United States Patent
Pak et al.

(10) Patent No.: US 12,250,878 B2
(45) Date of Patent: Mar. 11, 2025

(54) LIGHT-EMITTING DIODE AND AMINE COMPOUND FOR THE SAME

(71) Applicant: Samsung Display Co., Ltd., Yongin-si (KR)

(72) Inventors: Hankyu Pak, Suwon-si (KR); Eunjae Jeong, Hwaseong-si (KR); Sanghyun Han, Hwaseong-si (KR); Dongjun Kim, Suwon-si (KR); Minji Kim, Hwaseong-si (KR); Sohee Jo, Cheonan-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 786 days.

(21) Appl. No.: 17/445,484

(22) Filed: Aug. 19, 2021

(65) Prior Publication Data
US 2022/0199910 A1    Jun. 23, 2022

(30) Foreign Application Priority Data
Dec. 10, 2020 (KR) .................. 10-2020-0172684

(51) Int. Cl.
| | |
|---|---|
| H10K 85/60 | (2023.01) |
| C07D 405/12 | (2006.01) |
| C07D 409/12 | (2006.01) |
| C07F 7/08 | (2006.01) |
| H10K 85/40 | (2023.01) |
| H10K 50/15 | (2023.01) |

(52) U.S. Cl.
CPC ......... *H10K 85/636* (2023.02); *C07D 405/12* (2013.01); *C07D 409/12* (2013.01); *C07F 7/0812* (2013.01); *H10K 85/40* (2023.02); *H10K 50/15* (2023.02); *H10K 85/6572* (2023.02); *H10K 85/6574* (2023.02); *H10K 85/6576* (2023.02)

(58) Field of Classification Search
None
See application file for complete search history.

(56) References Cited

U.S. PATENT DOCUMENTS

| | | | |
|---|---|---|---|
| 4,720,432 A | 1/1988 | VanSlyke et al. | |
| 5,061,569 A | 10/1991 | VanSlyke et al. | |
| 6,242,115 B1 | 6/2001 | Thomson et al. | |
| 8,021,764 B2 | 9/2011 | Hwang et al. | |
| 9,978,949 B2 | 5/2018 | Mujica-Fernaud et al. | |
| 2020/0235297 A1 | 7/2020 | Miyake et al. | |

FOREIGN PATENT DOCUMENTS

| | | | | |
|---|---|---|---|---|
| CN | 110950829 A | * | 4/2020 | ........... C07D 311/96 |
| CN | 111018783 A | * | 4/2020 | ........... C07D 221/20 |
| CN | 112409314 A | * | 2/2021 | ........... C07D 311/96 |
| JP | H 11-144873 A | | 5/1999 | |
| JP | 2000-302756 A | | 10/2000 | |
| JP | 2003-133075 A | | 5/2003 | |
| JP | 2004-079265 A | | 3/2004 | |
| JP | 2006-151979 A | | 6/2006 | |
| KR | 10-1695270 B1 | | 1/2017 | |
| KR | 10-1716069 B1 | | 3/2017 | |
| KR | 10-1857518 B1 | | 5/2018 | |
| KR | 10-2078171 B1 | | 2/2020 | |
| KR | 10-2020-0100241 A | | 8/2020 | |

OTHER PUBLICATIONS

Machine translation of CN-111018783-A, translation generated May 2024, 23 pages. (Year: 2024).*
Machine translation of CN-110950829-A, translation generated May 2024, 36 pages. (Year: 2024).*

* cited by examiner

*Primary Examiner* — Robert S Loewe
(74) *Attorney, Agent, or Firm* — Womble Bond Dickinson

(57) ABSTRACT

A light-emitting diode may include a first electrode, a second electrode, and at least one functional layer disposed between the first electrode and the second electrode, the at least one functional layer including an amine compound represented by Formula 1. The light-emitting diode may exhibit high luminous efficiency properties and improved lifetime properties.

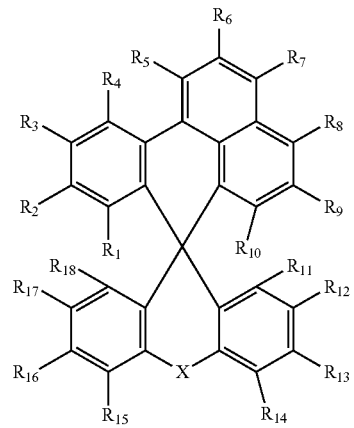

Formula 1

18 Claims, 6 Drawing Sheets

LIGHT-EMITTING DIODE AND AMINE COMPOUND FOR THE SAME

CROSS-REFERENCE TO RELATED APPLICATIONS

This application claims priority to and the benefit of Korean Patent Application No. 10-2020-0172684, filed on Dec. 10, 2020 in the Korean Intellectual Property Office, the entire content of which is hereby incorporated by reference.

BACKGROUND

1. Field

One or more embodiments of the present disclosure herein relate to a light emitting diode and an amine compound used (e.g., utilized) therein, and more particularly, to an amine compound used (e.g., utilized) in a hole transport region and a light-emitting diode including the same.

2. Description of the Related Art

Recently, the development of an organic electroluminescence display device, etc. as an image display has been actively conducted. The organic electroluminescence display device and/or the like is a display device including a self-luminescent device in which holes and electrons injected from a first electrode and a second electrode, respectively, recombine in an emission layer, and thereby a light-emitting material emits light in the emission layer to attain display of images.

In the application of a light-emitting diode to a display device, low driving voltage, high luminous efficiency, and/or long lifetime (lifespan) are required (or desired), and it is continuously required (or desired) to develop a material for the light-emitting diode that can stably (or suitably) achieve these desired characteristics.

In addition, to achieve a high efficiency light-emitting diode, a material for a hole transport region to inhibit exciton energy diffusion in an emission layer is desired (or continually being developed).

SUMMARY

One or more aspects of embodiments of the present disclosure are directed toward a light-emitting diode that exhibits excellent or improved luminous efficiency and lifetime (lifespan) properties.

The present disclosure also provides an amine compound which is a material for the light-emitting diode with high efficiency and long lifetime properties.

In one or more embodiments of the present disclosure, a light-emitting diode may include a first electrode, a second electrode on the first electrode, and at least one functional layer between the first electrode and the second electrode and including an amine compound represented by Formula 1:

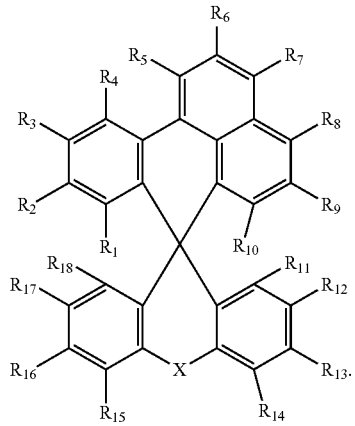

[Formula 1]

In Formula 1, X is O, S, $SiR_aR_b$, or $NR_c$, $R_1$ to $R_{18}$, $R_a$, $R_b$, and $R_c$ may each independently be a hydrogen atom, a deuterium atom, a halogen atom, a substituted or unsubstituted silyl group, a substituted or unsubstituted amine group, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms, and/or may be combined with an adjacent group to form a ring, and at least one selected from among $R_1$ to $R_{18}$ is represented by Formula 2:

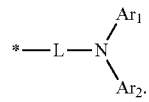

[Formula 2]

In Formula 2, L may be a direct linkage, a substituted or unsubstituted ring-forming arylene group having 6 to 30 carbon atoms, or a substituted or unsubstituted ring-forming heteroarylene group having 2 to 30 carbon atoms, and $Ar_1$ and $Ar_2$ may each independently be a substituted or unsubstituted ring-forming aryl group having 6 to 30 carbon atoms, or a substituted or unsubstituted ring-forming heteroaryl group having 2 to 30 carbon atoms.

In one or more embodiments, the at least one functional layer may include an emission layer, a hole transport region between the first electrode and the emission layer, and an electron transport region between the emission layer and the second electrode, and the hole transport region may include the amine compound.

In one or more embodiments, the hole transport region may include a hole injection layer on the first electrode and a hole transport layer on the hole injection layer, and the hole transport layer may include the amine compound.

In one or more embodiments, the amine compound represented by Formula 1 may be represented by any one selected from among Formula 1A to Formula 1D:

[Formula 1A]

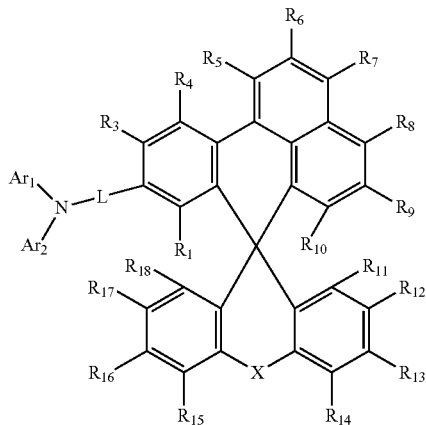

[Formula 1B]

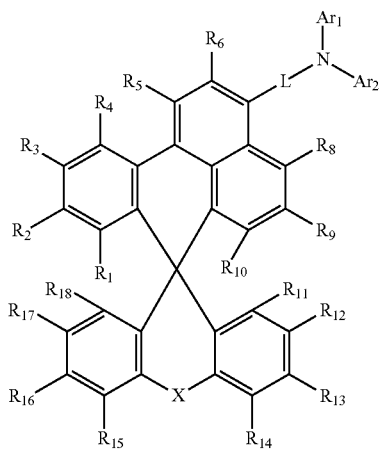

[Formula 1C]

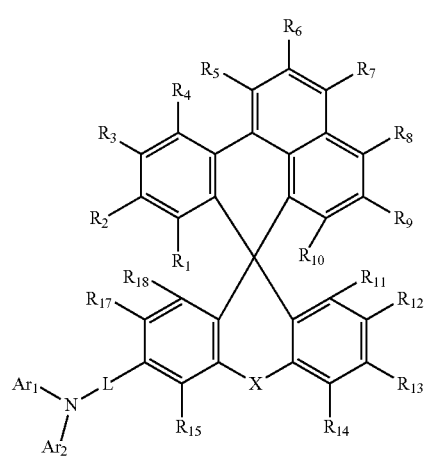

[Formula 1D]

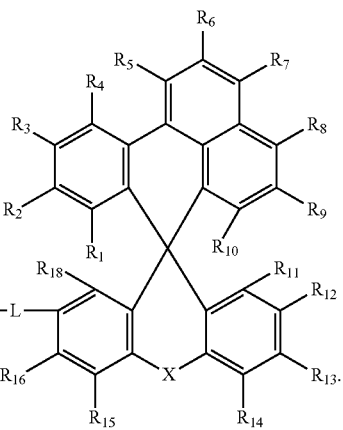

In Formula 1A to Formula 1D, X, $R_1$ to $R_{18}$, L, $Ar_1$, and $Ar_2$ are the same as defined in Formula 1 and Formula 2.

In one or more embodiments, a substituent represented by Formula 2 may be represented by Formula 2A or Formula 2B:

[Formula 2A]

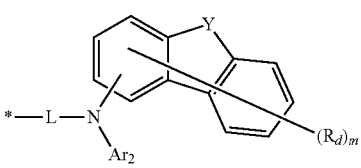

[Formula 2B]

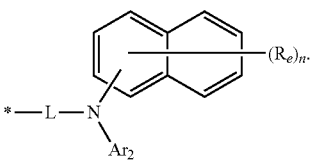

In Formula 2A and Formula 2B, Y may be O, S, $NAr_3$, or $CR_fR_g$, and $Ar_3$ may be a substituted or unsubstituted ring-forming aryl group having 6 to 30 carbon atoms, or a substituted or unsubstituted ring-forming heteroaryl group having 2 to 30 carbon atoms, and $R_d$, $R_e$, $R_f$ and $R_g$ may each independently be a hydrogen atom, a deuterium atom, a halogen atom, a substituted or unsubstituted silyl group, a substituted or unsubstituted amine group, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms, and/or may be combined with an adjacent group to form a ring, "m" and "n" may each independently be an integer of 0 to 7, and L and $Ar_2$ are the same as defined in Formula 2.

In one or more embodiments, X may be O, S, or $SiR_aR_b$.

In one or more embodiments, L may be a direct linkage.

In one or more embodiments, $Ar_1$ and $Ar_2$ may be different from each other.

In one or more embodiments, $Ar_1$ and $Ar_2$ may each independently be a substituted or unsubstituted phenyl group, a substituted or unsubstituted naphthyl group, a substituted or unsubstituted biphenyl group, a substituted or unsubstituted fluorenyl group, a substituted or unsubstituted carbazole group, a substituted or unsubstituted dibenzofuran group, or a substituted or unsubstituted dibenzothiophenyl group.

In one or more embodiments, $R_a$, $R_b$, and $R_c$ may each independently be a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms.

In one or more embodiments of the present disclosure, an amine compound represented by Formula 1 above is provided.

BRIEF DESCRIPTION OF THE DRAWINGS

The accompanying drawings are included to provide a further understanding of the present disclosure, and are incorporated in and constitute a part of this specification. The drawings illustrate embodiments of the present disclosure and, together with the description, serve to explain principles of the present disclosure. In the drawings.

DETAILED DESCRIPTION

Figure 1:
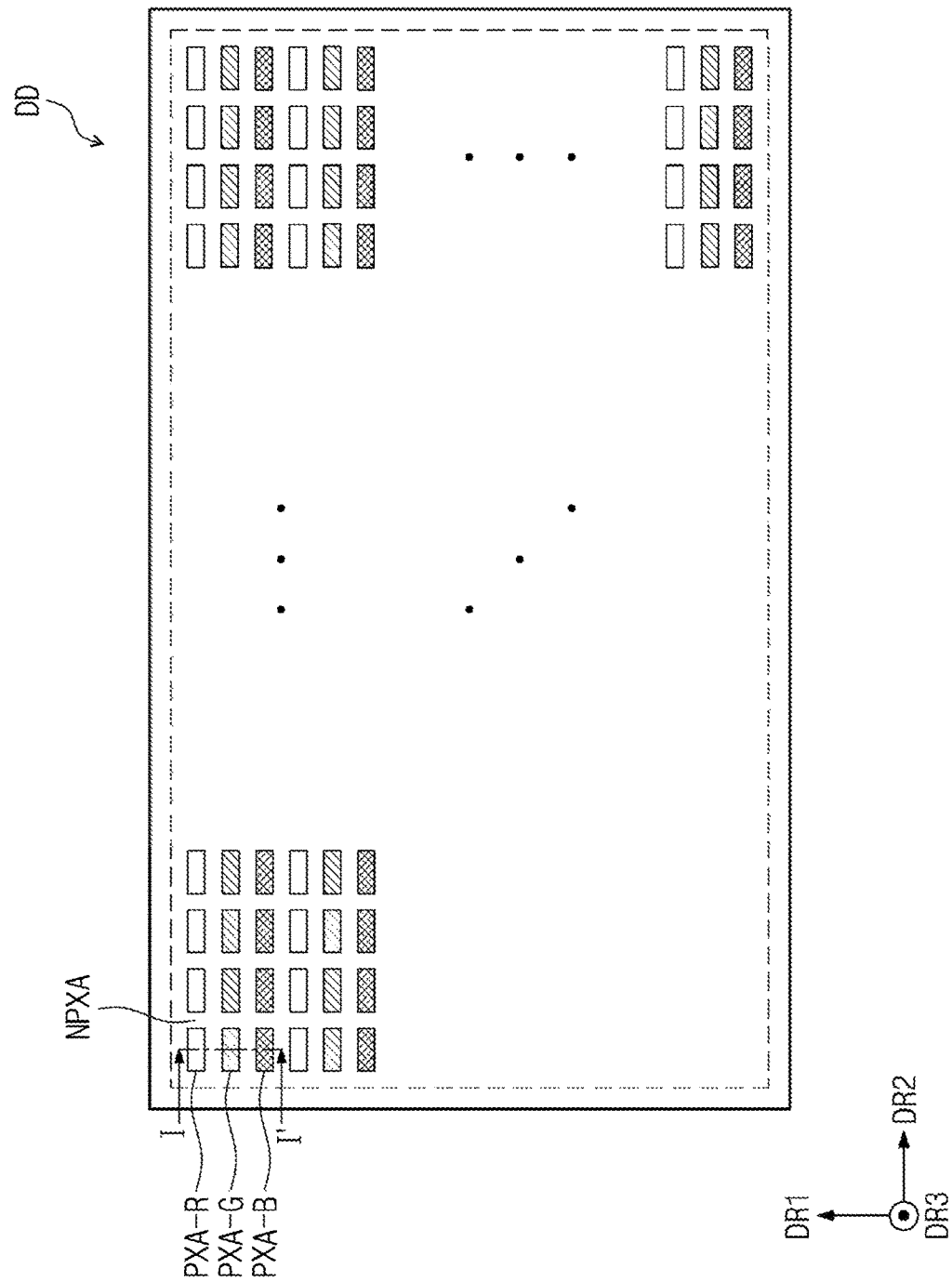
FIG. 1 is a plan view illustrating a display device according to one or more embodiments.

The present disclosure may be modified in many alternative forms, and thus specific embodiments will be exemplified in the drawings and described in more detail. It should be understood, however, that it is not intended to limit the present disclosure to the particular forms disclosed, but rather, is intended to cover all modifications, equivalents, and alternatives falling within the spirit and scope of the present disclosure.

When explaining each of drawings, like reference numerals are used for referring to like components. In the accompanying drawings, the dimensions of structures are exaggeratively illustrated for clarity of present disclosure. It will be understood that, although the terms "first," "second," etc. may be used herein to describe various elements, these elements should not be limited by these terms. These terms are only used to distinguish one element from another. For example, a first element may be referred to as a second element, and similarly, a second element may be referred to as a first element without departing from the scope of the present disclosure. The singular forms include the plural forms as well unless the context clearly indicates otherwise.

In this application, it will be further understood that the terms "include," "comprise," or "have" etc. specify the presence of a feature, a fixed number, a task (step), an operation, an element, a component, or a combination thereof disclosed in the specification, but do not exclude the possibility of presence or addition of one or more other features, fixed numbers, tasks (steps), operations, elements, components, or combinations thereof.

In this application, when a part such as a layer, a film, a region, or a plate is referred to as being "on" or "above" another part, it may be "directly on" the other part (without any intervening parts therebetween), or an intervening part may also be present. Similarly, when a part such as a layer, a film, a region, a plate is referred to as being "under" or "below" another part, it may be "directly under" the other part (without any intervening parts therebetween), or an intervening part may also be present. In addition, in this application, when a part is referred to as being disposed "on" another part, it may be disposed on the other part or under the other part as well.

In the specification, "disposed" may refer to being positioned and/or provided.

As used herein, the terms "use," "using," and "used" may be considered synonymous with the terms "utilize," "utilizing," and "utilized," respectively.

As used herein, expressions such as "at least one of", "one of", and "selected from", when preceding a list of elements, modify the entire list of elements and do not modify the individual elements of the list.

As used herein, the term "and/or" includes any and all combinations of one or more of the associated listed items.

Further, the use of "may" when describing embodiments of the present disclosure refers to "one or more embodiments of the present disclosure".

As used herein, the terms "substantially", "about", and similar terms are used as terms of approximation and not as terms of degree, and are intended to account for the inherent deviations in measured or calculated values that would be recognized by those of ordinary skill in the art. "About" or "approximately," as used herein, is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may mean within one or more standard deviations, or within ±30%, 20%, 10%, 5% of the stated value.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

In the specification, the term "substituted or unsubstituted" may refer to a group that is unsubstituted or that is substituted with one or more substituents selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the exemplified substituents may be substituted or unsubstituted. For example, a biphenyl group may be interpreted as an aryl group or a phenyl group substituted with a phenyl group.

In the specification, the phase "combined with an adjacent group to form a ring" may mean combining with an adjacent group to form a substituted or unsubstituted hydrocarbon ring, or a substituted or unsubstituted heterocycle. The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may each independently be a monocycle or a polycycle. In addition, the ring formed by combining adjacent groups may be connected to another ring to form a spiro structure.

In the specification, the term "adjacent group" may refer to a pair of substituent groups where the first substituent is connected to an atom which is directly connected to another atom substituted with the second substituent; a pair of substituent groups connected to the same atom; or a pair of substituent groups where the first substituent is sterically positioned at the nearest position to the second substituent. For example, in 1,2-dimethylbenzene, two methyl groups may be interpreted as "adjacent groups" to each other, and in 1,1-diethylcyclopentene, two ethyl groups may be interpreted as "adjacent groups" to each other. In addition, in 4,5-dimethylphenanthrene, two methyl groups may be interpreted as "adjacent groups" to each other.

In the specification, examples of the halogen atom may include a fluorine atom, a chlorine atom, a bromine atom, and an iodine atom.

In the specification, the alkyl group may be a linear, branched, or cyclic alkyl group. The number of carbon atoms of the alkyl group may be 1 to 50, 1 to 30, 1 to 20, 1 to 10, or 1 to 6. Examples of the alkyl group may include, but are not limited to, a methyl group, an ethyl group, an n-propyl group, an isopropyl group, an n-butyl group, a s-butyl group, a t-butyl group, an i-butyl group, a 2-ethylbutyl group, a 3,3-dimethylbutyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-t-butylcyclohexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantyl group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldocecyl group, a 2-octyldodecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-henicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, an n-triacontyl group, and the like.

In the specification, the hydrocarbon ring group refers to any functional group or substituent derived from an aliphatic hydrocarbon ring. The hydrocarbon ring group may be a saturated ring-forming hydrocarbon ring group having 5 to 20 carbon atoms (a saturated hydrocarbon ring group having 5 to 20 ring-forming carbon atoms).

In the specification, the aryl group refers to any functional group or substituent derived from an aromatic hydrocarbon ring. The aryl group may be a monocyclic aryl group or a polycyclic aryl group. The number of ring-forming carbon atoms of the aryl group may be 6 to 30, 6 to 20, or 6 to 15. Examples of the aryl group may include, but are not limited to, a phenyl group, a naphthyl group, a fluorenyl group, an anthracenyl group, a phenanthryl group, a biphenyl group, a terphenyl group, a quaterphenyl group, a quinquephenyl group, a sexiphenyl group, a triphenylenyl group, a pyrenyl group, a benzofluoranthenyl group, a chrysenyl group, and the like.

In the specification, the fluorenyl group may be substituted, and two substituents may be combined to form a spiro structure. When the fluorenyl group is substituted, it may be exemplified as follows. However, the embodiments of the present disclosure are not limited thereto.

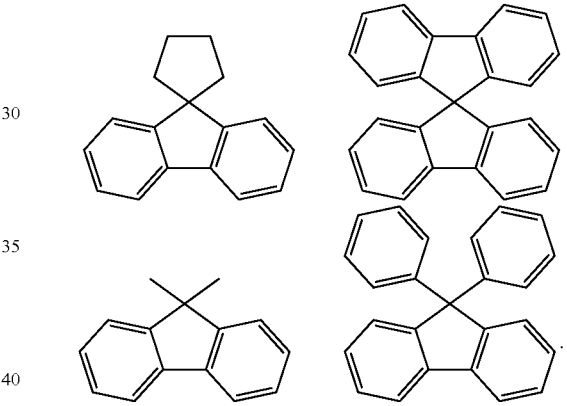

In the specification, the heterocyclic group refers to any functional group or substituent derived from a ring (e.g., a cyclic group) including one or more selected from among B, O, N, P, Si, and S as a heteroatom. The heterocyclic group includes an aliphatic heterocyclic group and an aromatic heterocyclic group. The aromatic heterocyclic group may be a heteroaryl group. The aliphatic heterocycle (e.g., the aliphatic heterocyclic group) and the aromatic heterocycle (e.g., the aromatic heterocyclic group) may each independently be a monocycle or a polycycle.

In the specification, the heterocyclic group may include one or more selected from among B, O, N, P, Si, and S as a heteroatom. If the heterocyclic group includes two or more heteroatoms, the two or more heteroatoms may be the same as or different from each other. The heterocyclic group may be a monocyclic heterocyclic group or a polycyclic heterocyclic group, and is a concept including a heteroaryl group. The number of ring-forming carbon atoms of the heterocyclic group may be 2 to 30, 2 to 20, or 2 to 10.

In the specification, the aliphatic heterocyclic group may include one or more selected from among B, O, N, P, Si, and S as a heteroatom. The number of ring-forming carbon atoms of the aliphatic heterocyclic group may be 2 to 30, 2 to 20, or 2 to 10. Examples of the aliphatic heterocyclic group may include, but are not limited to, an oxirane group, a thiirane group, a pyrrolidine group, a piperidine group, a tetrahydrofuranyl group, a tetrahydrothiophene group, a thiane group, a tetrahydropyran group, a 1,4-dioxane group, and the like.

In the specification, the heteroaryl group may include one or more selected from among B, O, N, P, Si, and S as a heteroatom. If the heteroaryl group includes two or more heteroatoms, the two or more heteroatoms may be the same as or different from each other. The heteroaryl group may be a monocyclic heterocyclic group or a polycyclic heterocyclic group. The number of ring-forming carbon atoms of the heteroaryl group may be 2 to 30, 2 to 20, or 2 to 10. Examples of the heteroaryl group may include, but are not limited to, thiophene, furan, pyrrole, imidazole, triazole, pyridine, bipyridine, pyrimidine, triazine, triazole, acridine, pyridazine, pyrazine, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isoxazole, oxazole, oxadiazole, thiadiazole, phenothiazine, dibenzosilole, dibenzofuran, and the like.

In the specification, the description for the aryl group described above may be applied to an arylene group except that the arylene group is a divalent group. The description for the heteroaryl group described above may be applied to a heteroarylene group except that the heteroarylene group is a divalent group.

In the specification, the silyl group includes an alkyl silyl group and an aryl silyl group. Examples of the silyl group may include, but are not limited to, a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like.

In the specification, the number of carbon atoms of the amino group may be 1 to 30, but is not particularly limited thereto. The amino group may include an alkyl amino group, an aryl amino group, and/or a heteroaryl amino group. Examples of the amino group may include, but are not limited to, a methylamino group, a dimethylamino group, a phenylamino group, a diphenylamino group, a naphthylamino group, a 9-methyl-anthracenylamino group, a triphenylamino group, and the like.

In the specification, the number of carbon atoms of the carbonyl group may be 1 to 40, 1 to 30, or 1 to 20, but is not particularly limited thereto. For example, it may include the structures below, but the embodiment of the present disclosure is not limited thereto:

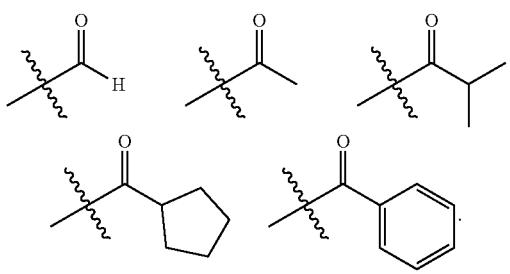

In the specification, the number of carbon atoms of the sulfinyl group and sulfonyl group may be 1 to 30, but is not particularly limited thereto. The sulfinyl group may include an alkyl sulfinyl group and an aryl sulfinyl group. The sulfonyl group may include an alkyl sulfonyl group and an aryl sulfonyl group.

In the specification, the thiol group may include an alkyl thio group and an aryl thio group. The thiol group may mean that a sulfur atom is bonded to the alkyl group or aryl group defined above. Examples of the thiol group may include, but are not limited to, a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, and the like.

In the specification, the oxy group may mean that an oxygen atom is bonded to the alkyl group or aryl group defined above. The oxy group may include an alkoxy group and an aryloxy group. The alkoxy group may be linear, branched, or cyclic. The carbon number of the alkoxy group may be, for example, 1 to 20 or 1 to 10, but is not particularly limited thereto. Examples of the oxy group may include, but are not limited to, methoxy, ethoxy, n-propoxy, isopropoxy, butoxy, pentyloxy, hexyloxy, octyloxy, nonyloxy, decyloxy, benzyloxy, and the like.

In the specification, the boron group may mean that a boron atom is bonded to the alkyl group or aryl group defined above. The boron group includes an alkyl boron group and an aryl boron group. Examples of the boron group may include, but are not limited to, a trimethylboron group, a triethylboron group, a t-butyldimethylboron group, a triphenylboron group, a diphenylboron group, a phenylboron group, and the like.

In the specification, the alkenyl group may be linear or branched. The number of carbon atoms is 2 to 30, 2 to 20, or 2 to 10, but is not particularly limited thereto. Examples of the alkenyl group may include, but are not limited to, a vinyl group, a 1-butenyl group, a 1-pentenyl group, a 1,3-butadienyl aryl group, a styrenyl group, a styrylvinyl group, and the like.

In the specification, the number of carbon atoms of the amine group may be 1 to 30, but is not particularly limited thereto. The amine group may include an alkyl amine group and/or an aryl amine group. Examples of the amine group may include, but are not limited to, a methylamine group, a dimethylamine group, a phenylamine group, a diphenylamine group, a naphthylamine group, a 9-methyl-anthracenylamine group, a triphenylamine group, and the like.

In the specification, the alkyl group in an alkylthio group, an alkylsulfoxy group, an alkylaryl group, an alkylamino group, an alkyl boron group, an alkyl silyl group, and/or an alkyl amine group is an example of the alkyl group described above.

In the specification, the aryl group in an aryloxy group, an arylthio group, an arylsulfoxy group, an arylamino group, an aryl boron group, an aryl silyl group, or an aryl amine group is an example of the aryl group described above.

In the specification, the direct linkage may mean a chemical bond (e.g., a single bond).

Meanwhile, in the specification, "$\dashv$" and "—·" means a position to be connected (e.g., a bonding site).

Hereinafter, embodiments of the present disclosure will be explained with reference to the drawings.

Figure 2:
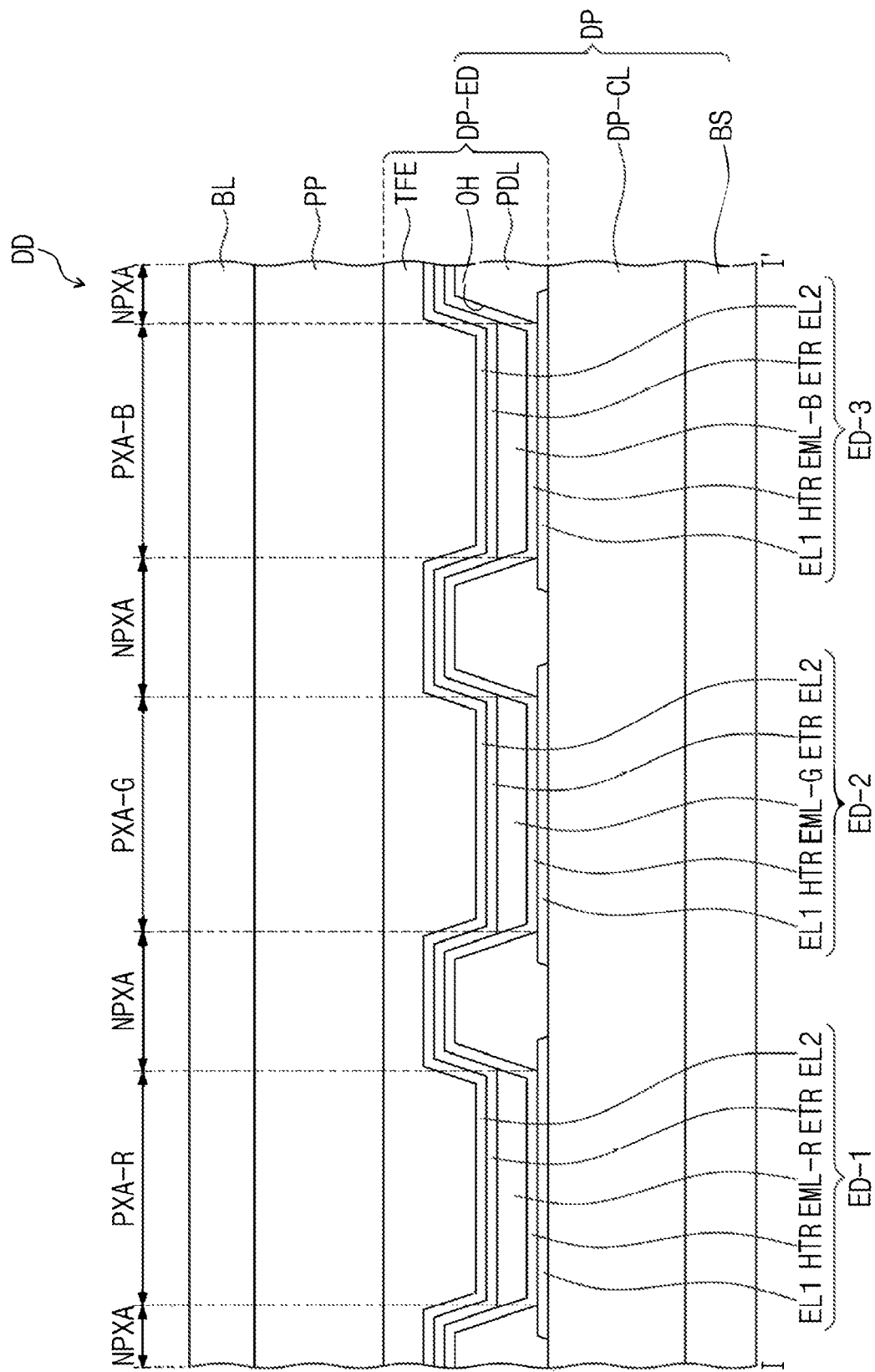
FIG. 2 is a cross-sectional view of a display device according to one or more embodiments.

FIG. 1 is a plan view illustrating one or more embodiments of a display device DD. FIG. 2 is a cross-sectional view of a display device DD according to one or more embodiments. FIG. 2 is a cross-sectional view illustrating a portion taken along line I-I' in FIG. 1.

The display device DD may include a display panel DP and an optical layer PP disposed on the display panel DP. The display panel DP includes light-emitting diodes ED-1, ED-2, and ED-3. The display device DD may include a plurality of light-emitting diodes ED-1, ED-2, and ED-3. The optical layer PP may be disposed on the display panel DP to control the reflected light by external light on the display panel DP. The optical layer PP may include, for example, a polarization layer and/or a color filter layer. In one or more embodiments, the optical layer PP may be omitted in the display device DD according to one or more embodiments.

A base substrate BL may be disposed on the optical layer PP. The base substrate BL may be a member configured to provide a base surface on which the optical layer PP is disposed. The base substrate BL may be a glass substrate, a metal substrate, a plastic substrate, and/or the like. However, the embodiment of the present disclosure is not limited thereto, and the base substrate BL may be an inorganic layer, an organic layer, or a composite material layer. In one or more embodiments, the base substrate BL may be omitted.

The display device DD according to one or more embodiments may further include a filling layer. The filling layer may be disposed between the display device layer DP-ED and the base substrate BL. The filling layer may be an organic material layer. The filling layer may include at least one of acrylic-based resin, silicone-based resin, or epoxy-based resin.

The display panel DP may include a base layer BS, a circuit layer DP-CL provided on the base layer BS, and a display device layer DP-ED. The display device layer DP-ED may include a pixel-defining film PDL, light-emitting diodes ED-1, ED-2, and ED-3 disposed between portions of the pixel-defining film PDL, and an encapsulating layer TFE disposed on the light-emitting diodes ED-1, ED-2, and ED-3.

The base layer BS may be a member configured to provide a base surface on which the display device layer DP-ED is disposed. The base layer BS may be a glass substrate, a metal substrate, a plastic substrate, and/or the like. However, the embodiment of the present disclosure is not limited thereto, and the base layer BS may be an inorganic layer, an organic layer, or a composite material layer (e.g., including an organic material and an inorganic material).

In one or more embodiments of the present disclosure, the circuit layer DP-CL is disposed on the base layer BS, and the circuit layer DP-CL may include a plurality of transistors. The transistors may each include a control electrode, an input electrode, and an output electrode. For example, the circuit layer DP-CL may include a switching transistor and a driving transistor for driving the light-emitting diodes ED-1, ED-2, and ED-3 of the display device layer DP-ED.

Each of the light-emitting diodes ED-1, ED-2, and ED-3 may have a structure of a light-emitting diode ED of one or more embodiments according to FIGS. 3 to 6 to be described below. Each of the light-emitting diodes ED-1, ED-2, and ED-3 may include a first electrode EL1, a hole transport region HTR, emission layers EML-R, EML-G, and EML-B, an electron transport region ETR, and a second electrode EL2.

In FIG. 2, the emission layers EML-R, EML-G, and EML-B of the light-emitting diodes ED-1, ED-2, and ED-3 are each disposed in an opening OH defined in the pixel-defining film PDL, and the hole transport region HTR, the electron transport region ETR, and the second electrode EL2 are provided as common layers in all of the light-emitting diodes ED-1, ED-2, and ED-3. However, the embodiment of the present disclosure is not limited thereto. In one or more embodiments, the hole transport region HTR and the electron transport region ETR may be patterned and provided in the opening OH defined in the pixel-defining film PDL. For example, in one or more embodiments, the hole transport region HTR, the emission layers EML-R, EML-G, and EML-B, and the electron transport region ETR, etc. of the light-emitting diodes ED-1, ED-2, and ED-3 may be patterned and provided by an inkjet printing method.

The encapsulating layer TFE may cover the light-emitting diodes ED-1, ED-2, and ED-3. The encapsulating layer TFE may seal the display device layer DP-ED. The encapsulating layer TFE may be a thin film encapsulating layer. The encapsulating layer TFE may be a single layer or a plurality of layers being stacked. The encapsulating layer TFE includes at least one insulating layer. The encapsulating layer TFE according to one or more embodiments may include at least one inorganic film (hereinafter, an encapsulating inorganic film). In one or more embodiments, the encapsulating layer TFE may include at least one organic film (hereinafter, an encapsulating organic film) and at least one encapsulating inorganic film.

The encapsulating inorganic film protects the display device layer DP-ED from moisture/oxygen, and the encapsulating organic film protects the display device layer DP-ED from foreign materials such as dust particles. The encapsulating inorganic film may include silicon nitride, silicon oxy nitride, silicon oxide, titanium oxide, aluminum oxide, and/or the like, but the embodiment of the present disclosure is not particularly limited thereto. The encapsulating organic film may include an acrylic-based compound, an epoxy-based compound, and/or the like. The encapsulating organic film may include a photopolymerizable organic material, but the embodiment of the present disclosure is not particularly limited thereto.

The encapsulating layer TFE may be disposed on the second electrode EL2 and may be disposed while filling (e.g., to fill) the opening OH.

Referring to FIGS. 1 and 2, the display device DD may include a non-light emitting region NPXA and light-emitting regions PXA-R, PXA-G, and PXA-B. The light-emitting regions PXA-R, PXA-G, and PXA-B may be a region in which light generated from the light-emitting diodes ED-1, ED-2, and ED-3 is emitted, respectively. The light-emitting regions PXA-R, PXA-G, and PXA-B may be spaced apart from each other on a plane (e.g., in plan view).

Each of the light-emitting regions PXA-R, PXA-G, and PXA-B may be a region separated by the pixel-defining film PDL. The non-light emitting region NPXA may be a region interposed between the neighboring light-emitting regions PXA-R, PXA-B, and PXA-G, and may be a region corresponding to the pixel-defining film PDL. Each of the light-emitting regions PXA-R, PXA-G, and PXA-B may correspond to a pixel. The pixel-defining film PDL may separate the light-emitting diodes ED-1, ED-2, and ED-3. Emission layers EML-R, EML-G and EML-B of the light-emitting diodes ED-1, ED-2 and ED-3 may be disposed and separated in the opening OH defined in the pixel-defining film PDL.

The light-emitting regions PXA-R, PXA-G, and PXA-B may be separated into a plurality of groups according to the color of light generated from the light-emitting diodes ED-1, ED-2, and ED-3. In the display device DD according to one or more embodiments illustrated in FIGS. 1 and 2, three light-emitting regions PXA-R, PXA-G, and PXA-B respectively emitting (e.g., to emit) red light, green light, and blue light are illustrated by way of example. For example, the display device DD according to one or more embodiments may include the red light-emitting region PXA-R, the green light-emitting region PXA-G, and the blue light-emitting region PXA-B, which are distinguished from each other.

In the display device DD according to one or more embodiments, the plurality of light-emitting diodes ED-1, ED-2, and ED-3 may emit light having different wavelength regions. For example, in one or more embodiments, the display device DD may include the first light-emitting diode ED-1 emitting (e.g., to emit) red light, the second light-emitting diode ED-2 emitting (e.g., to emit) green light, and the third light-emitting diode ED-3 emitting (e.g., to emit) blue light. For example, the red light-emitting region PXA-R, the green light-emitting region PXA-G, and the blue light-emitting region PXA-B of the display device DD may correspond to the first light-emitting diode ED-1, the second light-emitting diode ED-2, and the third light-emitting diode ED-3, respectively.

However, the embodiment of the present disclosure is not limited thereto, and the first to third light-emitting diodes ED-1, ED-2, and ED-3 may emit light of the same wavelength region, or at least one thereof may emit light of a different wavelength region. For example, all of the first to third light-emitting diodes ED-1, ED-2, and ED-3 may emit blue light.

The light-emitting regions PXA-R, PXA-G, and PXA-B in the display device DD according to one or more embodiments may be arranged in a stripe shape or pattern. Referring to FIG. 1, a plurality of red light-emitting regions PXA-R may be aligned with each other along a second direction axis DR2, a plurality of green light-emitting regions PXA-G may be aligned with each other along the second direction axis DR2, and a plurality of blue light-emitting regions PXA-B may be aligned with each other along the second direction axis DR2. In addition, a red light-emitting region PXA-R, a green light-emitting region PXA-G, and a blue light-emitting region PXA-B may be arranged by turns (e.g., alternatingly) with each other along a first direction axis DR1.

FIGS. 1 and 2 illustrate that all the light-emitting regions PXA-R, PXA-G, and PXA-B have similar areas, but the embodiment of the present disclosure is not limited thereto. The areas of the light-emitting regions PXA-R, PXA-G, and PXA-B may be different from each other depending on the wavelength region of the emitted light. As used herein, the areas of the light-emitting regions PXA-R, PXA-G, and PXA-B may mean areas as viewed on a plane defined by the first direction axis DR1 and the second direction axis DR2.

The arrangement of the light-emitting regions PXA-R, PXA-G, and PXA-B is not limited to the configuration illustrated in FIG. 1, and the arrangement order of the red light-emitting region PXA-R, the green light-emitting region PXA-G, and the blue light-emitting region PXA-B may be provided in various suitable combinations depending on the properties of display quality required (or desired) for the display device DD. For example, the light-emitting regions PXA-R, PXA-G, and PXA-B may be arranged in a PenTile®/PENTILE® configuration (PENTILE® is a registered trademark owned by Samsung Display Co., Ltd.) or a diamond configuration.

In one or more embodiments, the areas of the light-emitting regions PXA-R, PXA-G, and PXA-B may be different from each other. For example, in one or more embodiments, the area of the green light-emitting region PXA-G may be smaller than the area of the blue light-emitting region PXA-B, but the embodiment of the present disclosure is not limited thereto.

Hereinafter, FIGS. 3 to 6 are cross-sectional views schematically illustrating a light-emitting diode according to one or more embodiments. The light-emitting diode ED according to one or more embodiments may include a first electrode EL1, a second electrode EL2 facing the first electrodes EL1, and at least one functional layer disposed between the first electrode EL1 and the second electrode EL2. The at least one functional layer may include a hole transport region HTR, an emission layer EML, and an electron transport region ETR which are sequentially stacked. For example, a light-emitting diode ED according to one or more embodiments may include a first electrode EU, a hole transport region HTR, an emission layer EML, an electron transport region ETR, and a second electrode EL2 which are sequentially stacked.

Figure 3:
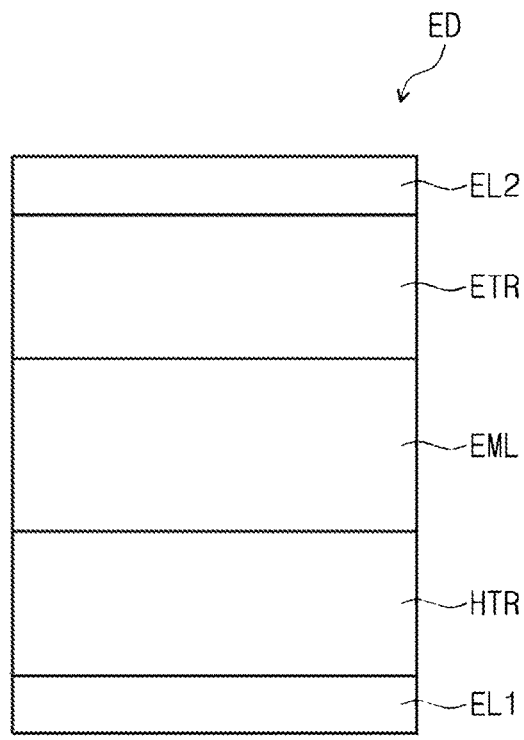
FIG. 3 is a cross-sectional view schematically illustrating a light-emitting diode according to one or more embodiments.
Figure 4:
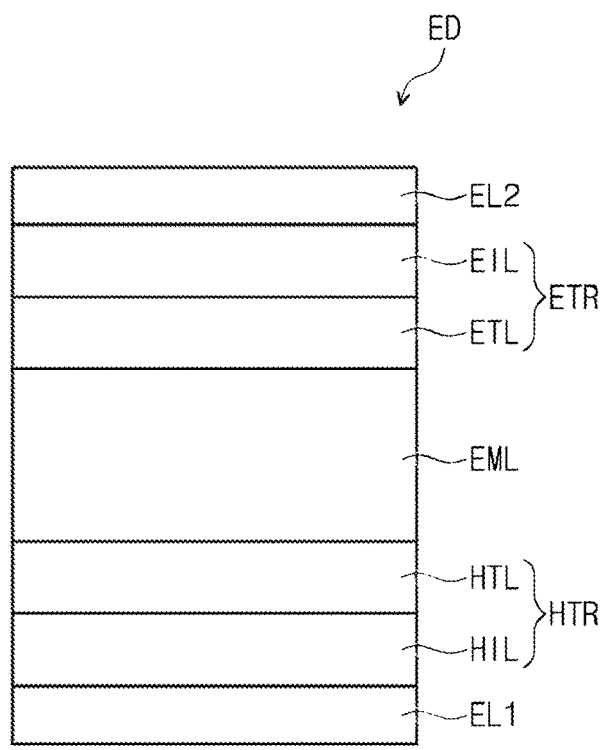
FIG. 4 is a cross-sectional view schematically illustrating a light-emitting diode according to one or more embodiments.
Figure 5:
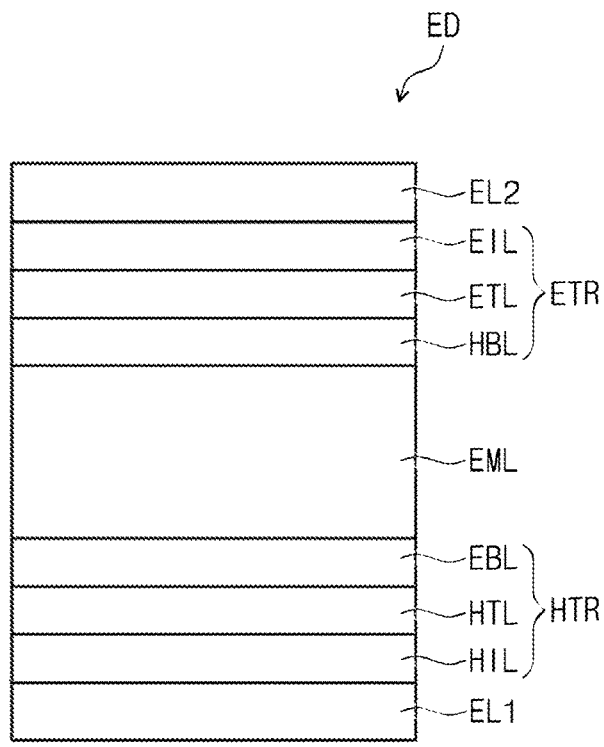
FIG. 5 is a cross-sectional view schematically illustrating a light-emitting diode according to one or more embodiments.
Figure 6:
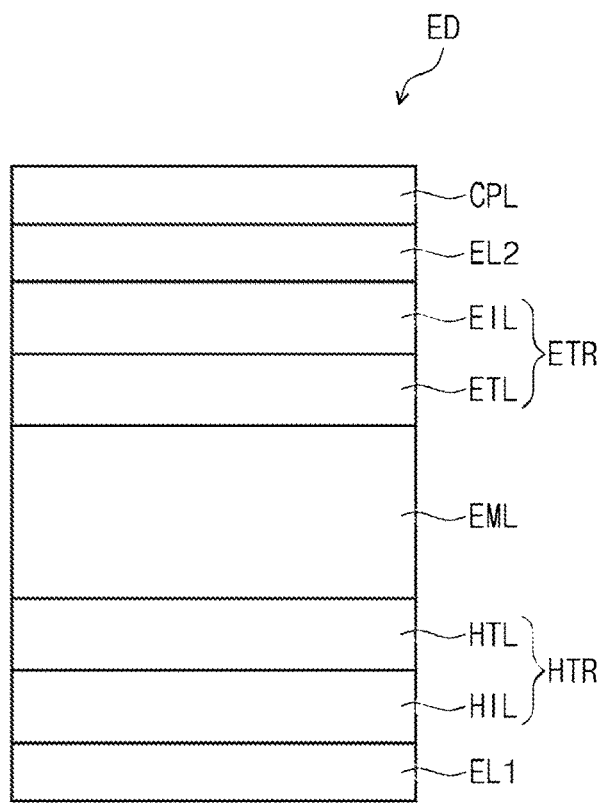
FIG. 6 is a cross-sectional view schematically illustrating a light-emitting diode according to one or more embodiments.

When compared with FIG. 3, FIG. 4 shows the cross-sectional view of the light-emitting diode ED according to one or more embodiments, wherein a hole transport region HTR includes a hole injection layer HIL and a hole transport layer HTL, and an electron transport region ETR includes an electron injection layer EIL and an electron transport layer ETL. When compared with FIG. 3, FIG. 5 shows the cross-sectional view of the light-emitting diode ED according to one or more embodiments, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. When compared with FIG. 4, FIG. 6 shows the cross-sectional view of the light-emitting diode ED according to one or more embodiments, which includes the capping layer CPL disposed on the second electrode EL2.

The light-emitting diode ED according to one or more embodiments may include an amine compound according to one or more embodiments to be described in more detail hereinbelow in at least one functional layer such as a hole transport region HTR, an emission layer EML, and/or an electron transport region ETR.

In the light-emitting diode ED according to one or more embodiments, the first electrode EL1 has conductivity. The first electrode EL1 may be formed of a metal material, a metal alloy, or any suitable conductive compound. The first electrode EL1 may be an anode or a cathode. However, the embodiment of the present disclosure is not limited thereto. In one or more embodiments, the first electrode EL1 may be a pixel electrode. The first electrode EL1 may be a transmissive electrode, a transflective electrode, or a reflective electrode. If the first electrode EL1 is the transmissive electrode, the first electrode EL1 may include transparent metal oxide such as indium tin oxide (ITO), indium zinc oxide (IZO), zinc oxide (ZnO), indium tin zinc oxide (ITZO), and/or the like. If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, W, a compound thereof, and/or a mixture thereof (for example, a mixture of Ag and Mg). In one or more embodiments, the first electrode EU may have a multilayered structure including a reflective film or a transflective film formed of any of the above-described materials and a transparent conductive film formed of indium tin oxide (ITO), indium zinc oxide (IZO), zinc oxide (ZnO), indium tin zinc oxide (ITZO), and/or the like. For example, the first electrode EL1 may have a three-layer structure of ITO/Ag/ITO, but the embodiment of the present disclosure is not limited thereto. In one or more embodiments, the first electrode EL1 may include the above-described metal material, a combination of two or more metal materials selected from the above-described metal materials, and/or an oxide of the above-described metal materials. A thickness of the first electrode EL1 may be about 700 Å to about 10000 Å. For example, the thickness of the first electrode EL1 may be about 1000 Å to about 3000 Å.

The hole transport region HTR is provided on the first electrode EL1. The hole transport region HTR may include at least one of a hole injection layer HIL, a hole transport layer HTL, a buffer layer, or a light-emitting auxiliary layer, or an electron blocking layer EBL. A thickness of the hole transport region HTR may be, for example, about 50 Å to about 15,000 Å.

The hole transport region HTR may have a single layer formed using (e.g., consisting of) a single material, a single layer formed using a plurality of different materials, or a multilayer structure having a plurality of layers formed using a plurality of different materials.

For example, the hole transport region HTR may have a structure of a single layer of a hole injection layer HIL or a hole transport layer HTL, and may have a structure of a single layer formed using a hole injection material and a hole transport material. Further, the hole transport regions HTR may have a structure of a single layer formed using a plurality of different materials, or a structure in which a hole injection layer HIL/hole transport layer HTL, a hole injection layer HIL/hole transport layer HTL/buffer layer, a hole injection layer HIL/buffer layer, a hole transport layer HTL/buffer layer, or a hole injection layer HIL/hole transport layer HTL/electron blocking layer EBL which are stacked in the stated order from the first electrode EL1, but the embodiment of the present disclosure is not limited thereto.

The hole transport region HTR may be formed by using one or more suitable methods such as a vacuum deposition method, a spin coating method, a cast method, a Langmuir-Blodgett (LB) method, an inkjet printing method, a laser printing method, and/or a laser induced thermal imaging (LITI) method.

In a light-emitting diode ED according to one or more embodiments, the hole transport region HTR may include the amine compound represented by Formula 1. In one or more embodiments, in a light-emitting diode ED according to one or more embodiments, the hole transport layer HTL may include the amine compound represented by Formula 1.

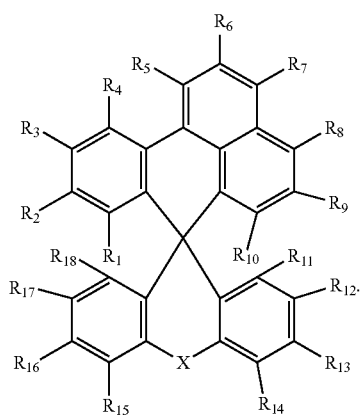

[Formula 1]

In Formula 1, any one of $R_1$ to $R_{18}$ is represented by Formula 2.

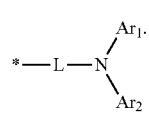

[Formula 2]

For example, the amine compound according to one or more embodiments may be in a form in which one amine derivative represented by Formula 2 is bonded in a condensed ring having a spiro structure represented by Formula 1. For example, the amine compound according to one or more embodiments may be a monoamine compound including one amine derivative (e.g., one amine group).

In Formula 1, any one of $R_1$ to $R_{18}$ may be represented by Formula 2, and the remainder may each independently be a hydrogen atom, a deuterium atom, a halogen atom, a substituted or unsubstituted silyl group, a substituted or unsubstituted amine group, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms, and/or may be combined with an adjacent group to form a ring. For example, any one of $R_1$ to $R_{18}$ may be represented by Formula 2, and the remainder may each independently be a hydrogen atom, or a substituted or unsubstituted aryl group. For example, any one of $R_1$ to $R_{18}$ may be represented by Formula 2, and the remainder may each independently be a hydrogen atom, or a substituted or unsubstituted phenyl group.

In Formula 1, X is O, S, $SiR_aR_b$, or $NR_c$.

For example, the amine compound according to one or more embodiments may be in a form in which one amine derivative represented by Formula 2 is bonded in a condensed ring having a spiro structure including a heteroatom represented by X. For example, X may be O, S, or $SiR_aR_b$.

$R_a$, $R_b$, and $R_c$ may each independently be a hydrogen atom, a deuterium atom, a halogen atom, a substituted or unsubstituted silyl group, a substituted or unsubstituted amine group, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms, and/or may be combined with an adjacent group to form a ring. For example, $R_a$, $R_b$, and $R_c$ may each independently be a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms. For example, $R_a$ and $R_b$ may each independently be a methyl group. However, the embodiment of the present disclosure is not limited thereto.

In Formula 2, L may be a direct linkage, a substituted or unsubstituted ring-forming arylene group having 6 to 30 carbon atoms, or a substituted or unsubstituted ring-forming heteroarylene group having 2 to 30 carbon atoms. For example, L may be a direct linkage. For example, N (nitrogen atom) of the amine group represented by Formula 2 may be directly combined with the condensed ring represented by Formula 1.

In one or more embodiments, in Formula 2, $Ar_1$ and $Ar_2$ are each independently a substituted or unsubstituted ring-forming aryl group having 6 to 30 carbon atoms, or a substituted or unsubstituted ring-forming heteroaryl group having 2 to 30 carbon atoms. For example, $Ar_1$ and $Ar_2$ may each independently be a substituted or unsubstituted phenyl group, a substituted or unsubstituted naphthyl group, a substituted or unsubstituted biphenyl group, a substituted or unsubstituted fluorenyl group, a substituted or unsubstituted carbazolyl group, a substituted or unsubstituted dibenzofuranyl group, or a substituted or unsubstituted dibenzothiophenyl group.

In one or more embodiments, $Ar_1$ and $Ar_2$ may each independently be a fluorenyl group in which two methyl groups are substituted at the carbon atom in position 9a.

In one or more embodiments, $Ar_1$ and $Ar_2$ may each independently be a substituted carbazole group in which a substituted or unsubstituted ring-forming aryl group having 6 to 30 carbon atoms, or a substituted or unsubstituted ring-forming heteroaryl group having 2 to 30 carbon atoms is substituted at the nitrogen atom in position 9. For example, $Ar_1$ and $Ar_2$ may each independently be a carbazole group substituted with a substituted or unsubstituted phenyl group, a carbazole group substituted with a substituted or unsubstituted biphenyl group, a carbazole group substituted with a substituted or unsubstituted dibenzofuran group, a carbazole group substituted with a substituted or unsubstituted dibenzothiophenyl group.

In one or more embodiments, $Ar_1$ and $Ar_2$ may each independently be an unsubstituted dibenzofuran group, a naphtho[1,2-b]benzofuran group, or a naphtho[2,3-b]benzofuran group.

In one or more embodiments, $Ar_1$ and $Ar_2$ may each independently be an unsubstituted dibenzothiophene group, a benzo[b]naphtho[2,1-d]thiophene group, or a benzo[b]naphtho[2,3-d]thiophene group.

In one or more embodiments, $Ar_1$ and $Ar_2$ may be different from each other. In one or more embodiments, $Ar_1$ may be a substituted or unsubstituted ring-forming aryl group having 6 to 30 carbon atoms, and $Ar_2$ may be a substituted or unsubstituted ring-forming heteroaryl group having 2 to 30 carbon atoms. For example, $Ar_1$ may be an unsubstituted naphthyl group, and $Ar_2$ may be an unsubstituted dibenzothiophene group.

In one or more embodiments, $Ar_1$ and $Ar_2$ each may be a substituted or unsubstituted ring-forming aryl group having 6 to 30 carbon atoms, and may be different from each other. For example, $Ar_1$ may be a naphthyl group in which a phenyl group is substituted, and $Ar_2$ may be an unsubstituted phenyl group.

In one or more embodiments, $Ar_1$ and $Ar_2$ each may be a substituted or unsubstituted ring-forming heteroaryl group having 2 to 30 carbon atoms, and may be different from each other. For example, $Ar_1$ may be a substituted or unsubstituted carbazole group, and $Ar_2$ may be a substituted or unsubstituted dibenzofuran group. However, the embodiment of the present disclosure is not limited thereto.

In one or more embodiments, the amine compound represented by Formula 1 may be represented by any one selected from among Formula 1-1 to Formula 1-4.

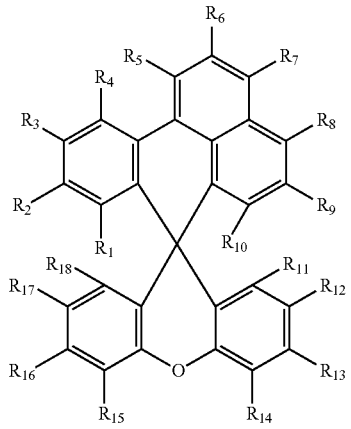

[Formula 1-1]


[Formula 1-2]

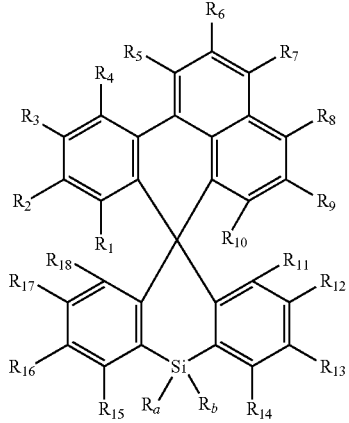

[Formula 1-3]

[Formula 1-4]

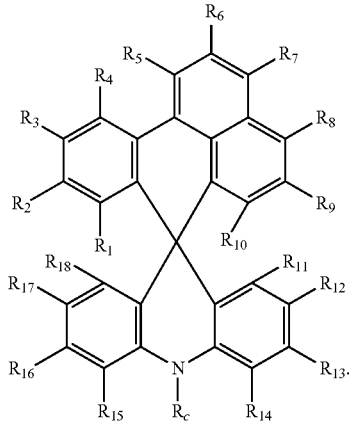

Formula 1-1 to Formula 1-4 embody when X is O, S, $SiR_aR_b$, or $NR_c$ in Formula 1, respectively.

In Formula 1-1 to Formula 1-4, $R_1$ to $R_{18}$, $R_a$, $R_b$, and $R_c$ are the same as defined In Formula 1.

In one or more embodiments, the amine compound represented by Formula 1 may be represented by any one selected from among Formula 1A to Formula 1D.

[Formula 1A]

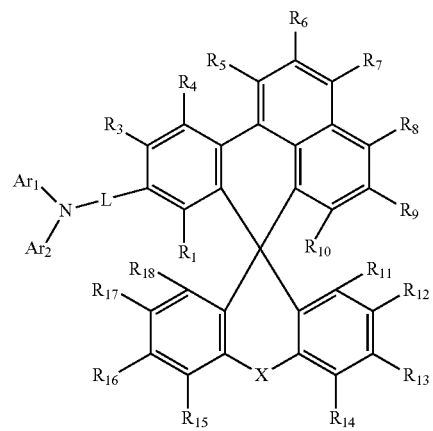

[Formula 1B]

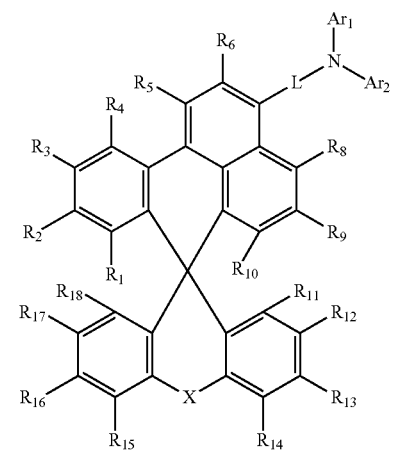

[Formula 1C]

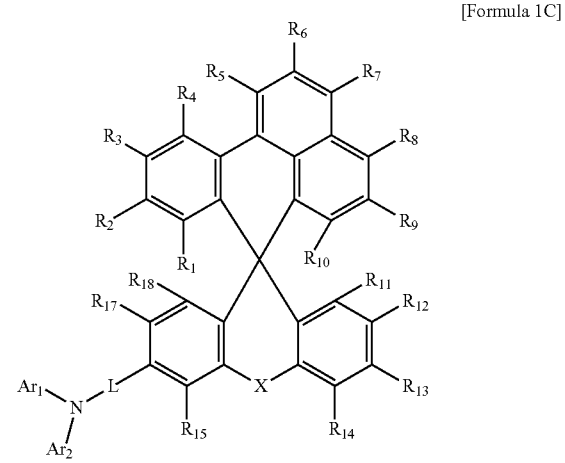

[Formula 1D]

Formula 1A to Formula 1D embody the structure in which the amine group represented by Formula 2 is connected to one selected from among $R_1$ to $R_{18}$ of Formula 1.

In one or more embodiments, Formula 1A is a structure in which the amine group represented by Formula 2 is connected to $R_2$ of Formula 1. Formula 1B is a structure in which the amine group represented by Formula 2 is connected to $R_7$ of Formula 1. Formula 1C is a structure in which the amine group represented by Formula 2 is connected to $R_{16}$ of Formula 1. Formula 1D is a structure in which the amine group represented by Formula 2 is connected to $R_{17}$ of Formula 1. However, the embodiment of the present disclosure is not limited thereto.

The amine compound according to one or more embodiments may have a structure disclosed in Formula 1A to Formula 1D, and thus hole transport ability of the amine compound may be improved.

In Formula 1A to Formula 1D, X, $R_1$ to $R_{18}$, L, $Ar_1$, and $Ar_2$ are the same as defined in Formula 1 and Formula 2.

In one or more embodiments, a substituent represented by Formula 2 may be represented by Formula 2A or Formula 2B.

[Formula 2A]

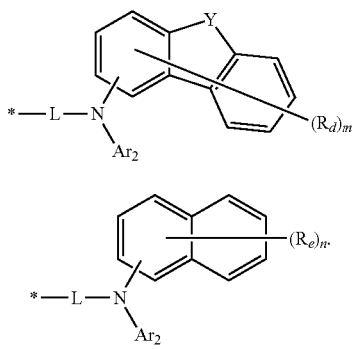

[Formula 2B]

a naphtho[2,3-b]benzofuran group

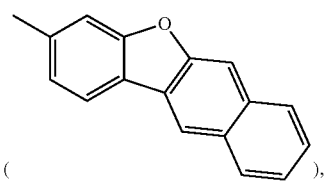 [SMILES: Cc1ccc2c(c1)oc1cc3ccccc3cc12]

( ), a benzo[b]naphtho[2,1-d]thiophene group

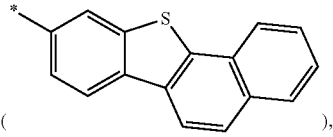

( ), or a benzo[b]naphtho[2,3-d]thiophene group

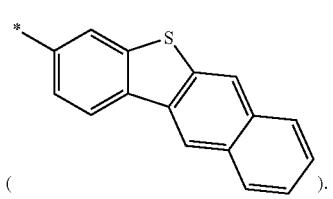 [SMILES: *c1ccc2c(c1)sc1cc3ccccc3cc12]

( ).

Formula 2A and Formula 2B embody $Ar_1$ In Formula 2.

In Formula 2A, Y may be O, S, $NAr_3$, or $CR_fR_g$. For example, An of Formula 2 may be a substituted or unsubstituted carbazole group, a substituted or unsubstituted dibenzofuran group, a substituted or unsubstituted dibenzothiophene group, or a substituted or unsubstituted fluorene group.

$R_d$ may be a hydrogen atom, a deuterium atom, a halogen atom, a substituted or unsubstituted silyl group, a substituted or unsubstituted amine group, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms, and/or may be combined with an adjacent group to form a ring.

"m" may be an integer of 0 to 7. For example, "m" may be 0, 1, or 2.

$Ar_3$ may be a substituted or unsubstituted ring-forming aryl group having 6 to 30 carbon atoms, or a substituted or unsubstituted ring-forming heteroaryl group having 2 to 30 carbon atoms.

$R_f$ and $R_g$ may each independently be a hydrogen atom, a deuterium atom, a halogen atom, a substituted or unsubstituted silyl group, a substituted or unsubstituted amine group, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms, and/or may be combined with an adjacent group to form a ring.

For example, when Y is O or S, "m" may be 0. For example, An may be an unsubstituted dibenzothiophenyl group or an unsubstituted dibenzofuranyl group.

For example, when Y is O or S, "m" may be 2, and two adjacent $R_d$ may be combined with each other to form a benzene ring. For example, An may be a naphtho[1,2-b]benzofuran group

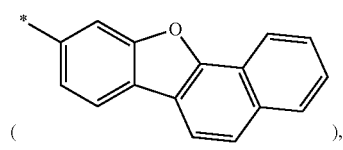

( ),

For example, when Y is N, "m" may be 0, and $Ar_3$ may be a substituted or unsubstituted phenyl group, an unsubstituted naphthyl group, an unsubstituted dibenzothiophene group, or an unsubstituted dibenzofuran group.

For example, when Y is C, "m" may be 0, and $R_f$ and $R_g$ each may be a methyl group.

In Formula 2B, $Ar_1$ may be a substituted or unsubstituted naphthyl group.

$R_e$ may be a hydrogen atom, a deuterium atom, a halogen atom, a substituted or unsubstituted silyl group, a substituted or unsubstituted amine group, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms, and/or may be combined with an adjacent group to form a ring.

"n" may be an integer of 0 to 7.

For example, "n" may be 0 or 1.

For example, when "n" is 1, $R_e$ may be a substituted or unsubstituted ring-forming aryl group having 6 to 30 carbon atoms, and for example, an unsubstituted phenyl group.

In Formula 2A and Formula 2B, L and $Ar_2$ are the same as defined in Formula 2.

The amine compound according to one or more embodiments, represented by Formula 1 may be represented by any one selected from among the amine compounds disclosed in Compound Group 1. The hole transport region HTR of a light-emitting diode ED according to one or more embodiments may include any one selected from among the amine compounds disclosed in Compound Group 1.

[Compound Group 1]
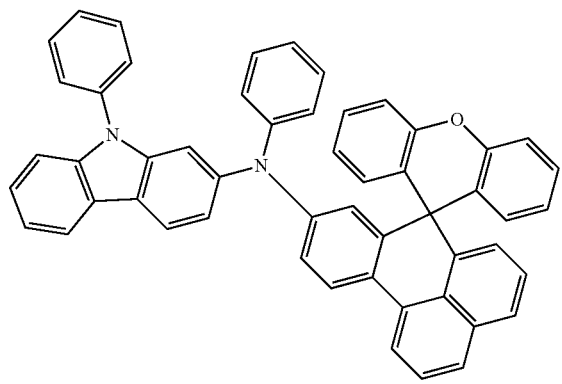
1
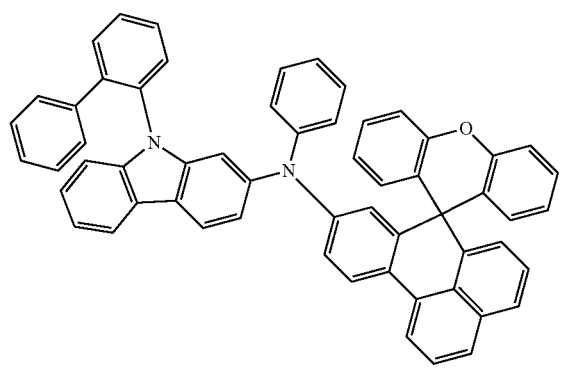
2
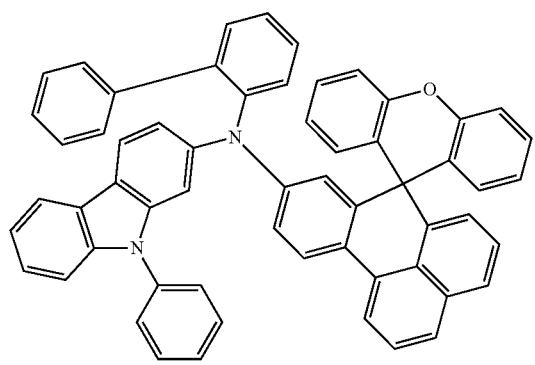
3
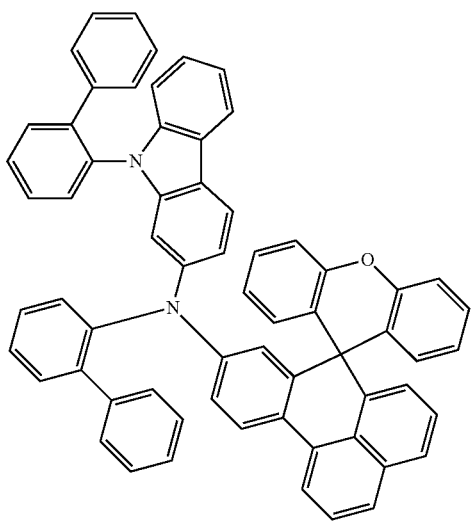
4
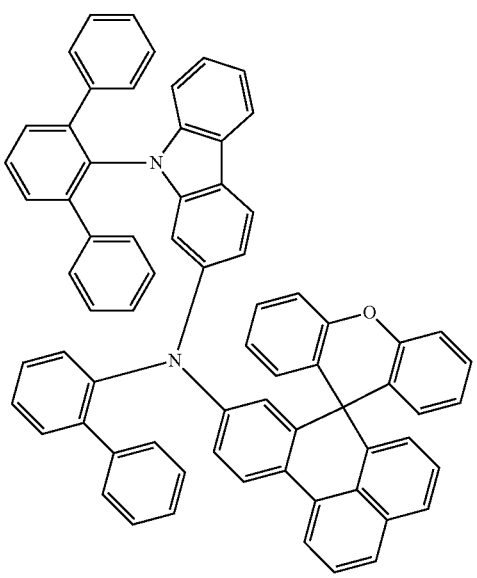
5
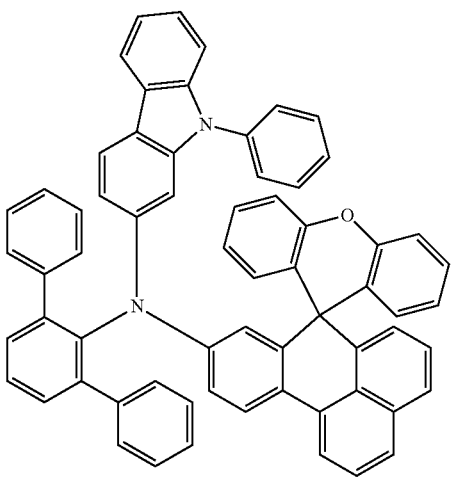
6

7
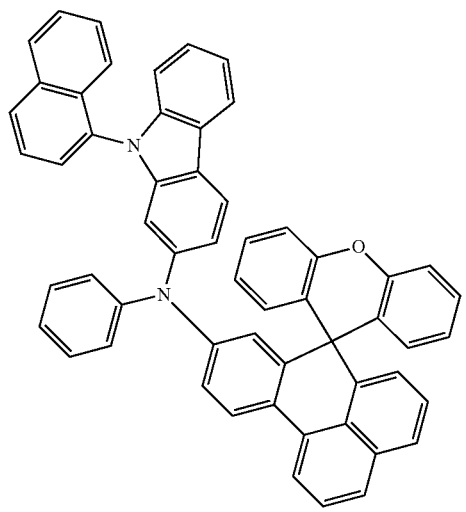
8
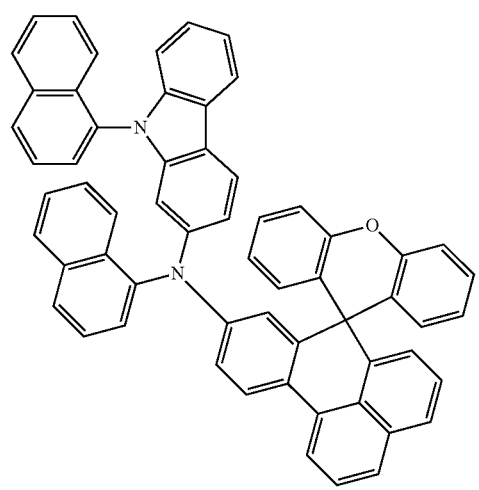
9
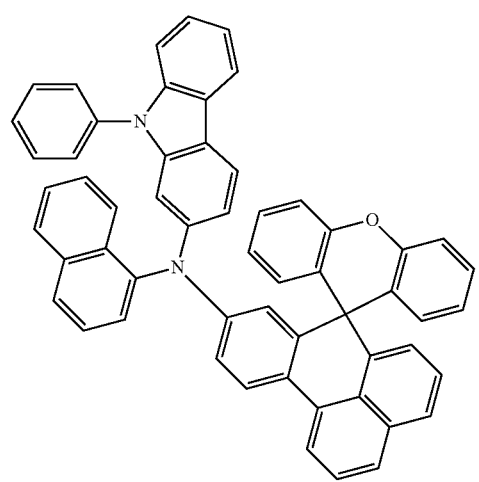
10
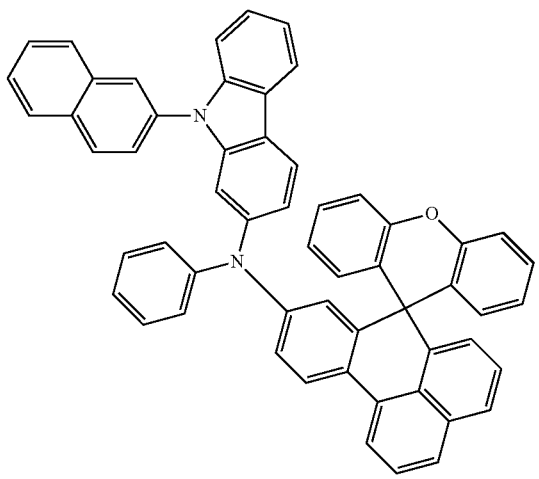
11
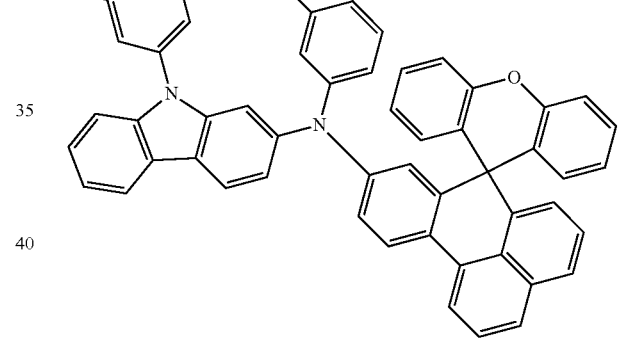
12
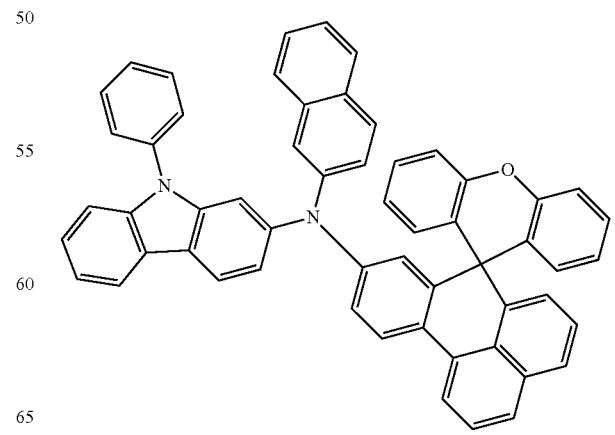

13
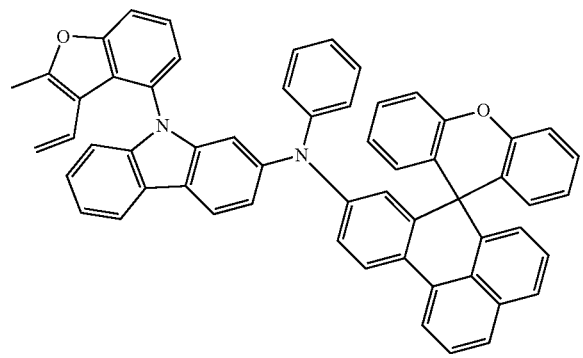
14
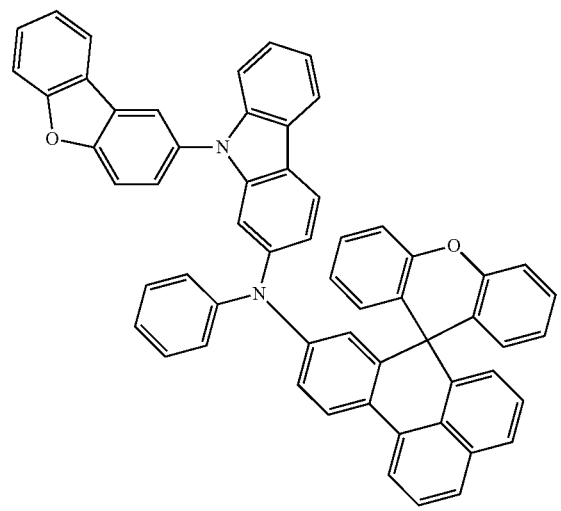
15
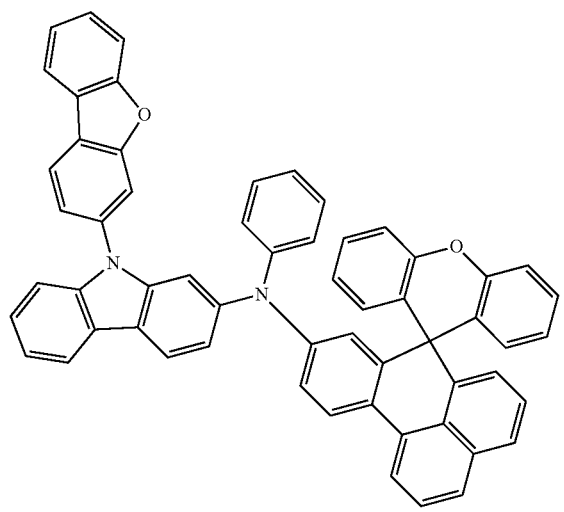
16
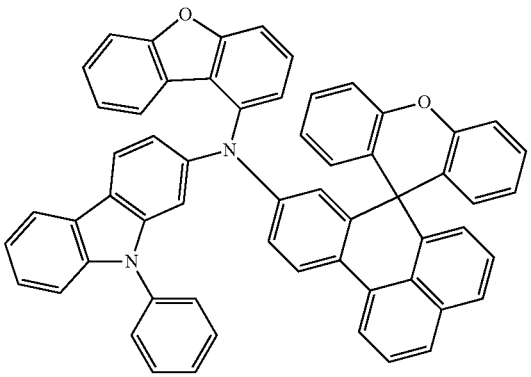
17
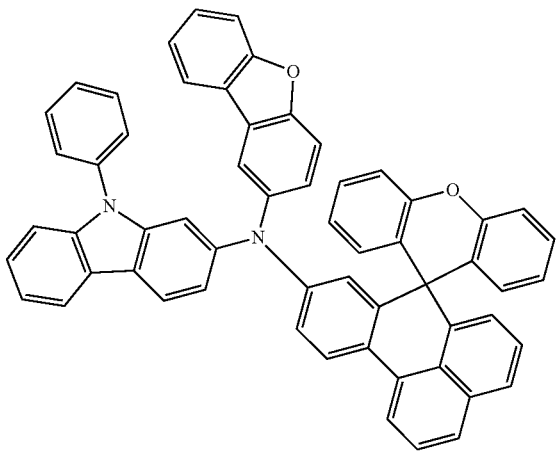
18
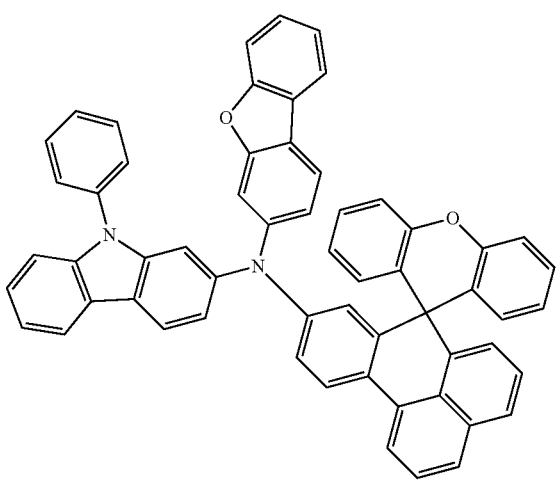

19
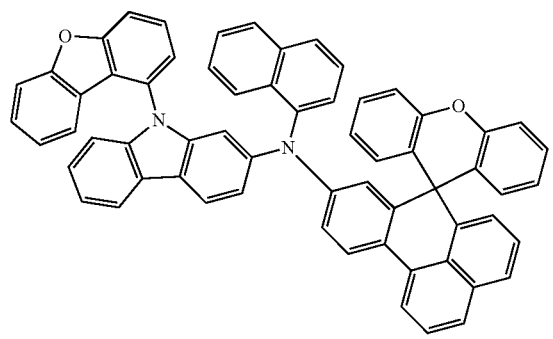
20
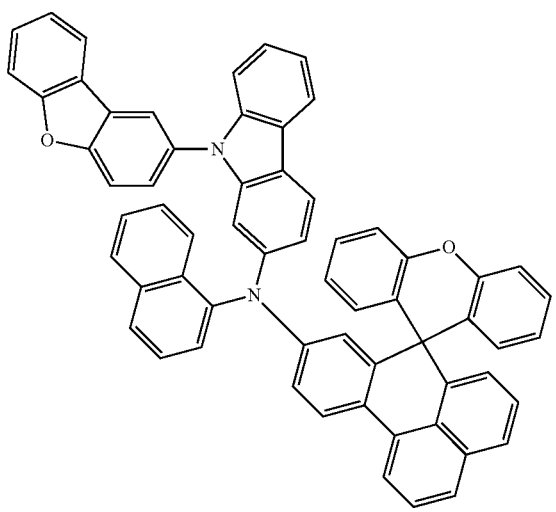
21
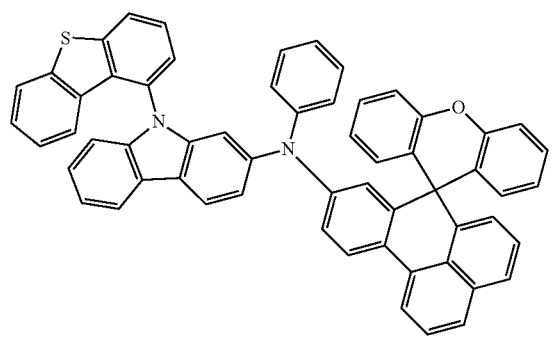
22
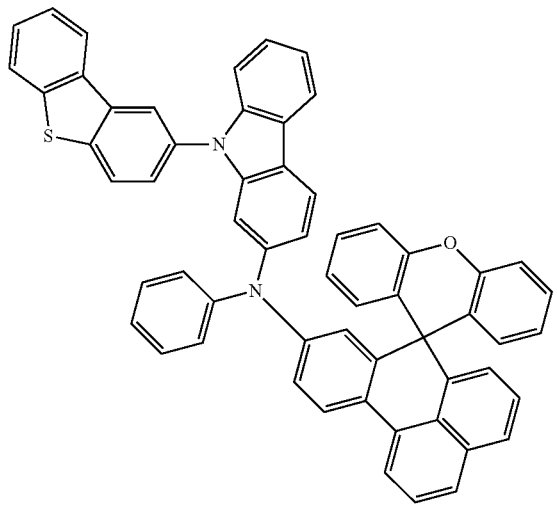
23
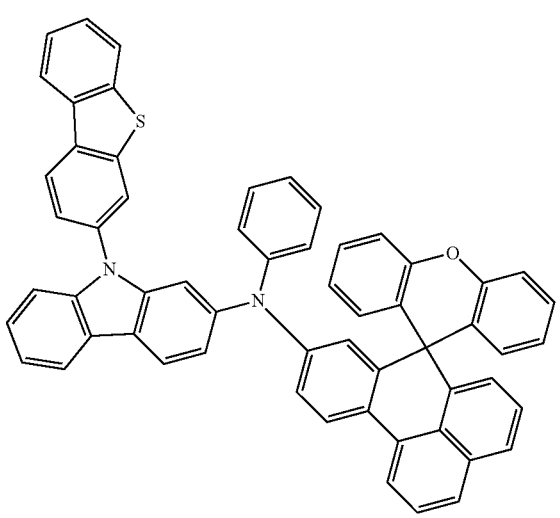
24
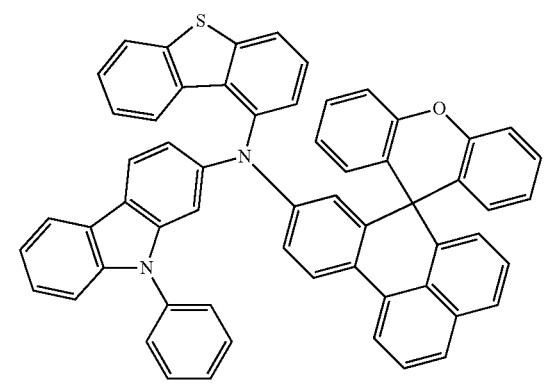

25
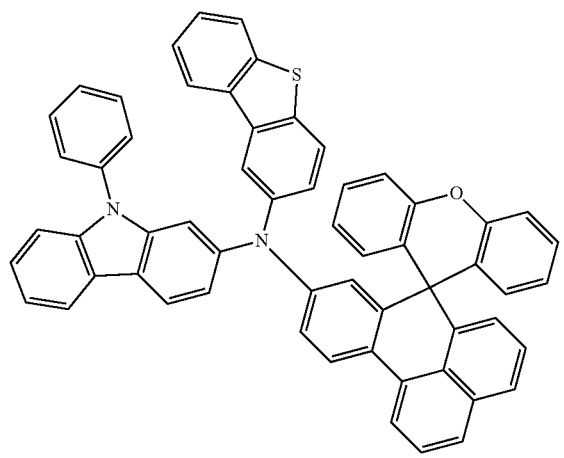
26
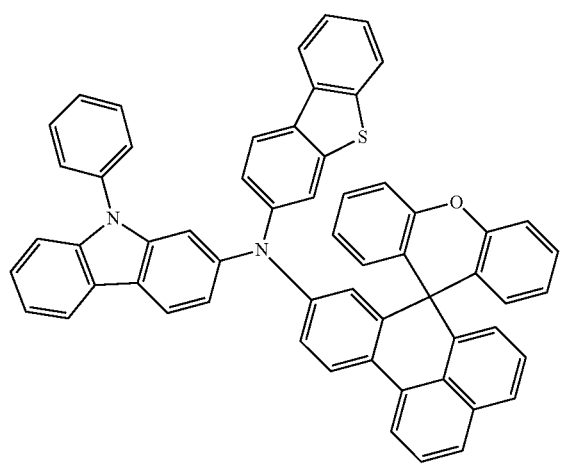
27
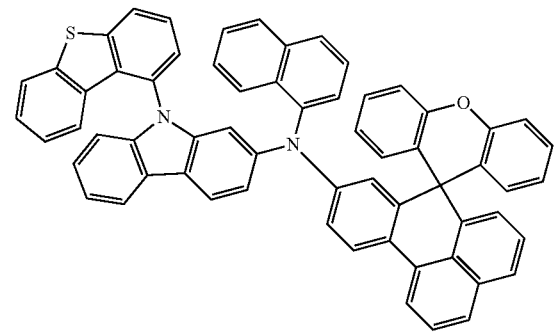
28
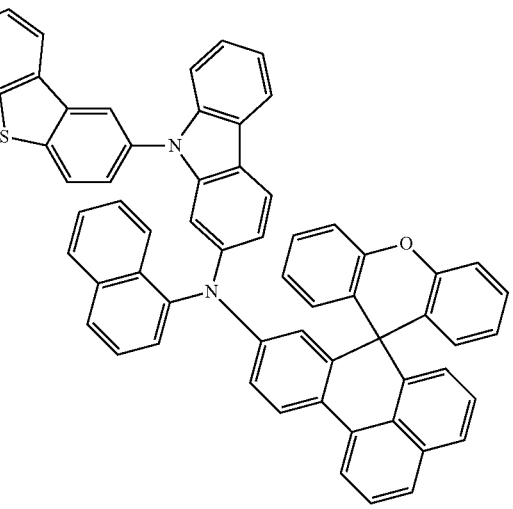
29
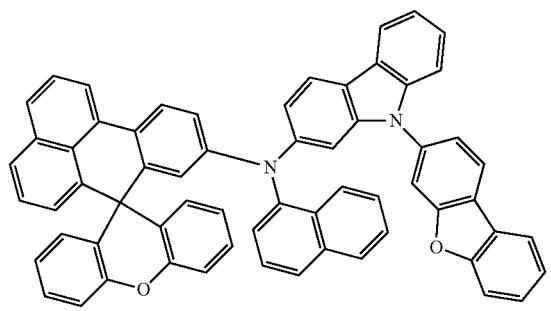
30
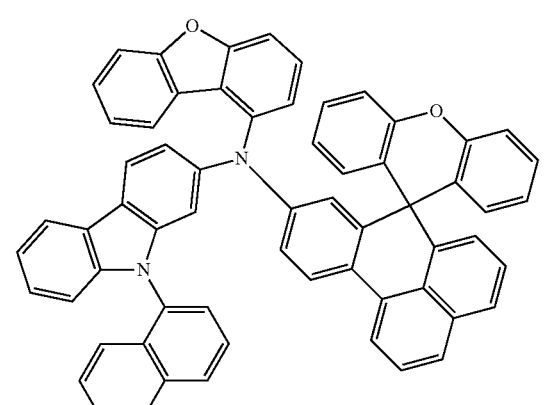

31
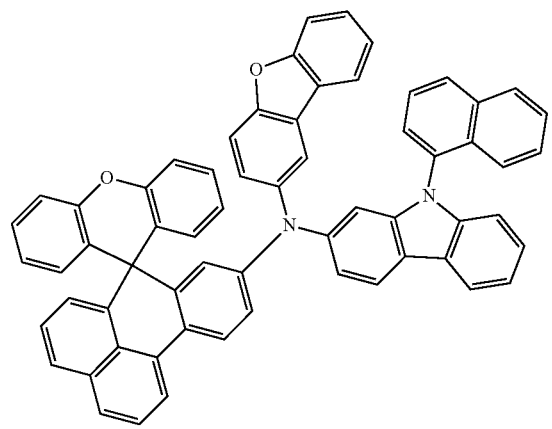
32
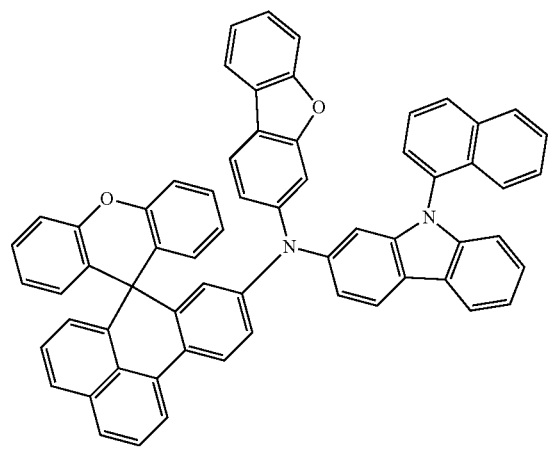
33
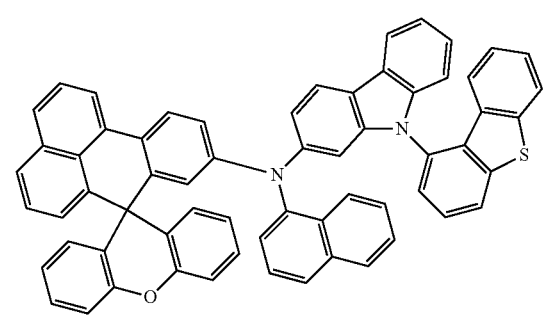
34
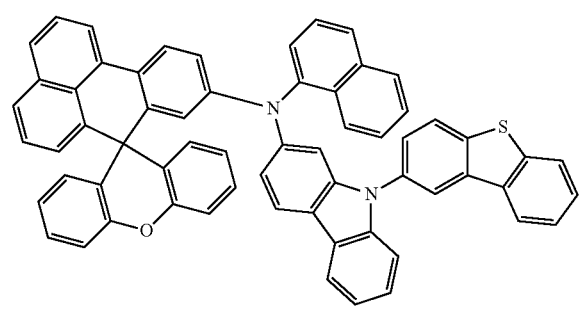
35
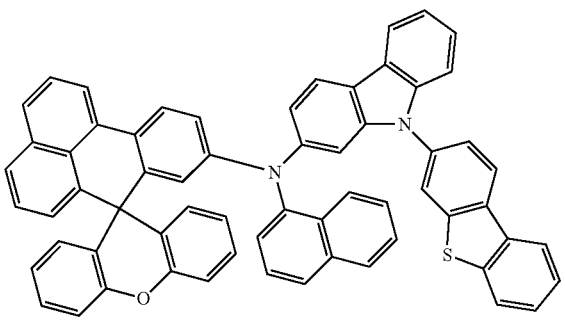
36
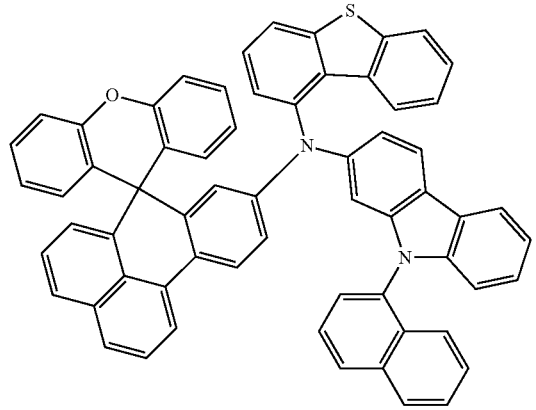
37
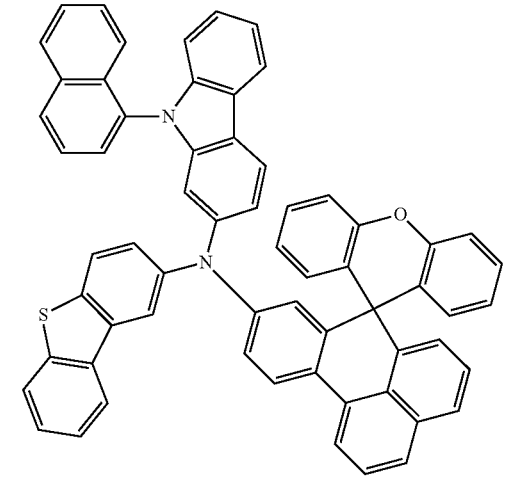
38
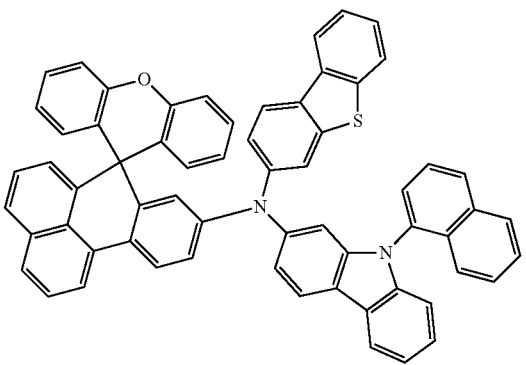

39
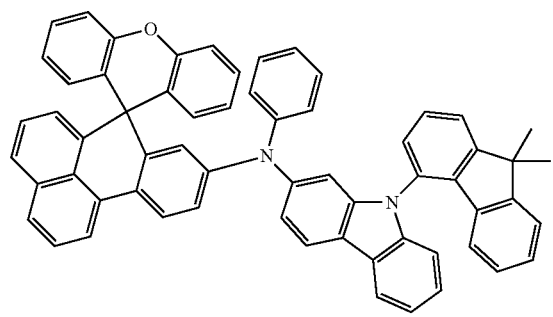
40
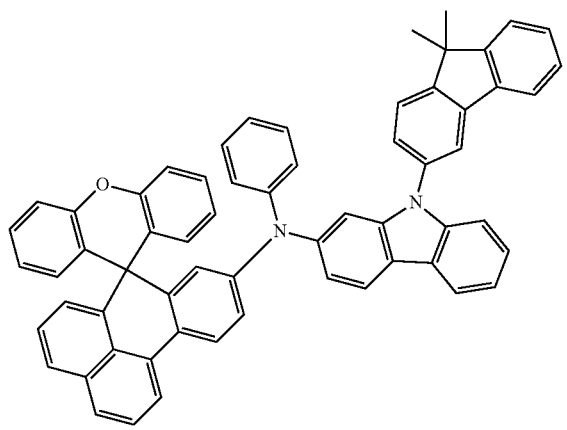
41
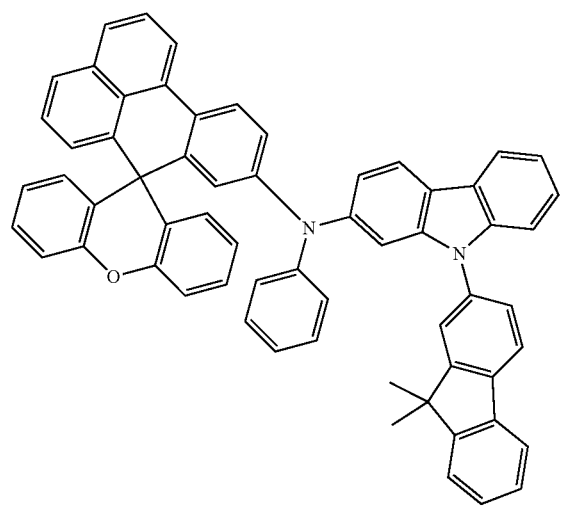
42
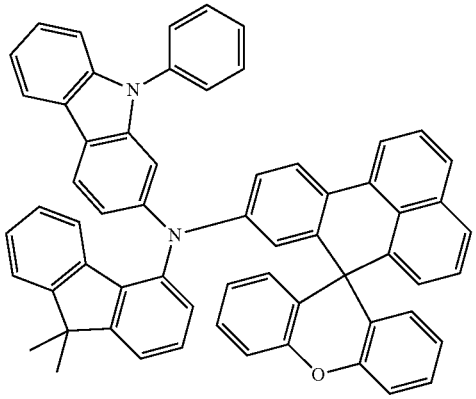
43
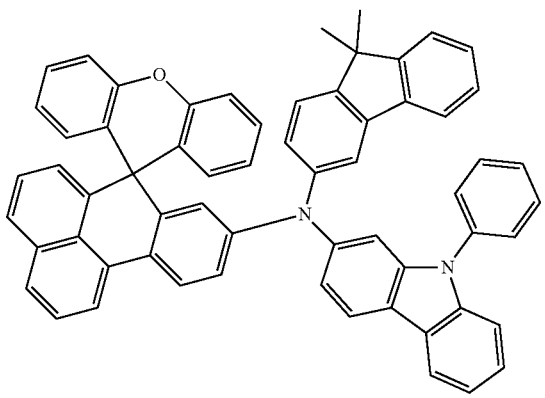
44
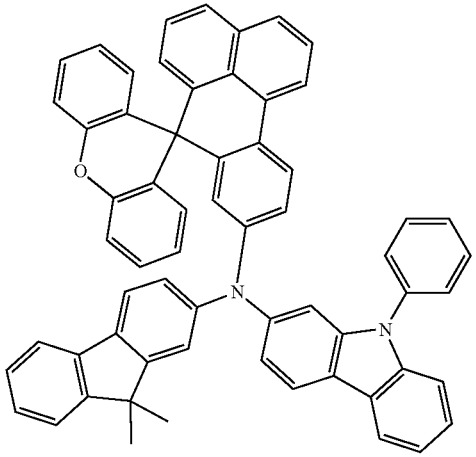
45
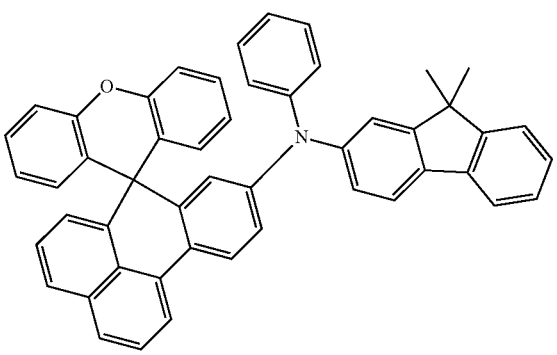

46
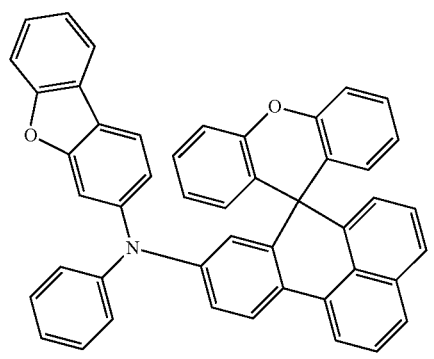
47
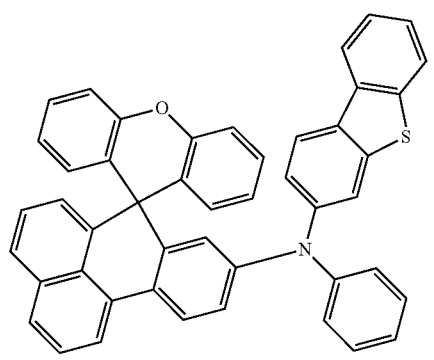
48
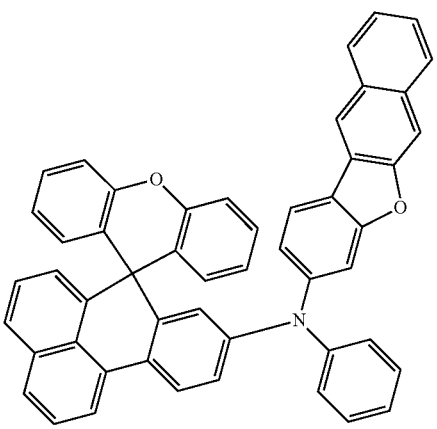
49
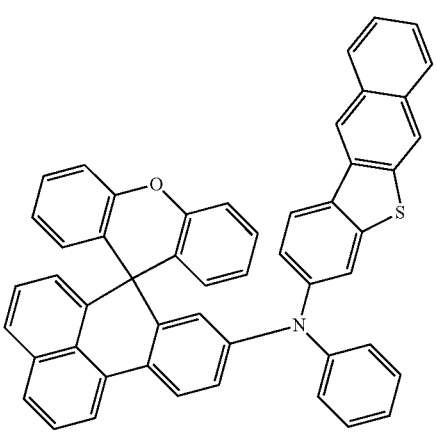
50
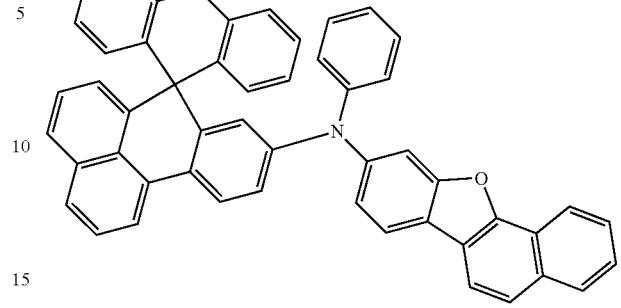
51
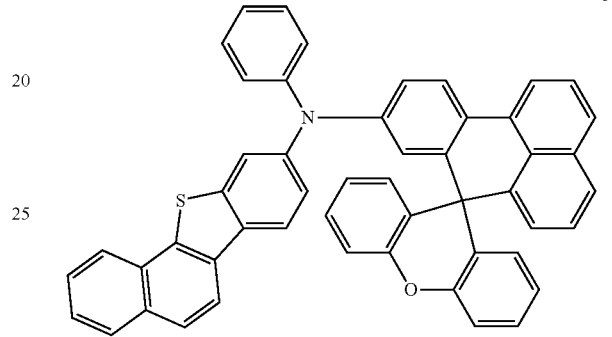
52
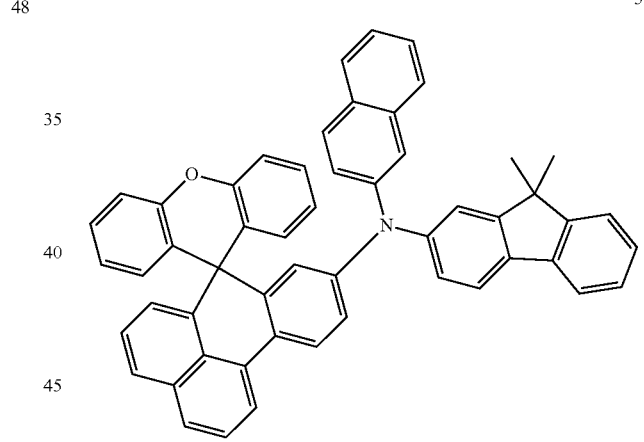
53
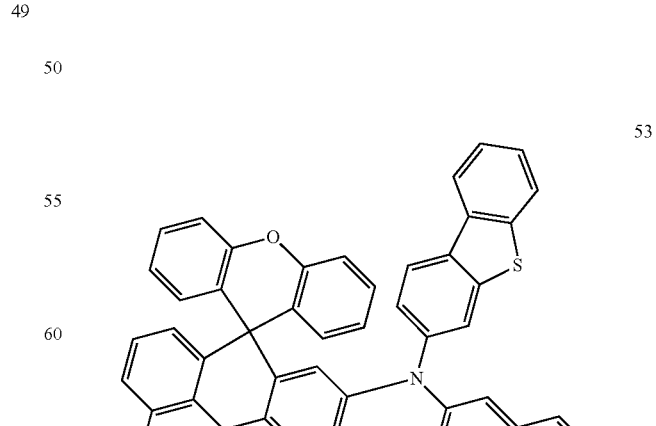

54
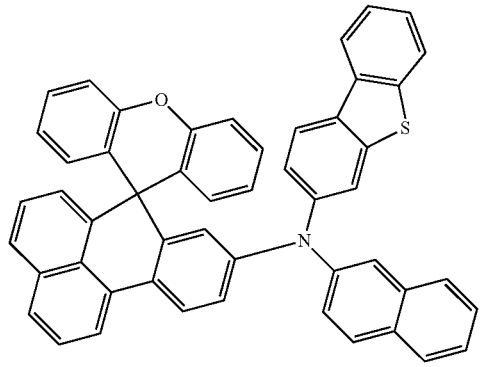
55
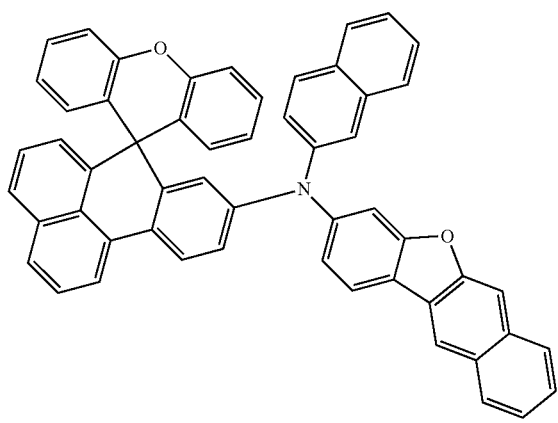
56
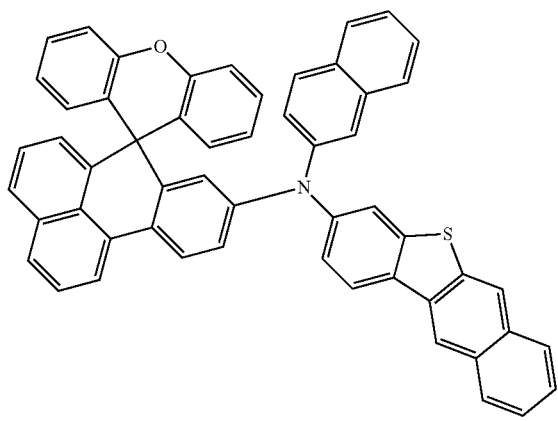
57
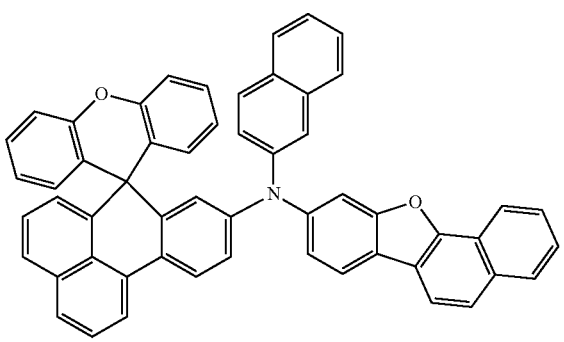
58
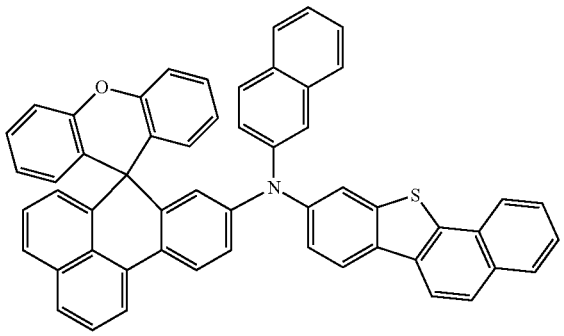
59
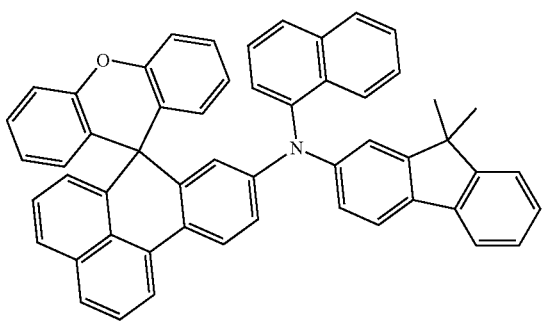
60
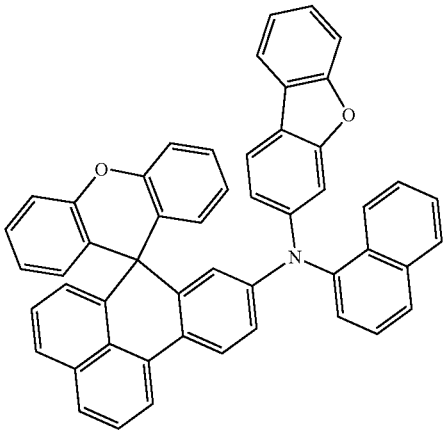
61
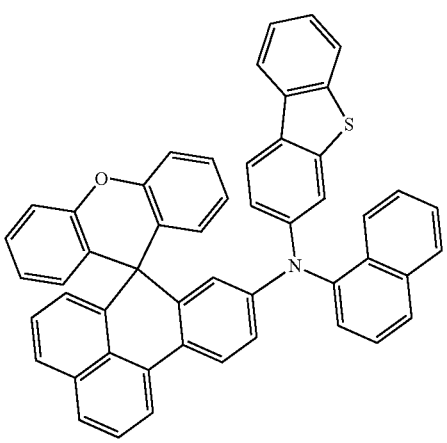

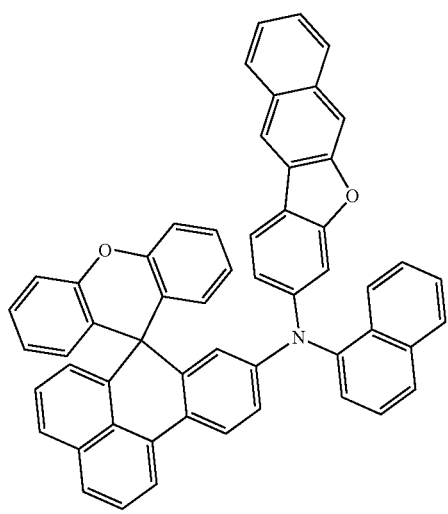
62
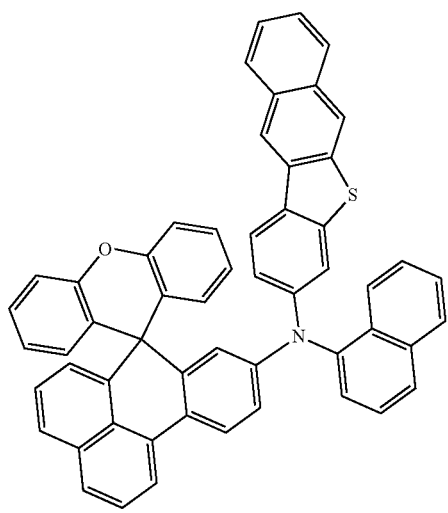
63
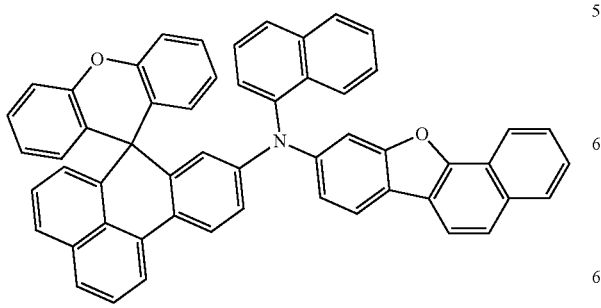
64
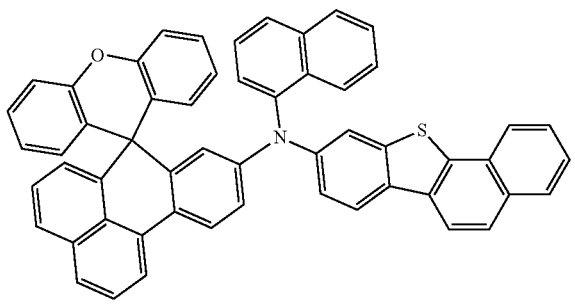
65
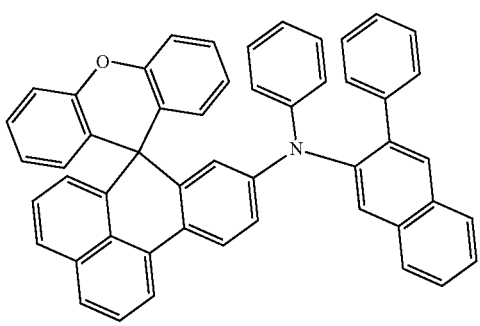
66
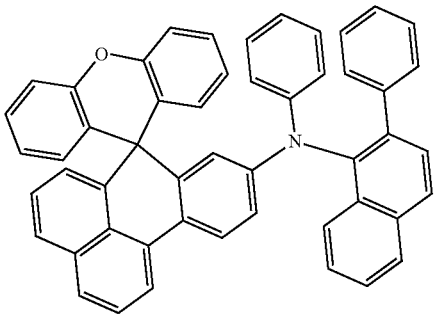
67

69
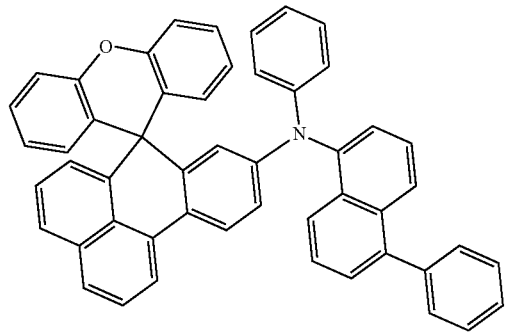
70
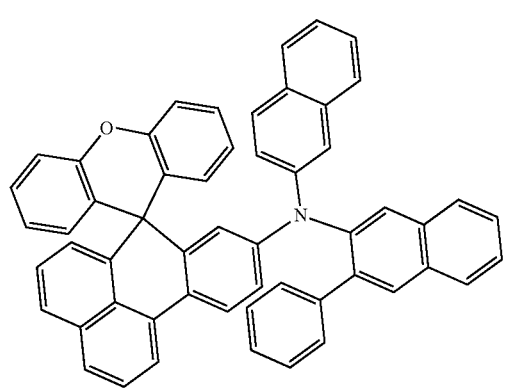
71
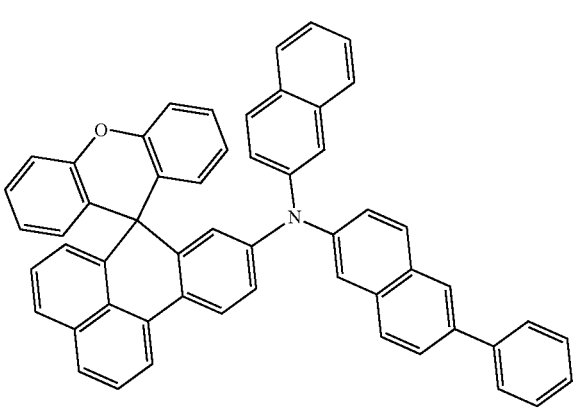
72
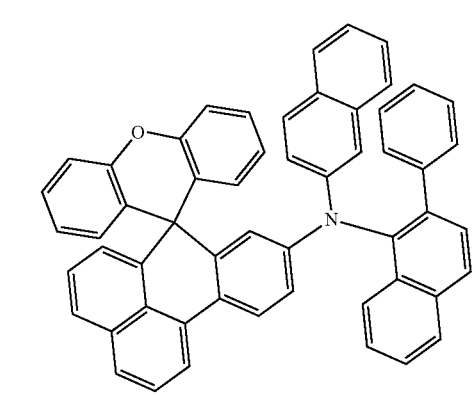
73
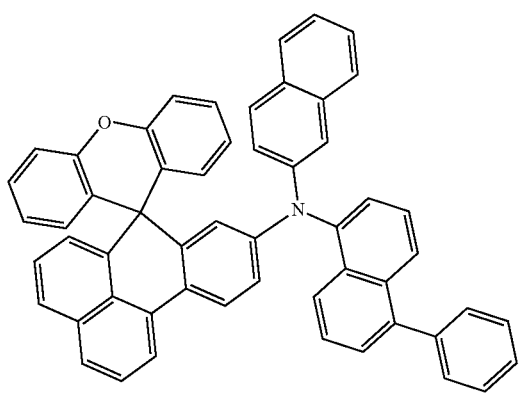
74
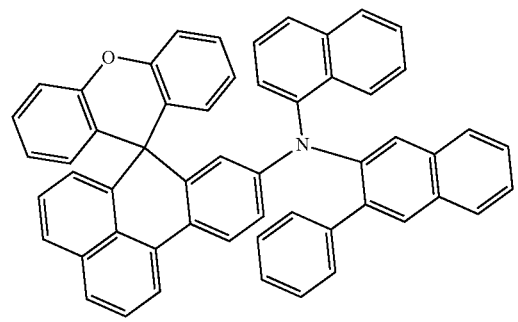
75
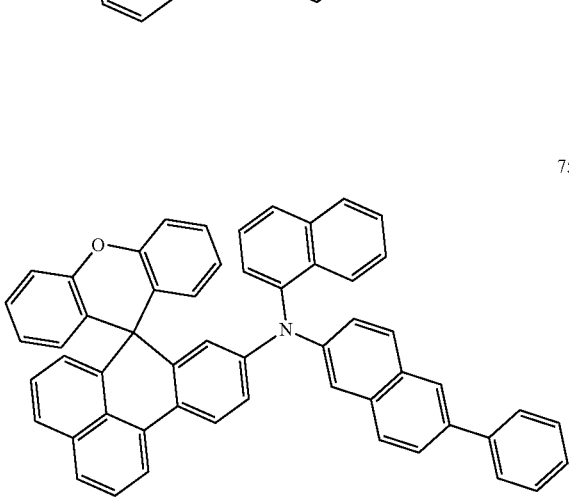
76
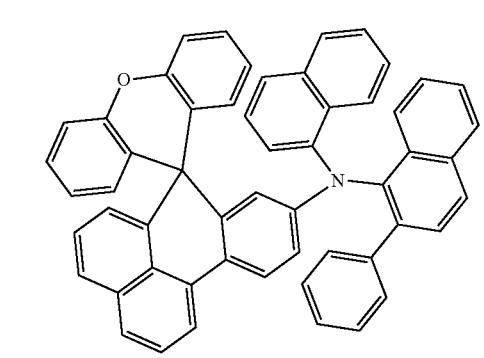

77
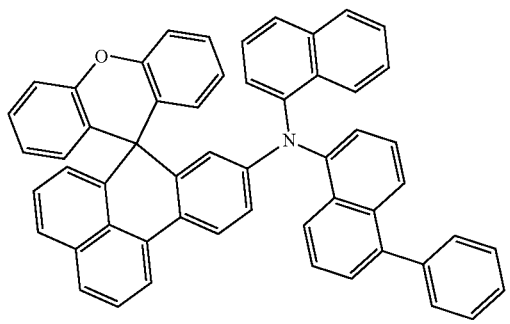
78
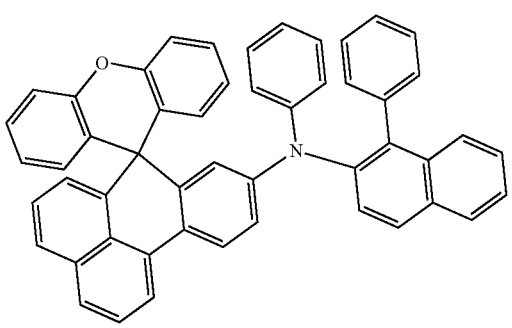
79
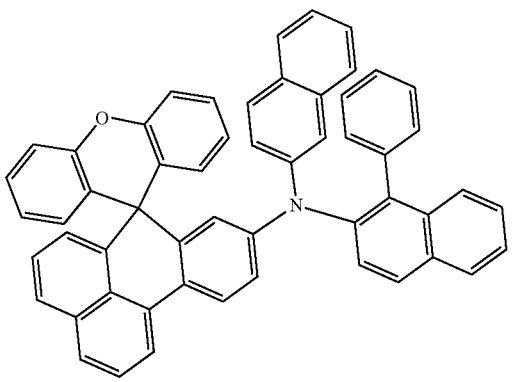
80
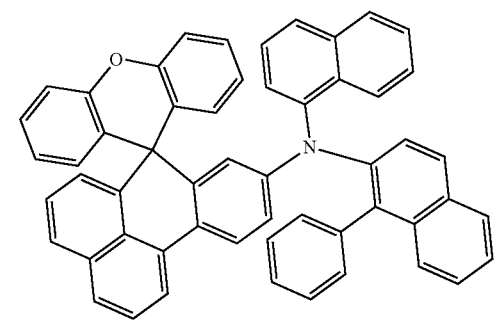
81
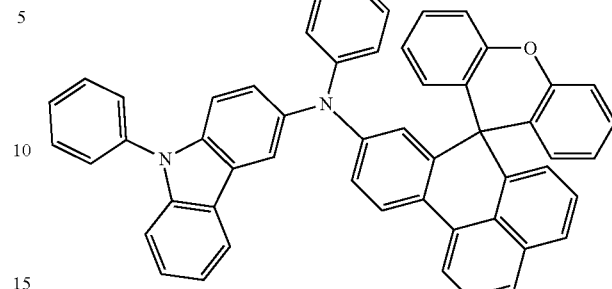
82
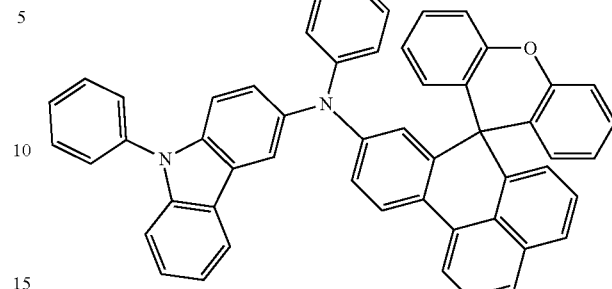
83
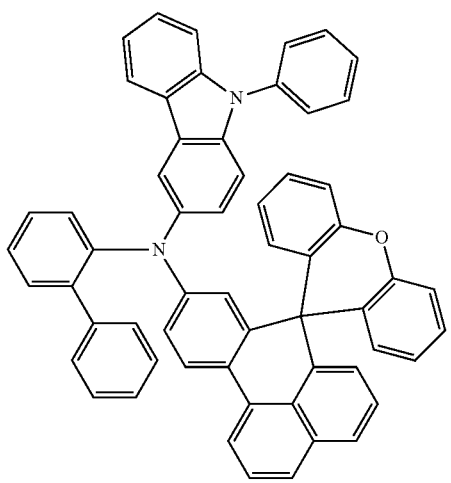

84
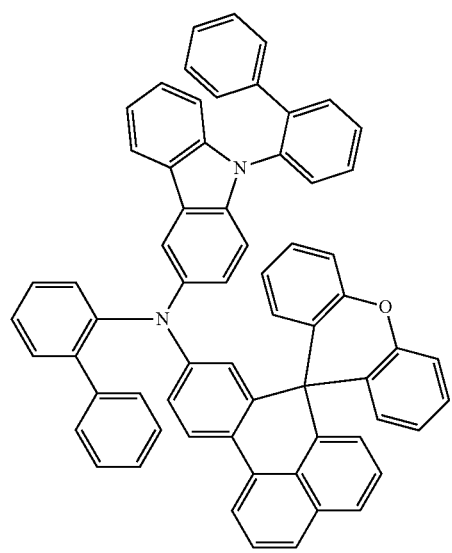
85
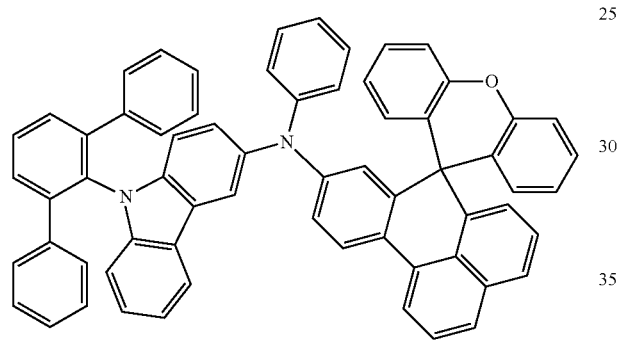
86
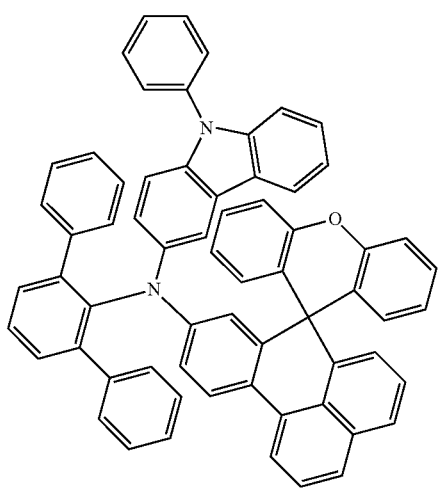
87
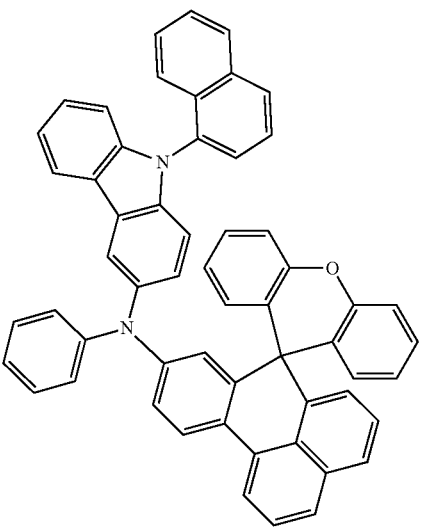
88
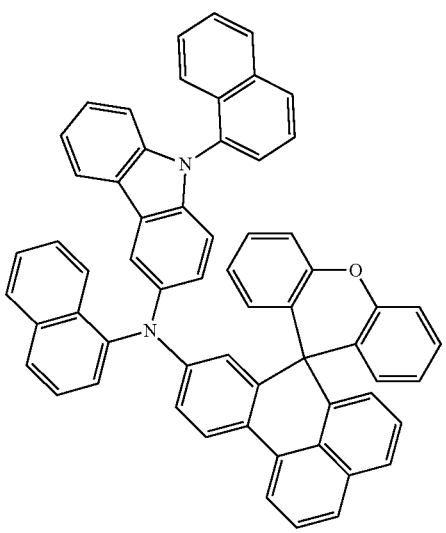
89
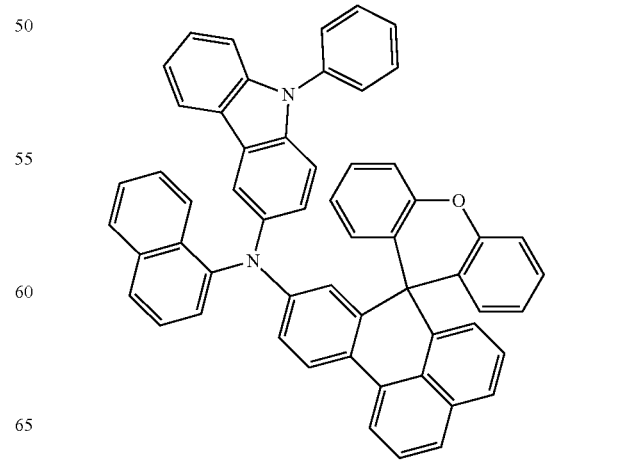

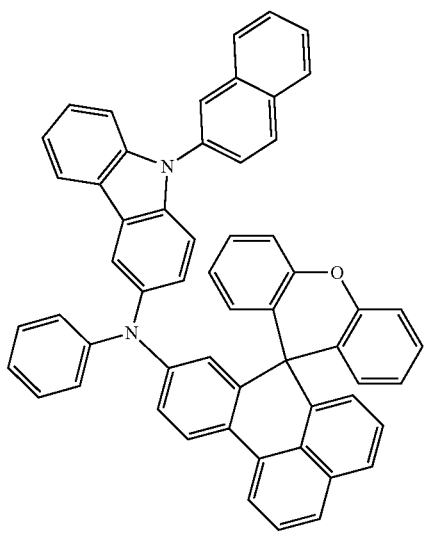
90
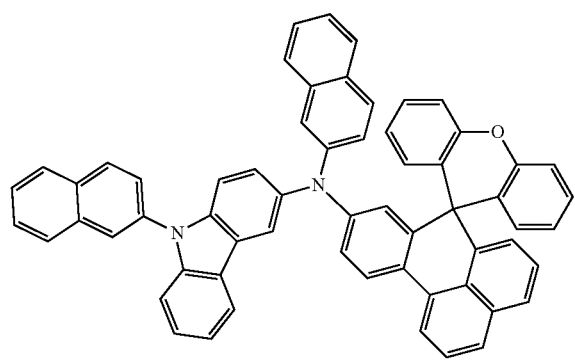
91
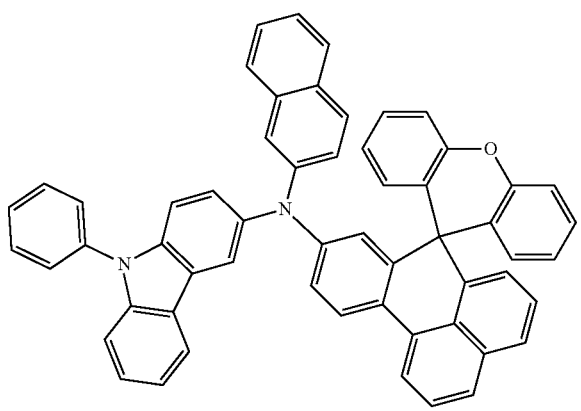
92
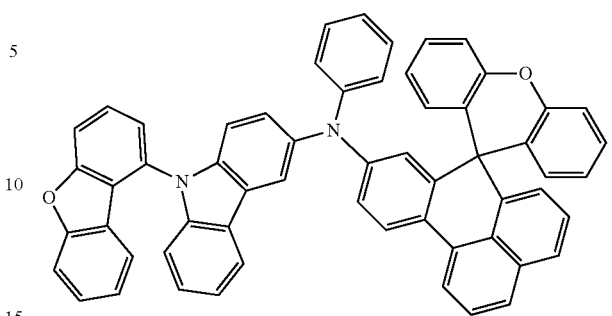
93
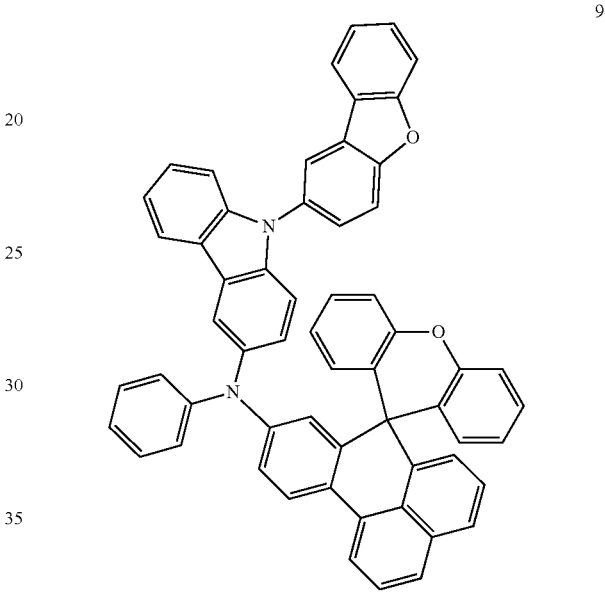
94
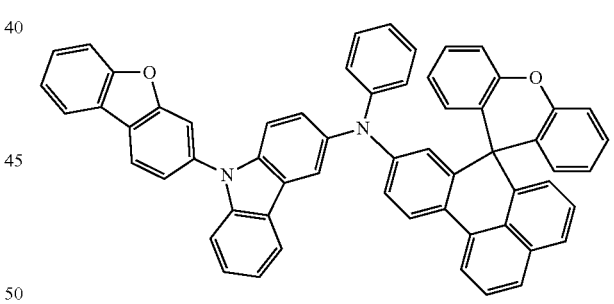
95
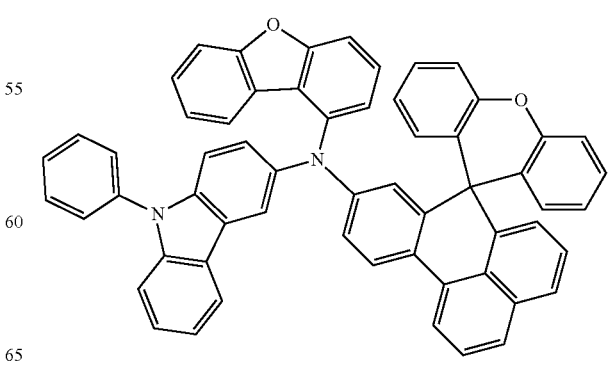
96

97
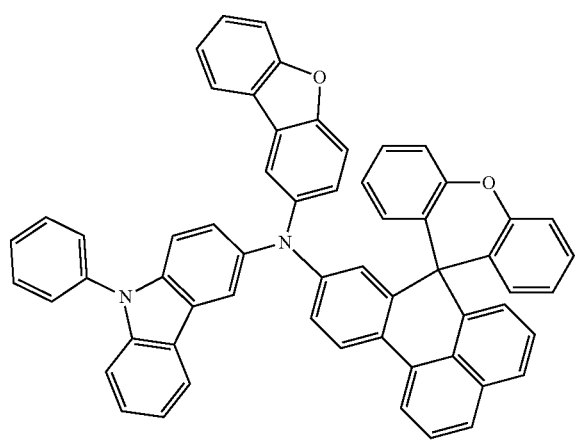
98
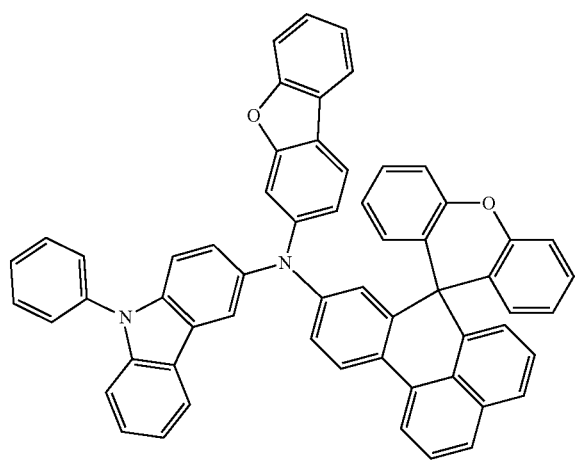
99
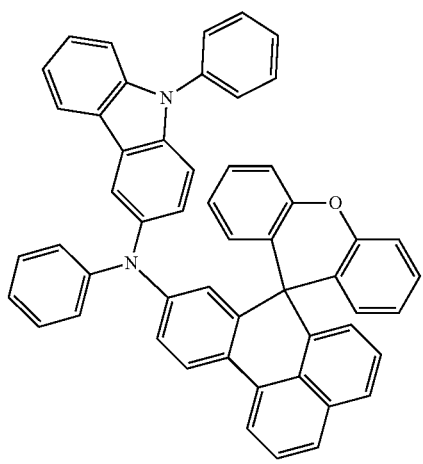
100
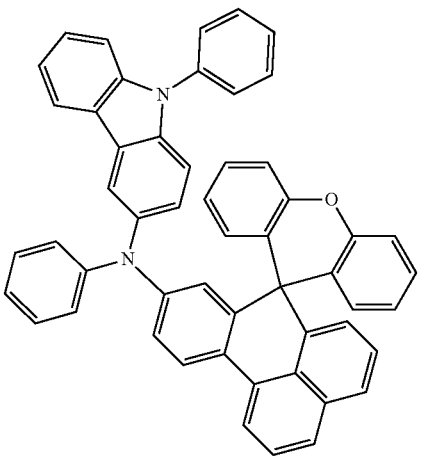
101
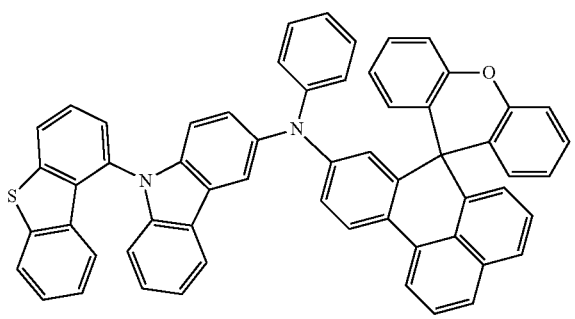
102
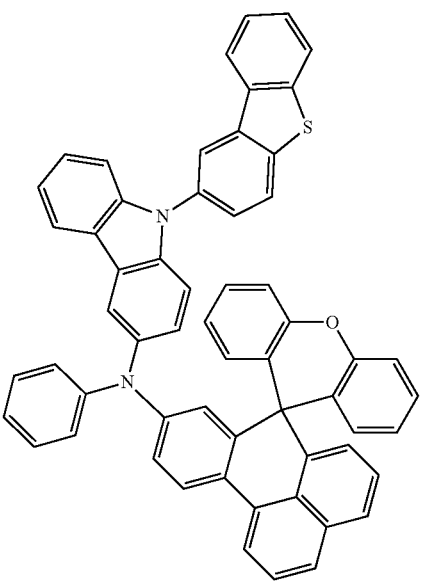

103
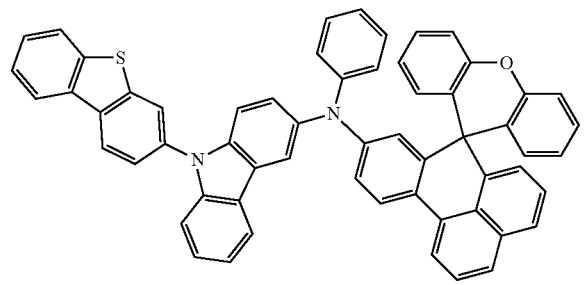
104
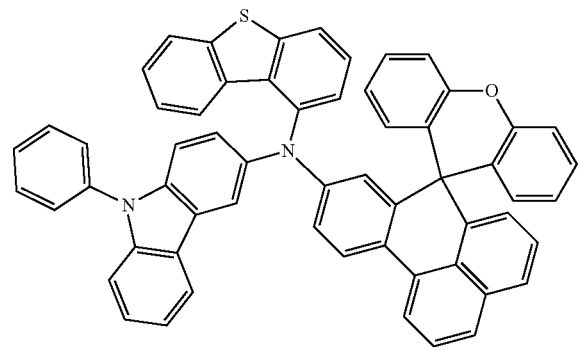
105
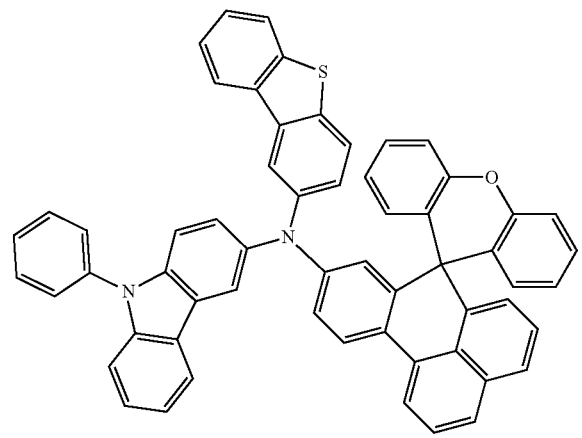
106
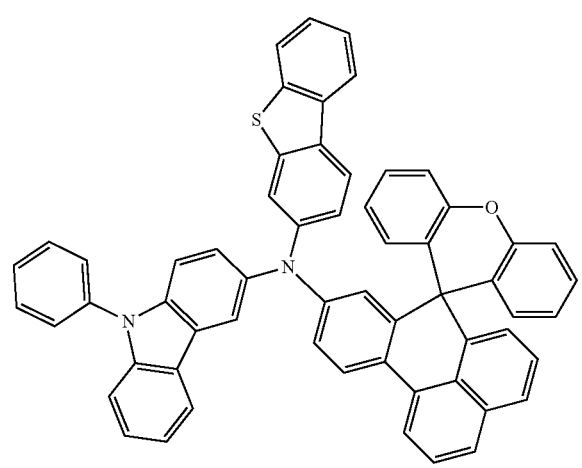
107
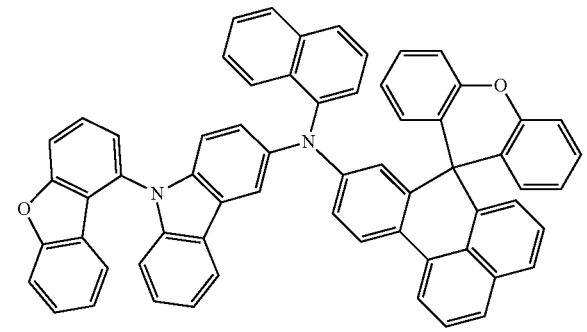
108
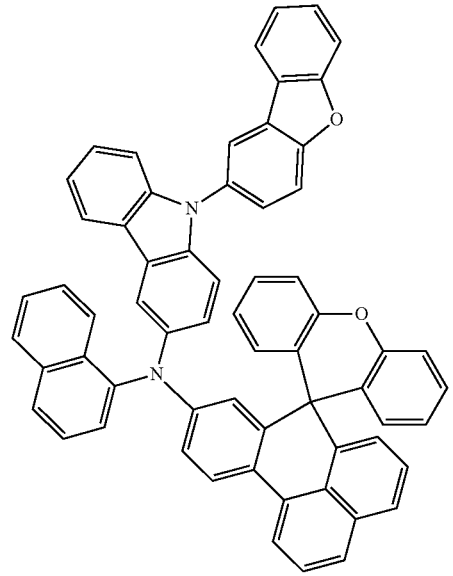
109
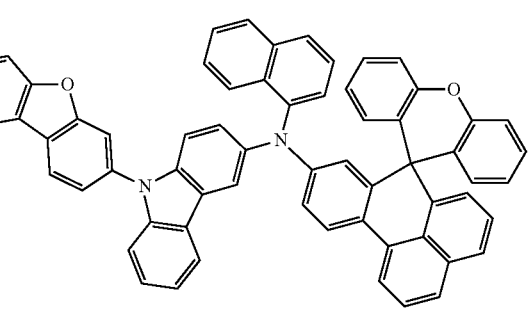
110
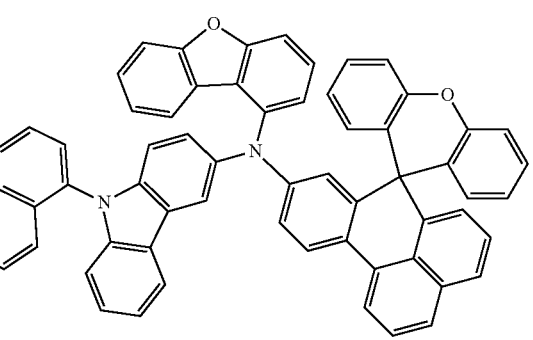

111
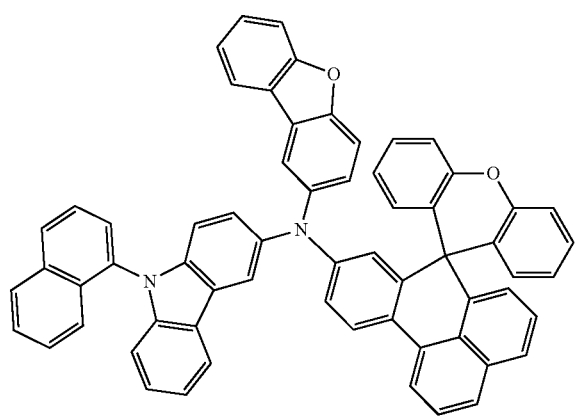
112
114
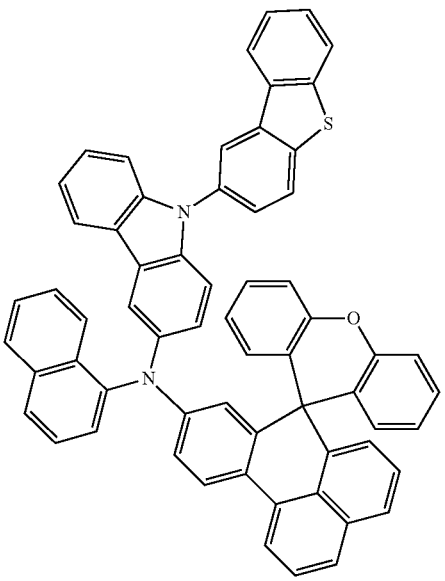
115
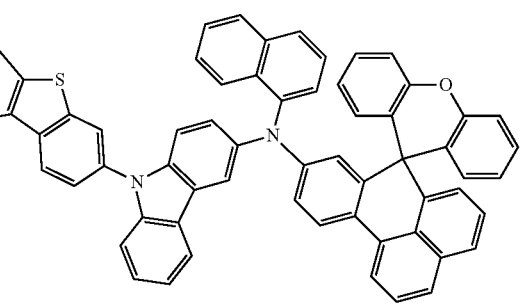
113
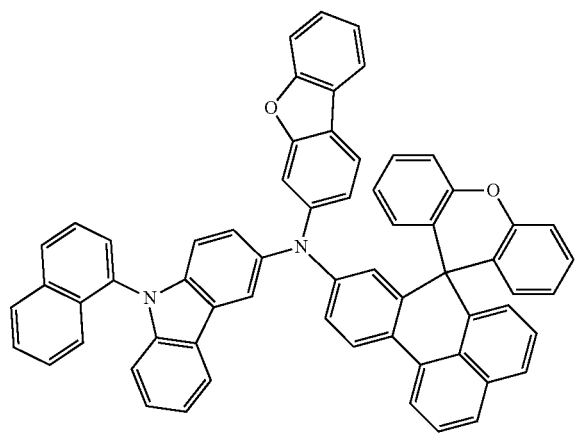
116
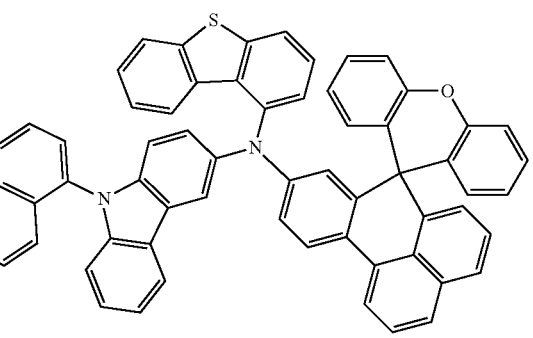

117
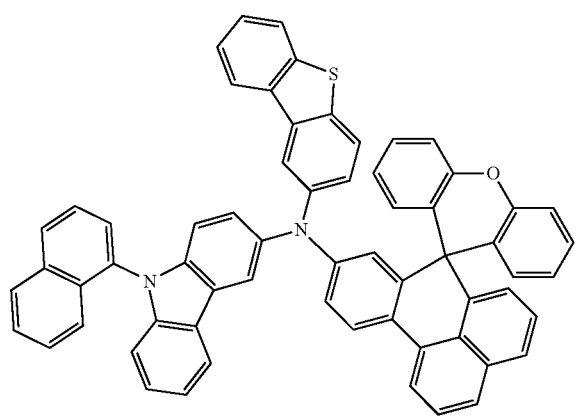
118
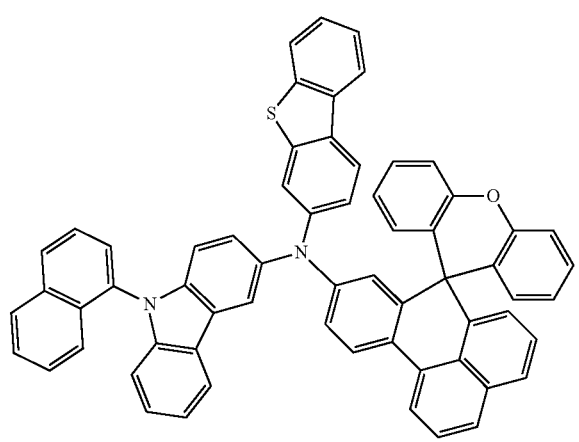
119
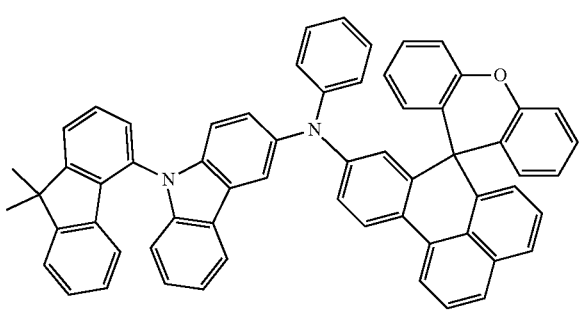
120
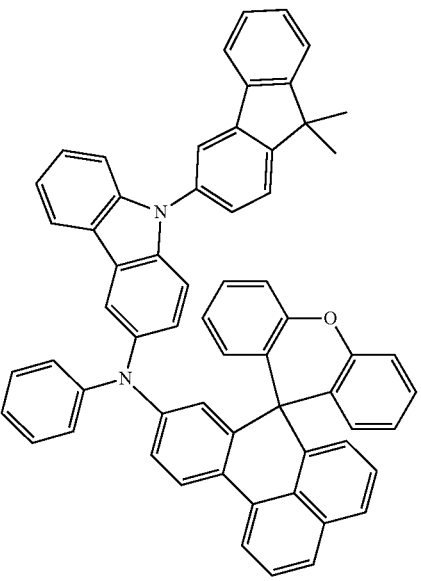
121
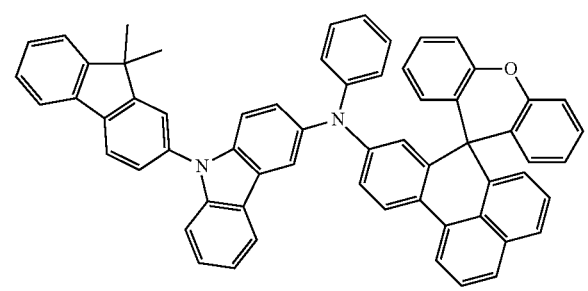
122
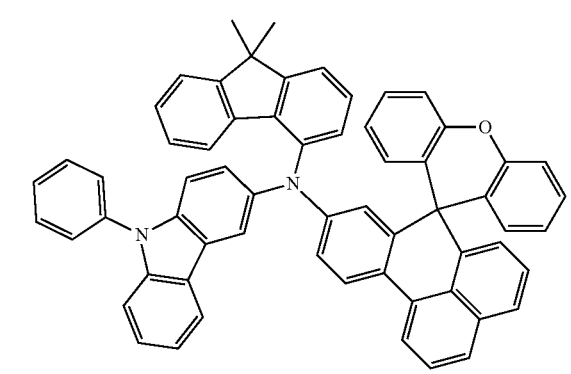

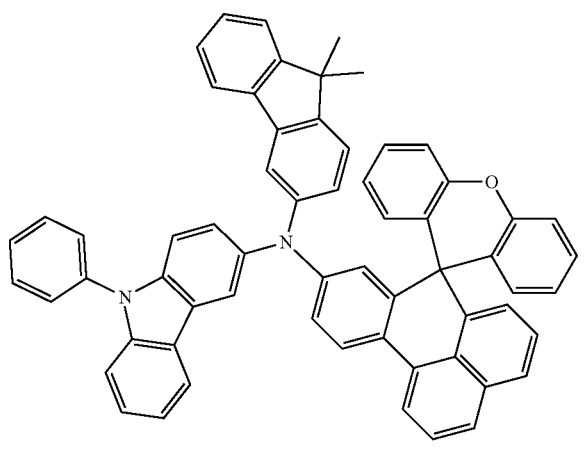
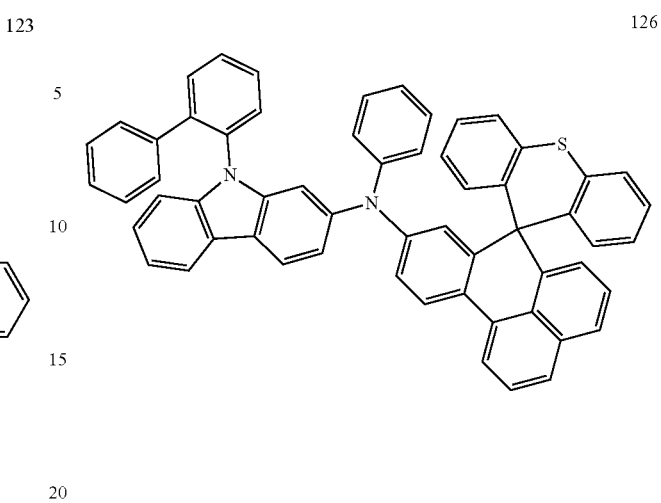

129
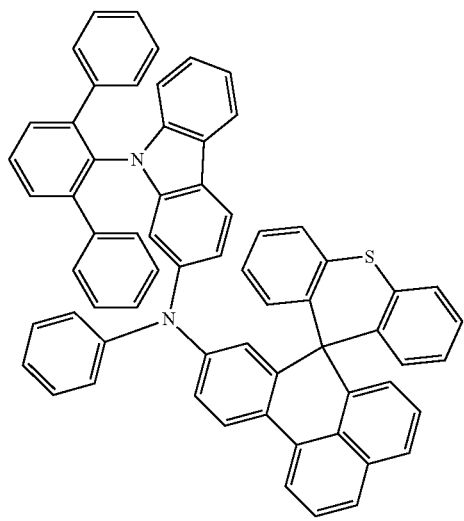
130
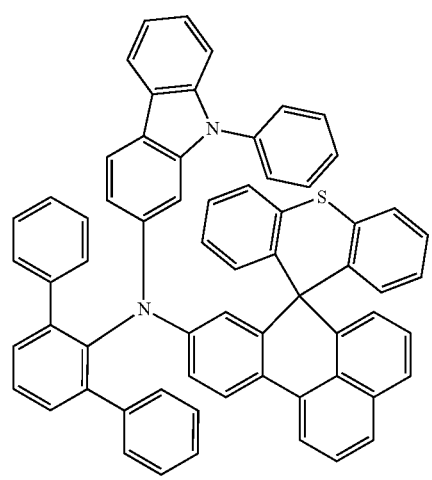
131
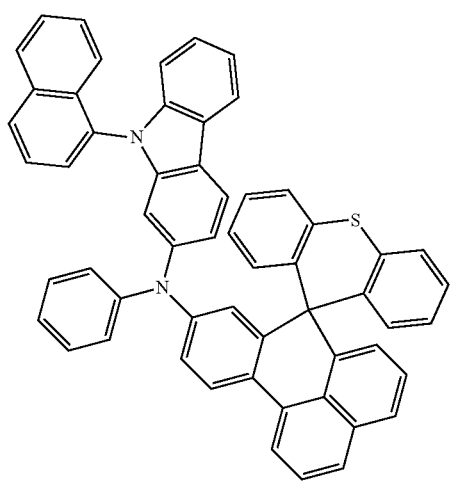
132
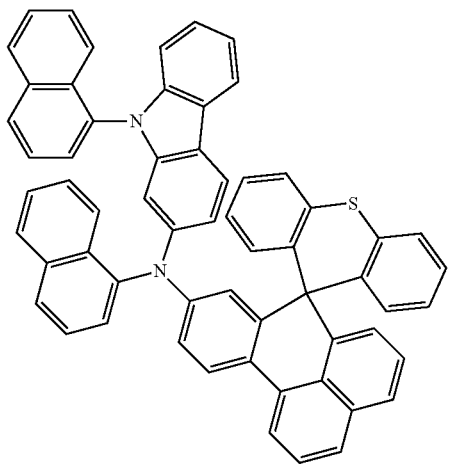
133
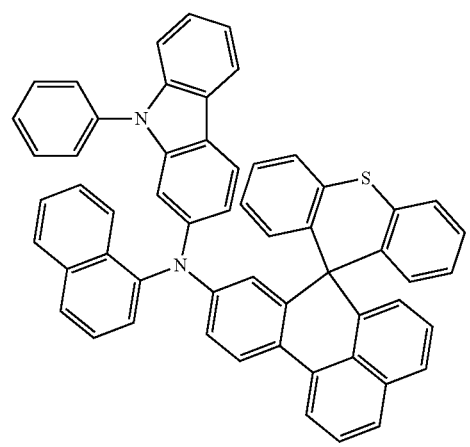
134
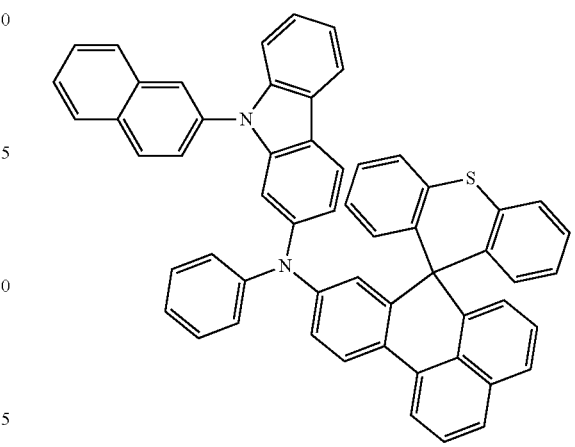

-continued
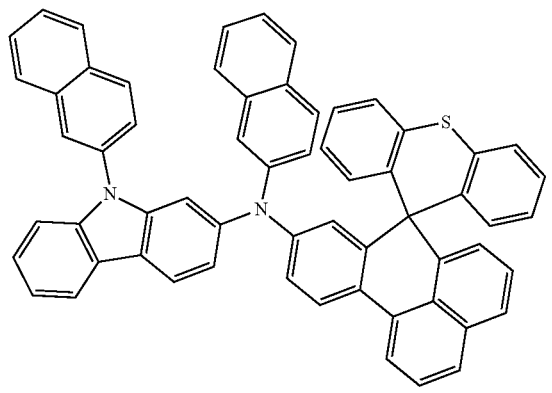
135

136
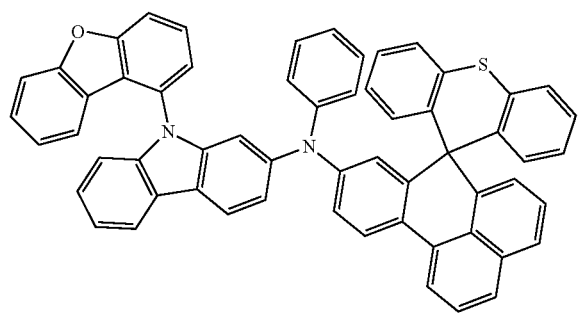
137
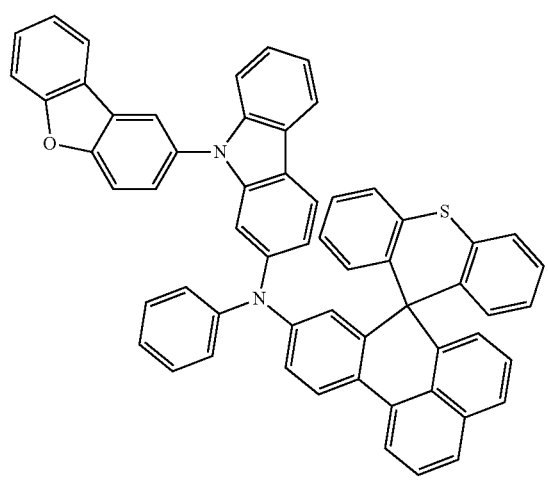
138
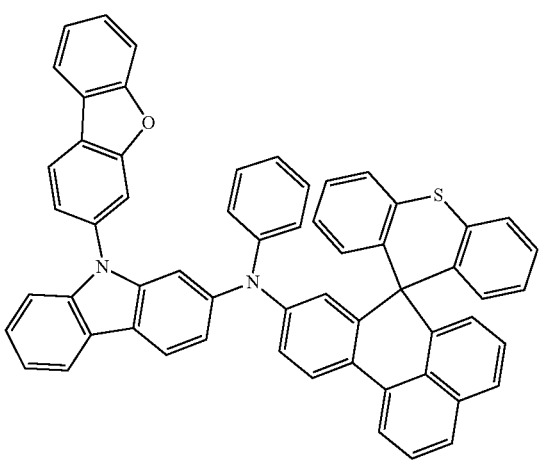
139
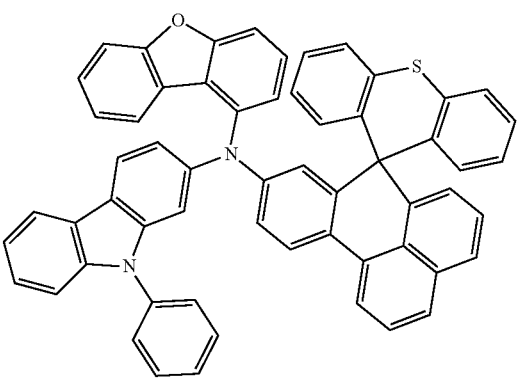
140
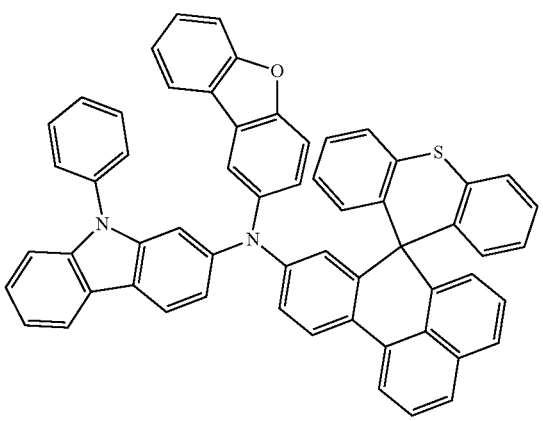
141

142
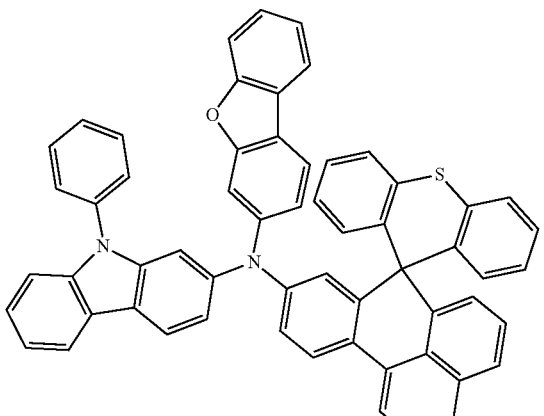
143
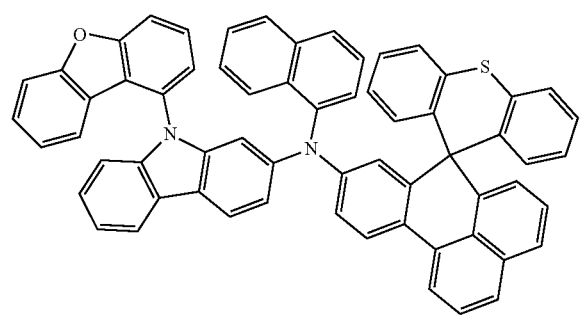
144
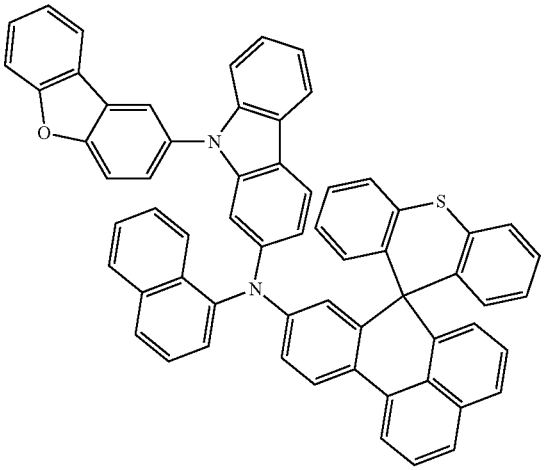
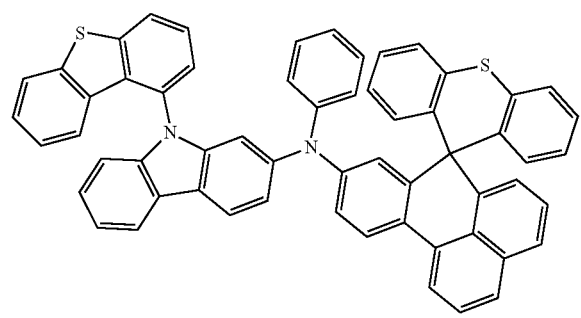
146
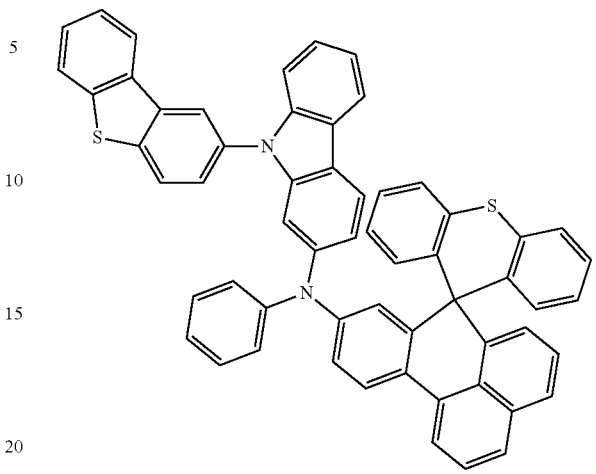
147
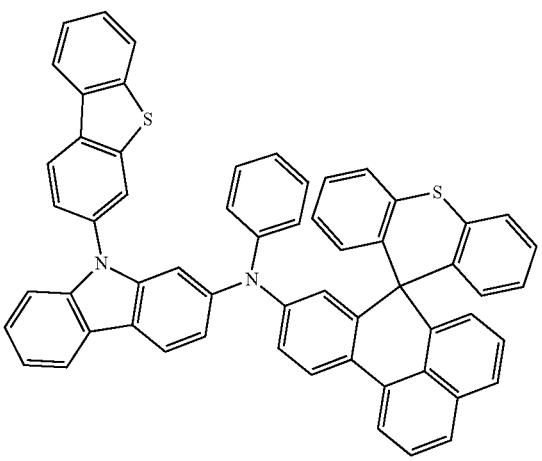
148
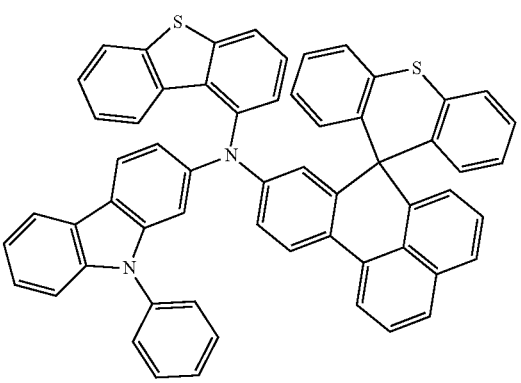

149
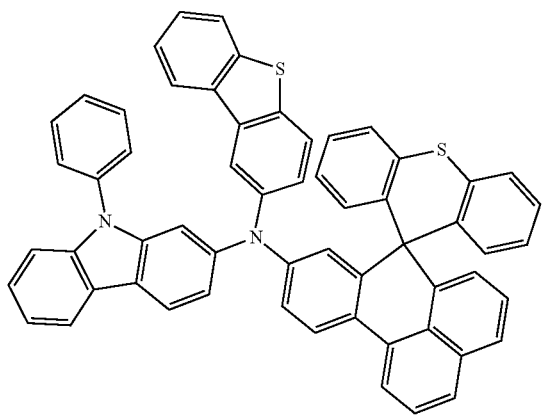
152
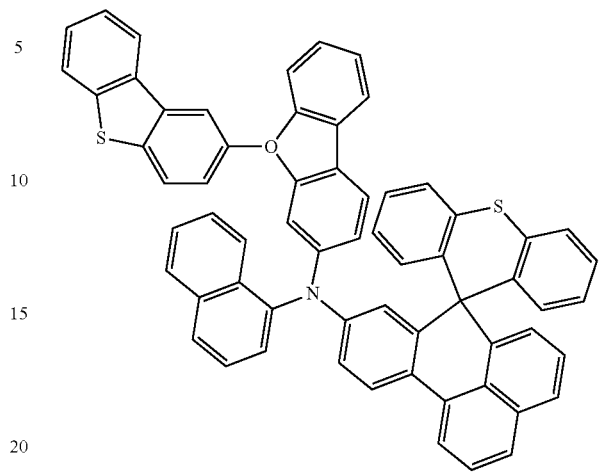
150
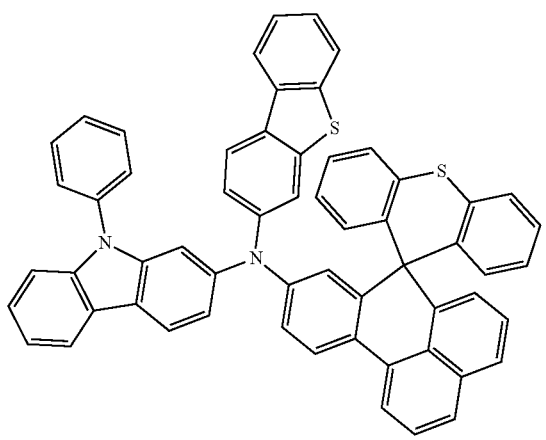
153
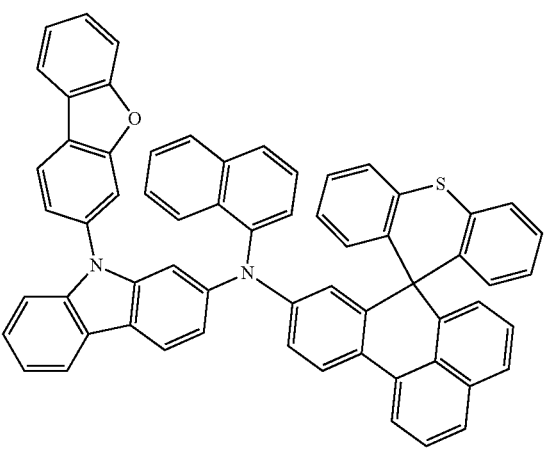
151
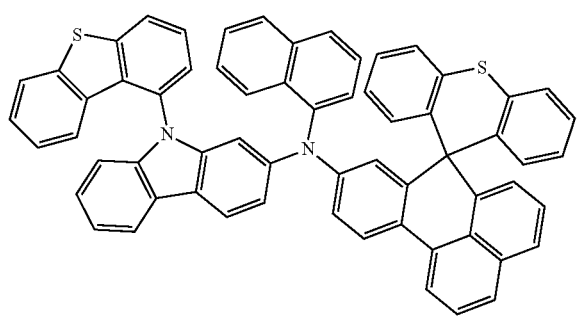
154
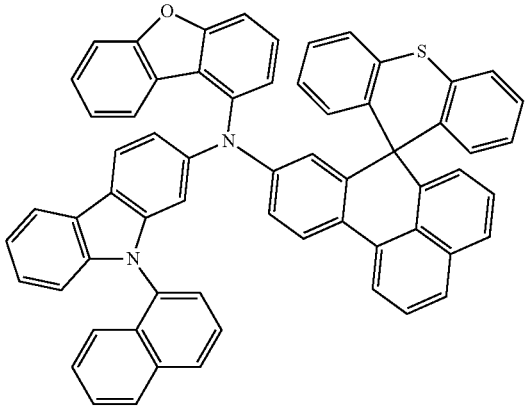

155
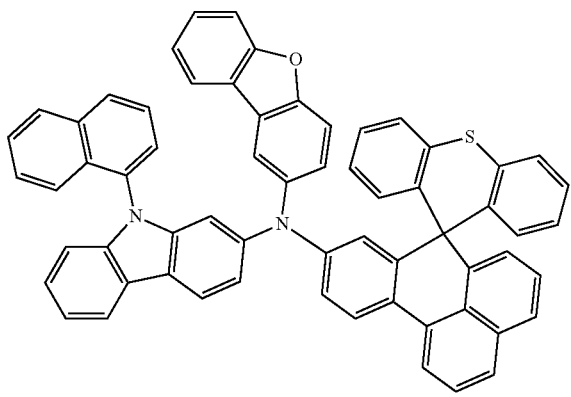
156
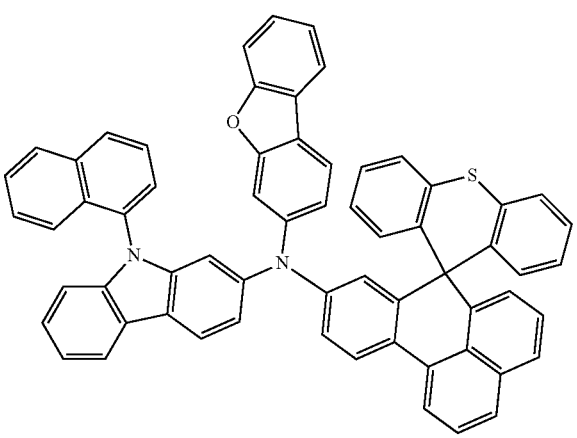
157
158
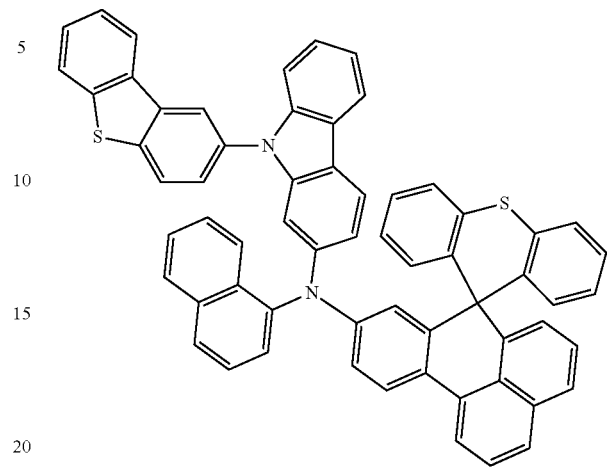
159
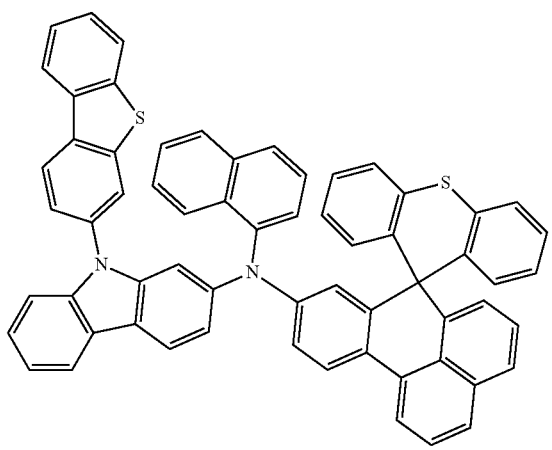
160
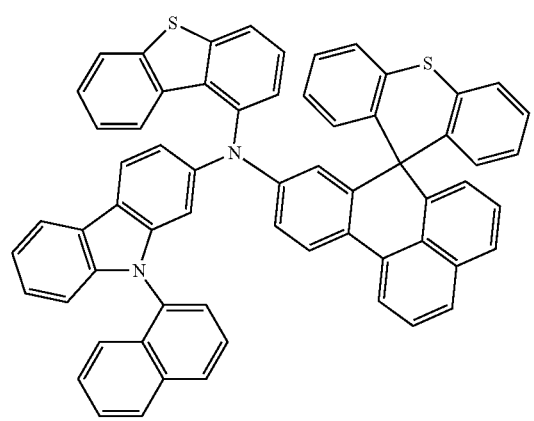

161
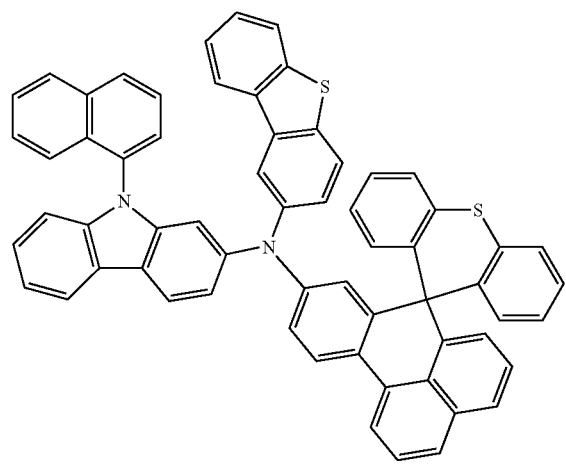
162
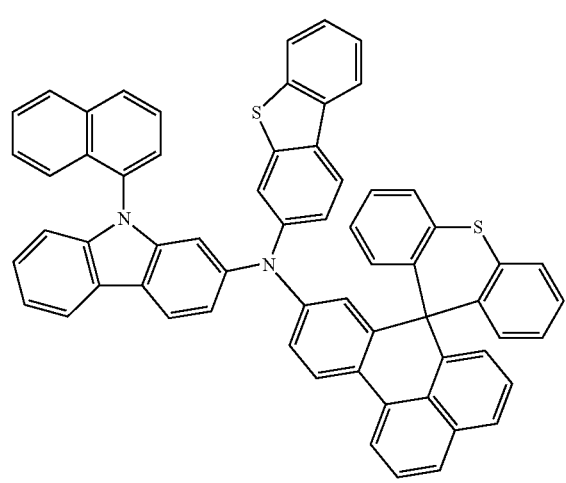
163
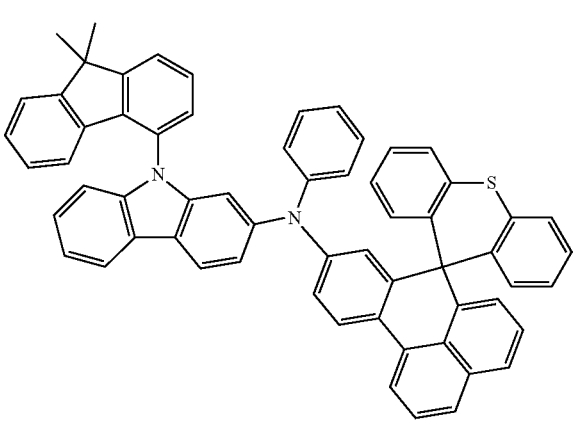
164
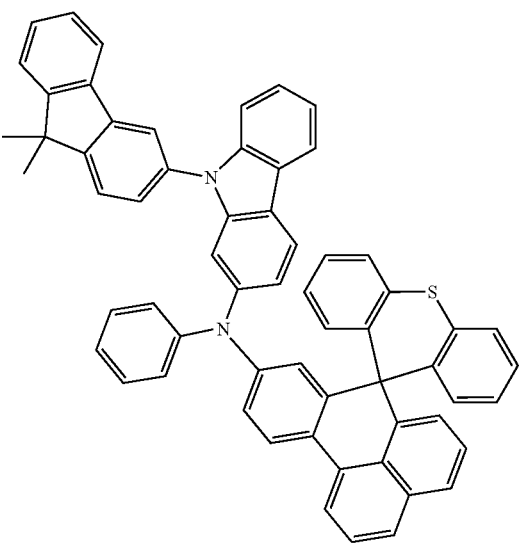
165
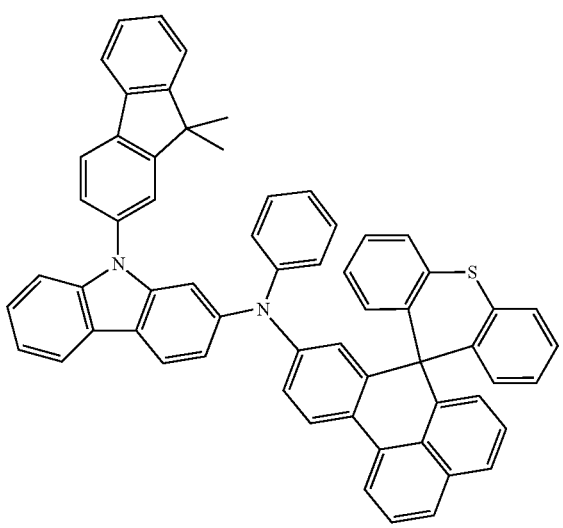
166
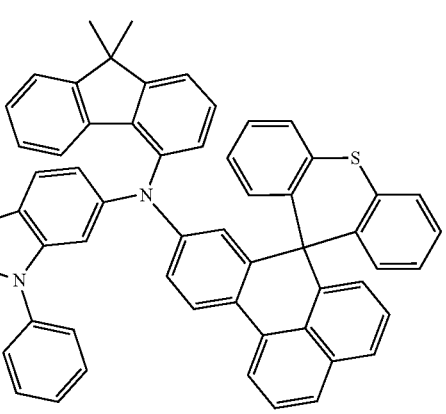

167
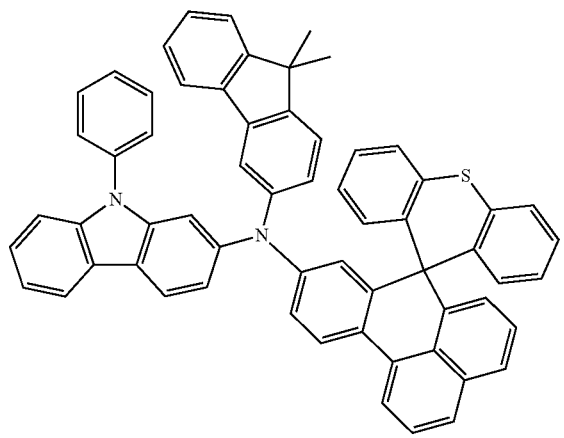
168
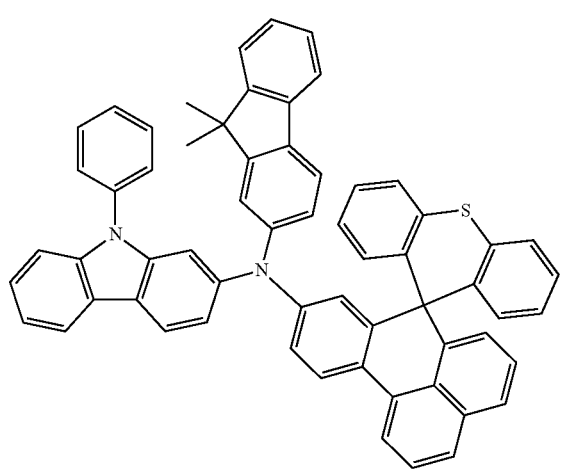
169
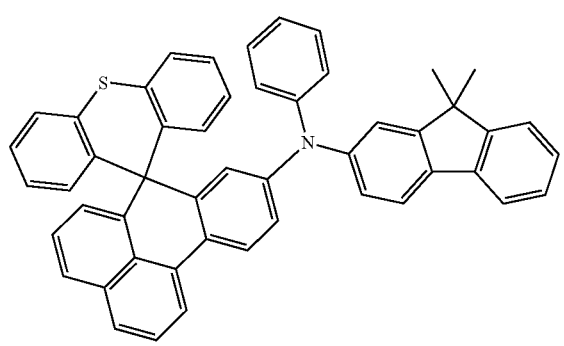
170
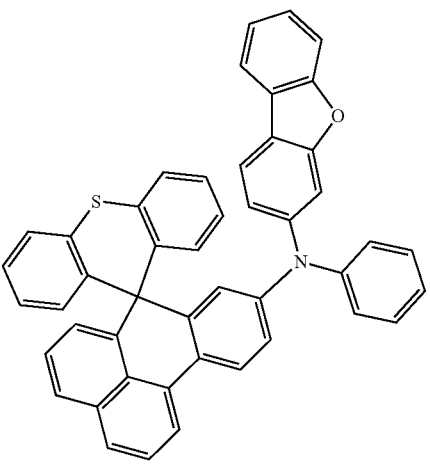
171
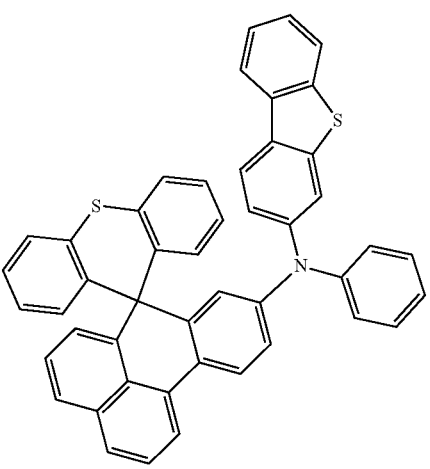
172
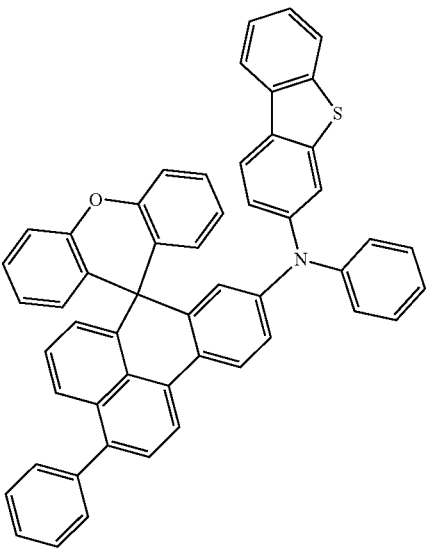

-continued
173
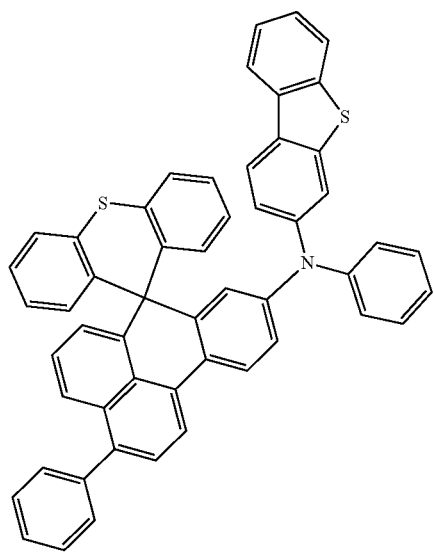
174
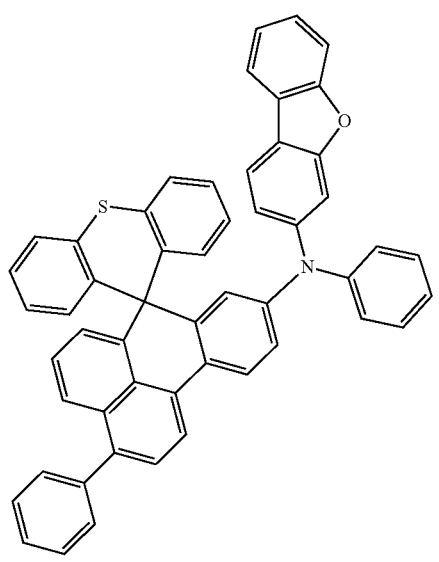
175
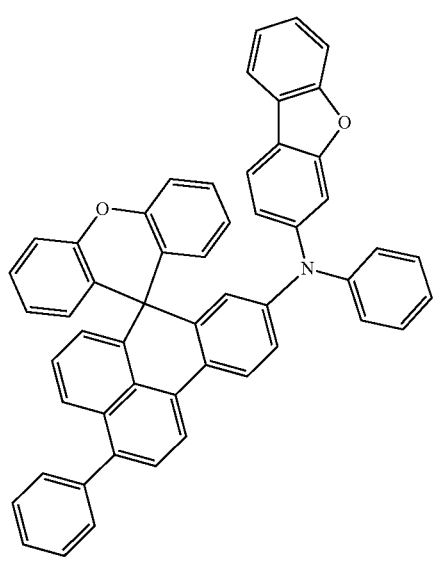
-continued
176
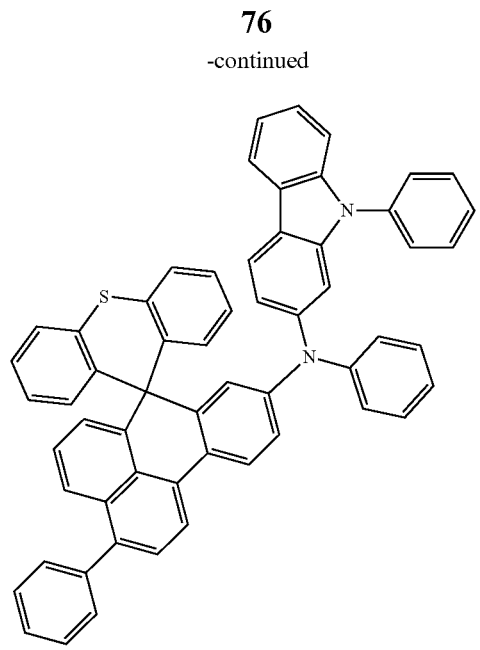
177
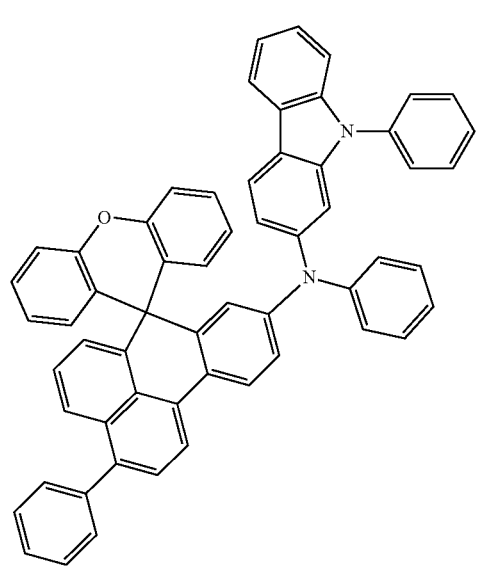
178
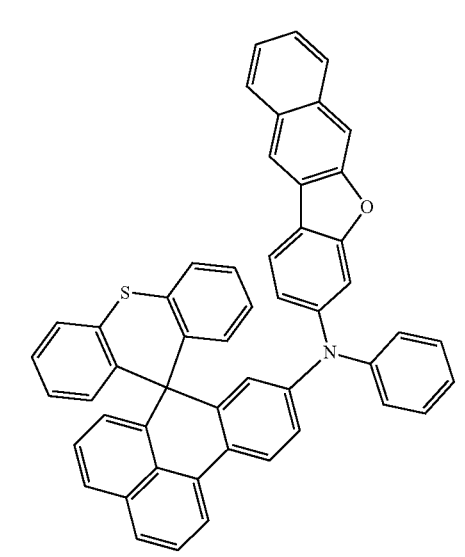

179
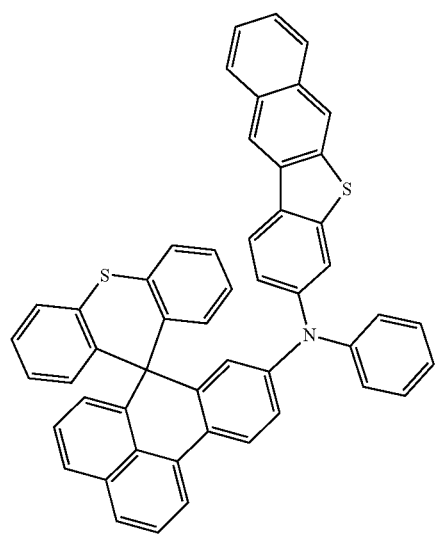
180
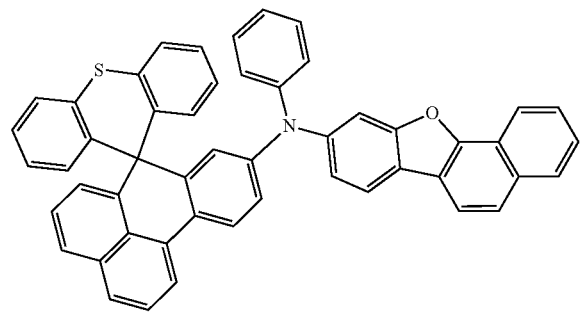
181
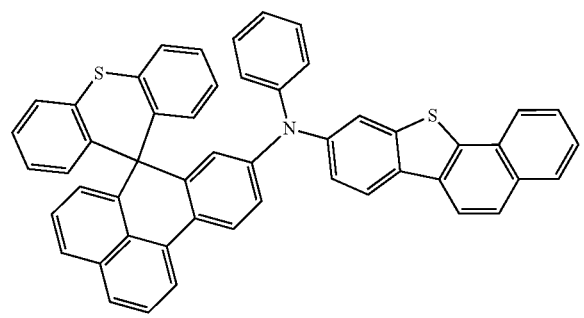
182
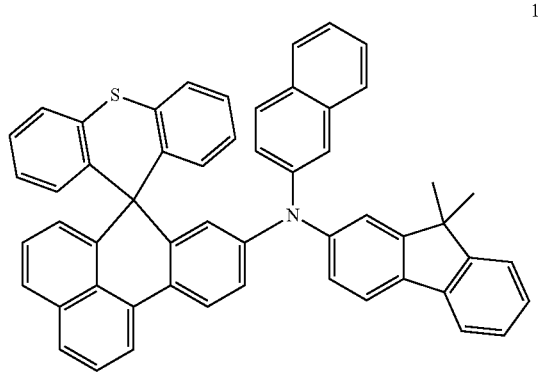
183
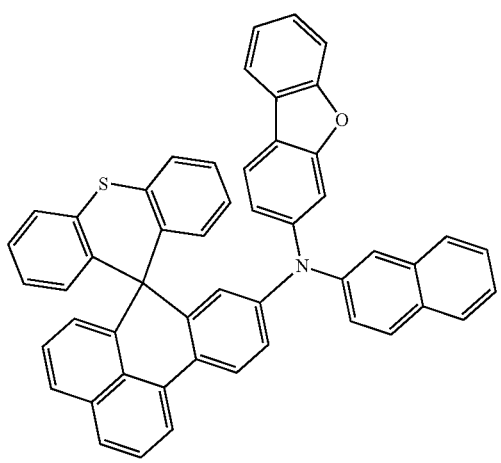
184
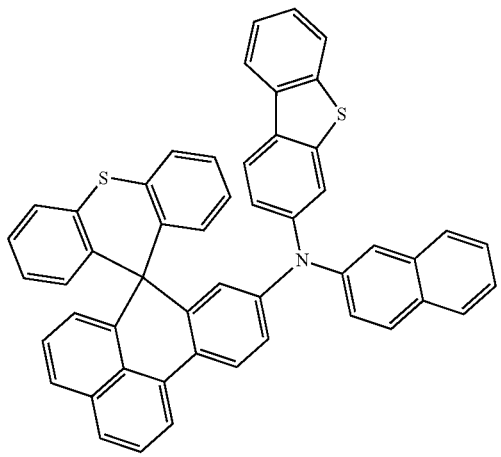
185
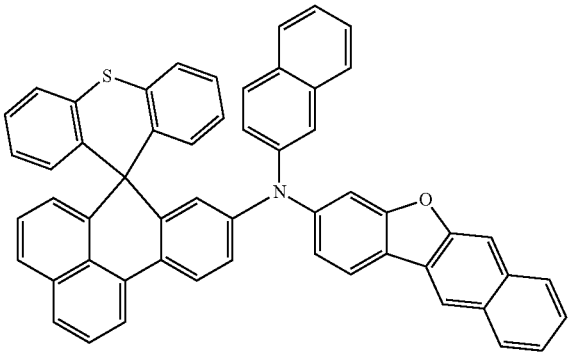

186
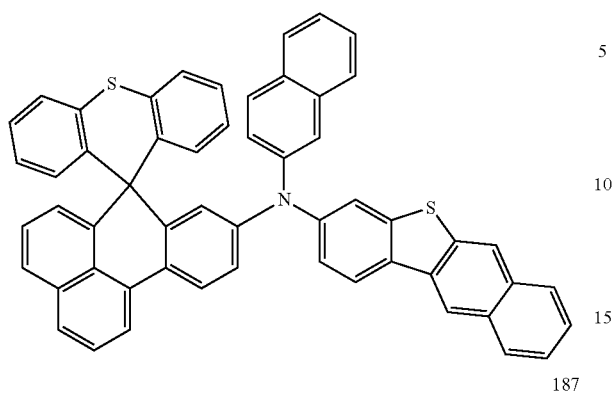
187
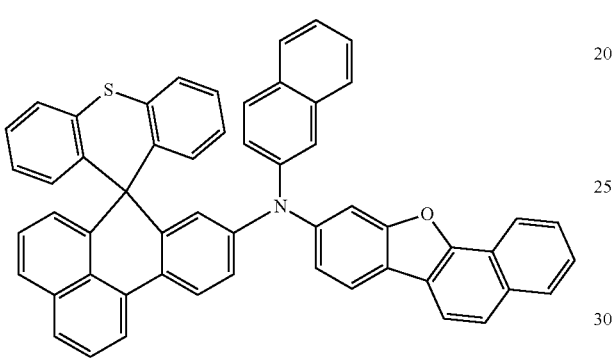
188
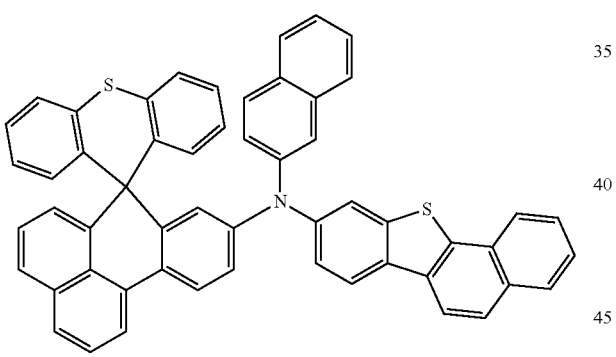
189
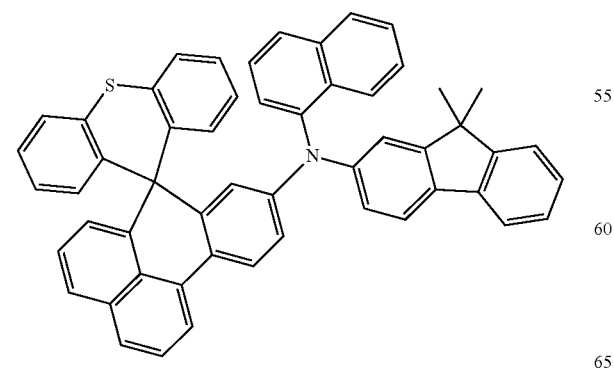
190
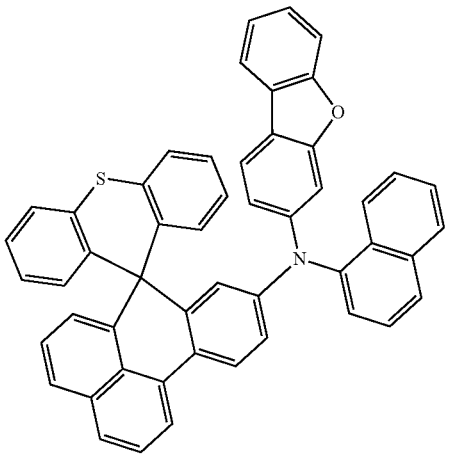
191
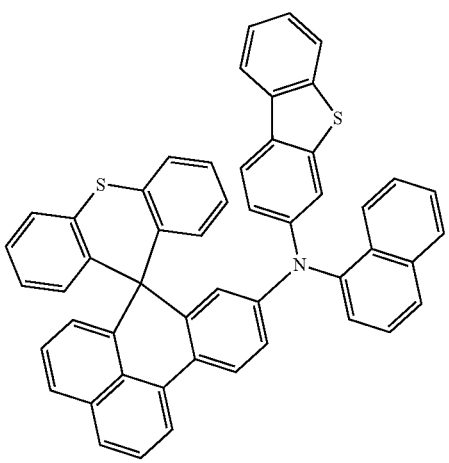
192
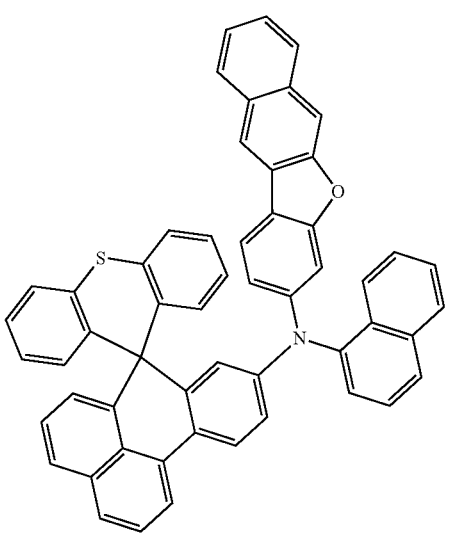

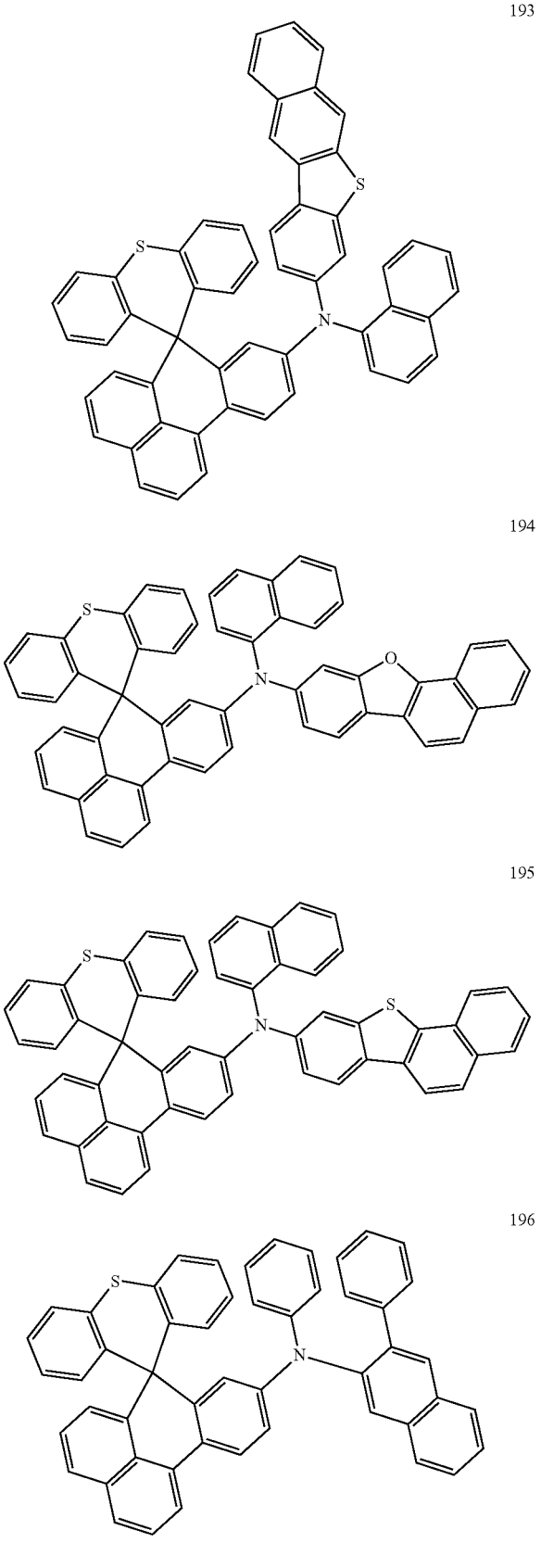
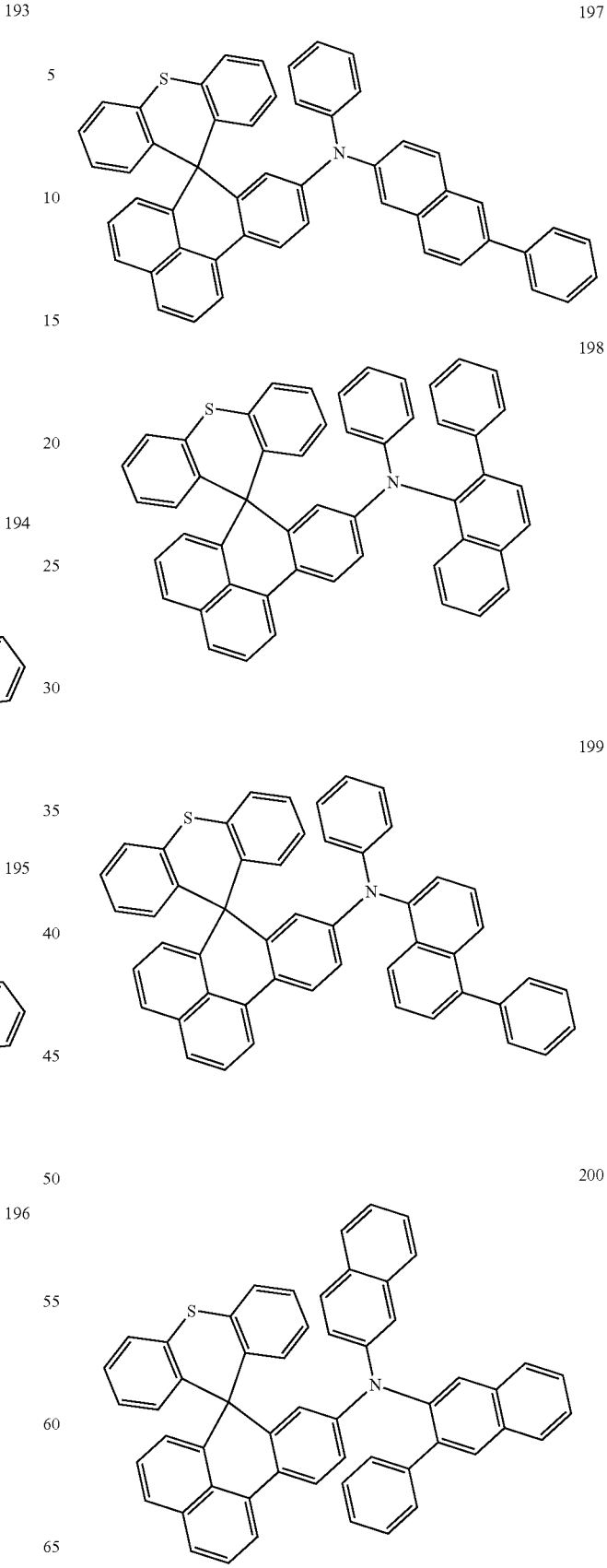

201
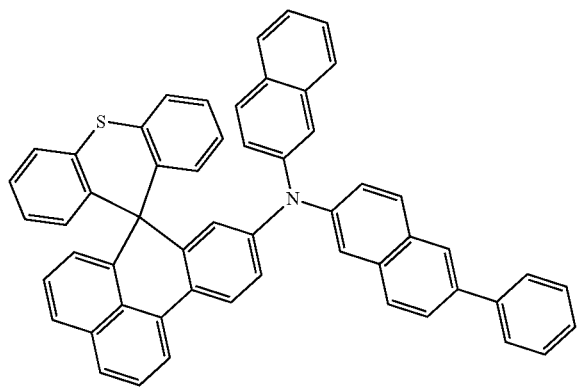
202
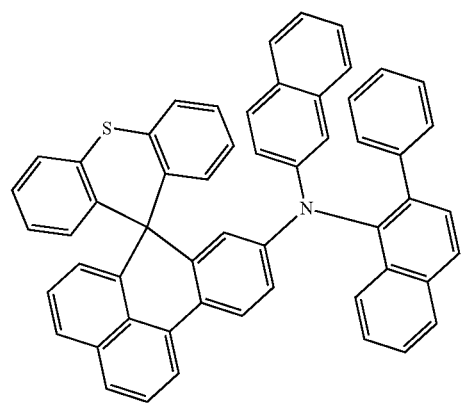
203
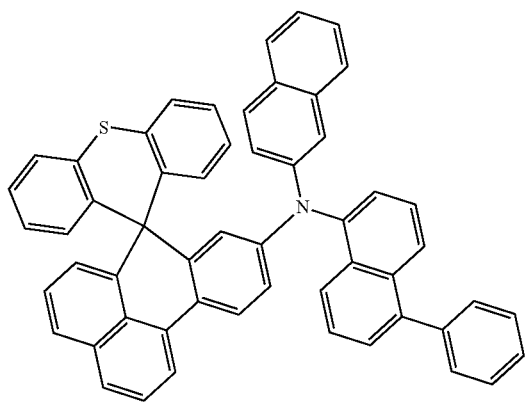
204
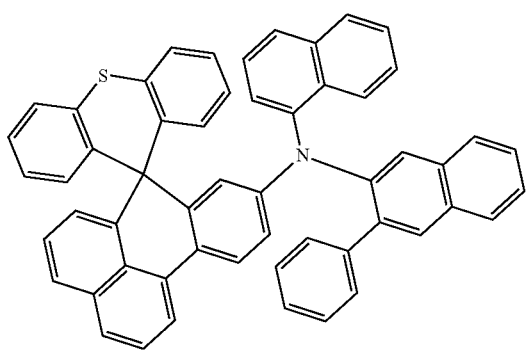
205
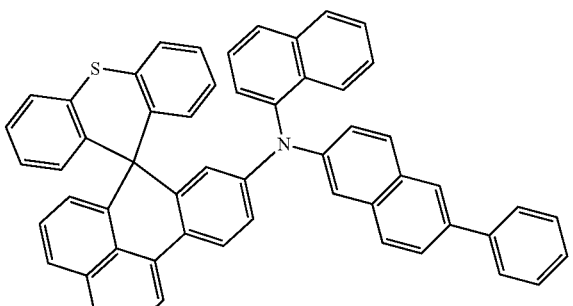
206
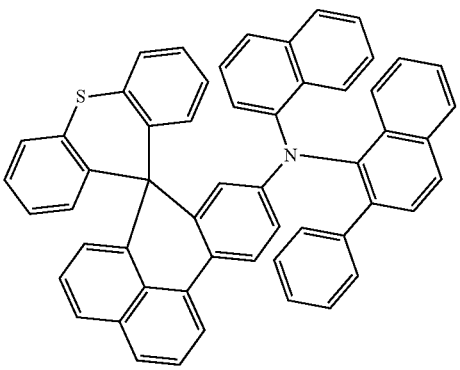
207
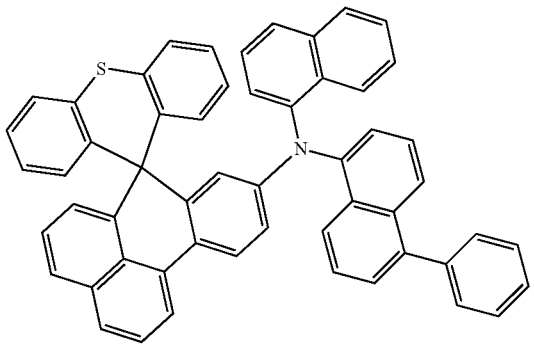
208
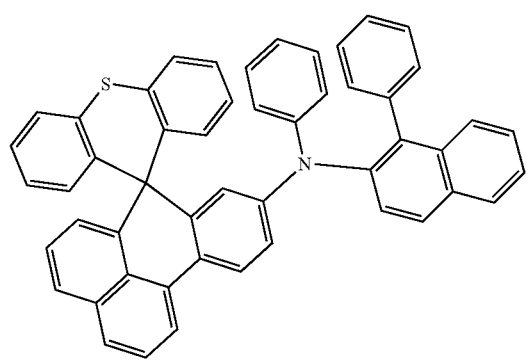

209
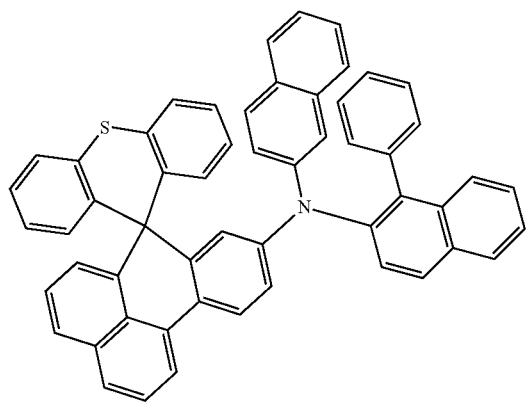
210
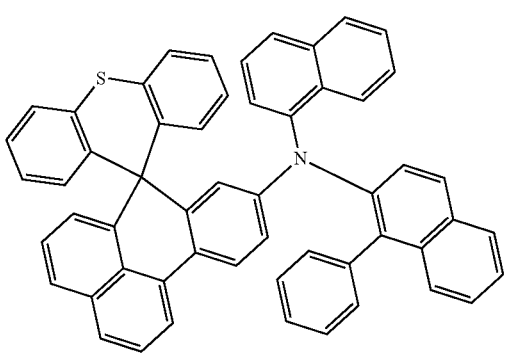
211
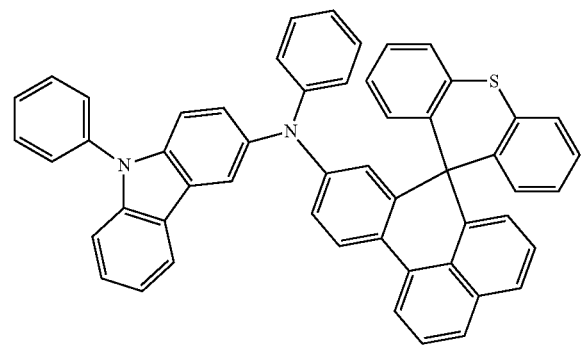
212
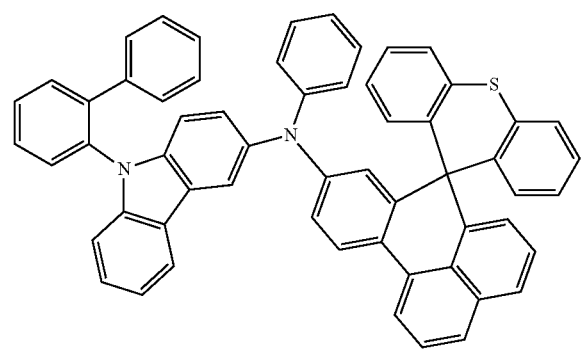
213
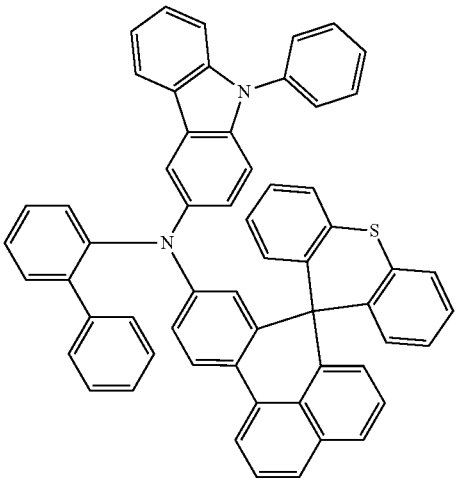
214
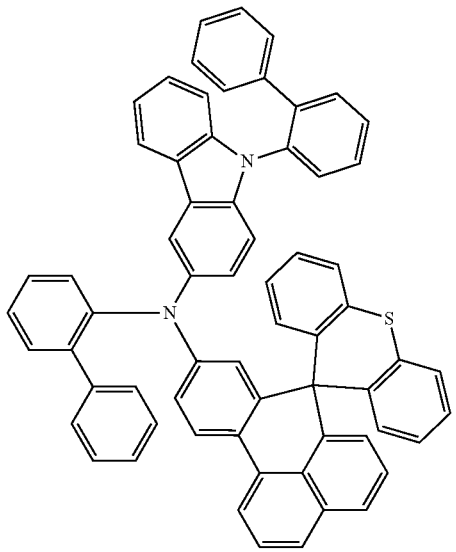
215
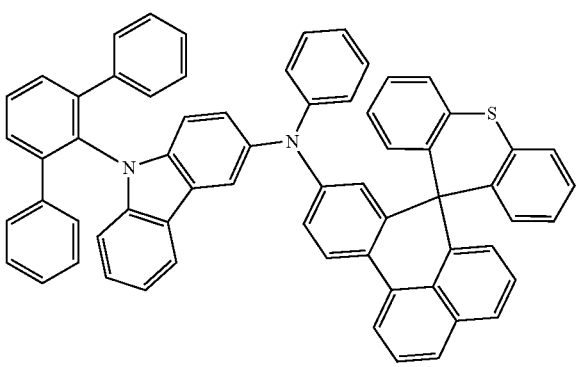

216
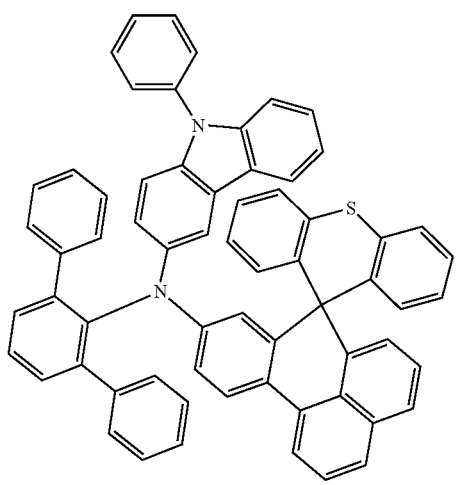
217
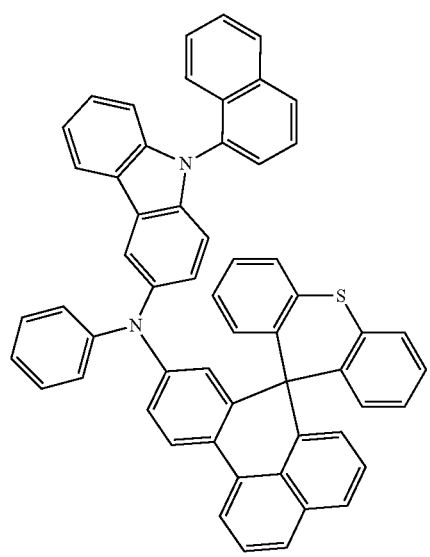
218
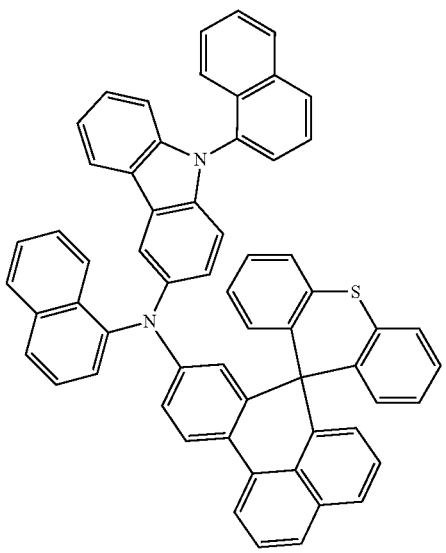
219
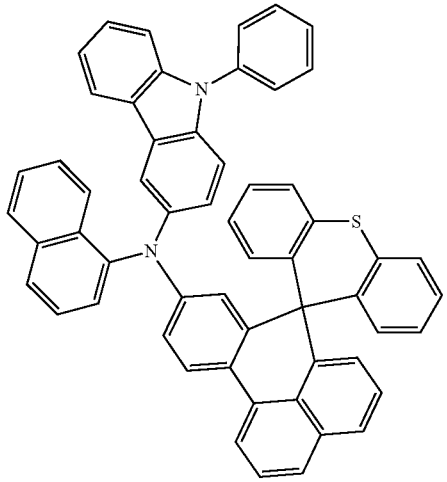
220
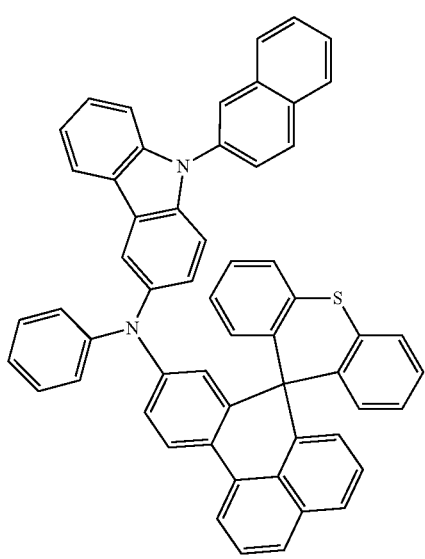
221
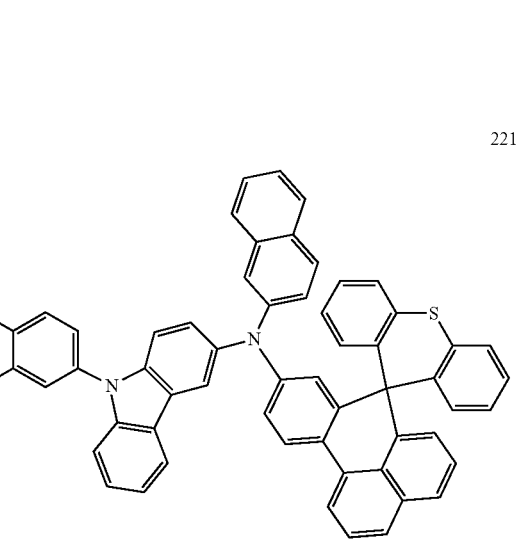

222
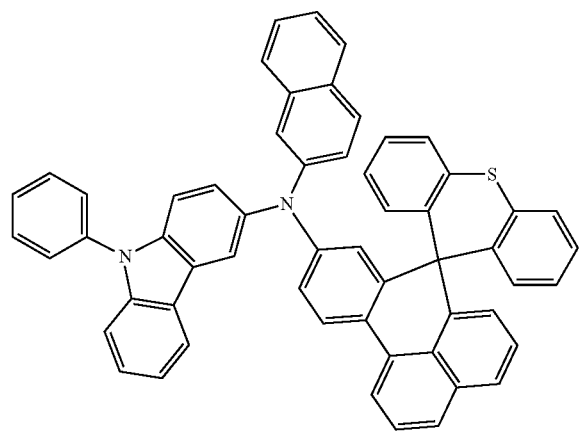
225
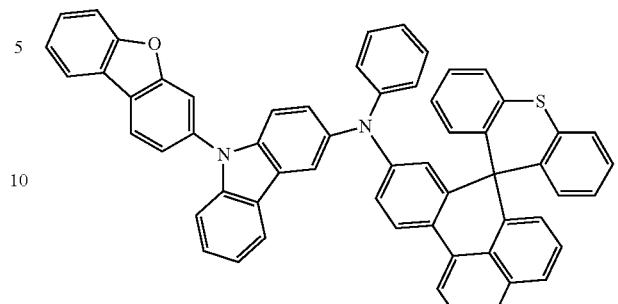
223
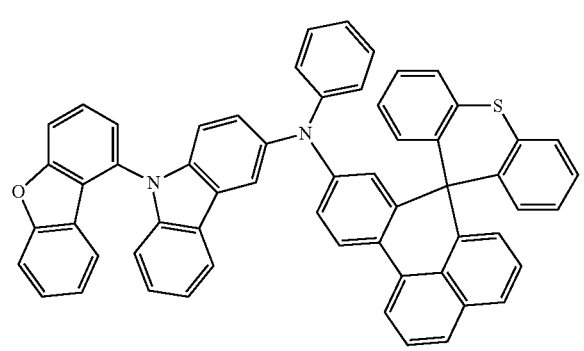
226
224
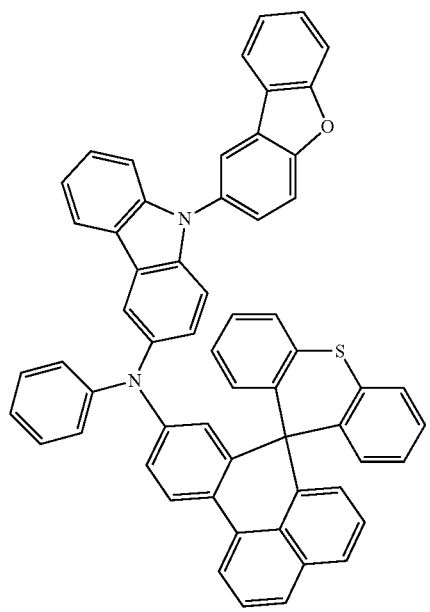
227
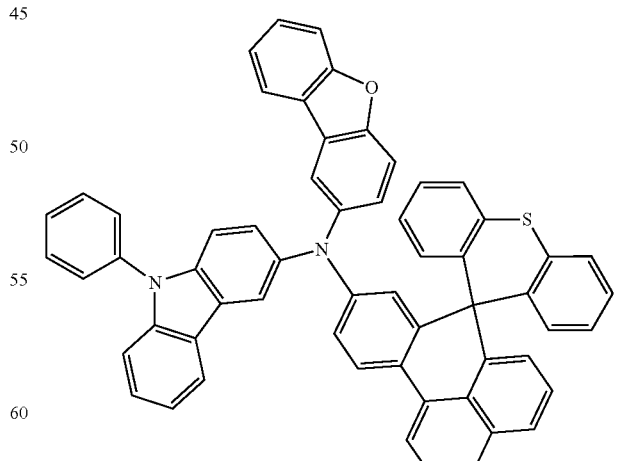

228
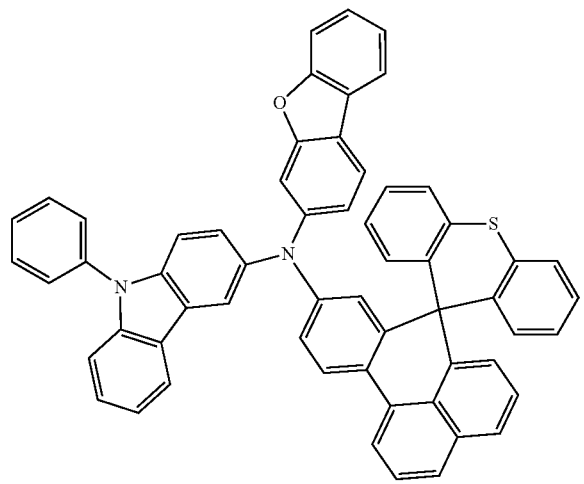
229
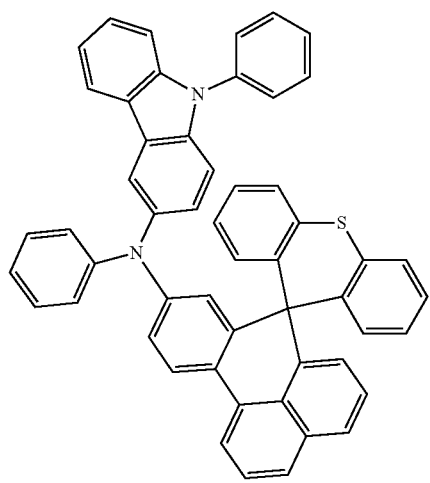
230
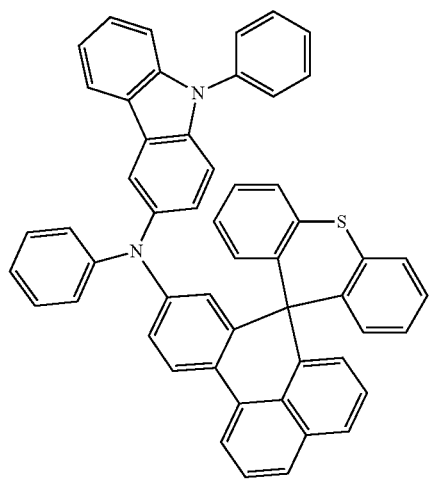
231
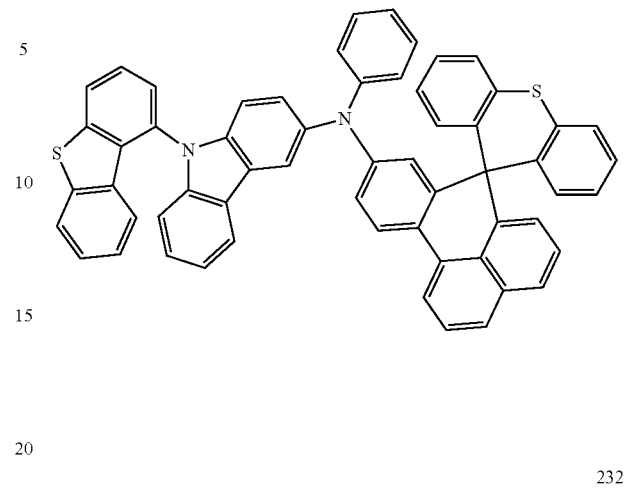
232
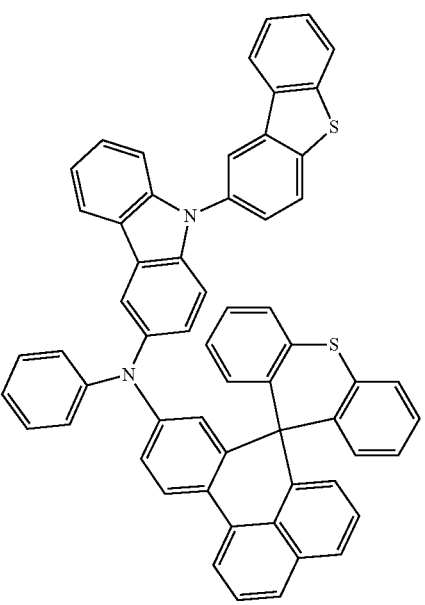
233
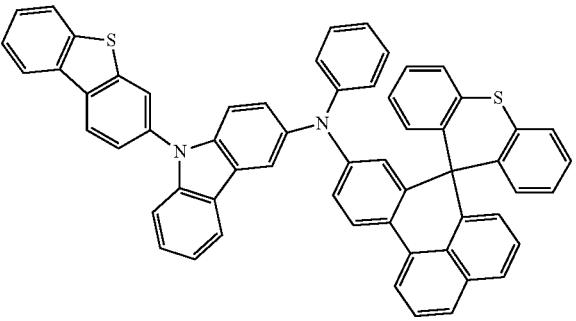

234
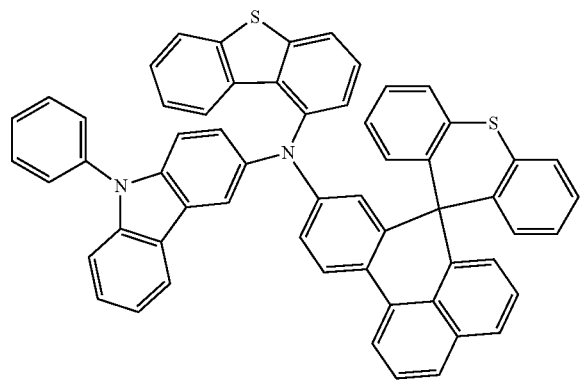
235
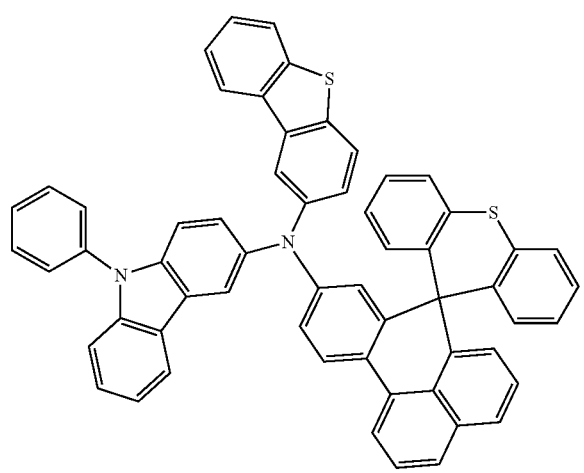
236
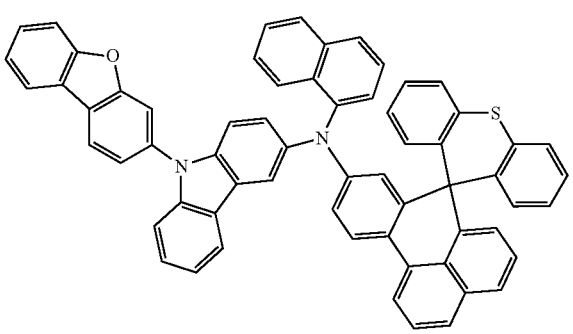
237
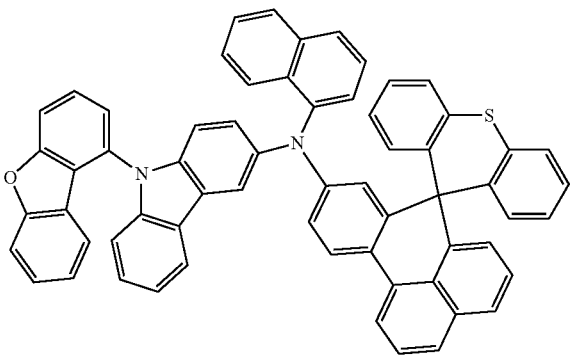
238
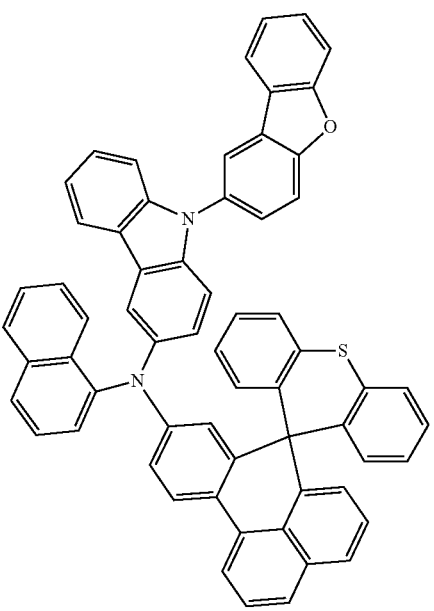
239

-continued
240
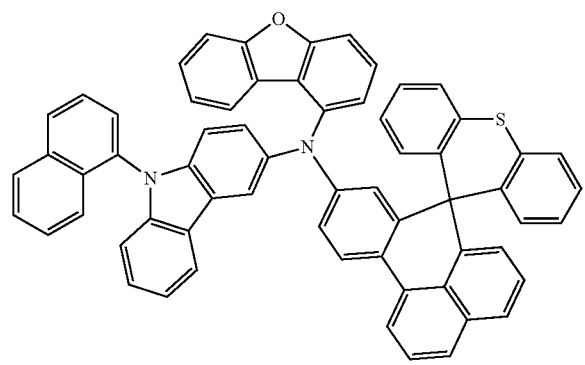
241
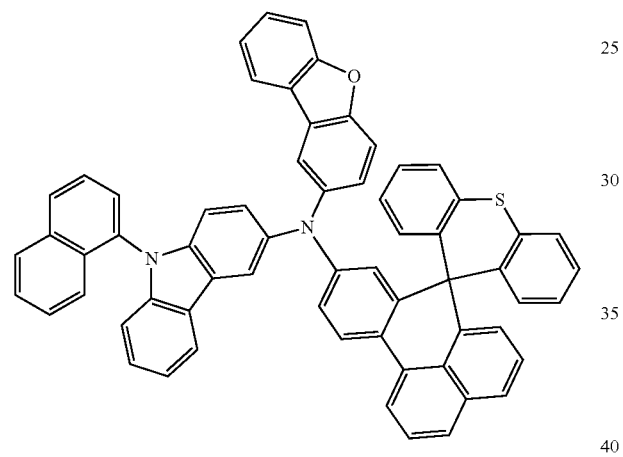
242
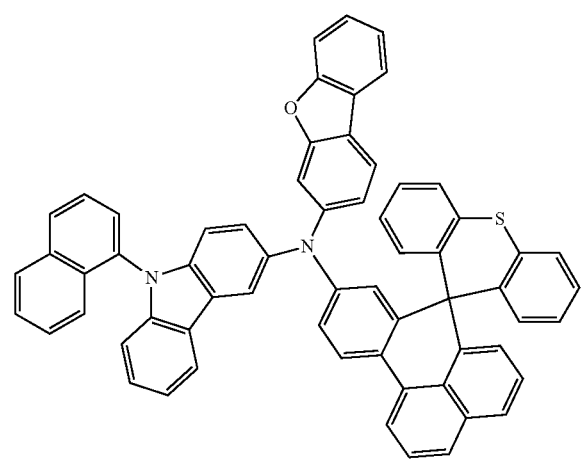
-continued
243
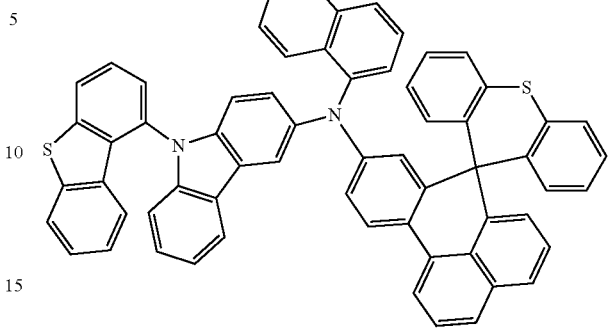
244
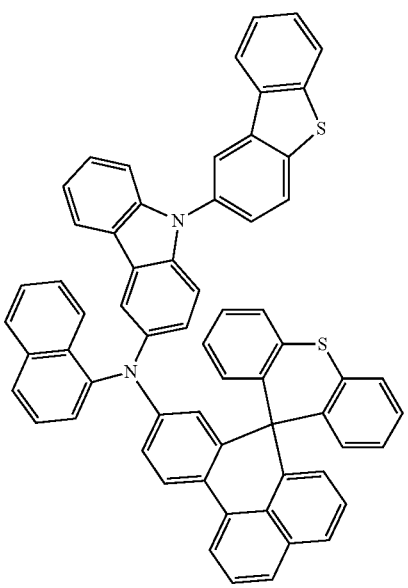
245
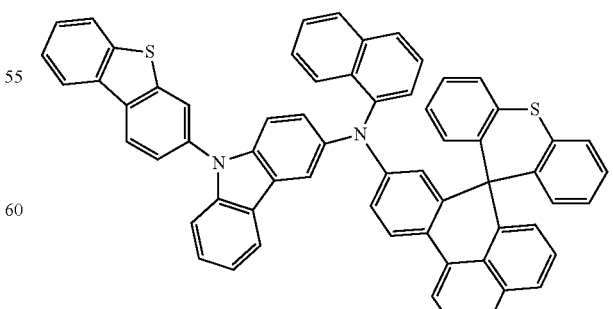

246 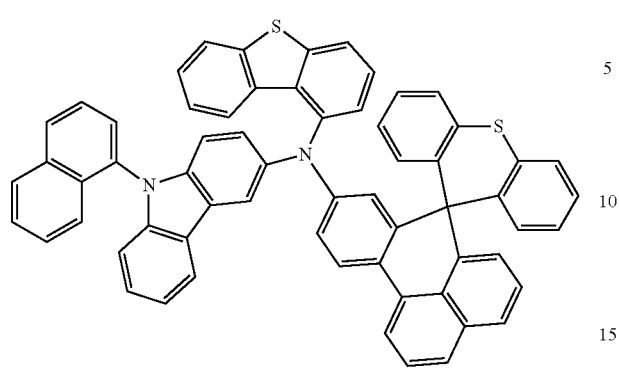
247 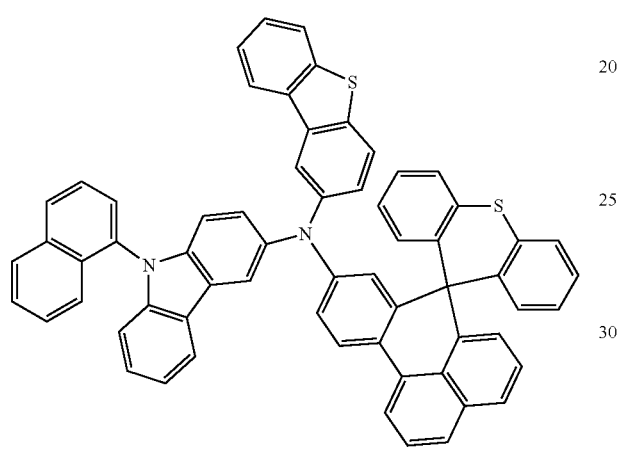
248 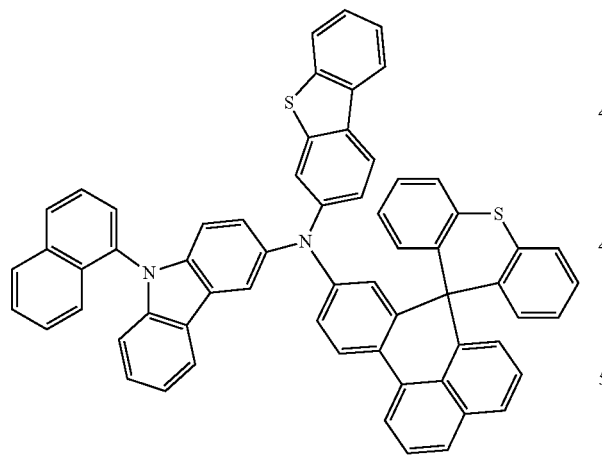
249 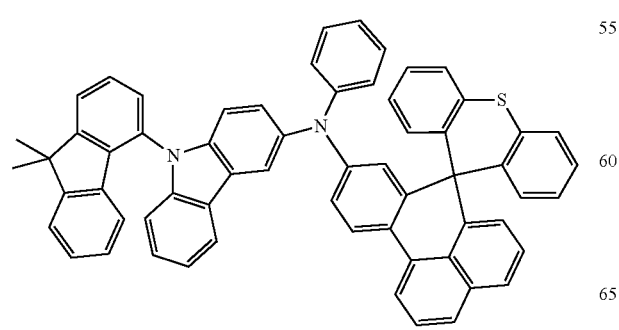
250 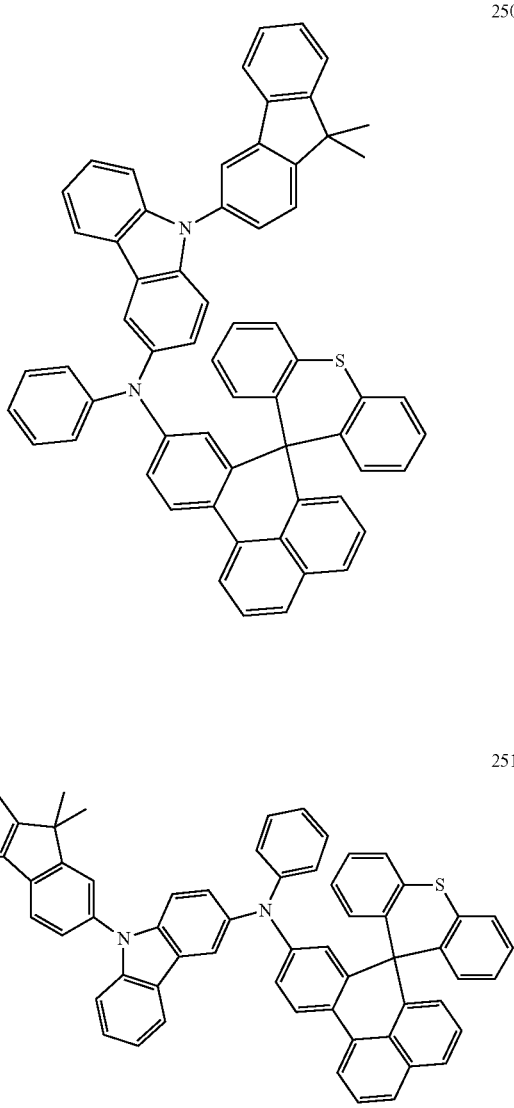
251
252 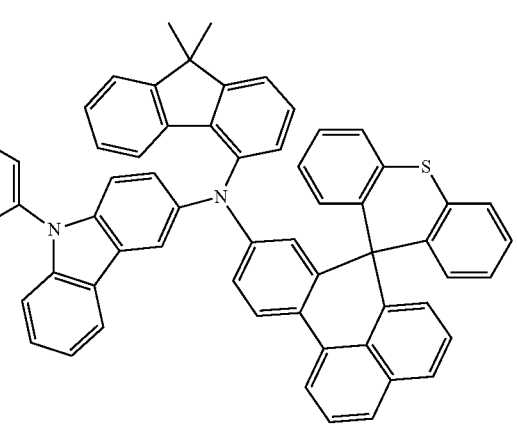

253
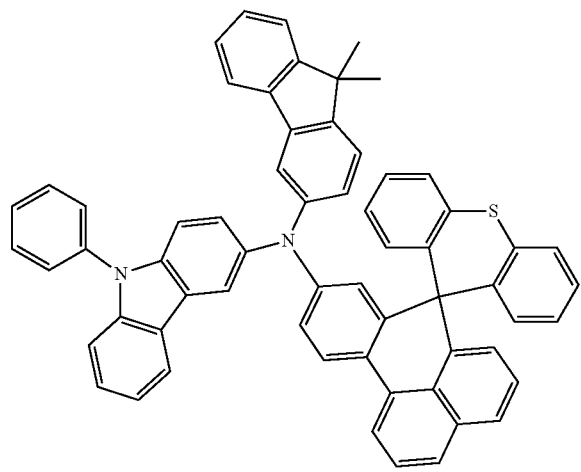
254
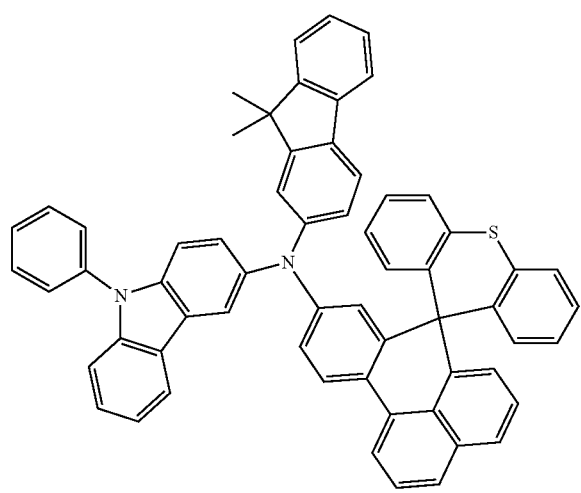
255
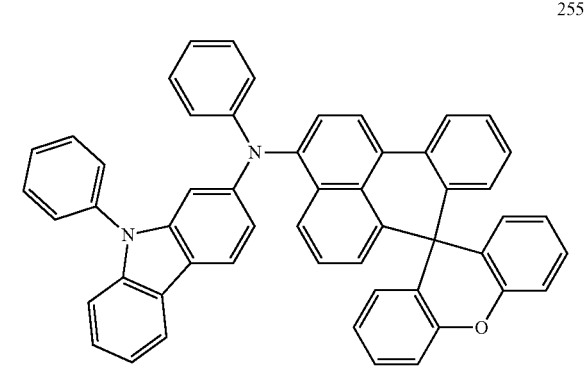
256
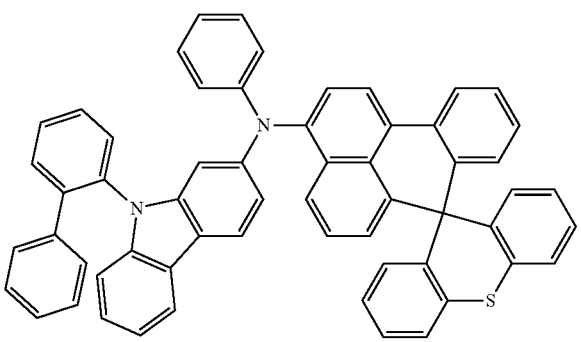
257
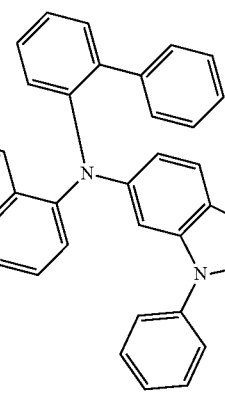
258
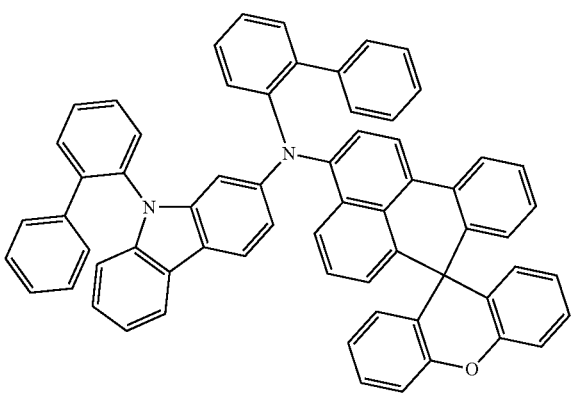
259

260
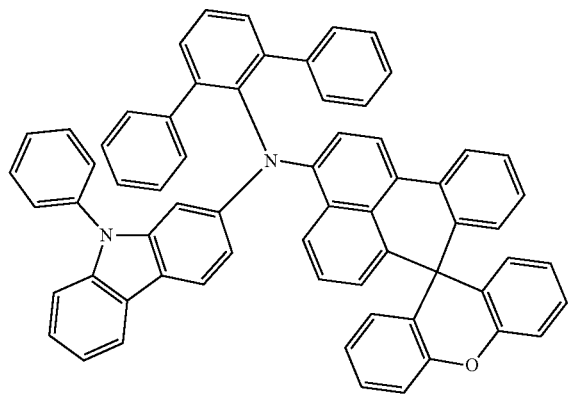
264
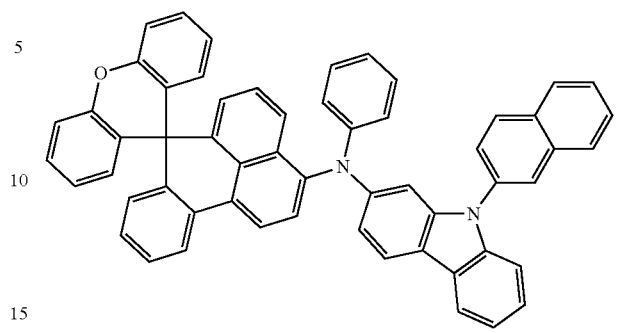
261
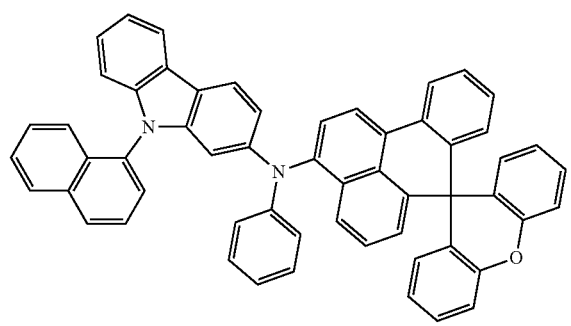
265
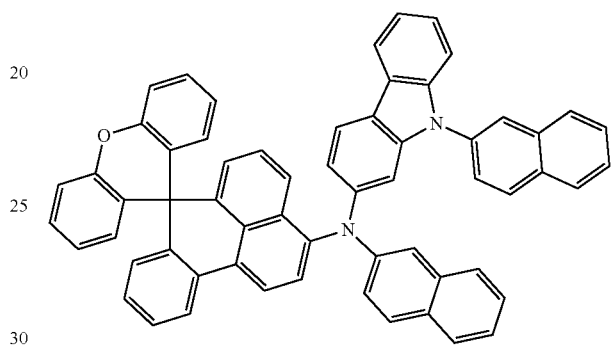
262
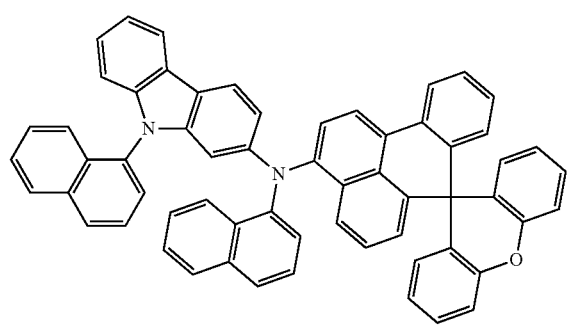
266
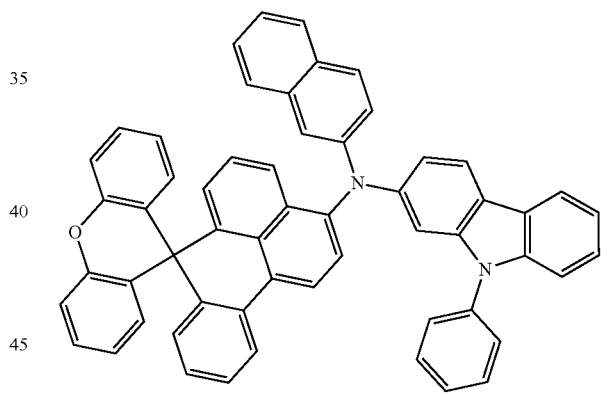
263
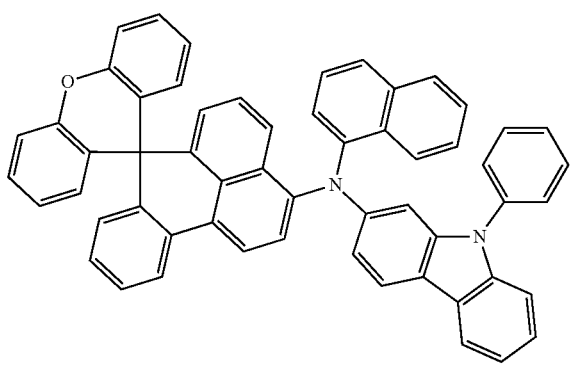
267
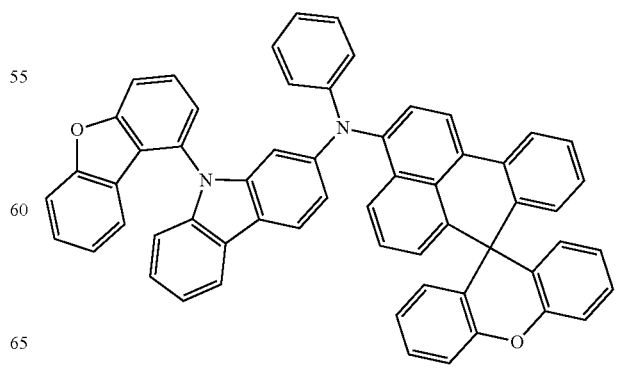

268
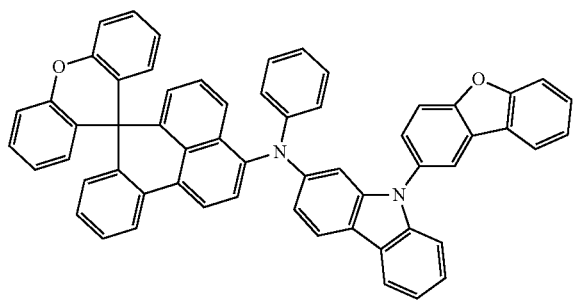
269
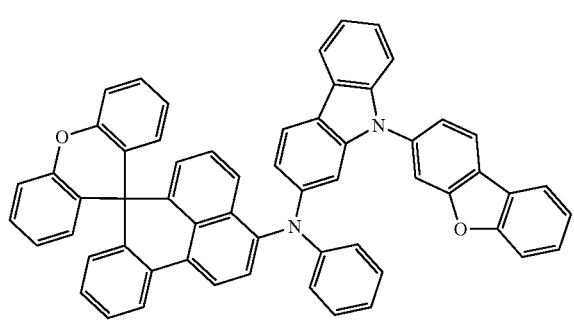
270
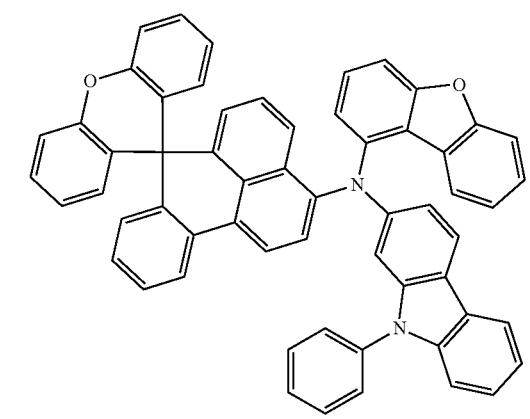
271
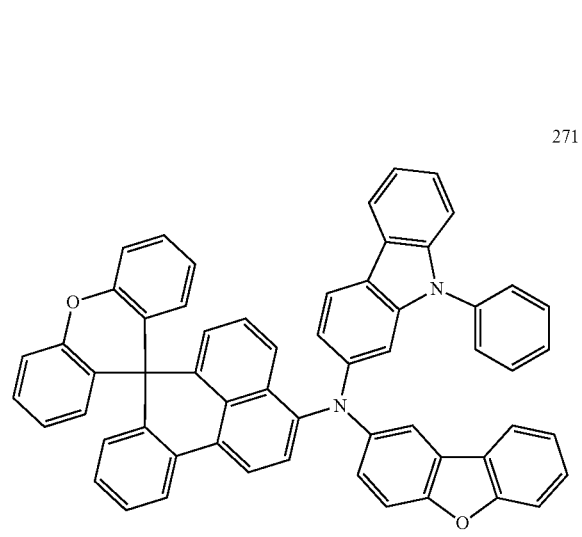
272
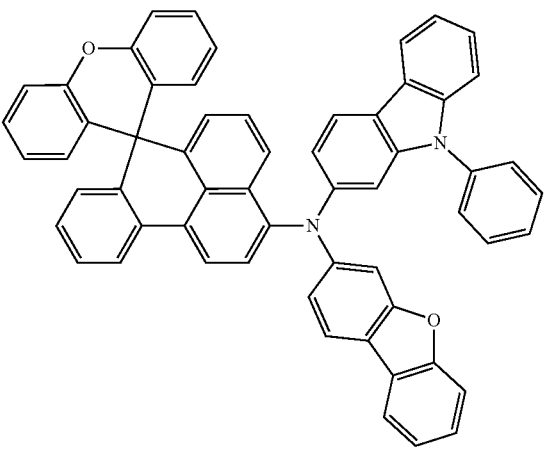
273
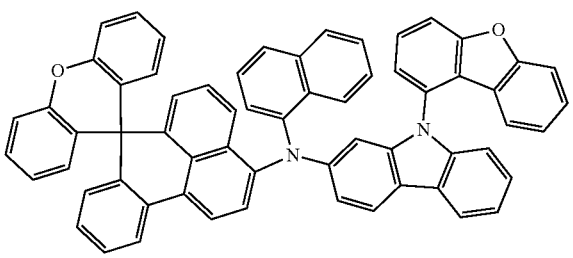
274
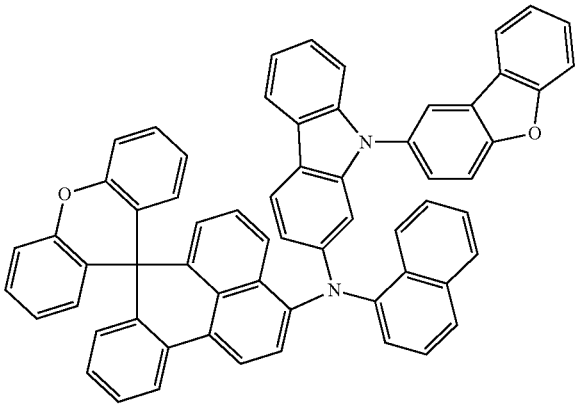
275
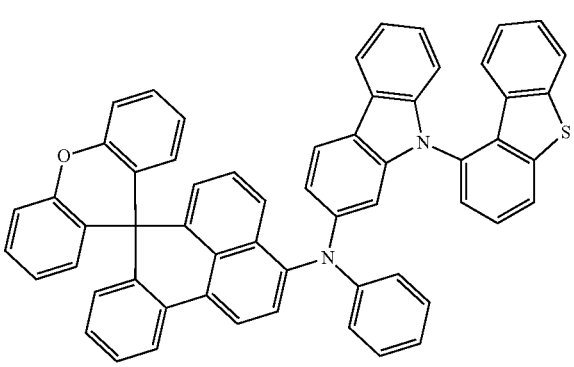

276
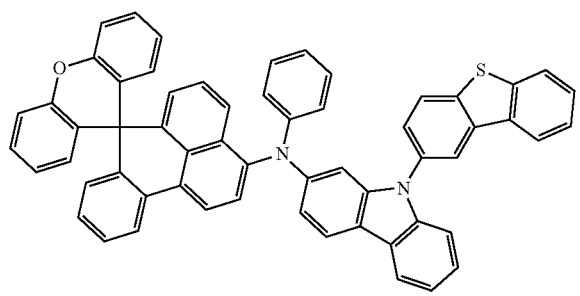
277
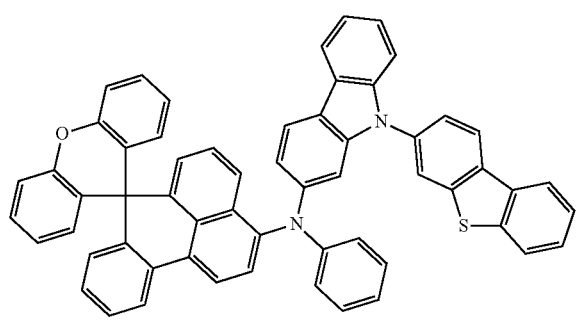
278
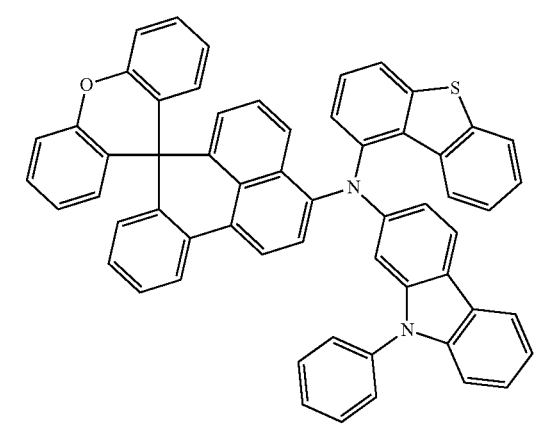
279
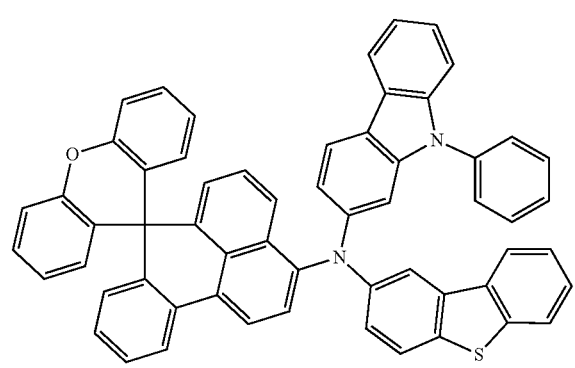
280
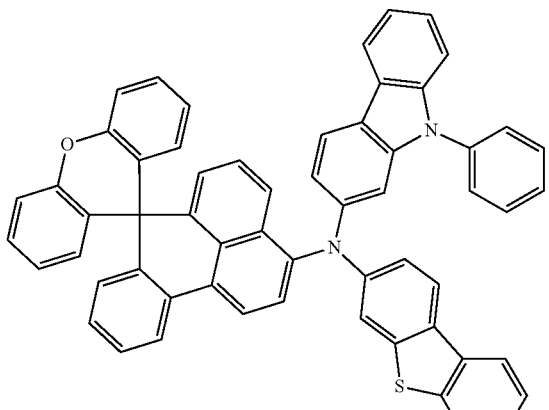
281
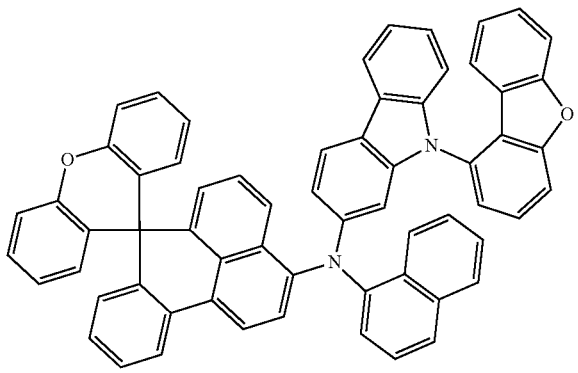
282
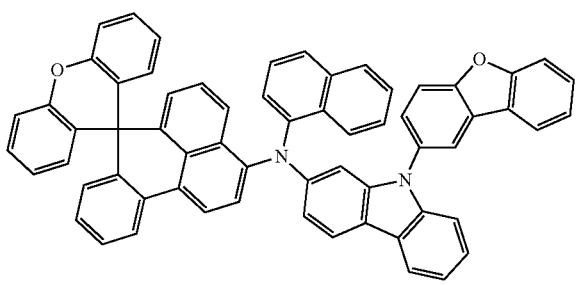
283
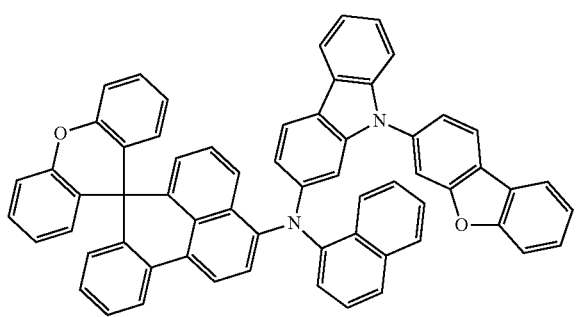

284
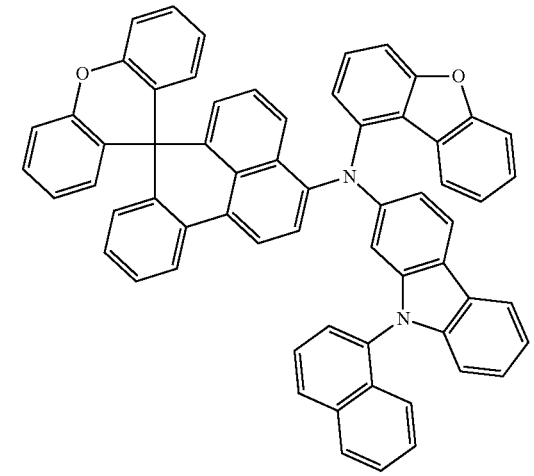
285
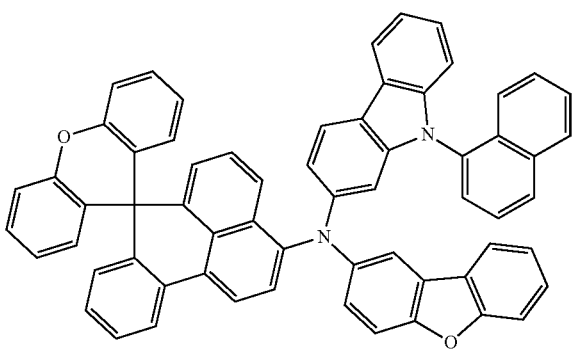
286
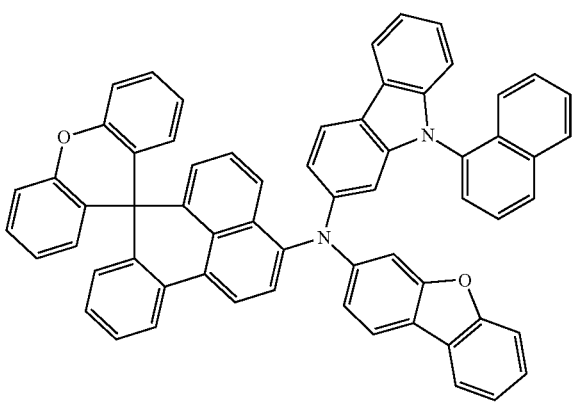
287
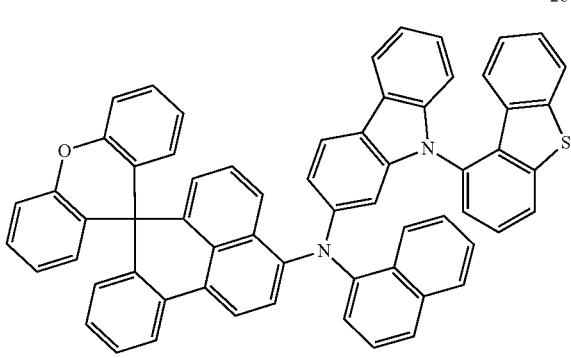
288
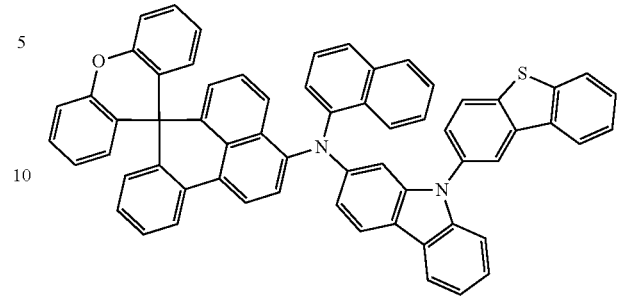
289
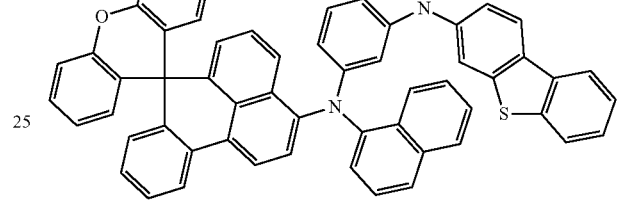
290
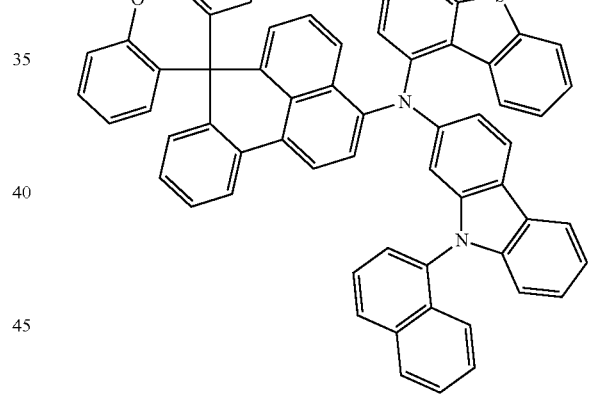
291
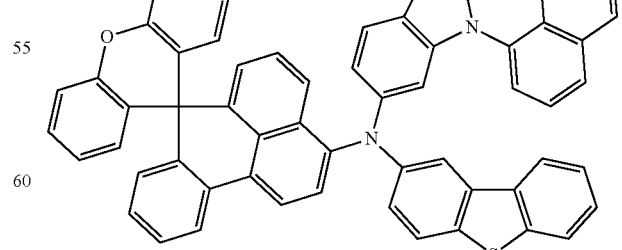

292
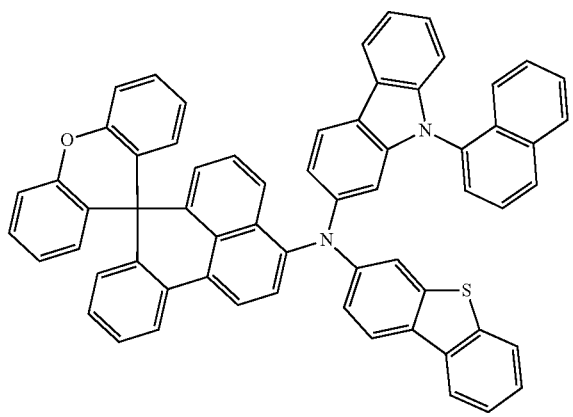
293
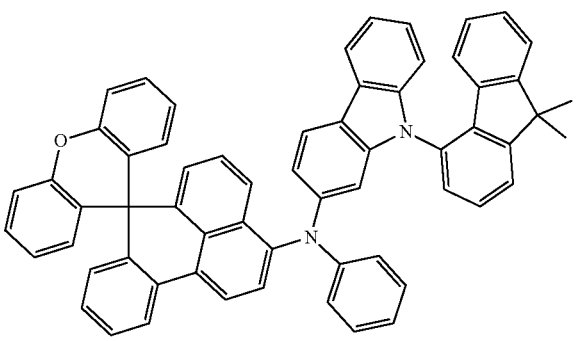
294
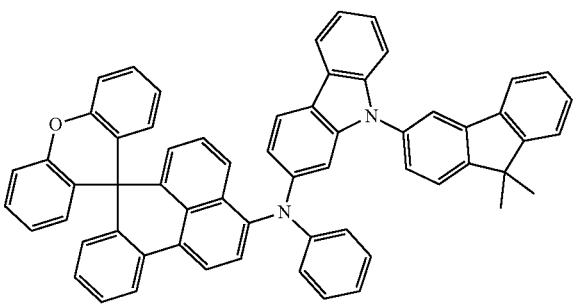
295
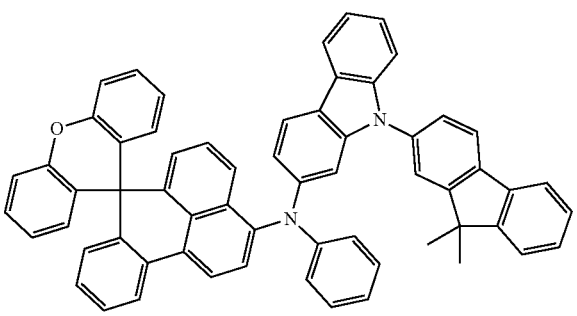
296
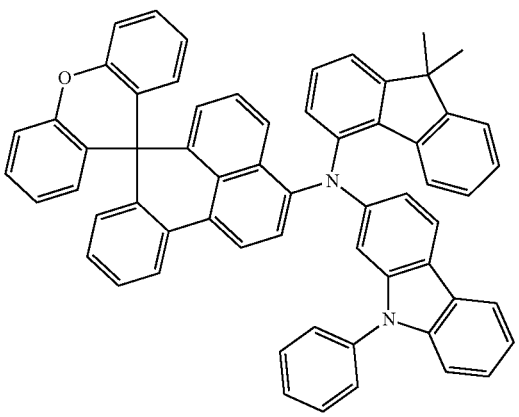
297
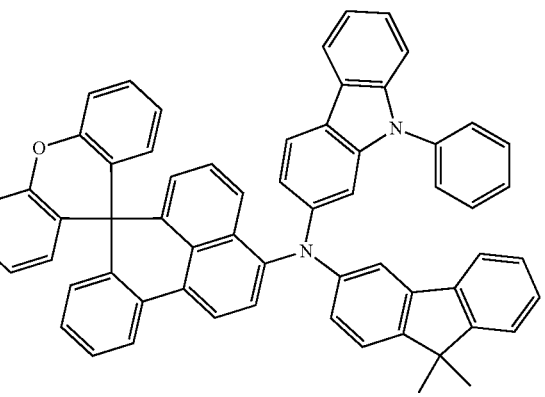
298
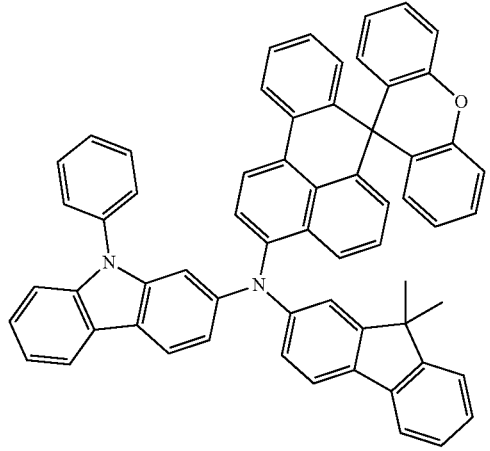
299
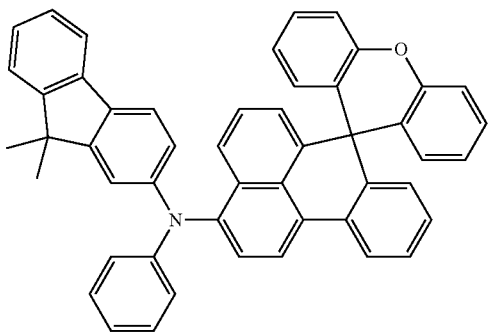

111
-continued
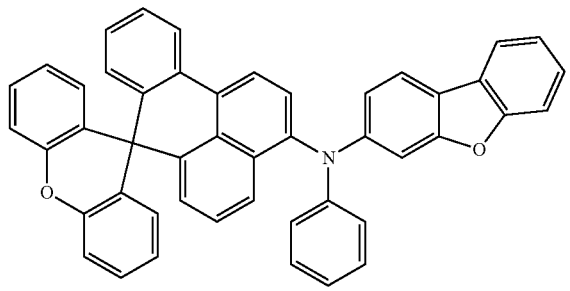
112
-continued
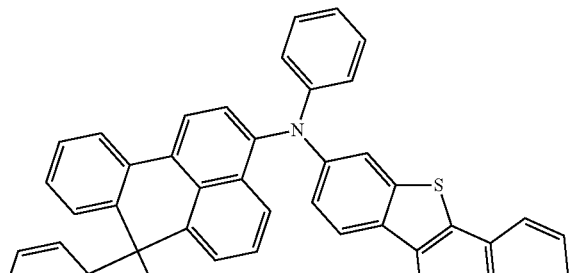
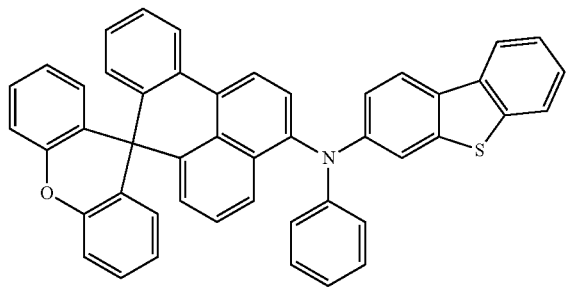

309
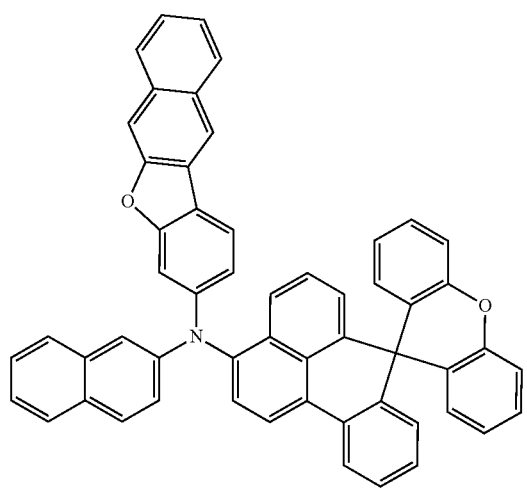
310
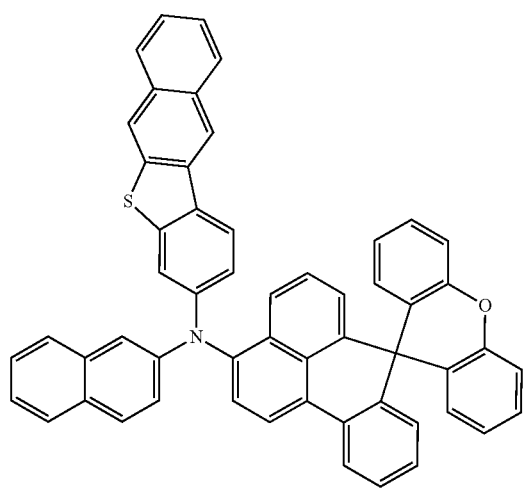
311
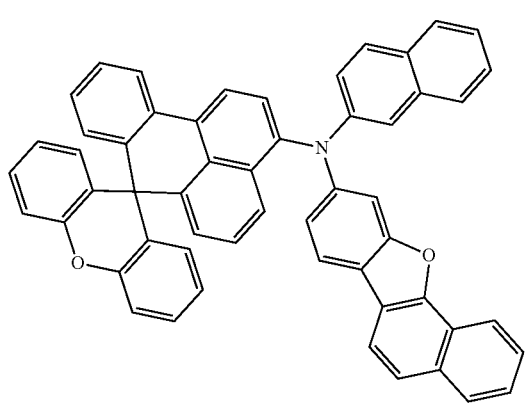
312
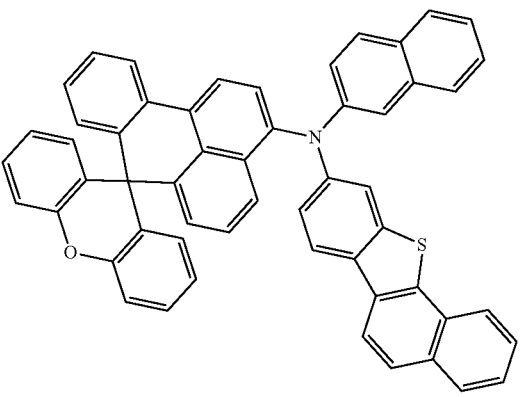
313
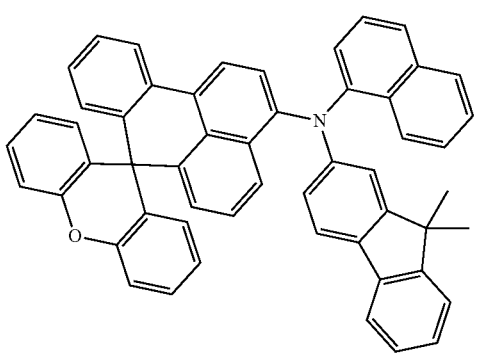
314
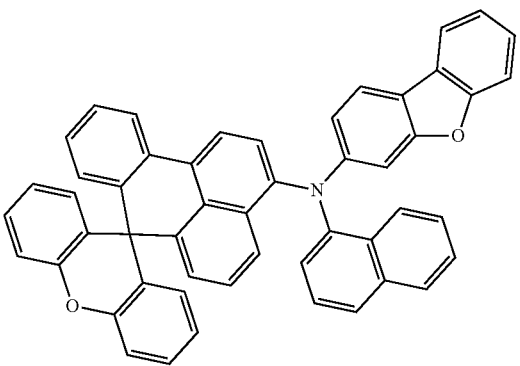
315
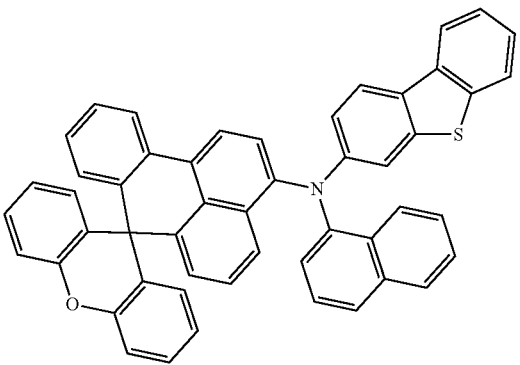

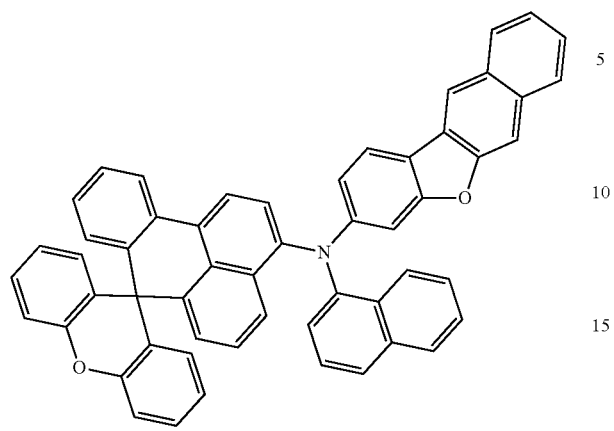
316
317
318
319
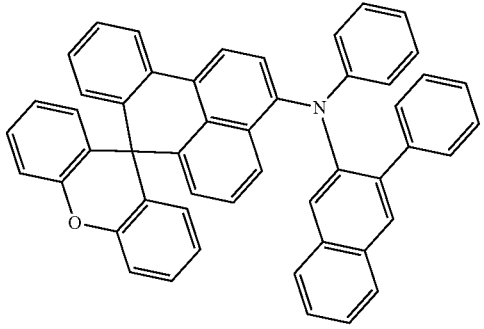
320
321
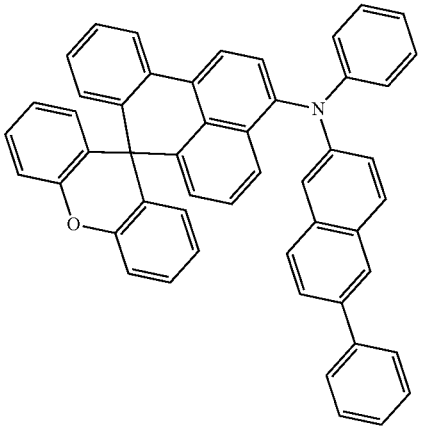
322
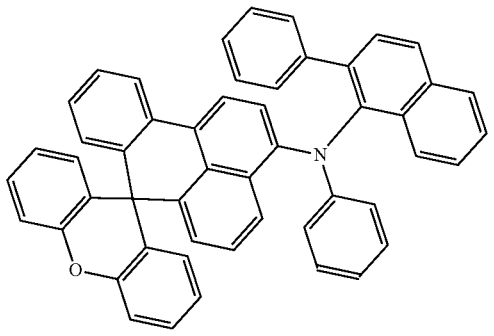
323
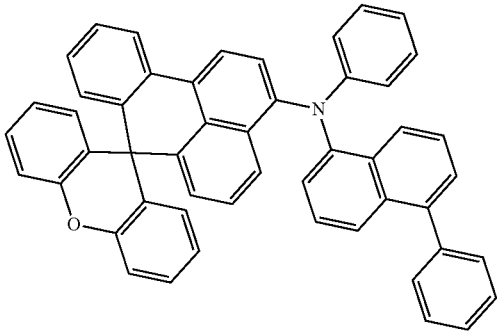

324
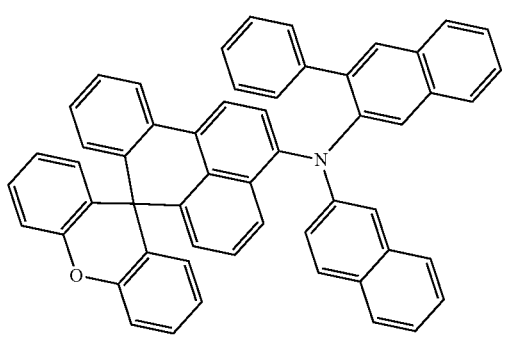
325
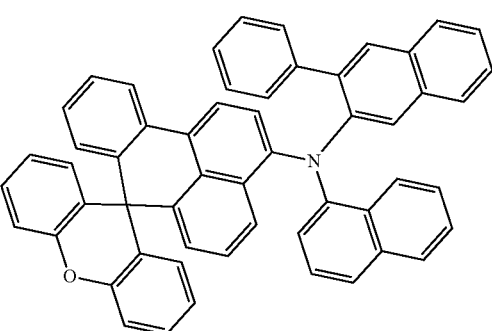
326
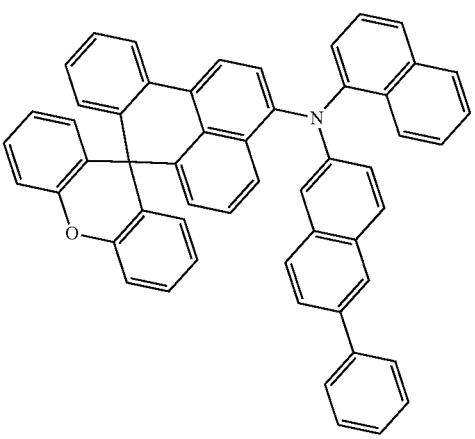
327
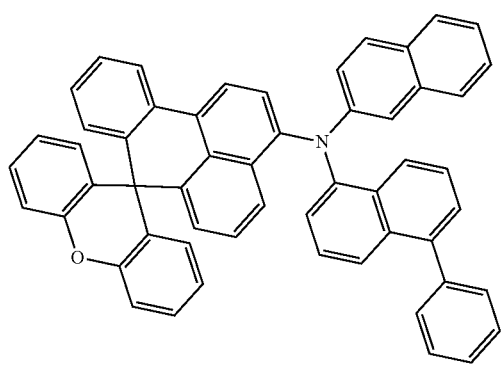
328
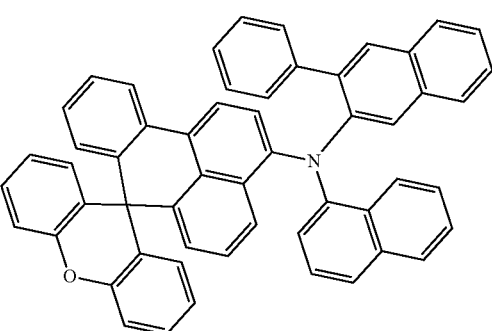
329
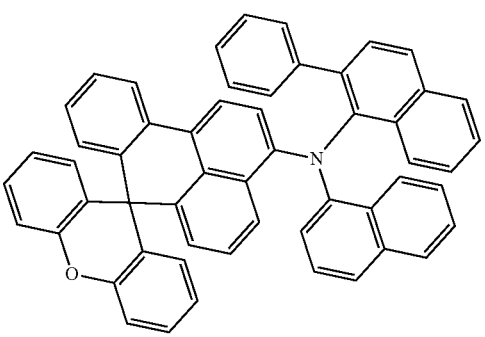
330
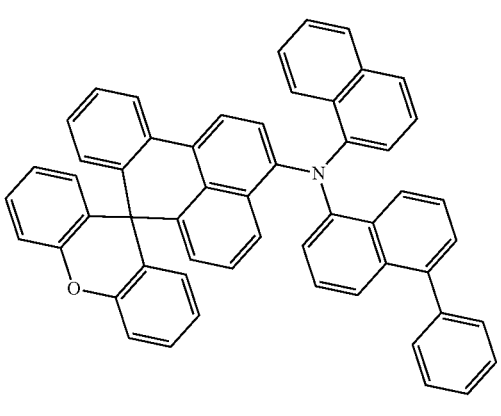
331
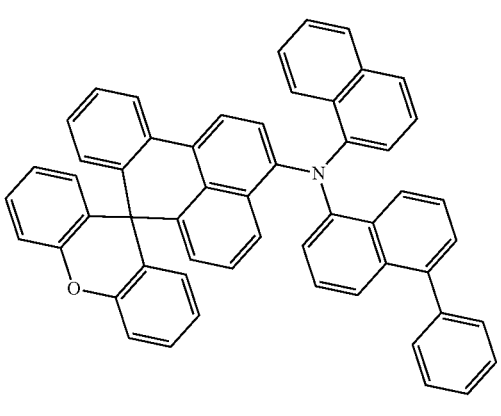

332
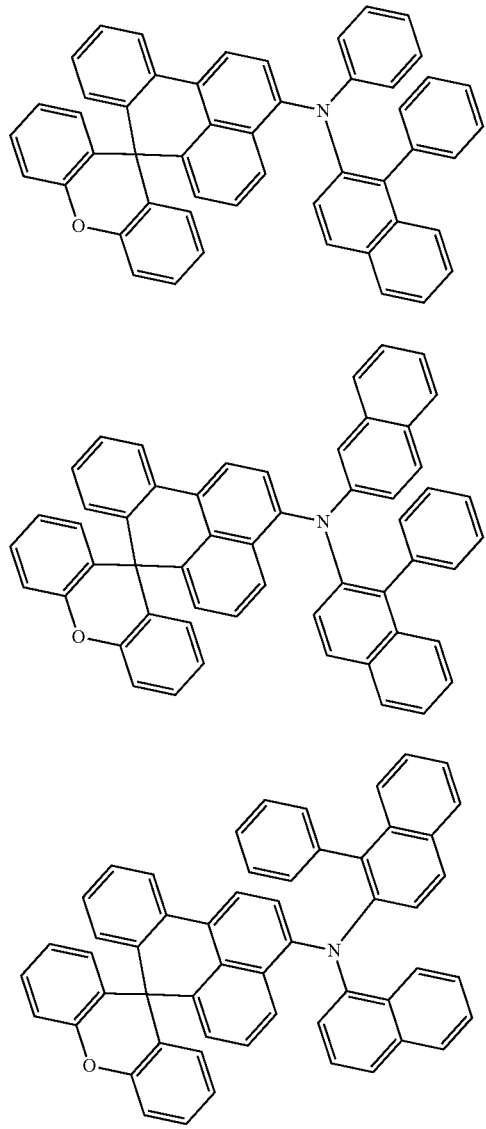
333
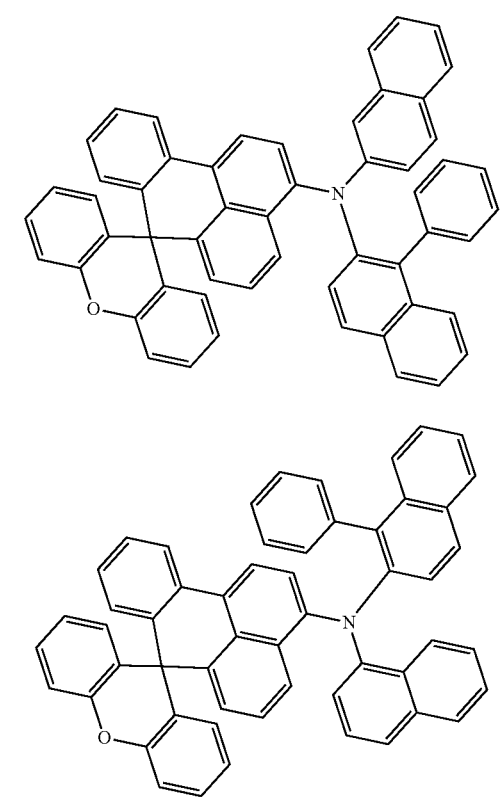
334
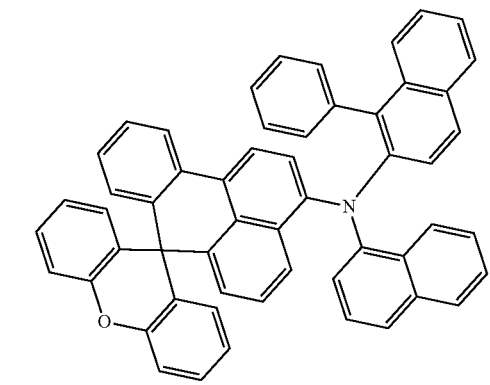
335
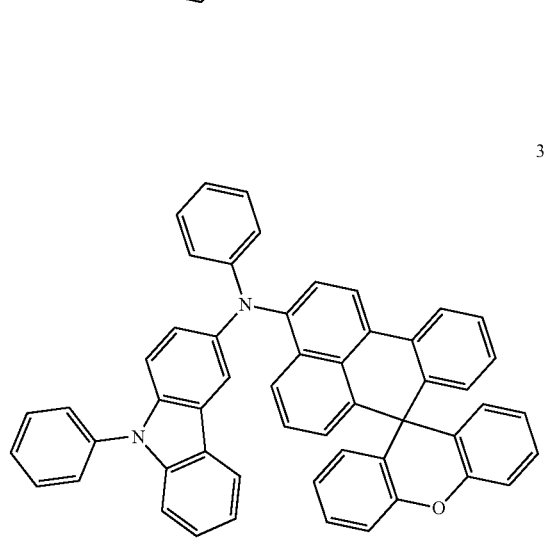
336
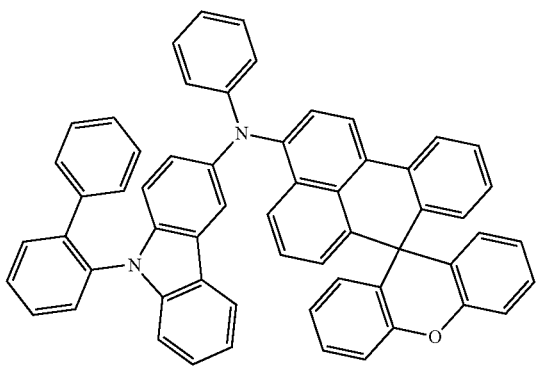
337
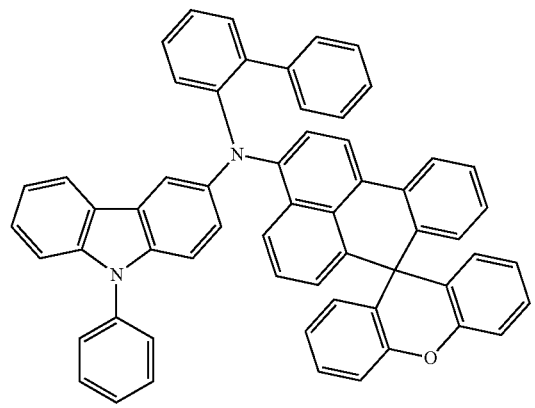
338
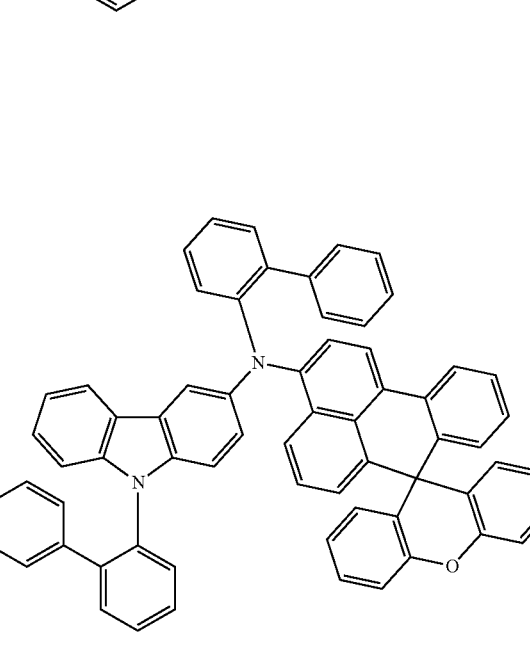

339
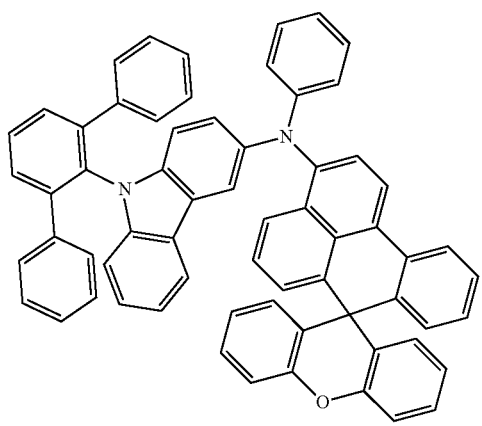
340
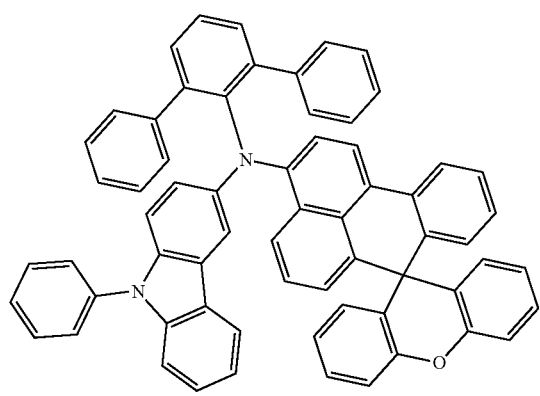
341
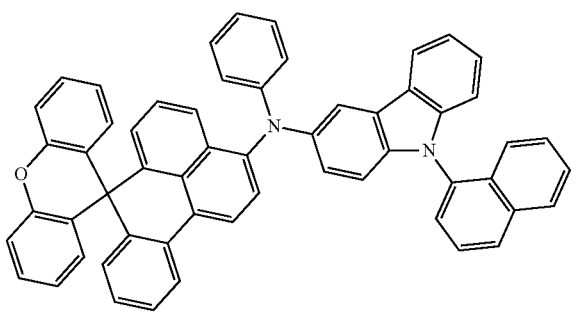
342
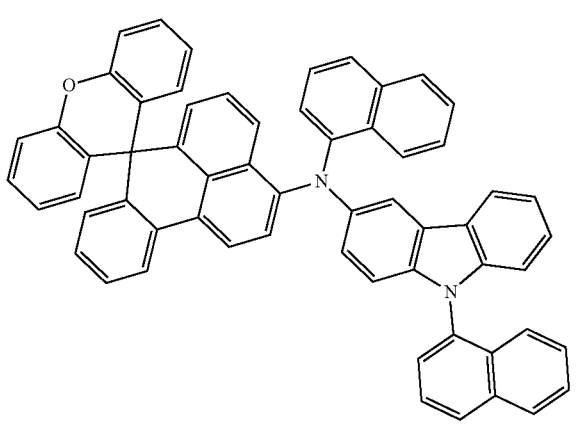
343
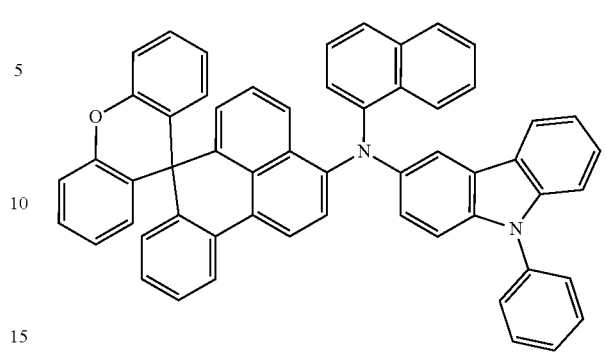
344
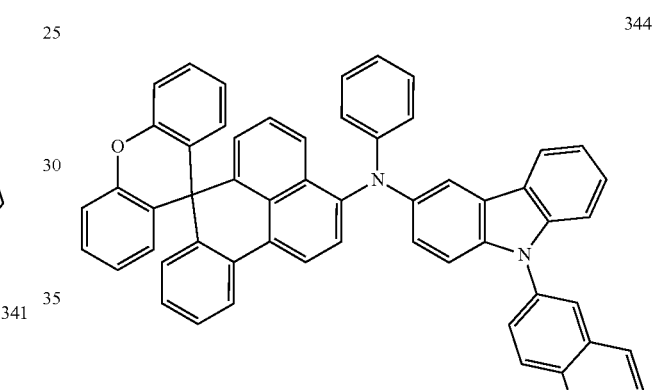
345
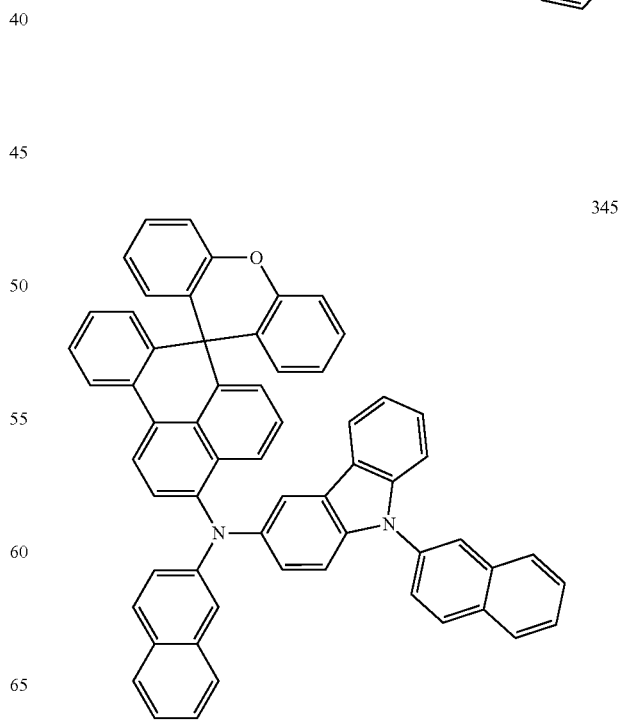

346
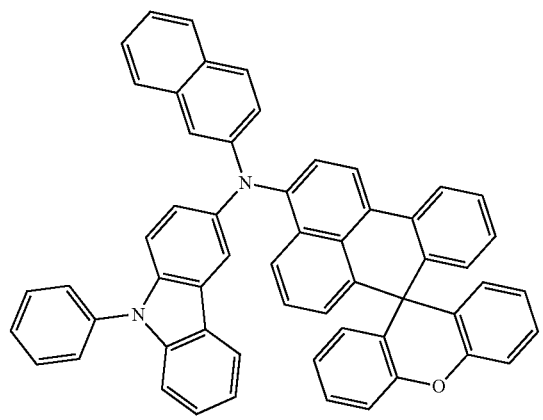
349
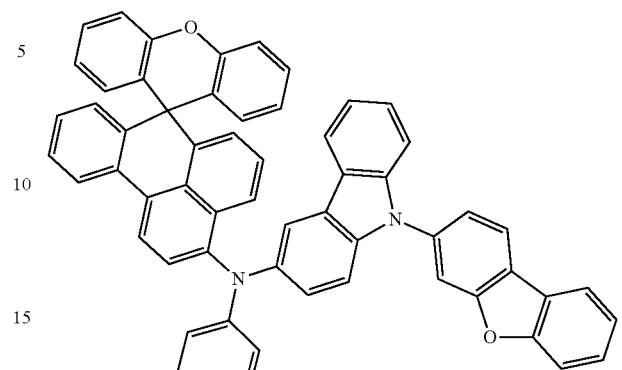
347
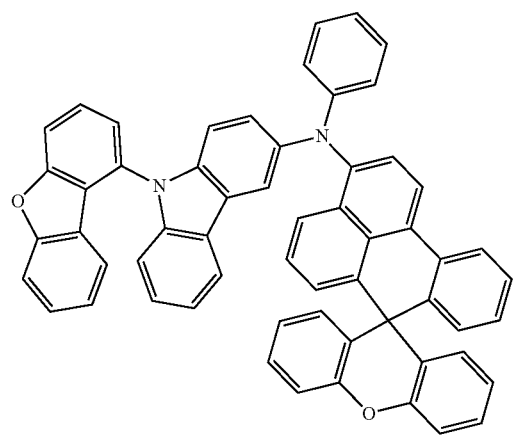
350
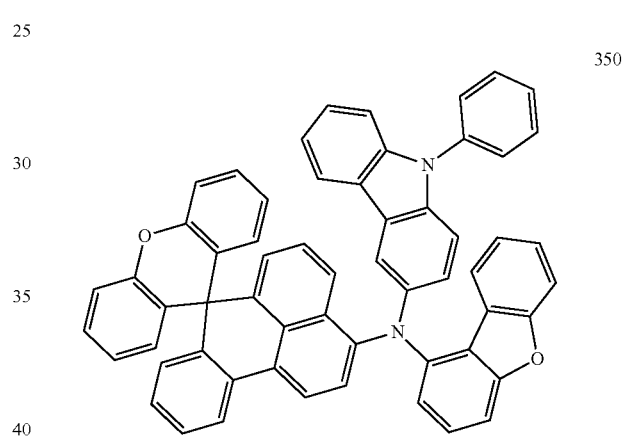
348
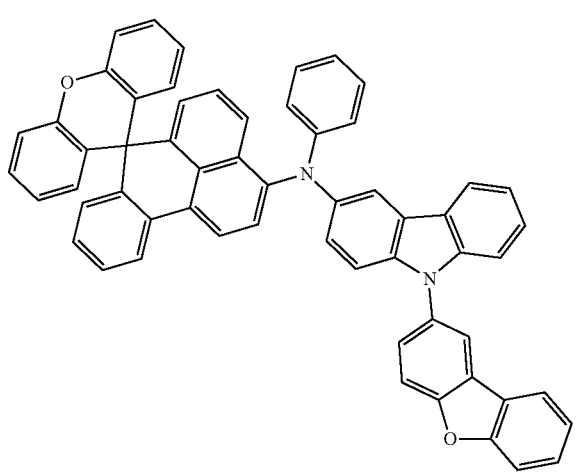
351
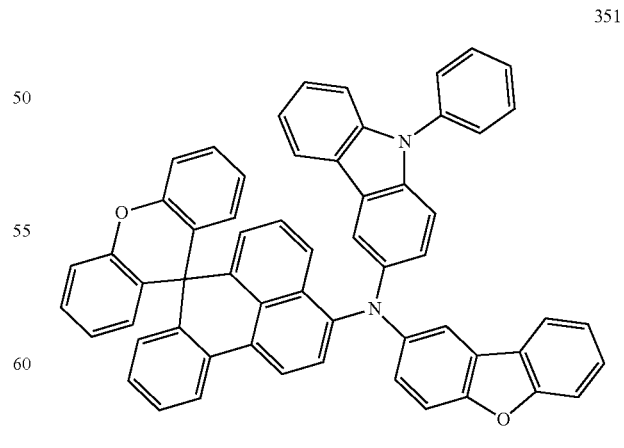

352
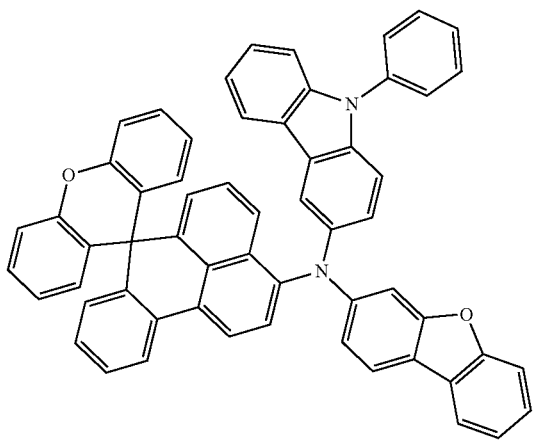
353
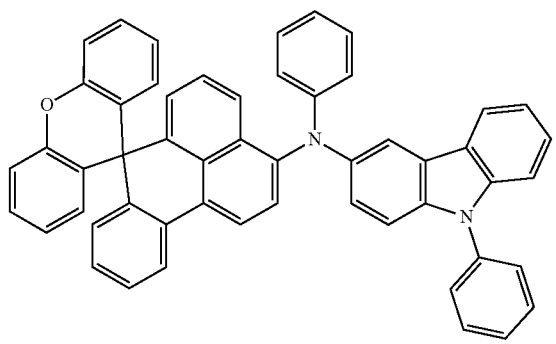
354
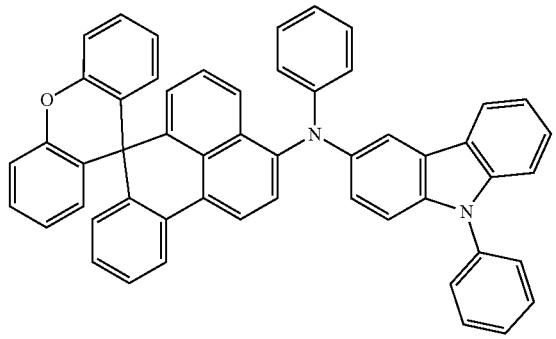
355
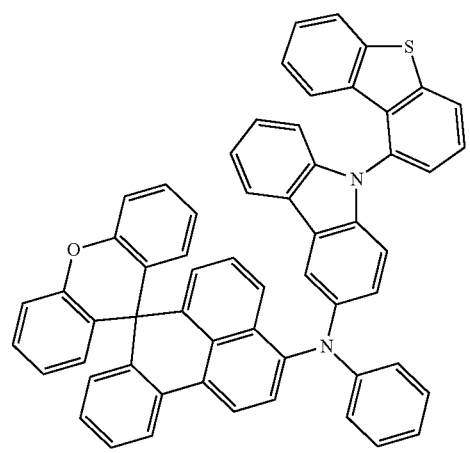
356
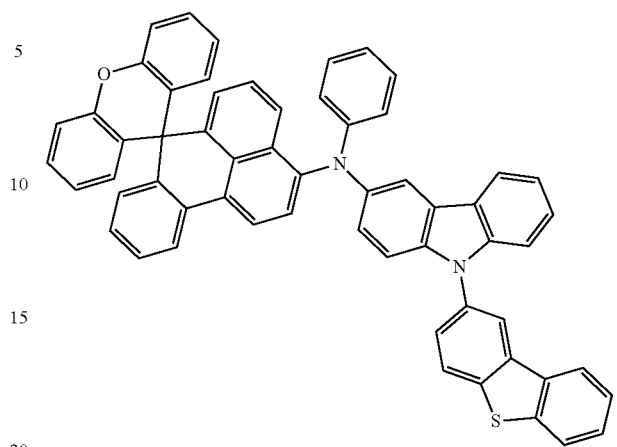
357
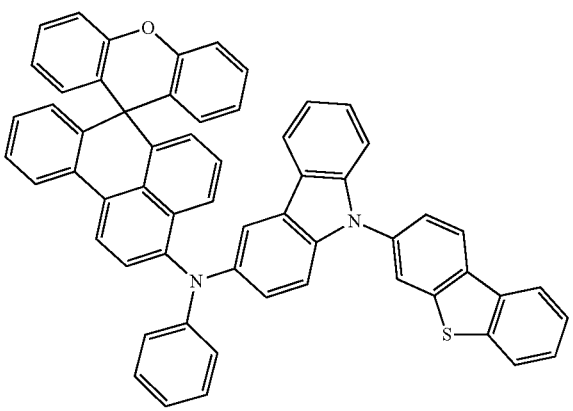
358
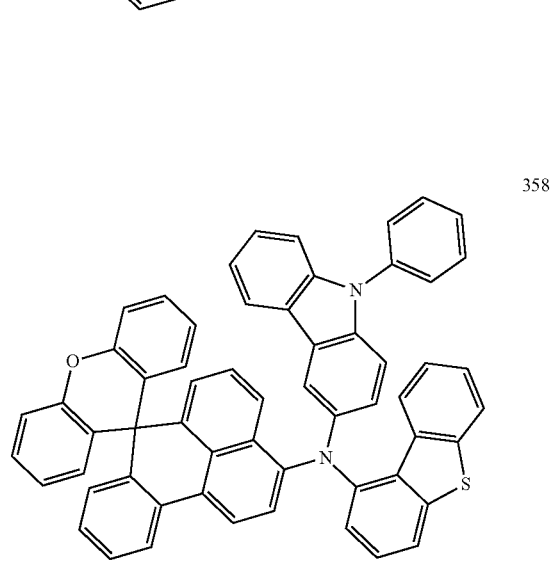

-continued
359
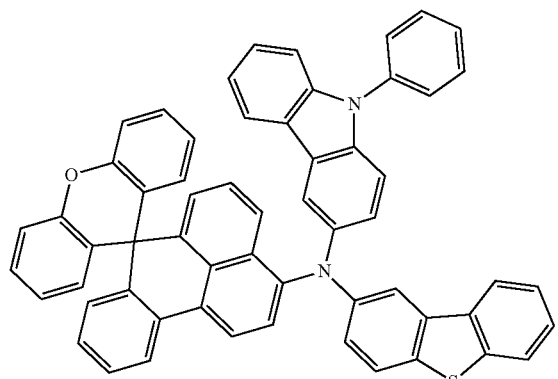
360
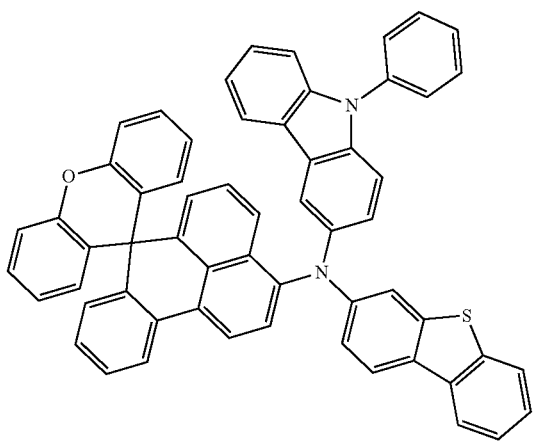
361
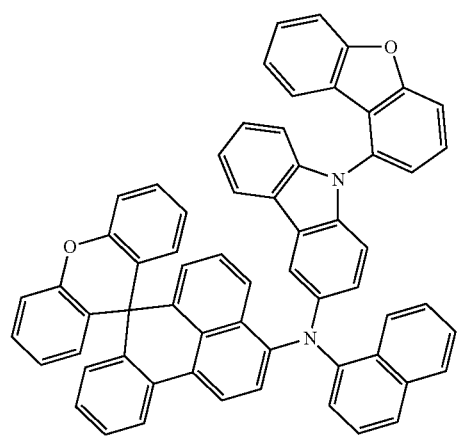
-continued
362
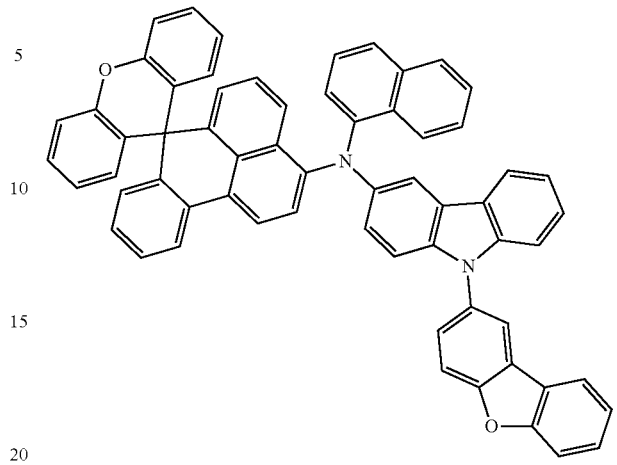
363
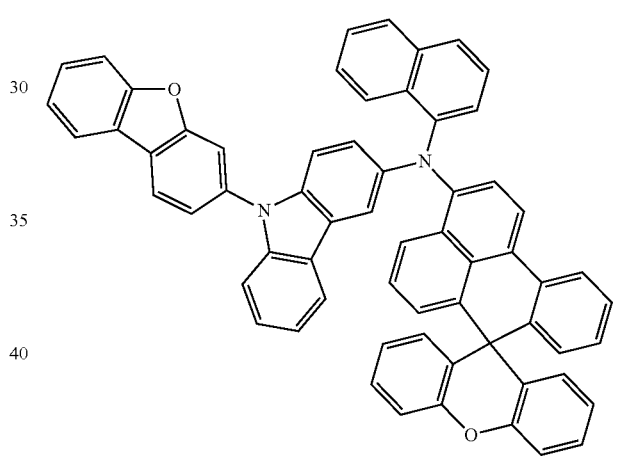
364
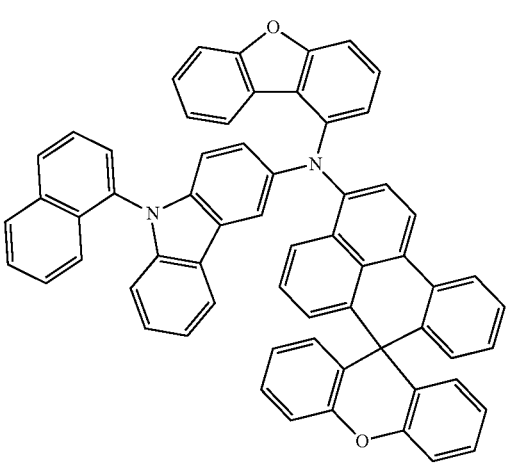

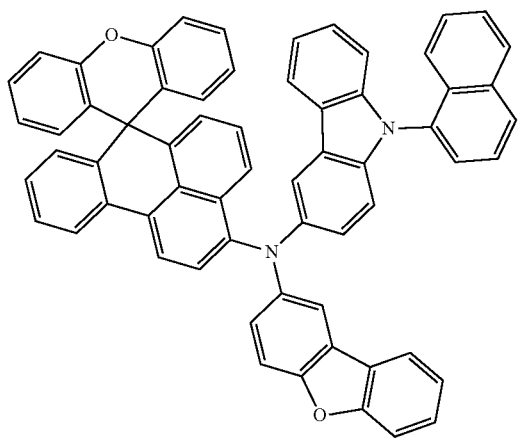
365
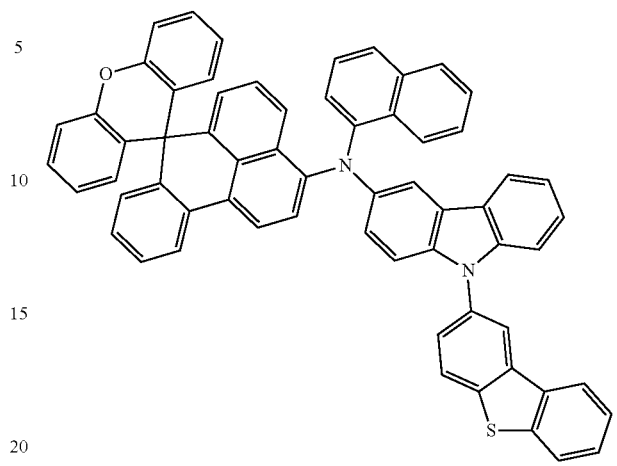
368
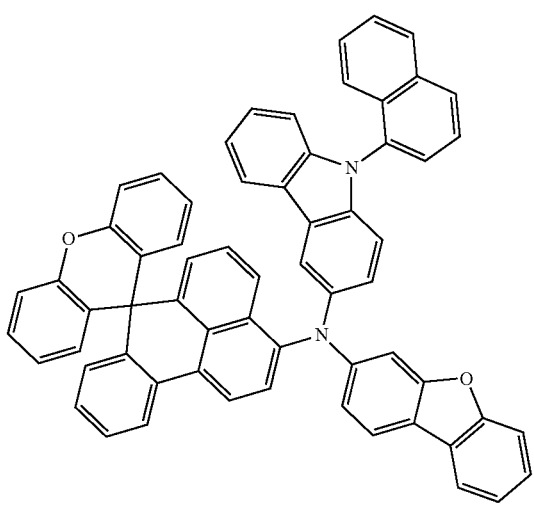
366
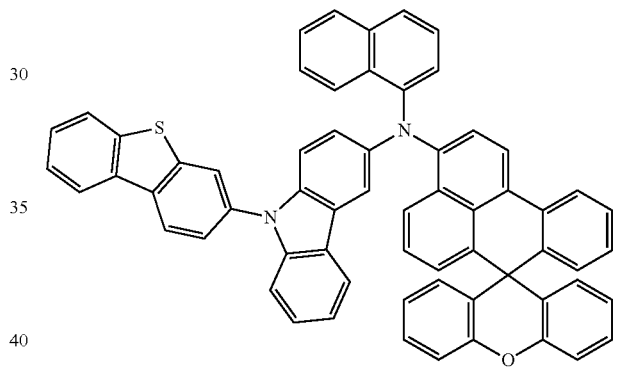
369
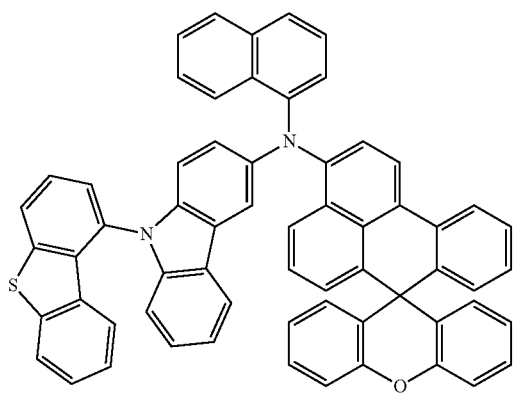
367
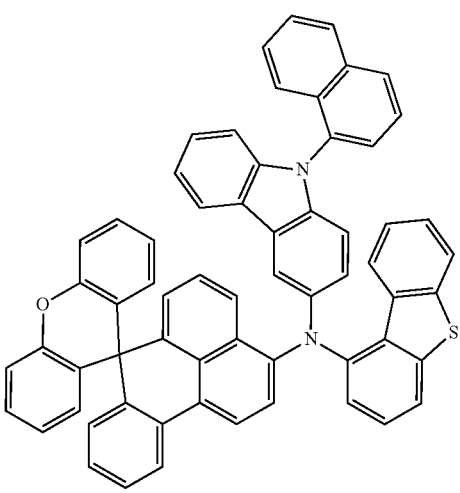
370

131
-continued
371
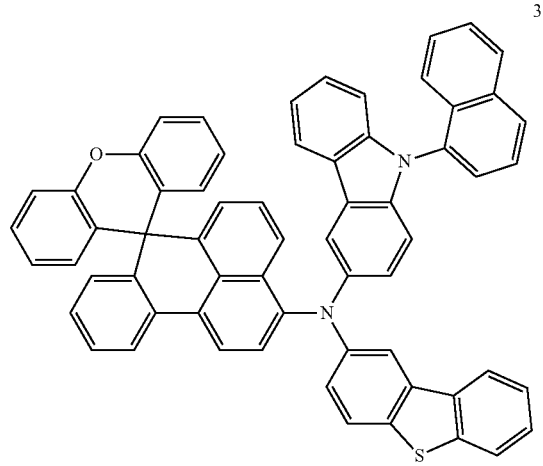
372
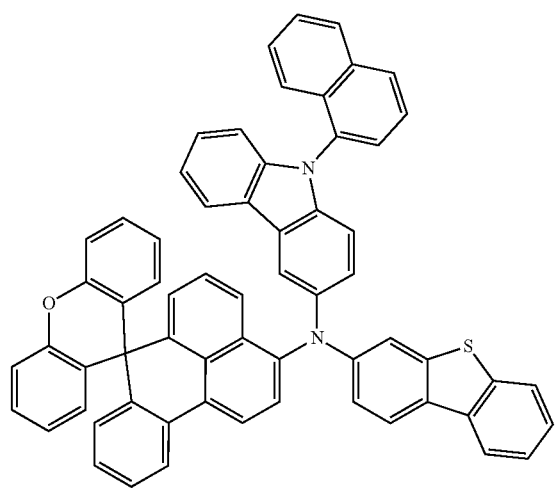
373
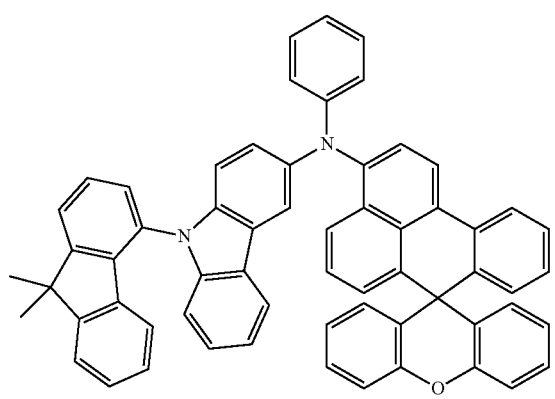
132
-continued
374
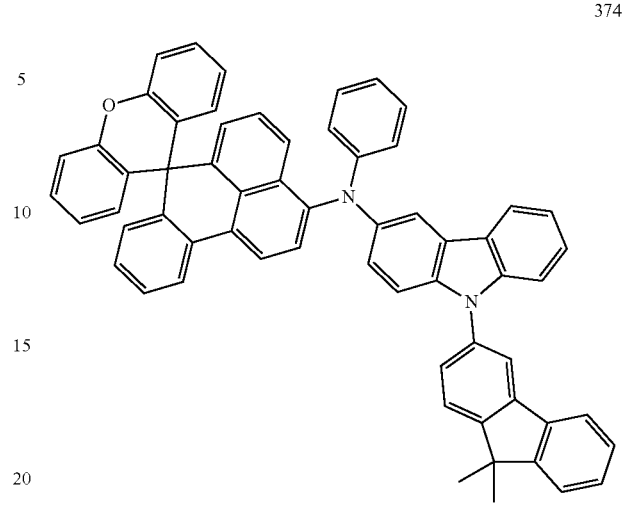
375
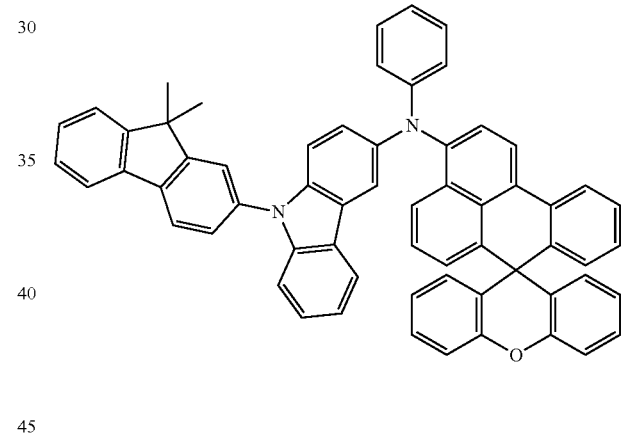
376
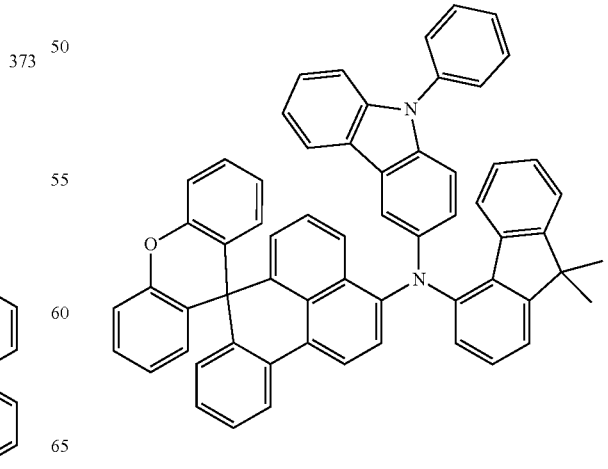

377
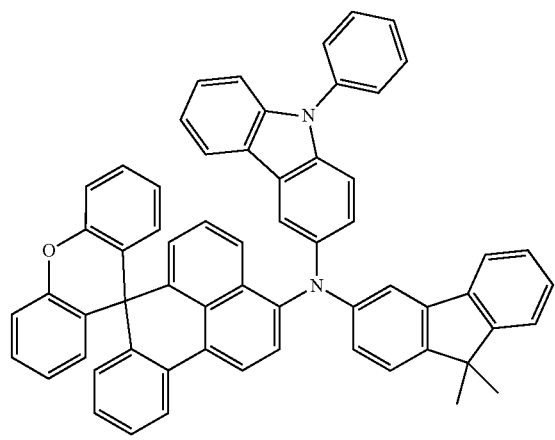
378
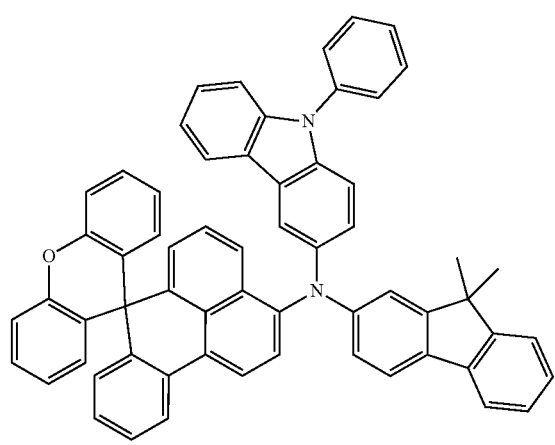
379
380
381
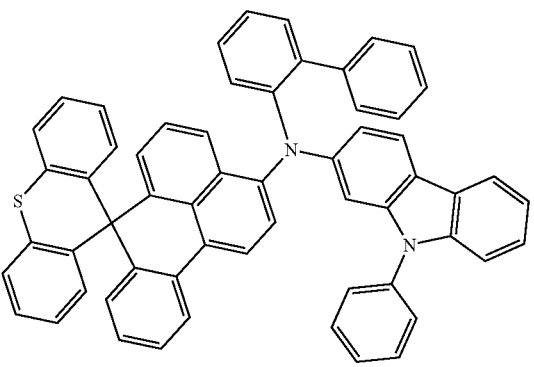
382
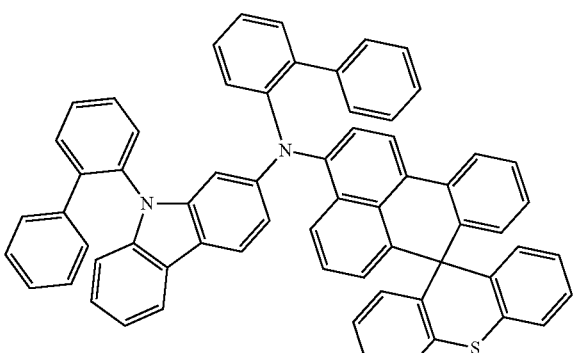
383
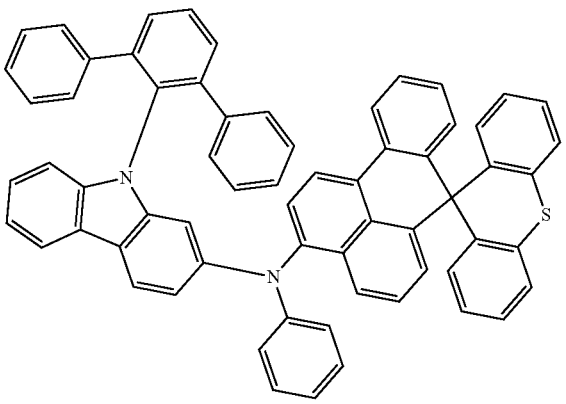
384
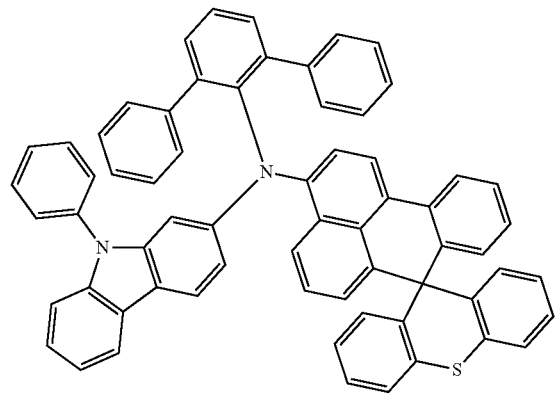

385
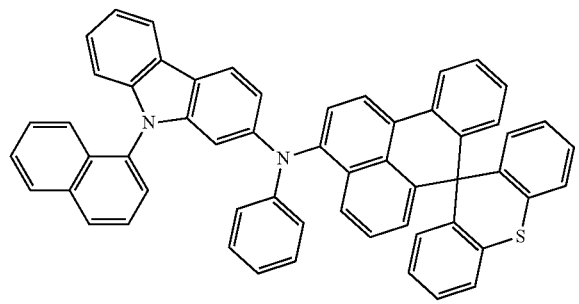
386
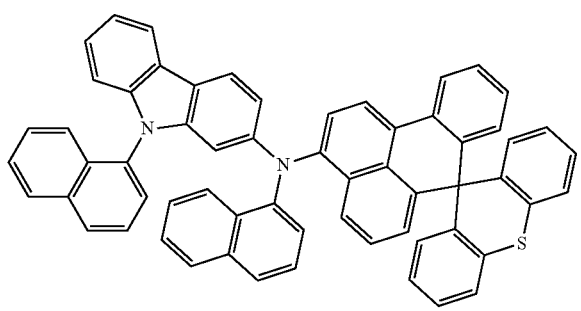
387
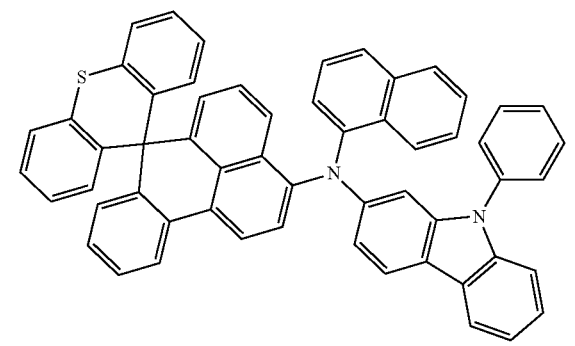
388
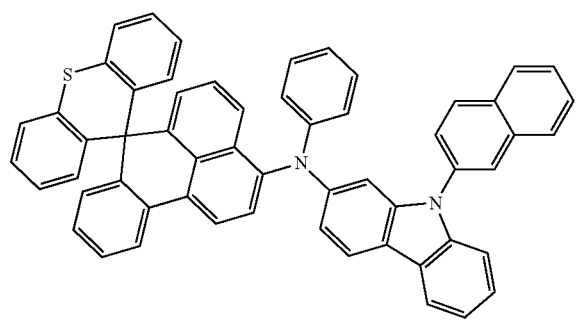
389
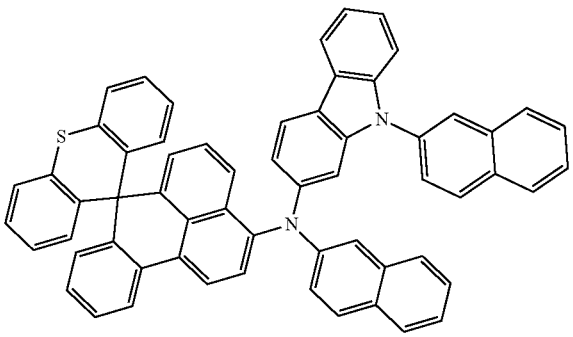
390
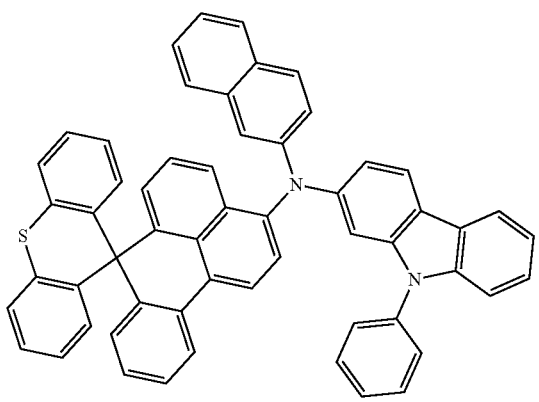
391
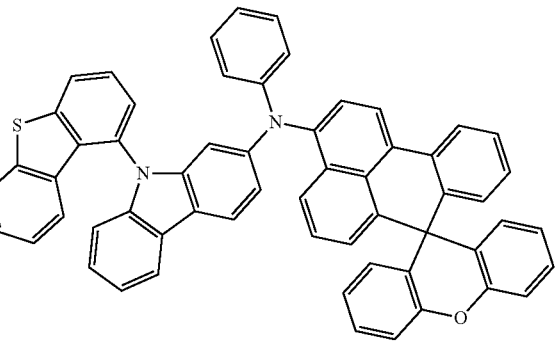
392
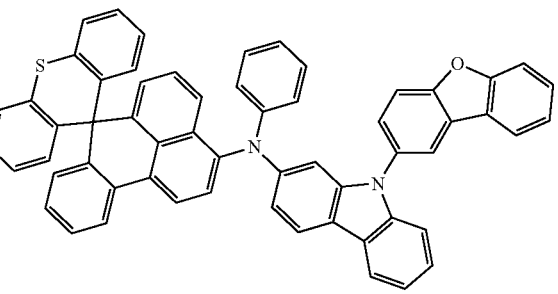

393
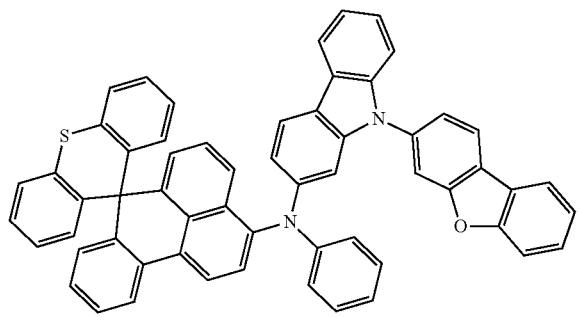
394
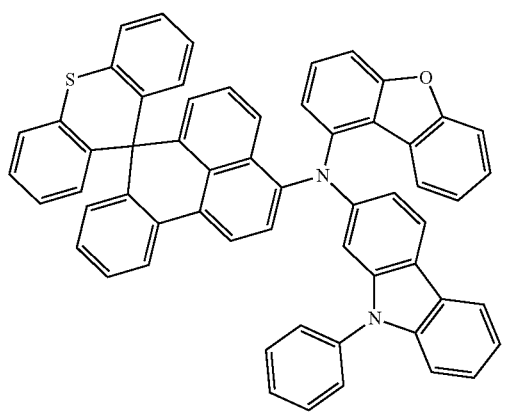
395
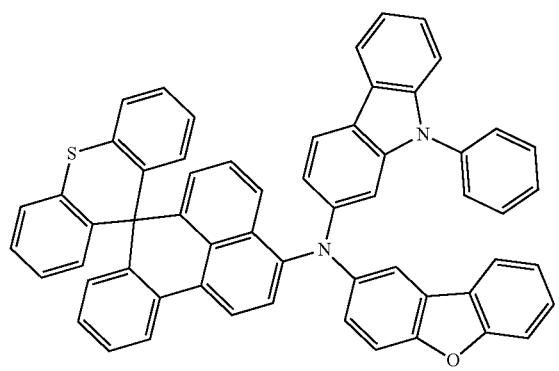
396
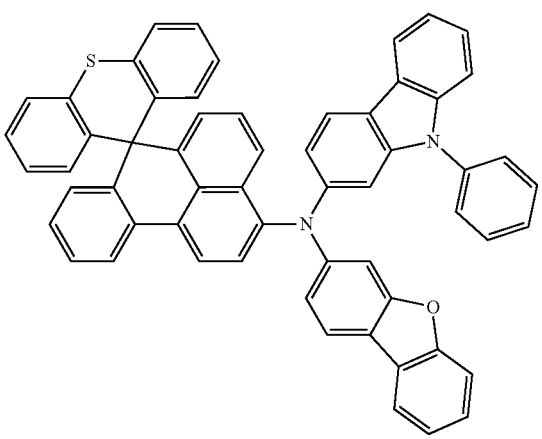
397
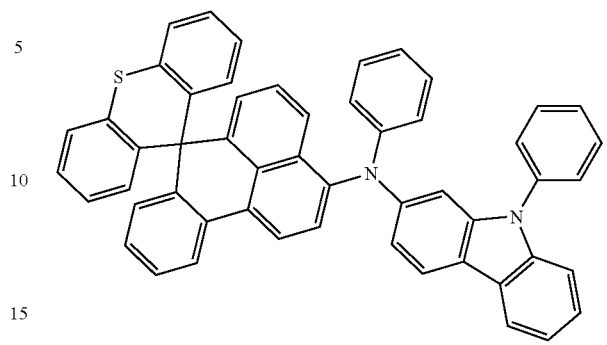
398
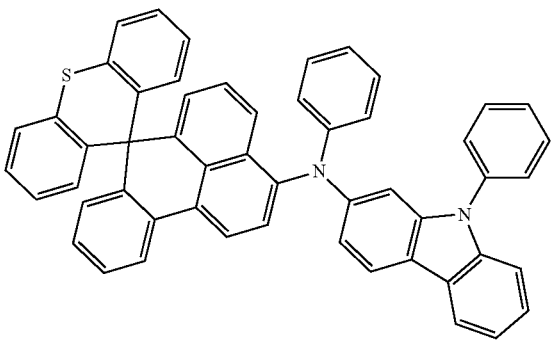
399
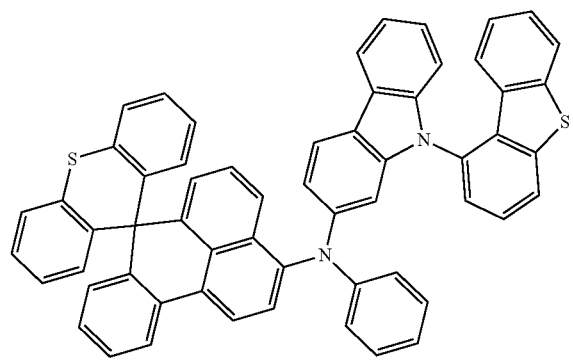
400
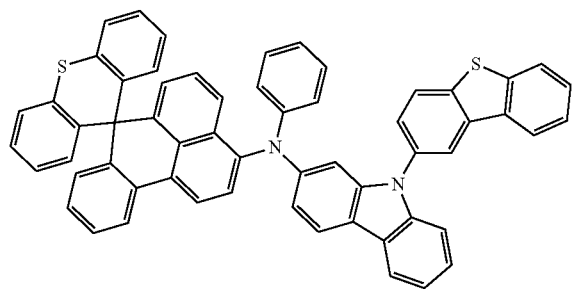

401
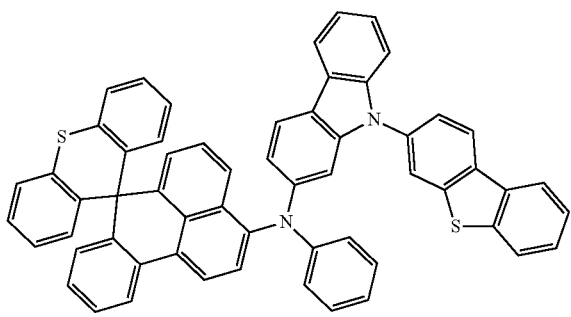
402
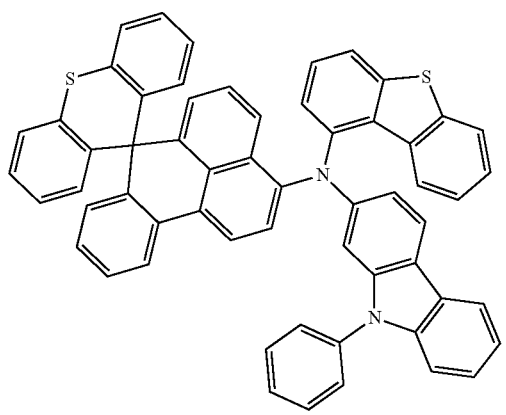
403
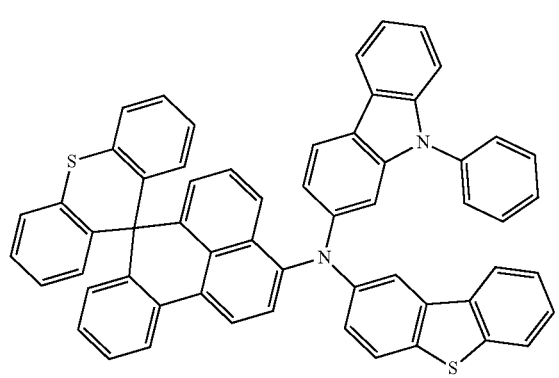
404
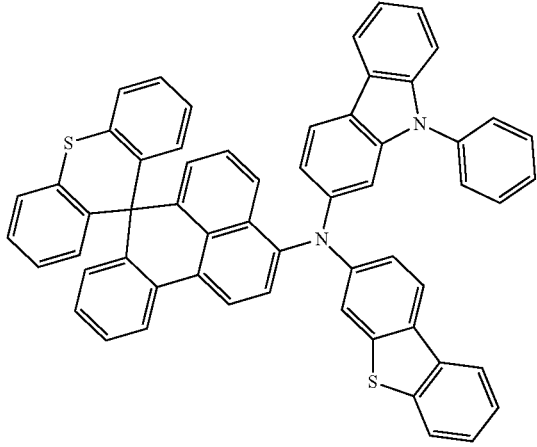
405
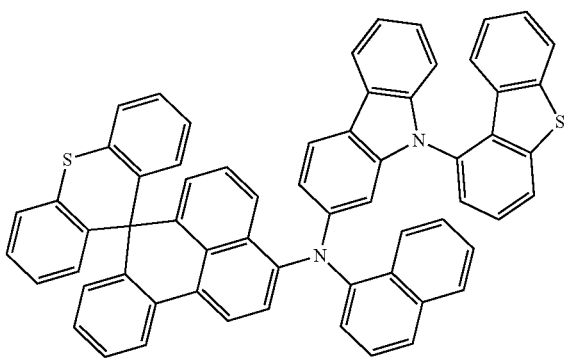
406
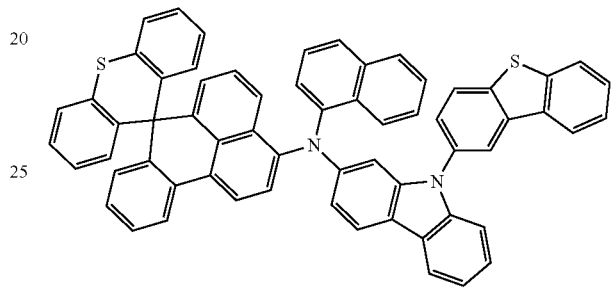
407
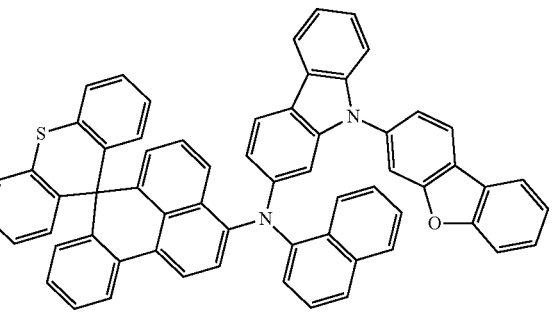
408
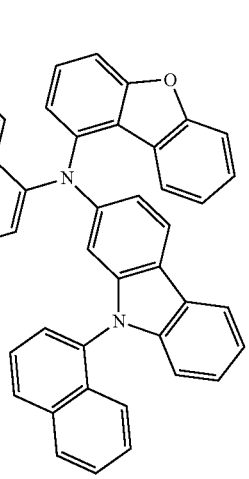

409
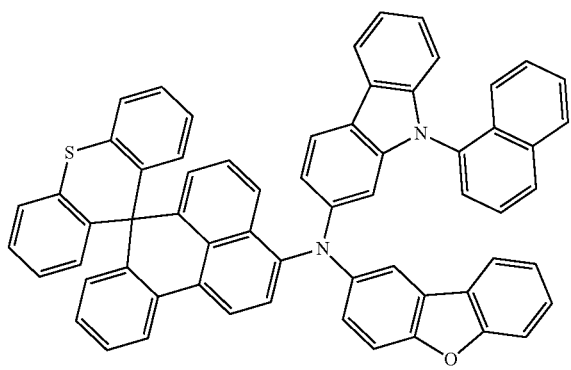
410
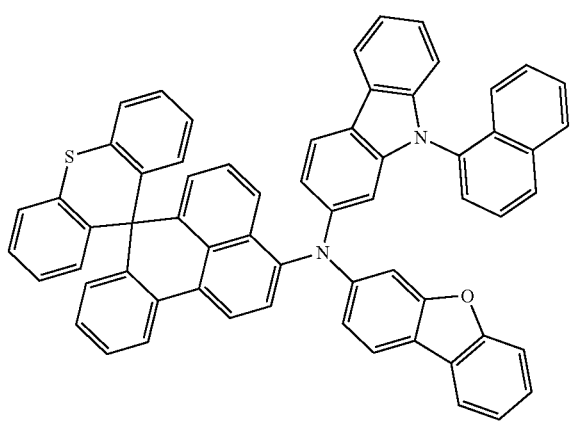
411
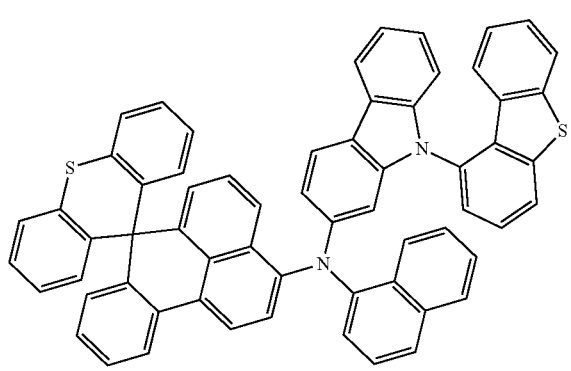
412
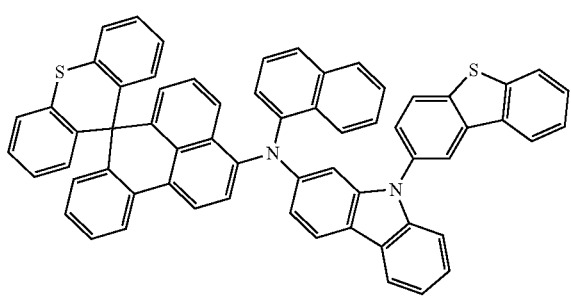
413
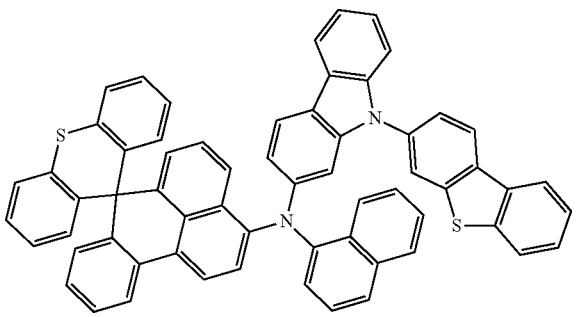
414
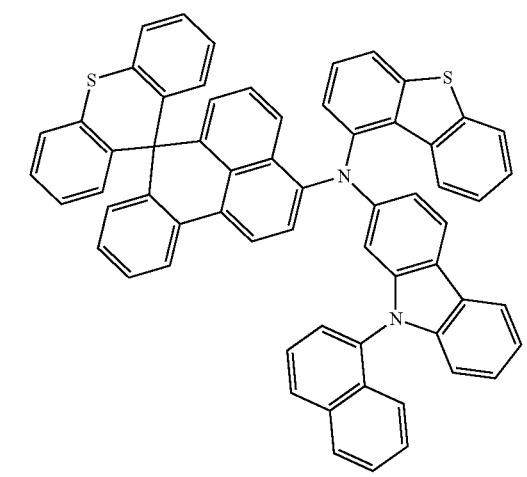
415
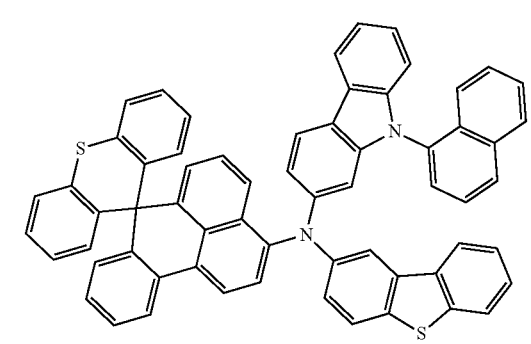
416
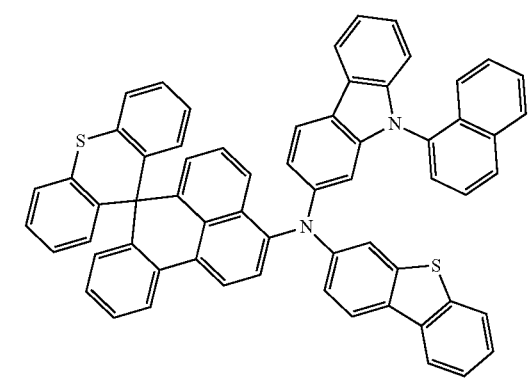

143
-continued
417
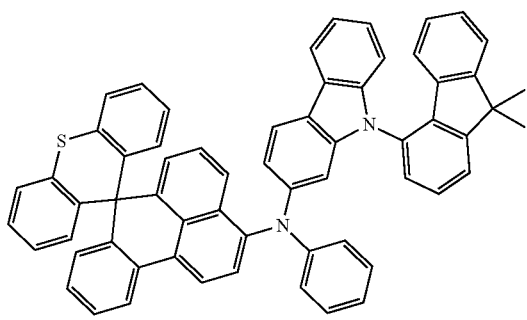
418
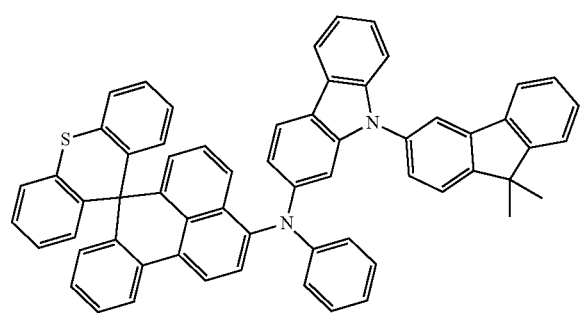
419
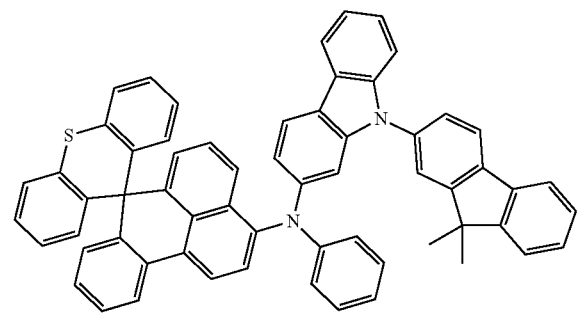
420
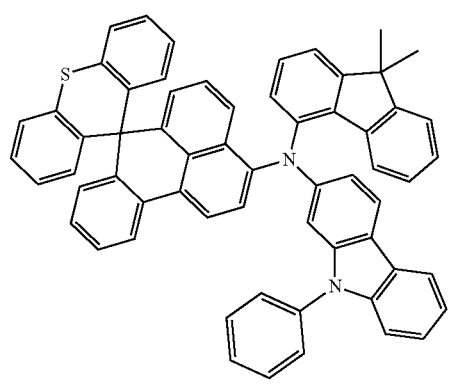
144
-continued
421
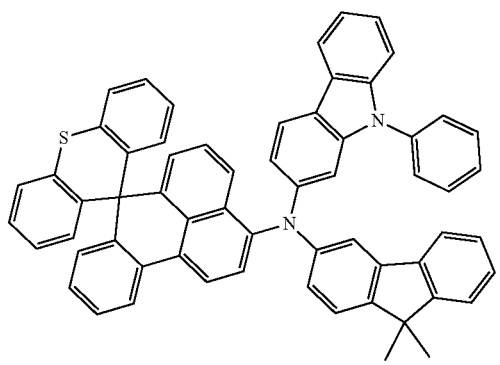
422
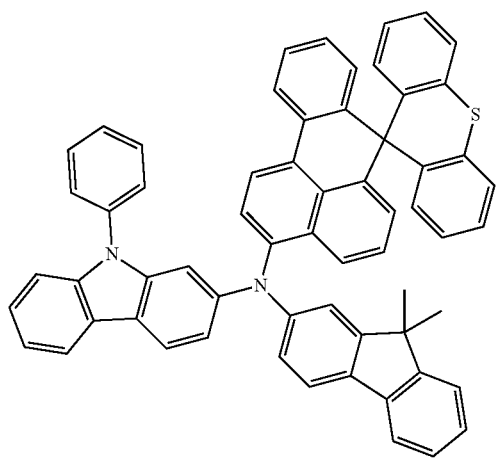
423
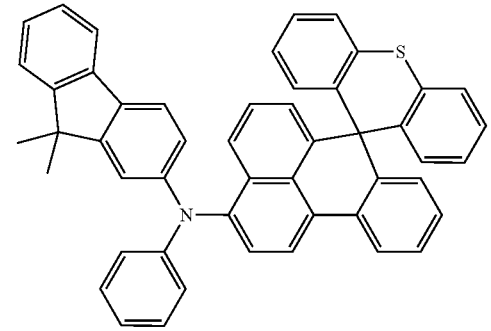
424
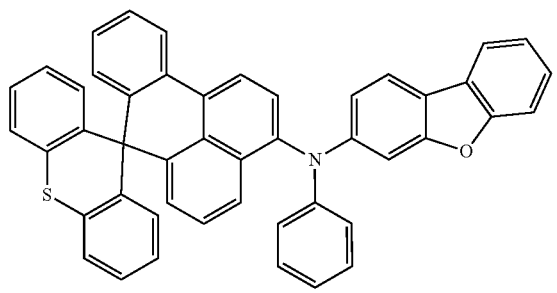

425
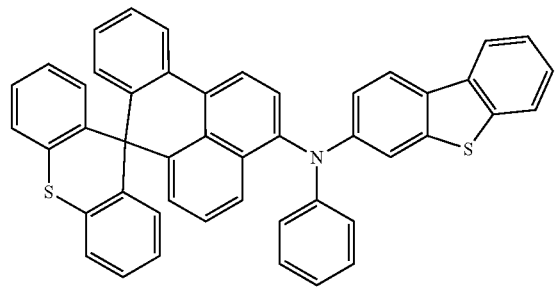
426
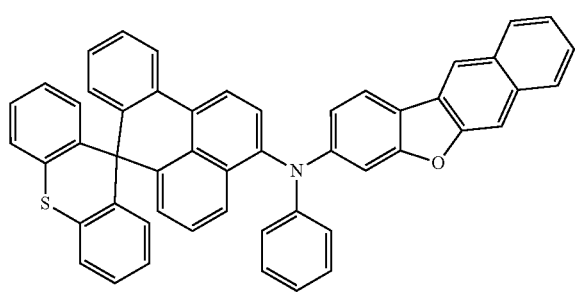
427
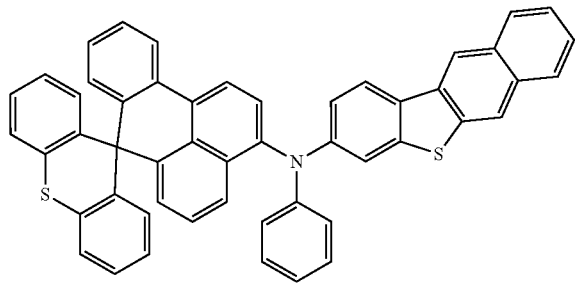
428
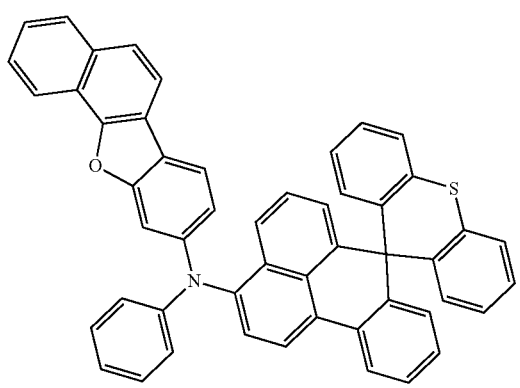
429
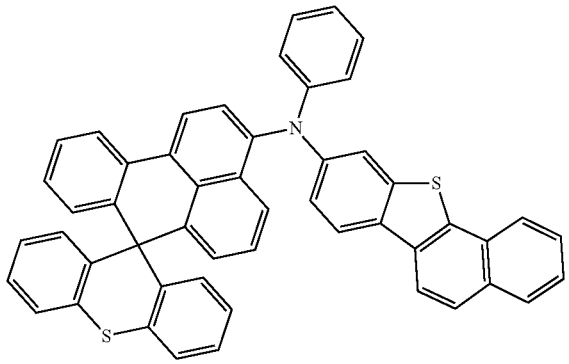
430
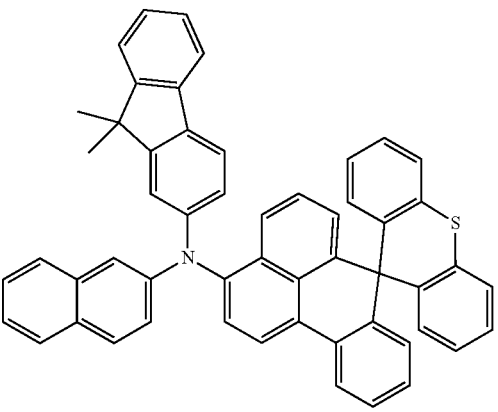
431
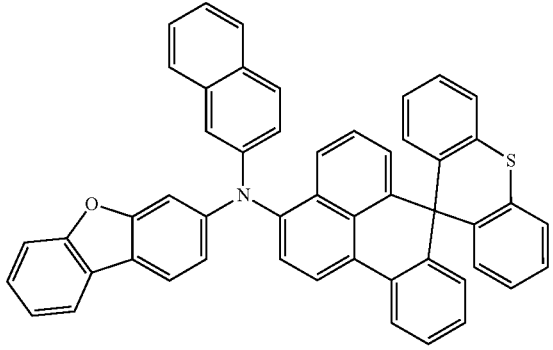
432
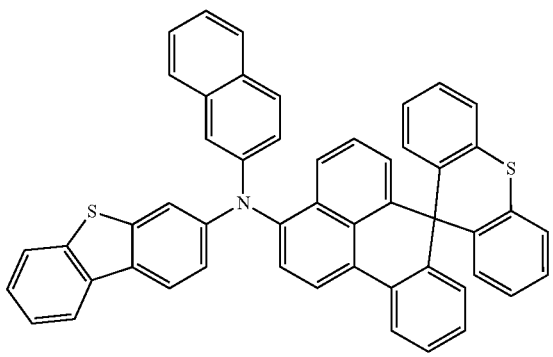

433
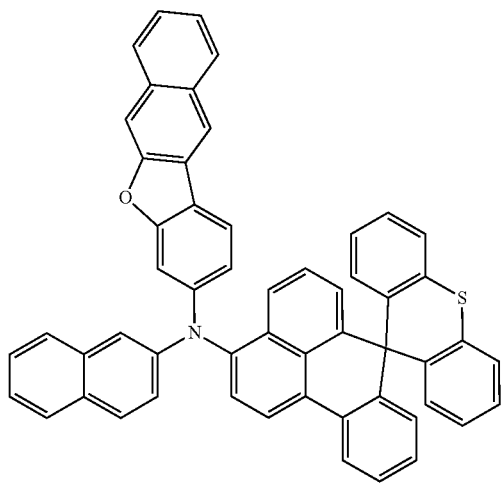
434
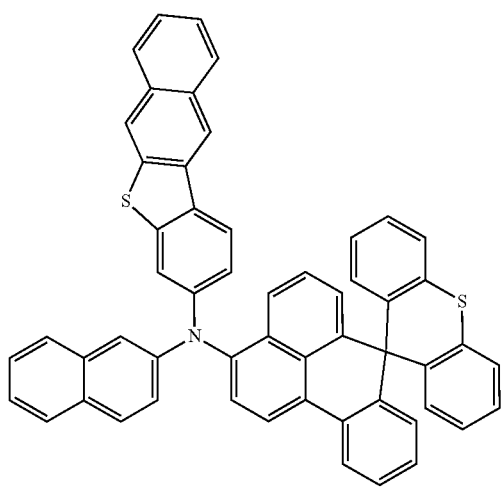
435
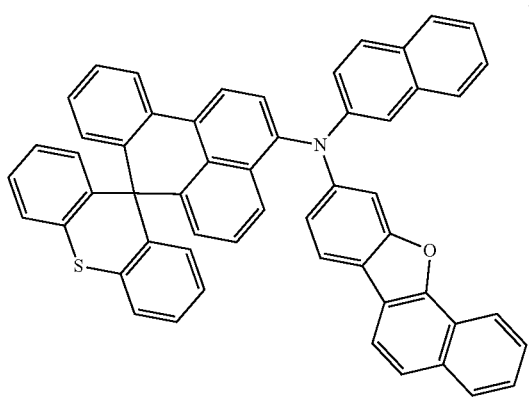
436
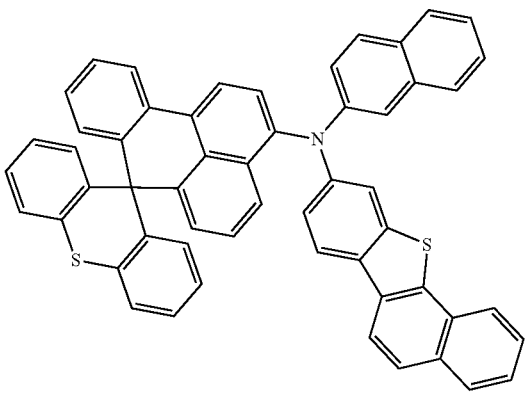
437
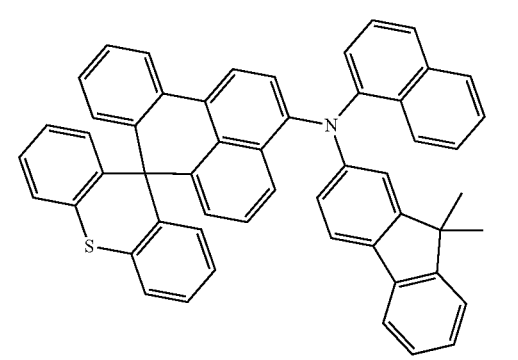
438
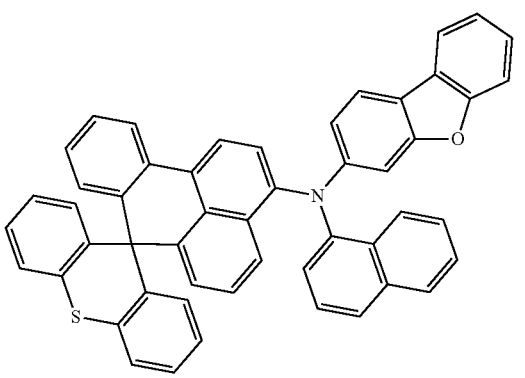
439
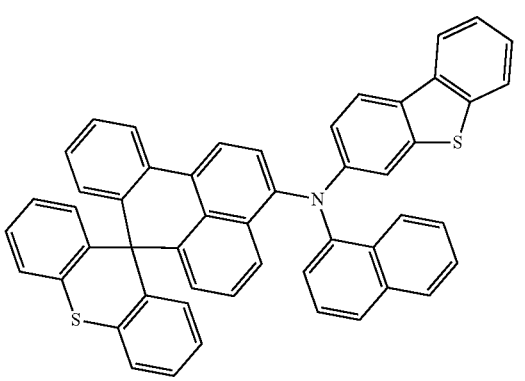

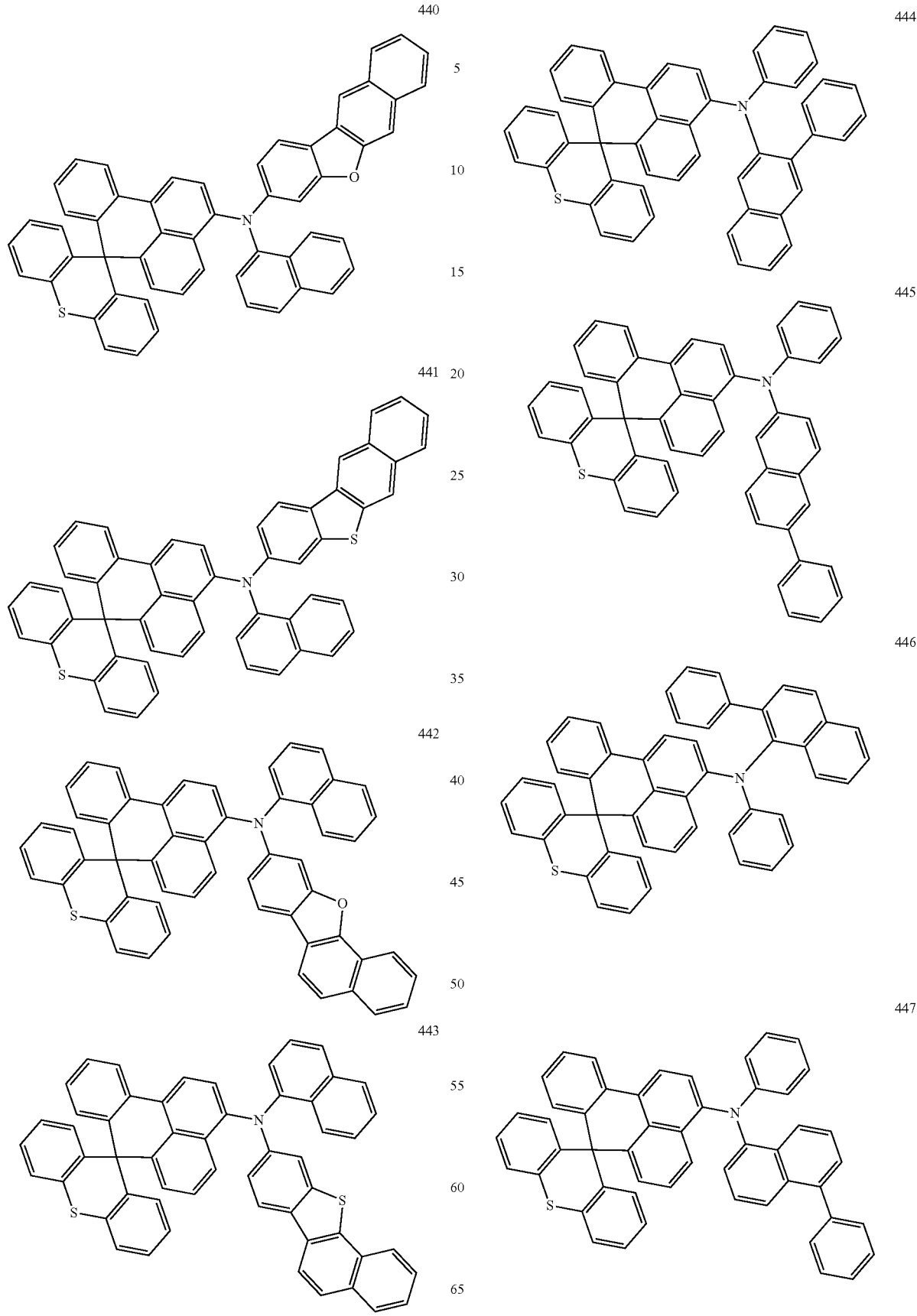

151
-continued
448
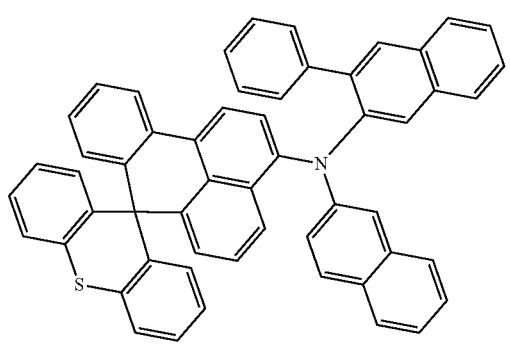
449
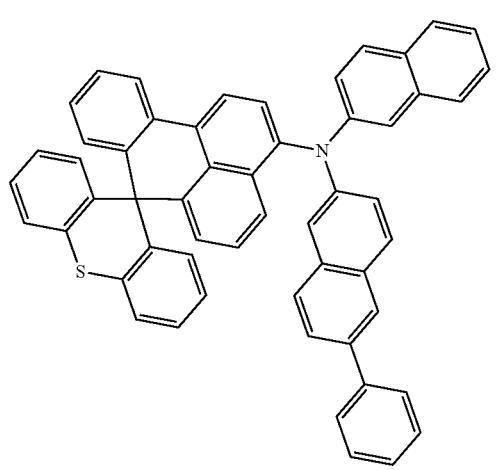
450
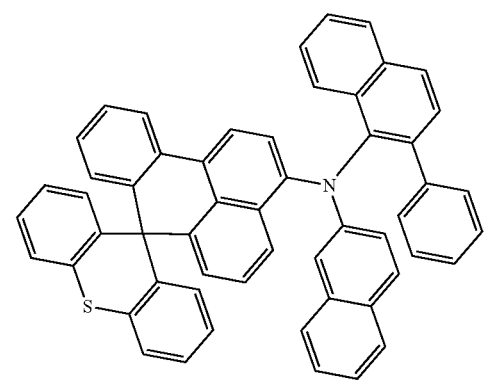
451
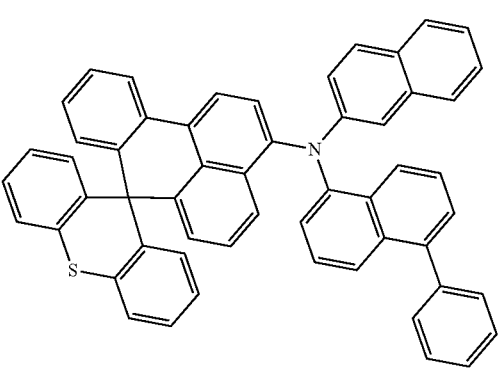
152
-continued
452
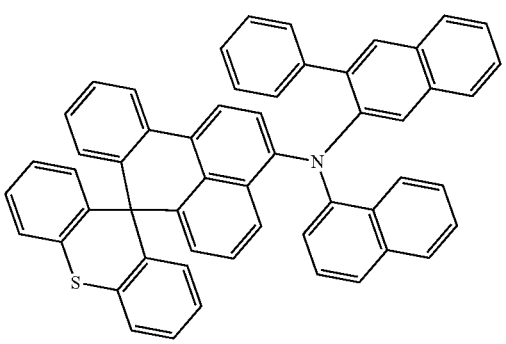
453
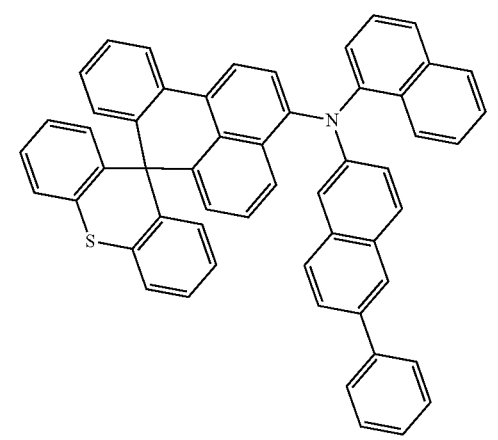
454
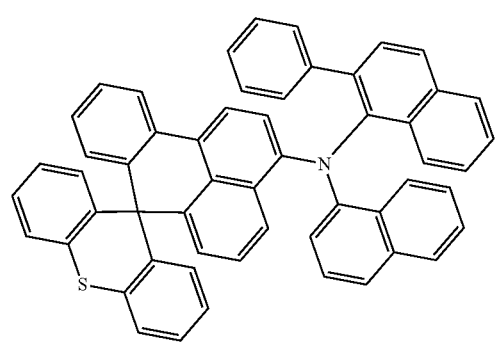
455
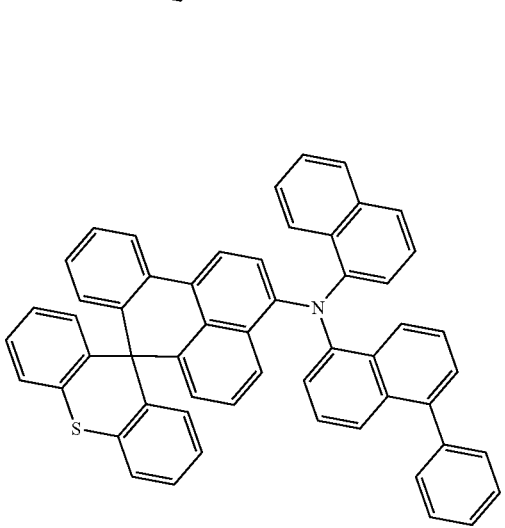

456
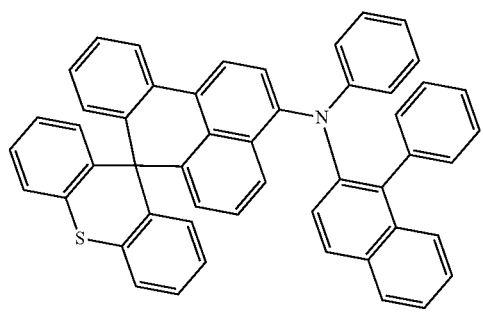
457
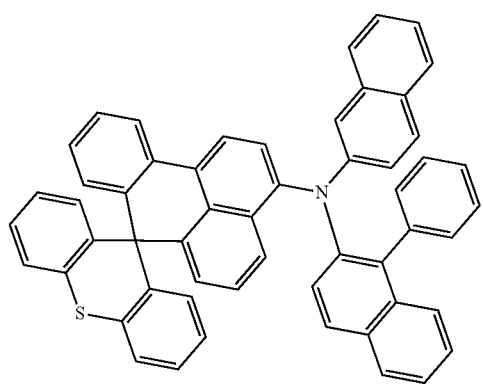
458
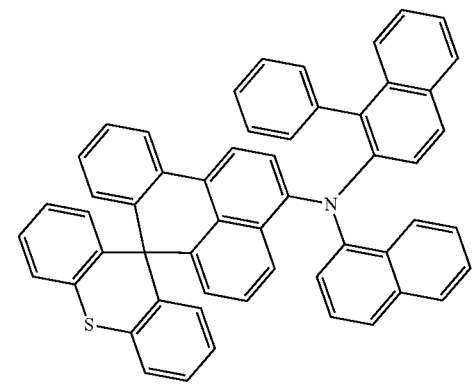
459
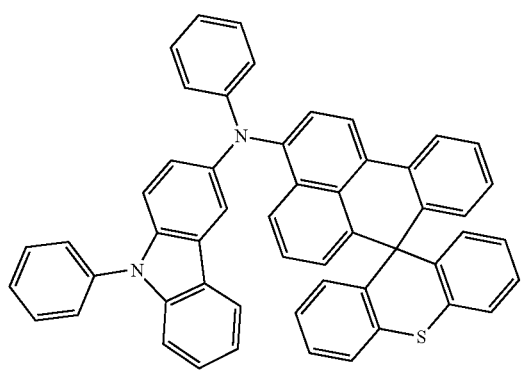
460
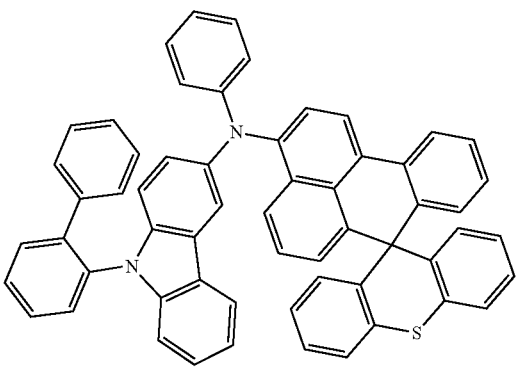
461
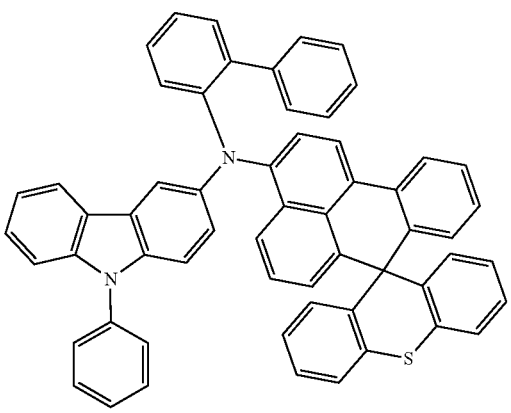
462
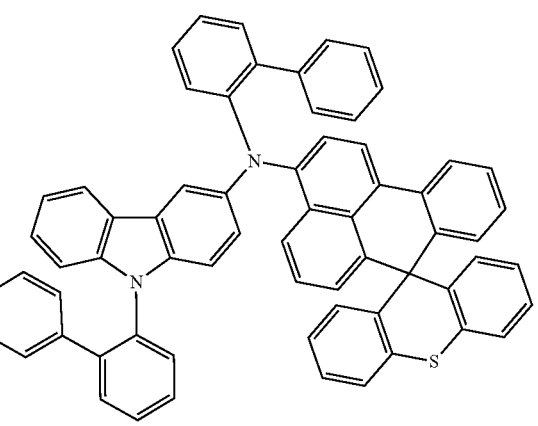

463
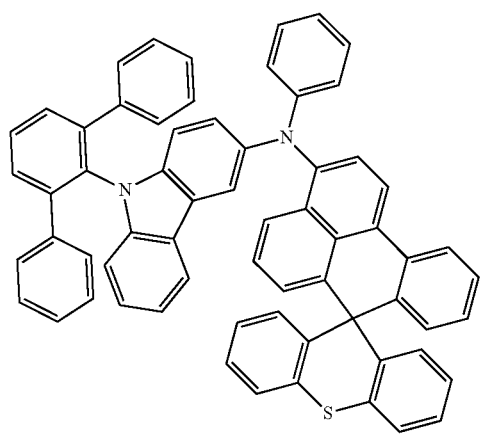
464
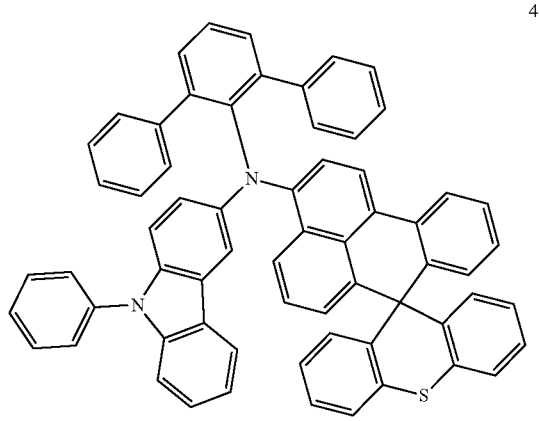
465
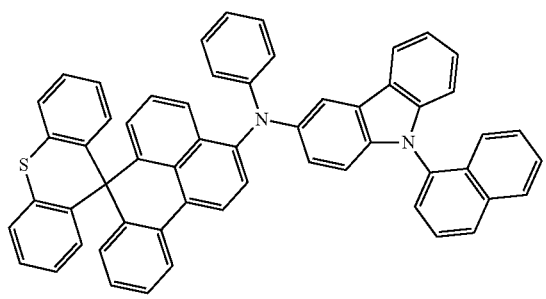
466
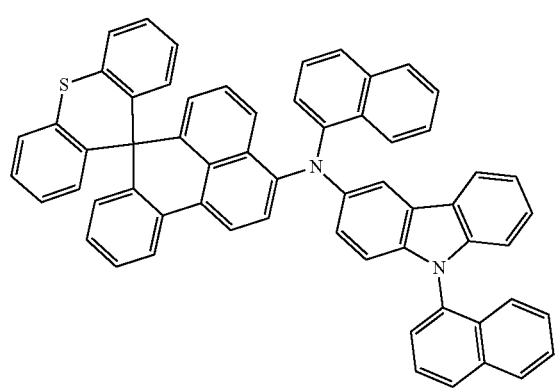
467
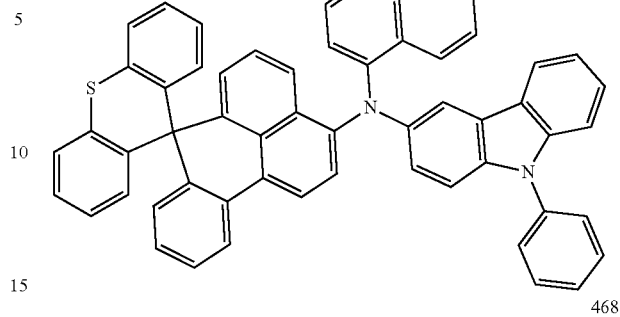
468
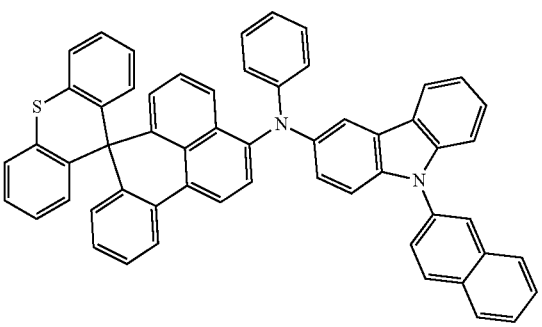
469
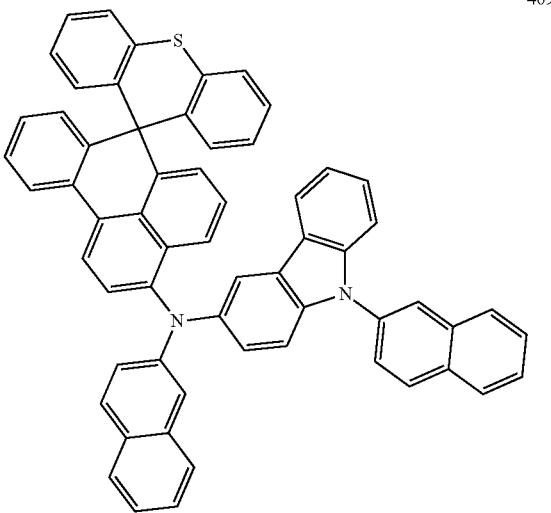
470
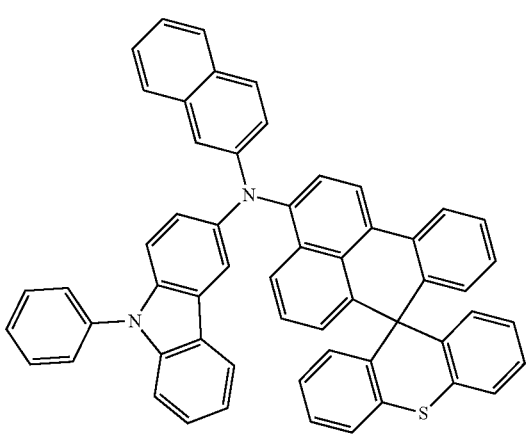

471
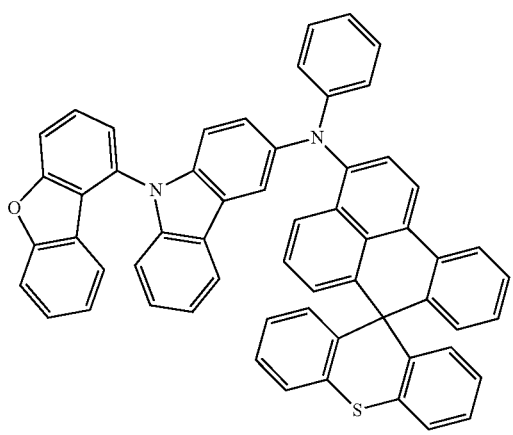
472
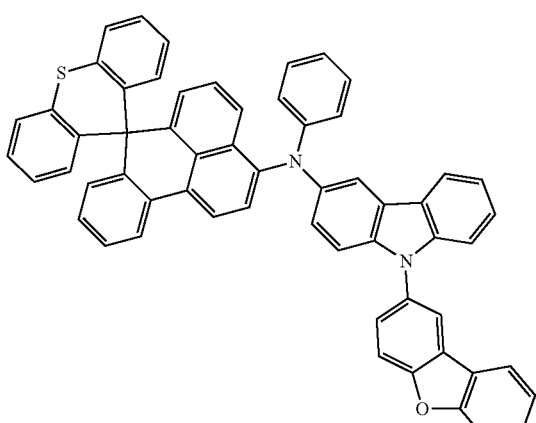
473
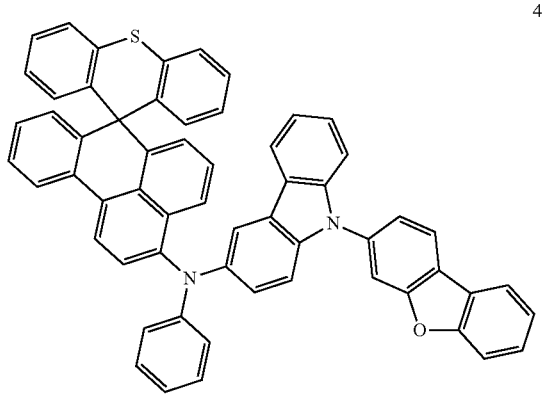
474
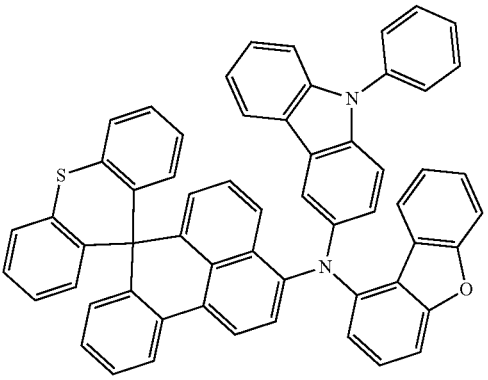
475
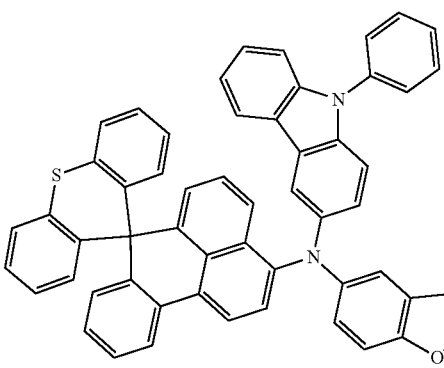
476
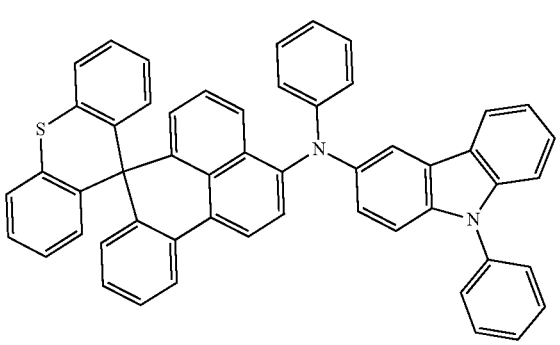
477

478
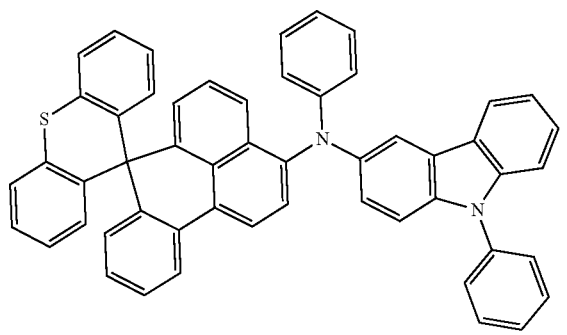
479
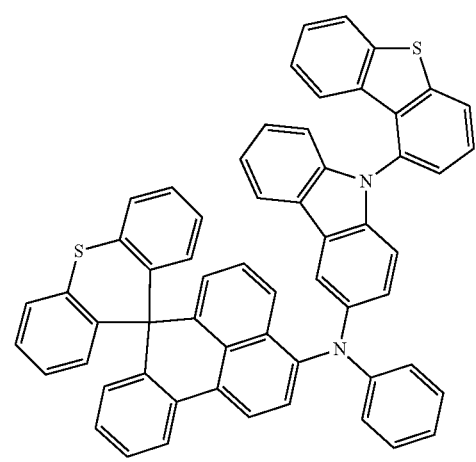
480
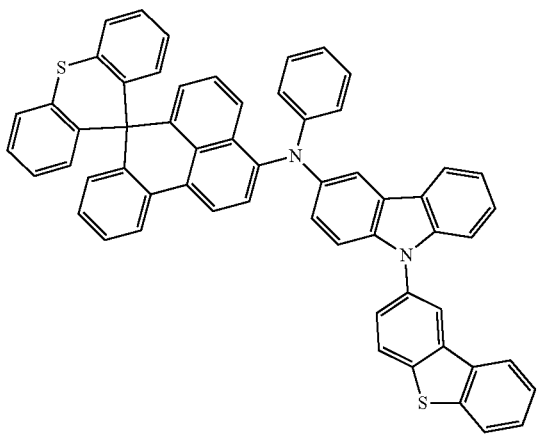
481
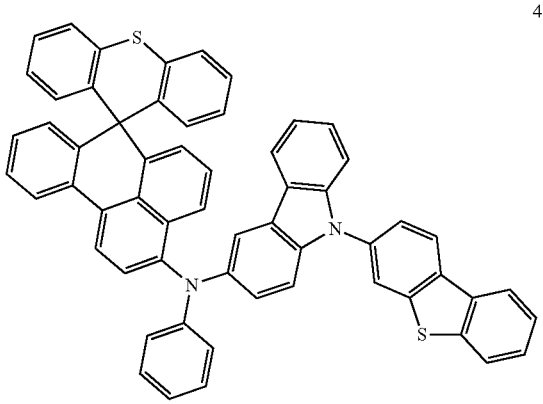
482
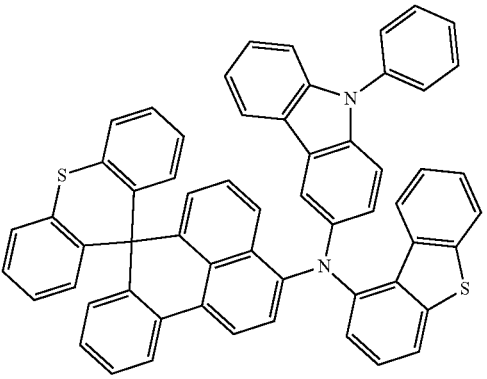
483
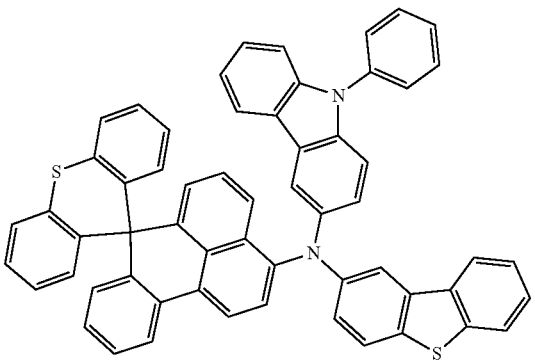
484
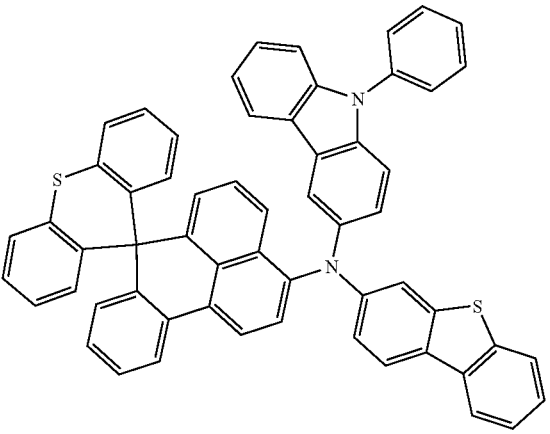

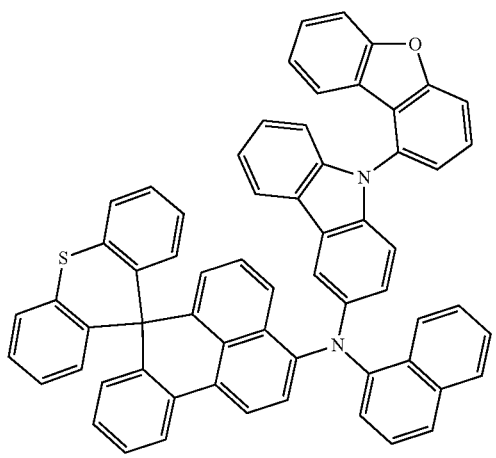
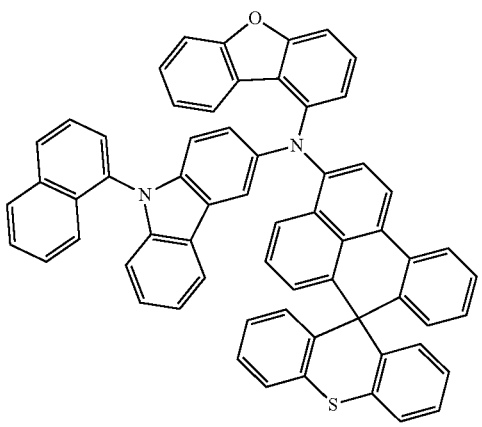

491
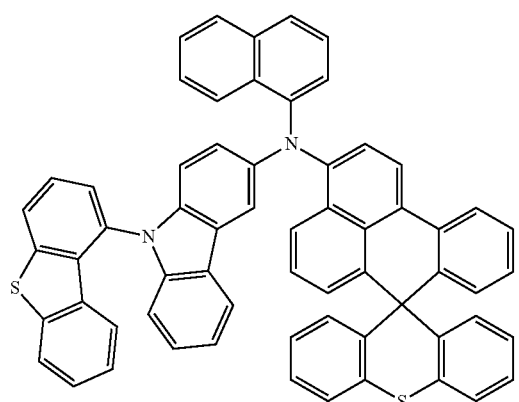
492
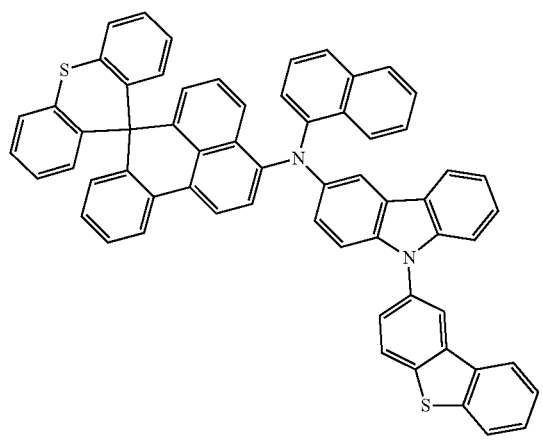
493
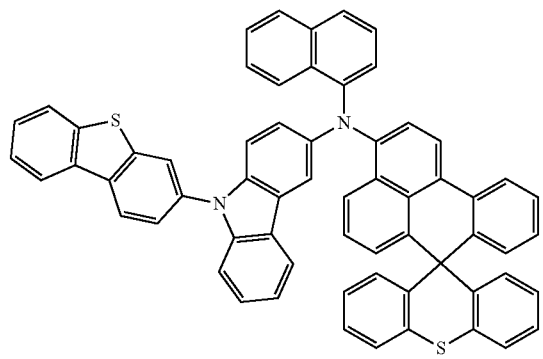
494
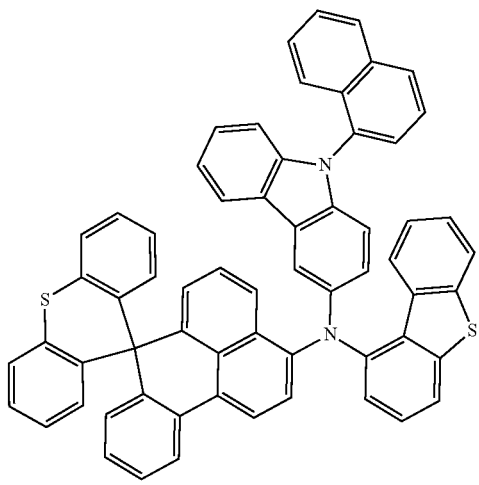
495
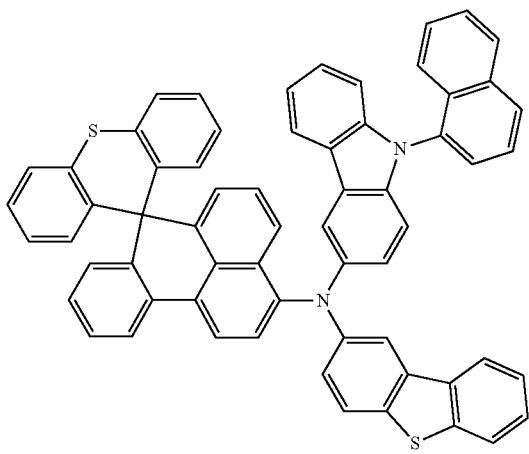
496
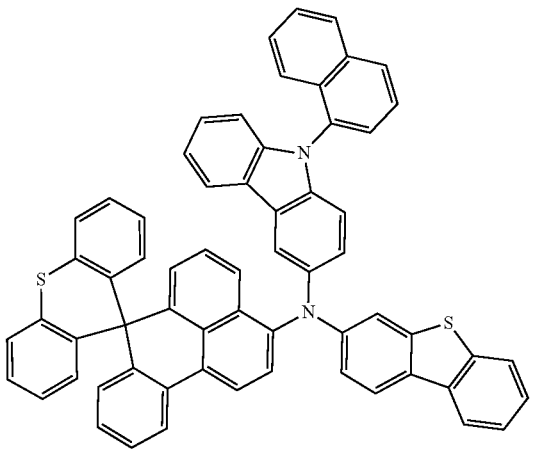

-continued
497
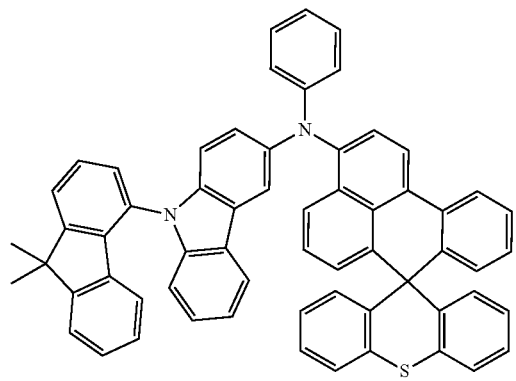
498
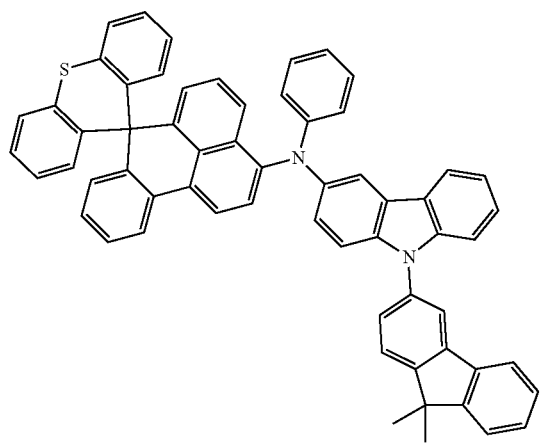
499
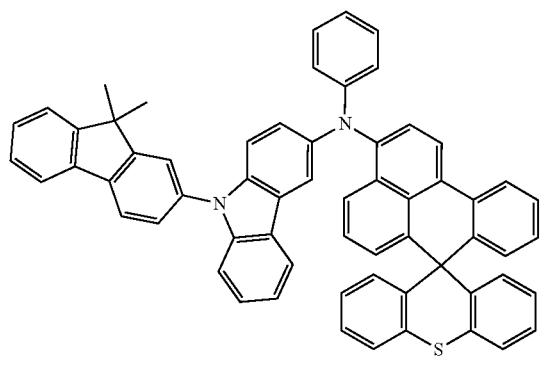
500
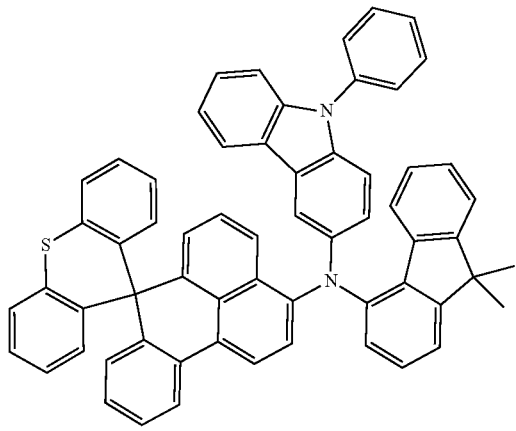
-continued
501
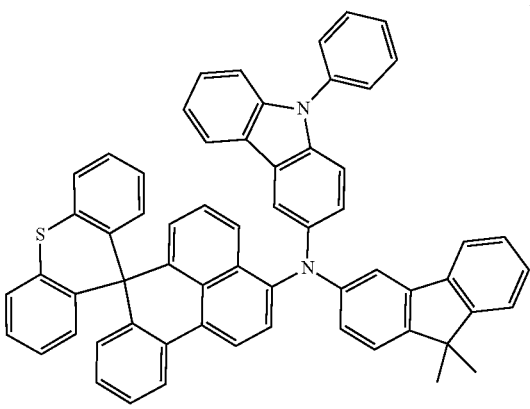
502
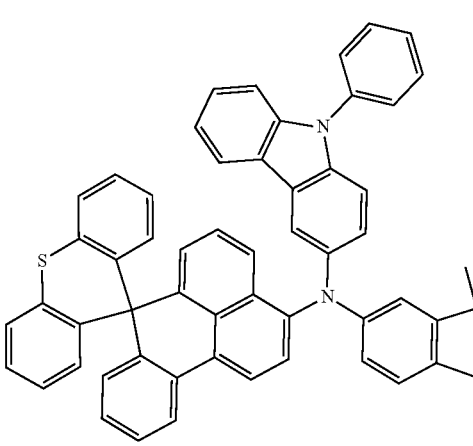
503
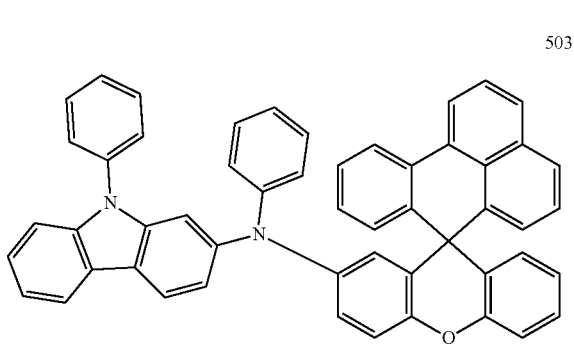
504
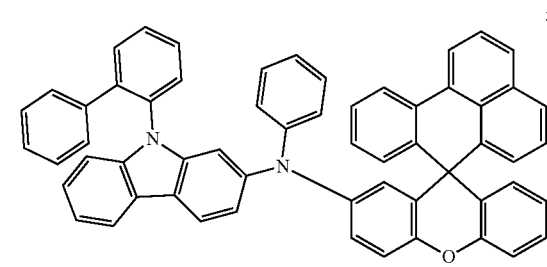

-continued
505
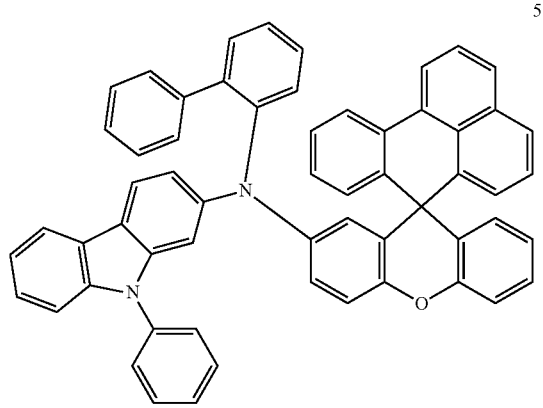
506
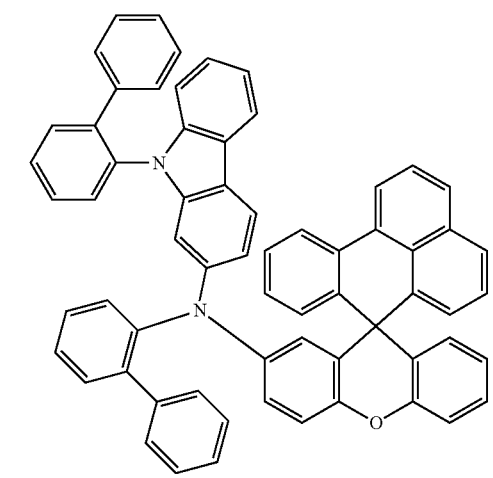
507
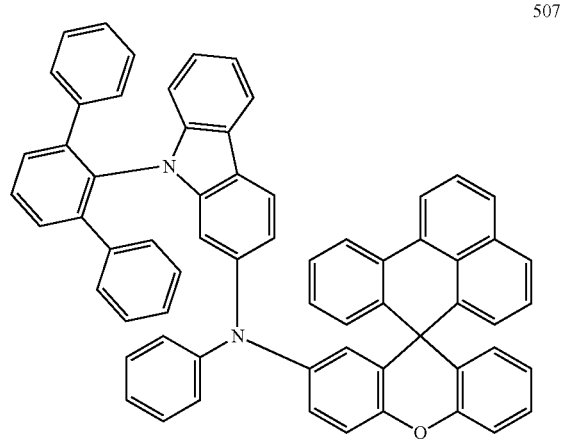
-continued
508
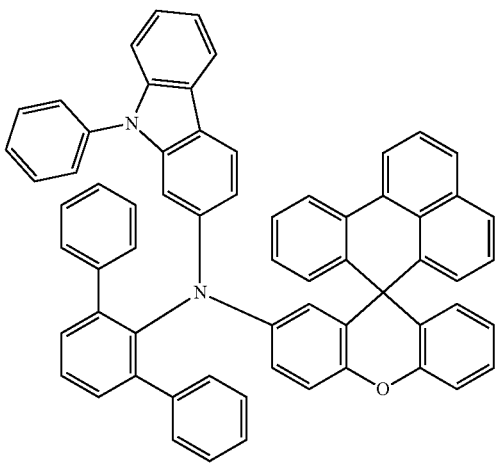
509
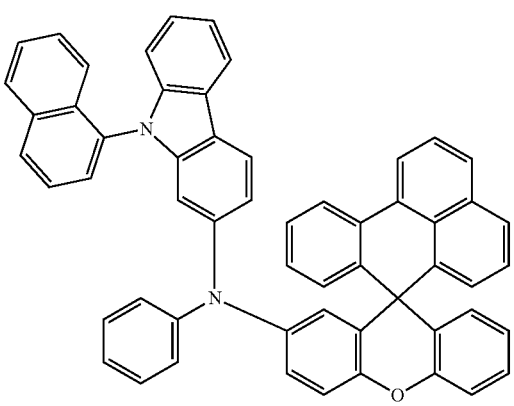
510
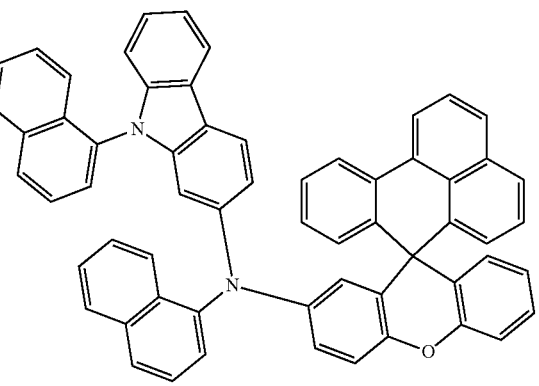
511
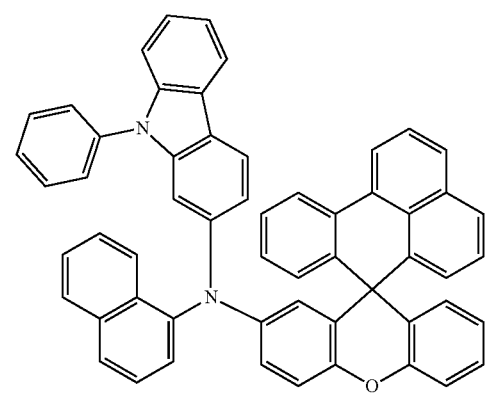

512
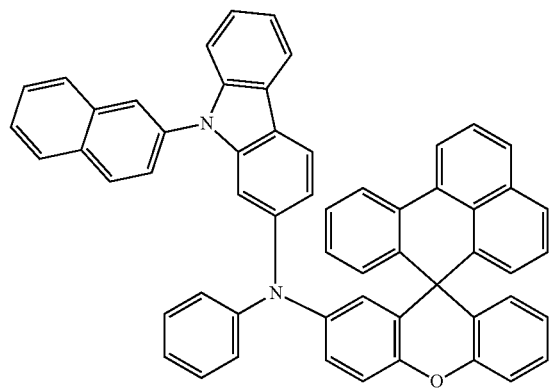
513
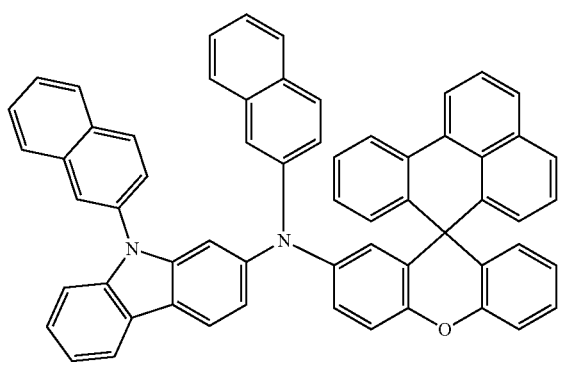
514
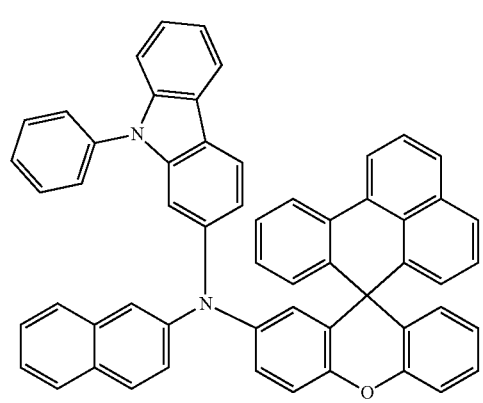
515
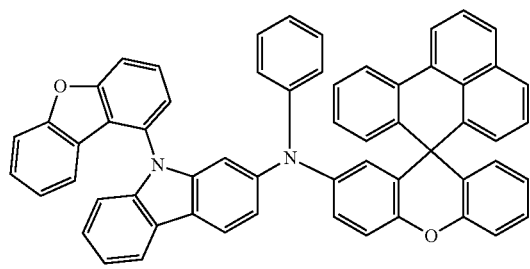
516
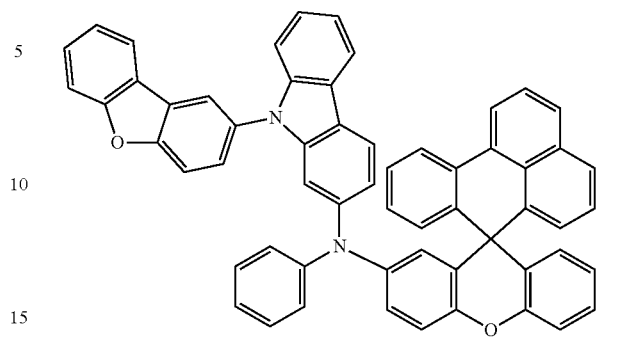
517
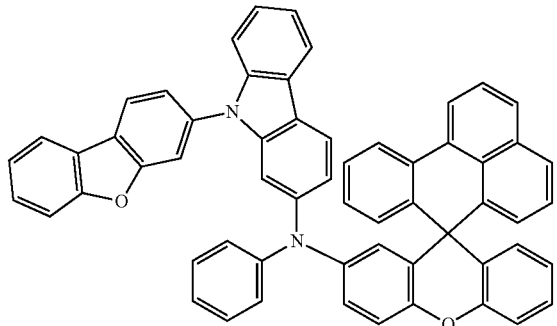
518
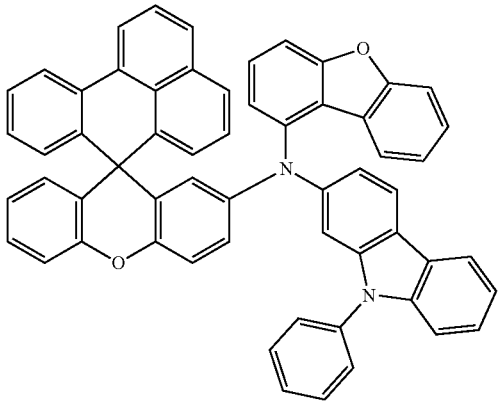
519
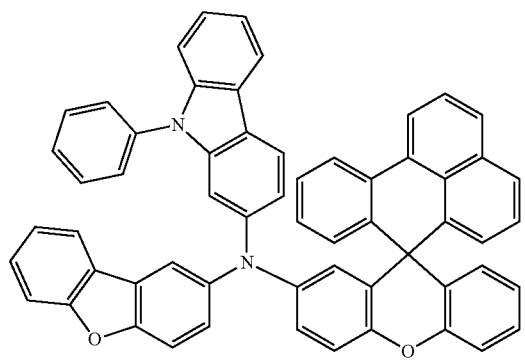

520
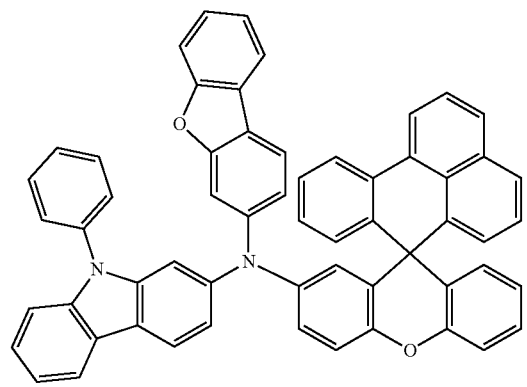
521
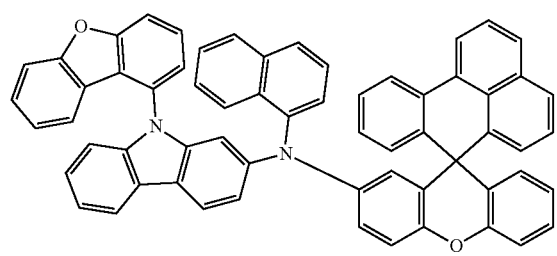
522
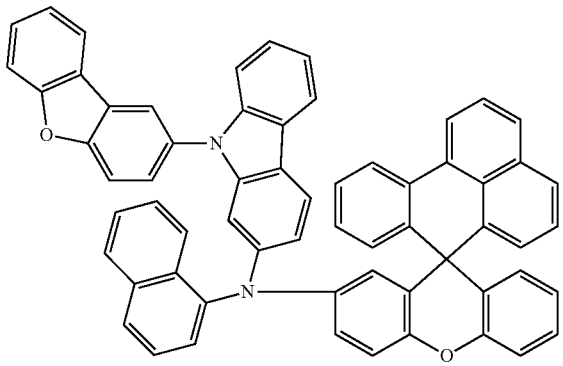
523
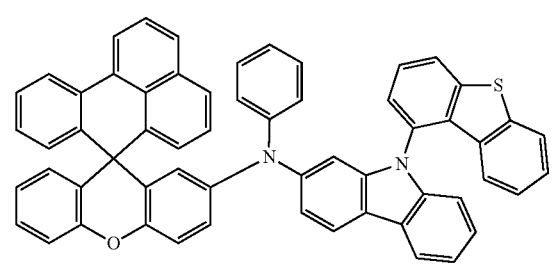
524
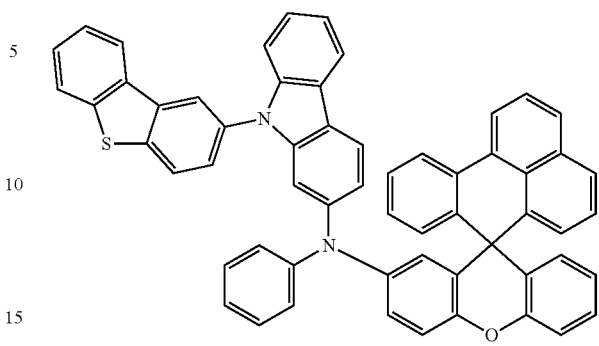
525
526
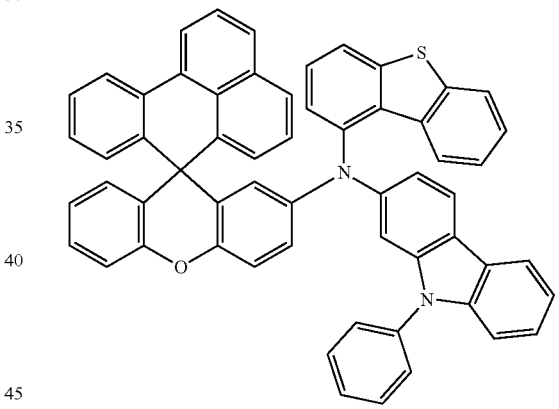
527
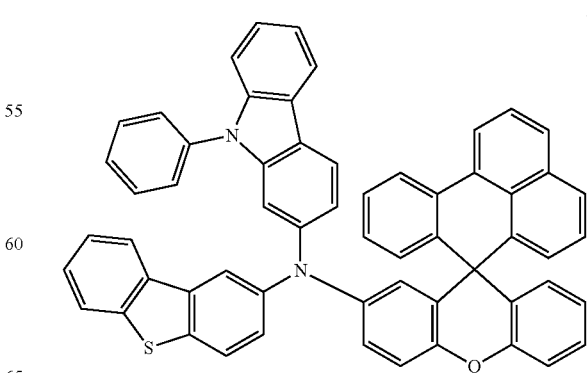

528
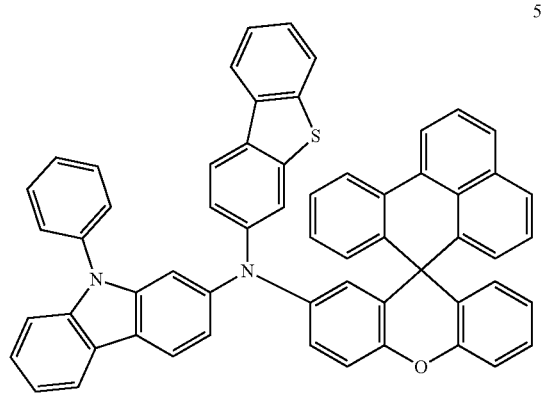
529
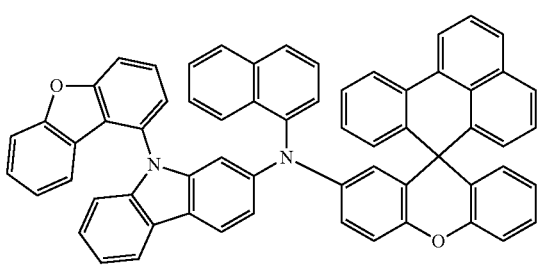
530
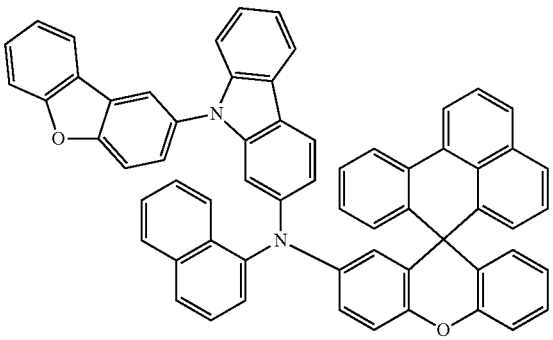
531
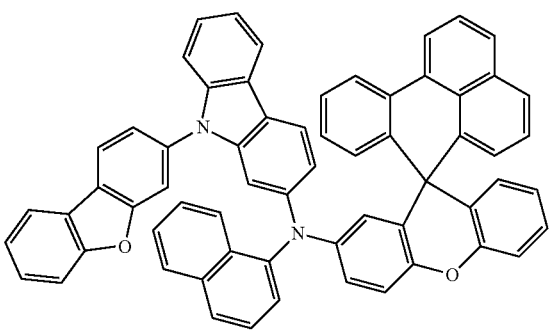
532
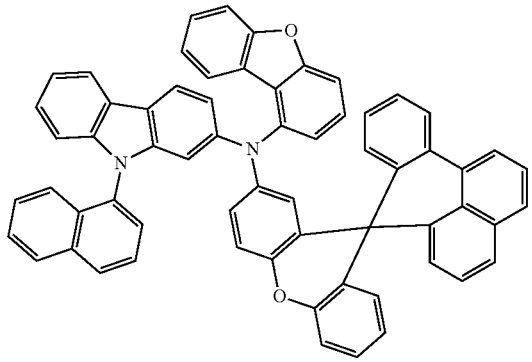
533
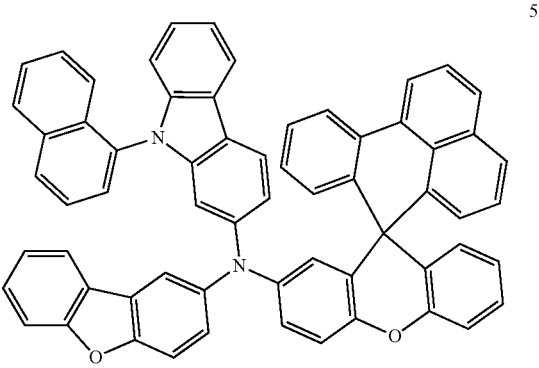
534
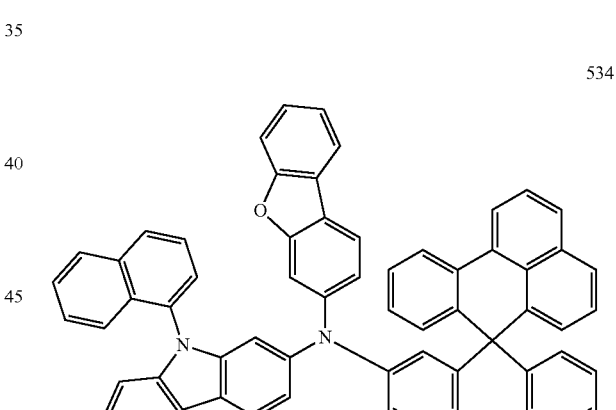
535
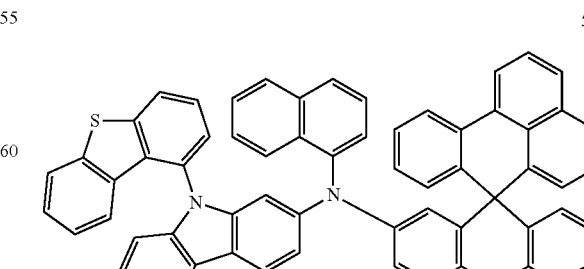

-continued
536
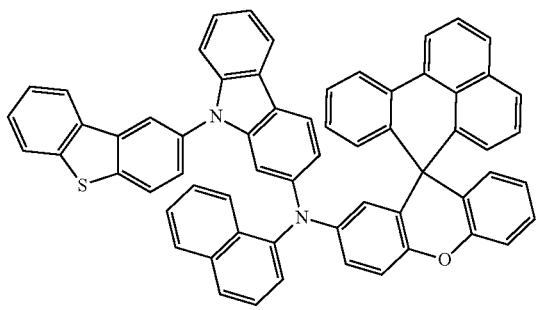
537
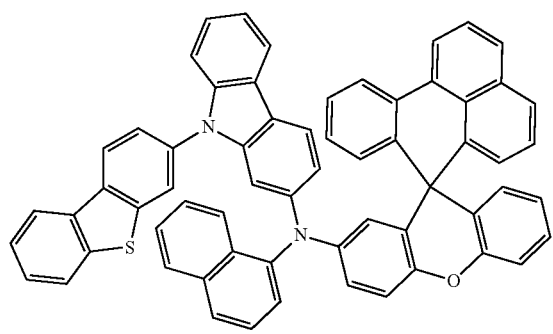
538
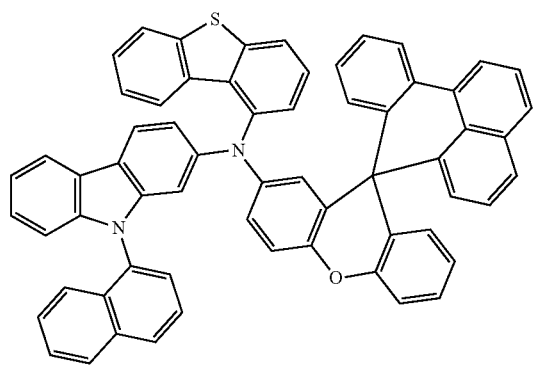
539
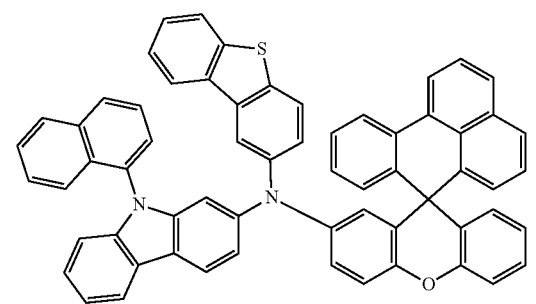
-continued
540
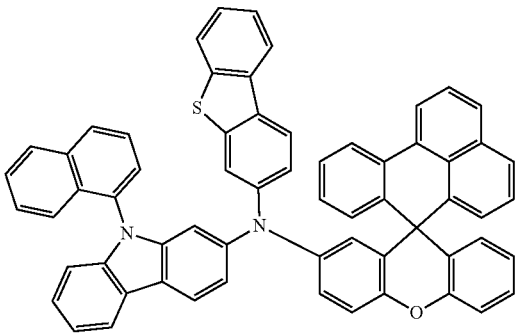
541
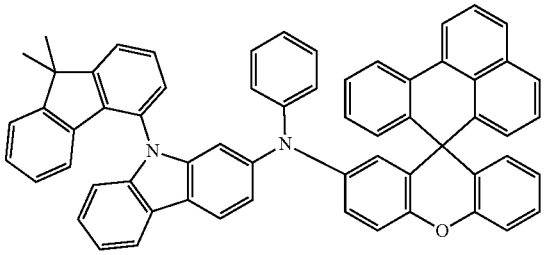
542
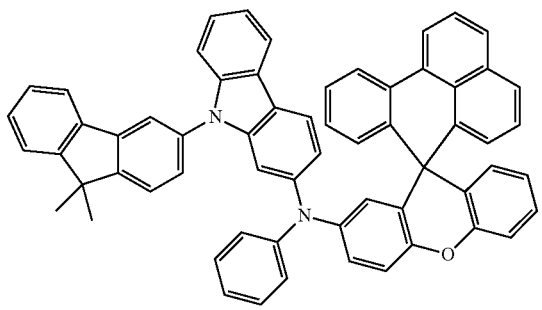
543
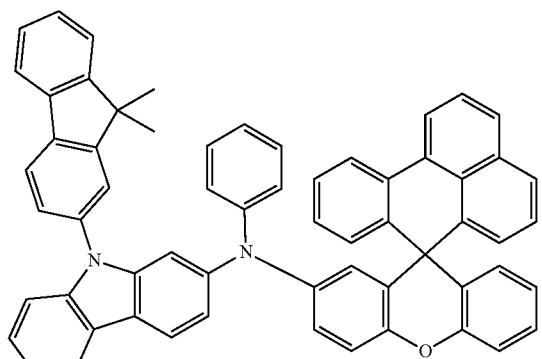

544
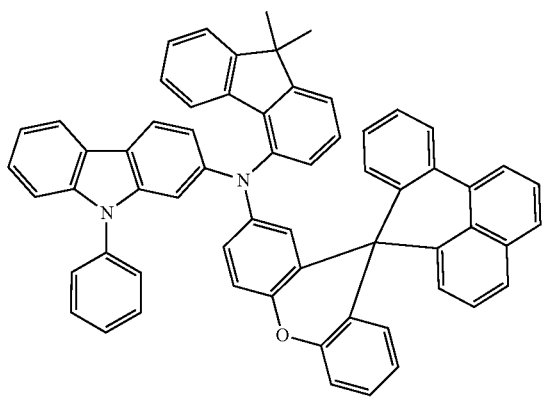
545
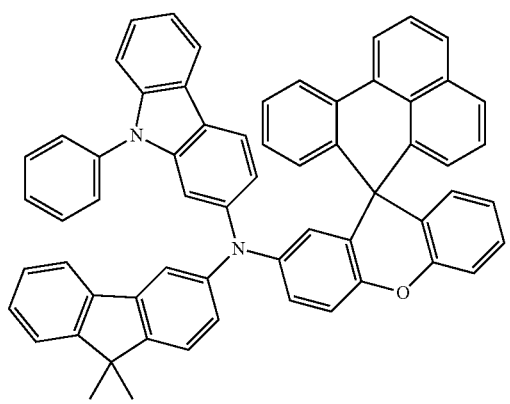
546
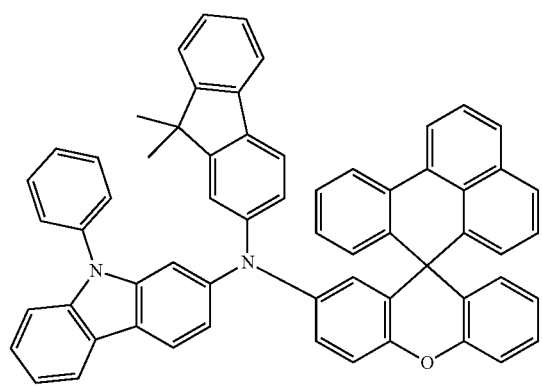
547
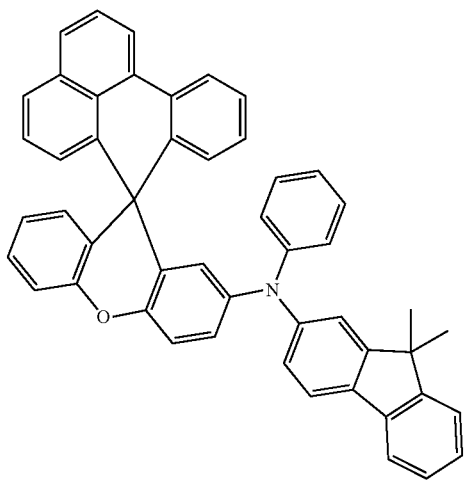
548
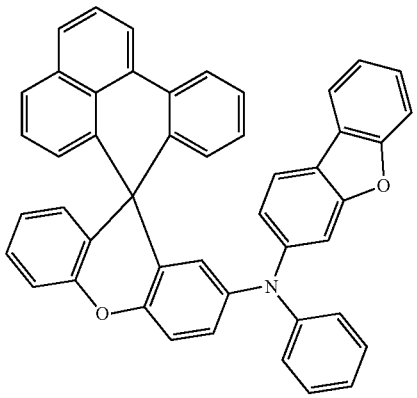
549
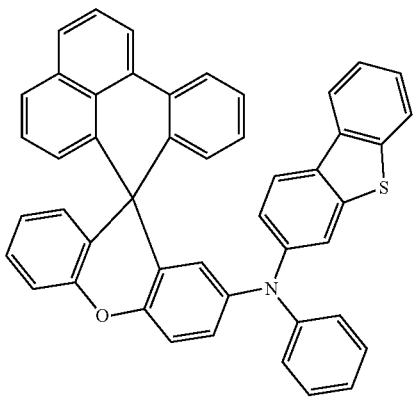

179
-continued
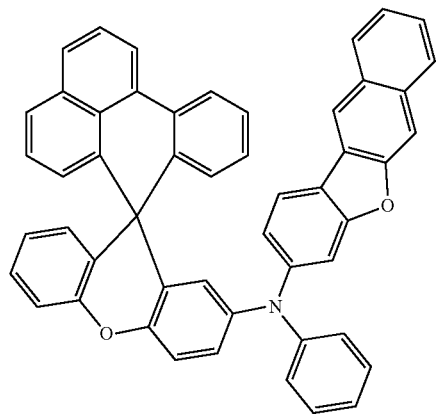
550
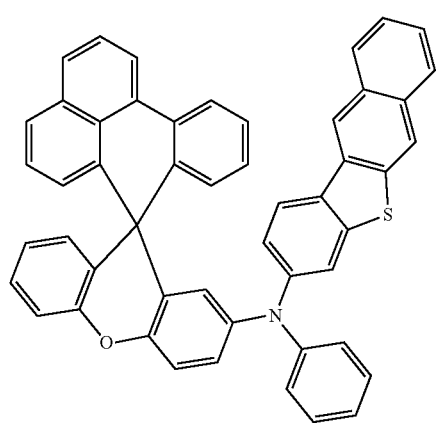
551
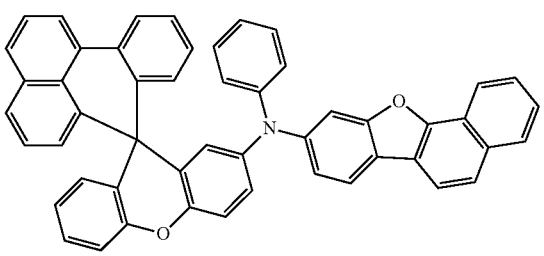
552
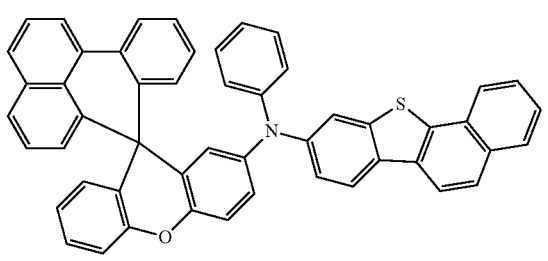
553
180
-continued
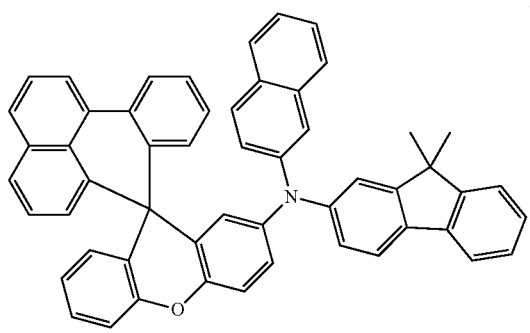
554
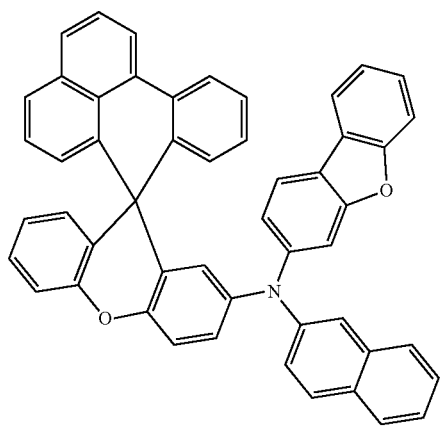
555
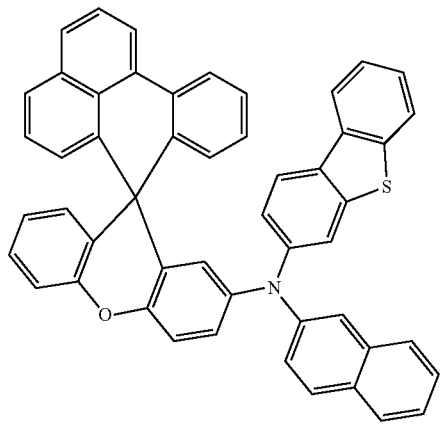
556

557
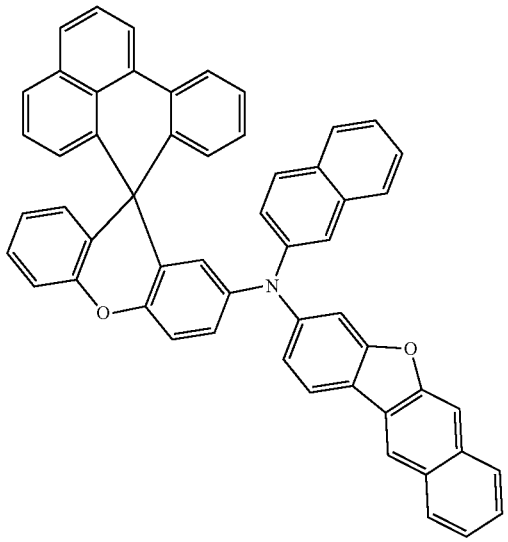
558
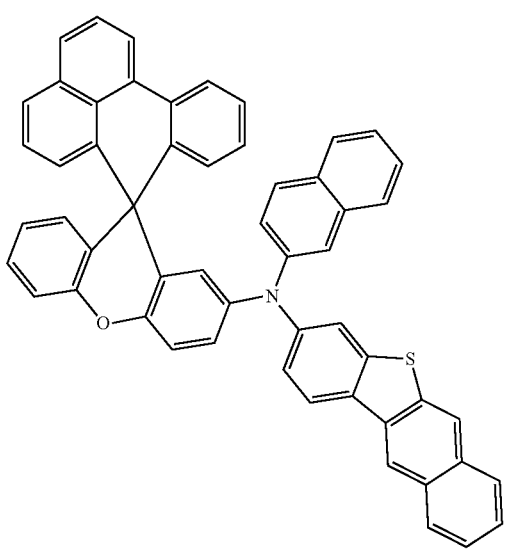
559
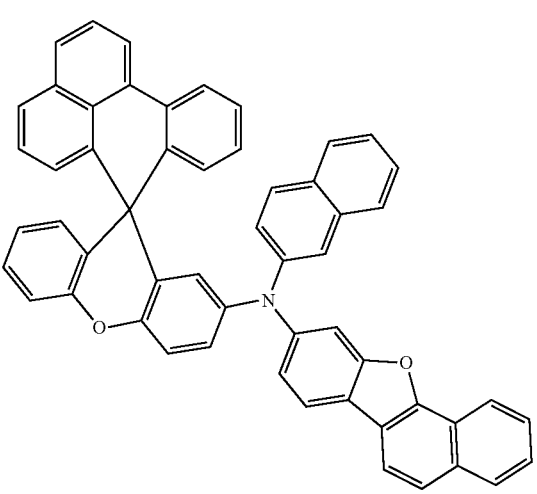
560
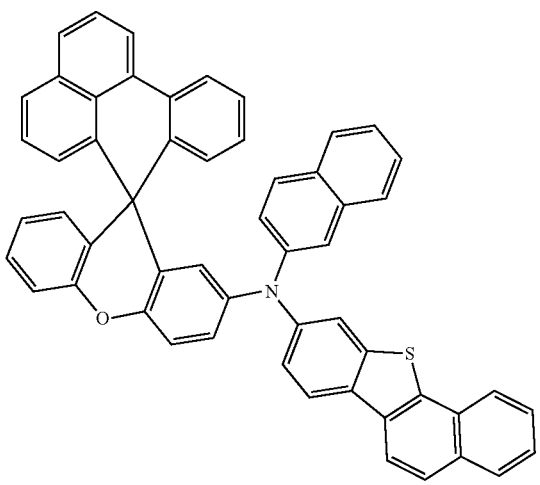
561
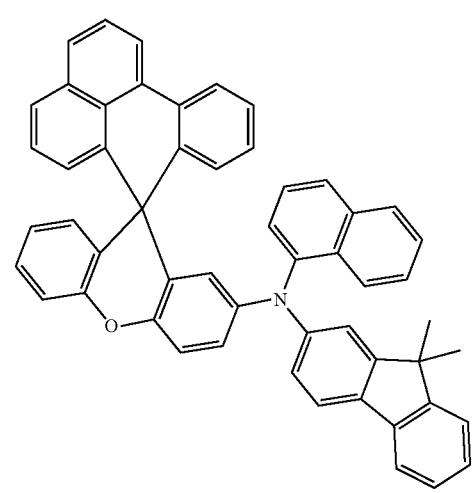
562
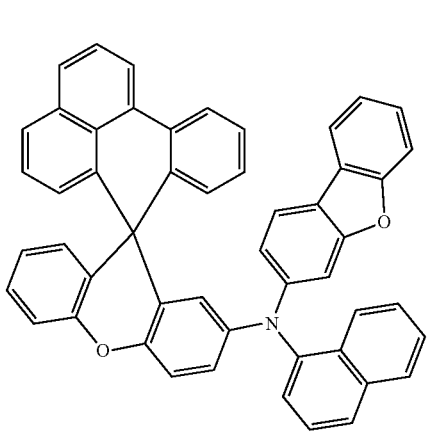

183
-continued
563
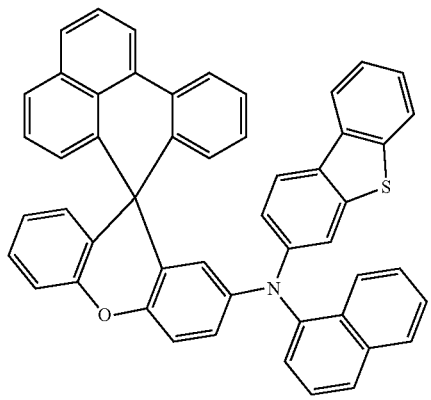
564
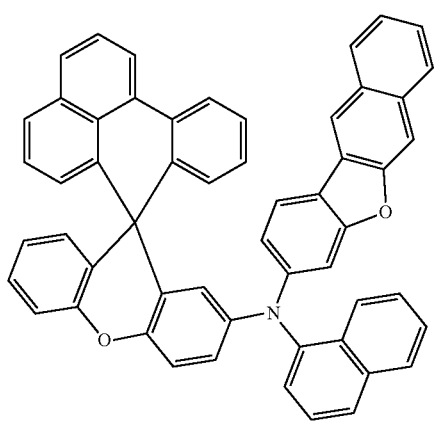
565
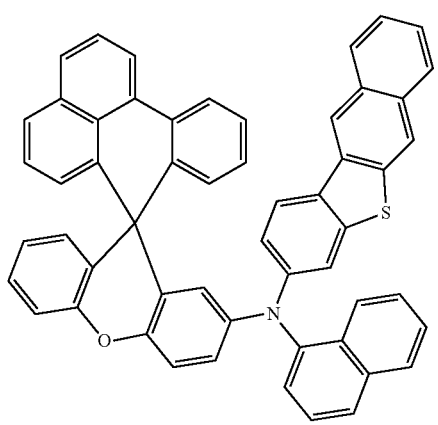
184
-continued
566
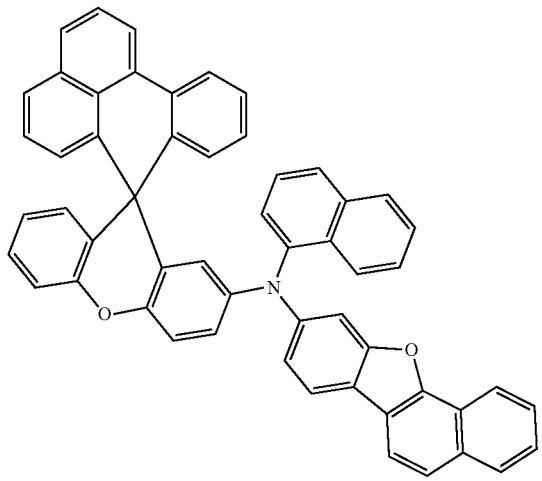
567
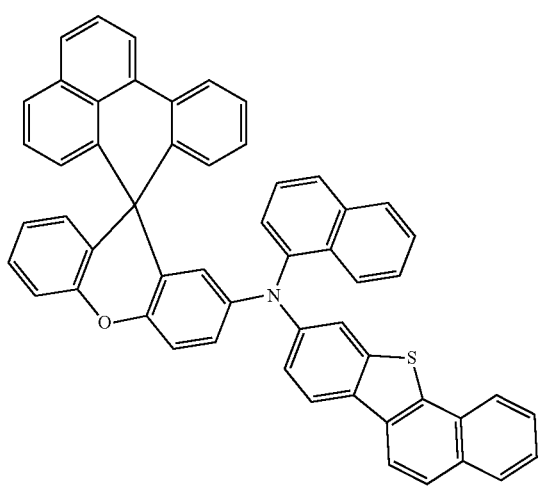
568
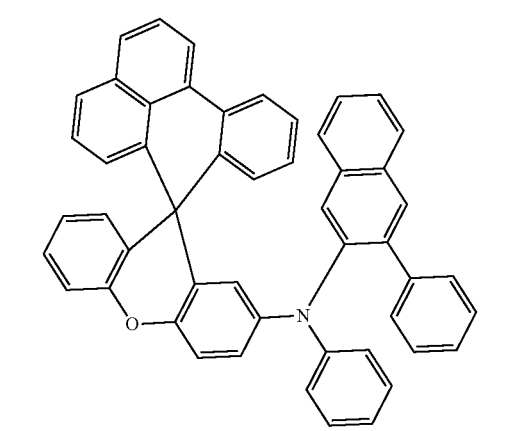

569
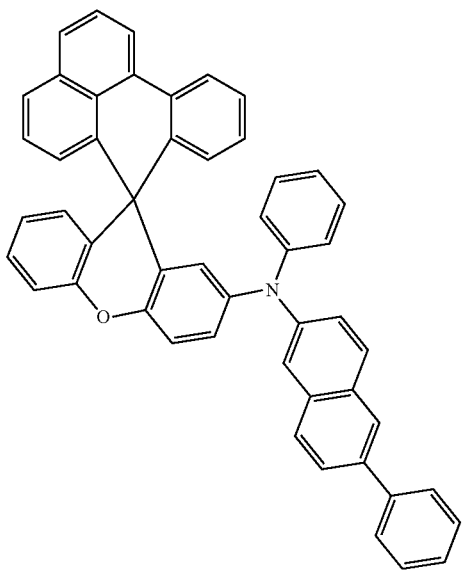
570
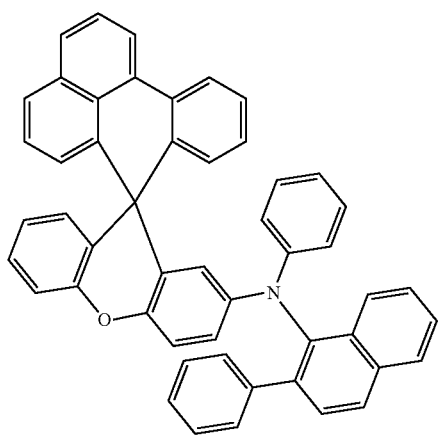
571
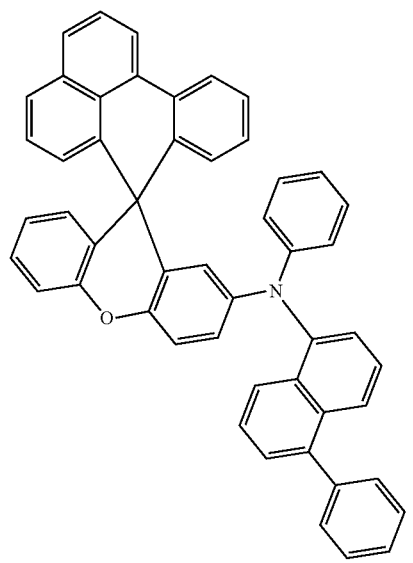
572
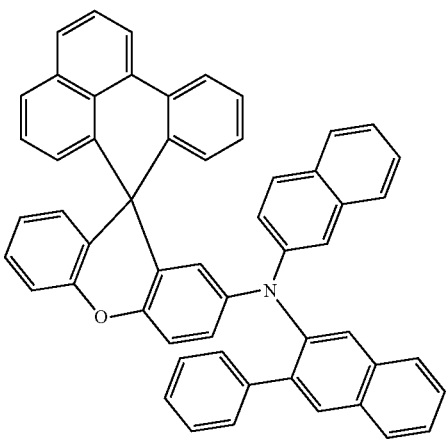
573
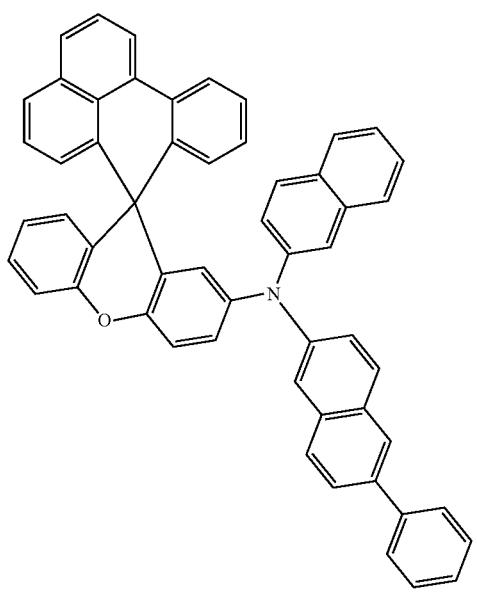
574
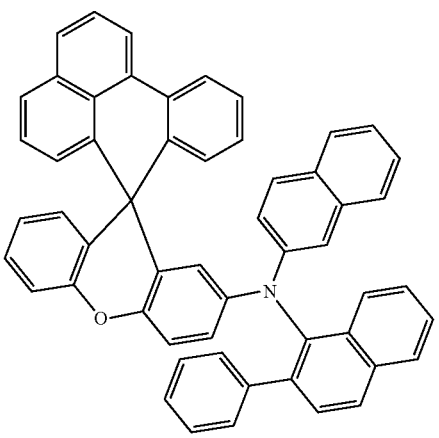

575
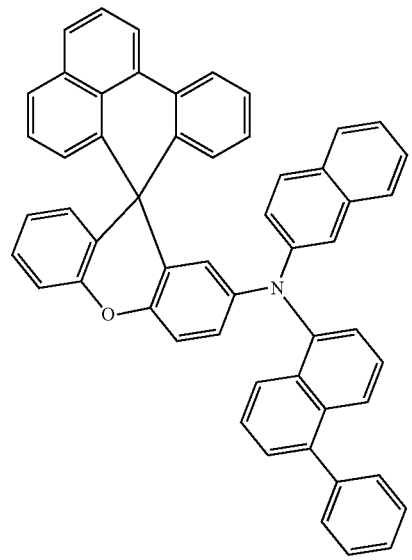
576
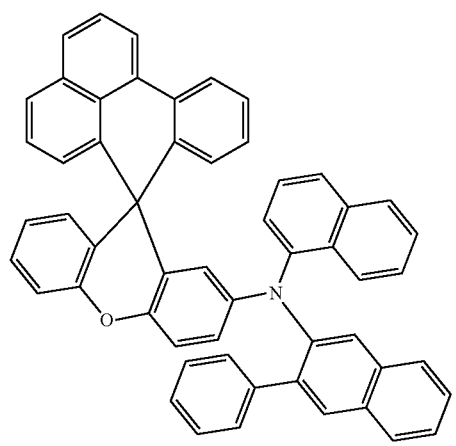
577
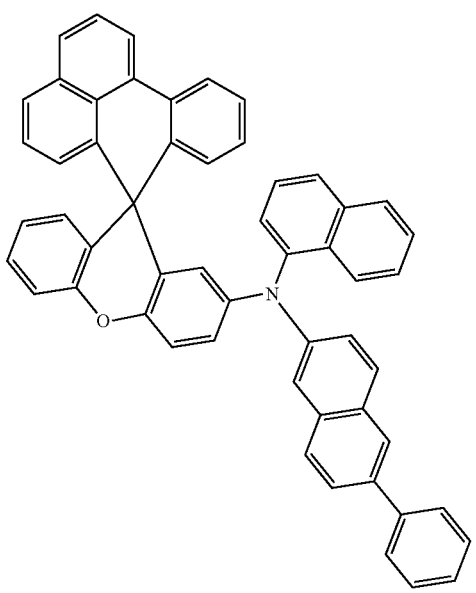
578
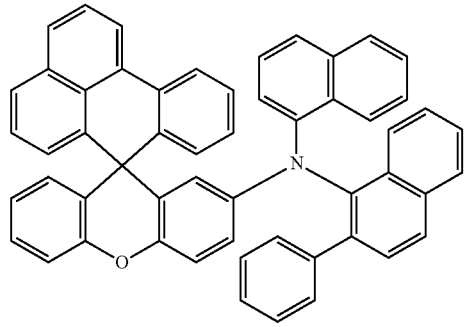
579
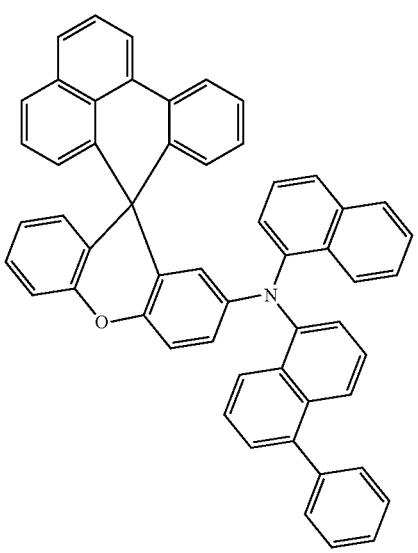
580
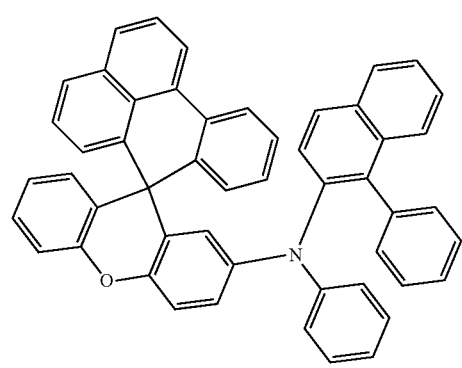

189
-continued
581
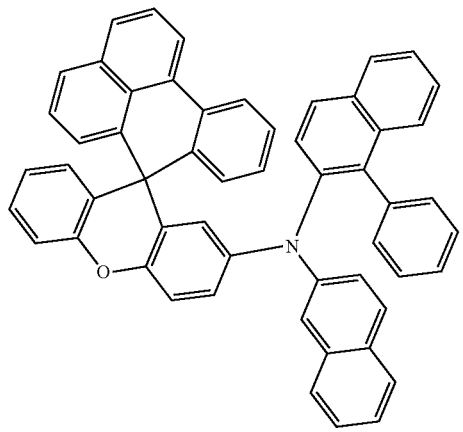
582
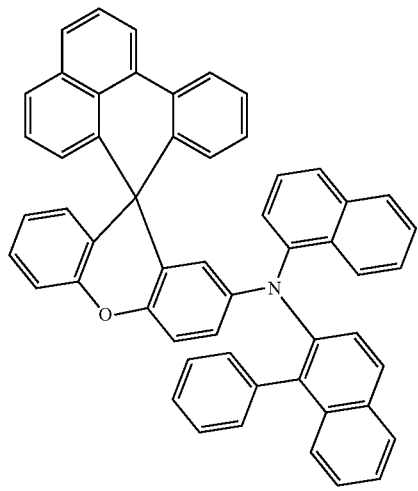
583
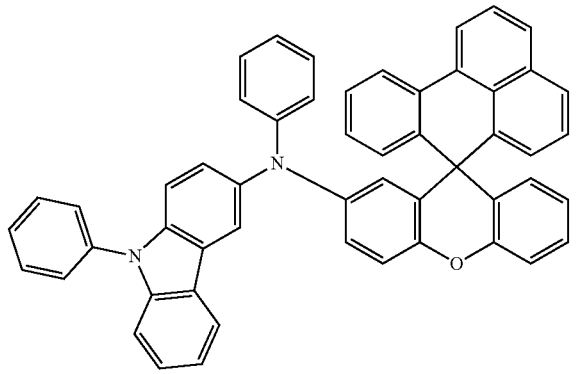
190
-continued
584
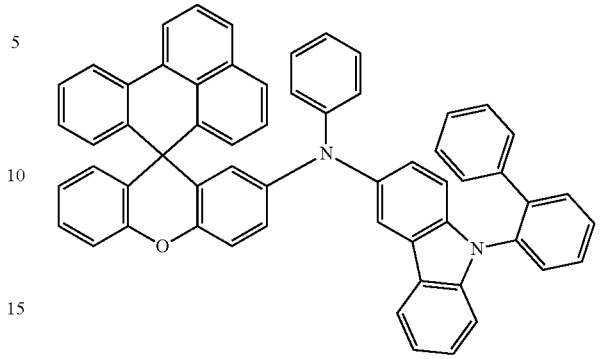
585
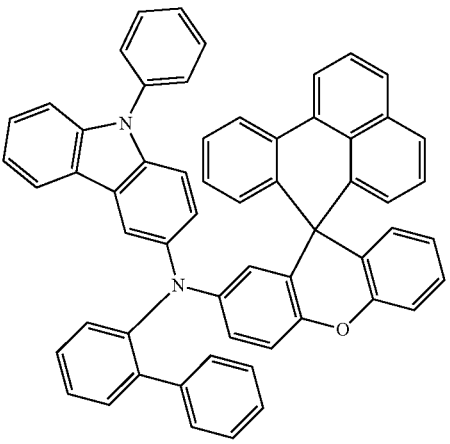
586
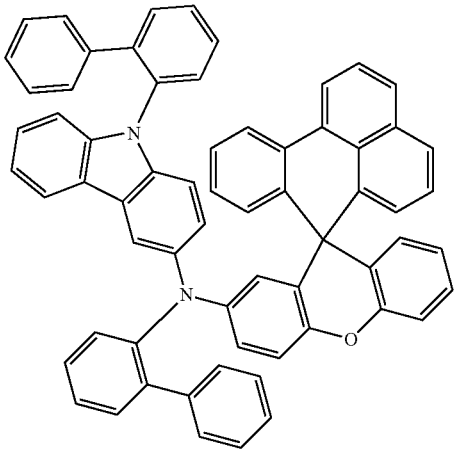

-continued
587
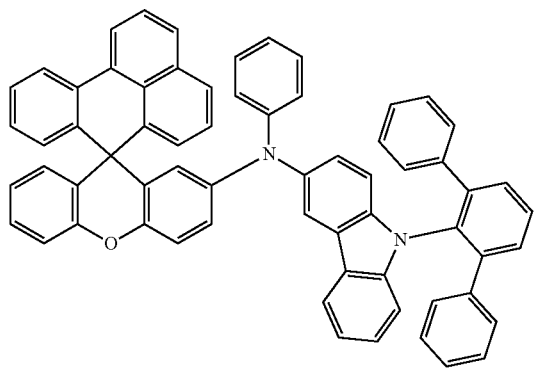
588
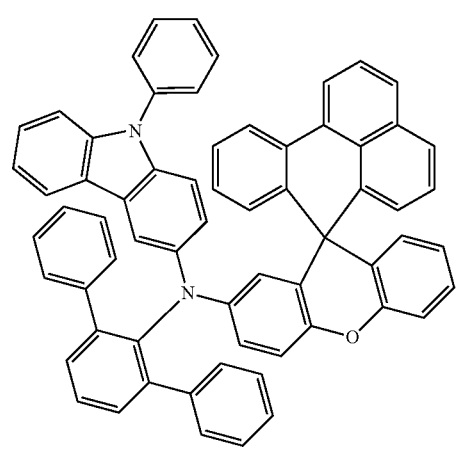
589
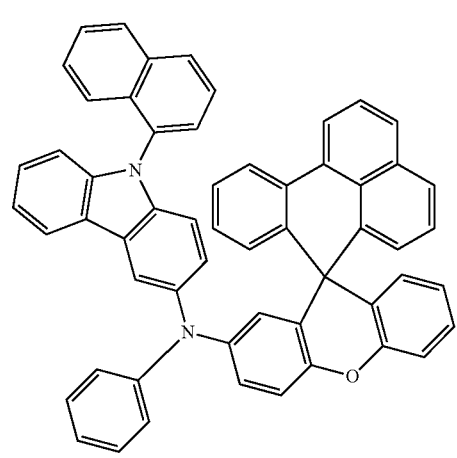
-continued
590
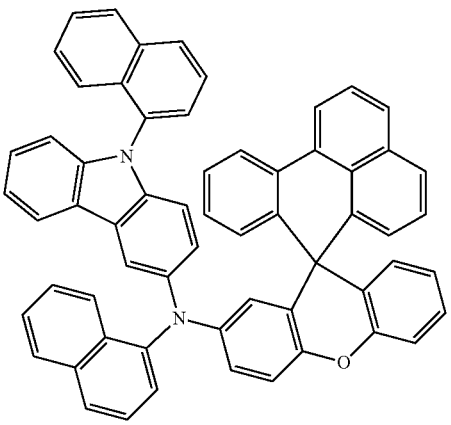
591
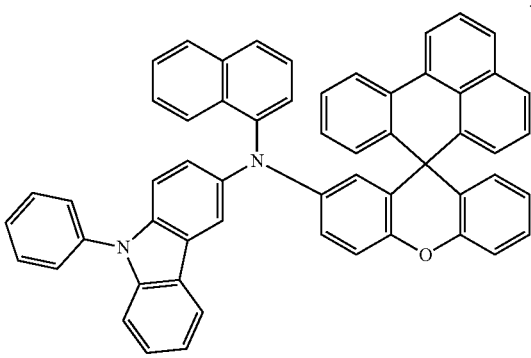
592
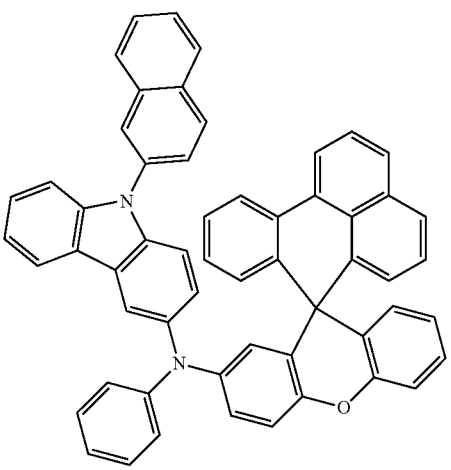
593
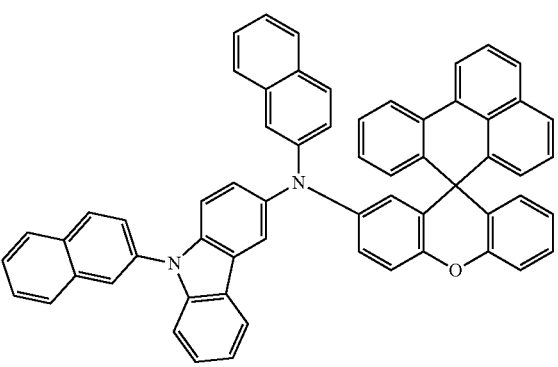

594
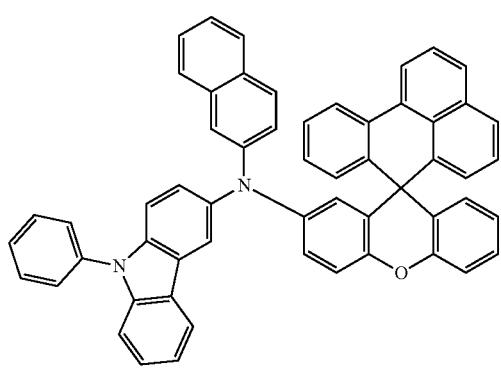
595
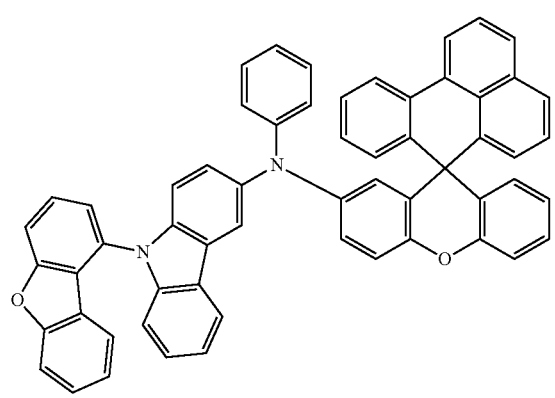
596
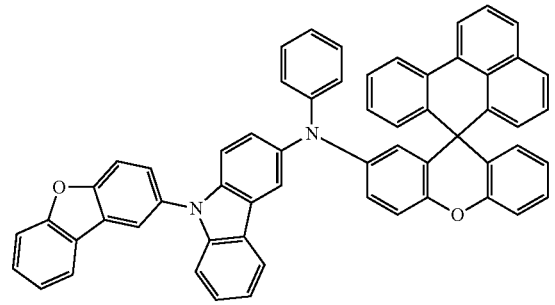
597
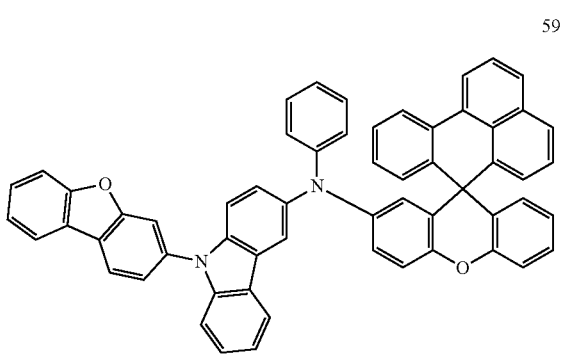
598
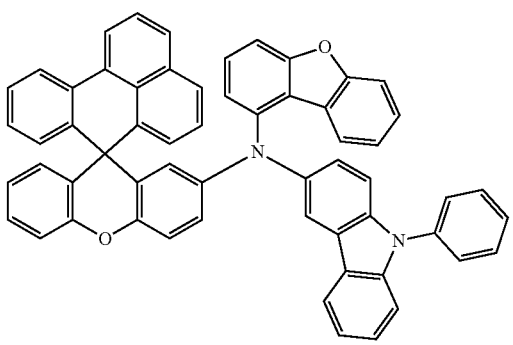
599
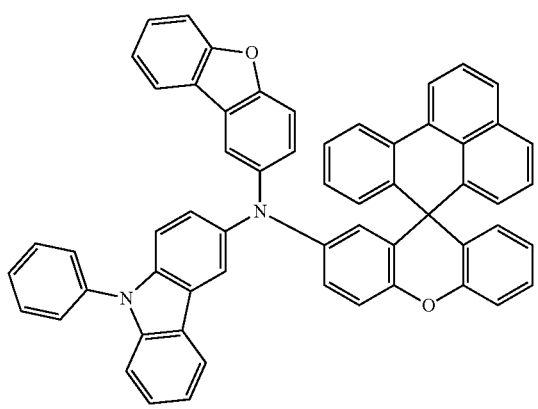
600
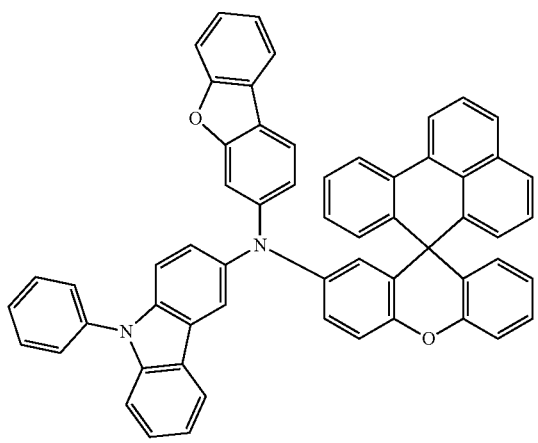
601
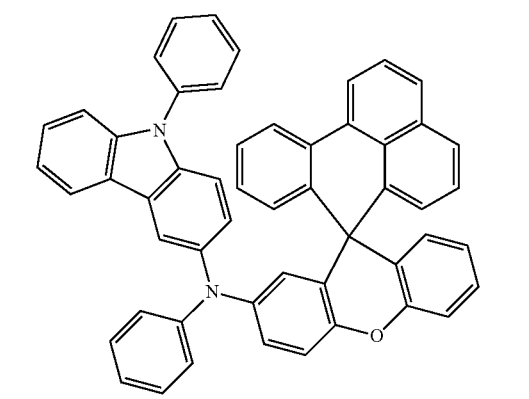

602
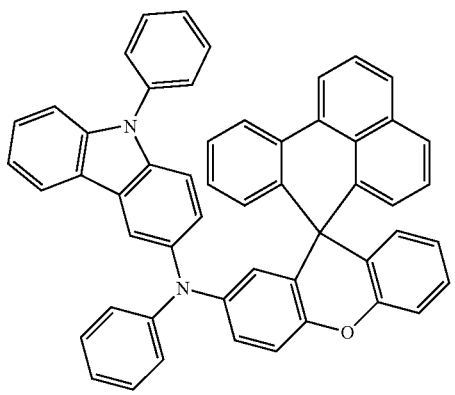
603
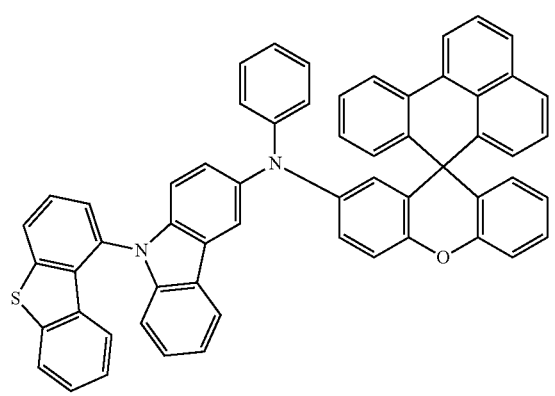
604
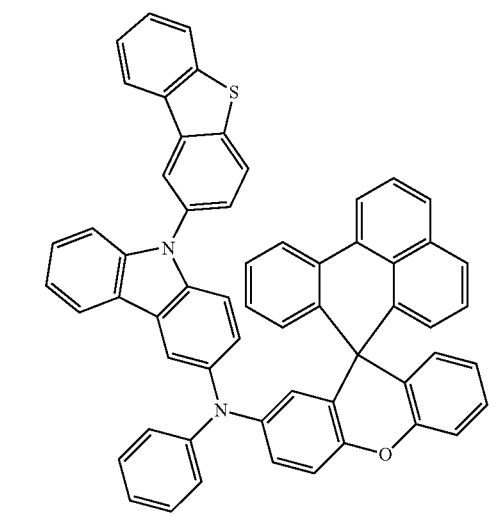
605
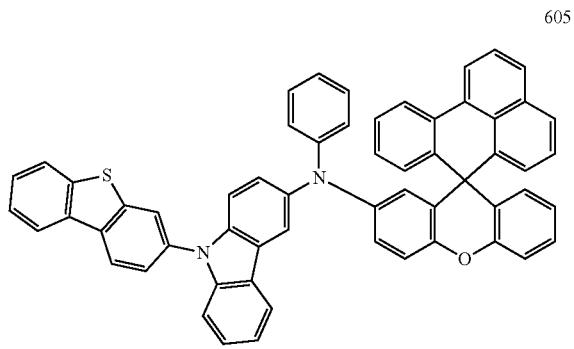
606
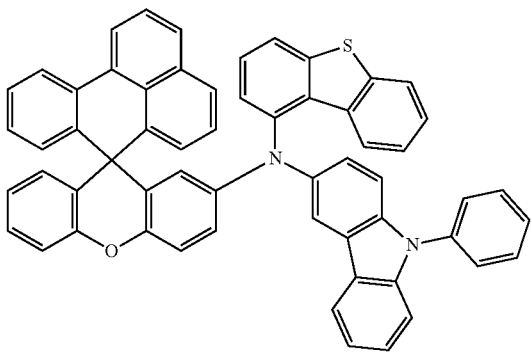
607
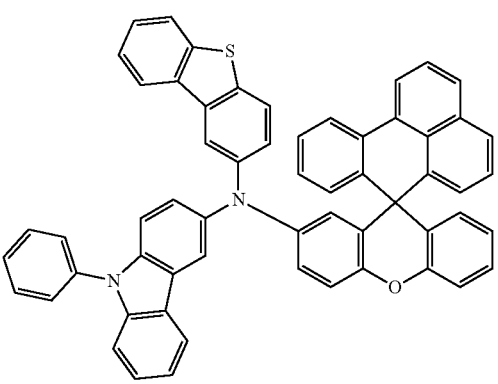
608
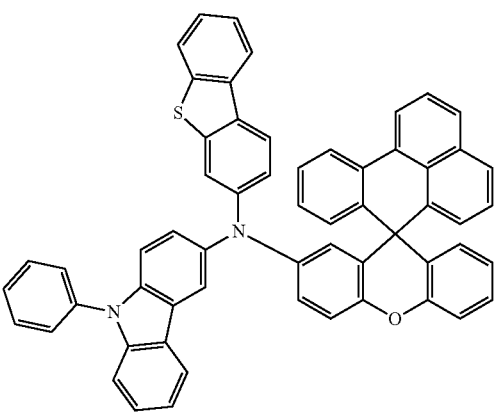
609
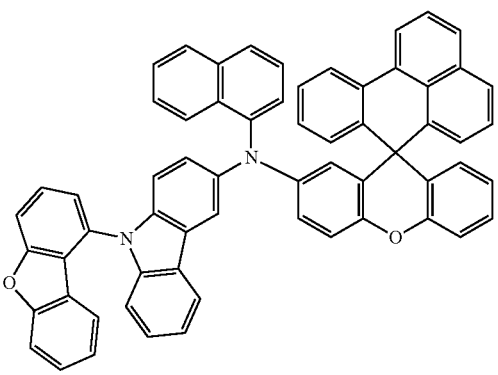

197
-continued
610
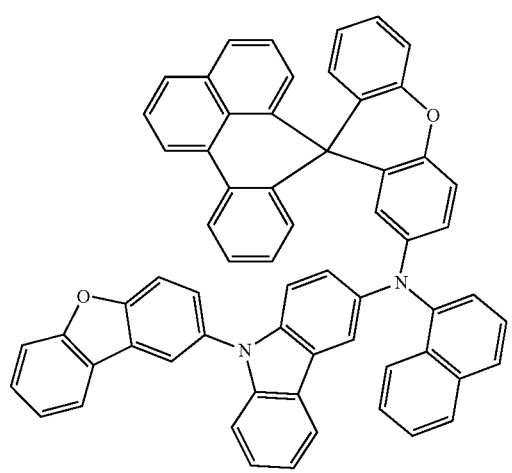
611
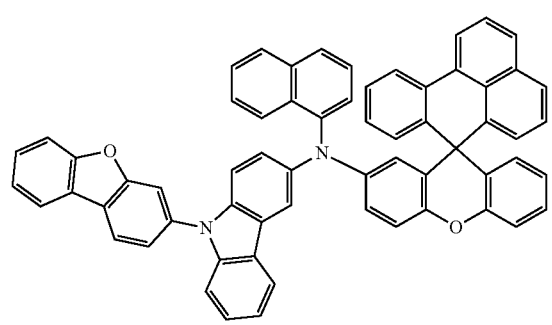
612
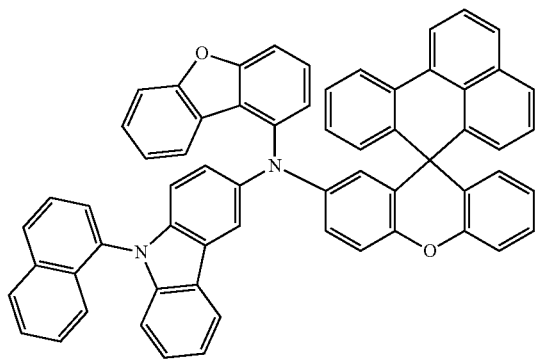
613
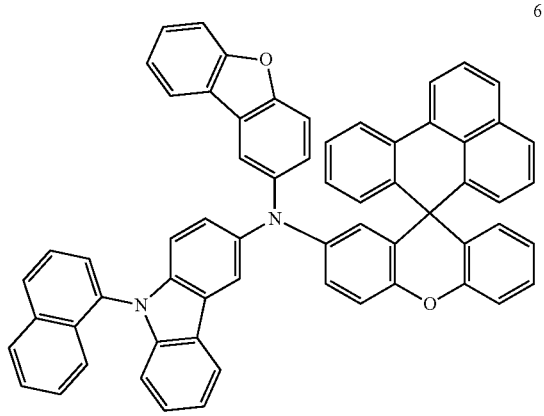
198
-continued
614
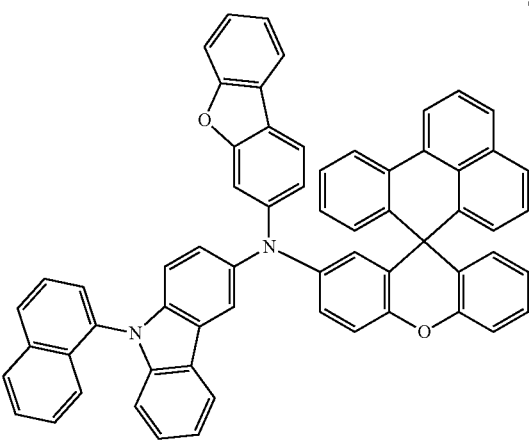
615
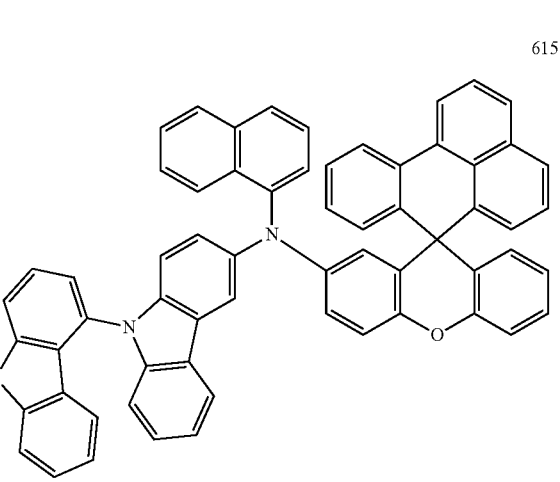
616
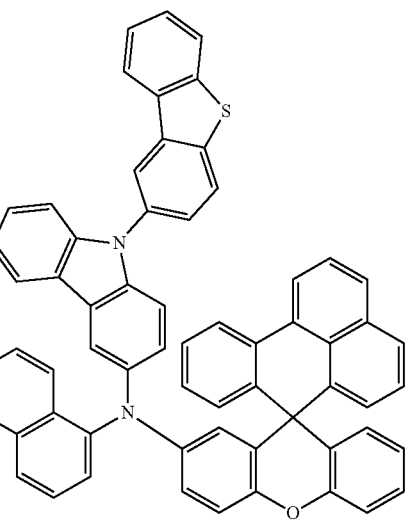

-continued
617
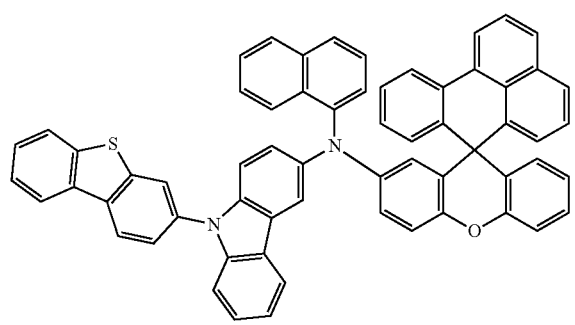
618
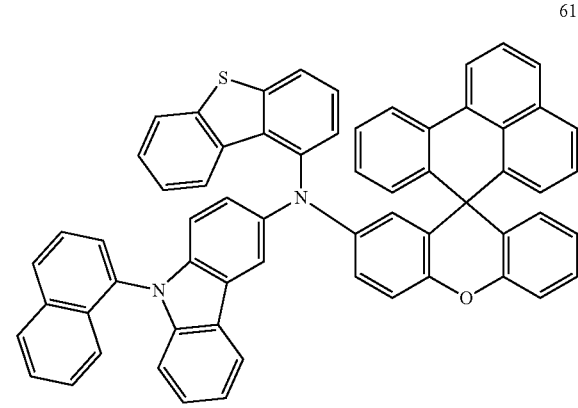
619
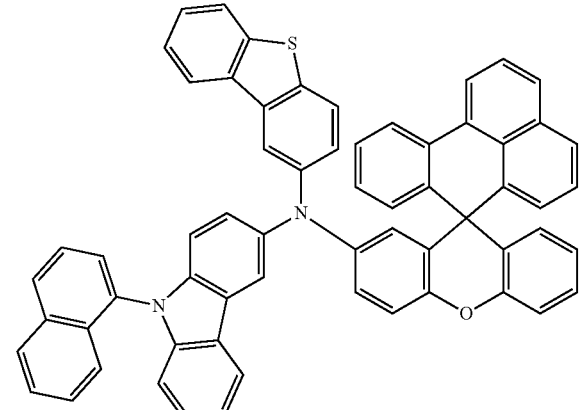
-continued
620
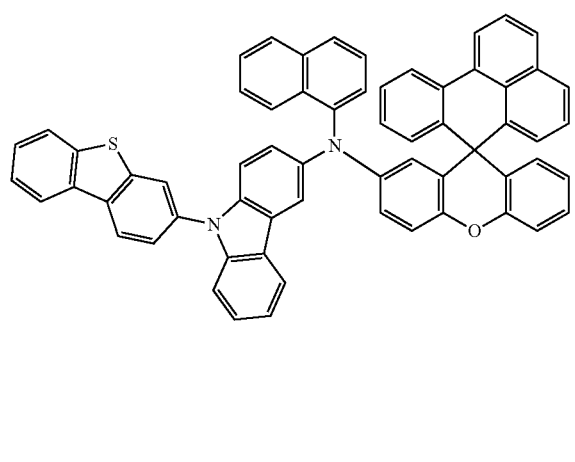
621
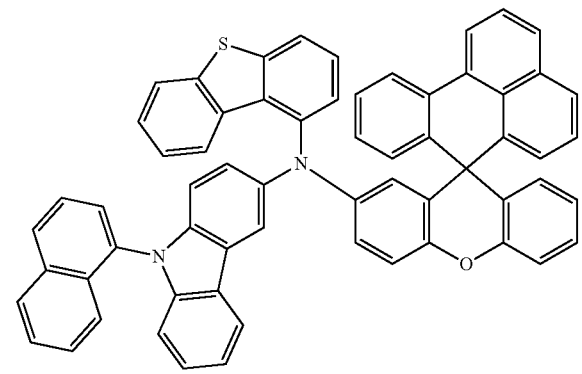
622
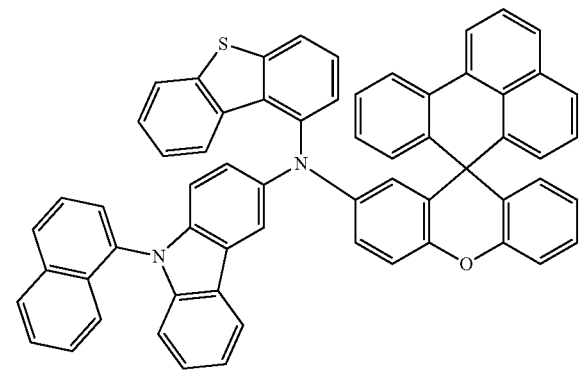
623
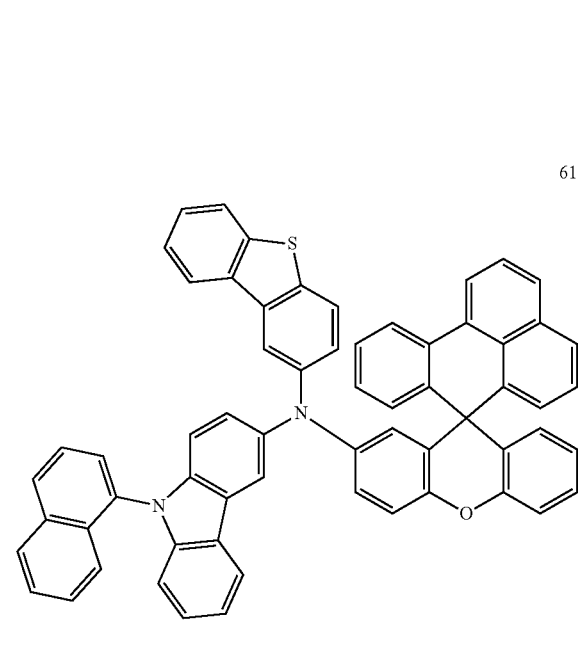

201
-continued
624
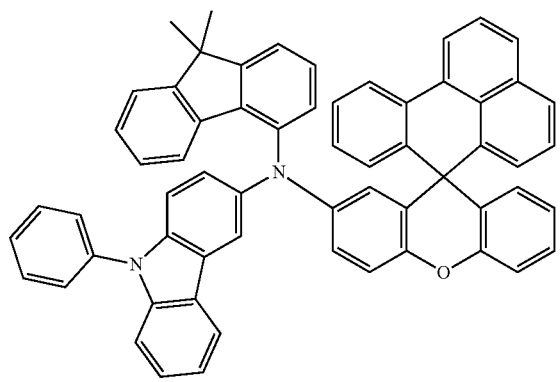
625
626
627
202
-continued
628
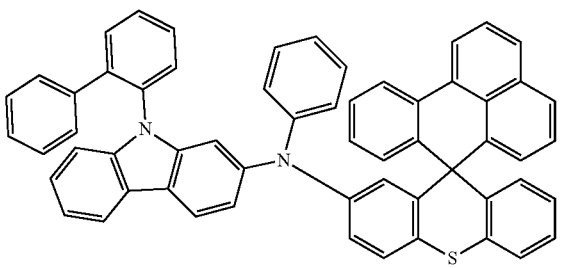
629
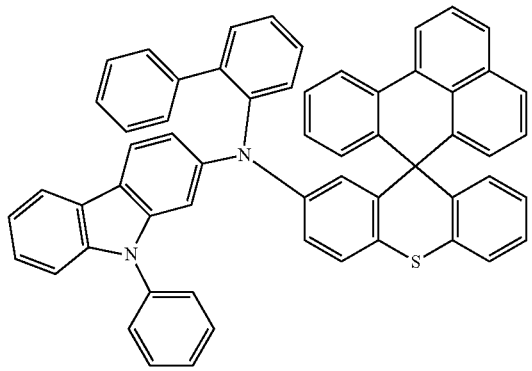
630
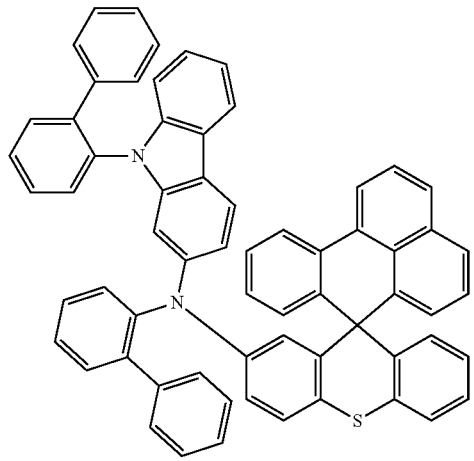
631
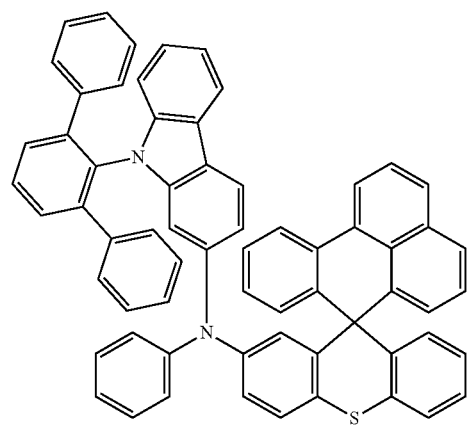

| 203 | 204 |
|---|---|
| -continued | -continued |
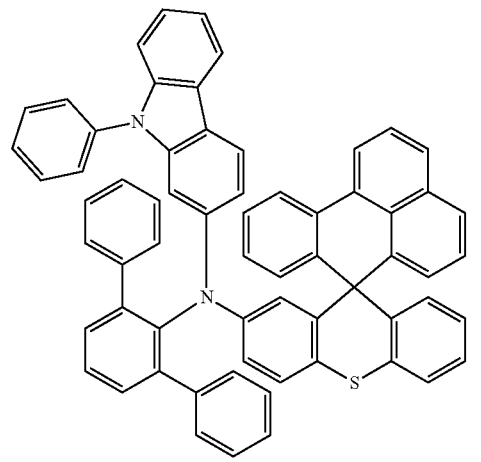
632
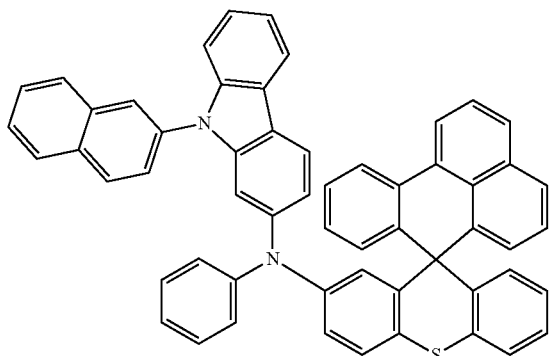
636
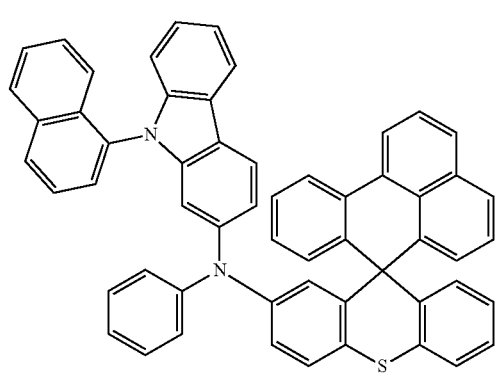
633
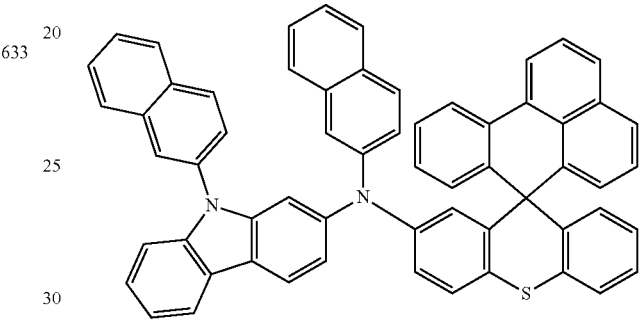
637
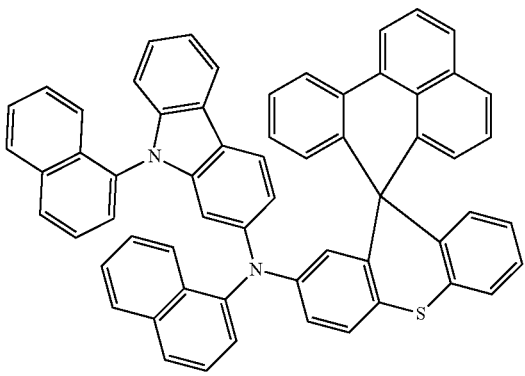
634
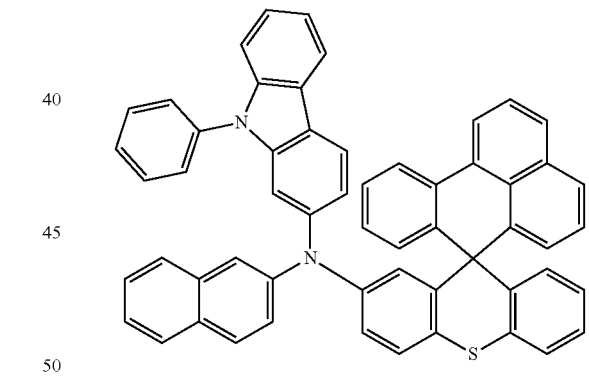
638
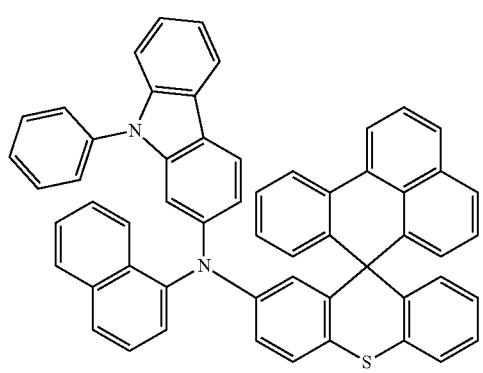
635
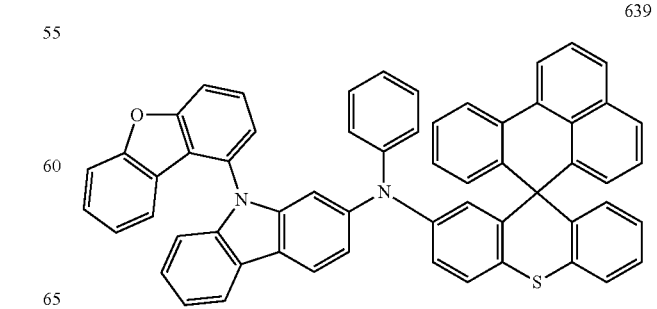
639

640
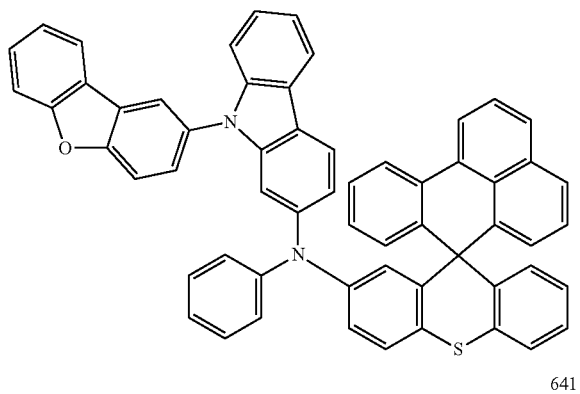
641
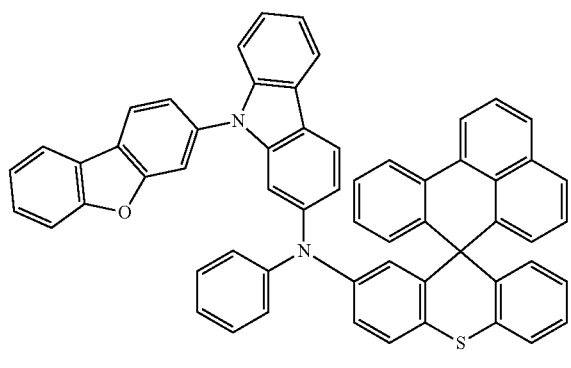
642
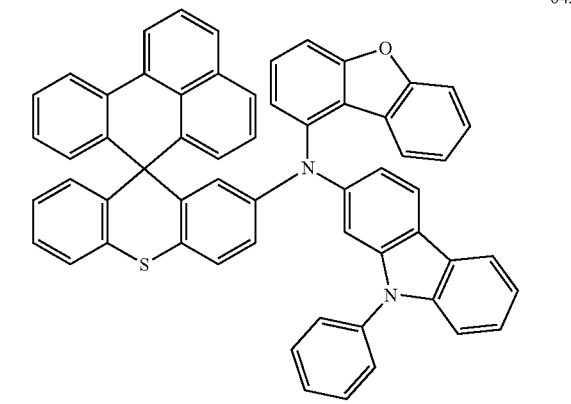
643
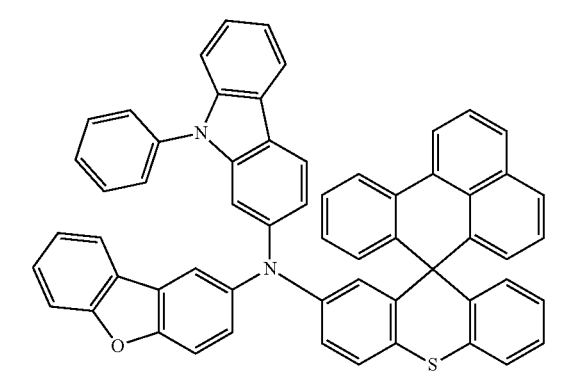
644
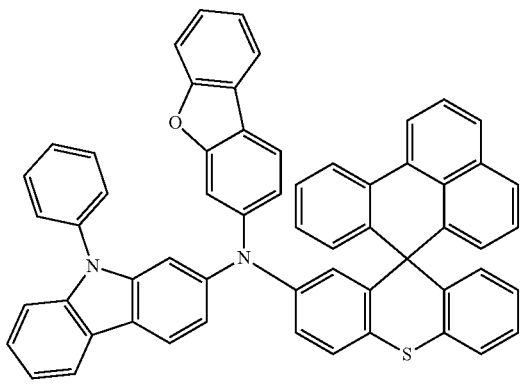
645
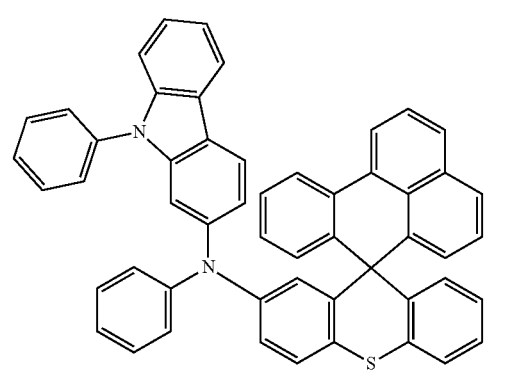
646
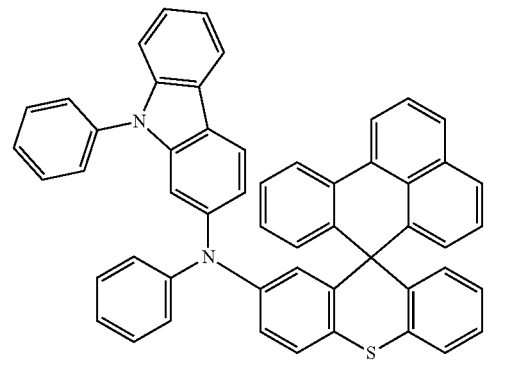
647
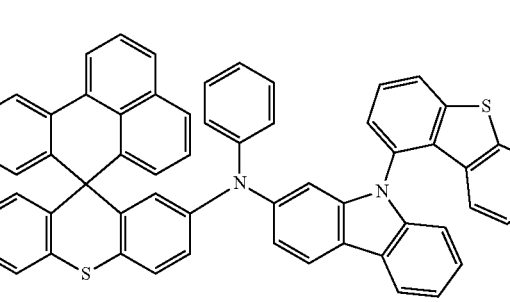

207
-continued
648
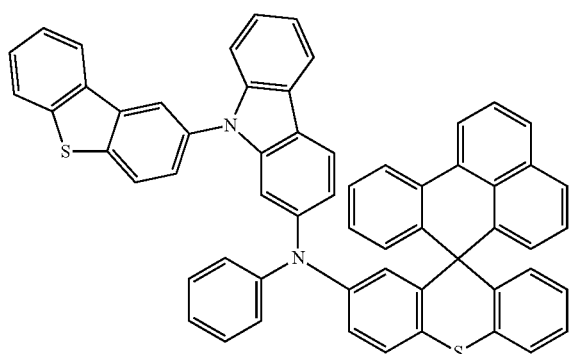
649
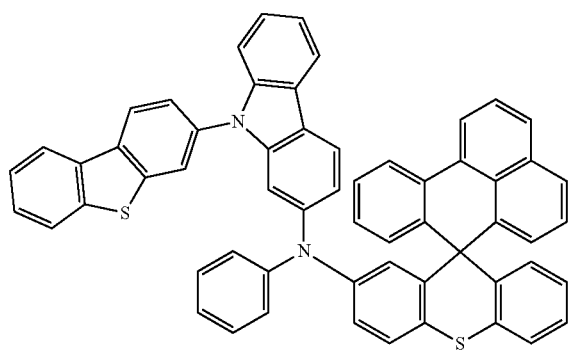
650
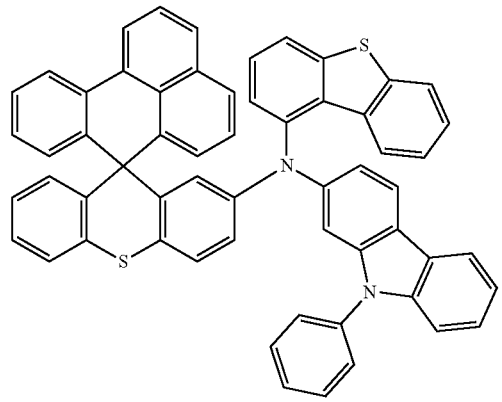
651
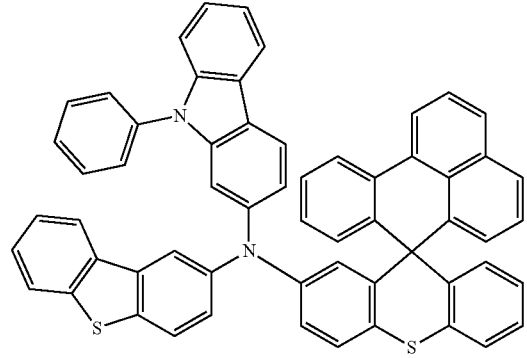
208
-continued
652
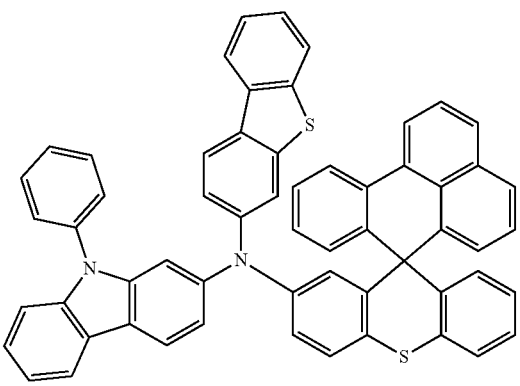
653
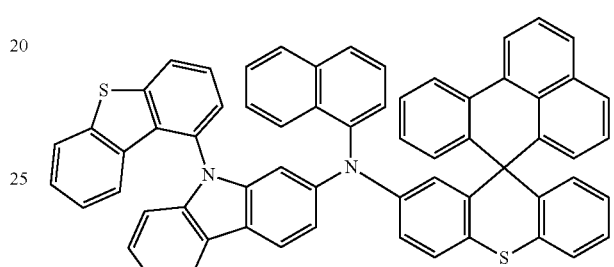
654
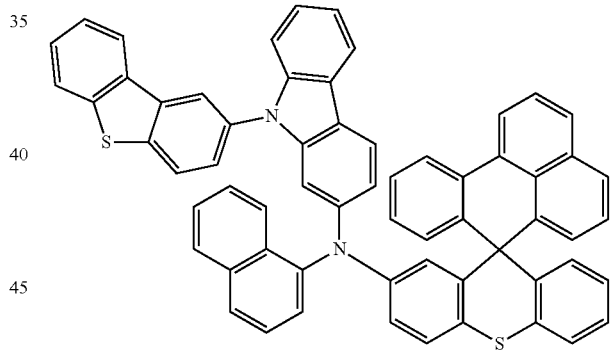
655
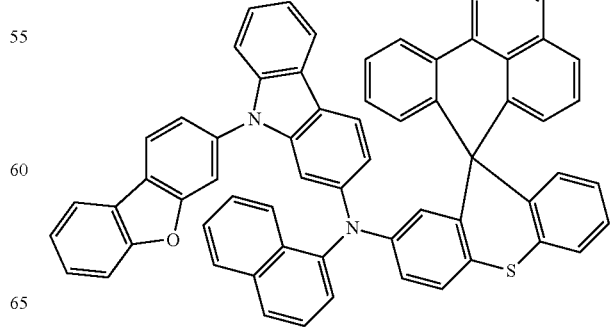

656
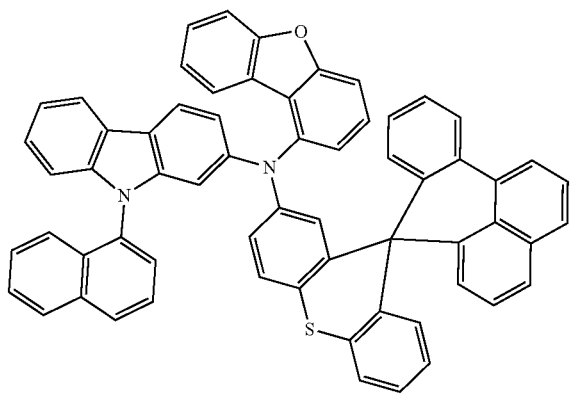
657
660
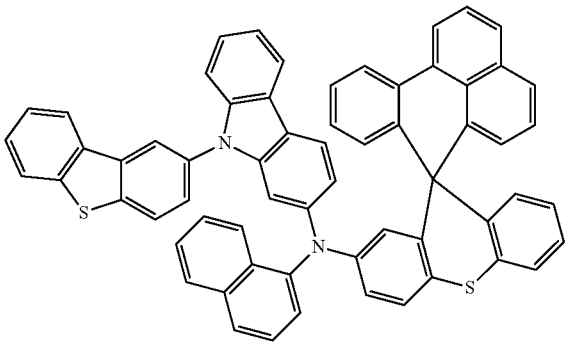
661
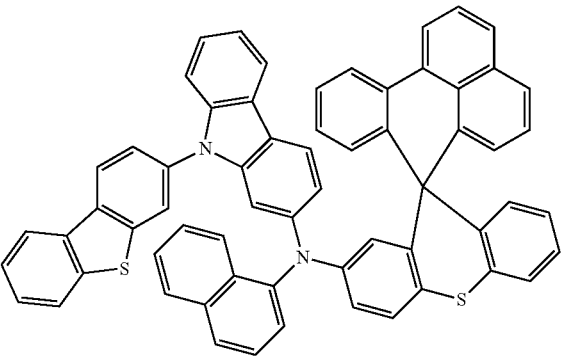
658
662
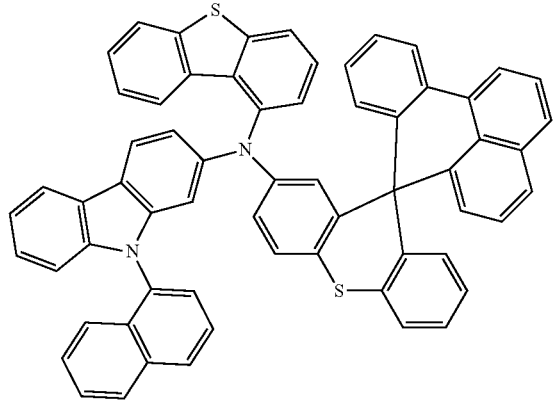
659
663
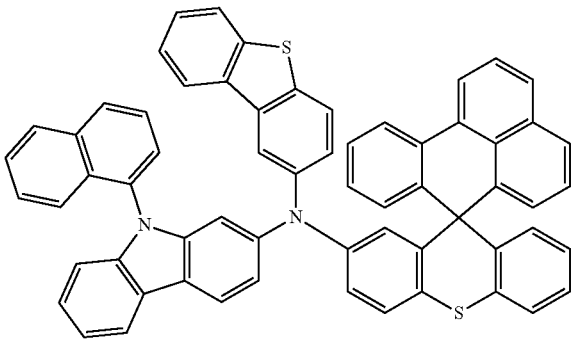

211
-continued
664
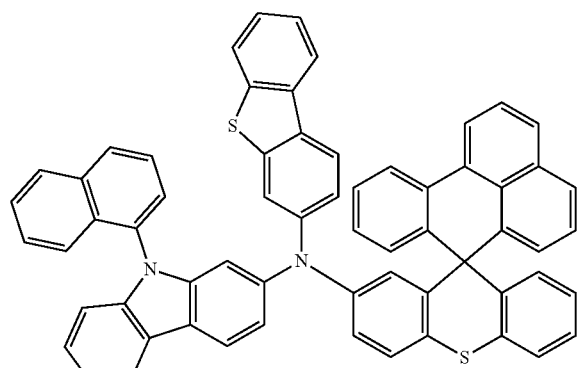
665
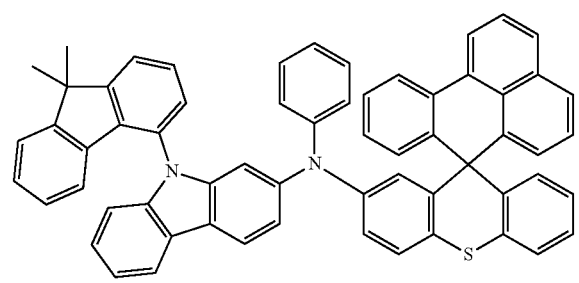
666
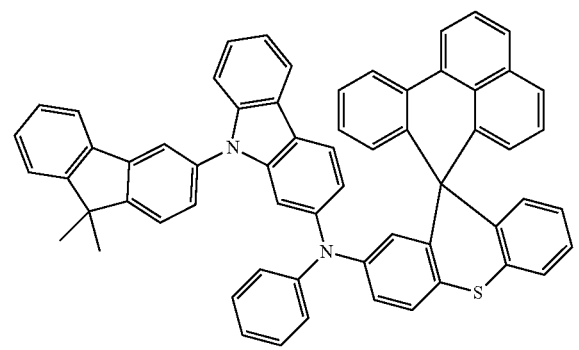
667
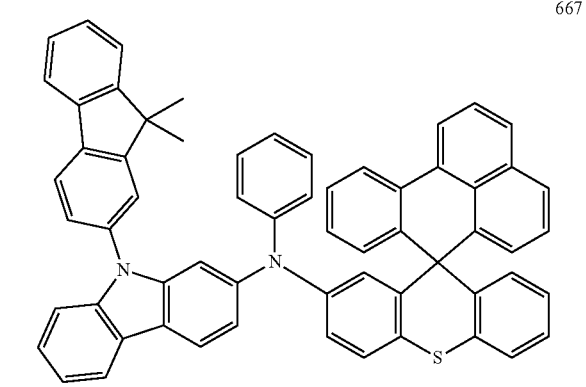
212
-continued
668
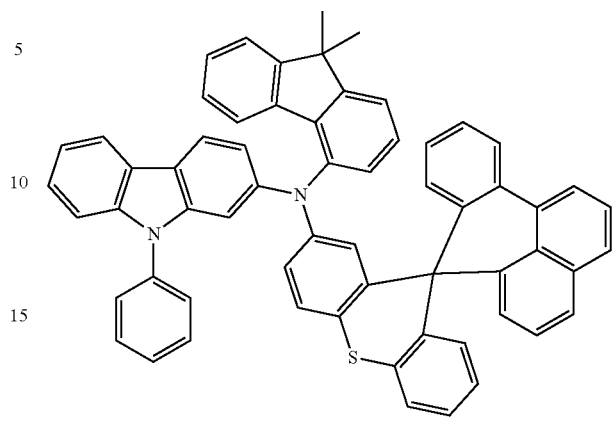
669
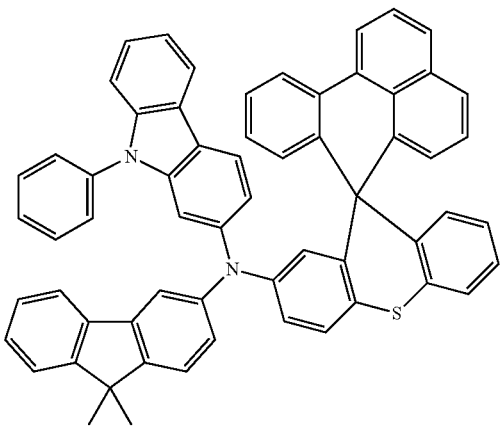
670
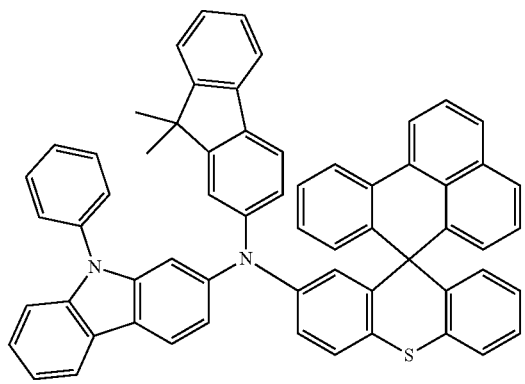

213
-continued
214
-continued
671
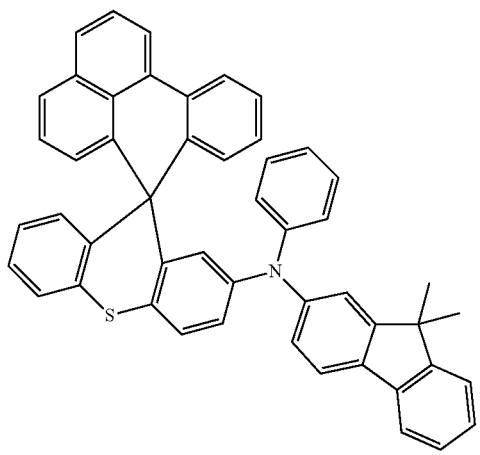
675
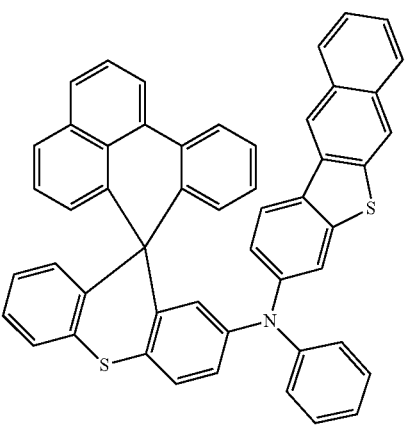
672
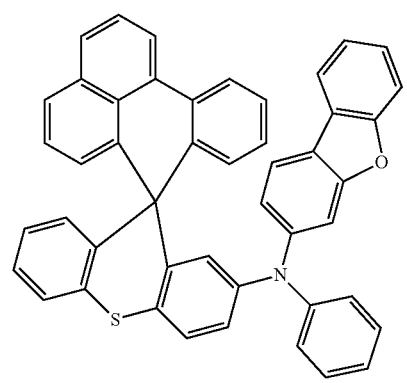
676
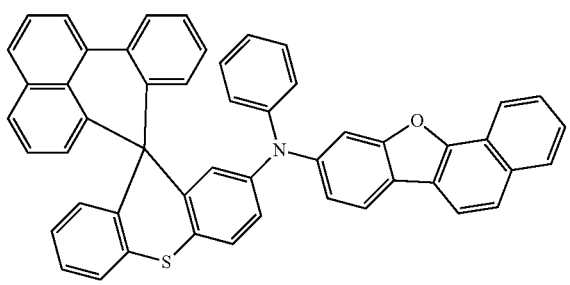
673
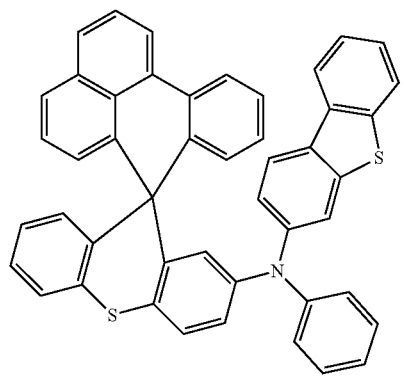
677
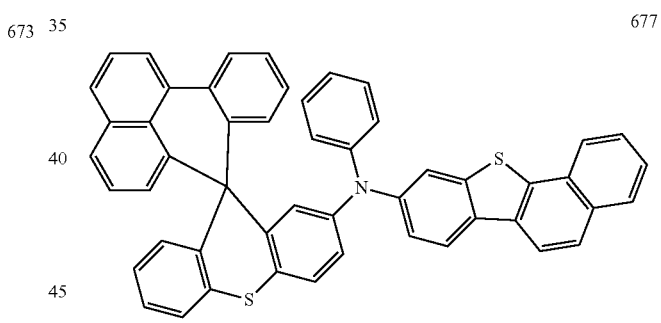
674
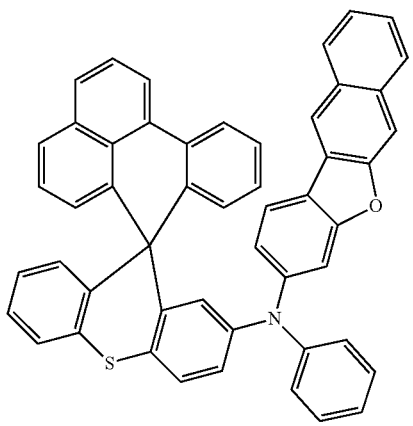
678
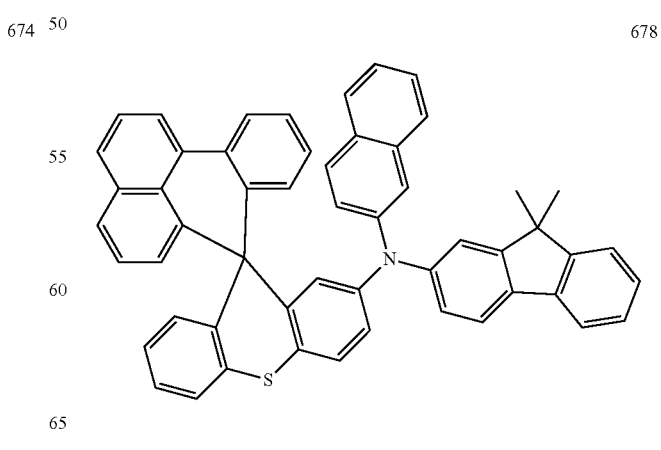

679
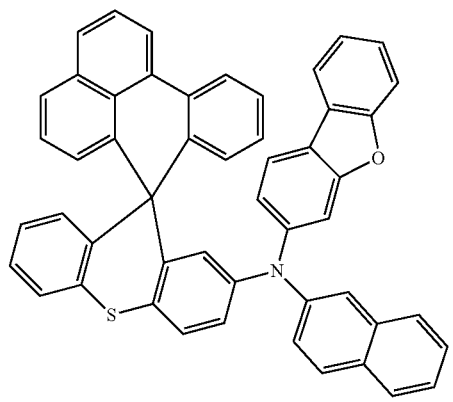
680
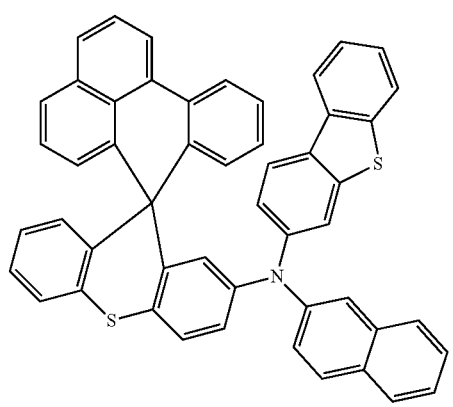
681
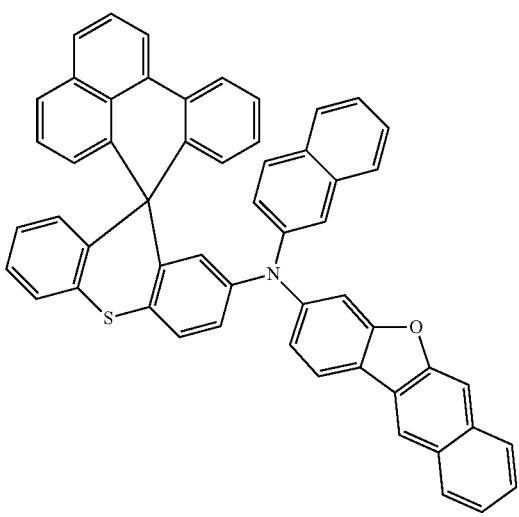
682
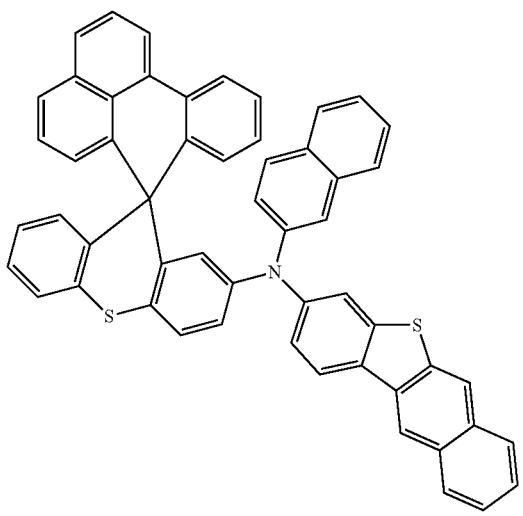
683
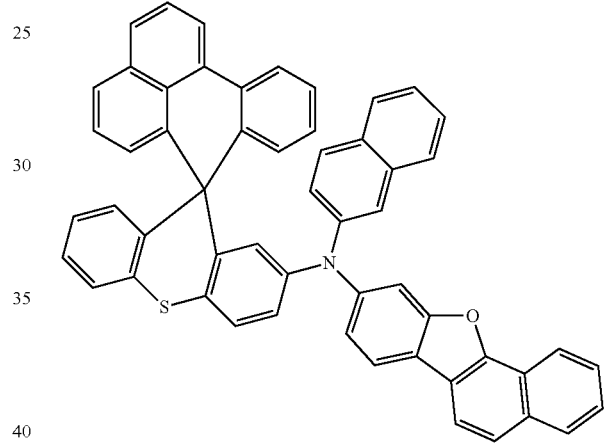
684
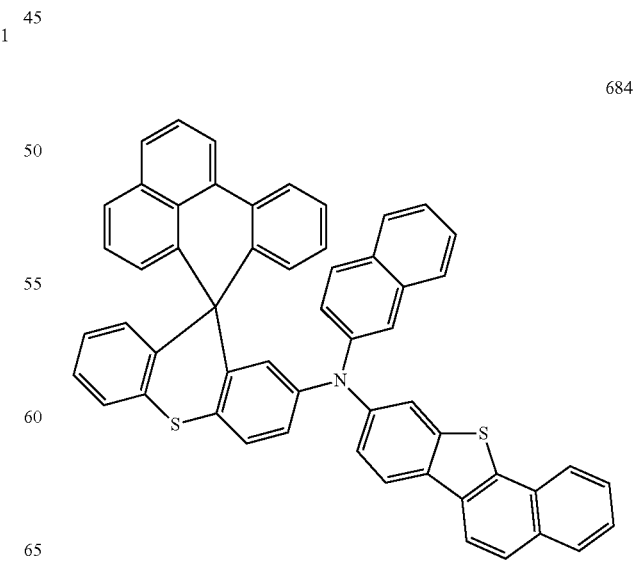

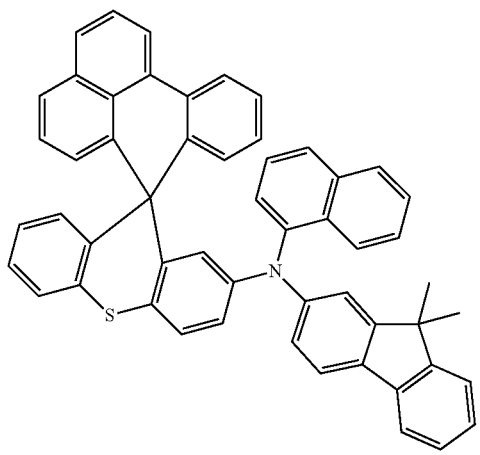
685
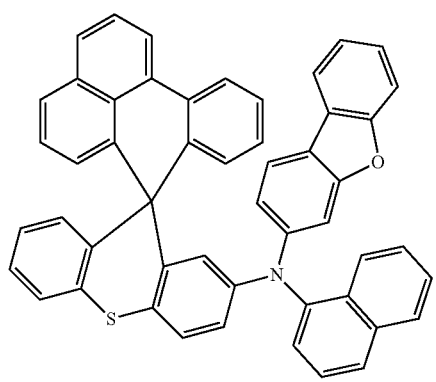
686
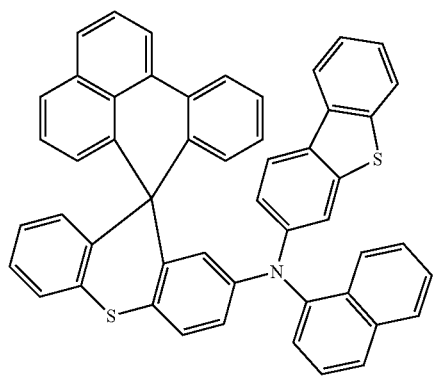
687
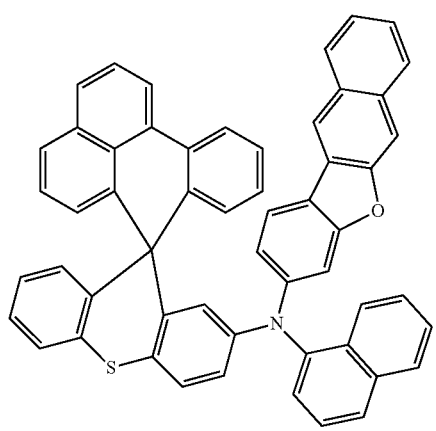
688
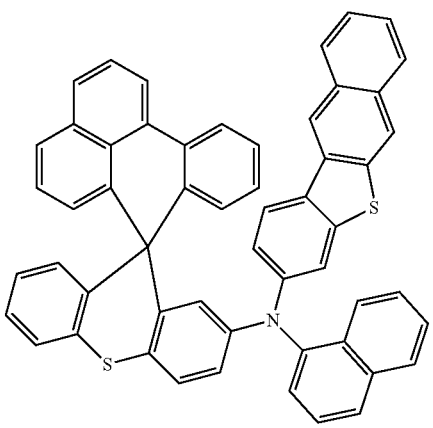
689
690
691

692
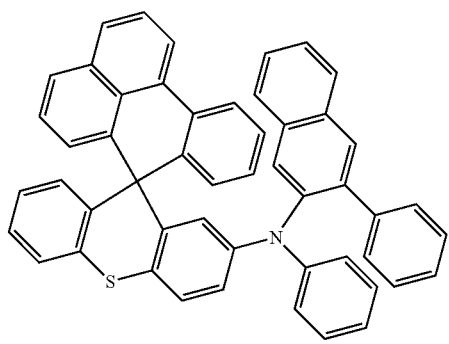
693
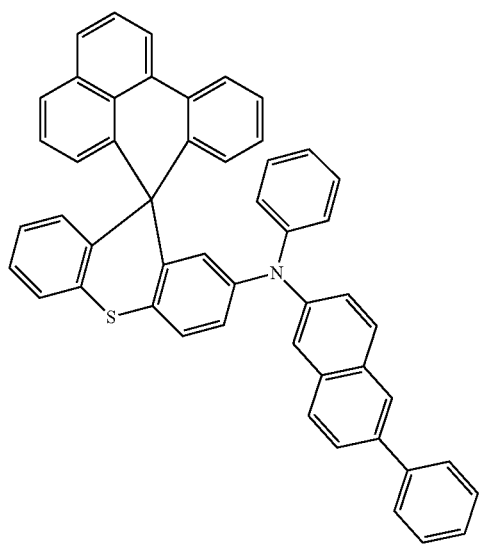
694
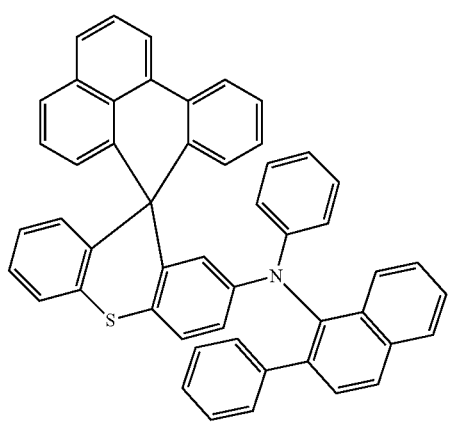
695
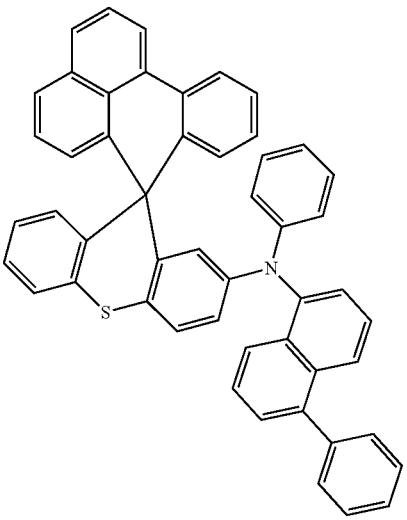
696
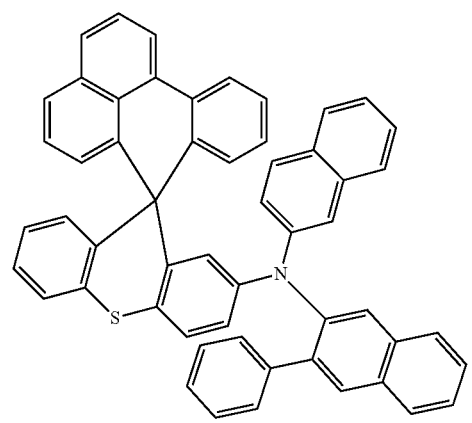
697
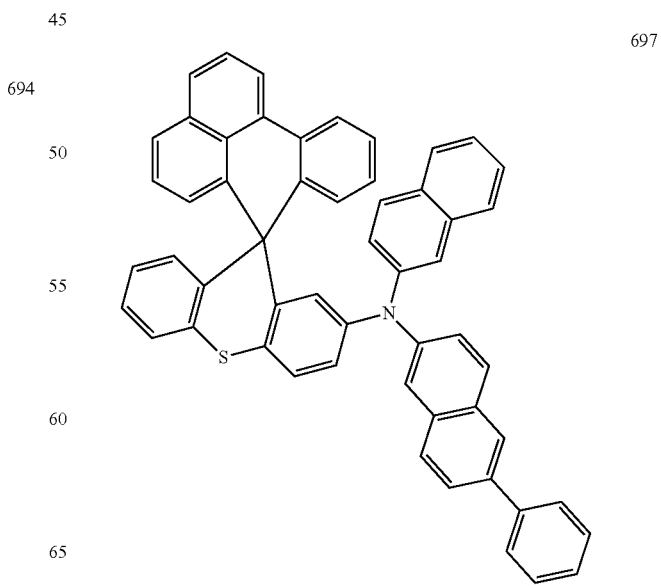

221
-continued
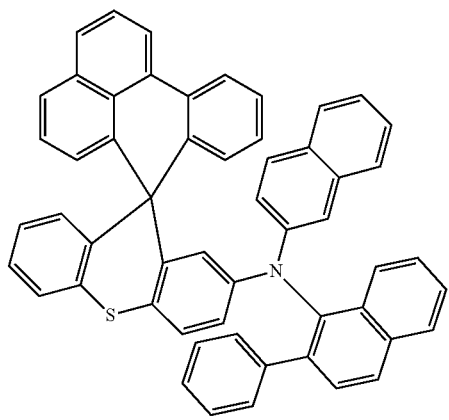
698
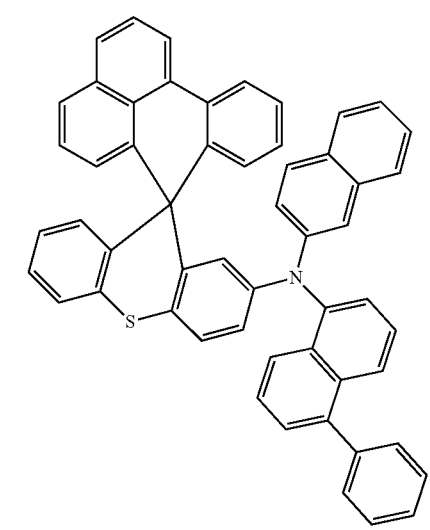
699
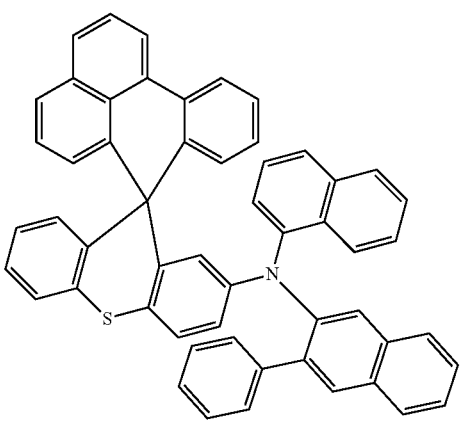
700
222
-continued
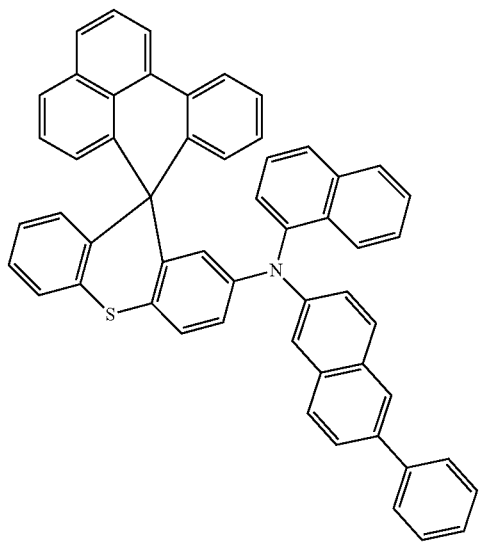
701
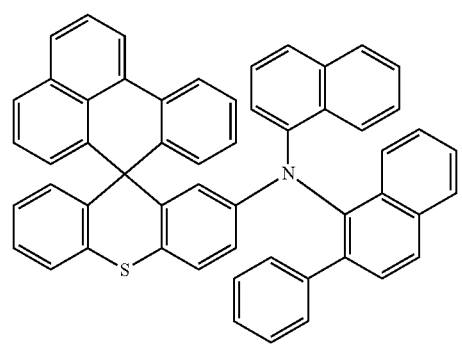
702
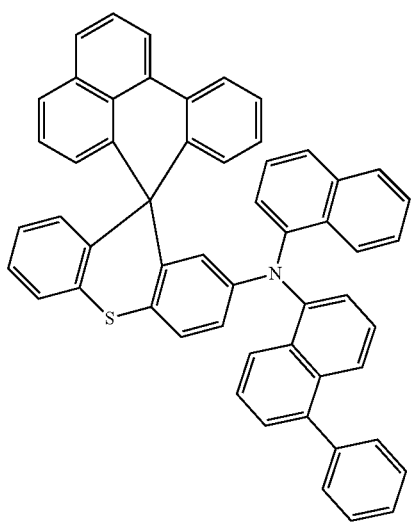
703

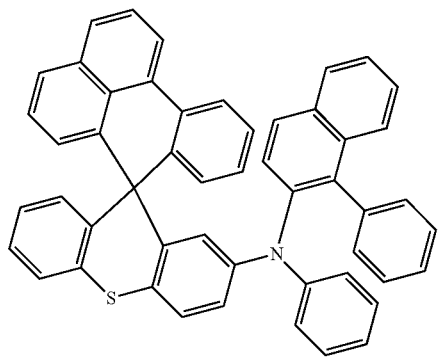
704
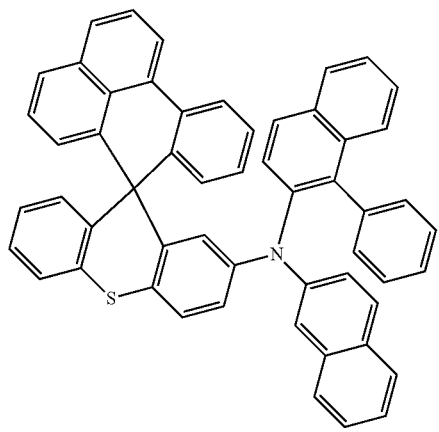
705
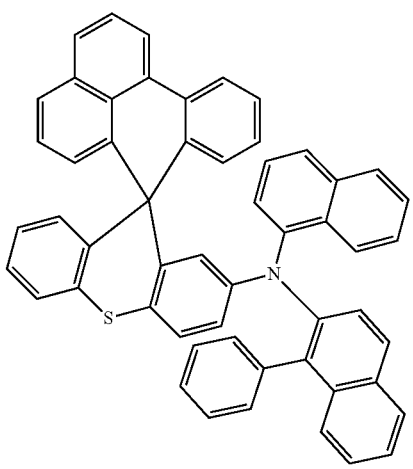
706
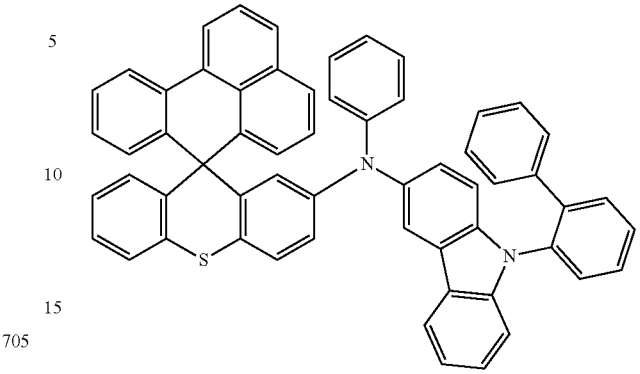
708
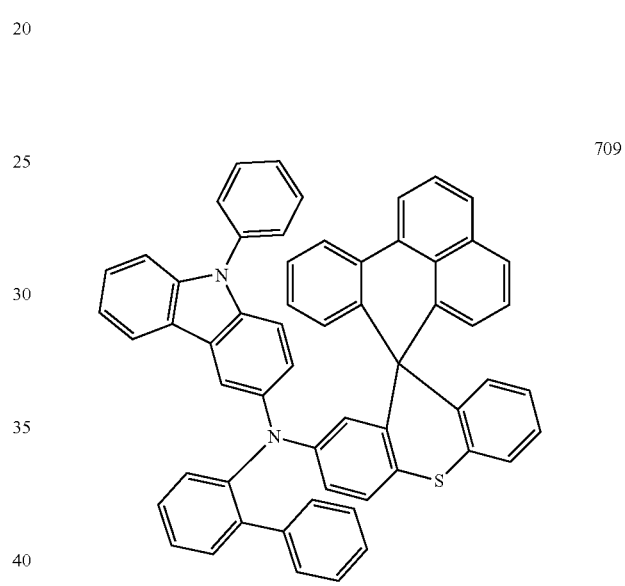
709
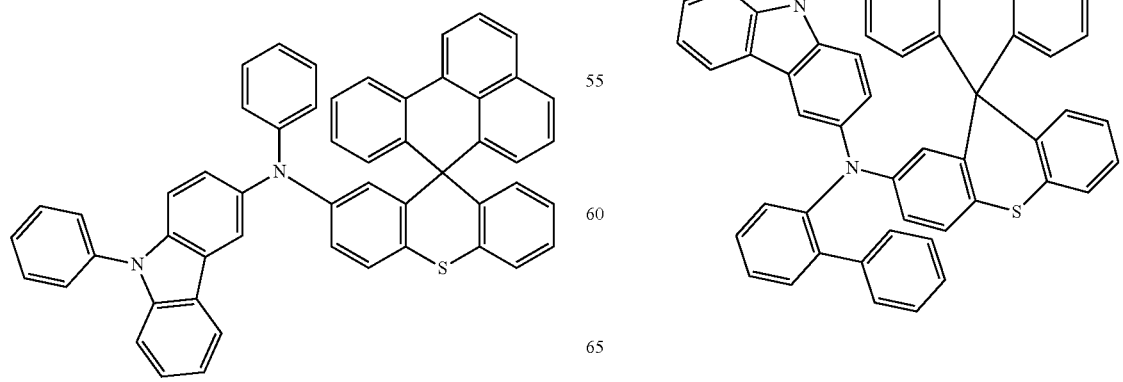
710

711
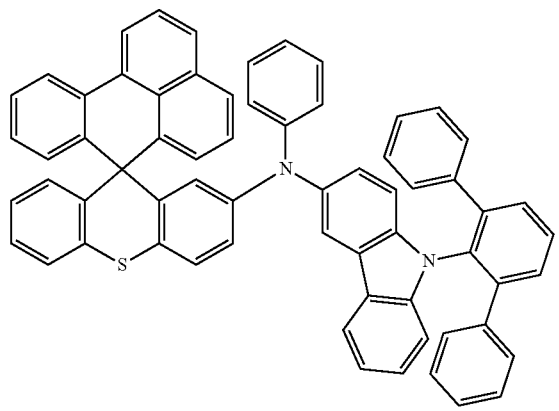
712
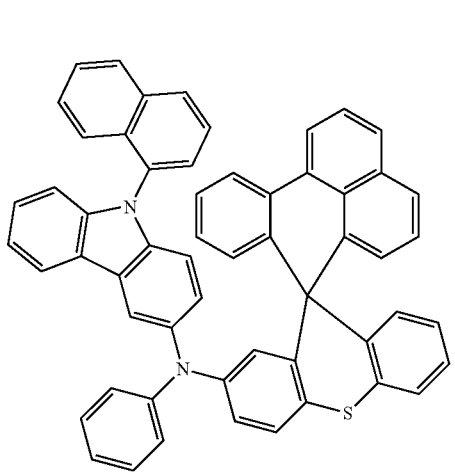
713
714
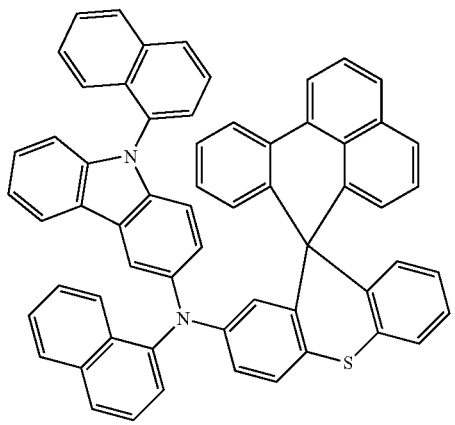
715
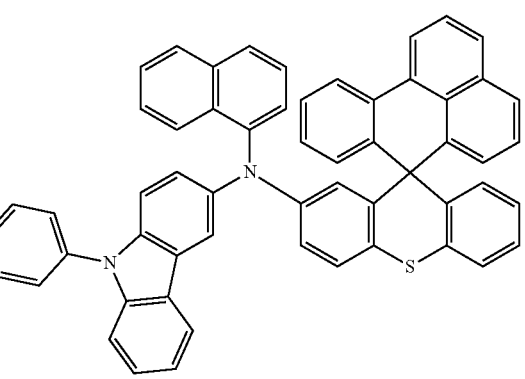
716
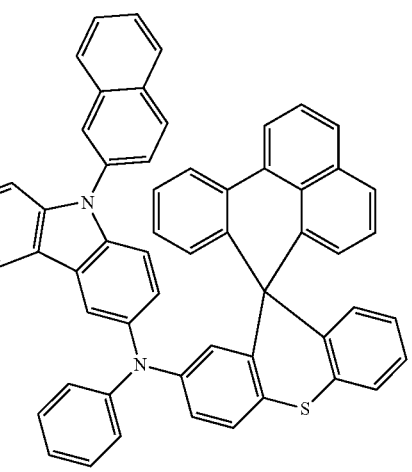

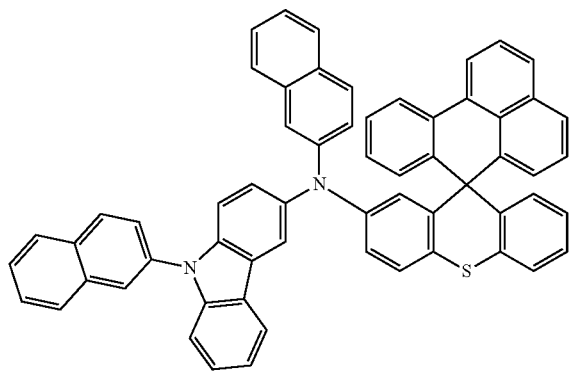
717
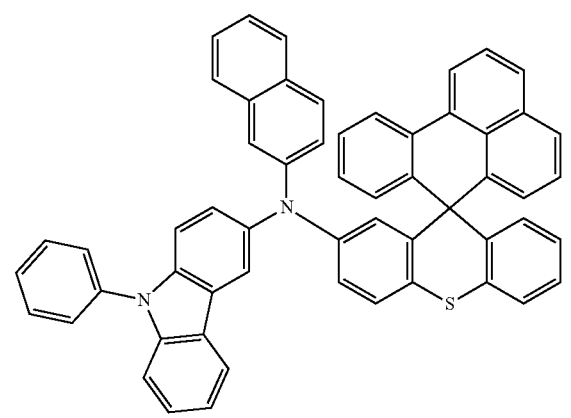
718
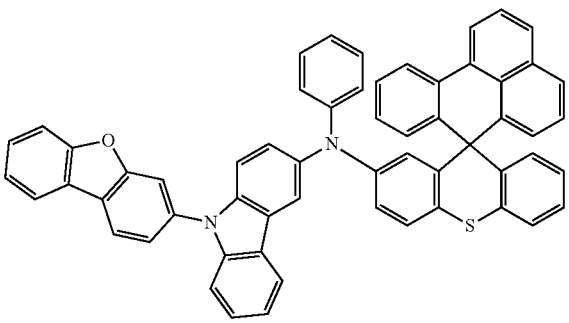
719
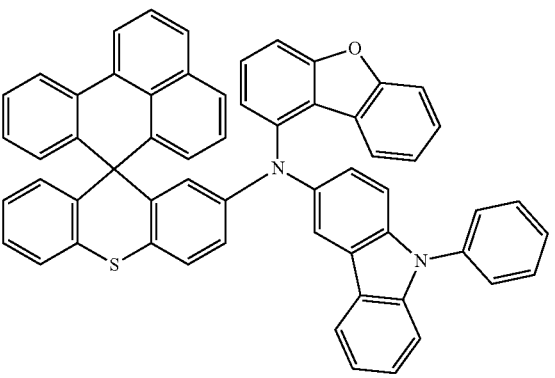
720
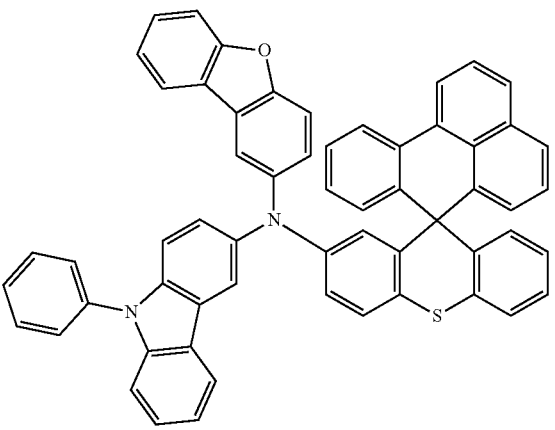
721
722
723

724
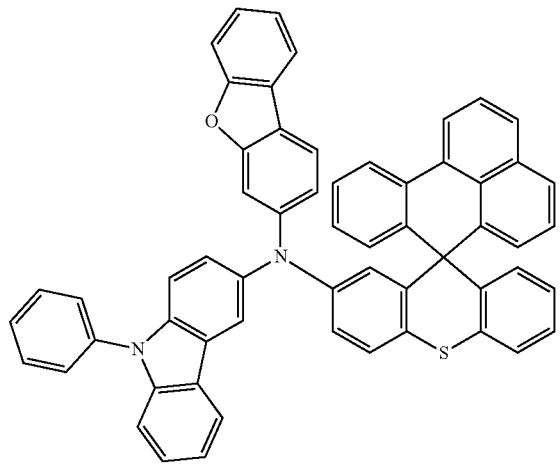
725
727
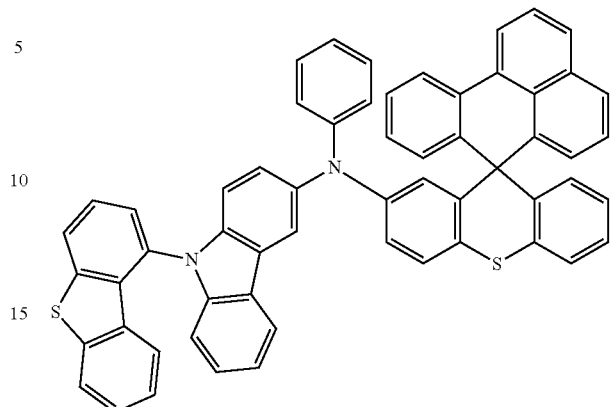
728
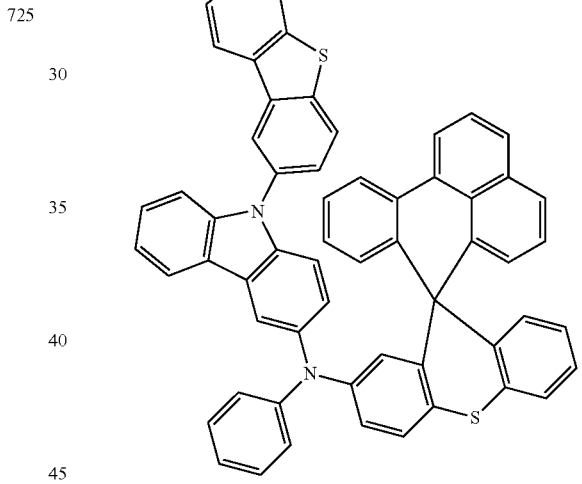
726
729
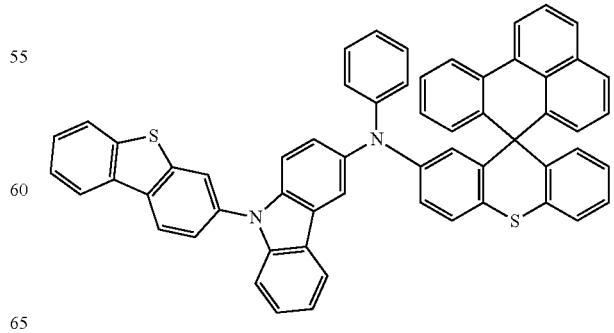

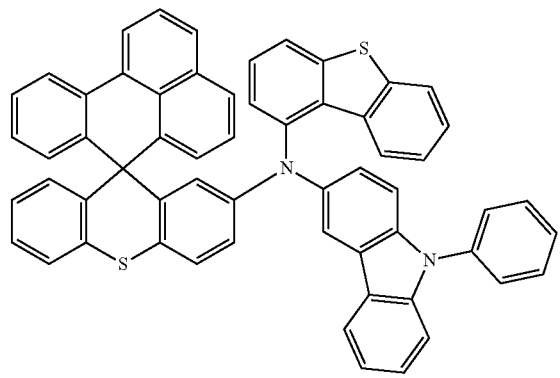
730
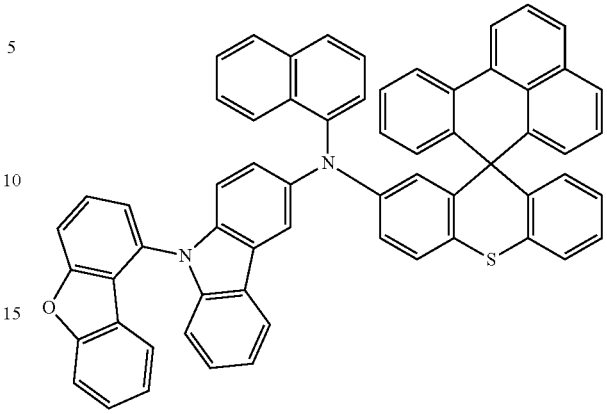
733
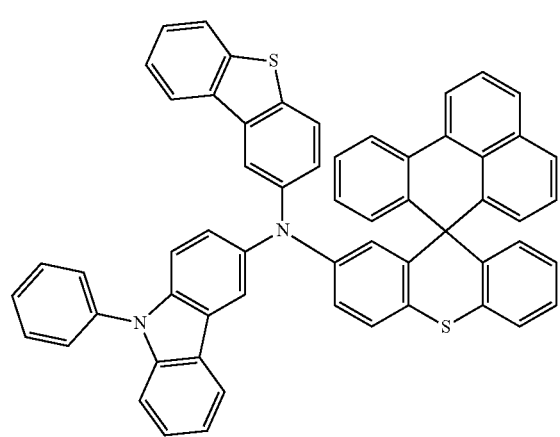
731
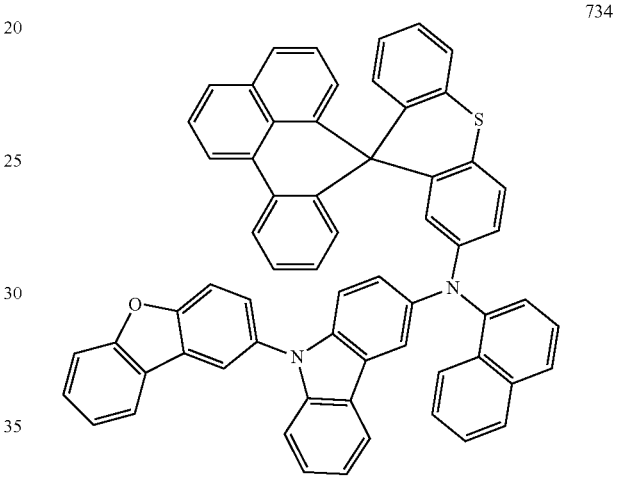
734
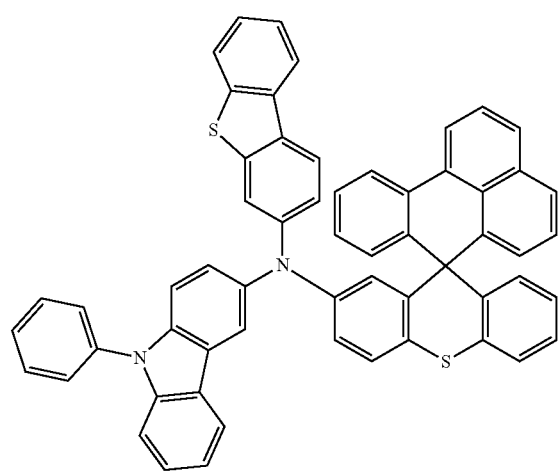
732
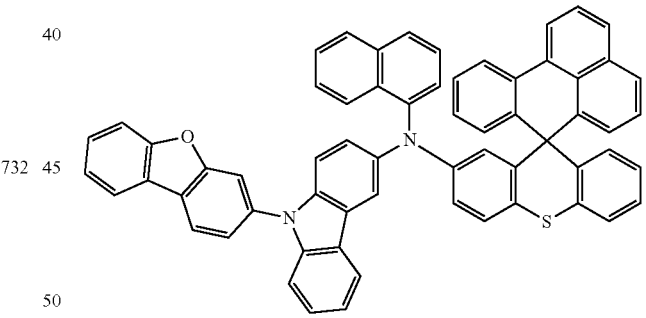
735
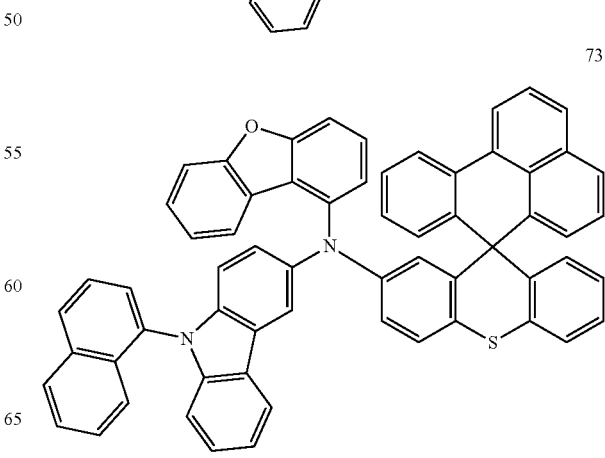
736

233
-continued
737
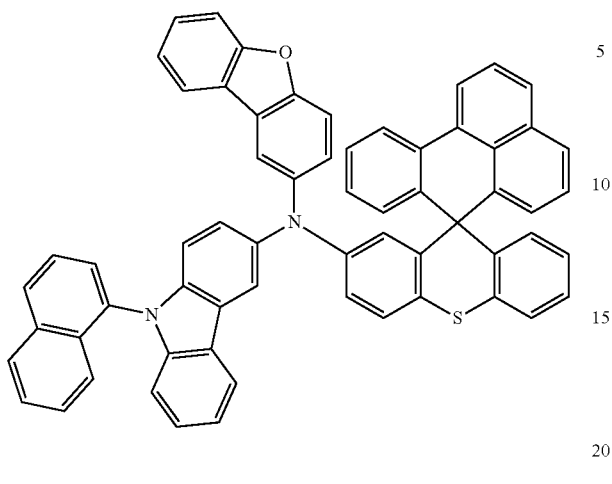
738
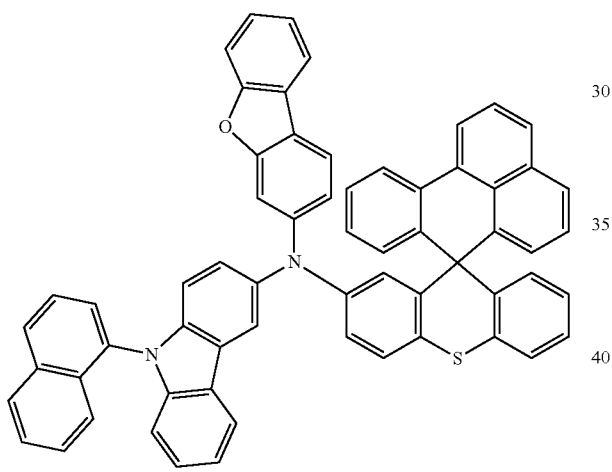
739
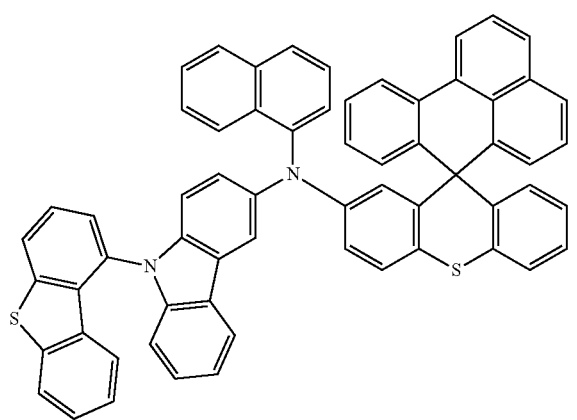
234
-continued
740
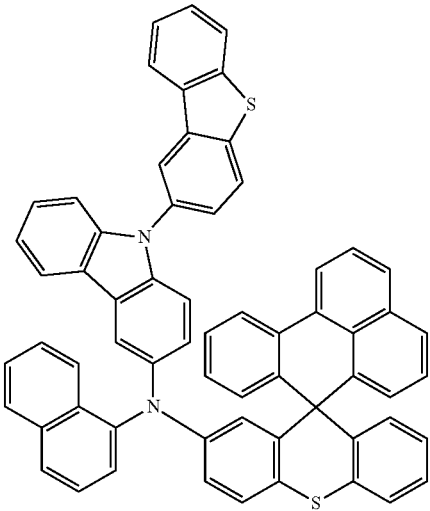
741
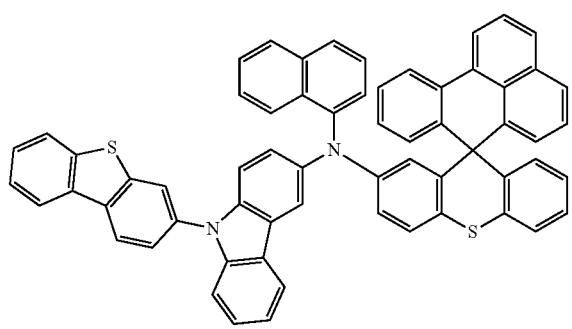
742
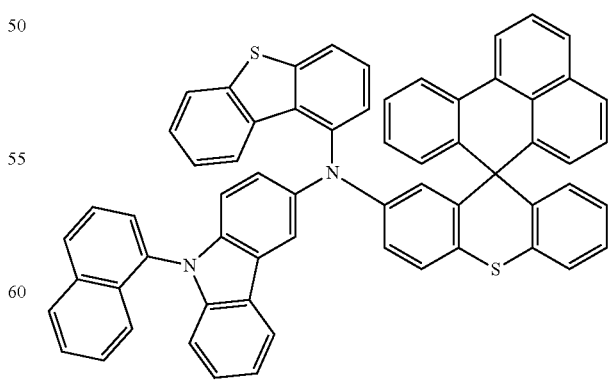

743
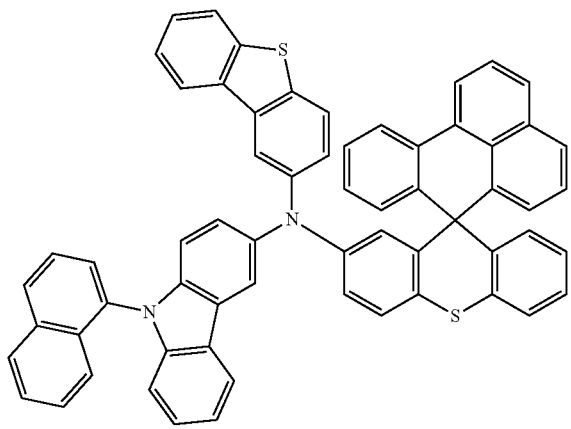
744
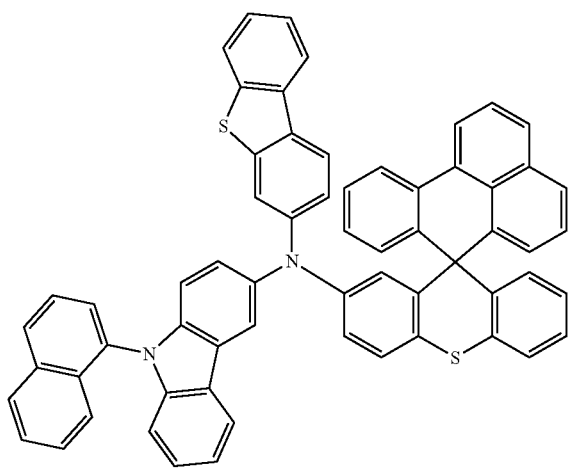
745
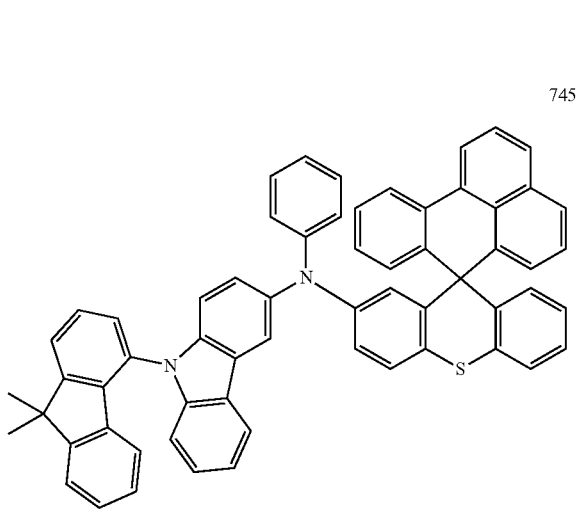
746
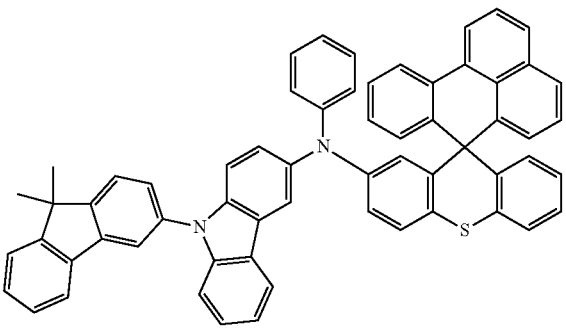
747
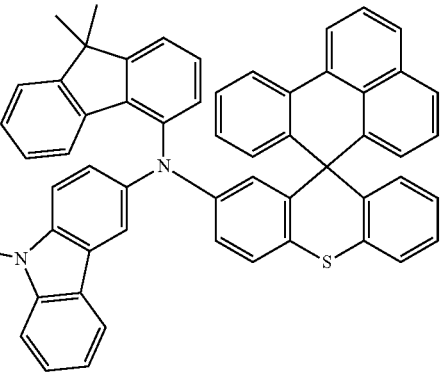
748
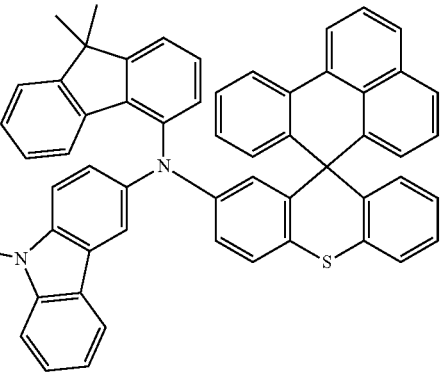
749
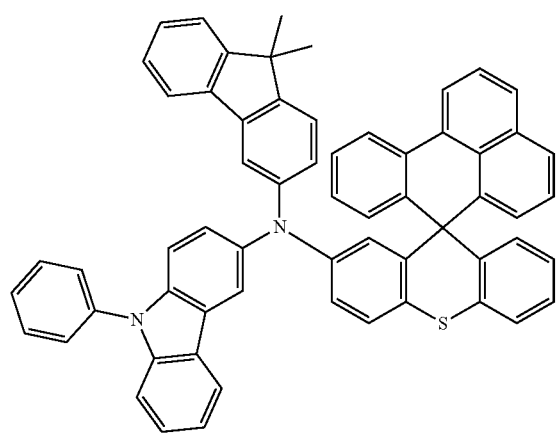

750
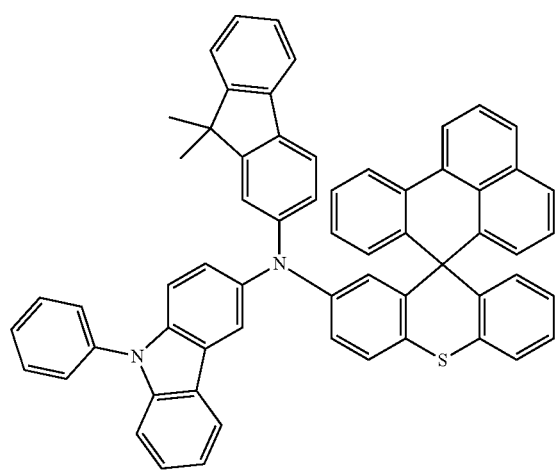
751
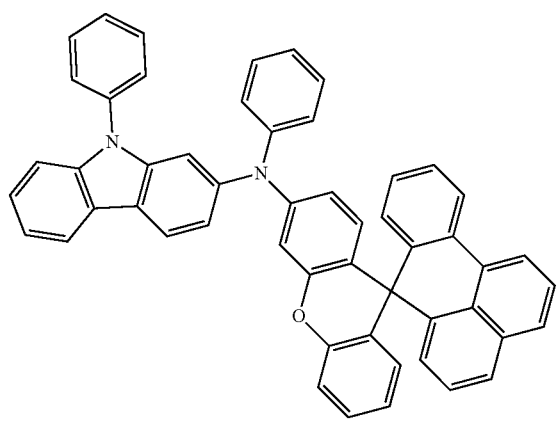
752
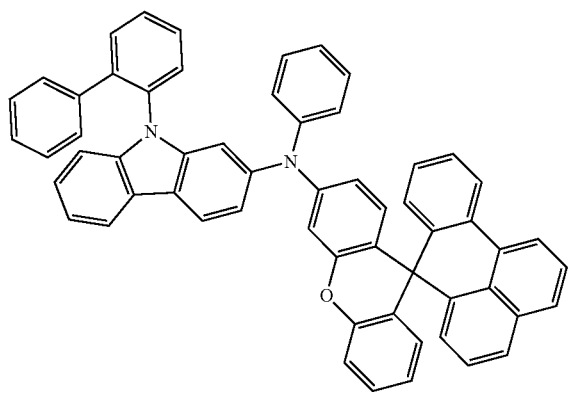
753
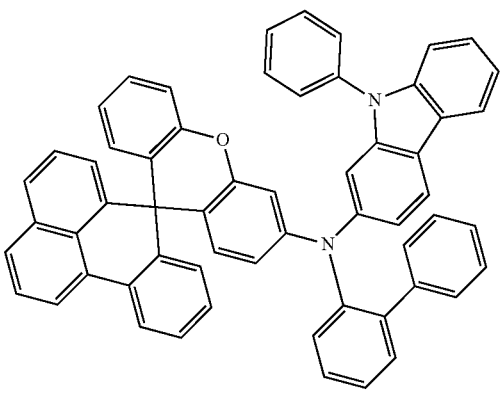
754
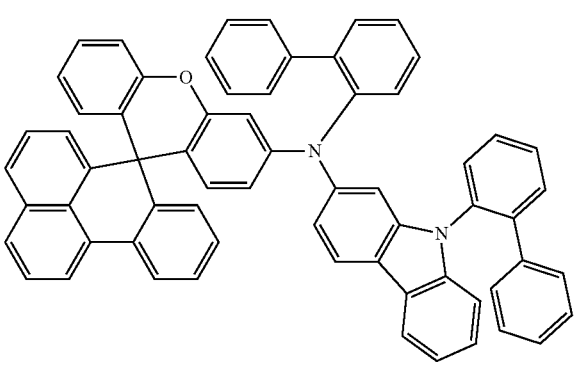
755
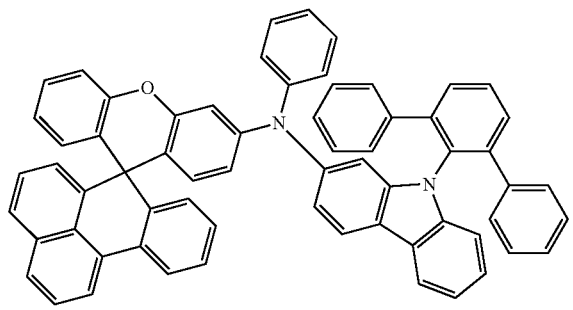
756
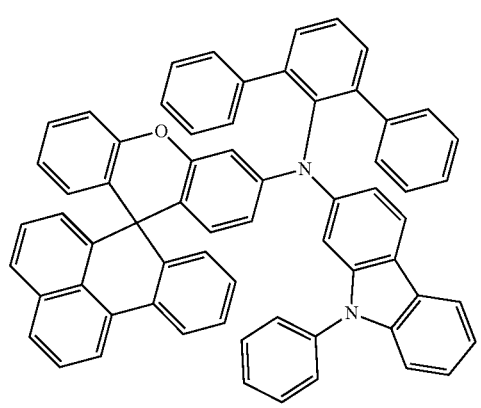

239
-continued
757
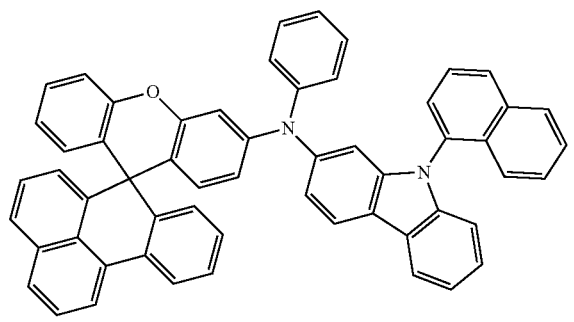
758
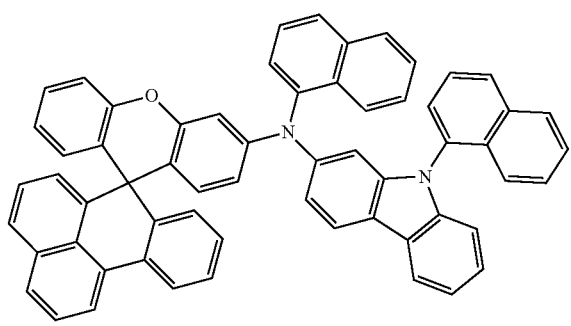
759
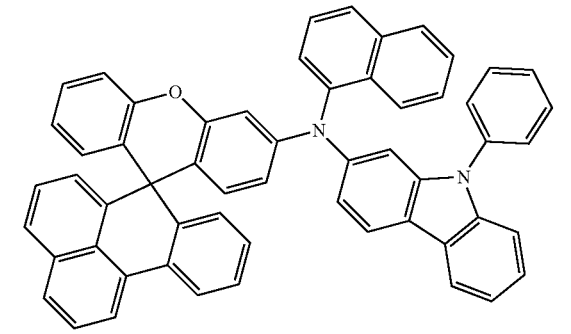
760
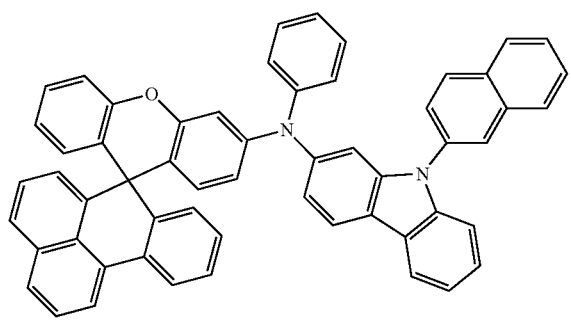
240
-continued
761
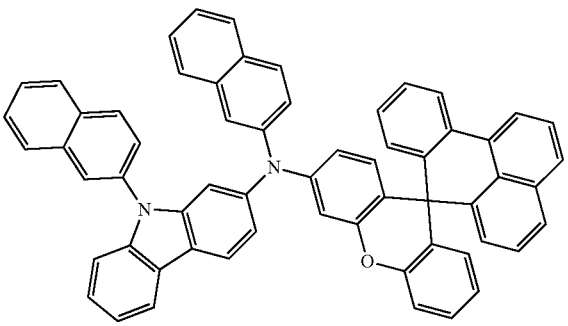
762
763
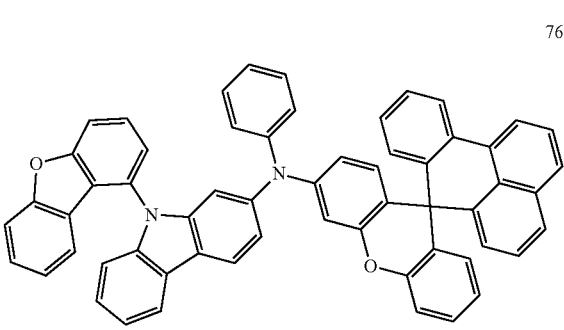
764
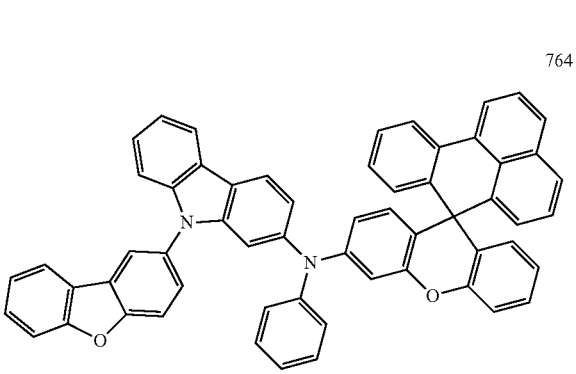

765
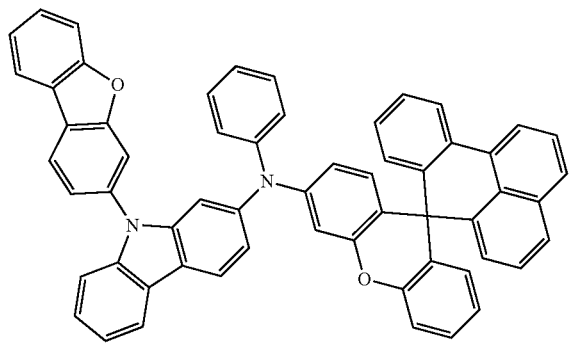
766
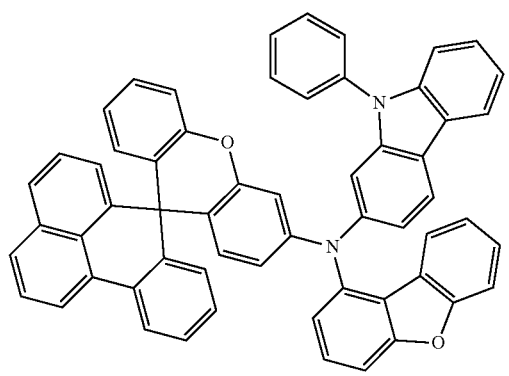
767
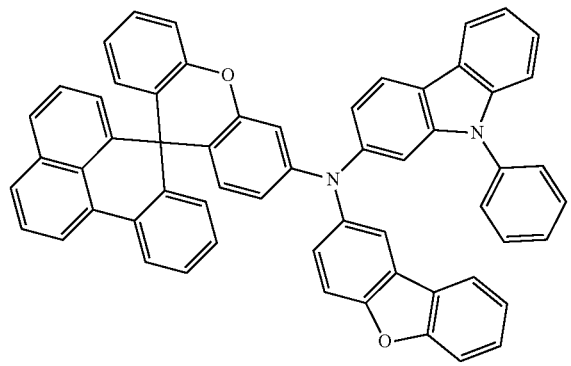
768
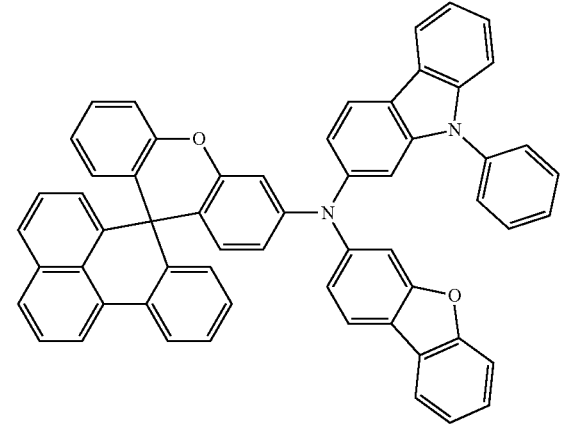
769
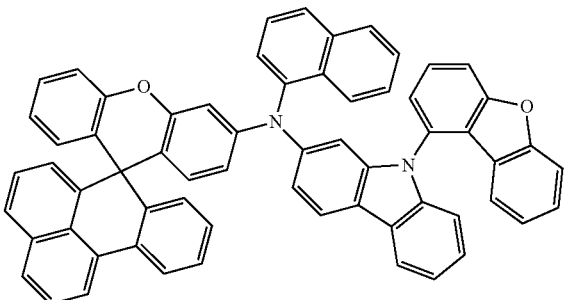
770
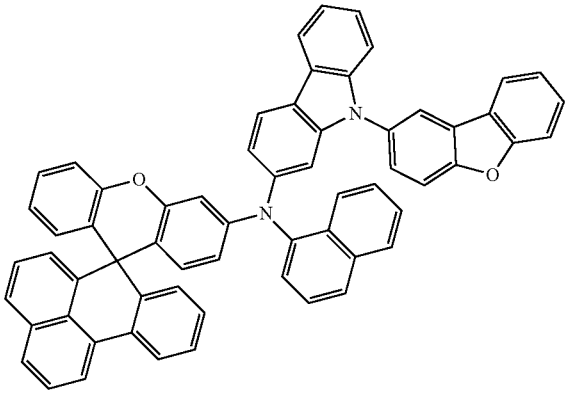
771
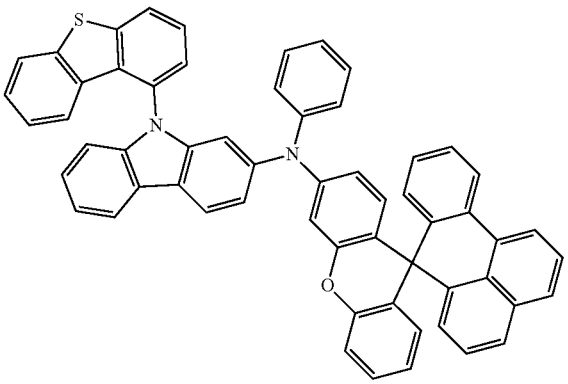
772
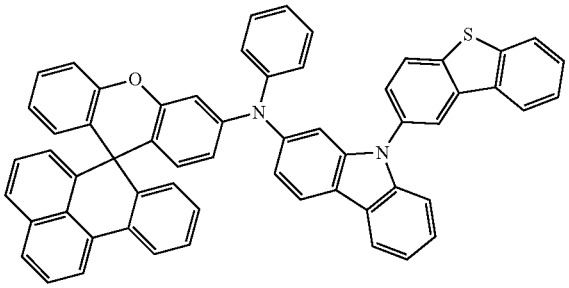

-continued
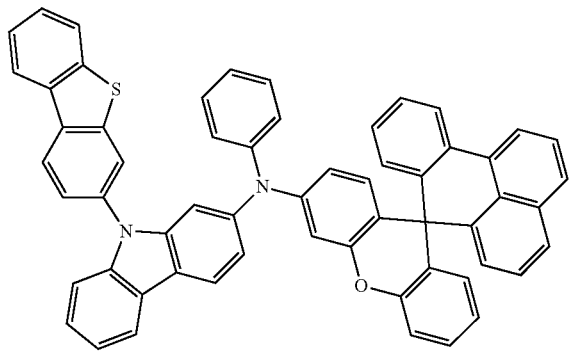
773
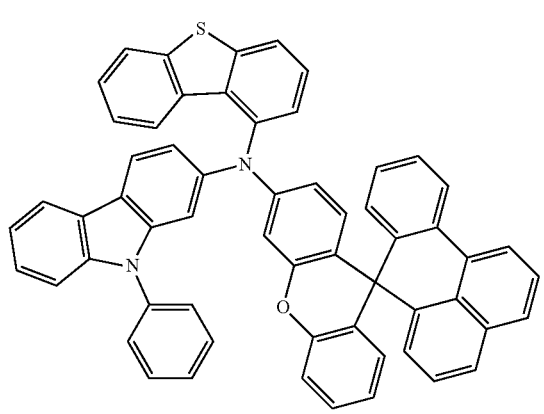
774
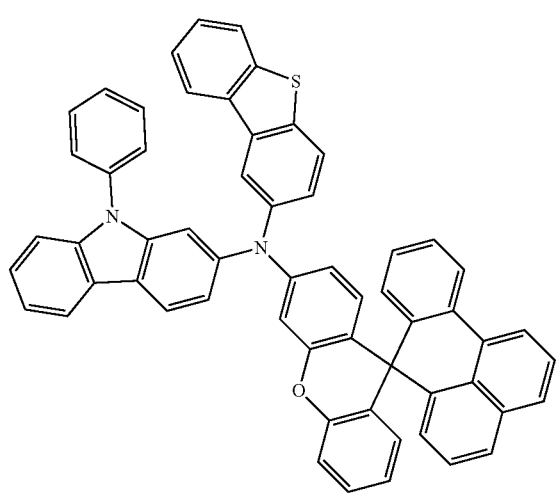
775
-continued
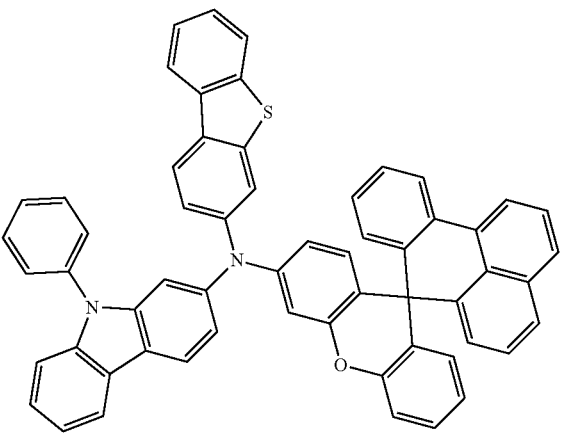
776
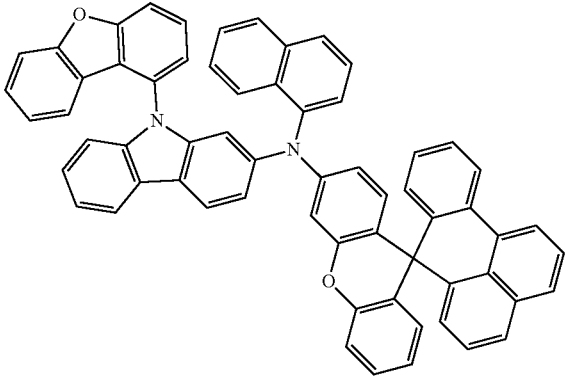
777
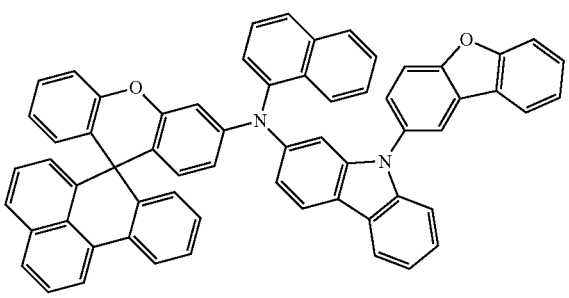
778

779
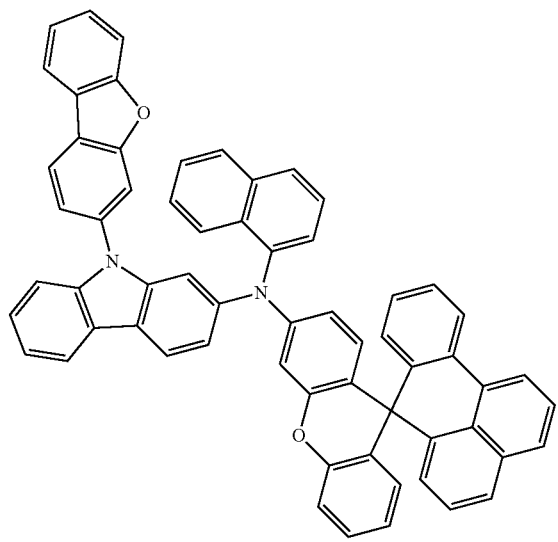
780
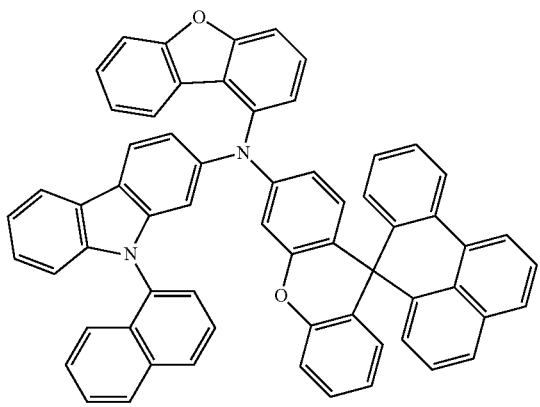
781
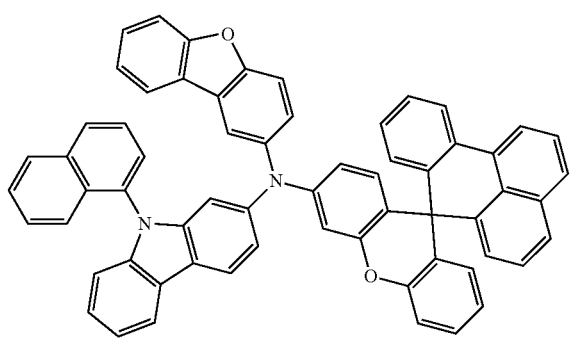
782
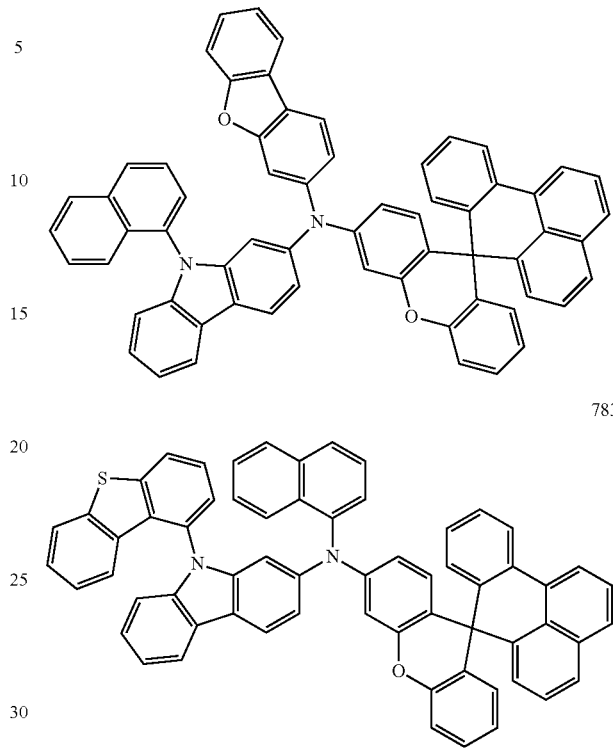
783
784
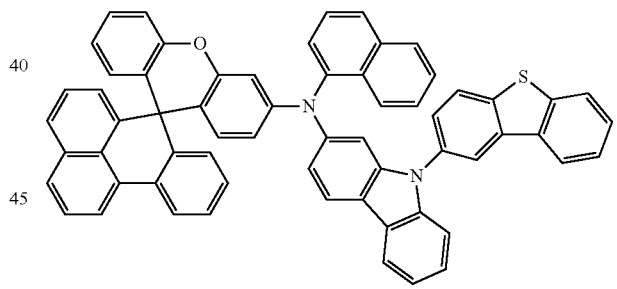
785
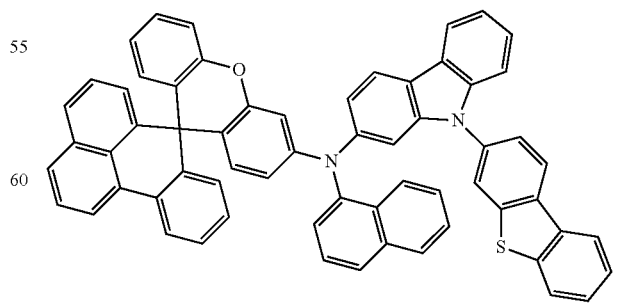

786
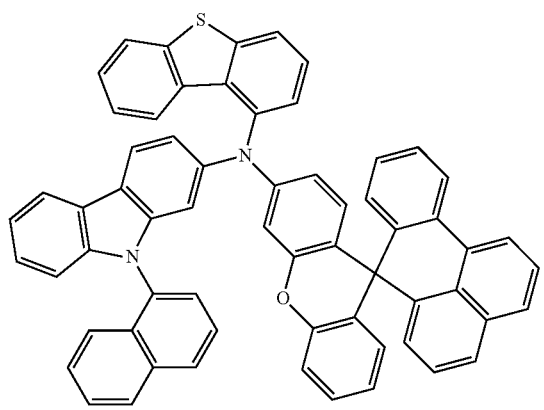
787
788
789
790
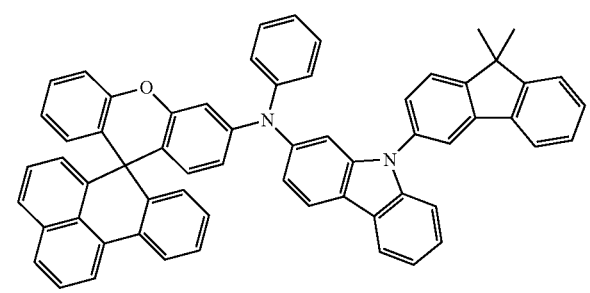
791
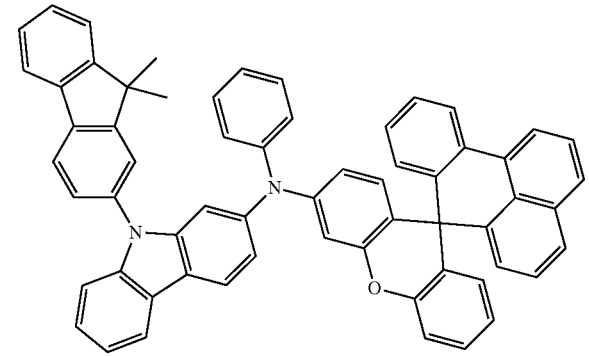
792
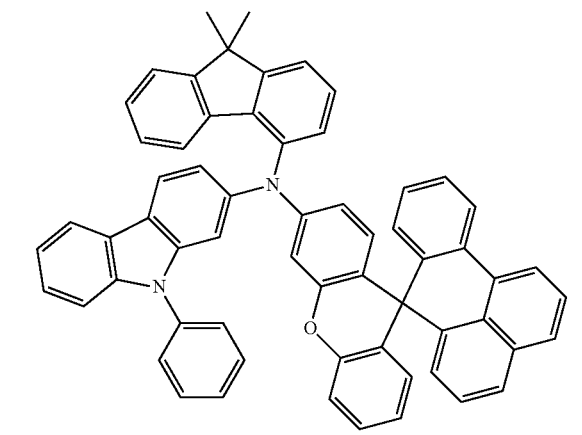
793
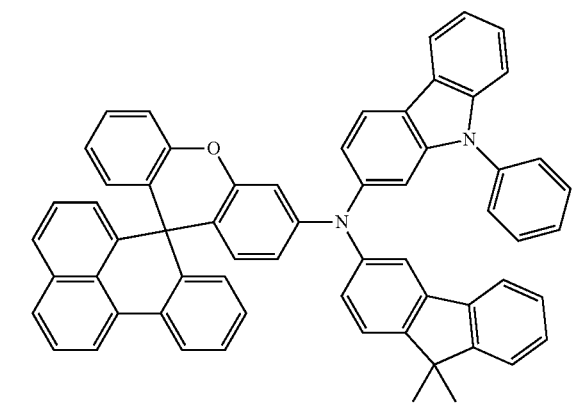

794
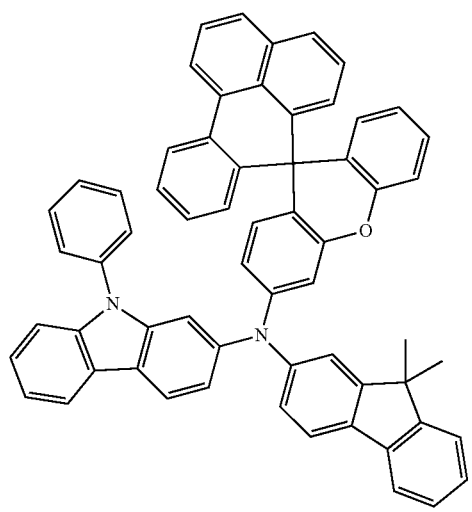
795
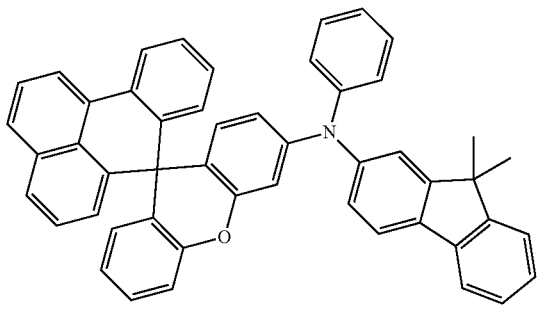
796
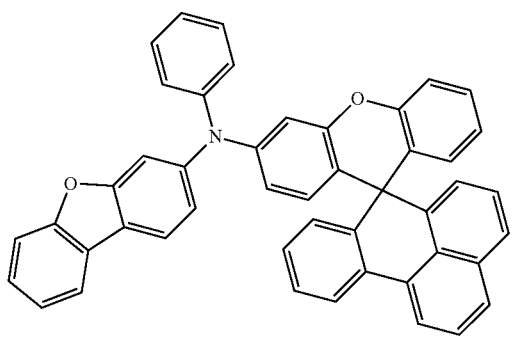
797
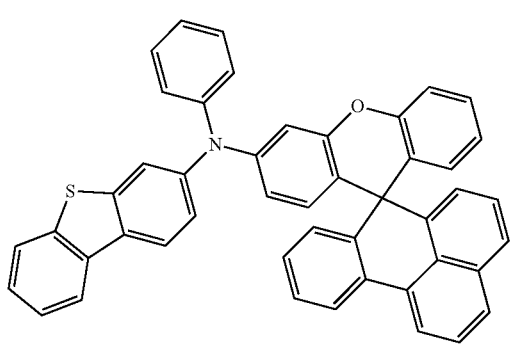
798
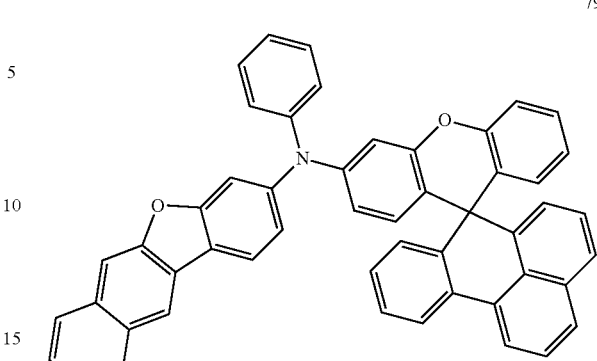
799
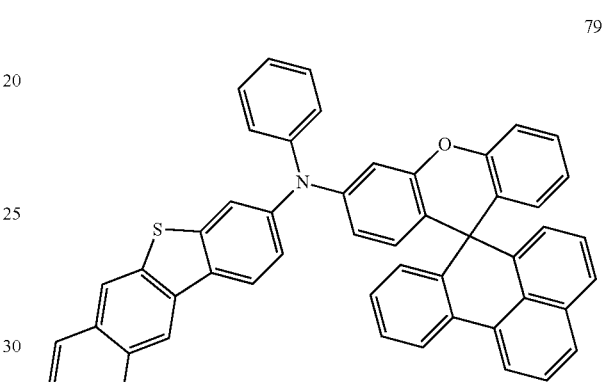
800
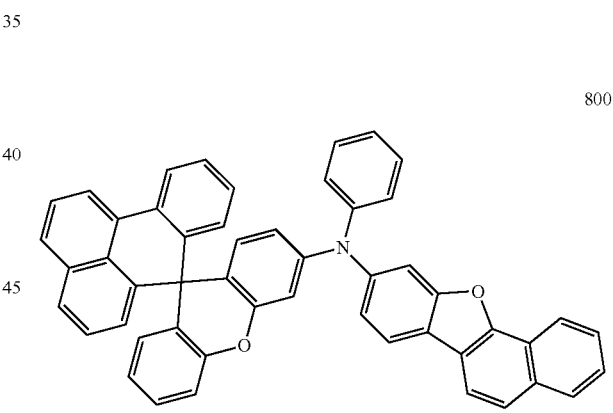
801
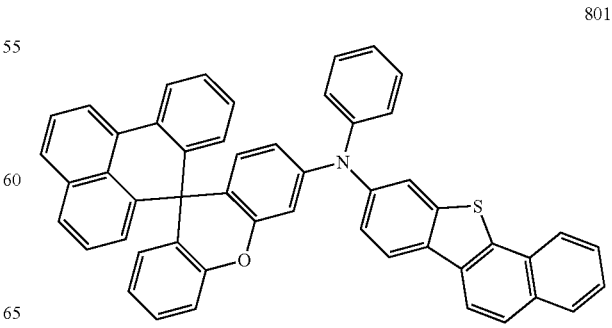

-continued
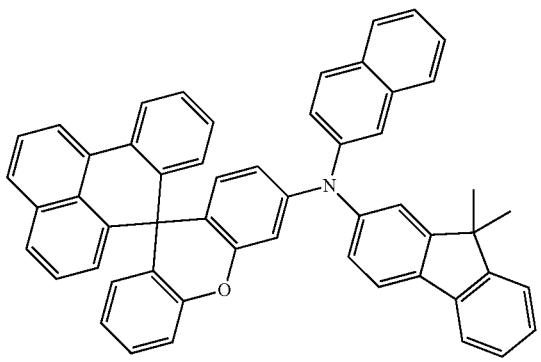
802
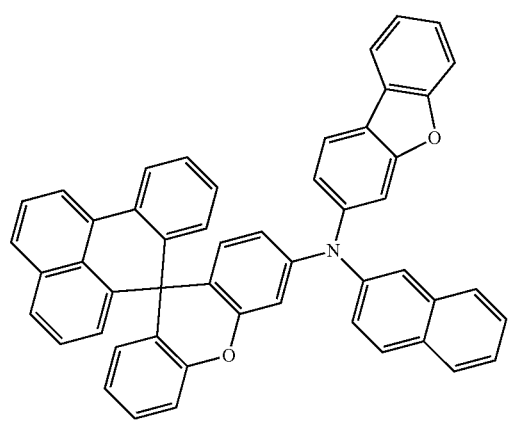
803
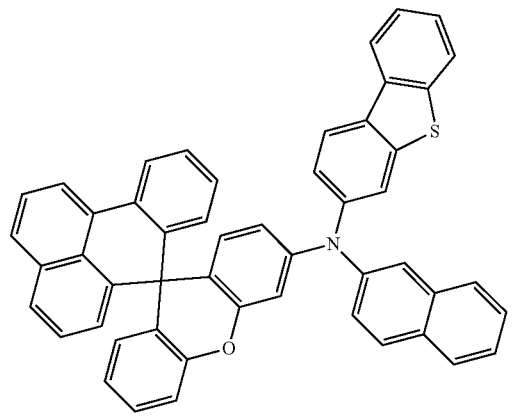
804
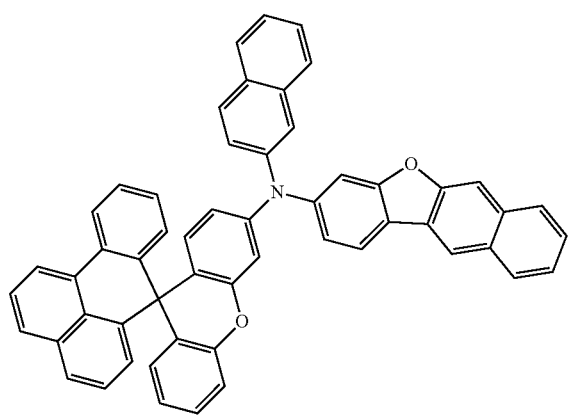
805
-continued
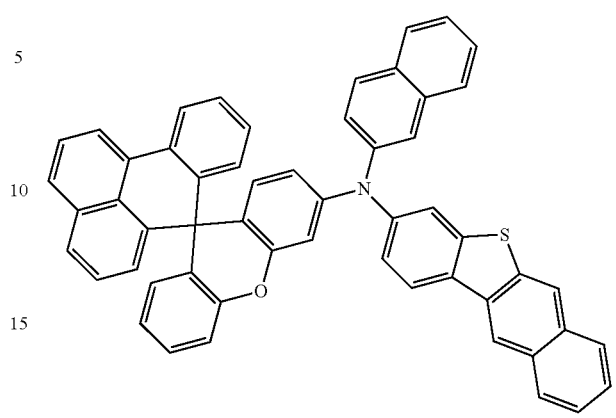
806
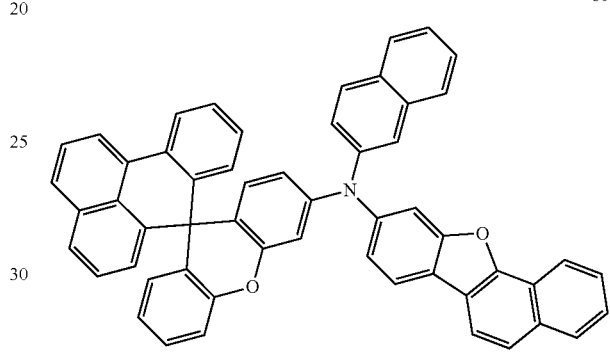
807
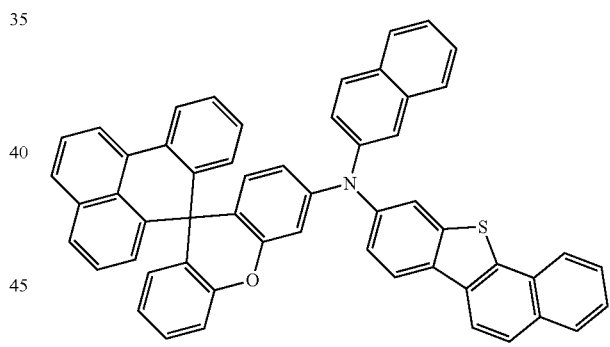
808
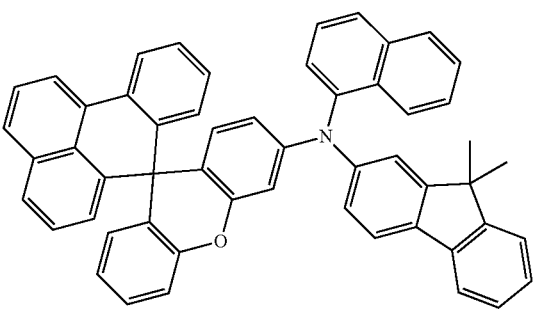
809

810
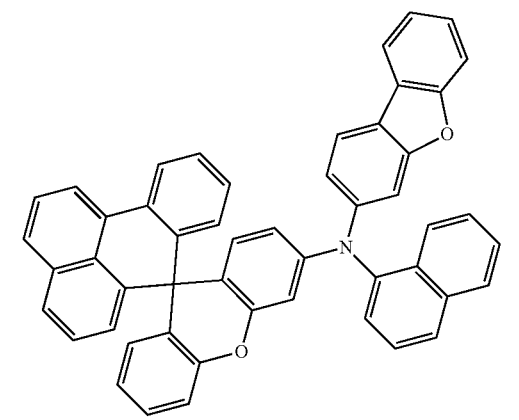
811
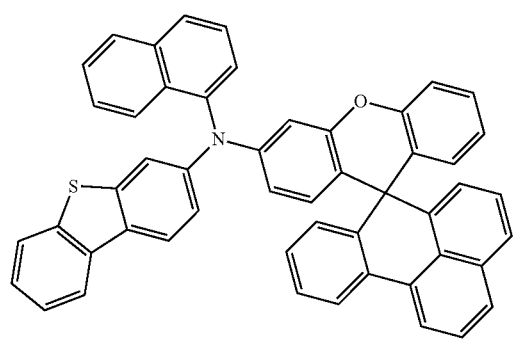
812
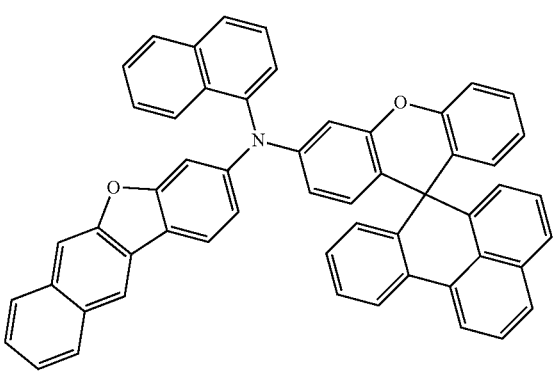
813
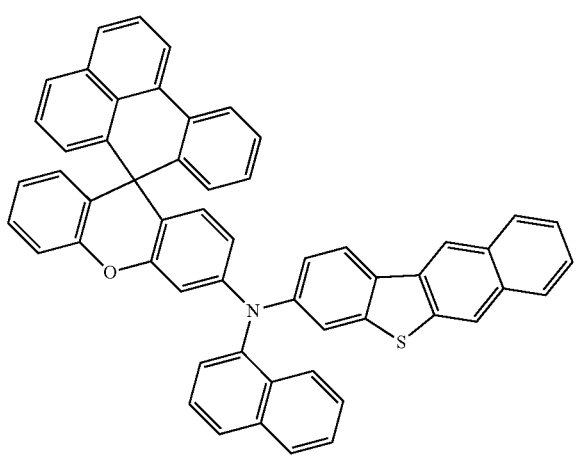
814
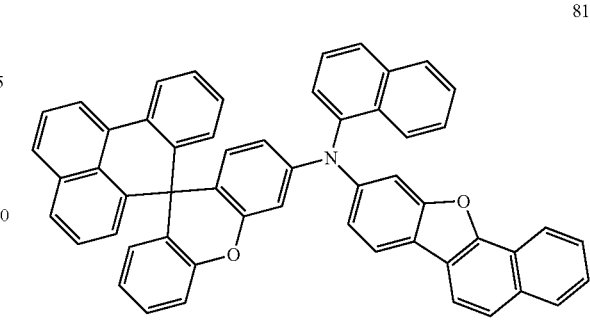
815
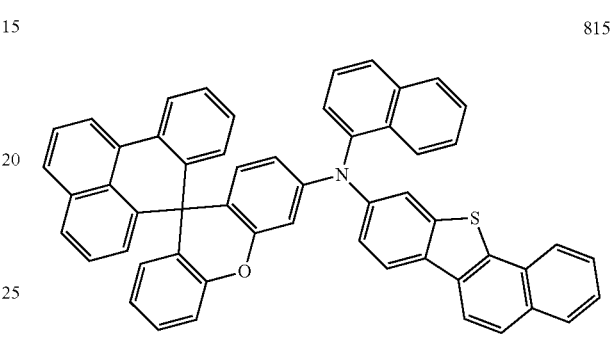
816
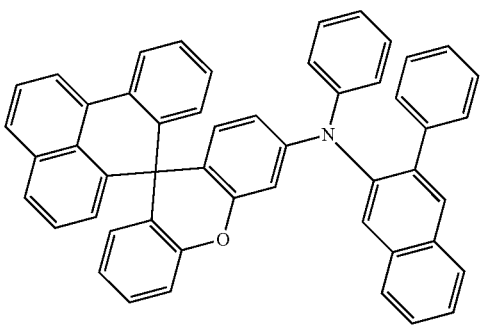
817
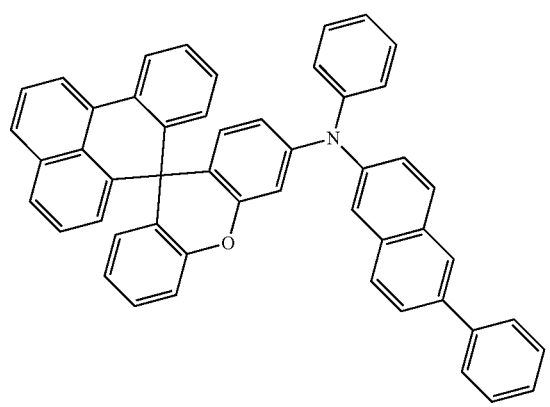

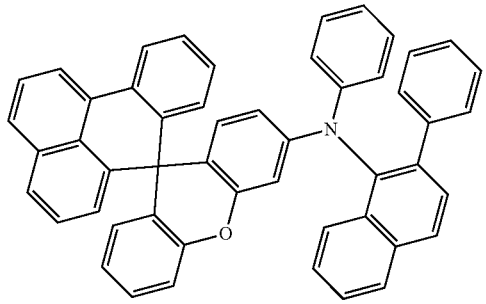
818
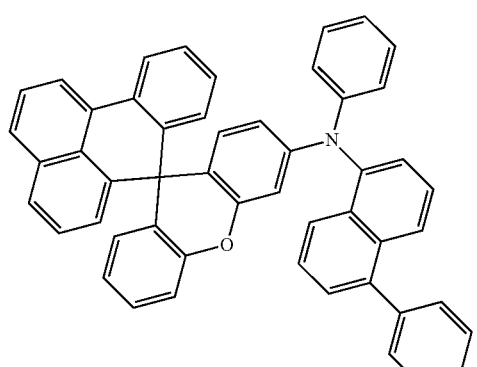
819
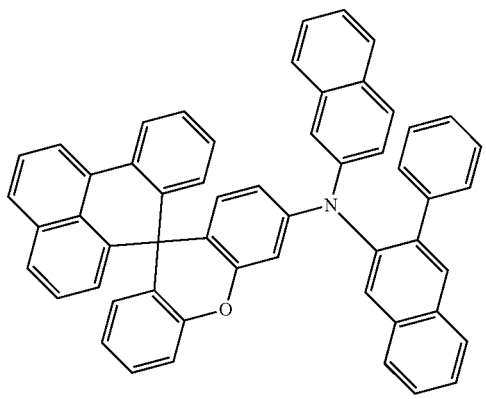
820
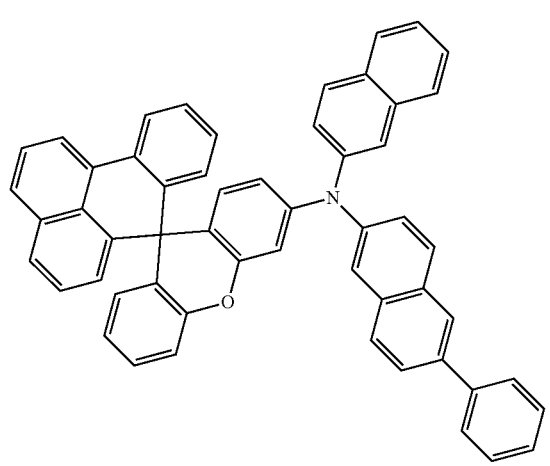
821
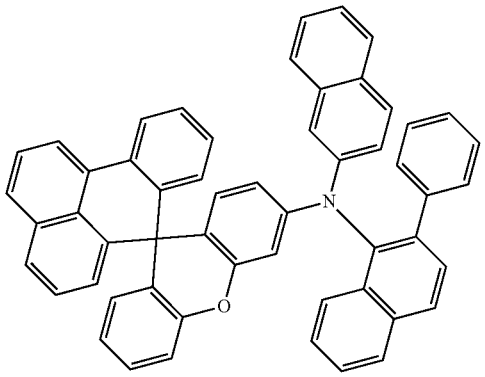
822
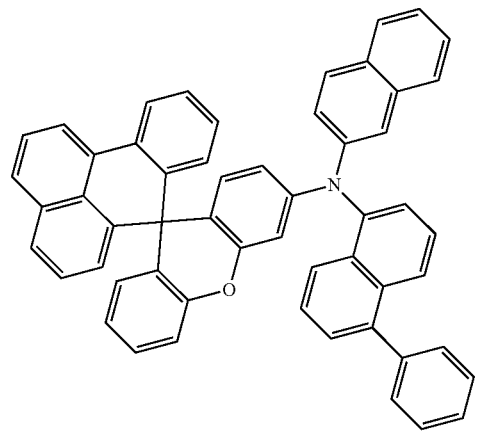
823
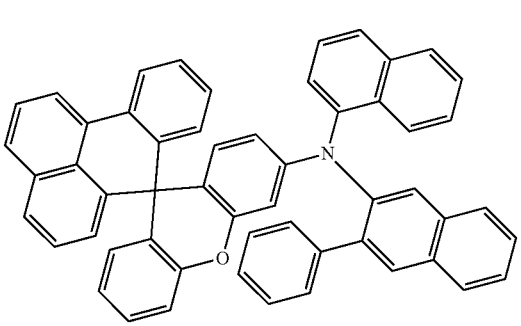
824
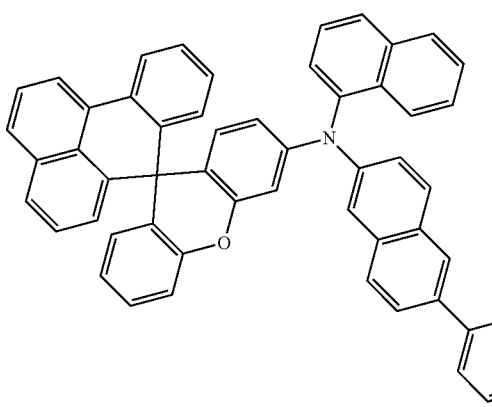
825

826
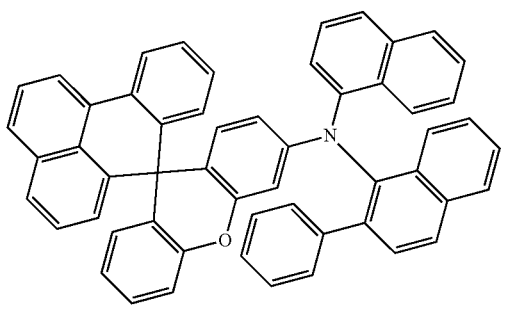
827
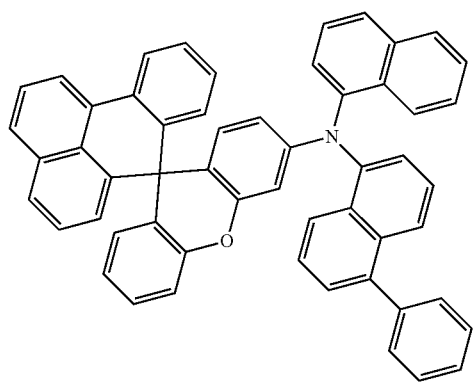
828
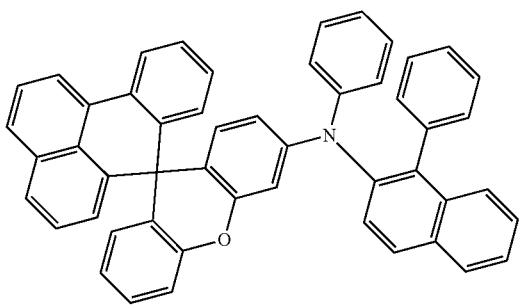
829
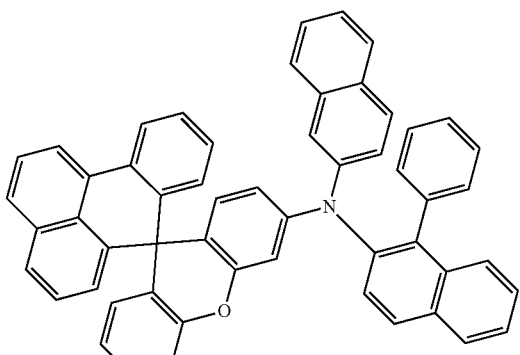
830
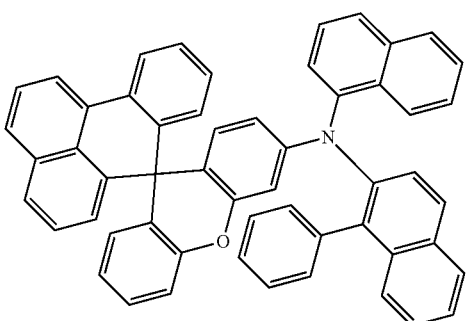
831
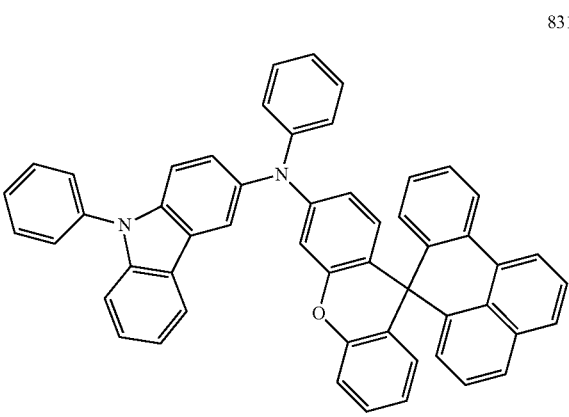
832
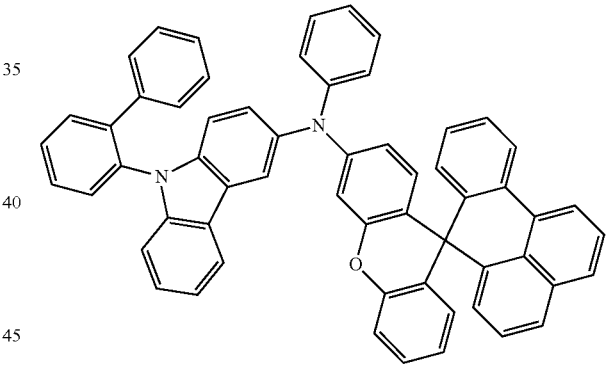
833
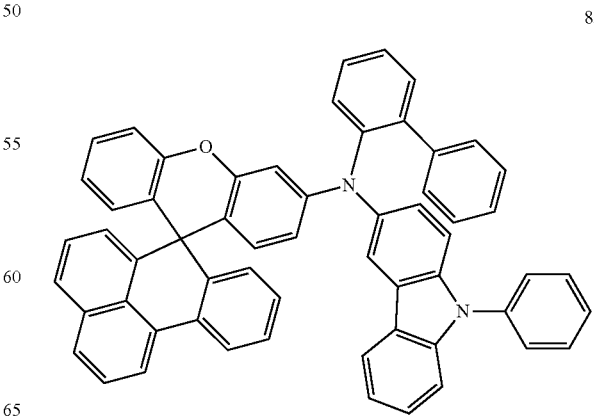

834
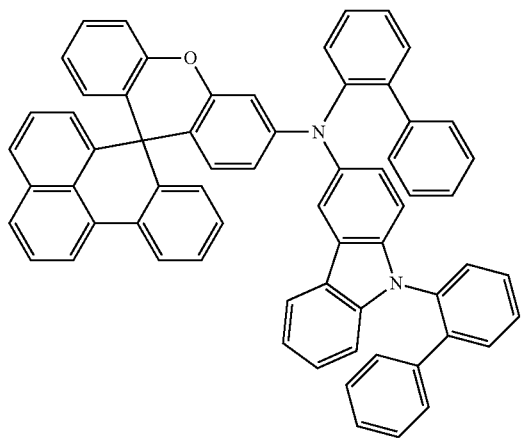
835
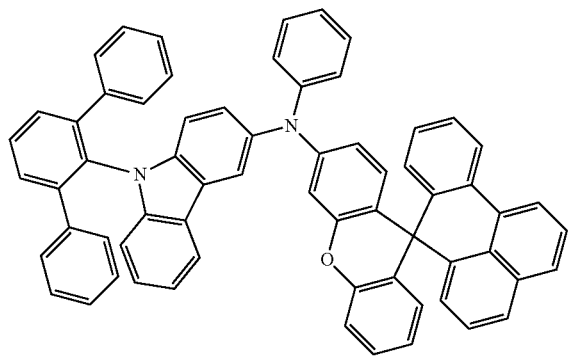
836
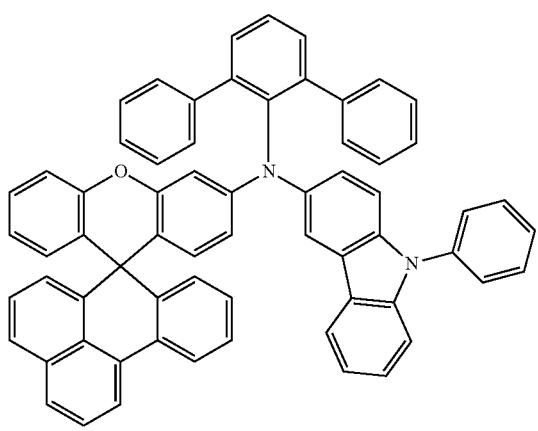
837
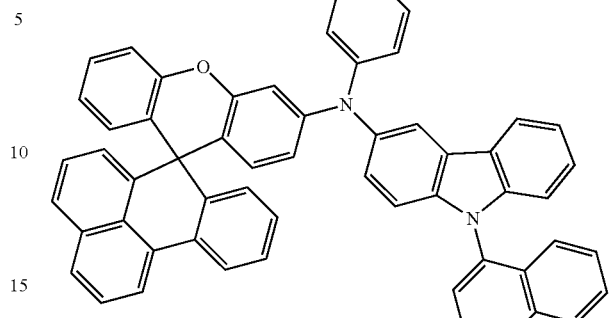
838
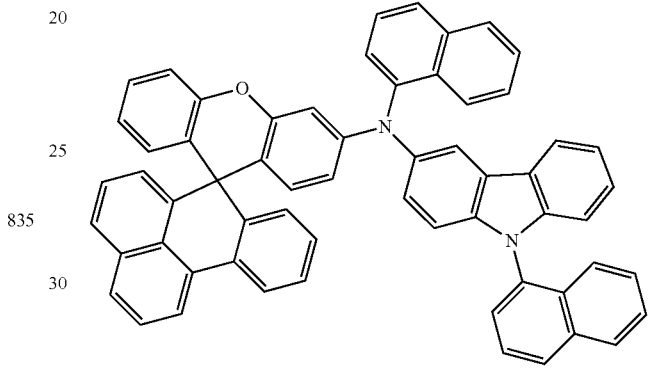
839
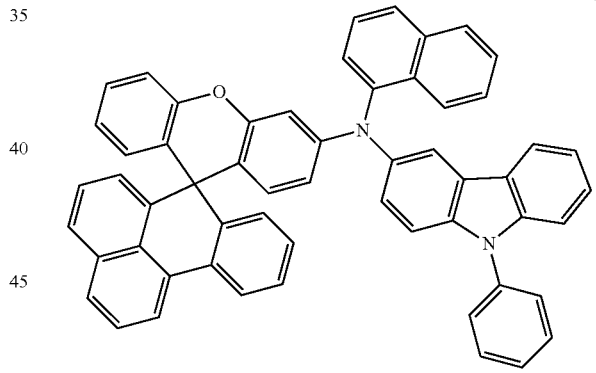
840
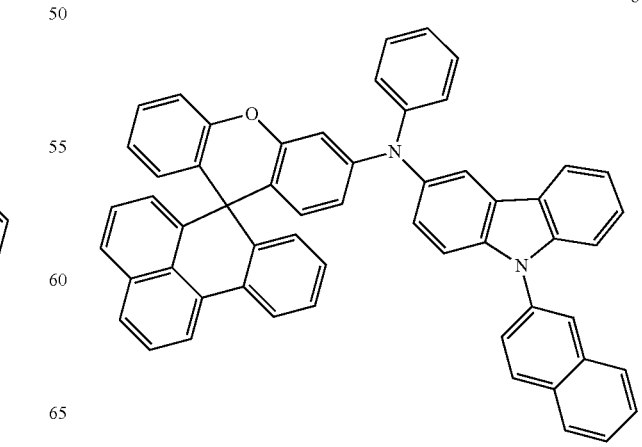

841
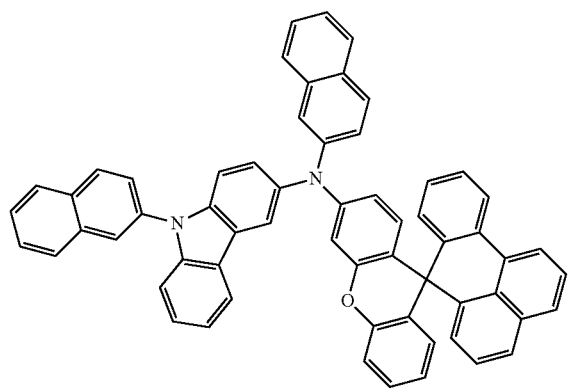
842
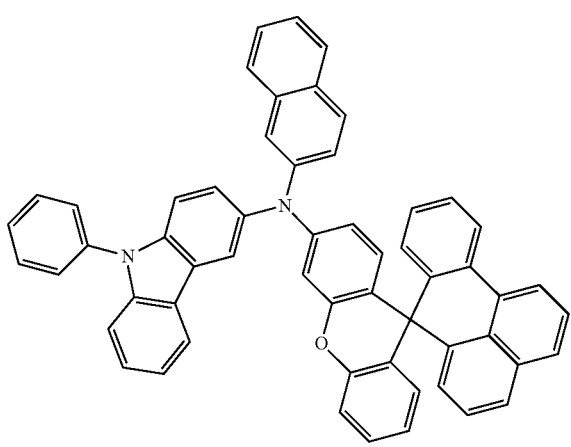
843
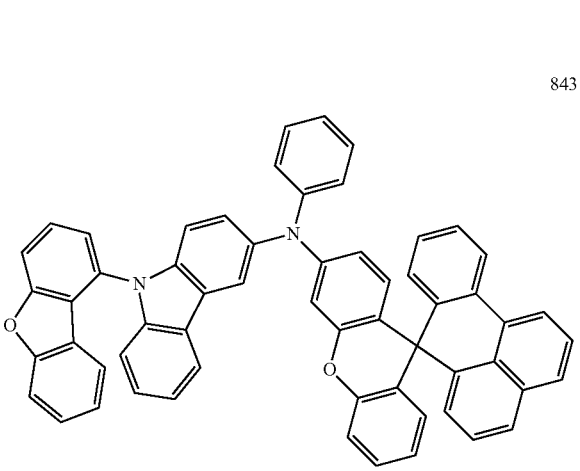
844
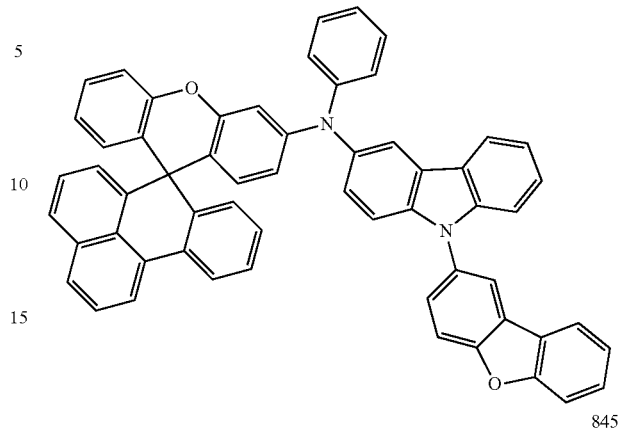
845
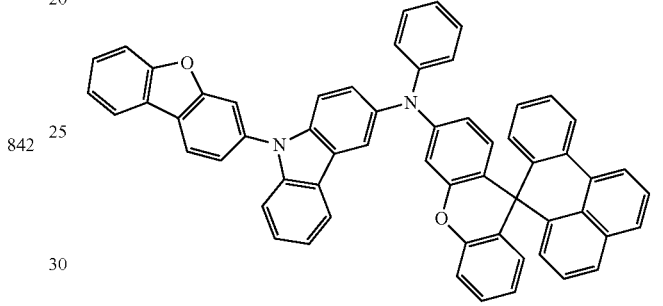
846
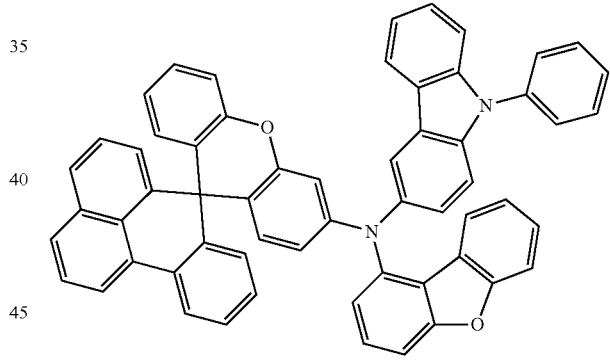
847
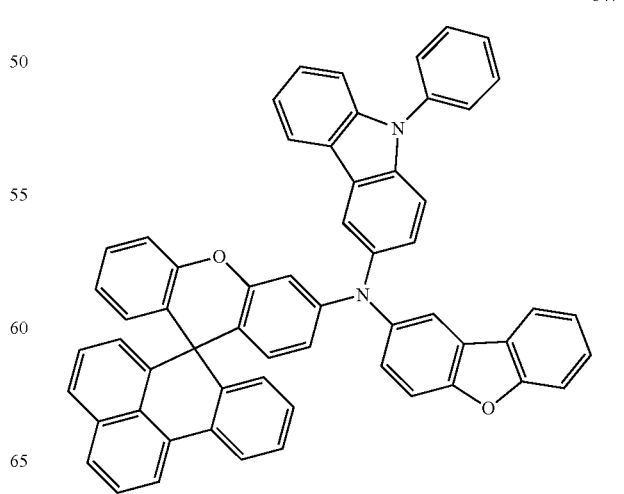

-continued
848
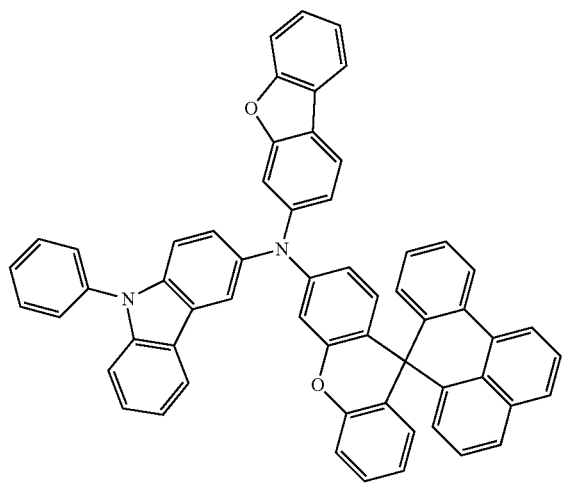
849
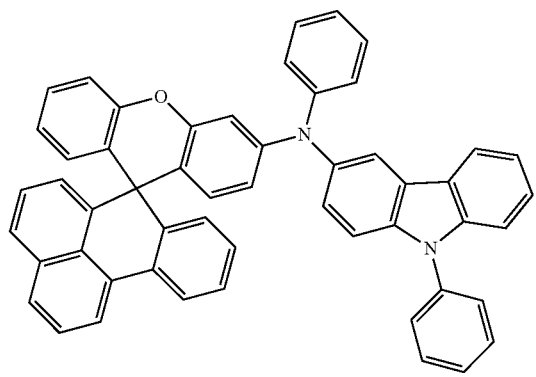
850
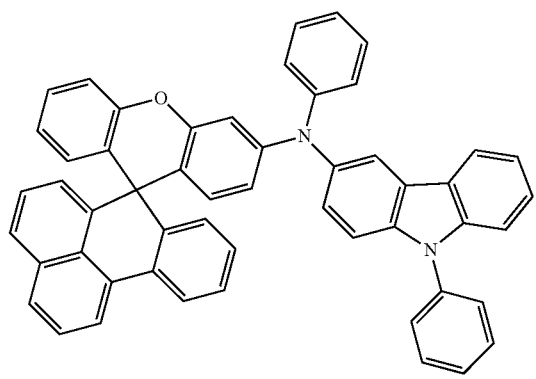
-continued
851
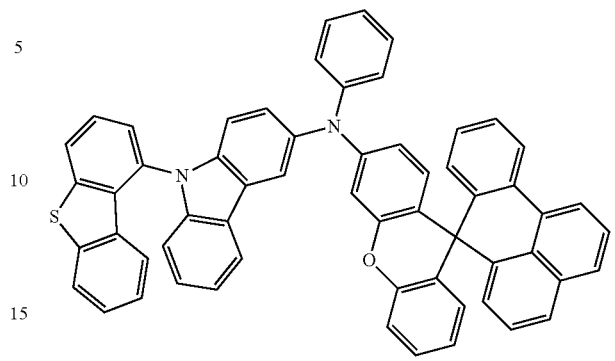
852
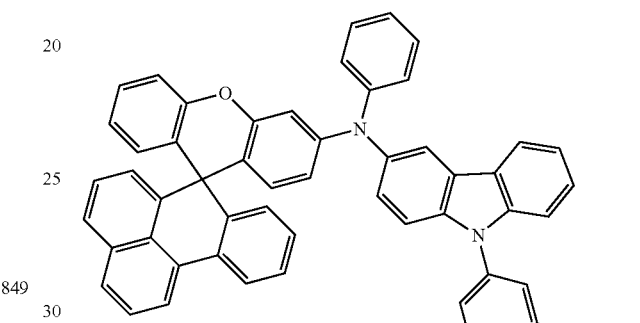
853
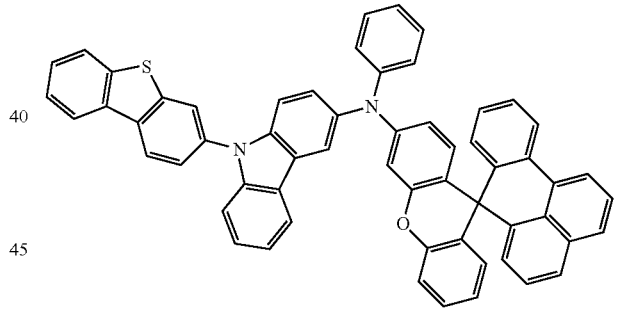
854
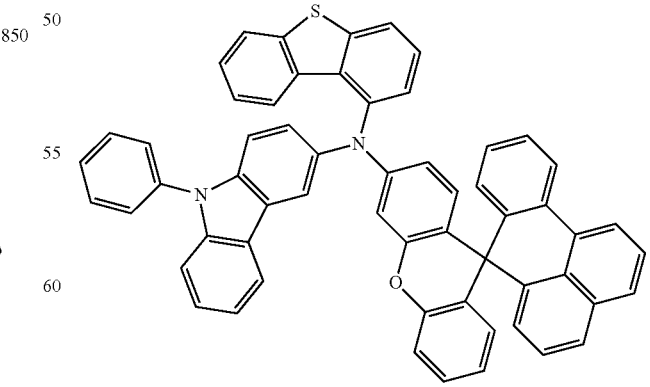

-continued
855
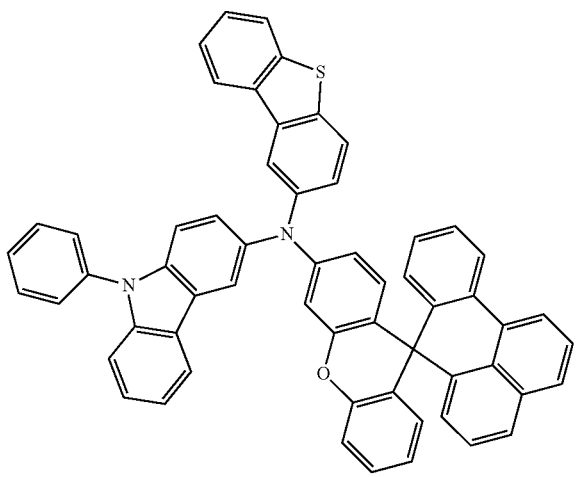
856
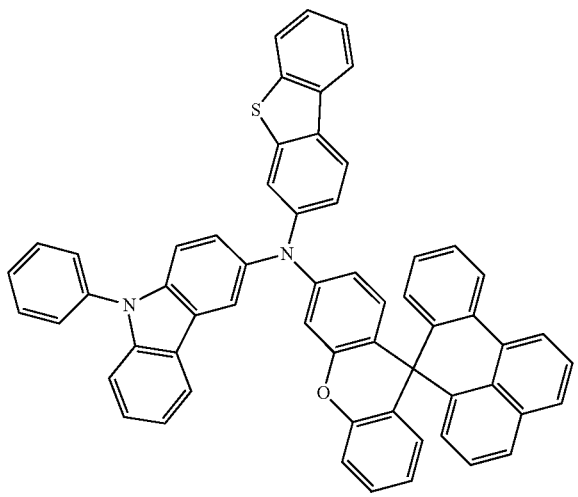
857
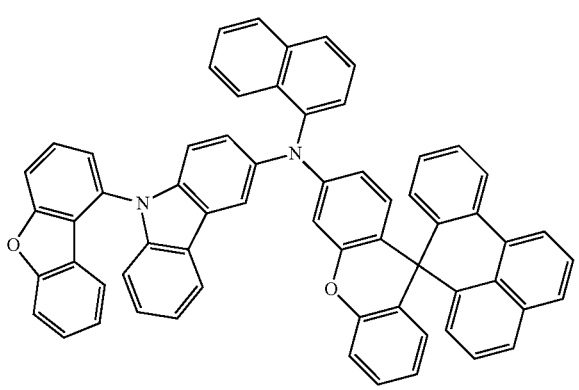
858
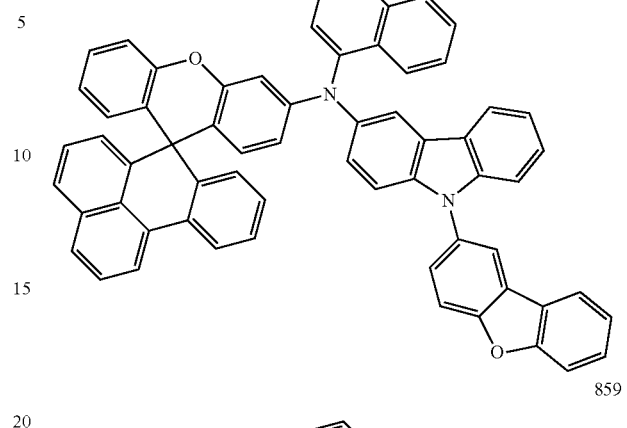
859
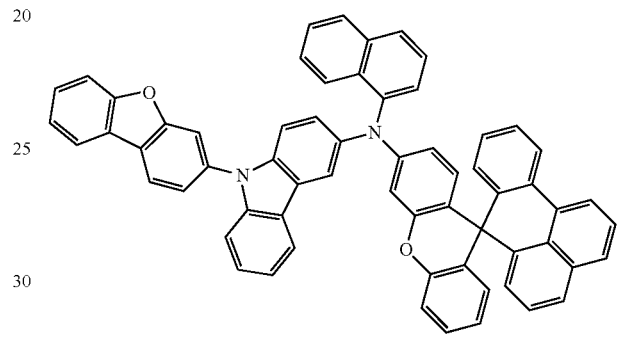
860
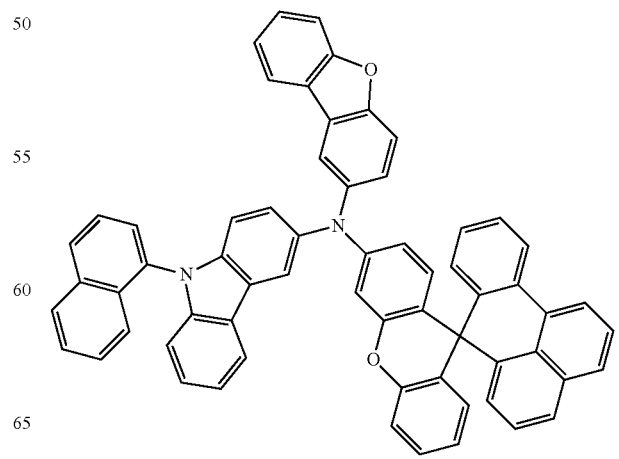
861

862
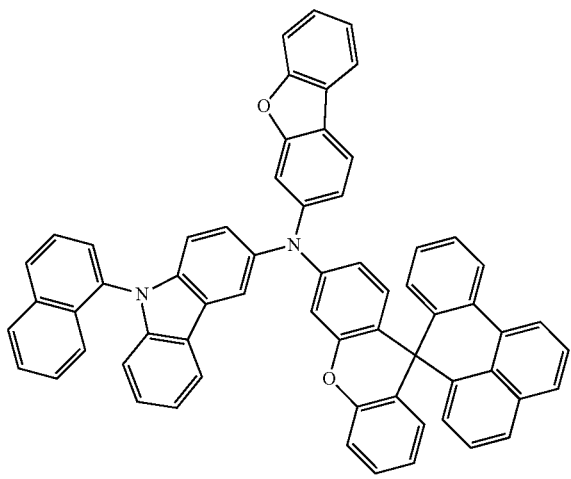
863
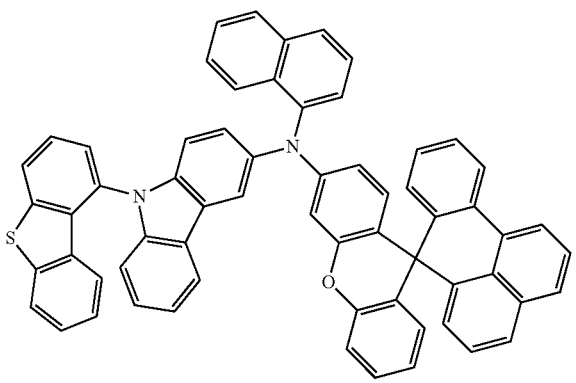
864
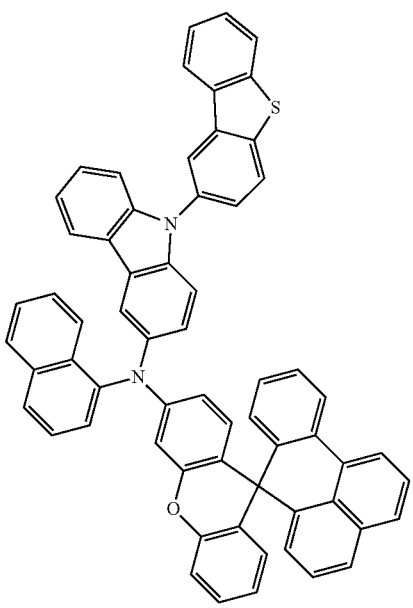
865
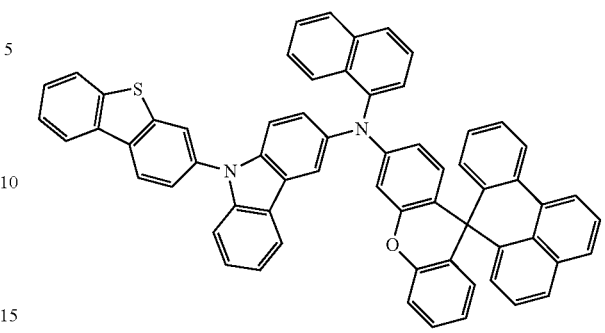
866
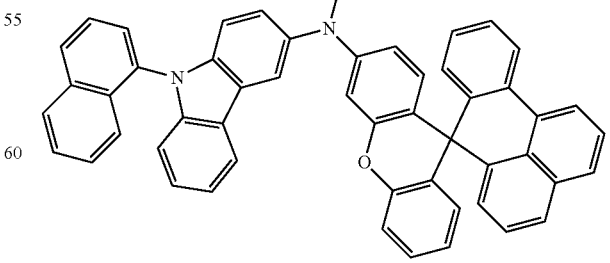
867

269
-continued
868
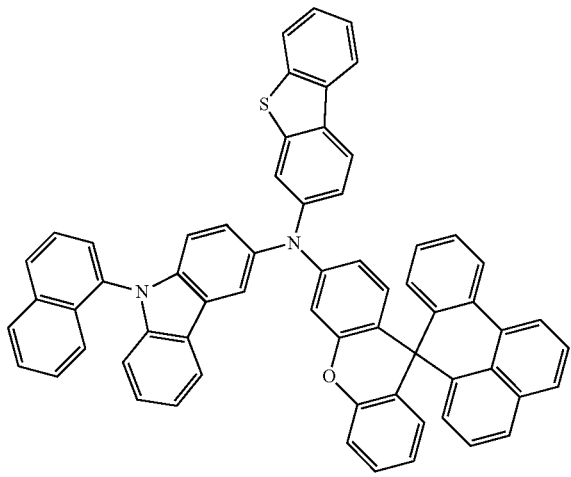
869
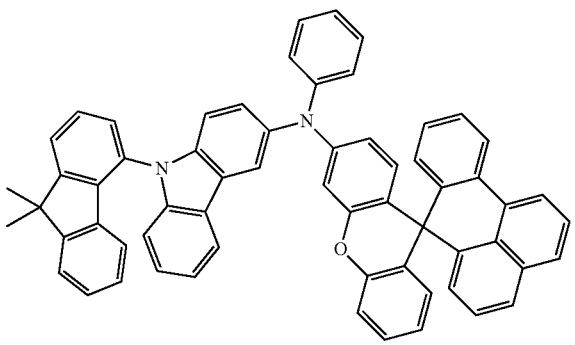
870
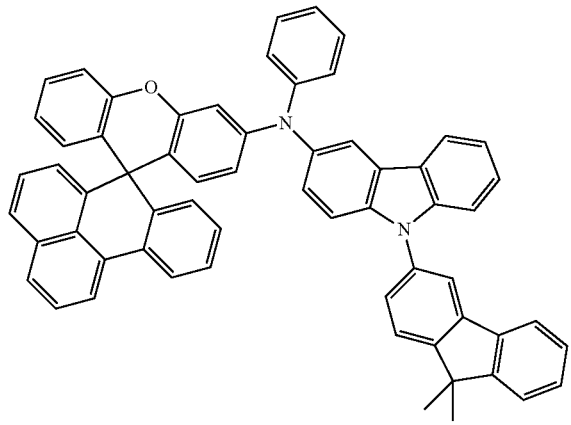
871
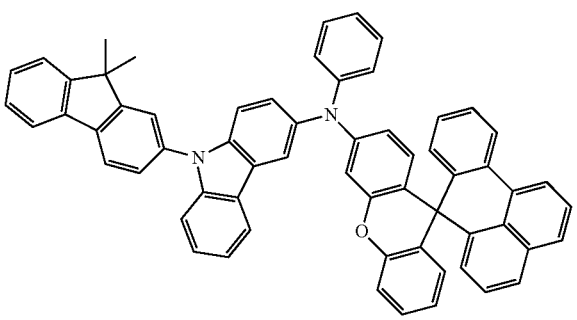
270
-continued
872
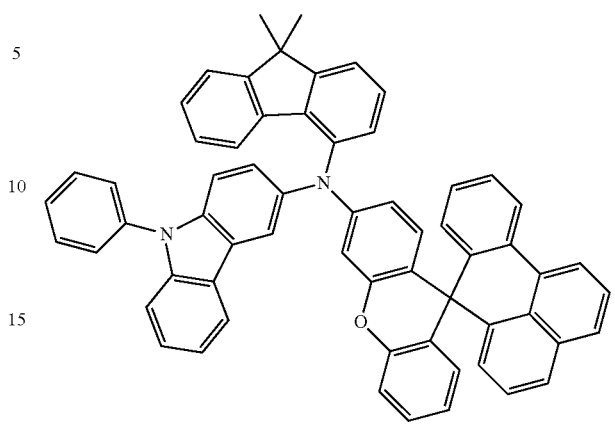
873
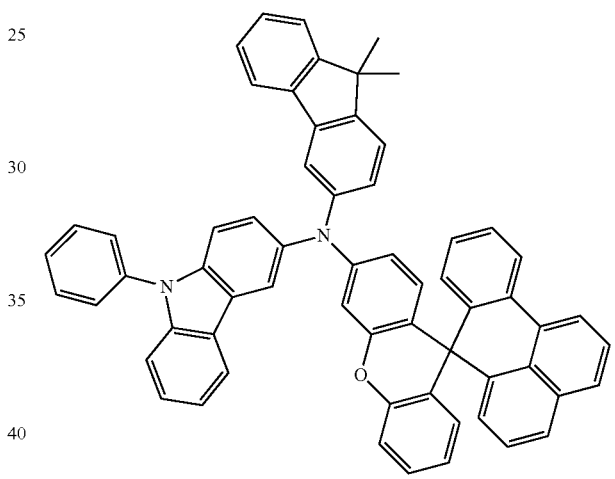
874
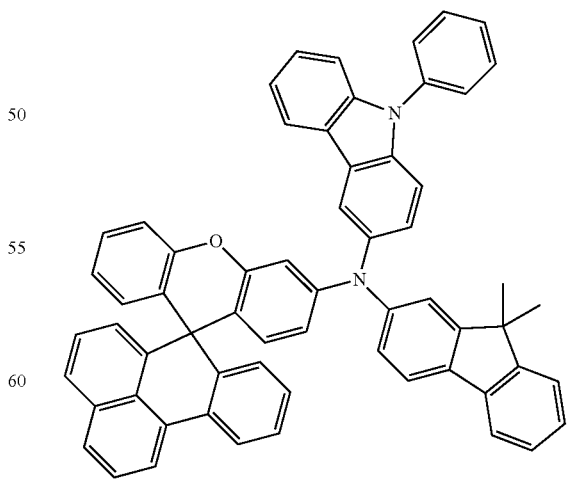

| 271 -continued | 272 -continued |
|---|---|
| 875 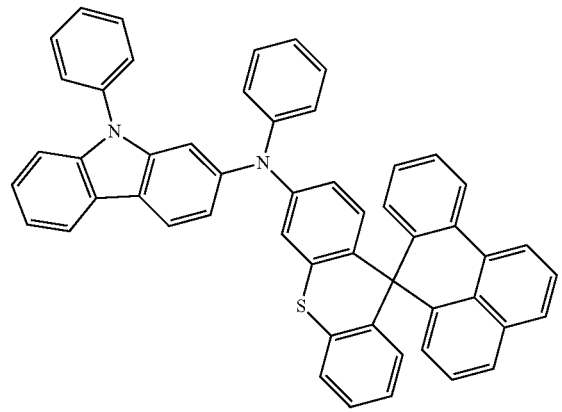 | 879 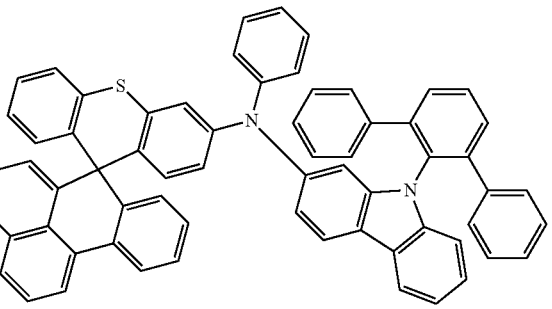 |
| 876 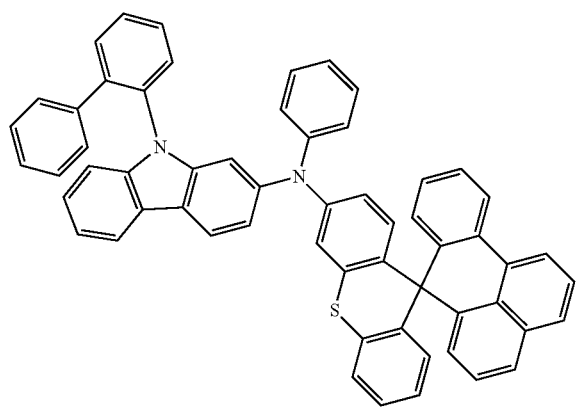 | 880 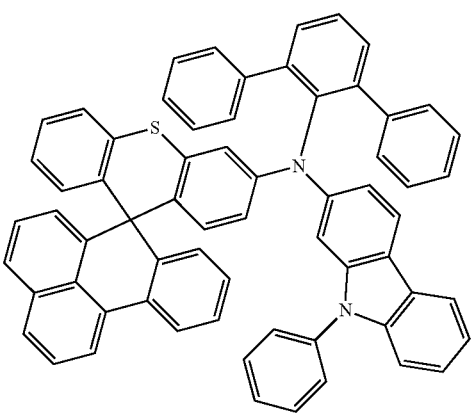 |
| 877 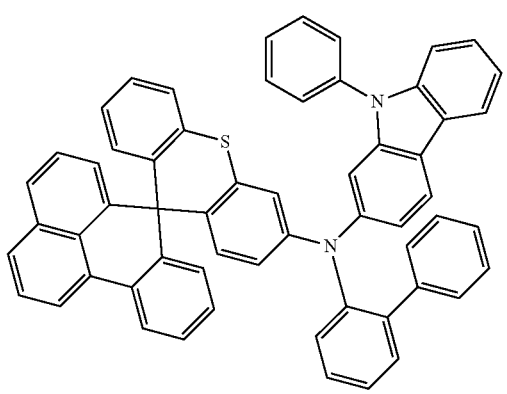 | 881 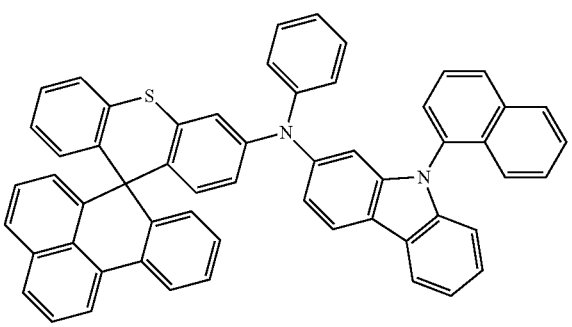 |
| 878 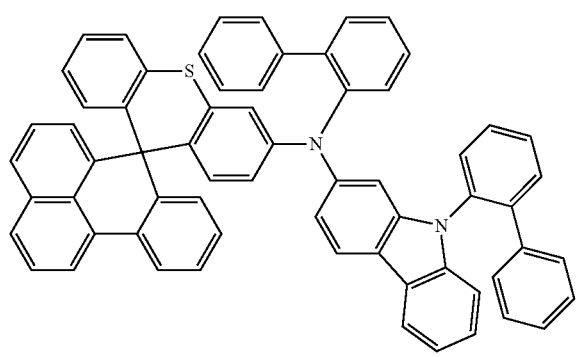 | 882 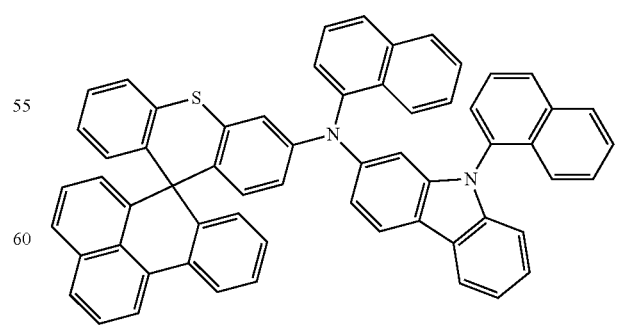 |

-continued
883
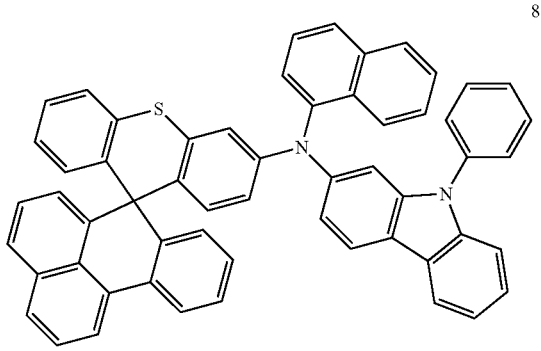
884
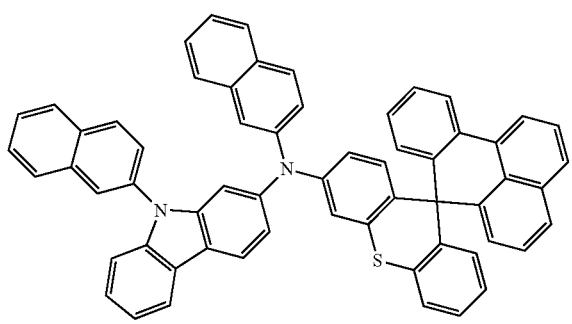
885
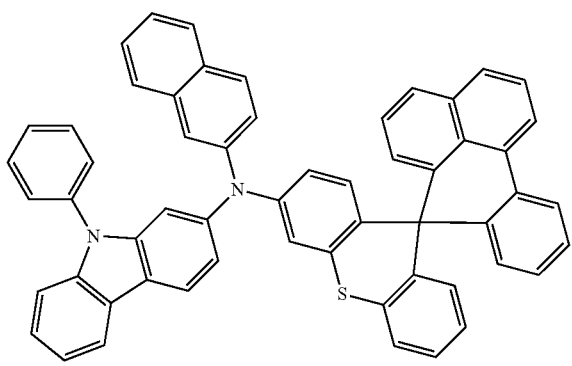
886
-continued
887
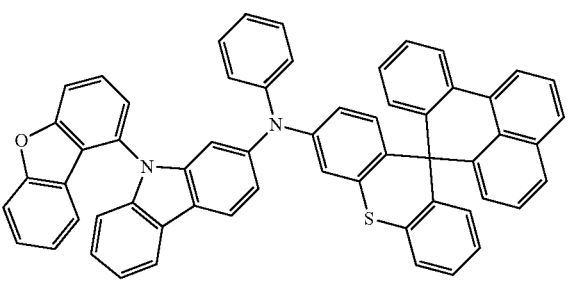
888
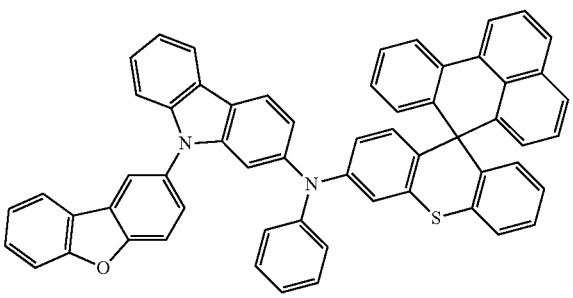
889
890
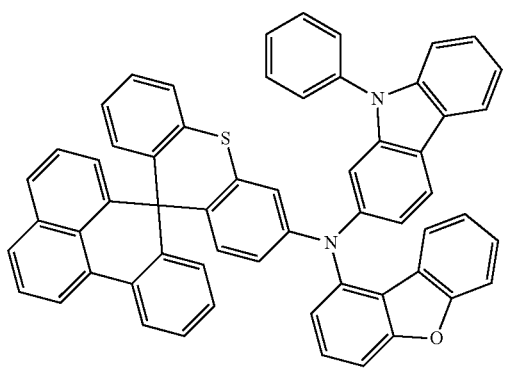

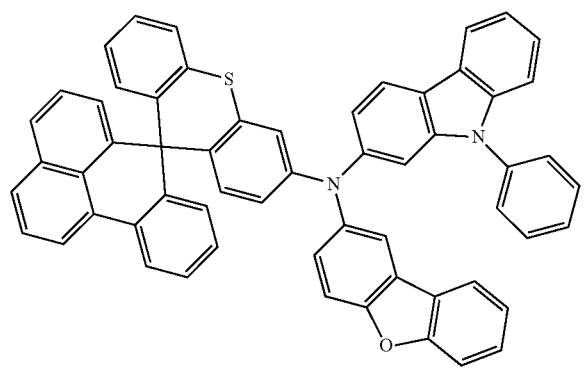
891
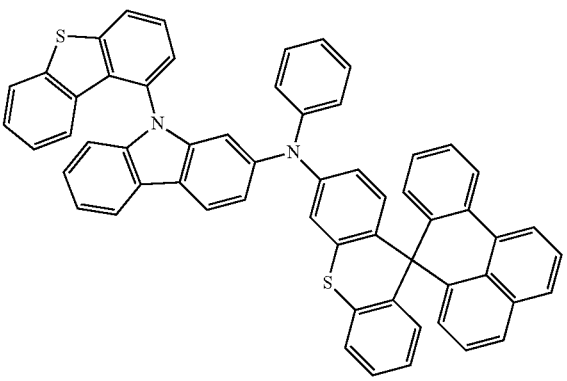
895
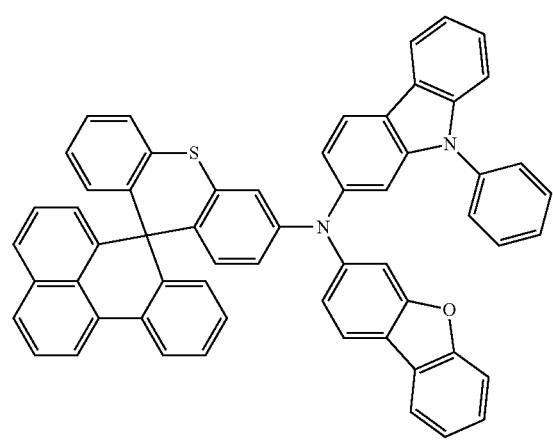
892
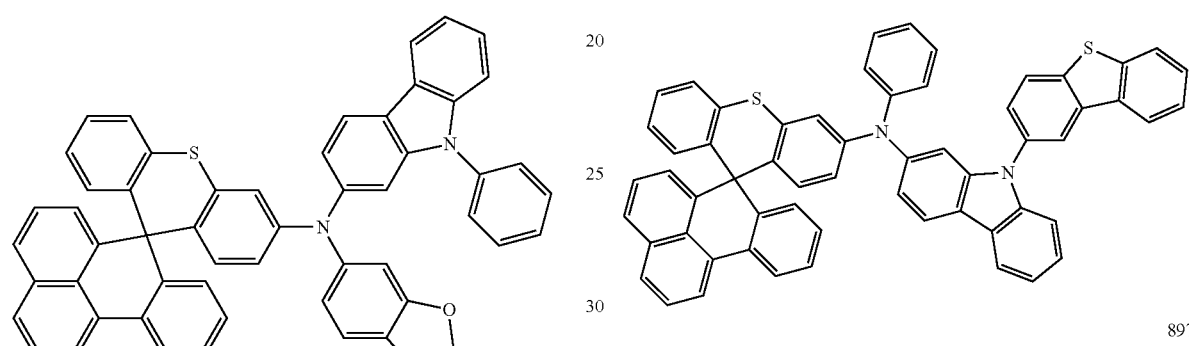
896
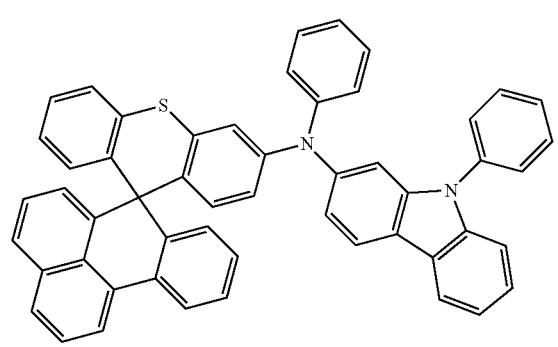
893
897
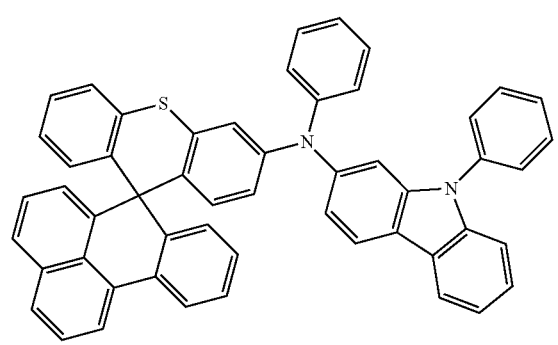
894
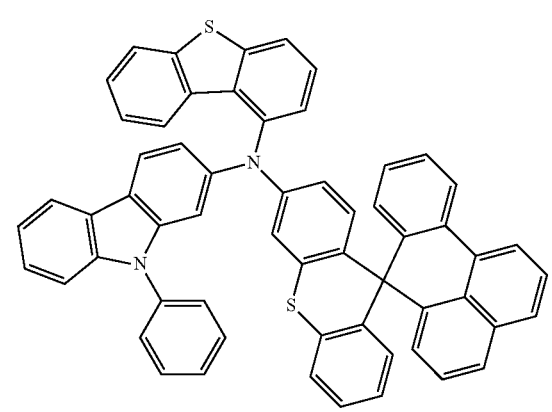
898

899
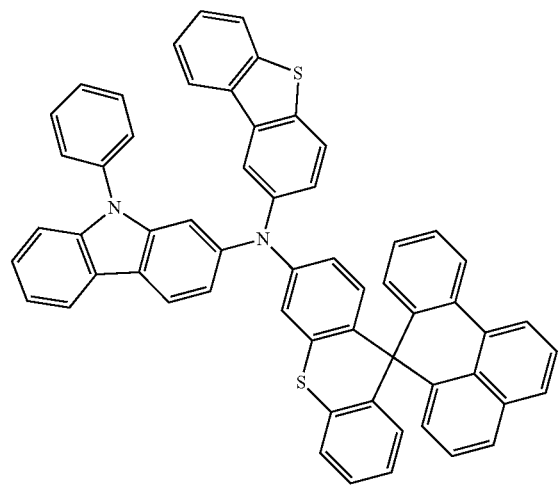
900
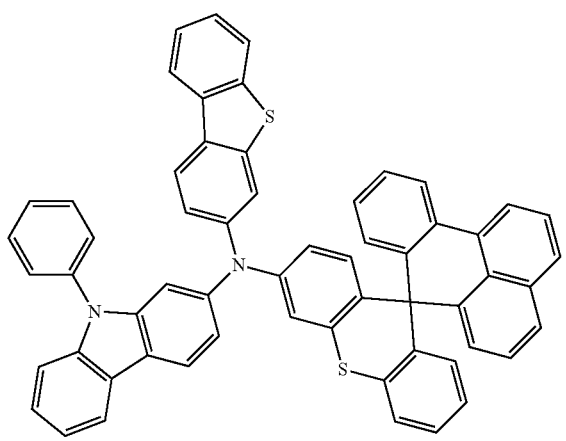
901
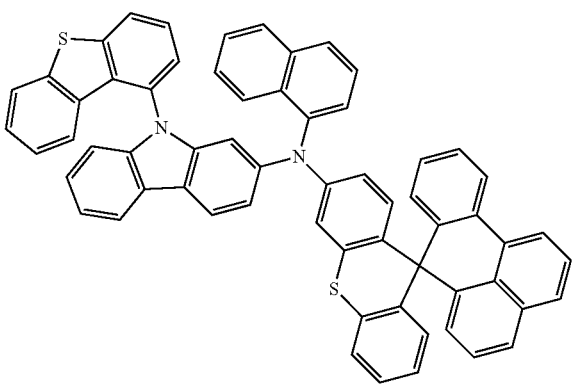
902
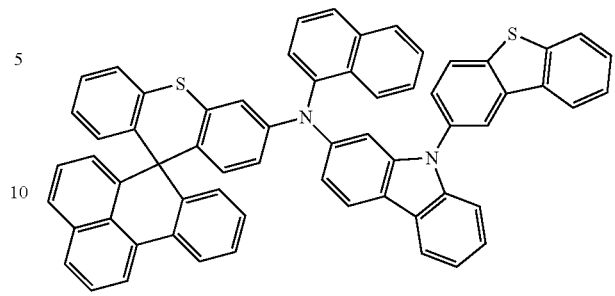
903
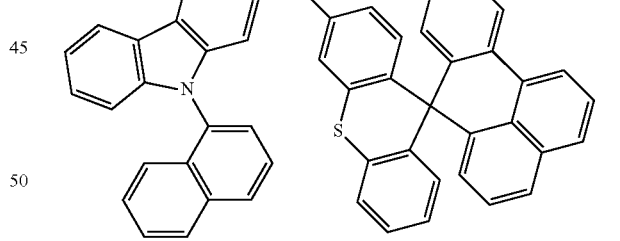
904
905
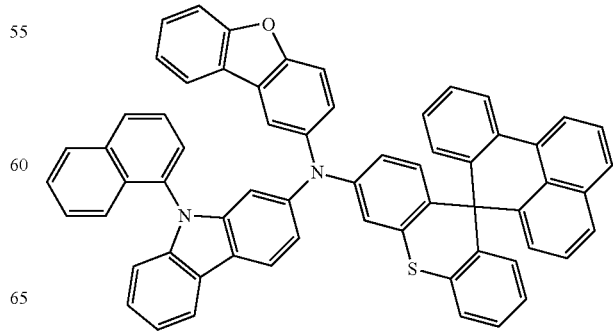

906
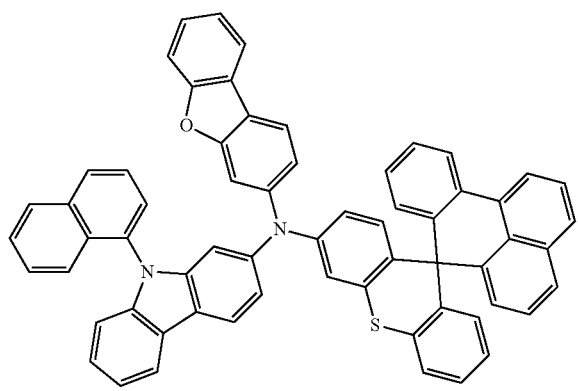
907
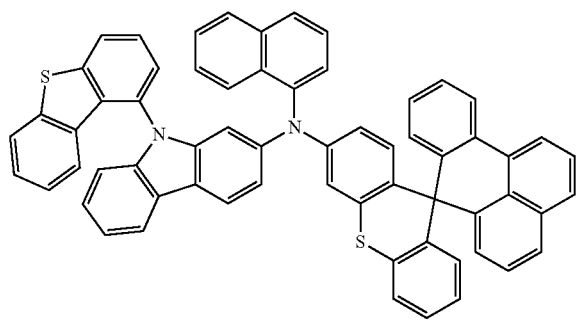
908
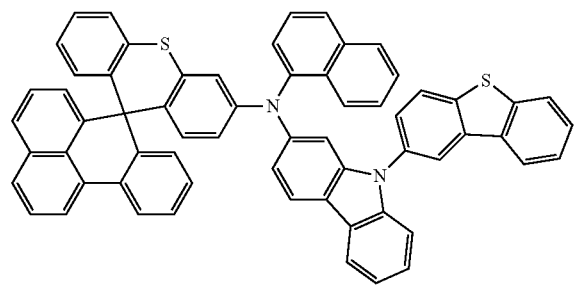
909
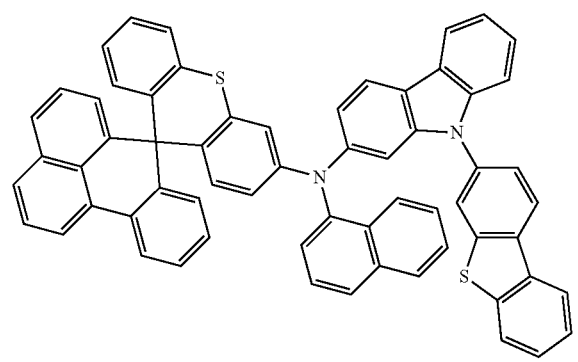
910
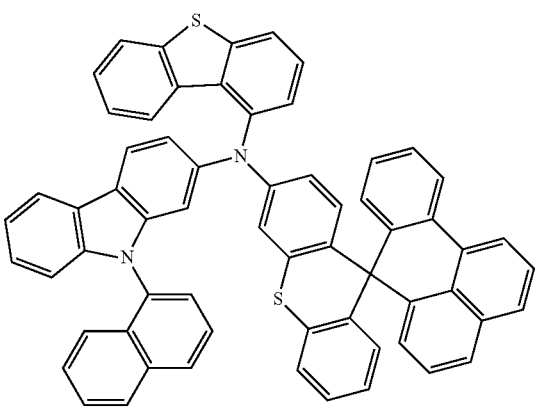
911
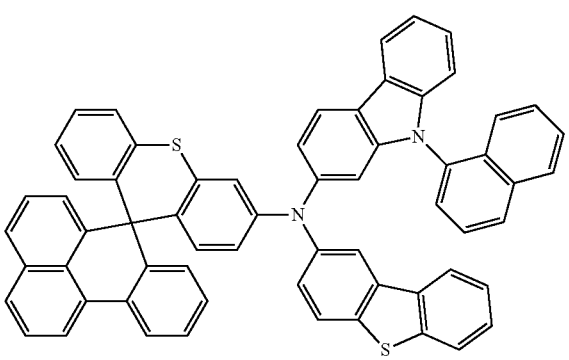
912
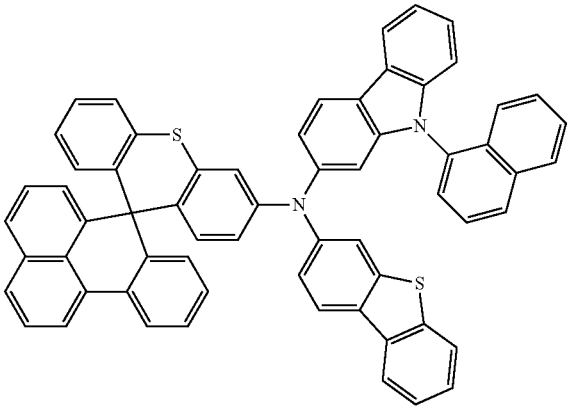
913
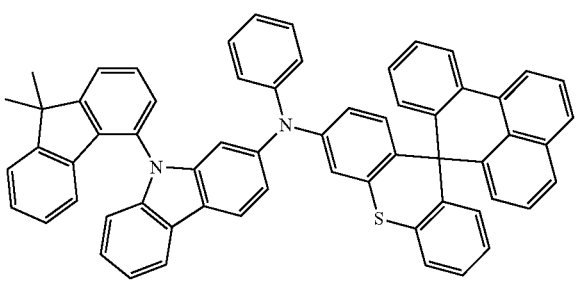

914
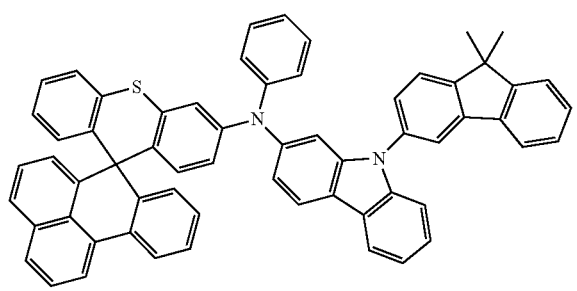
915
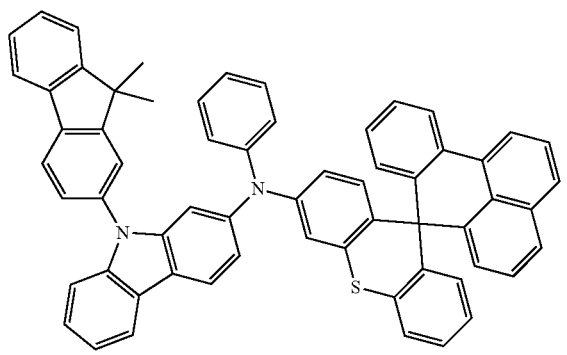
916
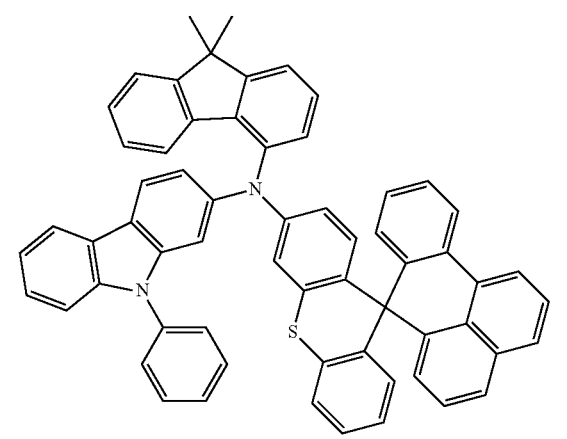
917
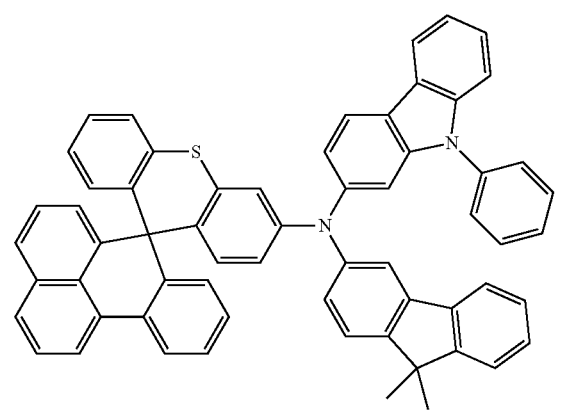
918
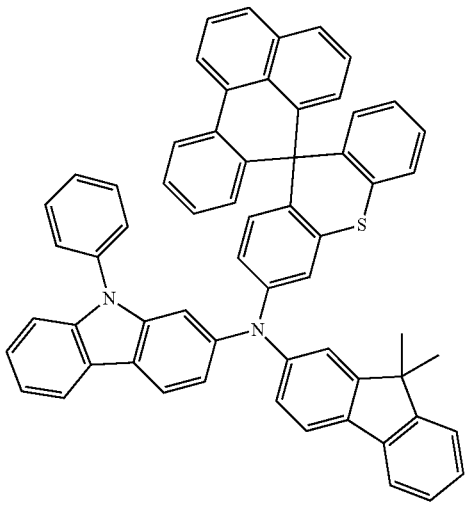
919
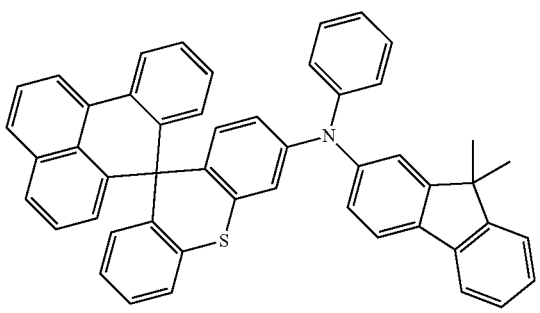
920
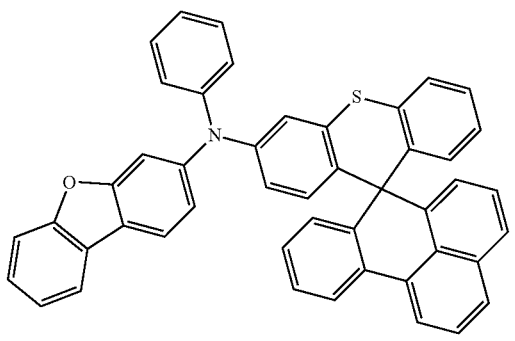
921
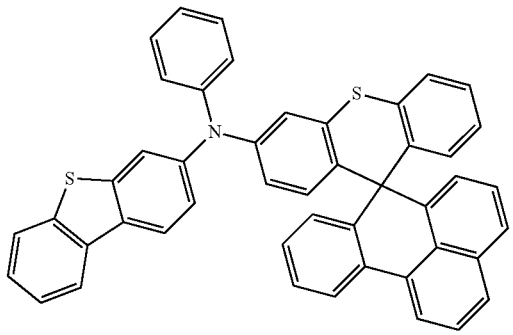

922
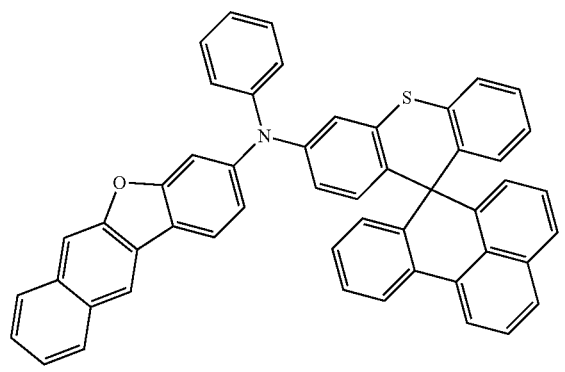
923
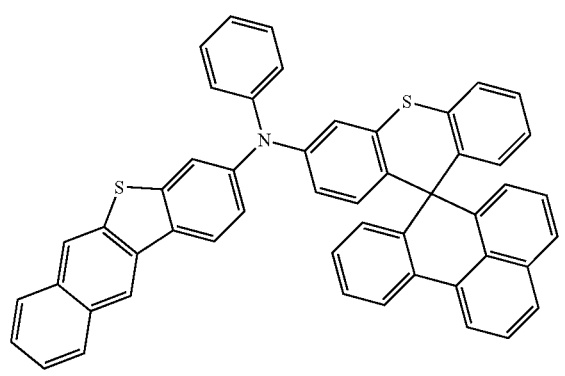
924
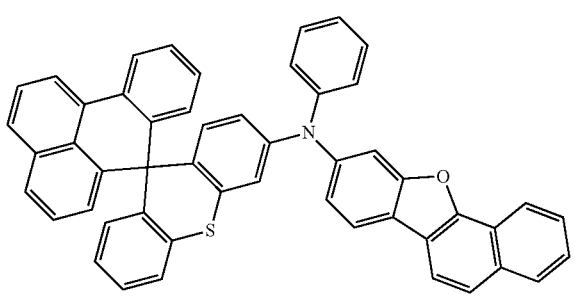
925
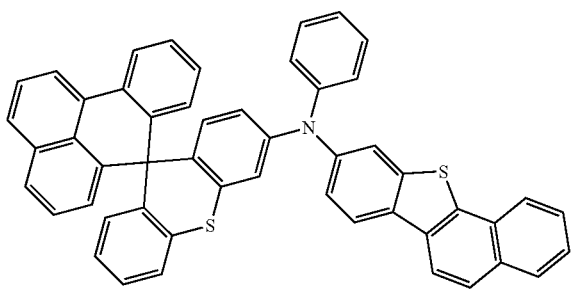
926
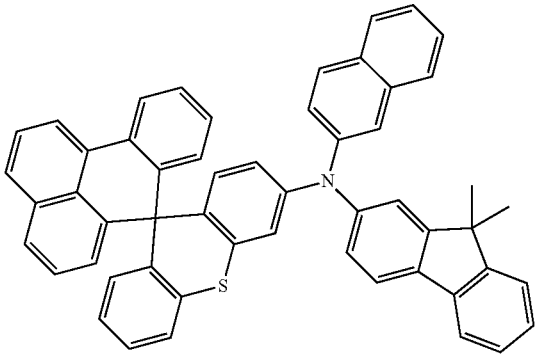
927
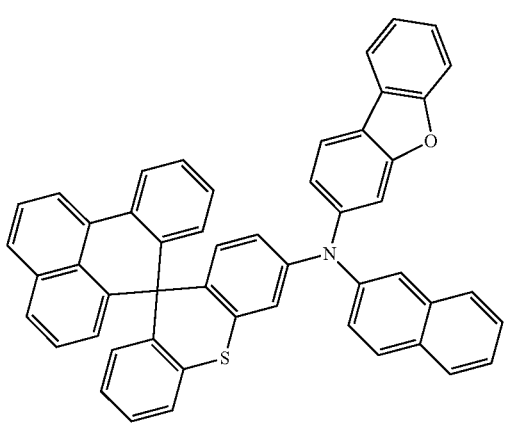
928
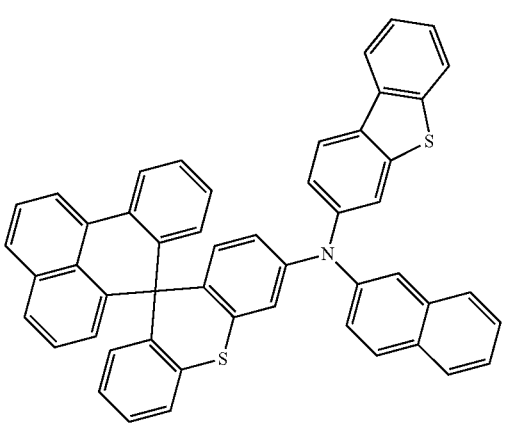
929
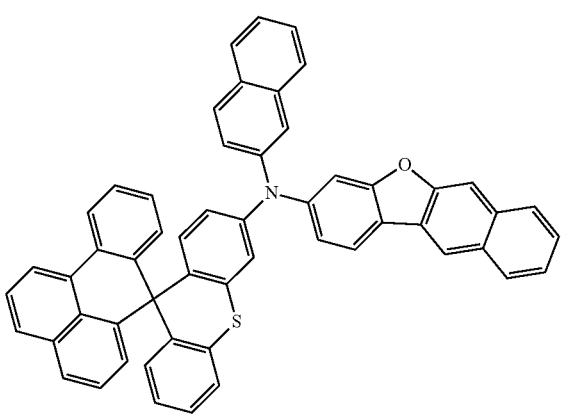

930
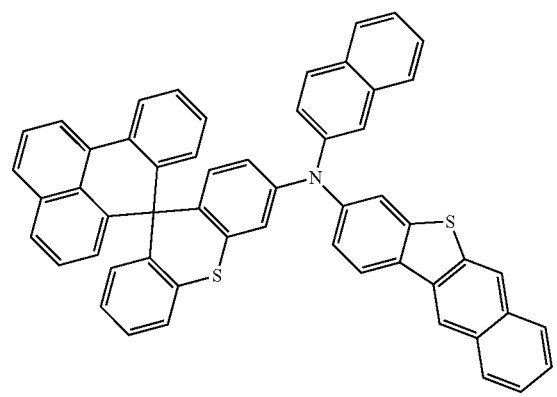
931
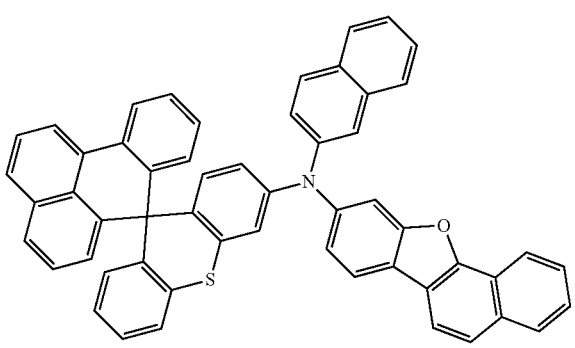
932
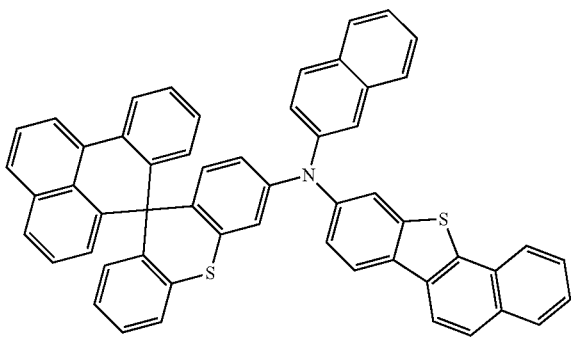
933
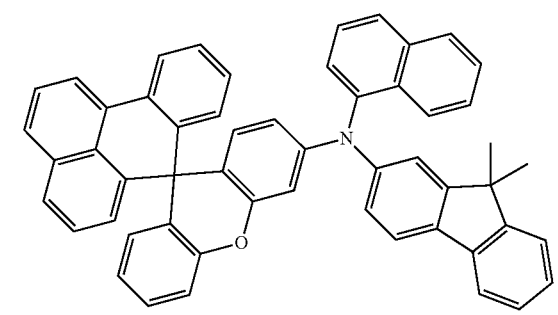
934
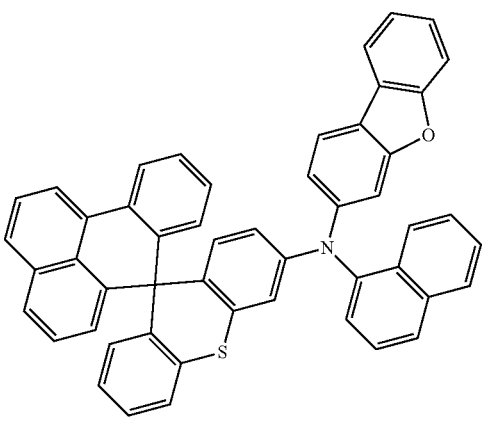
935
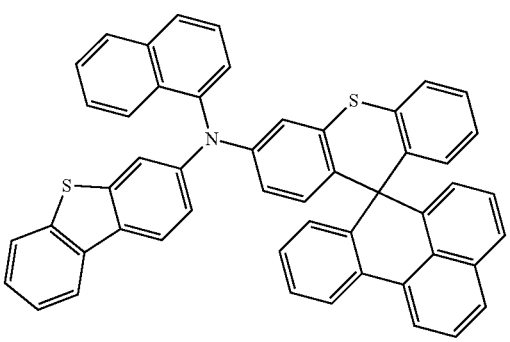
936
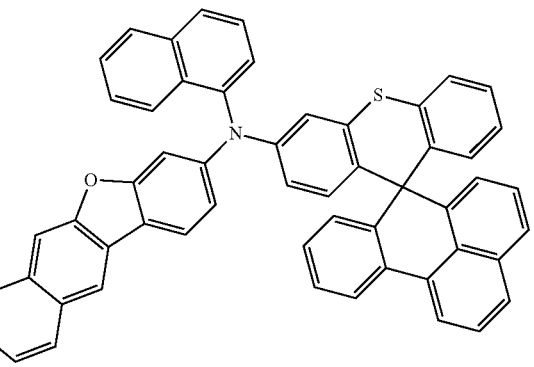
937
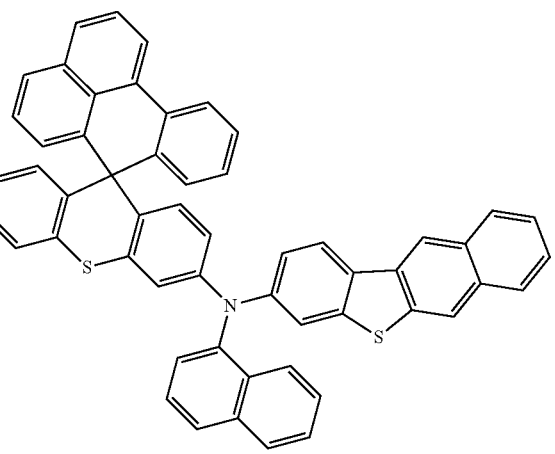

938
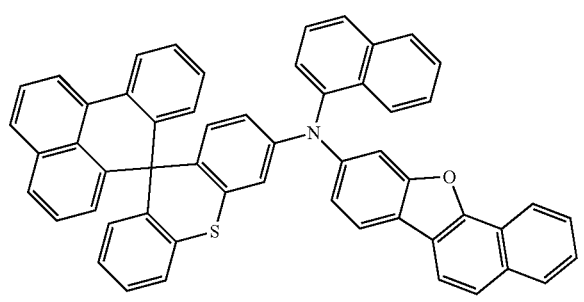
939
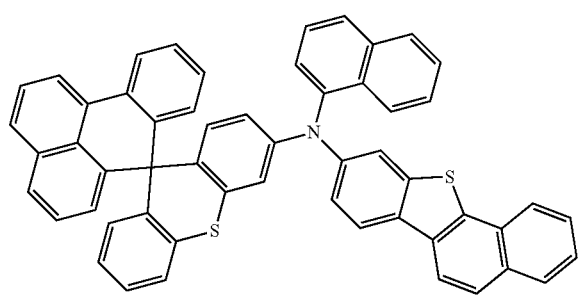
940
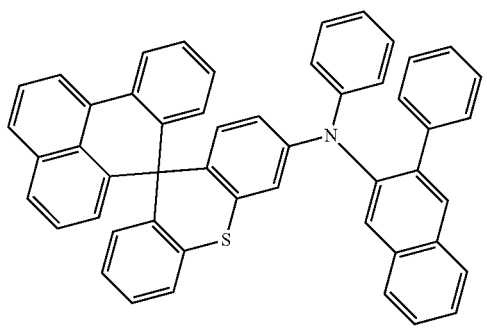
941
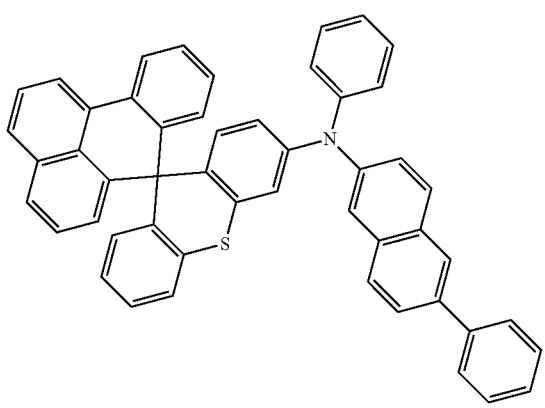
942
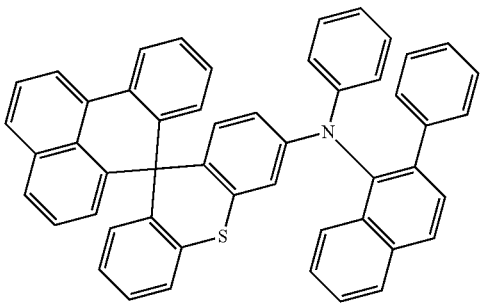
943
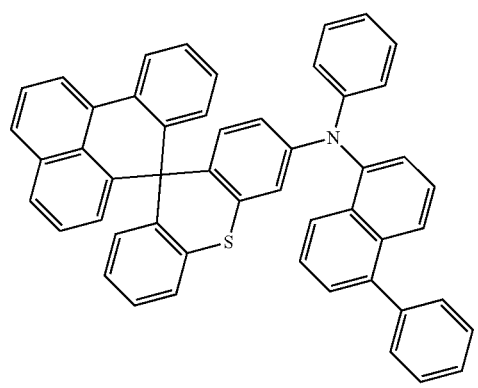
944
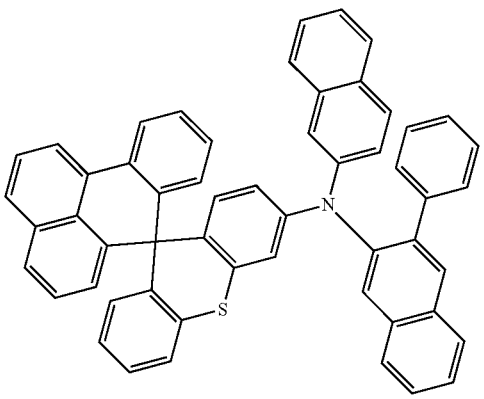
945
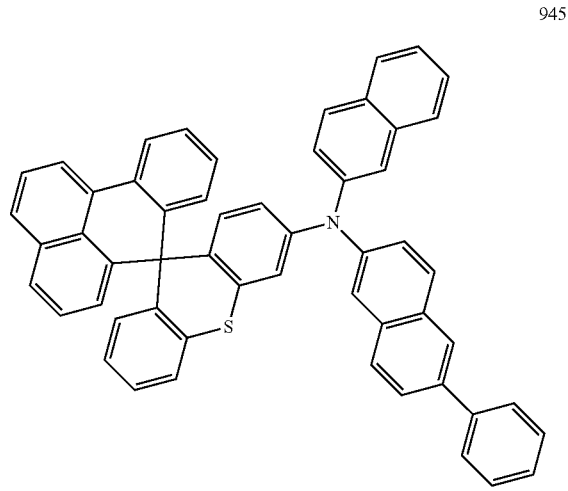

946
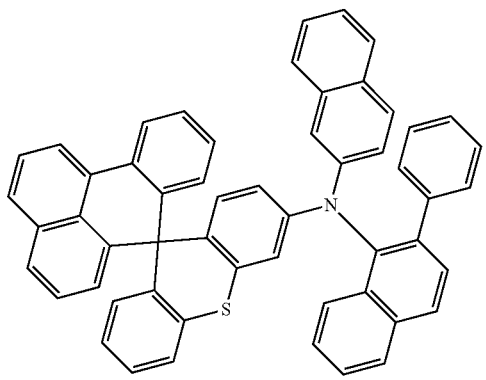
947
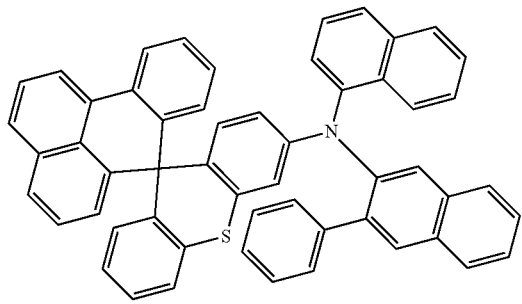
948
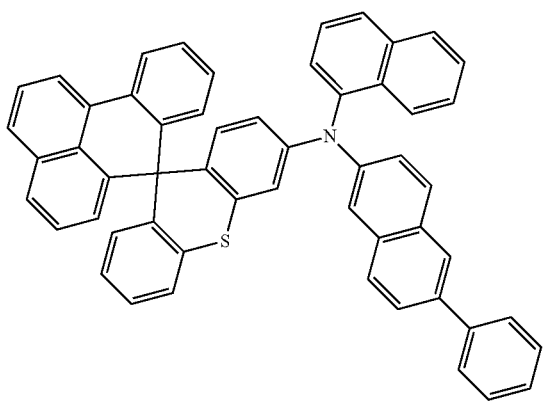
949
950
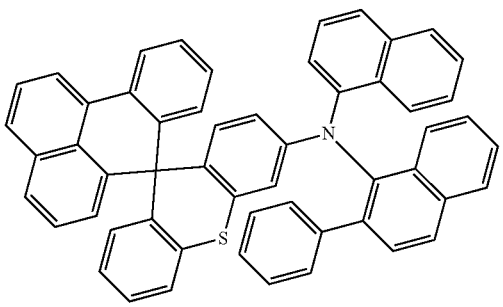
951
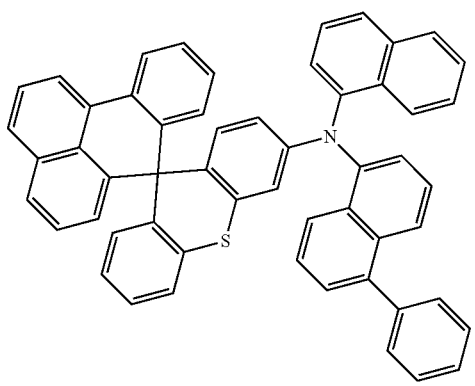
952
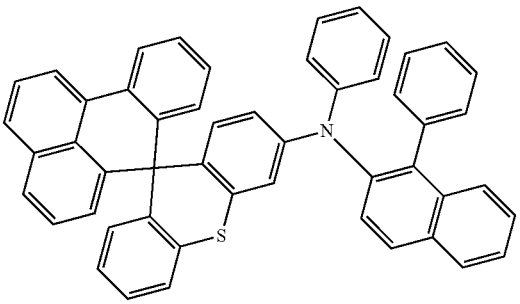
953
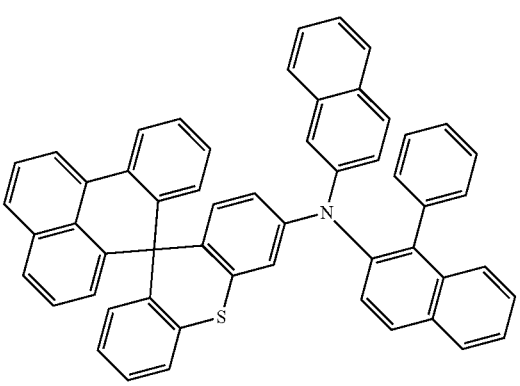

-continued
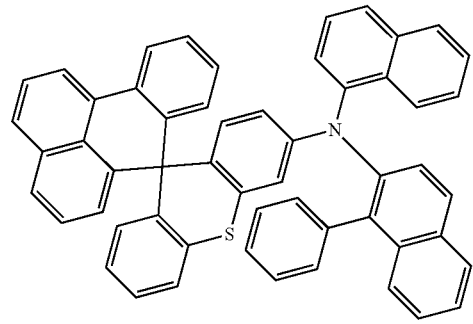
954
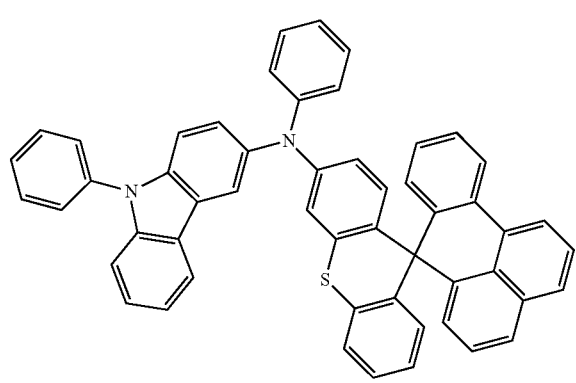
955
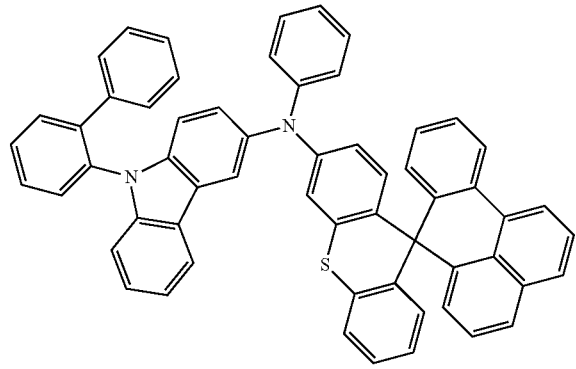
956
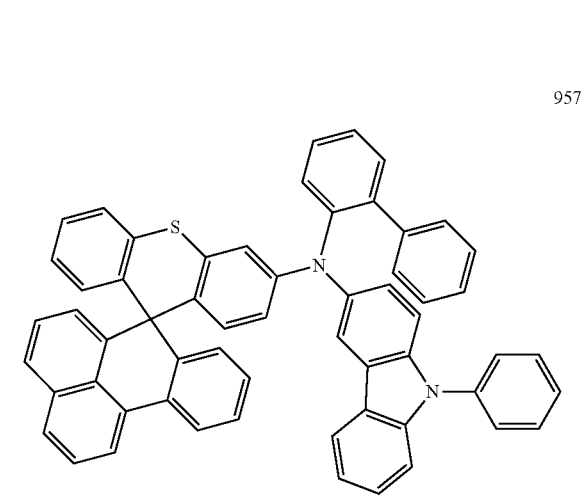
957
-continued
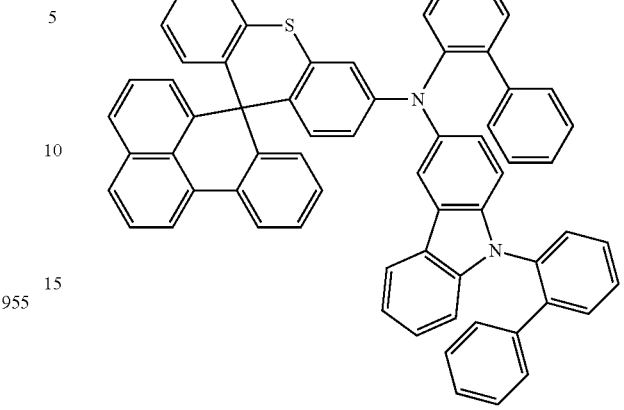
958
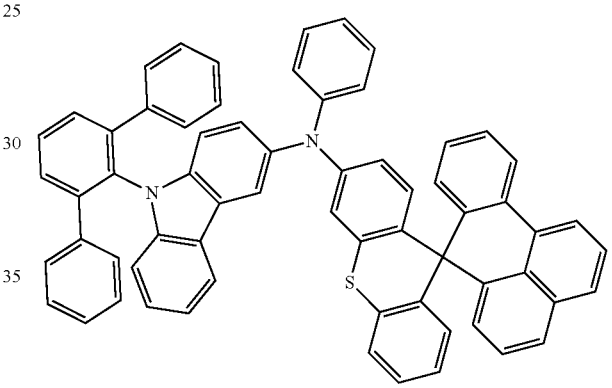
959
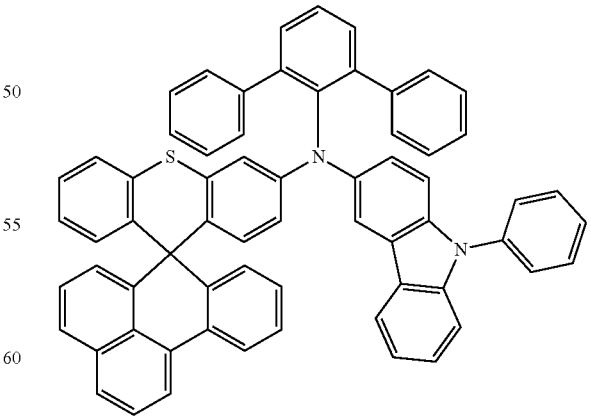
960

293
-continued
961
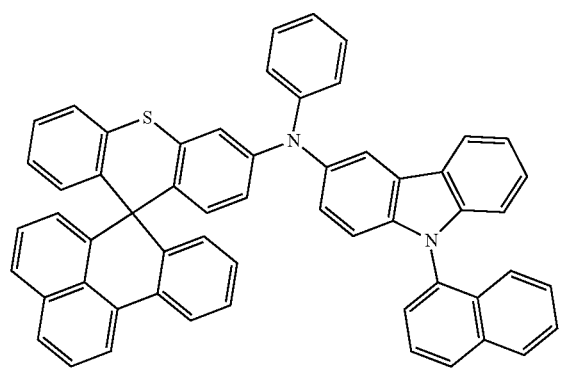
962
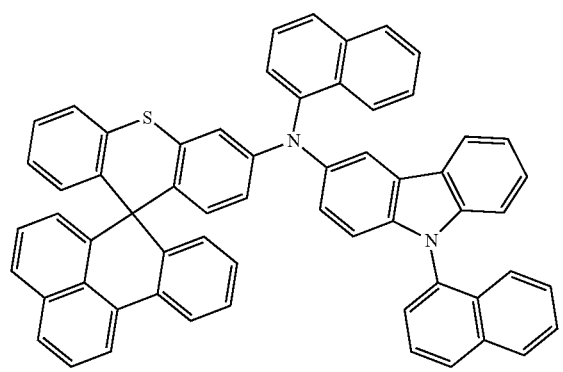
963
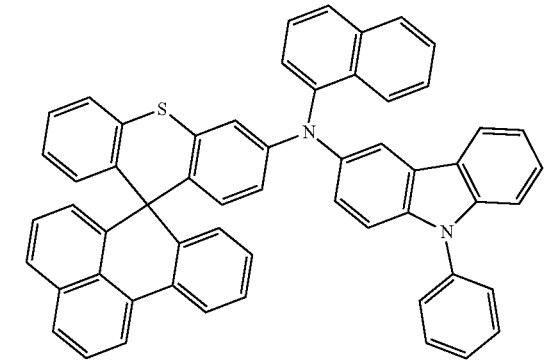
964
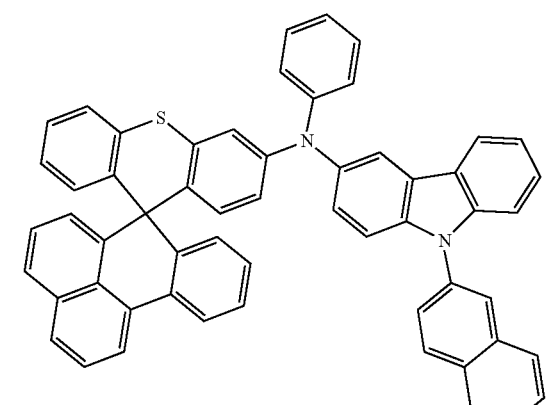
294
-continued
965
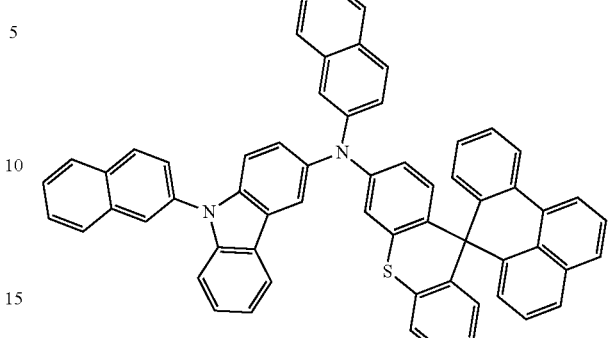
966
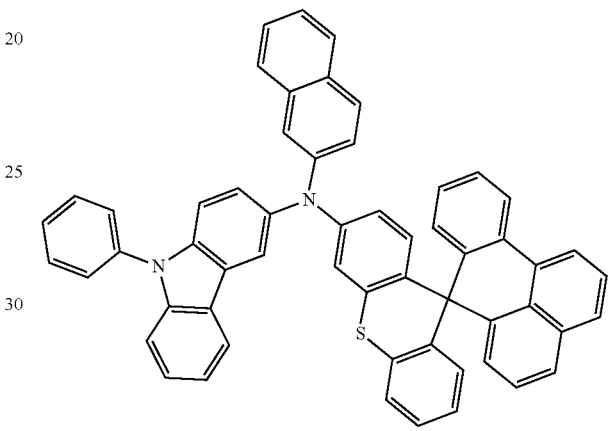
967
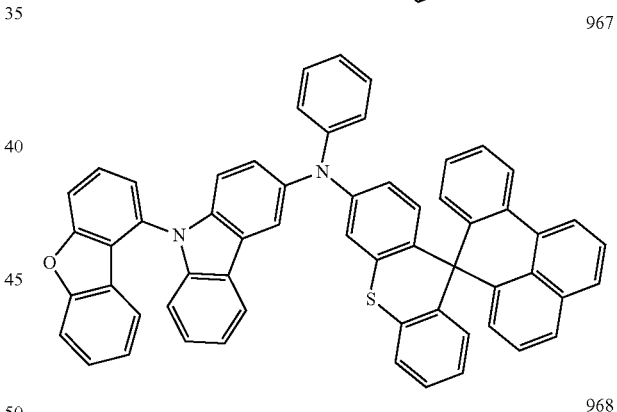
968
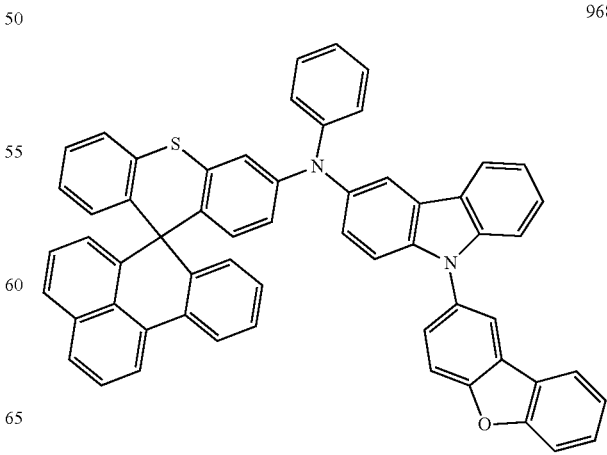

969
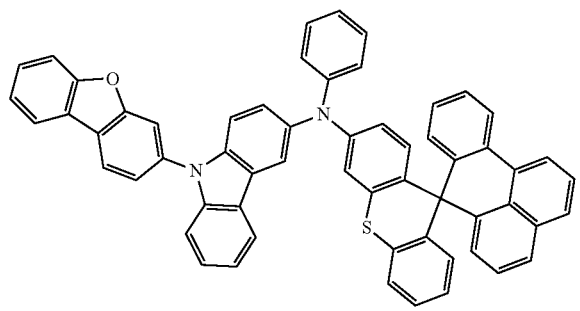
970
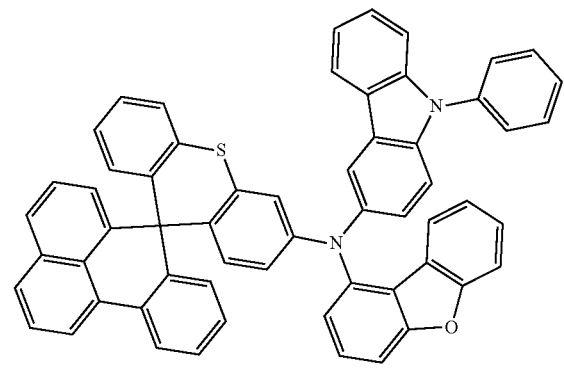
971
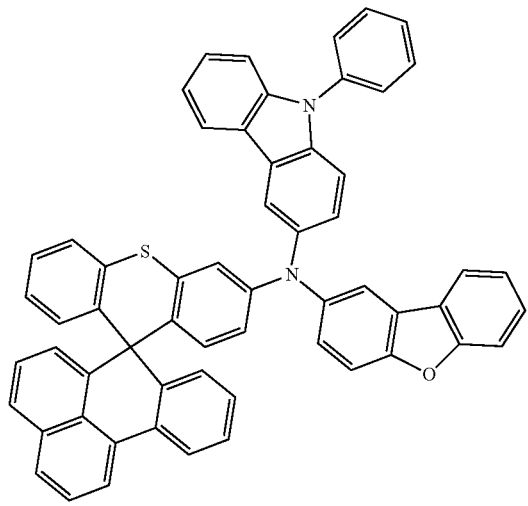
972
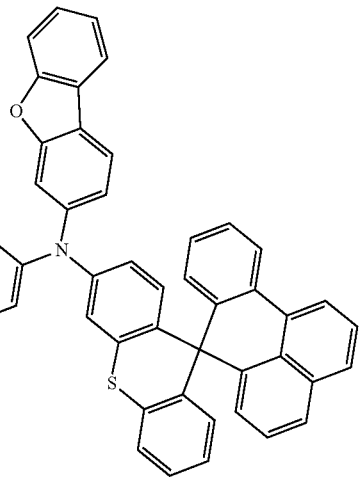
973
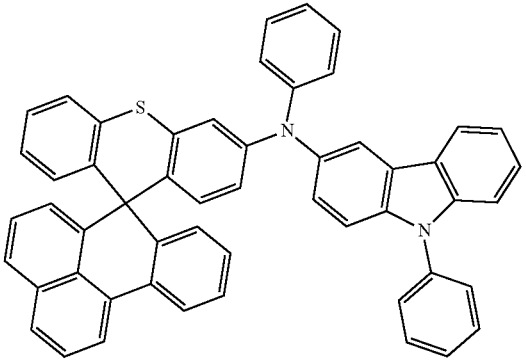
974
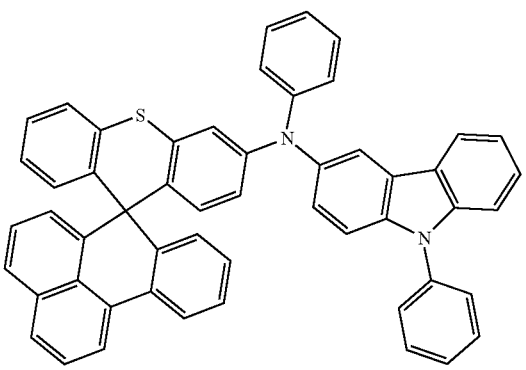
975
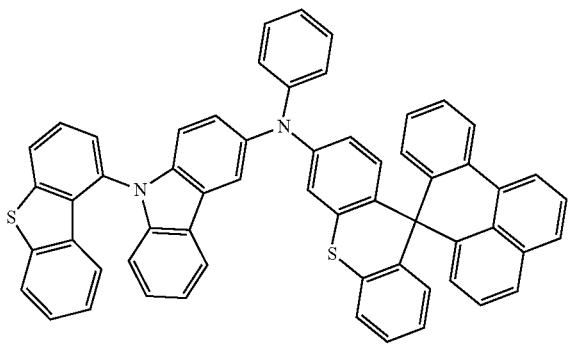

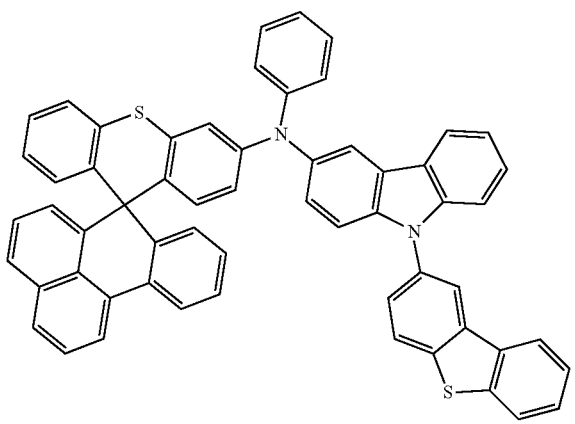
976
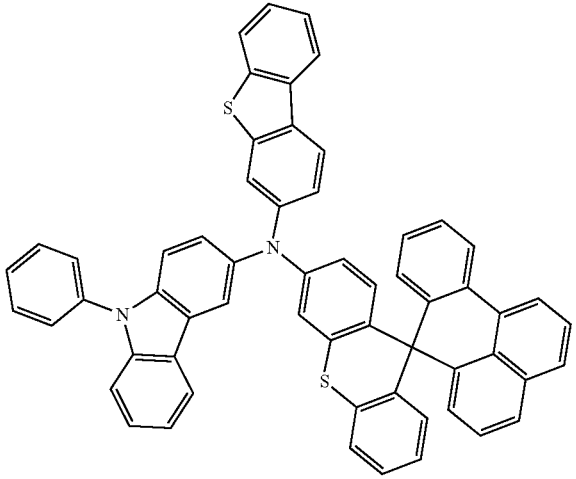
980
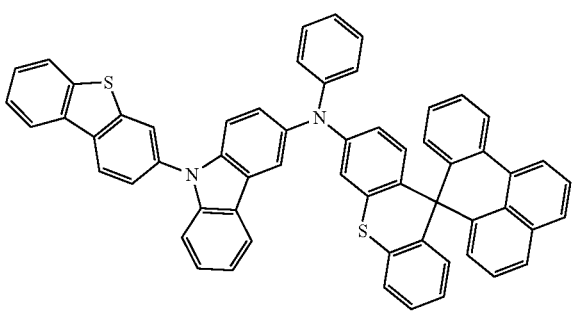
977
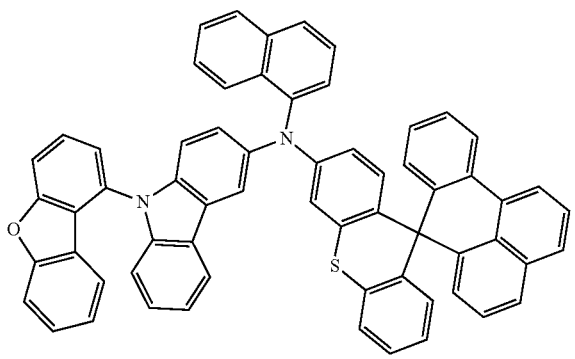
981
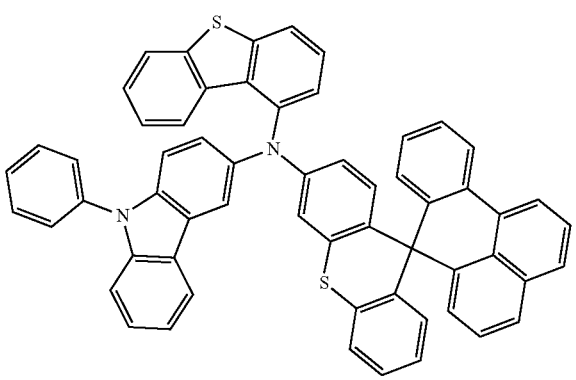
978
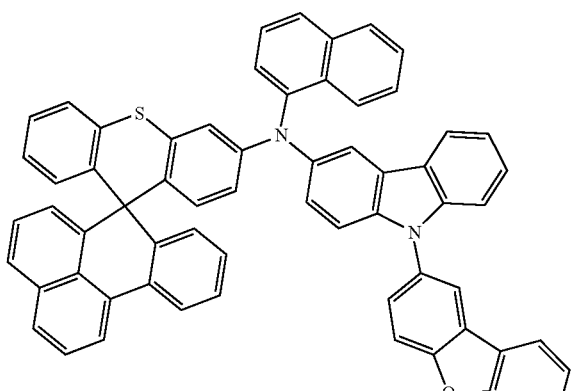
982
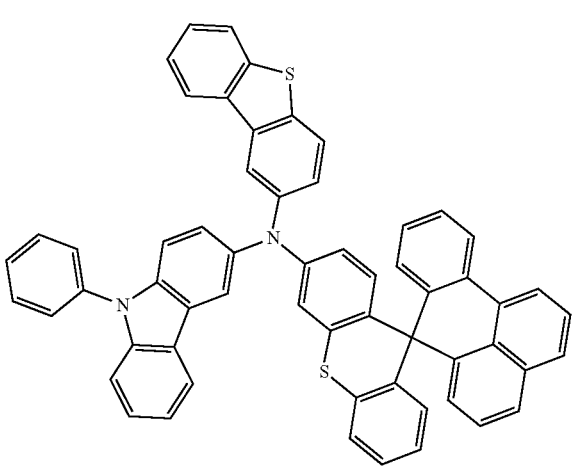
979
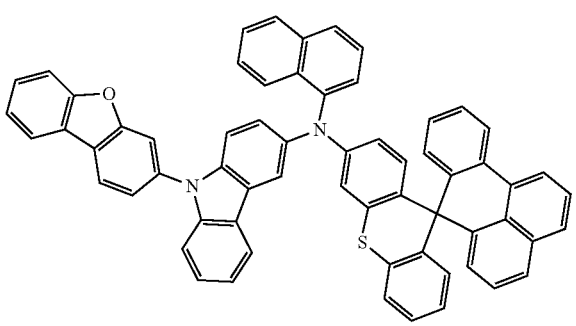
983

984
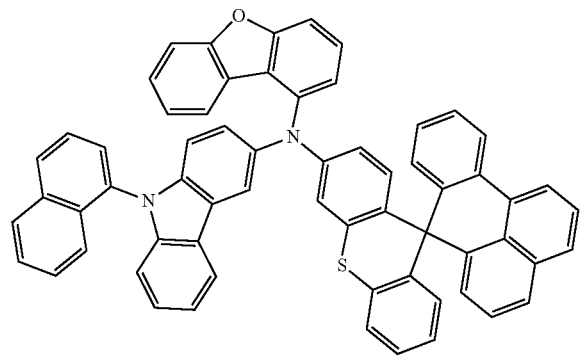
985
987
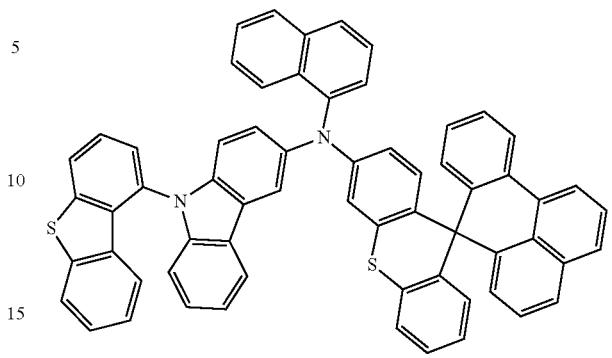
988
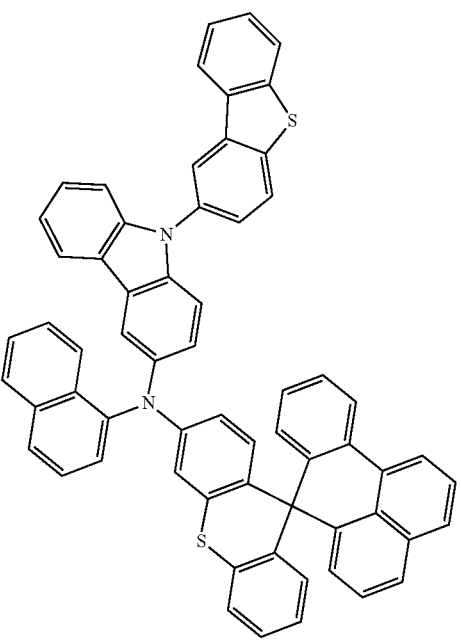
986
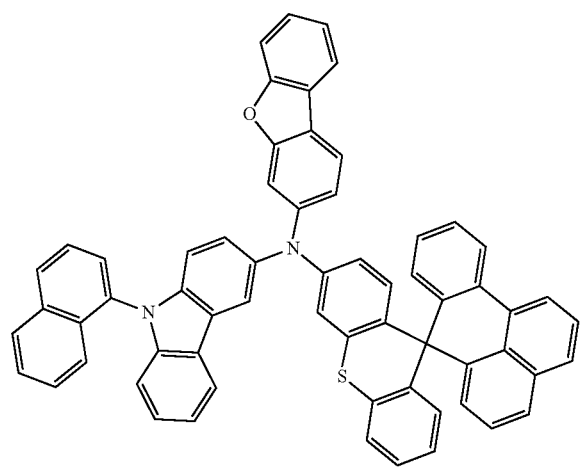
989
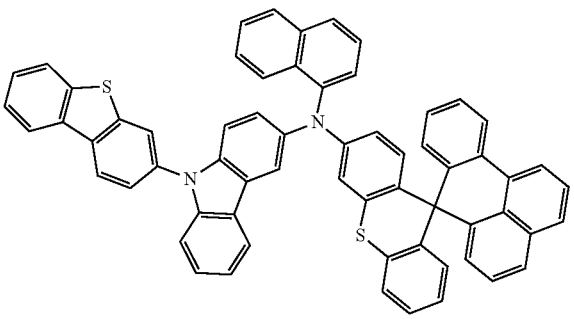

301
-continued
990
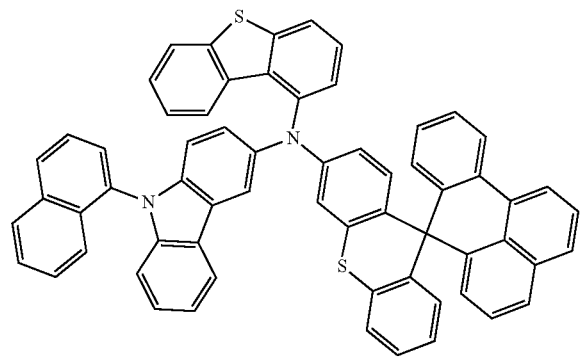
991
992
302
-continued
993
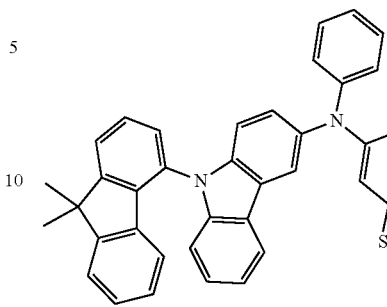
994
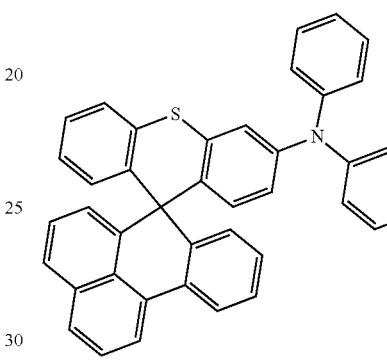
995
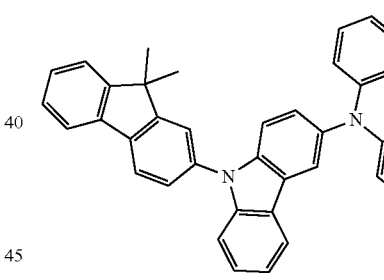
996
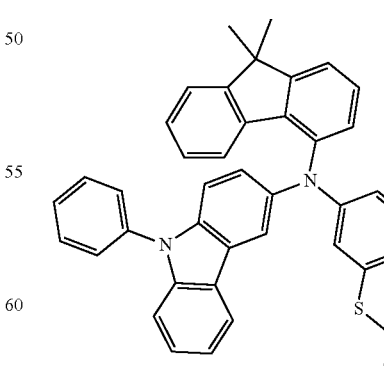

997
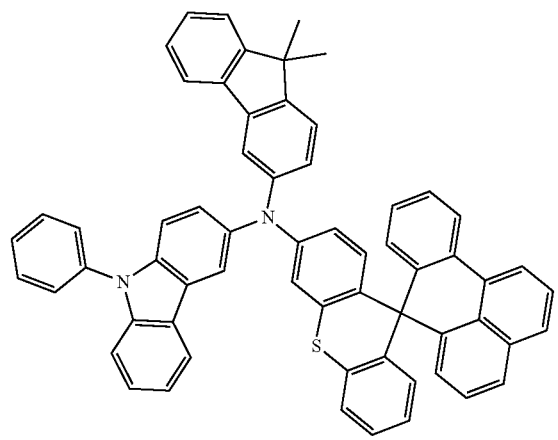
998
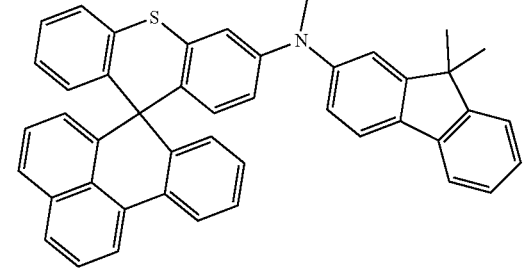
999
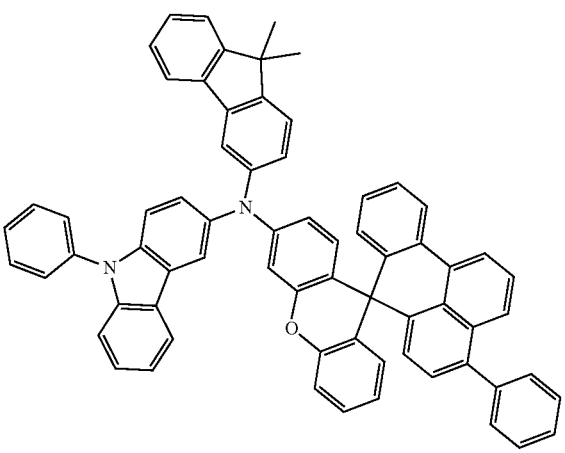
1000
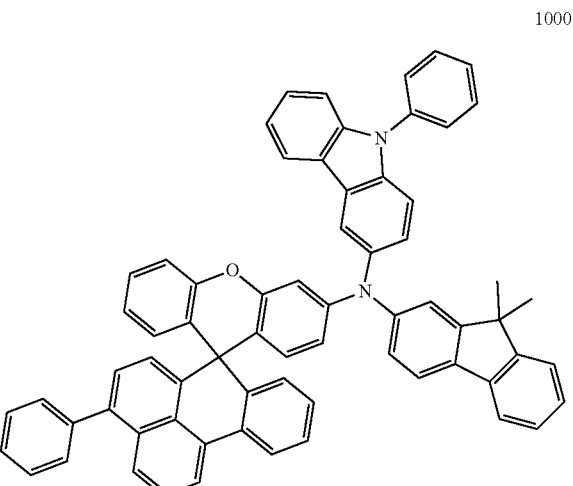
1001
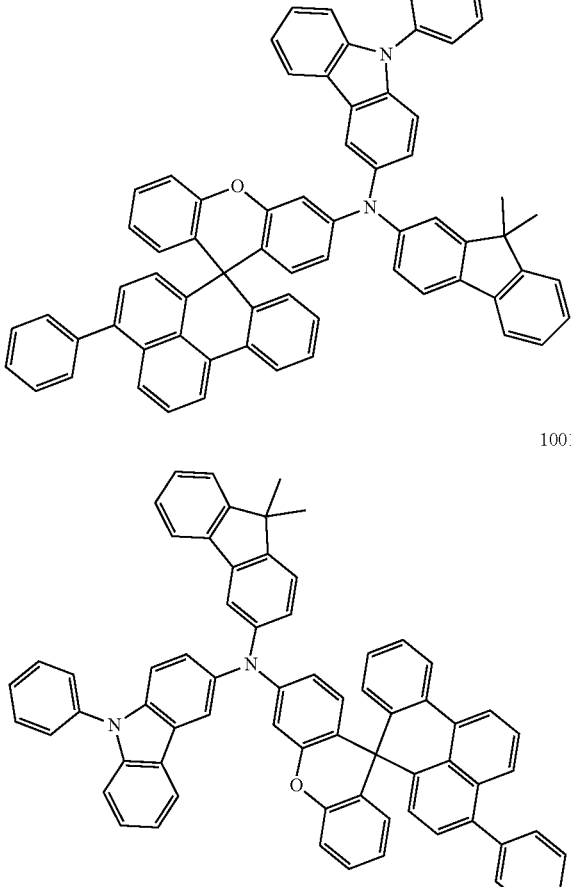
1002

-continued
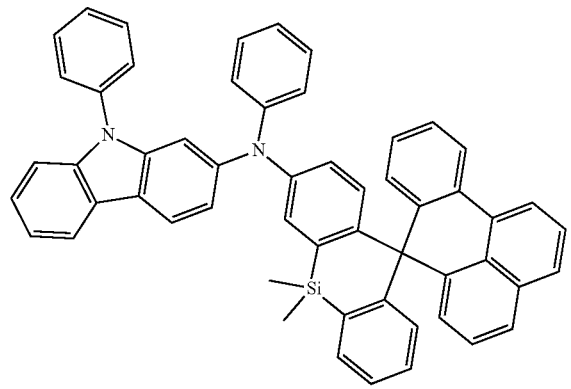
1003
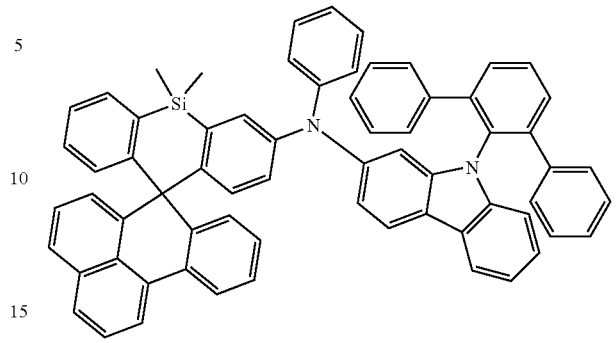
1007
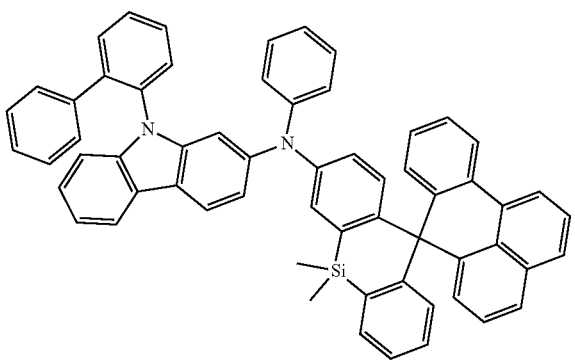
1004
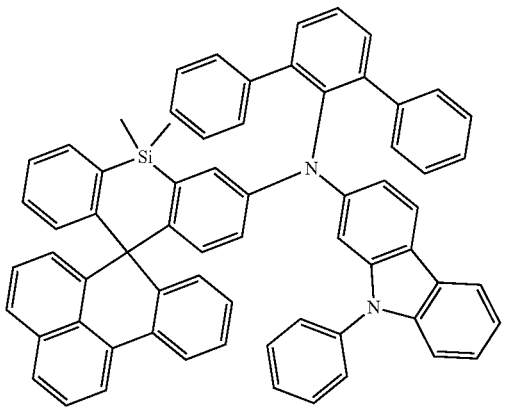
1008
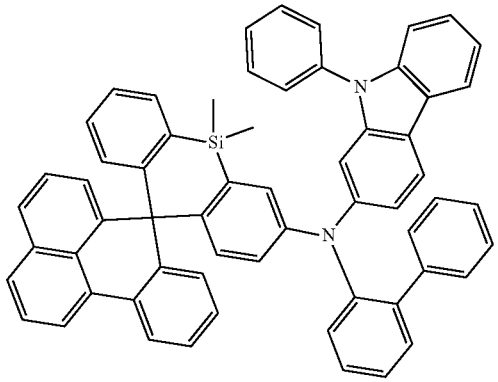
1005
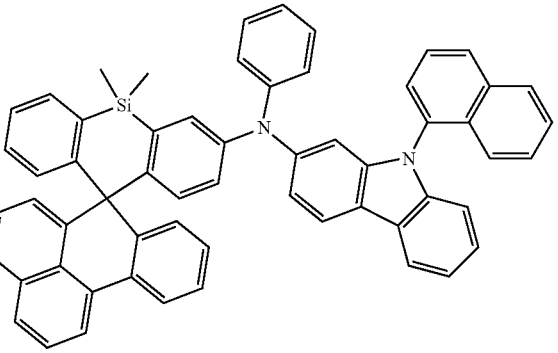
1009
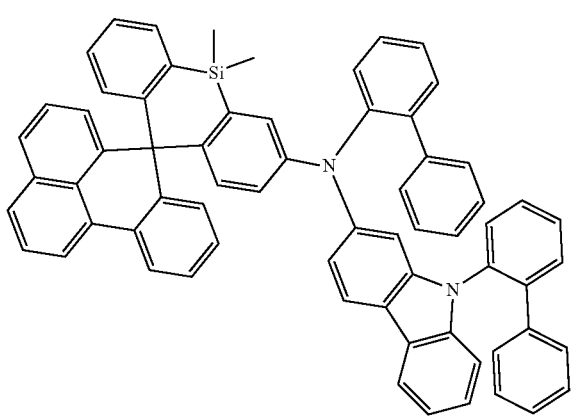
1006
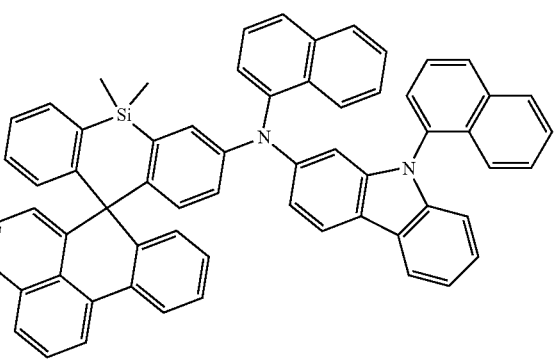
1010

1011
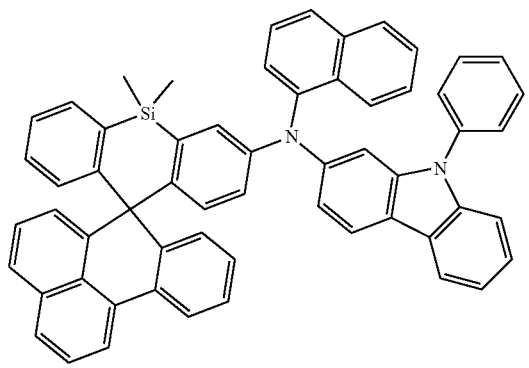
1012
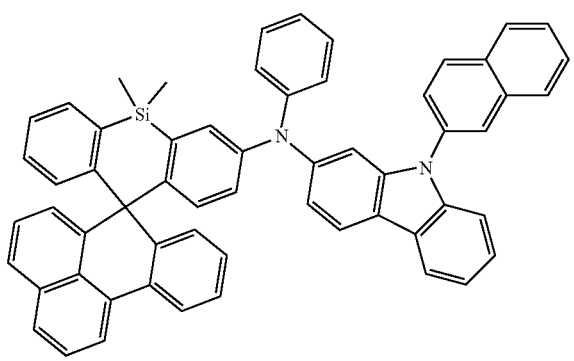
1013
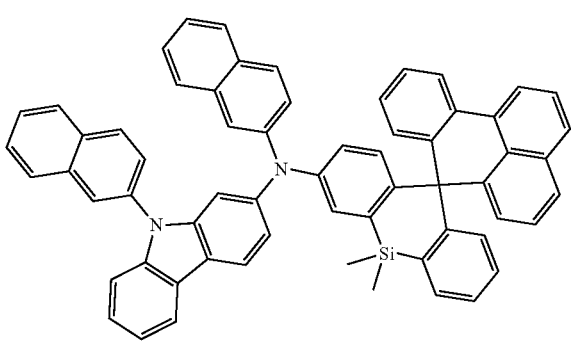
1014
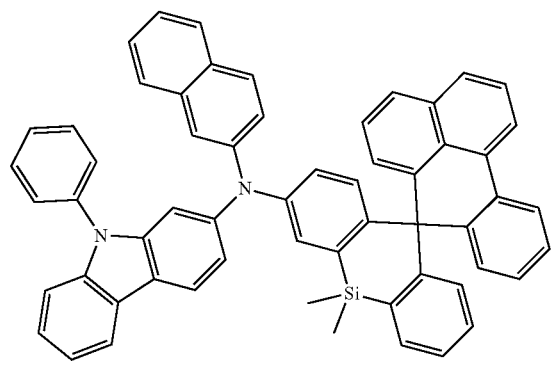
1015
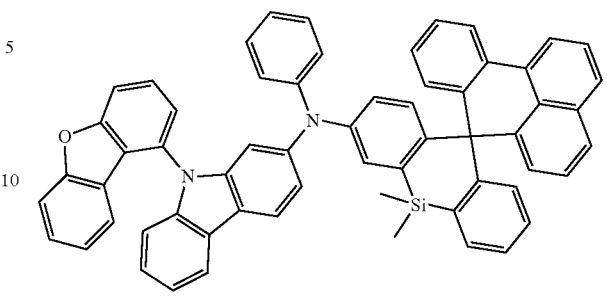
1016
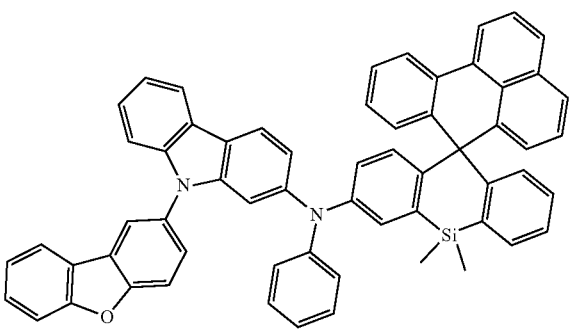
1017
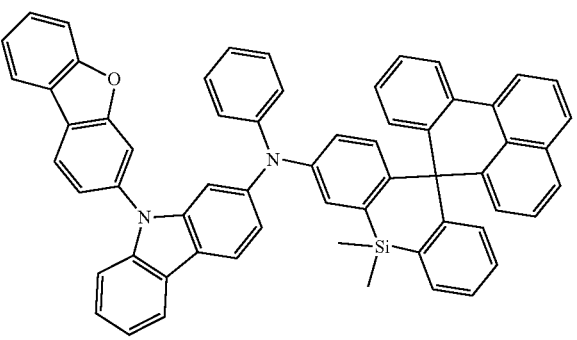
1018
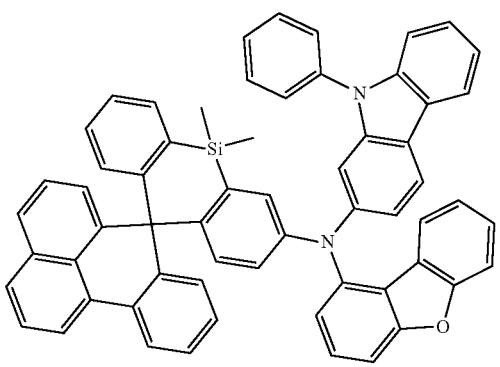

1019
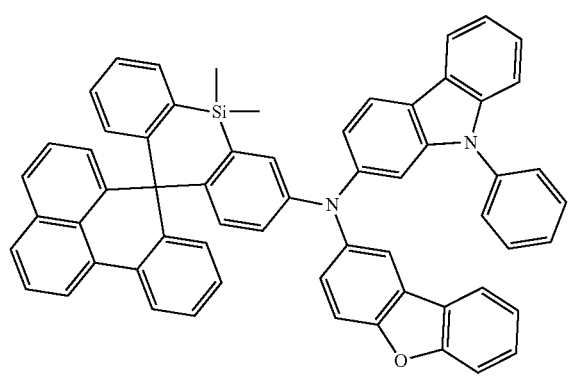
1020
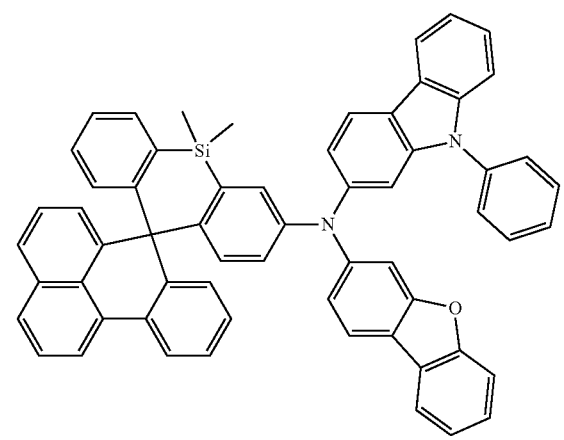
1021
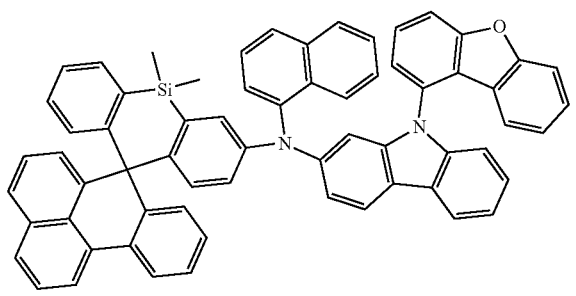
1022
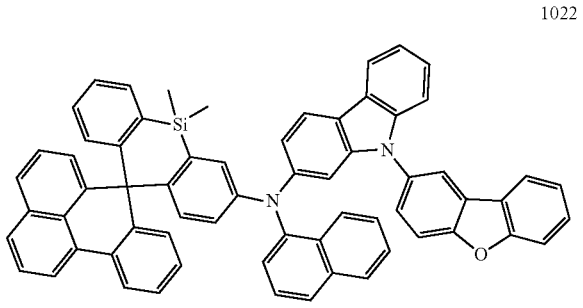
1023
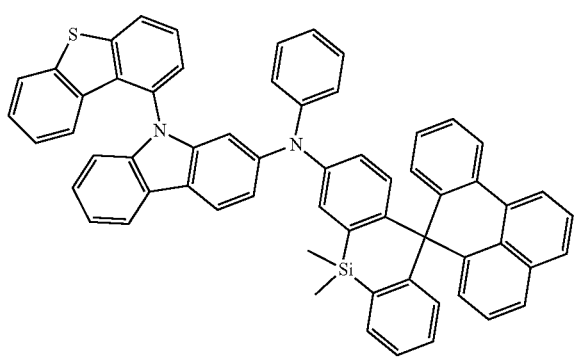
1024
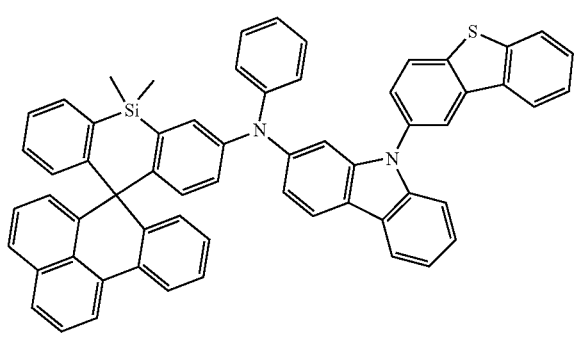
1025
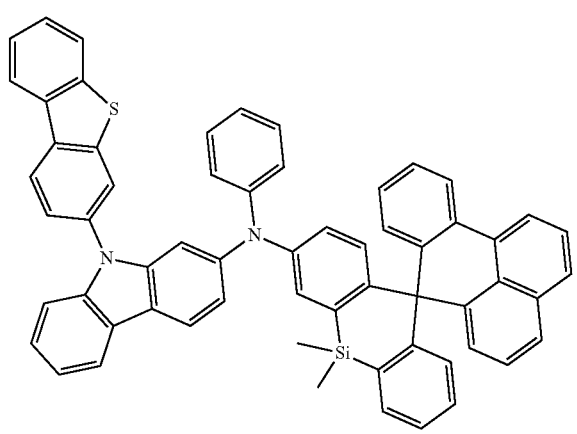
1026
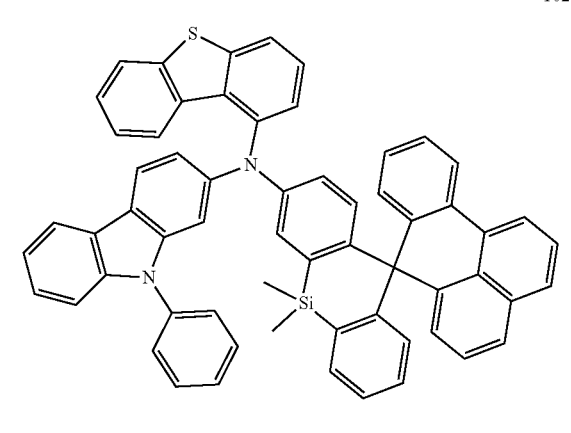

1027
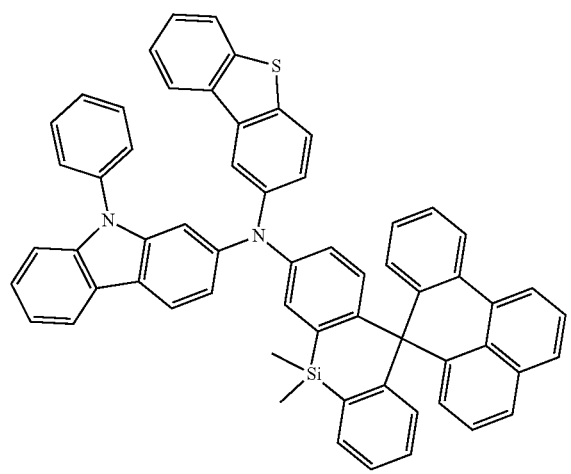
1028
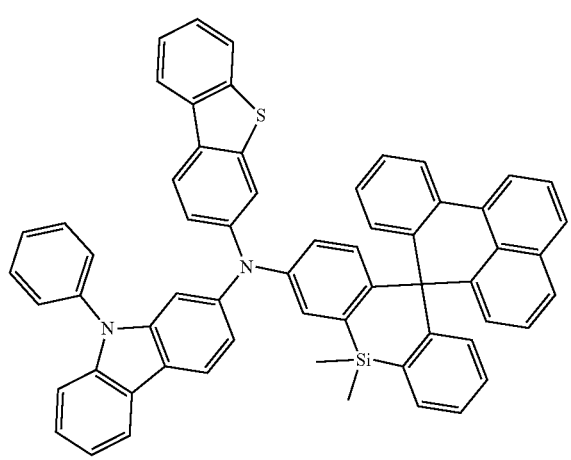
1029
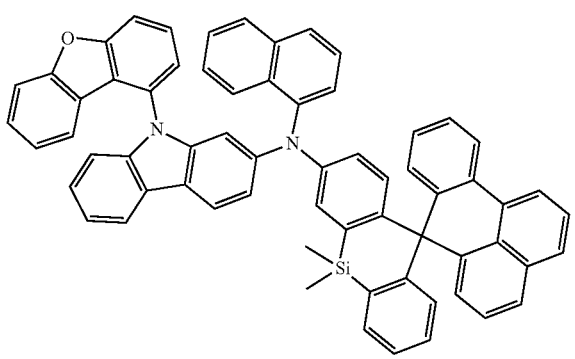
1030
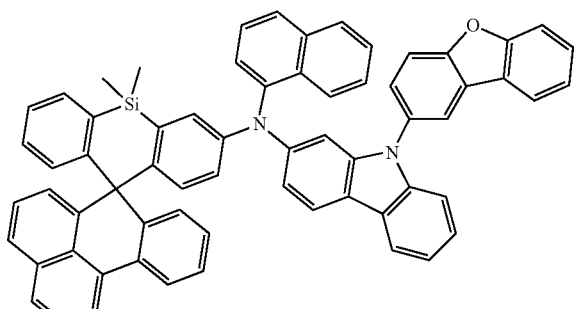
1031
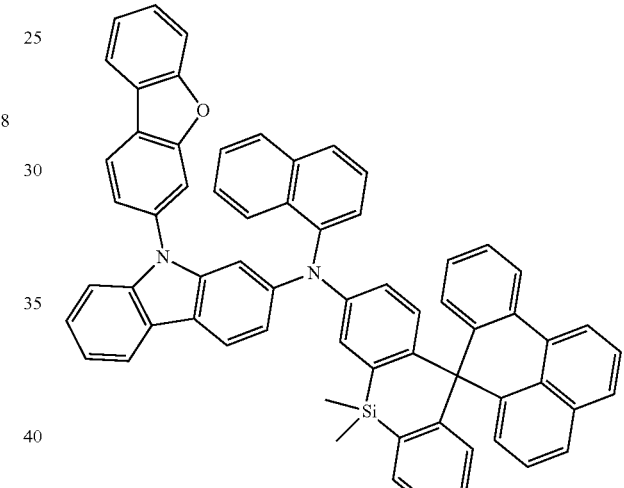
1032
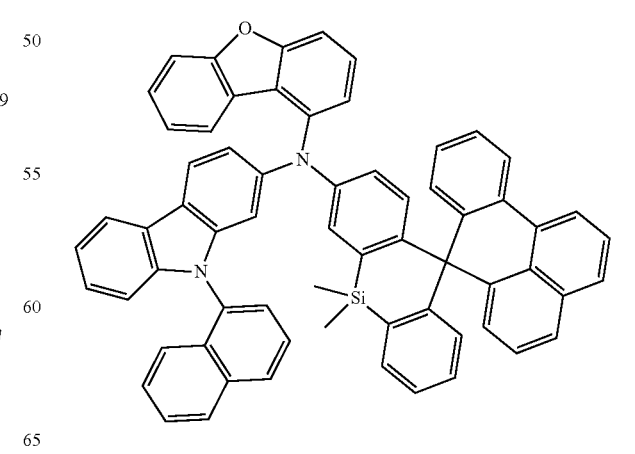

313
-continued
1033
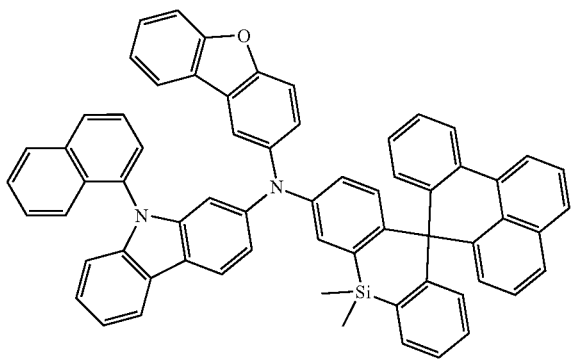
1034
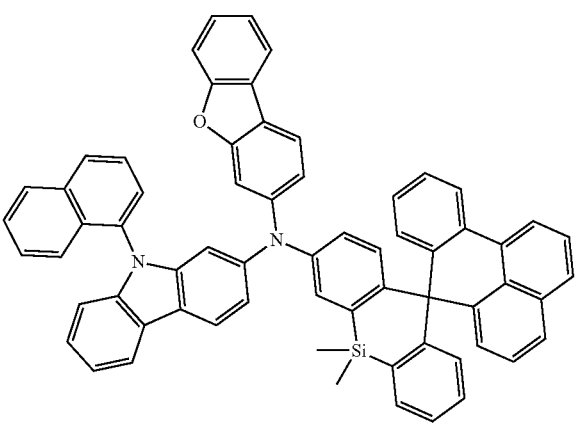
1035
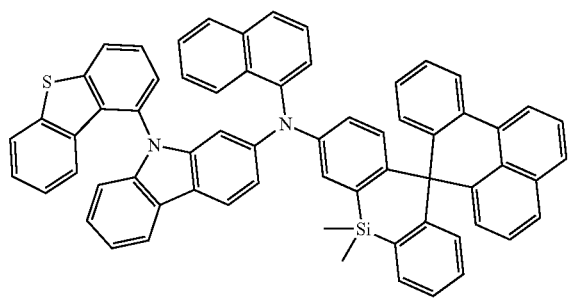
1036
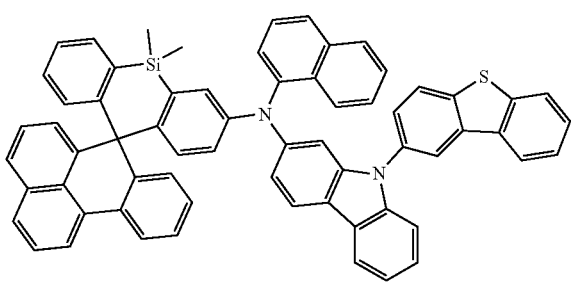
314
-continued
1037
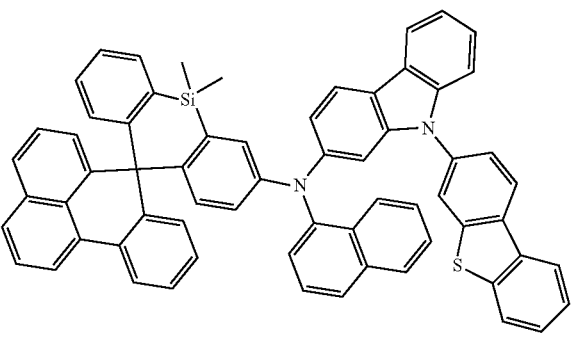
1038
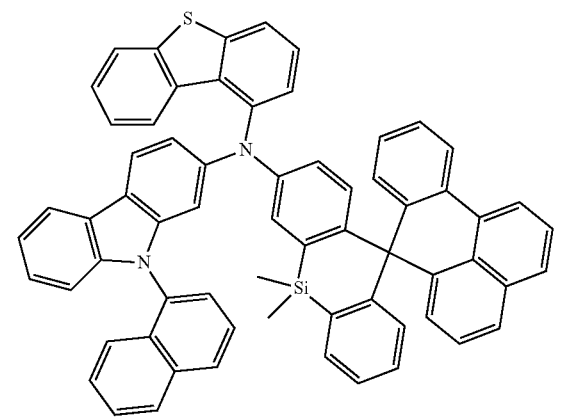
1039
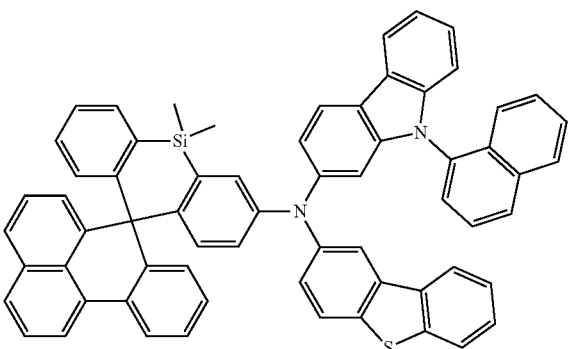
1040
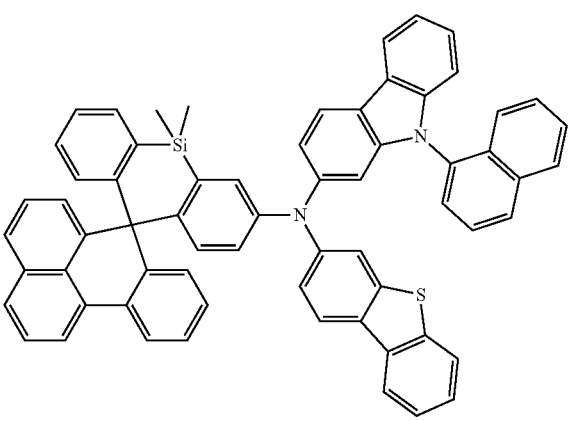

1041
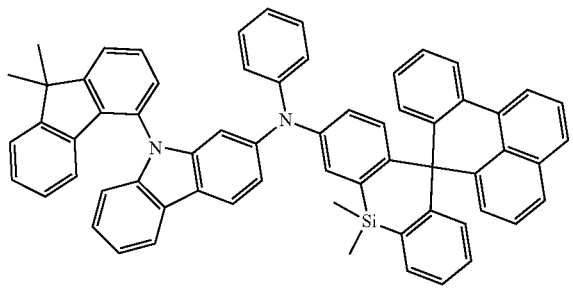
1042
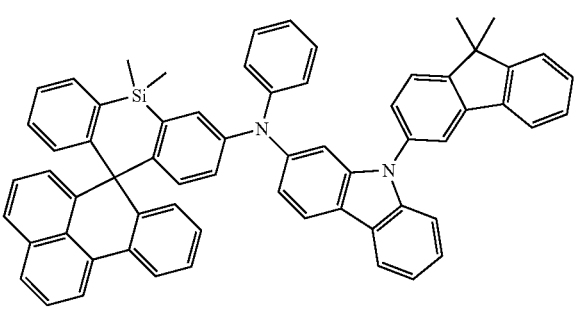
1043
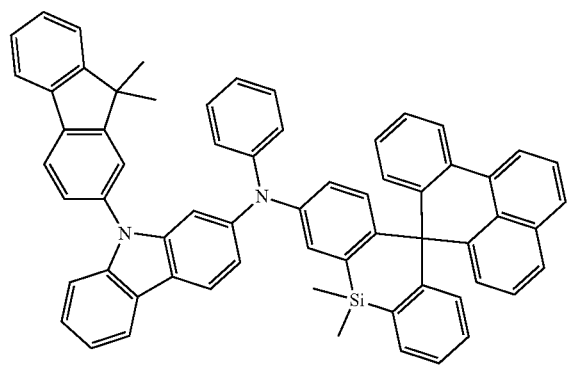
1044
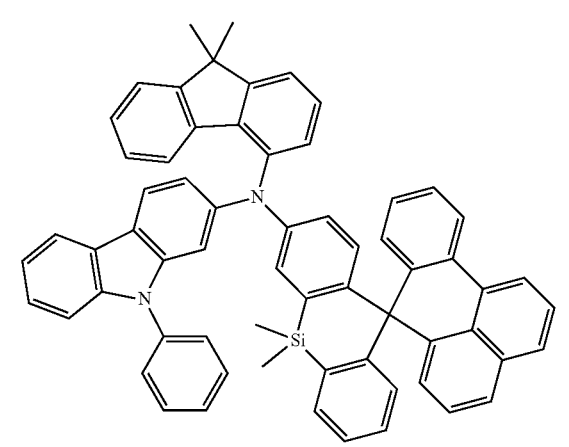
1045
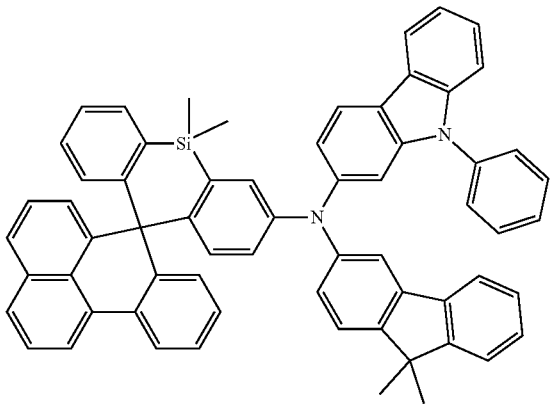
1046
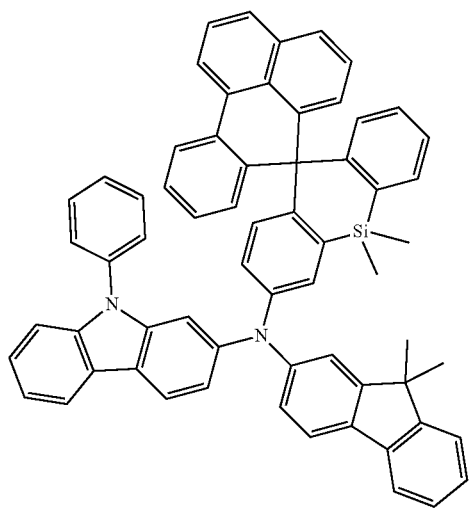
1047
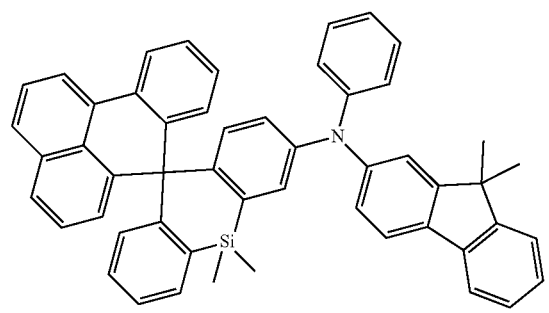
1048
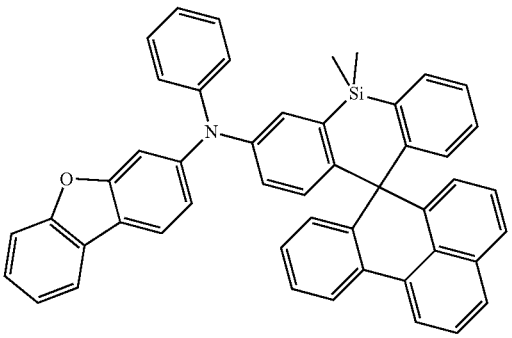

1049
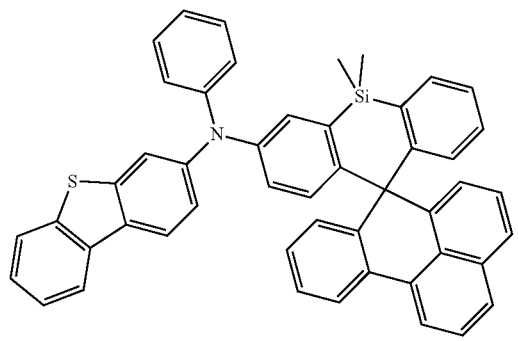
1050
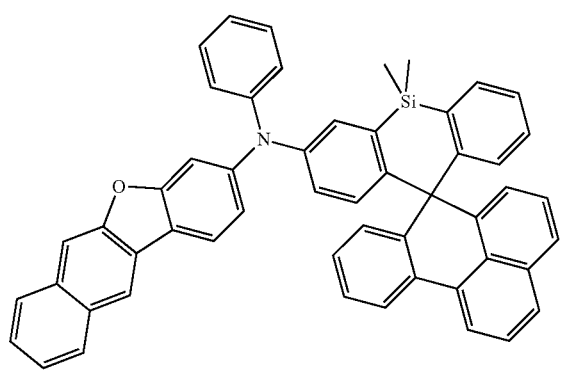
1051
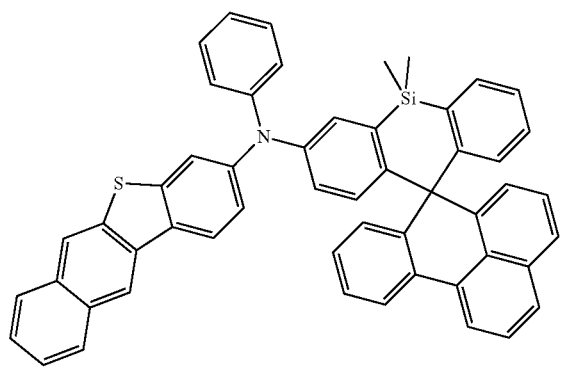
1052
1053
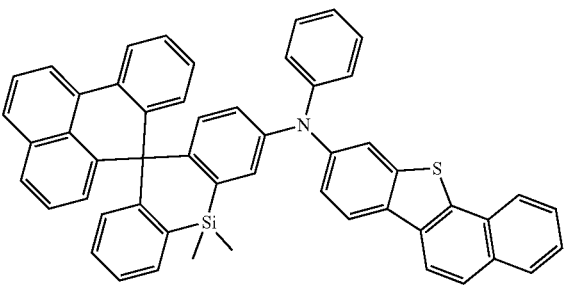
1054
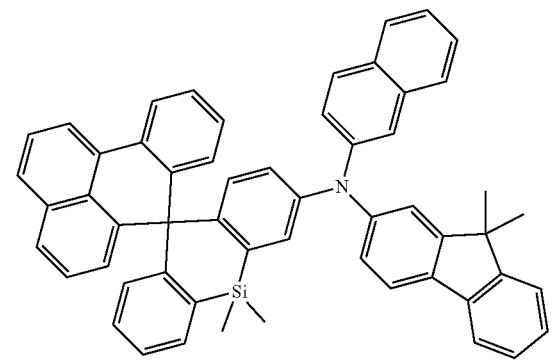
1055
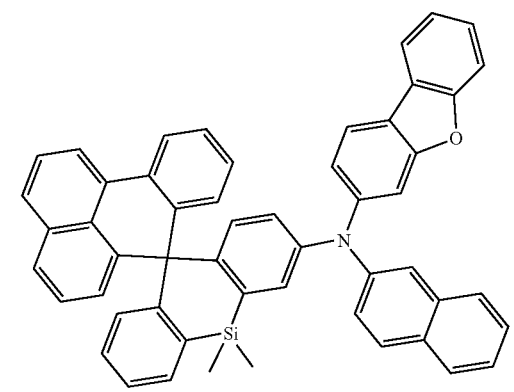
1056
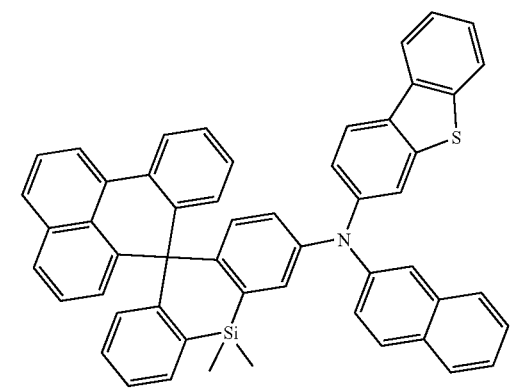

1057
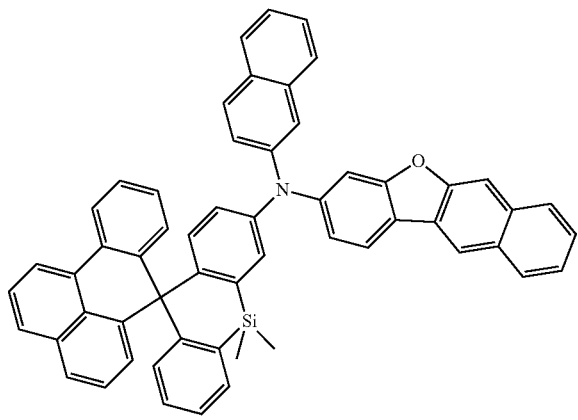
1058
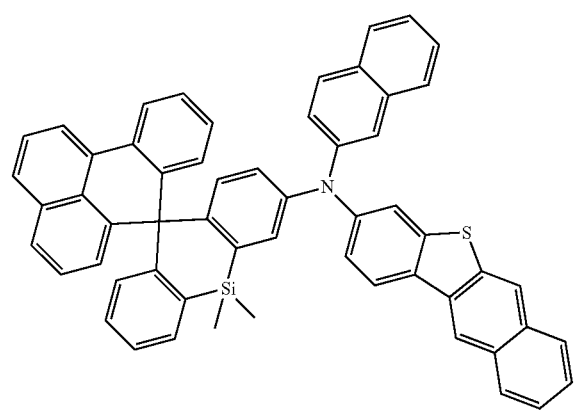
1059
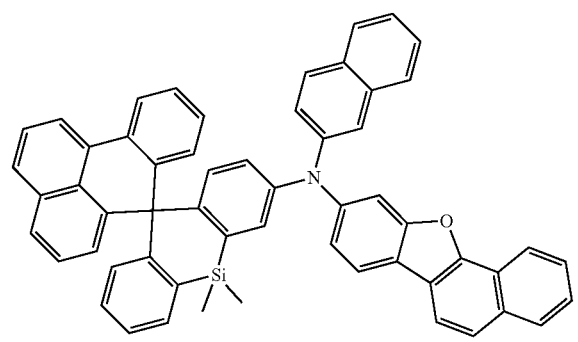
1060
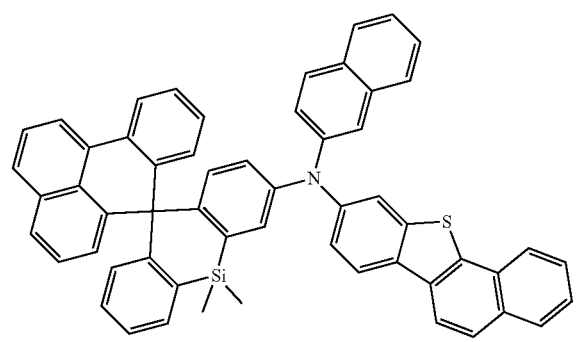
1061
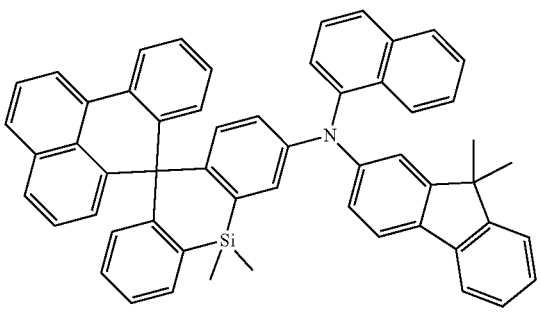
1062
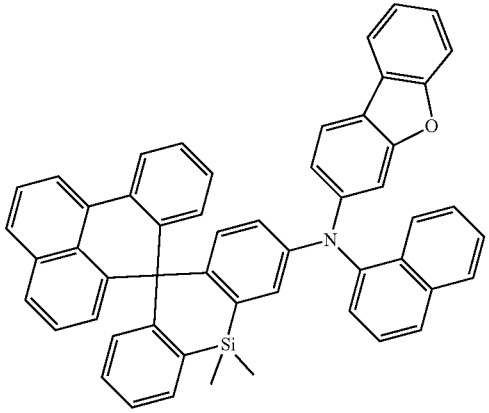
1063
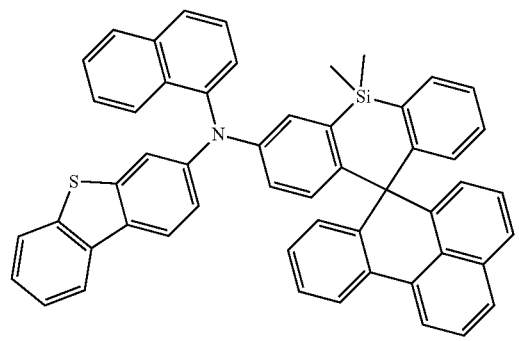
1064
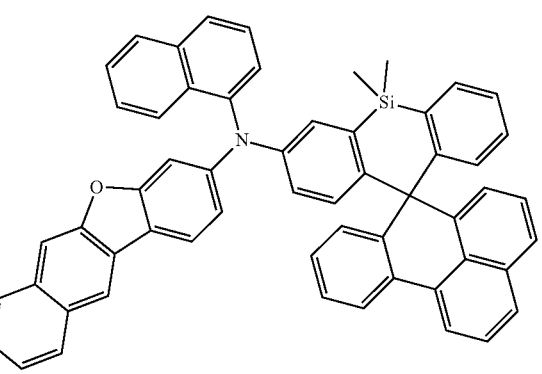

321
-continued
1065
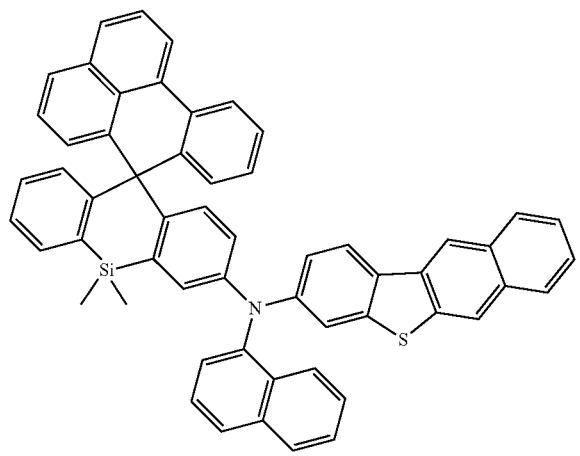
1066
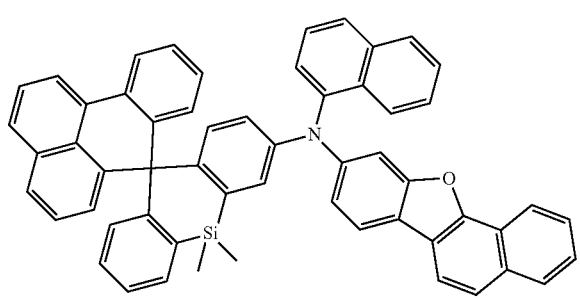
1067
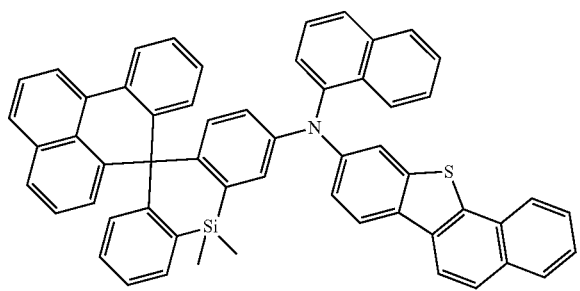
1068
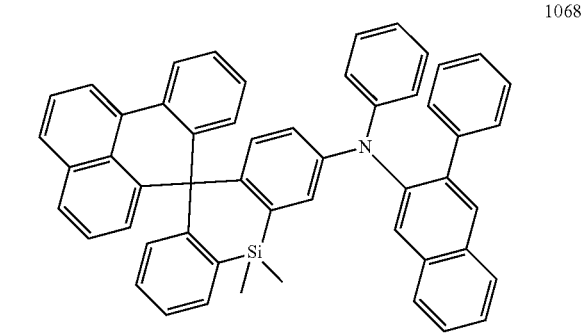
322
-continued
1069
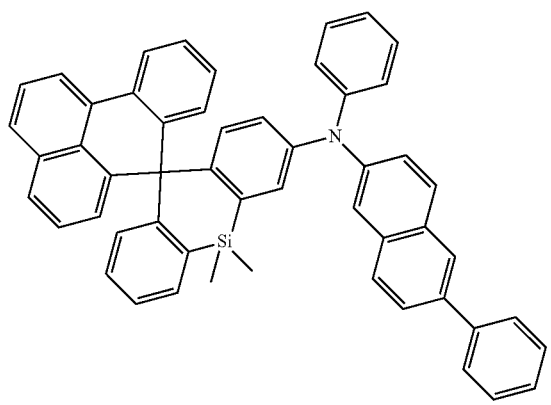
1070
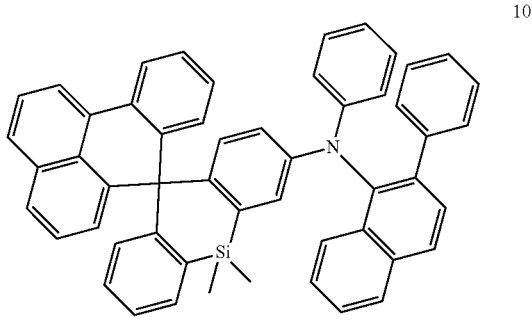
1071
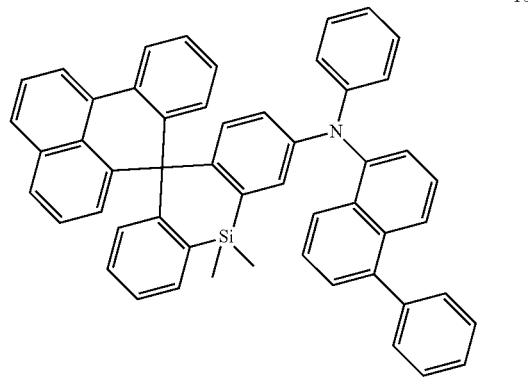
1072
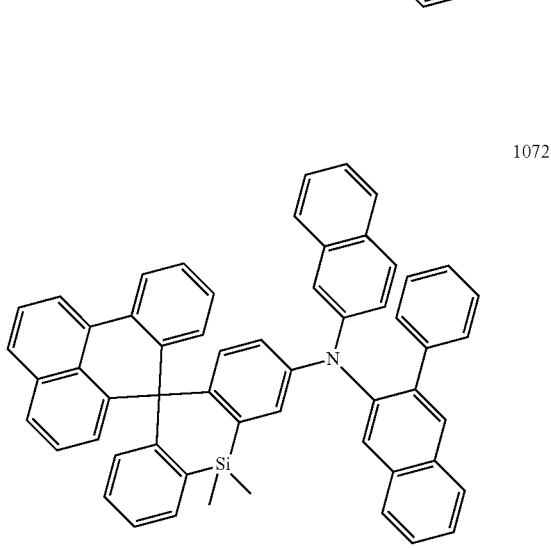

323
-continued
1073
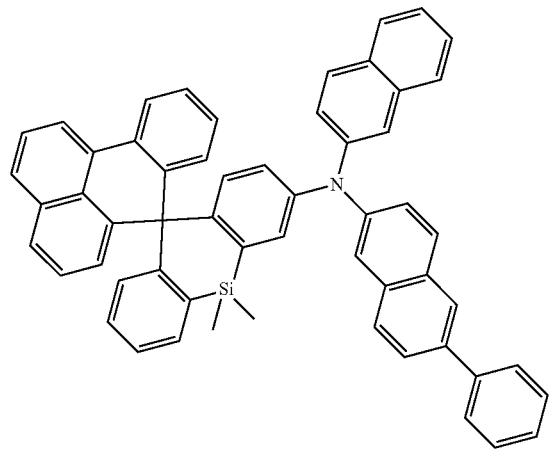
1074
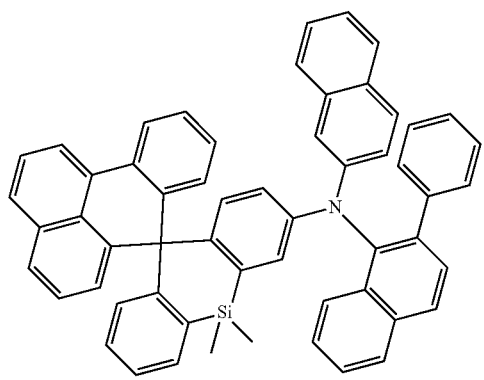
1075
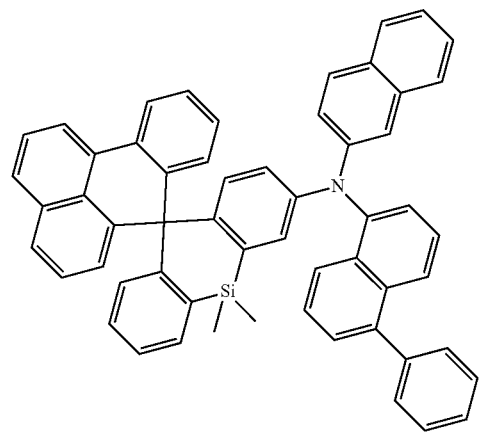
1076
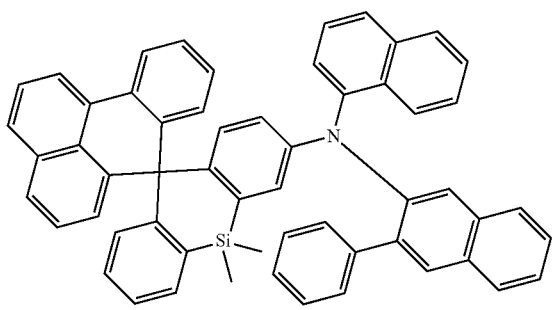
324
-continued
1077
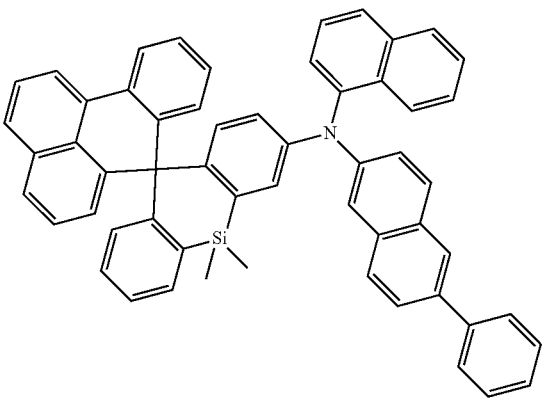
1078
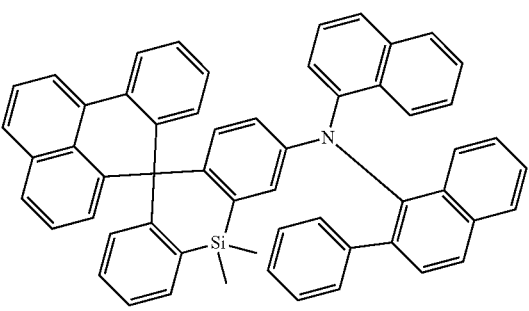
1079
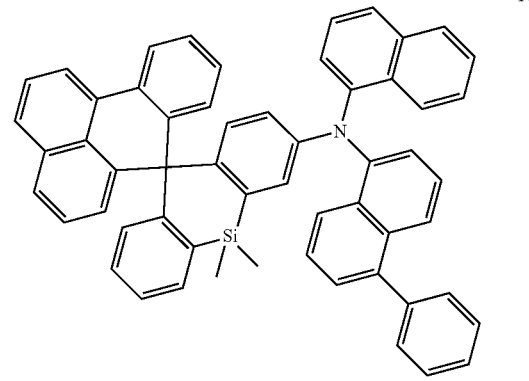
1080
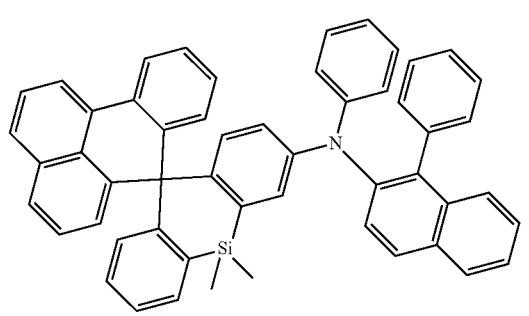

1081
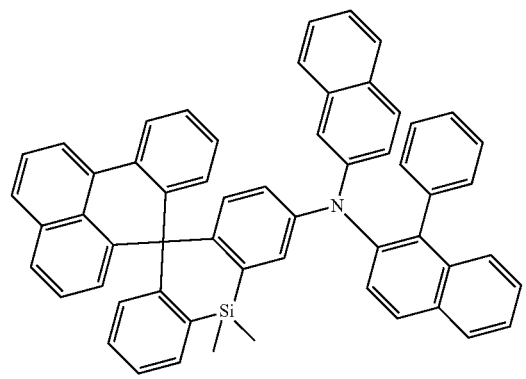
1082
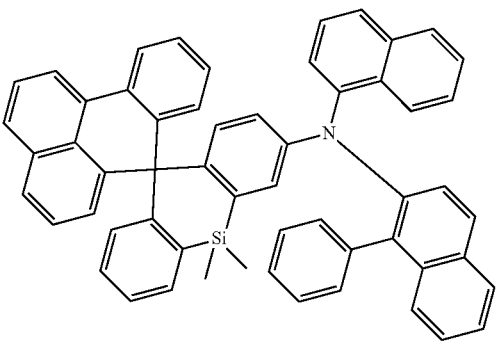
1083
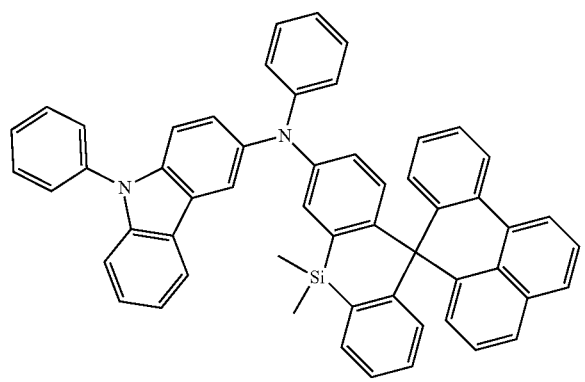
1084
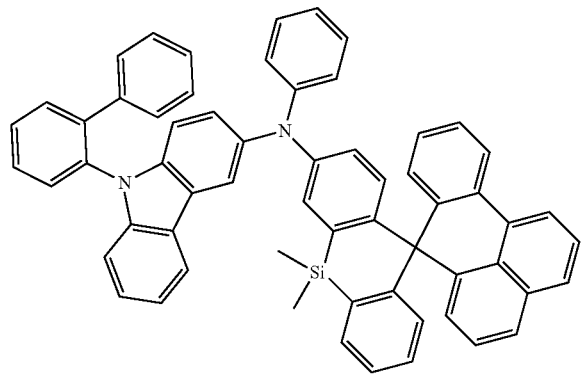
1085
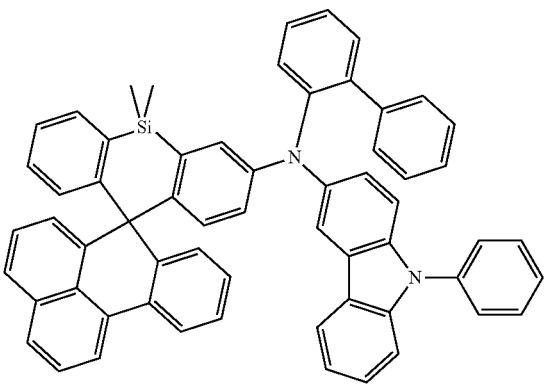
1086
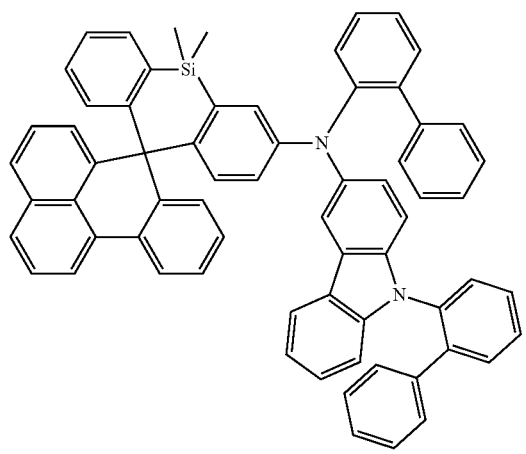
1087
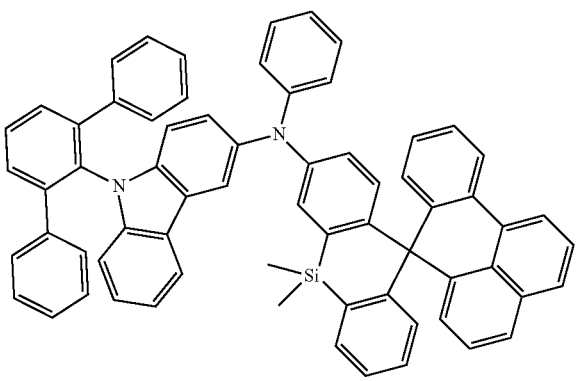

327
-continued
1088
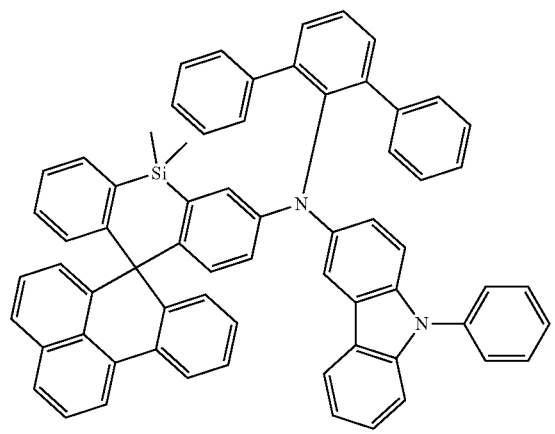
1089
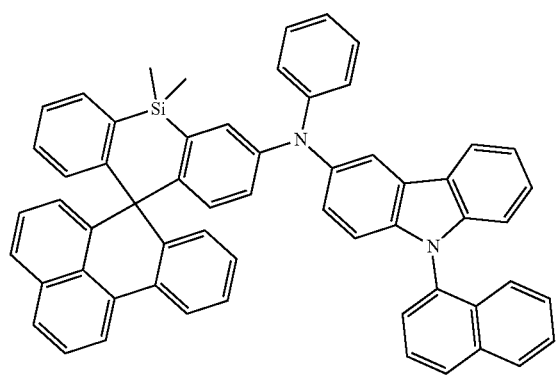
1090
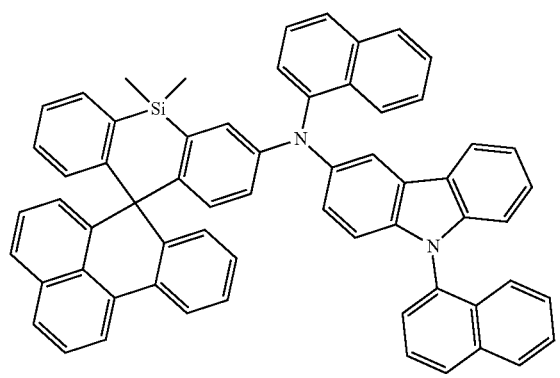
1091
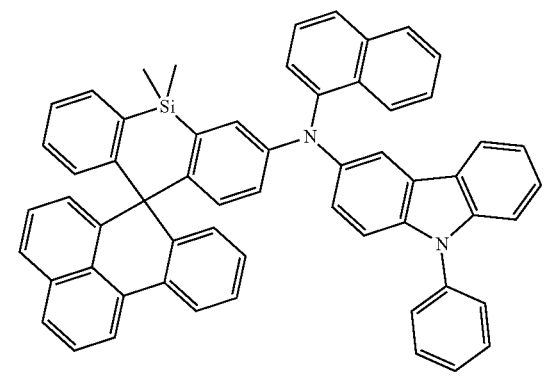
328
-continued
1092
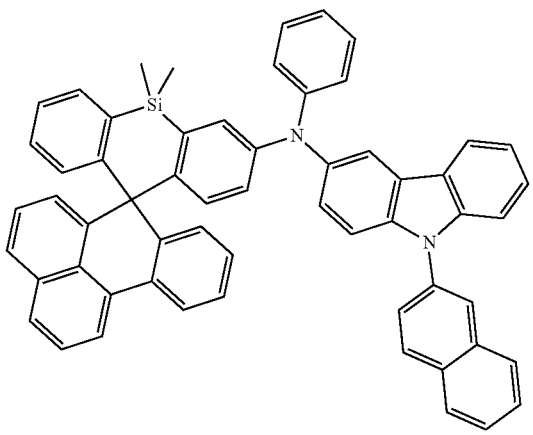
1093
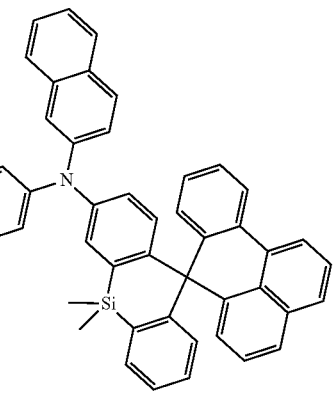
1094
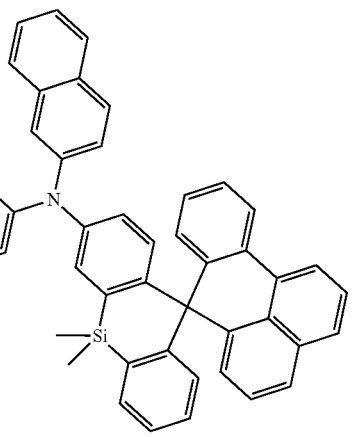

329
-continued
1095
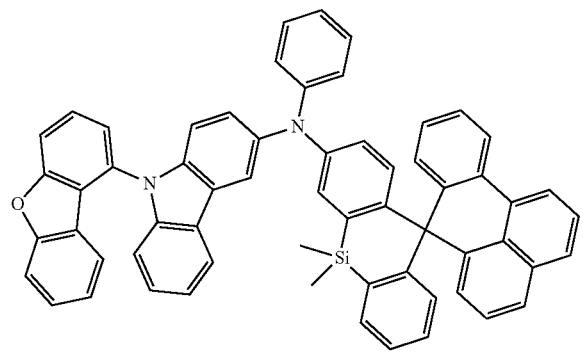
1096
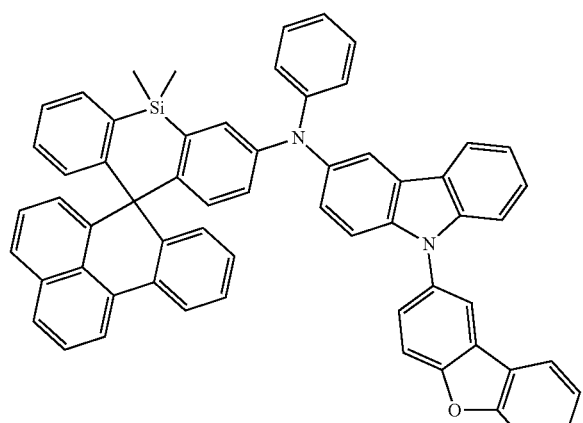
1097
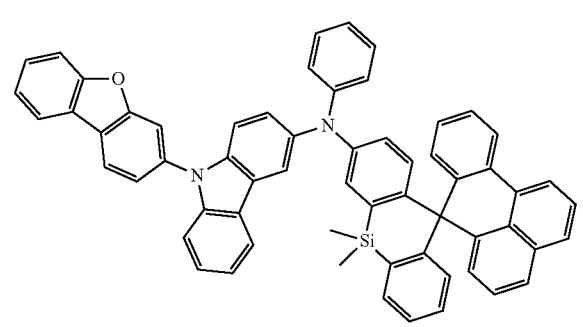
1098
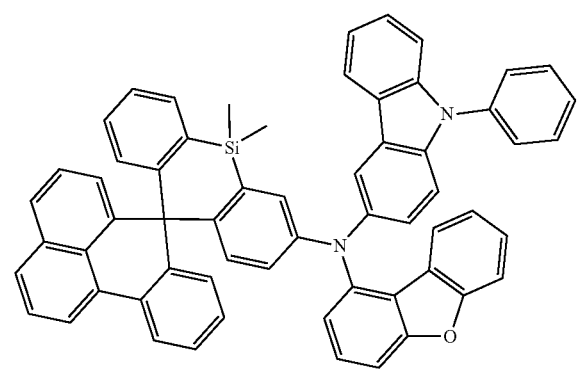
330
-continued
1099
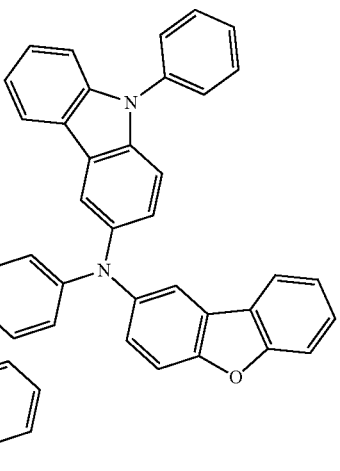
1100
1101

-continued
1102
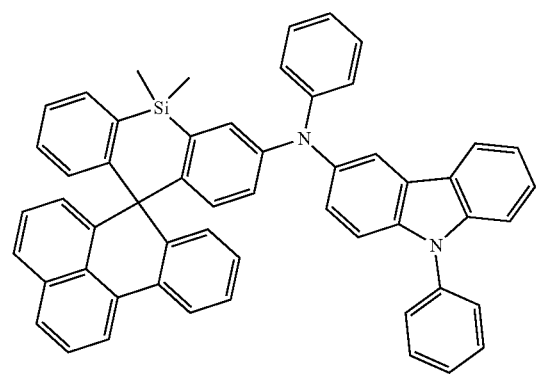
1103
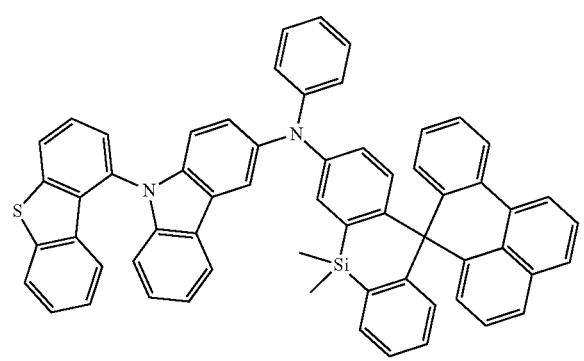
1104
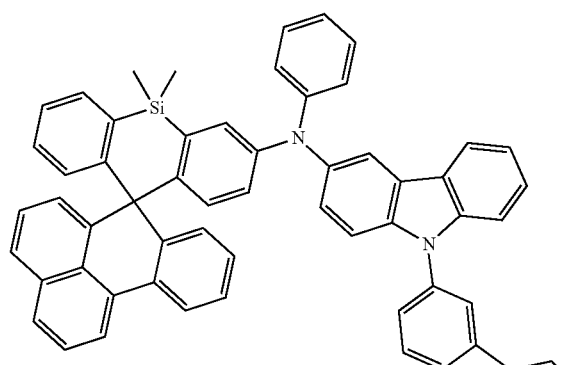
1105
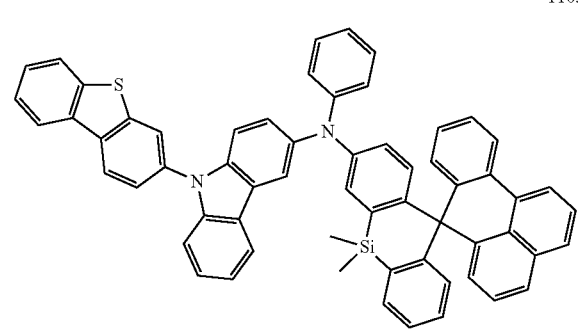
-continued
1106
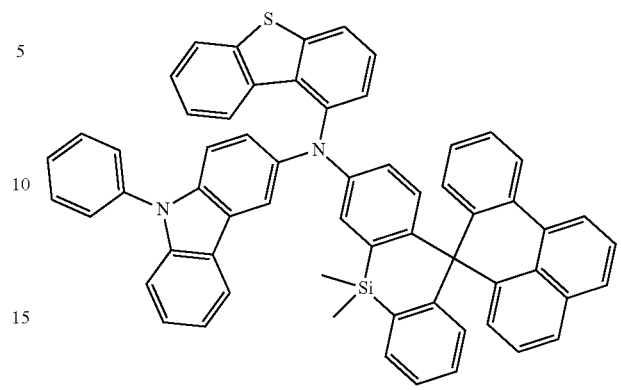
1107
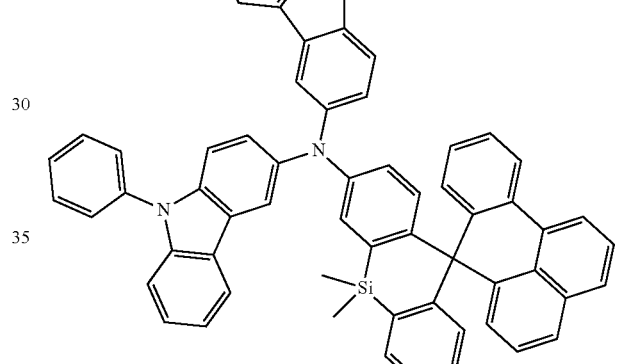
1108
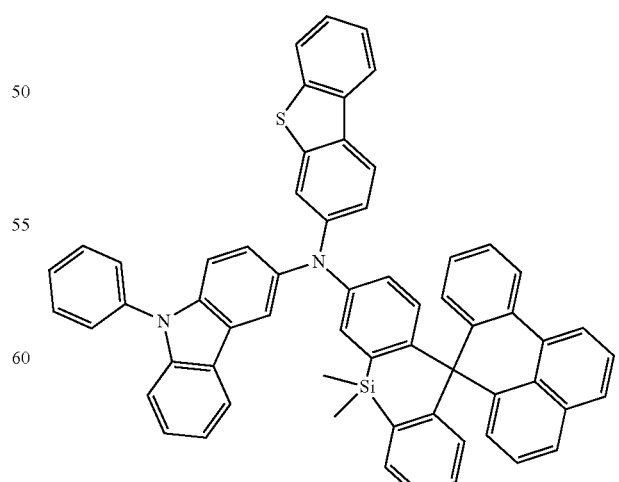

333
-continued
1109
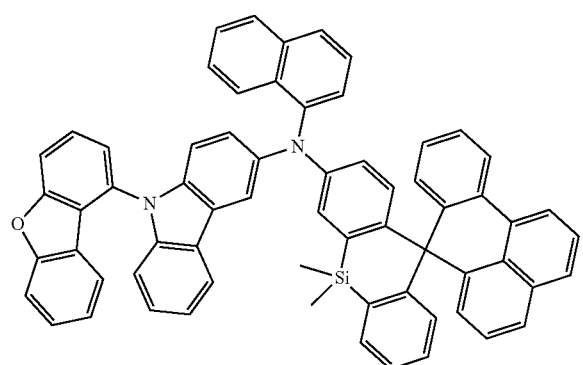
1110
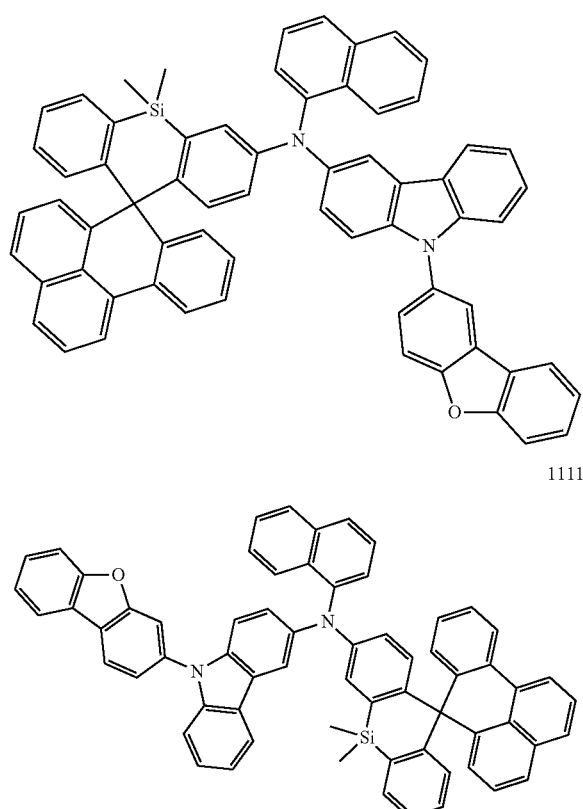
1111
1112
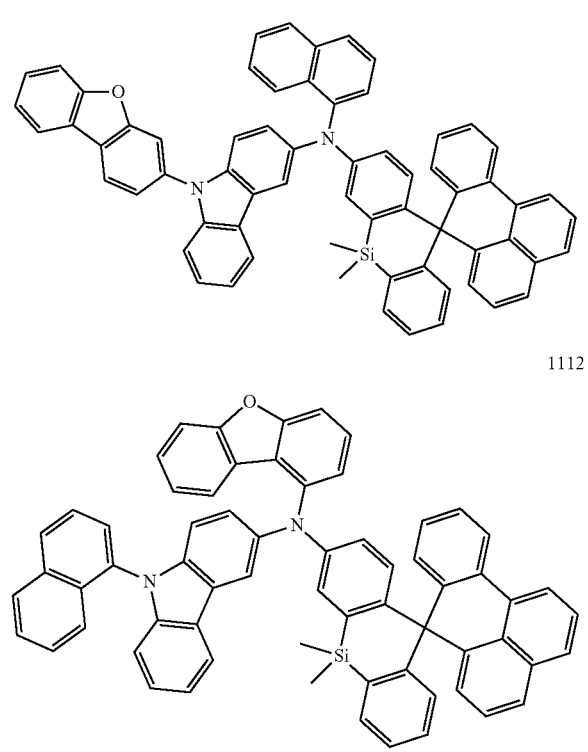
334
-continued
1113
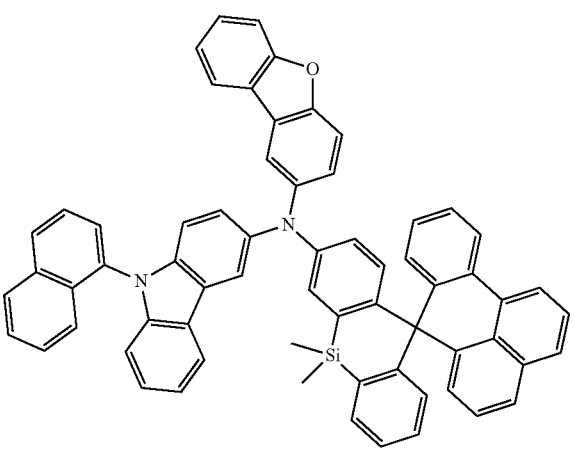
1114
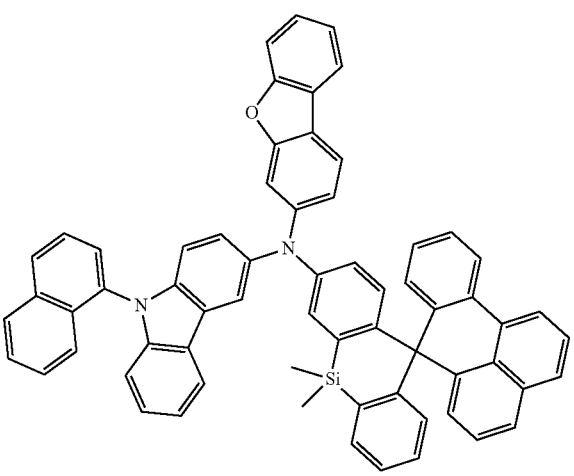
1115

335
-continued
1116
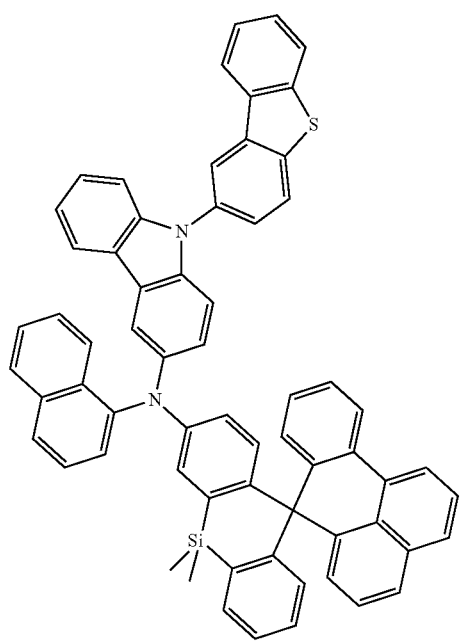
1117
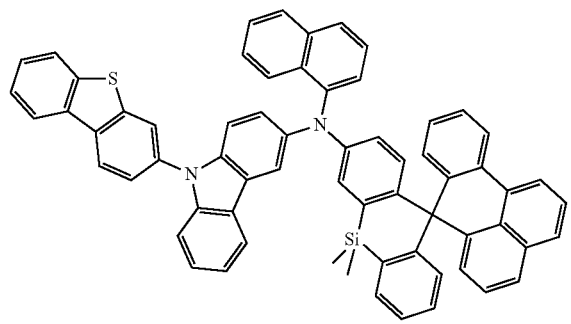
1118
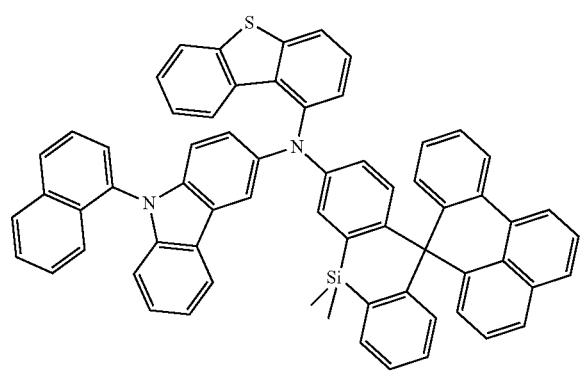
336
-continued
1119
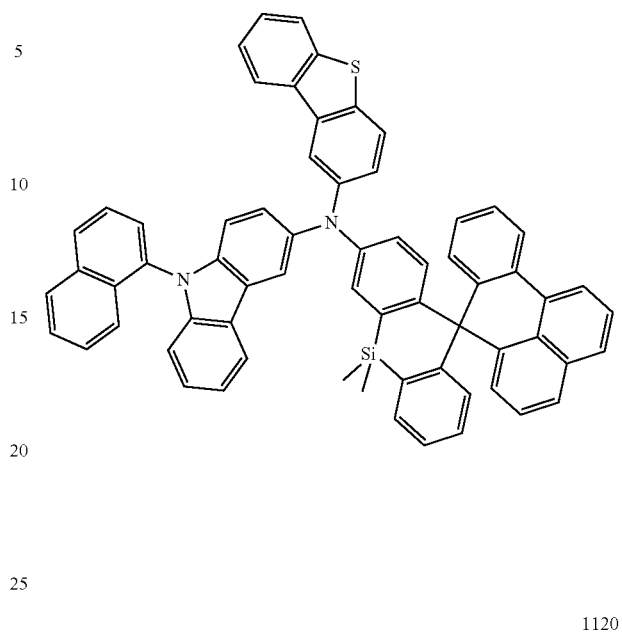
1120
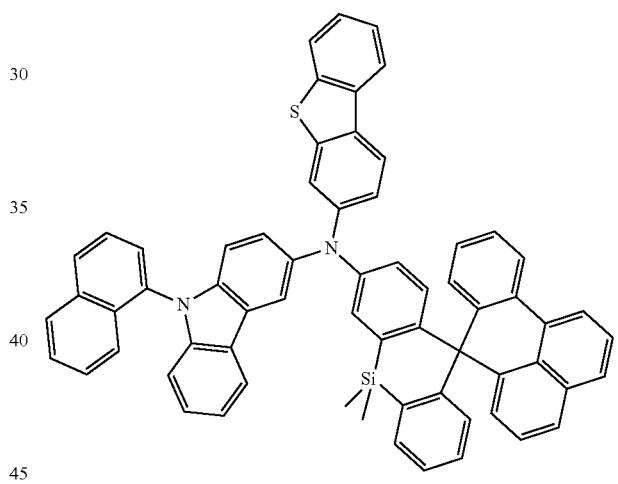
1121
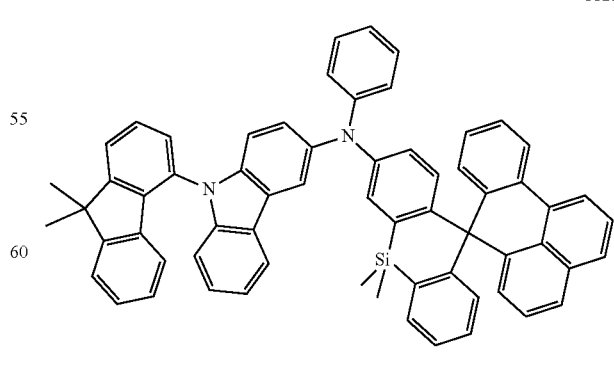

1122
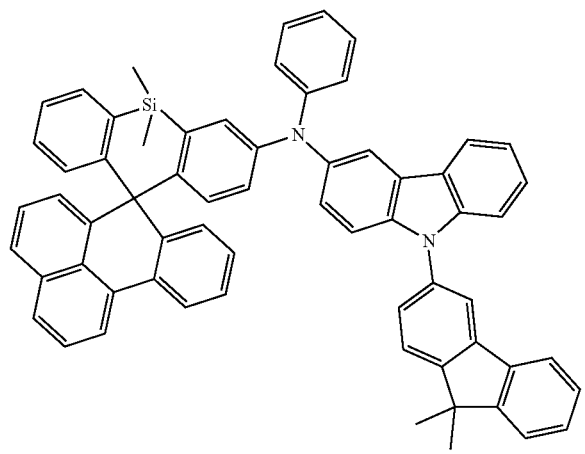
1123
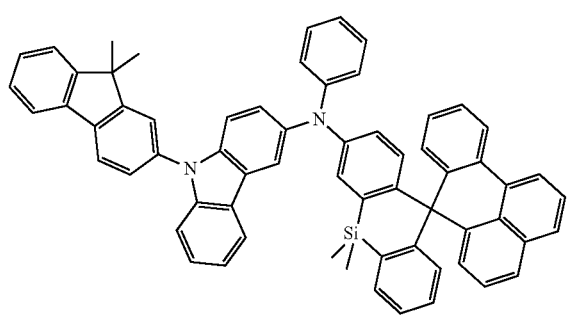
1124
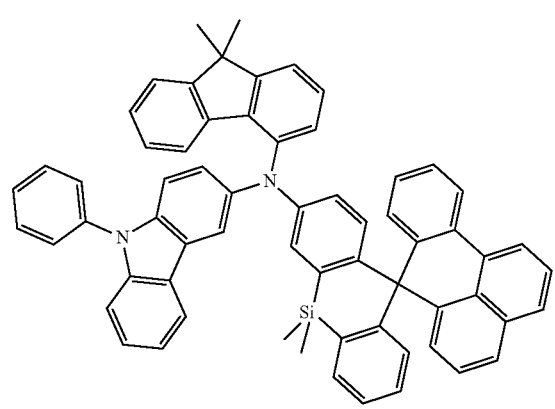
1125
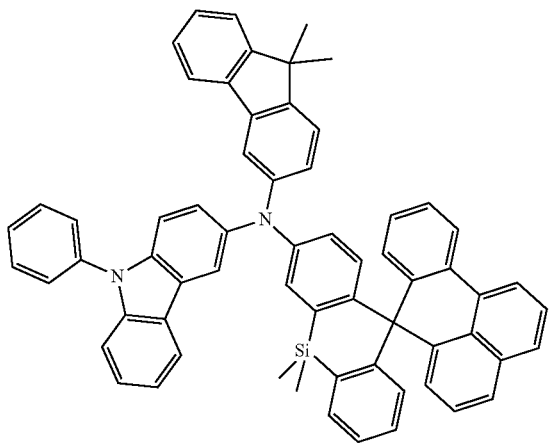
1126
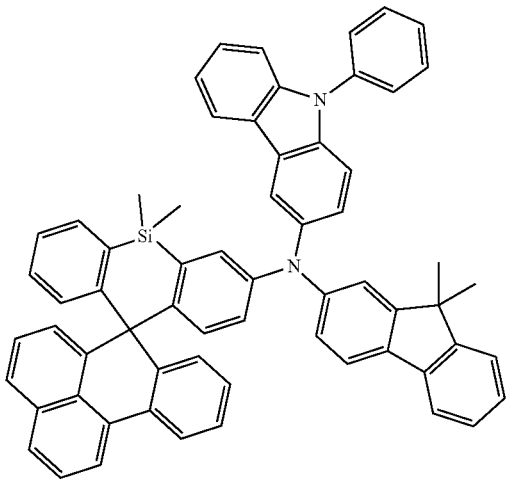
1127
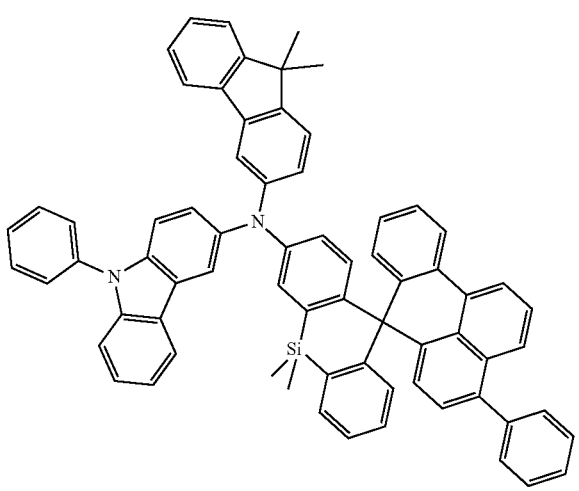

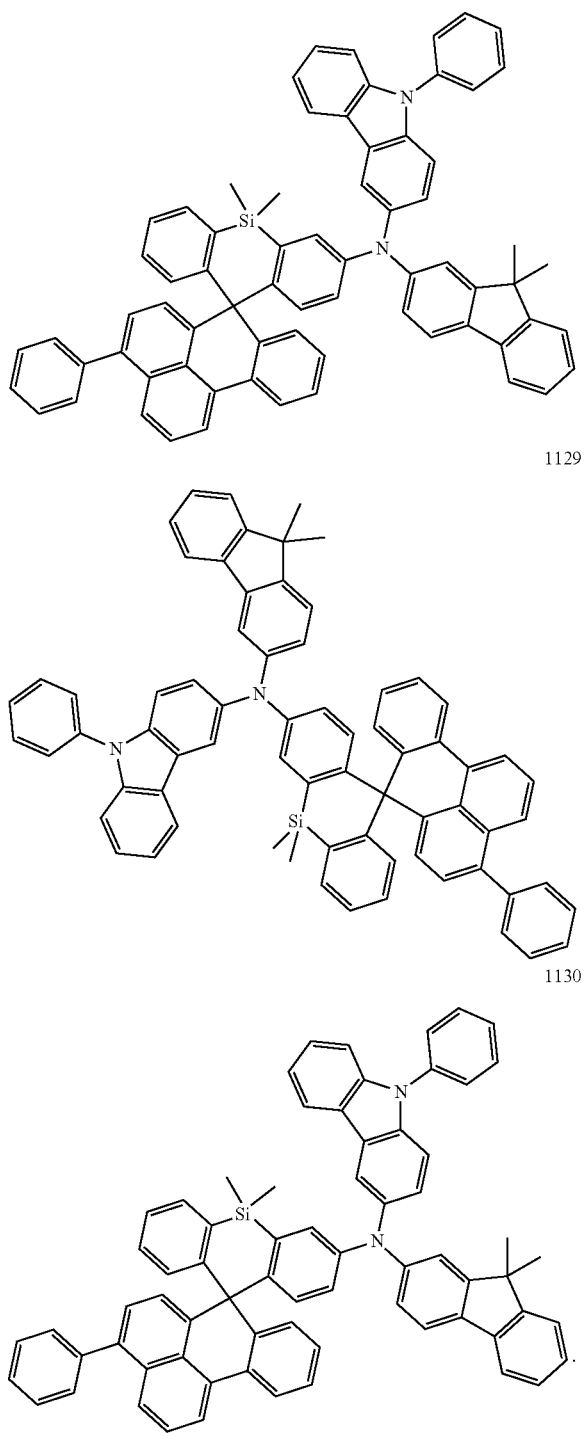

The amine compound according to one or more embodiments, represented by Formula 1 has a molecular structure in which an amine group is bonded to a condensed ring having a spiro structure including a heteroatom. For example, the amine compound according to one or more embodiments of the present disclosure includes a spiro structure (such as spiro[benzo[de]anthracene-7,9'-xanthene], spiro[benzo[de]anthracene-7,9'-thioxanthene], spiro[benzo[de]anthracene-7,10'-dibenzo[b,e]siline], and/or spiro[acridine-9,7'-benzo[de]anthracene], which contains a heteroatom that may increase band gap), and the spiro structure contains a heteroatom that has high glass transition temperature and high melting point characteristics, and may exhibit excellent (or improved) heat resistance and durability characteristics. In addition, hole transport ability may be improved by having a structure in which an amine group is substituted in a spiro structure of a compound containing a heteroatom.

If the amine compound according to one or more embodiments is used in the hole transport region, hole transportability may be increased, thereby improving the probability of recombination between holes and electrons in the emission layer, and thus luminous efficiency may be increased. In one or more embodiments, as described above, lifetime of the light-emitting diode according to one or more embodiments may also be improved by including the amine compound according to one or more embodiments with excellent (or improved) heat resistance and durability as a material for the light-emitting diode.

The light-emitting diode ED according to one or more embodiments may further include a material for the hole transport region described below in addition to the amine compound according to one or more embodiments described above.

The hole transport region HTR may include a compound represented by Formula H-1 below.

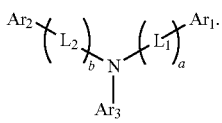

[Formula H-1]

In Formula H-1, $L_1$ and $L_2$ may each independently be a direct linkage, a substituted or unsubstituted ring-forming arylene group having 6 to 30 carbon atoms, or a substituted or unsubstituted ring-forming heteroarylene group having 2 to 30 carbon atoms. "a" and "b" may each independently be an integer of 0 to 10. Meanwhile, if "a" or "b" is an integer of 2 or more, a plurality of $L_1$ and $L_2$ may each independently be a substituted or unsubstituted ring-forming arylene group having 6 to 30 carbon atoms, or a substituted or unsubstituted ring-forming heteroarylene group having 2 to 30 carbon atoms.

In Formula H-1, $Ar_1$ and Are may each independently be a substituted or unsubstituted ring-forming aryl group having 6 to 30 carbon atoms, or a substituted or unsubstituted ring-forming heteroaryl group having 2 to 30 carbon atoms. In one or more embodiments, in Formula H-1, $Ar_3$ may be a substituted or unsubstituted ring-forming aryl group having 6 to 30 carbon atoms.

The compound represented by Formula H-1 may be a monoamine compound. In one or more embodiments, the compound represented by Formula H-1 may be a diamine compound in which at least one selected from among $Ar_1$ to $Ar_3$ contains an amine group as a substituent. In one or more embodiments, the compound represented by Formula H-1 may be a carbazole-based compound including a substituted or unsubstituted carbazole group in at least one of $Ar_1$ or $Ar_2$, or a fluorene-based compound including a substituted or unsubstituted fluorene group in at least one of $Ar_1$ or $Ar_2$.

The compound represented by Formula H-1 may be represented by any one selected from among the compounds in Compound Group H. However, the compounds listed in Compound Group H are illustrative, and the compound represented by Formula H-1 is not limited to those represented in Compound Group H.
[Compound Group H]
H-1-1
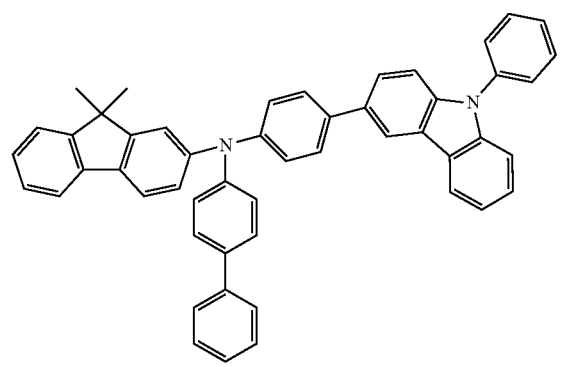
H-1-2
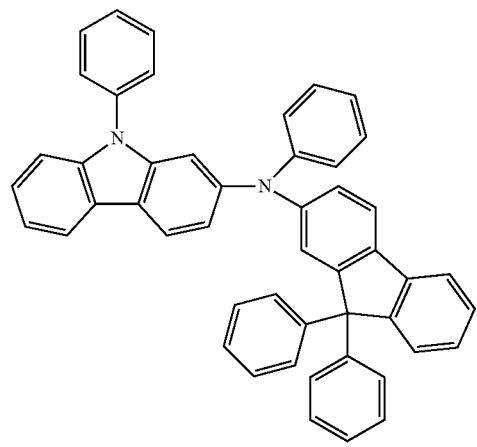
H-1-3
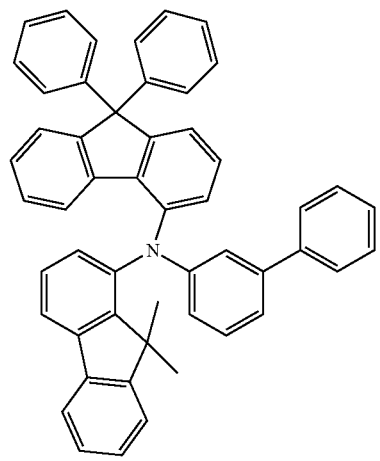
H-1-4
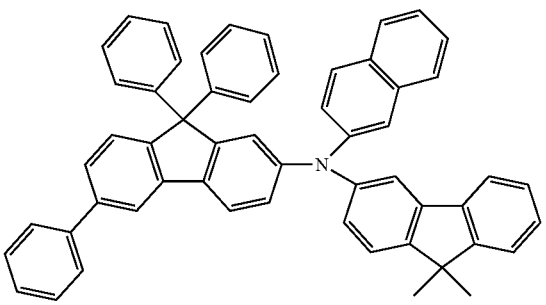
H-1-5
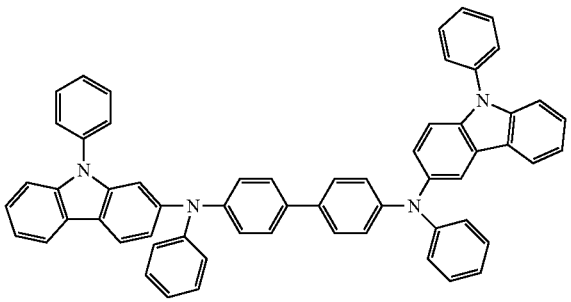
H-1-6
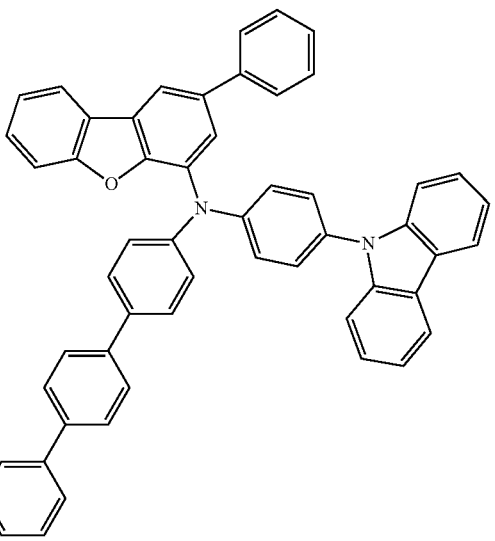

H-1-7
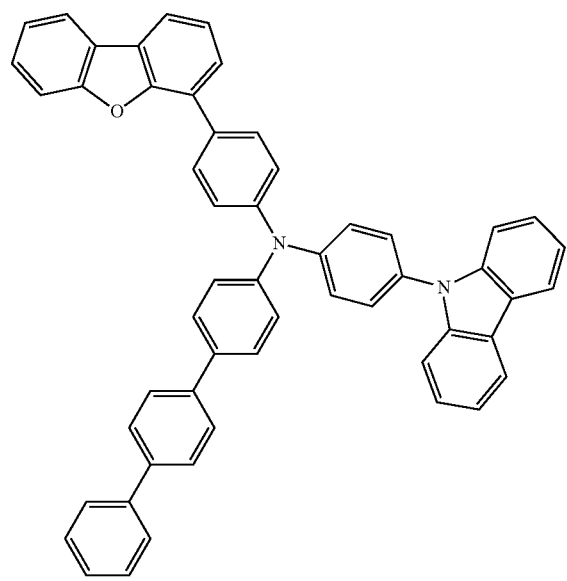
H-1-8
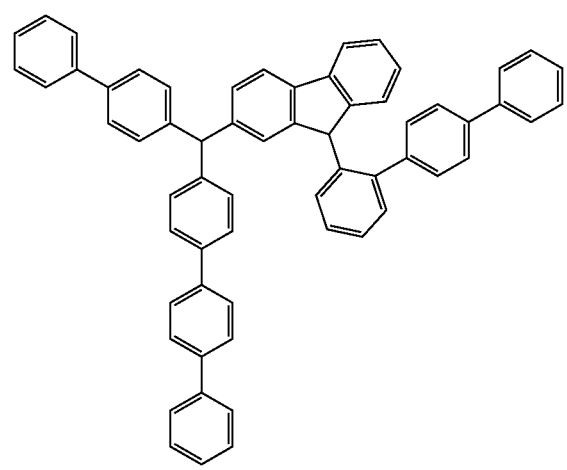
H-1-9
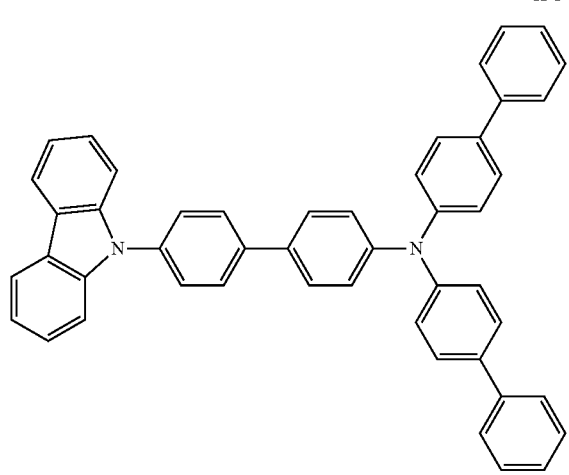
H-1-10
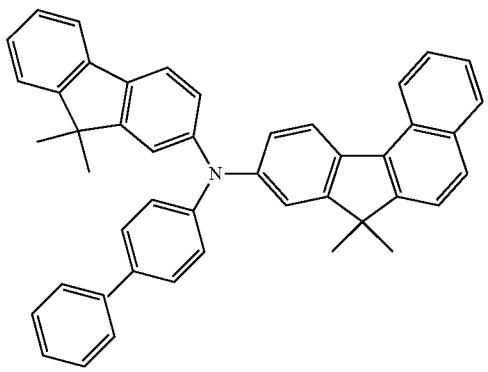
H-1-11
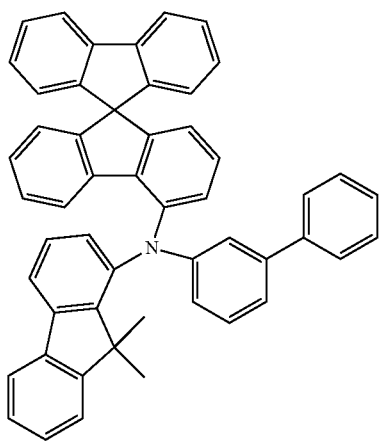
H-1-12
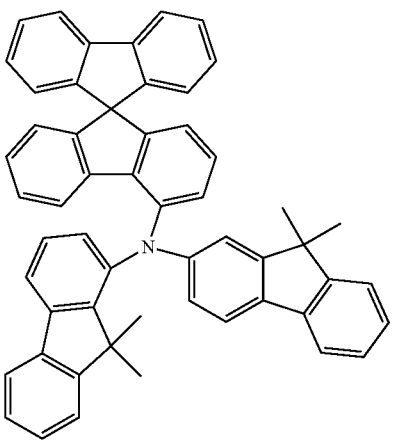
H-1-13
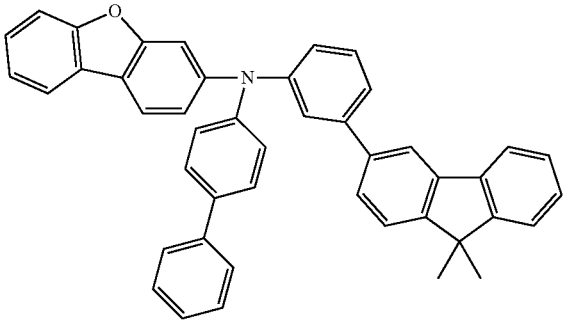

H-1-14

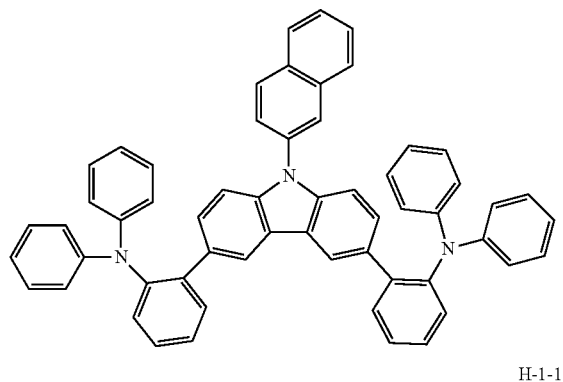

H-1-15

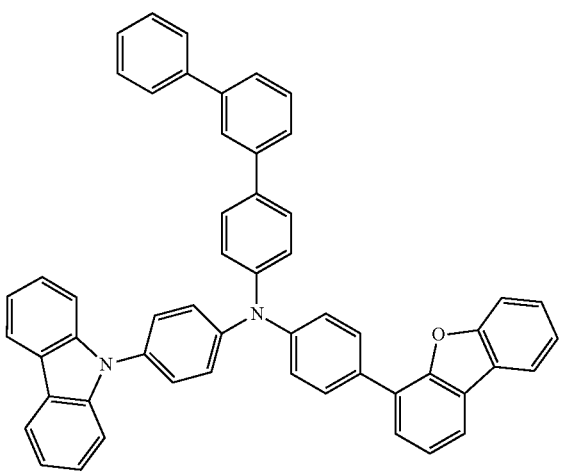

H-1-16

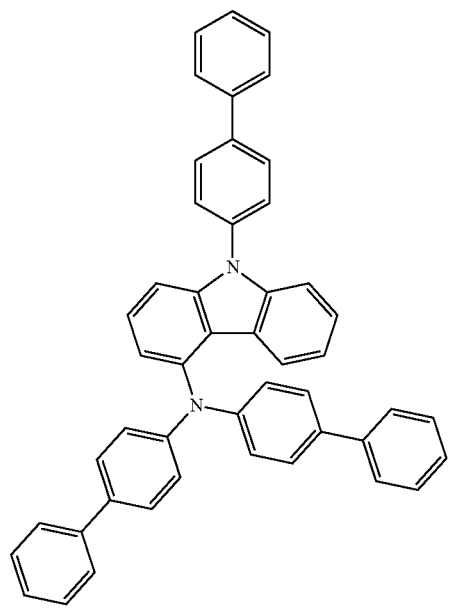

H-1-17

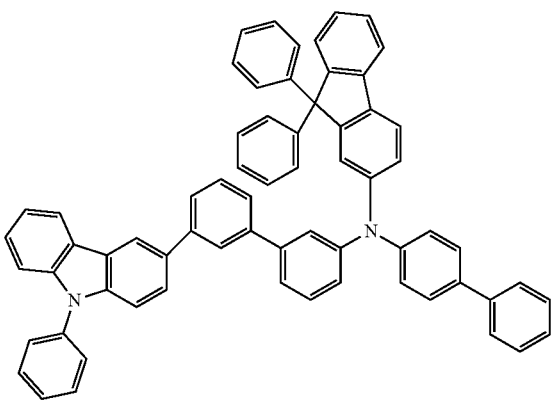

H-1-18

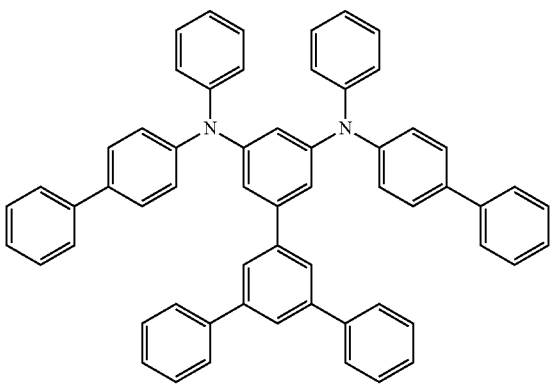

H-1-19

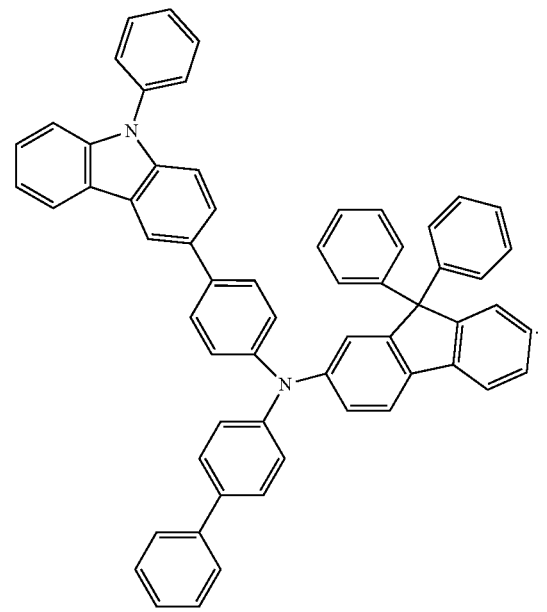

The hole transport region HTR may include a phthalocyanine compound such as copper phthalocyanine, $N^1,N^{1'}$-([1,1'-biphenyl]-4,4'-diyl)bis($N^1$-phenyl-$N^4,N^4$-di-m-tolyl-benzene-1,4-diamine) (DNTPD), 4,4',4''-[tris(3-methylphenyl)phenylamino] triphenylamine (m-MTDATA), 4,4'4''-tris(N,N-diphenylamino)triphenylamine (TDATA), 4,4',4''-tris[N(2-naphthyl)-N-phenylamino]-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonicacid (PANI/CSA), polyaniline/poly(4-styrenesulfonate) (PANI/PSS), N,N'-di(naphthalene-1-yl)-N,N'-diphenyl-benzidine (NPB), triphenylamine-containing polyetherketone (TPAPEK), 4-isopropyl-4'-methyldiphenyliodonium [tetrakis(pentafluorophenyl)borate], dipyrazino[2,3-f: 2',3'-h] quinoxaline-2,3,6,7,10,11-hexacarbonitrile (HATCN), and/or the like.

The hole transport region HTR may include a carbazole-based derivative (such as N-phenyl carbazole and/or polyvinyl carbazole), a fluorene-based derivative, N,N'-bis(3-methylphenyl)-N,N'-diphenyl-[1,1-biphenyl]-4,4'-diamine (TPD), a triphenylamine-based derivative (such as 4,4',4"-tris(N-carbazolyl)triphenylamine (TCTA)), N,N'-di(naphthalene-1-yl)-N,N'-diphenyl-benzidine (NPB), 4,4'-cyclohexylidene bis[N,N-bis(4-methylphenyl)benzeneamine] (TAPC), 4,4'-bis[N,N'-(3-tolyl)amino]-3,3'-dimethylbiphenyl (HMTPD), 1,3-bis(N-carbazolyl)benzene (mCP), and/or the like.

In one or more embodiments, the hole transport region HTR may include 9-(4-tert-Butylphenyl)-3,6-bis(triphenylsilyl)-9H-carbazole (CzSi), 9-phenyl-9H-3,9'-bicarbazole (CCP), 1,3-bis(1,8-dimethyl-9H-carbazol-9-yl)benzene (mDCP), and/or the like.

The hole transport region HTR may include one or more of the compounds of the hole transport region described above in at least one of the hole injection layer HIL, the hole transport layer HTL, or the electron blocking layer EBL.

A thickness of the hole transport region HTR may be about 100 Å to about 10000 Å, for example, about 100 Å to about 5000 Å. If the hole transport region HTR includes the hole injection layer HIL, the thickness of the hole injection layer HIL may be, for example, about 30 Å to about 1000 Å. If the hole transport region HTR includes the hole transport layer HTL, a thickness of the hole transport layer HTL may be about 30 Å to about 1000 Å. For example, if the hole transport region HTR includes the electron blocking layer EBL, a thickness of the electron blocking layer EBL may be about 10 Å to about 1000 Å. If the thicknesses of the hole transport region HTR, the hole injection layer HIL, the hole transport layer HTL, and the electron blocking layer EBL satisfy their respective above-described ranges, satisfactory (or suitable) hole transport properties may be obtained without a substantial increase of a driving voltage.

The hole transport region HTR may further include a charge generating material in addition to the above-described materials to improve conductivity. The charge generating material may be uniformly or non-uniformly dispersed in the hole transport region HTR. The charge generating material may be, for example, a p-dopant. The p-dopant may include at least one selected from among a halogenated metal compound, a quinone derivative, metal oxide, and a cyano group-containing compound, but the embodiment of the present disclosure is not limited thereto. For example, the p-type dopant may include a halogenated metal compound (such as CuI and/or RbI), a quinone derivative (such as tetracyanoquinodimethane (TCNQ) and/or 2,3,5,6-tetrafluoro-7,7',8,8-tetracyanoquinodimethane (F4-TCNQ)), a metal oxide (such as tungsten oxide and/or molybdenum oxide), a cyano group-containing compound (such as dipyrazino[2,3-f: 2',3'-h] quinoxaline-2,3,6,7,10,11-hexacarbonitrile (HATCN) and/or 4-[[2,3-bis[cyano-(4-cyano-2,3,5,6-tetrafluorophenyl)methylidene]cyclopropylidene]-cyanomethyl]-2,3,5,6-tetrafluorobenzonitrile (NDP9)), but the embodiment of the present disclosure is not limited thereto.

As described above, the hole transport region HTR may further include at least one of the buffer layer or the electron blocking layer EBL in addition to the hole injection layer HIL and the hole transport layer HTL. The buffer layer may compensate an optical resonance distance according to the wavelength of light emitted from the emission layer EML to increase light luminous efficiency. A material which may be included in the hole transport region HTR may be used as a material included in the buffer layer. The electron blocking layer EBL is a layer that serves to prevent or reduce the electron injection from the electron transport region ETR to the hole transport region HTR.

The emission layer EML is provided on the hole transport region HTR. The emission layer EML may have a thickness of, for example, about 100 Å to about 1000 Å or about 100 Å to about 300 Å. The emission layer EML may have a single layer formed using (e.g., consisting of) a single material, a single layer formed using a plurality of different materials, or a multilayer structure having a plurality of layers formed using a plurality of different materials.

In the light-emitting diode ED according to one or more embodiments, the emission layer EML may include an anthracene derivative, a pyrene derivative, a fluoranthene derivative, a chrysene derivative, a dihydrobenzanthracene derivative, and/or a triphenylene derivative. In one or more embodiments, the emission layer EML may include an anthracene derivative and/or a pyrene derivative.

In the light-emitting diode ED according to one or more embodiments shown in FIGS. 3 to 6, the emission layer EML may include a host and a dopant, and the emission layer EML may include the compound represented by Formula E-1. The compound represented by Formula E-1 may be used as a fluorescent host material.

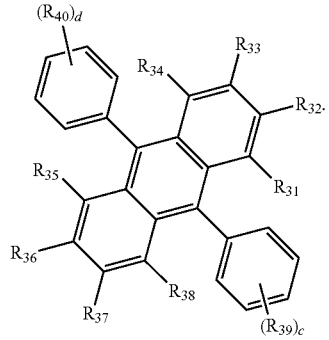

[Formula E-1]

In Formula E-1, $R_{31}$ to $R_{40}$ may each independently be a hydrogen atom, a deuterium atom, a halogen atom, a substituted or unsubstituted silyl group, a substituted or unsubstituted alkyl group having 1 to 10 carbon atoms, a substituted or unsubstituted ring-forming aryl group having 6 to 30 carbon atoms, or a substituted or unsubstituted ring-forming heteroaryl group having 2 to 30 carbon atoms, and/or may be combined with an adjacent group to form a ring. For example, $R_{31}$ to $R_{40}$ may be combined with an adjacent group to form a saturated hydrocarbon ring or an unsaturated hydrocarbon ring.

In Formula E-1, "c" and "d" may each independently be an integer of 0 to 5.

Formula E-1 may be represented by any one selected from among Compounds E1 to E19 below.

E1 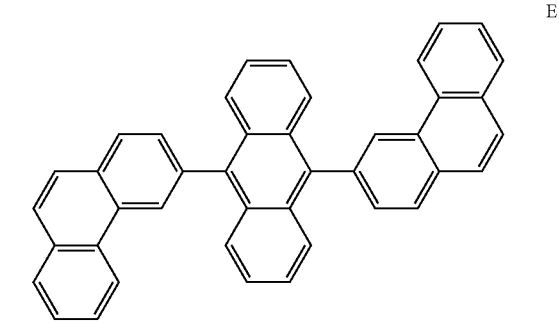
E2 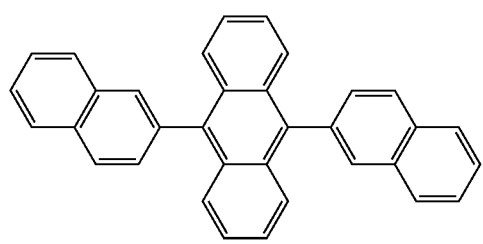
E3 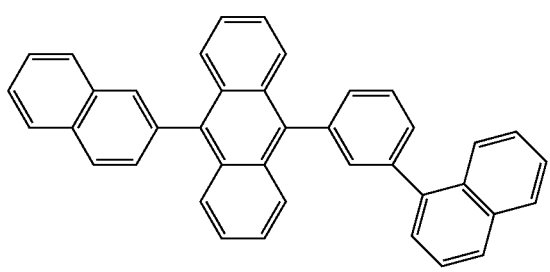
E4 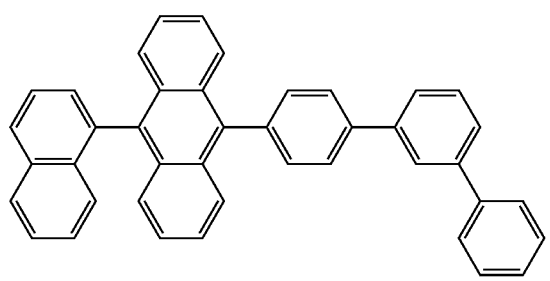
E5 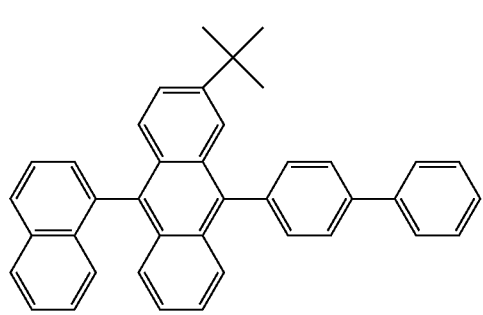
E6 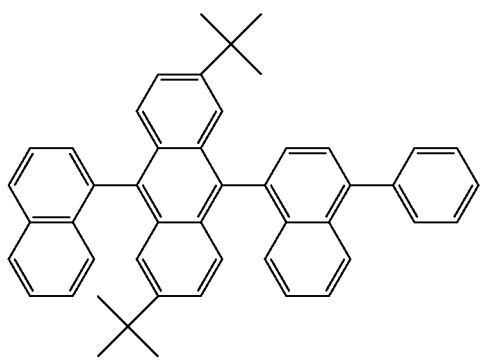
E7 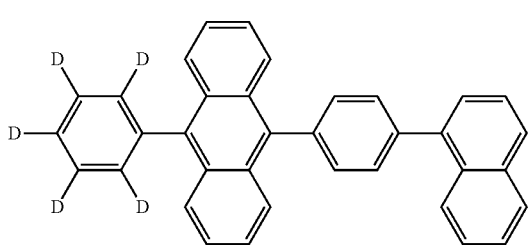
E8 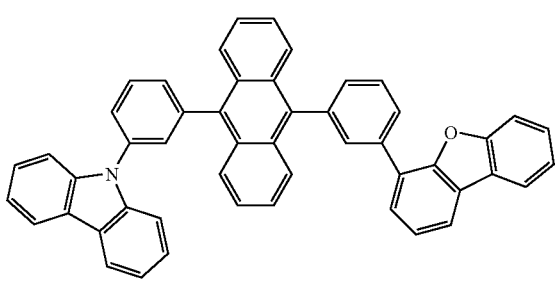
E9 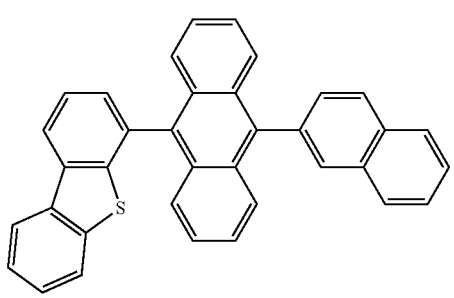
E10 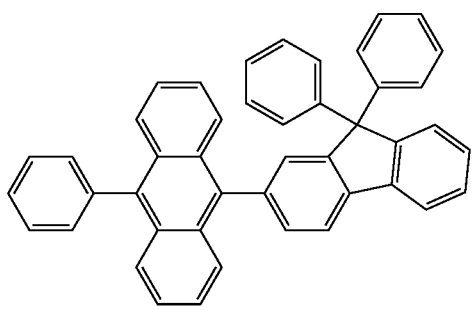

E11
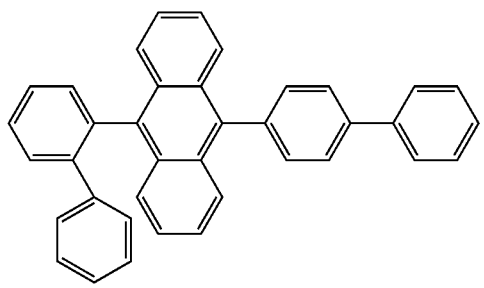
E12
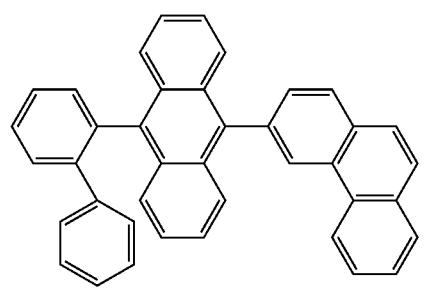
E13
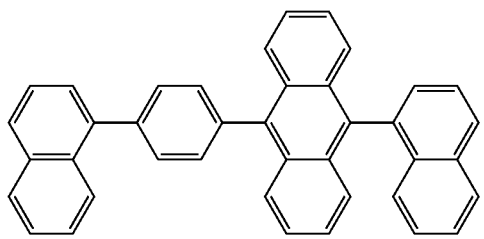
E14
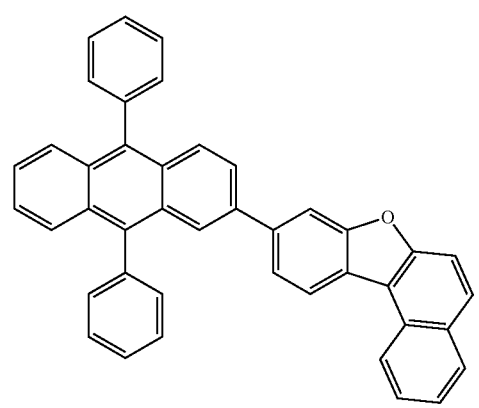
E15
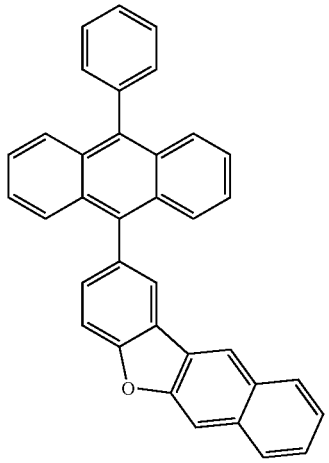
E16
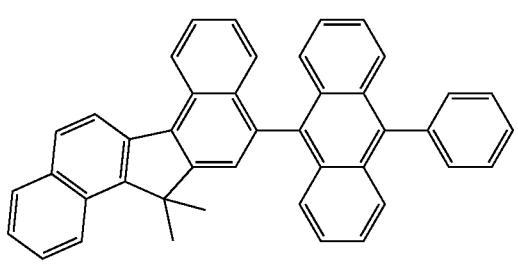
E17
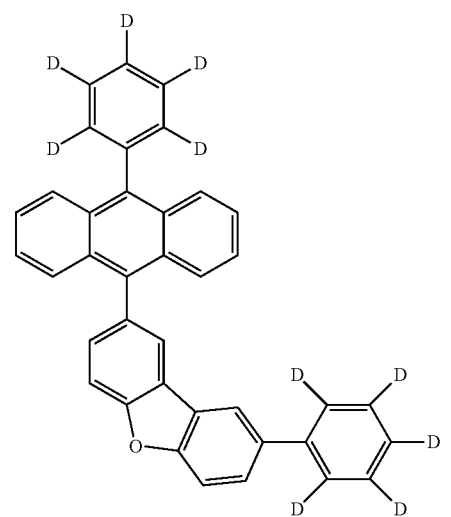
E18
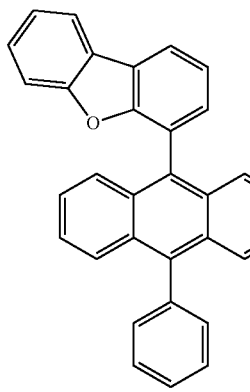

E19

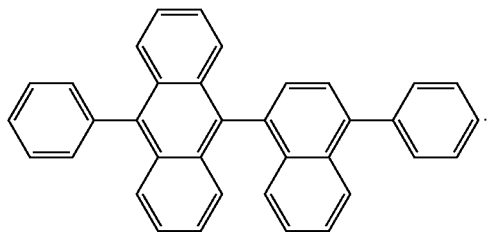

In one or more embodiments, the emission layer EML may include the compound represented by Formula E-2a or Formula E-2b. The compound represented by Formula E-2a or Formula E-2b may be used as a phosphorescent host material.

[Formula E-2a]

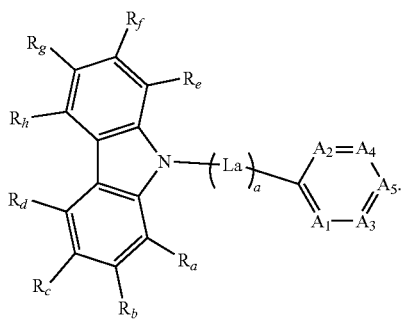

In Formula E-2a, "a" may be an integer of 0 to 10, and La may be a direct linkage, a substituted or unsubstituted ring-forming arylene group having 6 to 30 carbon atoms, or a substituted or unsubstituted ring-forming heteroarylene group having 2 to 30 carbon atoms. Meanwhile, if "a" is an integer of 2 or more, a plurality of La may each independently be a substituted or unsubstituted ring-forming arylene group having 6 to 30 carbon atoms, or a substituted or unsubstituted ring-forming heteroarylene group having 2 to 30 carbon atoms.

In one or more embodiments, in Formula E-2a, $A_1$ to $A_5$ may each independently be N or $CR_i$. $R_a$ to $R_i$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted ring-forming aryl group having 6 to 30 carbon atoms, or a substituted or unsubstituted ring-forming heteroaryl group having 2 to 30 carbon atoms, and/or may be combined with an adjacent group to form a ring. $R_a$ to $R_i$ may combined with an adjacent group to form a hydrocarbon ring or a hetero ring including N, O, S, and/or the like as a ring-forming atom.

Meanwhile, in Formula E-2a, two or three selected from among $A_1$ to $A_5$ may be N, and the remainder may be $CR_i$.

[Formula E-2b]

(Cbz1)─(L$_b$)$_b$─(Cbz2).

In Formula E-2b, Cbz1 and Cbz2 may each independently be an unsubstituted carbazole group, or a carbazole group substituted with a ring-forming aryl group having 6 to 30 carbon atoms. $L_b$ may be a direct linkage, a substituted or unsubstituted ring-forming arylene group having 6 to 30 carbon atoms, or a substituted or unsubstituted ring-forming heteroarylene group having 2 to 30 carbon atoms. If "b" is an integer of 0 to 10, and "b" is an integer of 2 or more, a plurality of $L_b$ may each independently be a substituted or unsubstituted ring-forming arylene group having 6 to 30 carbon atoms, or a substituted or unsubstituted ring-forming heteroarylene group having 2 to 30 carbon atoms.

The compound represented by Formula E-2a or Formula E-2b may be represented by any one selected from among the compounds in Compound Group E-2. However, the compounds listed in Compound Group E-2 are illustrative, and the compound represented by Formula E-2a or Formula E-2b is not limited to those represented in Compound Group E-2.

[Compound Group E-2]

E-2-1

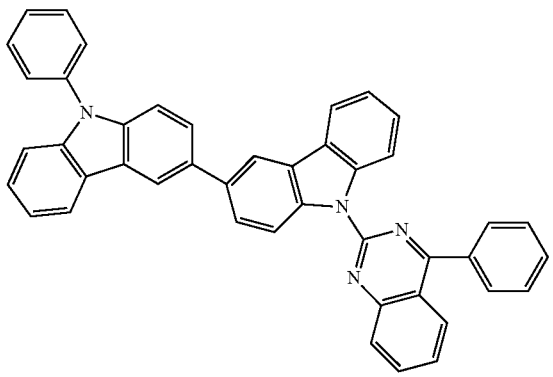

E-2-2

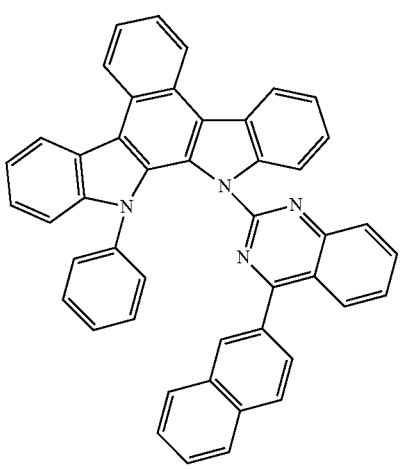

-continued
E-2-3
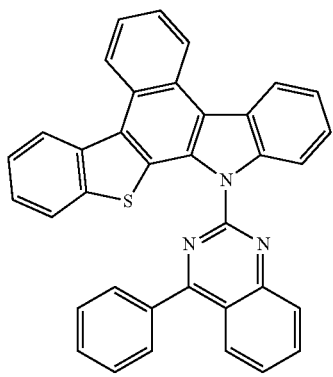
E-2-4
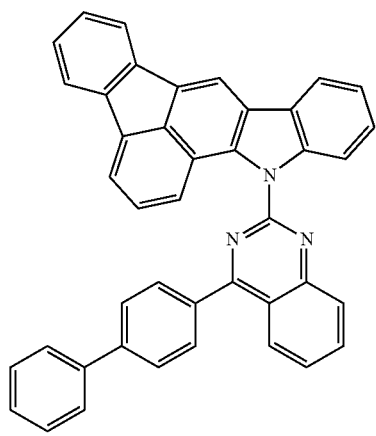
E-2-5
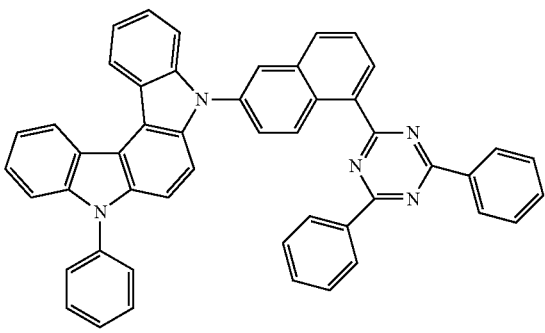
E-2-6
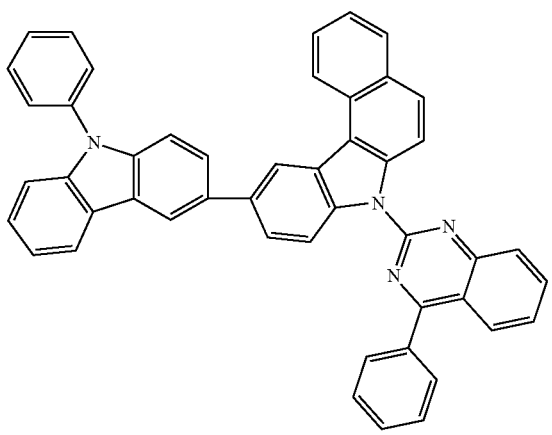
-continued
E-2-7
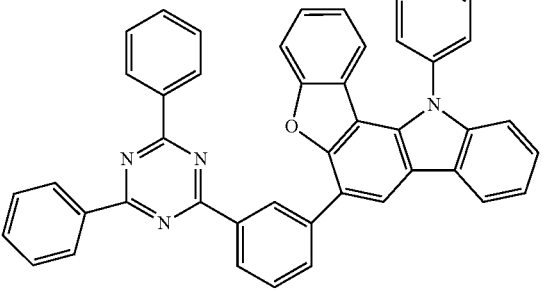
E-2-8
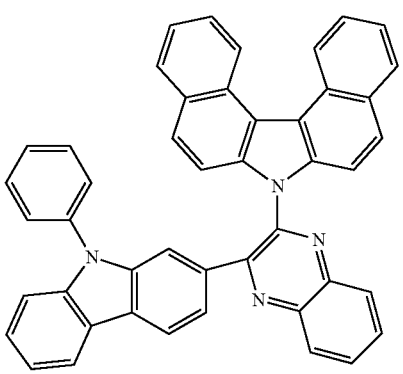
E-2-9
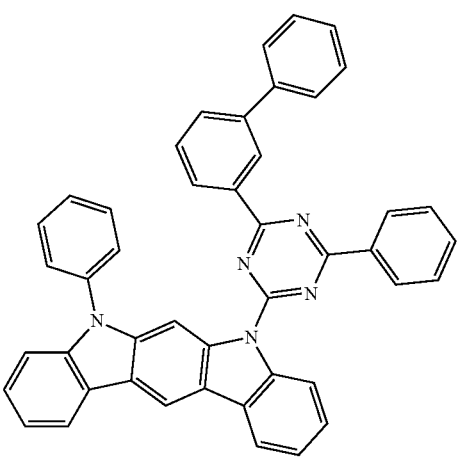

E-2-10
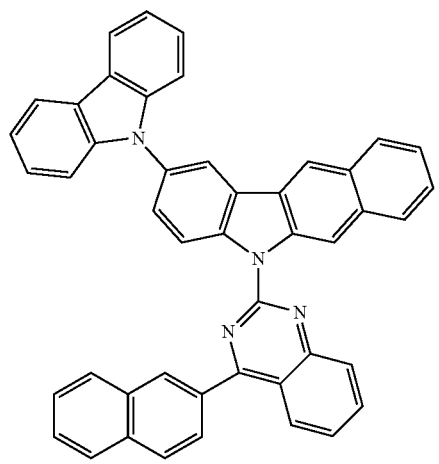
E-2-11
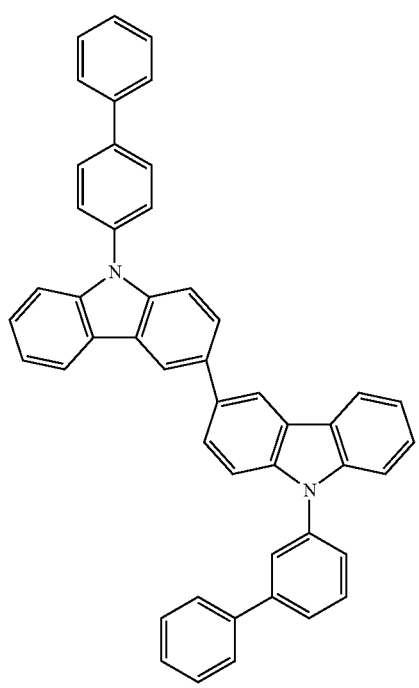
E-2-12
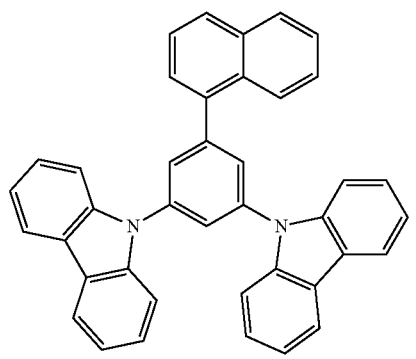
E-2-13
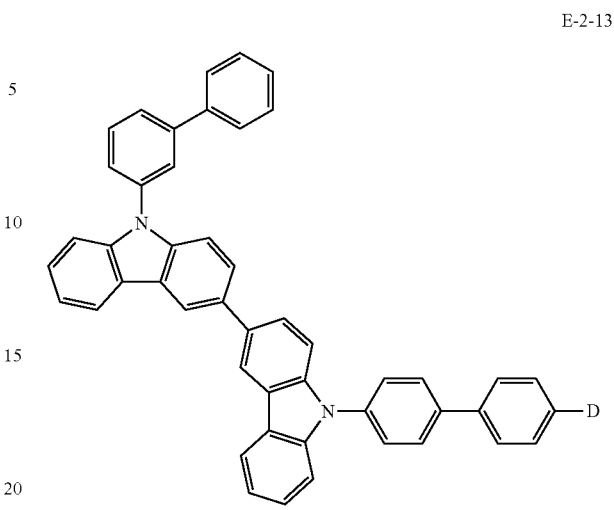
E-2-14
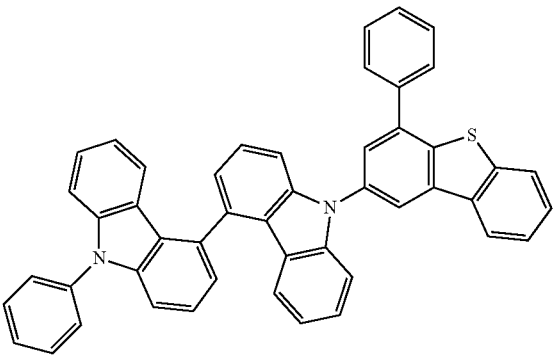
E-2-15

E-2-16
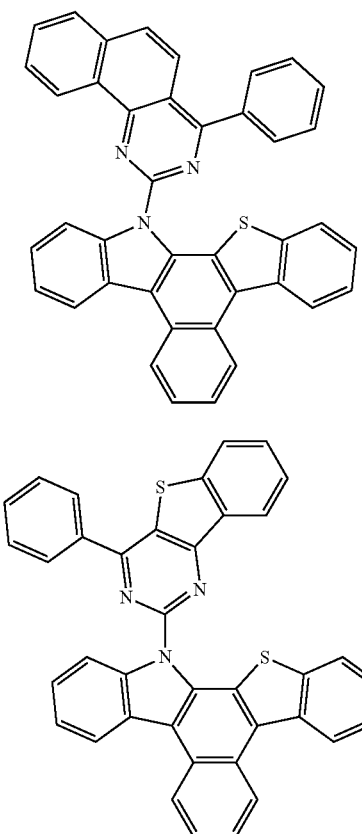
E-2-17
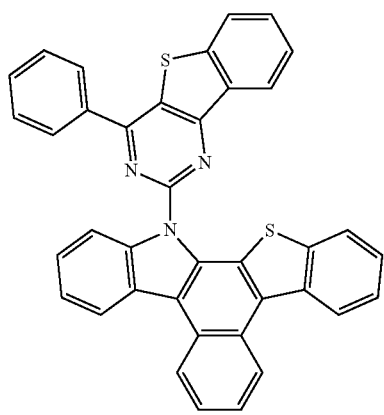
E-2-18
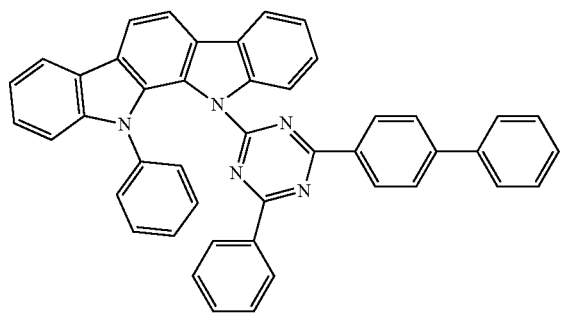
E-2-19
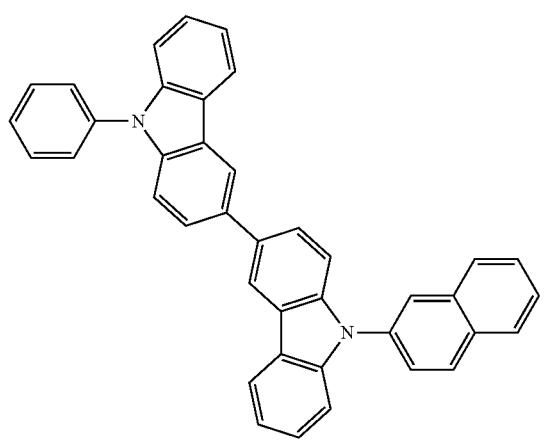
E-2-20
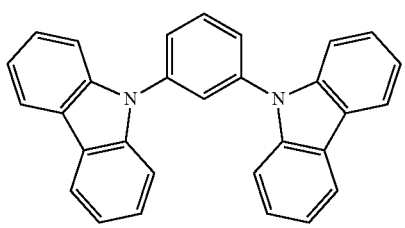
E-2-21
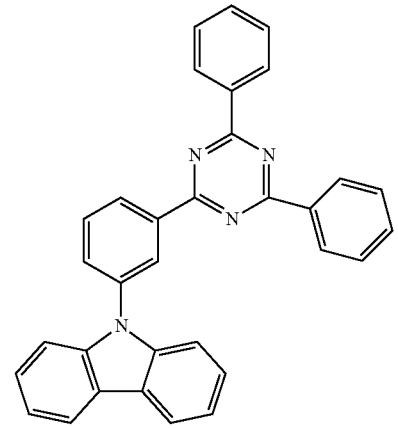
E-2-22
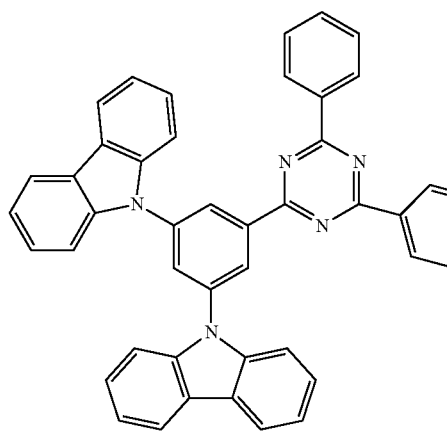
E-2-23
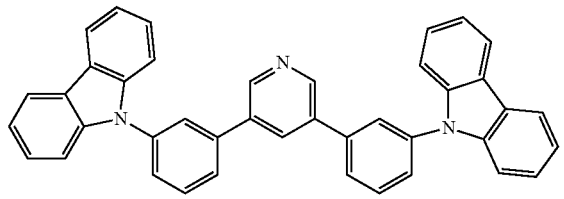

-continued

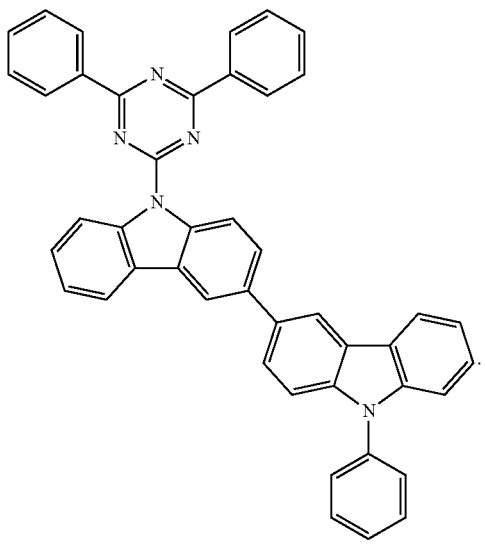

E-2-24

The emission layer EML may further include any suitable host material. For example, the emission layer EML may include, as the host material, at least one selected from among bis[2-(diphenylphosphino)phenyl] ether oxide (DPEPO), 4,4'-bis(N-carbazolyl)-1,1'-biphenyl (CBP), 1,3-bis(carbazol-9-yl)benzene (mCP), 2,8-bis(diphenylphosphoryl)dibenzo[b,d]furan (PPF), 4,4',4''-tris(carbazol-9-yl)-triphenylamine (TCTA), and 1,3,5-tris(1-phenyl-1H-benzo[d]imidazole-2-yl)benzene (TPBi). However, the embodiment of the present disclosure is not limited thereto, and for example, tris(8-hydroxyquinolino)aluminum ($Alq_3$), 9,10-di(naphthalene-2-yl)anthracene (DNA), 2-tert-butyl-9,10-di(naphthalene-2-yl)anthracene (TBDNA), distyrylarylene (DSA), 4,4'-bis(9-carbazolyl)-2,2'-dimethyl-biphenyl (CDBP), 2-methyl-9,10-di(naphthalene-2-yl)anthracene (MDNA), hexaphenyl cyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), and/or the like may be used as the host material.

The emission layer EML may include the compound represented by Formula M-a or Formula M-b. The compound represented by Formula M-a or Formula M-b may be used as a phosphorescent dopant material.

[Formula M-a]

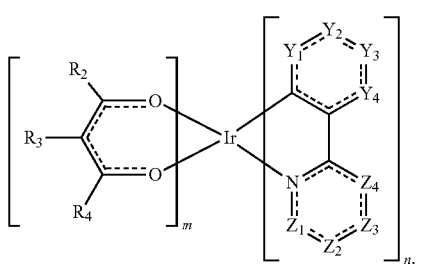

In Formula M-a, $Y_1$ to $Y_4$, and $Z_1$ to $Z_4$ may each independently be $CR_1$ or N, and $R_1$ to $R_4$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted ring-forming aryl group having 6 to 30 carbon atoms, or a substituted or unsubstituted ring-forming heteroaryl group having 2 to 30 carbon atoms, and/or may be combined with an adjacent group to form a ring. In Formula M-a, "m" is 0 or 1, and "n" is 2 or 3. In Formula M-a, when "m" is 0, "n" is 3, and when "m" is 1, "n" is 2.

The compound represented by Formula M-a may be used as a phosphorescent dopant.

The compound represented by Formula M-a may be represented by any one selected from among Compounds M-a1 to M-a19 below. However, Compounds M-a1 to M-a19 below are illustrative, and the compound represented by Formula M-a is not limited to those represented by Compounds M-a1 to M-a19 below.

M-a1

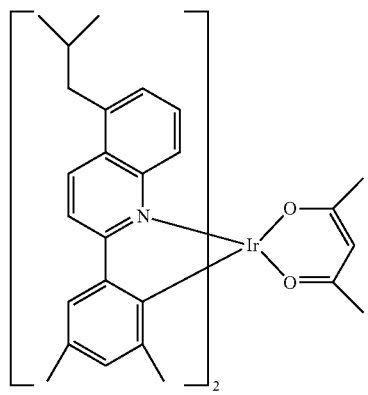

M-a2

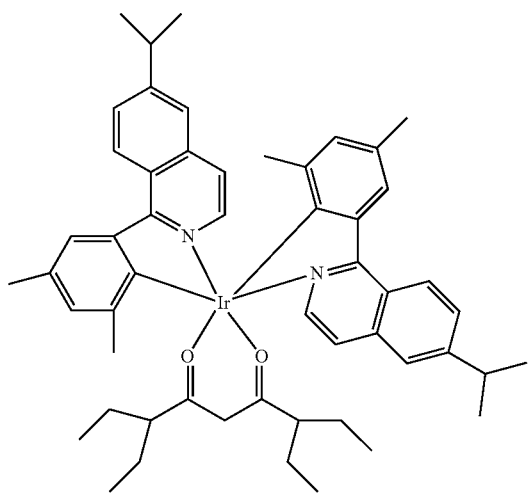

M-a3

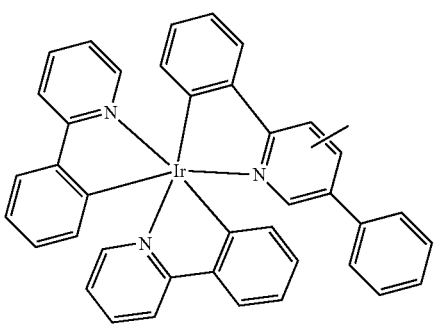

M-a4
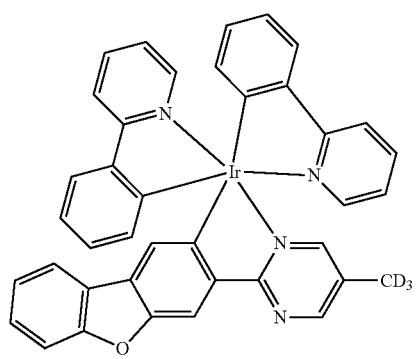
M-a5
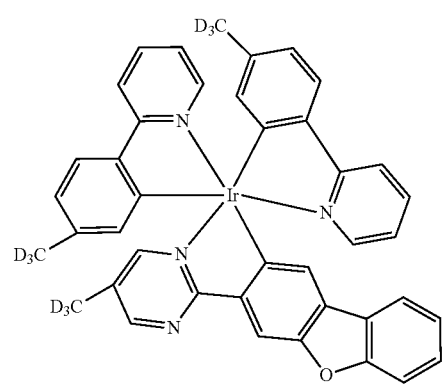
M-a6
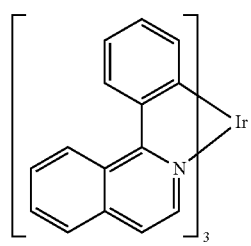
M-a7
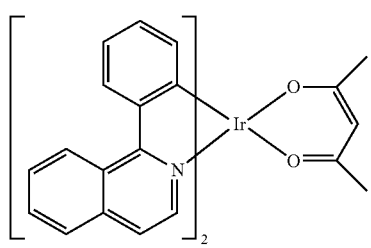
M-a8
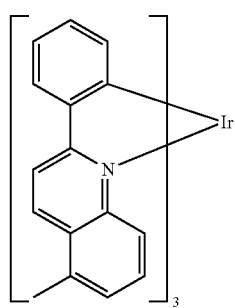
M-a9
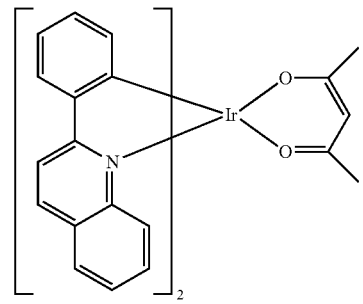
M-a10
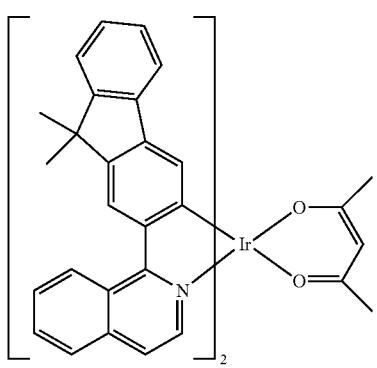
M-a11
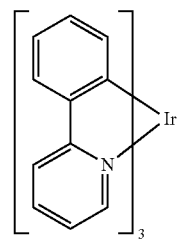
M-a12
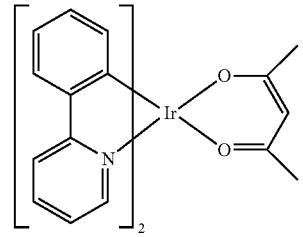
M-a13
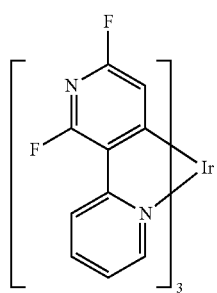

M-a14 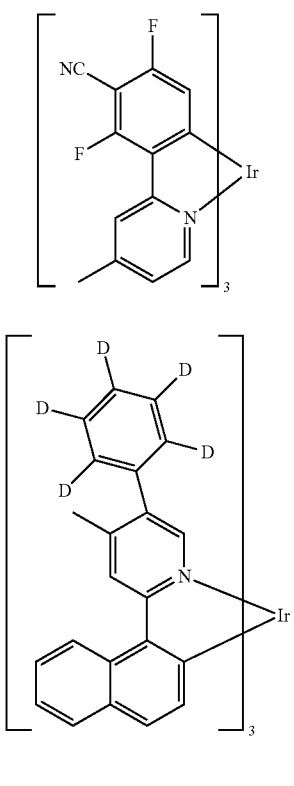

M-a15

M-a16 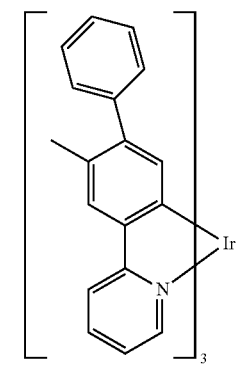

M-a17 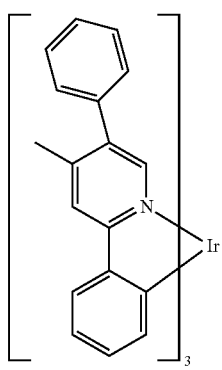

M-a18 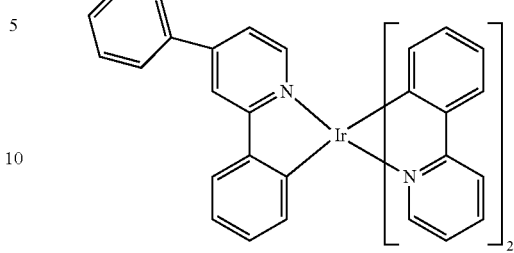

M-a19 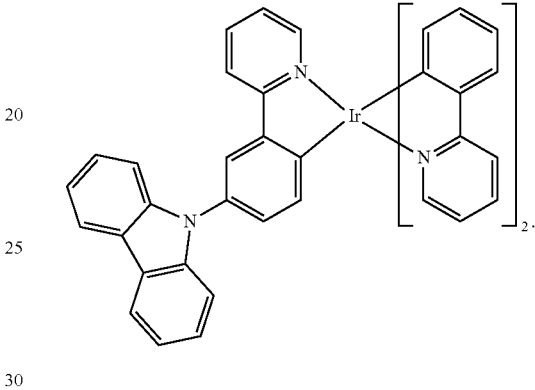

Compounds M-a1 and M-a2 may be used as a red dopant material, and Compounds M-a3 to M-a5 may be used as a green dopant material.

[Formula M-b]

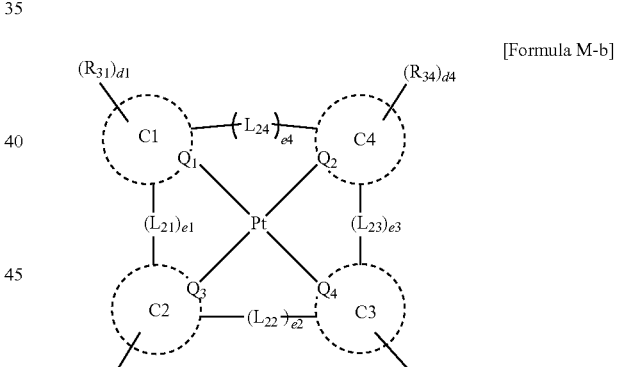

In Formula M-b, $Q_1$ to $Q_4$ are each independently C or N, and C1 to C4 are each independently a substituted or unsubstituted ring-forming hydrocarbon ring having 5 to 30 carbon atoms, or a substituted or unsubstituted ring-forming heterocycle having 2 to 30 carbon atoms. $L_{21}$ to $L_{24}$ are each independently a direct linkage,

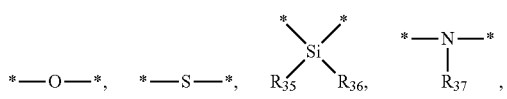

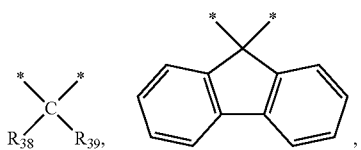

a substituted or unsubstituted divalent alkyl group having 1 to 20 carbon atoms, a substituted or unsubstituted ring-forming arylene group having 6 to 30 carbon atoms, or a substituted or unsubstituted ring-forming heteroarylene group having 2 to 30 carbon atoms, and e1 to e4 are each independently 0 or 1. $R_{31}$ to $R_{39}$ are each independently a hydrogen atom, a deuterium atom, a halogen atom, a cyano group, a substituted or unsubstituted amine group, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms, and/or combined with an adjacent group to form a ring, and d1 to d4 are each independently an integer of 0 to 4.

The compound represented by Formula M-b may be used as a blue phosphorescent dopant or a green phosphorescent dopant.

The compound represented by Formula M-b may be represented by any one selected from among the compounds below. However, the compounds below are illustrative, and the compound represented by Formula M-b is not limited to those represented in the compounds below.

M-b-1

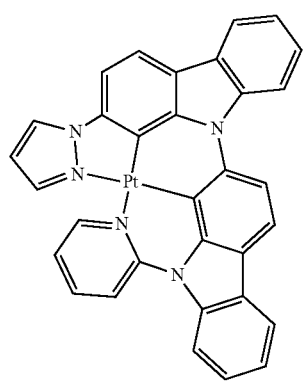

M-b-2

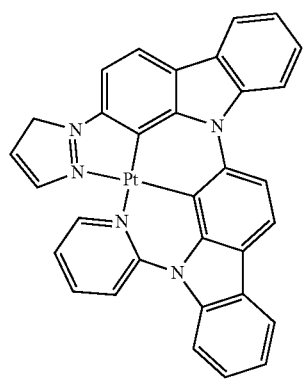

M-b-3

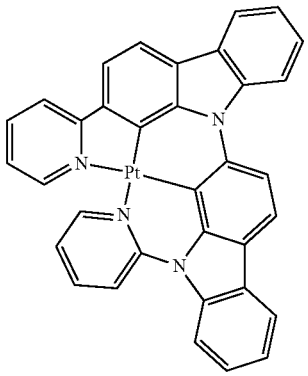

M-b-4

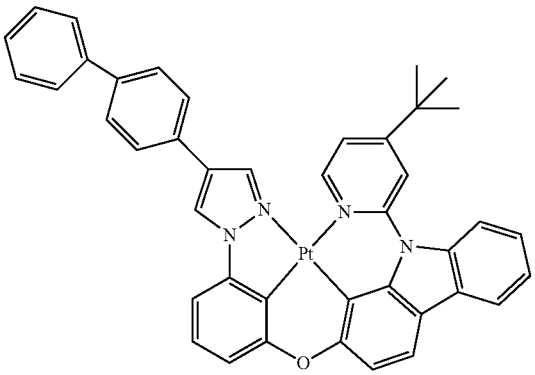

M-b-5

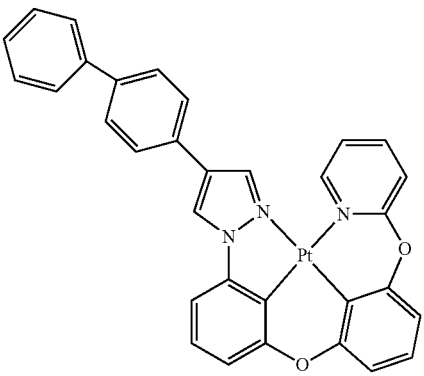

M-b-6

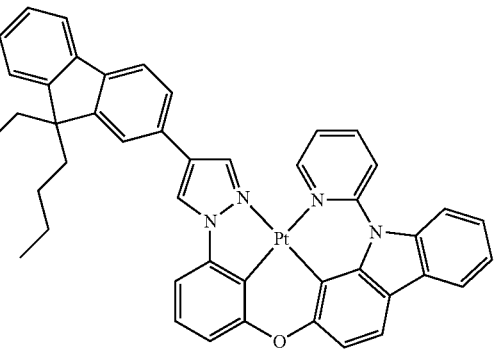

-continued

M-b-7
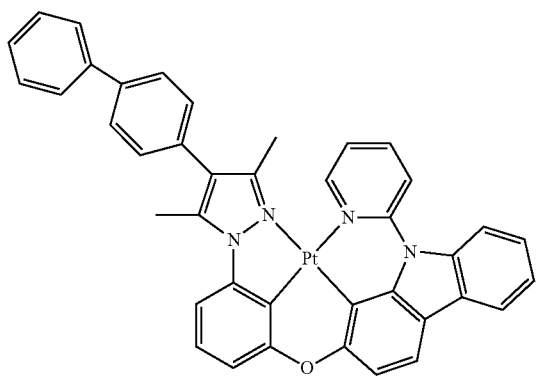

M-b-8
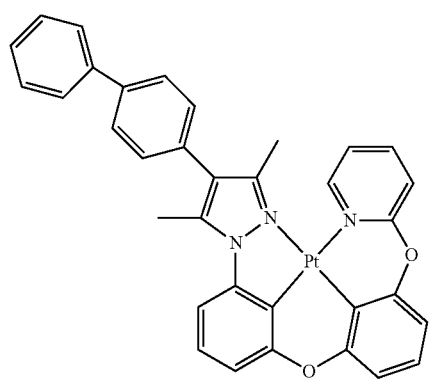

M-b-9
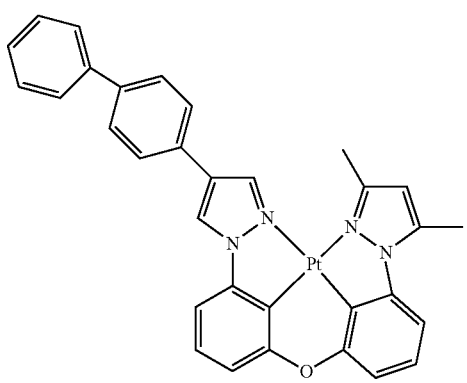

M-b-10
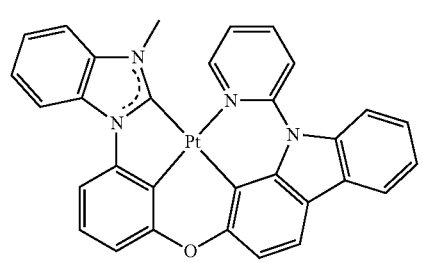

-continued

M-b-11
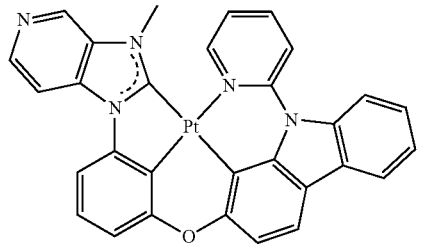

M-b-12
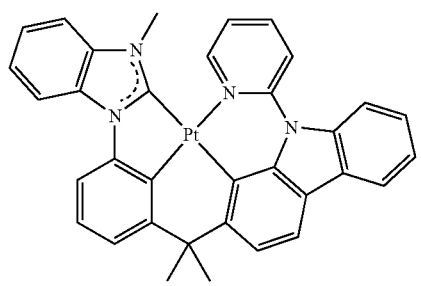

M-b-12
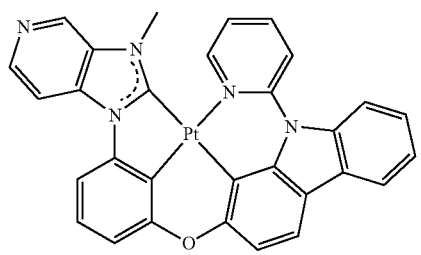

M-b-13
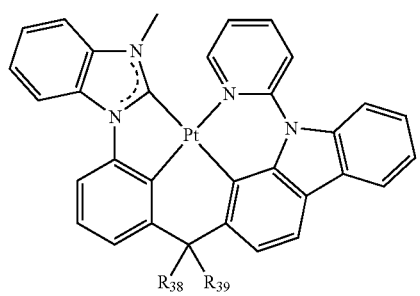

M-b-14

In the above compounds, R, $R_{38}$, and $R_{39}$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms.

The emission layer EML may include the compound represented by any one selected from among Formula F-a to Formula F-c below. The compound represented by Formula F-a to Formula F-c may be used as a fluorescent dopant material.

[Formula F-a]

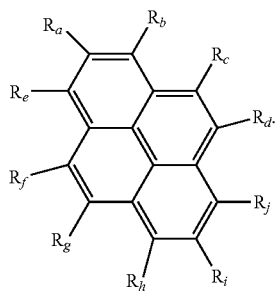

In Formula F-a, two selected from among $R_a$ to $R_j$ may each independently be substituted with •—$NAr_1Ar_2$. The remainder that are not substituted with •—$NAr_1Ar_2$ among $R_a$ to $R_j$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms.

In •—$NAr_1Ar_2$, $Ar_1$ and $Ar_2$ may each independently be a substituted or unsubstituted ring-forming aryl group having 6 to 30 carbon atoms, or a substituted or unsubstituted ring-forming heteroaryl group having 2 to 30 carbon atoms. For example, at least one of $Ar_1$ or $Ar_2$ may be a heteroaryl group containing 0 and/or S as a ring-forming atom.

[Formula F-b]

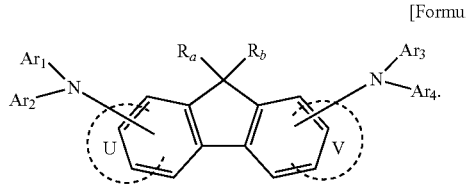

In Formula F-b, $R_a$ and $R_b$ may each independently be a hydrogen atom, a deuterium atom, a substituted or unsubstituted alkyl group having 1 to 20 carbon atoms, a substituted or unsubstituted alkenyl group having 2 to 20 carbon atoms, a substituted or unsubstituted ring-forming aryl group having 6 to 30 carbon atoms, or a substituted or unsubstituted ring-forming heteroaryl group having 2 to 30 carbon atoms, and/or may be combined with an adjacent group to form a ring.

In Formula F-b, U and V may each independently be a substituted or unsubstituted ring-forming hydrocarbon ring having 5 to 30 carbon atoms, or a substituted or unsubstituted ring-forming heterocycle having 2 to 30 carbon atoms.

In Formula F-b, the number of rings marked as U and V may each independently be 0 or 1. For example, if the number of U or V is 1 in Formula F-b, one ring forms a condensed ring at the portion indicated by U or V, and if the number of U or V is 0, it means that the ring indicated as U or V does not exist. In one or more embodiments, if the number of U is 0 and the number of V is 1, or the number of U is 1 and the number of V is 0, the condensed ring having a fluorene core of Formula F-b may be a tetracyclic compound. In one or more embodiments, if the numbers of U and V are both 0, the condensed ring of Formula F-b may be a tricyclic compound. Further, if the numbers of U and V are both 1, the condensed ring having a fluorene core of Formula F-b may be a pentacyclic compound.

[Formula F-c]

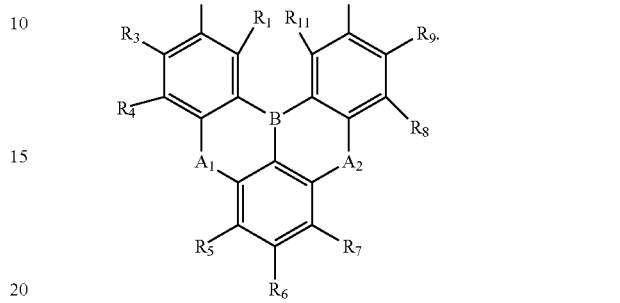

In Formula F-c, $A_1$ and $A_2$ may each independently be O, S, Se, or $NR_m$, and $R_m$ may be a hydrogen atom, a deuterium atom, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms. $R_1$ to $R_{11}$ are each independently a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms, and/or may be combined with an adjacent group to form a ring.

In Formula F-c, $A_1$ and $A_2$ may each independently be combined with substituents of an adjacent ring to form a condensed ring. For example, when $A_1$ and $A_2$ are each independently $NR_m$, $A_1$ may be combined with $R_4$ or $R_5$ to form a ring. In one or more embodiments, $A_2$ may be combined with $R_7$ or $R_8$ to form a ring.

In one or more embodiments, the emission layer EML may include, as a dopant material, a styryl derivative (for example, 1,4-bis[2-(3-N-ethylcarbazoryl)vinyl]benzene (BCzVB), 4-(di-p-tolylamino)-4'-[(di-p-tolylamino)styryl] stilbene (DPAVB), N-(4-((E)-2-(6-((E)-4-(diphenylamino) styryl)naphthalen-2-yl)vinyl)phenyl)-N-phenylbenzenamine (N-BDAVBi)), 4,4'-bis[2-(4-(N,N-diphenylamino) phenyl)vinyl]biphenyl (DPAVBi)), perylene and/or a derivative thereof (for example, 2,5,8,11-tetra-t-butylperylene (TBP)), pyrene and/or a derivative thereof (for example, 1,1-dipyrene, 1,4-dipyrenylbenzene, 1,4-bis(N,N-diphenylamino)pyrene), and/or the like.

The emission layer EML may include any suitable phosphorescent dopant material. For example, a metal complex including iridium (Ir), platinum (Pt), osmium (Os), gold (Au), titanium (Ti), zirconium (Zr), hafnium (Hf), europium (Eu), terbium (Tb), and/or thulium (Tm) may be used as a phosphorescent dopant. In one or more embodiments, iridium(III) bis(4,6-difluorophenylpyridinato-N,C2Ç (Flrpic), bis(2,4-difluorophenylpyridinato)-tetrakis(1-pyrazolyl)borate iriduim (III) (Fir6), or platinum octaethyl porphyrin (PtOEP) may be used as a phosphorescent dopant. However, the embodiment of the present disclosure is not limited thereto.

The emission layer EML may include a quantum dot material. The core of the quantum dot may be selected from Group II-VI compounds, Group III-VI compounds, Group compounds, Group III-V compounds, Group III-II-V compounds, Group IV-VI compounds, Group IV elements, Group IV compounds, and combinations thereof.

Group II-VI compounds may be selected from the group consisting of a binary compound selected from the group consisting of CdSe, CdTe, CdS, ZnS, ZnSe, ZnTe, ZnO, HgS, HgSe, HgTe, MgSe, MgS, and a mixture thereof; a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof; and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and a mixture thereof.

Group III-VI compounds may include a binary compound such as $In_2S_3$ and/or $In_2Se_3$; a ternary compound such as $InGaS_3$ and/or $InGaSe_3$; or any combination thereof.

Group compounds may be selected from a ternary compound selected from the group consisting of $AgInS$, $AgInS_2$, $CuInS$, $CuInS_2$, $AgGaS_2$, $CuGaS_2$, $CuGaO_2$, $AgGaO_2$, $AgAlO_2$, and a mixture thereof; and a quaternary compound such as $AgInGaS_2$ and/or $CuInGaS_2$.

Group III-V compounds may be selected from the group consisting of a binary compound selected from the group consisting of GaN, GaP, GaAs, GaSb, AlN, AlP, AlAs, AlSb, InN, InP, InAs, InSb, and a mixture thereof; a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and a mixture thereof; and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and a mixture thereof. In one or more embodiments, Group III-V compounds may further include a Group II metal. For example, InZnP and/or the like may be selected as Group III-II-V compounds.

Group IV-VI compounds may be selected from the group consisting of a binary compound selected from the group consisting of SnS, SnSe, SnTe, PbS, PbSe, PbTe, and a mixture thereof; a ternary compound selected from the group consisting of SnSeS, SnSeTe, SnSTe, PbSeS, PbSeTe, PbSTe, SnPbS, SnPbSe, SnPbTe, and a mixture thereof; and a quaternary compound selected from the group consisting of SnPbSSe, SnPbSeTe, SnPbSTe, and a mixture thereof. Group IV elements may be selected from the group consisting of Si, Ge, and a mixture thereof. Group IV compounds may be a binary compound selected from the group consisting of SiC, SiGe, and a mixture thereof.

In this case, the binary compound, the ternary compound, and/or the quaternary compound may be present in the particle in a uniform concentration, or may be present in the same particle while being divided to have partially different concentration distribution. In one or more embodiments, these compounds may have a core/shell structure in which one quantum dot surrounds another quantum dot. The core/shell structure may have a concentration gradient in which a concentration of an element present in the shell gradually decreases toward the core.

In some embodiments, the quantum dot may have a core-shell structure that includes a core including the aforementioned nanocrystal and a shell surrounding the core. The shell of the quantum dot may serve as a protective layer for maintaining characteristics of a semiconductor by preventing or reducing chemical modification of the core and/or a charging layer for imparting electrophoretic characteristics to the quantum dot. The shell may be a single layer or multiple layers. Examples of the shell of the quantum dot may include a metal oxide, a non-metal oxide, a semiconductor compound, and a combination thereof.

For example, the metal oxide and the non-metal oxide may be each independently a binary compound (such as $SiO_2$, $Al_2O_3$, $TiO_2$, $ZnO$, $MnO$, $Mn_2O_3$, $Mn_3O_4$, $CuO$, $FeO$, $Fe_2O_3$, $Fe_3O_4$, $CoO$, $Co_3O_4$, and/or $NiO$), or a ternary compound (such as $MgAl_2O_4$, $CoFe_2O_4$, $NiFe_2O_4$, and/or $CoMn_2O_4$), but the embodiment of the present disclosure is not limited thereto.

In one or more embodiments, the semiconductor compound may be exemplified as CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, and/or the like, but the embodiment of the present disclosure is not limited thereto.

The quantum dot may have a full width of half maximum (FWHM) of an emission wavelength spectrum of about 45 nm or less, for example, about 40 nm or less, or about 30 nm or less, and thereby improving color purity and/or color gamut in this range. In one or more embodiments, as light emitted through this quantum dot is emitted in all directions, an improved wide viewing angle may be obtained.

In one or more embodiments, the shape of the quantum dot is any suitable shape in the art, and is not particularly limited, but, for example, spherical, pyramidal, multi-arm, and/or cubic nanoparticles, nanotubes, nanowires, nanofibers, plate-shaped nanoparticles, and/or the like may be used.

The quantum dot may control the color of emitted light according to the particle size, and accordingly, the quantum dots may have various light-emitting colors such as blue, red, green, and/or the like.

In the light-emitting diode ED according to one or more embodiments shown in FIGS. 3 to 6, the electron transport region ETR is provided on the emission layer EML. The electron transport region ETR may include at least one of the hole blocking layer HBL, the electron transport layer ETL, or the electron injection layer EIL, but the embodiment of the present disclosure is not limited thereto.

The electron transport region ETR may have a single layer formed using (e.g., consisting of) a single material, a single layer formed using a plurality of different materials, or a multilayer structure having a plurality of layers formed using a plurality of different materials.

For example, the electron transport region ETR may have a structure of a single layer of an electron injection layer EIL or an electron transport layer ETL, and may have a structure of a single layer formed using an electron injection material and an electron transport material. Further, the electron transport region ETR may have a single layer structure formed using a plurality of different materials, or a structure in which an electron transport layer ETL/electron injection layer EIL, or a hole blocking layer HBL/electron transport layer ETL/electron injection layer EIL are stacked in the stated order from the emission layer EML, but the embodiment of the present disclosure is not limited thereto. A thickness of the electron transport region ETR may be, for example, about 1000 Å to about 1500 Å.

The electron transport region ETR may be formed by using one or more suitable methods such as a vacuum deposition method, a spin coating method, a cast method, a Langmuir-Blodgett (LB) method, an inkjet printing method, a laser printing method, and/or a laser induced thermal imaging (LITI) method.

The electron transport region ETR may include the compound represented by Formula ET-1.

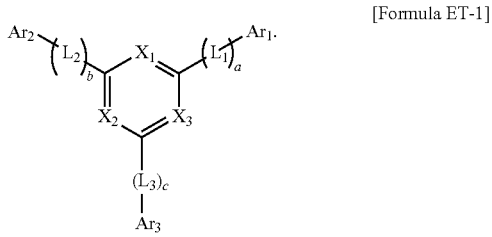

[Formula ET-1]

In Formula ET-1, at least one selected from among Xi to X3 is N, and the remainder are CRa. $R_a$ may be a hydrogen atom, a deuterium atom, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms. $Ar_1$ to Ara may each independently be a hydrogen atom, a deuterium atom, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms.

In Formula ET-1, "a" to "c" may each independently be an integer of 0 to 10. In Formula ET-1, $L_1$ to $L_3$ may each independently be a direct linkage, a substituted or unsubstituted ring-forming arylene group having 6 to 30 carbon atoms, or a substituted or unsubstituted ring-forming heteroarylene group having 2 to 30 carbon atoms. Meanwhile, if "a" to "c" are integer of 2 or more, $L_1$ to $L_3$ may each independently be a substituted or unsubstituted ring-forming arylene group having 6 to 30 carbon atoms, or a substituted or unsubstituted ring-forming heteroarylene group having 2 to 30 carbon atoms.

The electron transport region ETR may include an anthracene-based compound. However, the embodiment of the present disclosure is not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazol-1-yl)phenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), beryllium bis(benzoquinolin-10-olate) ($Bebq_2$), 9,10-di(naphthalene-2-yl)anthracene (ADN), 1,3-bis[3,5-di(pyridin-3-yl)phenyl]benzene (BmPyPhB), or a mixture thereof.

In one or more embodiments, the electron transport region ETR may include a halogenated metal (such as LiF, NaCl, CsF, RbCl, RbI, CuI, and/or KI), a lanthanide metal (such as Yb), and/or a co-deposited material of the above halogenated metal and lanthanide metal as well. For example, the electron transport region ETR may include KI:Yb, RbI:Yb, and/or the like as a co-deposited material. In one or more embodiments, a metal oxide (such as $Li_2O$ and/or BaO), 8-hydroxyl-lithium quinolate (Liq), and/or the like may be used in the electron transport region ETR, but the embodiment of the present disclosure is not limited thereto. The electron transport region ETR may also be formed using a mixture material of an electron transport material and an insulating organo metal salt. The organo metal salt may be a material having an energy band gap of about 4 eV or more. In one or more embodiments, the organo metal salt may include, for example, metal acetate(s), metal benzoate(s), metal acetoacetate(s), metal acetylacetonate(s), and/or metal stearate(s).

The electron transport region ETR may further include at least one of 2,9-dimethyl-4,7-diphenyl-1,10-phenanthroline (BCP) or 4,7-diphenyl-1,10-phenanthroline (Bphen) in addition to the above-described materials, but the embodiment of the present disclosure is not limited thereto.

The electron transport region ETR may include the aforementioned compounds of the electron transport region in at least one of the electron injection layer EIL, the electron transport layer ETL, or the hole blocking layer HBL.

If the electron transport region ETR includes the electron transport layer ETL, a thickness of the electron transport layer ETL may be about 100 Å to about 1000 Å, for example, about 150 Å to about 500 Å. If the thickness of the electron transport layer ETL satisfies the above-described range, satisfactory (or suitable) electron transport properties may be obtained without a substantial increase of a driving voltage. If the electron transport region ETR includes the electron injection layer EIL, a thickness of the electron injection layer EIL may be about 1 Å to about 100 Å, for example, about 3 Å to about 90 Å. If the thickness of the electron injection layer EIL satisfies the above-described range, satisfactory (or suitable) electron injection properties may be obtained without a substantial increase of a driving voltage.

A second electrode EL2 is provided on the electron transport region ETR. The second electrode EL2 may be a common electrode. The second electrode EL2 may be a cathode or an anode, but the embodiment of the present disclosure is not limited thereto. For example, if the first electrode EL1 is an anode, the second electrode EL2 may be a cathode, and if the first electrode EU is a cathode, the second electrode EL2 may be an anode.

The second electrode EL2 may be a transmissive electrode, a transflective electrode, or a reflective electrode. If the second electrode EL2 is the transmissive electrode, the second electrode EL2 may include transparent metal oxide such as indium tin oxide (ITO), indium zinc oxide (IZO), zinc oxide (ZnO), indium tin zinc oxide (ITZO), and/or the like.

If the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/$A_1$, Mo, Ti, Yb, W, a compound thereof, and/or a mixture thereof (for example, AgMg, AgYb, or MgAg). In one or more embodiments, the second electrode EL2 may have a multilayered structure including a reflective film or a transflective film formed using any of the above materials and a transparent conductive film formed using indium tin oxide (ITO), indium zinc oxide (IZO), zinc oxide (ZnO), indium tin zinc oxide (ITZO), and/or the like. For example, the second electrode EL2 may include at least one selected from the above-described metal materials, a combination of two or more metal materials selected from the above-described metal materials, and/or an oxide of the above-described metal materials.

In one or more embodiments, the second electrode EL2 may be connected (e.g., coupled) with an auxiliary electrode. If the second electrode EL2 is connected (e.g., coupled) with the auxiliary electrode, the resistance of the second electrode EL2 may decrease.

In one or more embodiments, the capping layer CPL may be further disposed on the second electrode EL2 of the light-emitting diode ED according to one or more embodiments. The capping layer CPL may include multiple layers or a single layer.

In one or more embodiments, the capping layer CPL may be an organic layer or an inorganic layer. For example, if the capping layer CPL includes an inorganic material, the inorganic material may include an alkali metal compound such as LiF, and/or an alkaline earth metal compound such as $MgF_2$, SiON, SiNx, SiOy, and/or the like.

For example, if the capping layer CPL includes an organic material, the organic material may include α-NPD, NPB, TPD, m-MTDATA, $Alq_3$, CuPc, N4,N4,N4',N4'-tetra (biphenyl-4-yl) biphenyl-4,4'-diamine (TPD15), $4,4^1,4"$-tris (carbazol sol-9-yl) triphenylamine (TCTA), etc., an epoxy resin, and/or acrylate such as methacrylate. However, the embodiment of the present disclosure is not limited thereto, and the capping layer CPL may include at least one selected from among Compounds P1 to P5 below.

P1

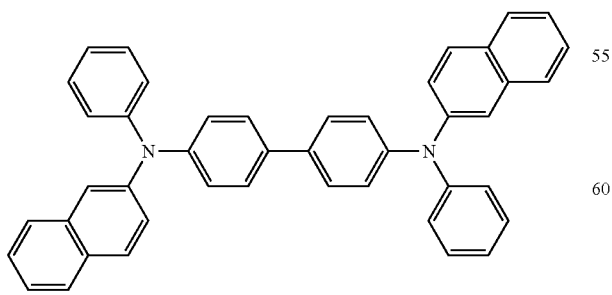

P2

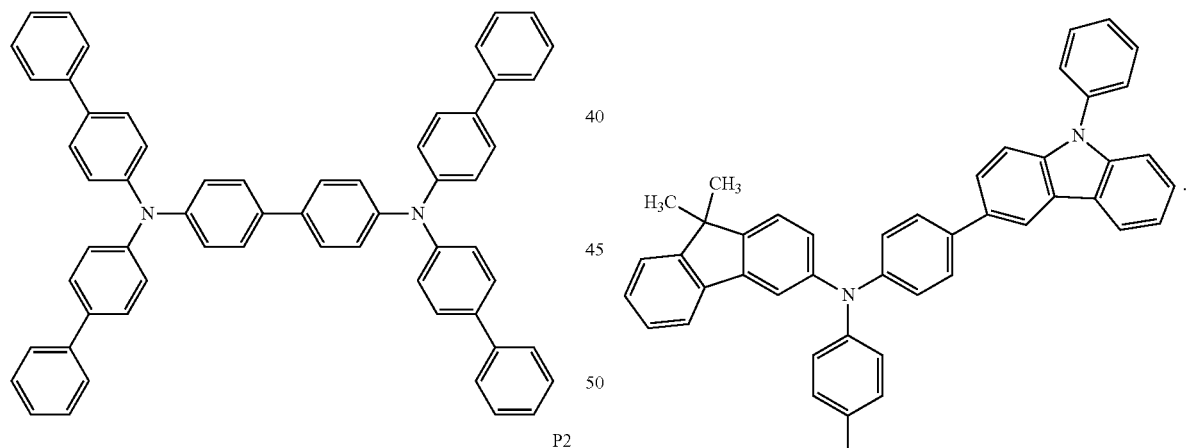

P3

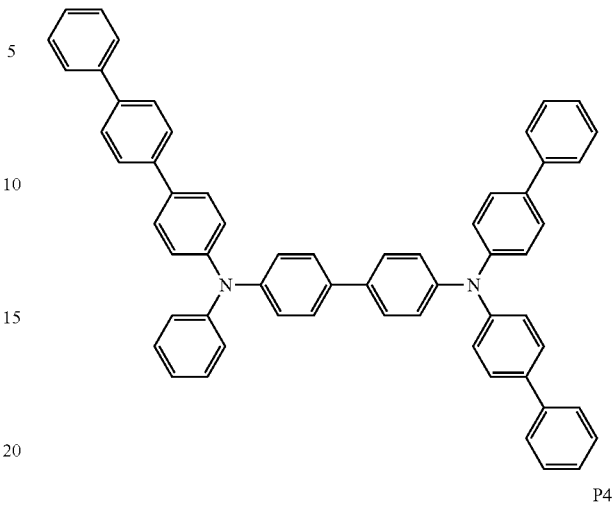

P4

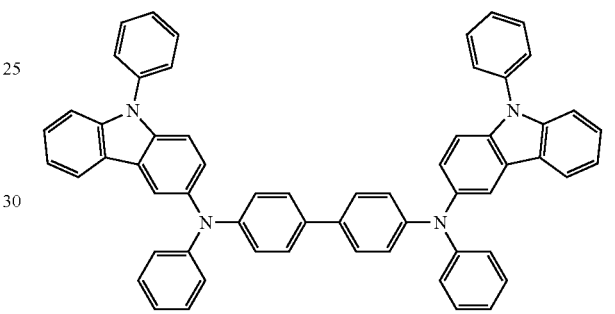

P4

The refractive index of the capping layer CPL may be about 1.6 or more. In one or more embodiments, for light having the wavelength range of about 550 nm to about 660 nm, the refractive index of the capping layer CPL may be about 1.6 or more.

Figure 7:
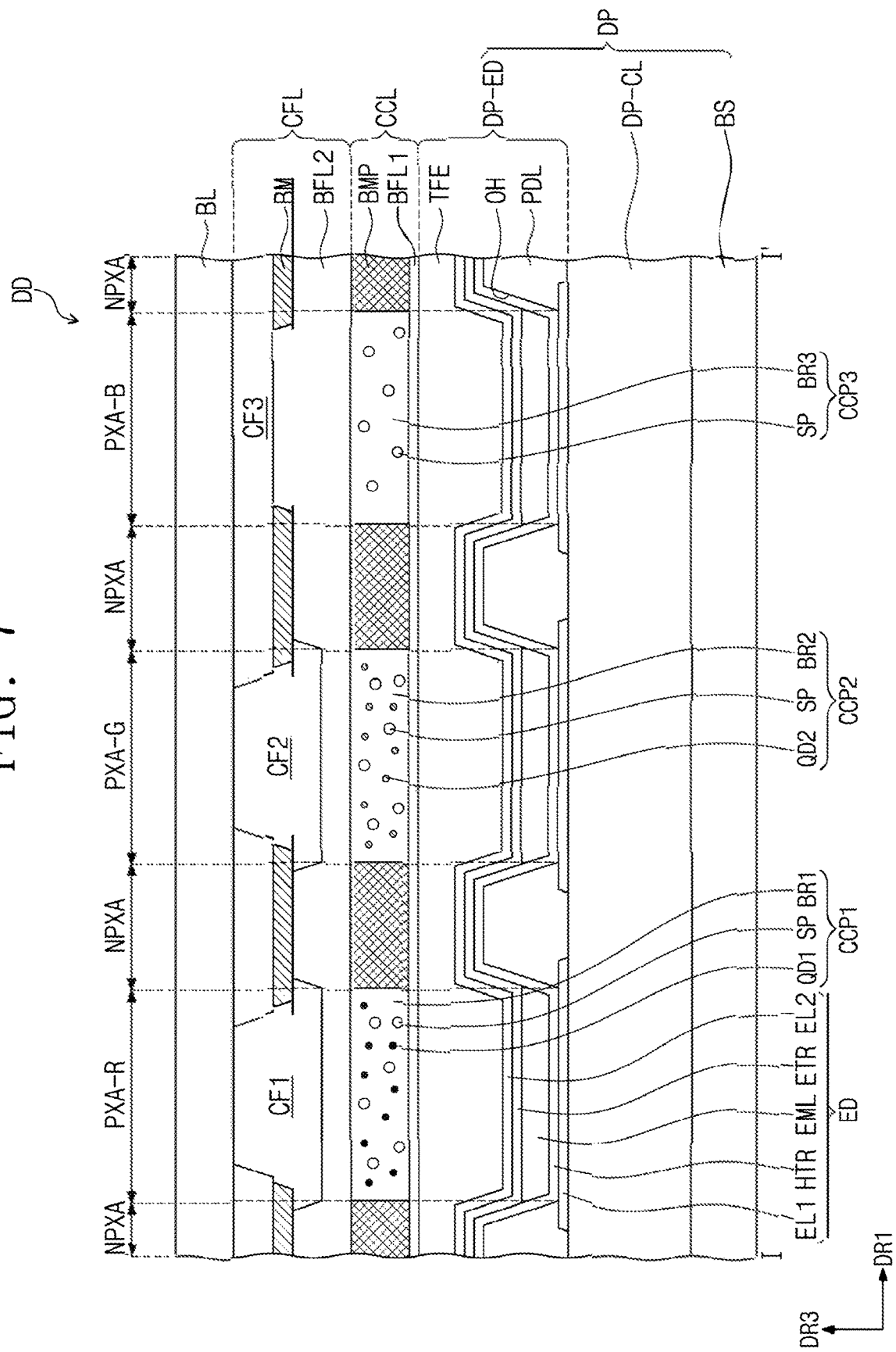
FIG. 7 is a cross-sectional view of a display device according to one or more embodiments.
Figure 8:
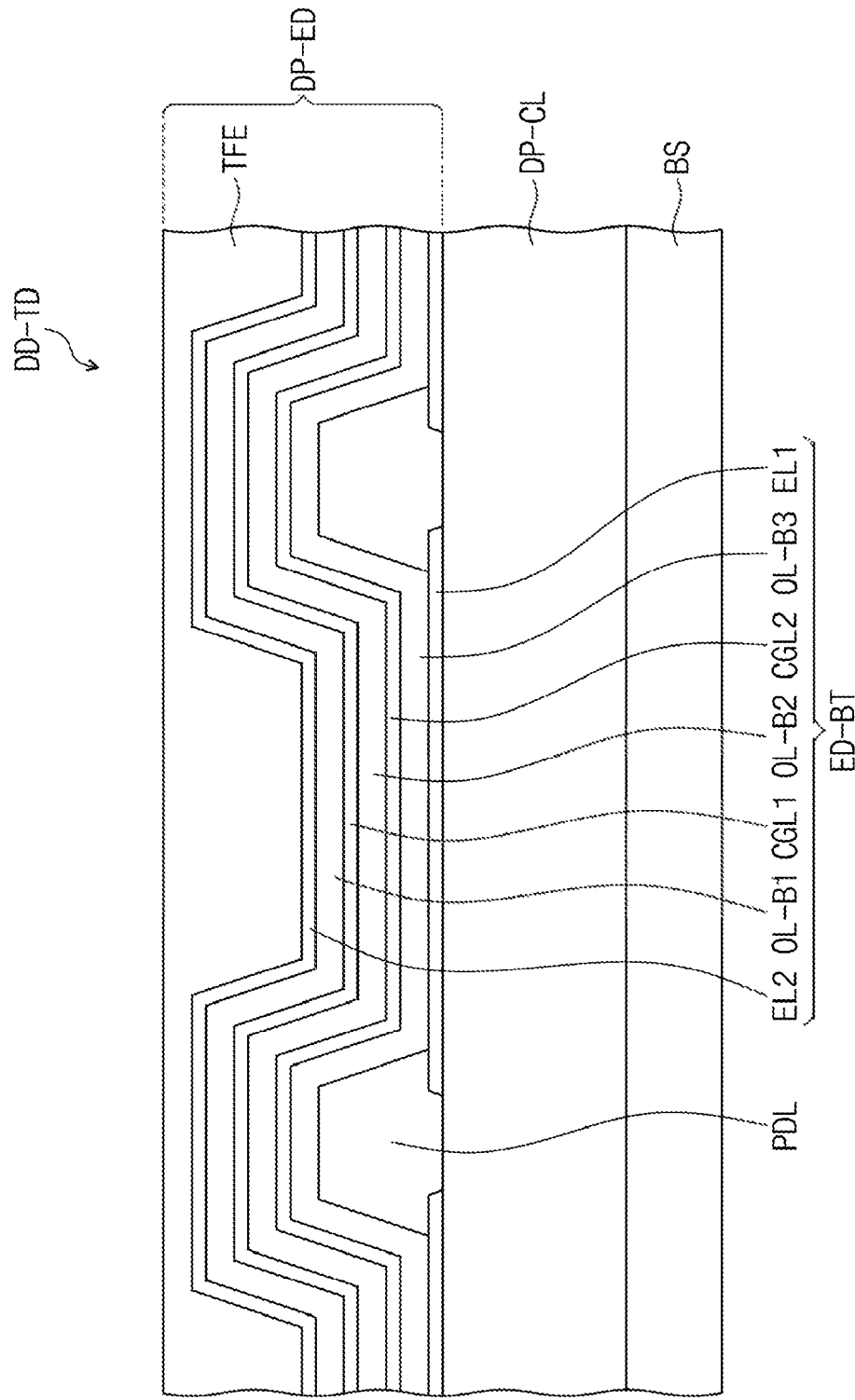
FIG. 8 is a cross-sectional view of a display device according to one or more embodiments.

FIGS. 7 and 8 are each a cross-sectional view of a display device according to one or more embodiments. In the description for the display device according to one or more embodiments described with reference to FIGS. 7 and 8, the descriptions that overlap with those described in FIGS. 1 to 6 will not be provided again, and differences will be mainly described.

Referring to FIG. 7, the display device DD according to one or more embodiments may include a display panel DP including a display device layer DP-ED, a light control layer CCL disposed on the display panel DP, and a color filter layer CFL.

In one or more embodiments illustrated in FIG. 7, the display panel DP may include a base layer BS, a circuit layer DP-CL provided on the base layer BS, and a display device layer DP-ED, and the display device layer DP-ED may include a light-emitting diode ED.

The light-emitting diode ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. The structure of the light-emitting diode in FIGS. 3 to 6 described above may be equally applicable to the structure of the light-emitting diode ED illustrated in FIG. 7.

Referring to FIG. 7, the emission layer EML may be disposed in the opening OH defined in the pixel-defining film PDL. For example, the emission layer EML separated by the pixel-defining film PDL and provided corresponding to respective light-emitting regions PXA-R, PXA-G, and PXA-B may emit light of the same wavelength region. In the display device DD according to one or more embodiments, the emission layer EML may emit blue light. In one or more embodiments, the emission layer EML may be provided as a common layer over all of the light-emitting regions PXA-R, PXA-G, and PXA-B.

The light control layer CCL may be disposed on the display panel DP. The light control layer CCL may include a light conversion body. The light conversion body may be a quantum dot, a phosphor, and/or the like. The light conversion body may convert the wavelength of received light to emit the converted light. For example, the light control layer CCL may be a layer including a quantum dot or a layer including a phosphor.

The light control layer CCL may include a plurality of light control portions CCP1, CCP2, and CCP3. The light control portions CCP1, CCP2, and CCP3 may be spaced apart from each other.

Referring to FIG. 7, a division pattern BMP may be disposed between the light control portions CCP1, CCP2, and CCP3 which are spaced apart from each other, but the embodiment of the present disclosure is not limited thereto. In FIG. 7, the division pattern BMP is illustrated to be non-overlapping with the light control portions CCP1, CCP2, and CCP3, but in one or more embodiments, at least part of edges of the light control portions CCP1, CCP2, and CCP3 may overlap the division pattern BMP.

The light control layer CCL may include a first light control portion CCP1 including a first quantum dot QD1 configured to convert first color light provided by the light-emitting diode ED into second color light, a second light control portion CCP2 including a second quantum dot QD2 configured to convert the first color light into third color light, and a third light control portion CCP3 configured to transmit the first color light.

In one or more embodiments, the first light control portion CCP1 may provide red light which is second color light, and the second light control portion CCP2 may provide green light which is third color light. The third light control portion CCP3 may transmit and provide blue light which is first color light provided by the light-emitting diode ED. For example, the first quantum dot QD1 may be a red quantum dot, and the second quantum dot QD2 may be a green quantum dot. The same description as described above may be applied to the quantum dots QD1 and QD2.

In one or more embodiments, the light control layer CCL may further include a scatterer SP. The first light control portion CCP1 may include the first quantum dot QD1 and the scatterer SP, the second light control portion CCP2 may include the second quantum dot QD2 and the scatterer SP, and the third light control portion CCP3 may not include a quantum dot but may include the scatterer SP.

The scatterer SP may be an inorganic particle. For example, the scatterer SP may include at least one of $TiO_2$, ZnO, $Al_2O_3$, $SiO_2$, or hollow silica. The scatterer SP may include at least one of $TiO_2$, ZnO, $Al_2O_3$, $SiO_2$, or hollow silica, or may be a mixture of two or more materials selected from $TiO_2$, ZnO, $Al_2O_3$, $SiO_2$, and hollow silica.

The first light control portion CCP1, the second light control portion CCP2, and the third light control portion CCP3 may include base resins BR1, BR2, and BR3 which respectively disperse the quantum dots QD1 and QD2, and the scatterer SP. In one or more embodiments, the first light control portion CCP1 may include the first quantum dot QD1 and the scatterer SP dispersed in the first base resin BR1, the second light control portion CCP2 may include the second quantum dot QD2 and the scatterer SP dispersed in the second base resin BR2, and the third light control portion CCP3 may include the scatterer SP dispersed in the third base resin BR3. The base resins BR1, BR2, and BR3 are media in which the quantum dots QD1 and QD2, and the scatterer SP are dispersed, and may be made of one or more suitable resin compositions which may be generally referred to as binders. For example, the base resins BR1, BR2, and BR3 may be acrylic-based resins, urethane-based resins, silicone-based resins, epoxy-based resins, and/or the like. The base resins BR1, BR2, and BR3 may be transparent resins. In one or more embodiments, each of the first base resin BR1, the second base resin BR2, and the third base resin BR3 may be the same as or different from each other.

The light control layer CCL may include a barrier layer BFL1. The barrier layer BFL1 may serve to prevent or reduce penetration of moisture and/or oxygen (hereinafter referred to as "moisture/oxygen"). The barrier layer BFL1 may be disposed on the light control portions CCP1, CCP2, and CCP3 to prevent or reduce the light control portions CCP1, CCP2, and CCP3 from being exposed to moisture/oxygen. Meanwhile, the barrier layer BFL1 may cover the light control portions CCP1, CCP2, and CCP3. In one or more embodiments, a barrier layer BFL2 may be provided between the color filter layer CFL and the light control portions CCP1, CCP2, and CCP3 as well.

The barrier layers BFL1 and BFL2 may include at least one inorganic layer. For example, the barrier layers BFL1 and BFL2 may include an inorganic material. For example, the barrier layers BFL1 and BFL2 may include silicon nitride, aluminum nitride, zirconium nitride, titanium nitride, hafnium nitride, tantalum nitride, silicon oxide, aluminum oxide, titanium oxide, tin oxide, cerium oxide, and/or silicon oxynitride, or a thin metal film which ensures light transmittance, etc. Meanwhile, the barrier layers BFL1 and BFL2 may further include an organic film. The barrier layers BFL1 and BFL2 may be comprised of a single layer or a plurality of layers.

In a display device DD according to one or more embodiments, the color filter layer CFL may be disposed on the light control layer CCL. For example, the color filter layer CFL may be directly disposed on the light control layer CCL. In this case, the barrier layer BFL2 may be omitted.

The color filter layer CFL may include a light-shielding portion BM and filters CF—B, CF-G, and CF-R. The color filter layer CFL may include a first filter CF1 configured to transmit second color light, a second filter CF2 configured to transmit third color light, and a third filter CF3 configured to transmit first color light. For example, the first filter CF1 may be a red filter, the second filter CF2 may be a green filter, and the third filter CF3 may be a blue filter. Each of the filters CF1, CF2, and CF3 may include a photosensitive polymer resin and a pigment and/or dye. The first filter CF1 may include a red pigment and/or dye, the second filter CF2 may include a green pigment and/or dye, and the third filter CF3 may include a blue pigment and/or dye. However, the embodiment of the present disclosure is not limited thereto, and the third filter CF3 may not include a pigment or a dye. The third filter CF3 may include a photosensitive polymer resin and may not include a pigment or a dye. The third filter CF3 may be transparent. The third filter CF3 may be formed of a transparent photosensitive resin.

In one or more embodiments, the first filter CF1 and the second filter CF2 may be a yellow filter. The first filter CF1 and the second filter CF2 may not be distinguished from each other and may be provided integrally.

The light-shielding portion BM may be a black matrix. The light-shielding portion BM may include an organic light-shielding material or an inorganic light-shielding material including a black pigment and/or a black dye. The light-shielding portion BM may prevent or reduce light leakage, and separate the boundary between the adjacent filters CF1, CF2, and CF3. In one or more embodiments, the light-shielding portion BM may be formed of a blue filter.

The first to third filters CF1, CF2, and CF3 may be disposed to respectively correspond to a red light-emitting region PXA-R, a green light-emitting region PXA-G, and a blue light-emitting region PXA-B.

A base substrate BL may be disposed on the color filter layer CFL. The base substrate BL may be a member providing a base surface on which the color filter layer CFL, the light control layer CCL, and/or the like are disposed. The base substrate BL may be a glass substrate, a metal substrate, a plastic substrate, and/or the like. However, the embodiment of the present disclosure is not limited thereto, and the base substrate BL may be an inorganic layer, an organic layer, or a composite material layer (e.g., including an organic material and an inorganic material). In one or more embodiments, the base substrate BL may be omitted.

FIG. 8 is a cross-sectional view illustrating a portion of the display device according to one or more embodiments. FIG. 8 illustrates a cross-sectional view of a portion corresponding to the display panel DP of FIG. 7. In the display device DD-TD according to one or more embodiments, a light-emitting diode ED-BT may include a plurality of light-emitting structures OL-B1, OL-B2, and OL-B3. The light-emitting diode ED-BT may include a first electrode EL1 and a second electrode EL2 that face each other, and a plurality of light-emitting structures OL-B1, OL-B2, and OL-B3 that are provided by sequentially stacking in a thickness direction between the first electrode EL1 and the second electrode EL2. Each of the light-emitting structures OL-B1, OL-B2, and OL-B3 may include the emission layer EML (FIG. 7), and the hole transport region HTR and the electron transport region ETR with the emission layer EML (FIG. 7) interposed therebetween.

For example, the light-emitting diode ED-BT included in the display device DD-TD according to one or more embodiments may be a light-emitting diode having a tandem structure including a plurality of emission layers.

In one or more embodiments illustrated in FIG. 8, all light emitted from respective light-emitting structures OL-B1, OL-B2, and OL-B3 may be blue light. However, the embodiment of the present disclosure is not limited thereto, and the wavelength ranges of light emitted from each of the light-emitting structures OL-B1, OL-B2, and OL-B3 may be different from each other. For example, the light emitting diode ED-BT including the plurality of light-emitting structures OL-B1, OL-B2, and OL-B3 that emit light of different wavelength regions may emit white light.

A charge generating layer CGL may be disposed between the adjacent light-emitting structures OL-B1, OL-B2, and OL-B3. The charge generating layer CGL may include a p-type charge generating layer and/or an n-type charge generating layer.

At least one selected from among the light-emitting structures OL-B1, OL-B2, and OL-B3 included in the display device DD-TD according to one or more embodiments may include the aforementioned amine compound according to one or more embodiments.

The light-emitting diode ED according to one or more embodiments of the present disclosure may include the aforementioned amine compound according to one or more embodiments in at least one functional layer disposed between the first electrode EL1 and the second electrode EL2, and thereby exhibiting improved luminous efficiency and improved lifetime properties. The light-emitting diode ED according to one or more embodiments may include the aforementioned amine compound according to one or more embodiments in at least one of the hole transport region HTR, the emission layer EML, or the electron transport region ETR disposed between the first electrode EL1 and the second electrode EL2, or in the capping layer CPL.

For example, the amine compound according to one or more embodiments may be included in the hole transport region HTR of the light-emitting diode ED according to one or more embodiments, and the light-emitting diode according to one or more embodiments may exhibit excellent luminous efficiency and long lifetime properties.

The amine compound according to one or more embodiments described above has a molecular structure in which an amine derivative and a condensed ring with at least one heteroatom are bonded and thus has excellent durability and heat resistance, and thereby may exhibit improved lifetime properties. In one or more embodiments, the amine compound according to one or more embodiments may contribute to long lifetime properties and high efficiency properties of the light-emitting diode by improving stability and hole transport ability of the material.

Hereinafter, the amine compound according to one or more embodiments of the present disclosure and the light-emitting diode according to one or more embodiments will be described in more detail with reference to Examples and Comparative Examples. However, the Examples shown below are illustrative and are designed to assist in understanding of the present disclosure, and the scope of the present disclosure is not limited thereto.

EXAMPLES

1. Synthesis of Amine Compound

First, the synthetic method of the amine compound according to the embodiment will be explained in more detail referring to the synthetic methods of Compound 1, Compound 5, Compound 9, Compound 12, Compound 136, Compound 222, Compound 390, Compound 886, and Compound 1014 in Compound Group 1. In one or more embodiments, the synthetic methods of the amine compound explained below are illustrative, and the synthetic method of the amine compound according to one or more embodiments of the present disclosure is not limited thereto.

Synthesis of Compound 1

The amine compound 1 according to one or more embodiments may be synthesized by, for example, the tasks (steps) of the Scheme 1.

1-1. Synthesis of Intermediate 1a 1,8-dibromonaphthalene (1.0 eq.), bis(pinacolato)diboron (1.2 eq.), potassium acetate (4.0 eq.), and palladium acetate (0.05 eq.) were dissolved in 1,4-dioxane, and then stirred at about 80° C. for about 3 hours under a nitrogen atmosphere. After cooling, followed by washing with ethyl acetate and water three times, the resulting organic layer was dried over MgSO$_4$, and then dried under reduced pressure. Intermediate 1a was obtained by column chromatography. (yield: 85%).

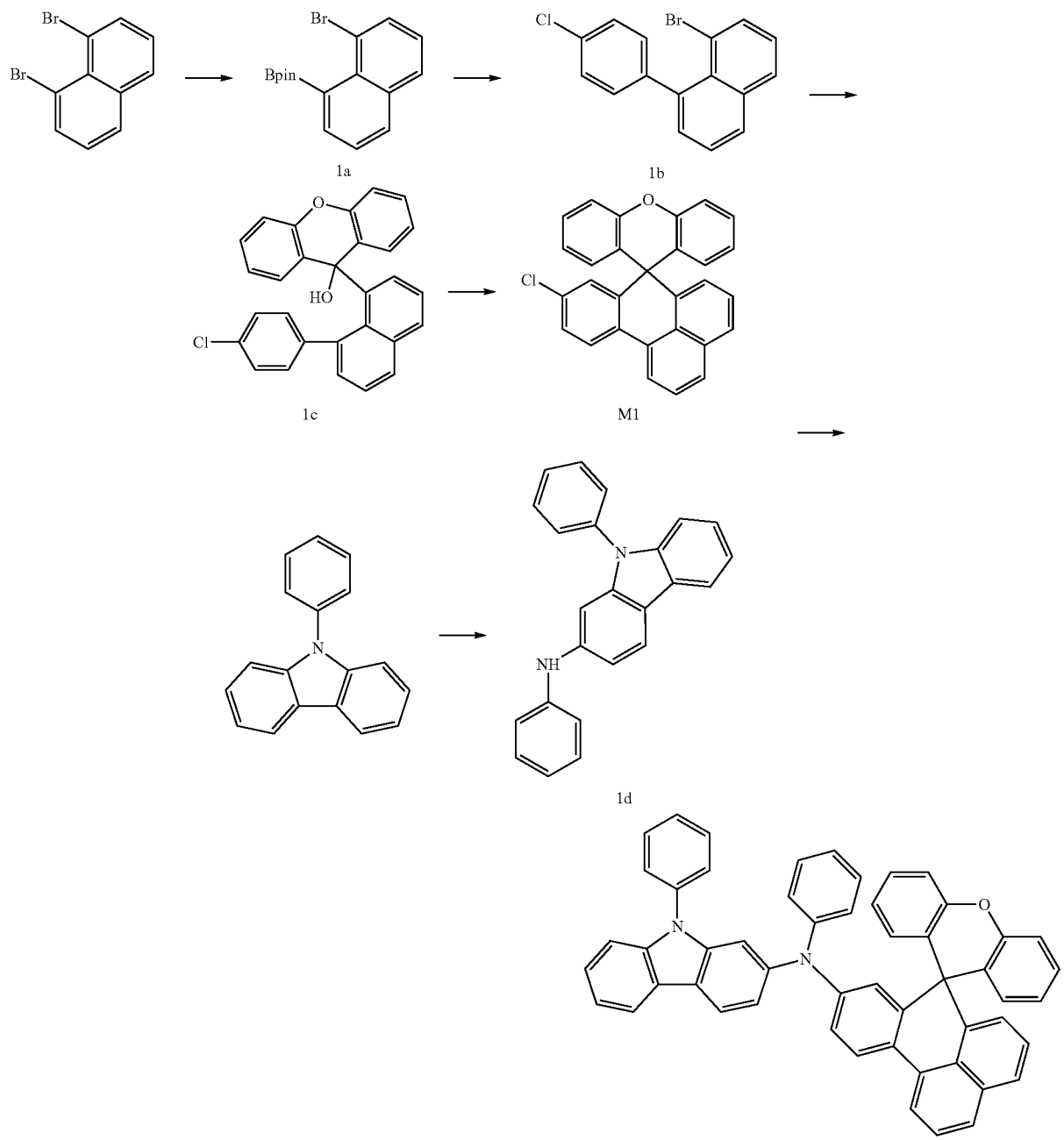

1-2. Synthesis of Intermediate 1b

Intermediate 1a (1.0 eq.), 1-bromo-4-chlorobenzene (1.2 eq.), tetrakis(triphenylphosphine)palladium (0.05 eq.), and potassium carbonate (2.0 eq.) were dissolved in THF:H$_2$O in a volume ratio of 4:1, and then stirred at about 80° C. about for 12 hours under a nitrogen atmosphere. After cooling, followed by washing with ethyl acetate and water three times, the resulting organic layer was dried over MgSO$_4$, and then dried under reduced pressure. Intermediate 1b was obtained by column chromatography. (yield: 66%).

1-3. Synthesis of Intermediate 1c

Anhydrous THF was added dropwise to Intermediate 1b (1.0 eq.), and then cooled to about −78° C. under a nitrogen atmosphere. n-BuLi (1.1 eq.) was slowly added dropwise to the cooled solution, and then stirred at about −78° C. for about 1 hour. 9H-xanthen-9-one (1.1 eq.) was slowly added dropwise to this solution, and then stirred at room temperature for about 3 hours. After cooling, followed by washing with ethyl acetate and water three times, the resulting organic layer was dried over MgSO$_4$, and then dried under reduced pressure. Intermediate 1c was obtained by column chromatography. (yield: 82%).

1-4. Synthesis of Intermediate M1

Intermediate 1c (1.0 eq.) was dissolved in 9:1 volume ratio of acetic acid:hydrochloric acid, and then stirred at about 80° C. for about 2 hours under a nitrogen atmosphere. After cooling, followed by washing with ethyl acetate and water three times, the resulting organic layer was dried over MgSO$_4$, and then dried under reduced pressure. Intermediate M1 was obtained by column chromatography. (yield: 78%).

1-5. Synthesis of Intermediate 1d

Aniline (1.0 eq.), 2-bromo-9-phenyl-9H-carbazole (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, and then stirred at about 90° C. for about 2 hours under a nitrogen atmosphere. After cooling, followed by washing with ethyl acetate and water three times, the resulting organic layer was dried over MgSO$_4$, and then dried under reduced pressure. Intermediate 1d was obtained by column chromatography. (yield: 78%).

1-6. Synthesis of Compound 1

Intermediate M1 (1.0 eq.), Intermediate 1d (1.0 eq.), tris(dibenzylideneacetone)dipalladium(0) (0.05 eq.), tri-tert-butylphosphine (0.10 eq.), and sodium tert-butoxide (2.0 eq.) were dissolved in toluene, and then stirred at about 90° C. for about 2 hours under a nitrogen atmosphere. After cooling, followed by washing with ethyl acetate and water three times, the resulting organic layer was dried over MgSO$_4$, and then dried under reduced pressure. Compound 1 was obtained by column chromatography. (yield: 75%). By FAB-MS measurement, mass number m/z=714.27 was observed as the molecular ion peak, and Compound 1 was identified.

Synthesis of Compound 5

The amine Compound 5 according to one or more embodiments may be synthesized by, for example, the tasks of the Scheme 2.

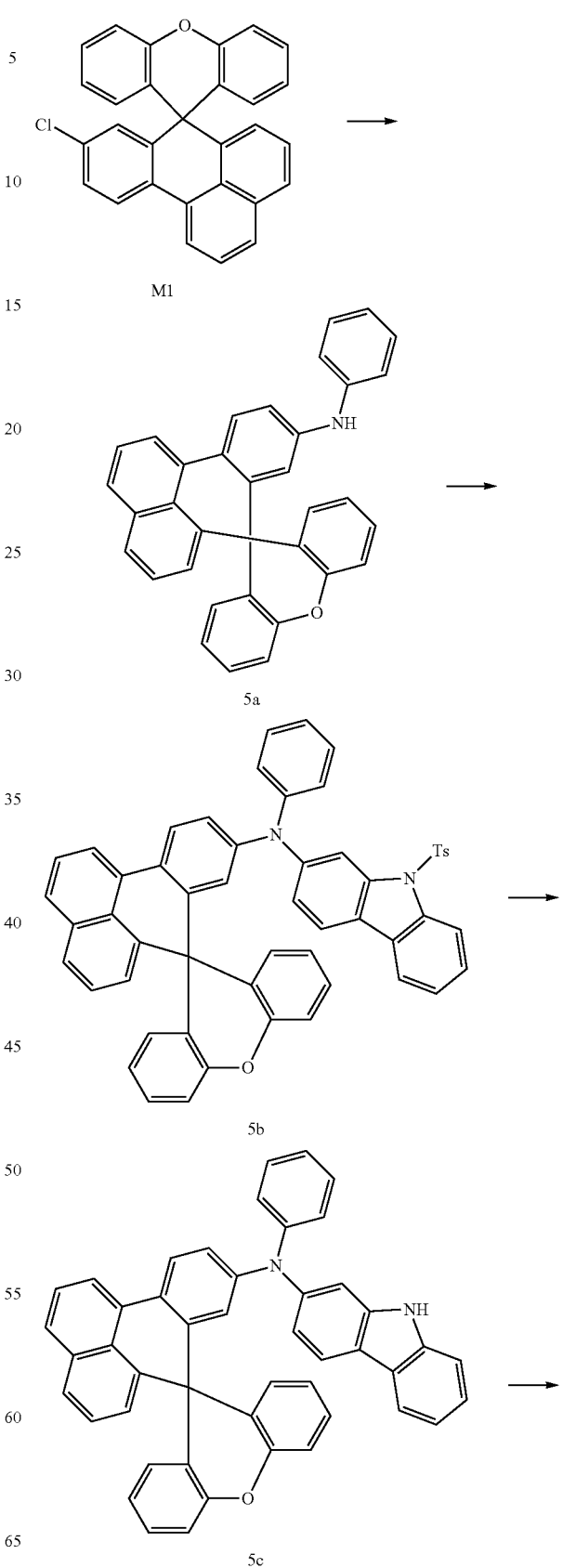

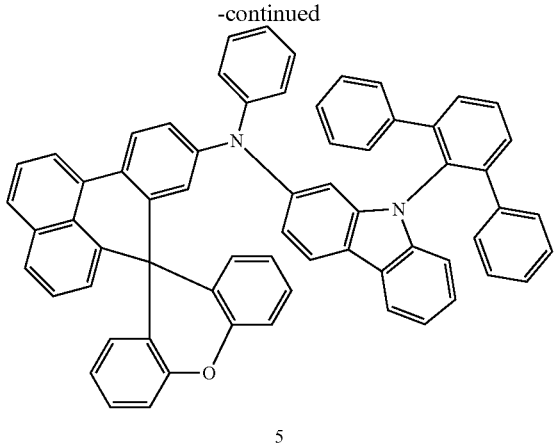

5

2-1. Synthesis of Intermediate 5a

Intermediate M1 (1.0 eq.), aniline (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, and then stirred at about 80° C. for about 2 hours under a nitrogen atmosphere. After cooling, followed by washing with ethyl acetate and water three times, the resulting organic layer was dried over $MgSO_4$, and then dried under reduced pressure. Intermediate 5a was obtained by column chromatography. (yield: 88%).

2-2. Synthesis of Intermediate 5b

Intermediate 5a (1.0 eq.), 2-bromo-9-tosyl-9H-carbazole (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, and then stirred at about 70° C. for about 15 minutes under a nitrogen atmosphere. After cooling, followed by washing with ethyl acetate and water three times, the resulting organic layer was dried over $MgSO_4$, and then dried under reduced pressure. Intermediate 5b was obtained by column chromatography. (yield: 75%).

2-3. Synthesis of Intermediate 5c

DMSO/EtOH in a volume ratio of 4:1 was added dropwise to Intermediate 5b (1.0 eq.) and KOH (3.0 eq.), and then stirred at room temperature for about 4 hours. After washing with ethyl acetate and water 5 times, the resulting organic layer was dried over $MgSO_4$, and then dried under reduced pressure. Intermediate 5c was obtained by column chromatography. (yield: 75%).

2-4. Synthesis of Compound 5

Intermediate 5c (1.0 eq.), 2'-iodo-1,1':3',1''-terphenyl (10 eq.), CuI (0.2 eq.), 1,10-phenanthroline (0.40 eq.), and sodium tert-butoxide (3.0 eq.) were dissolved in DMF, and then stirred at about 160° C. for about 24 hours under a nitrogen atmosphere. After cooling, followed by washing with ethyl acetate and water 5 times, the resulting organic layer was dried over $MgSO_4$, and then dried under reduced pressure. Compound 5 was obtained by column chromatography. (yield: 32%). By FAB-MS measurement, mass number m/z=866.33 was observed as the molecular ion peak, and Compound 5 was identified.

Synthesis of Compound 9

The amine Compound 9 according to one or more embodiments may be synthesized by, for example, the tasks of the Scheme 3.

[Scheme 3]

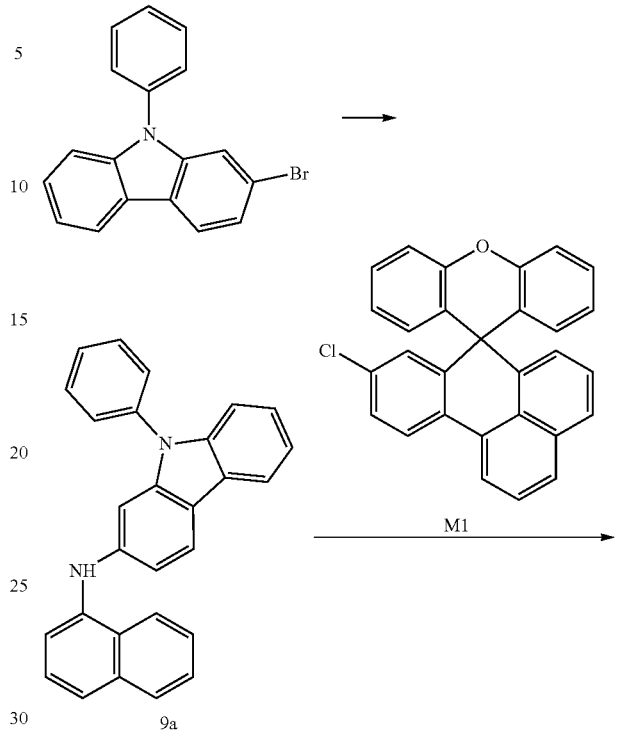

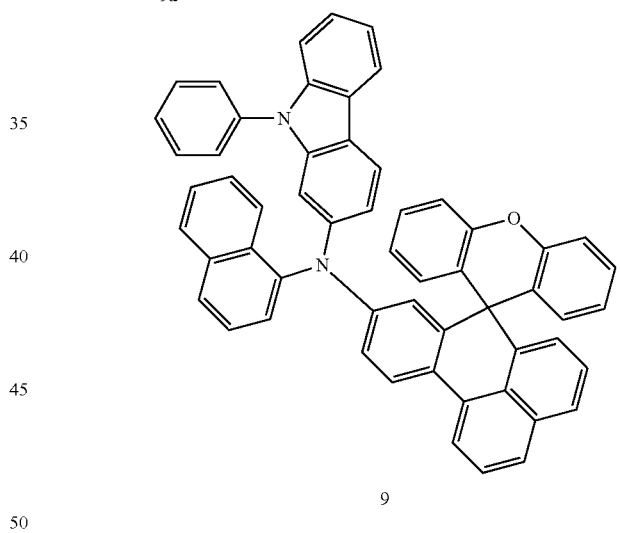

9

3-1. Synthesis of Intermediate 9a 2-bromo-9-phenyl-9H-carbazole (1.0 eq.), naphthalen-1-amine (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, and then stirred at about 80° C. for about 2 hour under a nitrogen atmosphere. After cooling, followed by washing with ethyl acetate and water 3 times, the resulting organic layer was dried over $MgSO_4$, and then dried under reduced pressure. Intermediate 9a was obtained by column chromatography. (yield: 85%).

3-2. Synthesis of Compound 9

Intermediate M1 (1.0 eq.), Intermediate 9a (1.0 eq.), tris(dibenzylideneacetone)dipalladium(0) (0.05 eq.), tri-tert-butylphosphine (0.10 eq.), and sodium tert-butoxide (2.0 eq.) were dissolved in toluene, and then stirred at about 90°

C. for about 2 hours under a nitrogen atmosphere. After cooling, followed by washing with ethyl acetate and water 3 times, the resulting organic layer was dried over MgSO$_4$, and then dried under reduced pressure. Compound 9 was obtained by column chromatography. (yield: 75%). By FAB-MS measurement, mass number m/z=764.28 was observed as the molecular ion peak, and Compound 9 was identified.

Synthesis of Compound 12

The amine Compound 12 according to one or more embodiments may be synthesized by, for example, the tasks of the Scheme 4.

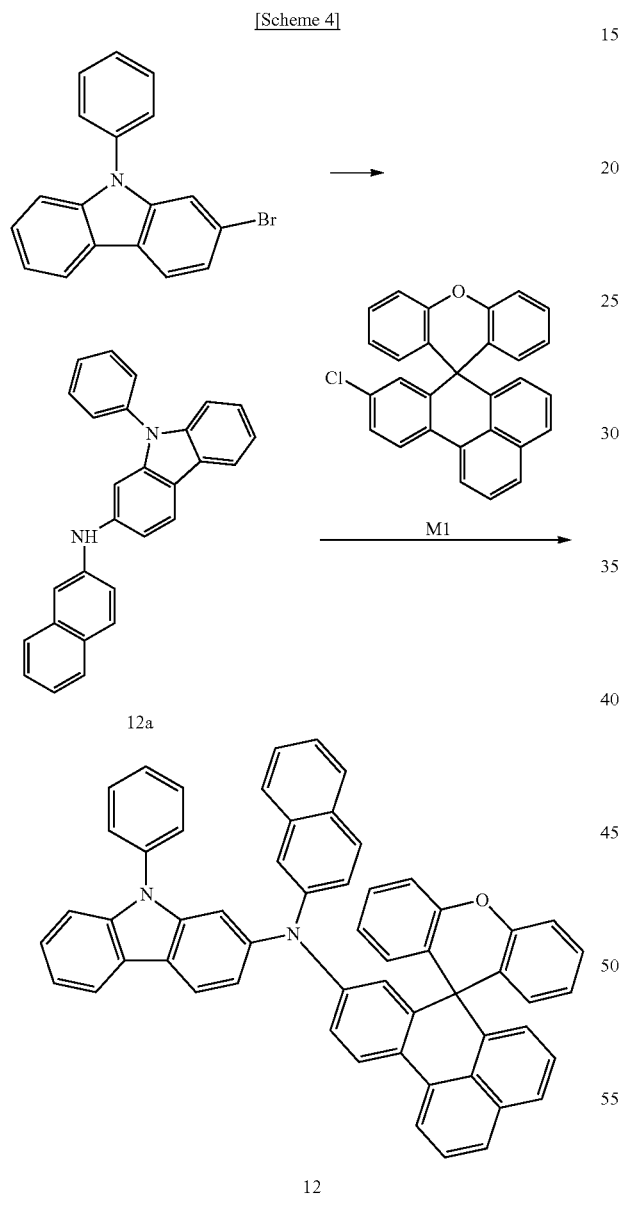

12a

12

4-1. Synthesis of Intermediate 12a 2-bromo-9-phenyl-9H-carbazole (1.0 eq.), naphthalen-2-amine (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, and then stirred at about 80° C. for about 2 hour under a nitrogen atmosphere. After cooling, followed by washing with ethyl acetate and water 3 times, the resulting organic layer was dried over MgSO$_4$, and then dried under reduced pressure. Intermediate 12a was obtained by column chromatography. (yield: 85%).

4-2. Synthesis of Compound 12

Intermediate M1 (1.0 eq.), Intermediate 12a (1.0 eq.), tris(dibenzylideneacetone)dipalladium(0) (0.05 eq.), tri-tert-butylphosphine (0.10 eq.), and sodium tert-butoxide (2.0 eq.) were dissolved in toluene, and then stirred at about 90° C. for about 2 hours under a nitrogen atmosphere. After cooling, followed by washing with ethyl acetate and water 3 times, the resulting organic layer was dried over MgSO$_4$, and then dried under reduced pressure. Compound 12 was obtained by column chromatography. (yield: 74%). By FAB-MS measurement, mass number m/z=764.28 was observed as the molecular ion peak, and Compound 12 was identified.

Synthesis of Compound 136

The amine compound 136 according to one or more embodiments may be synthesized by, for example, the tasks of the Scheme 5.

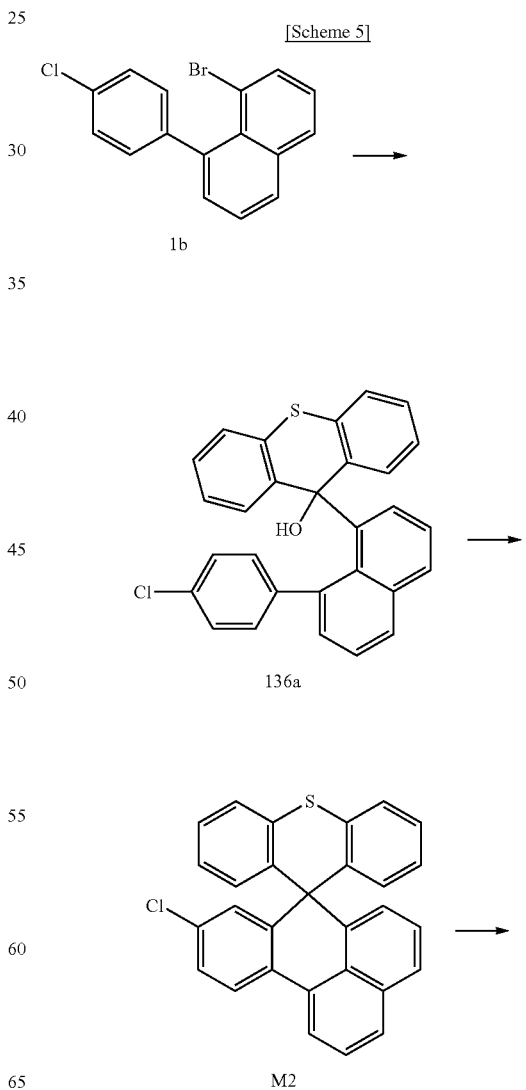

1b

136a

M2

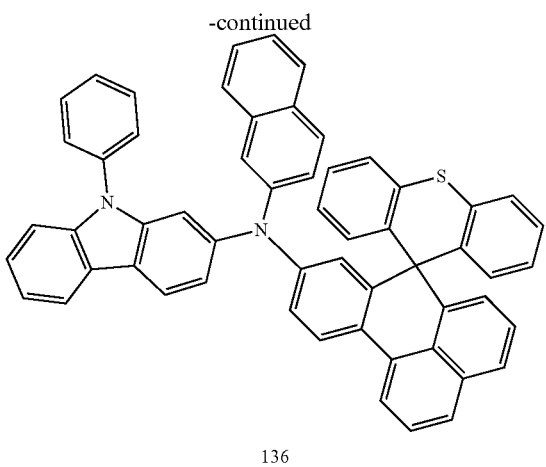

136

5-1. Synthesis of Intermediate 136a

Anhydrous THF was added dropwise to Intermediate 1 b (1.0 eq.), and then cooled to about −78° C. under a nitrogen atmosphere. n-BuLi (1.1 eq.) was slowly added dropwise to the cooled solution, and then stirred at about −78° C. for about 1 hour. 9H-thioxanthen-9-one (1.1 eq.) was slowly added dropwise to this solution, and then stirred at room temperature for about 3 hours. After cooling, followed by washing with ethyl acetate and water three times, the resulting organic layer was dried over MgSO₄, and then dried under reduced pressure. Intermediate 136a was obtained by column chromatography. (yield: 82%).

5-2. Synthesis of Intermediate M2

Intermediate 136a (1.0 eq.) was dissolved in 9:1 volume ratio of acetic acid:hydrochloric acid, and then stirred at about 80° C. for about 2 hours under a nitrogen atmosphere. After cooling, followed by washing with ethyl acetate and water 3 times, the resulting organic layer was dried over MgSO₄, and then dried under reduced pressure. Intermediate M2 was obtained by column chromatography. (yield: 78%).

5-3. Synthesis of Compound 136

Intermediate M2 (1.0 eq.), Intermediate 12a (1.0 eq.), tris(dibenzylideneacetone)dipalladium(0) (0.05 eq.), tri-tert-butylphosphine (0.10 eq.), and sodium tert-butoxide (2.0 eq.) were dissolved in toluene, and then stirred at about 90° C. for about 2 hours under a nitrogen atmosphere. After cooling, followed by washing with ethyl acetate and water 3 times, the resulting organic layer was dried over MgSO₄, and then dried under reduced pressure. Compound 136 was obtained by column chromatography. (yield: 75%). By FAB-MS measurement, mass number m/z=780.26 was observed as the molecular ion peak, and Compound 136 was identified.

Synthesis of Compound 222

The amine Compound 222 according to one or more embodiments may be synthesized by, for example, the tasks of the Scheme 6.

[Scheme 6]

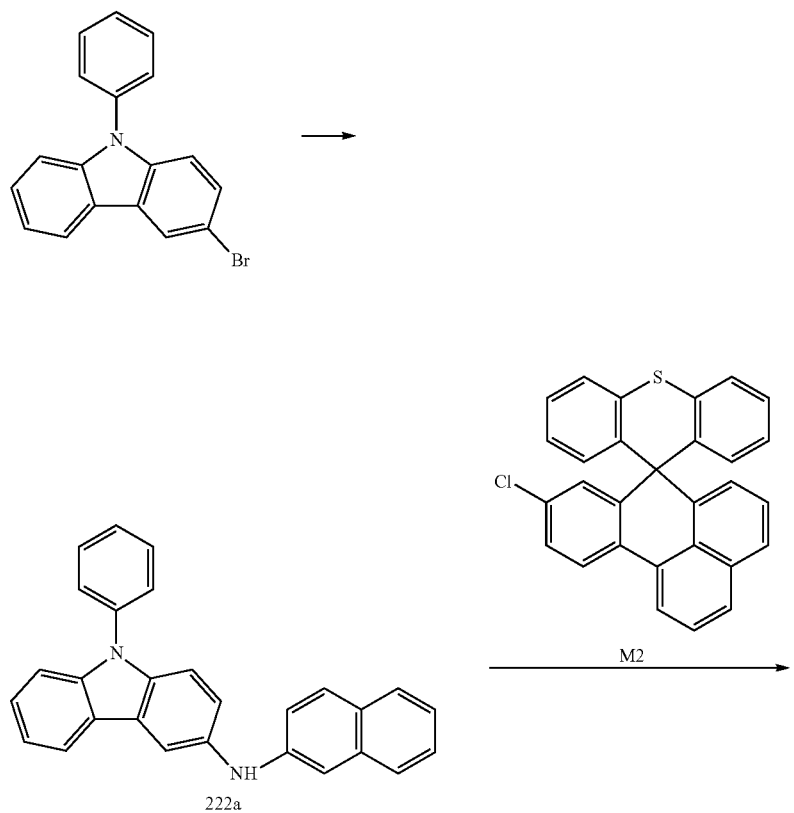

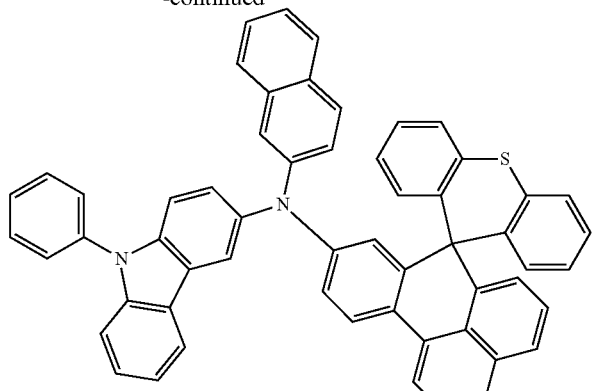

222

6-1. Synthesis of Intermediate 222a 3-bromo-9-phenyl-9H-carbazole (1.0 eq.), naphthalen-2-amine (1.1 eq.), tris(dibenzylideneacetone)dipalladium(0) (0.05 eq.), tri-tert-butylphosphine (0.10 eq.), and sodium tert-butoxide (2.0 eq.) were dissolved in toluene, and then stirred at about 80° C. for about 2 hour under a nitrogen atmosphere. After cooling, followed by washing with ethyl acetate and water 3 times, the resulting organic layer was dried over MgSO$_4$, and then dried under reduced pressure. Intermediate 222a was obtained by column chromatography. (yield: 85%).

6-2. Synthesis of Compound 222

Intermediate M2 (1.0 eq.), Intermediate 222a (1.0 eq.), tris(dibenzylideneacetone)dipalladium(0) (0.05 eq.), tri-tert-butylphosphine (0.10 eq.), and sodium tert-butoxide (2.0 eq.) were dissolved in toluene, and then stirred at about 90° C. for about 2 hours under a nitrogen atmosphere. After cooling, followed by washing with ethyl acetate and water 3 times, the resulting organic layer was dried over MgSO$_4$, and then dried under reduced pressure. Compound 222 was obtained by column chromatography. (yield: 75%). By FAB-MS measurement, mass number m/z=780.26 was observed as the molecular ion peak, and Compound 222 was identified.

Synthesis of Compound 390

The amine Compound 390 according to one or more embodiments may be synthesized by, for example, the tasks of the Scheme 7.

[Scheme 7]

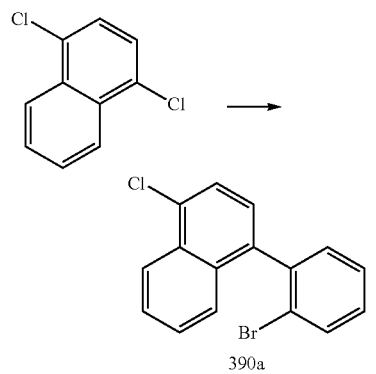

390a

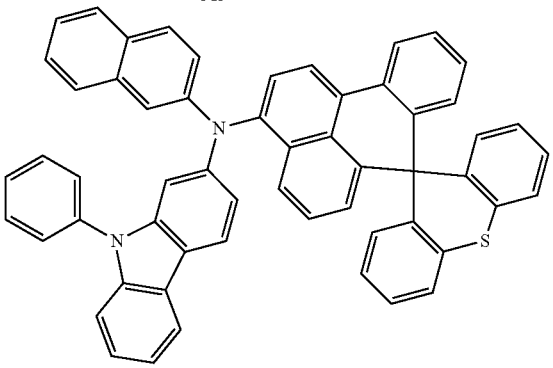

7-1. Synthesis of Intermediate 390a 1,4-dichloronaphthalene (1.0 eq.), (2-bromophenyl)boronic acid (1.2 eq.), tetrakis(triphenylphosphine)palladium (0.05 eq.), and potassium carbonate (2.0 eq.) were dissolved in dioxane:H$_2$O in a volume ratio of 4:1, and then stirred at about 110° C. for about 12 hours under a nitrogen atmosphere. After cooling, followed by washing with ethyl acetate and water 3 times, the resulting organic layer was dried over MgSO$_4$, and then dried under reduced pressure. Intermediate 390a was obtained by column chromatography. (yield: 52%).

7-2. Synthesis of Intermediate 390b

Anhydrous THF was added dropwise to Intermediate 390a (1.0 eq.), and then cooled to about −78° C. under a nitrogen atmosphere. n-BuLi (1.1 eq.) was slowly added dropwise to the cooled solution, and then stirred at about −78° C. for about 1 hour. 9H-xanthen-9-one (1.1 eq.) was slowly added dropwise to this solution, and then stirred at room temperature for about 3 hours. After cooling, followed by washing with ethyl acetate and water three times, the resulting organic layer was dried over MgSO$_4$, and then dried under reduced pressure. Intermediate 390b was obtained by column chromatography. (yield: 82%).

7-3. Synthesis of Intermediate M3

Intermediate 390b (1.0 eq.) was dissolved in 9:1 volume ratio of acetic acid:hydrochloric acid, and then stirred at about 80° C. for about 2 hours under a nitrogen atmosphere. After cooling, followed by washing with ethyl acetate and water 3 times, the resulting organic layer was dried over MgSO$_4$, and then dried under reduced pressure. Intermediate M3 was obtained by column chromatography. (yield: 78%).

7-4. Synthesis of Compound 390

Intermediate M3 (1.0 eq.), Intermediate 12a (1.0 eq.), tris(dibenzylideneacetone)dipalladium(0) (0.05 eq.), tri-tert-butylphosphine (0.10 eq.), and sodium tert-butoxide (2.0 eq.) were dissolved in toluene, and then stirred at about 90° C. for about 2 hours under a nitrogen atmosphere. After cooling, followed by washing with ethyl acetate and water 3 times, the resulting organic layer was dried over MgSO$_4$, and then dried under reduced pressure. Compound 390 was obtained by column chromatography. (yield: 75%). By FAB-MS measurement, mass number m/z=780.26 was observed as the molecular ion peak, and Compound 390 was identified.

Synthesis of Compound 886

The amine Compound 886 according to one or more embodiments may be synthesized by, for example, the tasks of the Scheme 8.

[Scheme 8]

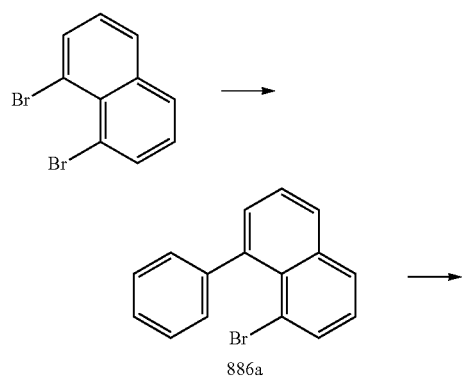

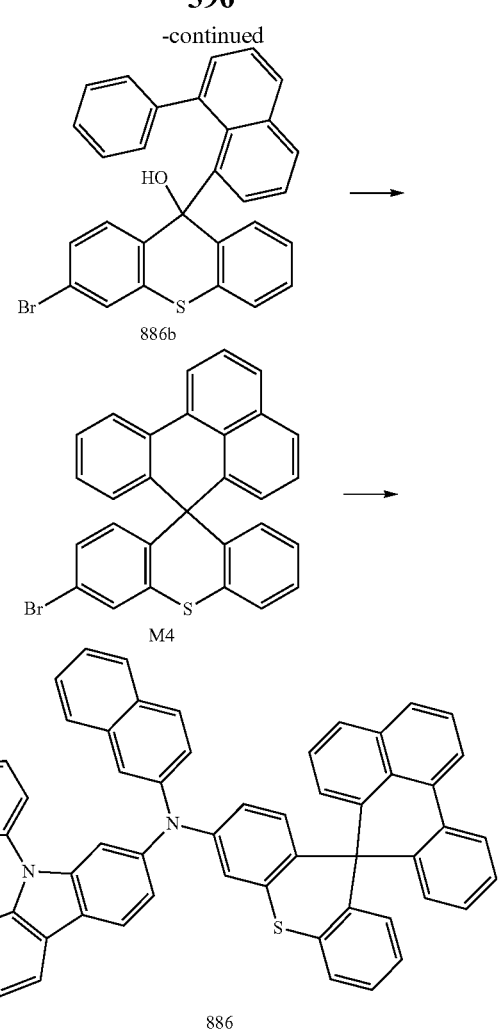

8-1. Synthesis of Intermediate 886a 1,8-dibromonaphthalene (1.0 eq.), phenylboronic acid (1.1 eq.), tetrakis(triphenylphosphine)palladium (0.05 eq.), and potassium carbonate (2.0 eq.) were dissolved in THF:H$_2$O in a volume ratio of 4:1, and then stirred at about 80° C. about for 12 hours under a nitrogen atmosphere. After cooling, followed by washing with ethyl acetate and water 3 times, the resulting organic layer was dried over MgSO$_4$, and then dried under reduced pressure. Intermediate 886a was obtained by column chromatography. (yield: 66%).

8-2. Synthesis of Intermediate 886b

Anhydrous THF was added dropwise to Intermediate 886a (1.0 eq.), and then cooled to about −78° C. under a nitrogen atmosphere. n-BuLi (1.1 eq.) was slowly added dropwise to the cooled solution, and then stirred at about −78° C. for about 1 hour. 9H-thioxanthen-9-one (1.1 eq.) was slowly added dropwise to this solution, and then stirred at room temperature for about 3 hours. After cooling, followed by washing with ethyl acetate and water three times, the resulting organic layer was dried over MgSO$_4$, and then dried under reduced pressure. Intermediate 886b was obtained by column chromatography. (yield: 82%).

8-3. Synthesis of Intermediate M4

Intermediate 886b (1.0 eq.) was dissolved in 9:1 volume ratio of acetic acid:hydrochloric acid, and then stirred at about 80° C. for about 2 hours under a nitrogen atmosphere. After cooling, followed by washing with ethyl acetate and water 3 times, the resulting organic layer was dried over MgSO$_4$, and then dried under reduced pressure. Intermediate M4 was obtained by column chromatography. (yield: 78%).

8-4. Synthesis of Compound 886

Intermediate M4 (1.0 eq.), Intermediate 12a (1.0 eq.), tris(dibenzylideneacetone)dipalladium(0) (0.05 eq.), tri-tert-butylphosphine (0.10 eq.), and sodium tert-butoxide (2.0 eq.) were dissolved in toluene, and then stirred at about 90° C. for about 2 hours under a nitrogen atmosphere. After cooling, followed by washing with ethyl acetate and water 3 times, the resulting organic layer was dried over MgSO$_4$, and then dried under reduced pressure. Compound 886 was obtained by column chromatography. (yield: 75%). By FAB-MS measurement, mass number m/z=780.26 was observed as the molecular ion peak, and Compound 886 was identified.

Synthesis of Compound 1014

The amine Compound 1014 according to one or more embodiments may be synthesized by, for example, the tasks of the Scheme 9.

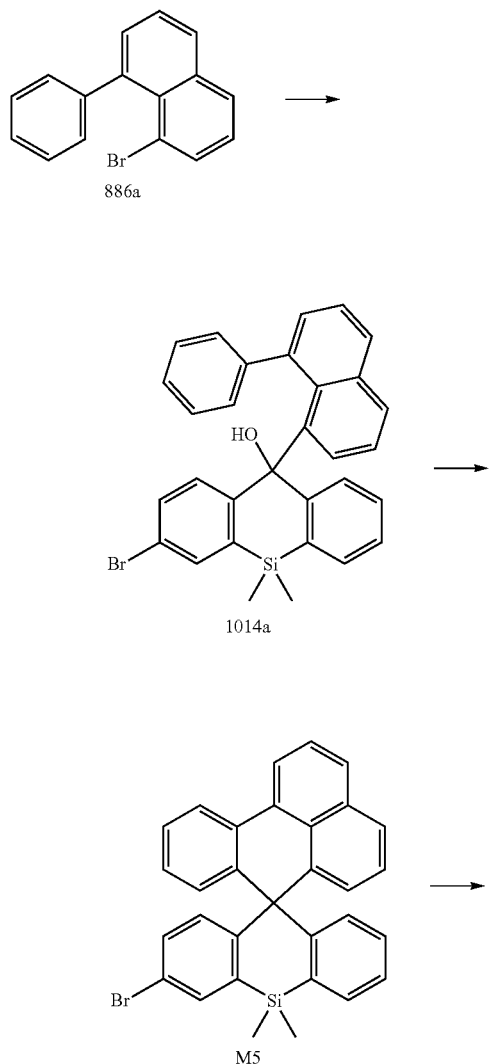

-continued

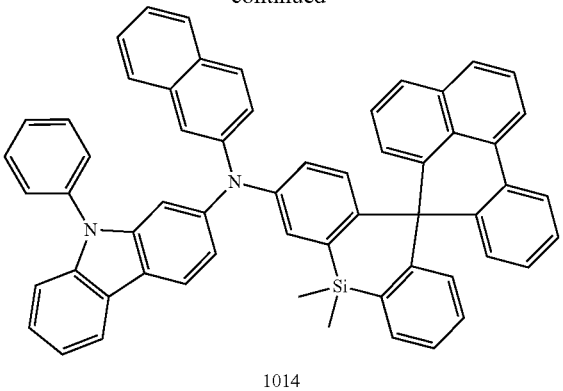

1014

9-1. Synthesis of Intermediate 1014a

Anhydrous THF was added dropwise to Intermediate 886a (1.0 eq.), and then cooled to about −78° C. under a nitrogen atmosphere. n-BuLi (1.1 eq.) was slowly added dropwise to the cooled solution, and then stirred at about −78° C. for about 1 hour. 3-bromo-5,5-dimethyldibenzo[b,e]silin-10(5H)-one (1.1 eq.) was slowly added dropwise to this solution, and then stirred at room temperature for about 3 hours. After cooling, followed by washing with ethyl acetate and water three times, the resulting organic layer was dried over MgSO$_4$, and then dried under reduced pressure. Intermediate 1014a was obtained by column chromatography. (yield: 82%).

9-2. Synthesis of Intermediate M5

Intermediate 1014a (1.0 eq.) was dissolved in 9:1 volume ratio of acetic acid:hydrochloric acid, and then stirred at about 80° C. for about 2 hours under a nitrogen atmosphere. After cooling, followed by washing with ethyl acetate and water 3 times, the resulting organic layer was dried over MgSO$_4$, and then dried under reduced pressure. Intermediate M5 was obtained by column chromatography. (yield: 78%).

9-3. Synthesis of Compound 1014

Intermediate M5 (1.0 eq.), Intermediate 12a (1.0 eq.), tris(dibenzylideneacetone)dipalladium(0) (0.05 eq.), tri-tert-butylphosphine (0.10 eq.), and sodium tert-butoxide (2.0 eq.) were dissolved in toluene, and then stirred at about 90° C. for about 2 hours under a nitrogen atmosphere. After cooling, followed by washing with ethyl acetate and water 3 times, the resulting organic layer was dried over MgSO$_4$, and then dried under reduced pressure. Compound 1014 was obtained by column chromatography. (yield: 75%). By FAB-MS measurement, mass number m/z=806.31 was observed as the molecular ion peak, and Compound 1014 was identified.

2. Manufacture and Evaluation of Light-Emitting Diode (Manufacture of Light-Emitting Diode)

Light-emitting diodes according to one or more embodiments including the amine compound according to one or more embodiments in the hole transport layer were manufactured by a method below. The light-emitting diode of Examples 1 to 9 were manufactured using the amine compound of Compound 1, Compound 5, Compound 9, Compound 12, Compound 136, Compound 222, Compound 390, Compound 886, and Compound 1014 described above, respectively, as materials for a hole transport layer.

Example Compounds
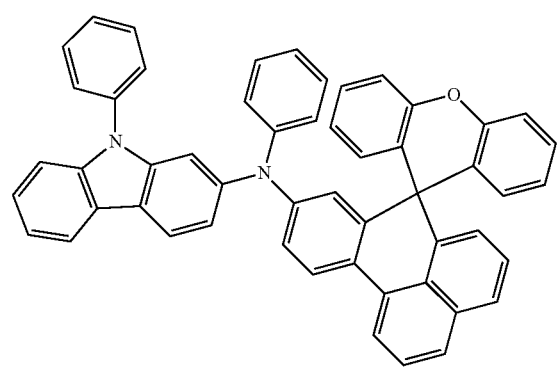
1
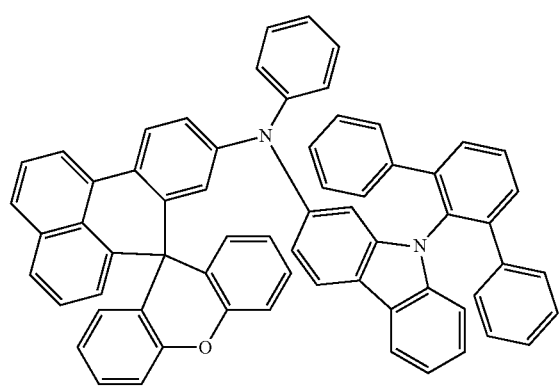
5
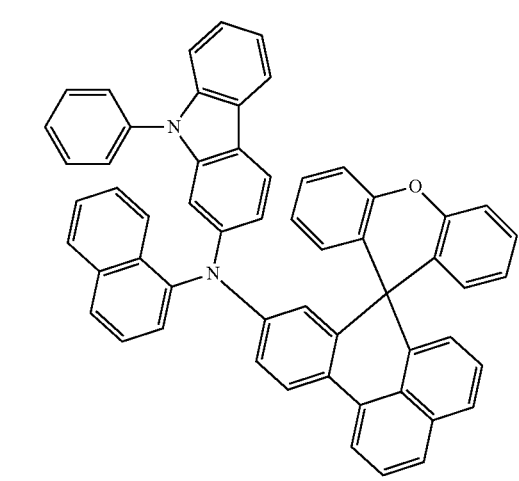
9
-continued
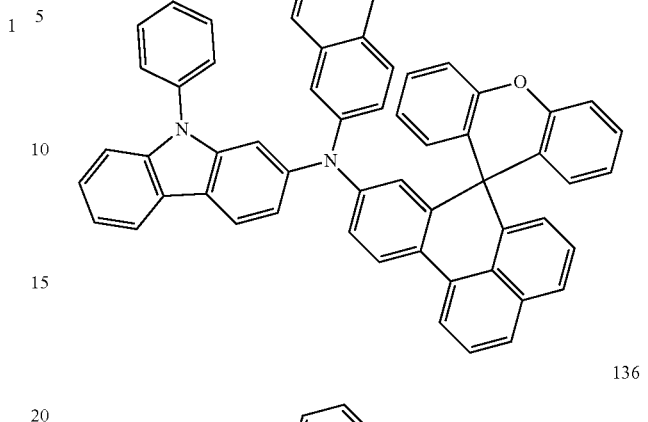
12
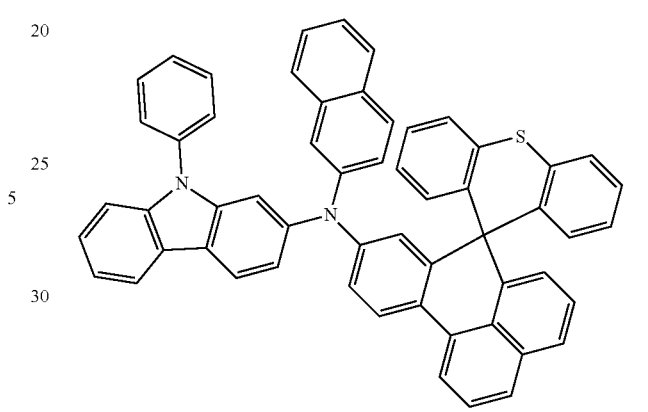
136
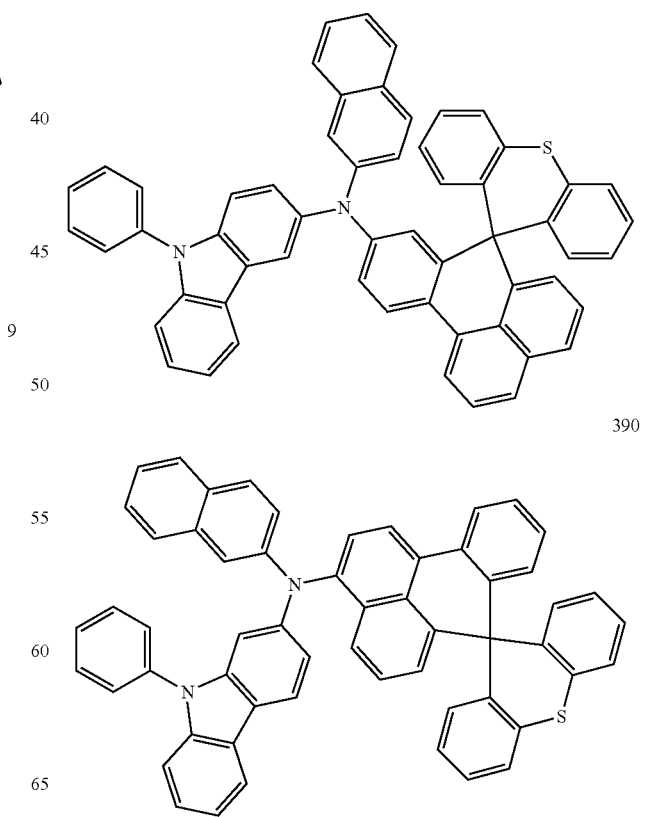
222
390

-continued
886
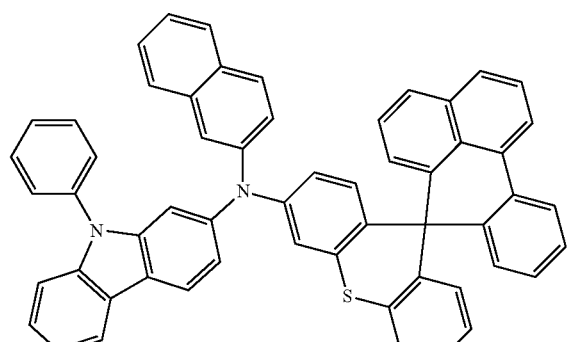
1014
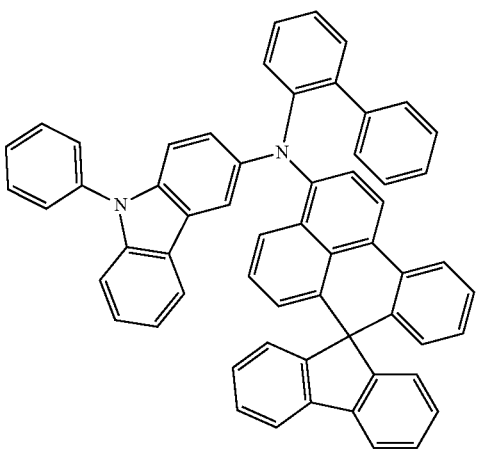
In Comparative Examples 1 to 5, light-emitting diodes were manufactured using Comparative Compounds C1 to C5 below respectively as materials for a hole transport layer.
(Comparative Compounds)
C1
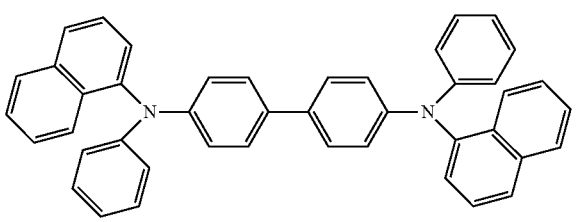
C2
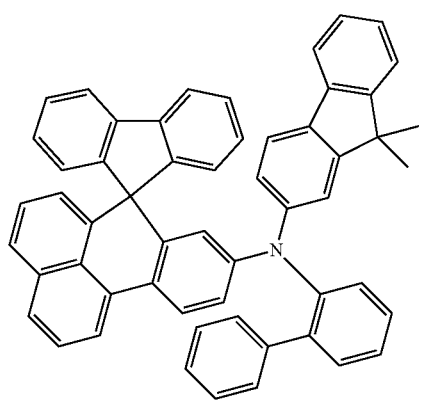
-continued
C3
C4
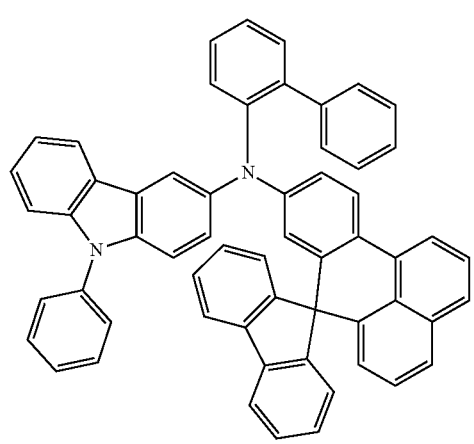
C5
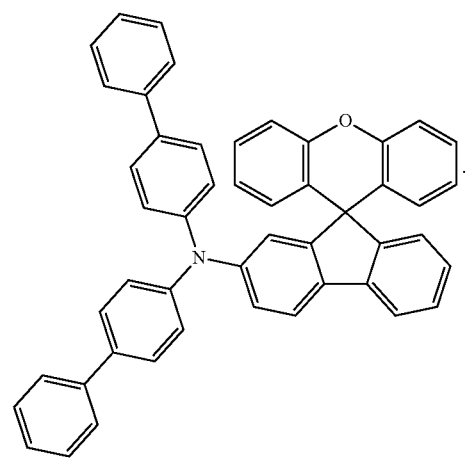

(Other Compounds Used in Device Manufacturing)

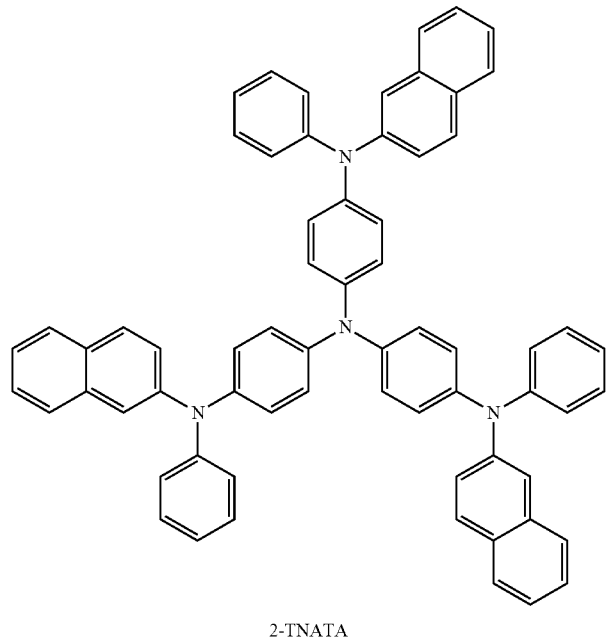

2-TNATA

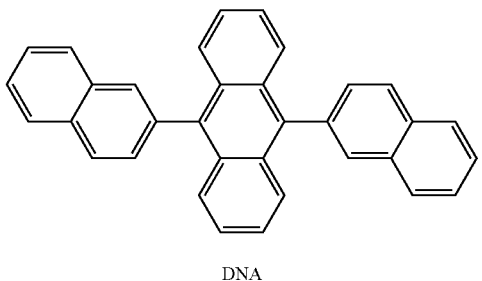

DNA

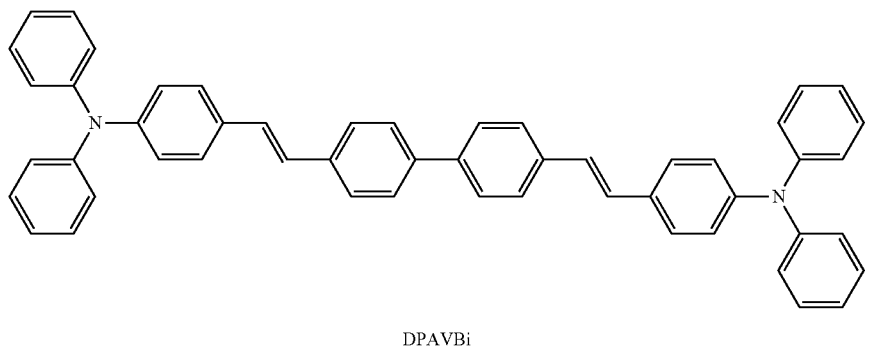

DPAVBi

An ITO glass substrate of about 15 Ω/cm² (about 1,200 Å thickness) made by Corning Co. was cut to a size of 50 mm×50 mm×0.7 mm, and cleansed by ultrasonic waves using isopropyl alcohol and pure water for about five minutes, respectively. After cleansing by ultrasonic waves, the glass substrate was irradiated with ultraviolet rays for about 30 minutes and treated with ozone. Then, 2-TNATA was deposited to form a 600 Å-thick hole injection layer. Next, a corresponding one of the Example compounds or Comparative Compounds was deposited to form a 300 Å-thick hole transport layer.

Then, DNA and DPAVBi as a blue, fluorescent dopant were co-deposited in a weight ratio of about 98:2 to form a 300 Å-thick emission layer. Next, Alq₃ was deposited to a thickness of about 300 Å to form an electron transport layer, and LiF was deposited to a thickness of about 10 Å to form an electron injection layer.

Next, Al was provided in a thickness of about 3000 Å to form a second electrode.

In Examples, a hole injection layer, a hole transport layer, an emission layer, an electron transport layer, an electron injection layer, and a second electrode were formed using a vacuum deposition device.

(Evaluation of Characteristics of Light-Emitting Diode)

The evaluation results of the light-emitting diodes for Examples 1 to 9 and Comparative Examples 1 to 5 are shown in Table 1. The driving voltage, luminance, luminous efficiency, and half-life of the light-emitting elements manufactured are compared and shown in Table 1. The luminous efficiency represents an efficiency value at current density of about 50 mA/cm², and half-life represents a luminance half-life at about 100 mA/cm² in the characteristics evaluation results for Examples and Comparative Examples shown in Table 1. Meanwhile, it was confirmed that all of the manufactured devices exhibited a blue light-emitting color.

TABLE 1

| Device Fabrication example | Hole transport layer material | Driving voltage (V) | Luminance (cd/m$^2$) | Luminous efficiency (cd/A) | Half-life (hr@100 mA/cm$^2$) |
|---|---|---|---|---|---|
| Example 1 | Example Compound 1 | 4.20 | 3630 | 7.00 | 290 |
| Example 2 | Example compound 5 | 4.25 | 3620 | 6.90 | 350 |
| Example 3 | Example compound 9 | 4.12 | 3650 | 7.10 | 340 |
| Example 4 | Example Compound 12 | 4.10 | 3655 | 7.40 | 350 |
| Example 5 | Example Compound 136 | 4.15 | 3680 | 7.50 | 350 |
| Example 6 | Example Compound 222 | 4.20 | 3755 | 7.51 | 375 |
| Example 7 | Example Compound 390 | 4.24 | 3740 | 7.20 | 350 |
| Example 8 | Example Compound 886 | 4.45 | 3350 | 6.90 | 290 |
| Example 9 | Example Compound 1014 | 4.35 | 3550 | 6.95 | 295 |
| Comparative Example 1 | Comparative Compound C1 | 6.01 | 2625 | 5.29 | 258 |
| Comparative Example 2 | Comparative Compound C2 | 5.22 | 2854 | 6.12 | 234 |
| Comparative Example 3 | Comparative Compound C3 | 4.95 | 3050 | 6.20 | 220 |
| Comparative Example 4 | Comparative Compound C4 | 4.80 | 3205 | 6.90 | 220 |
| Comparative Example 5 | Comparative Compound C5 | 5.20 | 3050 | 6.95 | 225 |

Referring to the results in Table 1, it could be confirmed that the light-emitting diodes of Examples using the amine compound according to one or more embodiments of the present disclosure as materials for a hole transport layer exhibit a lower voltage, higher luminance properties, excellent device efficiency, and improved device lifetime properties. For example, referring to Table 1, it may be seen that Examples 1 to 9 exhibit a lower voltage, a higher luminance, a longer life, and a higher efficiency properties than Comparative Examples 1 to 5. For luminous efficiency, the average luminous efficiency value of the light-emitting diodes of Examples 1 to 9 is higher than the average luminous efficiency value of the light-emitting diodes of Comparative Examples 1 to 5.

It may be seen that compared to Comparative Compound C1, Example Compounds exhibited high durability by having a molecular structure in which the amine derivative is bonded to the condensed ring having a spiro structure containing a heteroatom, and thus lifetime properties were particularly improved, and Example Compounds exhibited improved luminance properties and high luminous efficiency properties due to the stable molecular structure.

In one or more embodiments, it may be seen that Comparative Example compound C2 to C4 have a molecular structure in which the amine derivative is bonded to the condensed ring having a spiro structure similar to the Example compounds, but Example Compounds have a heteroatom in the spiro structure, and thus exhibit improved lifetime properties and high luminous efficiency properties compared to Comparative Compounds C2 to C4.

As described above, Examples 1 to 9 exhibit results in which luminous efficiency and luminous lifetime are improved at the same time (e.g., concurrently) compared to Comparative Examples 1 to 5. For example, the amine compound according to embodiments having a structure in which the amine derivative and the spiro-type condensed ring substituted with at least one heteroatom are bonded may be used, and thus device efficiency and device lifetime of the light-emitting diode according to one or more embodiments may be improved at the same time.

The amine compound according to one or more embodiments may have a molecular structure in which the amine group is bonded to the condensed ring having a spiro structure containing a heteroatom, thereby contributing to low driving voltage, long lifetime, and high efficiency properties of the light-emitting diode. In one or more embodiments, the light-emitting diode according to one or more embodiments may include the amine compound according to one or more embodiments, thereby exhibiting long lifetime and high efficiency properties at the same time.

The light-emitting diode according to one or more embodiments may include the amine compound according to one or more embodiments in a hole transport region, thereby exhibiting high efficiency and long lifetime properties.

The amine compound according to one or more embodiments may improve luminous efficiency and device lifetime of the light-emitting diode.

Although the embodiments of the present disclosure have been described herein, it is understood that various changes and modifications can be made by those skilled in the art within the spirit and scope of the present disclosure defined by the following claims or the equivalents.

Therefore, the technical scope of the present disclosure should not be limited to the content described in the detailed description of the specification, but should be determined by the claims and their equivalents.

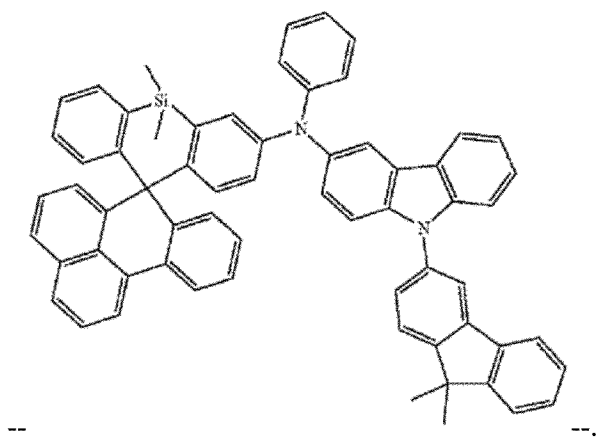

What is claimed is:
1. A light-emitting diode comprising:
a first electrode;
a second electrode on the first electrode; and
at least one functional layer between the first electrode and the second electrode, the at least one functional layer comprising an amine compound represented by Formula 1:

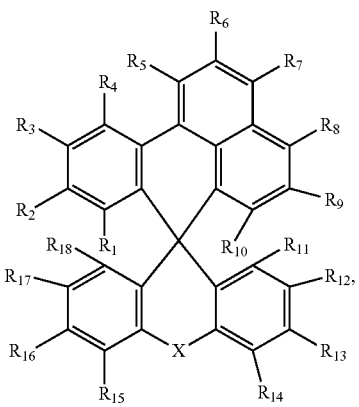

Formula 1 wherein, in Formula 1,

X is O, S, SiR$_a$R$_b$, or NR$_c$,

R$_1$ to R$_{18}$, R$_a$, R$_b$, and R$_c$ are each independently a hydrogen atom, a deuterium atom, a halogen atom, a substituted or unsubstituted silyl group, a substituted or unsubstituted amine group, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms, and/or combined with an adjacent group to form a ring, and at least one selected from among R$_1$ to R$_{18}$ is represented by Formula 2:

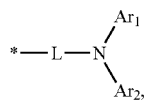

Formula 2 wherein, in Formula 2,

L is a direct linkage, a substituted or unsubstituted ring-forming arylene group having 6 to 30 carbon atoms, or a substituted or unsubstituted ring-forming heteroarylene group having 2 to 30 carbon atoms, and Ar$_1$ and Ar$_2$ are each independently a substituted or unsubstituted ring-forming aryl group having 6 to 30 carbon atoms, or a substituted or unsubstituted ring-forming heteroaryl group having 2 to 30 carbon atoms, and wherein when X is O, S, or NR$_c$, then Ar$_1$ and Ar$_2$ are each independently a substituted or unsubstituted naphthyl group, a substituted or unsubstituted fluorenyl group, a substituted or unsubstituted carbazolyl group, a substituted or unsubstituted dibenzofuranyl group, or a substituted or unsubstituted dibenzothiophenyl group, provided that Ar$_1$ and Ar$_2$ are not a substituted or unsubstituted fluorenyl group at the same time.

2. The light-emitting diode of claim 1, wherein the at least one functional layer comprises an emission layer, a hole transport region between the first electrode and the emission layer, and an electron transport region between the emission layer and the second electrode, and the hole transport region comprises the amine compound.

3. The light-emitting diode of claim 2, wherein the hole transport region comprises a hole injection layer on the first electrode and a hole transport layer on the hole injection layer, and the hole transport layer comprises the amine compound.

4. The light-emitting diode of claim 1, wherein the amine compound represented by Formula 1 is represented by any one selected from among Formula 1A to Formula 1D:

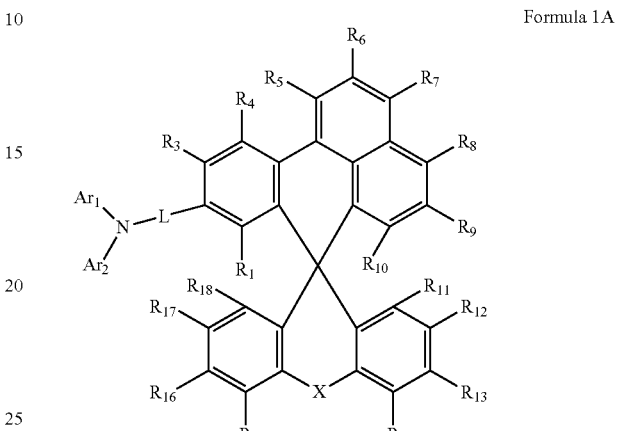

Formula 1A

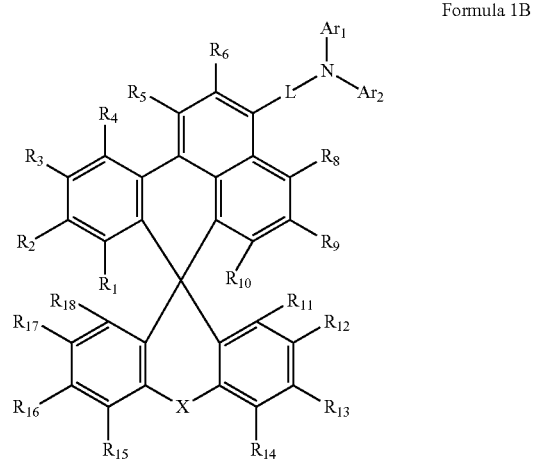

Formula 1B

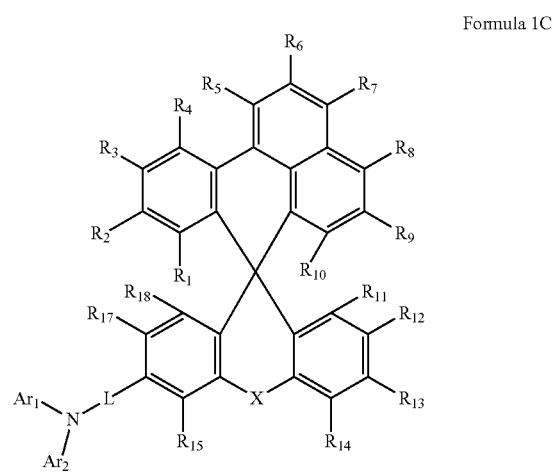

Formula 1C

-continued

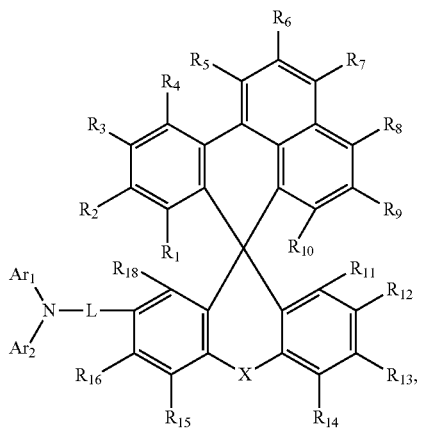

Formula 1D and
wherein, in Formula 1A to Formula 1D, X, $R_1$ to $R_{18}$, L, $Ar_1$, and $Ar_2$ are the same as defined in Formula 1 and Formula 2.

5. The light-emitting diode of claim 1, wherein a substituent represented by Formula 2 is represented by Formula 2A or Formula 2B:

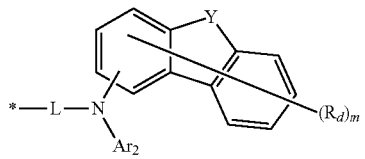

Formula 2A

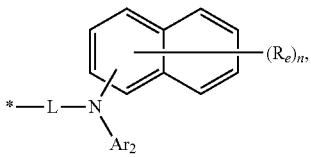

Formula 2B and
wherein, in Formula 2A and Formula 2B,
Y is O, S, $NAr_3$, or $CR_fR_g$,
$Ar_3$ is a substituted or unsubstituted ring-forming aryl group having 6 to 30 carbon atoms, or a substituted or unsubstituted ring-forming heteroaryl group having 2 to 30 carbon atoms,
$R_d$, $R_e$, $R_f$ and $R_g$ are each independently a hydrogen atom, a deuterium atom, a halogen atom, a substituted or unsubstituted silyl group, a substituted or unsubstituted amine group, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms, and/or combined with an adjacent group to form a ring,
"m" and "n" are each independently an integer of 0 to 7, and
L and $Ar_2$ are the same as defined in Formula 2.

6. The light-emitting diode of claim 1, wherein X is O, S, or $SiR_aR_b$.

7. The light-emitting diode of claim 1, wherein L is a direct linkage.

8. The light-emitting diode of claim 1, wherein $Ar_1$ and $Ar_2$ are different from each other.

9. The light-emitting diode of claim 1, wherein $R_a$, $R_b$, and $R_c$ are each independently a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms.

10. The light-emitting diode of claim 1, wherein the amine compound represented by Formula 1 is represented by any one selected from among the compounds in Compound Group 1:

[Compound Group 1]

8

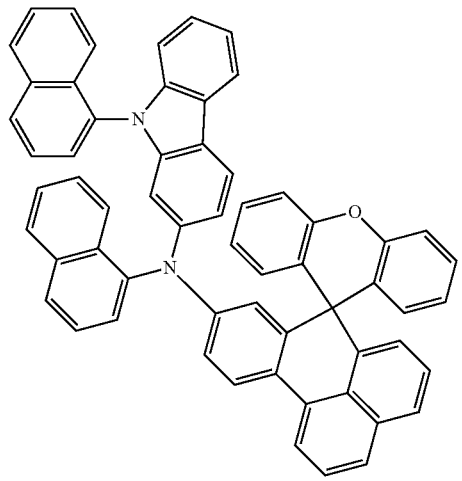

9

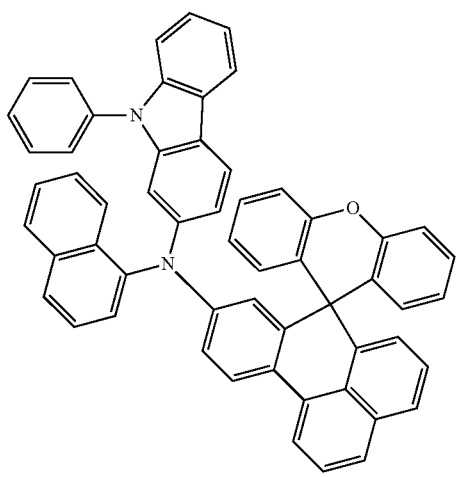

411
16
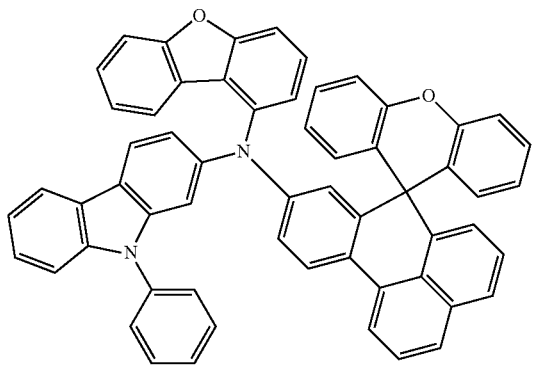
17
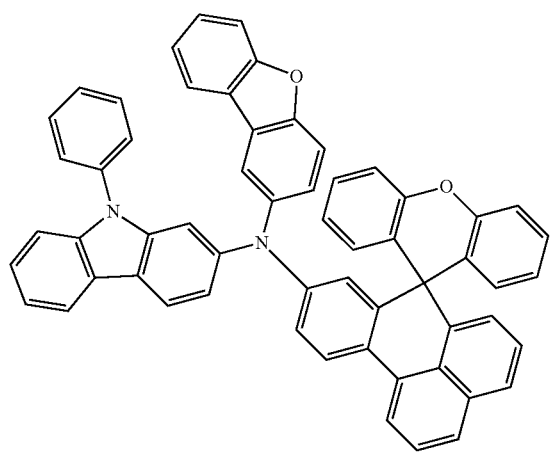
18
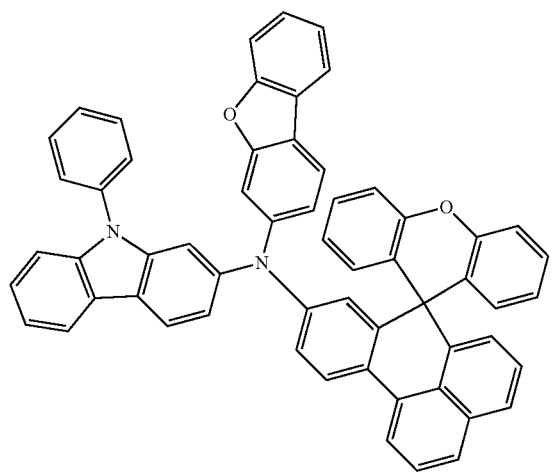
412
19
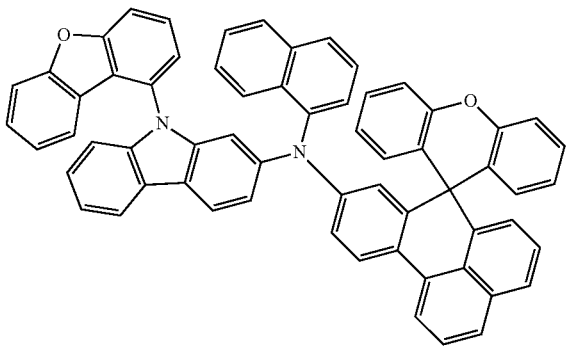
20
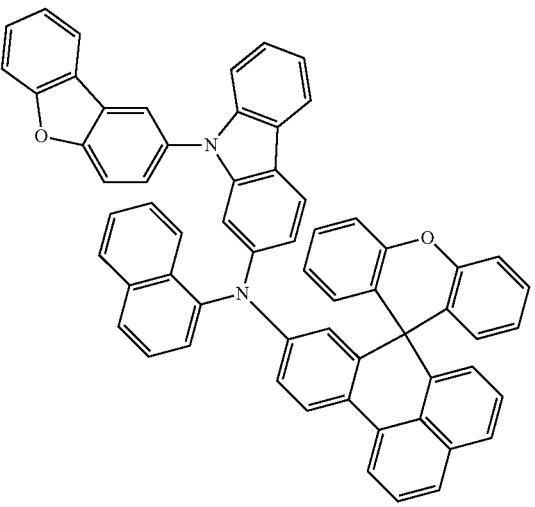
24
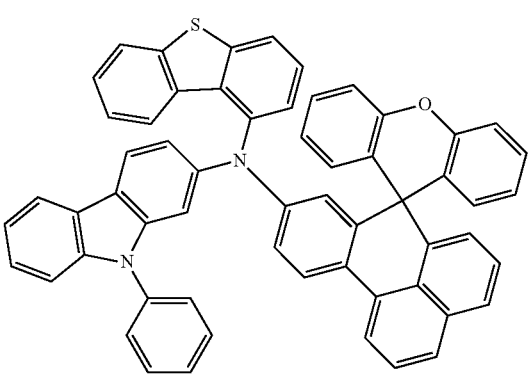

-continued
25
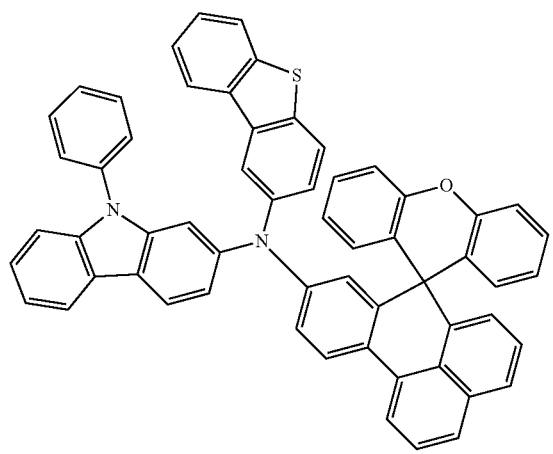
26
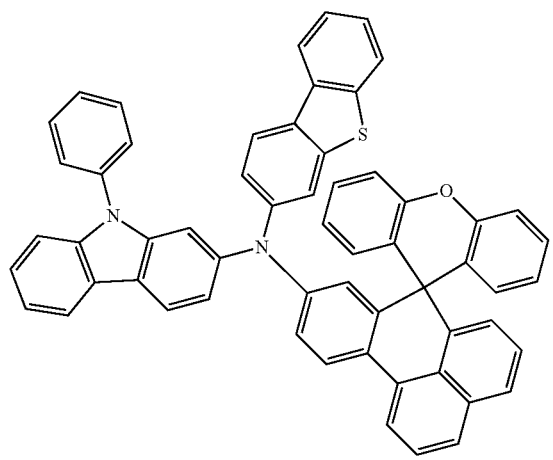
27
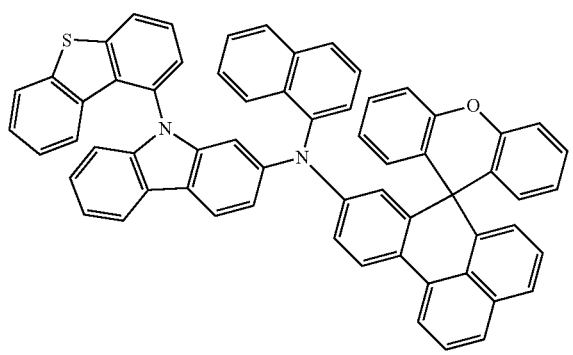
-continued
28
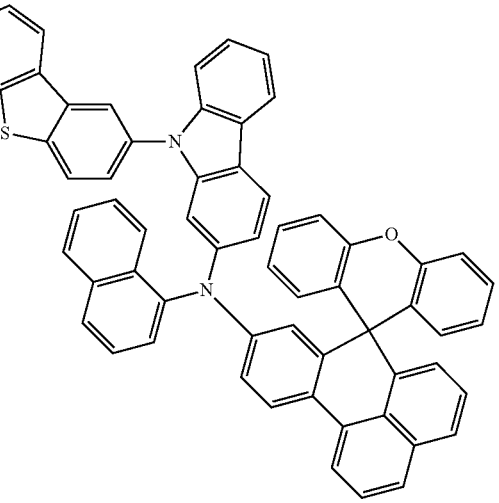
29
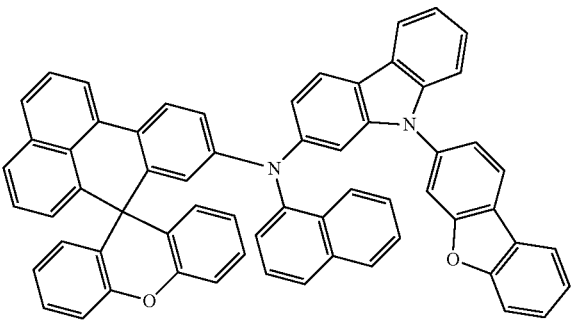
30
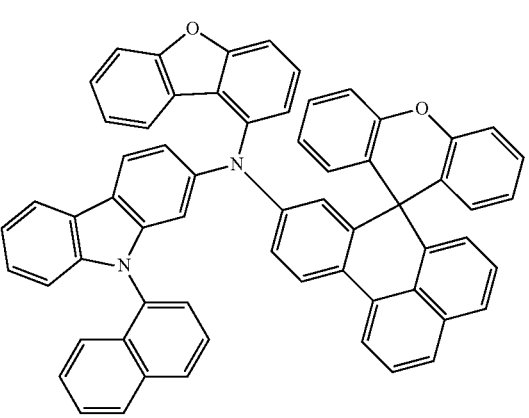

31
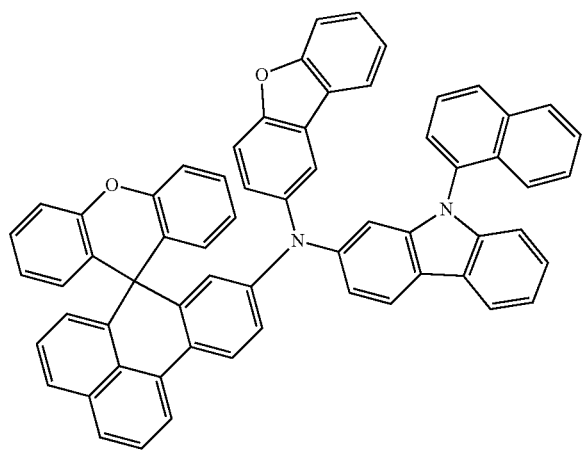
32
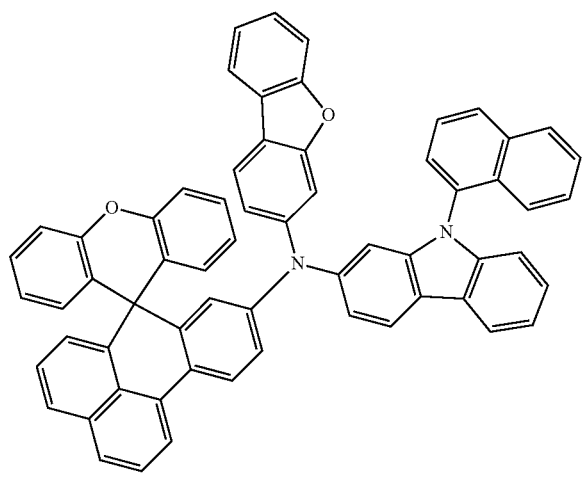
33
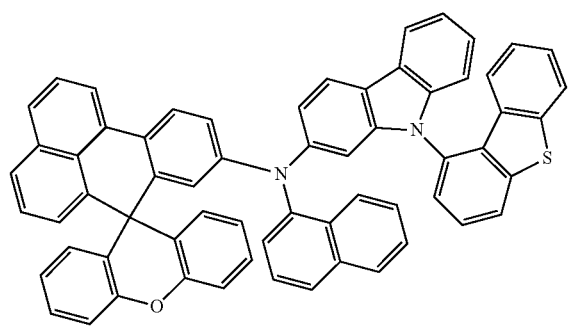
34
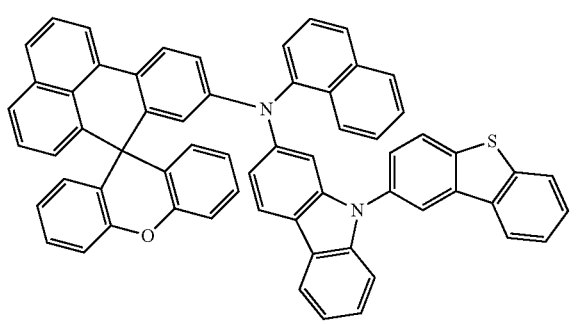
35
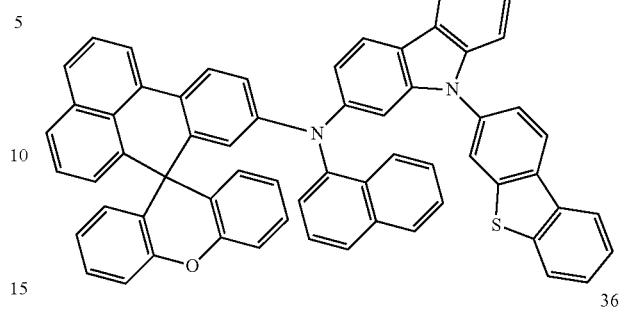
36
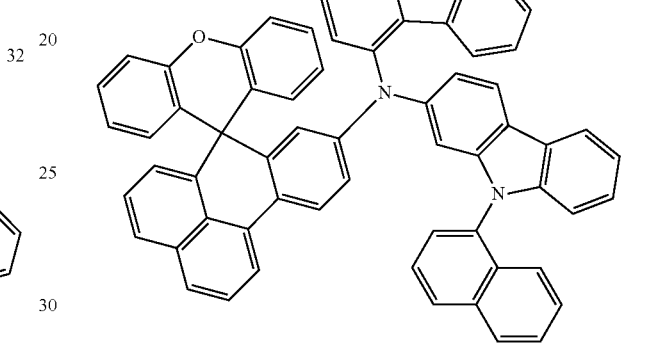
37
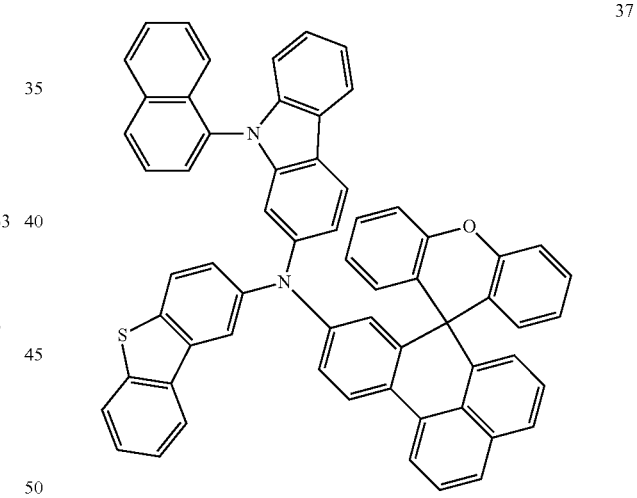
38
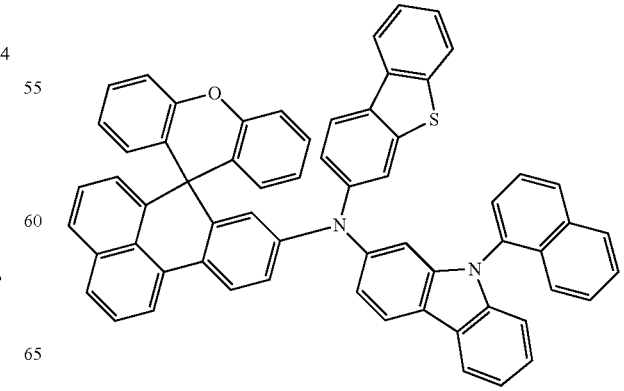

417
-continued
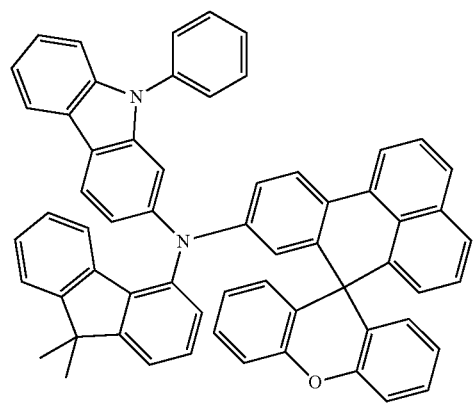
42
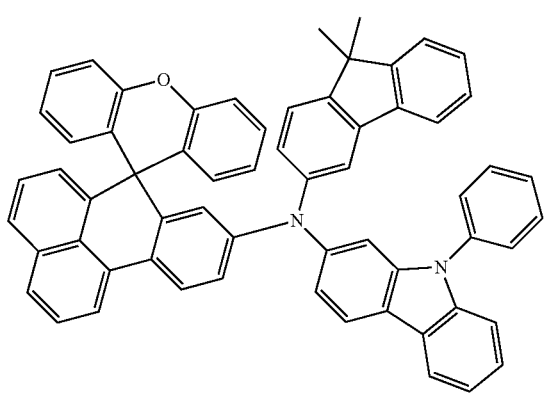
43

44
418
-continued

52

53
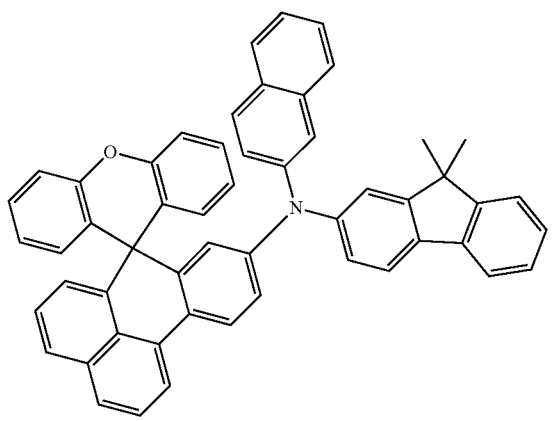
54
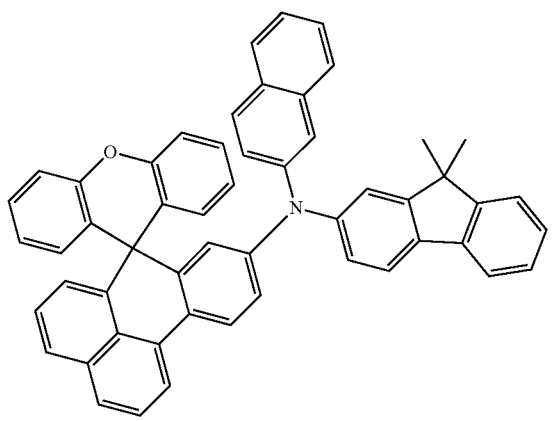
55

419
-continued
56
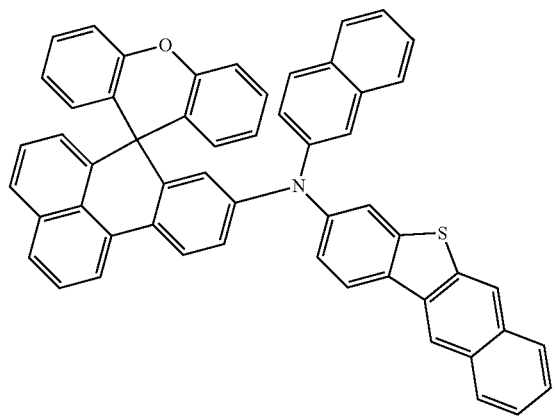
57
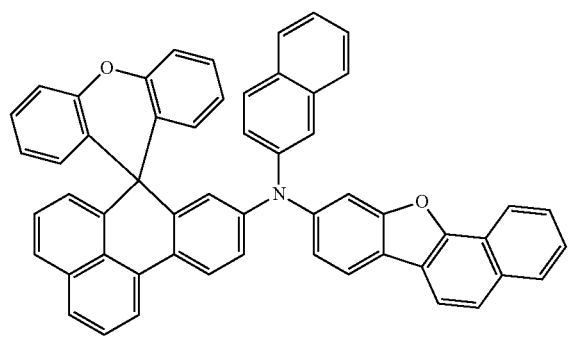
58
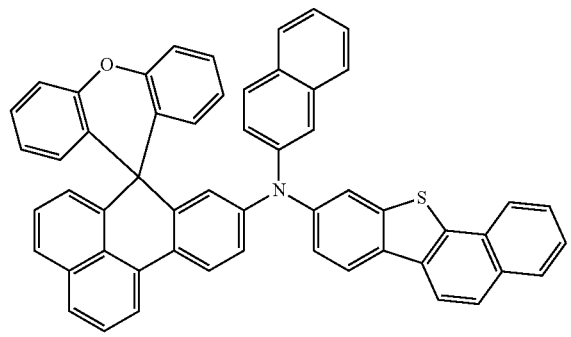
59
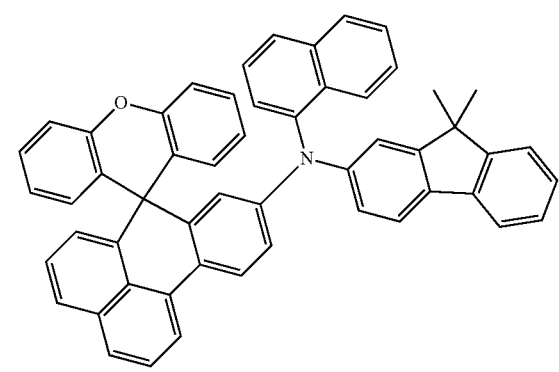
420
-continued
60
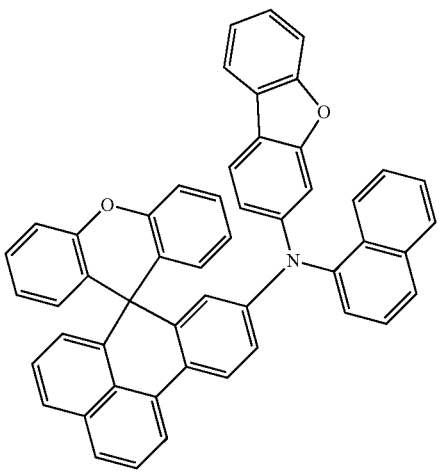
61
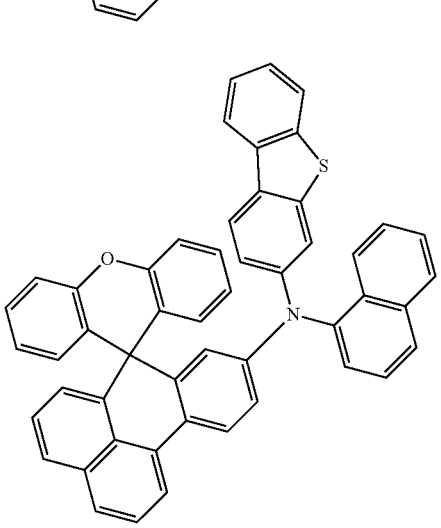
62
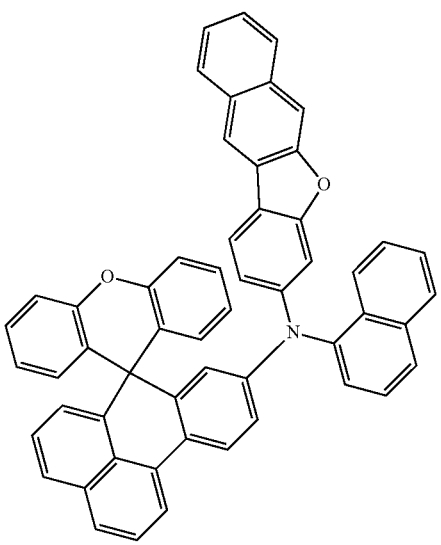

-continued
63
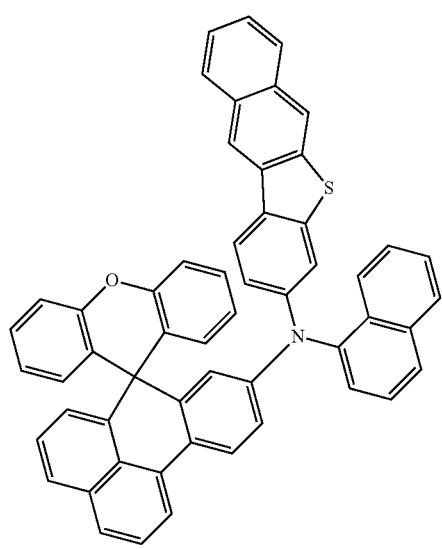
64
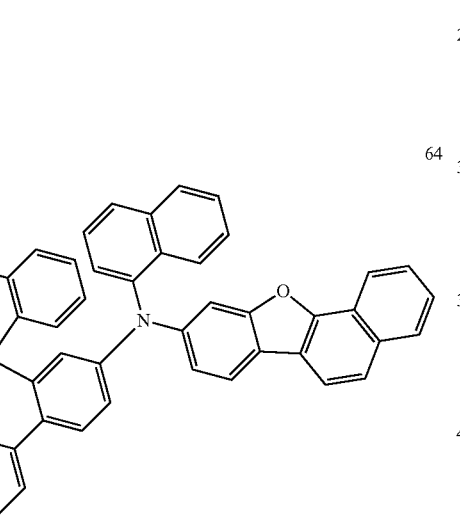
65
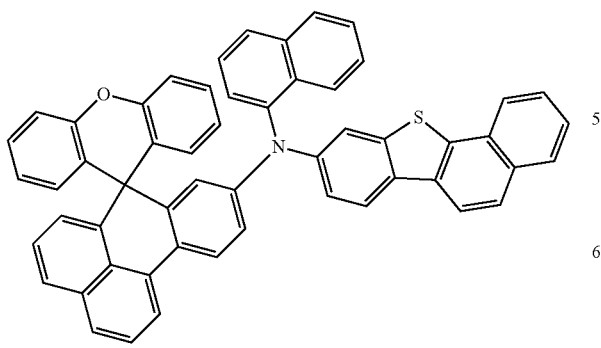
-continued
70
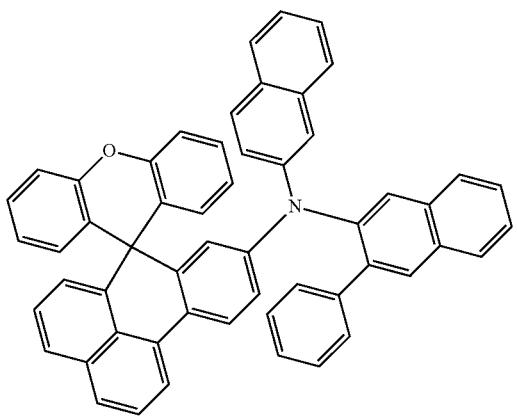
71
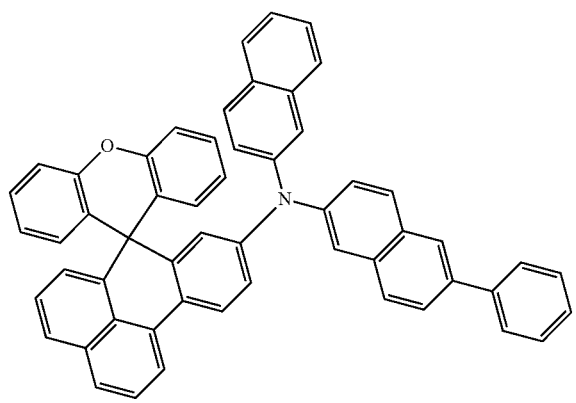
72
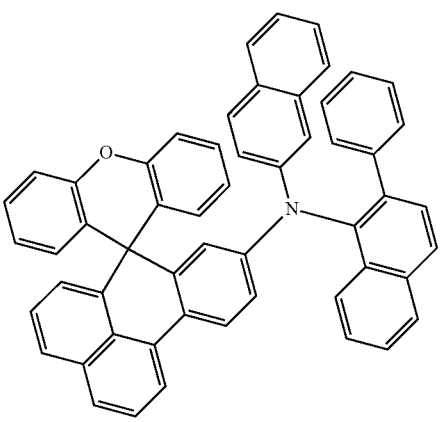

73
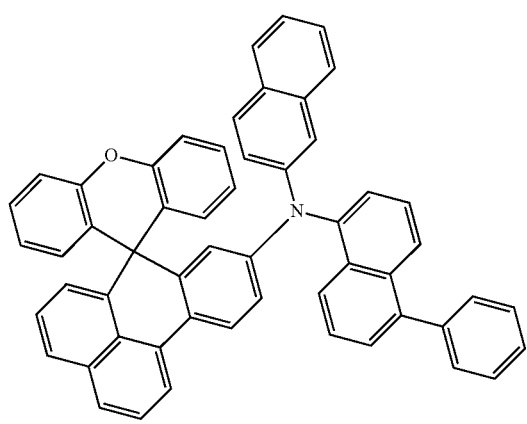
74
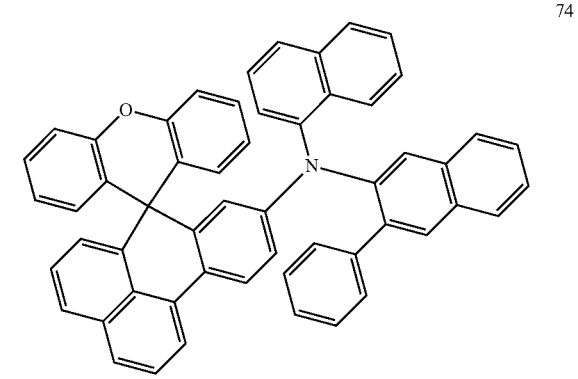
75
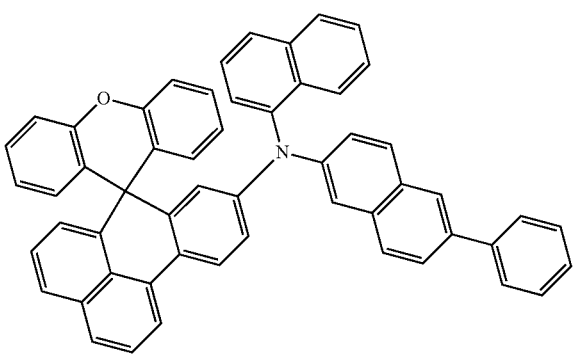
76
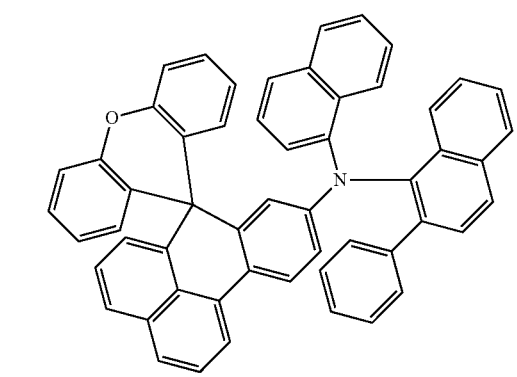
77
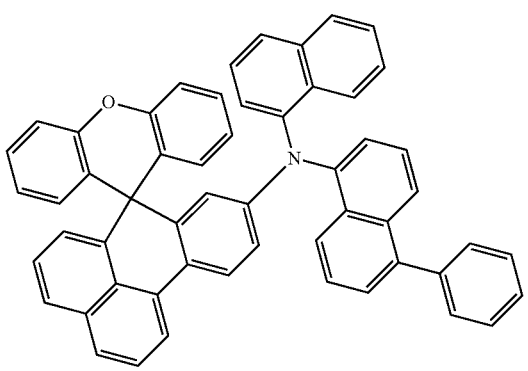
79
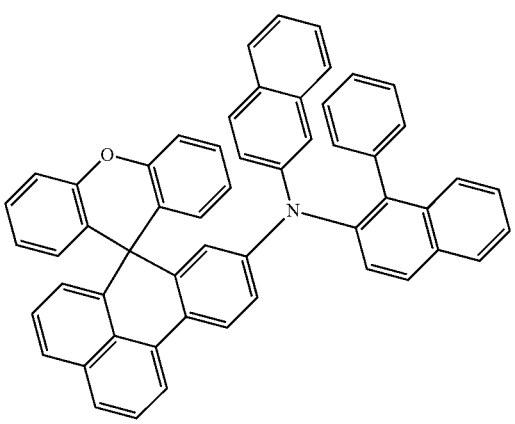
80
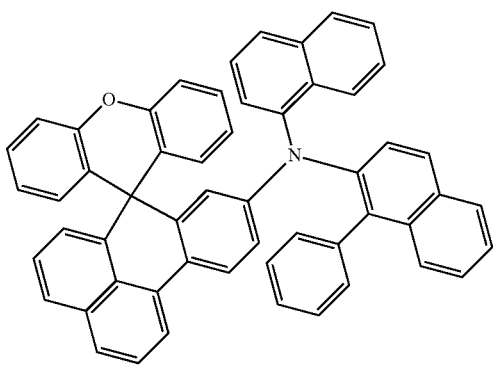

88
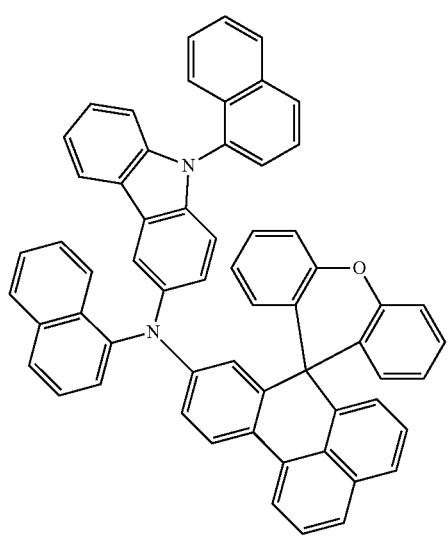
89
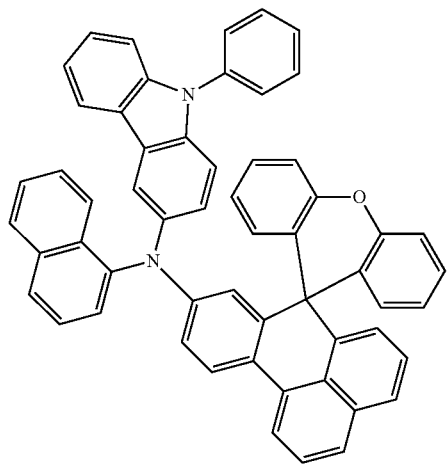
91
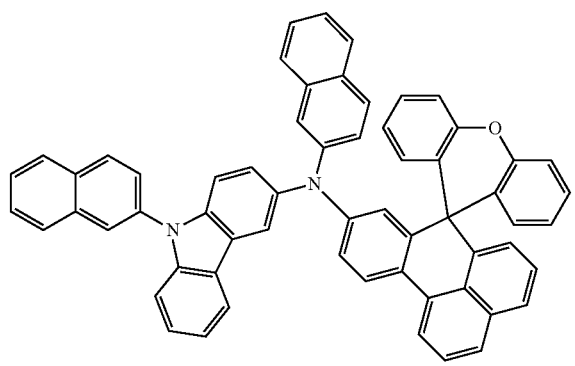
92
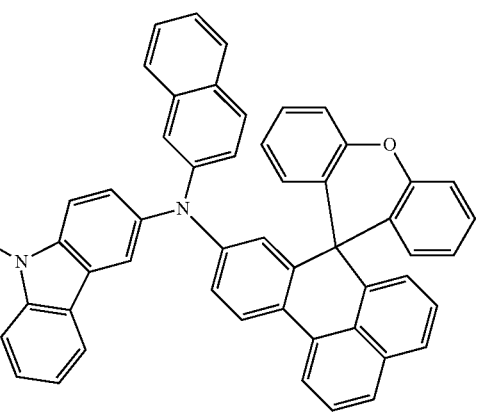
96
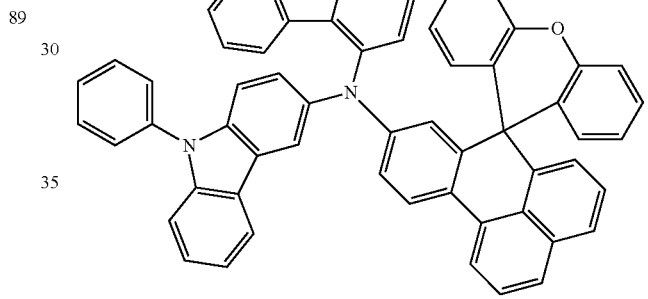
97
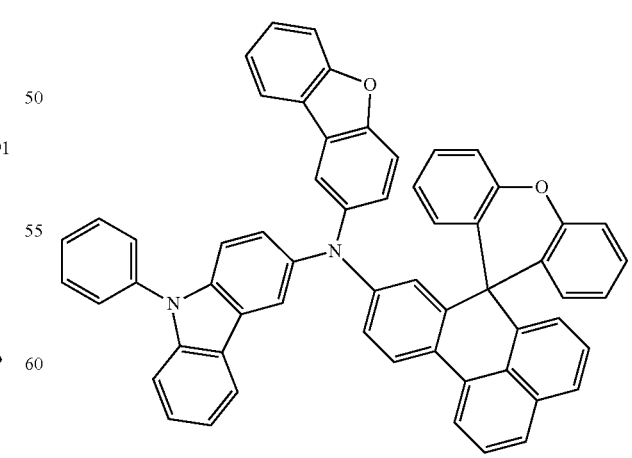

427
-continued
98
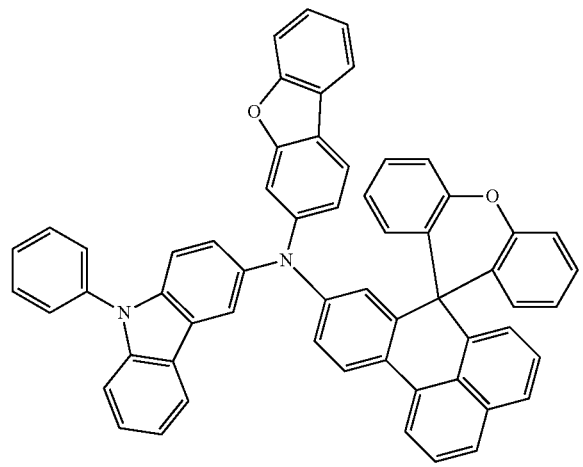
104
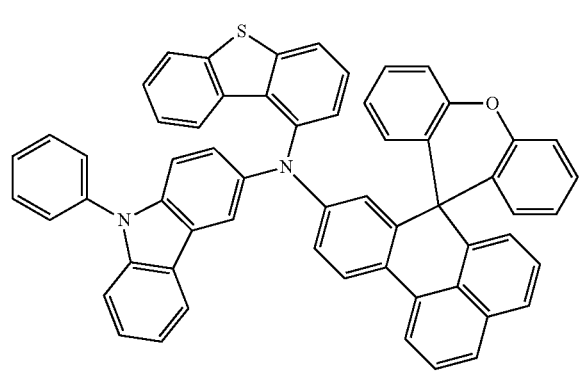
105
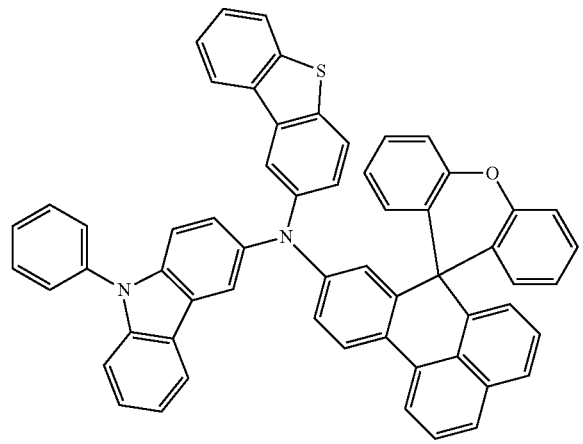
428
-continued
106
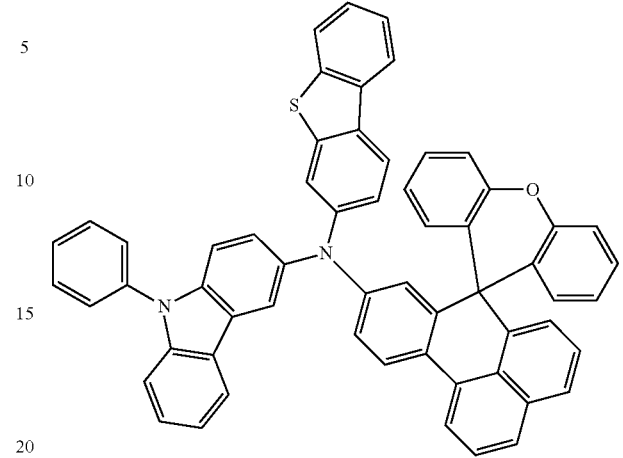
107
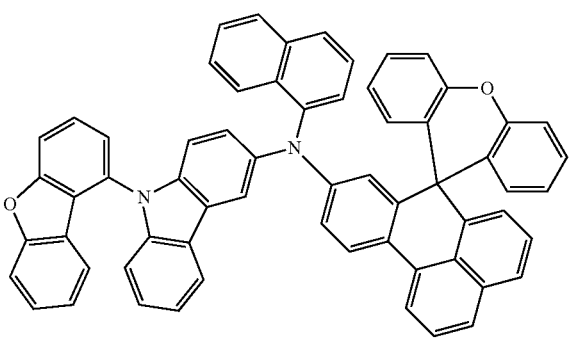
108
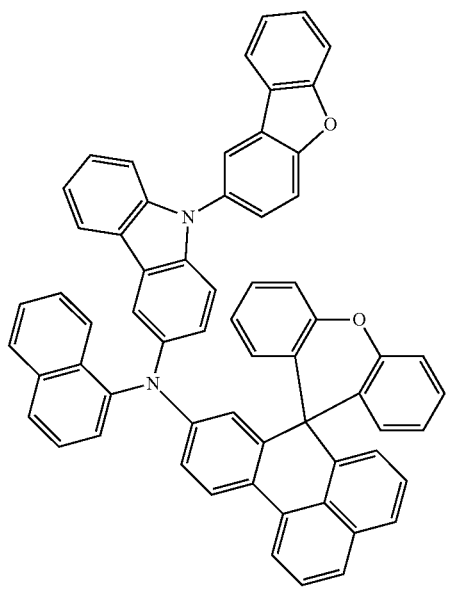

109
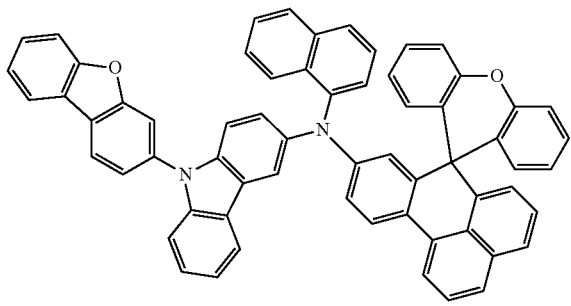
110
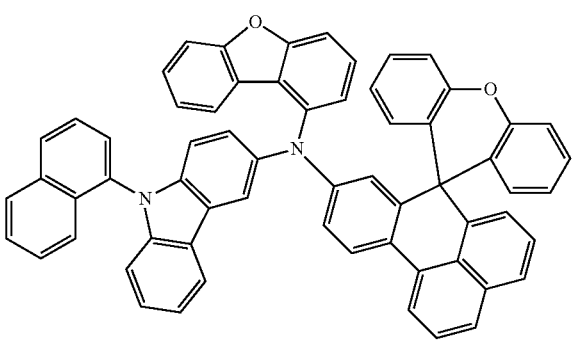
111
113
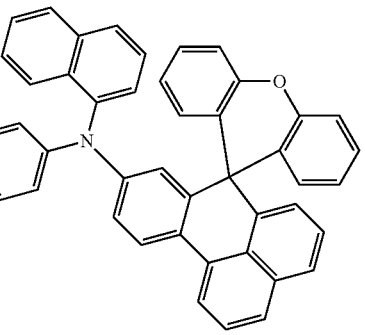
114
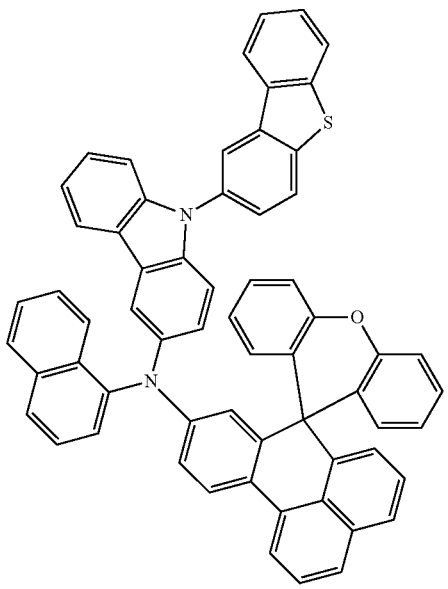
115
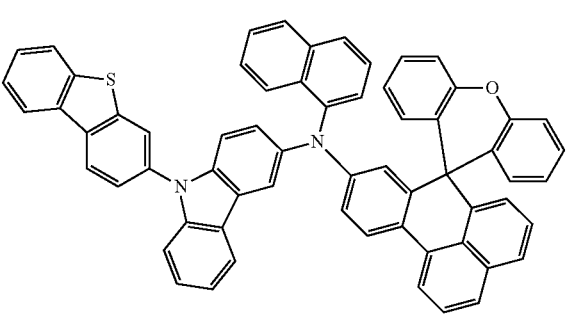
112
116
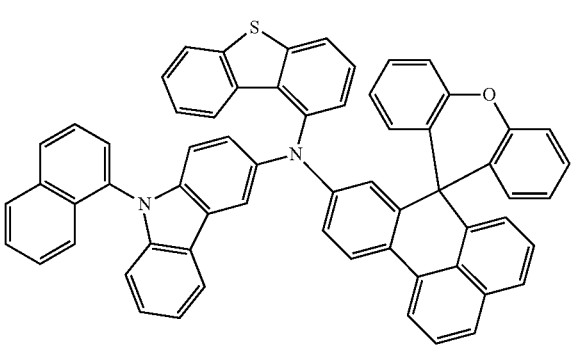

-continued
117
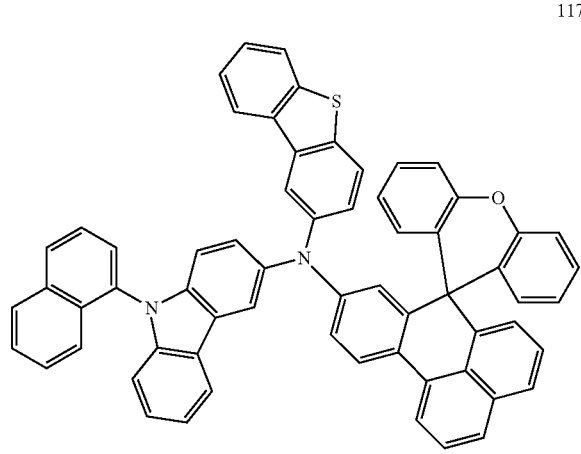
118
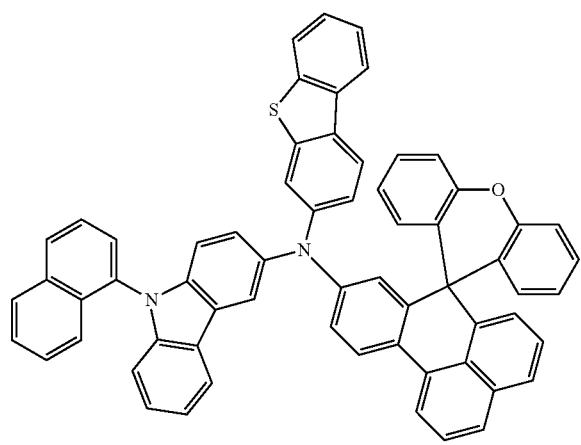
122
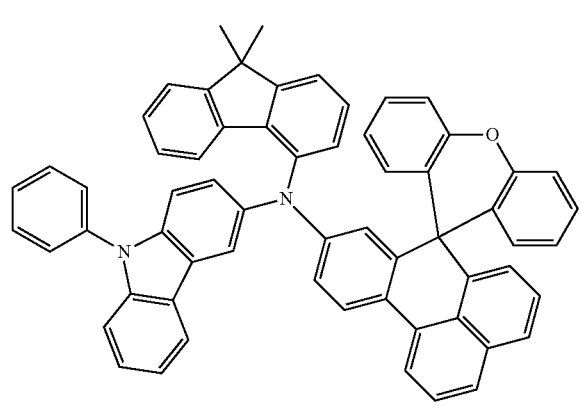
-continued
123
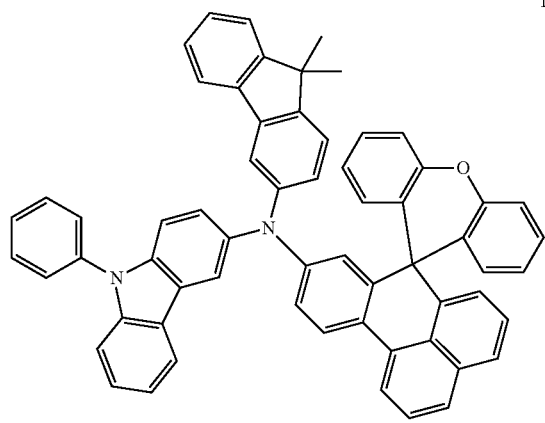
124
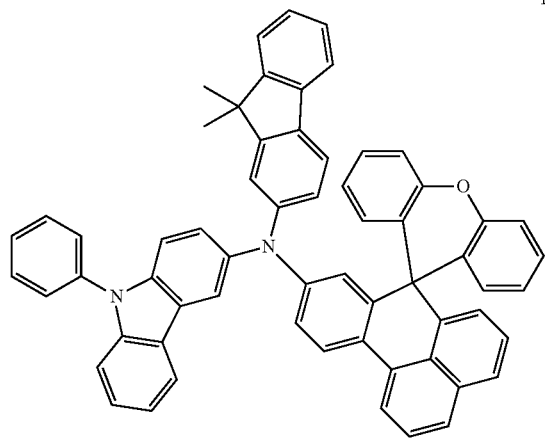
132
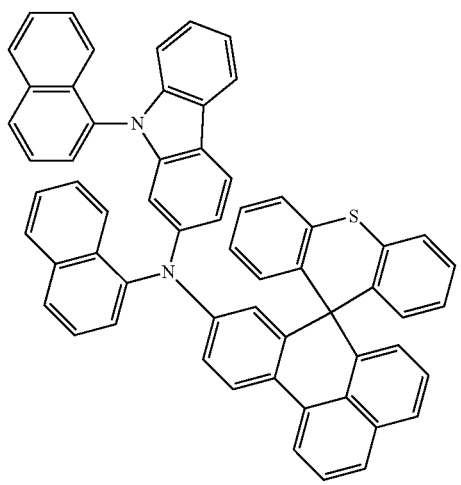

433
-continued
133
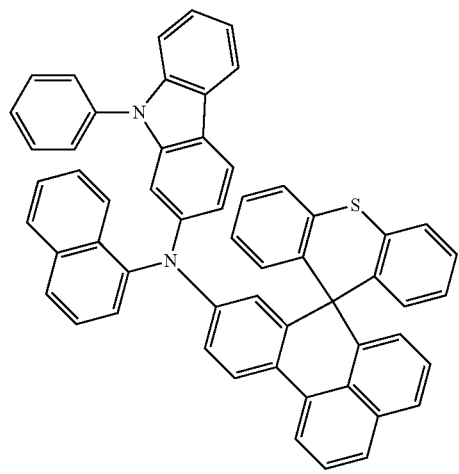
135
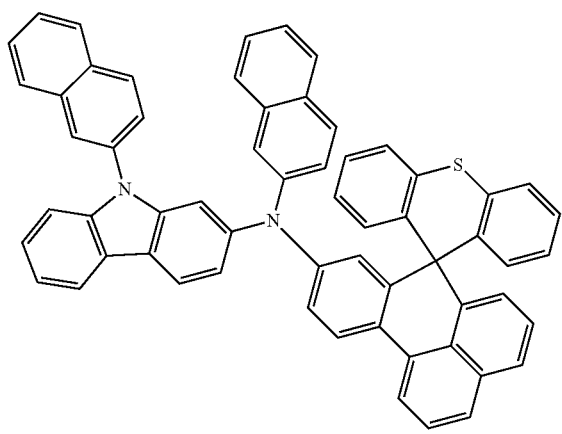
136
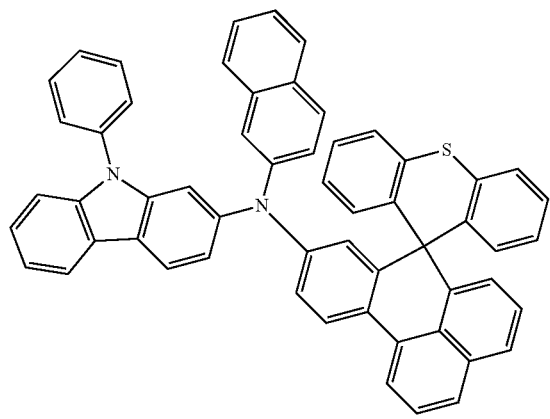
434
-continued
140
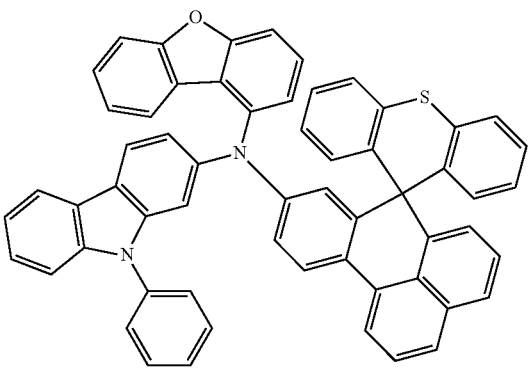
141
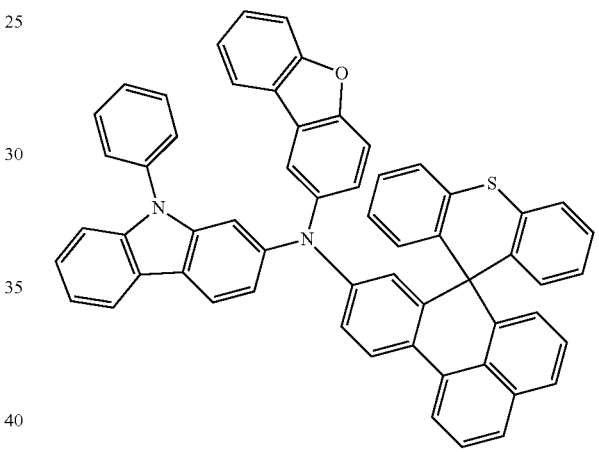
142
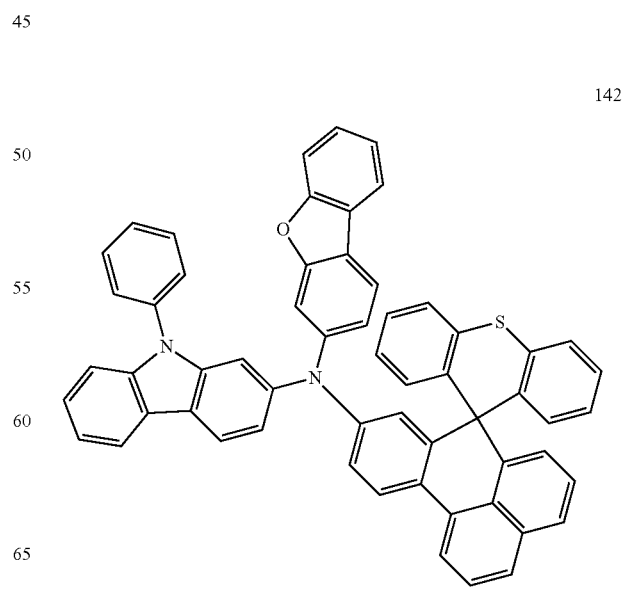

143
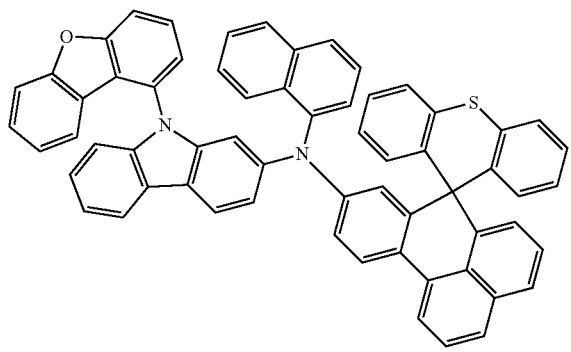
144
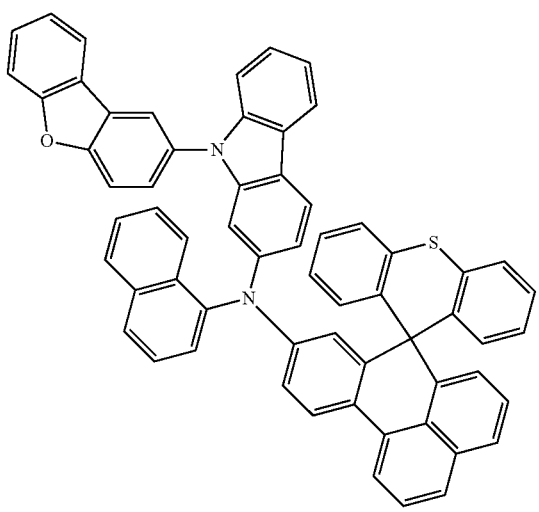
148
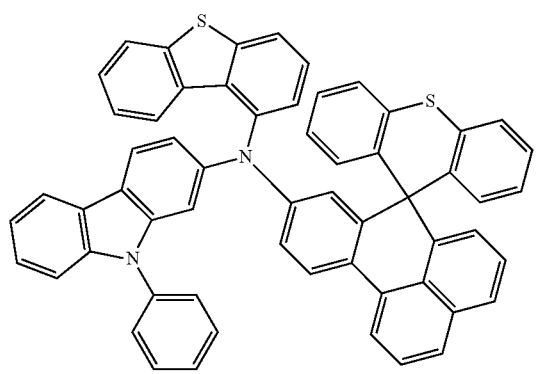
149
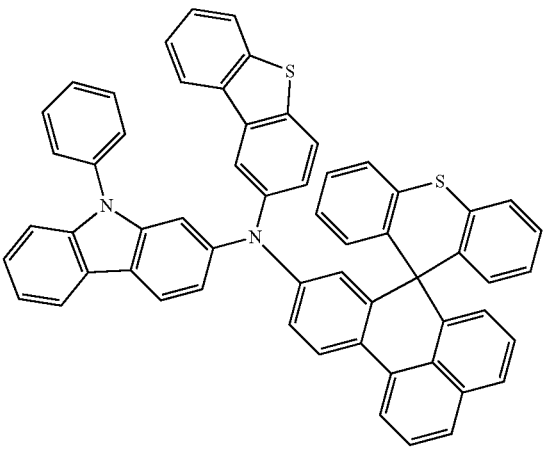
150
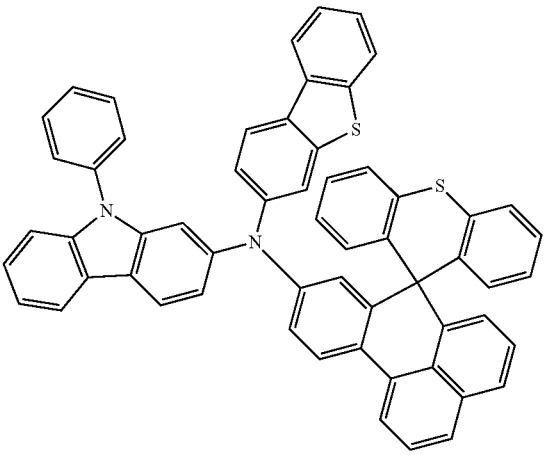
151
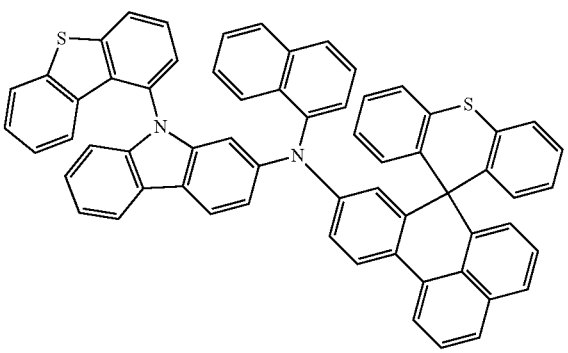

-continued
152
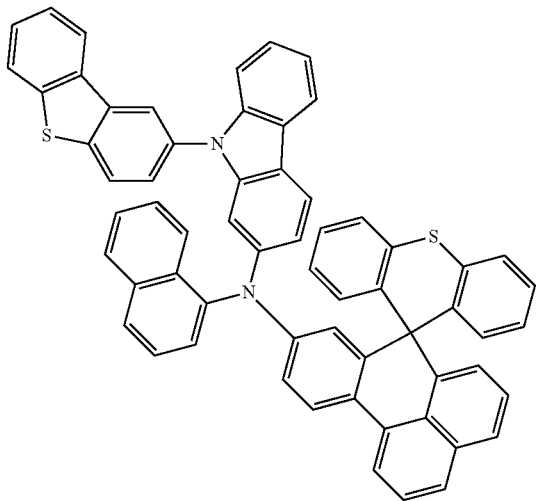
153
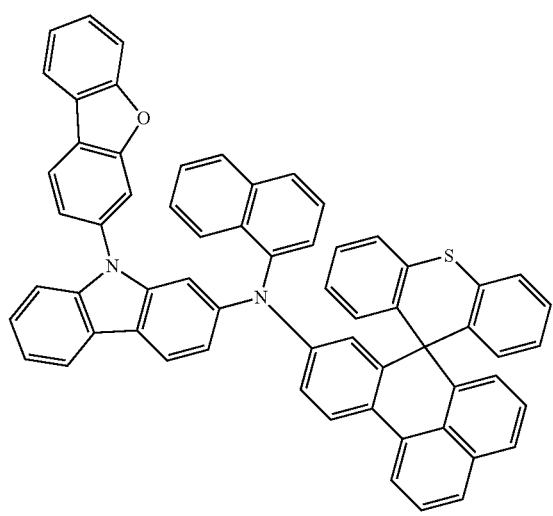
154
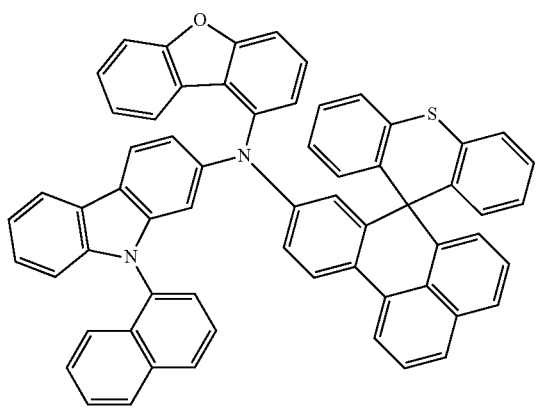
-continued
155
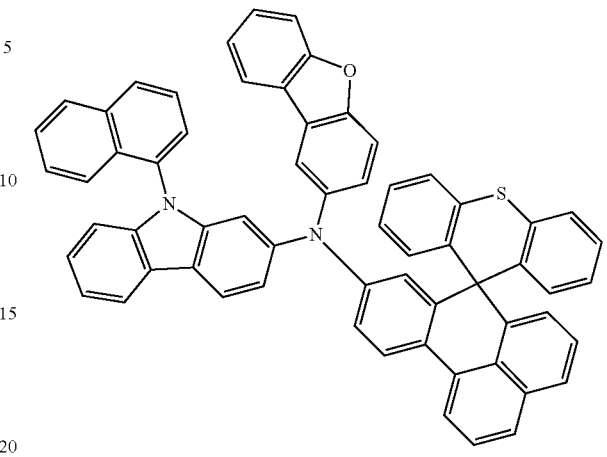
156
157
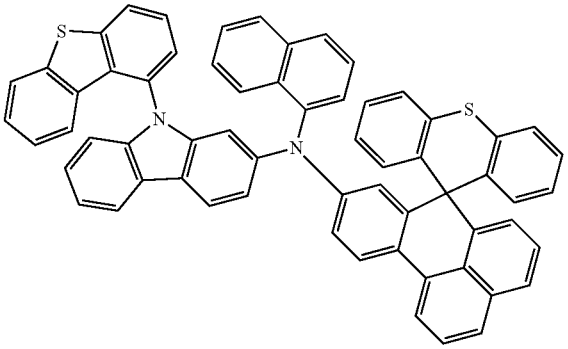

158
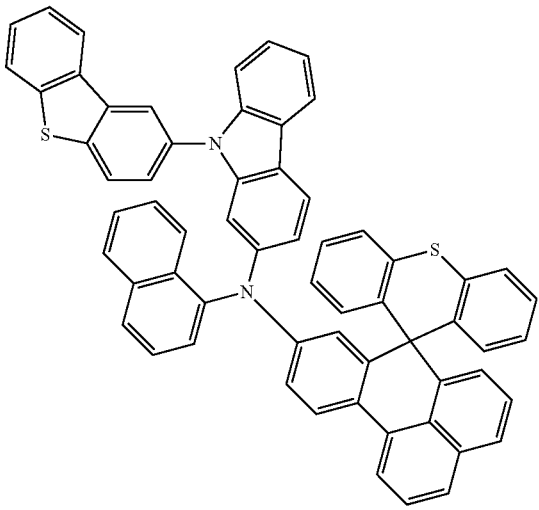
159
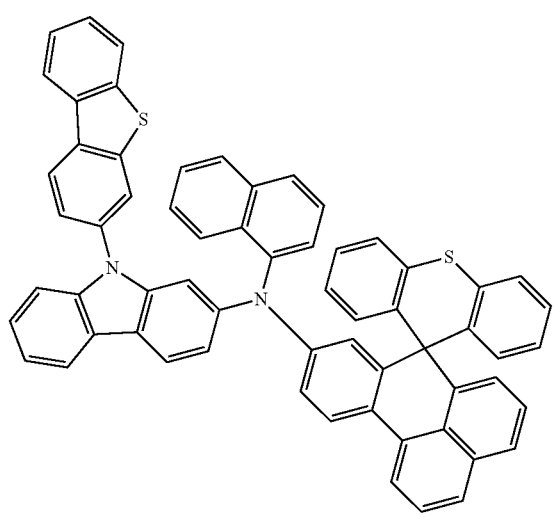
160
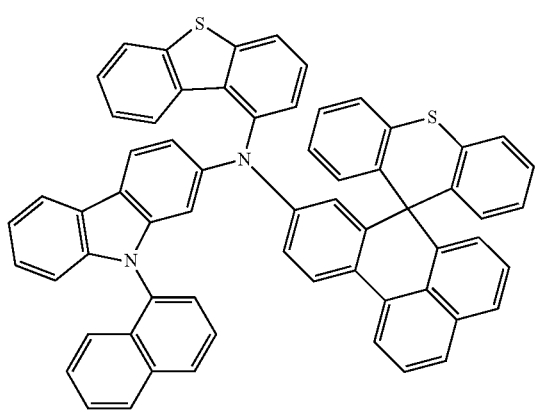
161
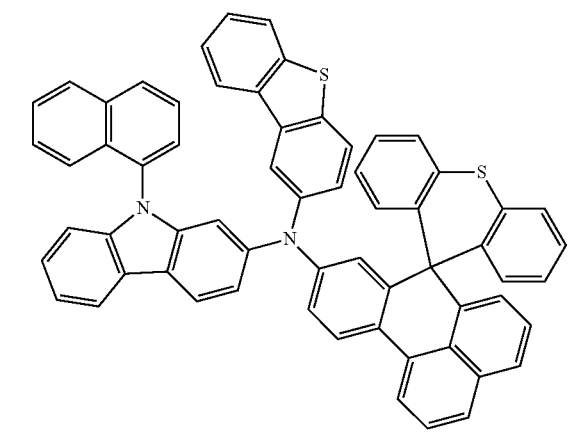
162
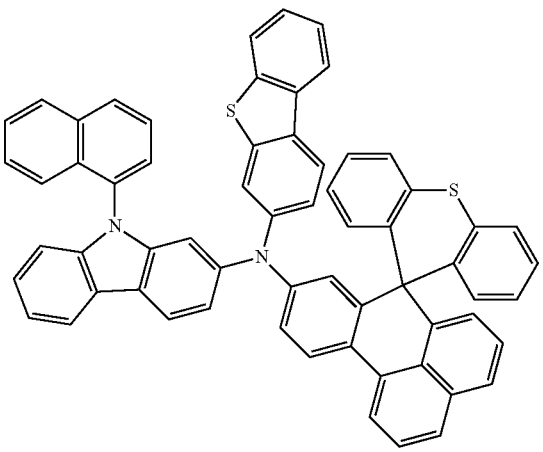
166
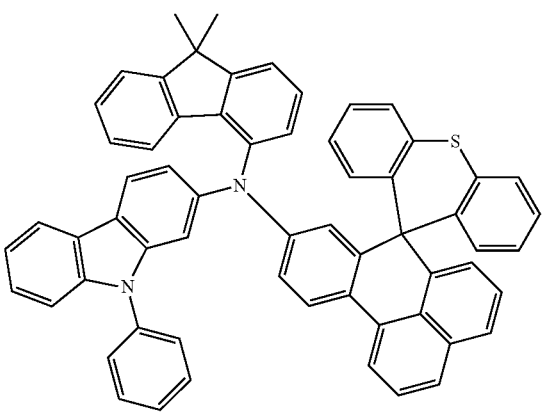

-continued
167
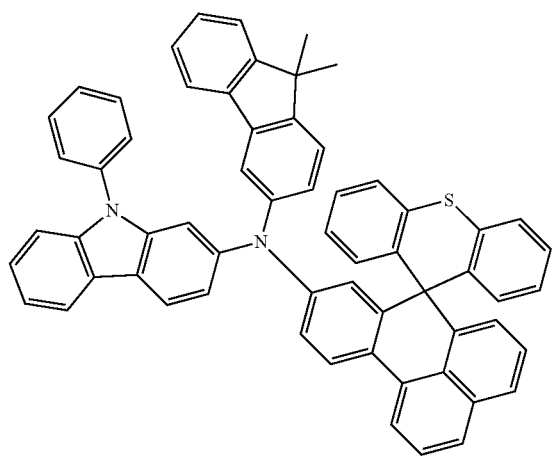
168
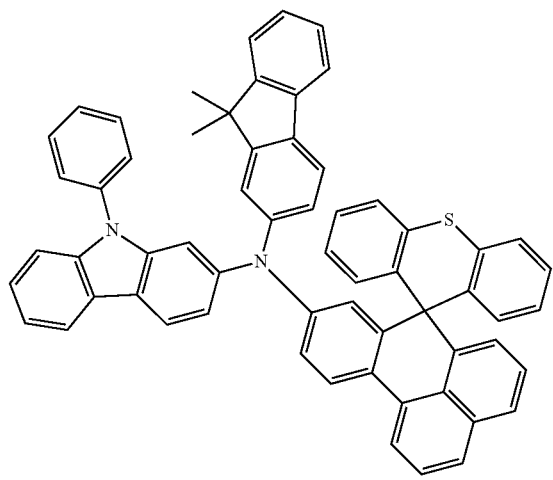
182
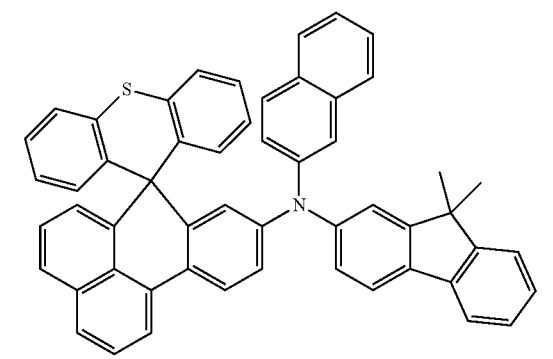
-continued
183
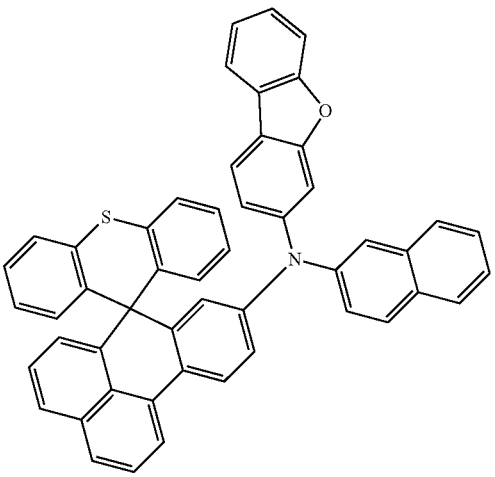
184
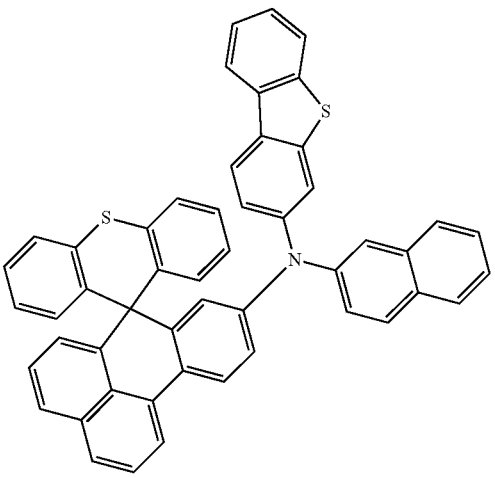
185
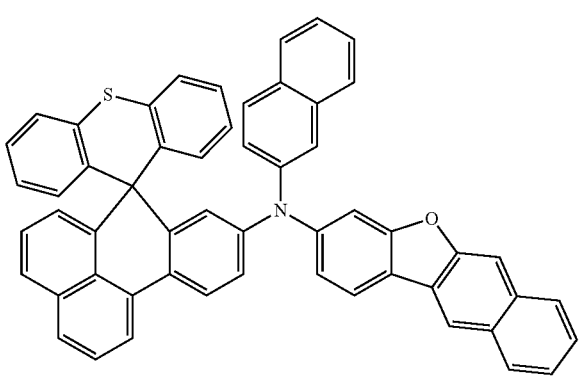

186
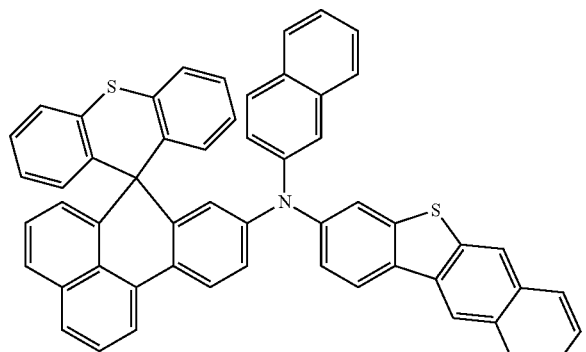
187
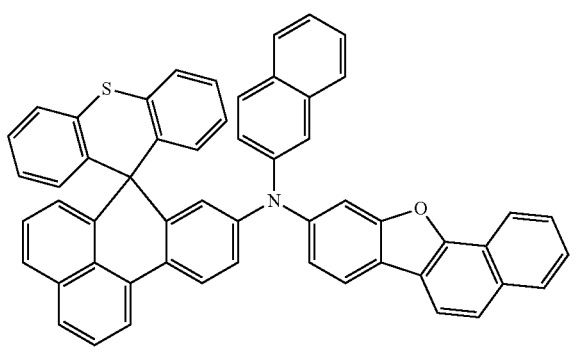
188
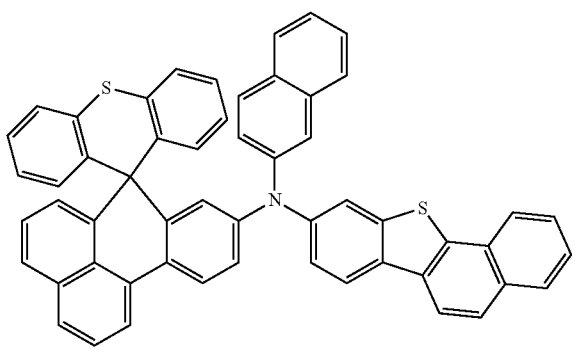
189
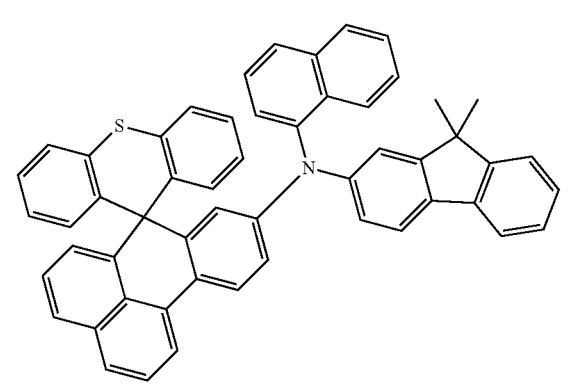
190
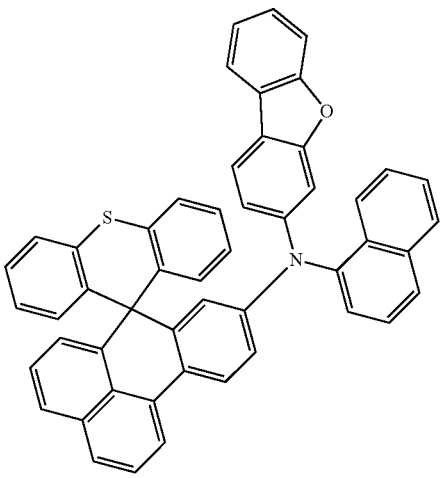
191
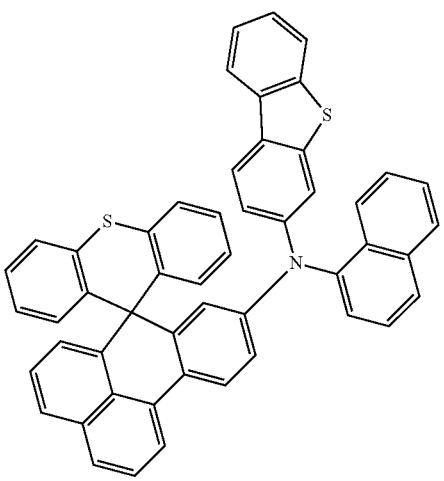
192
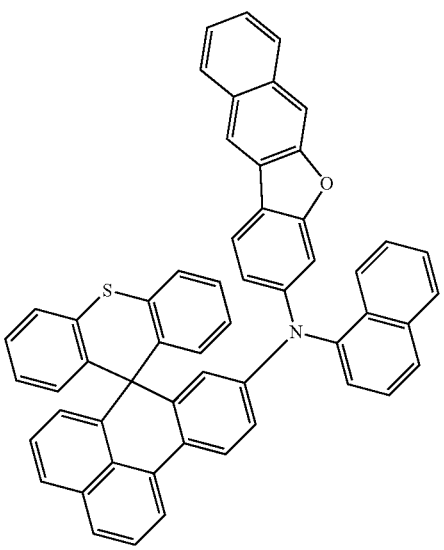

193
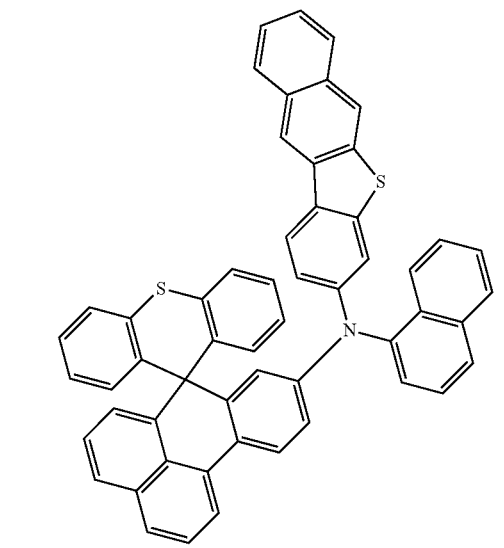
194
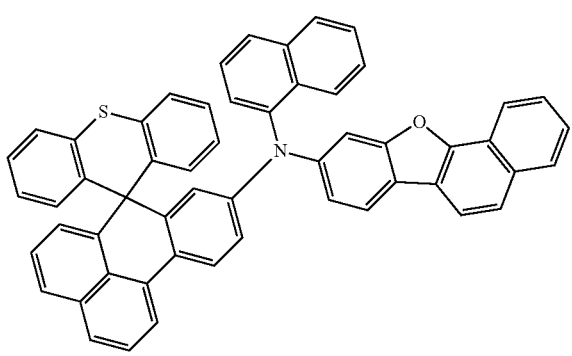
195
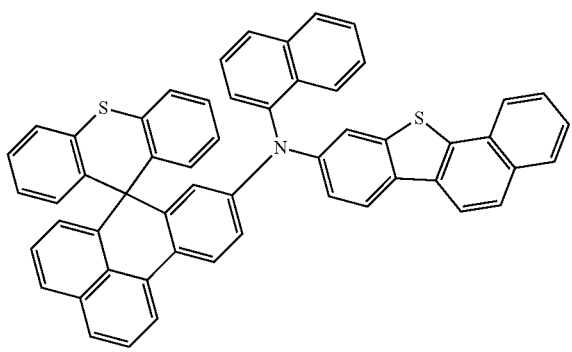
198
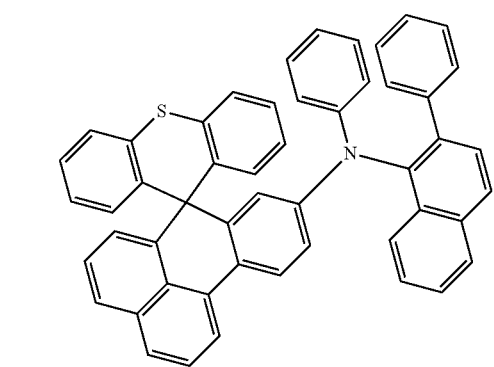
199
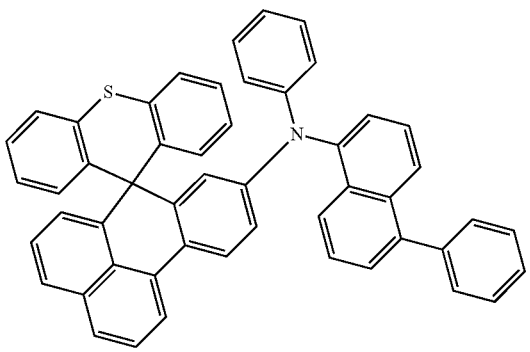
200
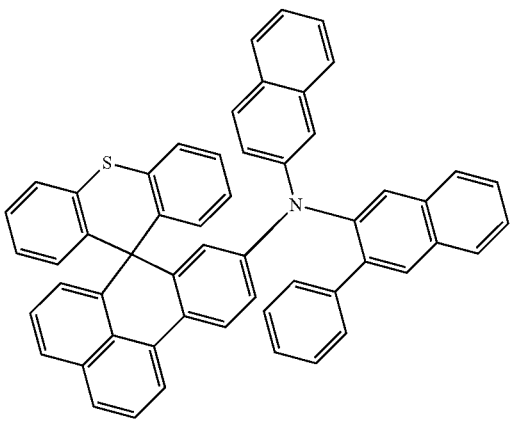
201
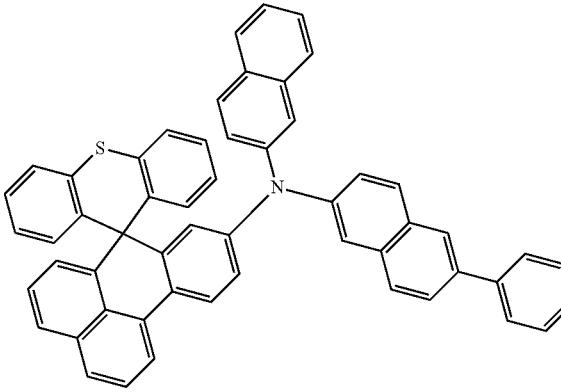
202
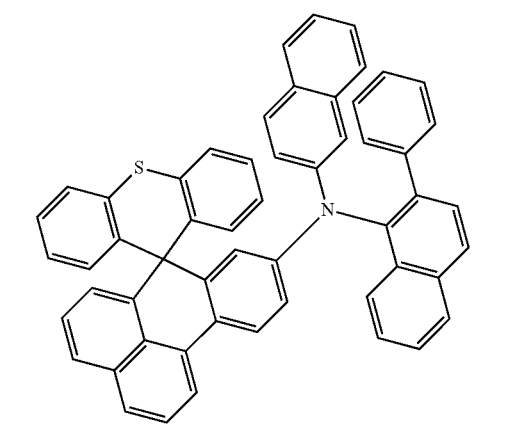

203
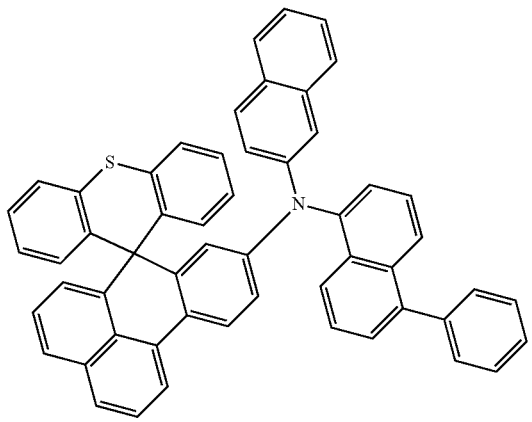
204
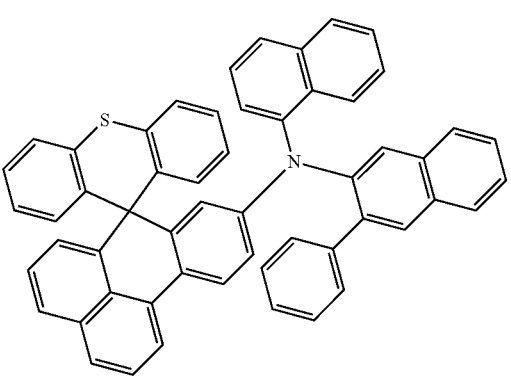
205
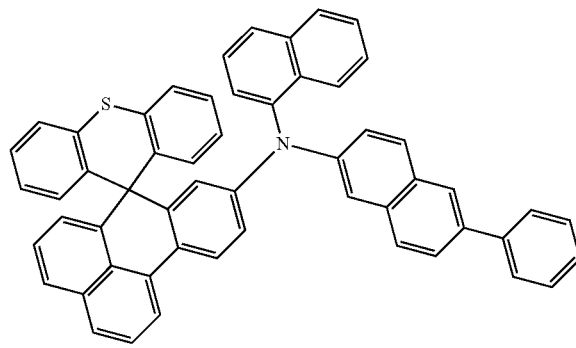
206
207
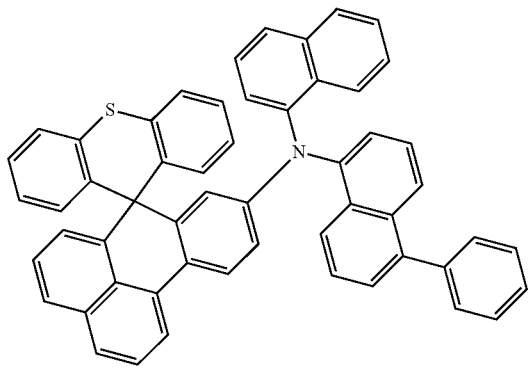
209
210
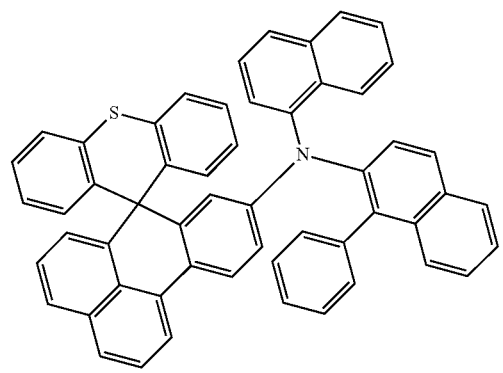

-continued
218
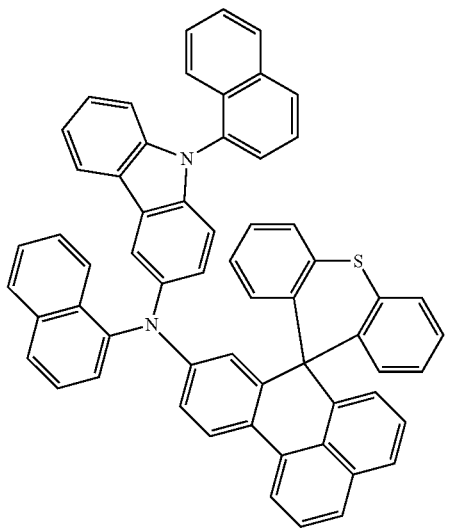
219
222
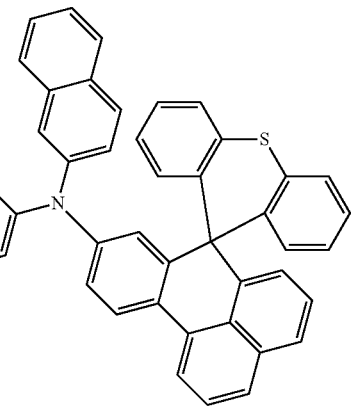
227
221
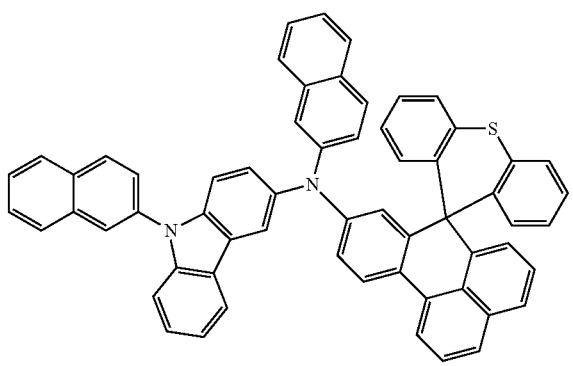
228
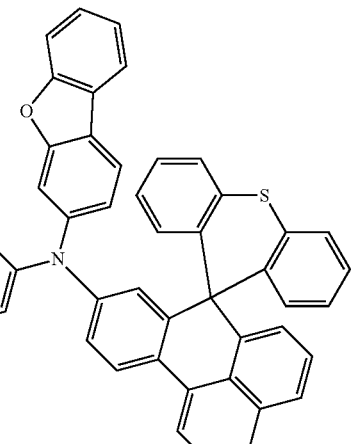

234
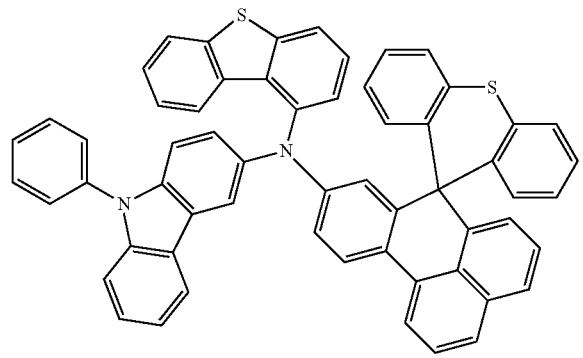
235
237
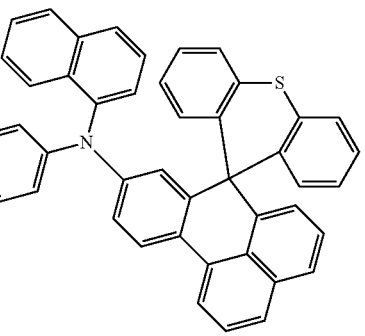
238
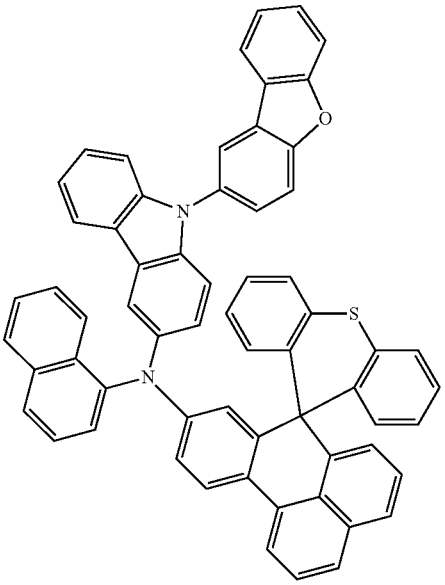
236
239
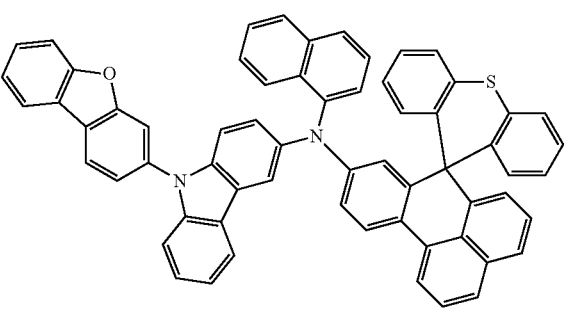
240
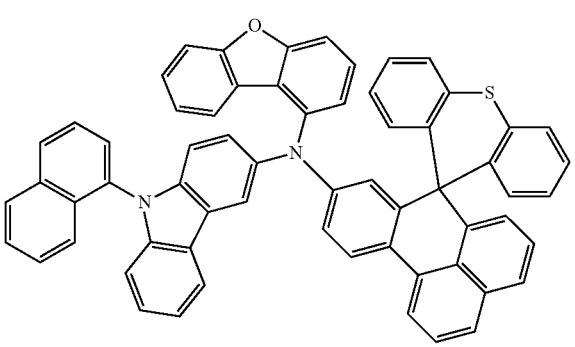

241
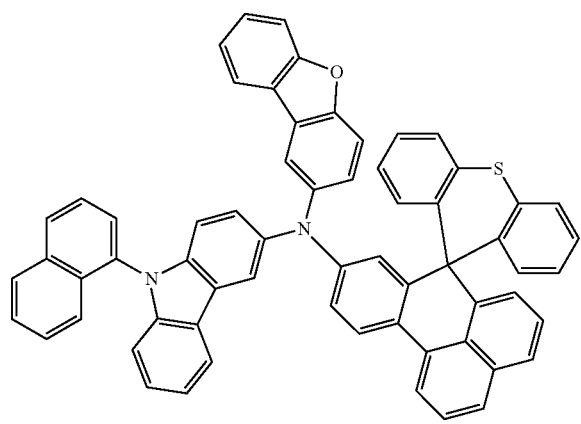
242
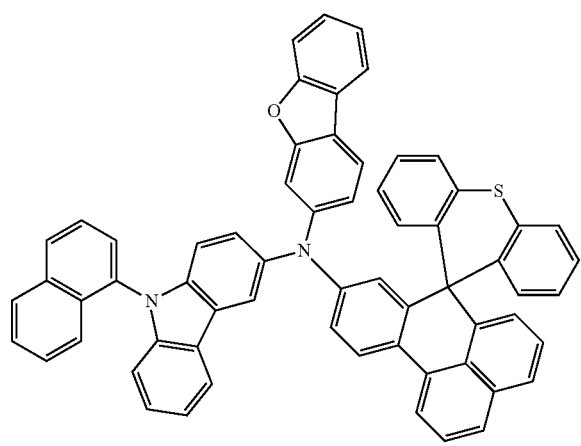
243
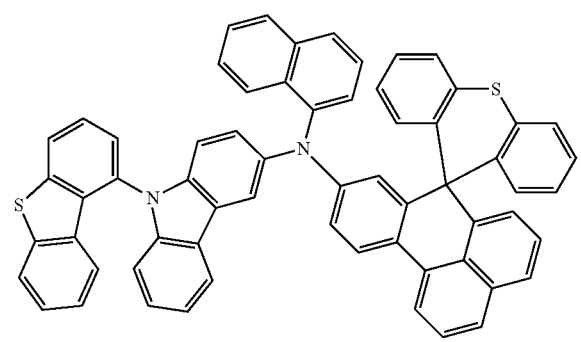
244
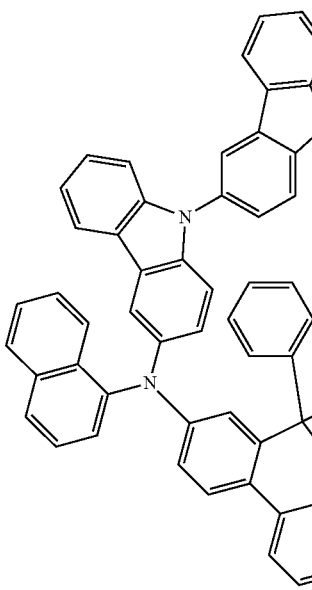
245
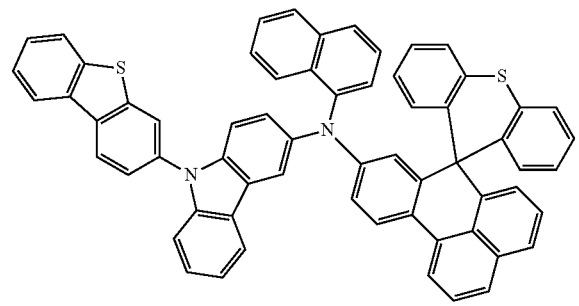
246
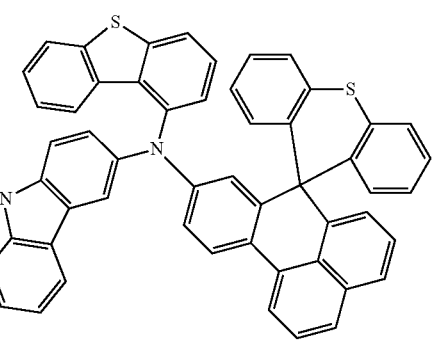

-continued
247
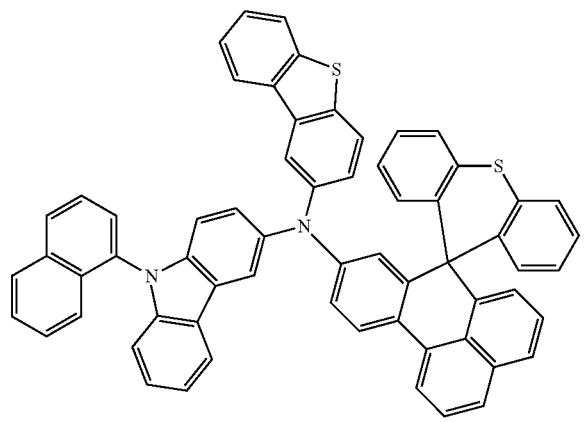
248
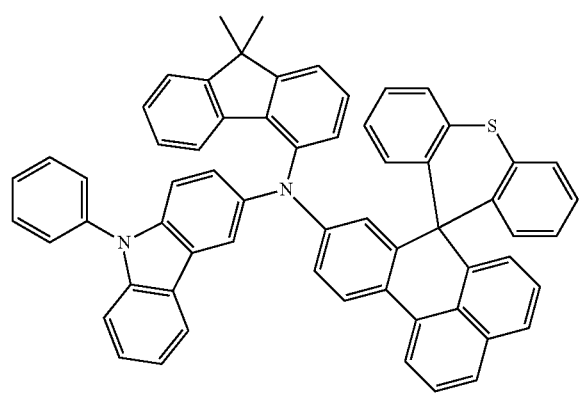
252
-continued
253
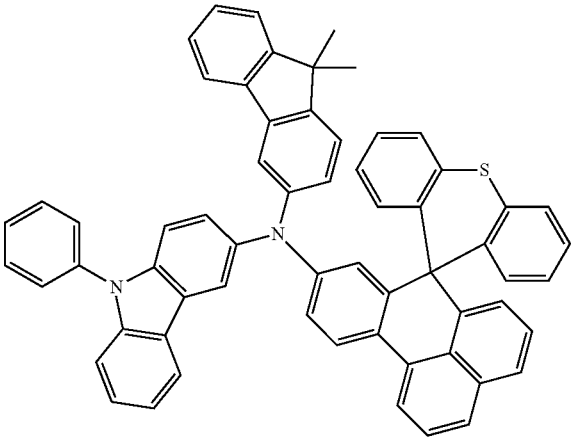
254
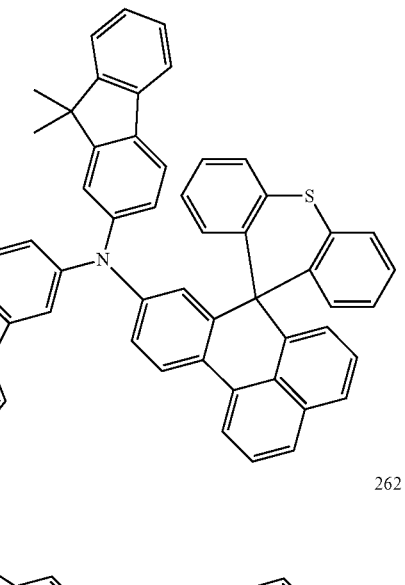
262
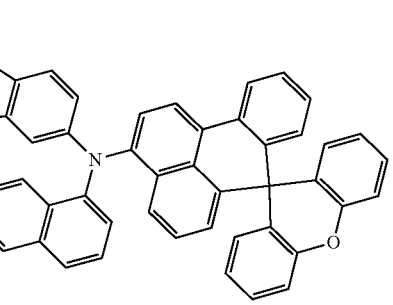
263
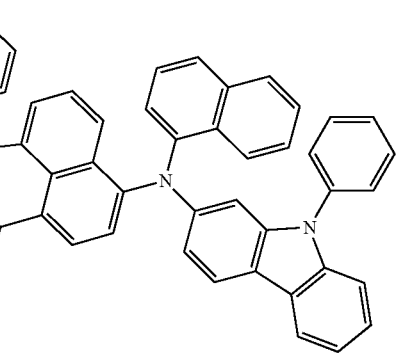

-continued
265
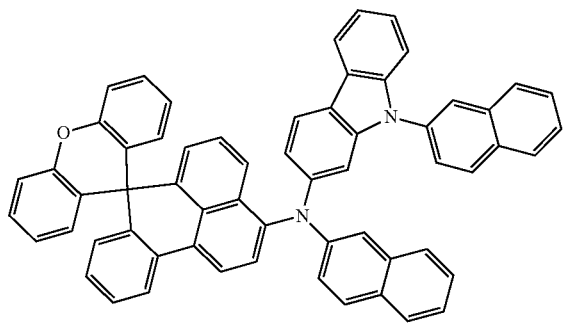
266
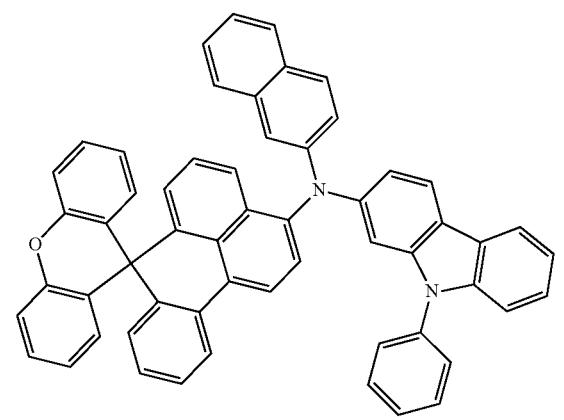
270
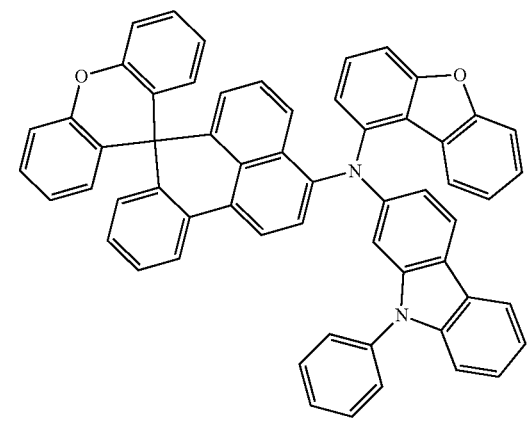
271
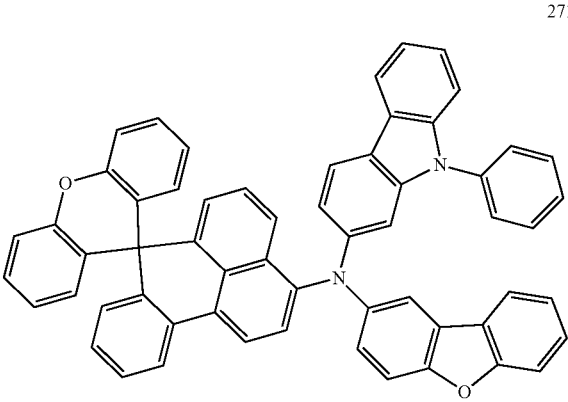
-continued
272
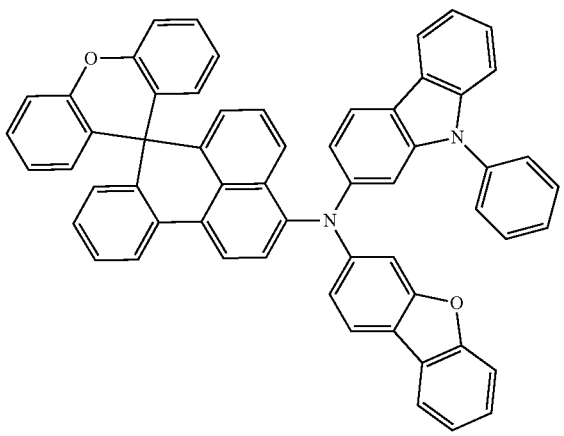
273
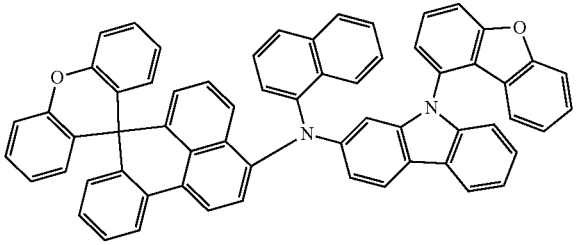
274
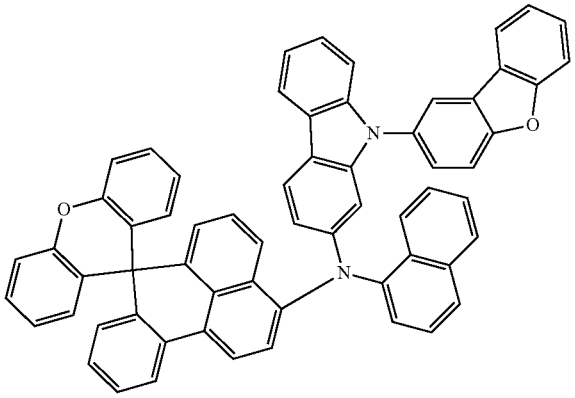
278
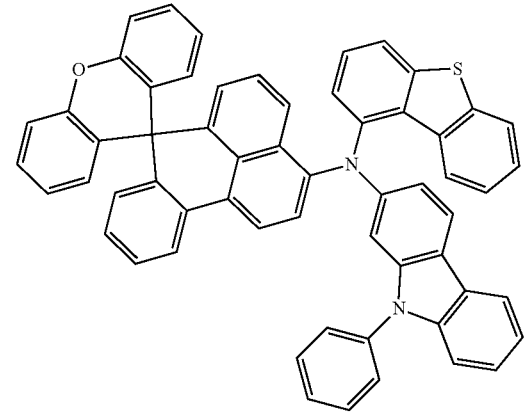

279
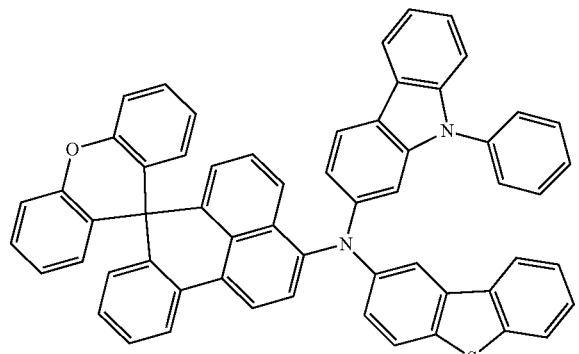
280
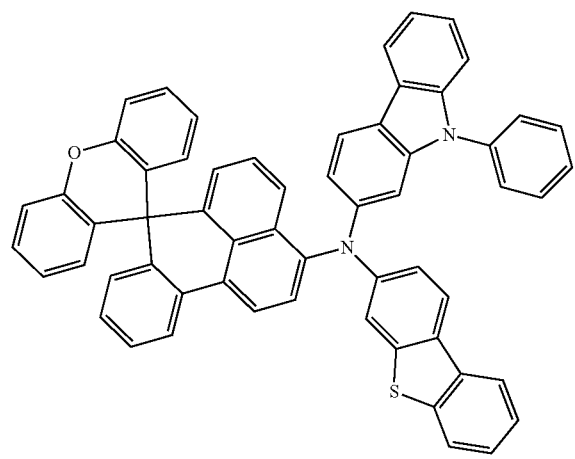
281
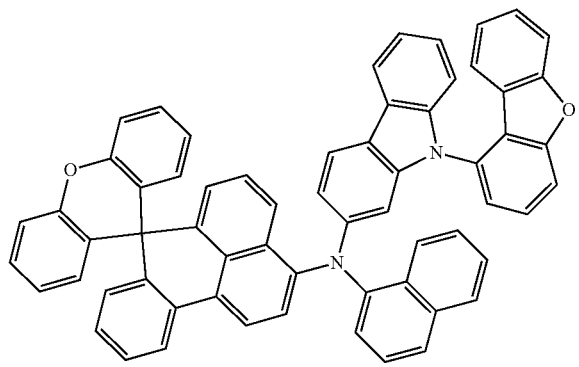
282
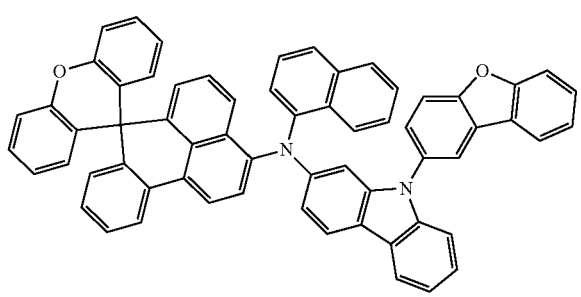
283
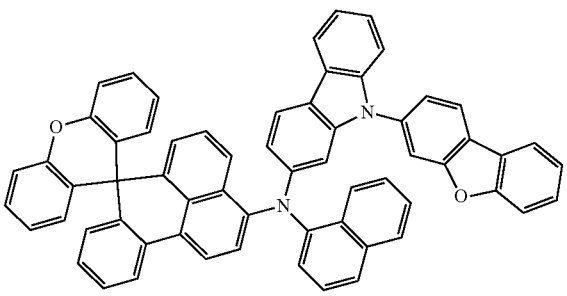
284
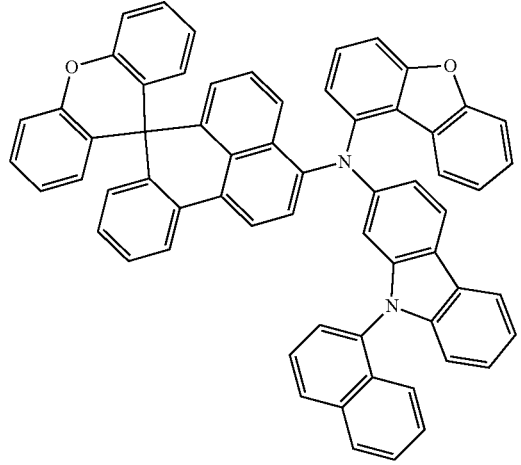
285
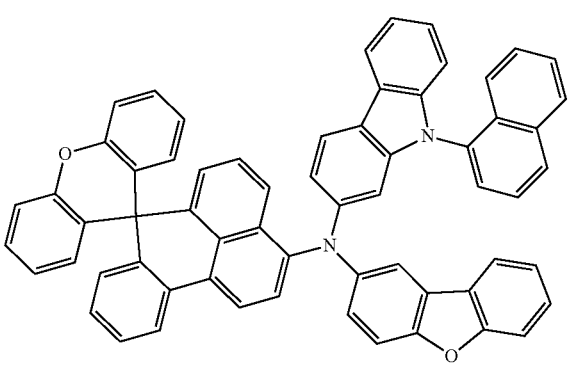
286
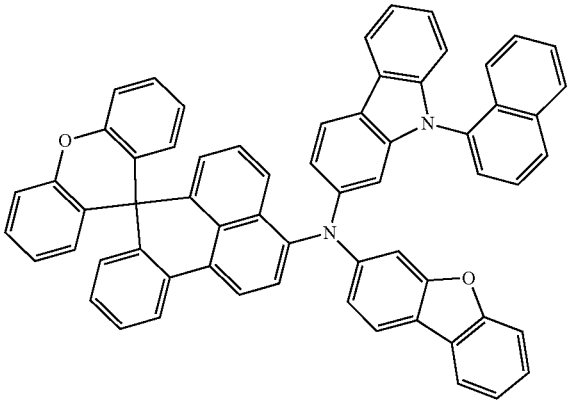

287
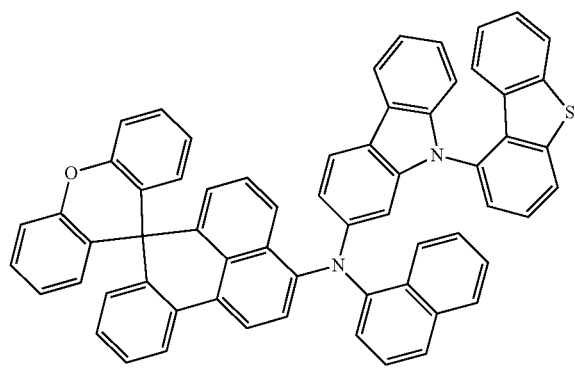
288
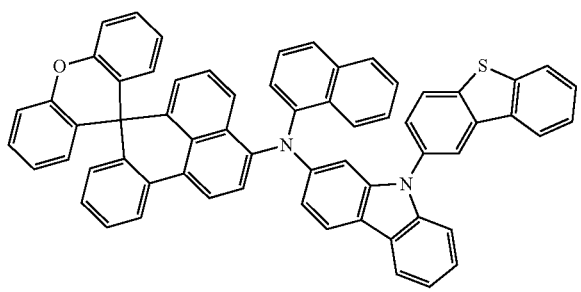
289
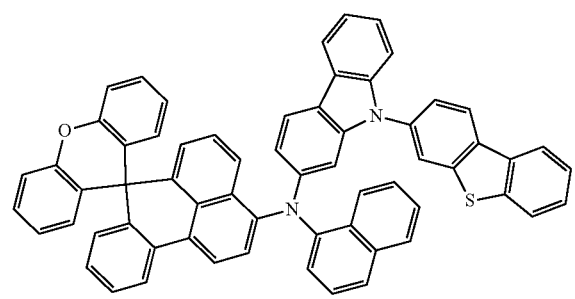
290
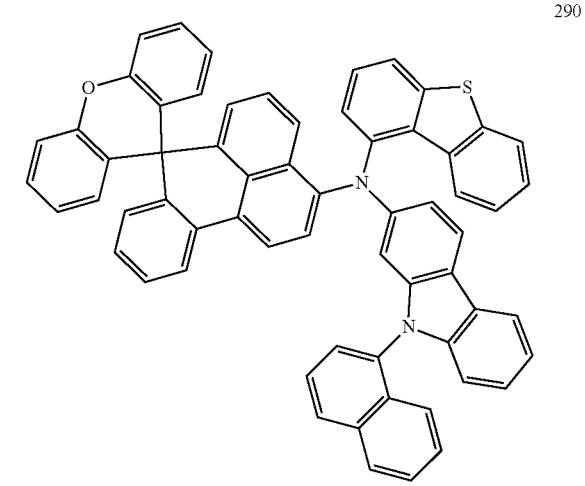
291
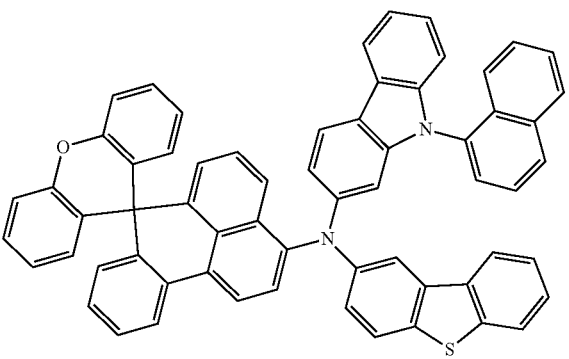
292
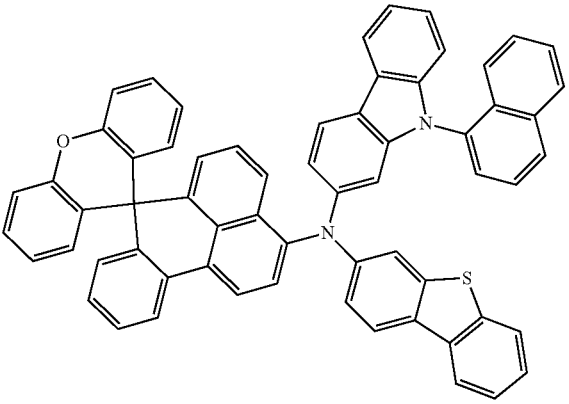
296
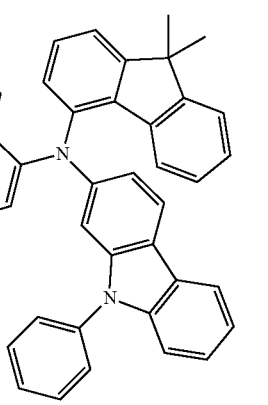
297
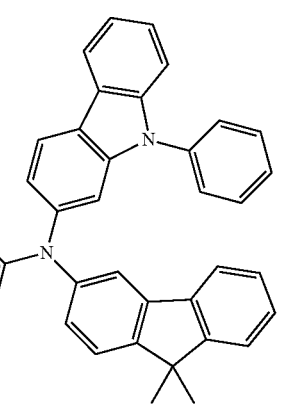

298
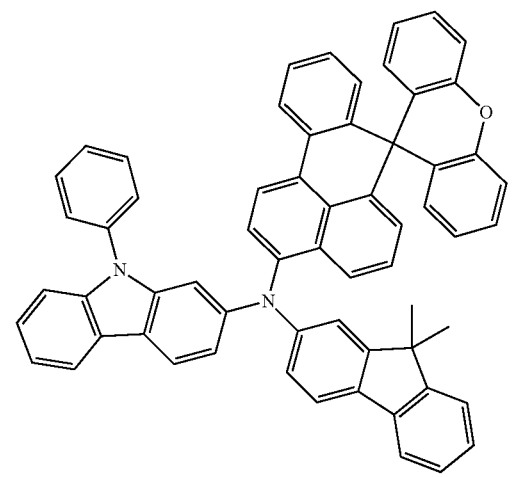
306
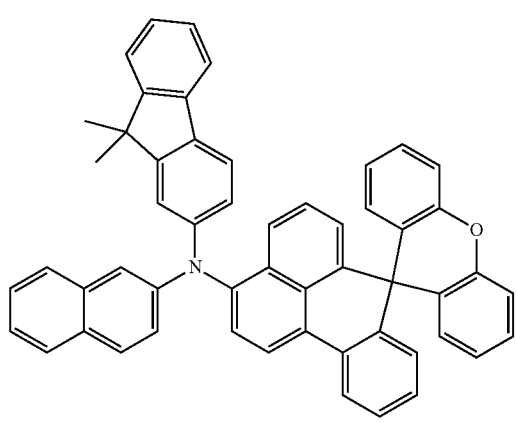
307
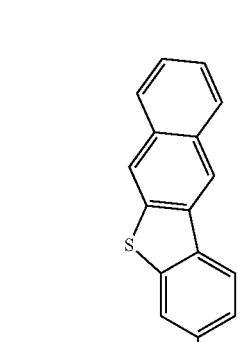
308
309
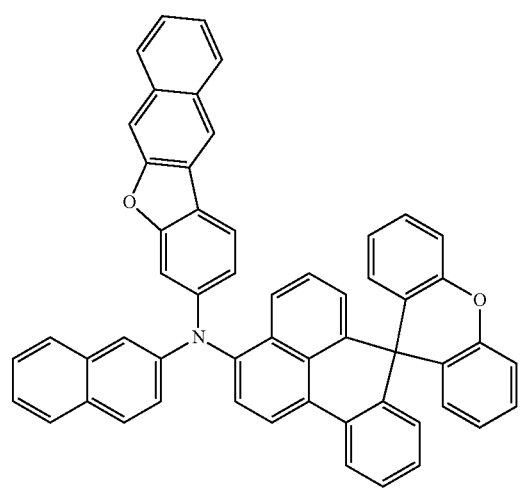
310
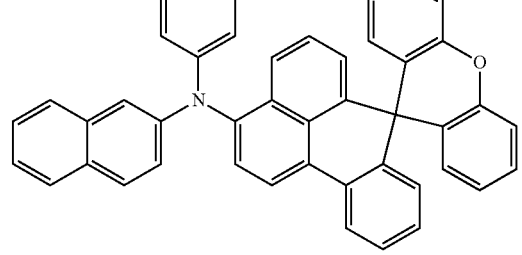
311
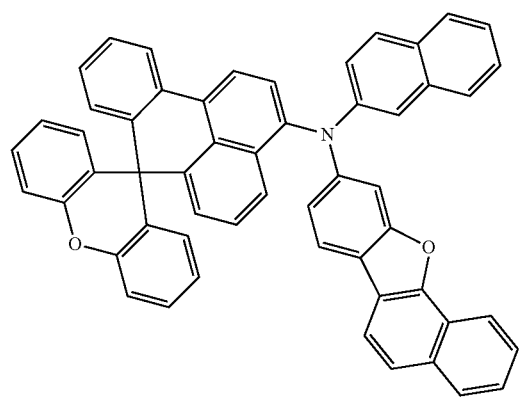

| 312 | 316 |
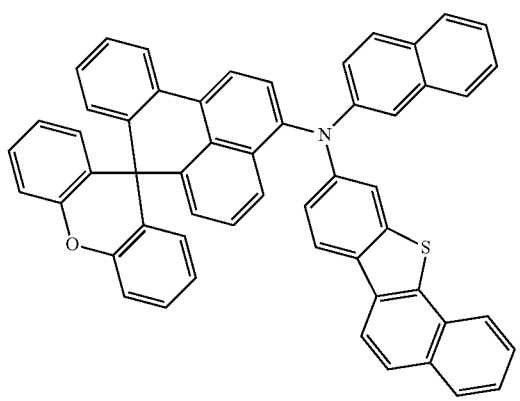
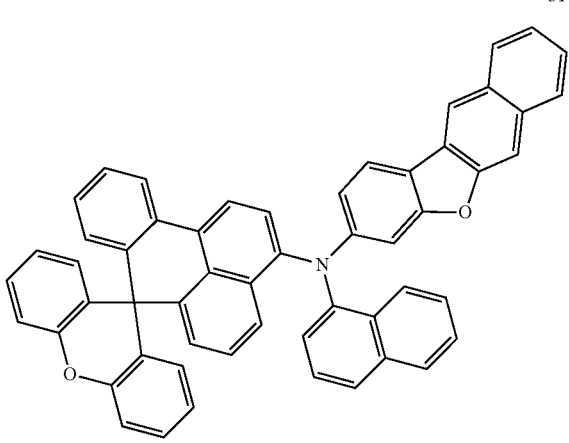
| 313 | 317 |
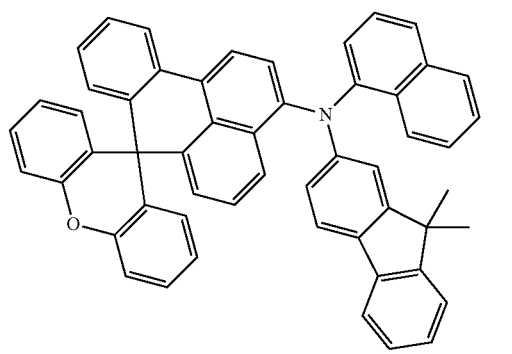
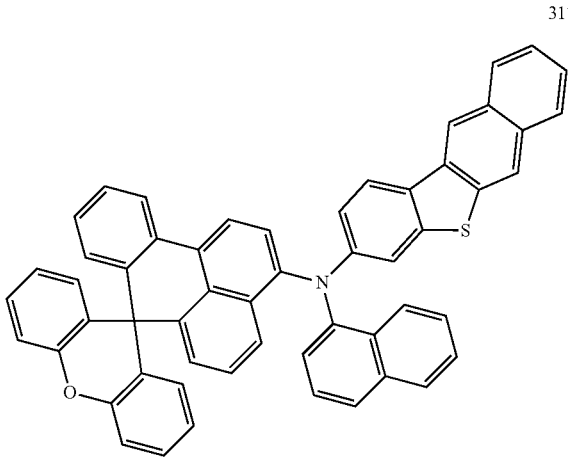
| 314 | 318 |
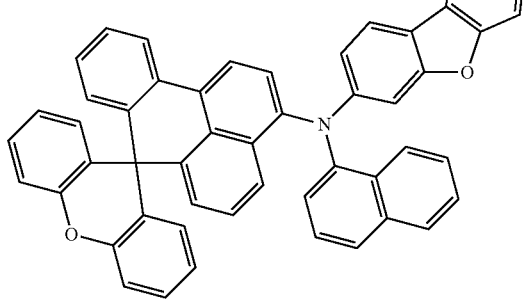
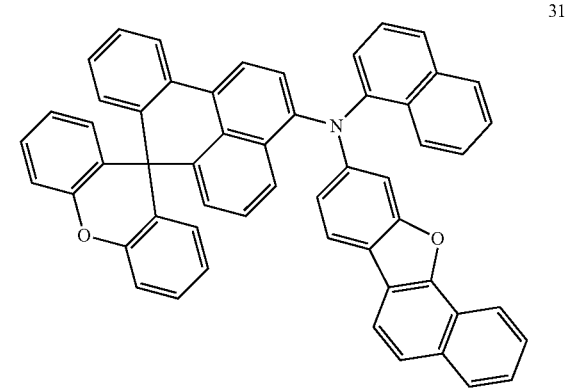
| 315 | 319 |
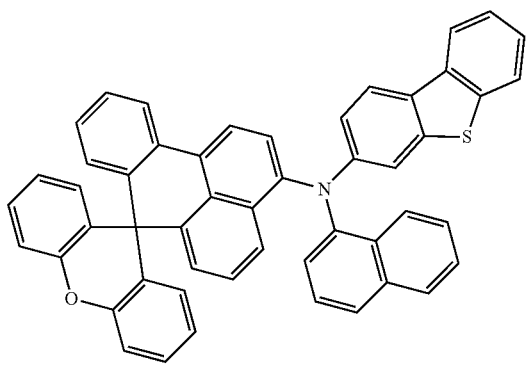
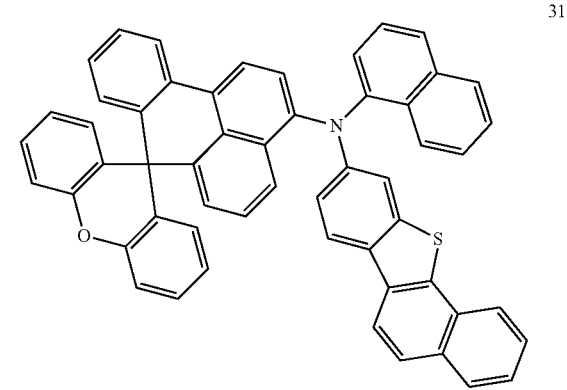

467
-continued
324
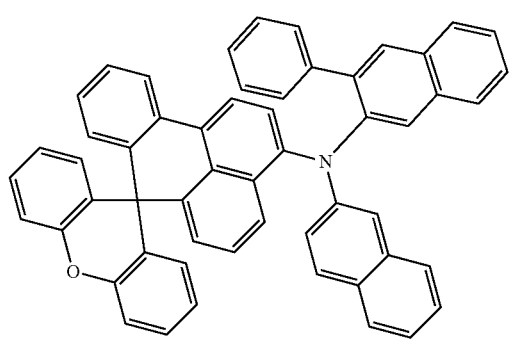
325
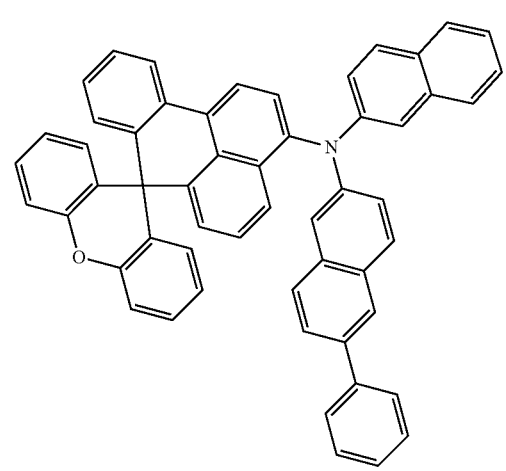
326
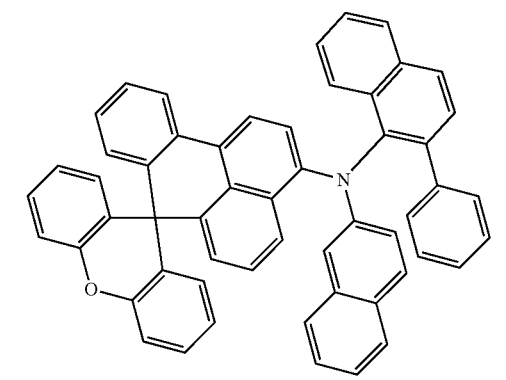
327
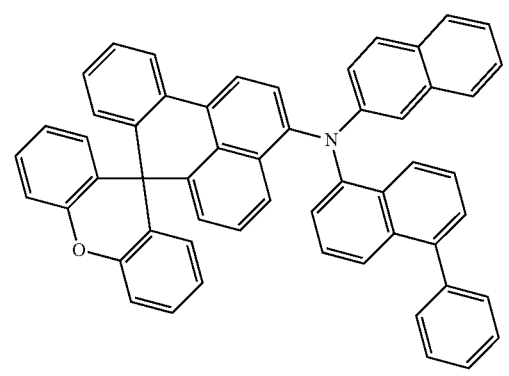
468
-continued
328
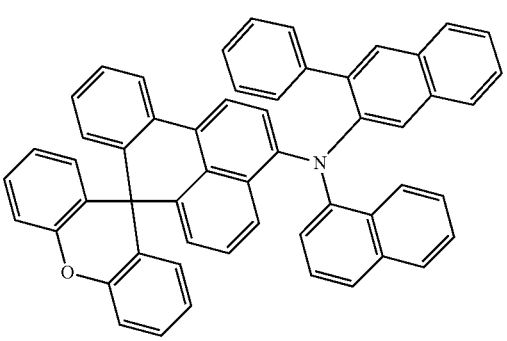
329
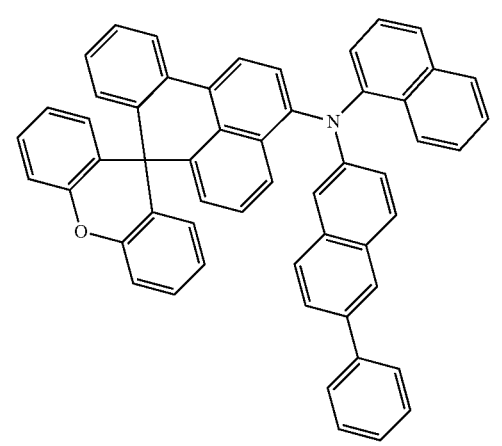
330
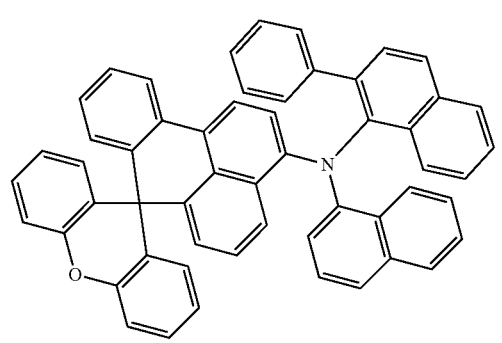
331
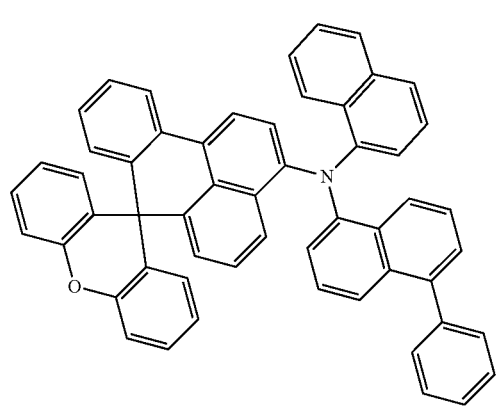

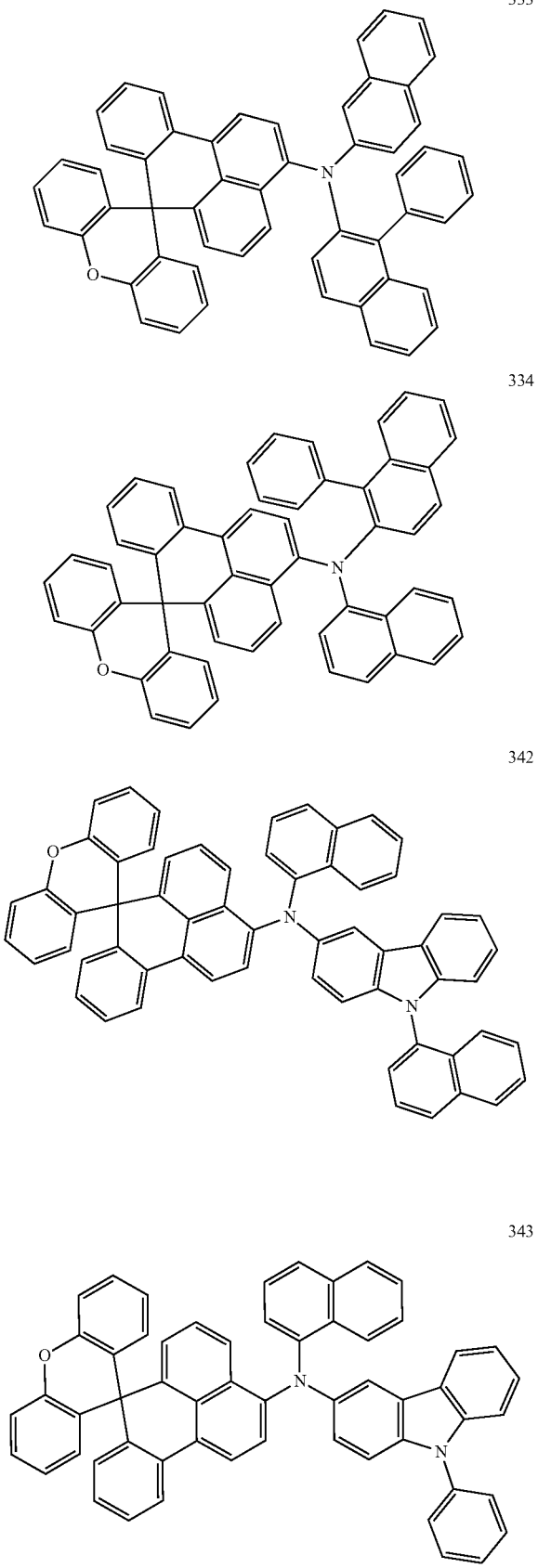

351
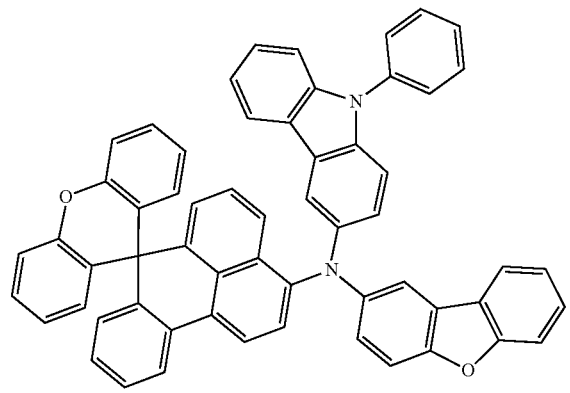
352
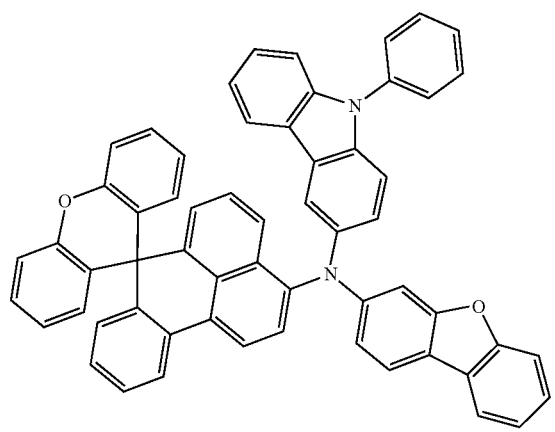
358
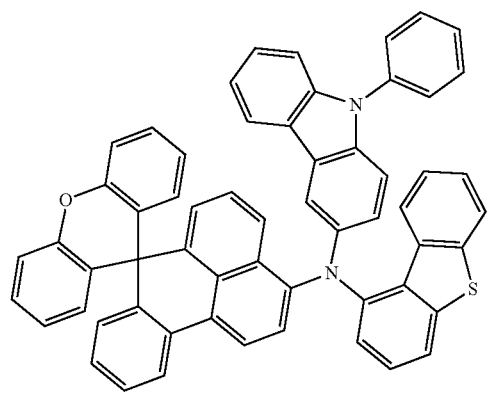
359
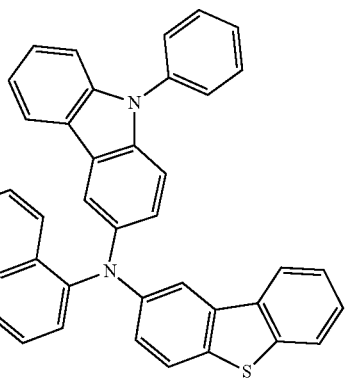
360
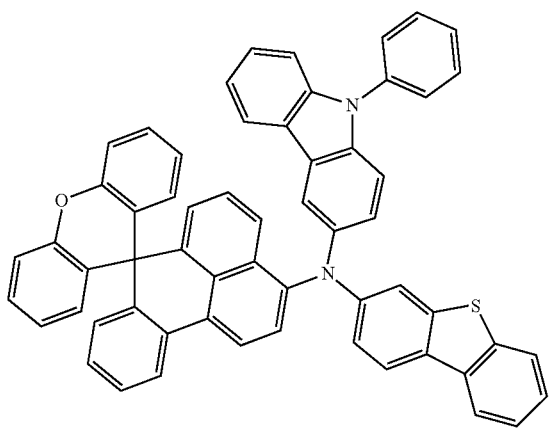
361
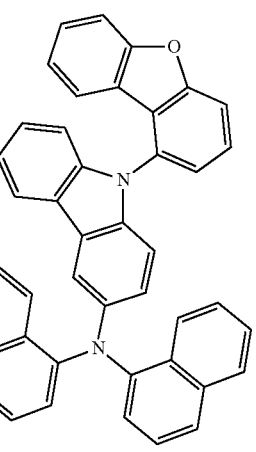

362
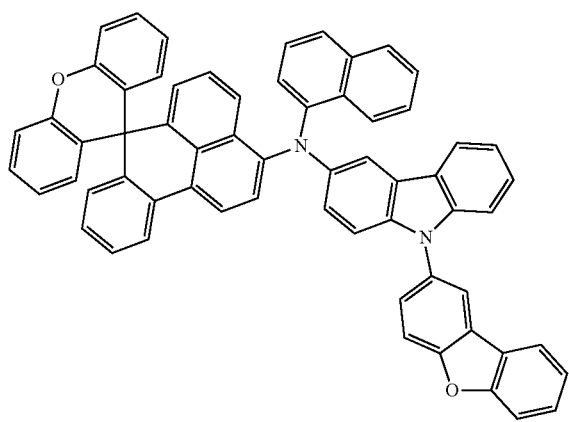
365
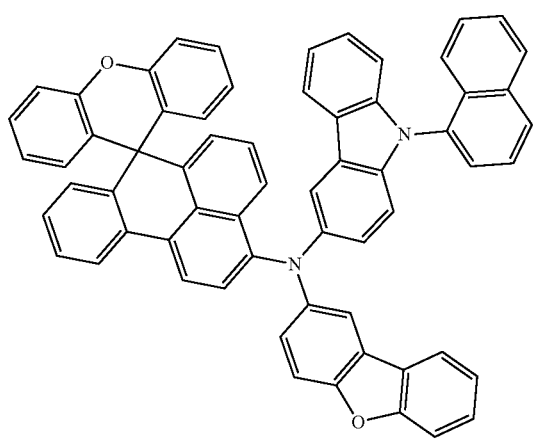
363
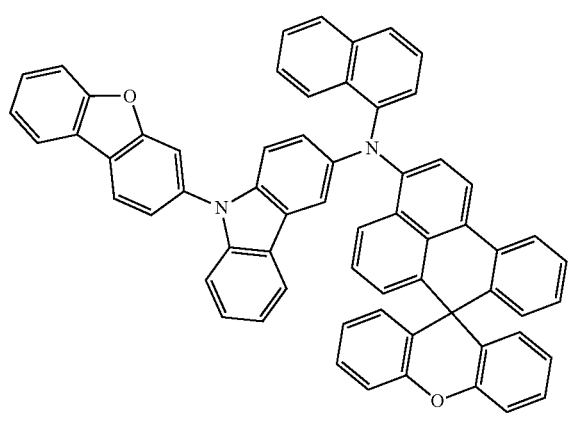
366
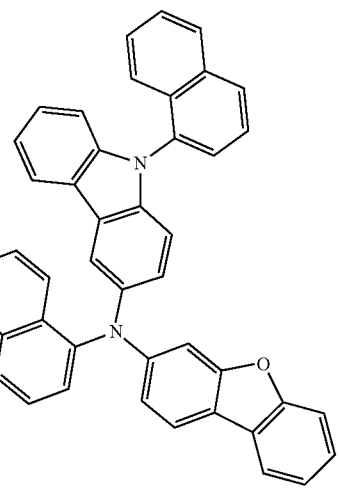
364
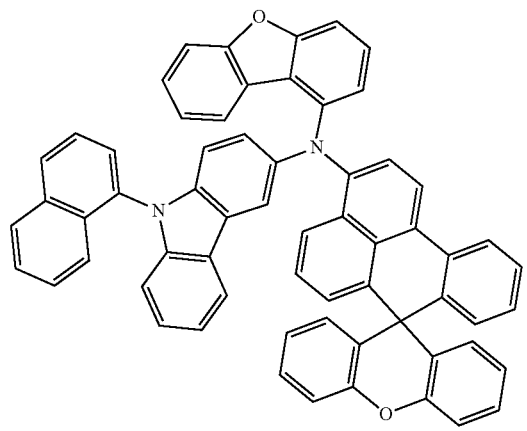
367
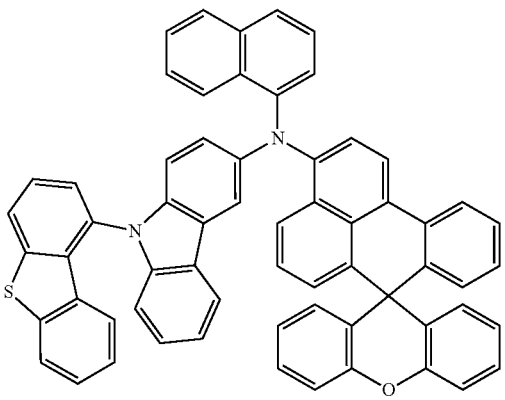

-continued
368
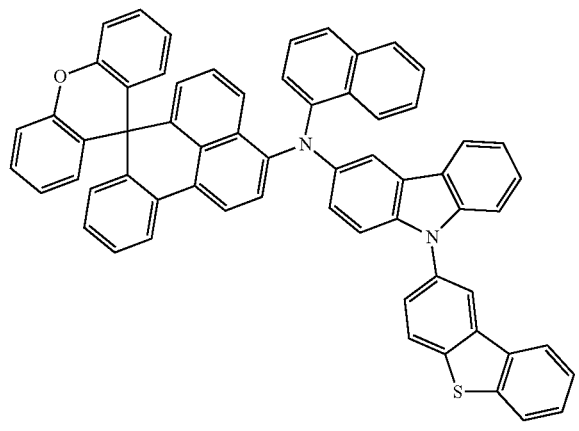
369
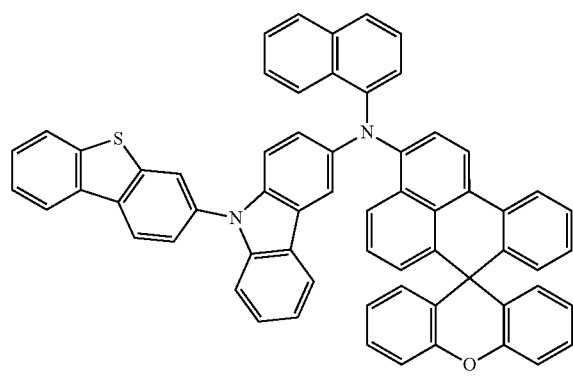
370
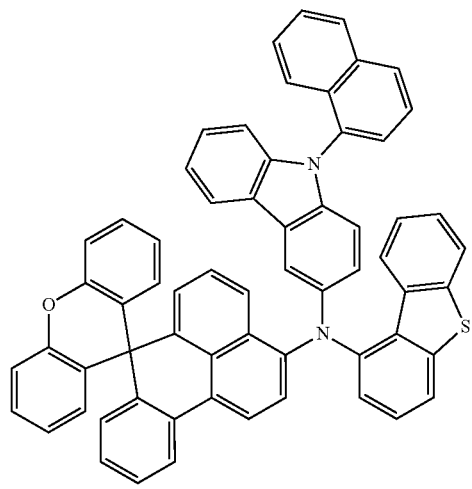
-continued
371
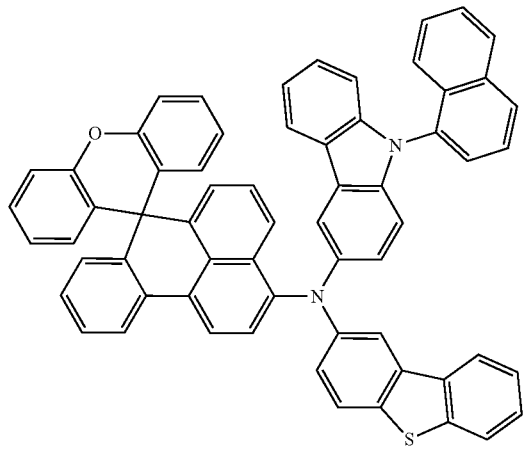
372
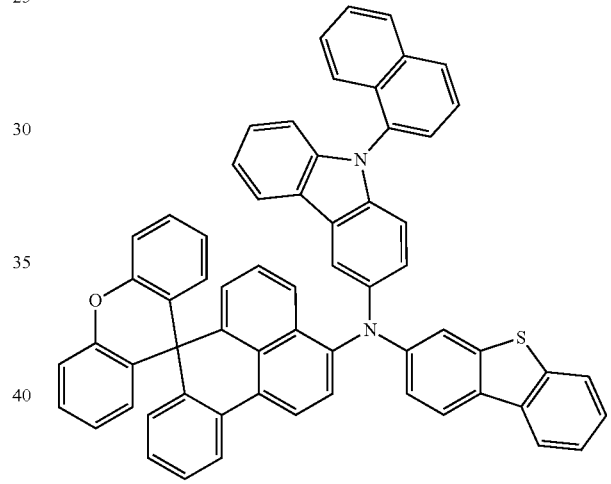
376
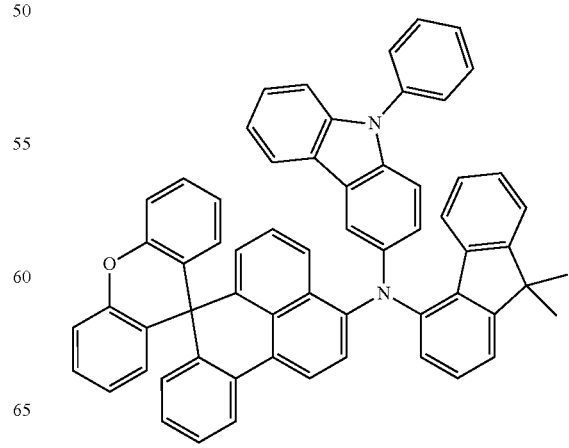

377
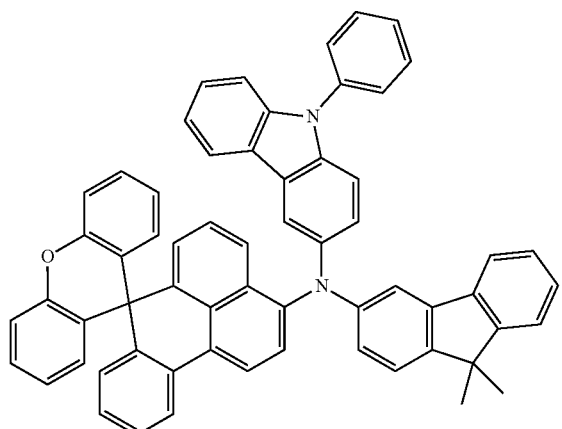
378
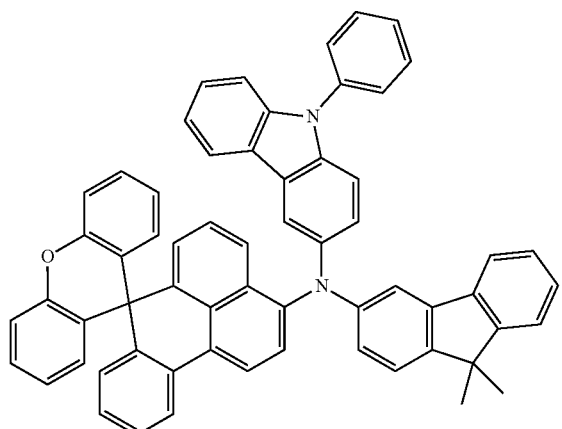
386
387
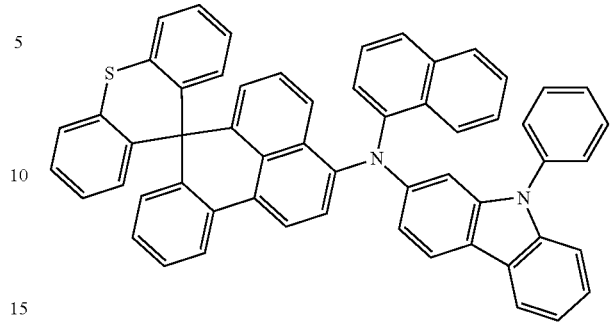
389
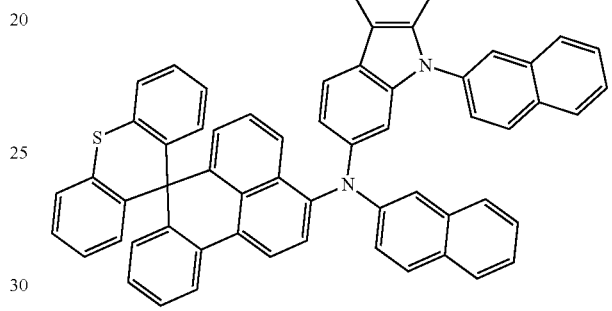
390
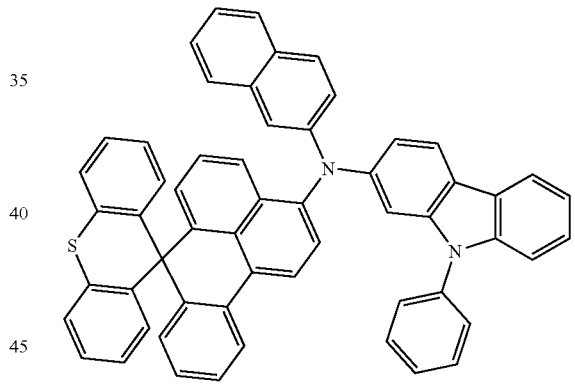
394
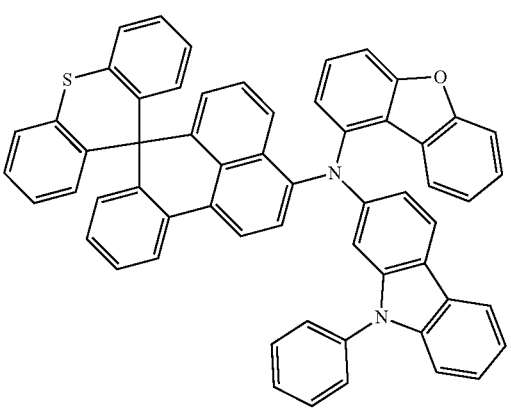

479
-continued
395
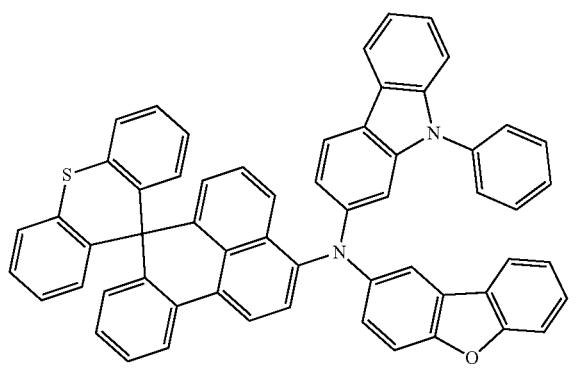
396
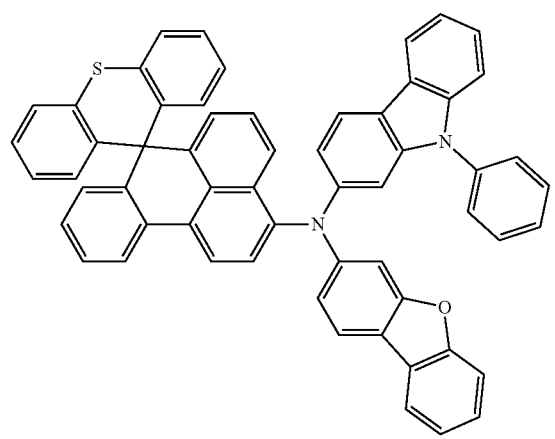
402
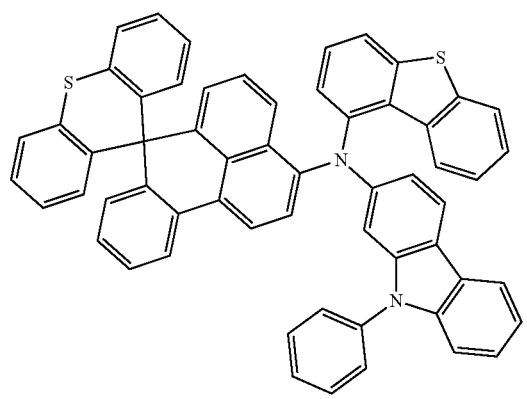
403
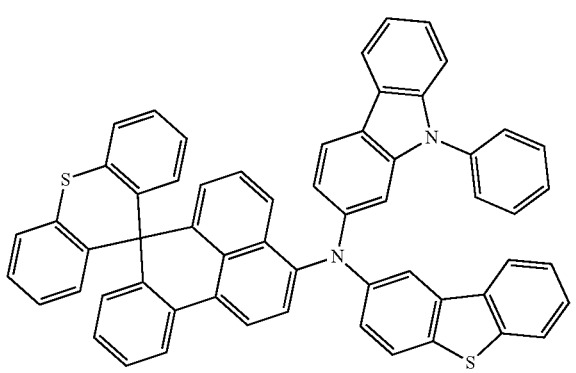
480
-continued
404
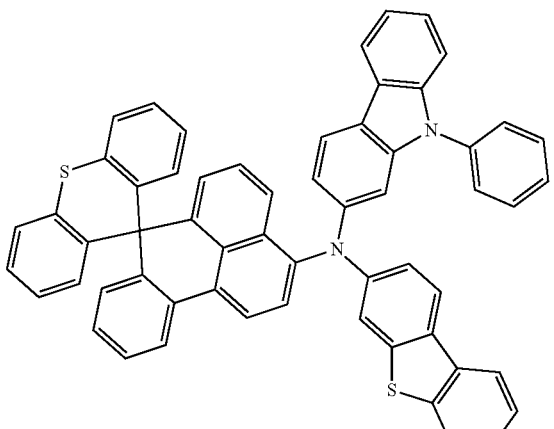
405
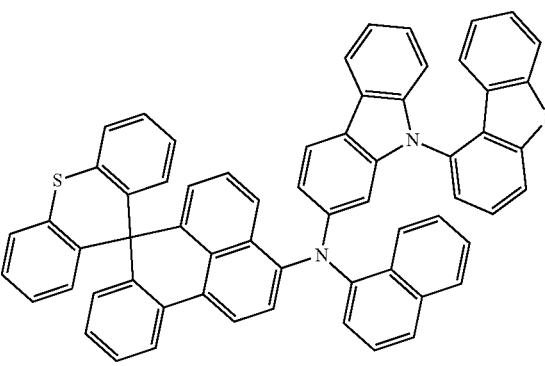
406
407
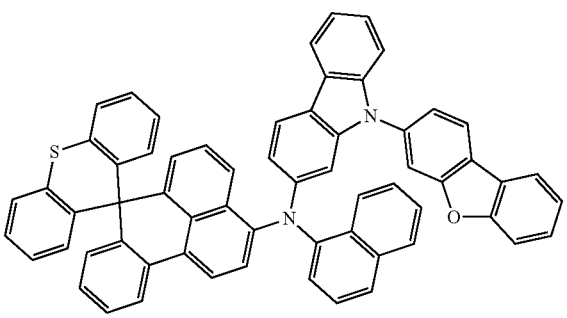

408
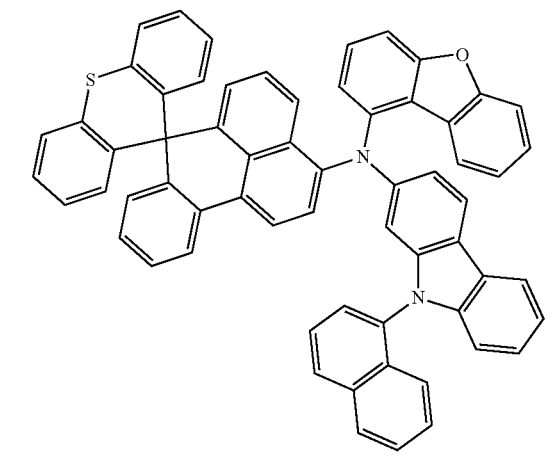
409
410
411
412
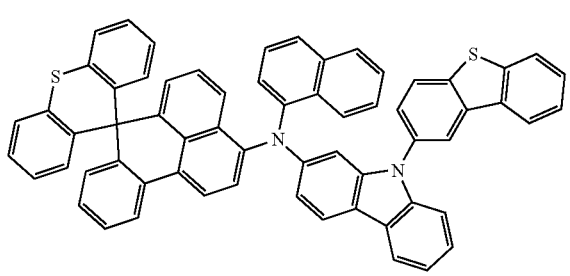
413
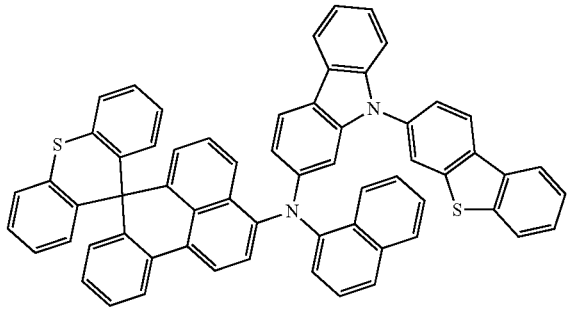
414
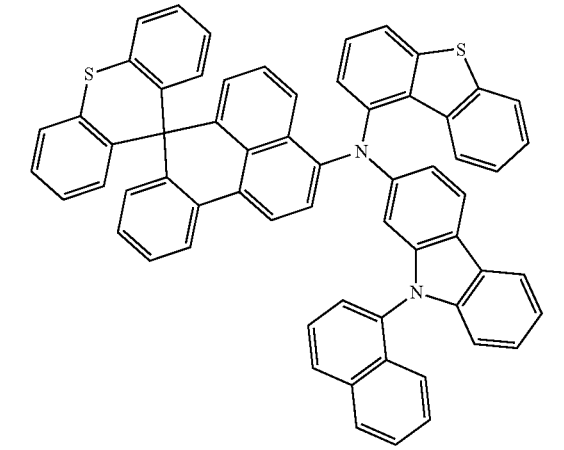
415
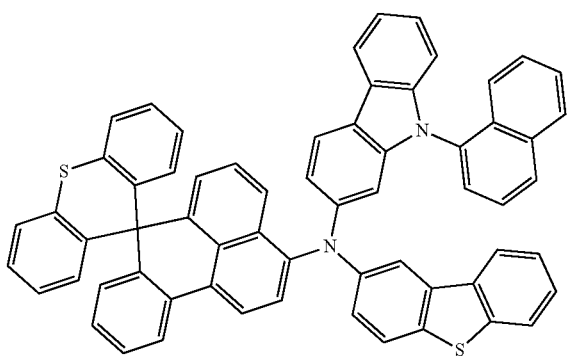

416
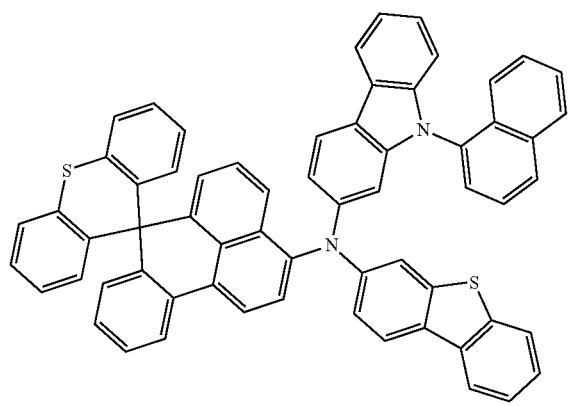
420
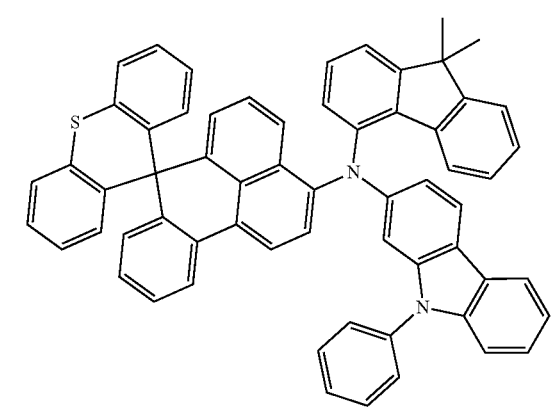
421
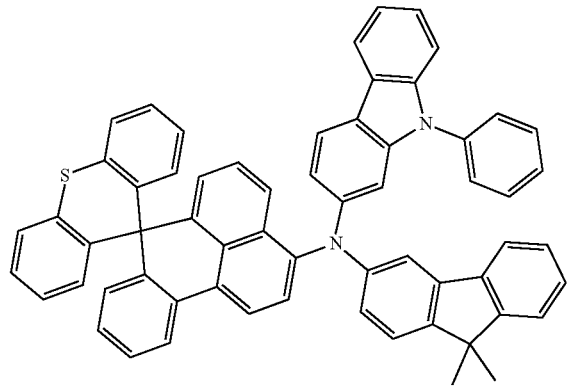
422
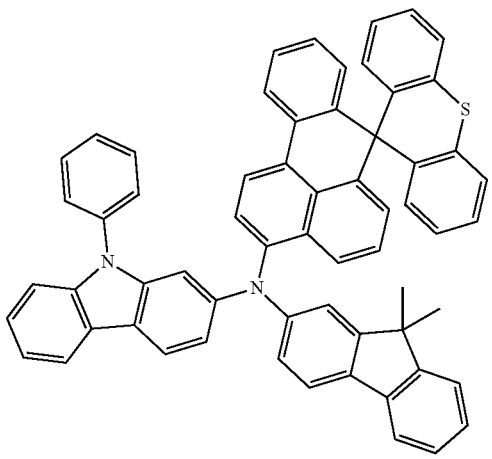
430
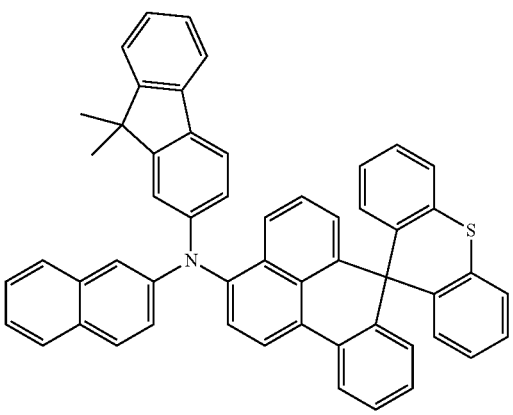
431
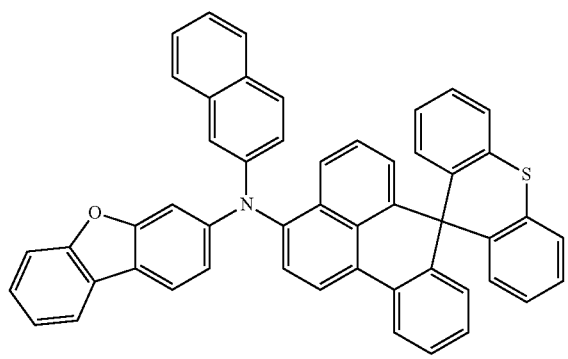
432
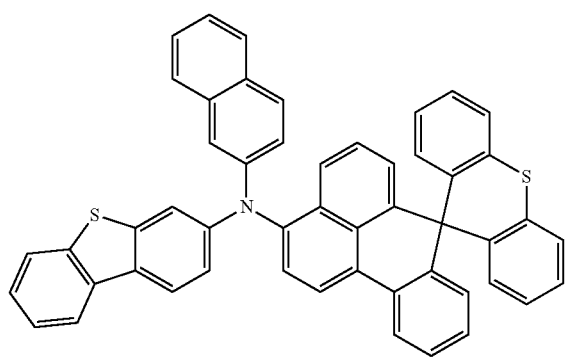

485
-continued
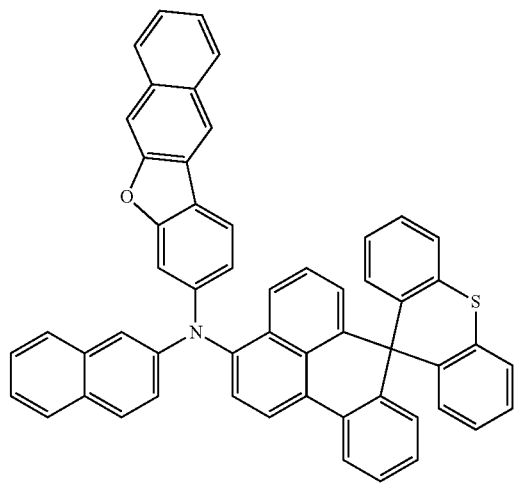
433
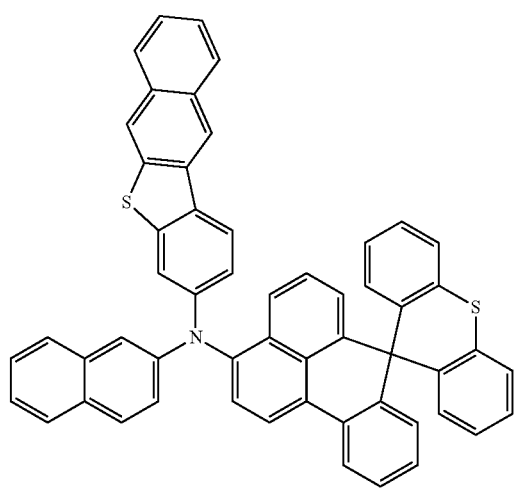
434
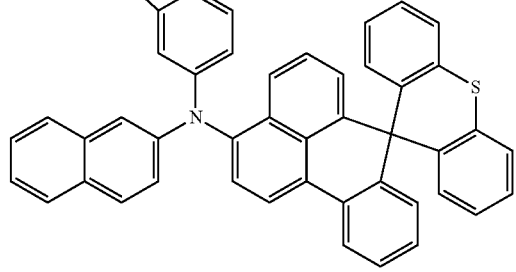
435
486
-continued
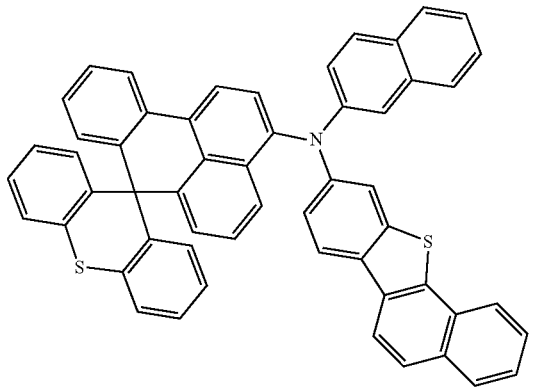
436
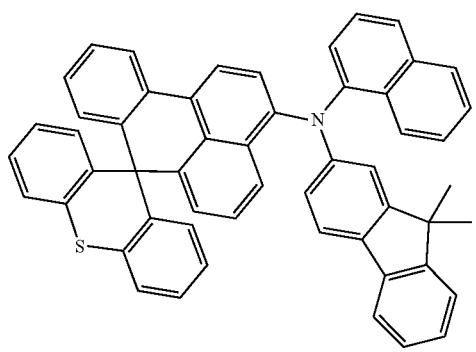
437
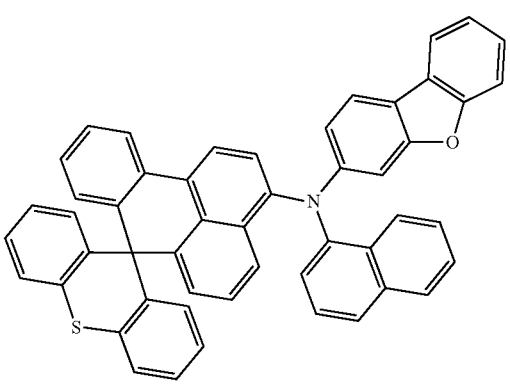
438
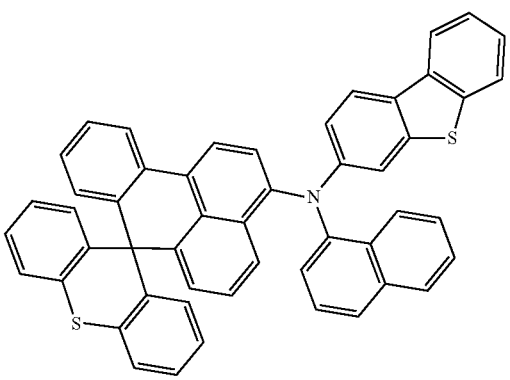
439

440
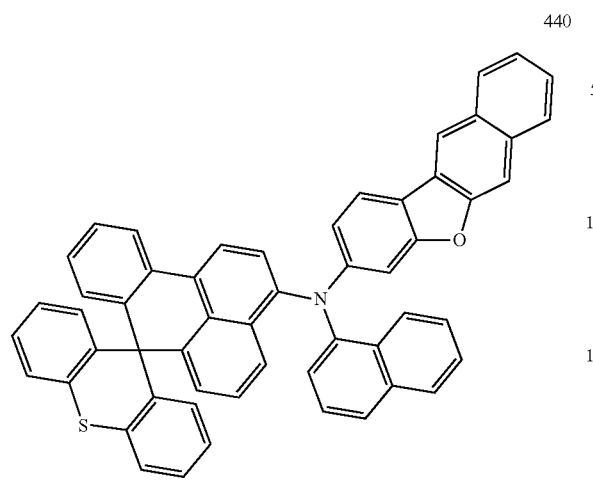
441
442
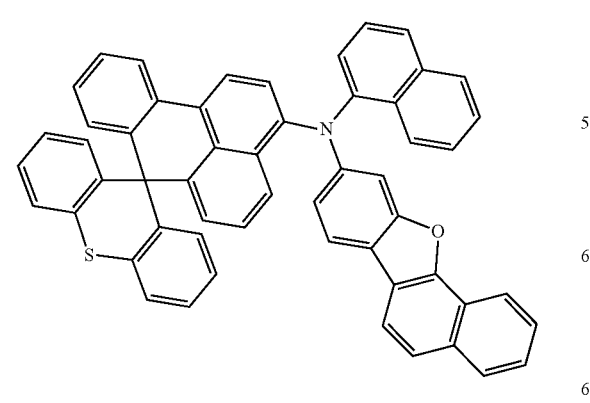
443
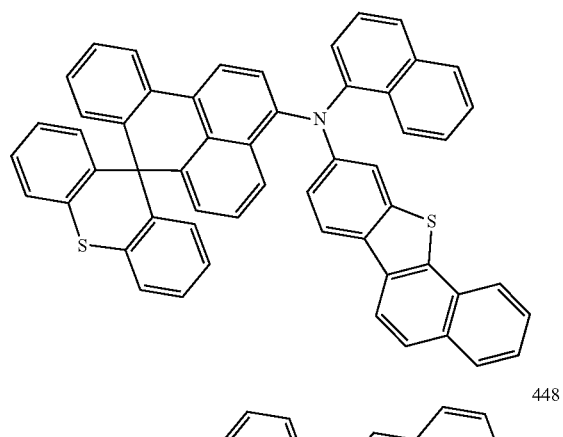
448
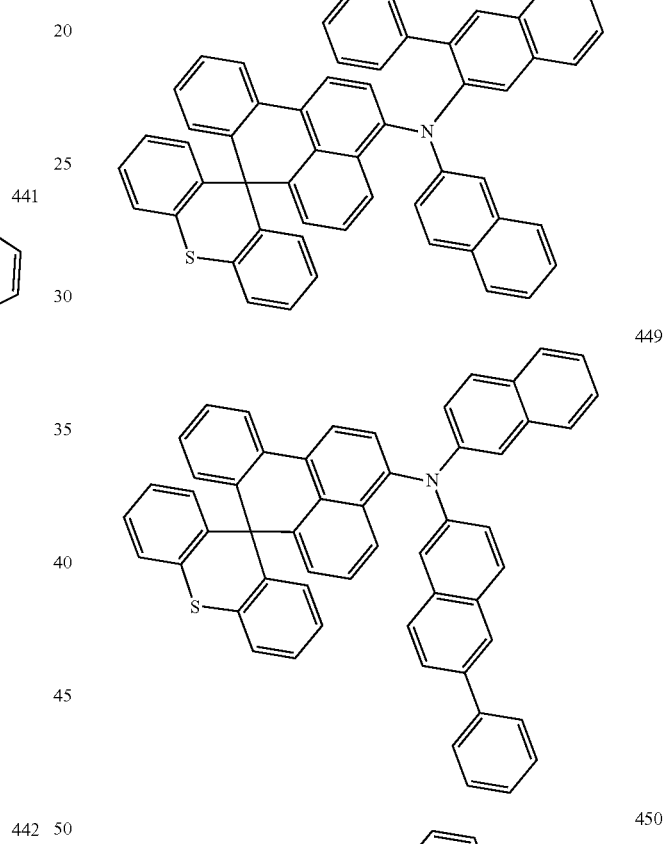
449
450
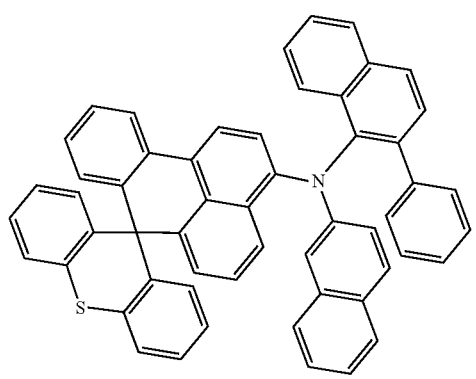

451
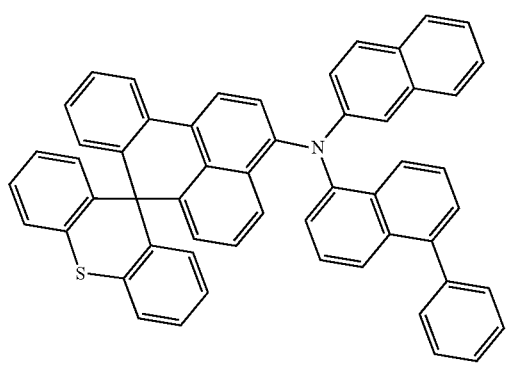
452
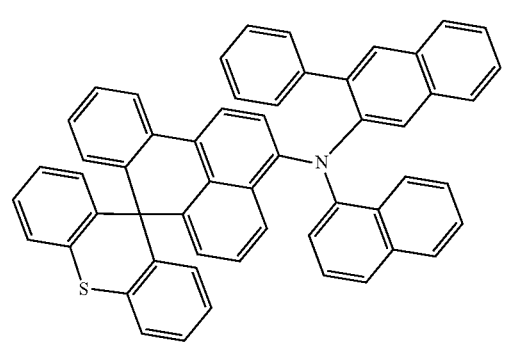
453
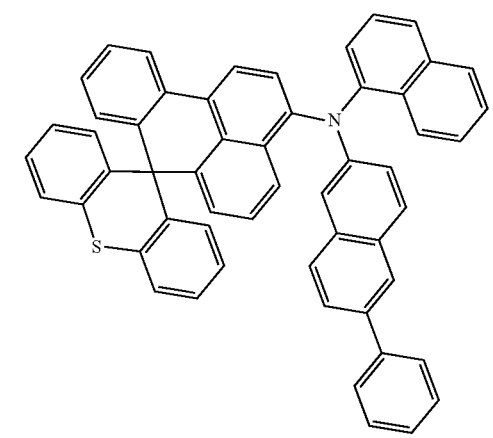
454
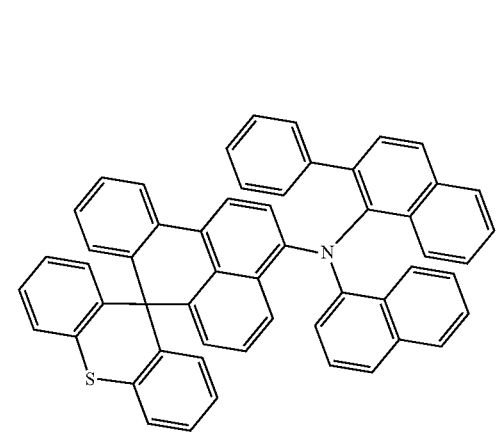
455
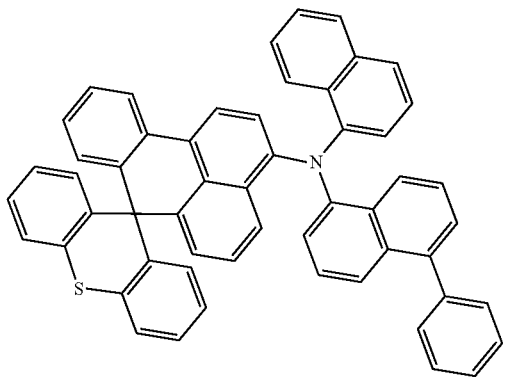
457

458
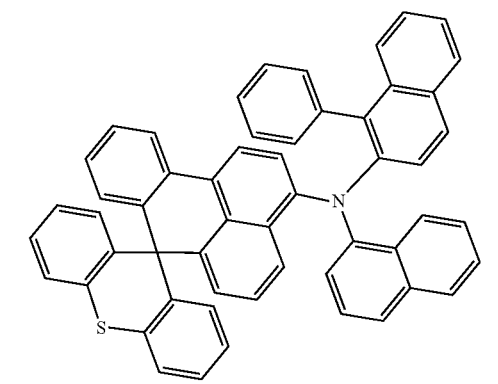

466
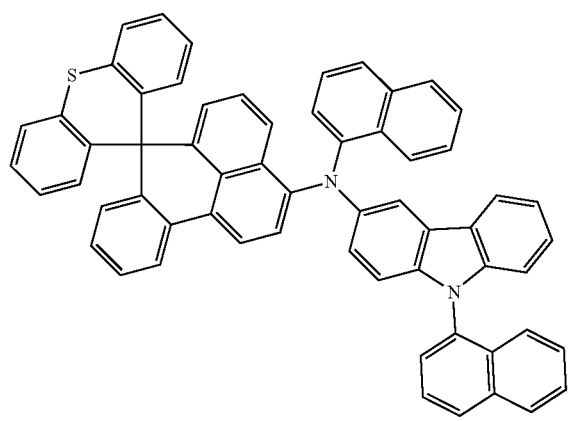
467
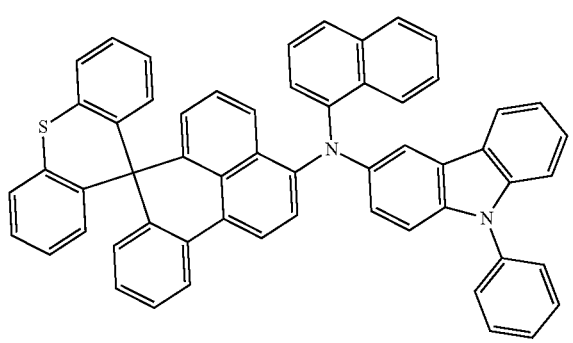
469
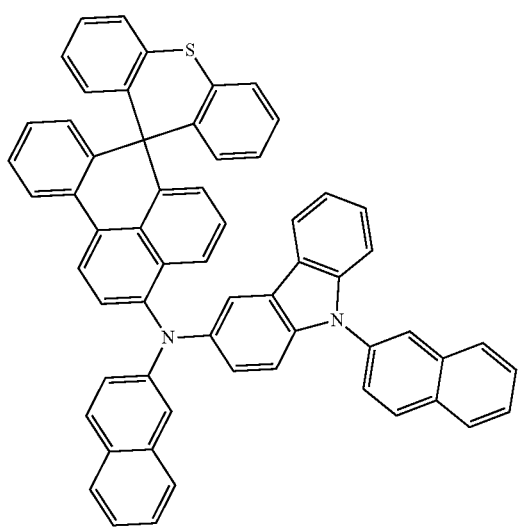
470
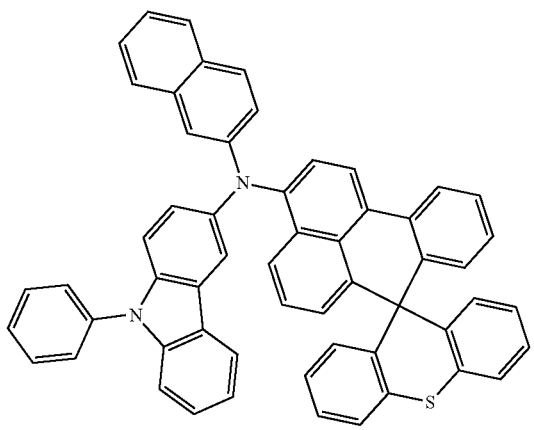
474
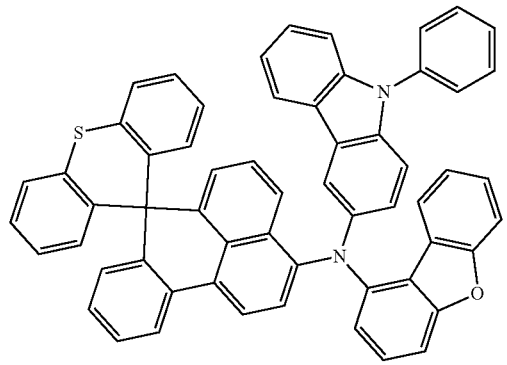
475
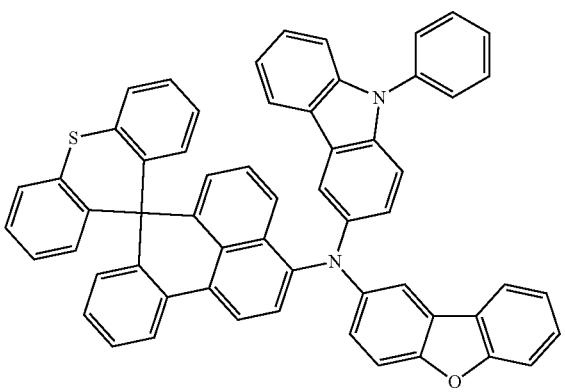

476
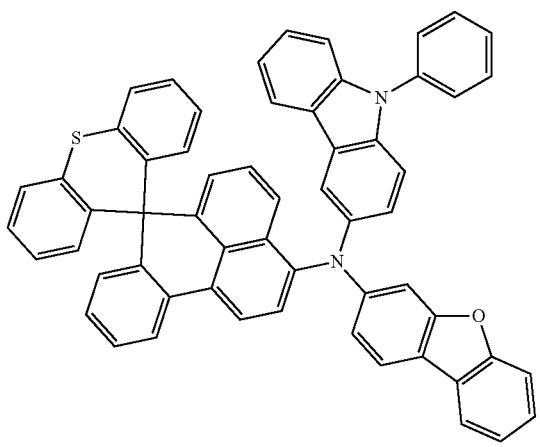
484
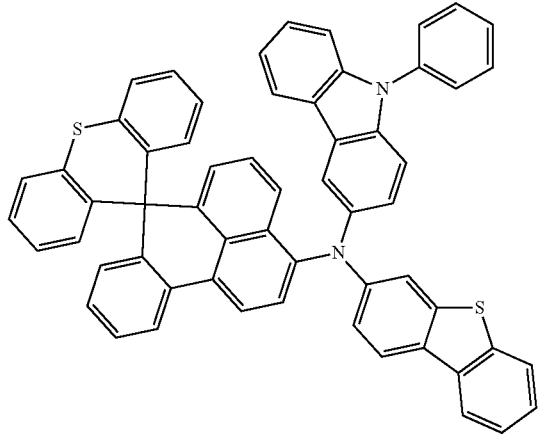
482
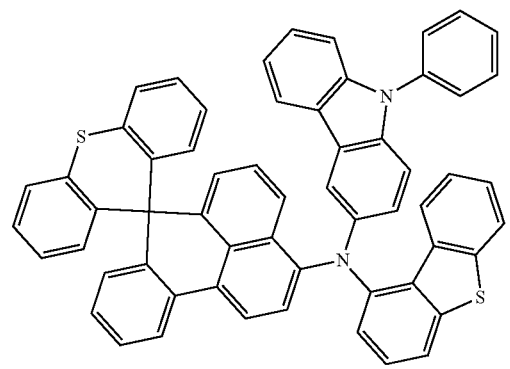
485
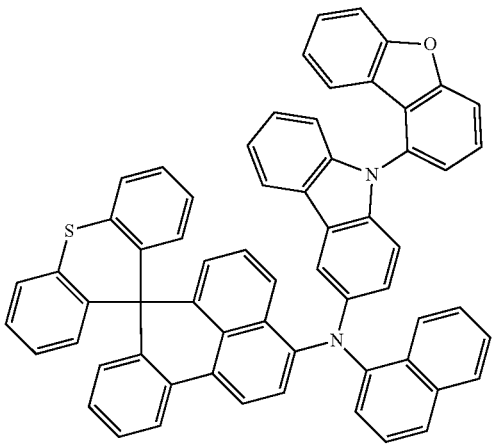
483
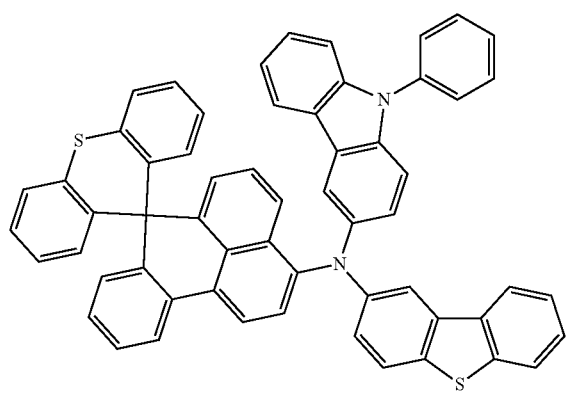
486
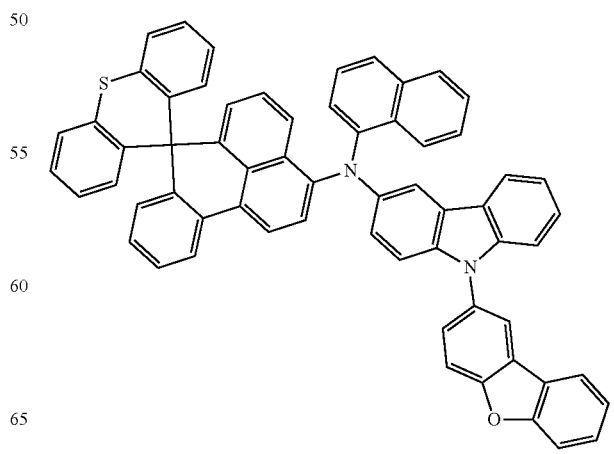

-continued
487
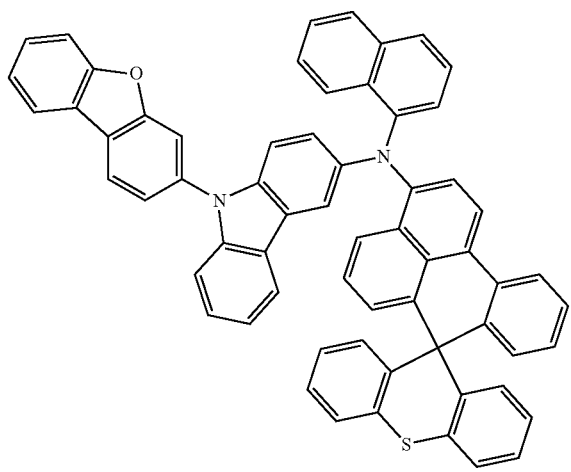
488
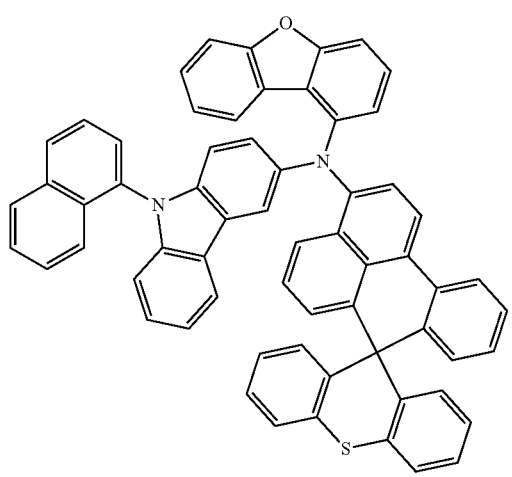
489
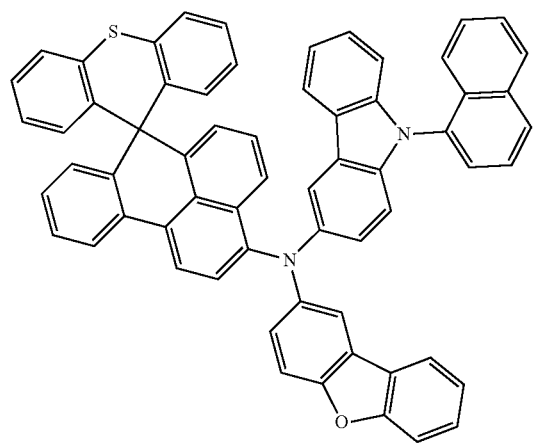
-continued
490
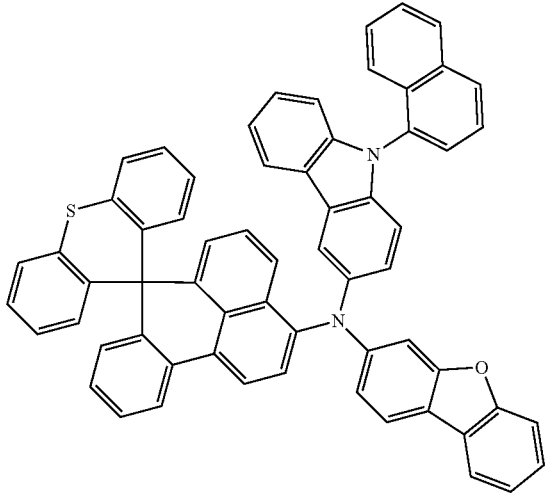
491
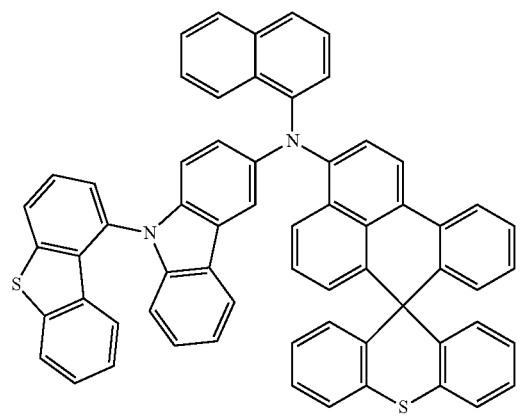
492
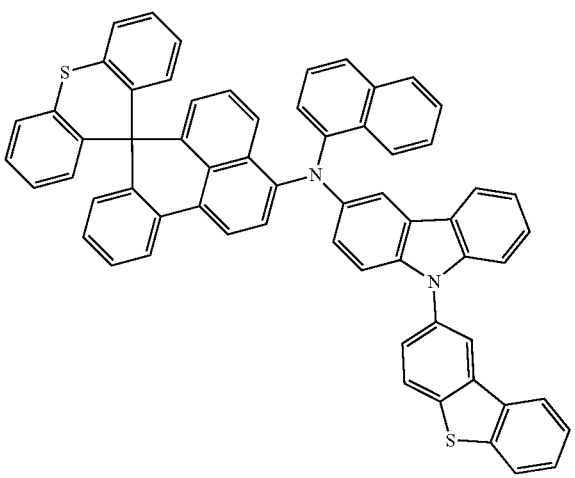

497
-continued
498
-continued
493
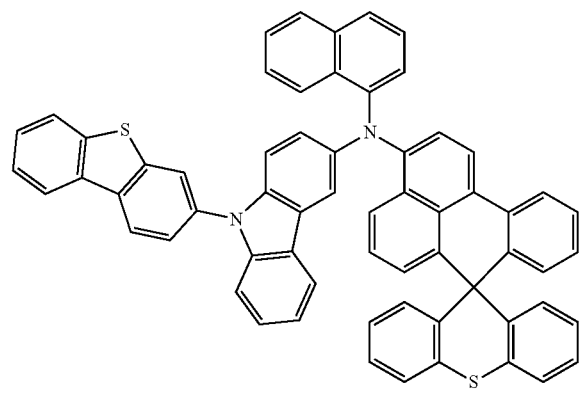
496
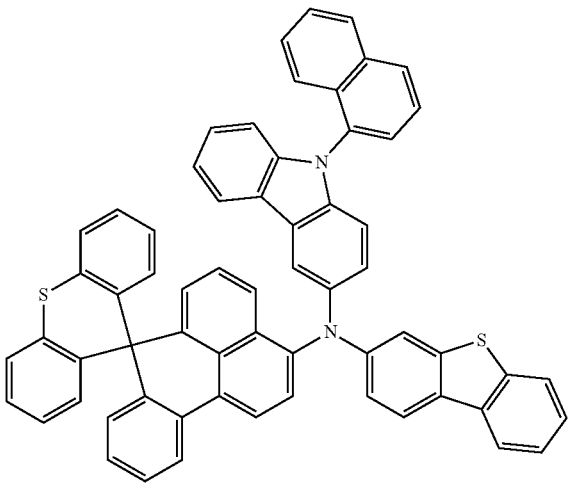
494
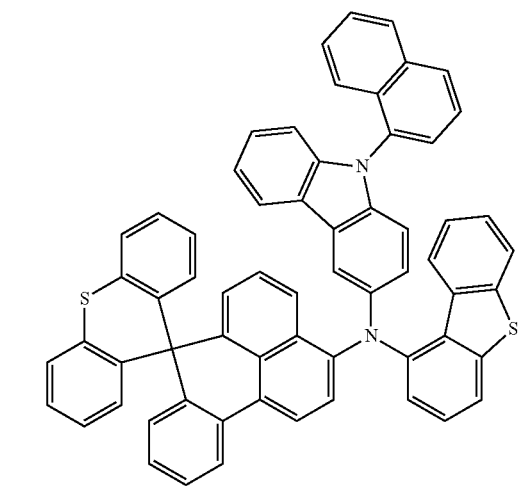
500
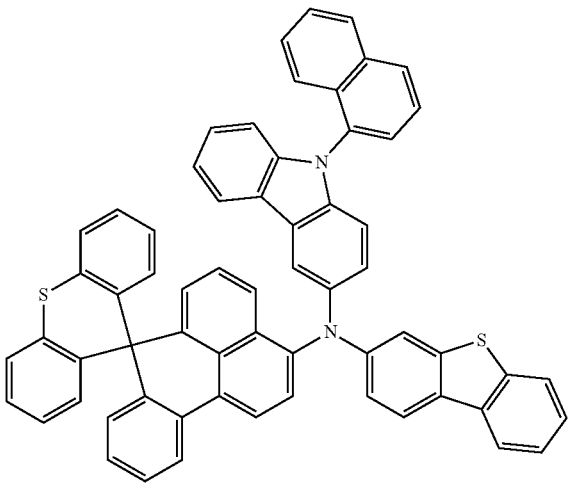
495
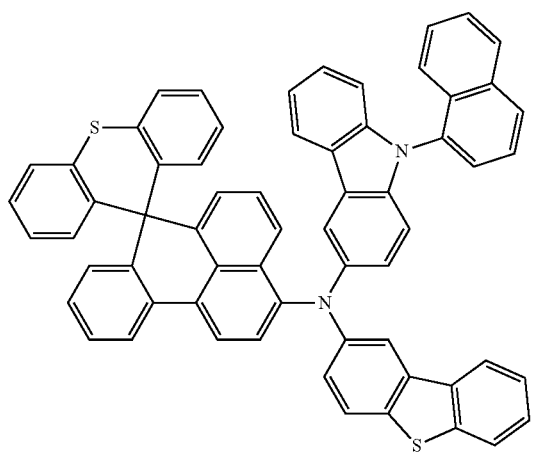
501
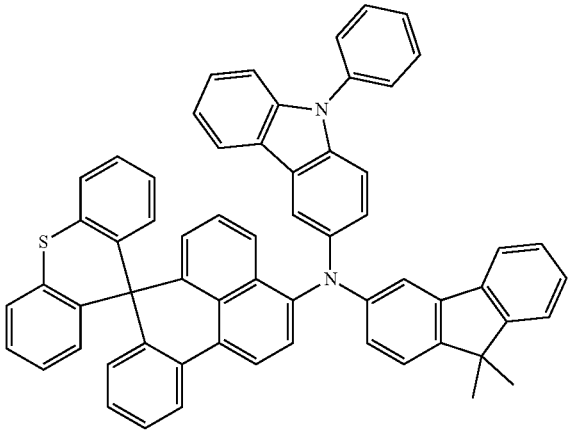

499
-continued
502
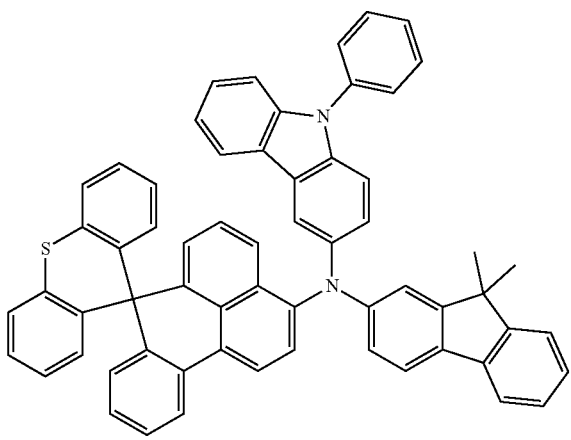
510
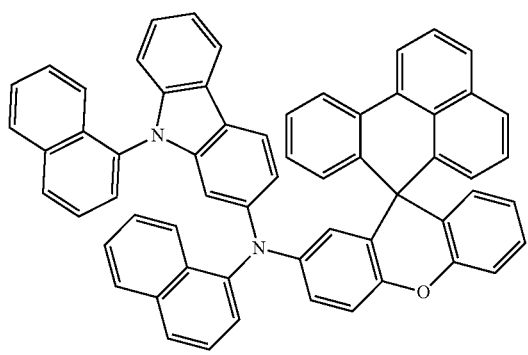
511
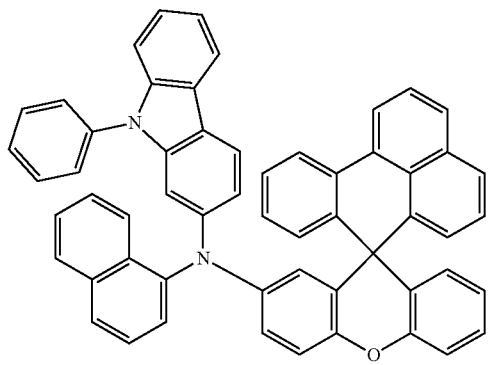
513
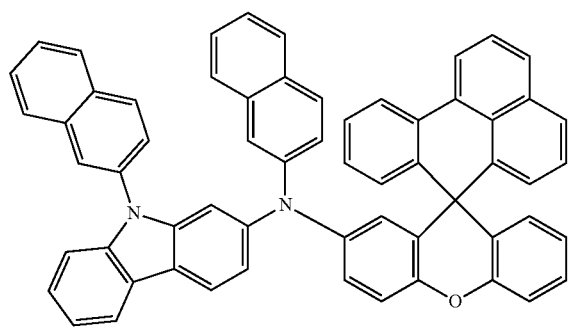
500
-continued
514
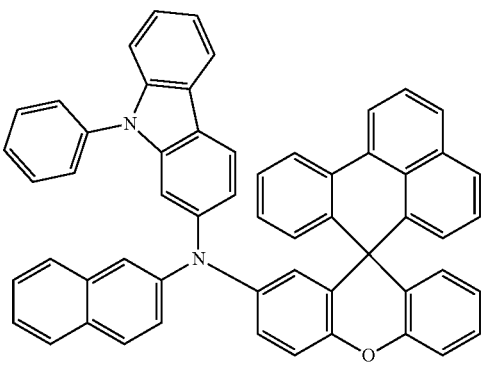
518
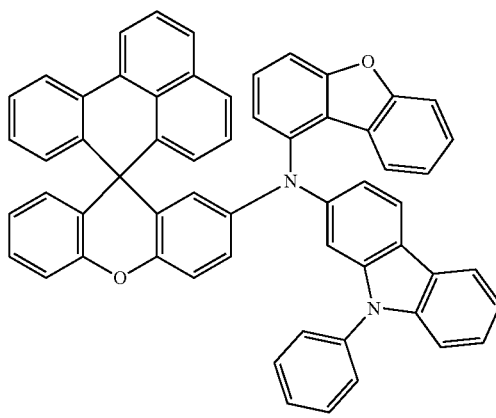
519
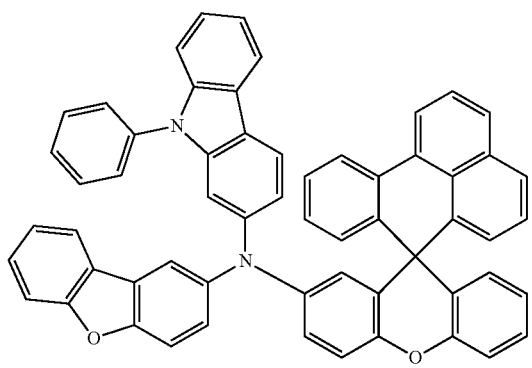
520
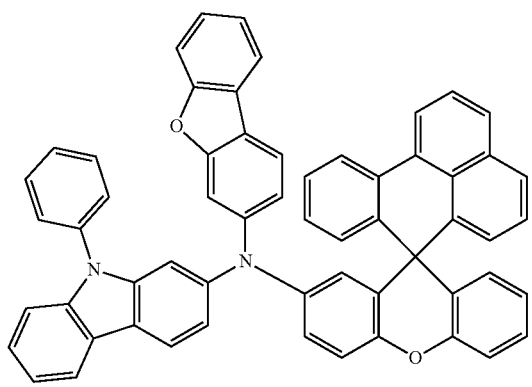

-continued
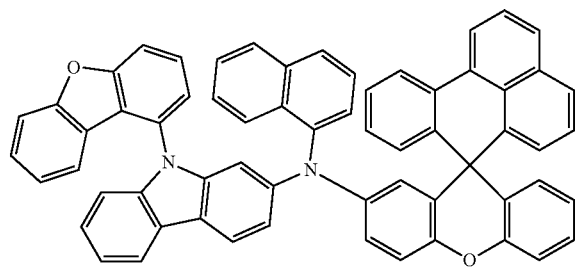
521
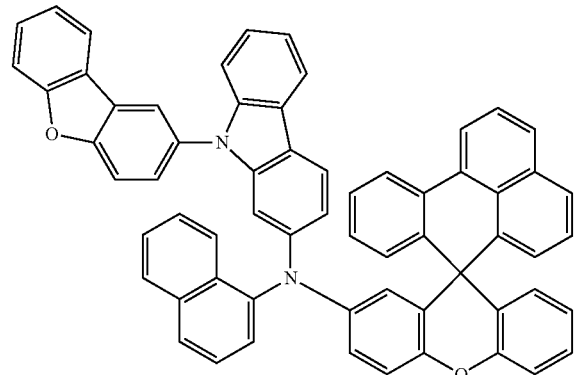
523
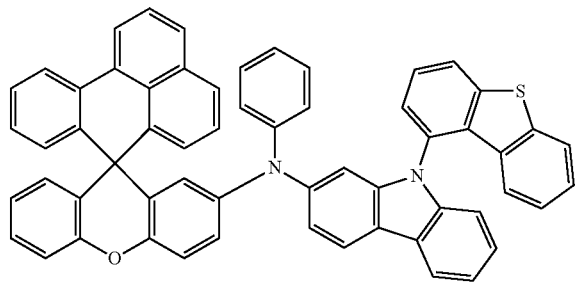
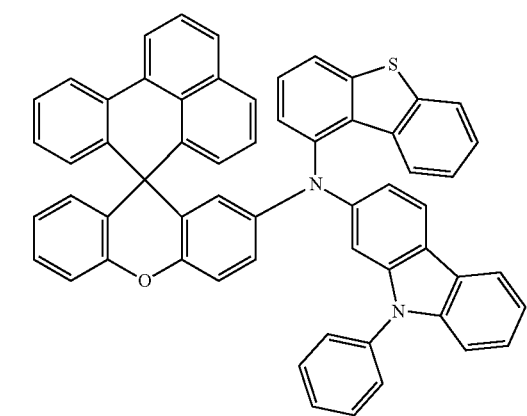
526
-continued
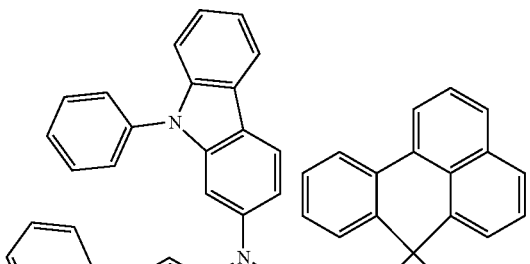
527
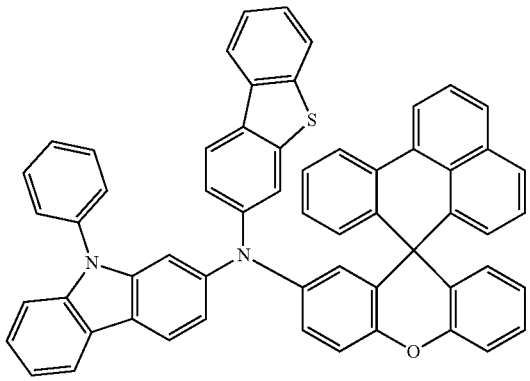
528
529
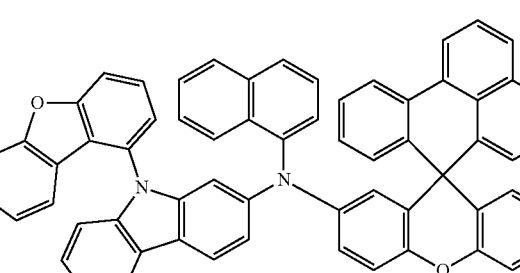
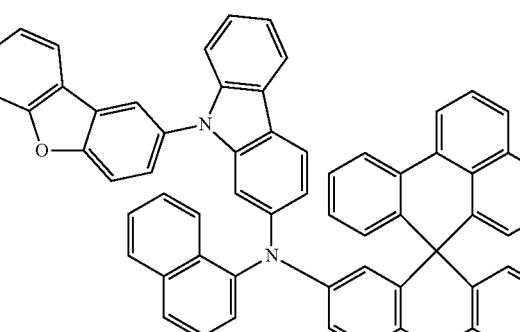
530

-continued
531
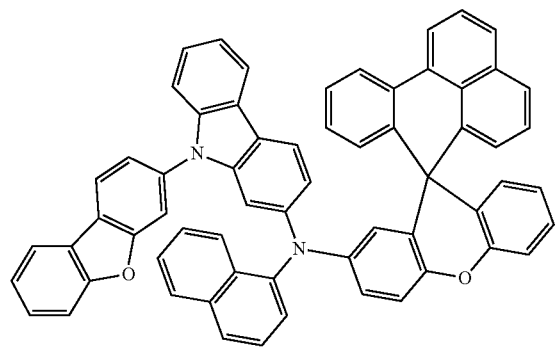
532
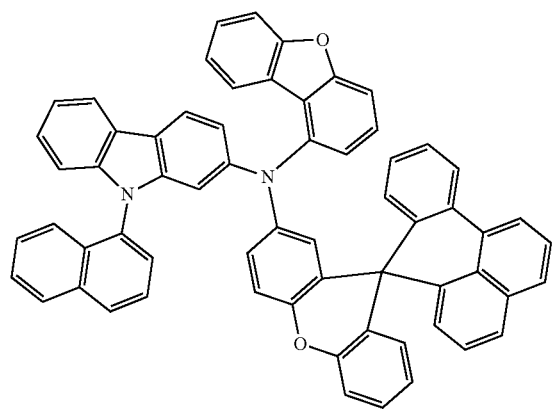
533
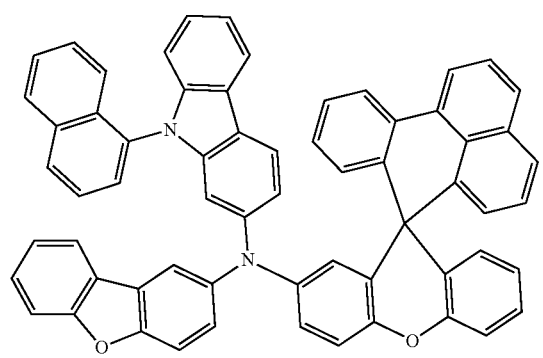
534
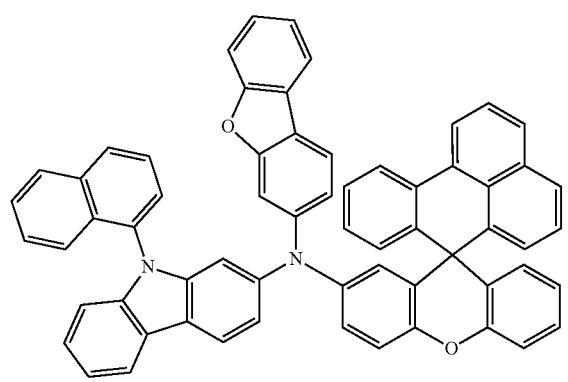
535
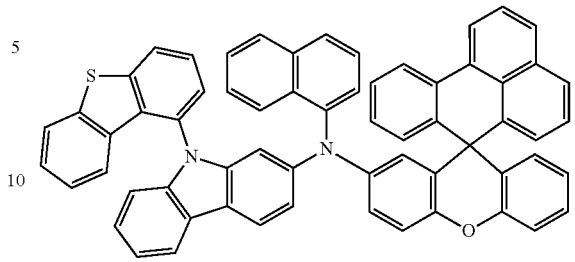
536
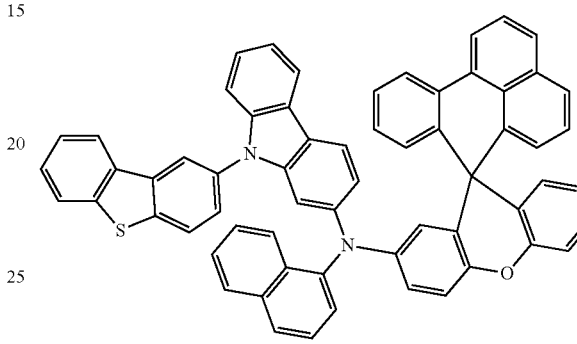
537
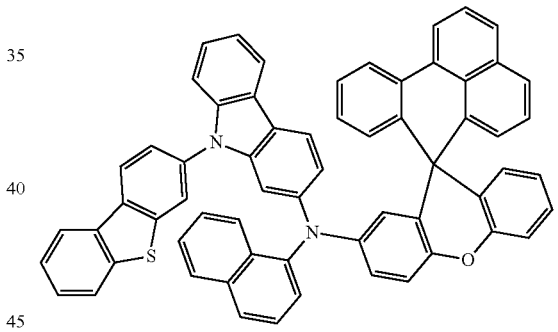
538
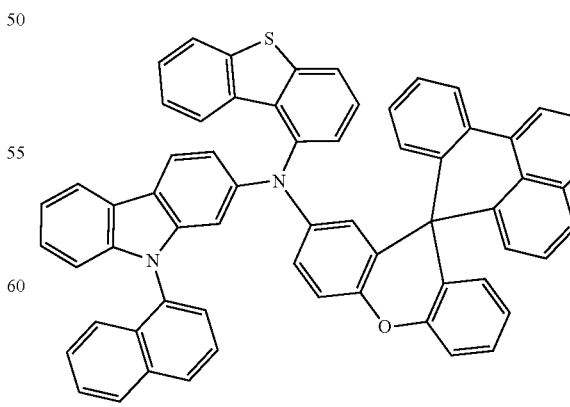

505
-continued
539
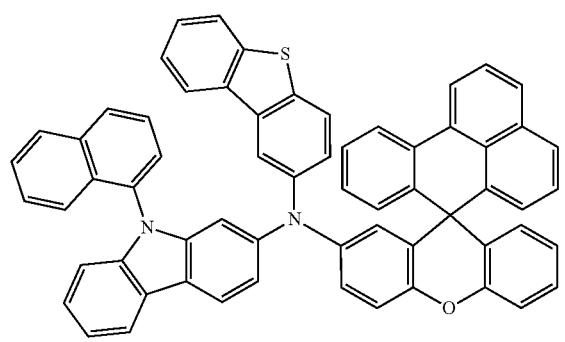
540
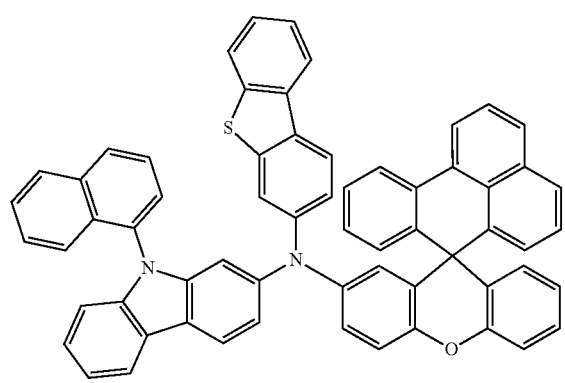
544
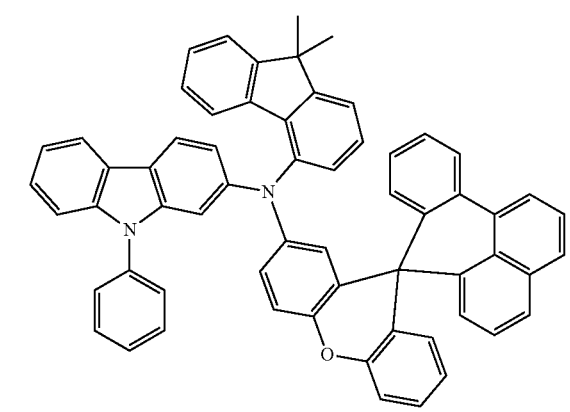
545
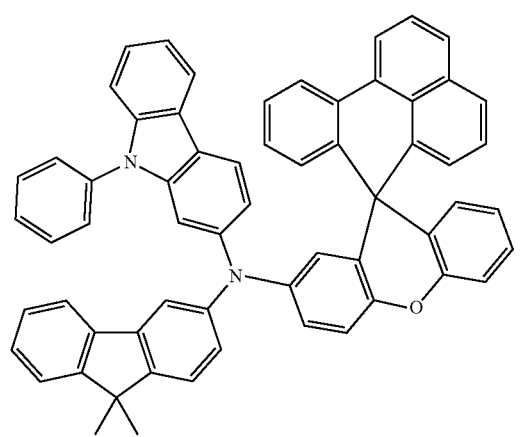
506
-continued
546
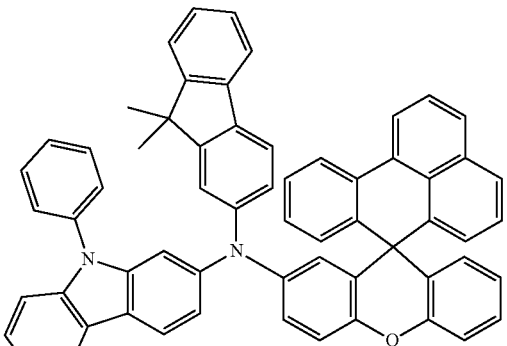
554
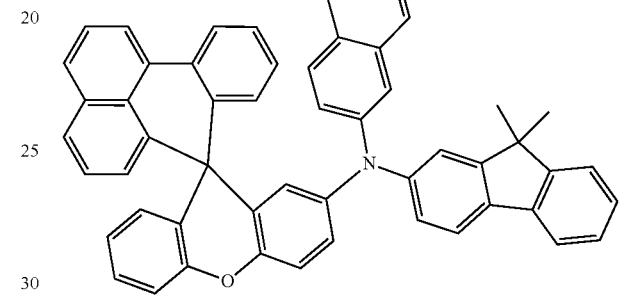
555
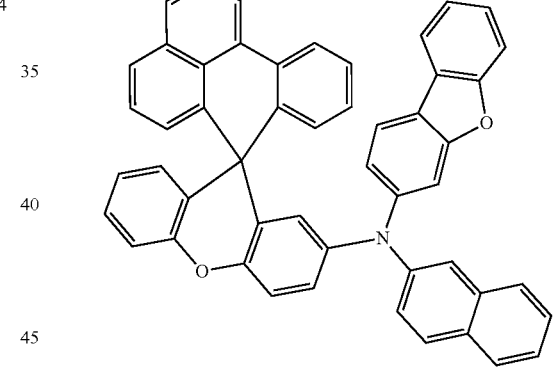
556
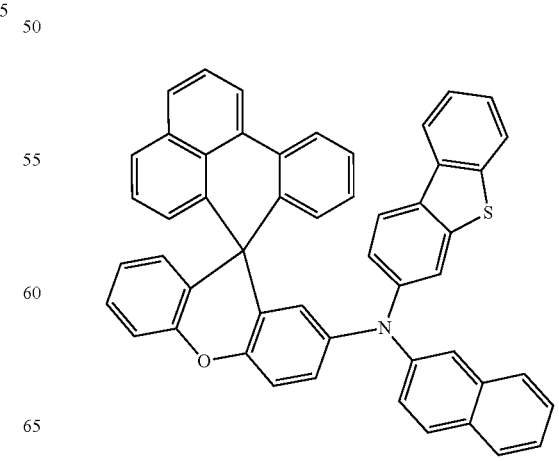

557
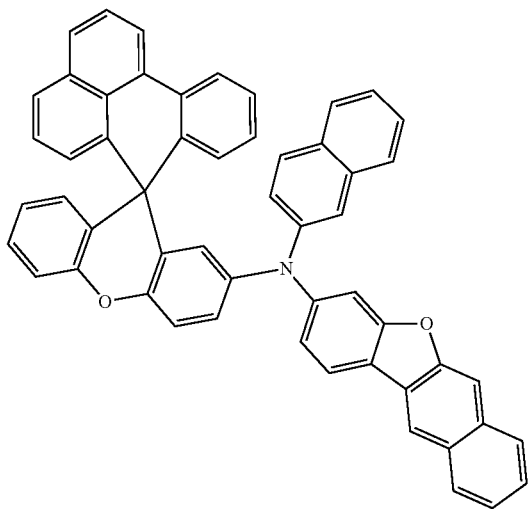
558
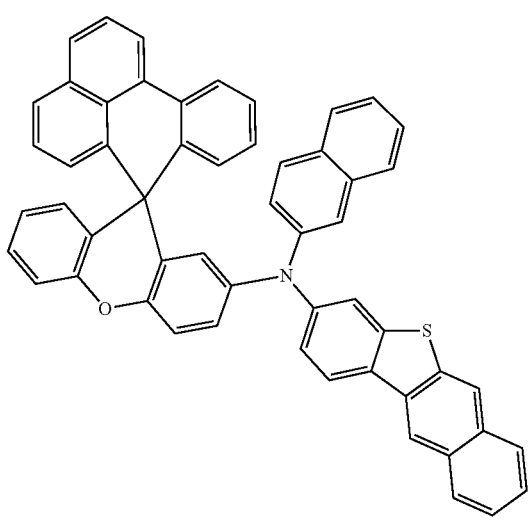
559
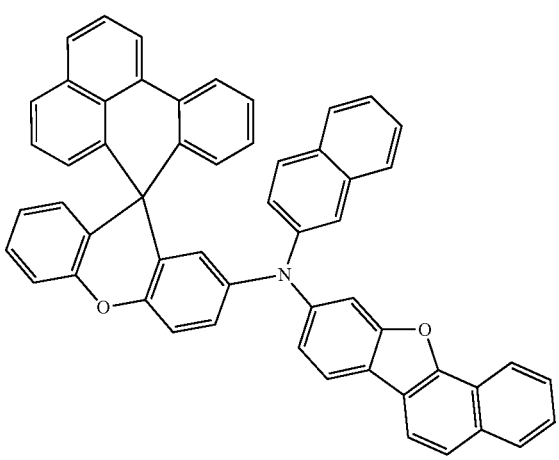
560
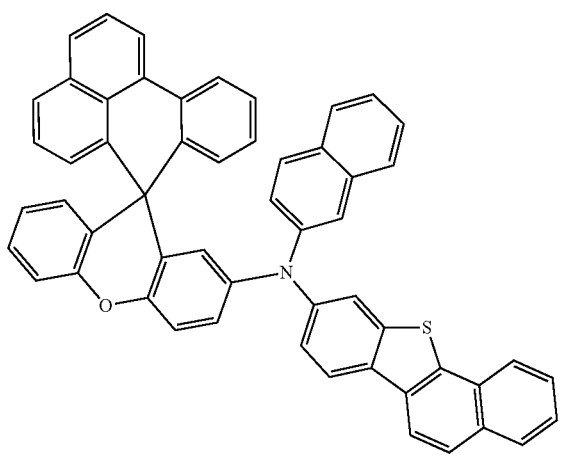
561
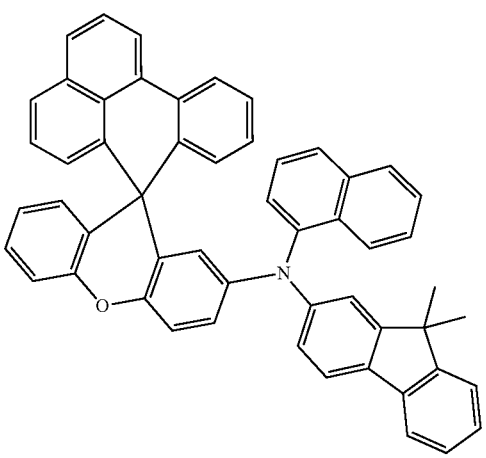
562
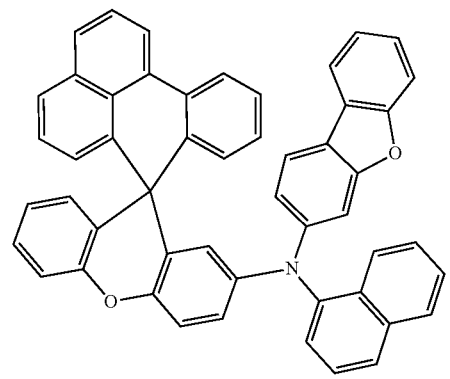

509
-continued
563
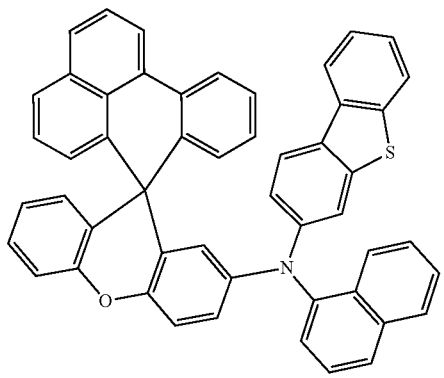
564
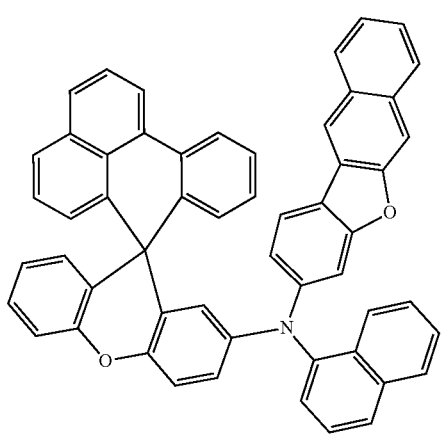
565
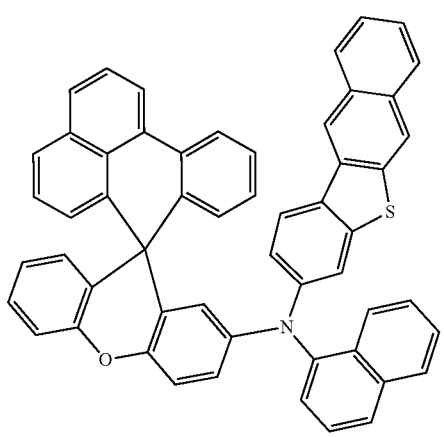
510
-continued
566
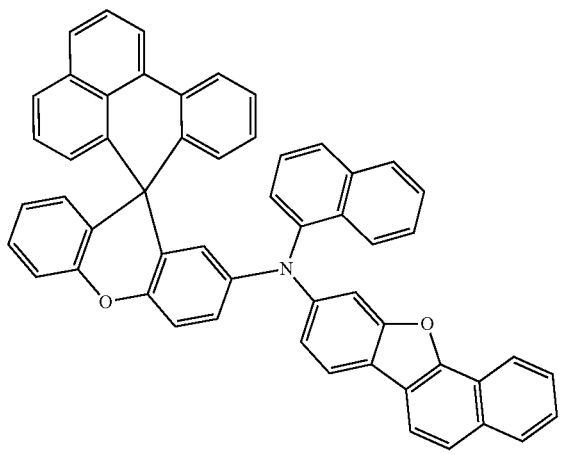
567
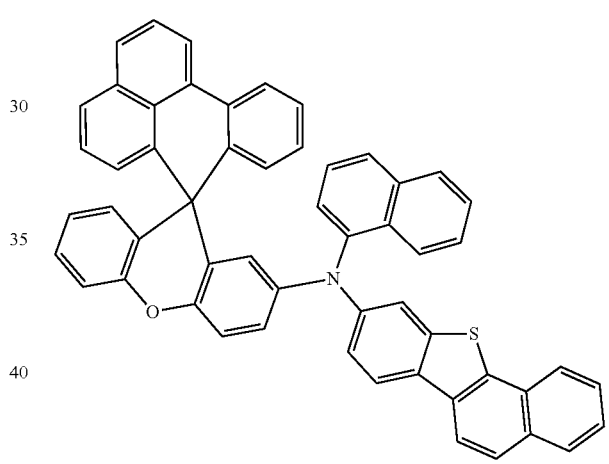
572
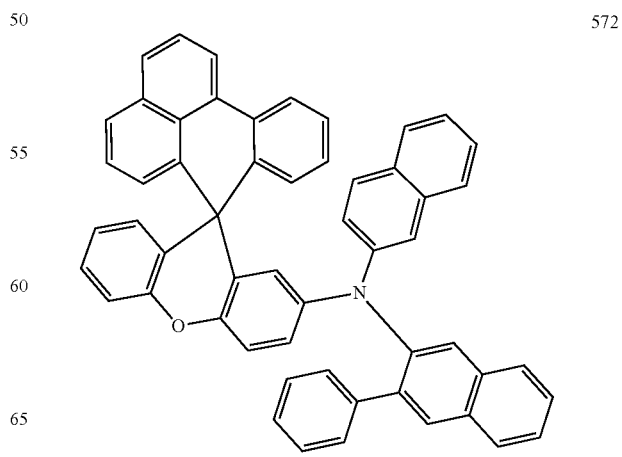

511
-continued
573
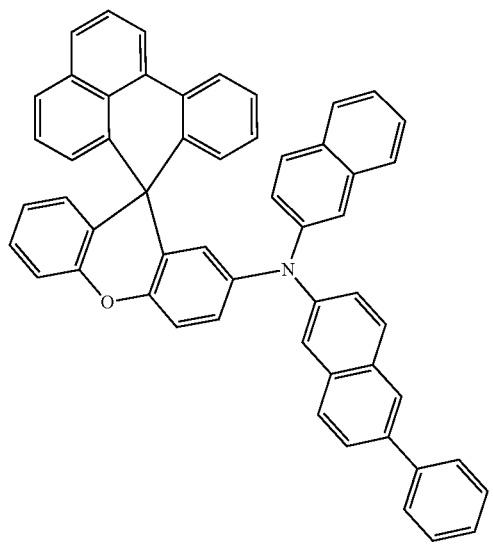
574
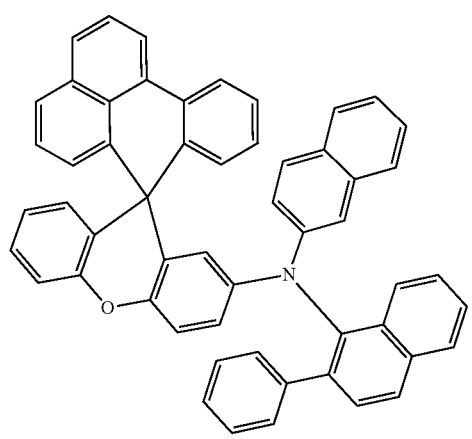
575
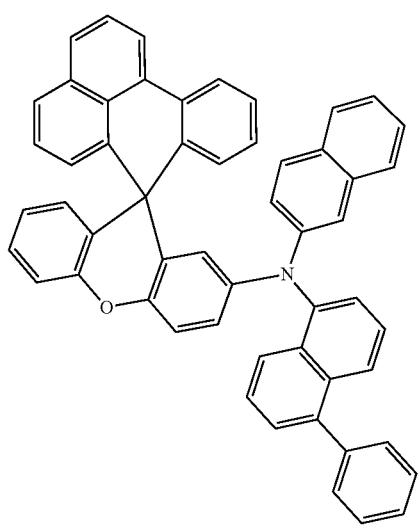
512
-continued
576
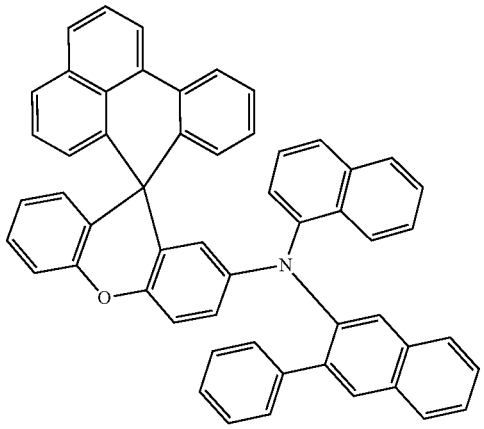
577
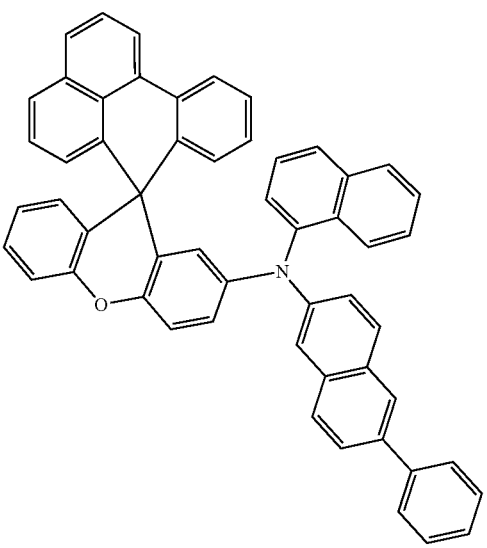
578
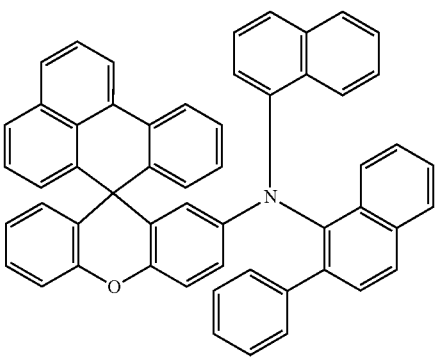

513
-continued
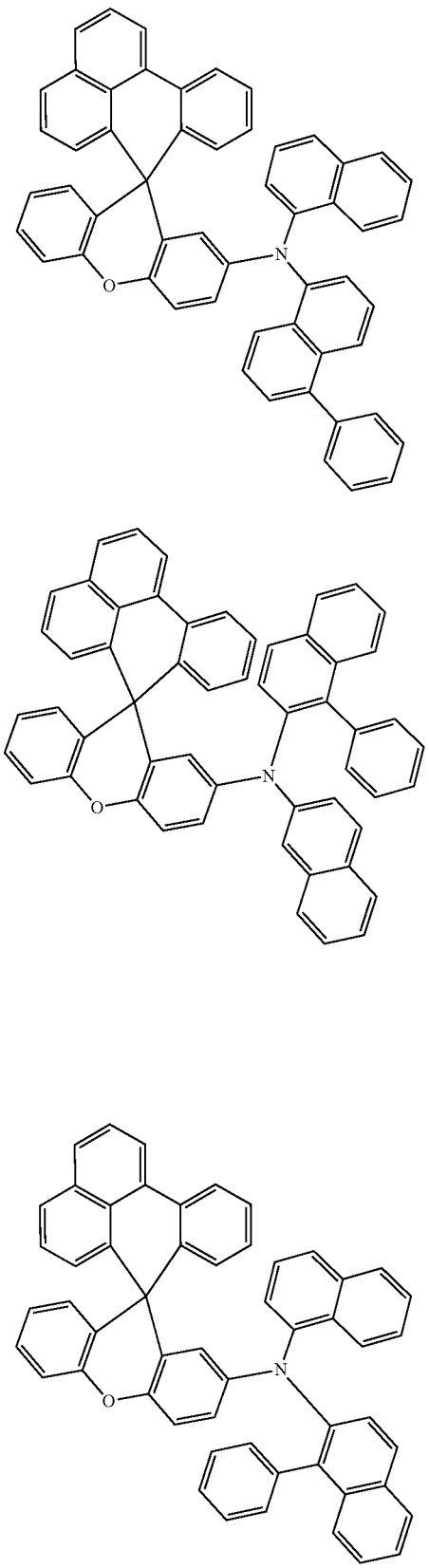
514
-continued
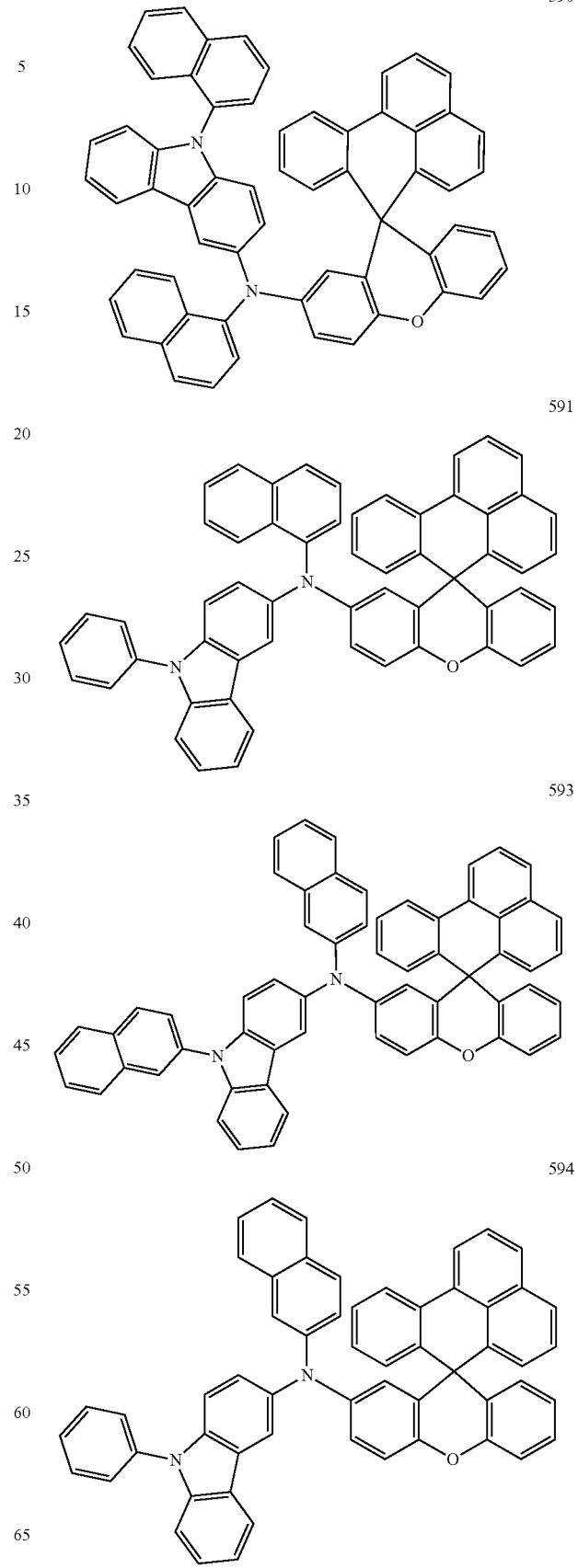

598
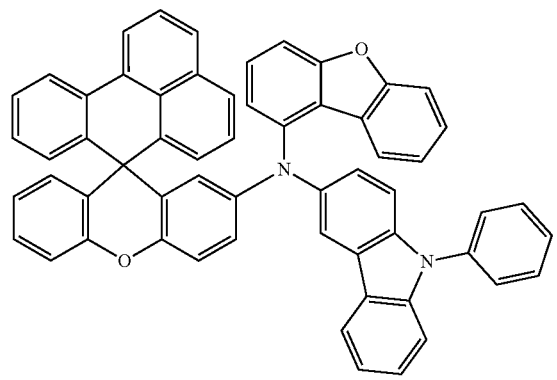
599
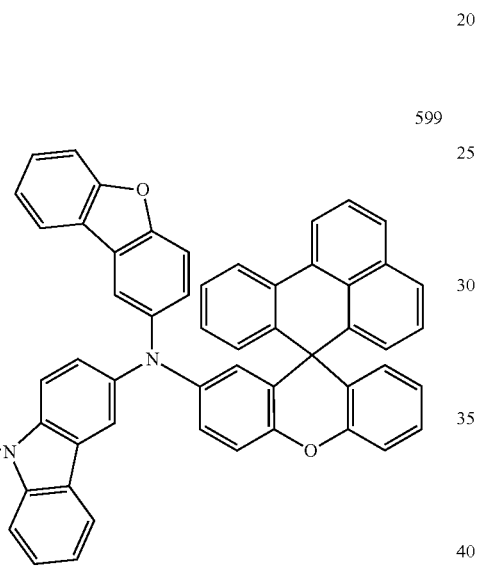
600
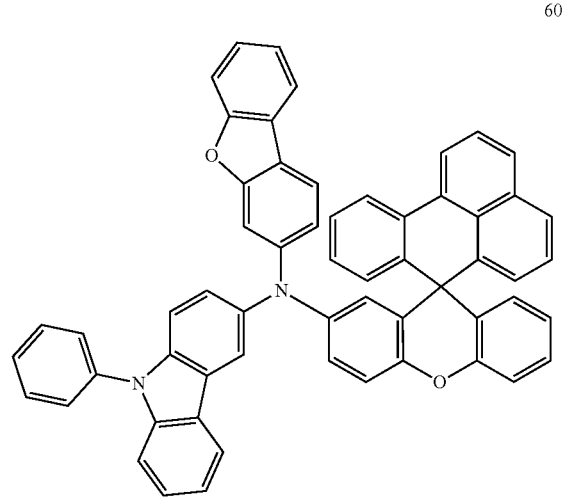
606
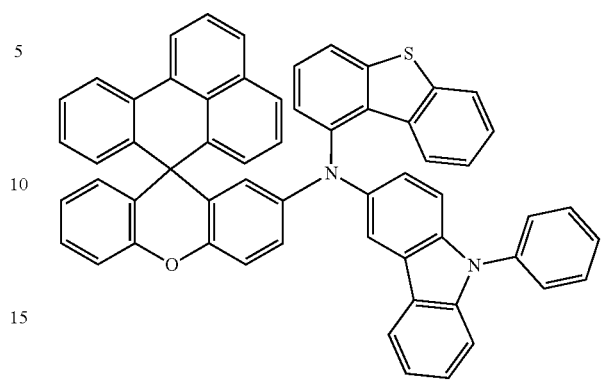
607
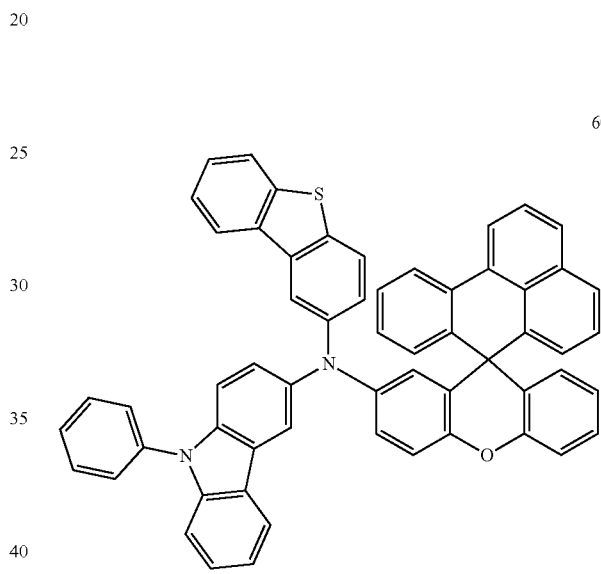
608
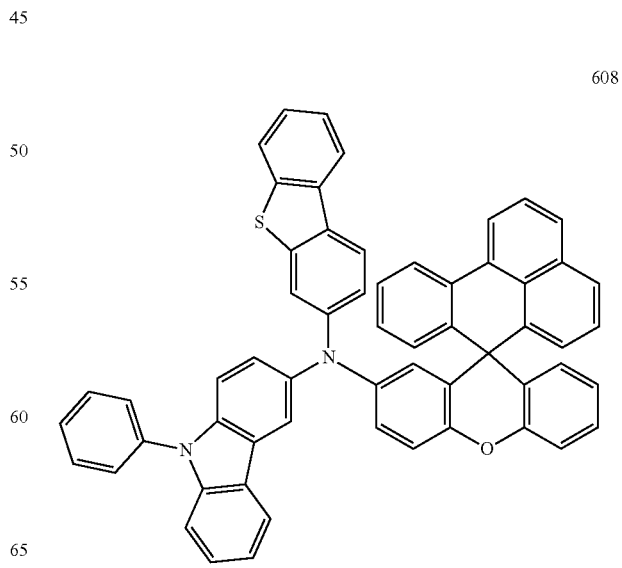

609
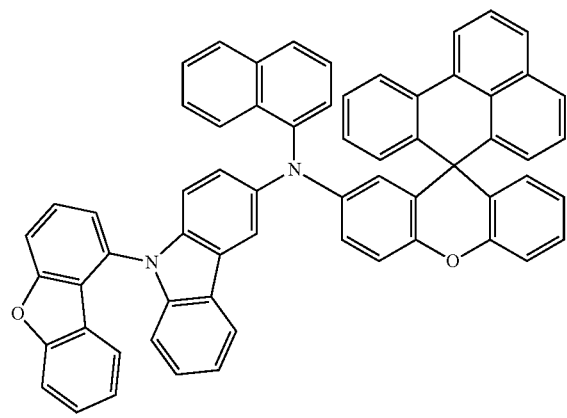
610
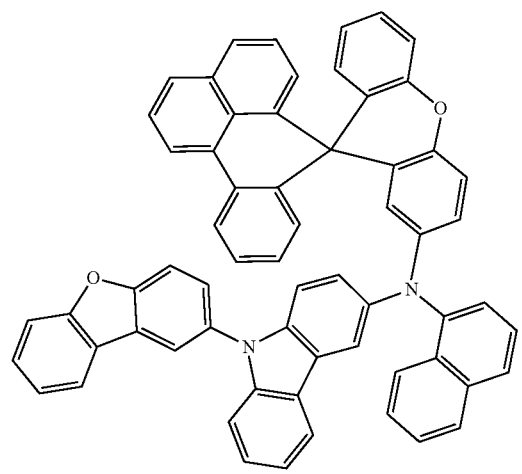
611
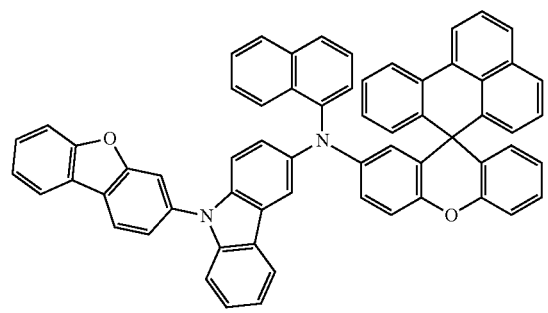
612
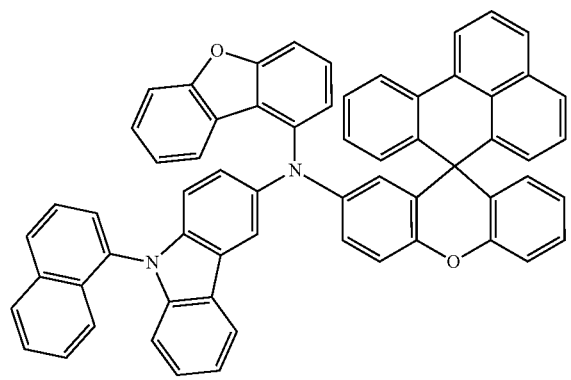
613
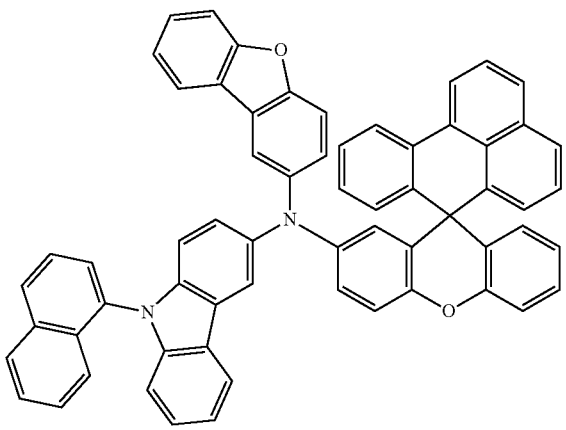
614
615
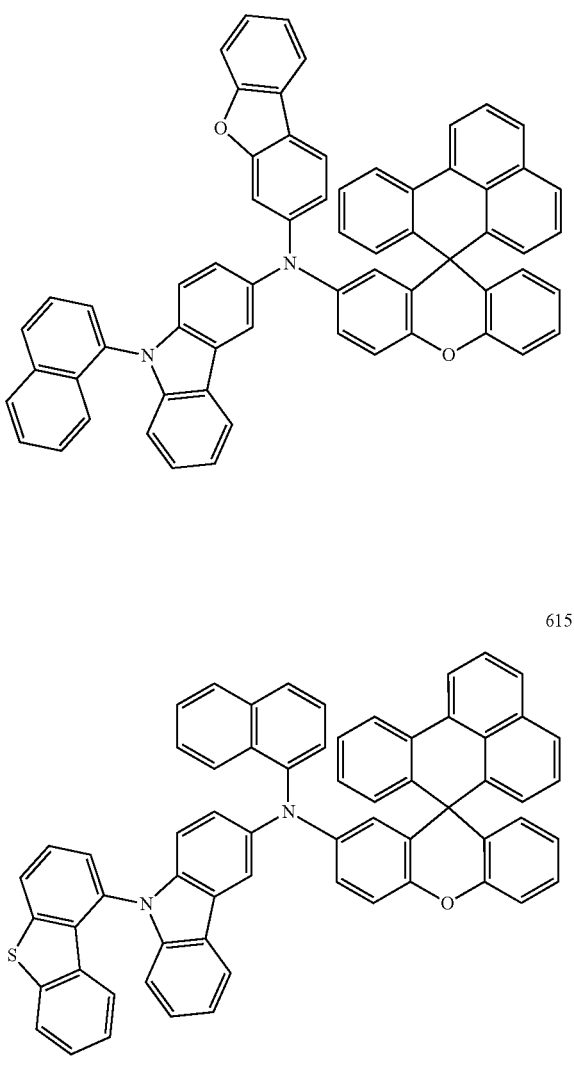

-continued
616
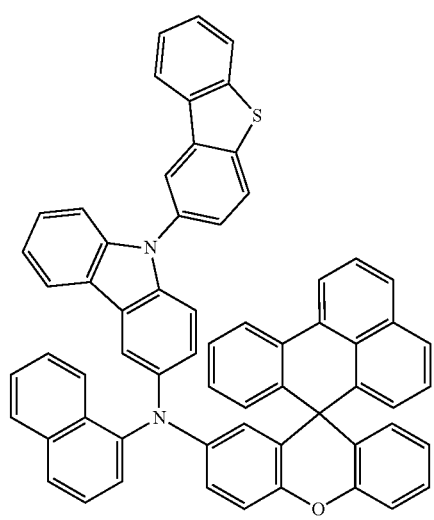
617
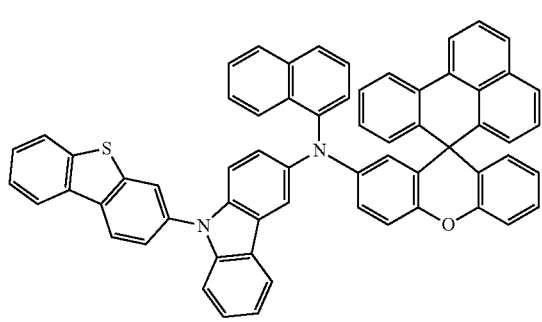
618
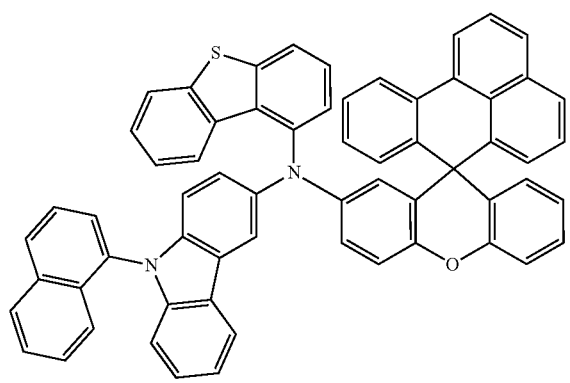
-continued
619
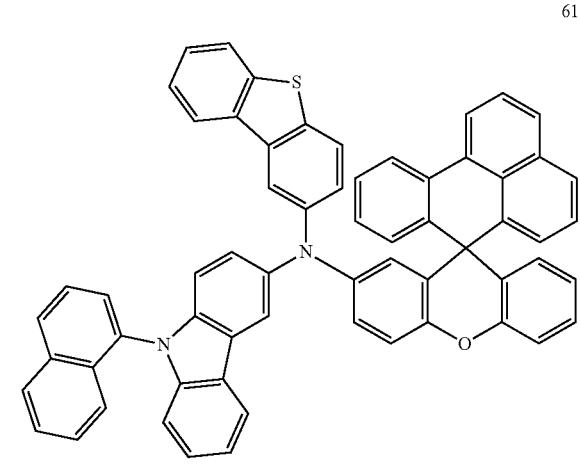
620
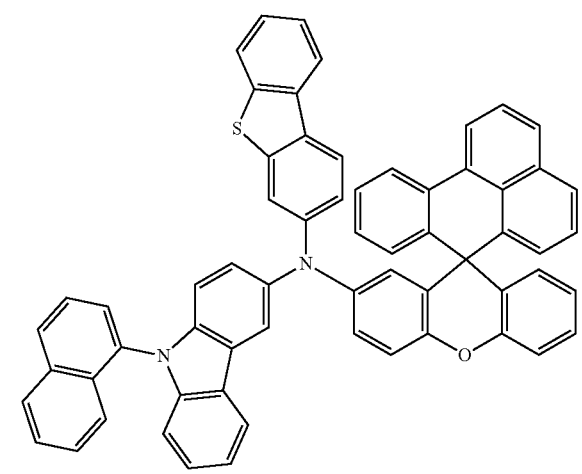
624
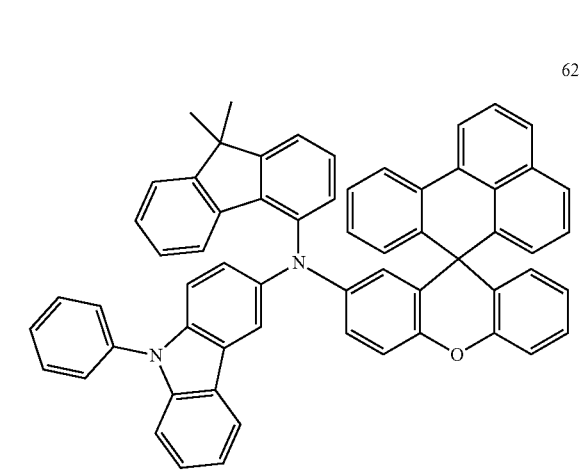

521
-continued
625
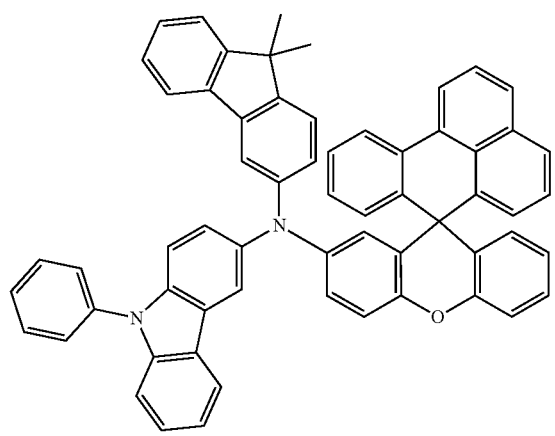
626
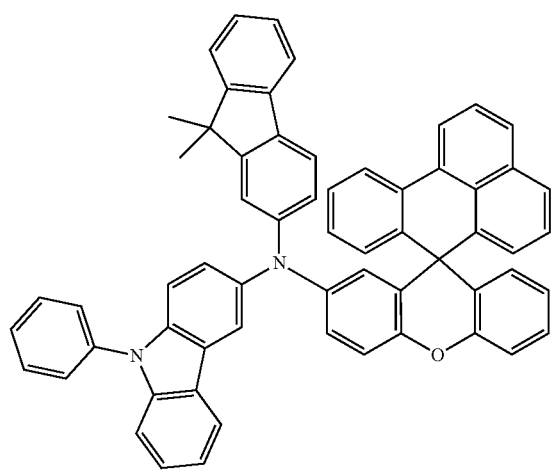
634
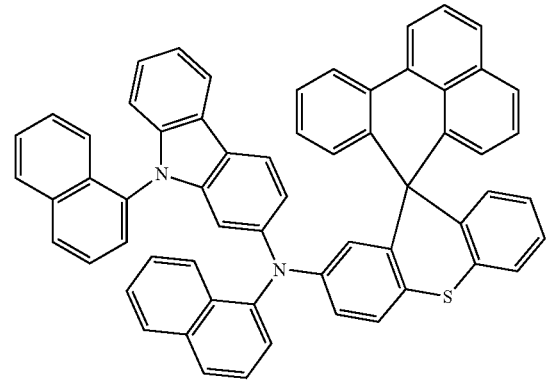
522
-continued
635
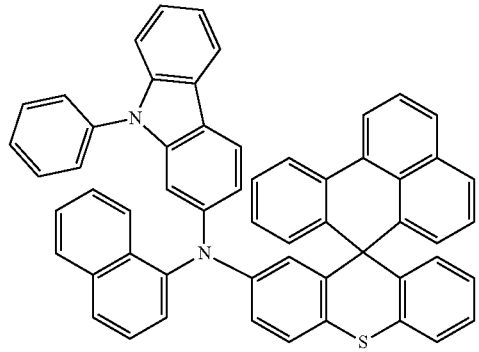
637
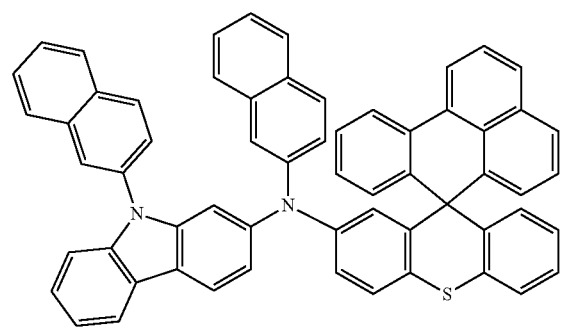
638
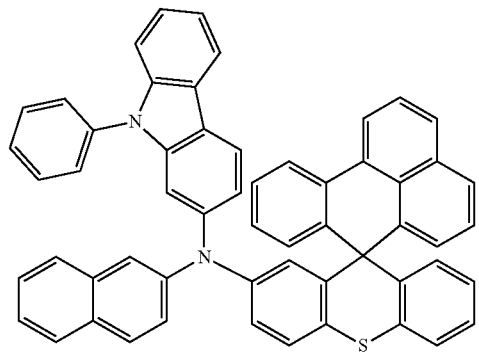
642
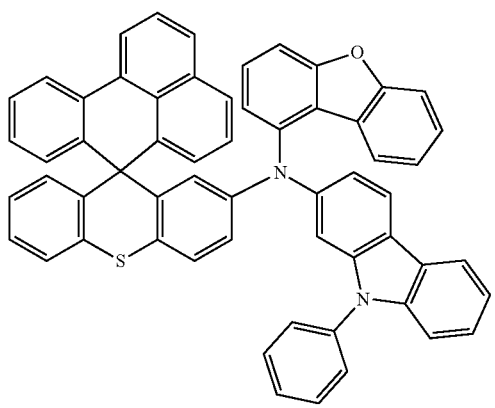

523
-continued
643
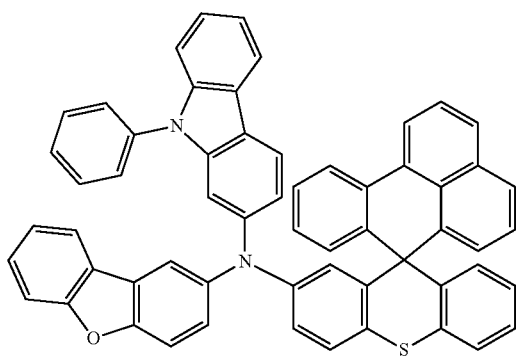
644
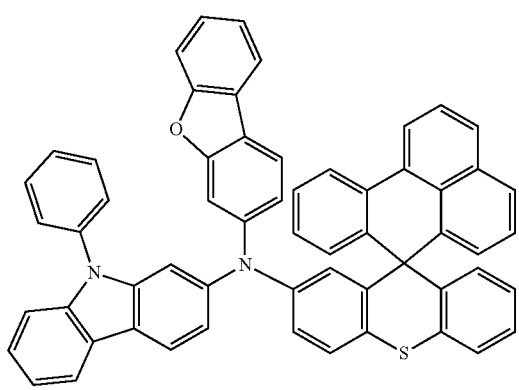
650
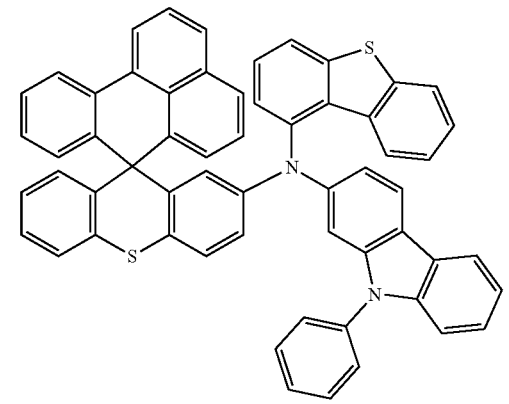
651
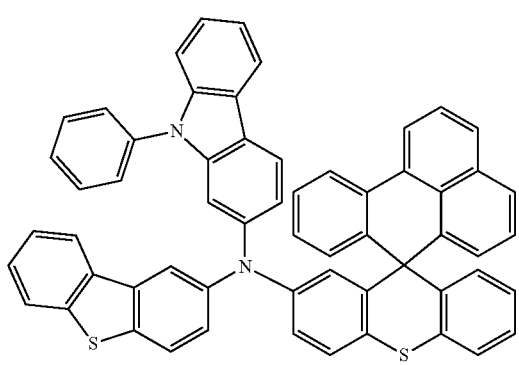
524
-continued
652
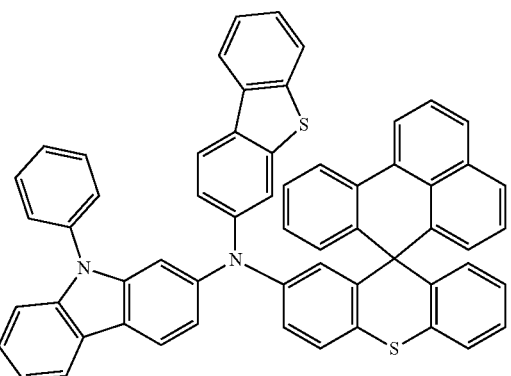
653
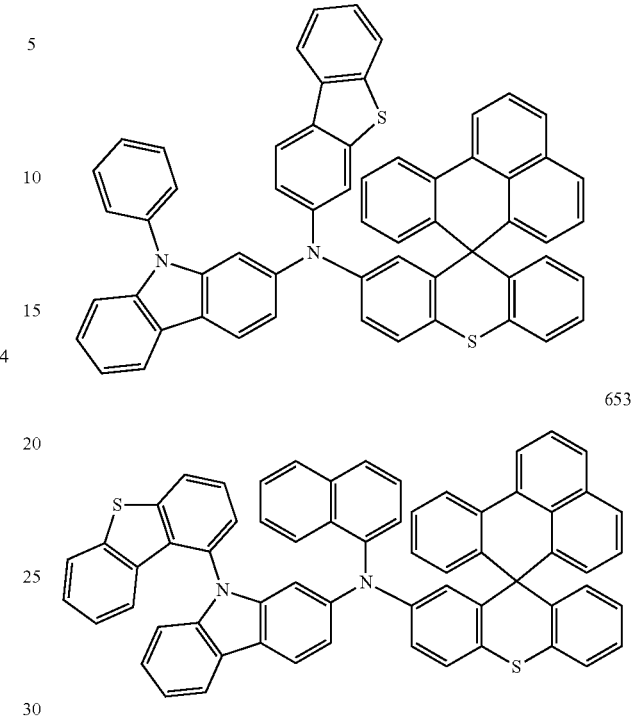
654
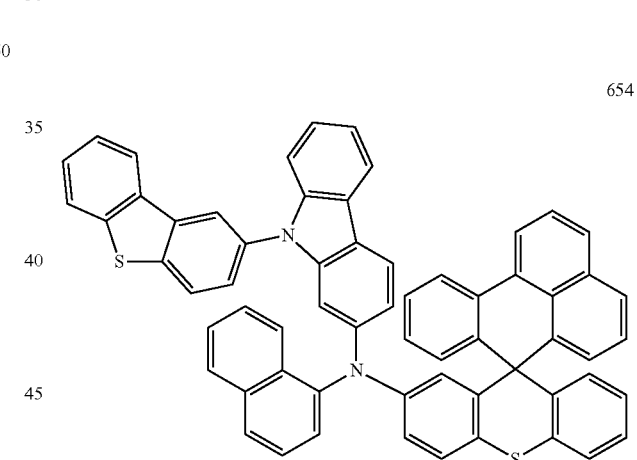
655
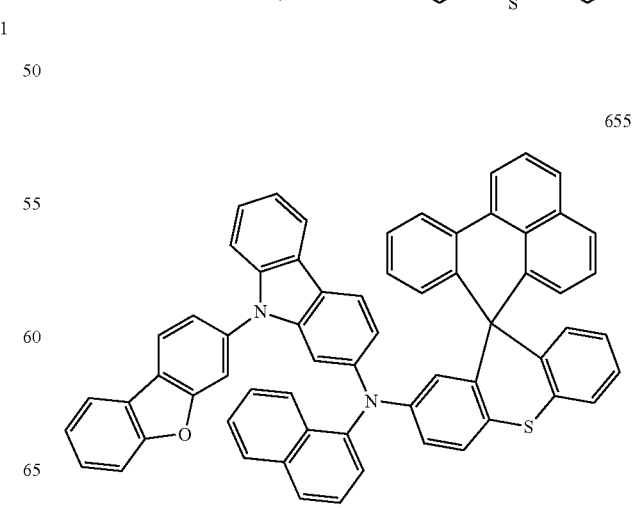

656
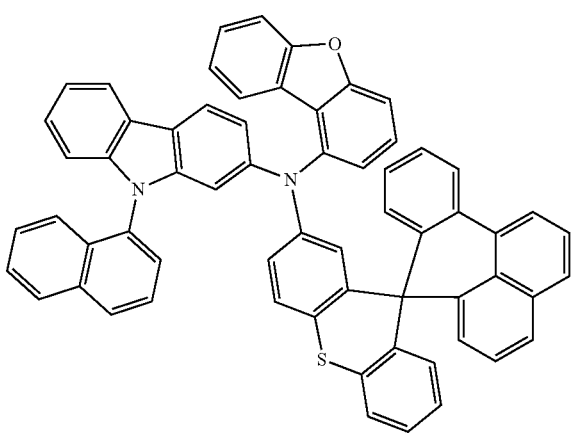
657
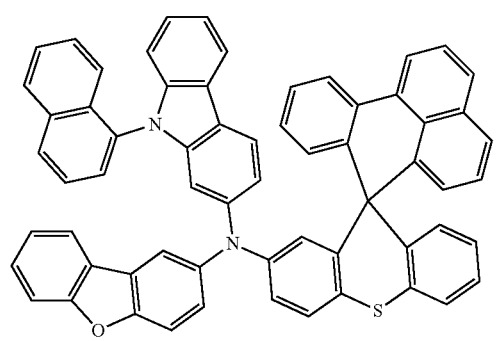
658
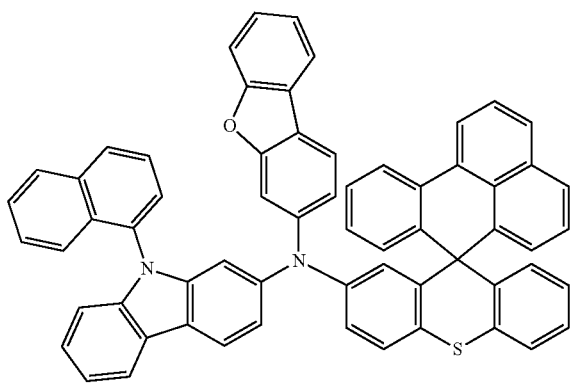
659
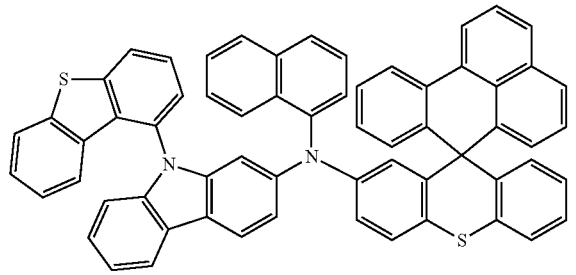
660
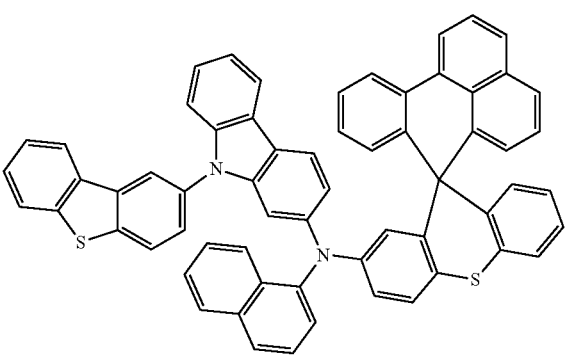
661
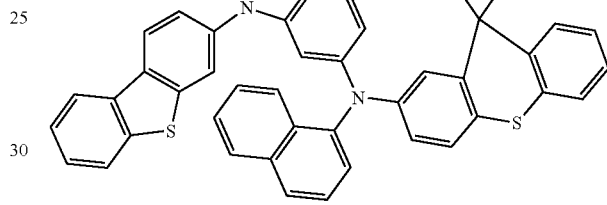
662
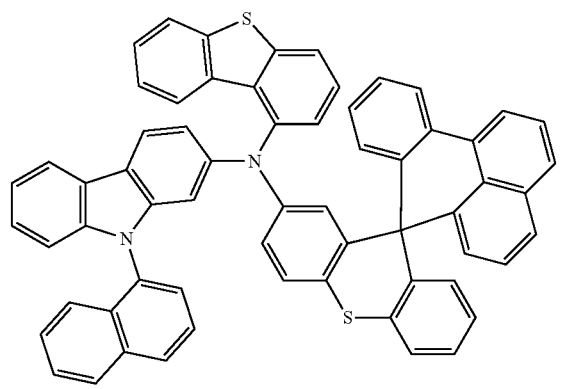
663
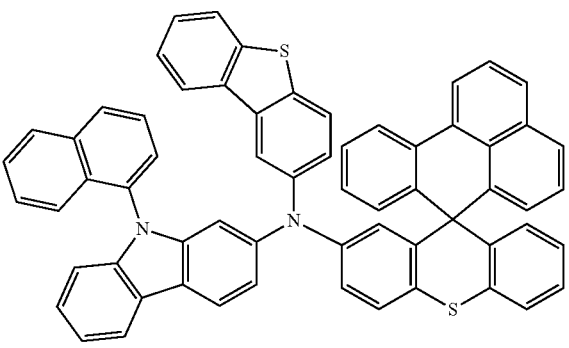

527
-continued
528
-continued
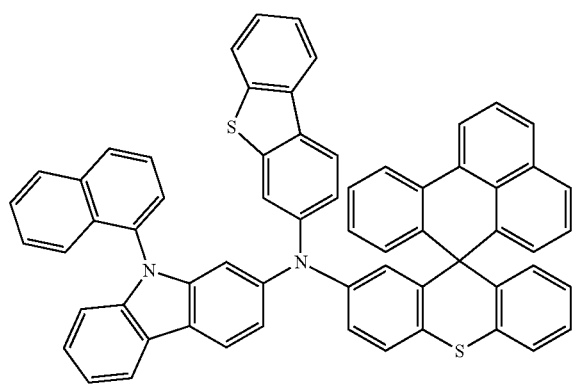
664
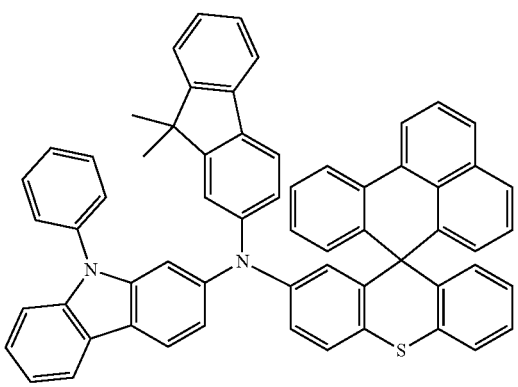
670
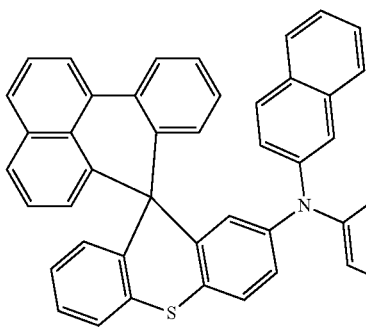
668
678
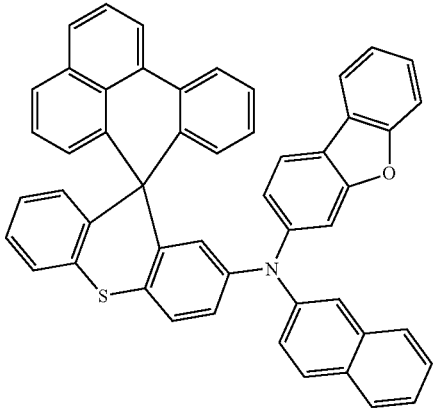
679
669
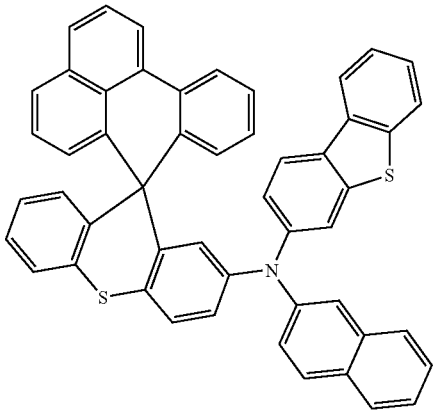
680

529
-continued
681
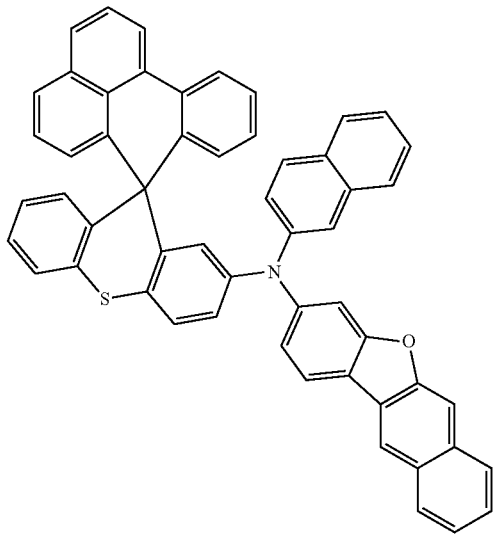
682
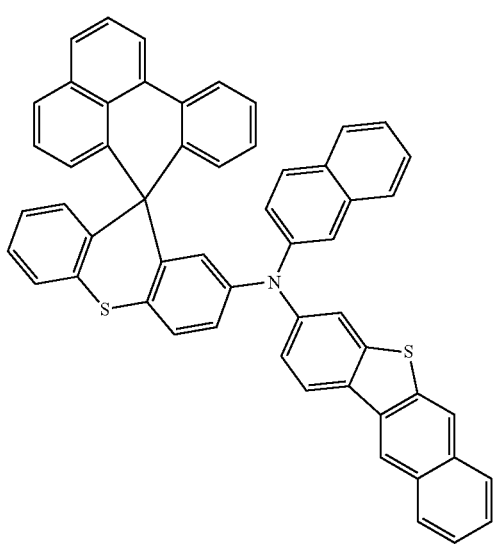
683
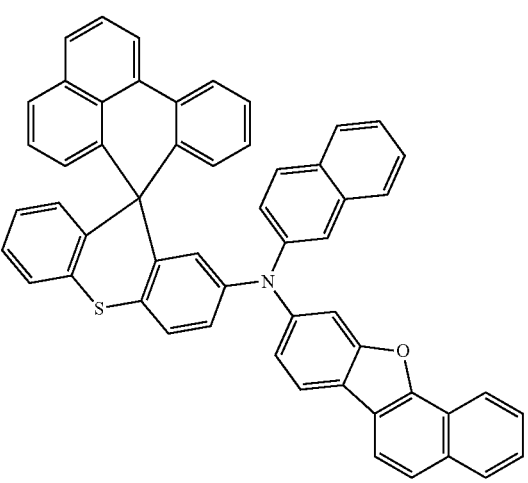
530
-continued
684
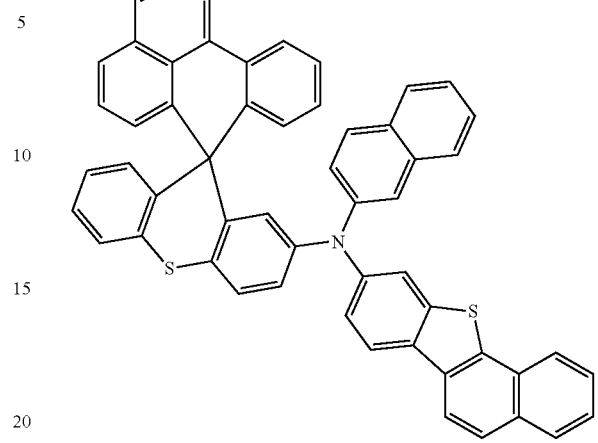
685
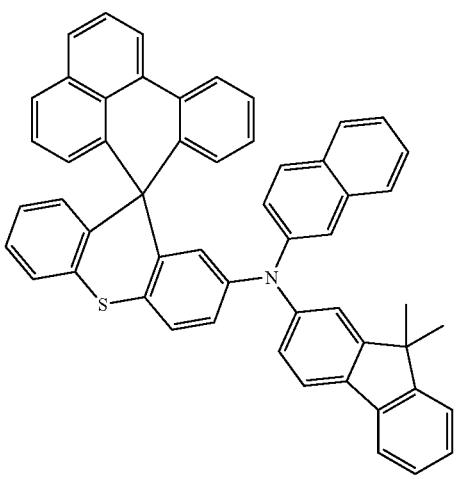
686
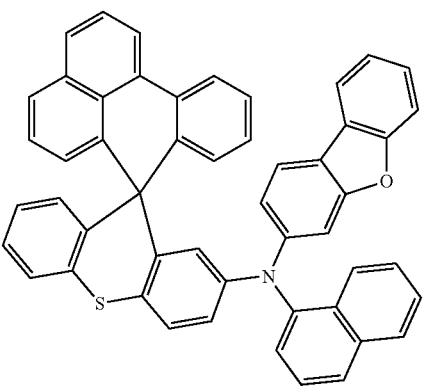

531
-continued
687
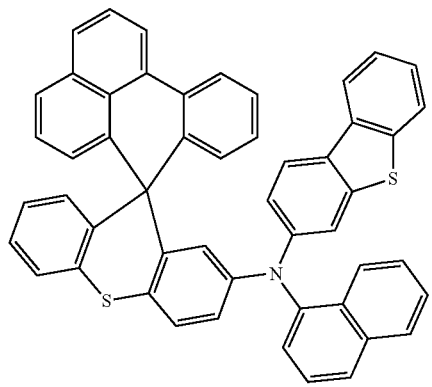
688
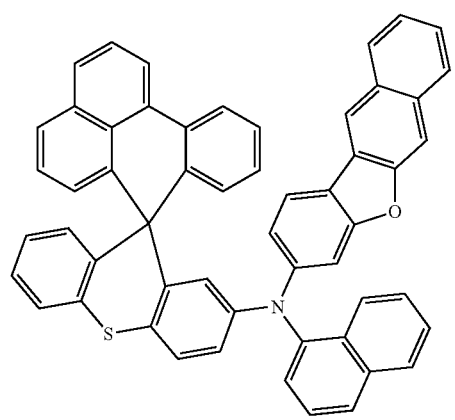
689
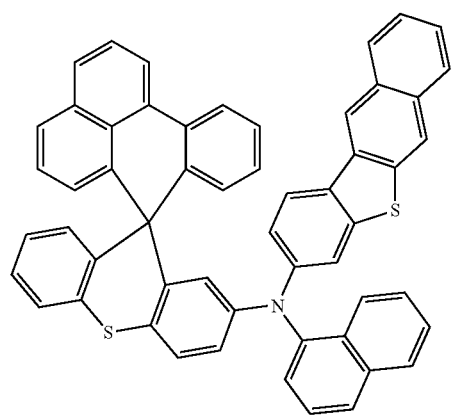
532
-continued
690
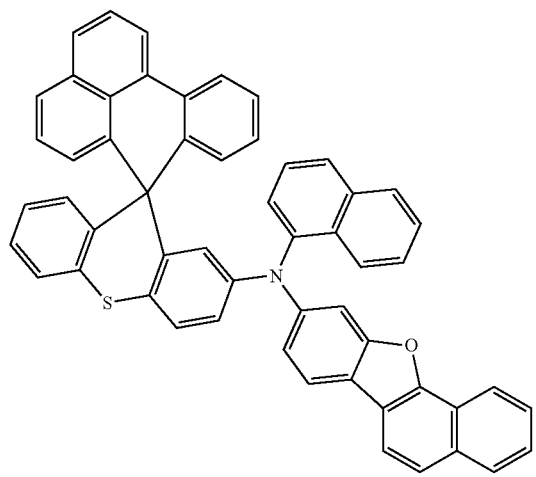
691
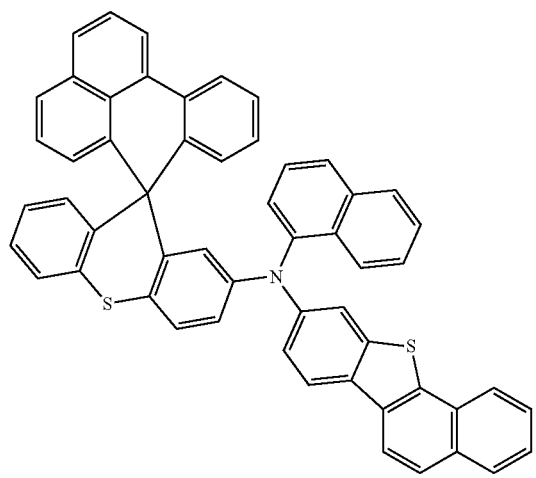
696
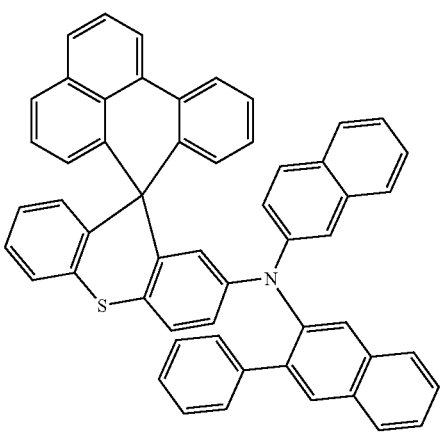

-continued
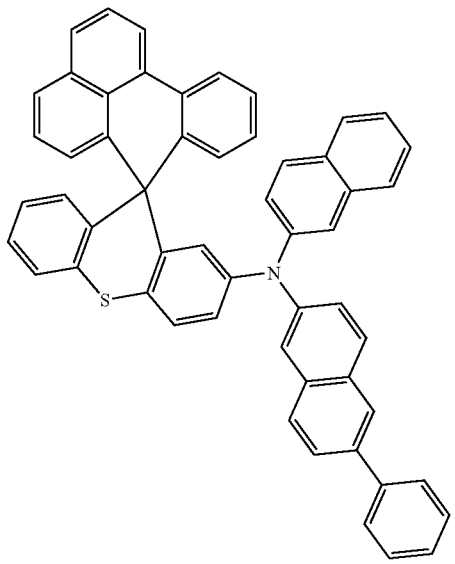
697
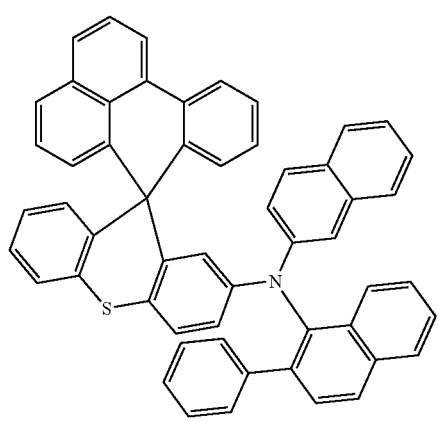
698
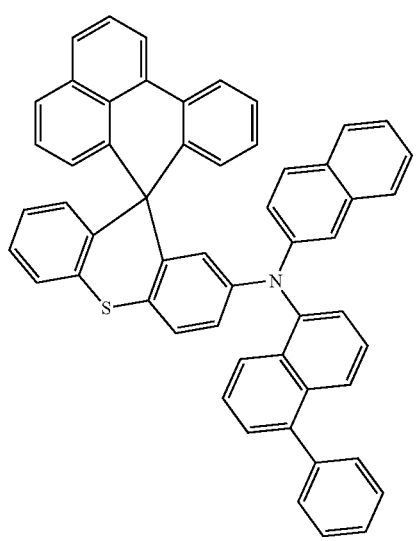
699
-continued
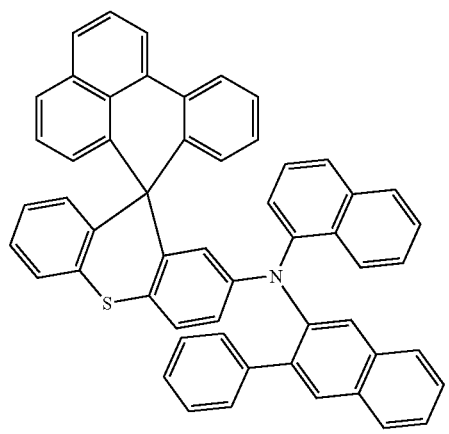
700
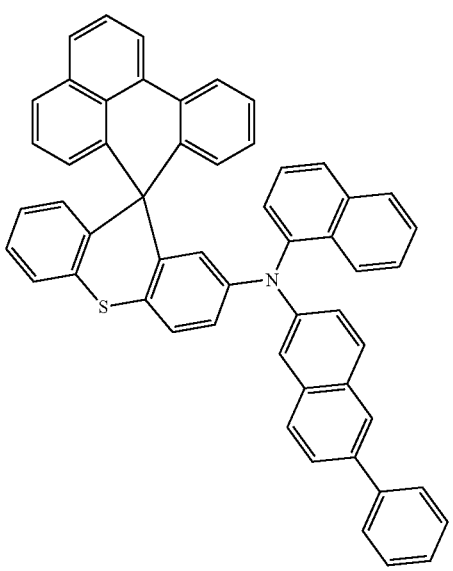
701
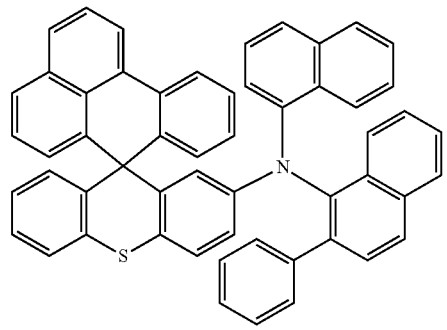
702

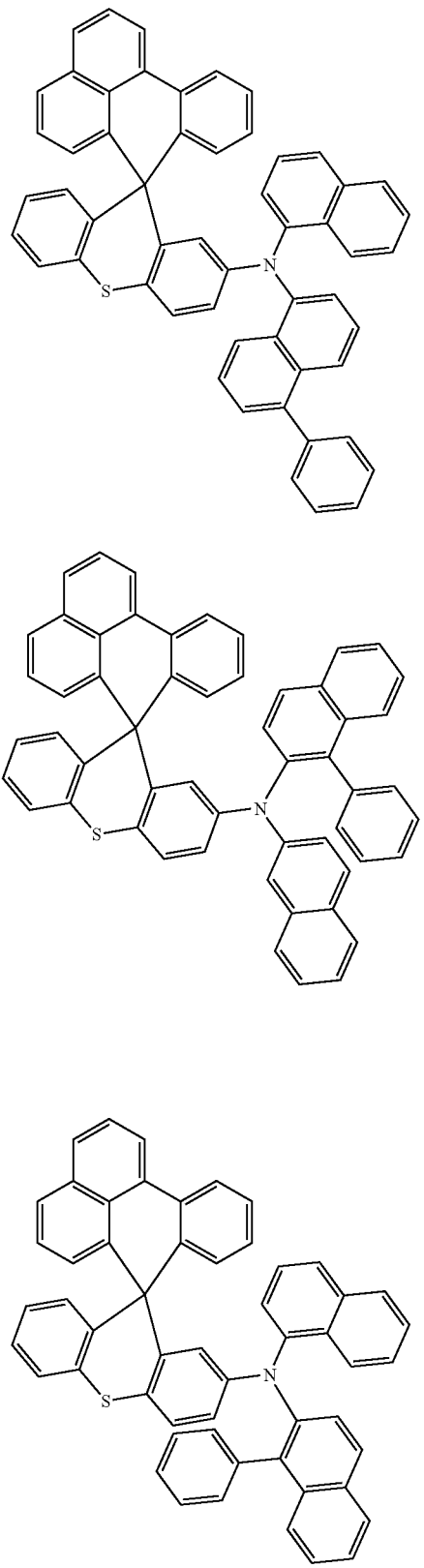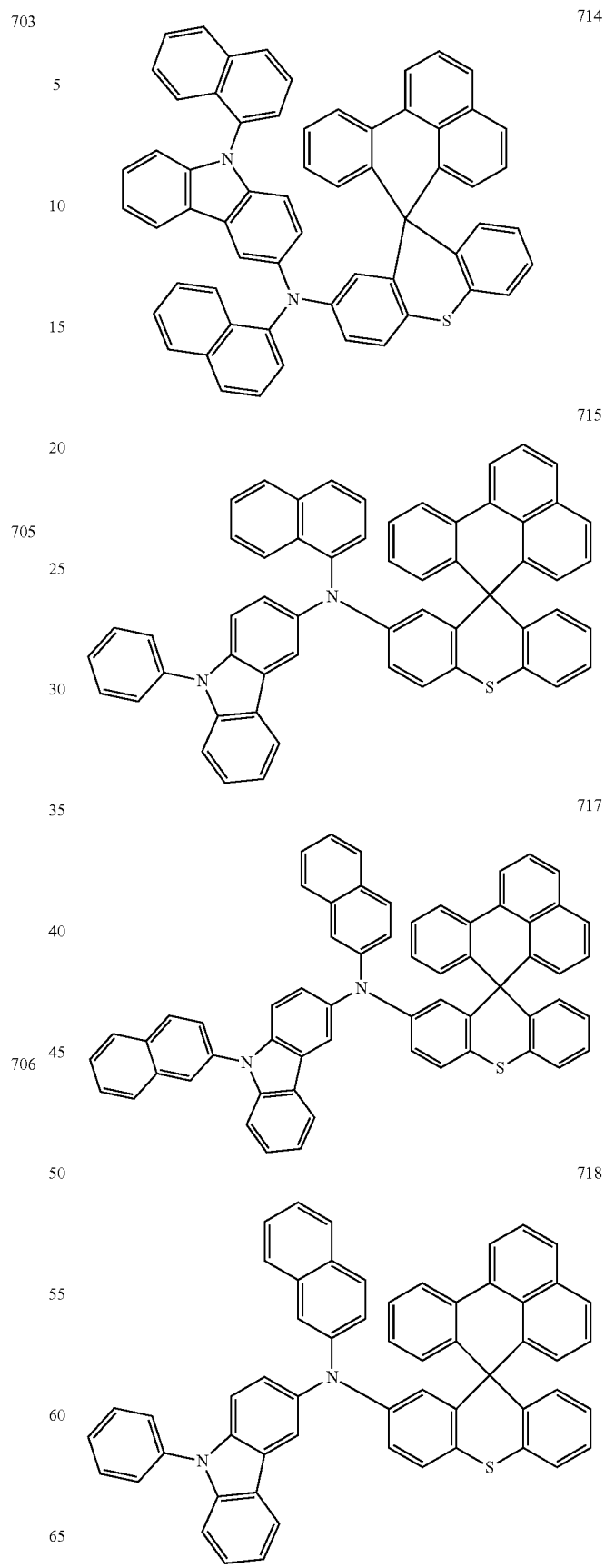

722
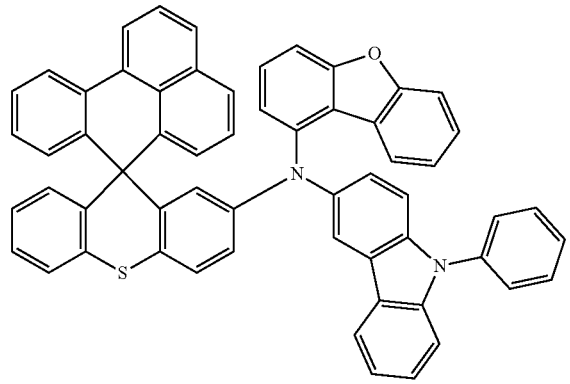
730
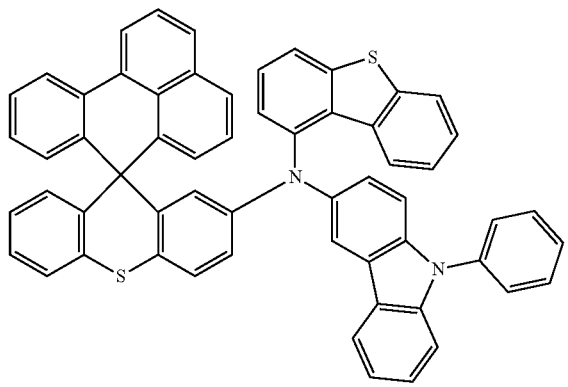
723
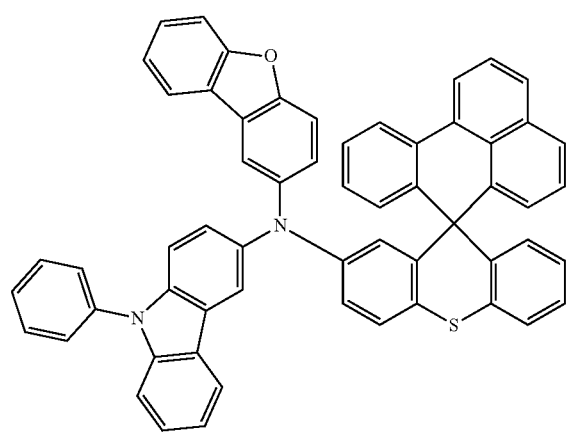
731
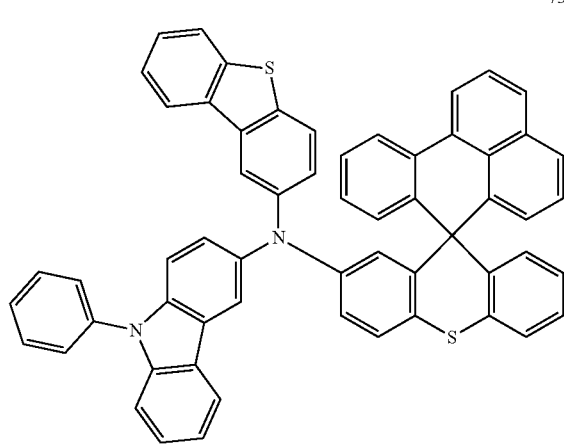
724
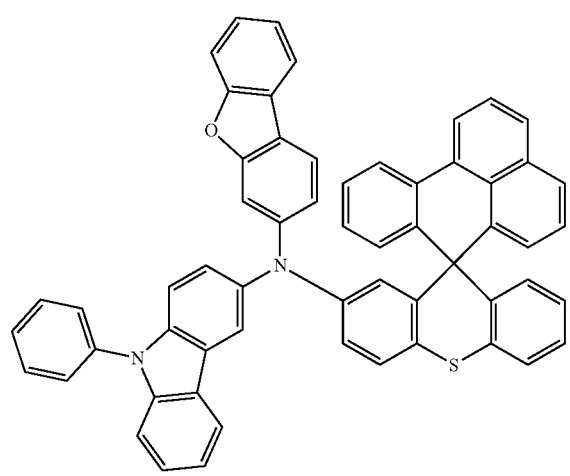
732
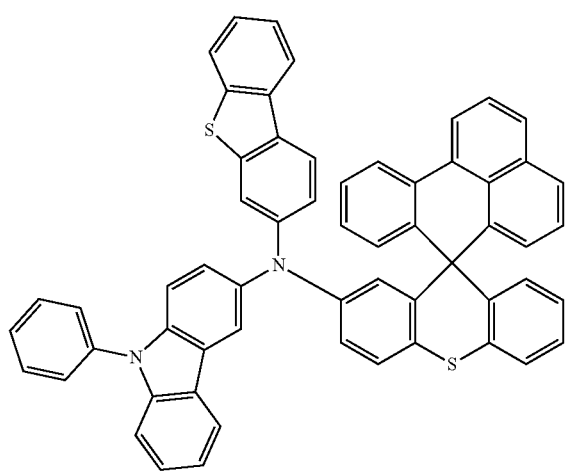

733
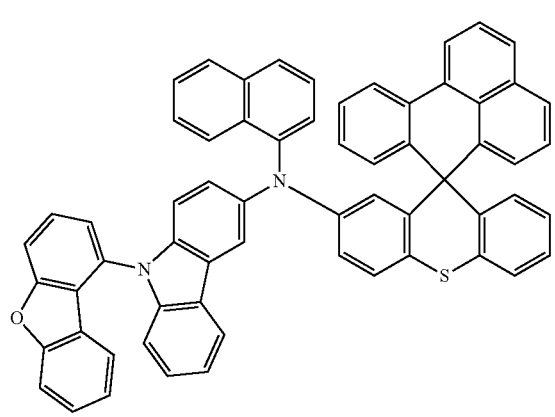
737
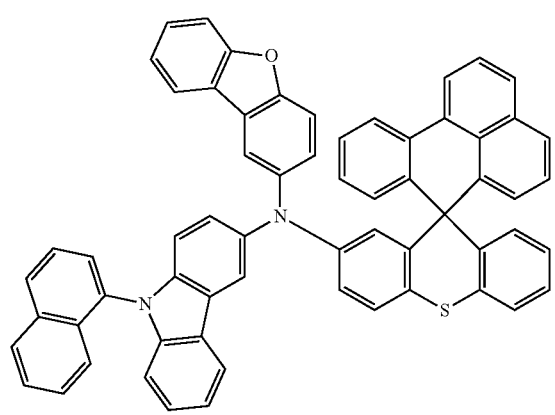
734
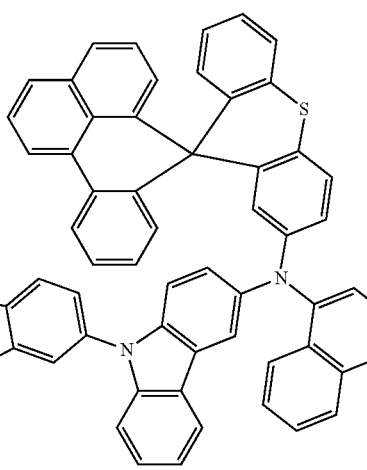
738
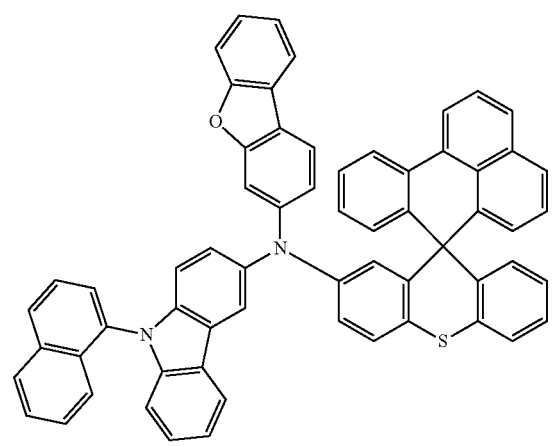
735
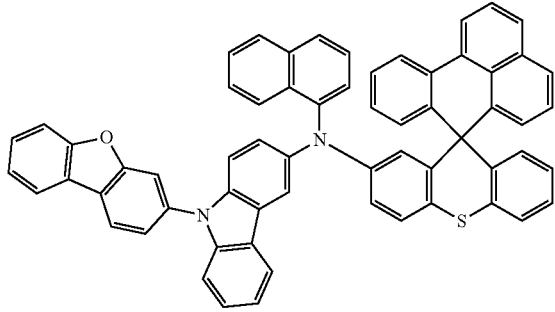
736
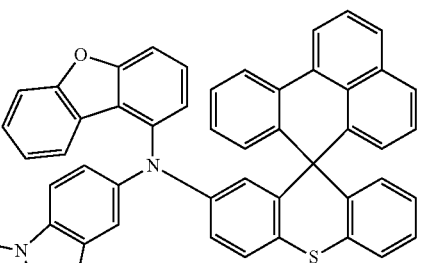
739
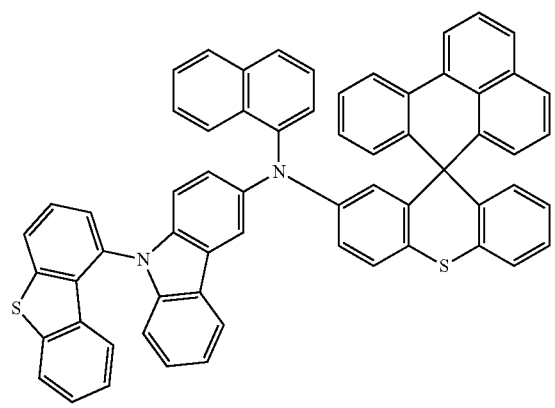

740
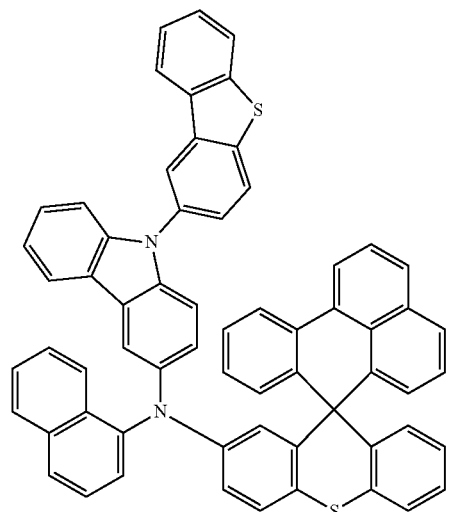
741
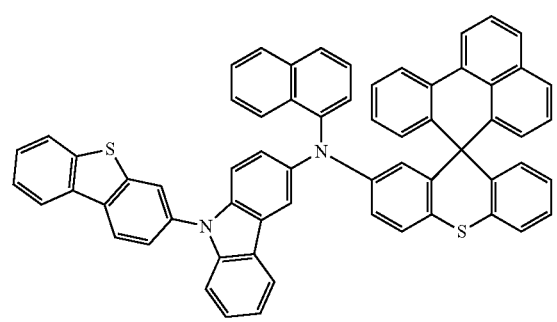
742
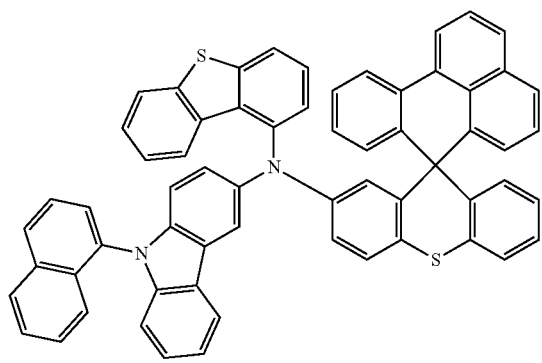
743
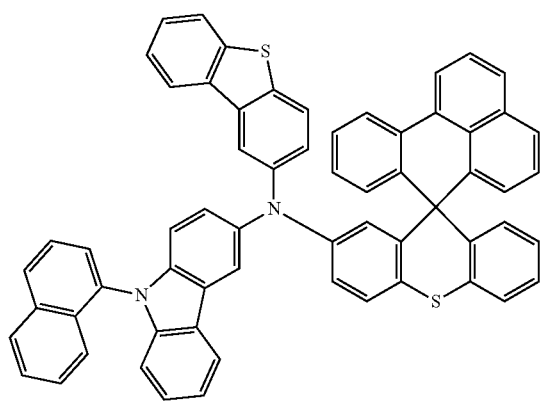
744
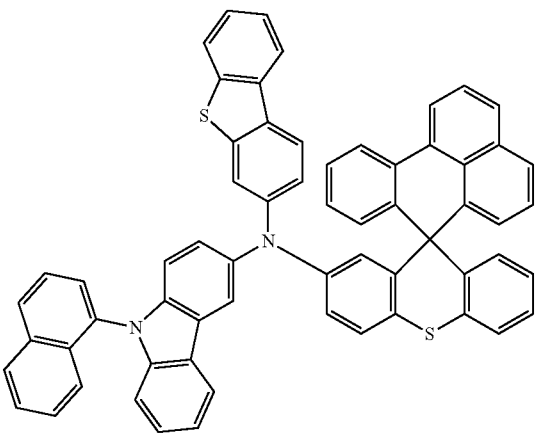
748
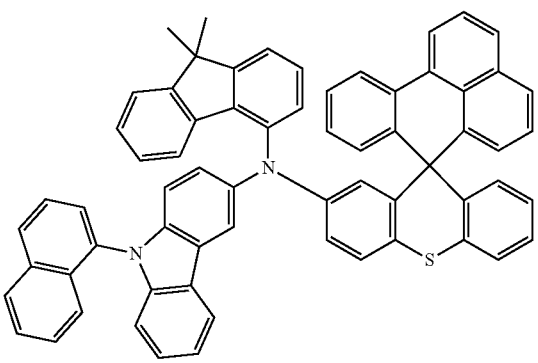
749
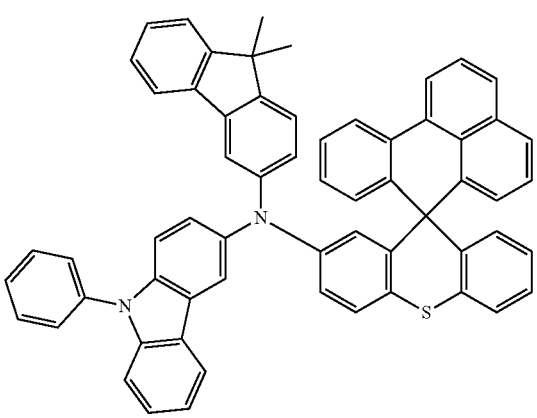

750
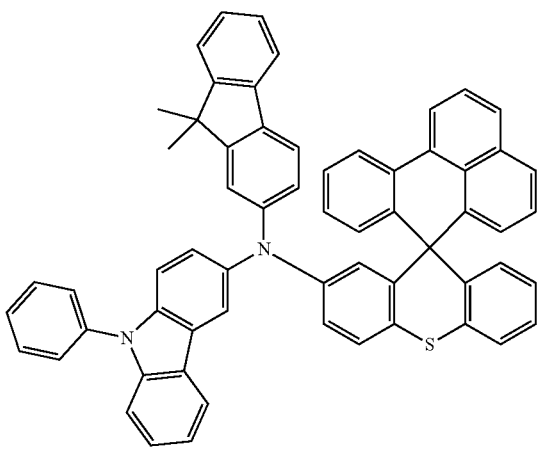
758
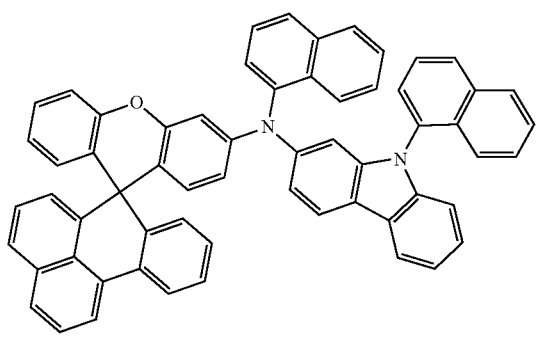
759
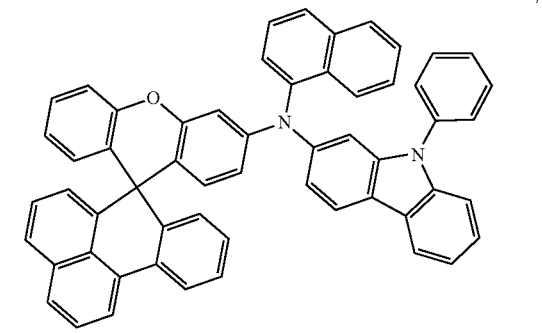
761
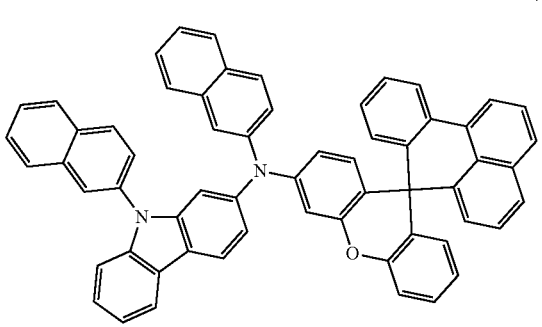
762
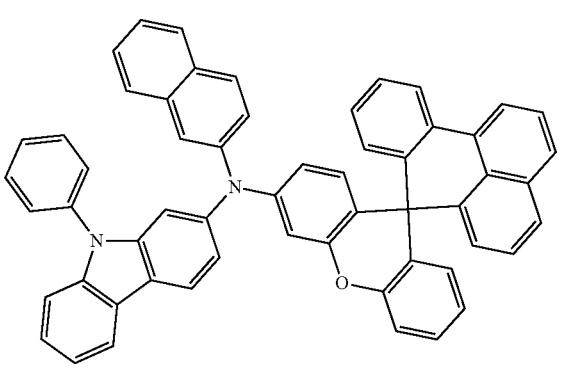
766
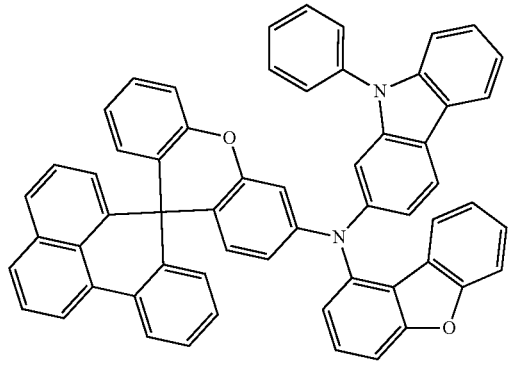
767
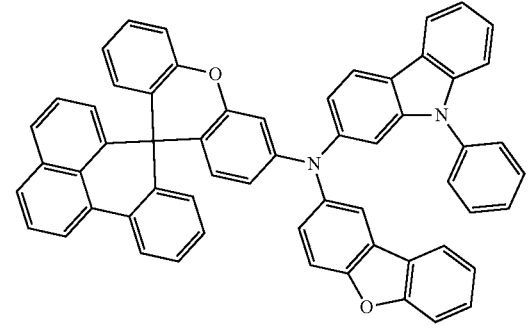
768
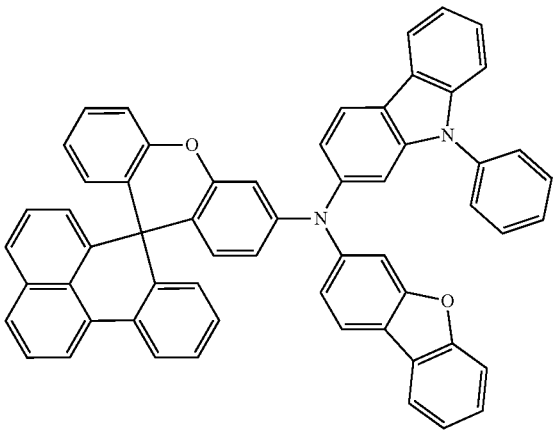

545
-continued
769
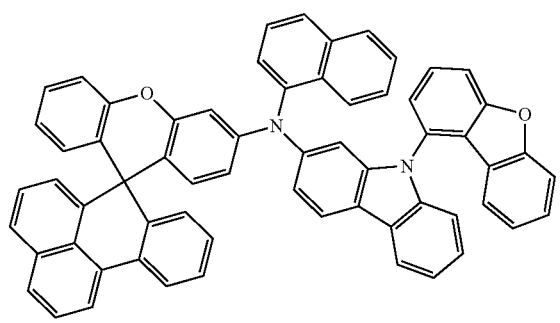
770
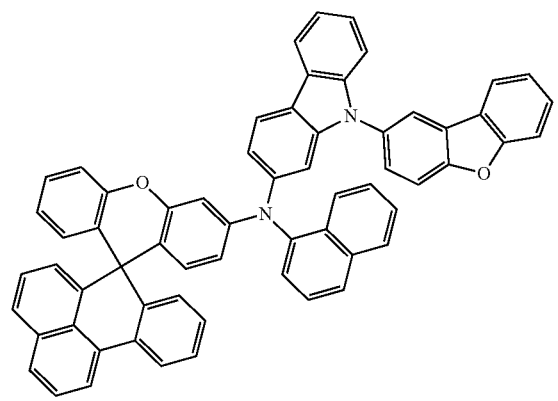
774
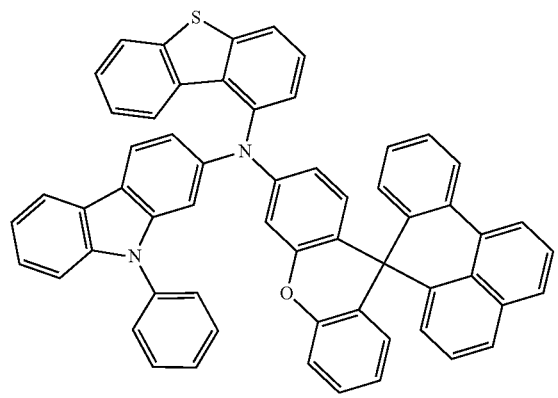
546
-continued
775
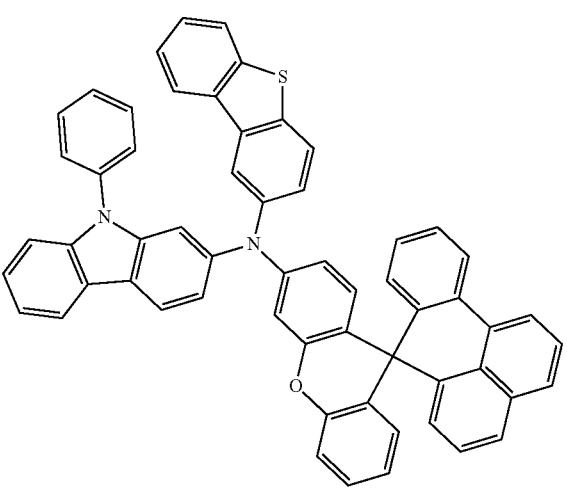
776
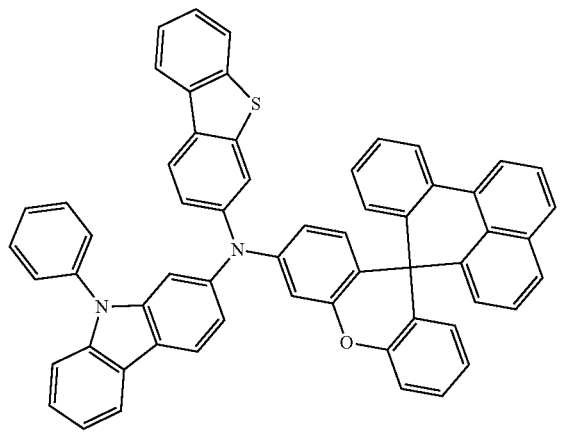
777
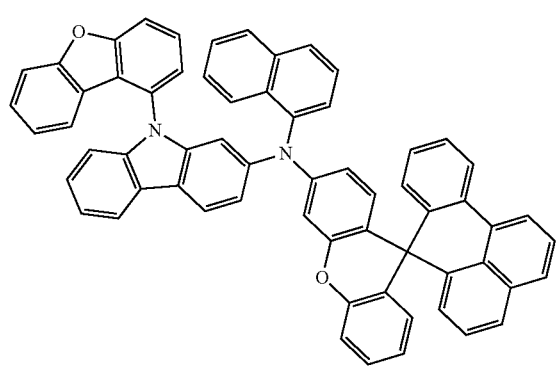

778
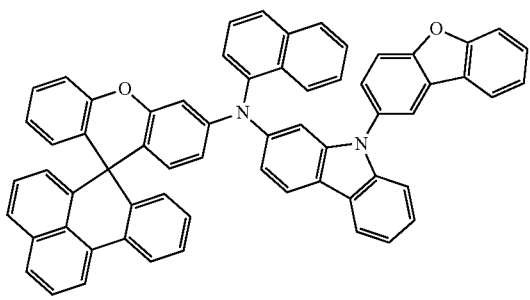
779
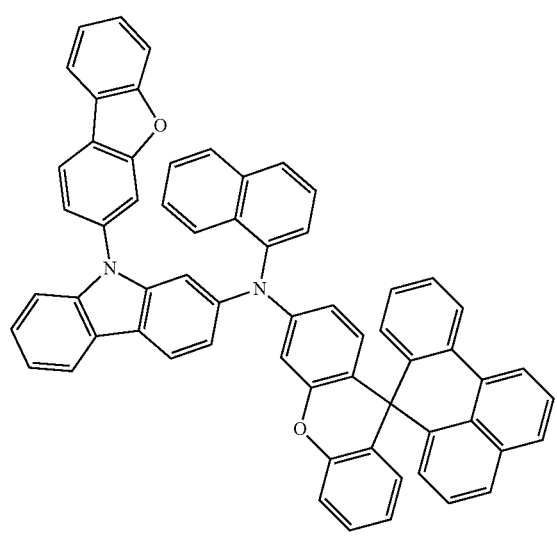
780
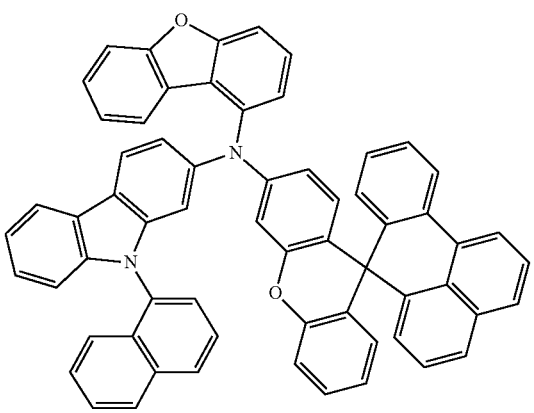
781
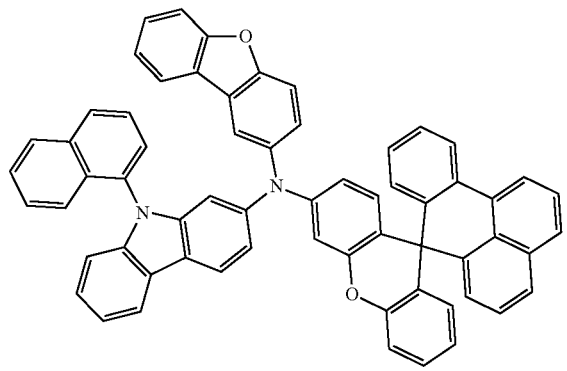
782
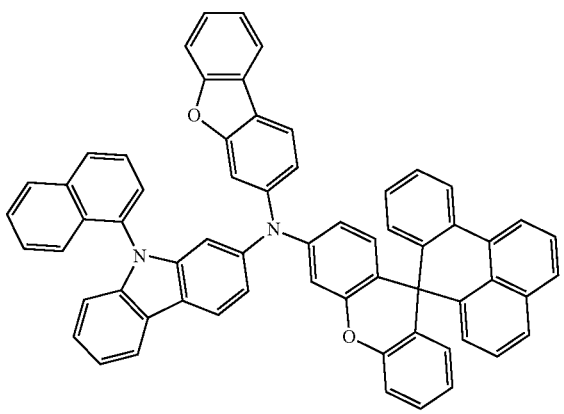
783
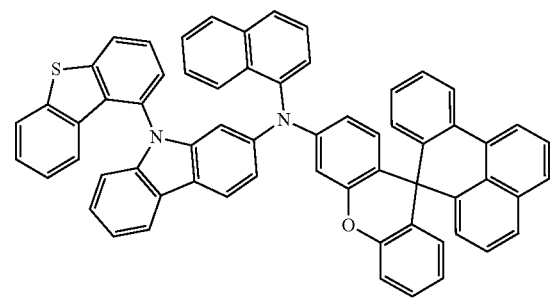
784
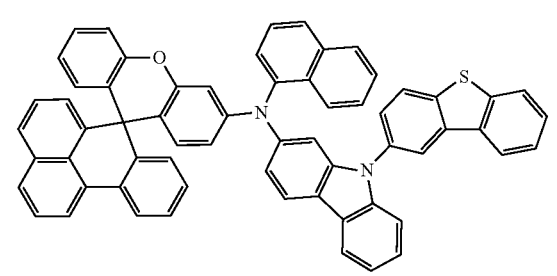

549
-continued
785
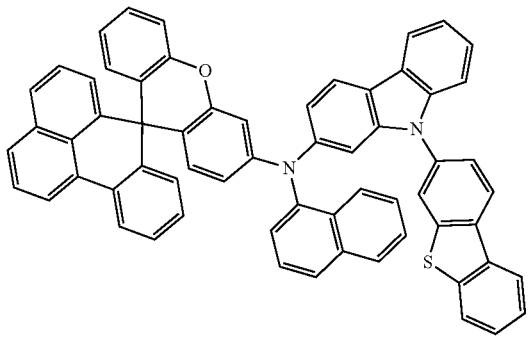
786
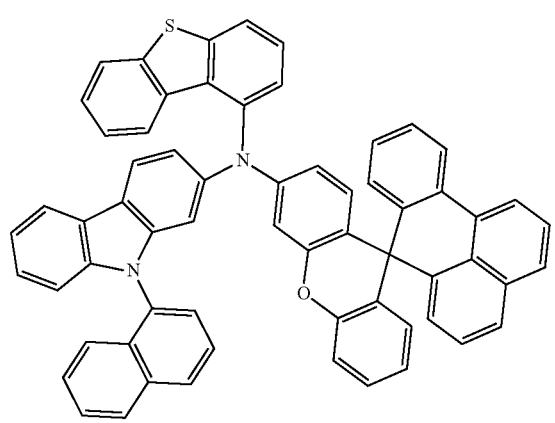
787
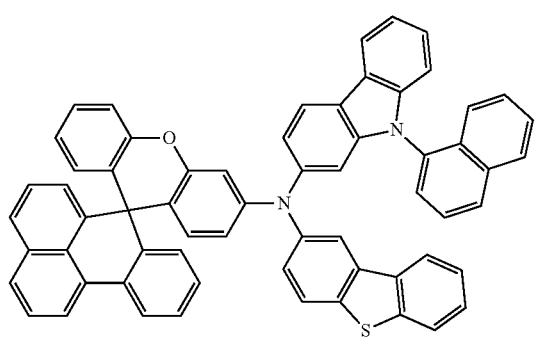
788
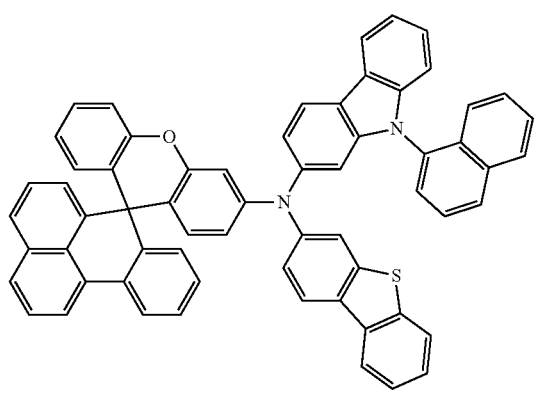
550
-continued
792
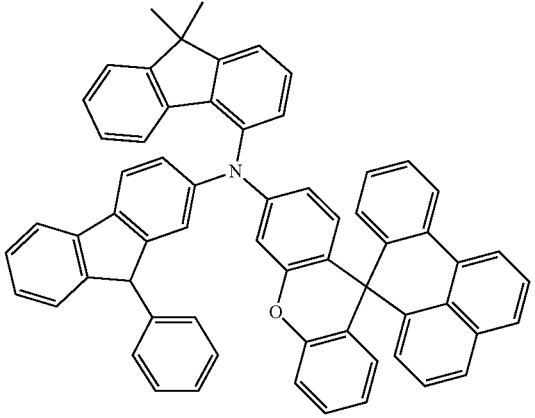
793
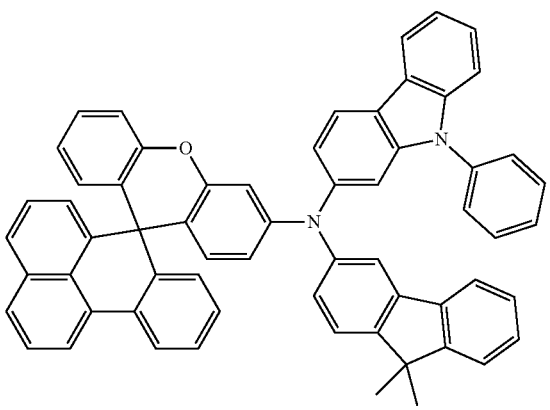
794
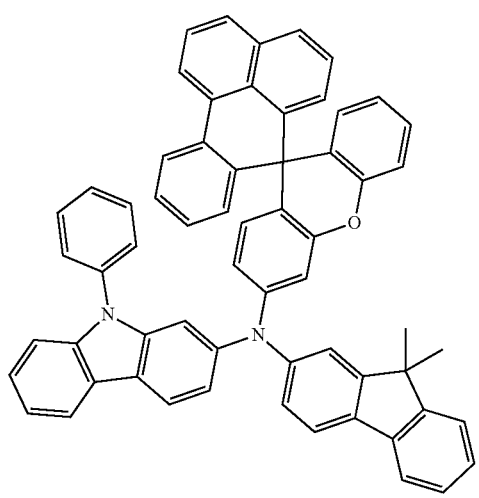

-continued
802
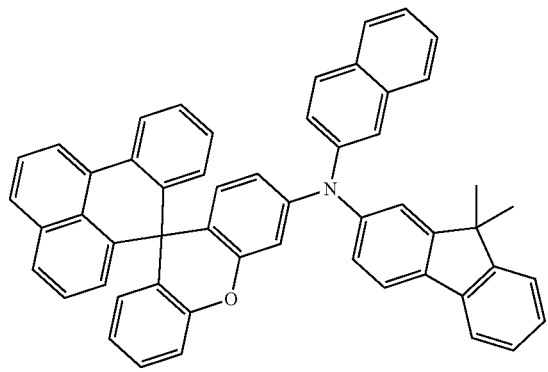
803
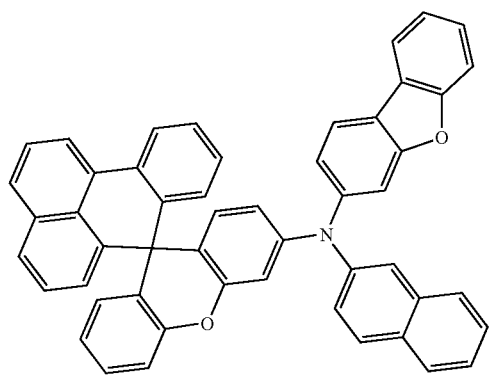
804
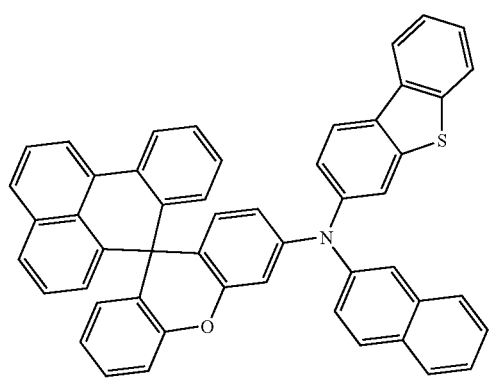
805
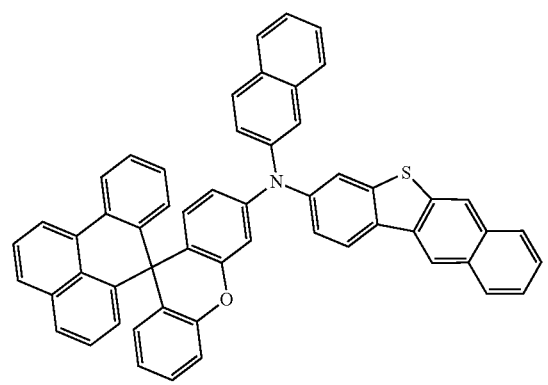
-continued
806
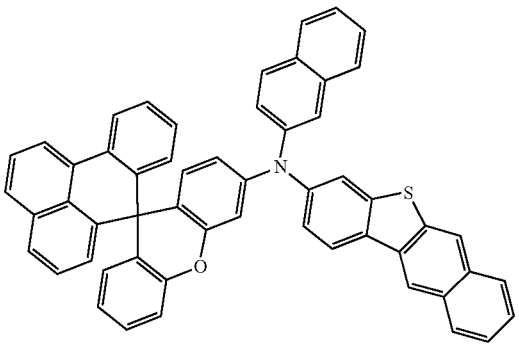
807
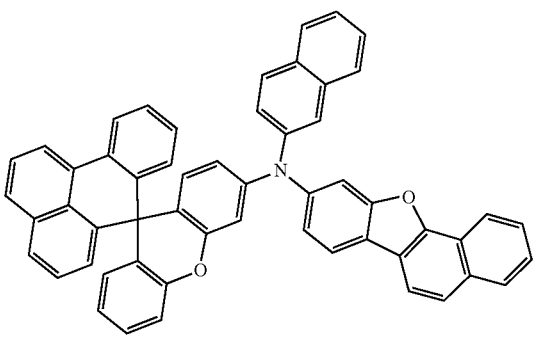
808
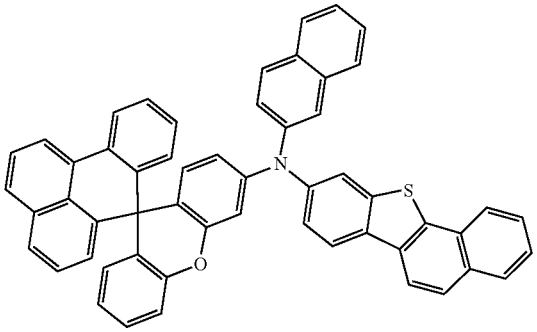
809
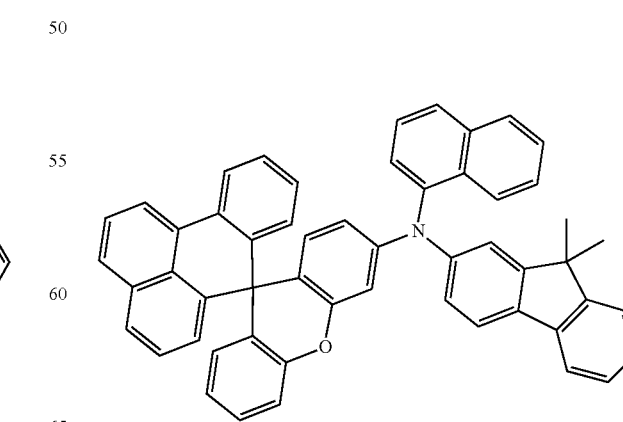

553
-continued
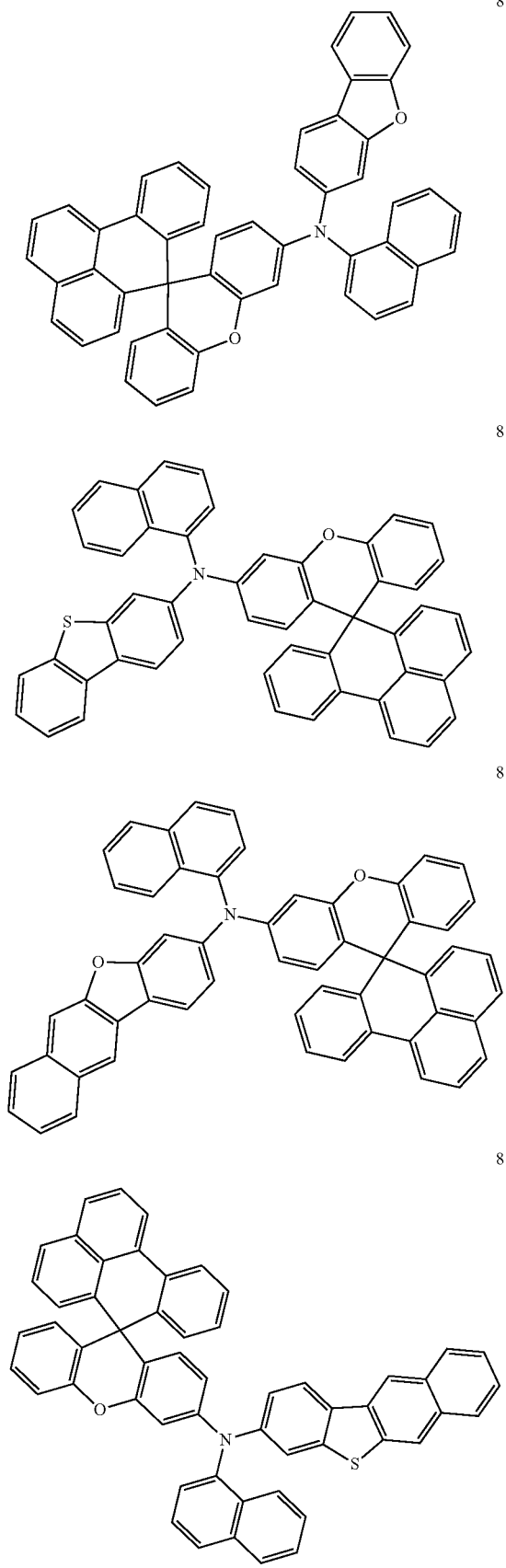
554
-continued
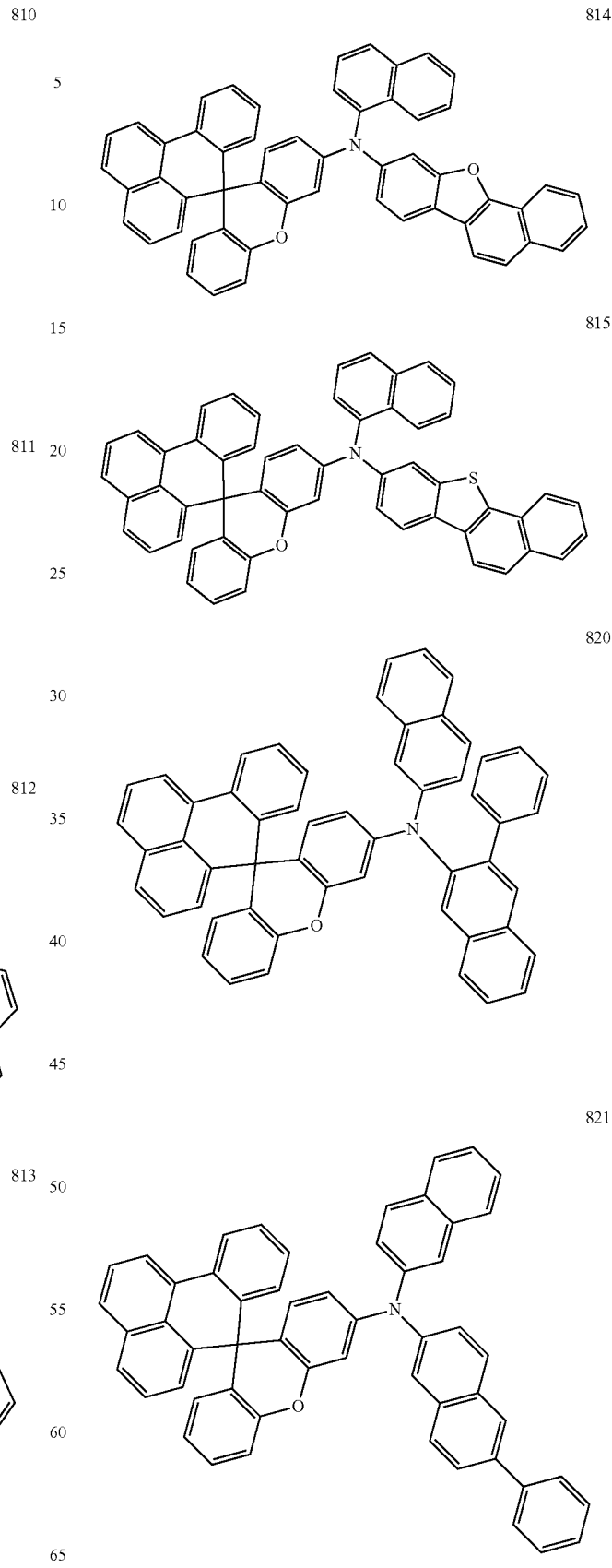

555
-continued
822
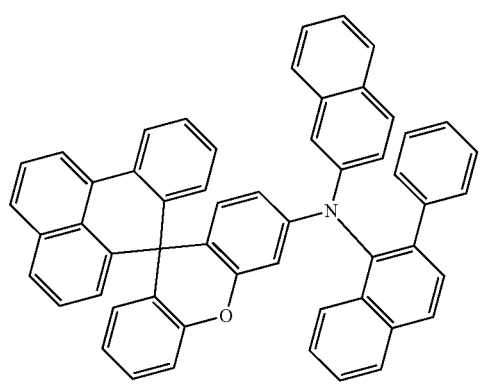
823
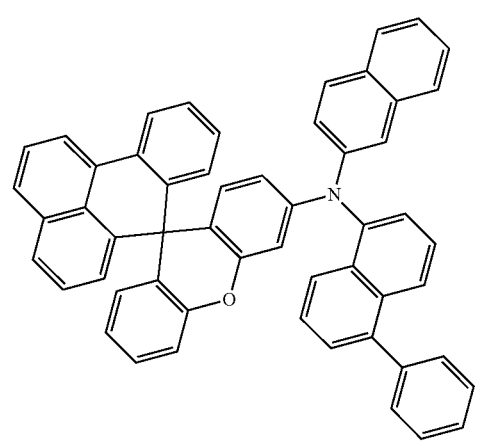
824
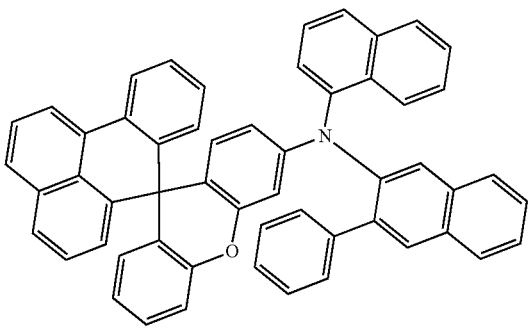
825
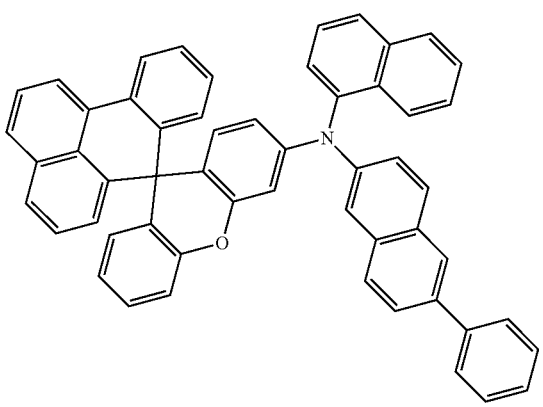
556
-continued
826
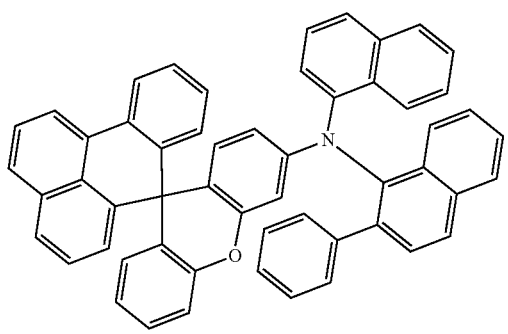
827
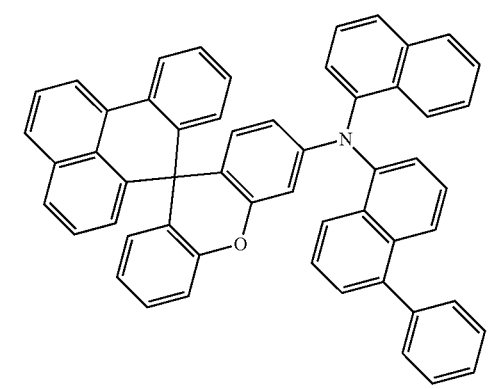
829
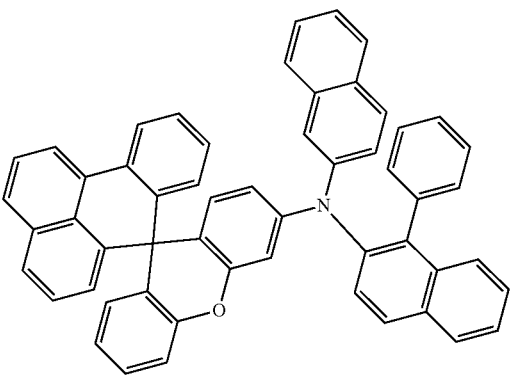
830
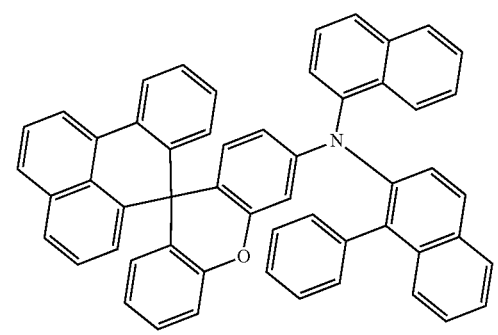

838
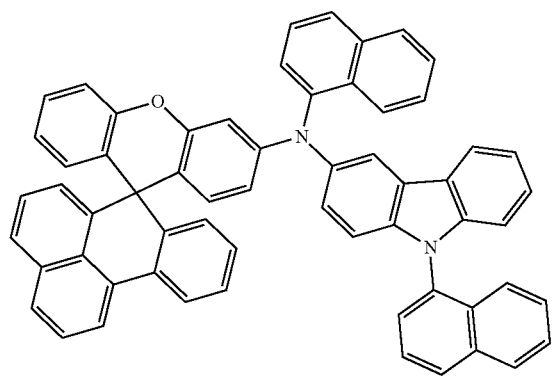
839
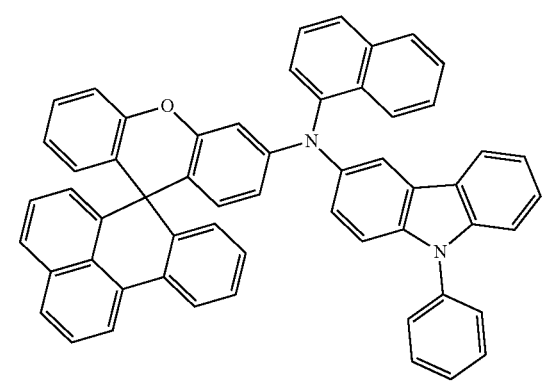
841
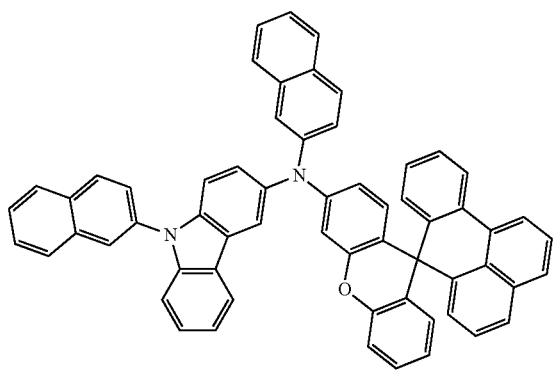
842
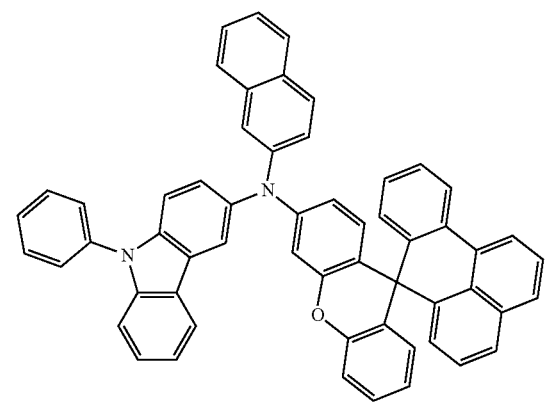
846
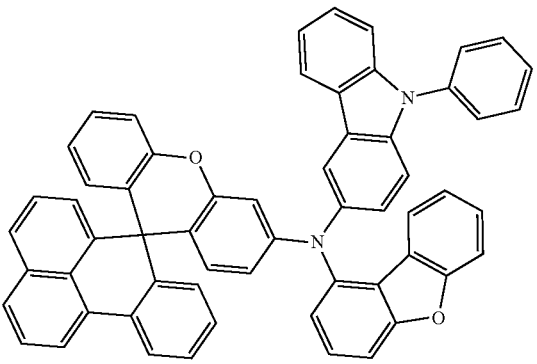
847
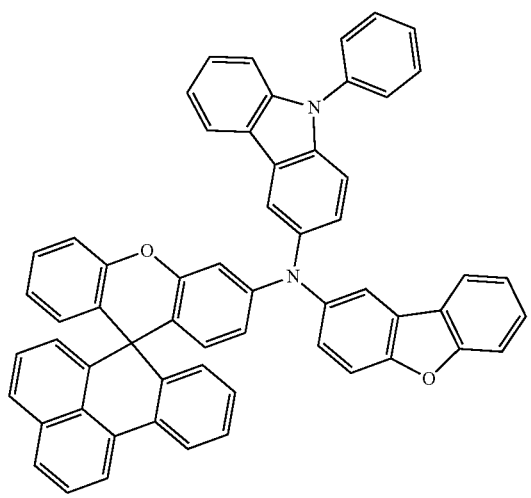
848
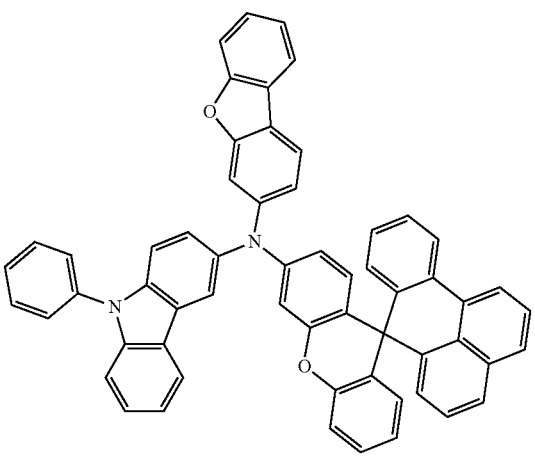

854
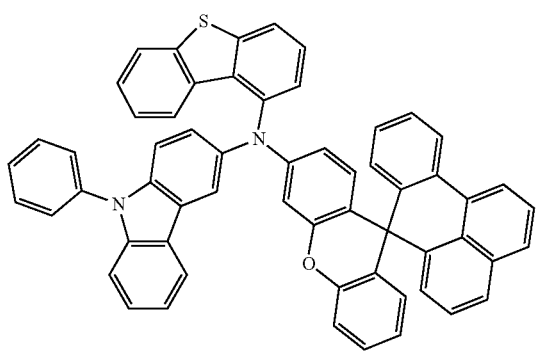
855
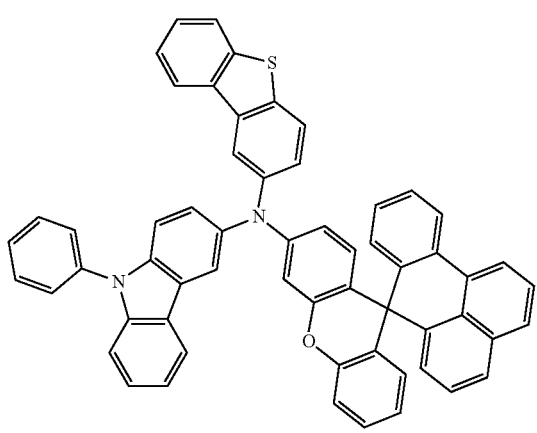
856
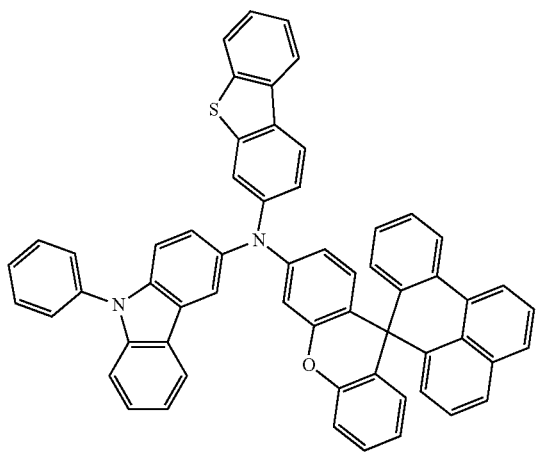
857
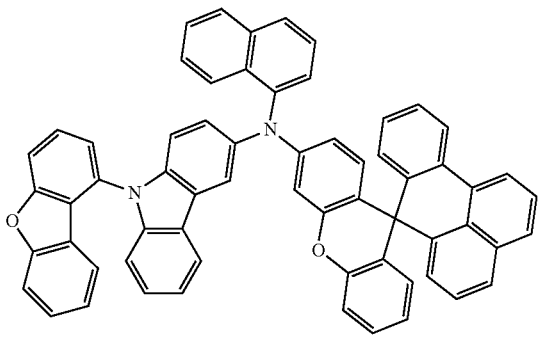
858
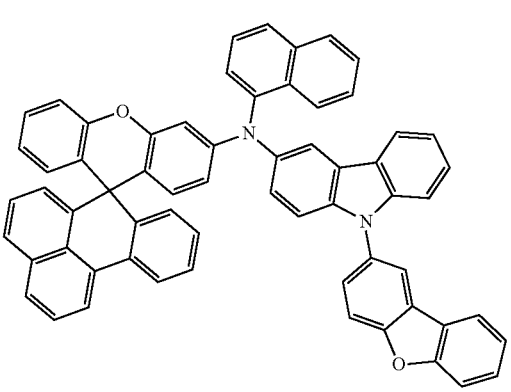
859
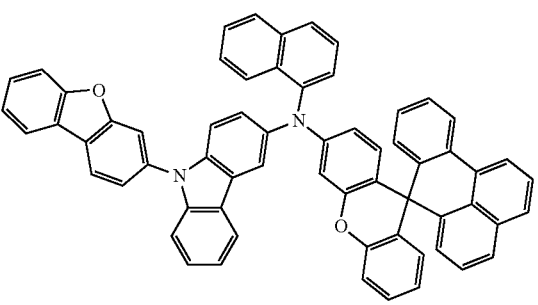
860
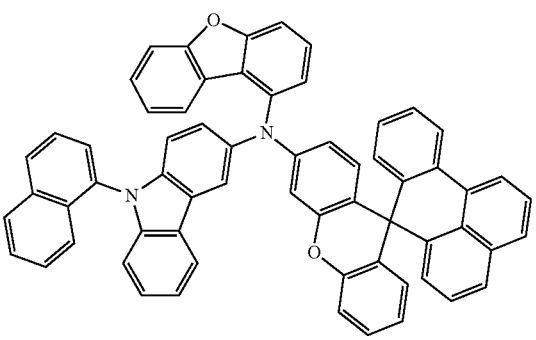
861
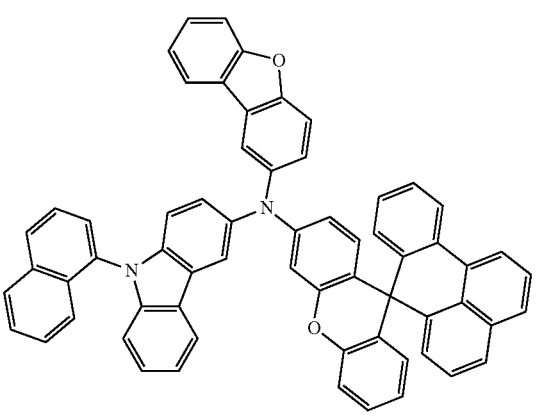

-continued
862
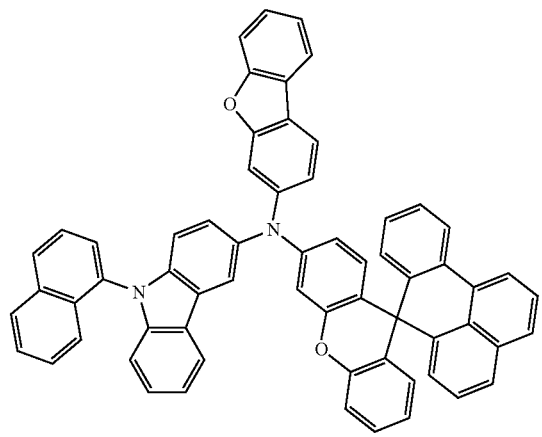
863
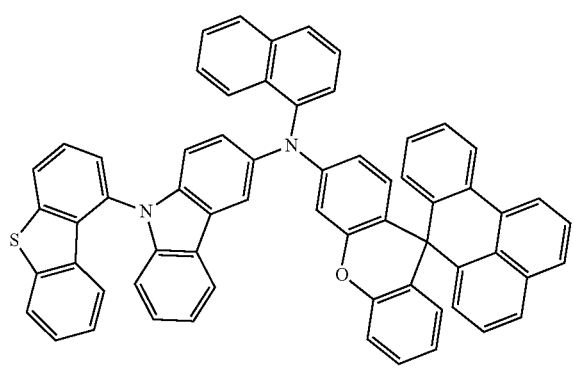
864
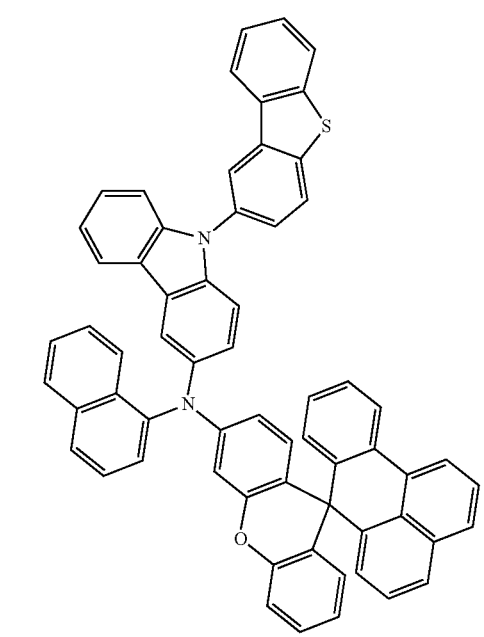
-continued
865
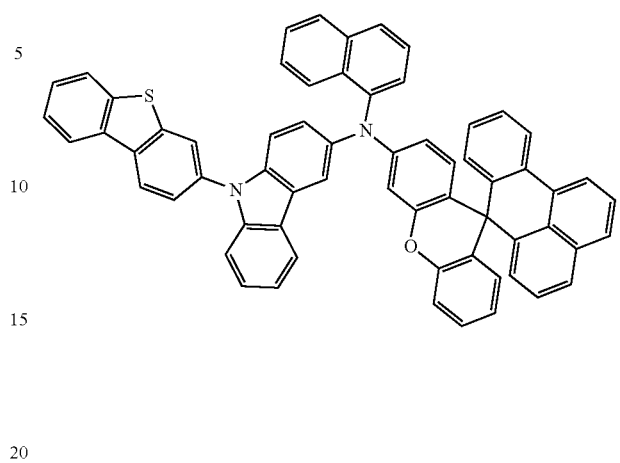
866
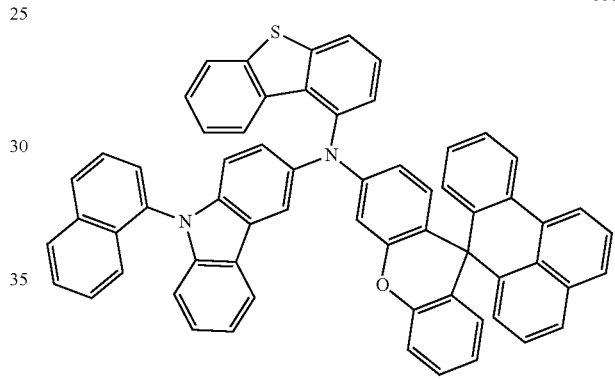
867
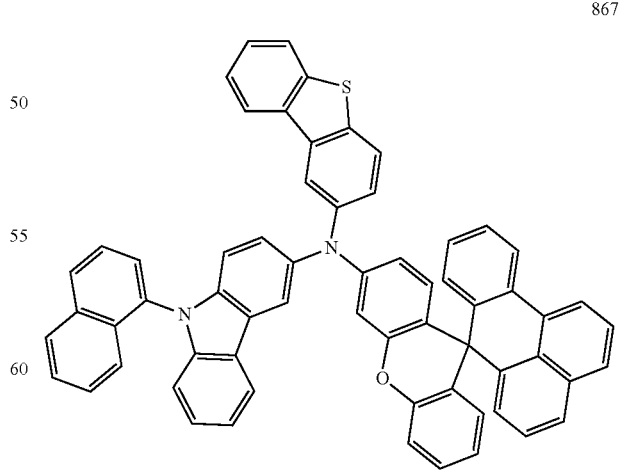

563
-continued
868
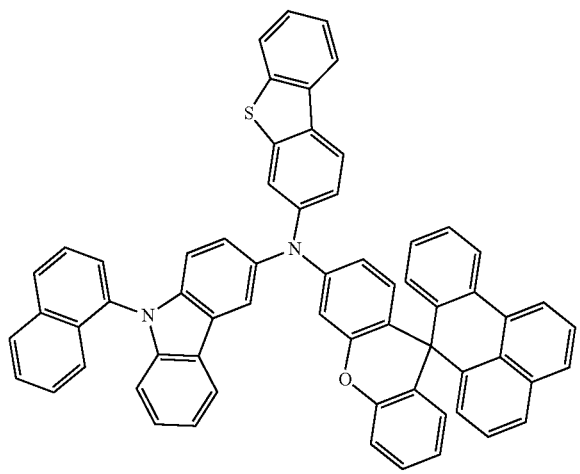
872
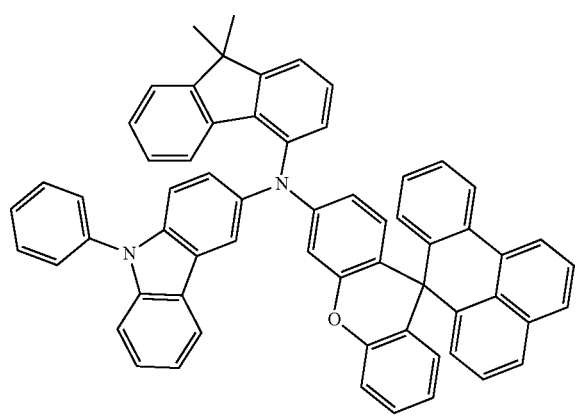
873
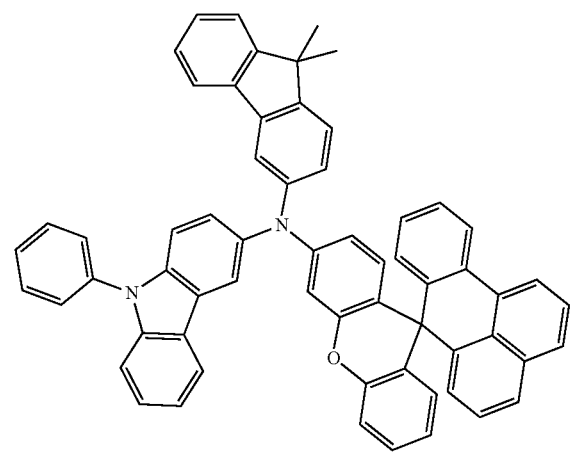
564
-continued
874
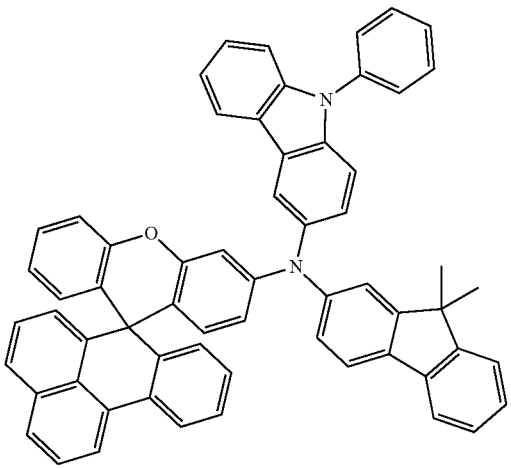
877
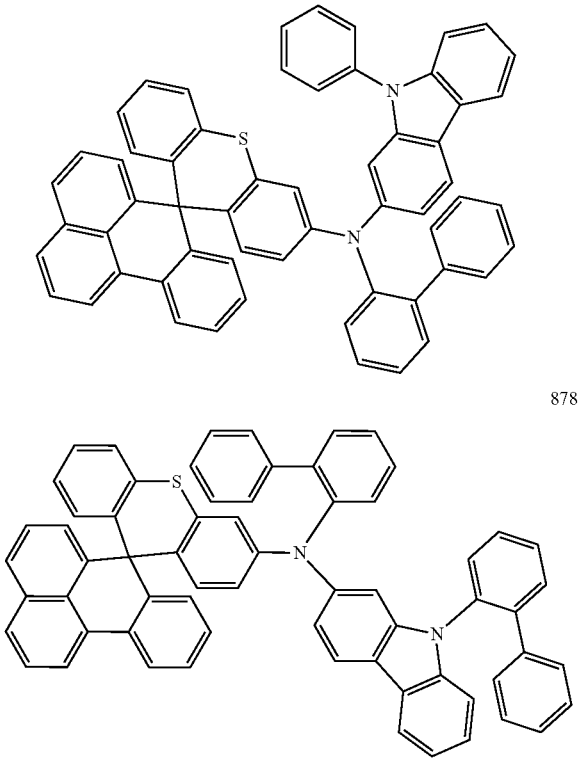
878
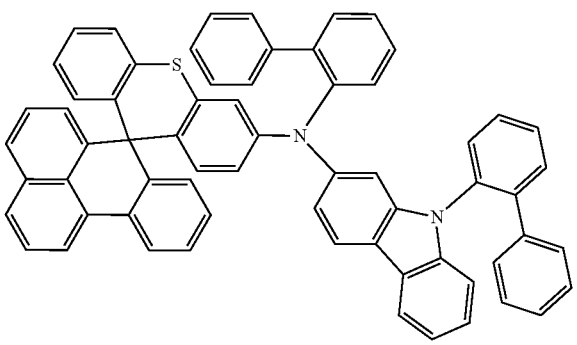
882
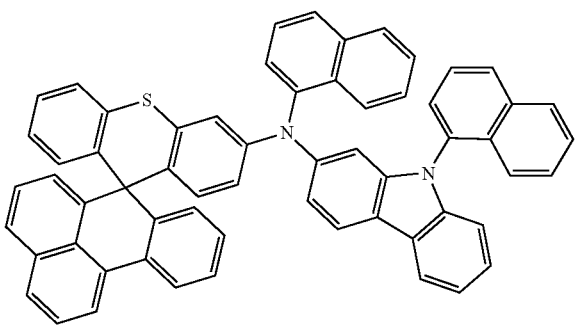

565
-continued
883
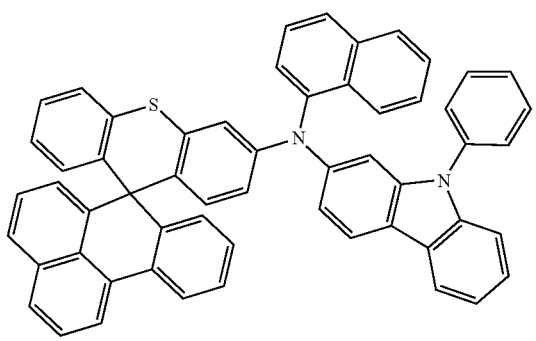
885
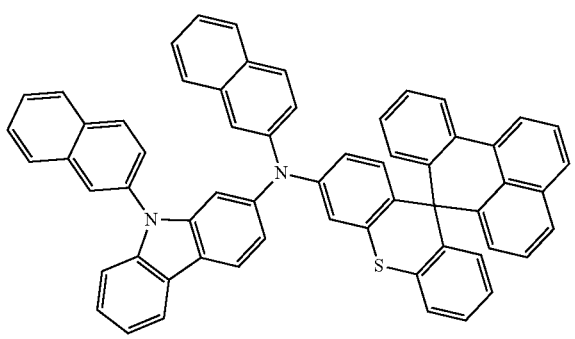
886
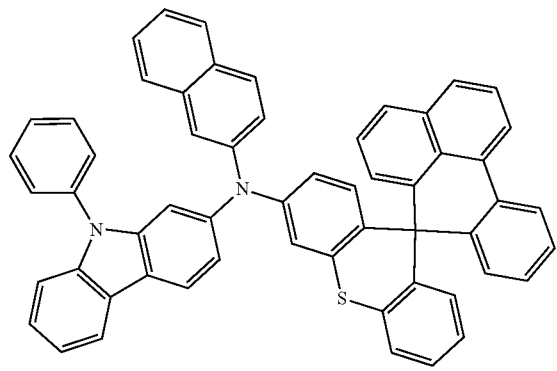
890
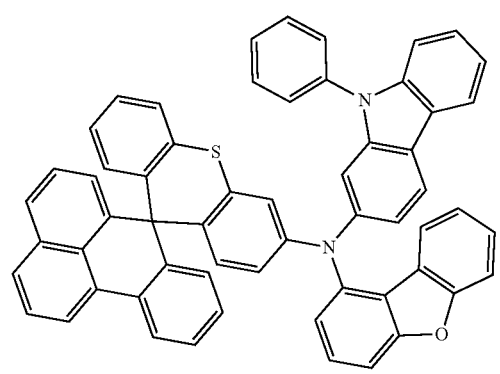
566
-continued
891
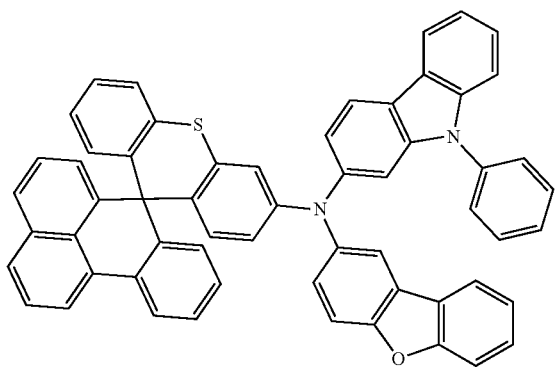
892
898
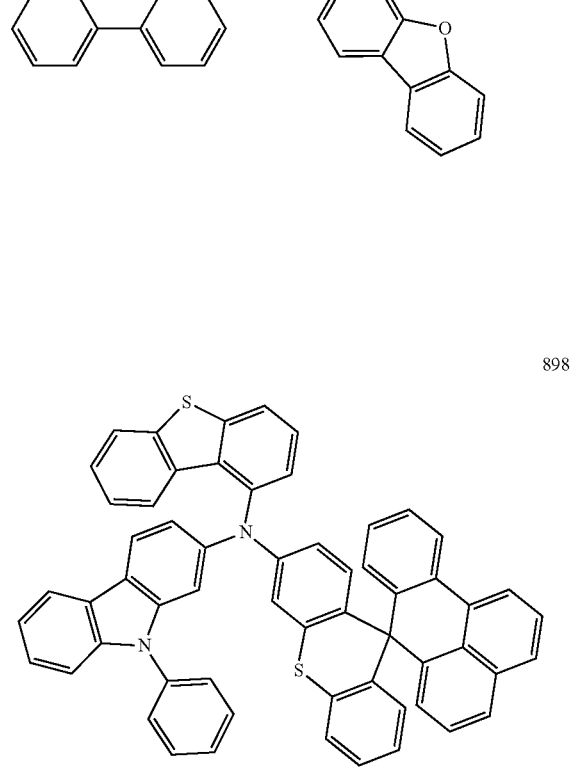

567
-continued
568
-continued
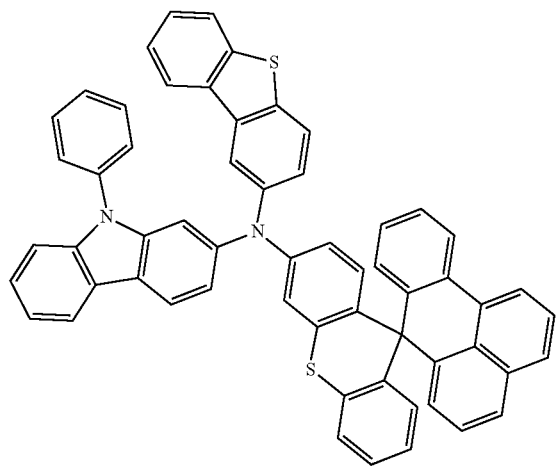
899
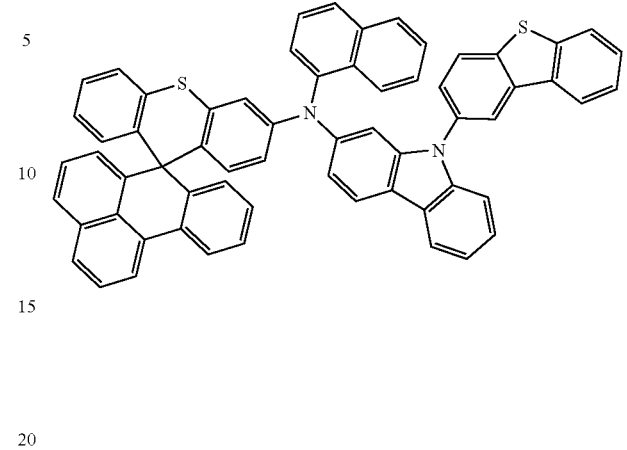
902
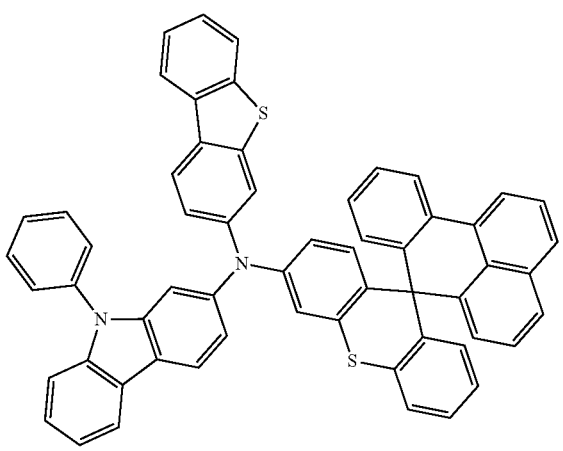
900
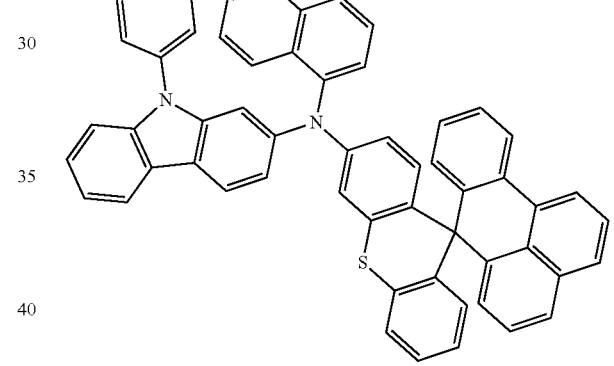
903
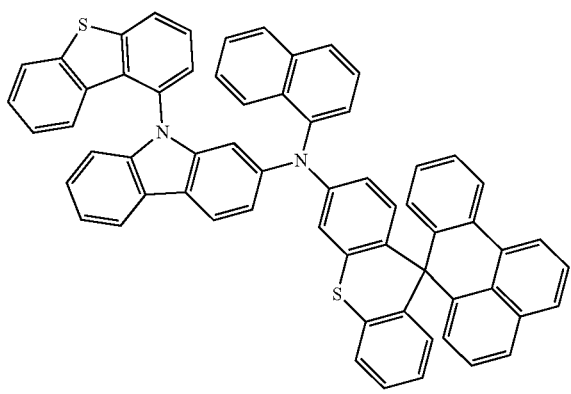
901
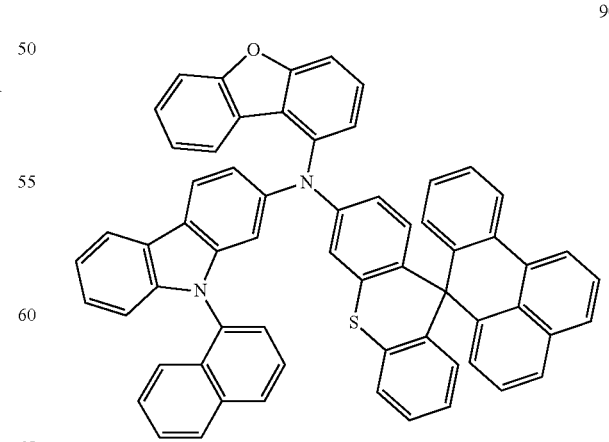
904

569
-continued
905
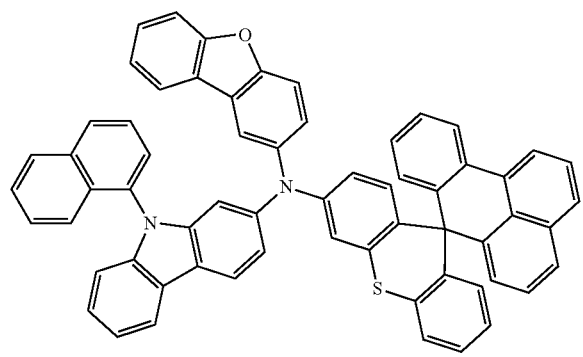
906
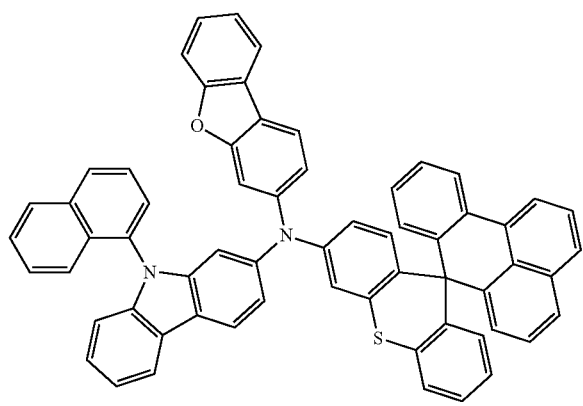
907
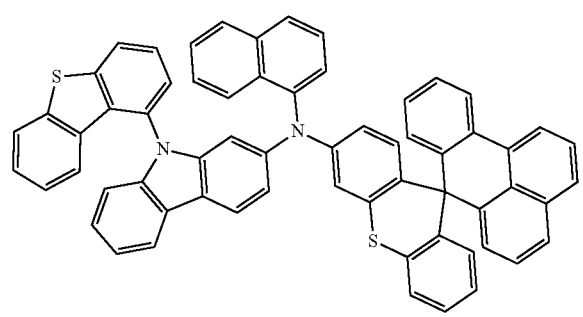
908
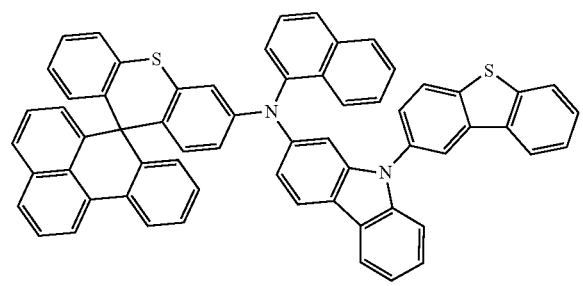
570
-continued
909
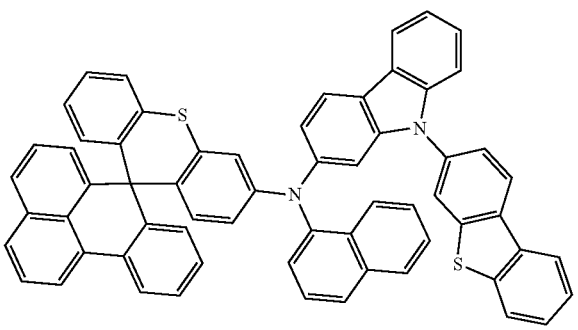
910
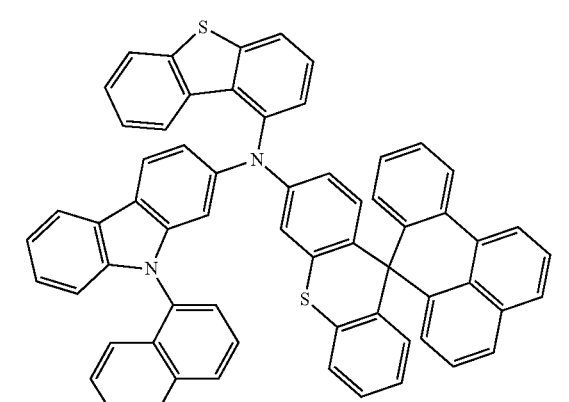
911
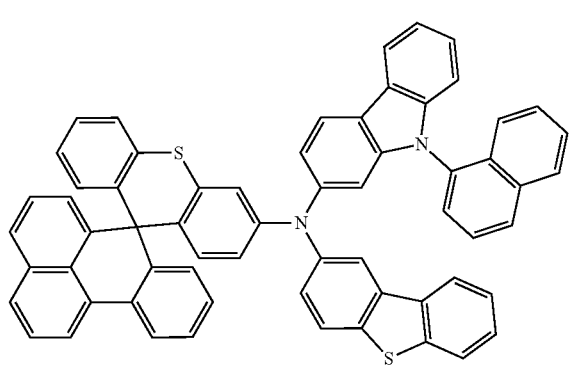
912
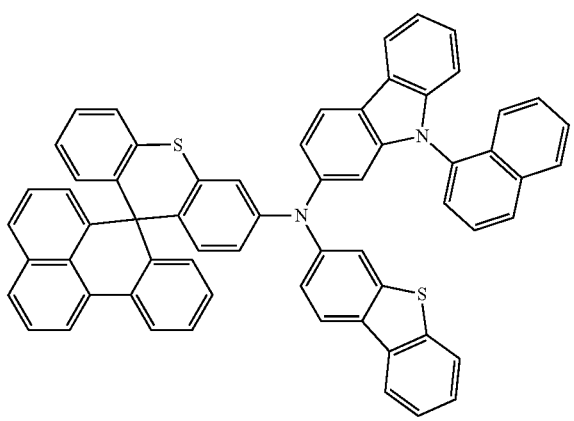

916
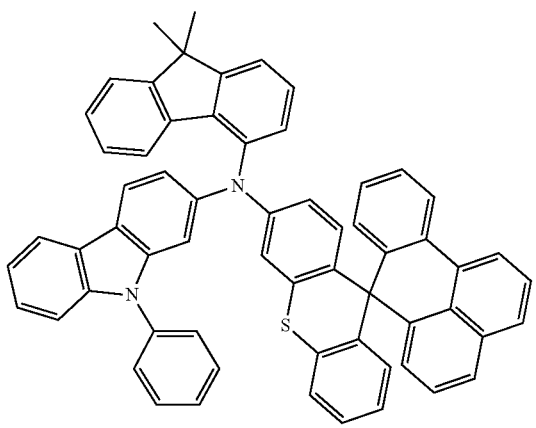
917
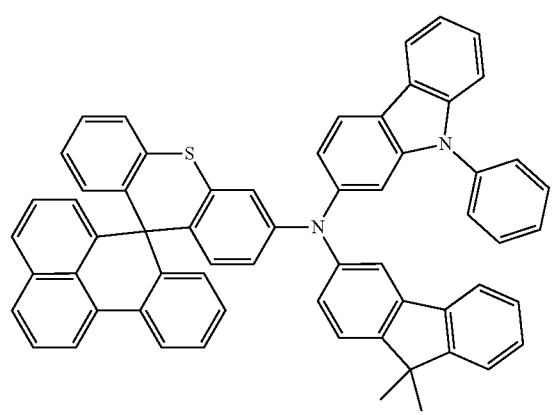
918
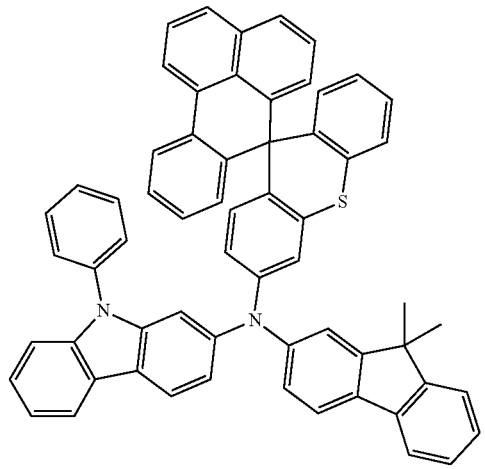
926
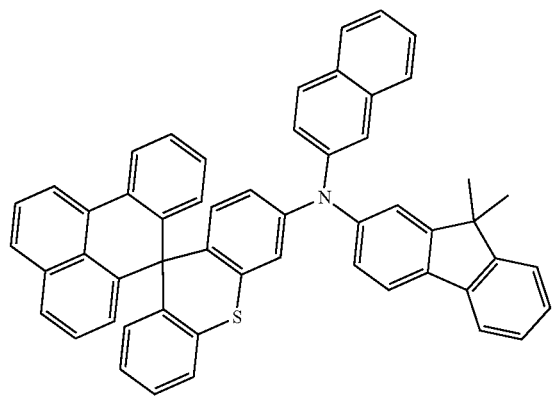
927
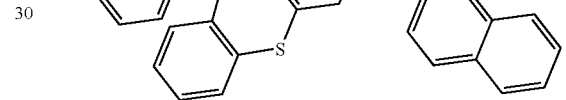
928
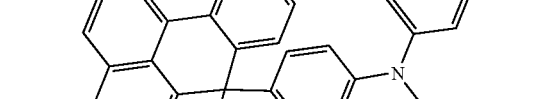
929
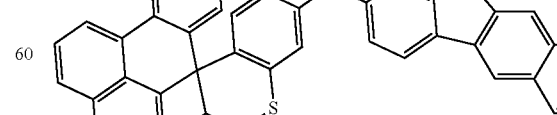

-continued
930
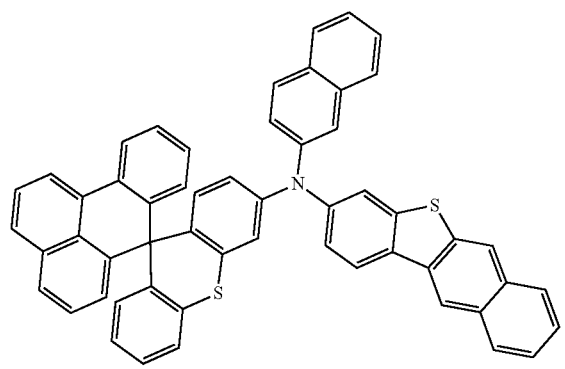
931
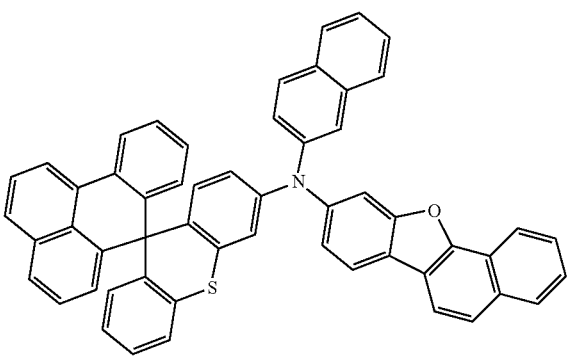
932
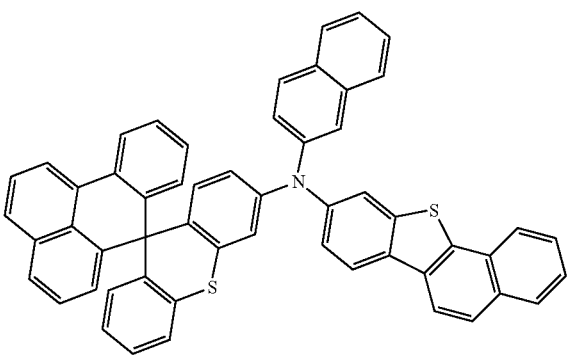
933
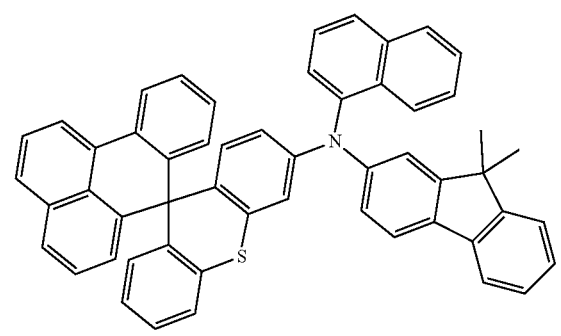
-continued
934
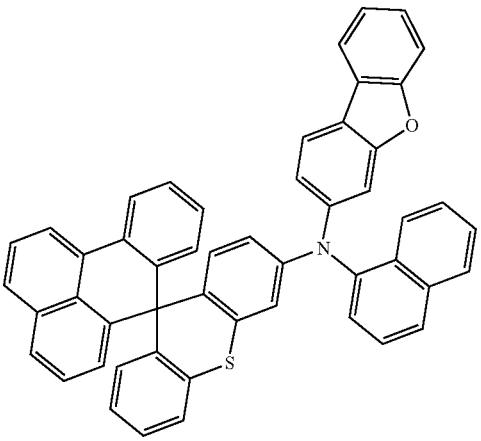
935
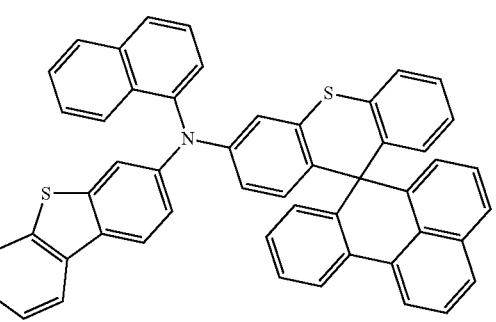
936
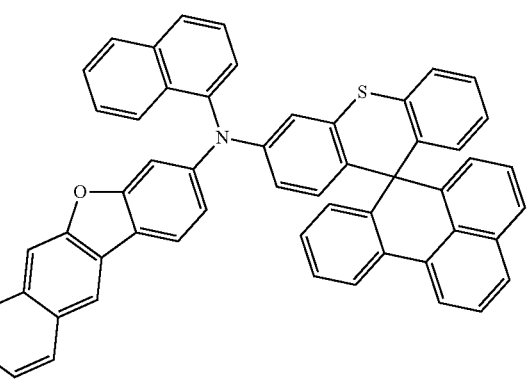
937
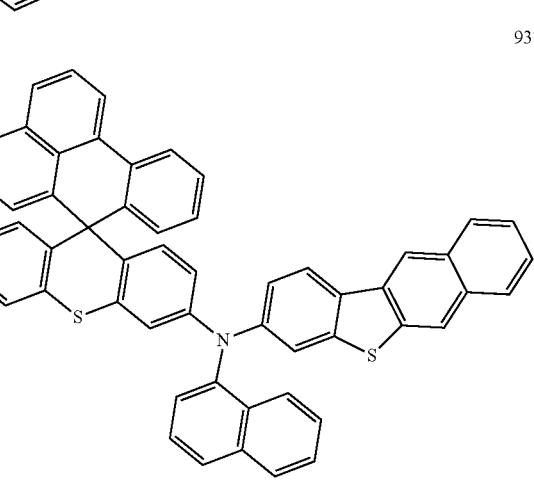

938
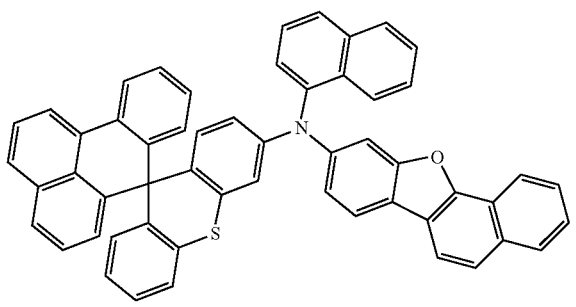
939
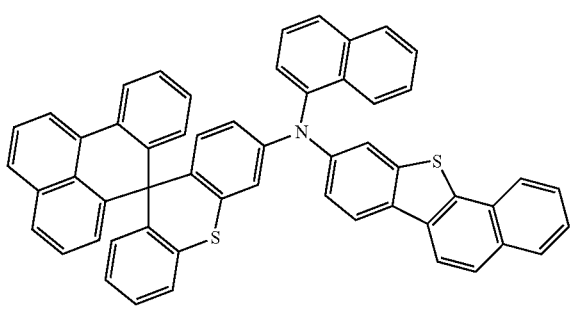
944
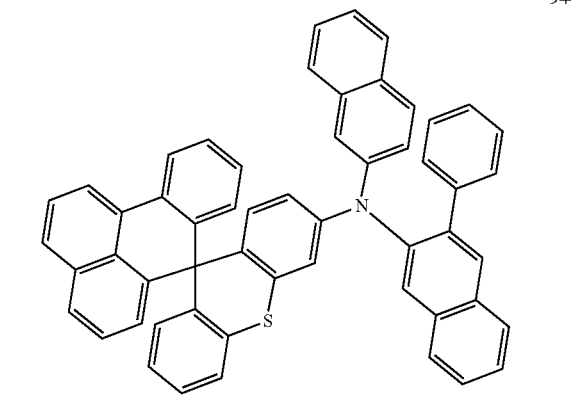
945
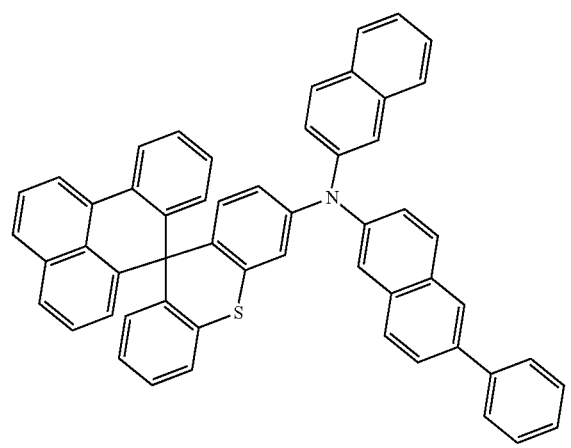
946
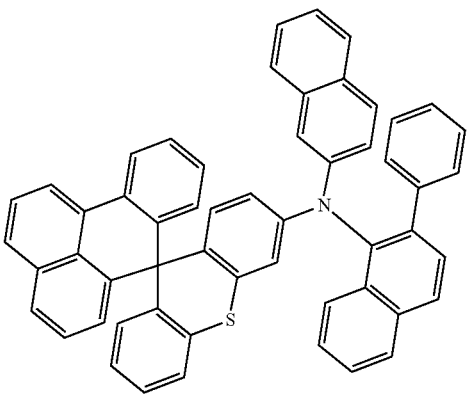
947
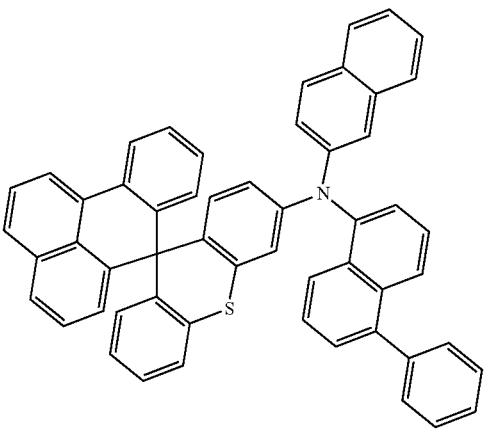
948
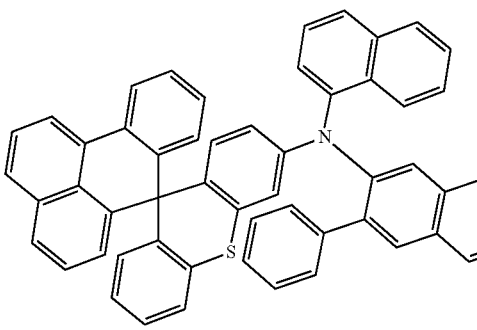
949
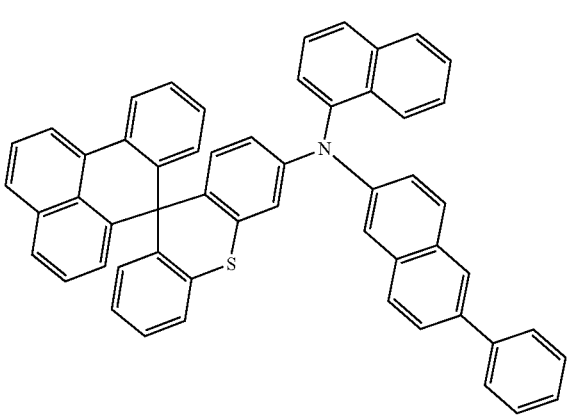

950
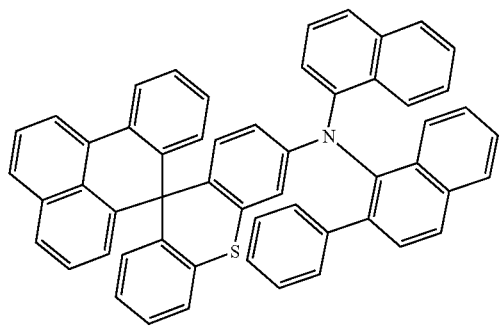
951
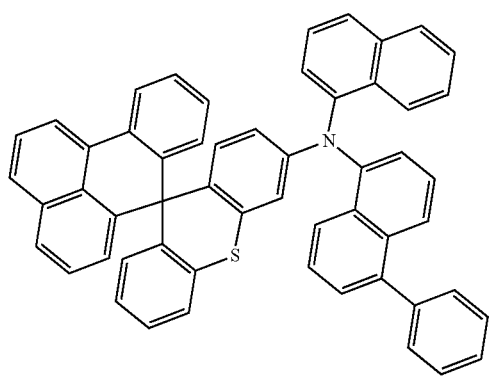
953
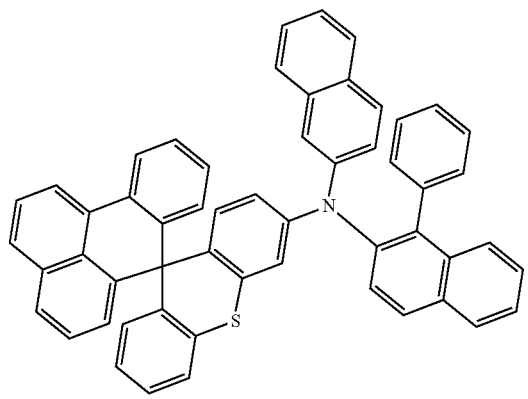
954
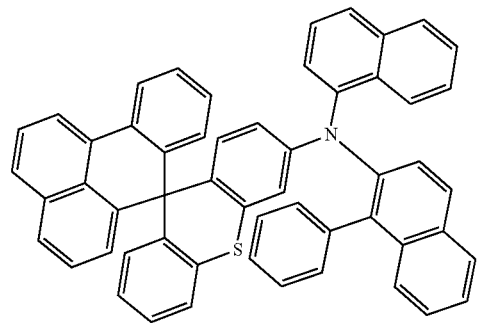
962
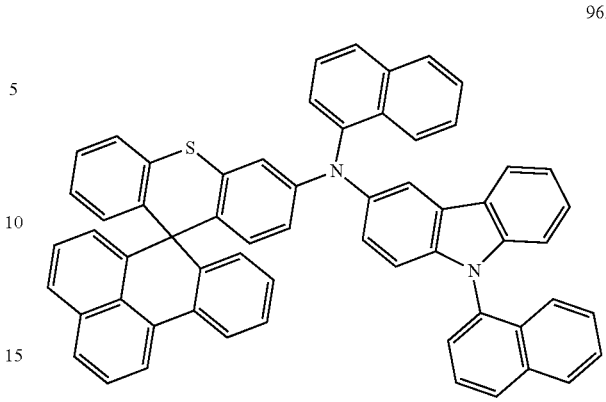
963
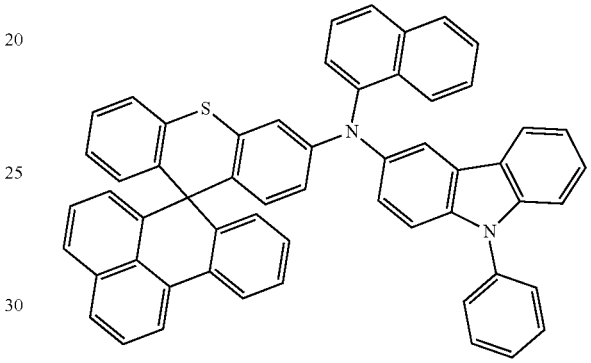
965
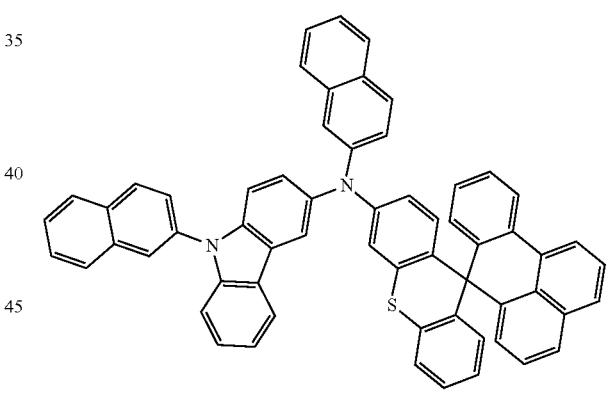
966

579
-continued
970
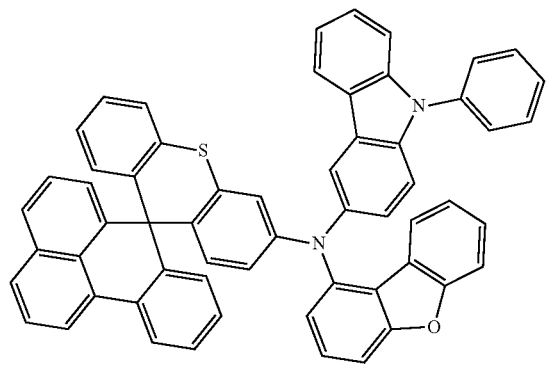
971
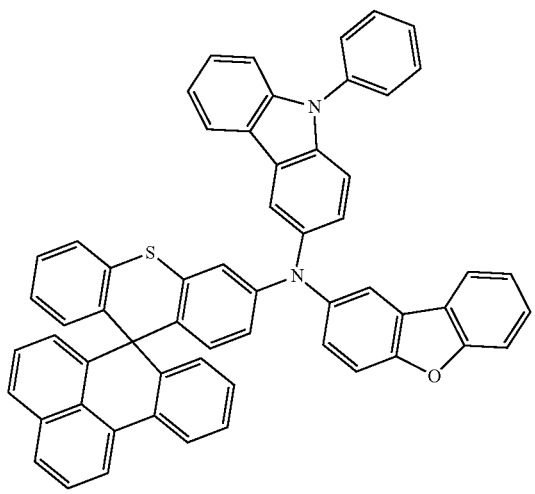
972
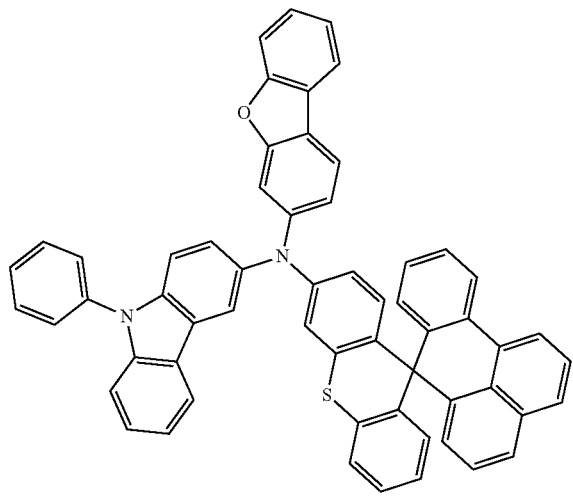
580
-continued
978
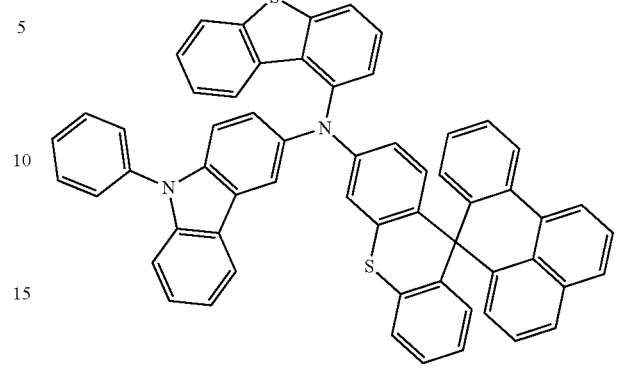
979
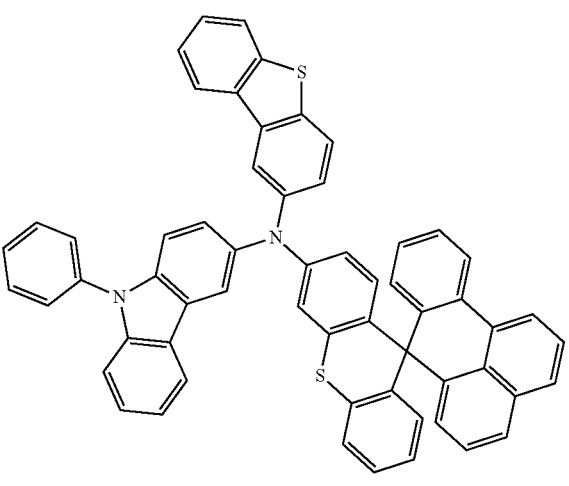
980
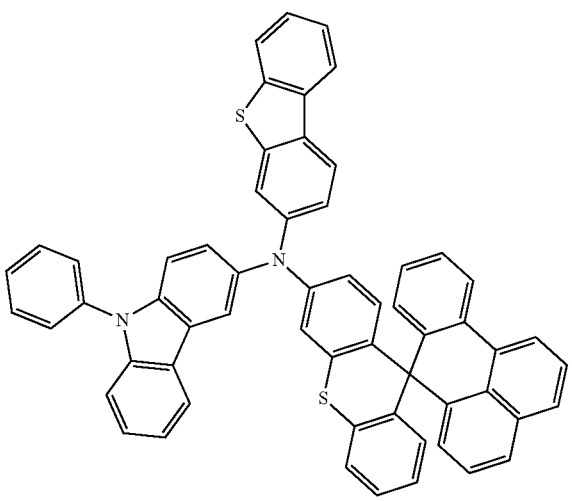

-continued
981
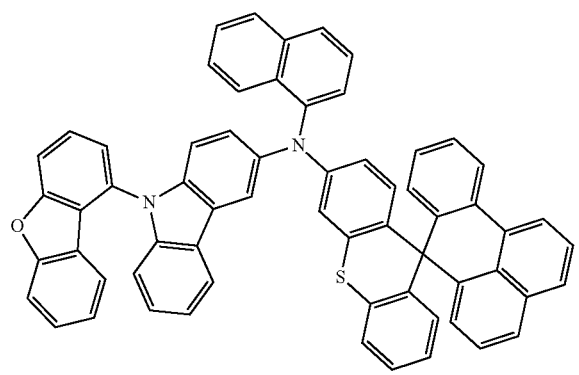
982
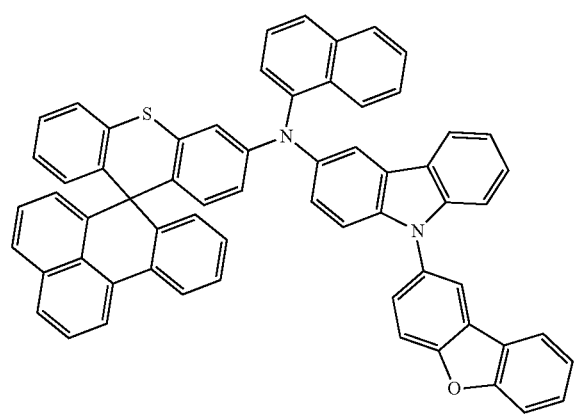
983
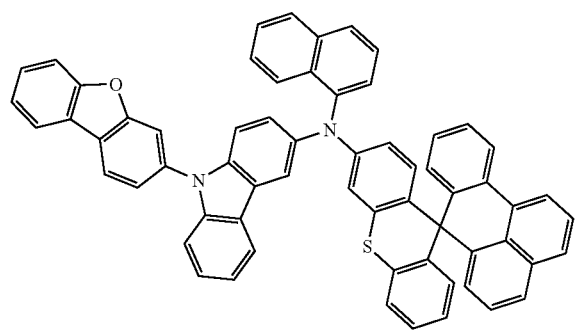
984
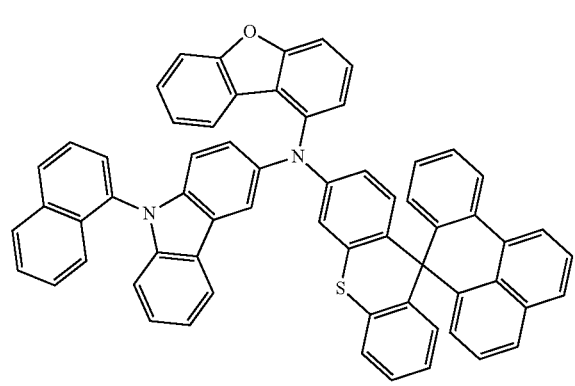
-continued
985
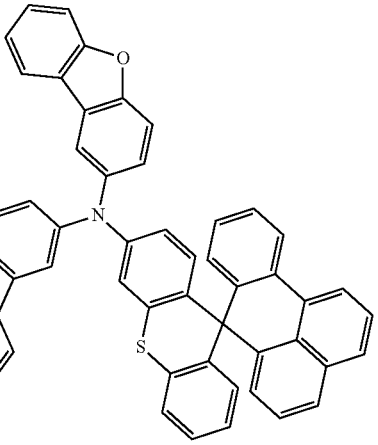
986
987
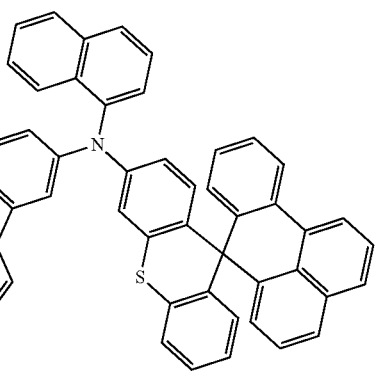

988
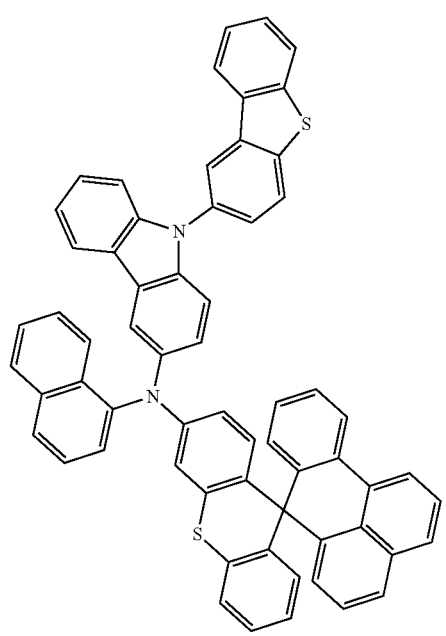
989
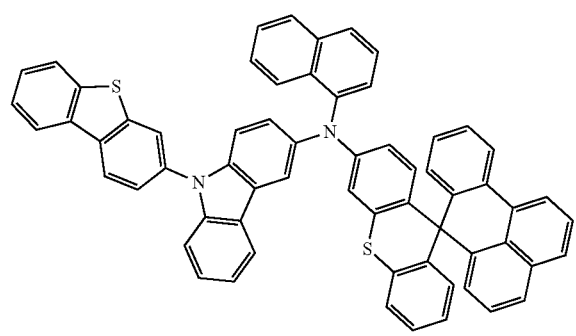
990
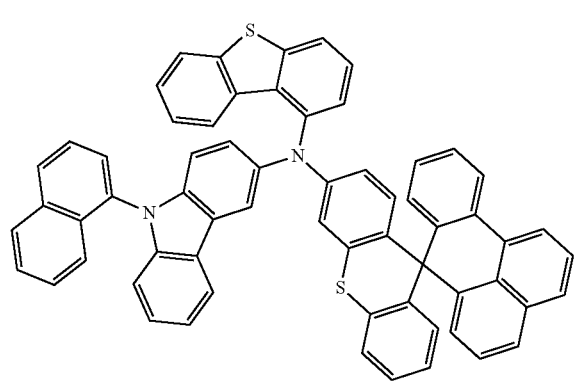
991
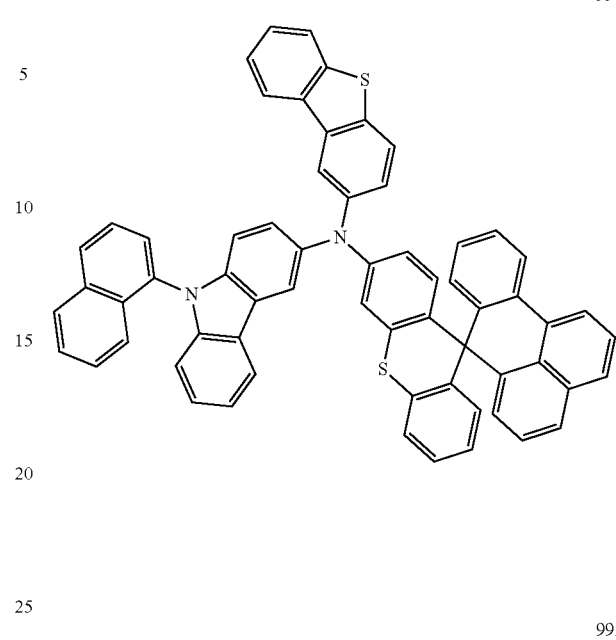
992
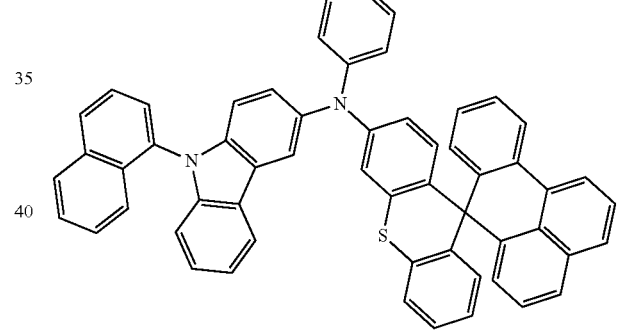
996
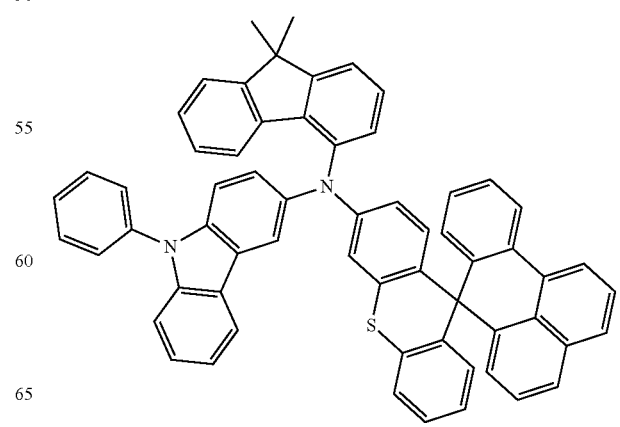

997
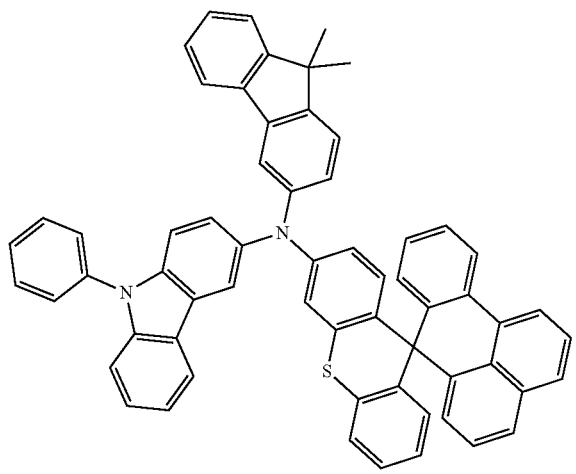
1000
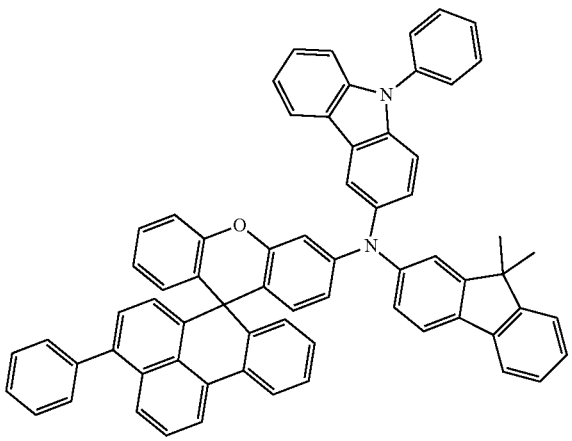
998
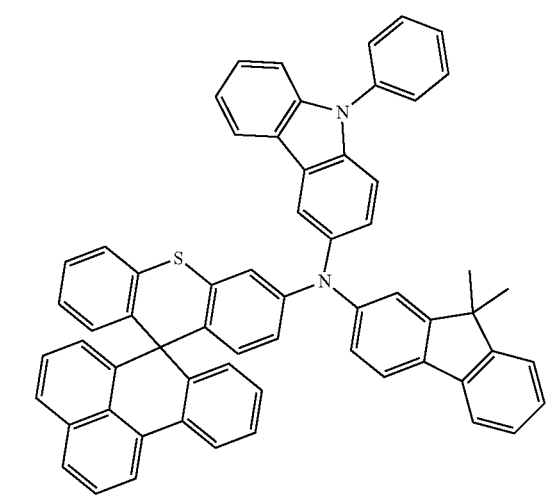
1001
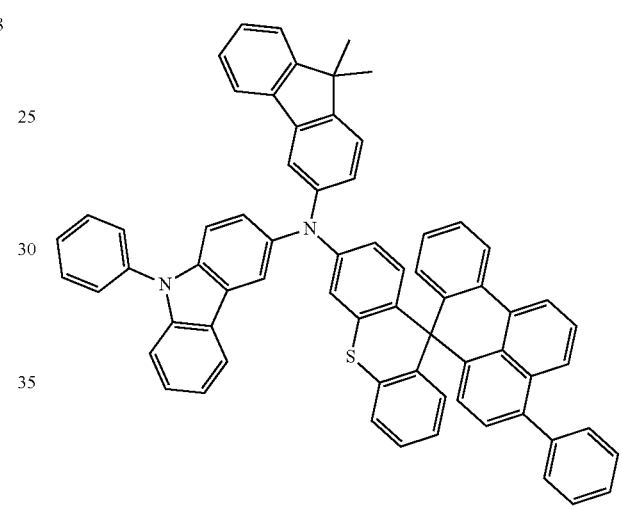
999
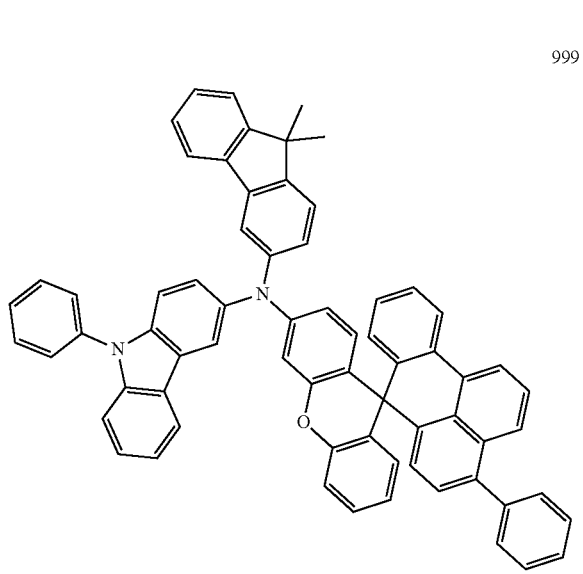
1002
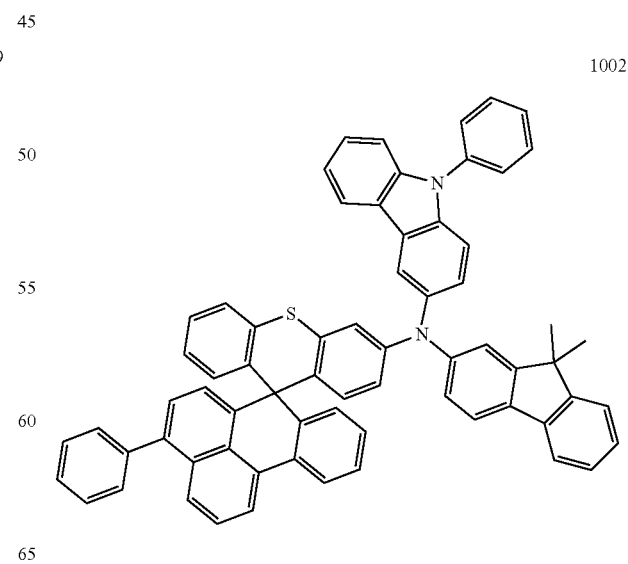

-continued
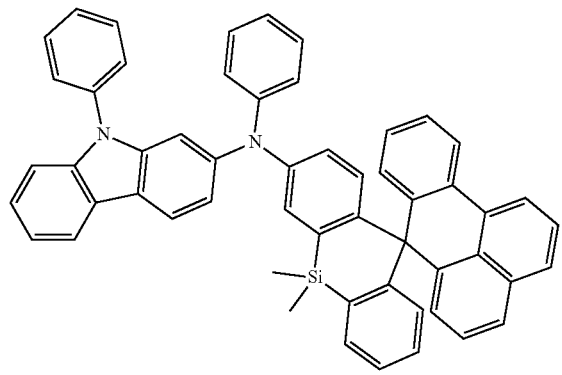
1003
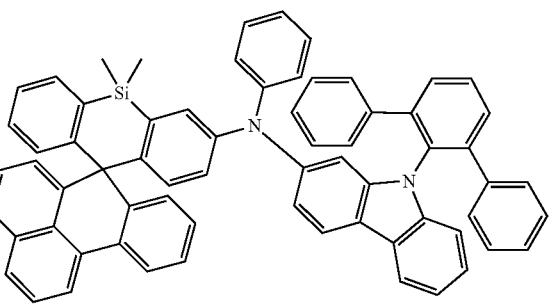
1007
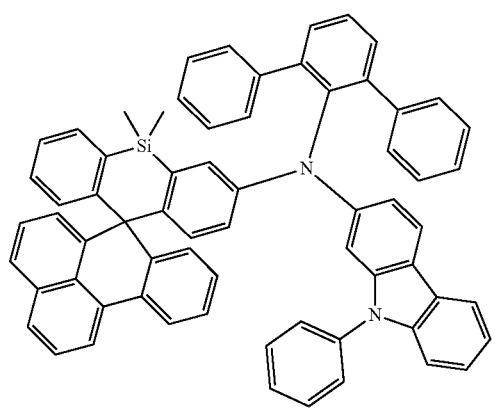
1004
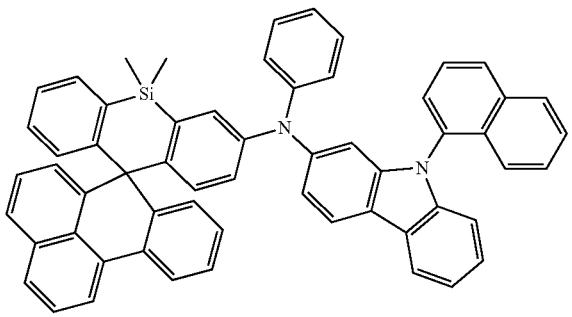
1008
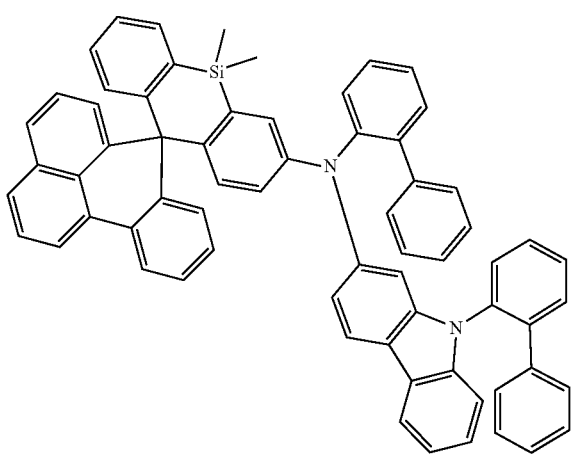
1005
1006
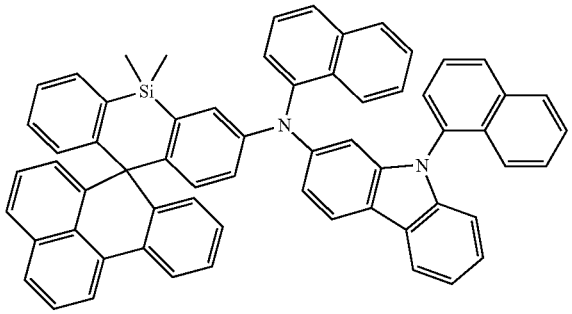
1009
1010

589
-continued
1011
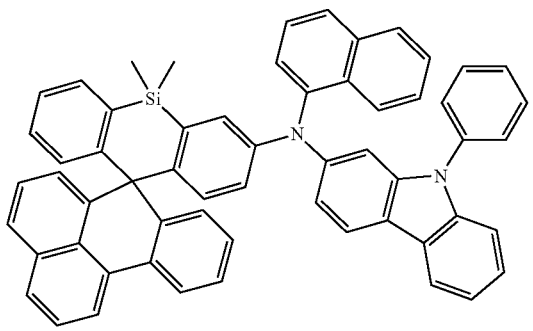
1012
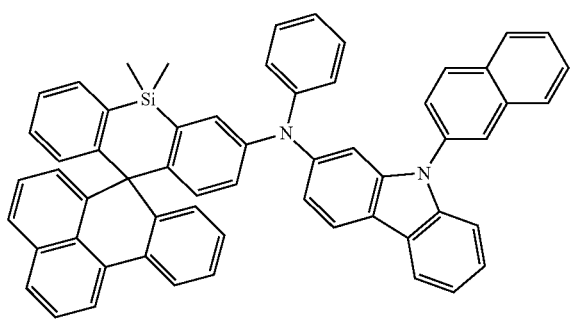
1013
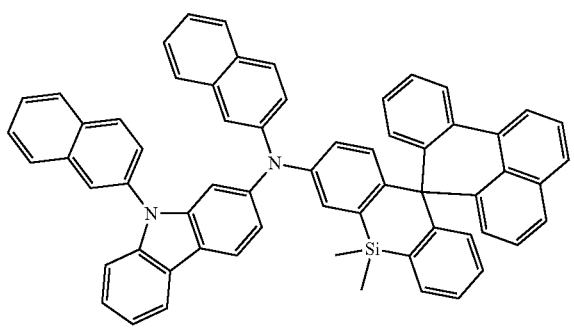
1014
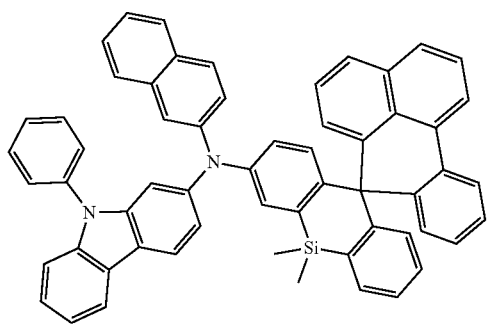
590
-continued
1015
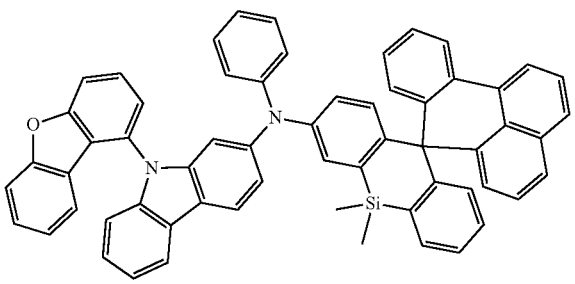
1016
1017
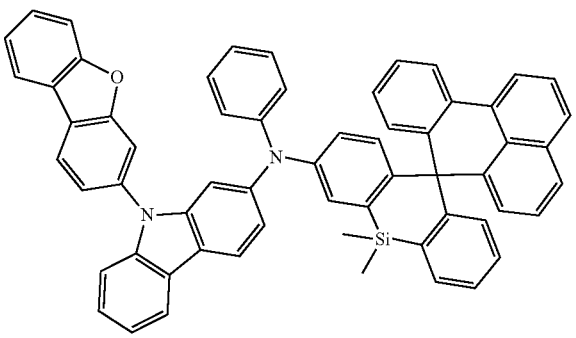
1018
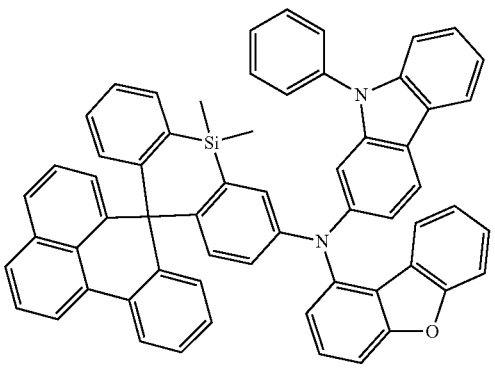

591
-continued
1019
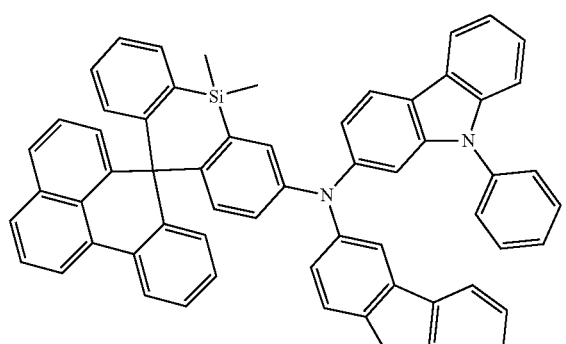
1020
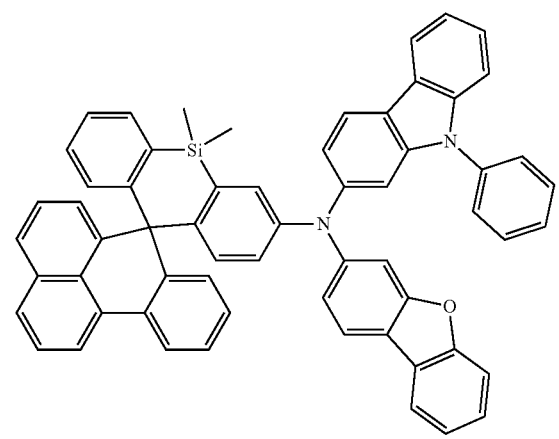
1021
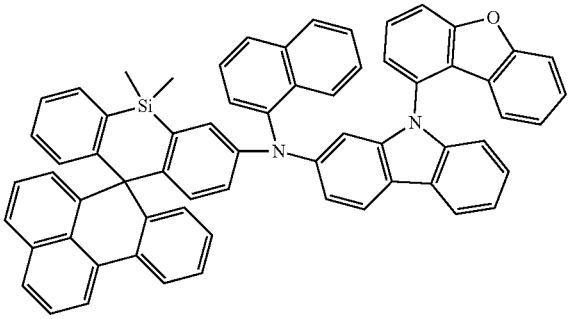
1022
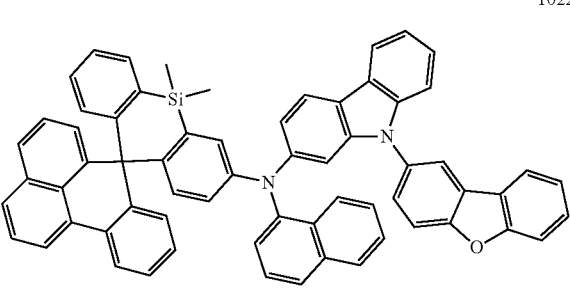
592
-continued
1023
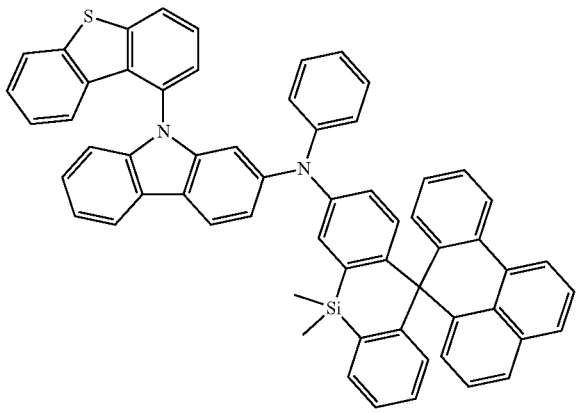
1024
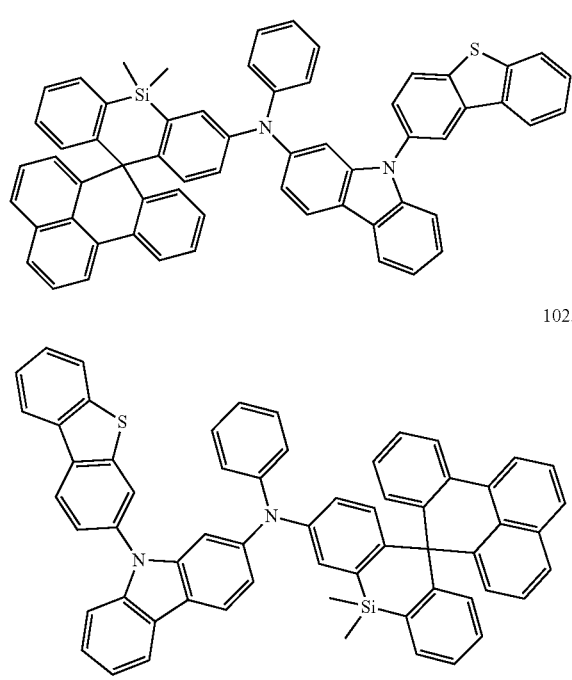
1025
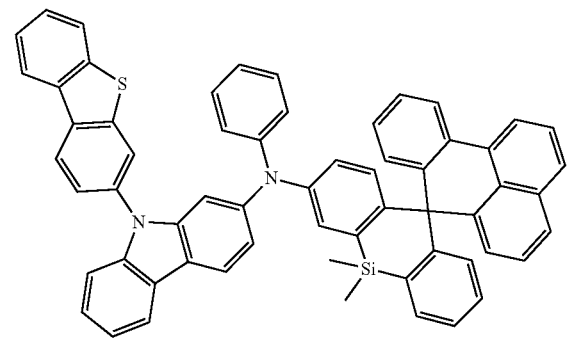
1026
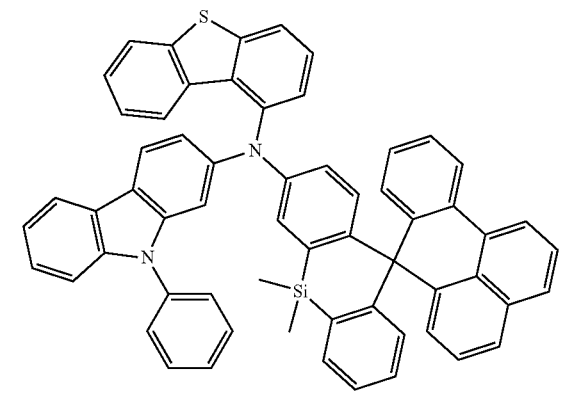

-continued
1027
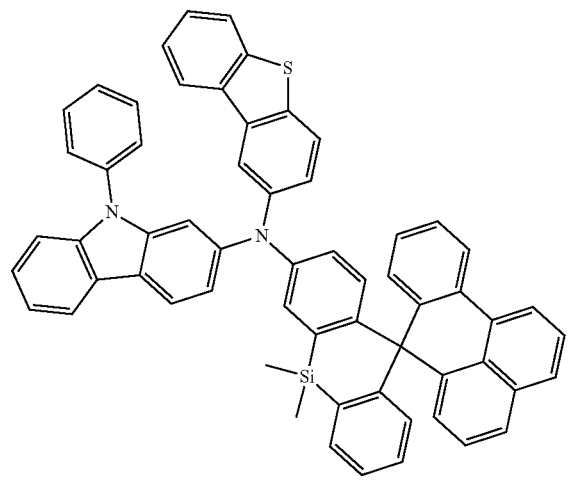
1028
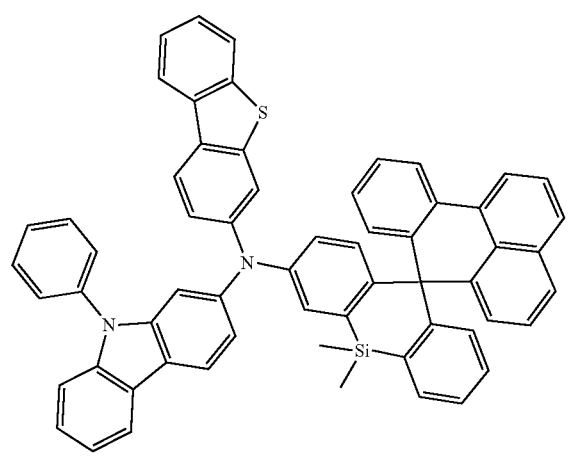
1029
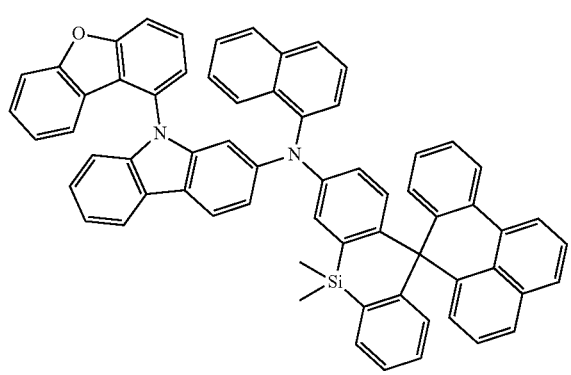
1030
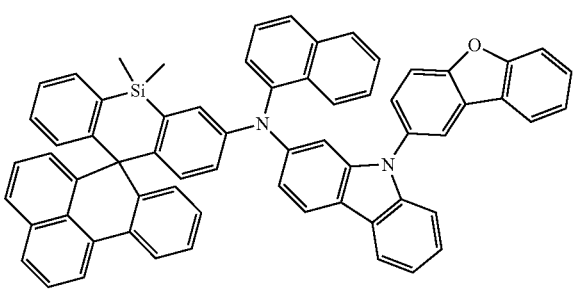
-continued
1031
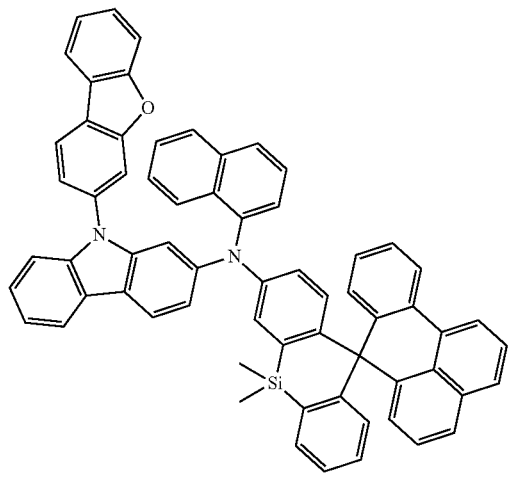
1032
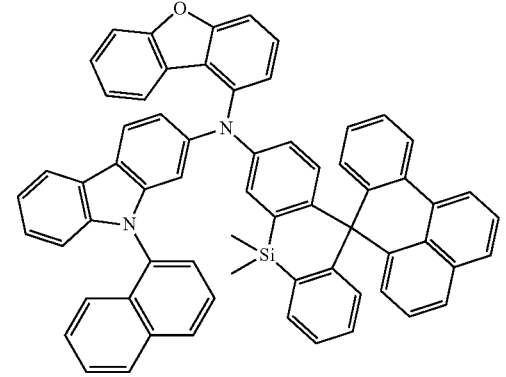
1033
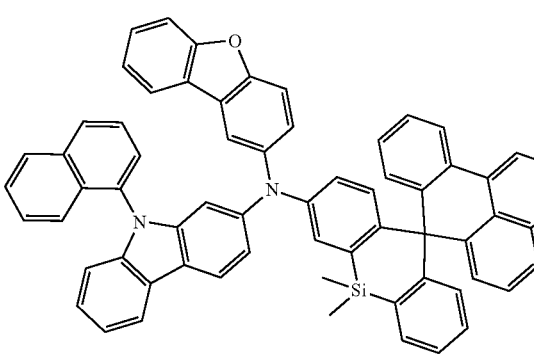
1034
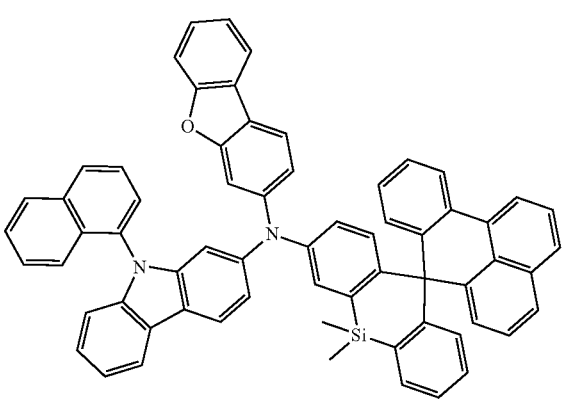

1035
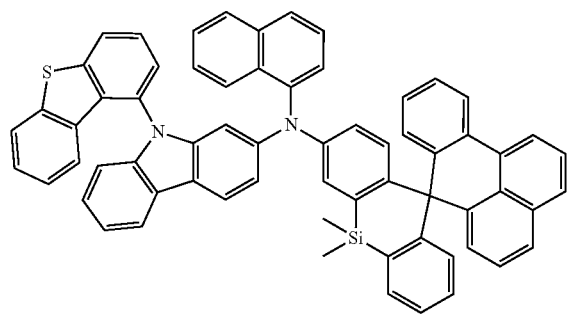
1036
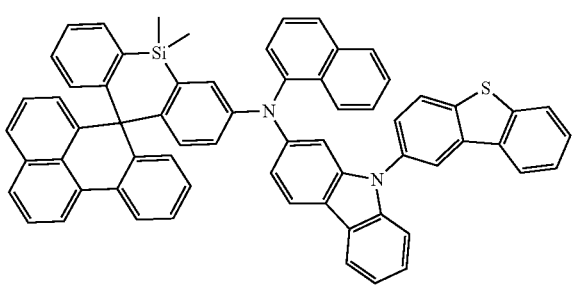
1037
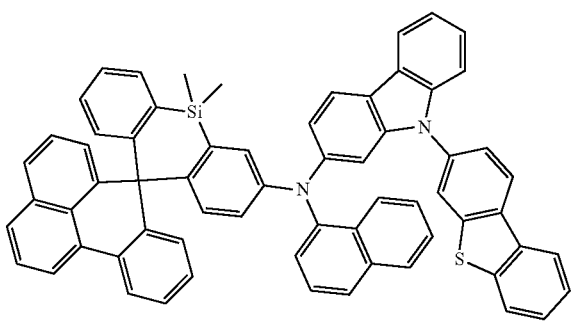
1038
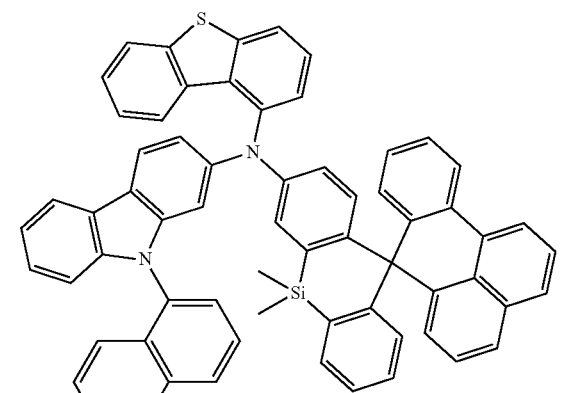
1039
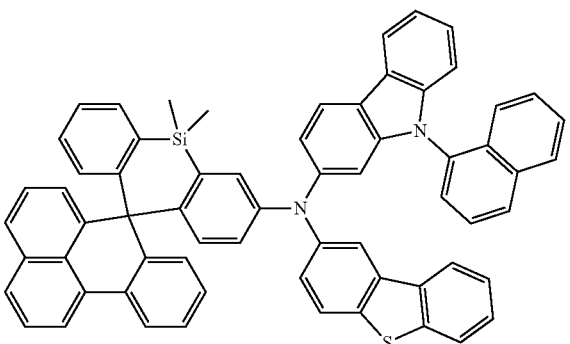
1040
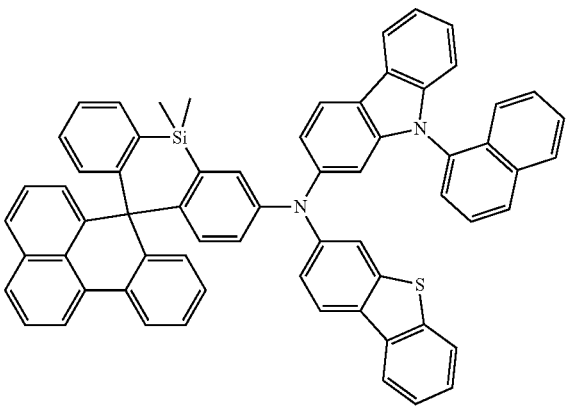
1041
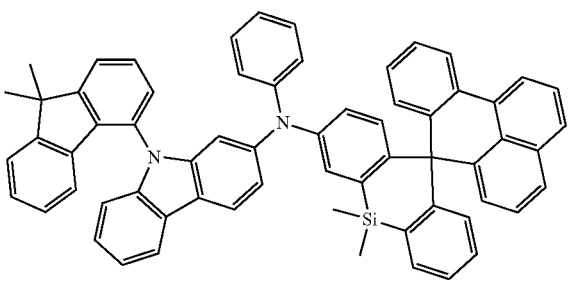
1042
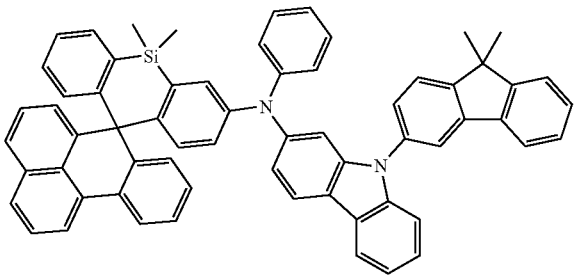

597
-continued
1043
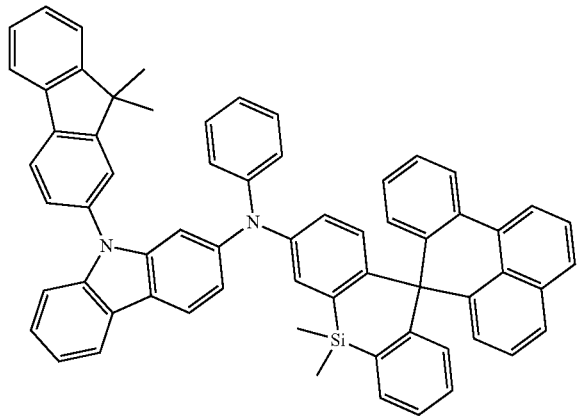
1044
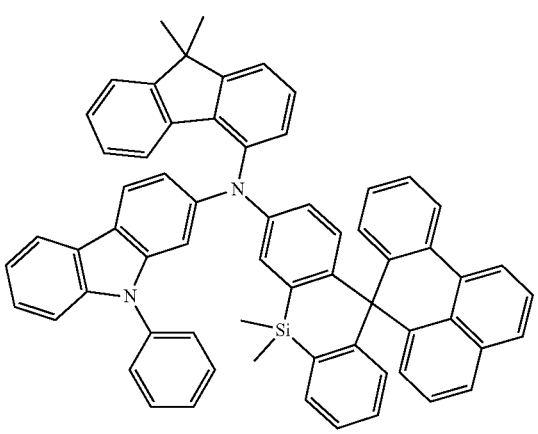
1045
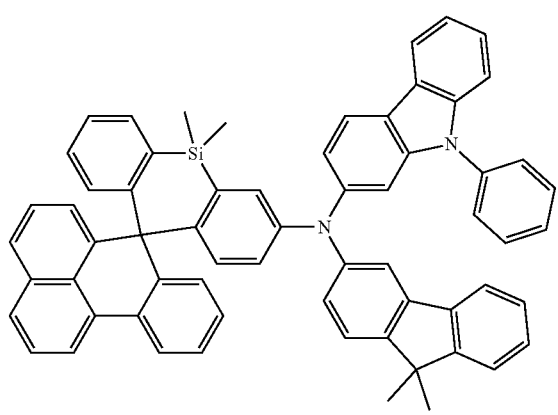
598
-continued
1046
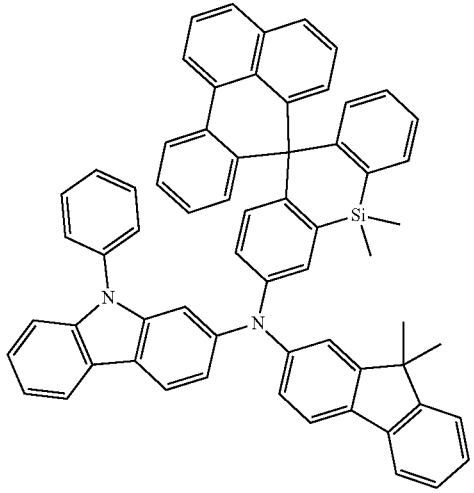
1047
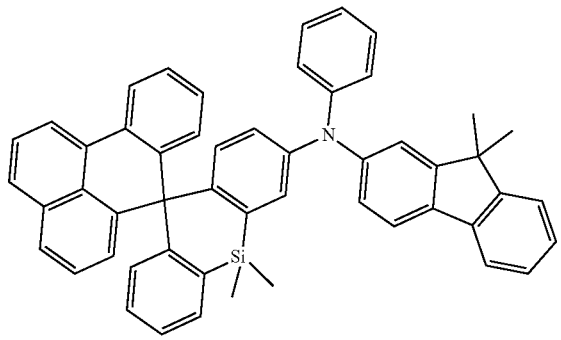
1048
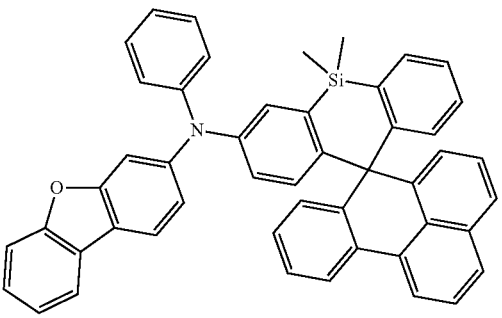
1049
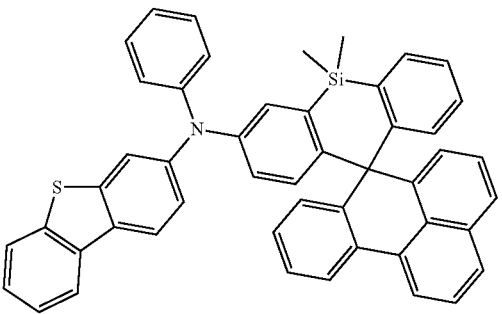

1050
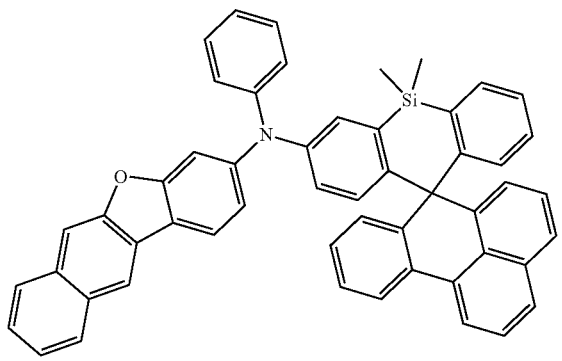
1051
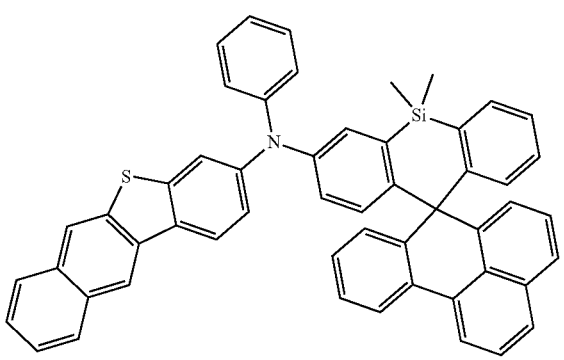
1052
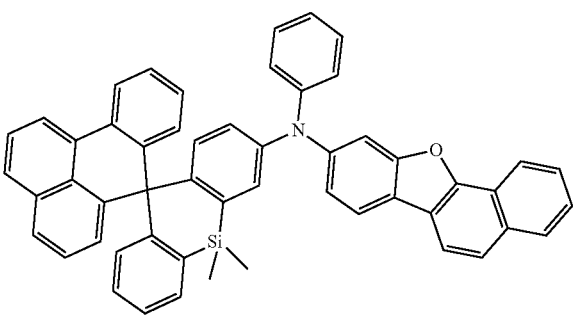
1053
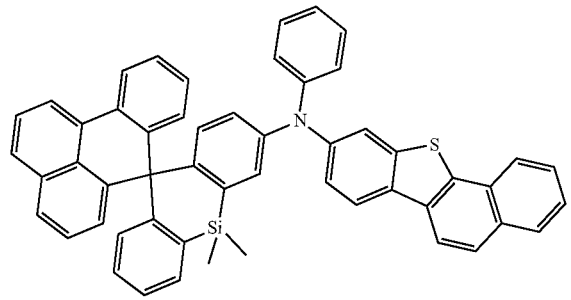
1054
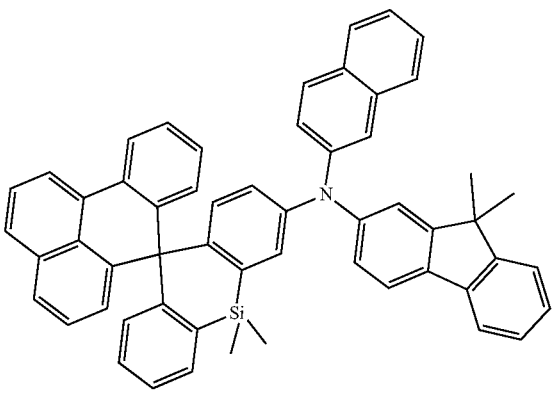
1055
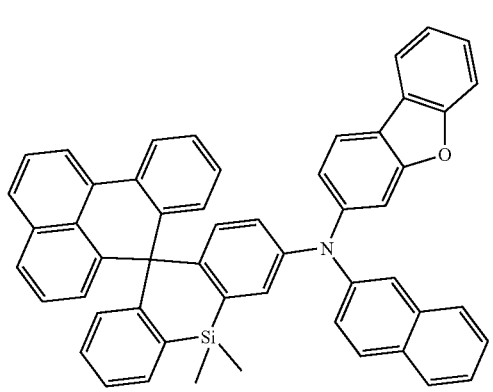
1056
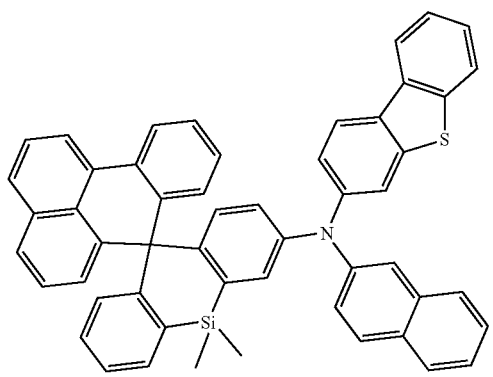
1057
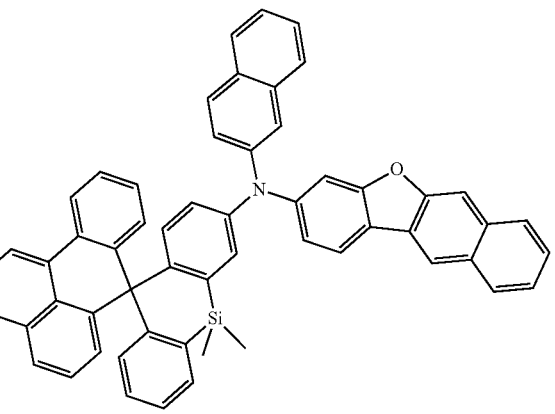

601
-continued
1058
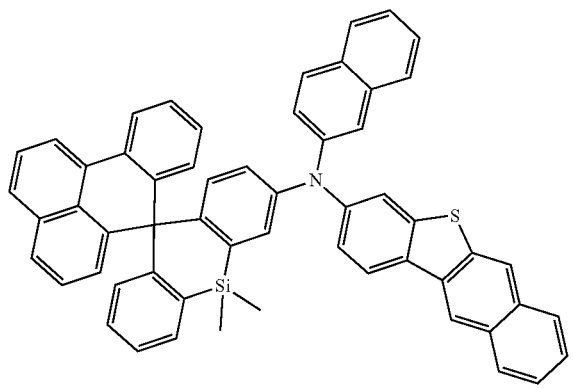
1059
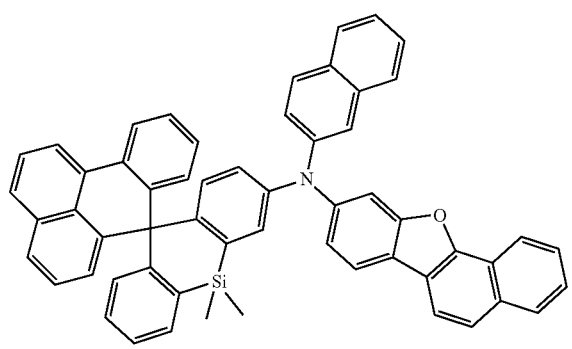
1060
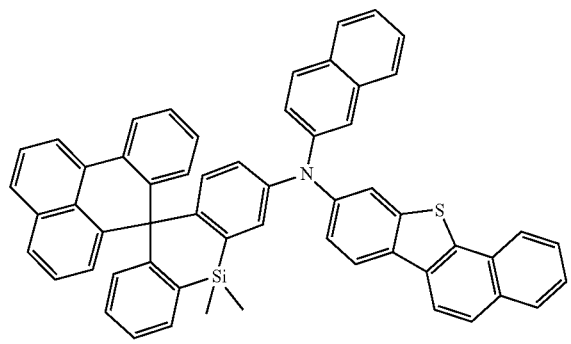
1061
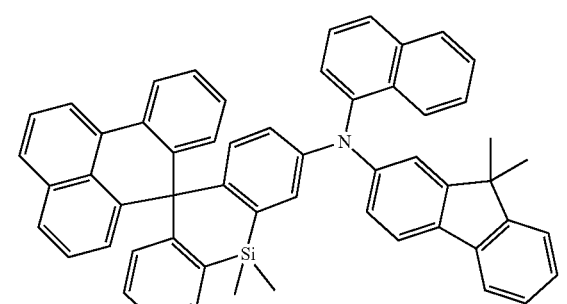
602
-continued
1062
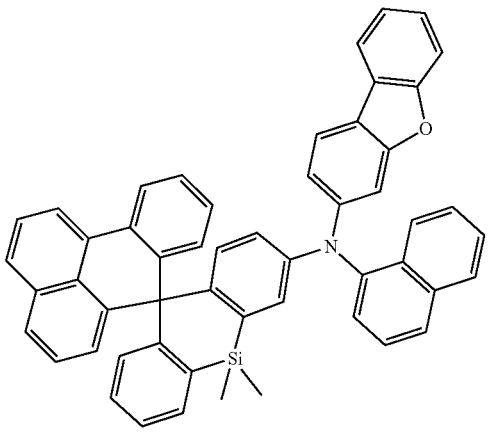
1063
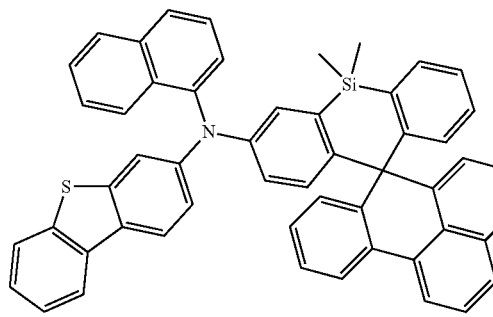
1064
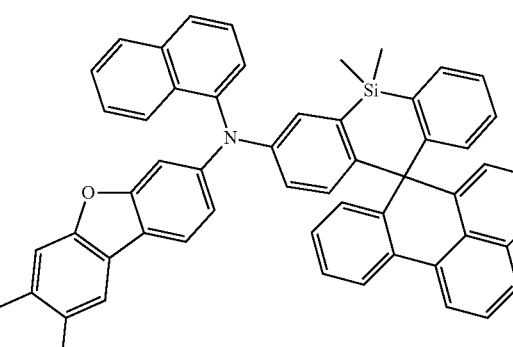
1065
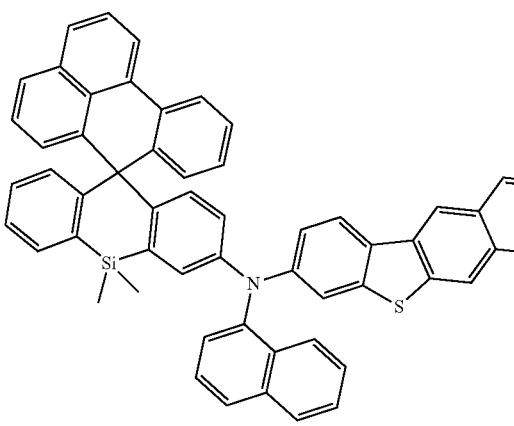

1066
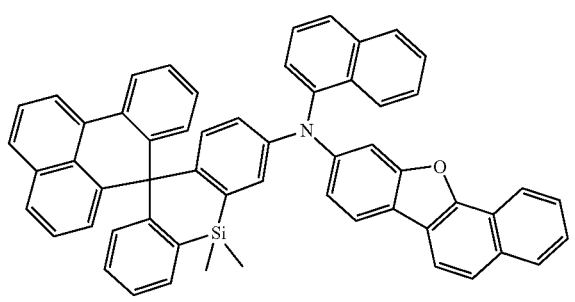
1067
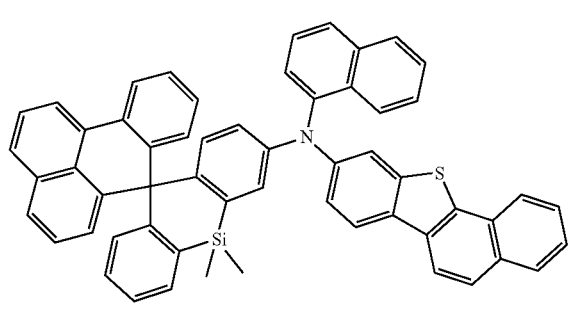
1068
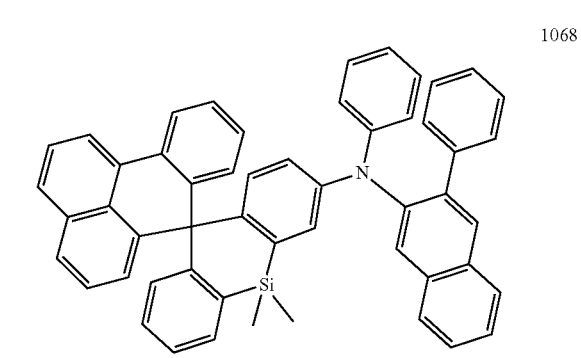
1069
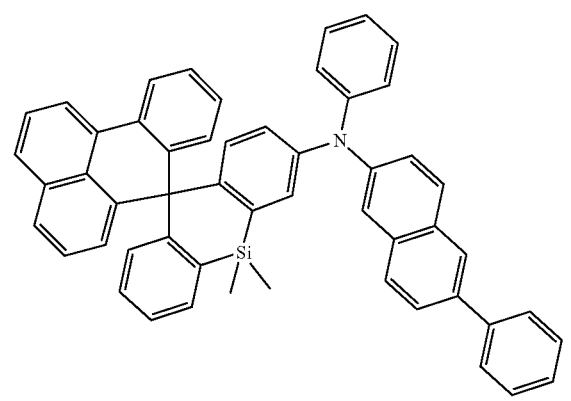
1070
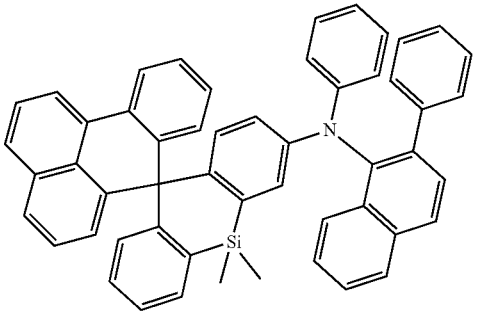
1071
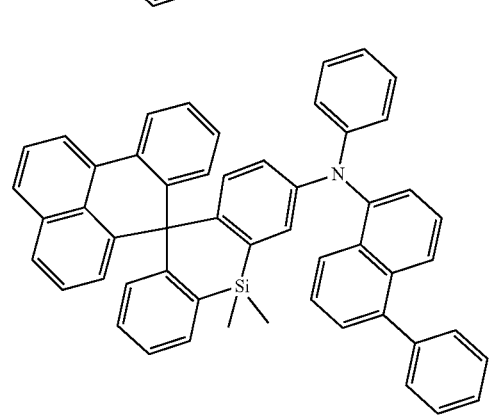
1072
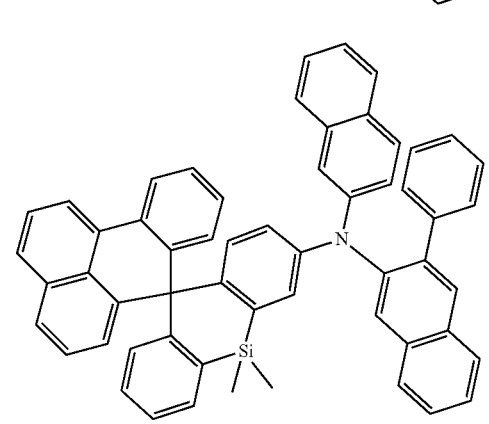
1073
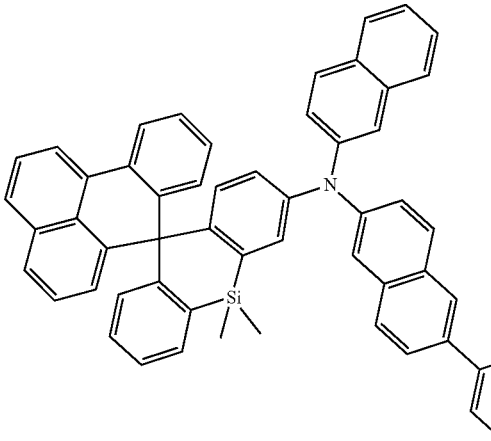

1074
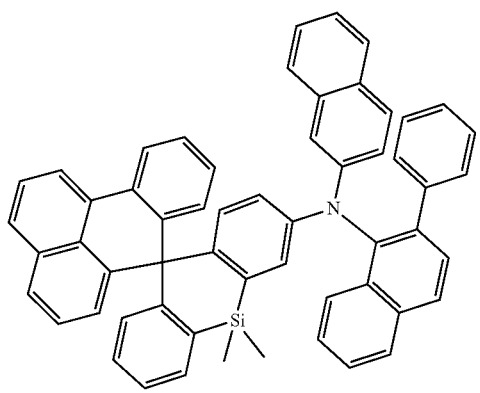
1075
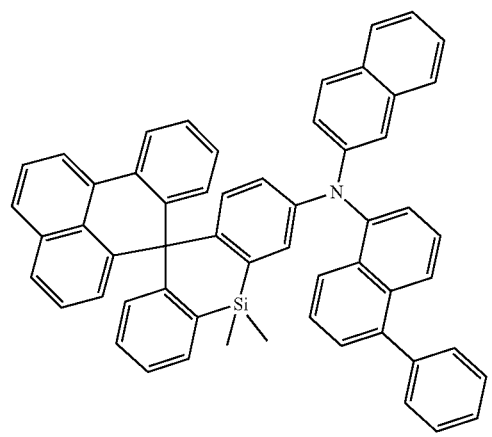
1076
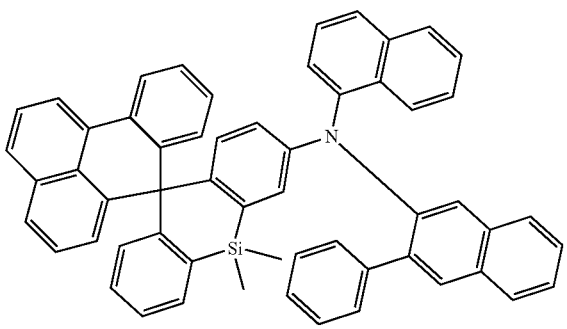
1077
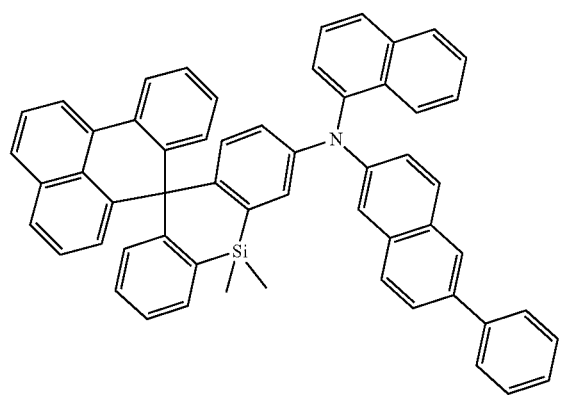
1078
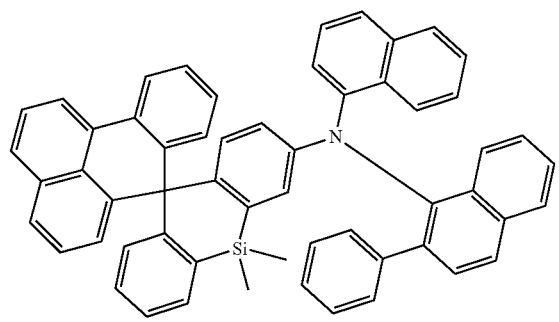
1079
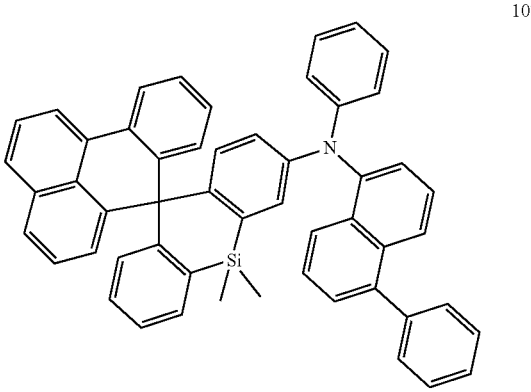
1080
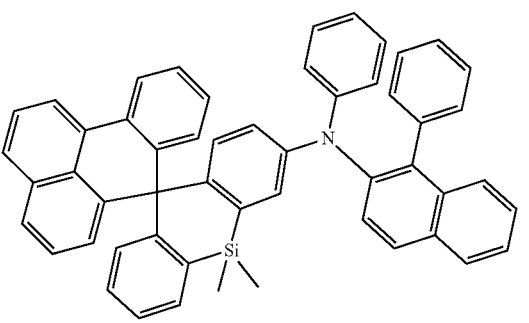
1081
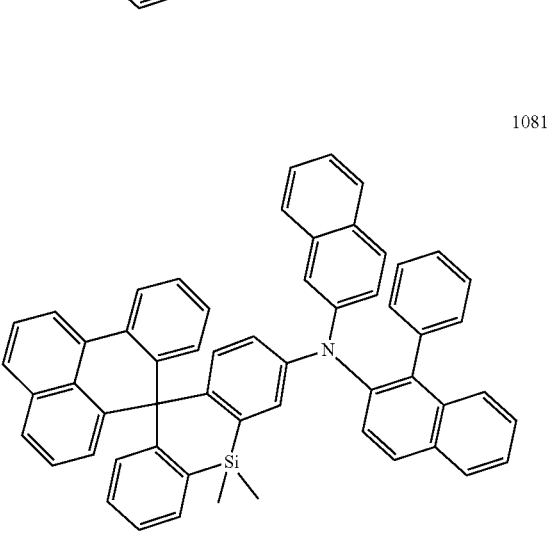

1082
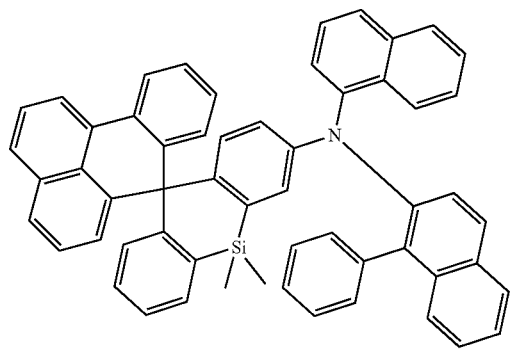
1083
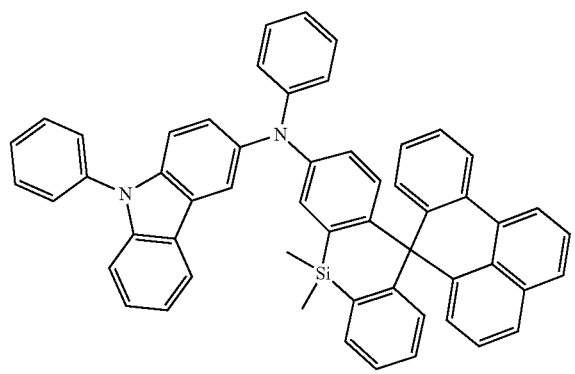
1084
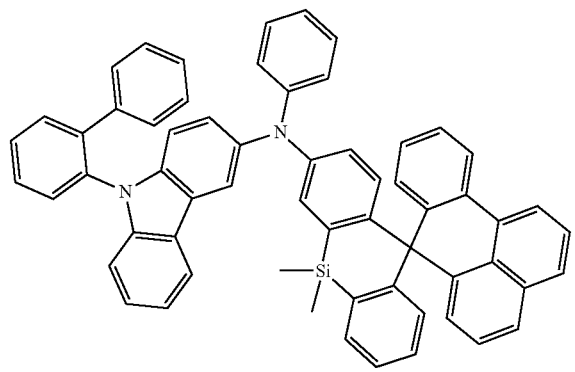
1085
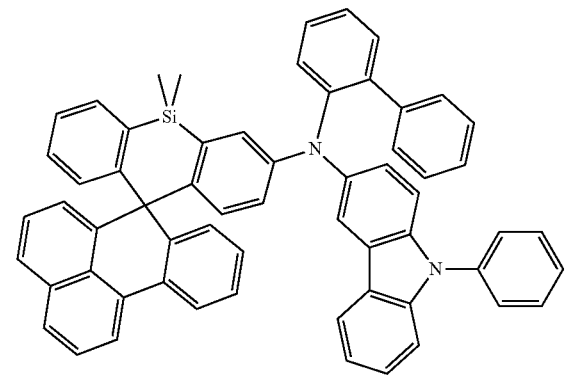
1086
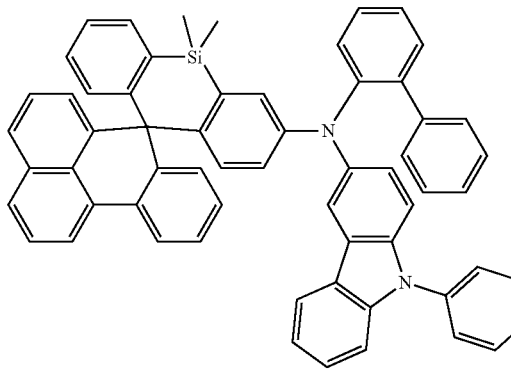
1087
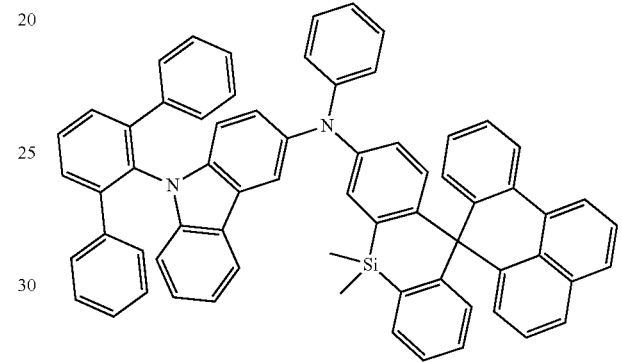
1088
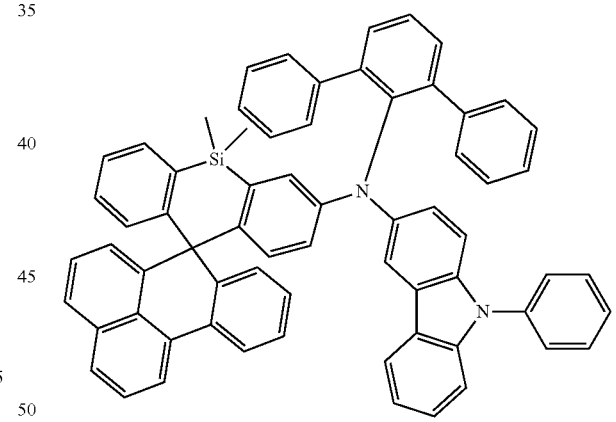
1089
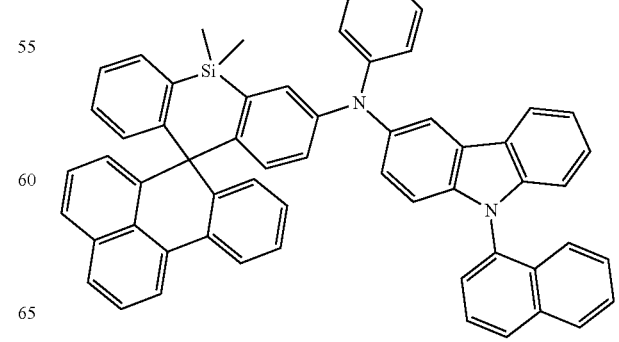

1090
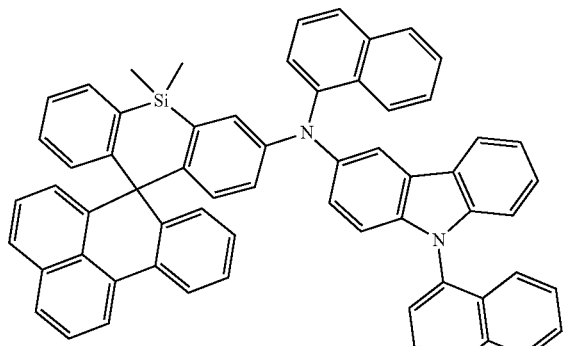
1091
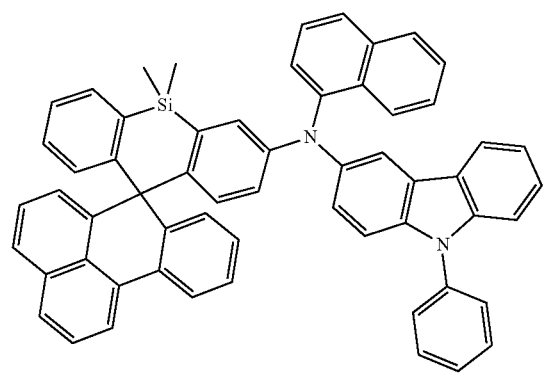
1092
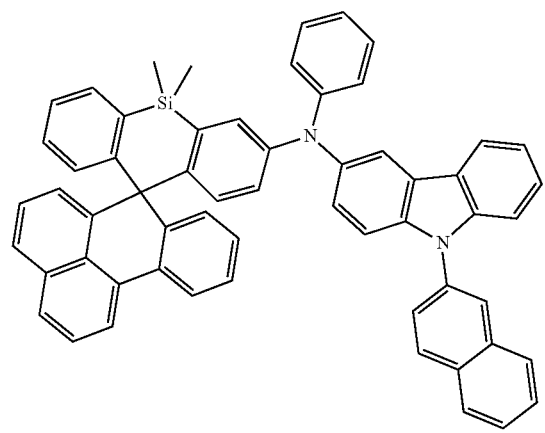
1093
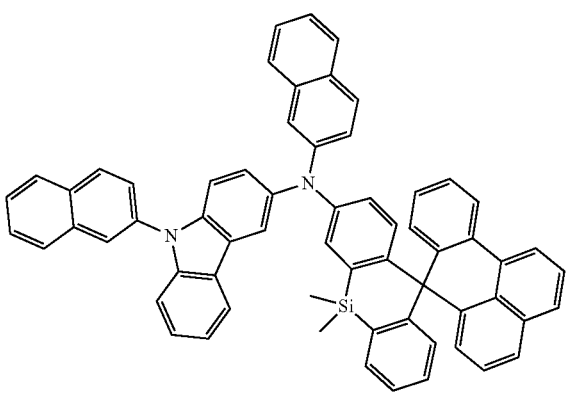
1094
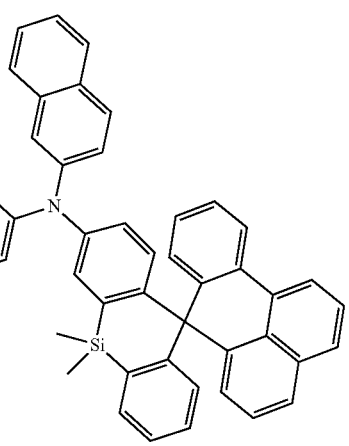
1095
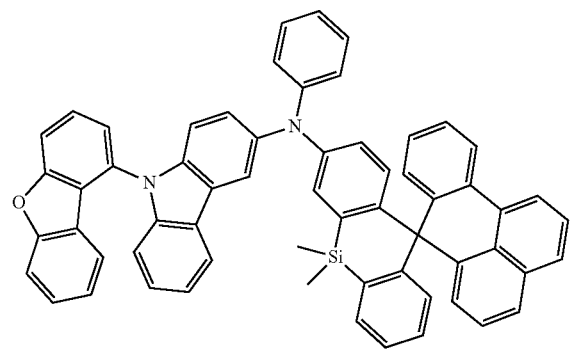
1096
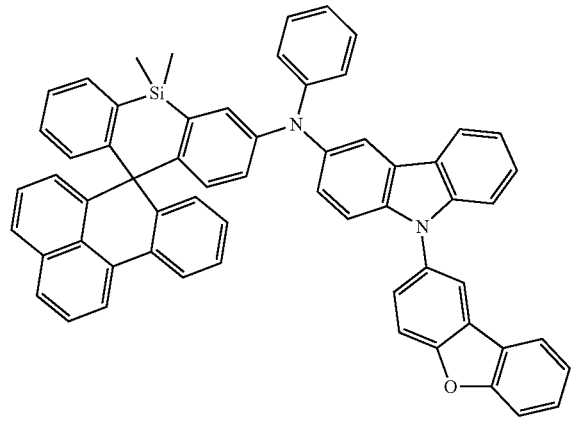
1097
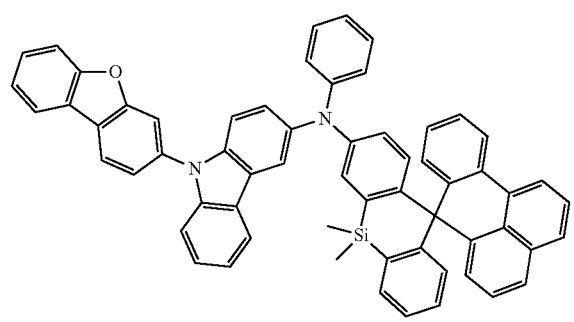

611
-continued
1098
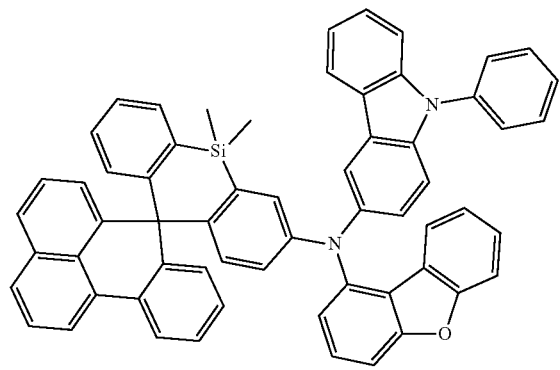
1099
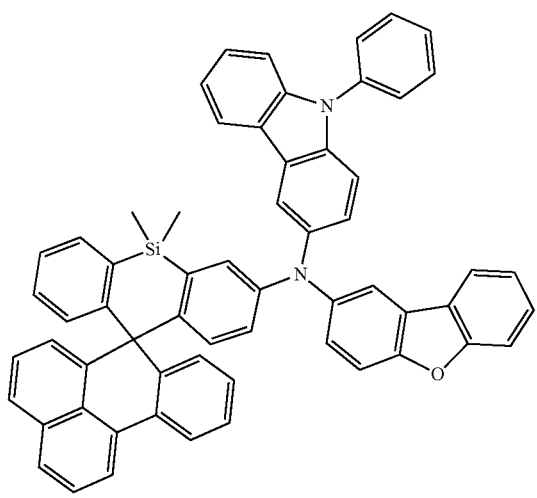
1100
612
-continued
1101
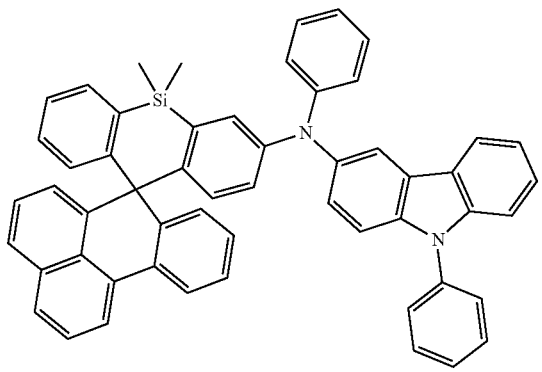
1102
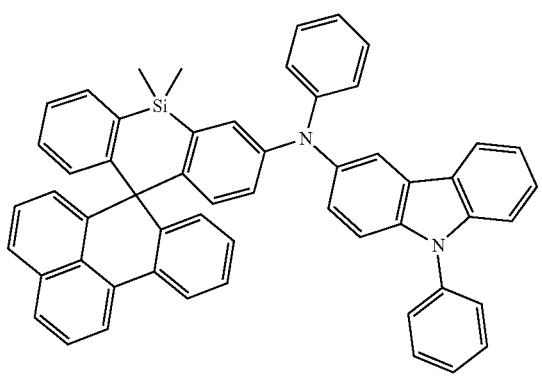
1103
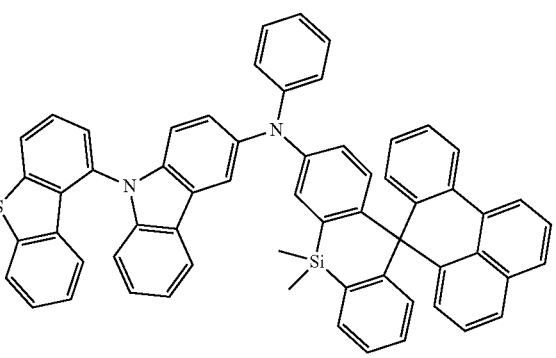
1104
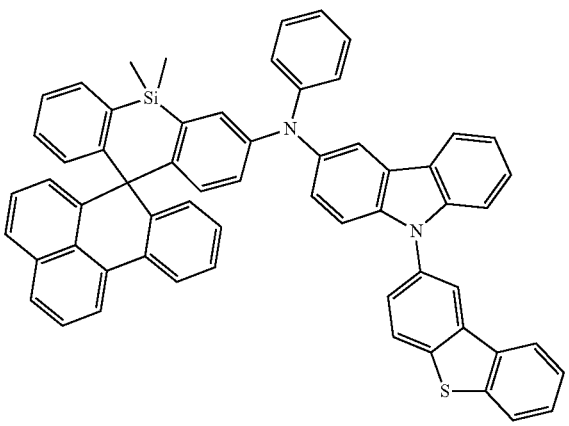

613
-continued
1105
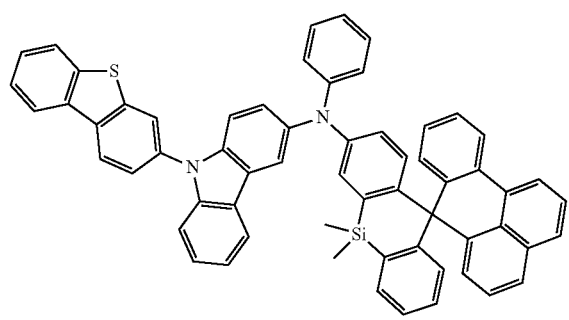
1106
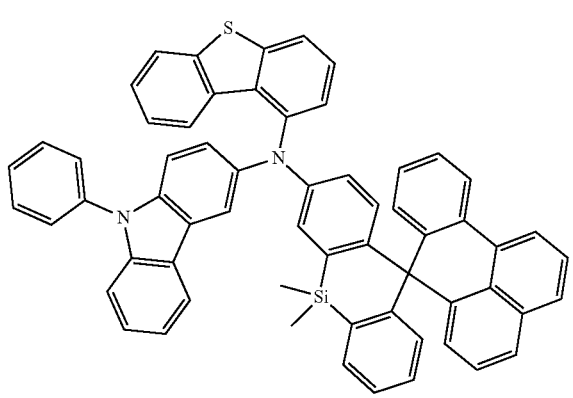
1107
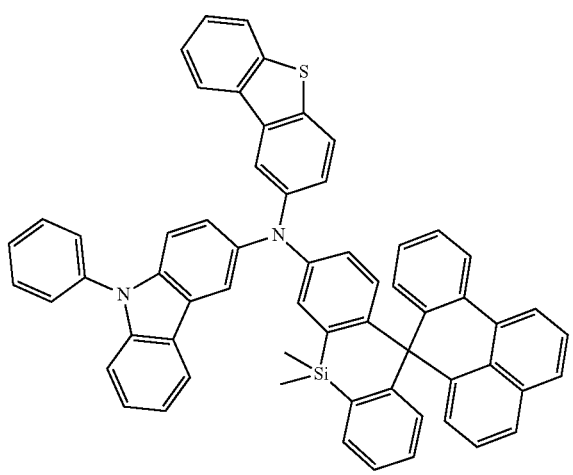
614
-continued
1108
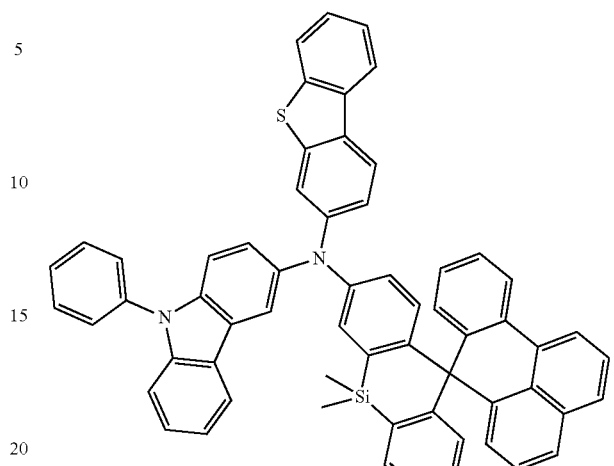
1109
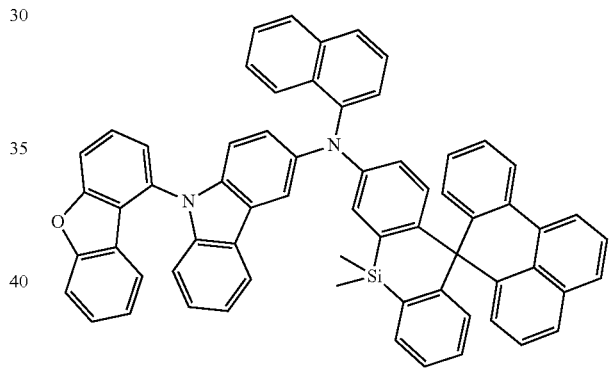
1110
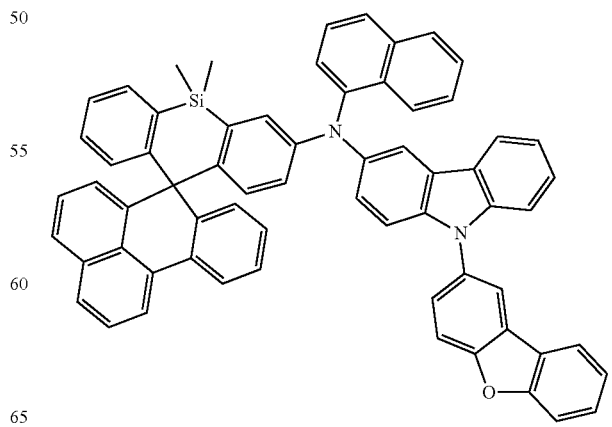

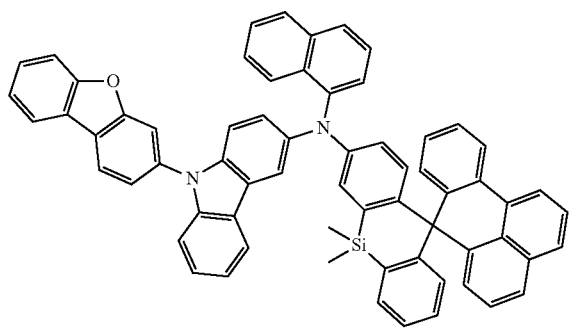
1111
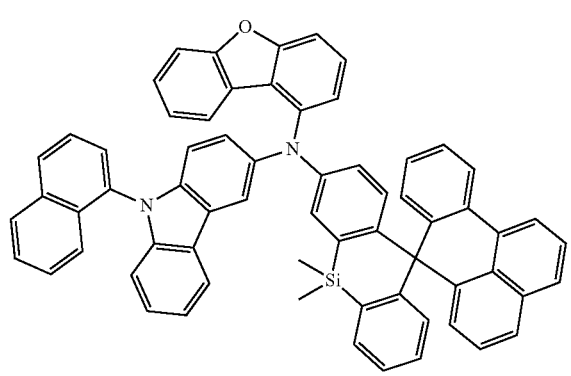
1112
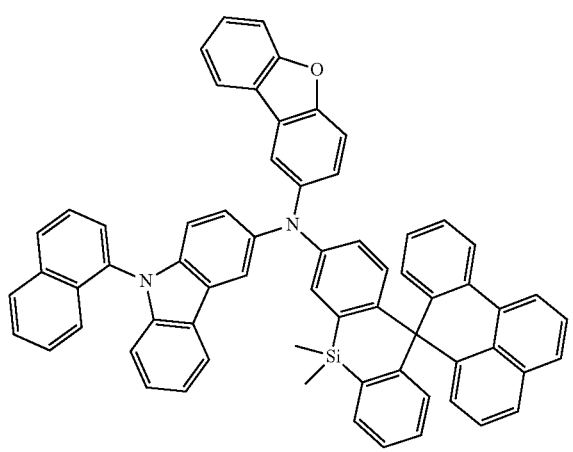
1113
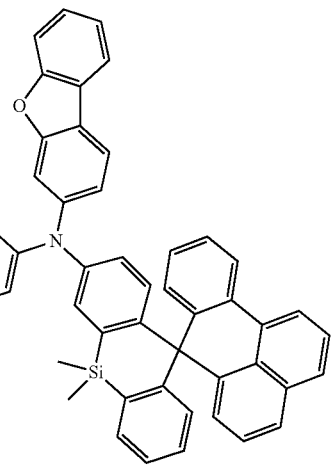
1114
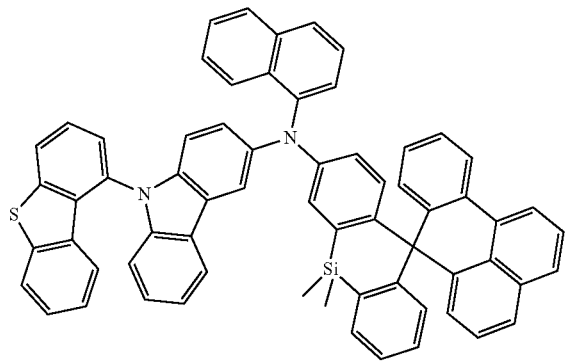
1115
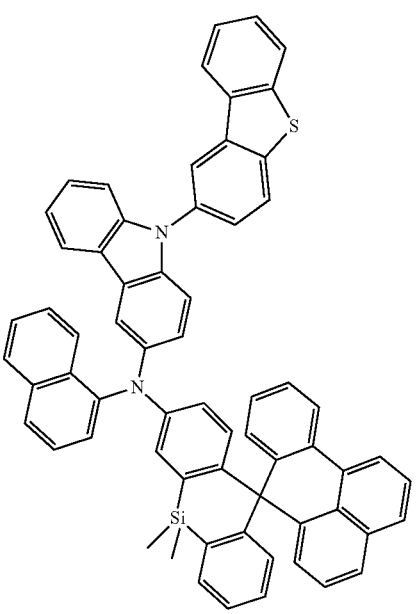
1116

1117
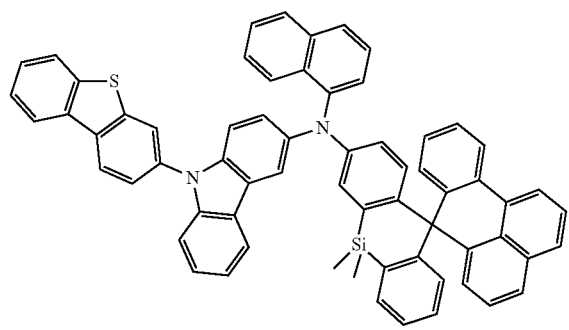
1118
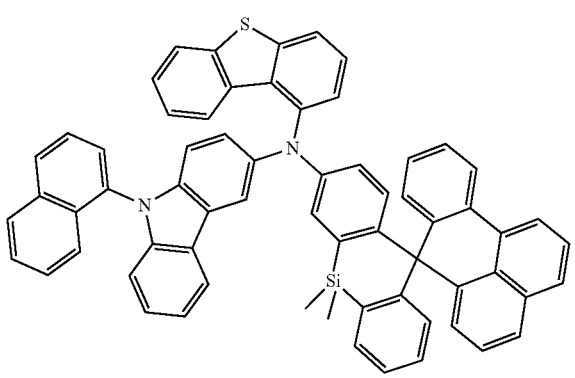
1119
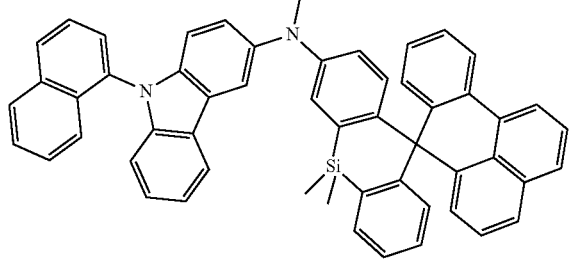
1120
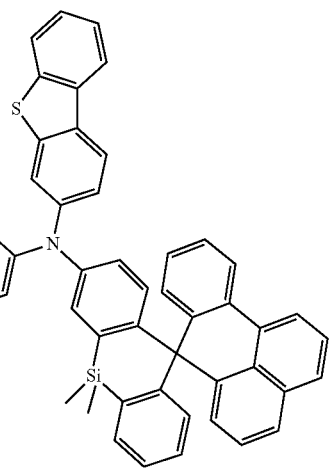
1121
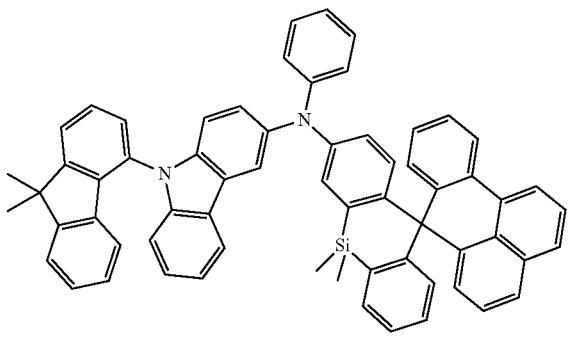
1122
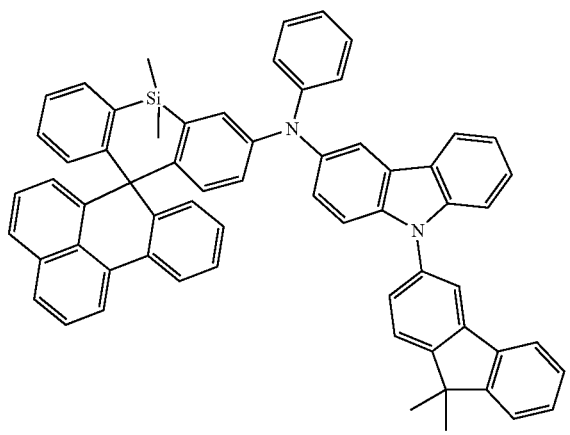
1123
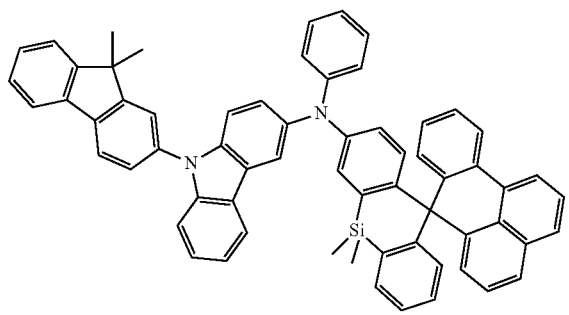

-continued
1124
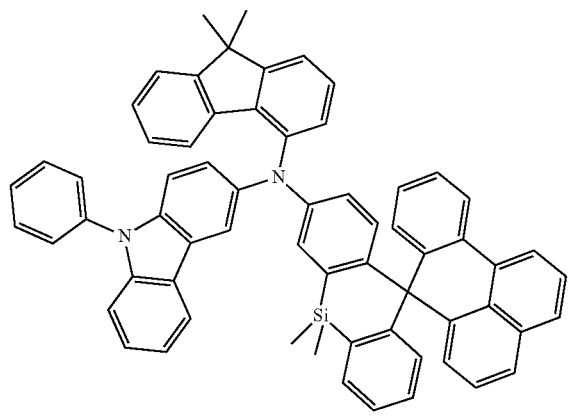
1125
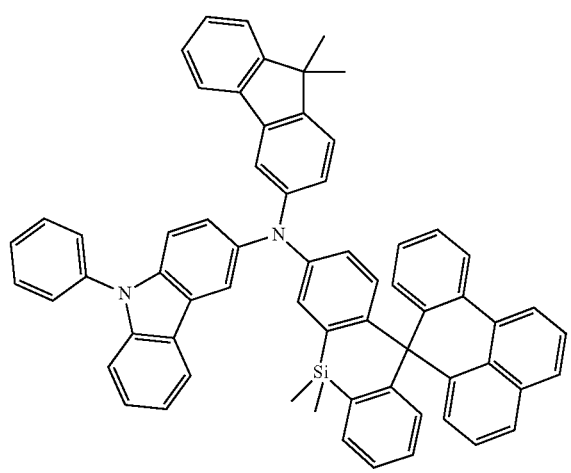
1126
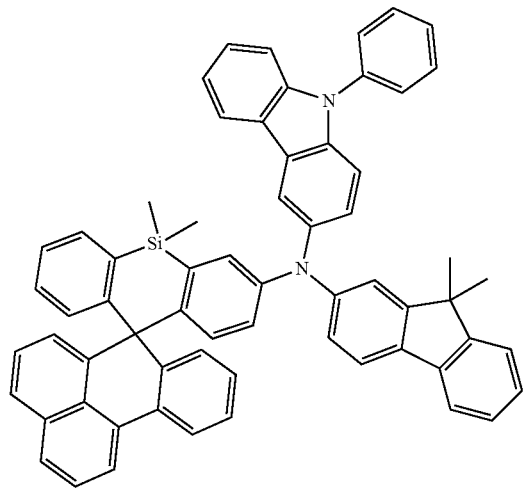
-continued
1127
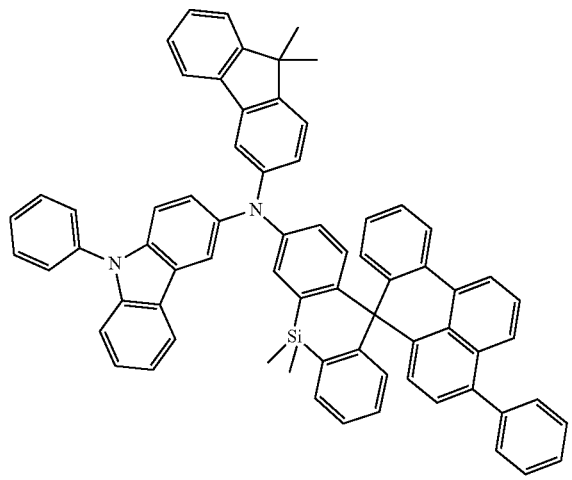
1128
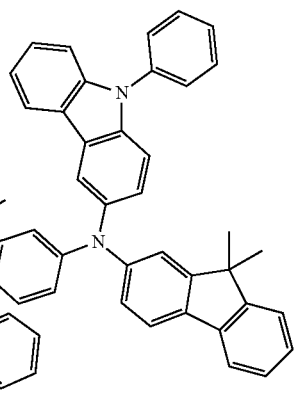
1129
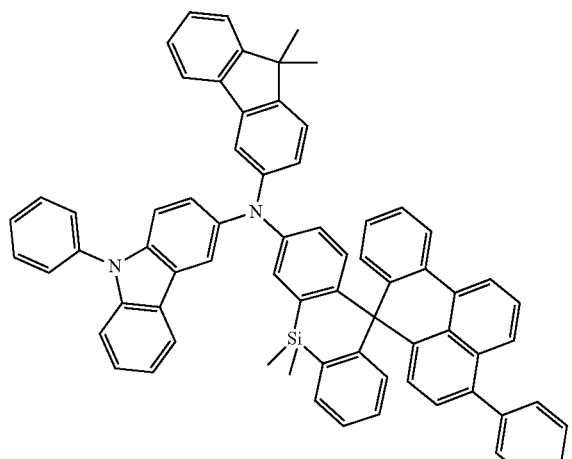

-continued

1130

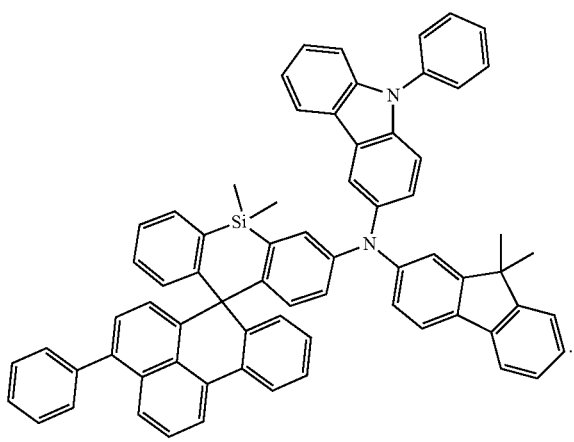

11. An amine compound represented by Formula 1:

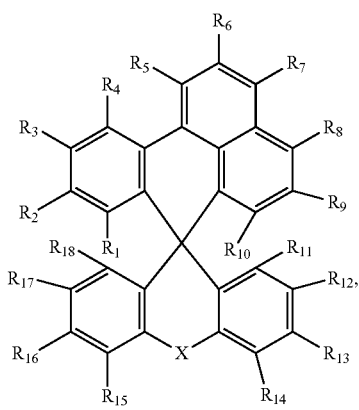

Formula 1 wherein, in Formula 1,
X is O, S, SiR$_a$R$_b$, or NR$_c$,
R$_1$ to R$_{18}$, R$_a$, R$_b$, and R$_c$ are each independently a hydrogen atom, a deuterium atom, a halogen atom, a substituted or unsubstituted silyl group, a substituted or unsubstituted amine group, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms, and/or combined with an adjacent group to form a ring, and
at least one selected from among R$_1$ to R$_{18}$ is represented by Formula 2:

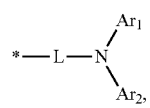

Formula 2 wherein, in Formula 2,
L is a direct linkage, a substituted or unsubstituted ring-forming arylene group having 6 to 30 carbon atoms, or a substituted or unsubstituted ring-forming heteroarylene group having 2 to 30 carbon atoms, Ar$_1$ and Ar$_2$ are each independently a substituted or unsubstituted ring-forming aryl group having 6 to 30 carbon atoms, or a substituted or unsubstituted ring-forming heteroaryl group having 2 to 30 carbon atoms, and wherein when X is O, S, or NR$_c$, then Ar$_1$ and Ar$_2$ are each independently a substituted or unsubstituted naphthyl group, a substituted or unsubstituted fluorenyl group, a substituted or unsubstituted carbazolyl group, a substituted or unsubstituted dibenzofuranyl group, or a substituted or unsubstituted dibenzothiophenyl group, provided that Ar$_1$ and Ar$_2$ are not a substituted or unsubstituted fluorenyl group at the same time.

12. The amine compound of claim 11, wherein the amine compound represented by Formula 1 is represented by any one selected from among Formula 1A to Formula 1D:

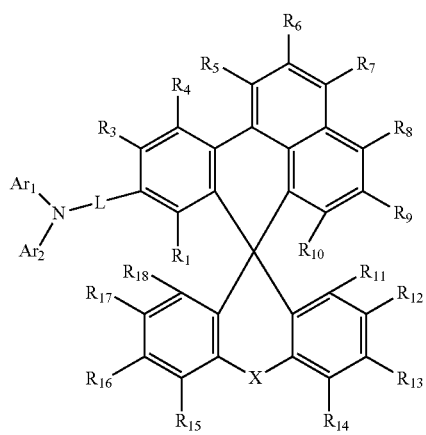

Formula 1A

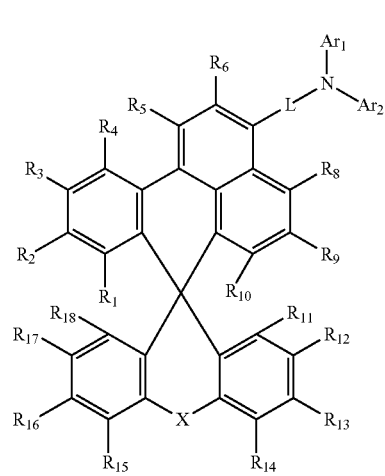

Formula 1B

Formula 1C

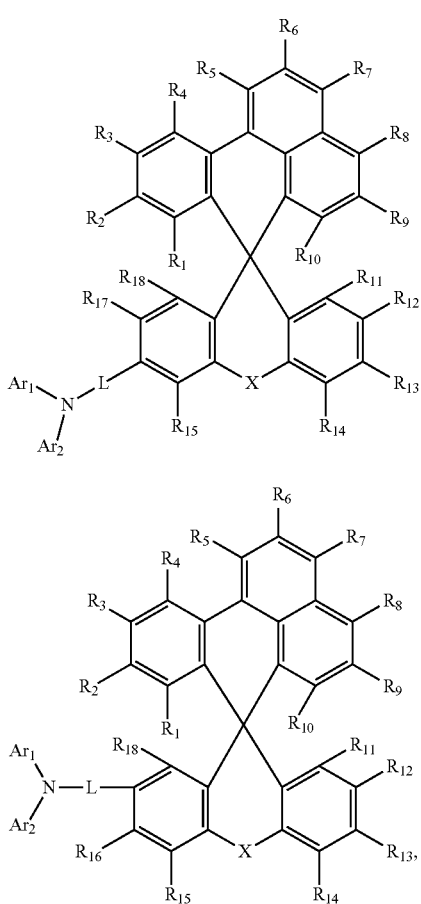

Formula 1D and
wherein, in Formula 1A to Formula 1D, X, $R_1$ to $R_{18}$, L, $Ar_1$, and $Ar_2$ are the same as defined in Formula 1 and Formula 2.

13. The amine compound of claim 11, wherein a substituent represented by Formula 2 is represented by Formula 2A or Formula 2B:

Formula 2A

Formula 2B

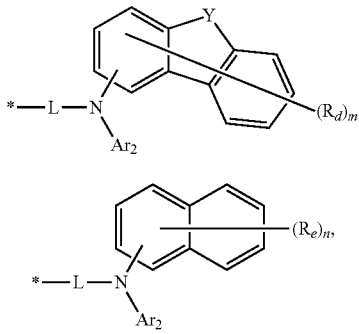

and
wherein, in Formula 2A and Formula 2B,
Y is O, S, $NAr_3$, or $CR_fR_g$,
$Ar_3$ is a substituted or unsubstituted ring-forming aryl group having 6 to 30 carbon atoms, or a substituted or unsubstituted ring-forming heteroaryl group having 2 to 30 carbon atoms, $R_d$, $R_e$, $R_f$ and $R_g$ are each independently a hydrogen atom, a deuterium atom, a halogen atom, a substituted or unsubstituted silyl group, a substituted or unsubstituted amine group, a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms, and/or combined with an adjacent group to form a ring, "m" and "n" are each independently an integer of 0 to 7, and L and $Ar_2$ are the same as defined in Formula 2.

14. The amine compound of claim 11, wherein X is O, S, or $SiR_aR_b$.

15. The amine compound of claim 11, wherein L is a direct linkage.

16. The amine compound of claim 11, wherein $Ar_1$ and $Ar_2$ are different from each other.

17. The amine compound of claim 11, wherein $R_a$, $R_b$, and $R_c$ are each independently a substituted or unsubstituted alkyl group having 1 to 20 carbon atoms, a substituted or unsubstituted ring-forming aryl group having 6 to 30 carbon atoms, or a substituted or unsubstituted ring-forming heteroaryl group having 2 to 30 carbon atoms.

18. The amine compound of claim 11, wherein the amine compound represented by Formula 1 is represented by any one selected from among the compounds in Compound Group 1:

[Compound Group 1]

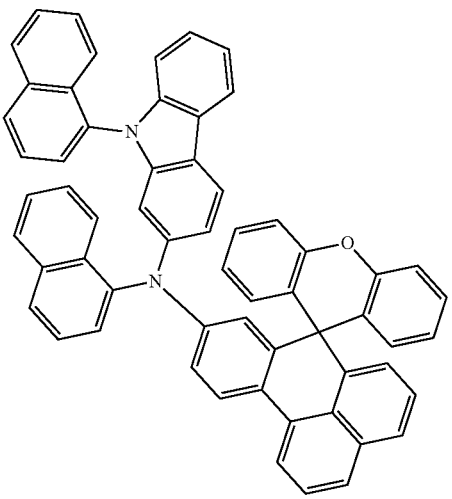

9
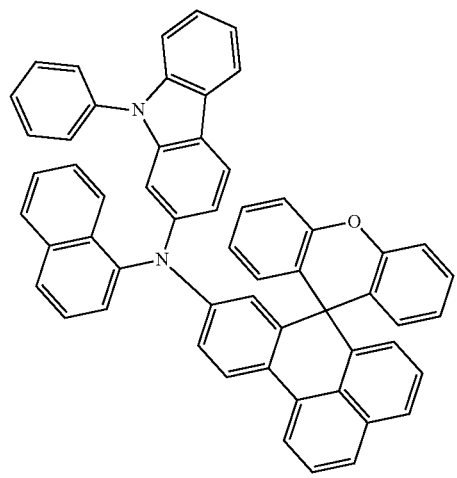
11
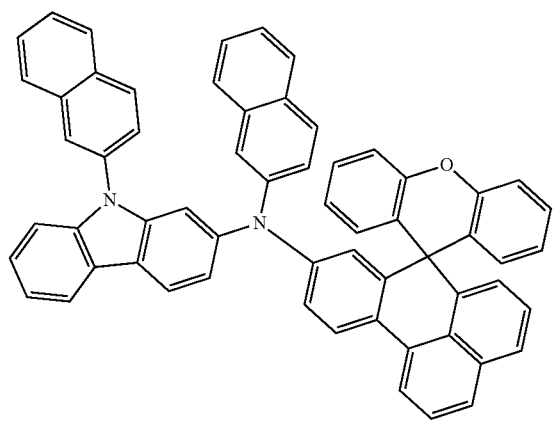
12
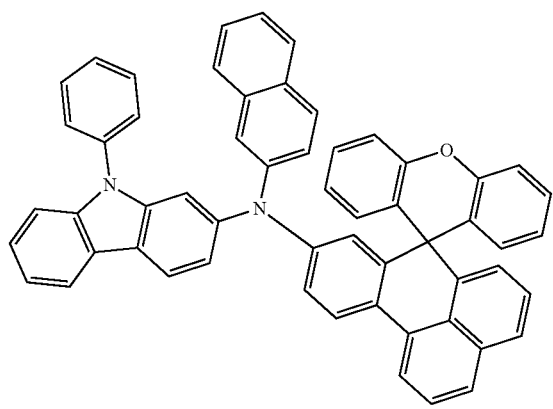
16
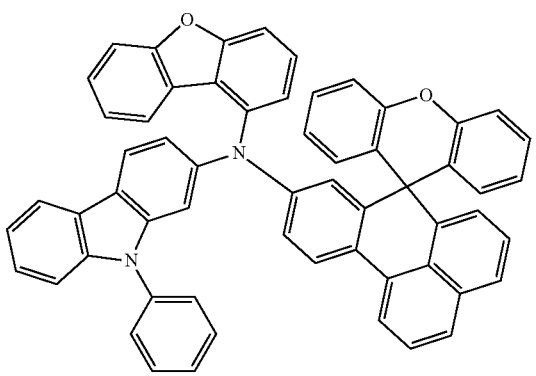
17
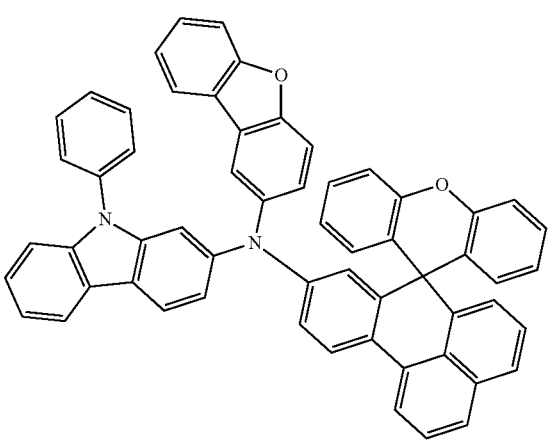
18
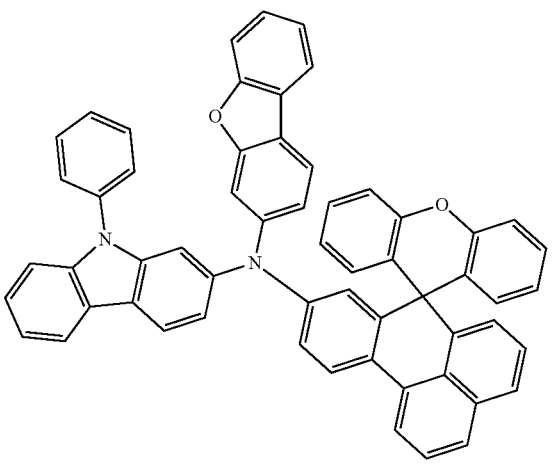

19
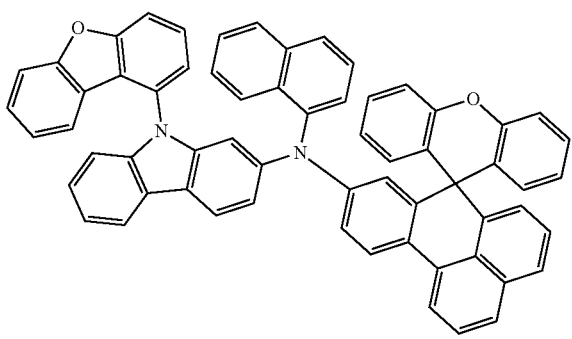
20
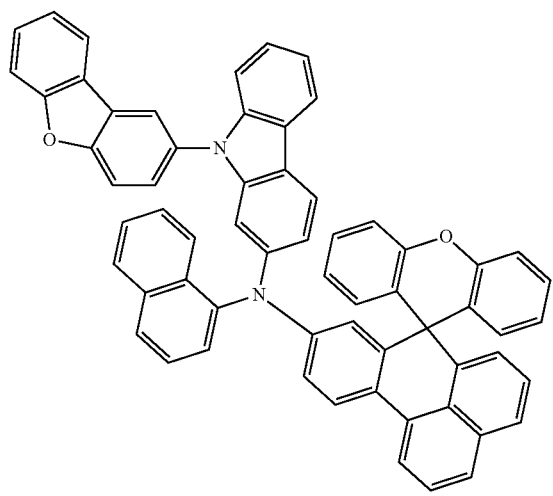
24
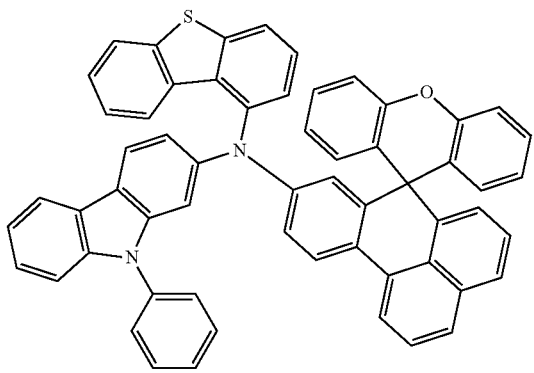
25
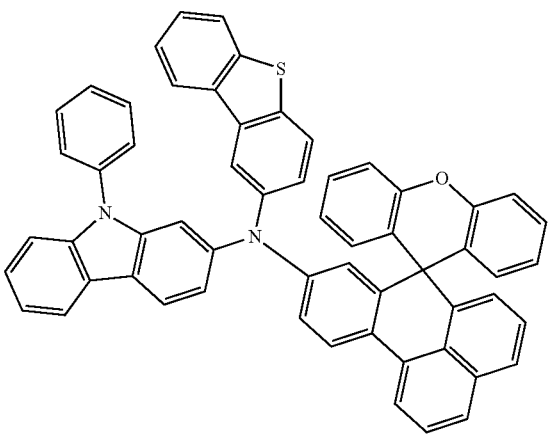
26
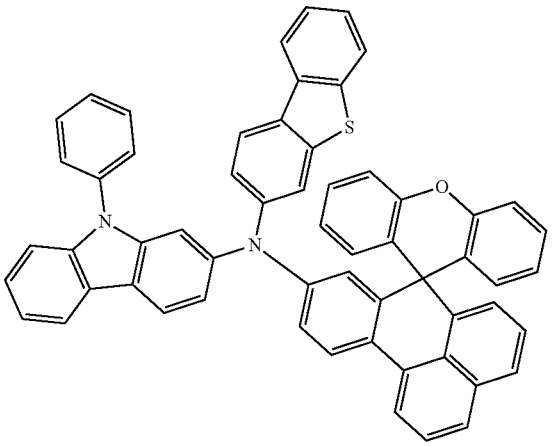
27
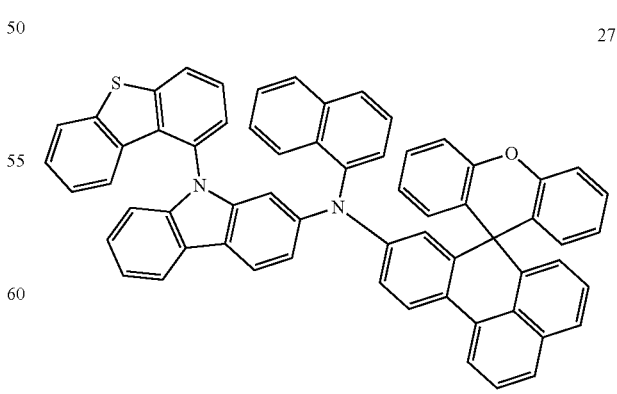

28
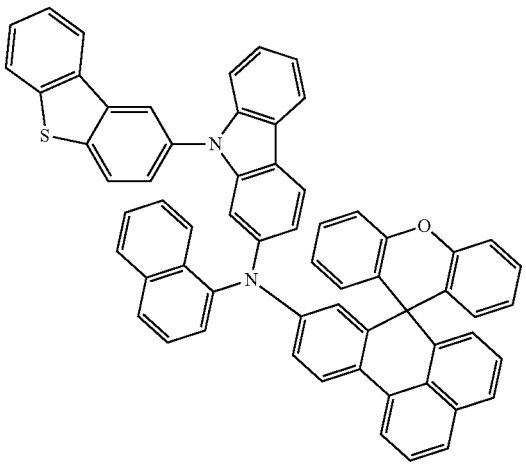
29
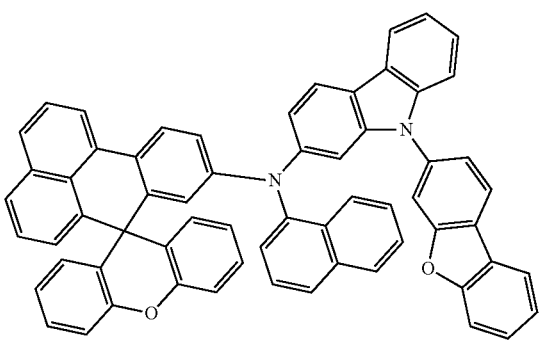
30
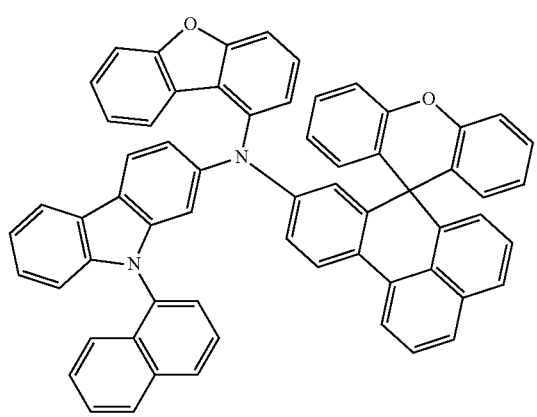
31
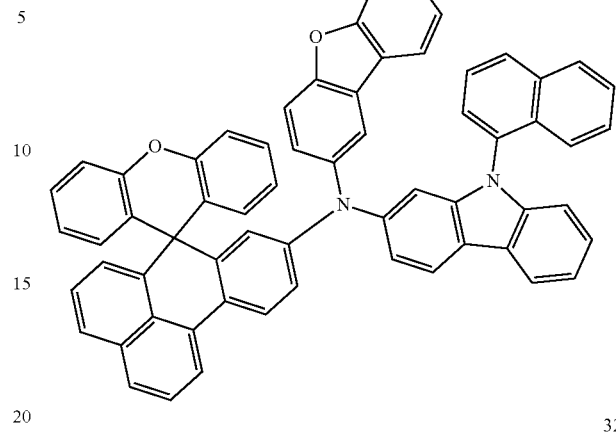
32
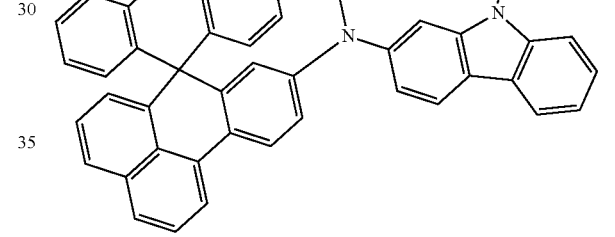
33
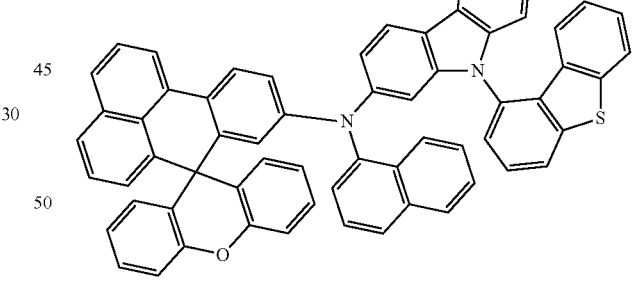
34
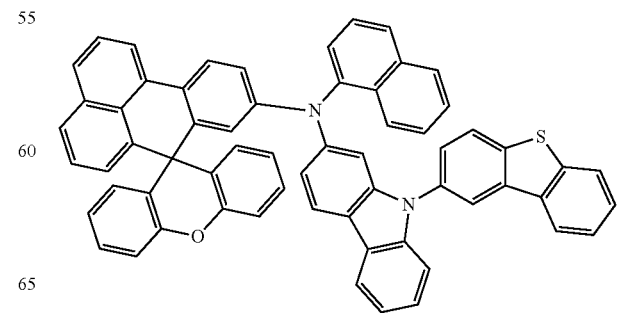

631
-continued
35
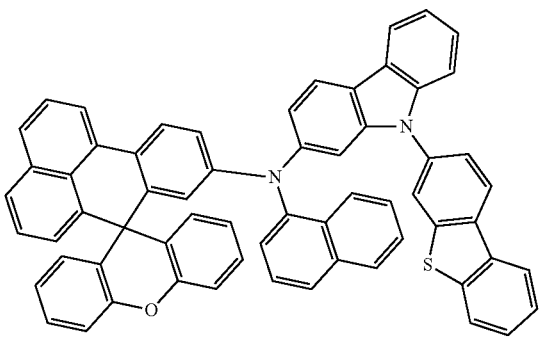
36
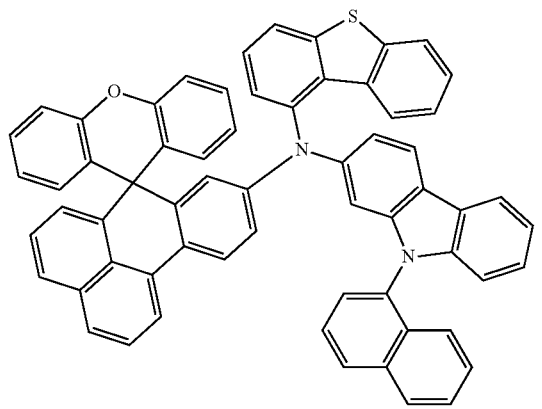
37
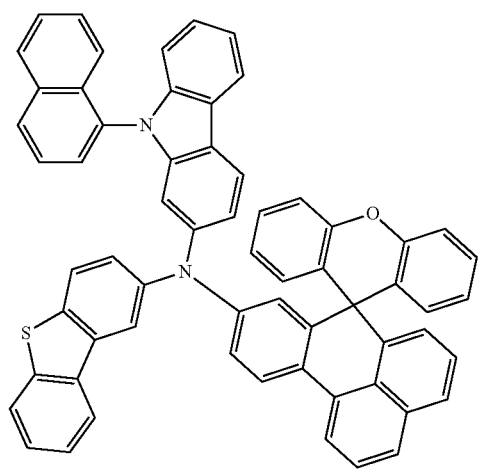
632
-continued
38
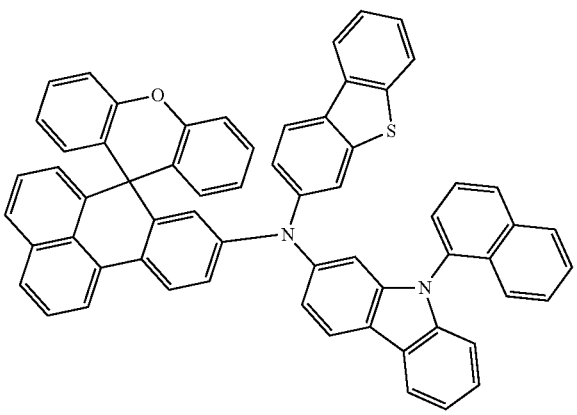
42
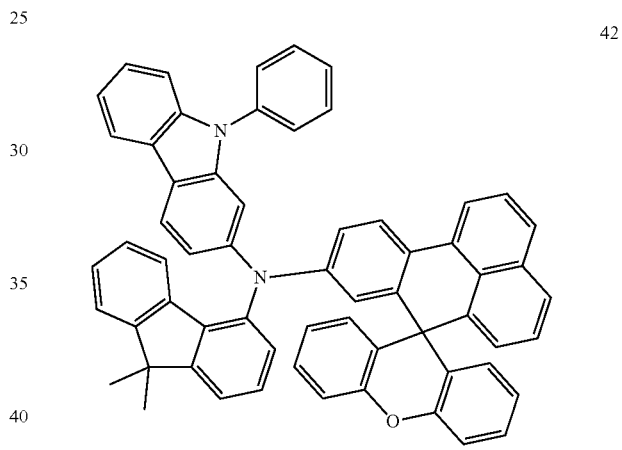
43
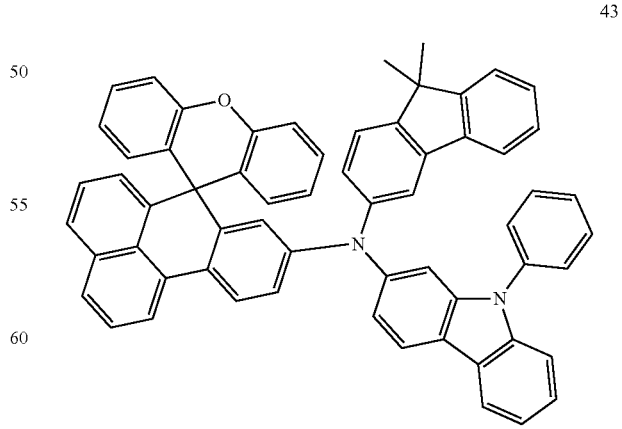

-continued
44
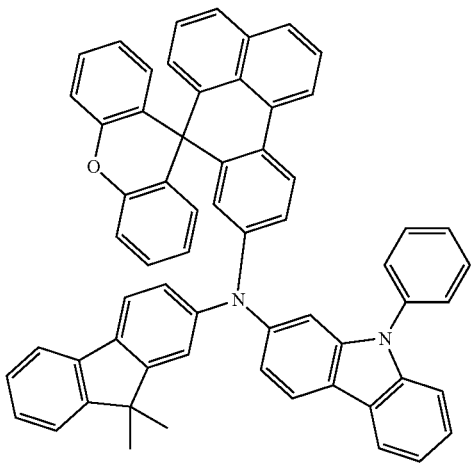
52
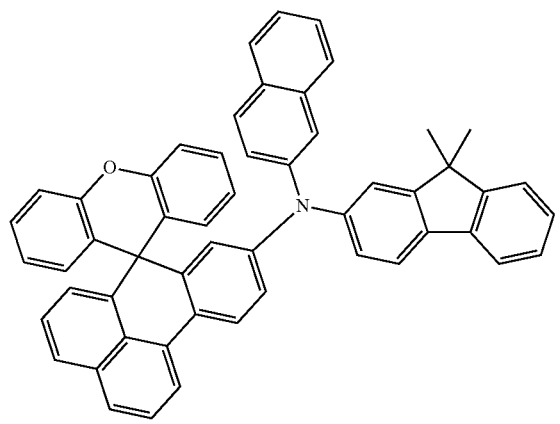
53
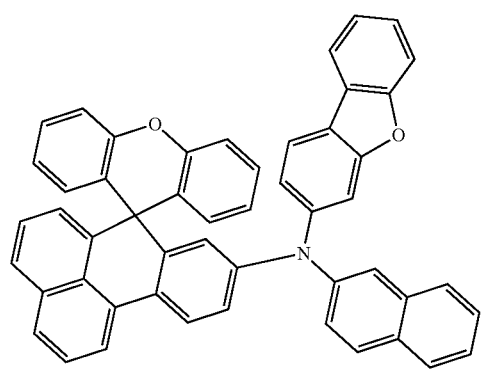
54
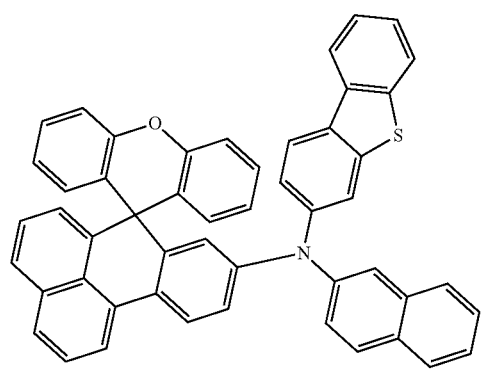
-continued
55
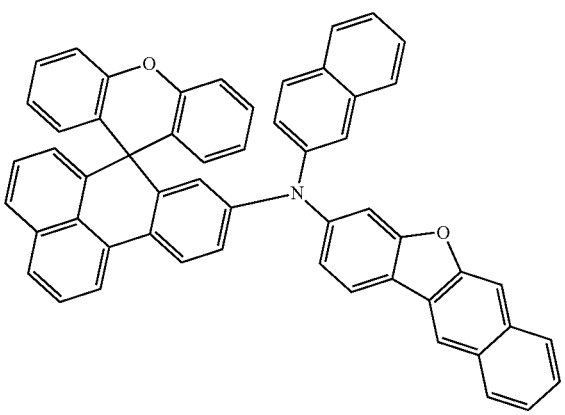
56
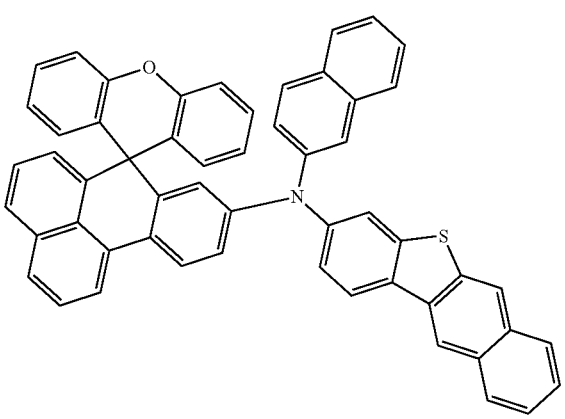
57
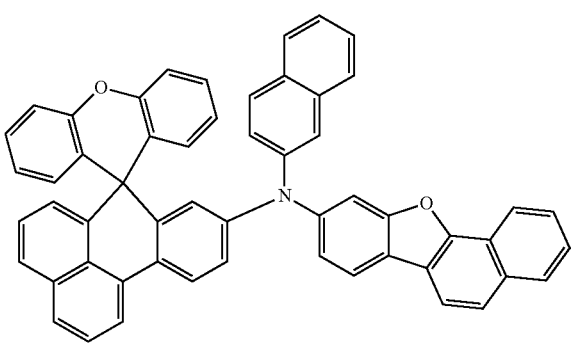
58
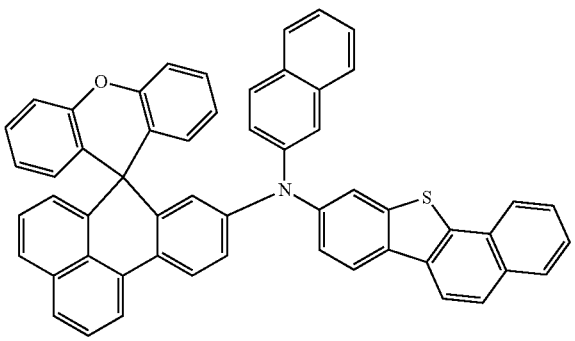

59
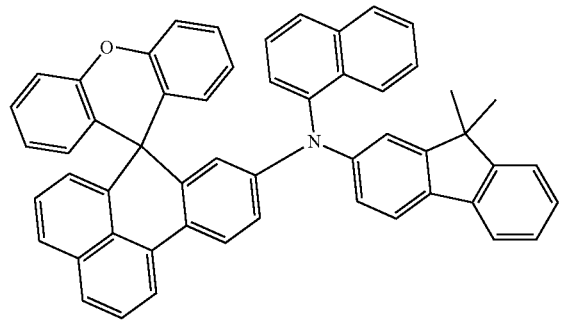
60
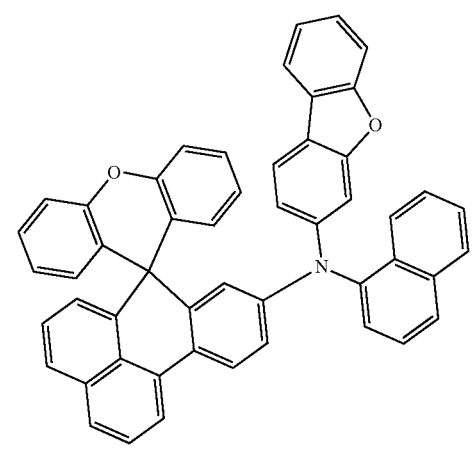
61
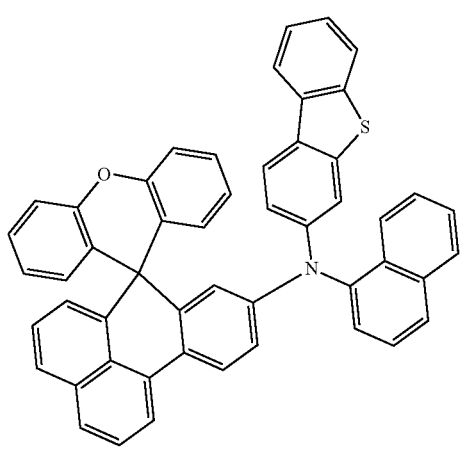
62
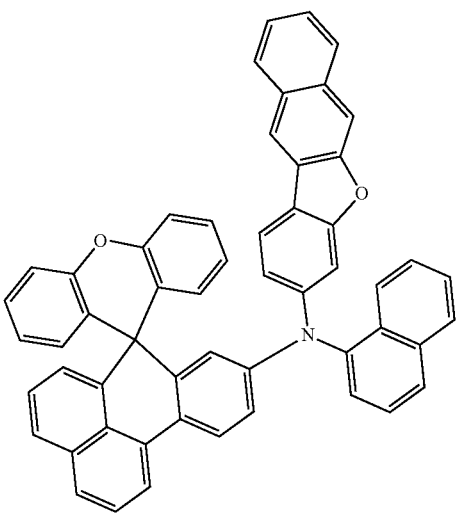
63
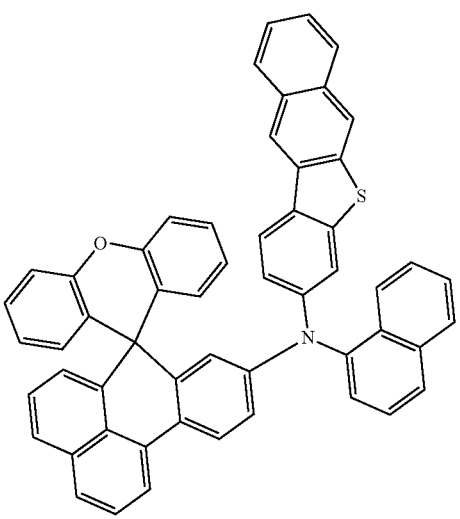
64
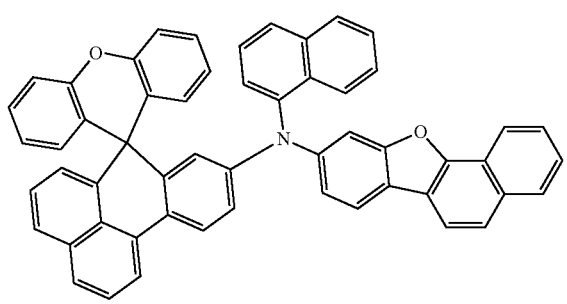

637
-continued
65
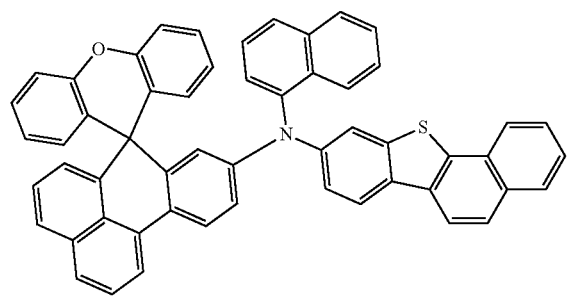
70
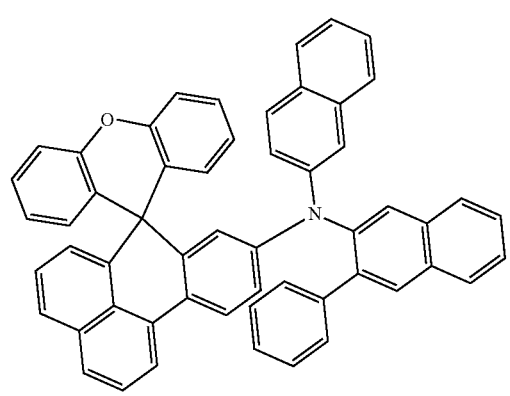
71
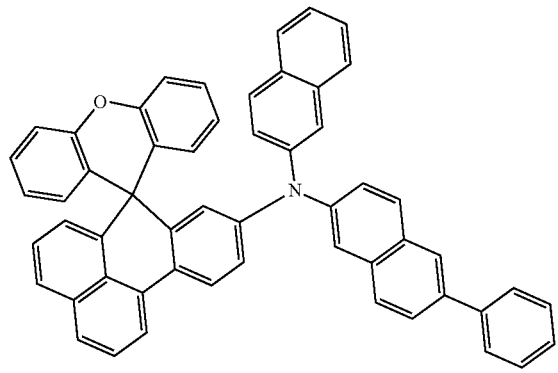
72
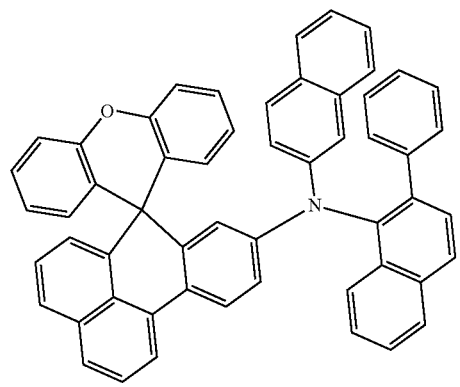
638
-continued
73
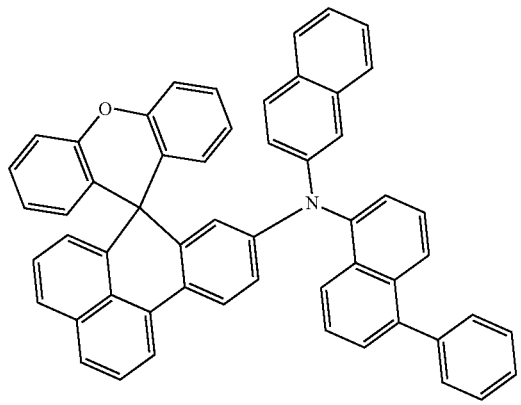
74
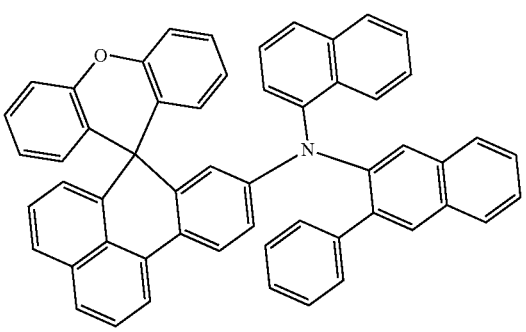
75
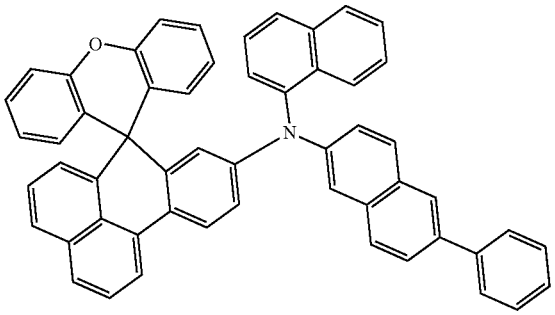
76
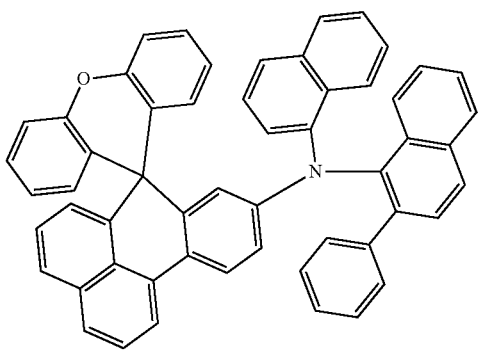

-continued
77
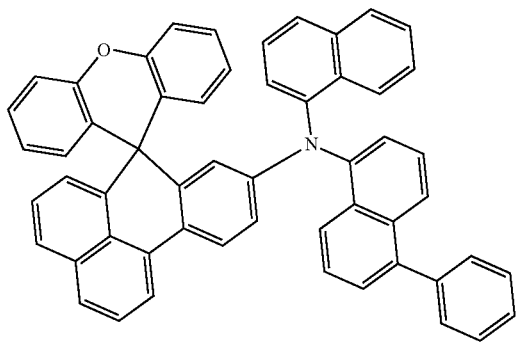
79
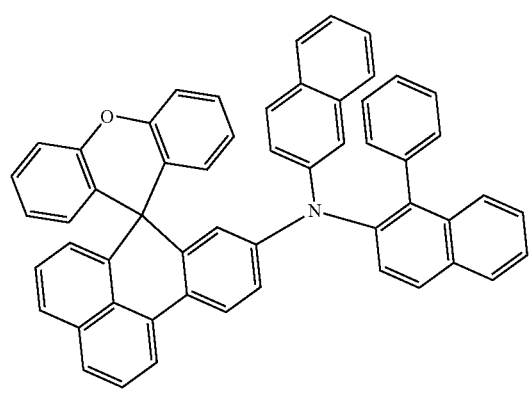
80
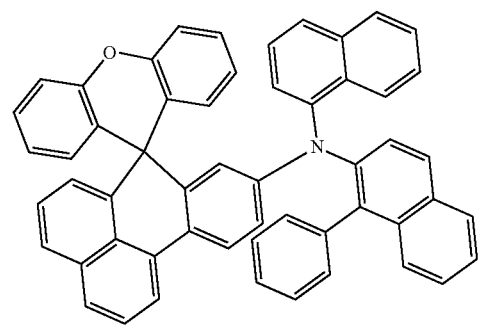
88
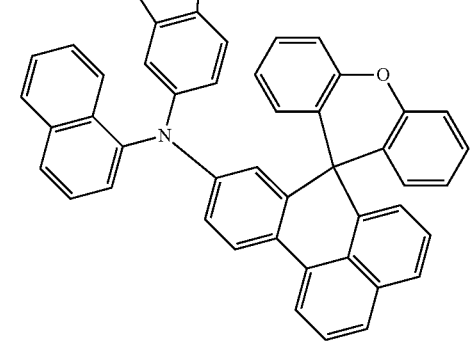
-continued
89
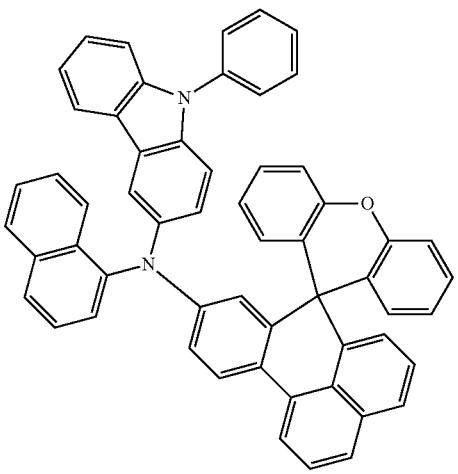
91
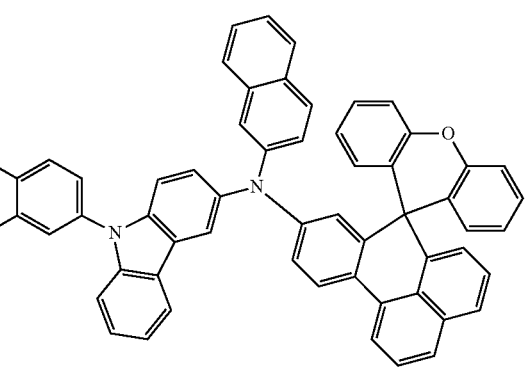
92
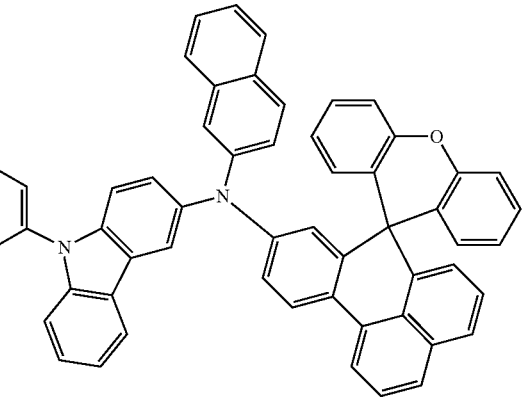
96
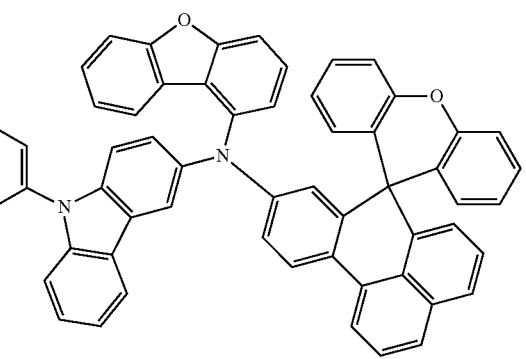

-continued
97
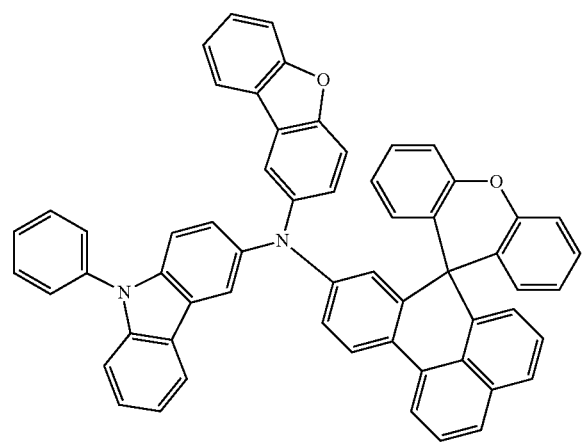
98
105
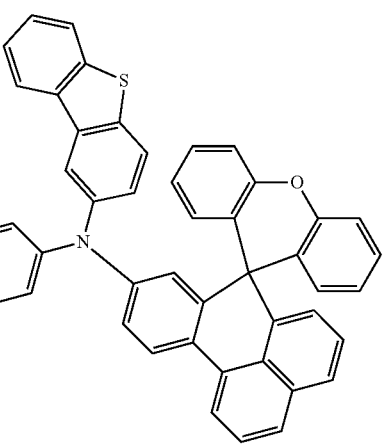
106
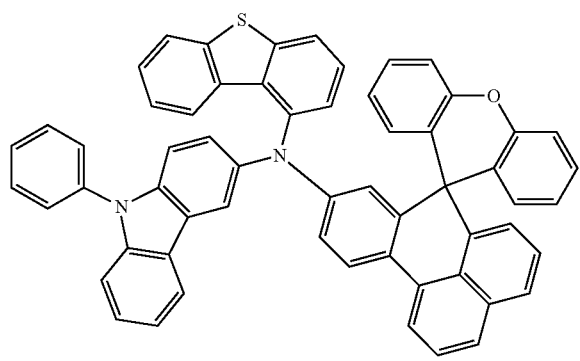
104
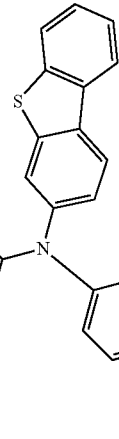
107
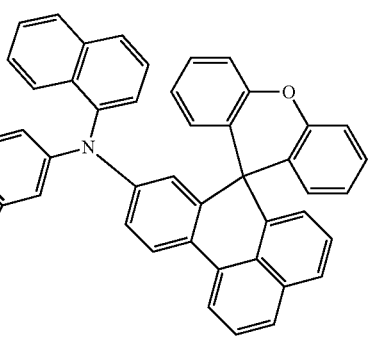

108
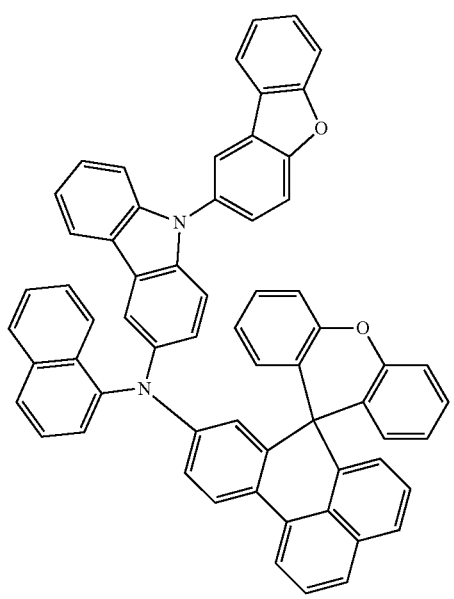
109
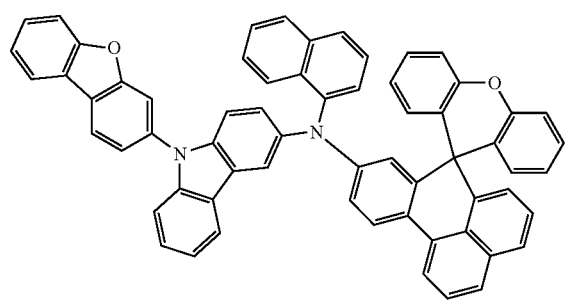
110
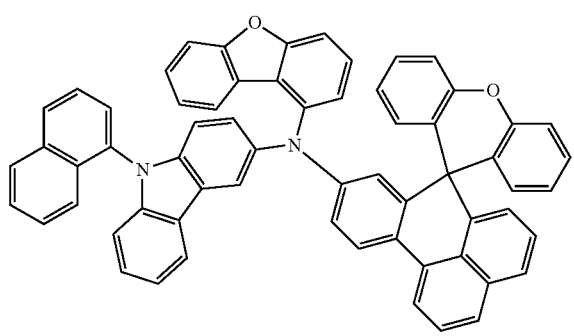
111
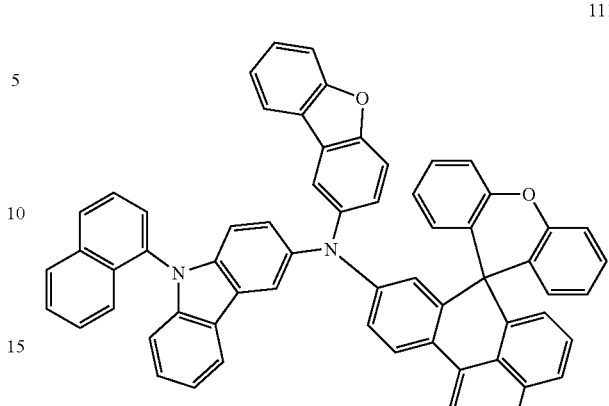
112
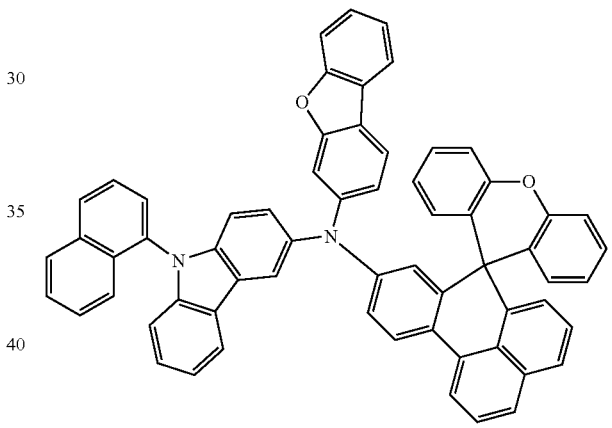
113
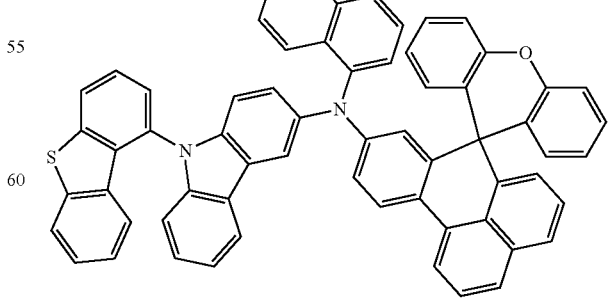

114
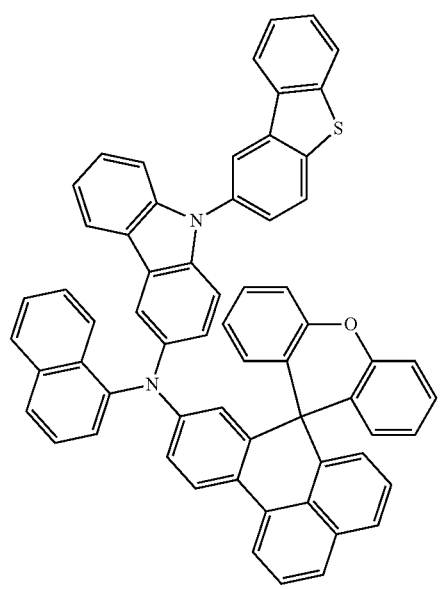
115
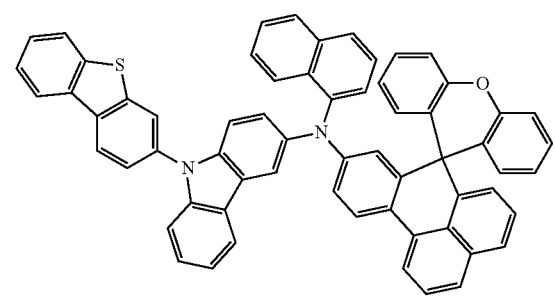
116
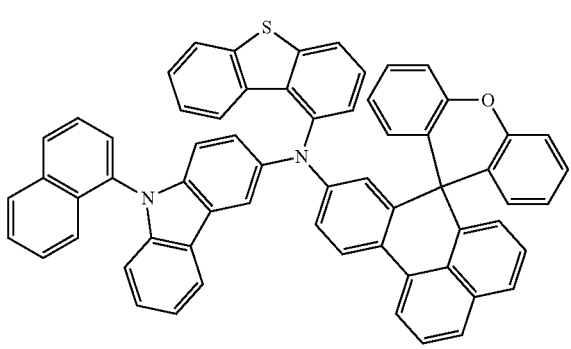
117
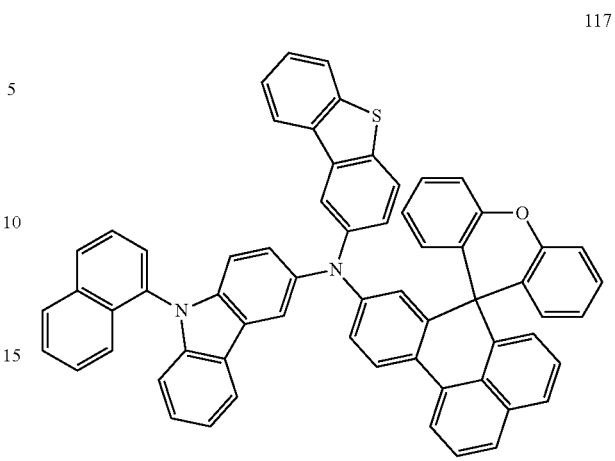
118
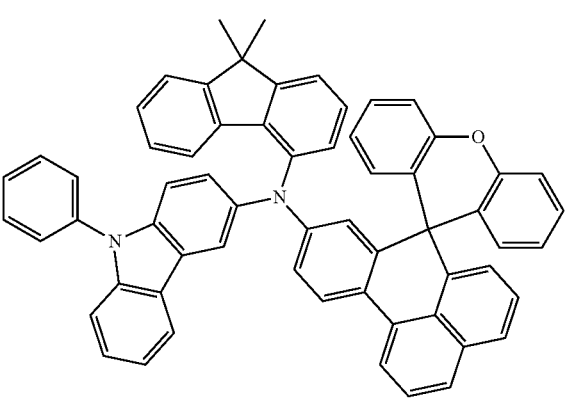
122

123
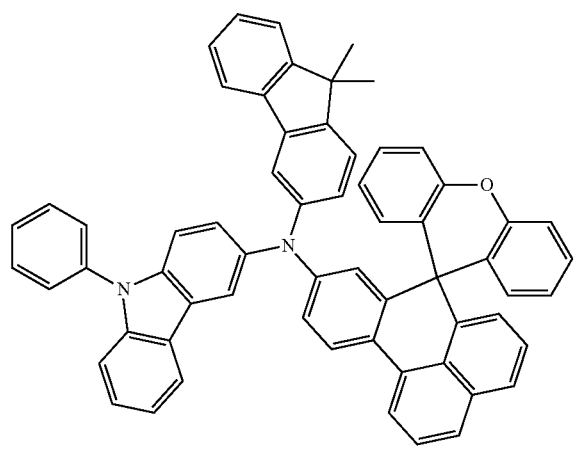
124
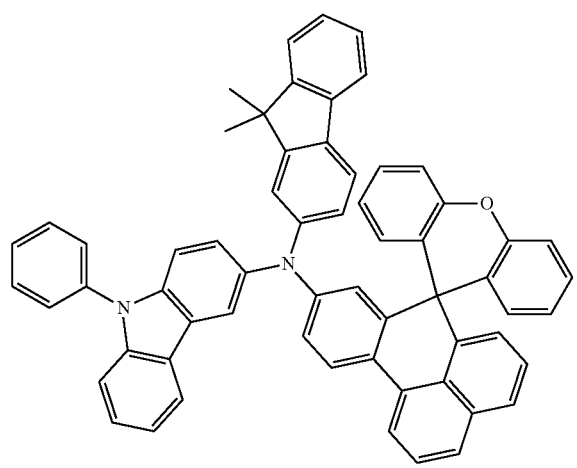
132
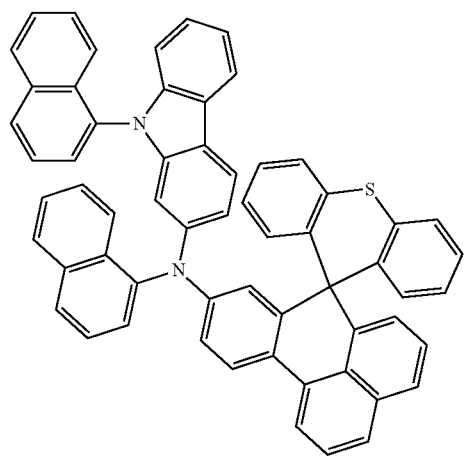
133
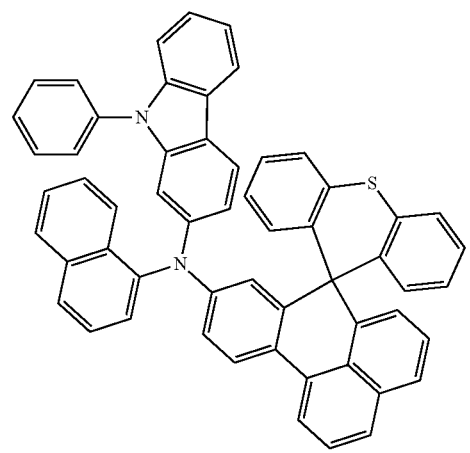
135
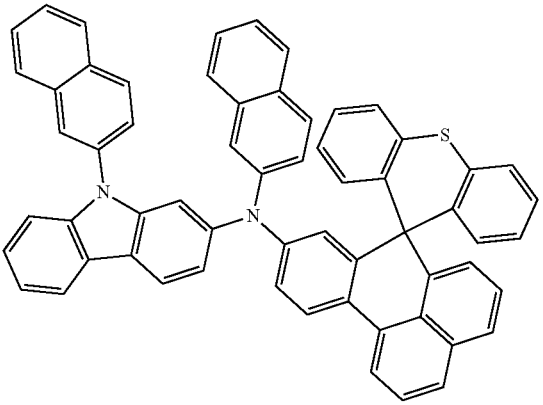
136
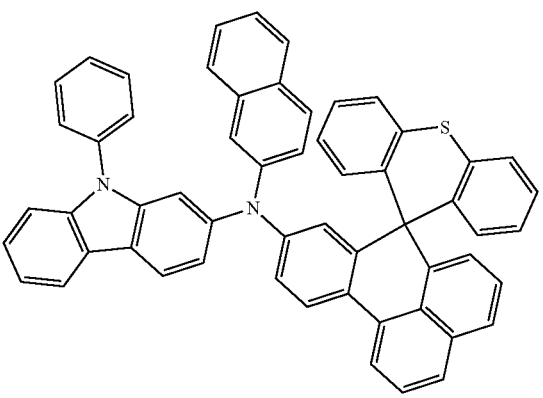

140
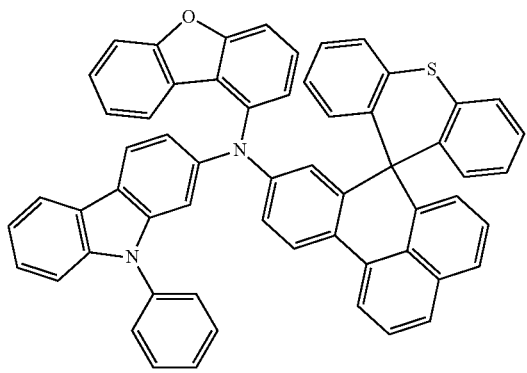
141
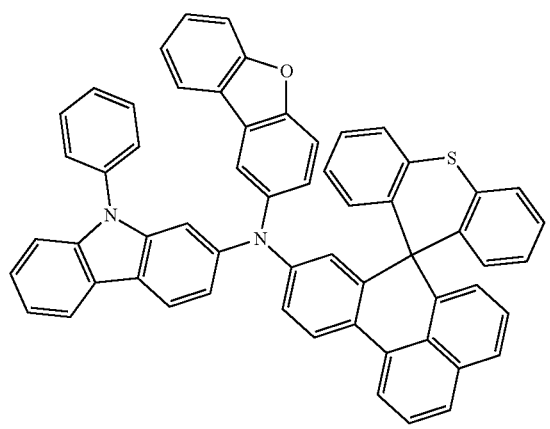
142
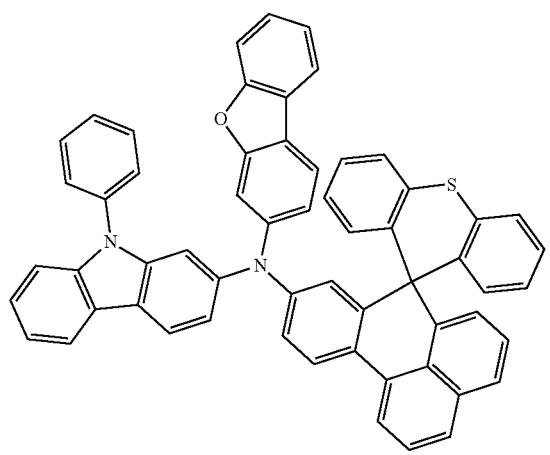
143
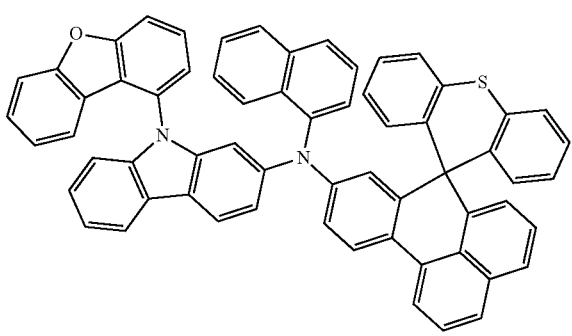
144
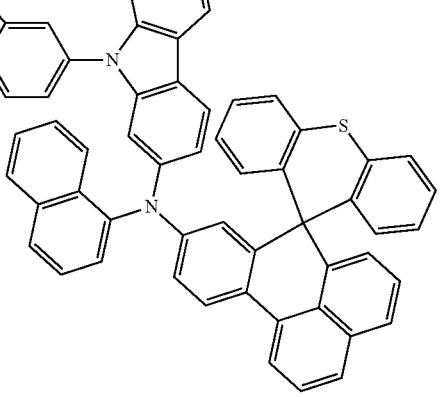
148
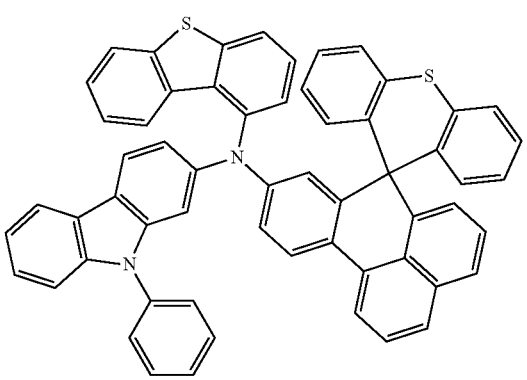
149
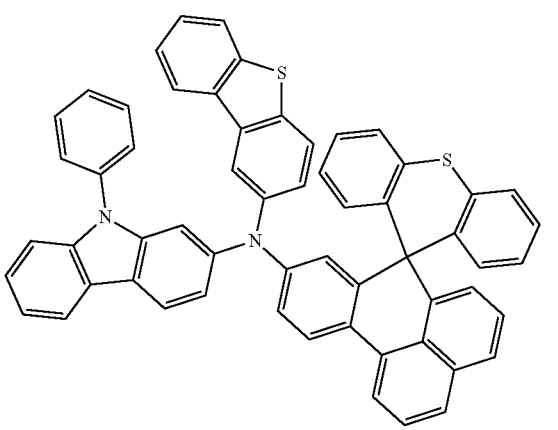

651
150
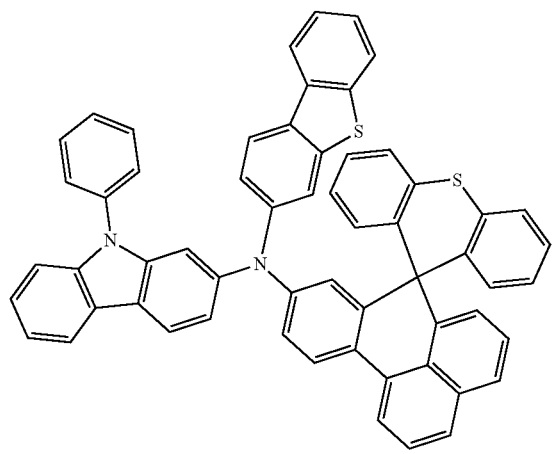
151
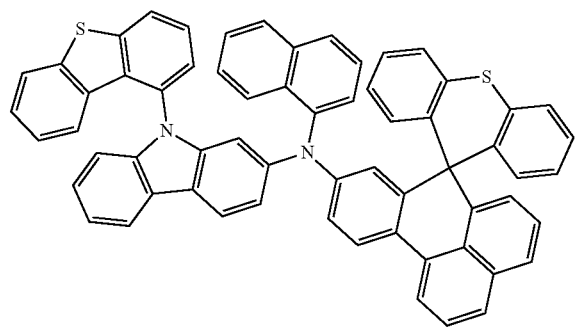
152
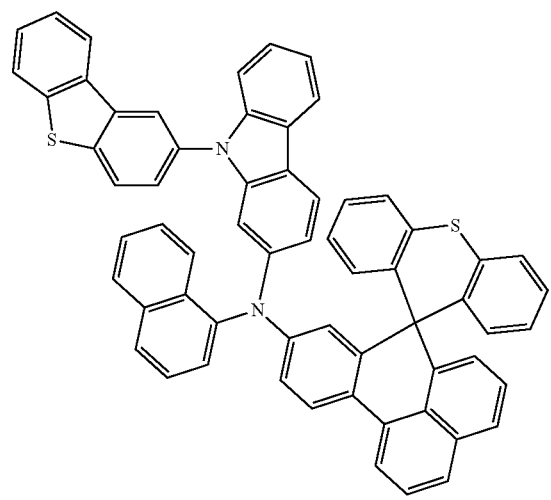
652
153
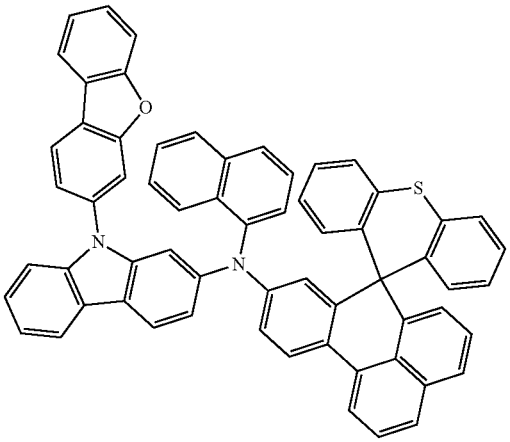
154
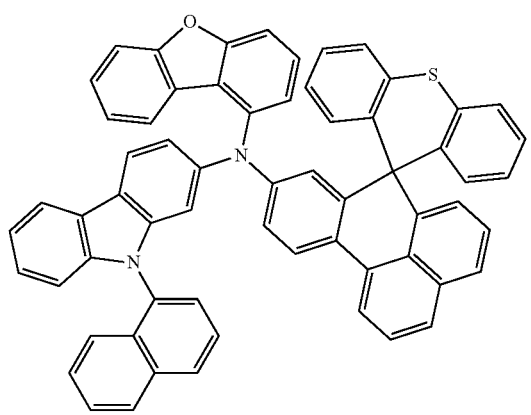
155
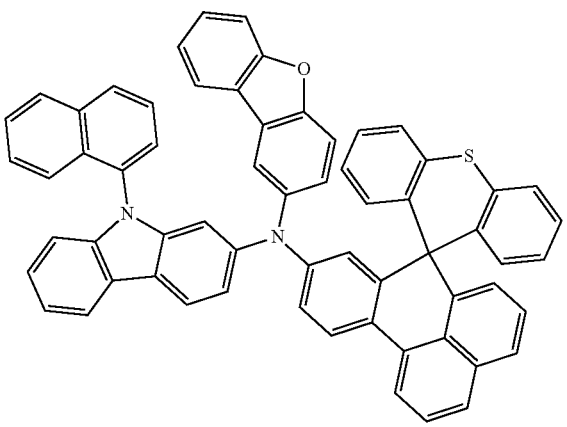

156
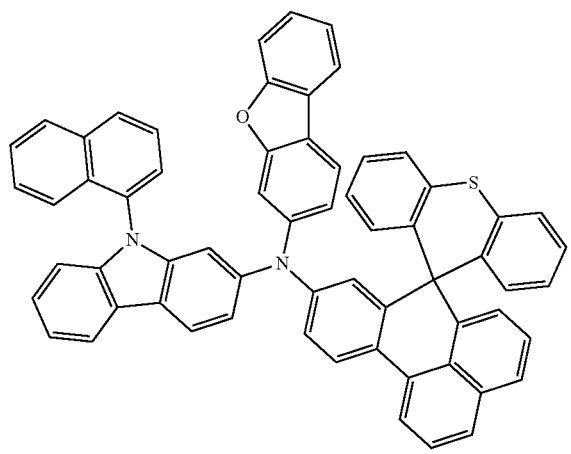
159
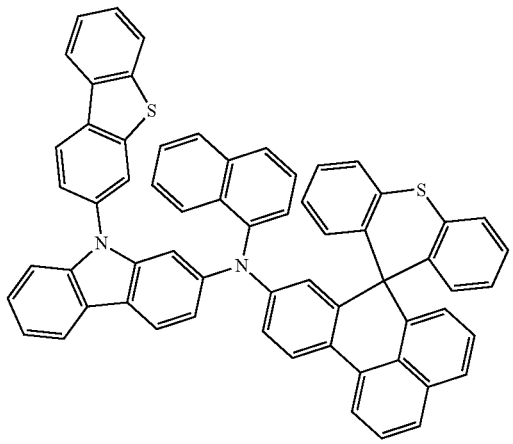
157
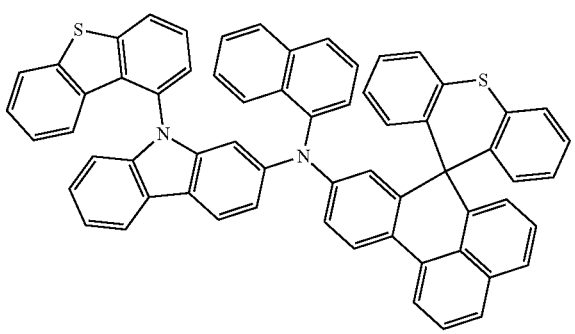
160
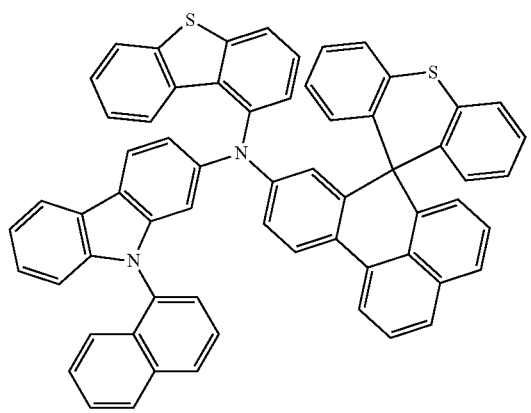
158
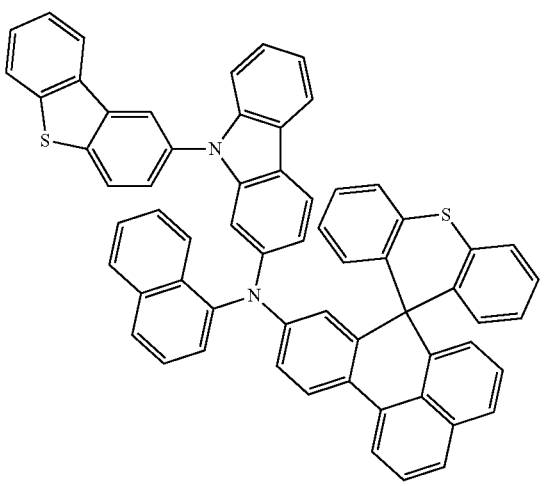
161
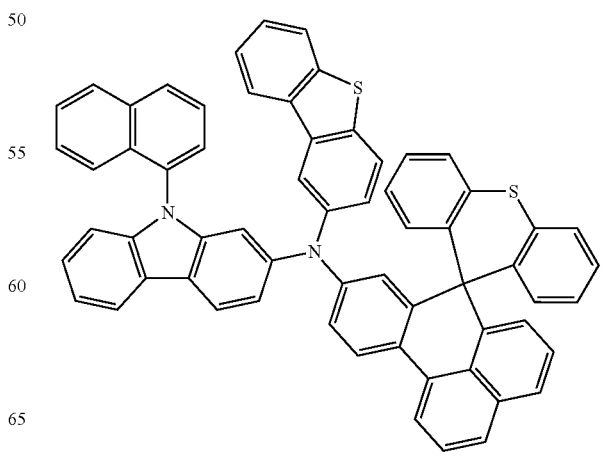

-continued
162
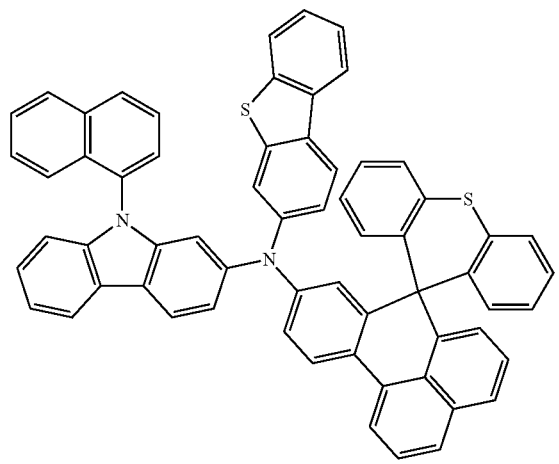
166
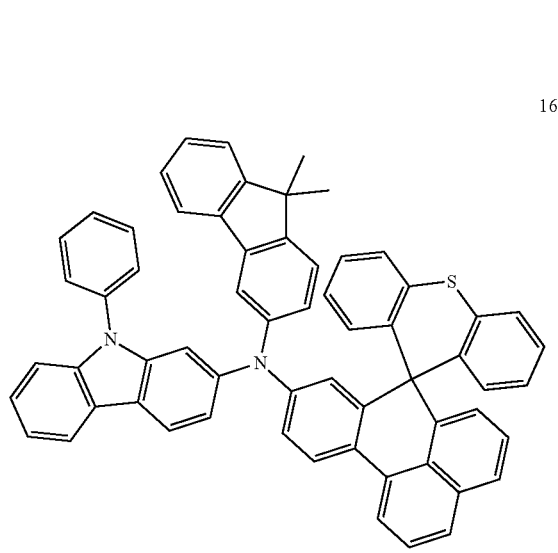
167
168
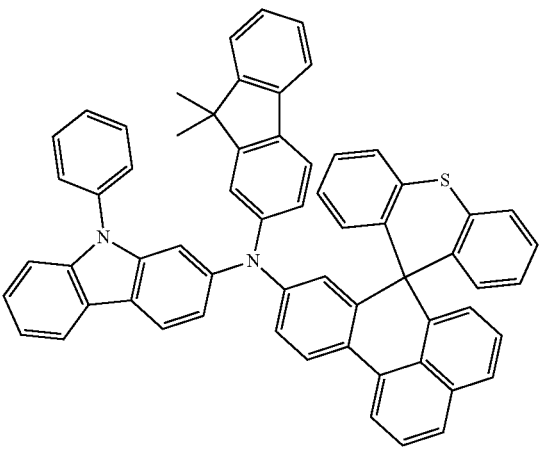
182
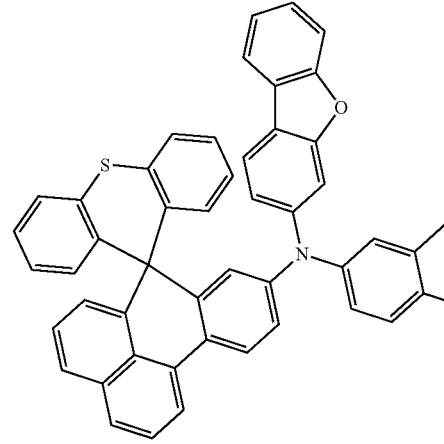
183

184
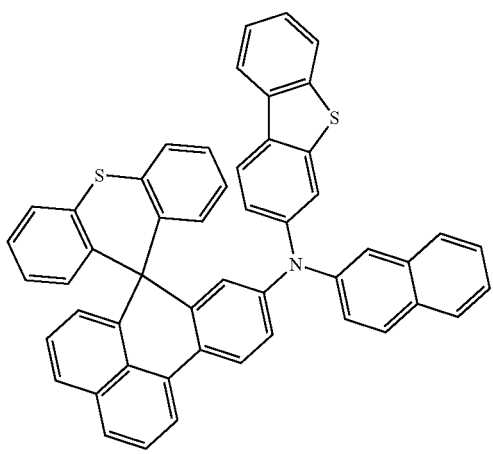
188
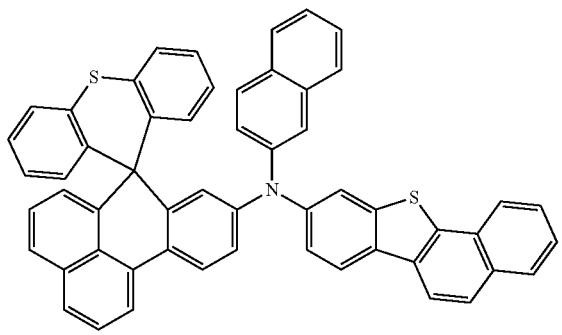
185
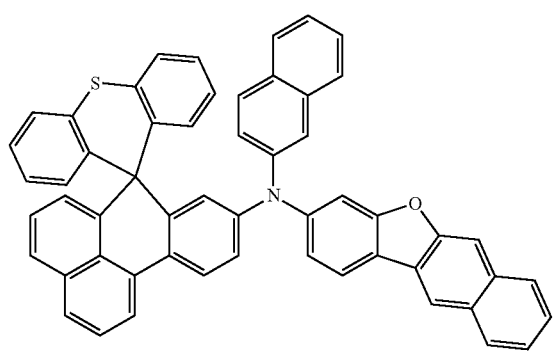
189
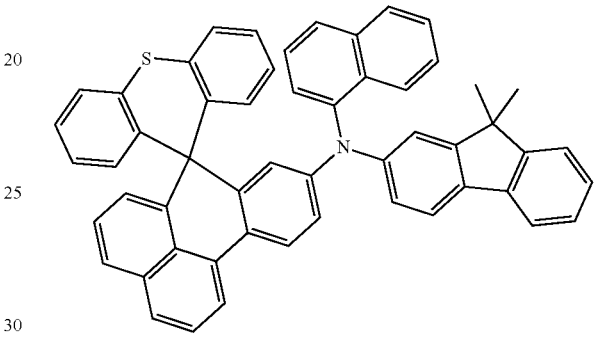
186
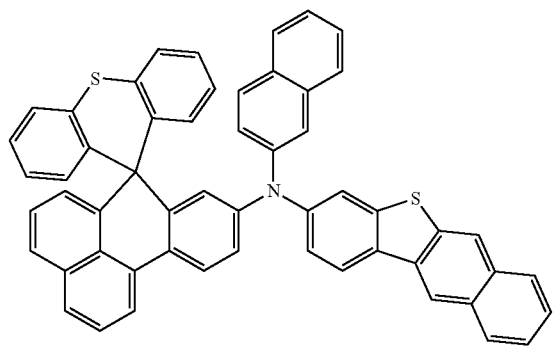
190
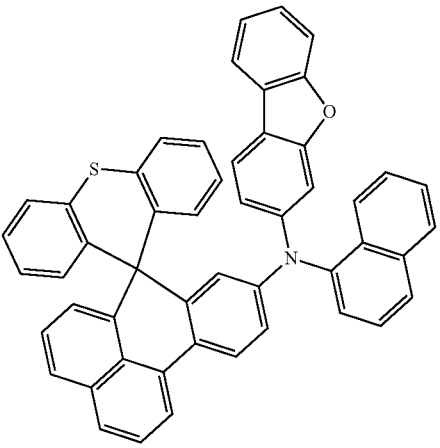
187
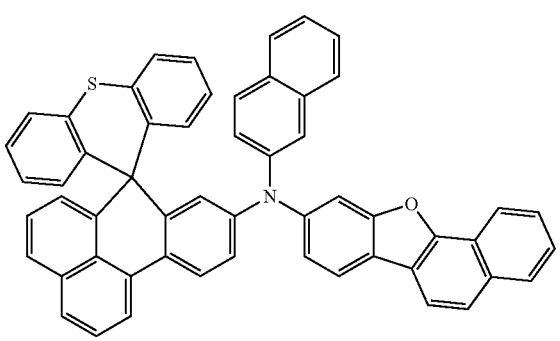
191
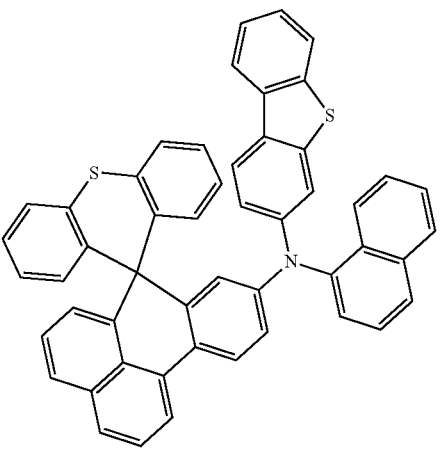

192
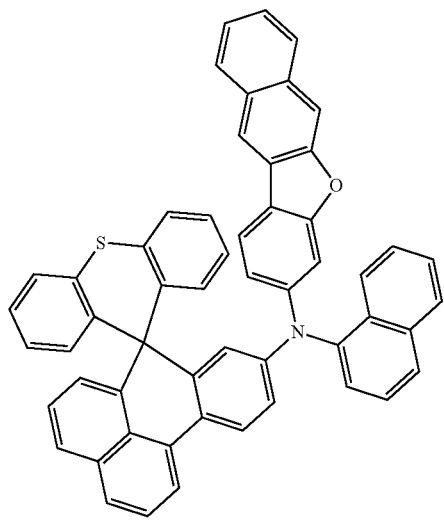
193
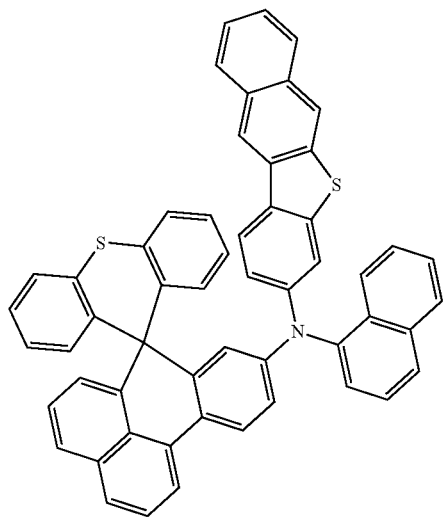
194
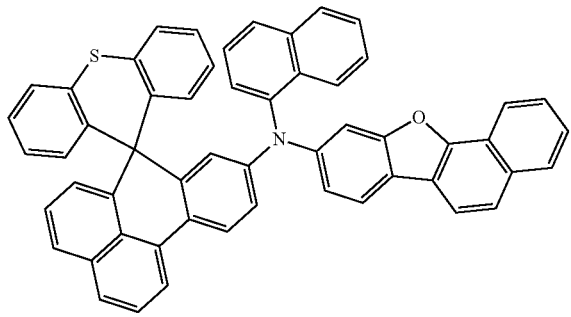
195
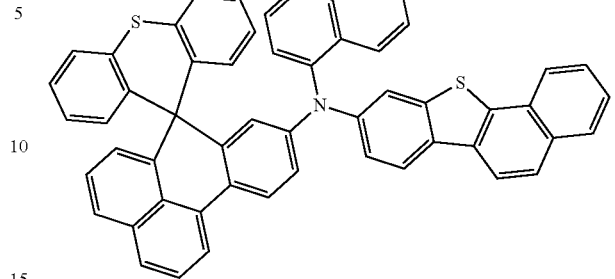
200
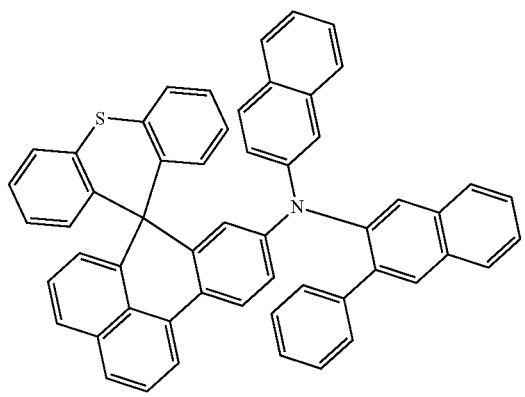
201
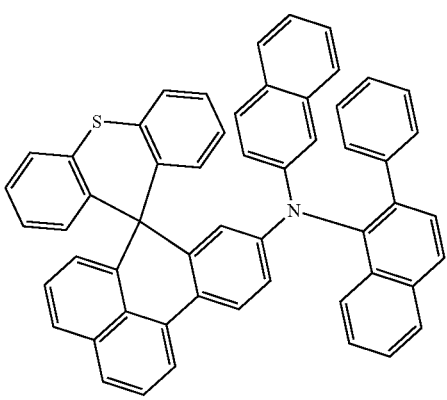
202

203
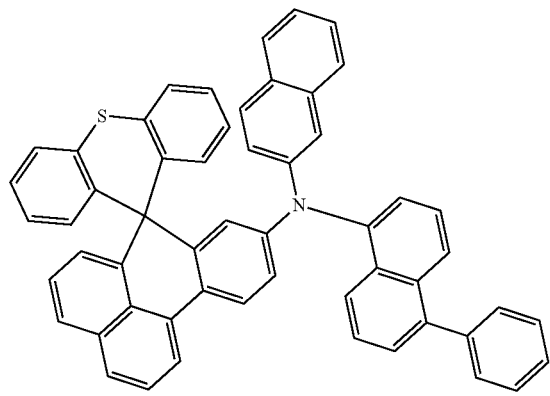
204
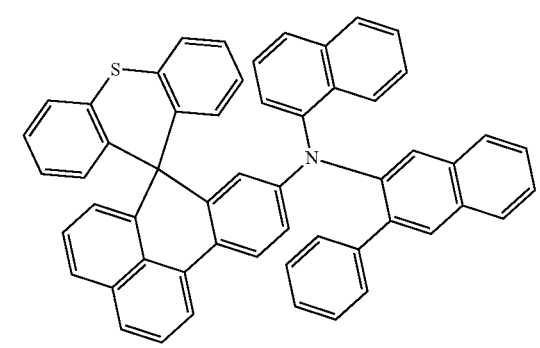
205
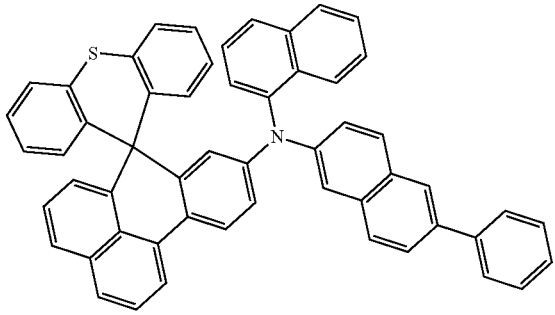
206
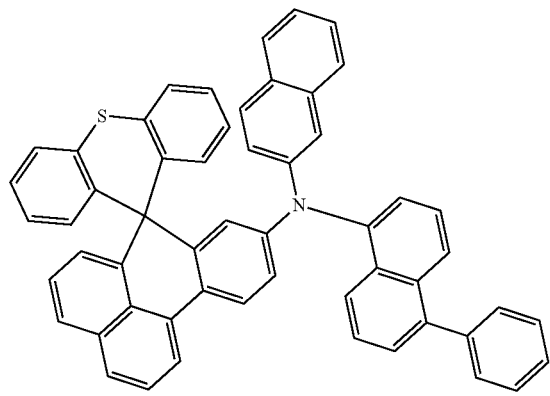
207
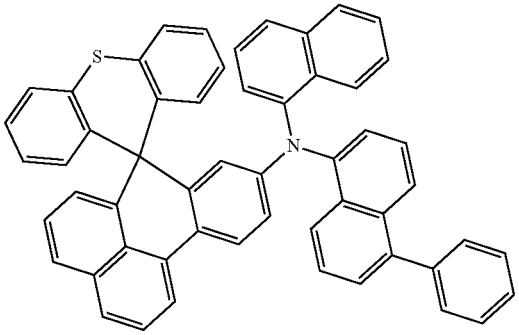
209
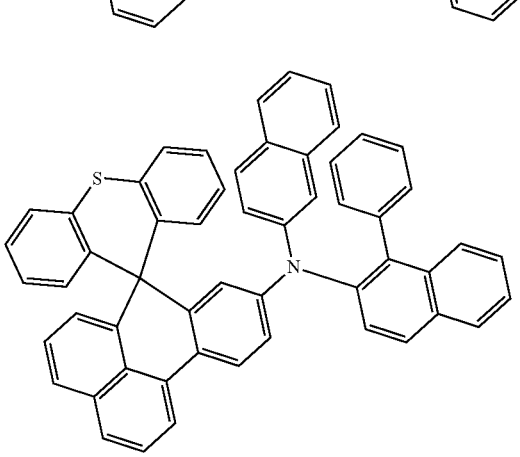
210
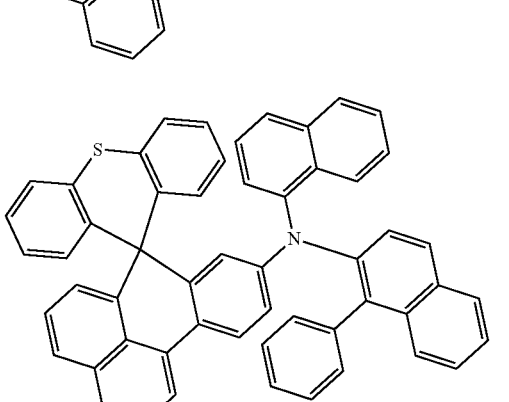
218
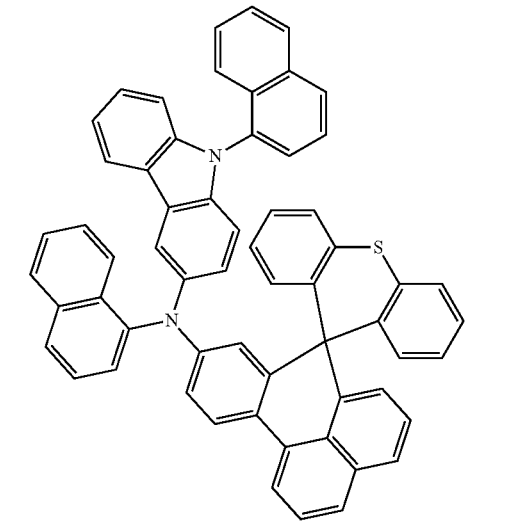

219
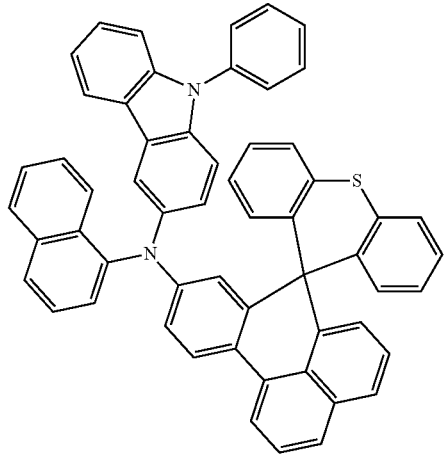
221
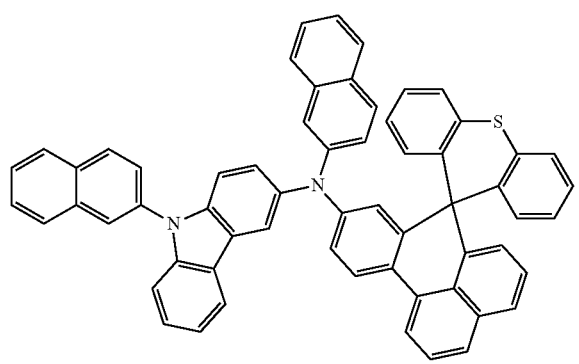
222
227
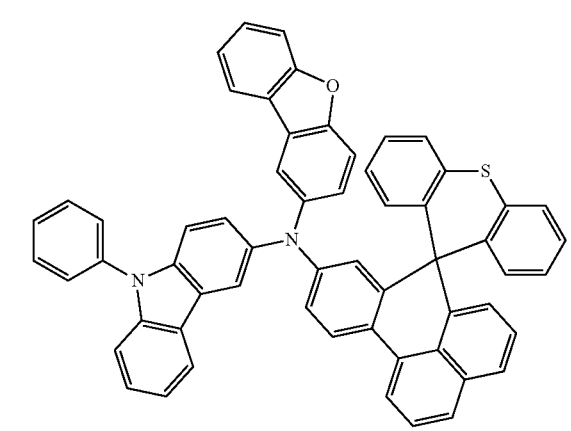
228
226
234
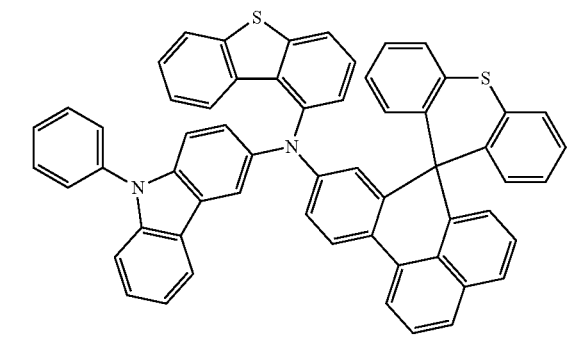

235
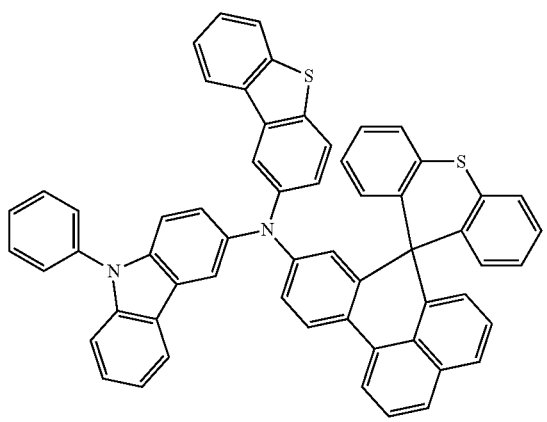
236
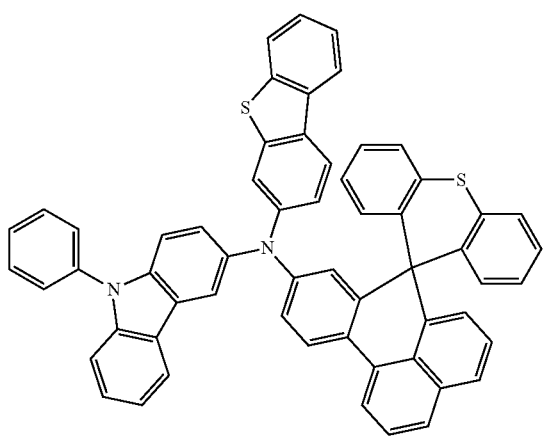
237
238
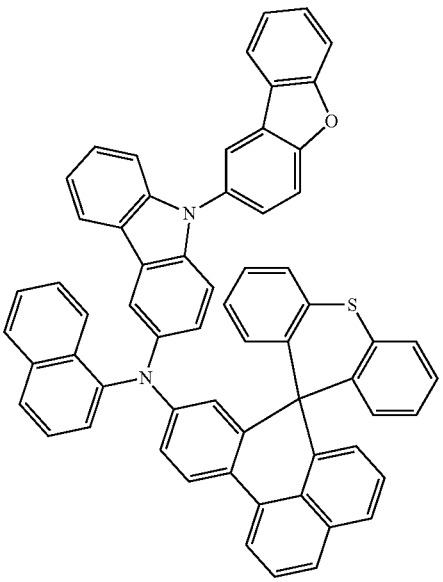
239
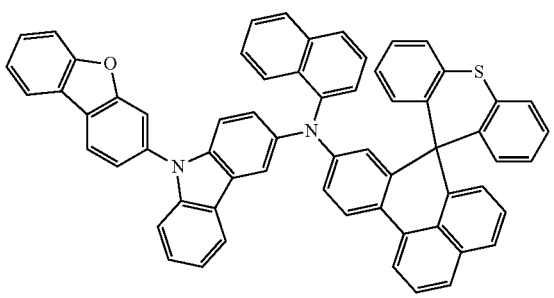
240
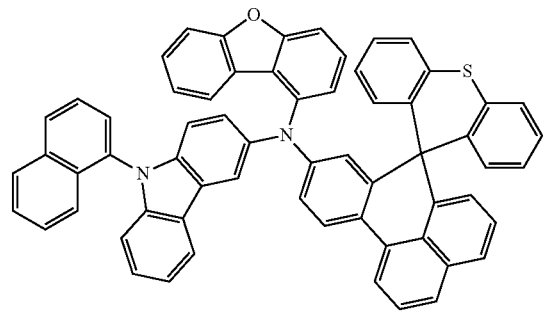
241
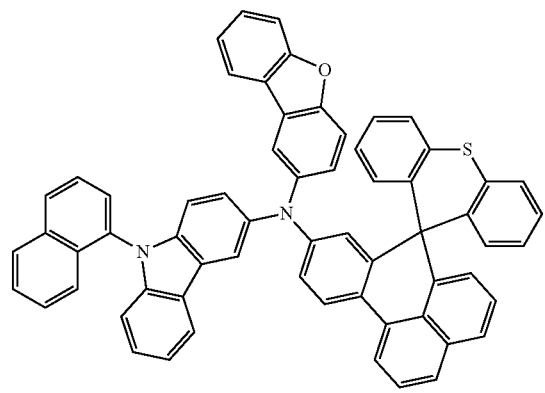

242
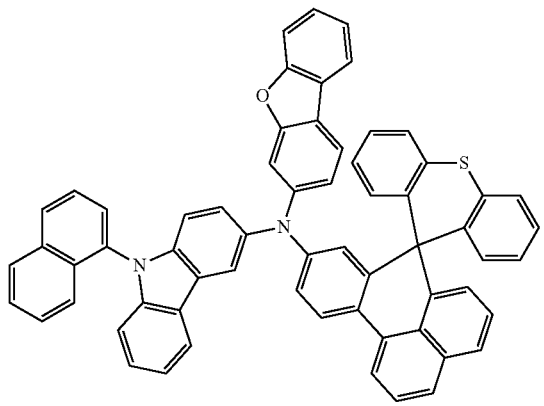
243
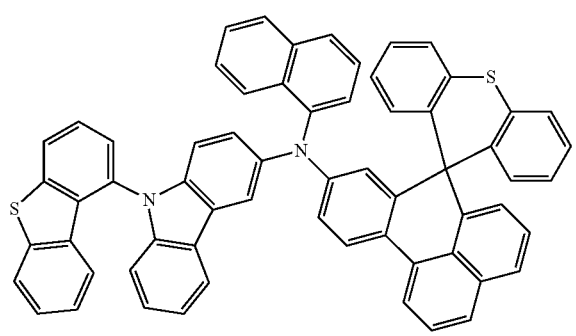
244
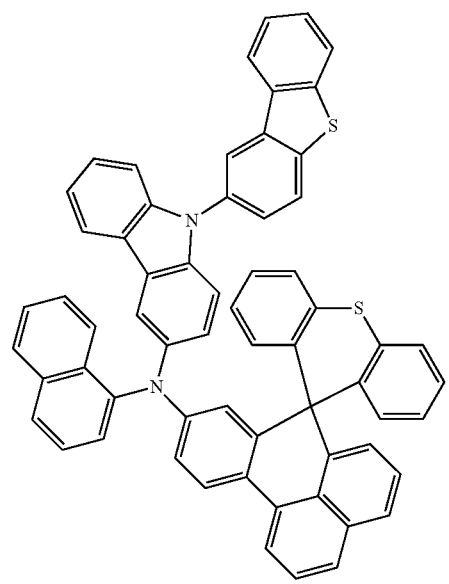
245
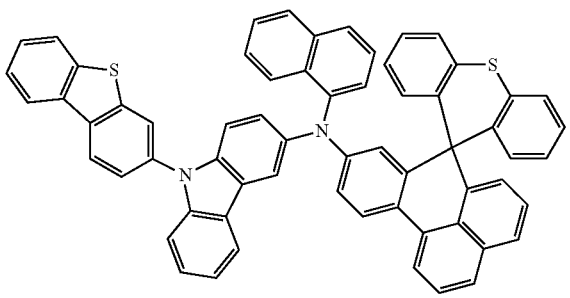
246
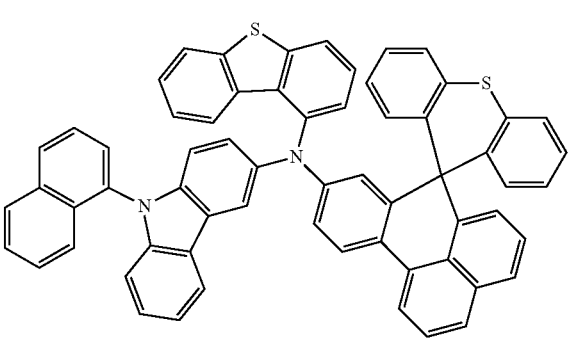
247
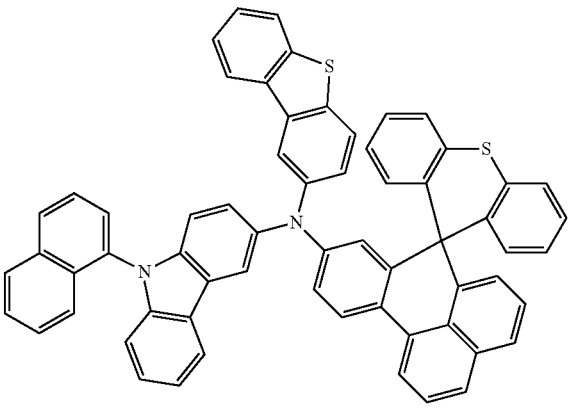
248
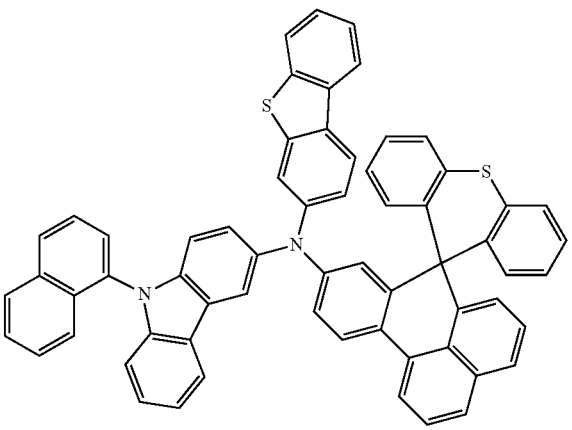

-continued
252
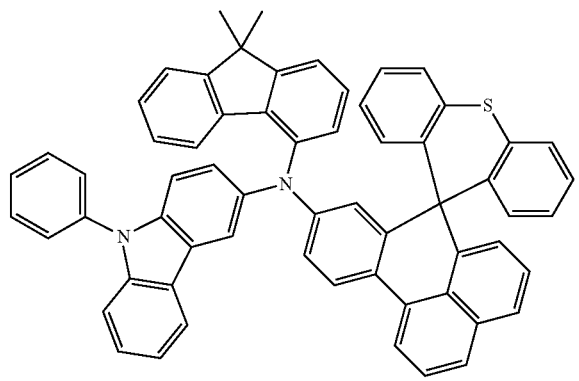
253
254
262
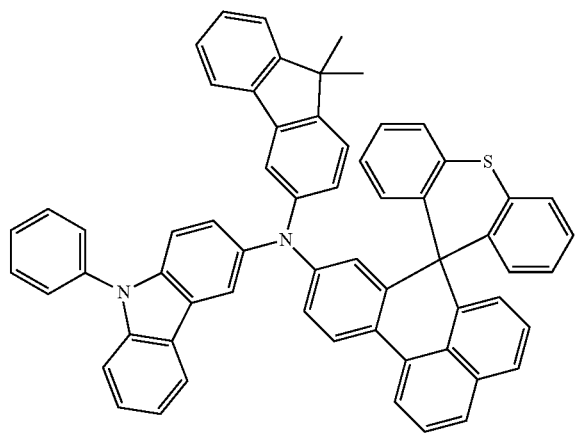
-continued
263
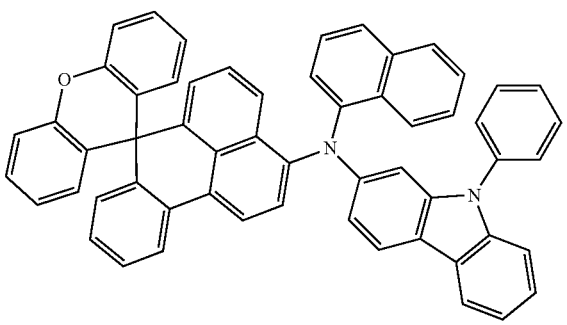
265
266
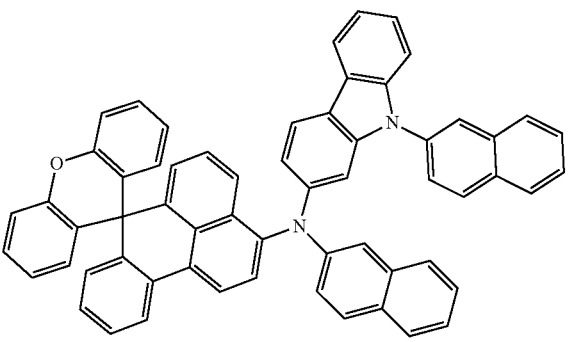
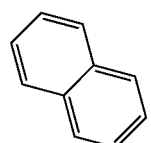
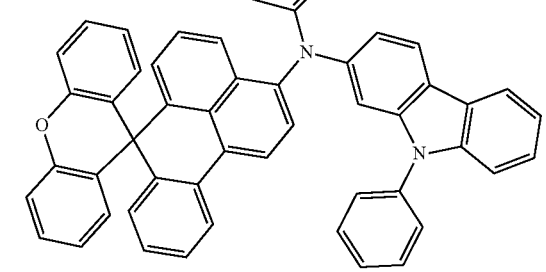
270
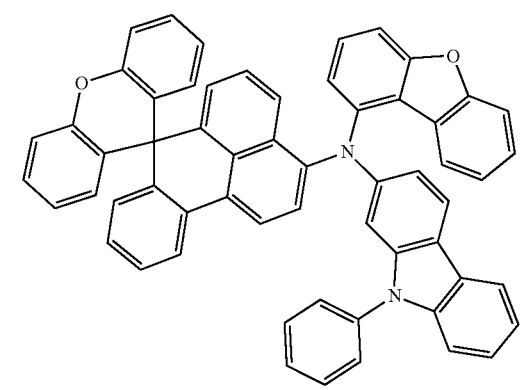

671
-continued
271
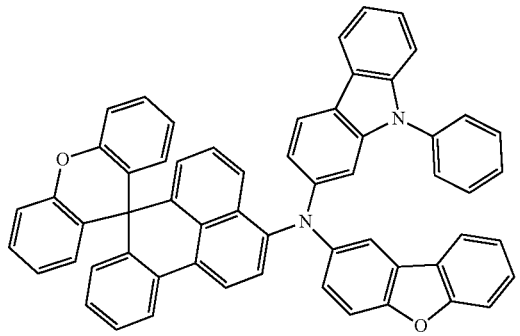
272
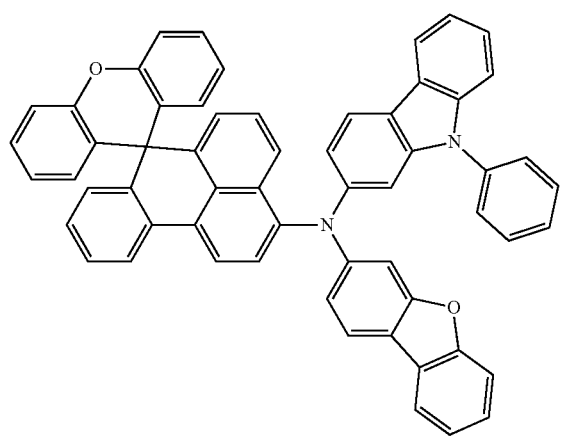
273
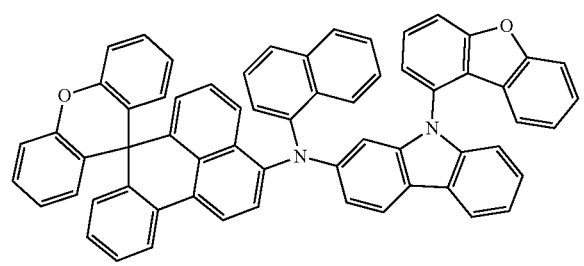
274
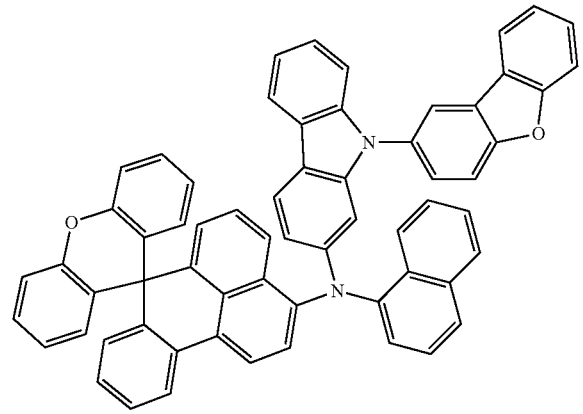
672
-continued
278
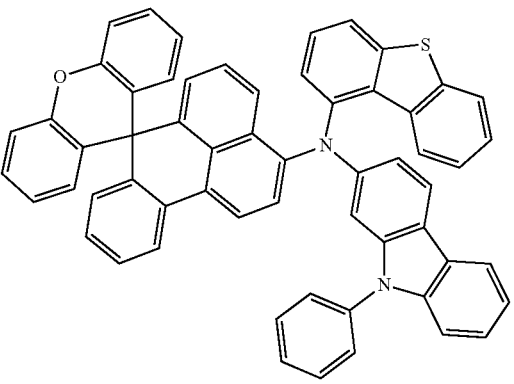
279
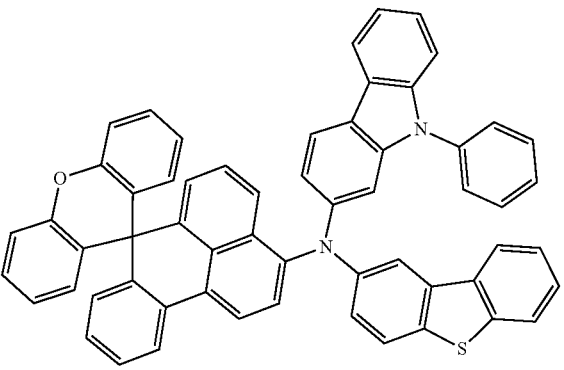
280
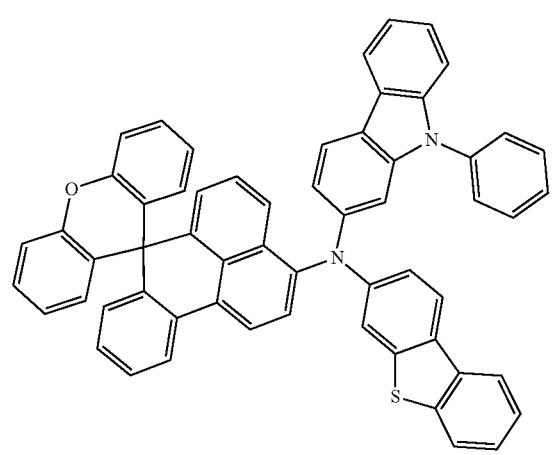
281
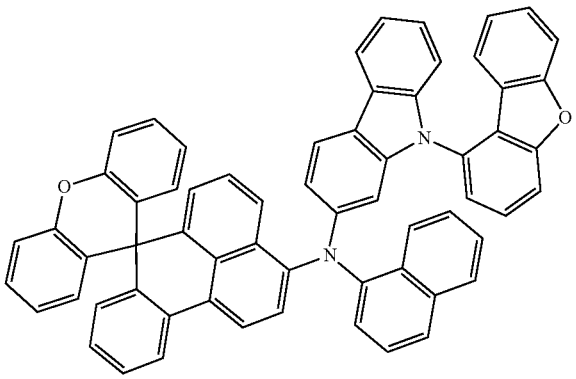

282
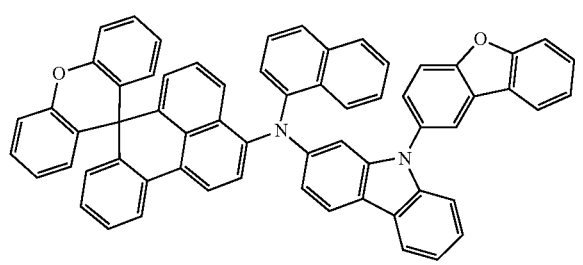
283
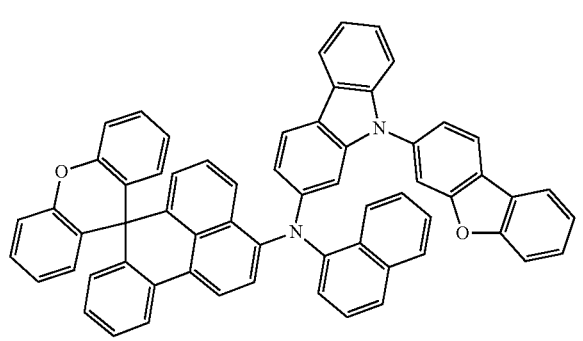
284
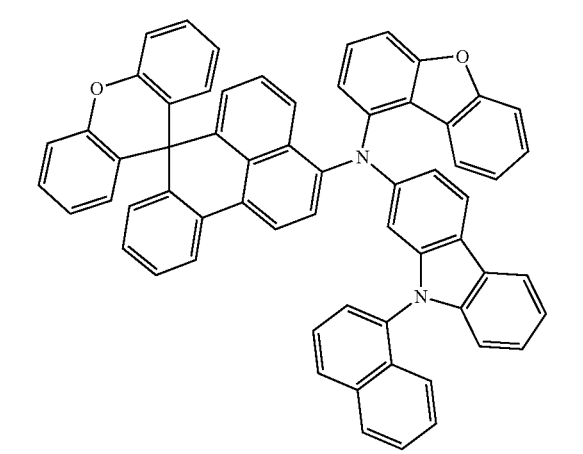
285
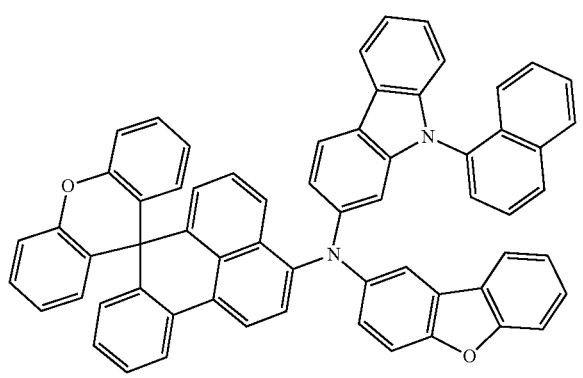
286
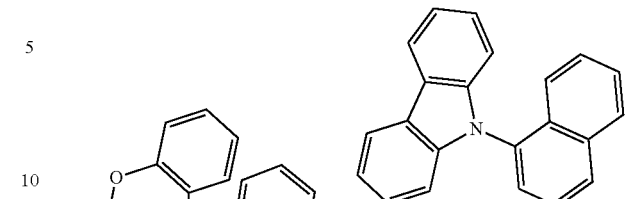
287
288
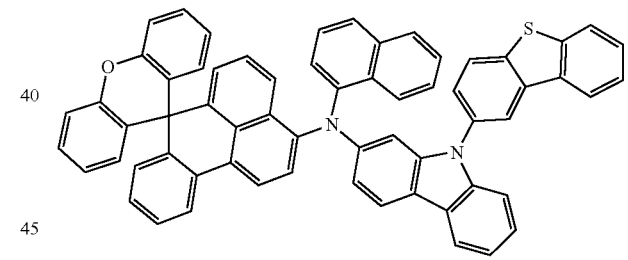
289
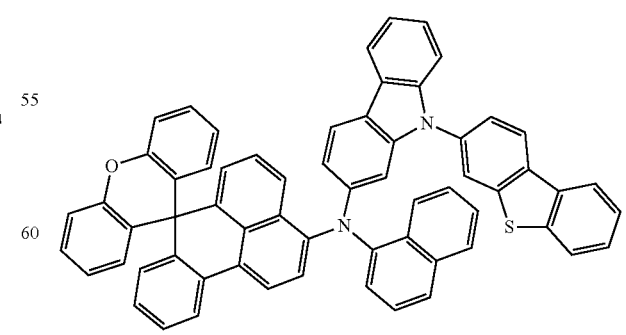

290
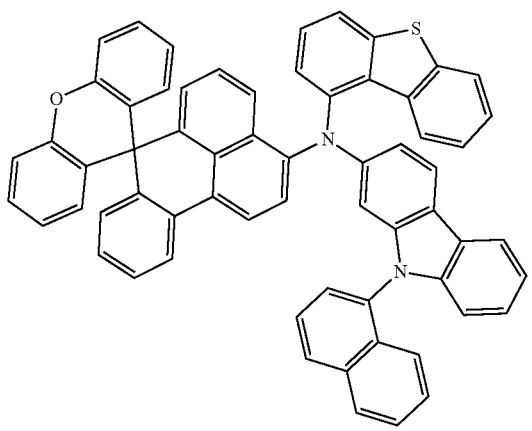
291
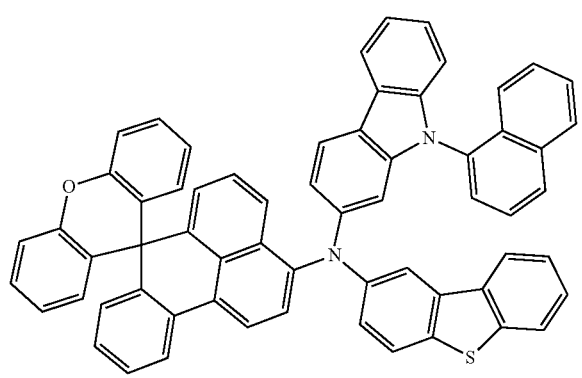
292
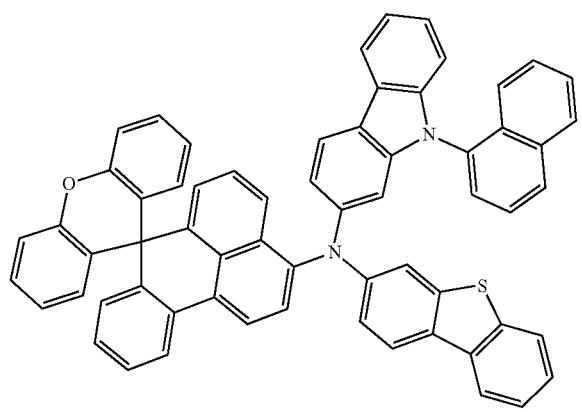
296
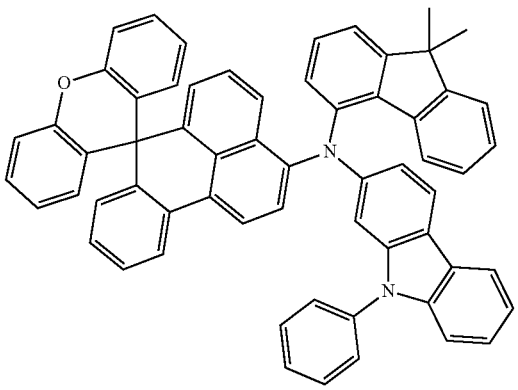
297
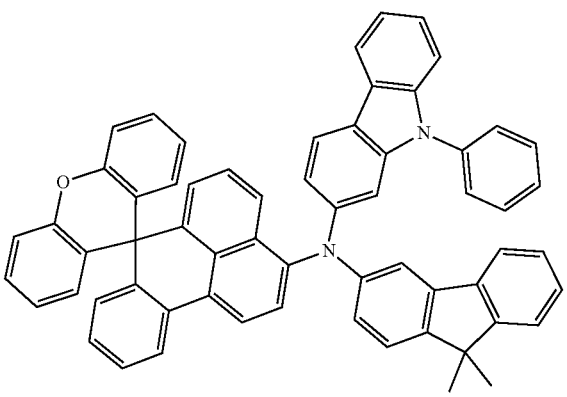
298
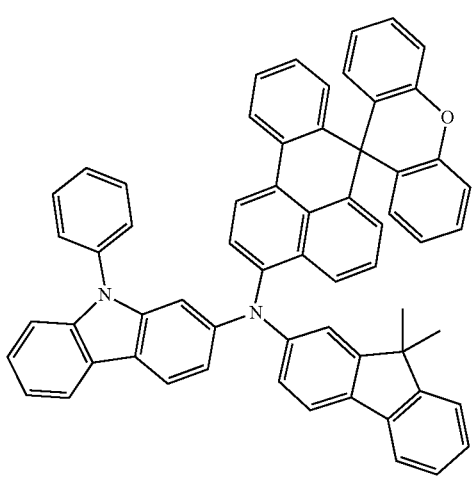

677
-continued
306
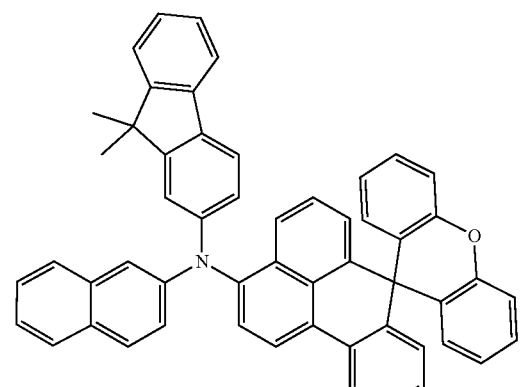
307
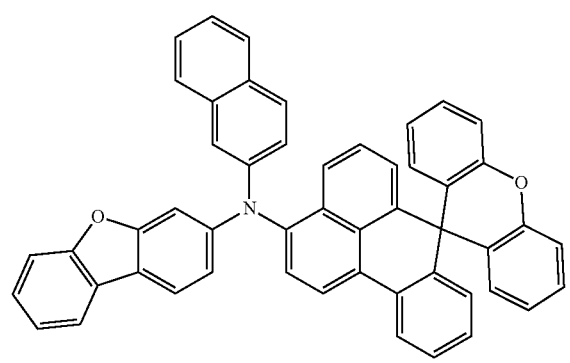
307
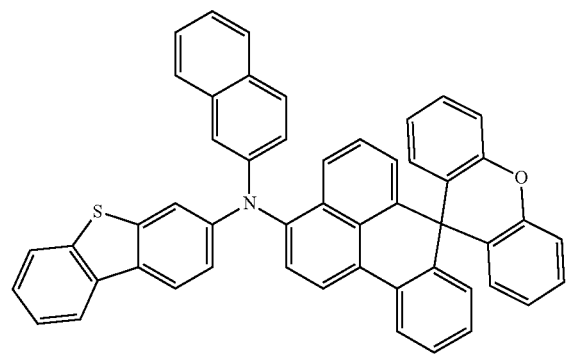
309
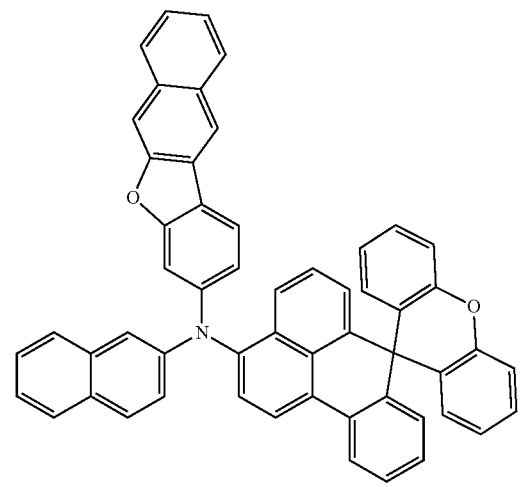
678
-continued
310
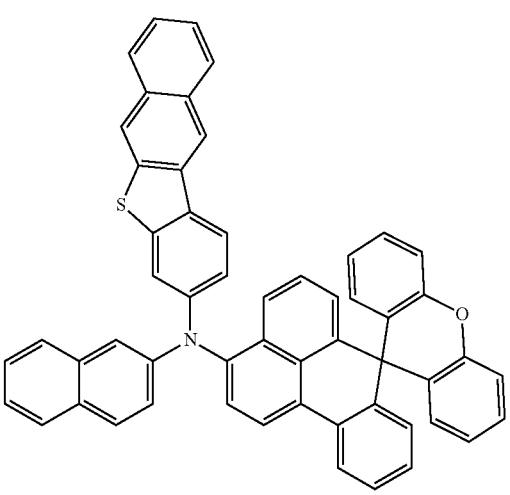
311
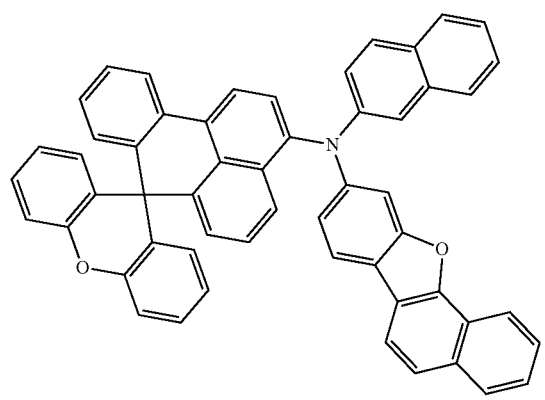
312
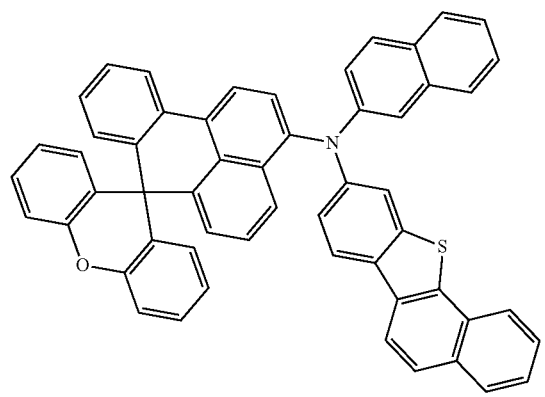

313
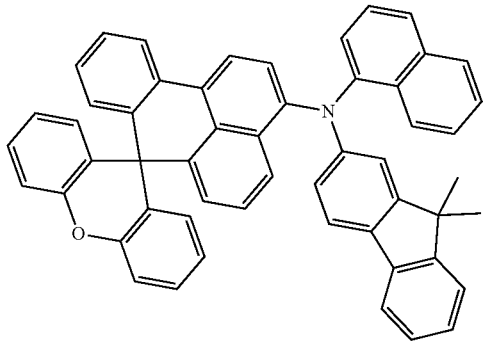
314
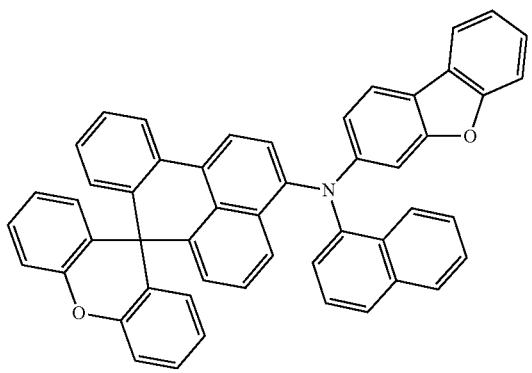
315
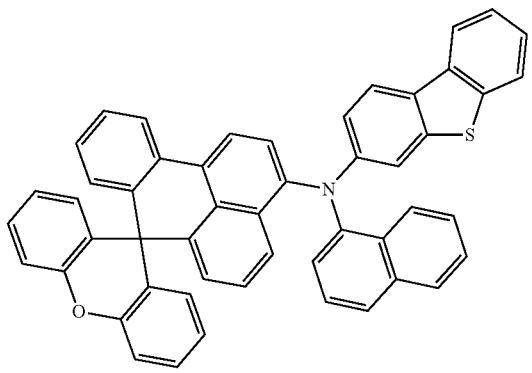
316
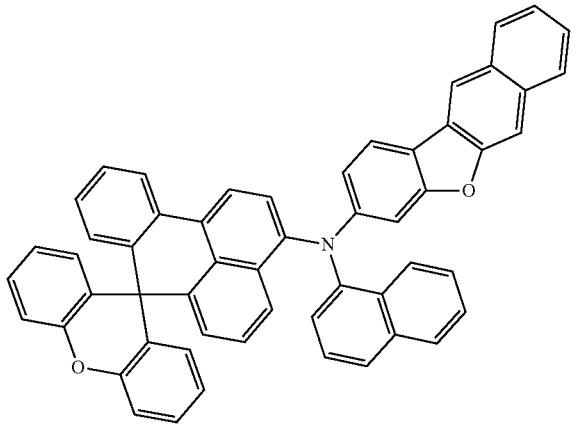
317
318
319
324
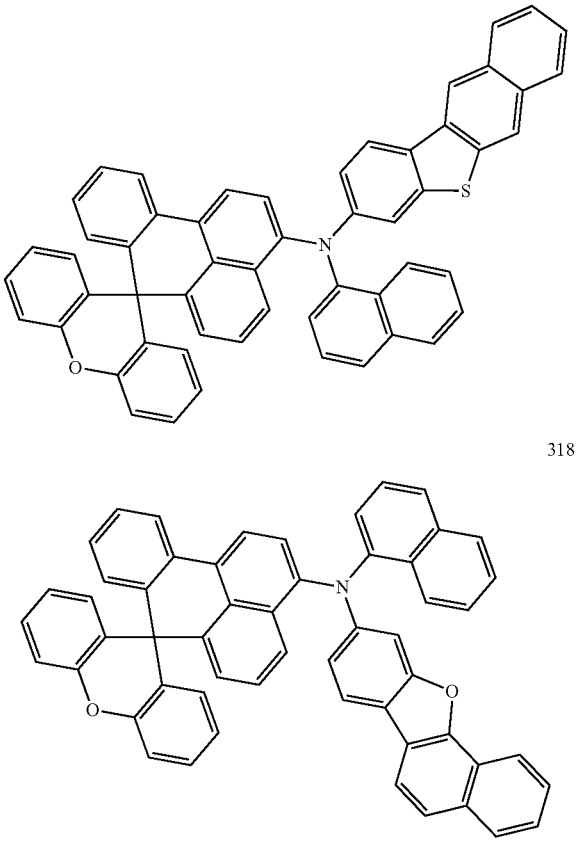

325
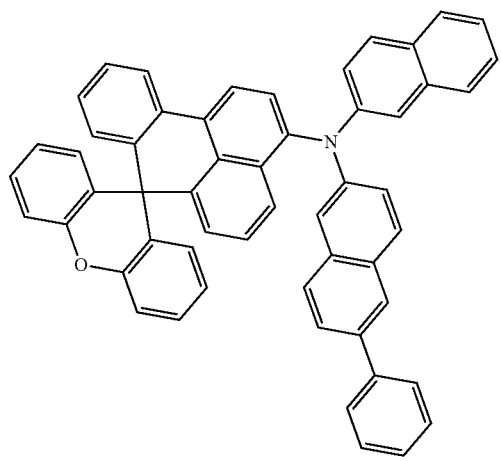
326
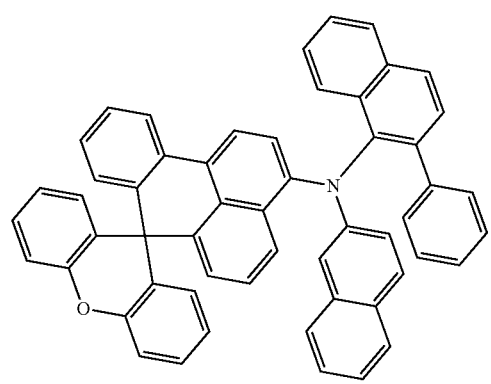
327
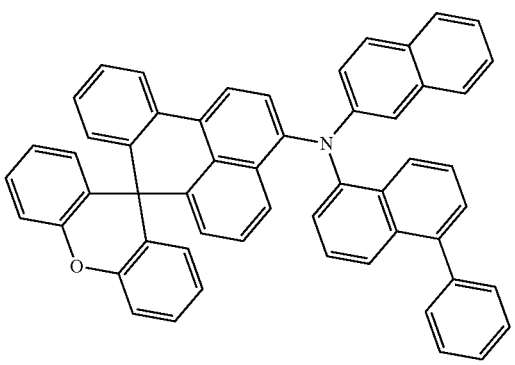
328
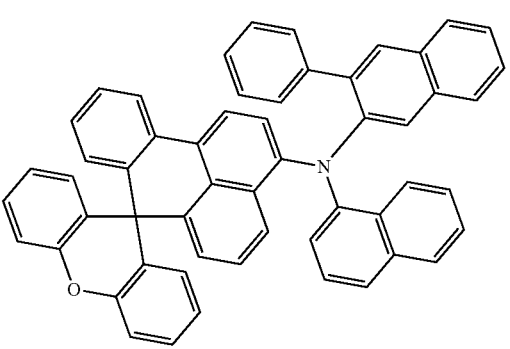
329
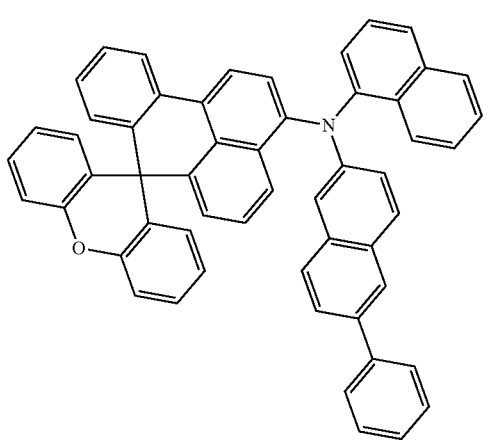
330
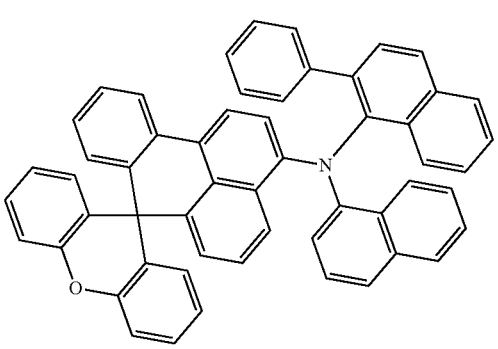
331
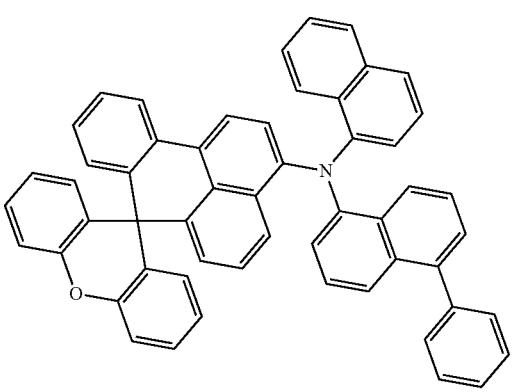
333
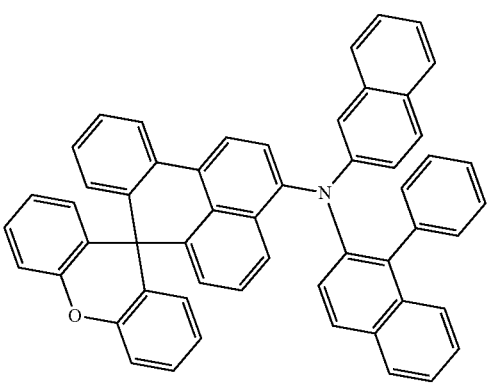

334
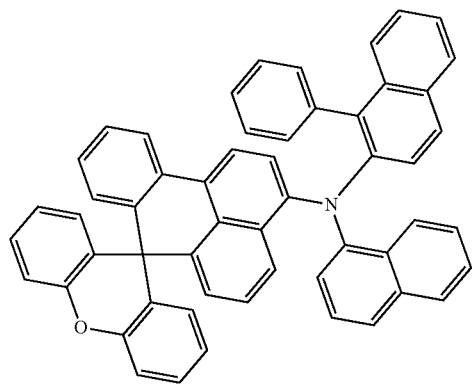
342
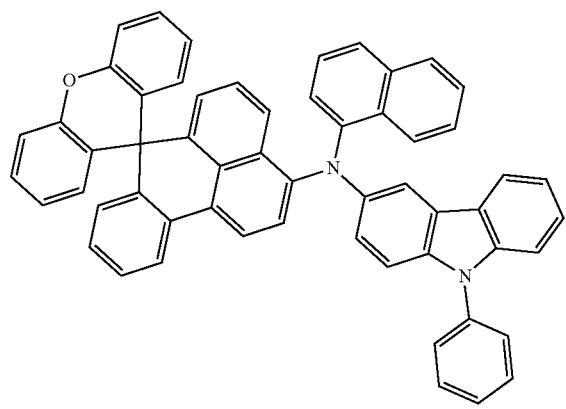
343
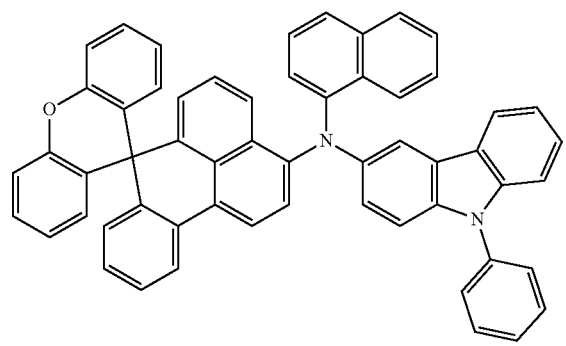
345
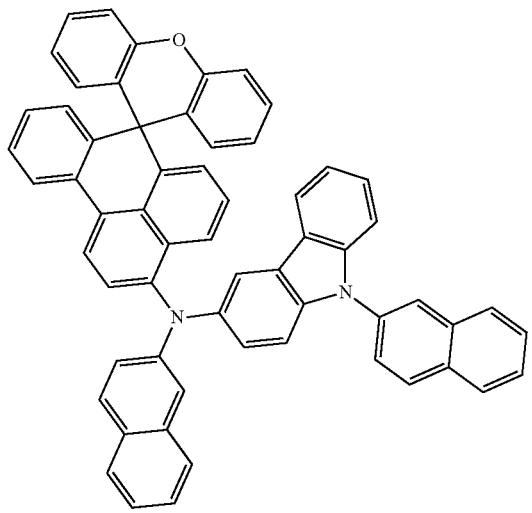
346
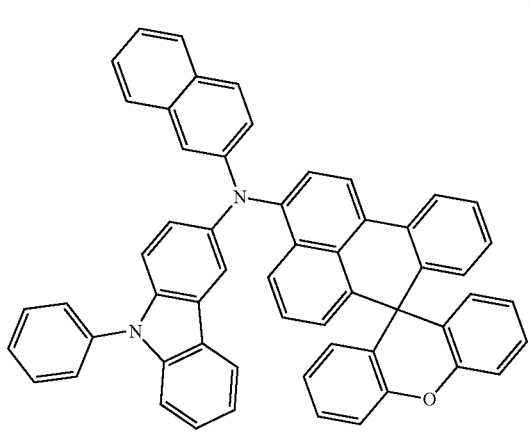
350
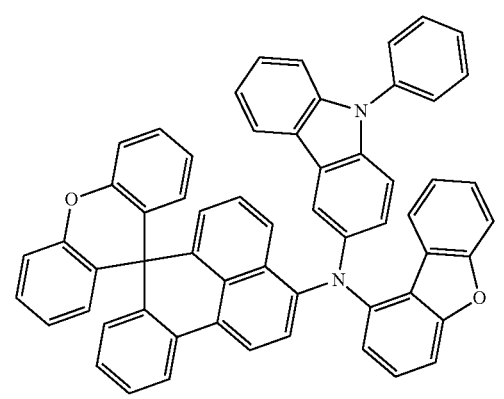

351
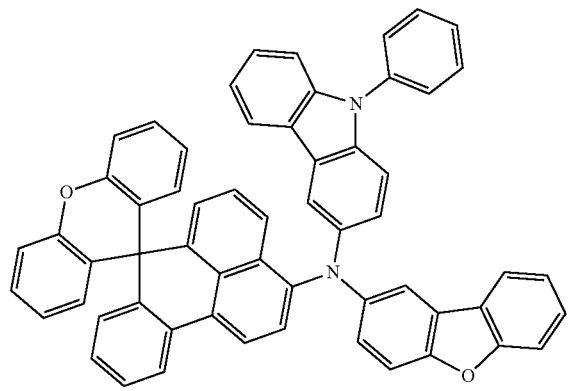
352
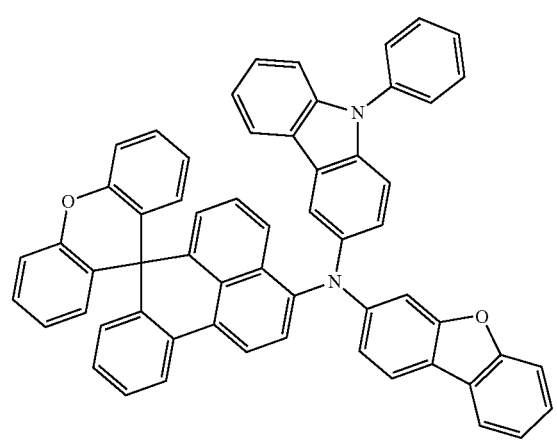
358
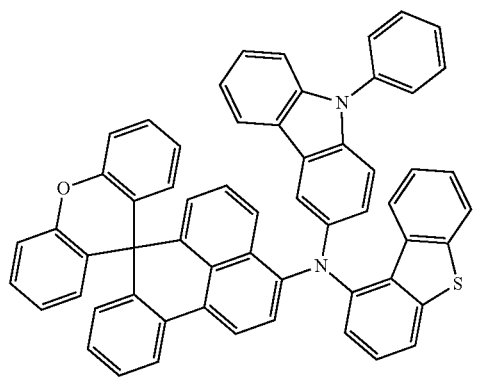
359
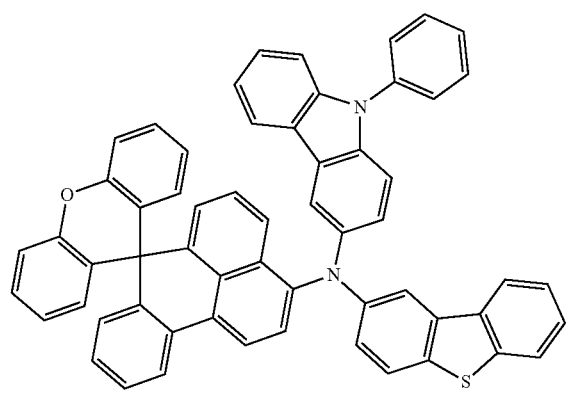
360
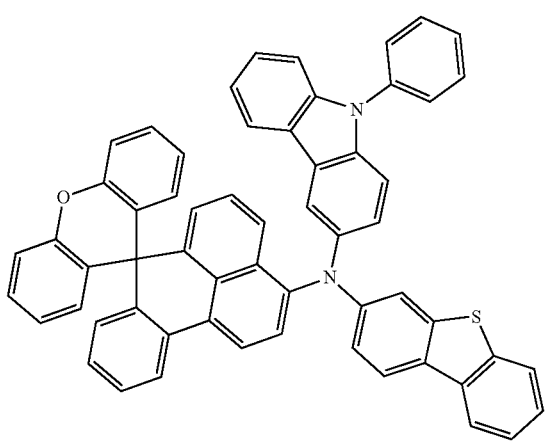
361
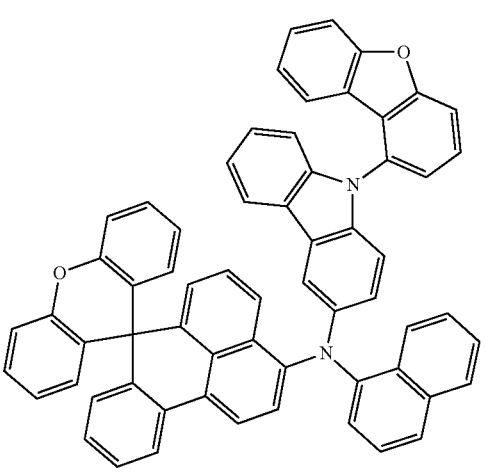
362
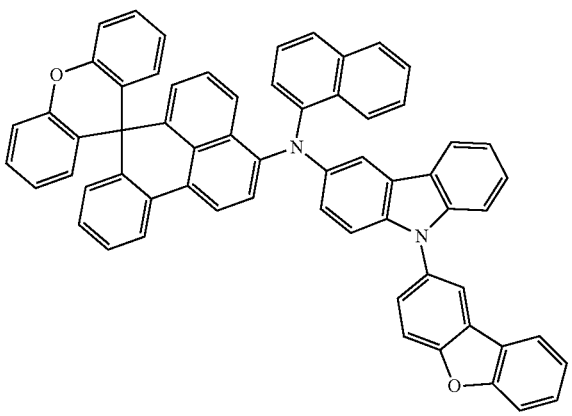

-continued
363
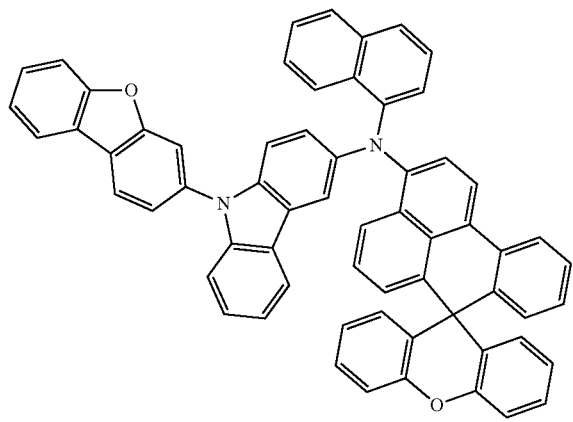
364
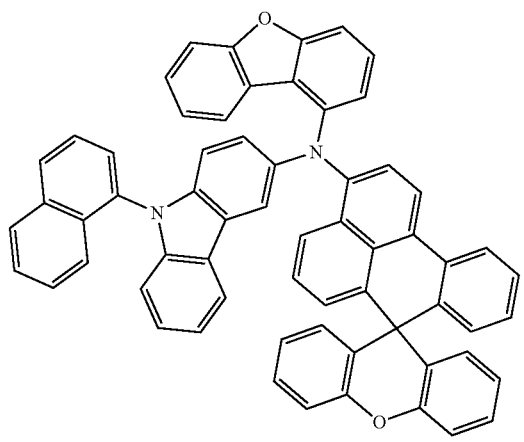
365
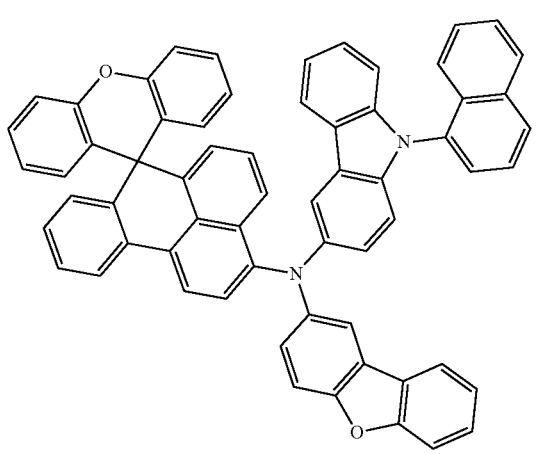
-continued
366
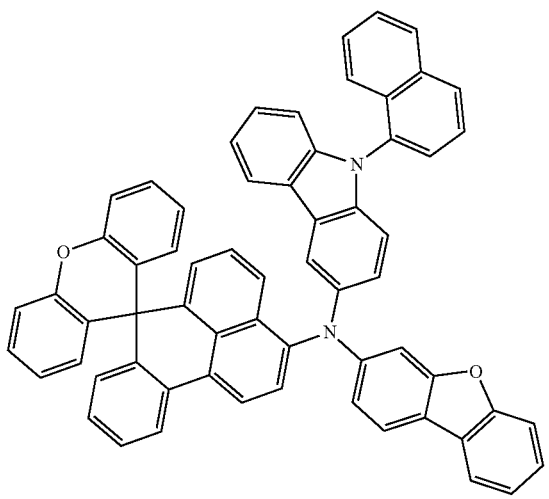
367
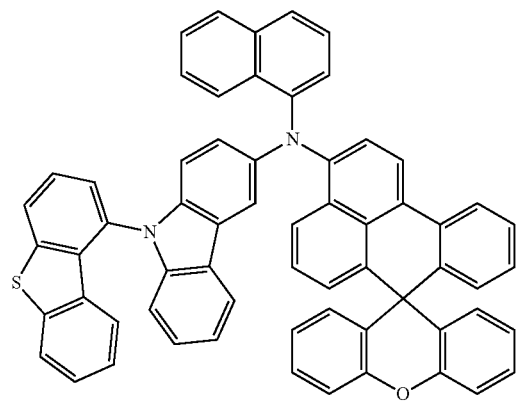
368
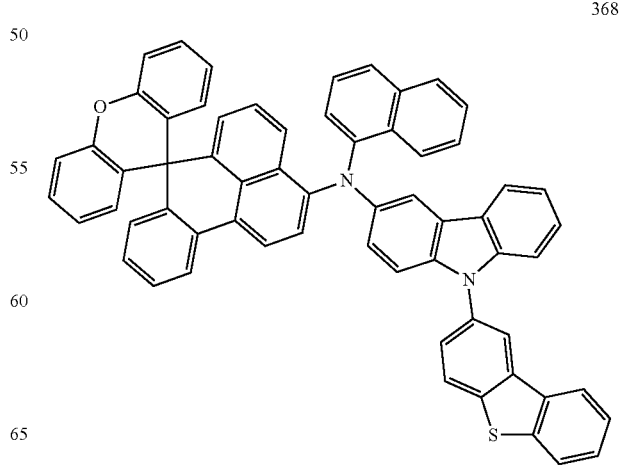

689
-continued
370
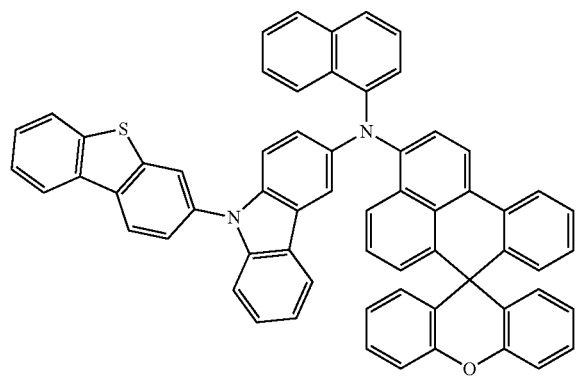
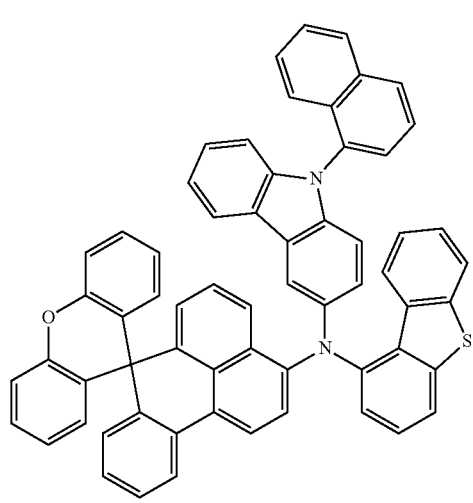
371
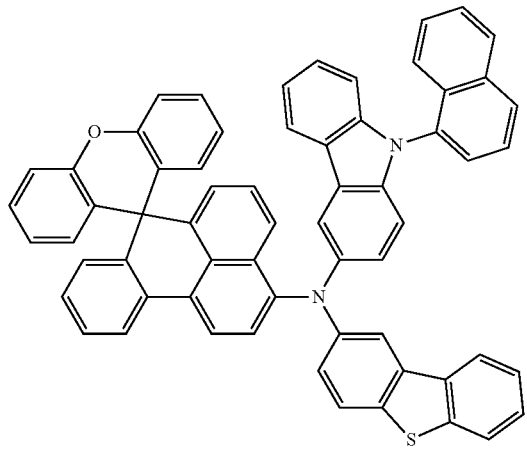
690
-continued
372
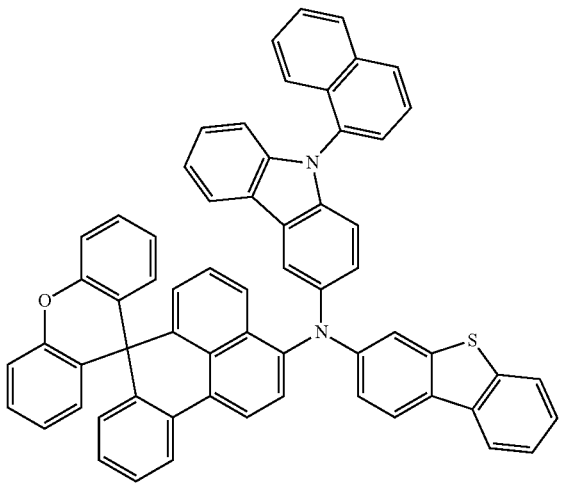
376
377
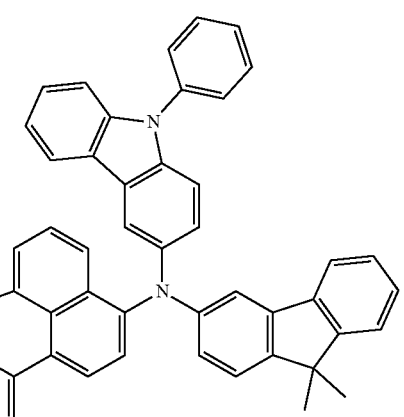

-continued
378
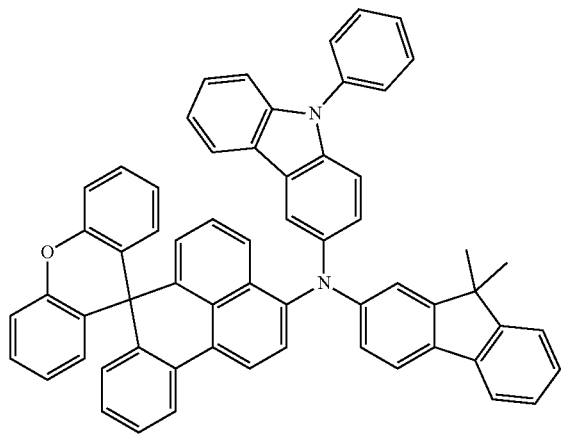
386
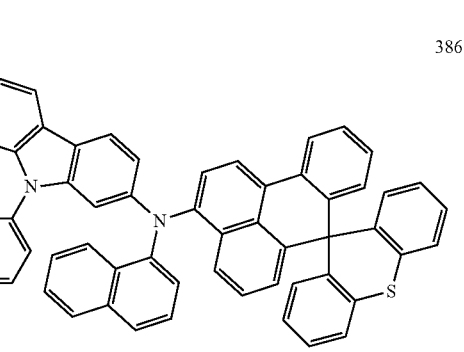
387
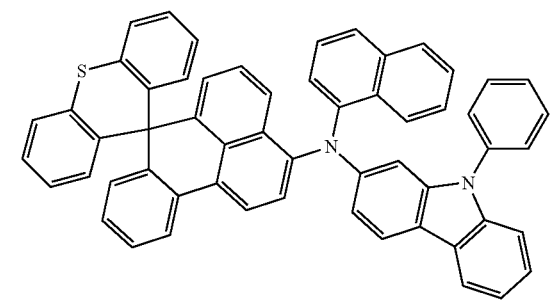
389
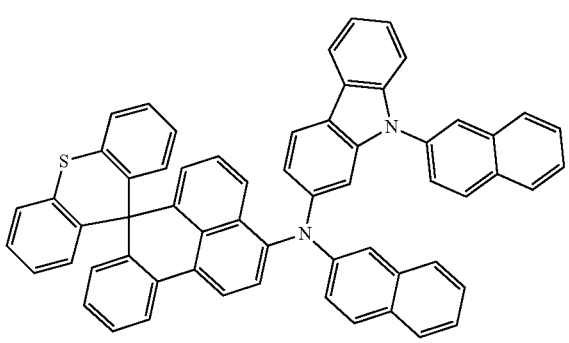
-continued
390
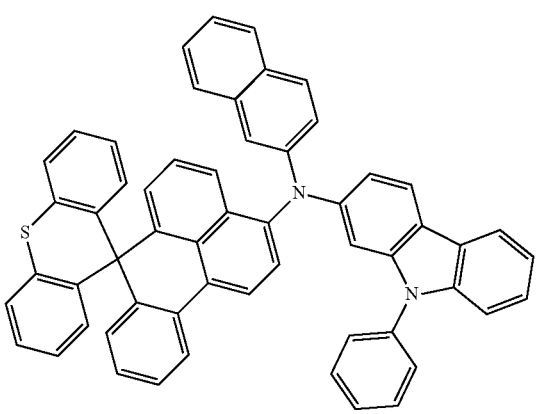
394
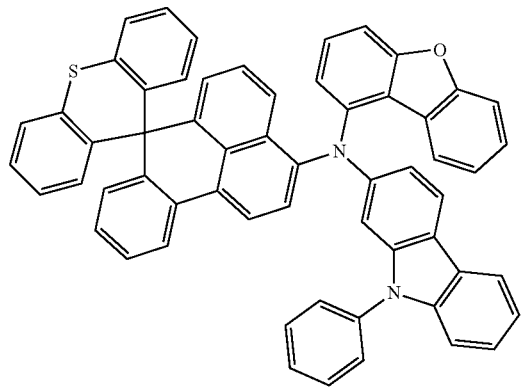
395
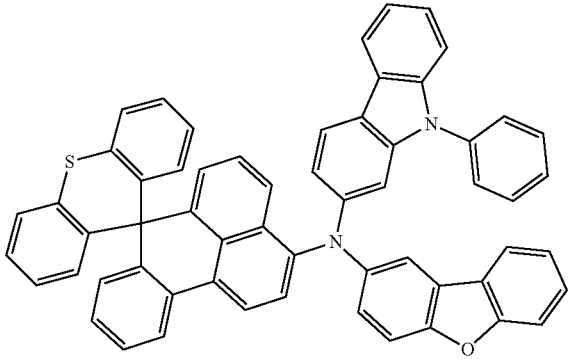

396
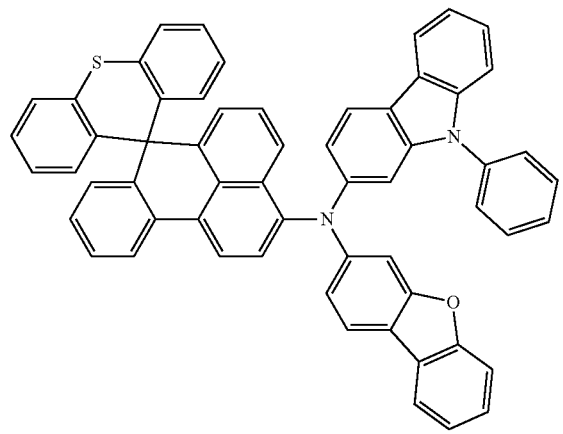
402
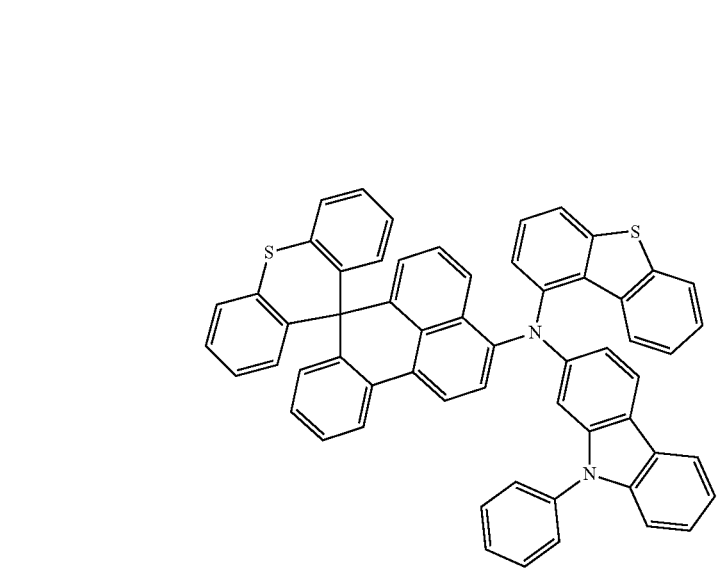
403
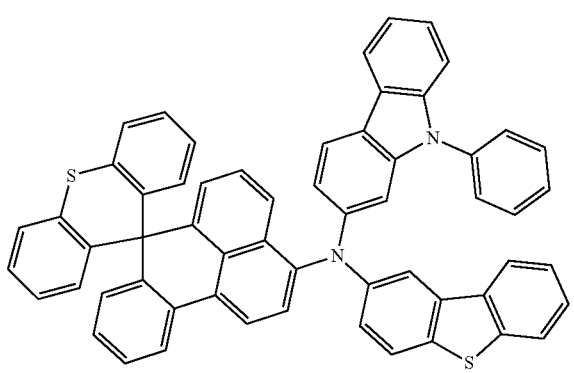
404
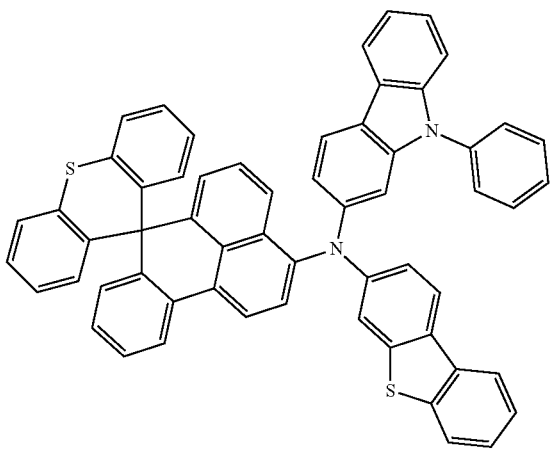
405
406
407
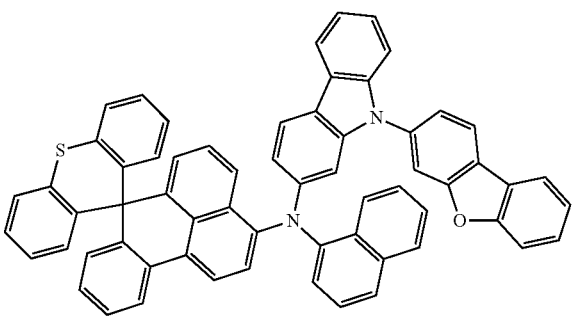

408
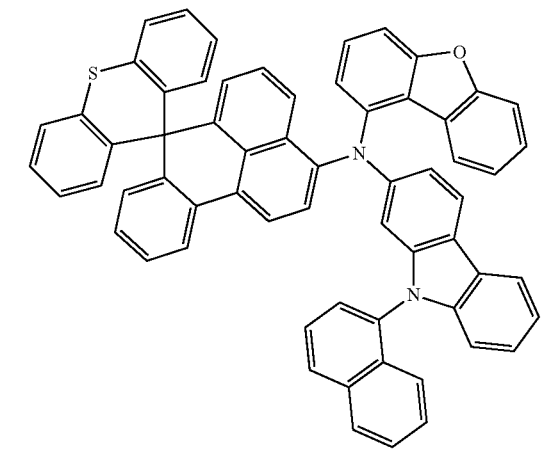
409
412
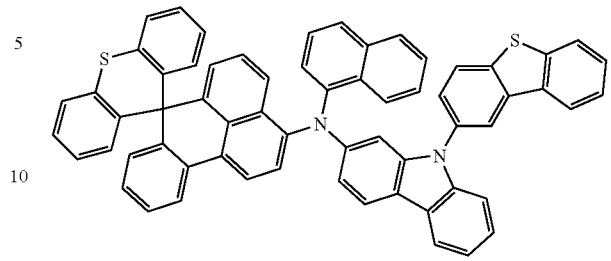
413
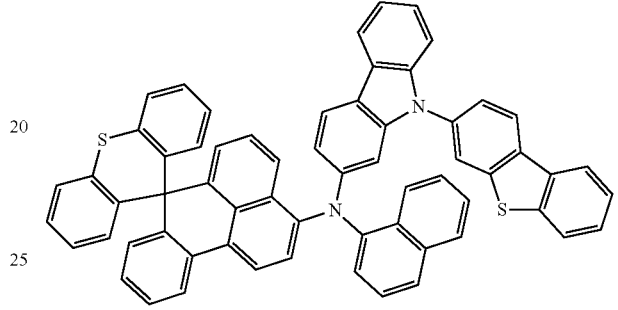
410
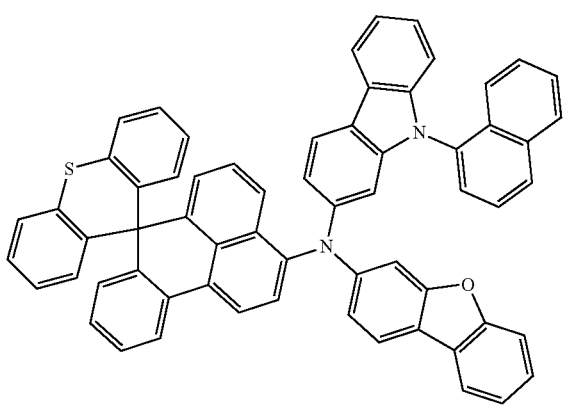
414
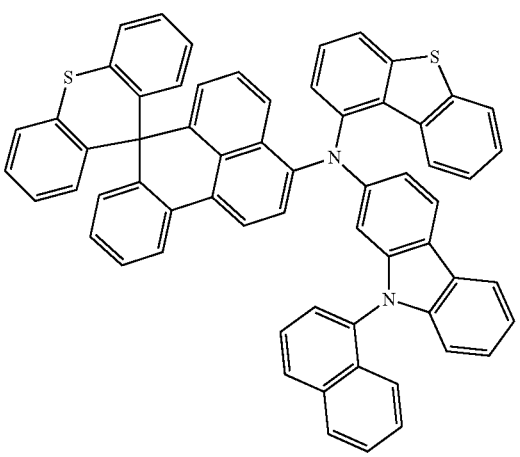
411
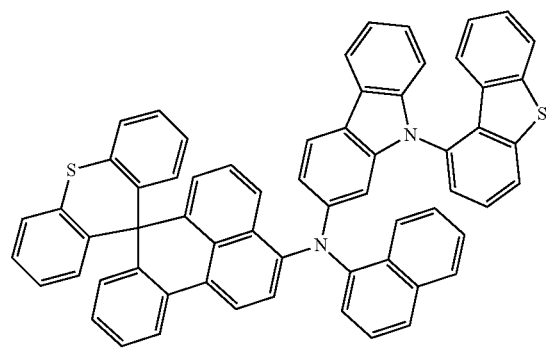
415
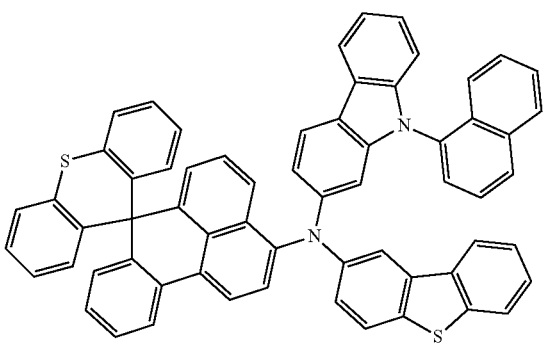

697
-continued
416
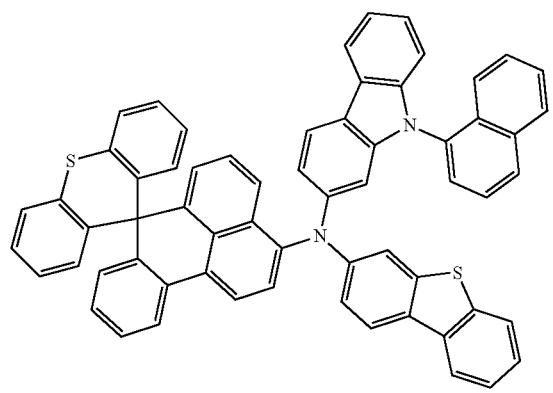
420
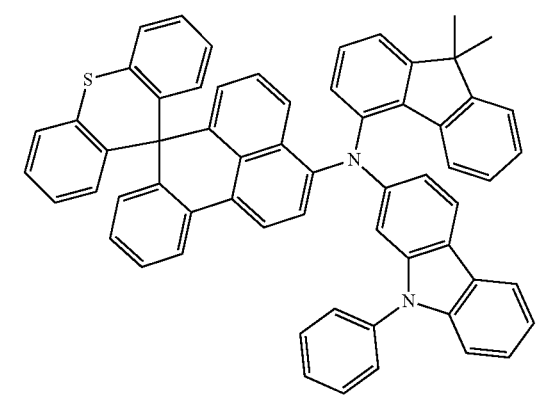
421
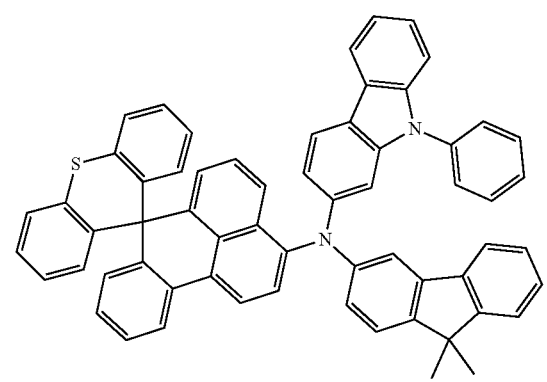
698
-continued
422
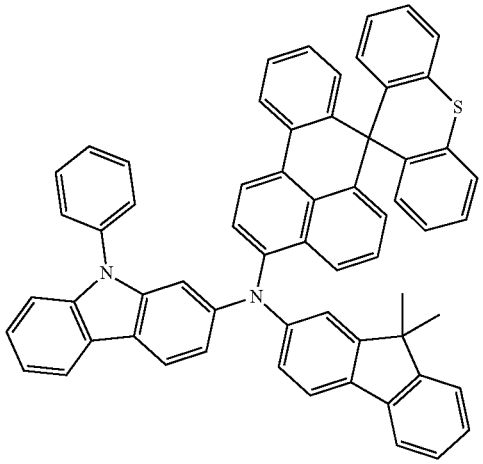
430
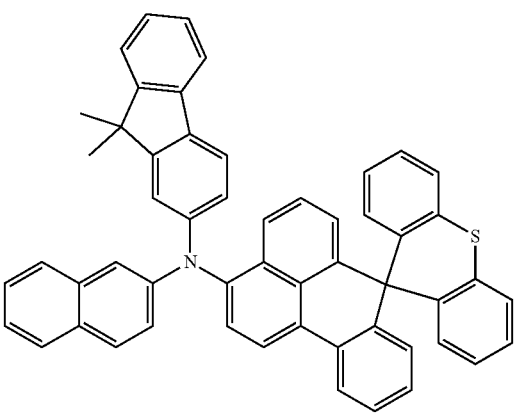
431
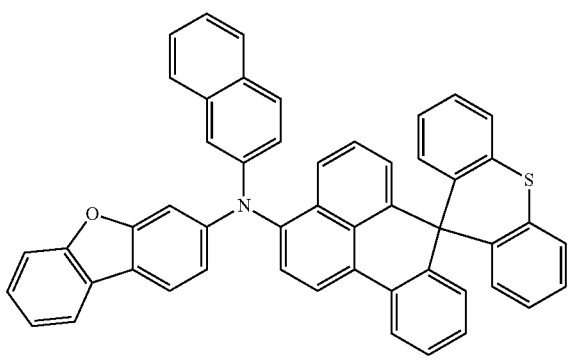
432
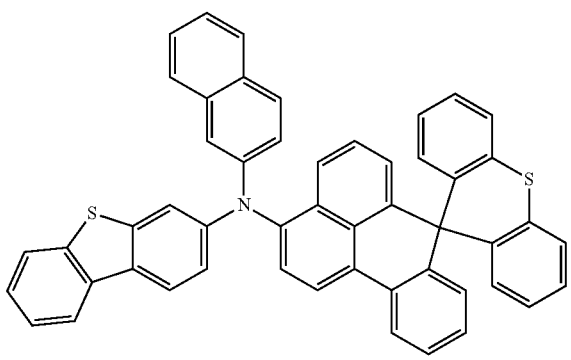

433
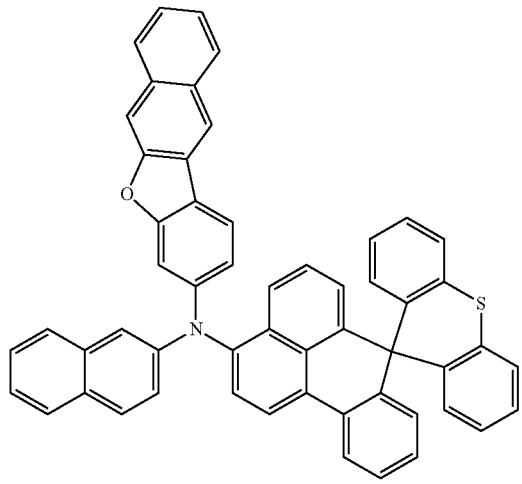
434
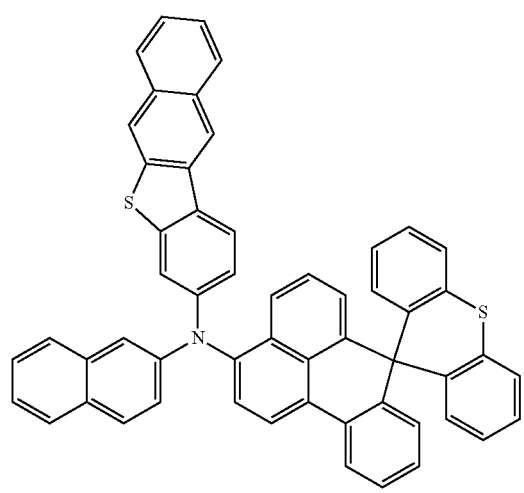
435
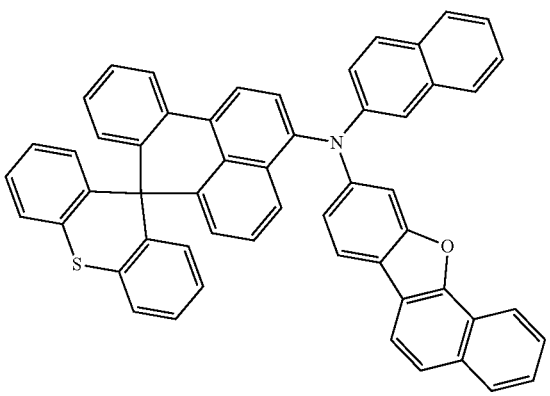
436
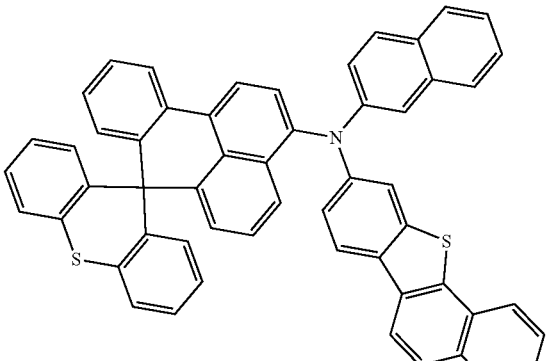
437
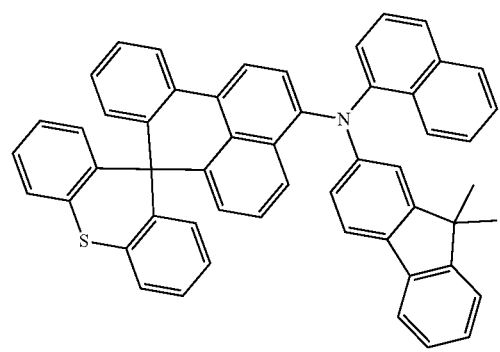
438
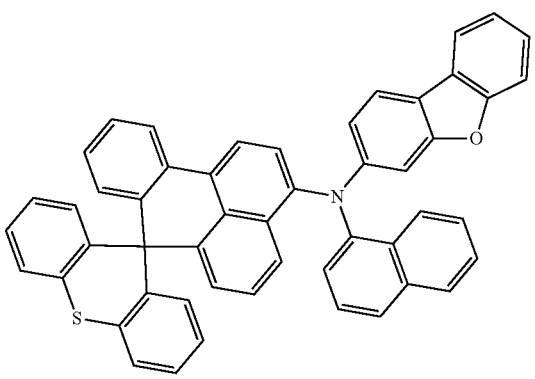
439
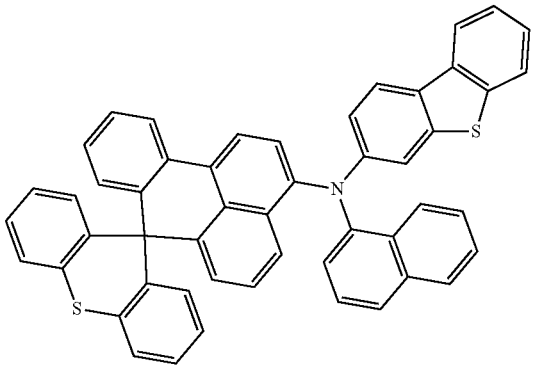

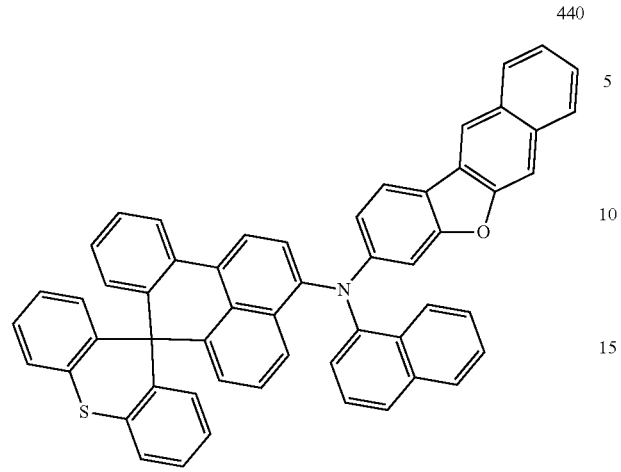
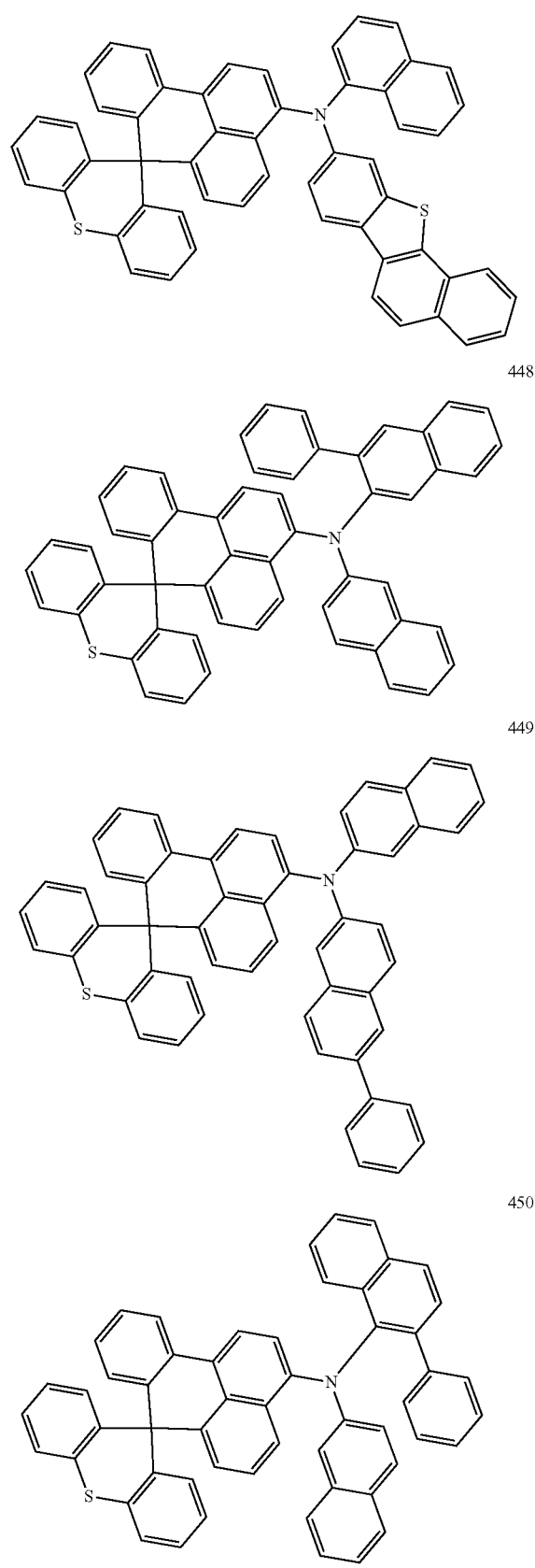

703 -continued
451
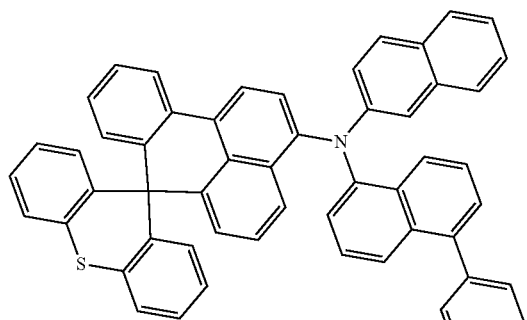
452
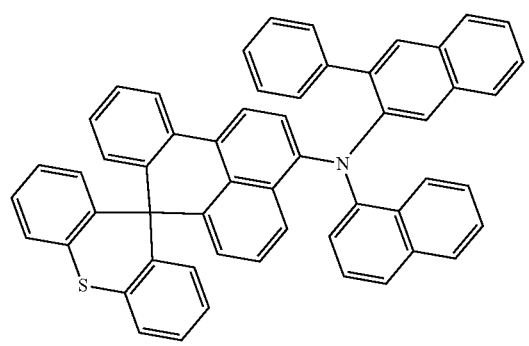
453
454
704 -continued
455
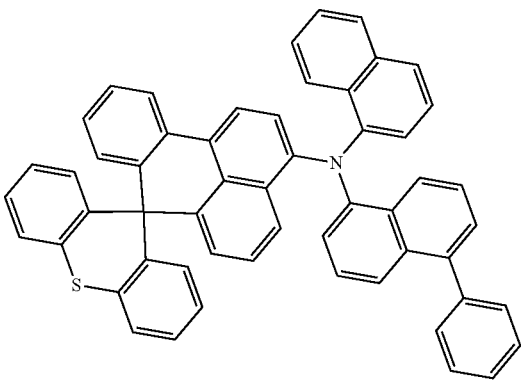
457
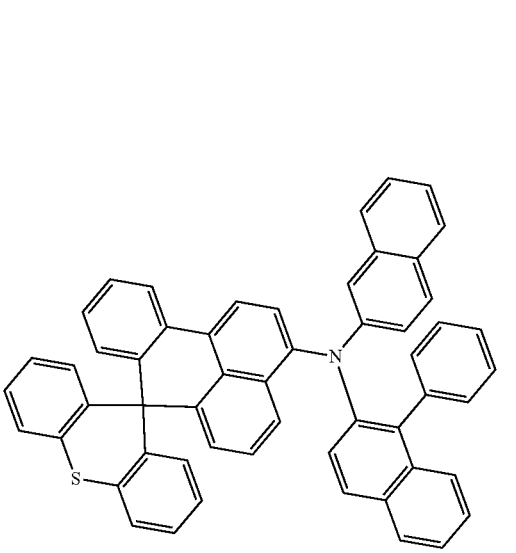
458
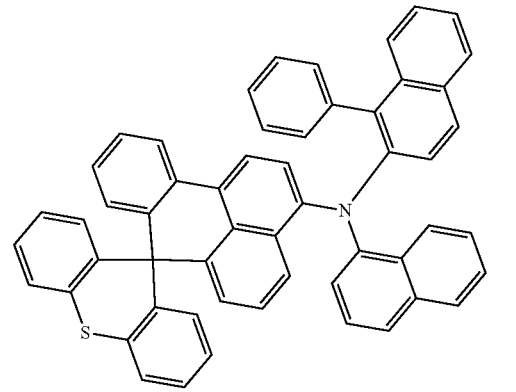

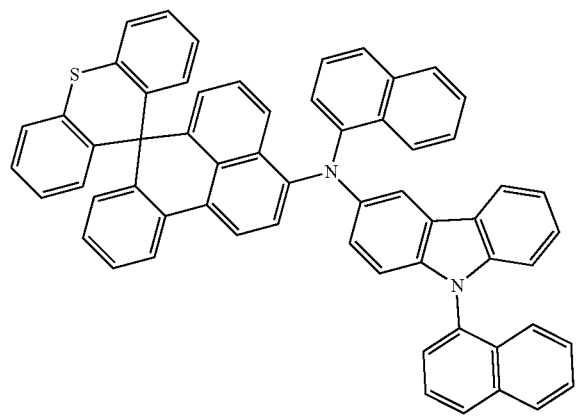
466
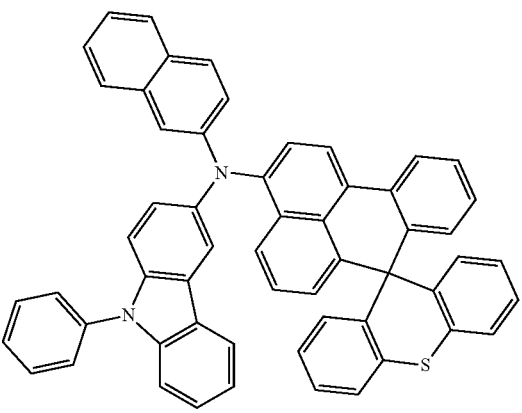
470
467
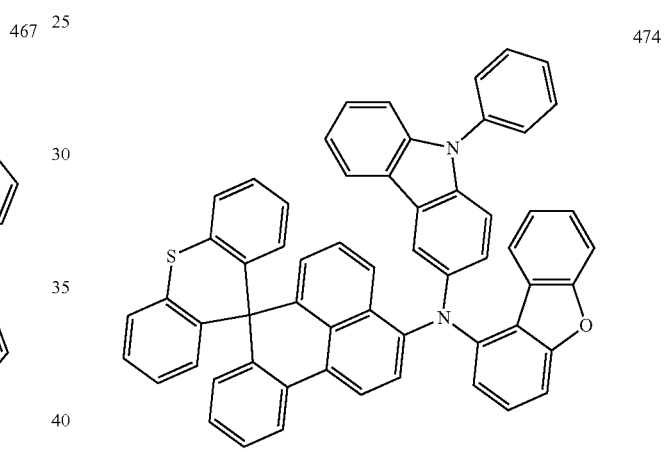
474
469
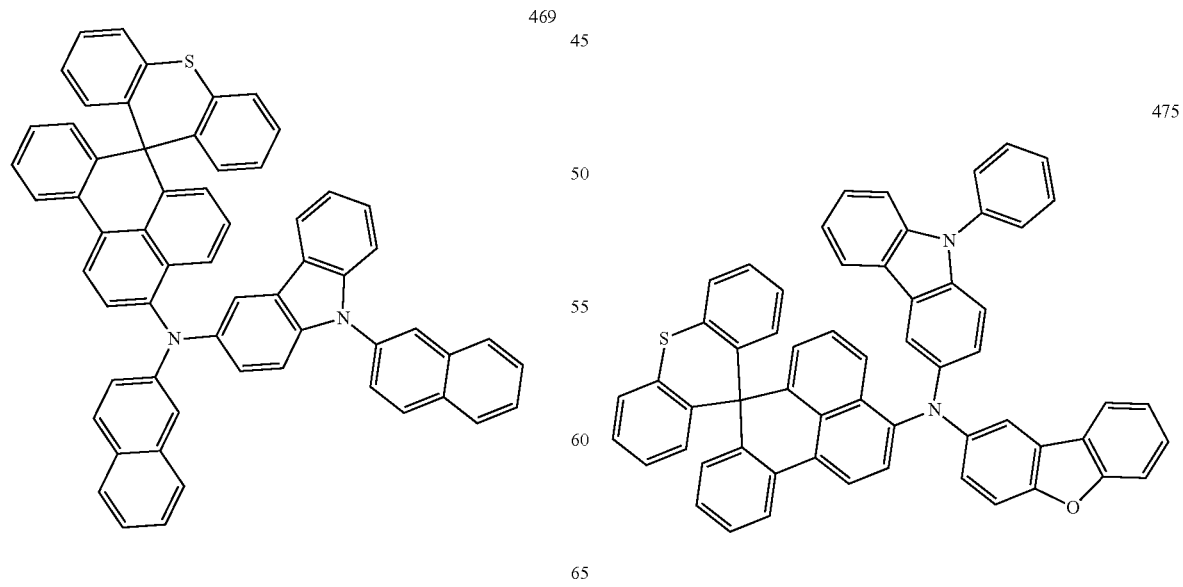
475

-continued
476
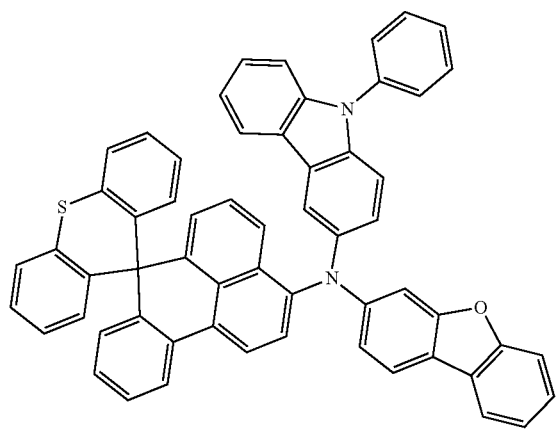
482
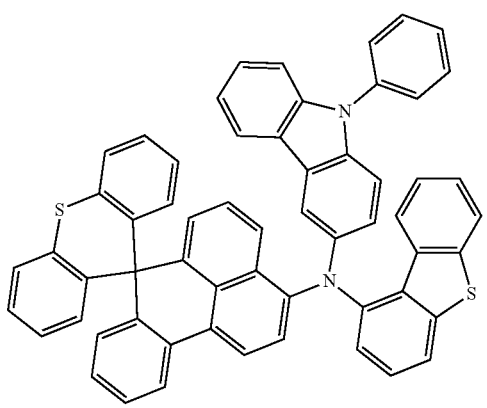
483
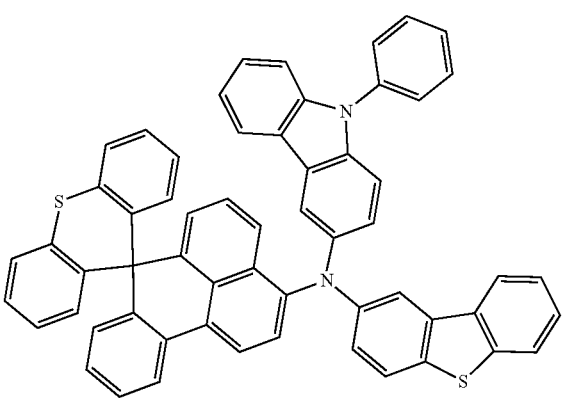
-continued
484
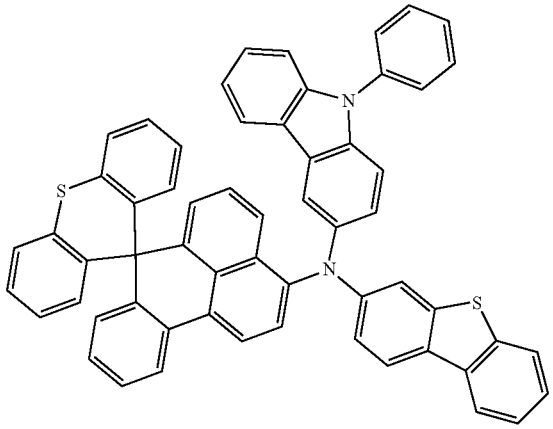
485
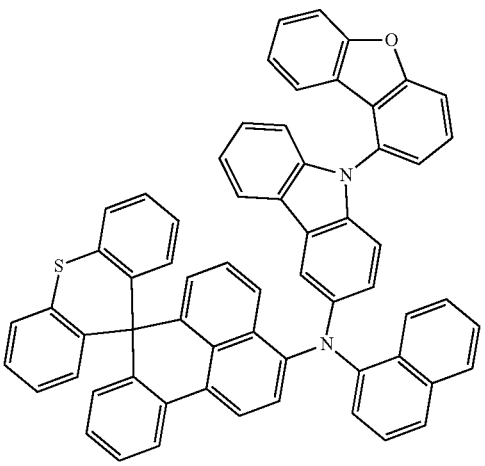
486
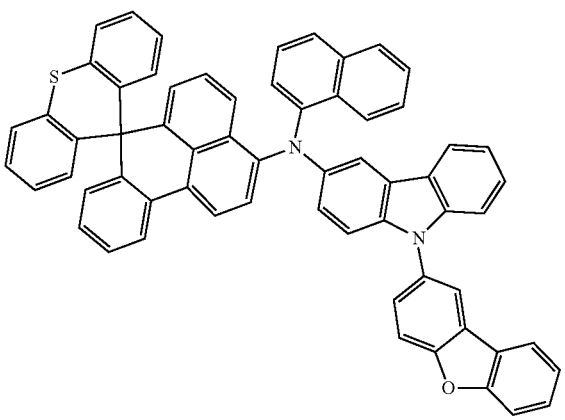

-continued
487
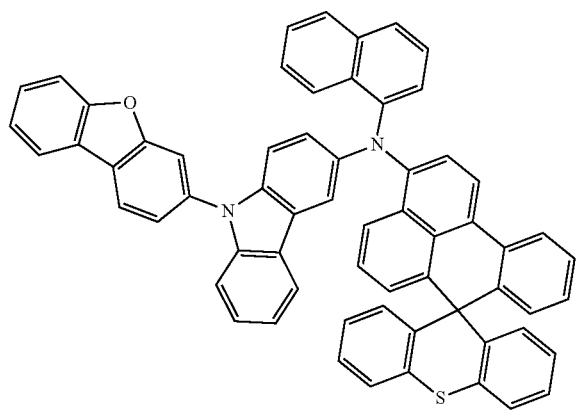
488
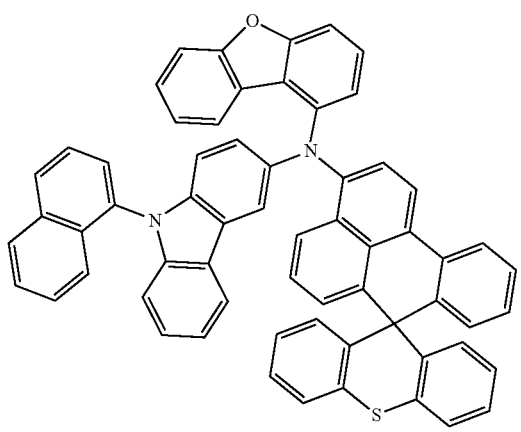
489
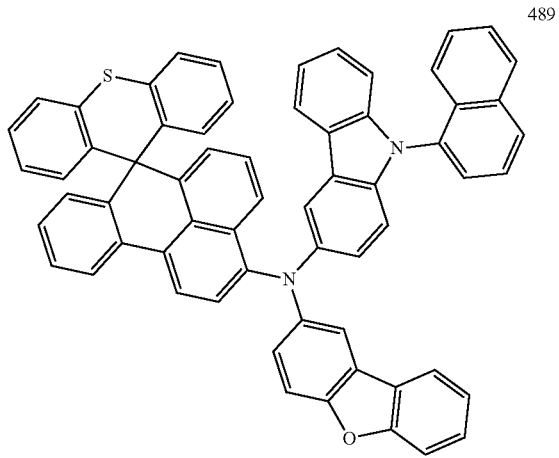
-continued
490
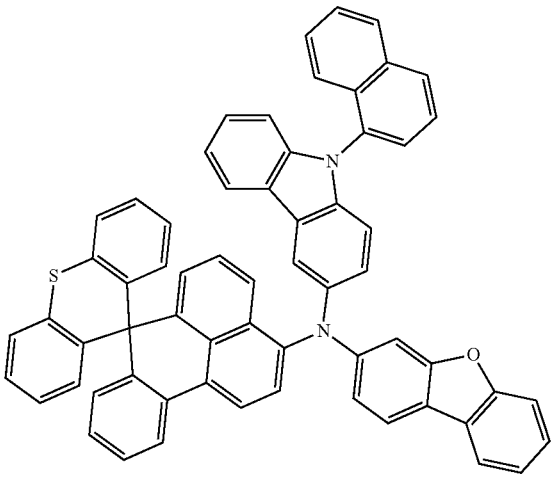
491
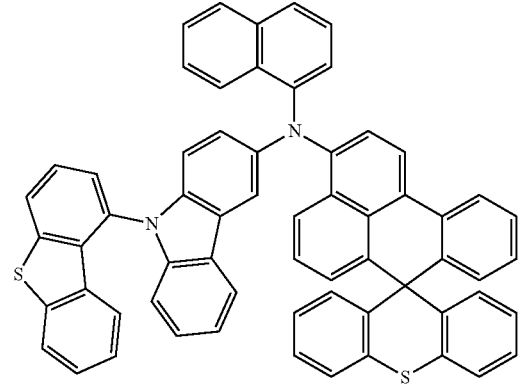
492
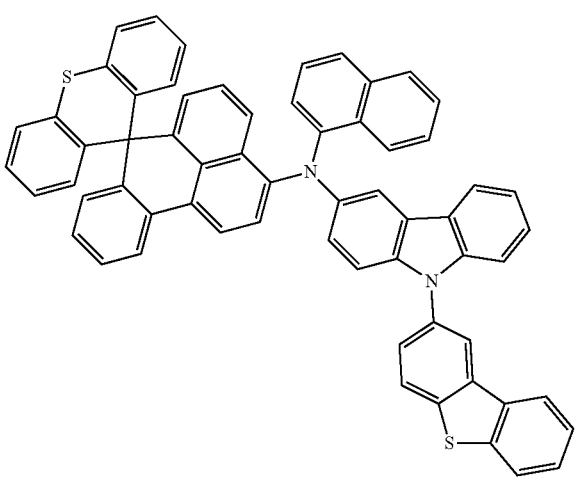

711
-continued
493
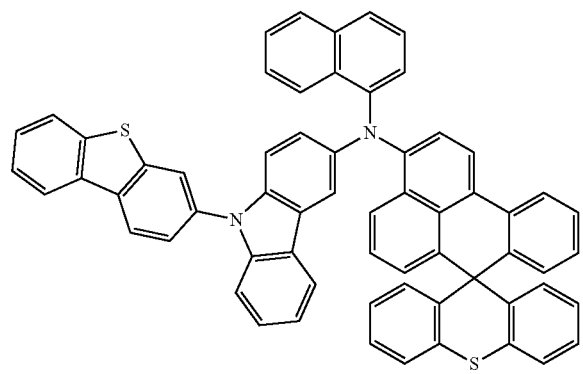
494
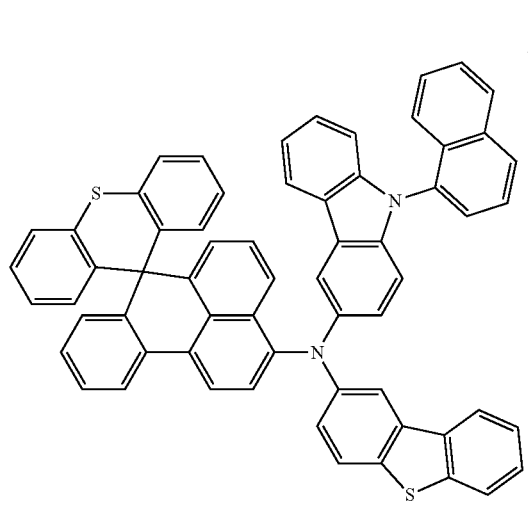
495
712
-continued
496
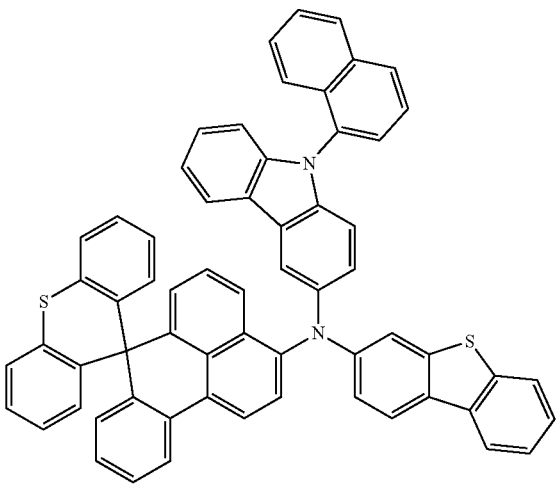
500
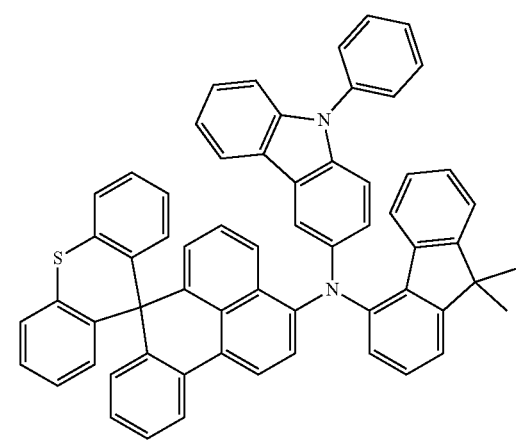
501
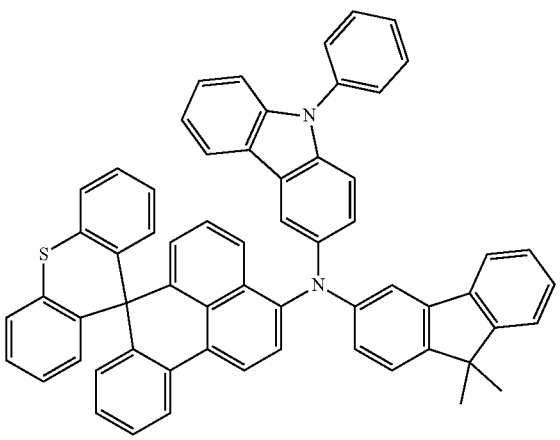

713
-continued
502
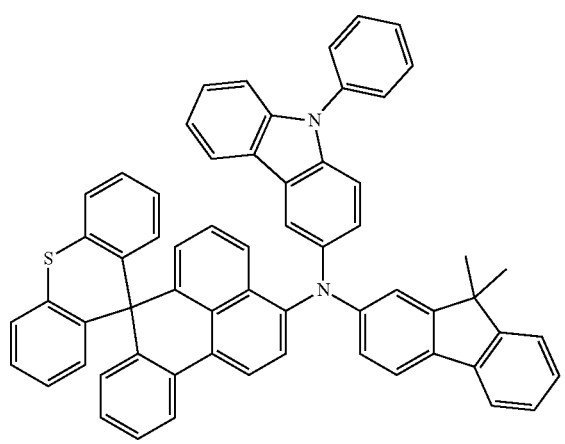
510
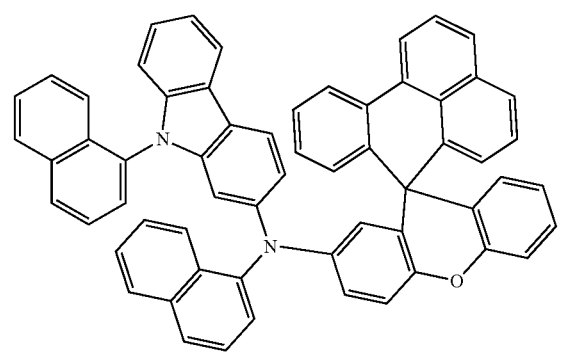
511
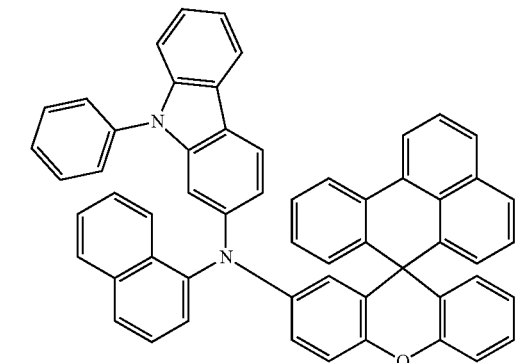
513
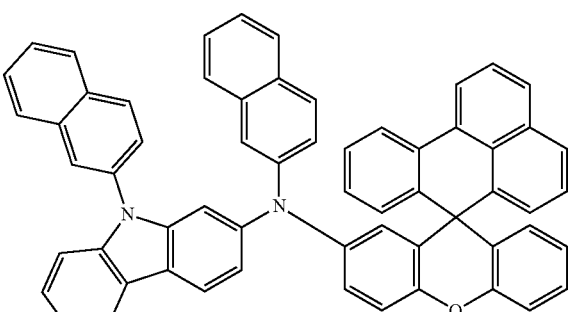
714
-continued
514
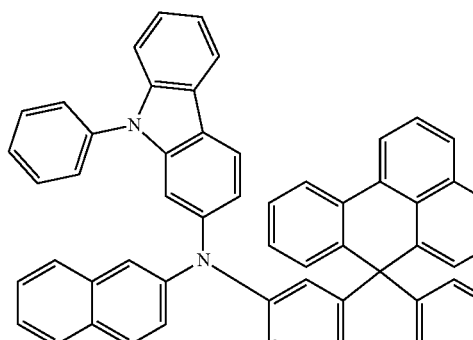
518
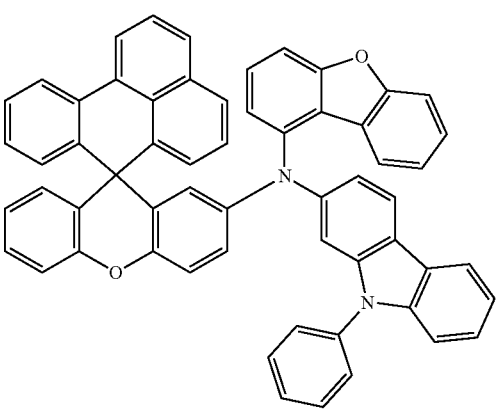
519
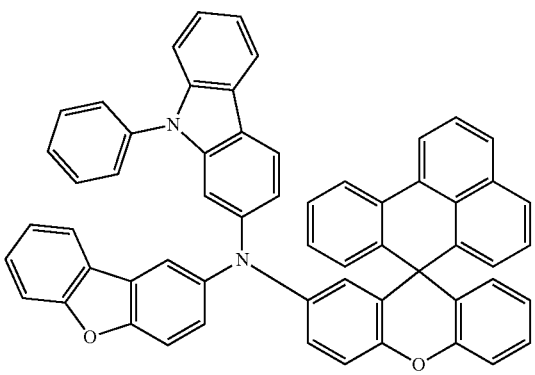
520
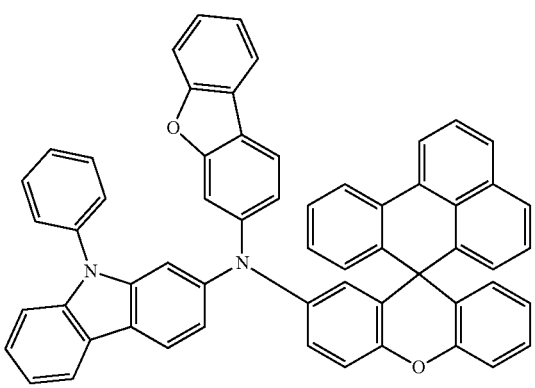

521
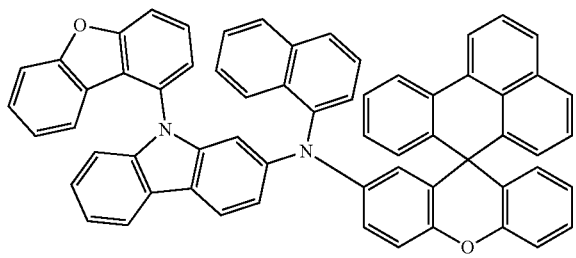
522
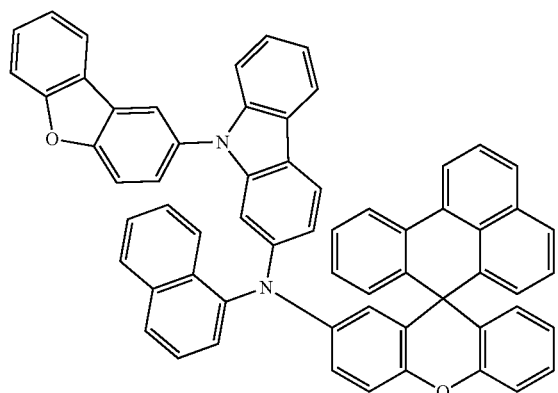
523
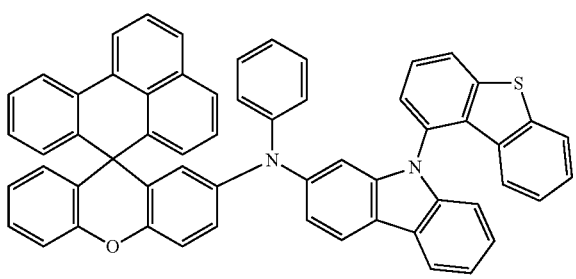
526
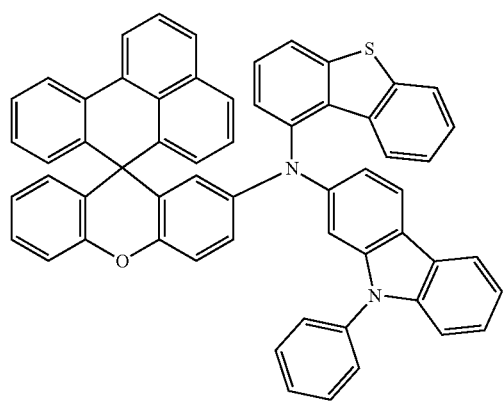
527
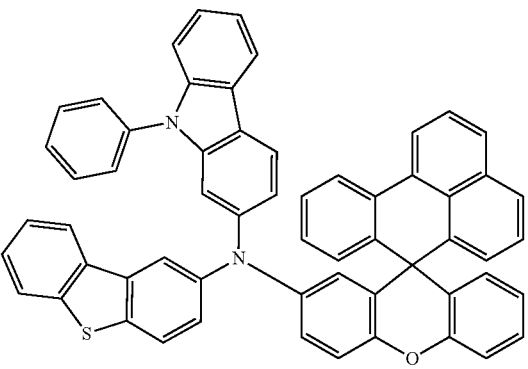
528
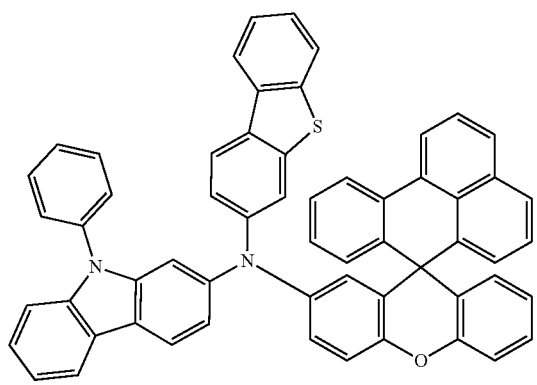
529
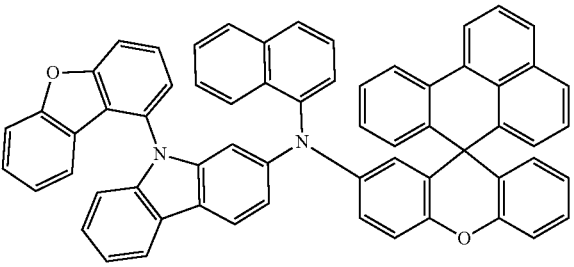
530
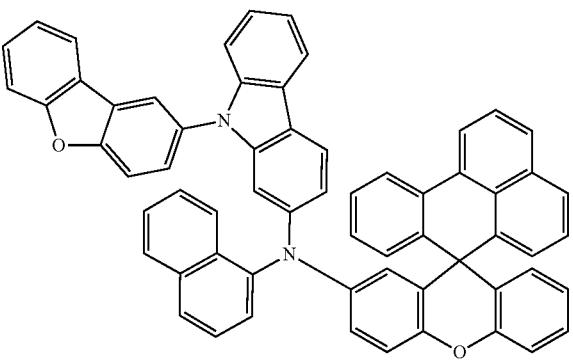

-continued
531
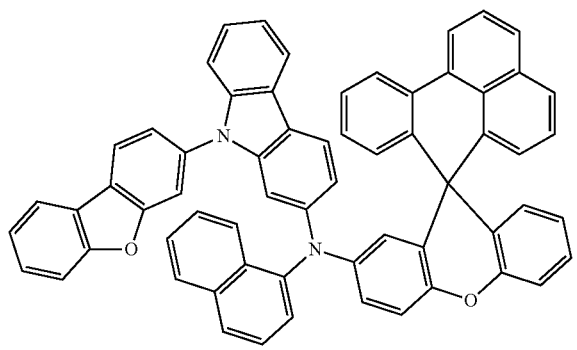
535
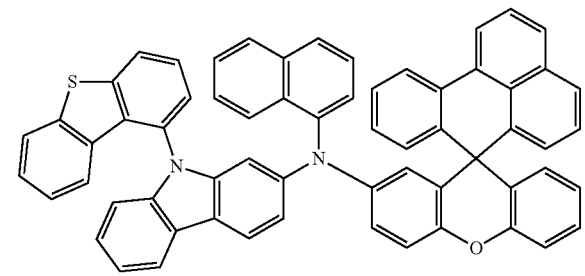
532
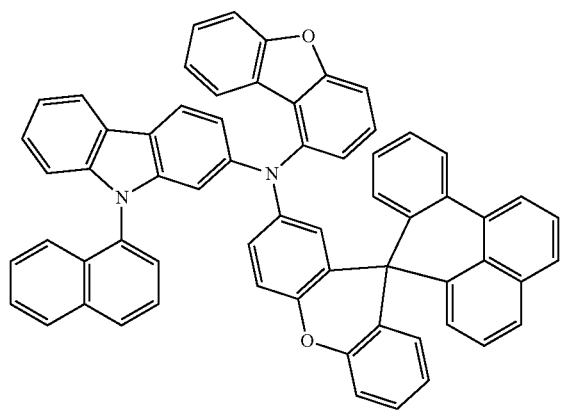
536
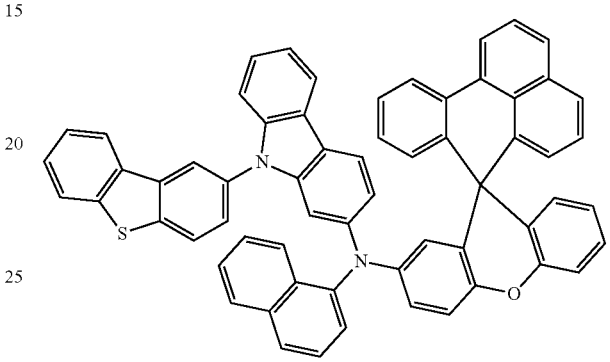
533
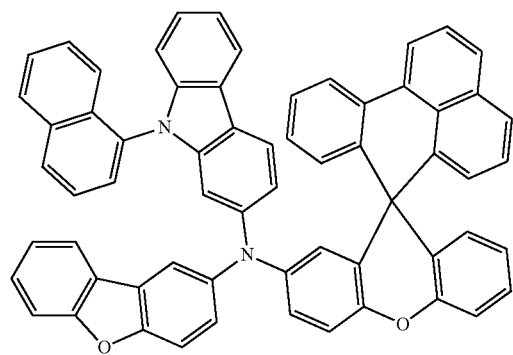
537
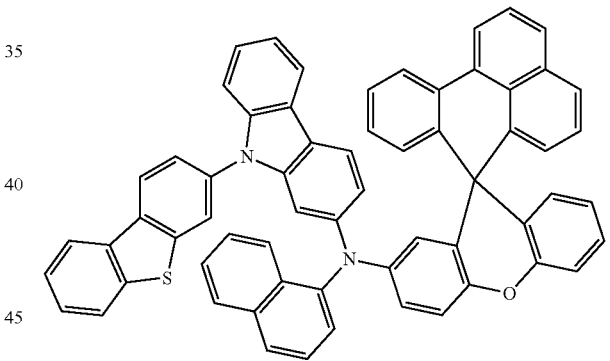
534
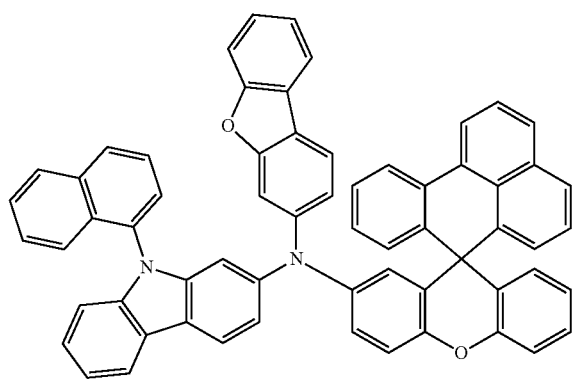
538
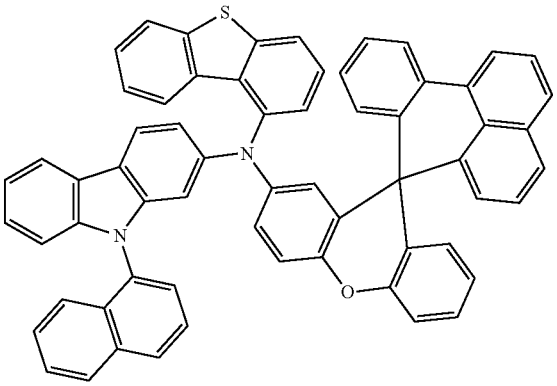

719
-continued
539
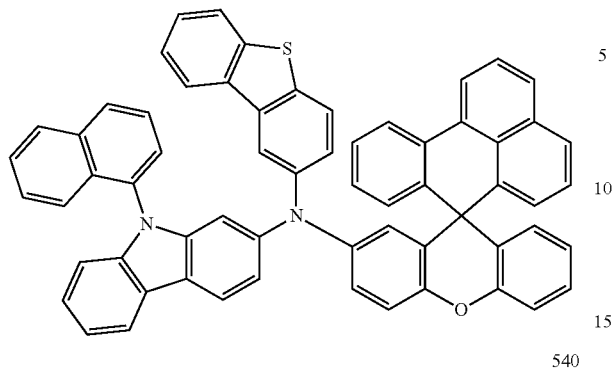
540
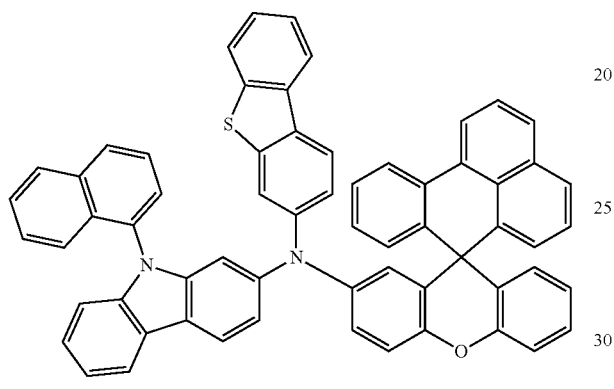
544
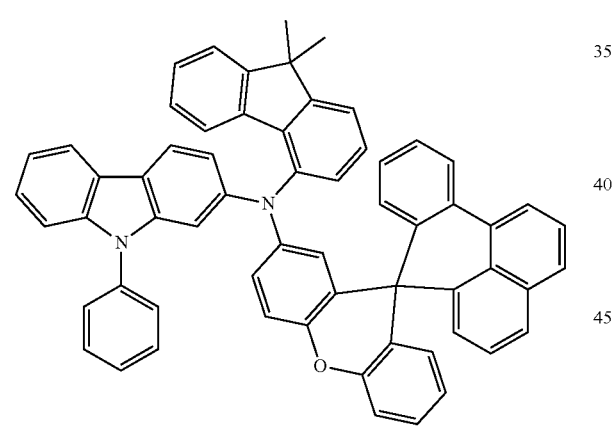
545
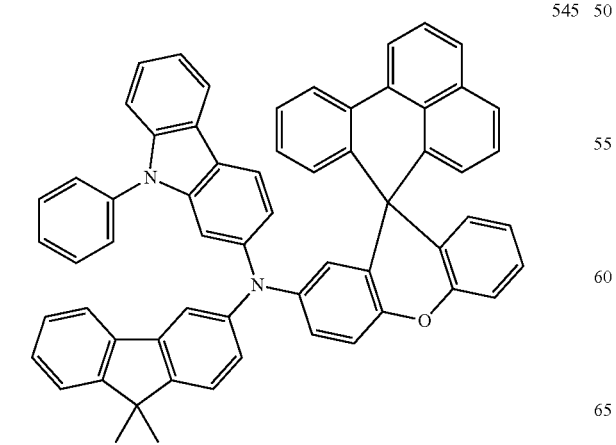
720
-continued
546
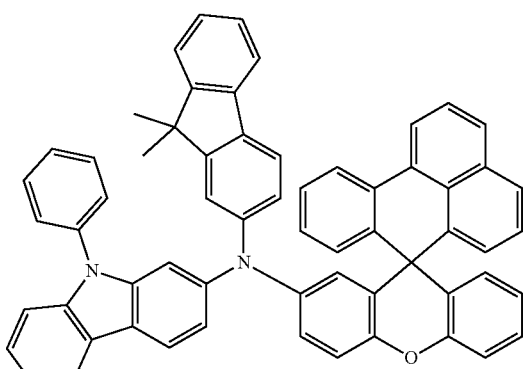
554
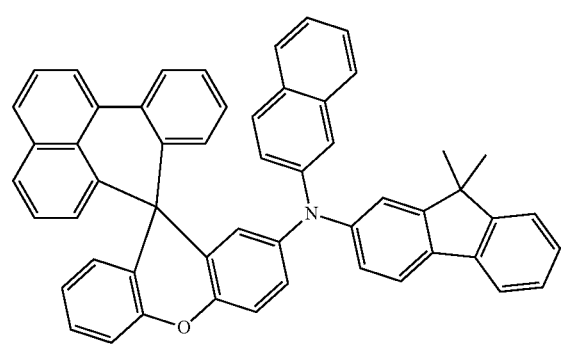
555
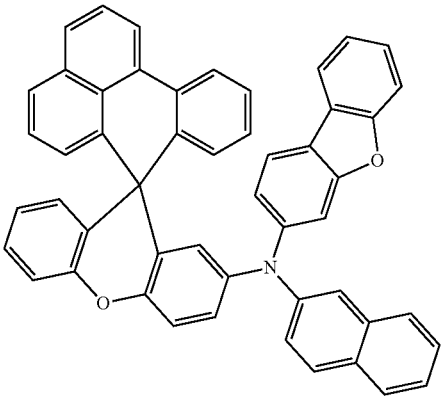
556
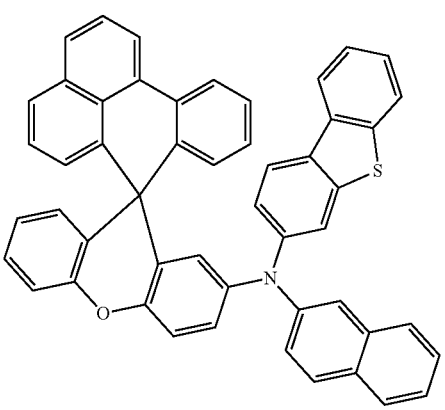

557
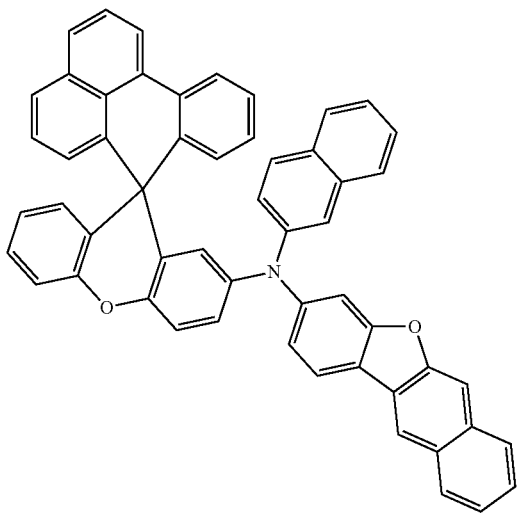
558
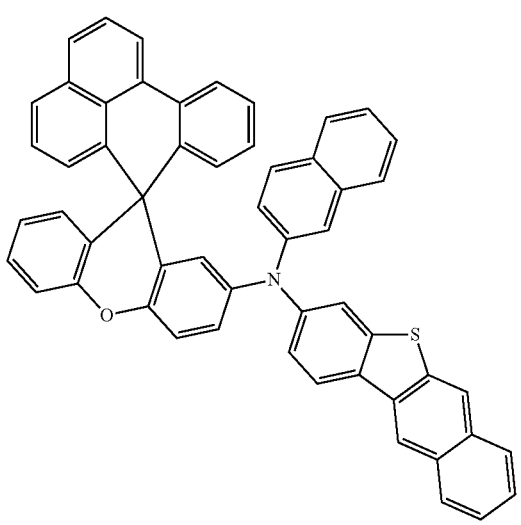
559
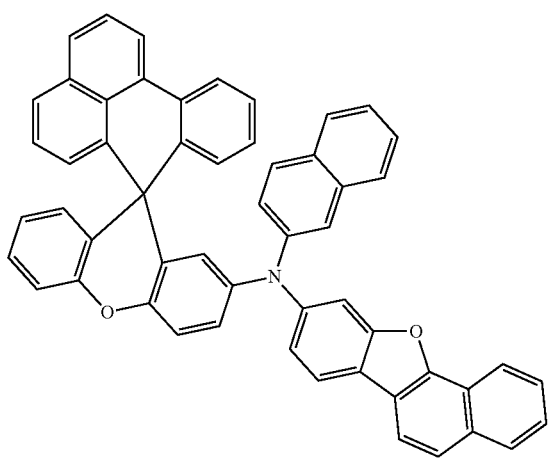
560
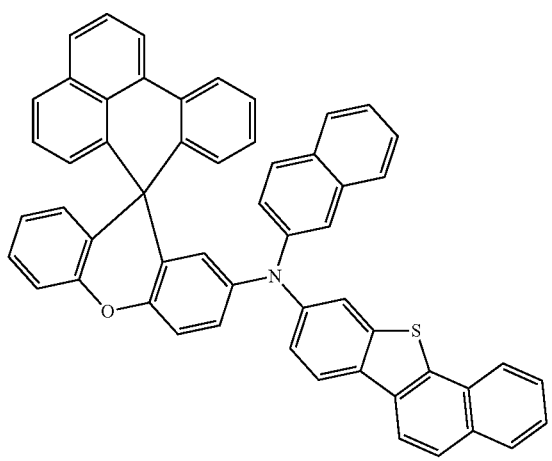
561
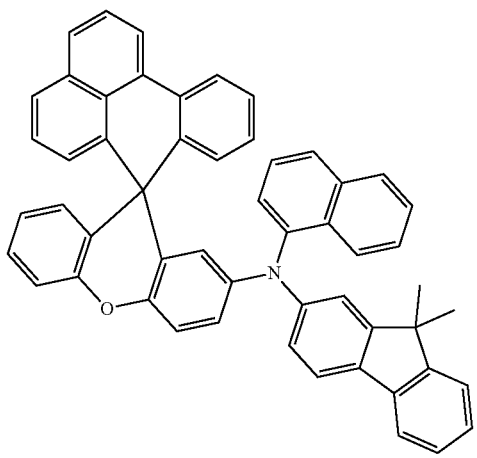
562
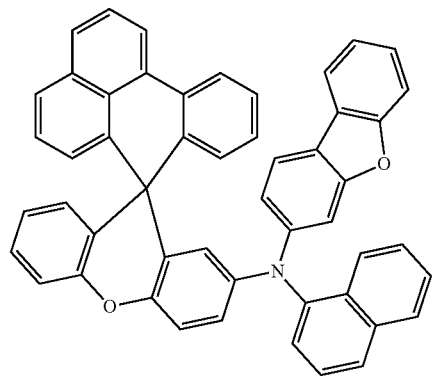

723
-continued
563
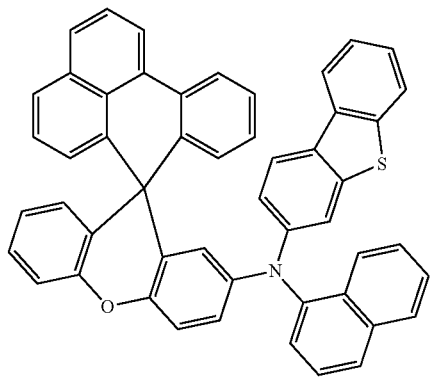
564
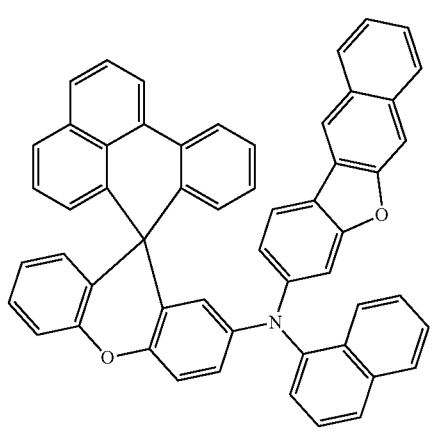
565
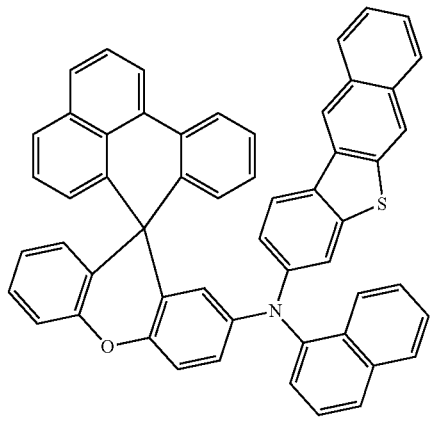
724
-continued
566
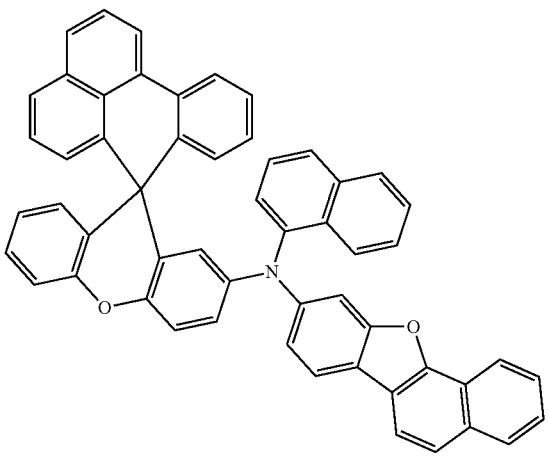
567
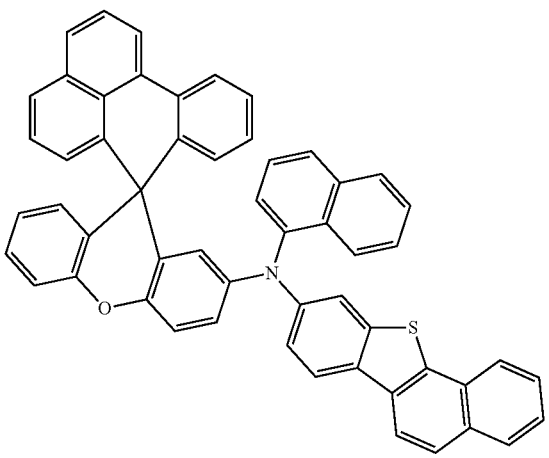
572
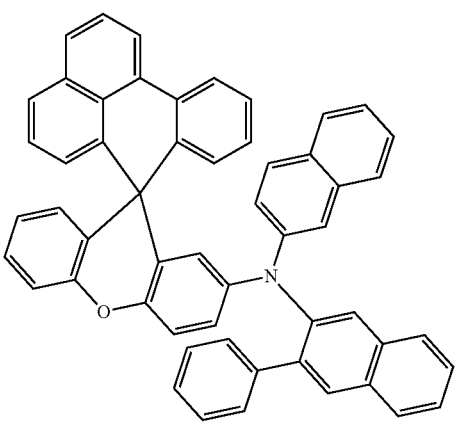

725
-continued
726
-continued
573
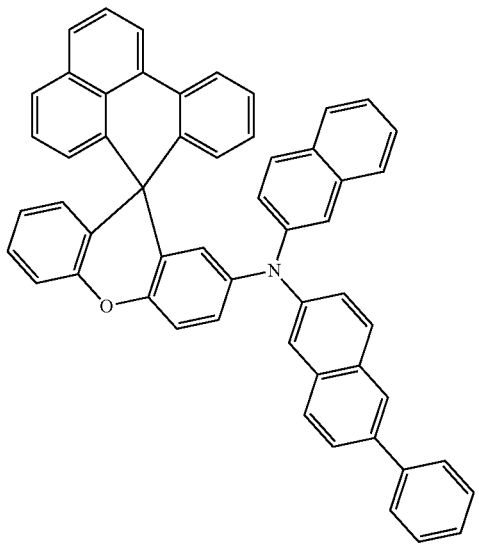
576
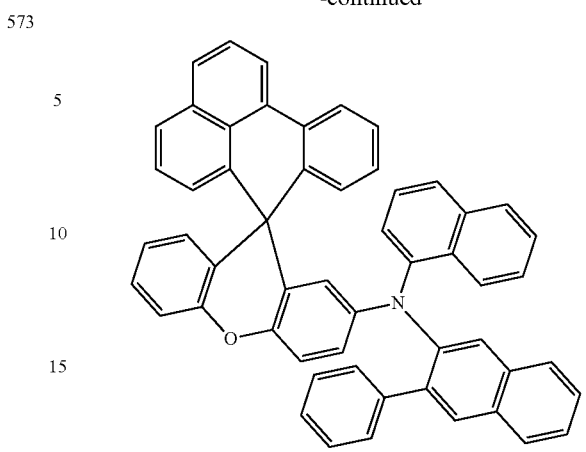
574
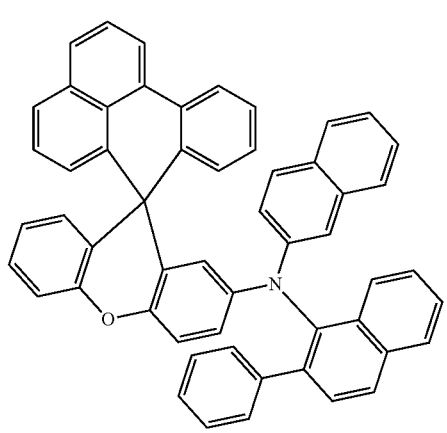
577
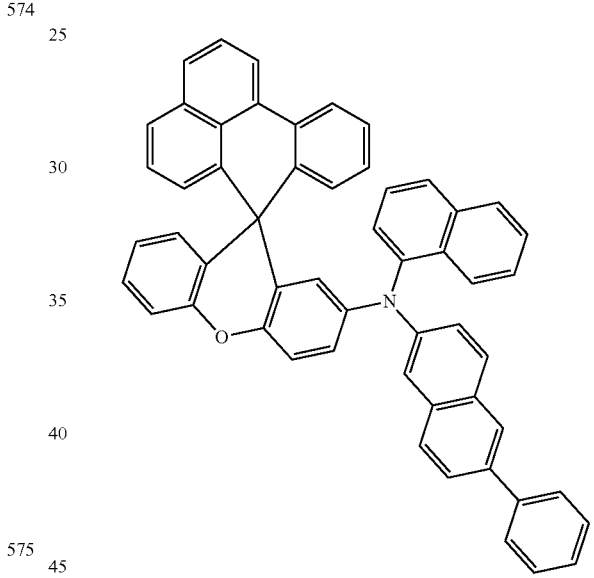
575
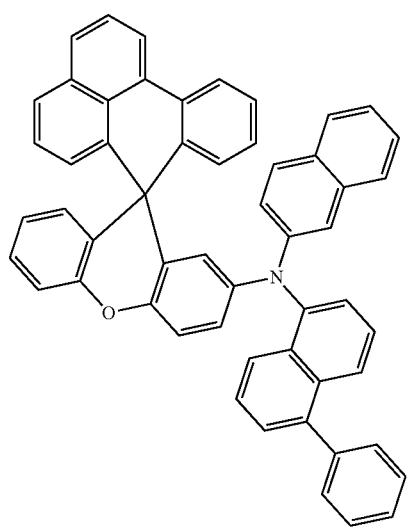
578
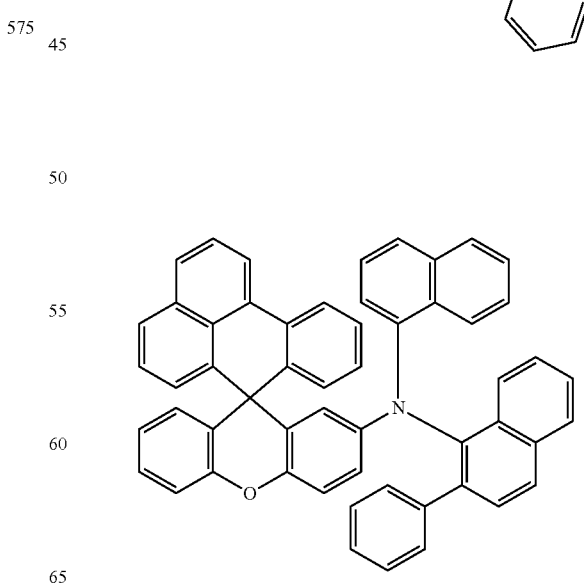

727
-continued
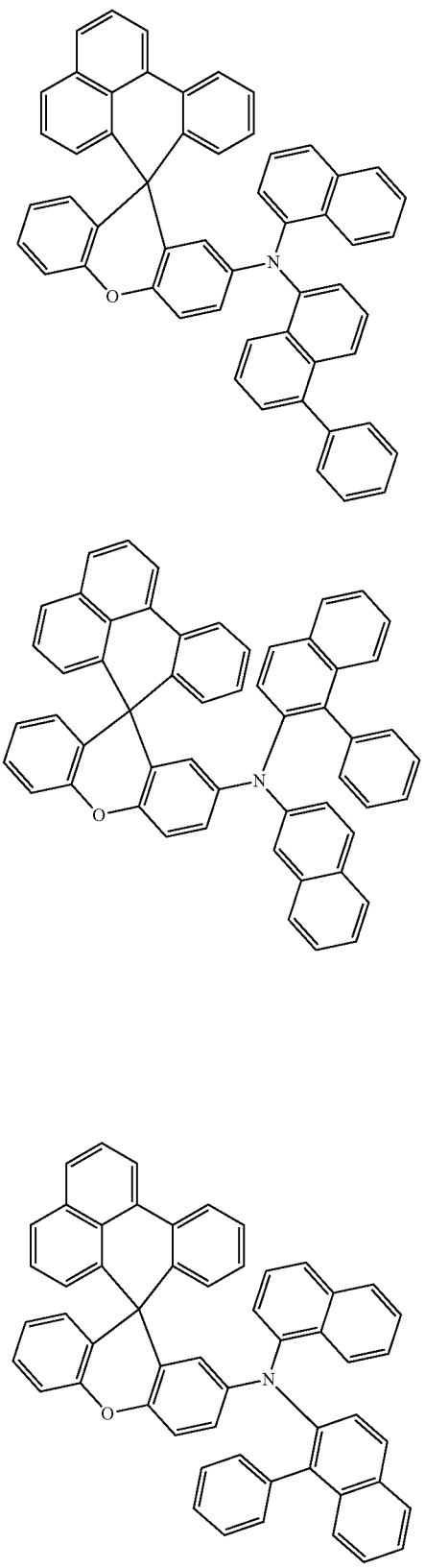
728
-continued
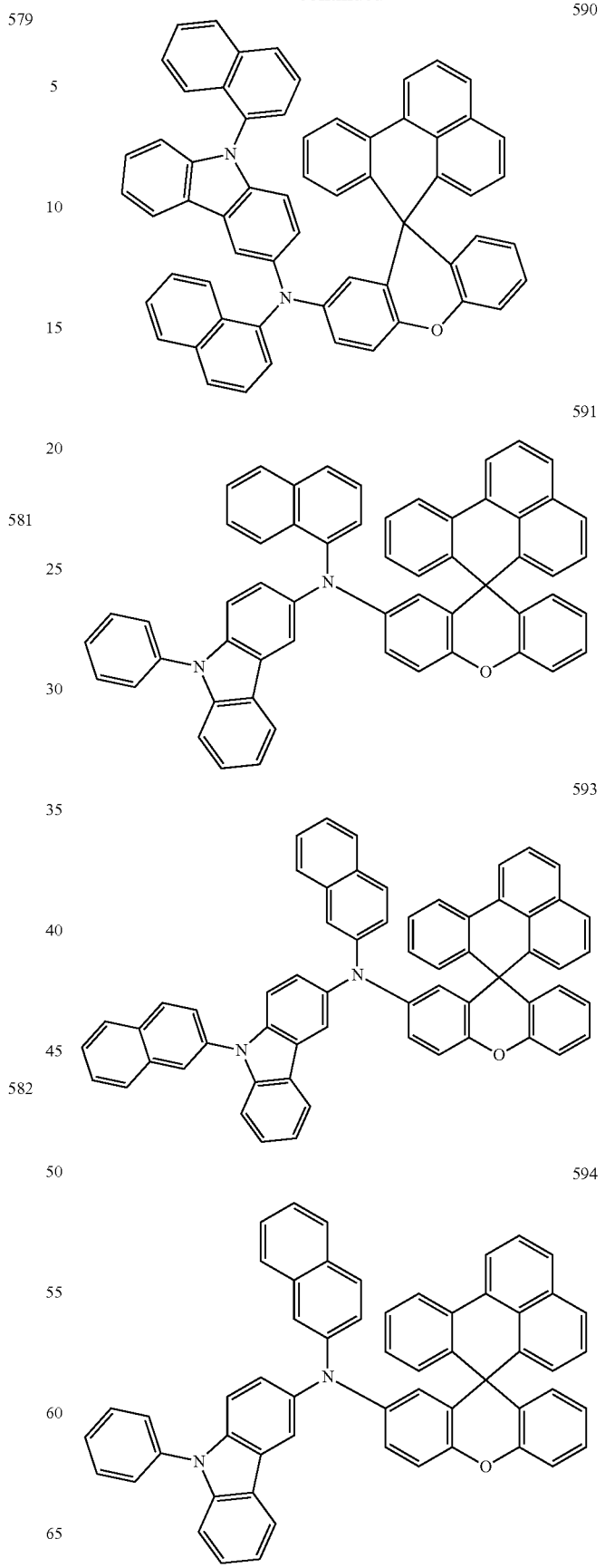

-continued
598
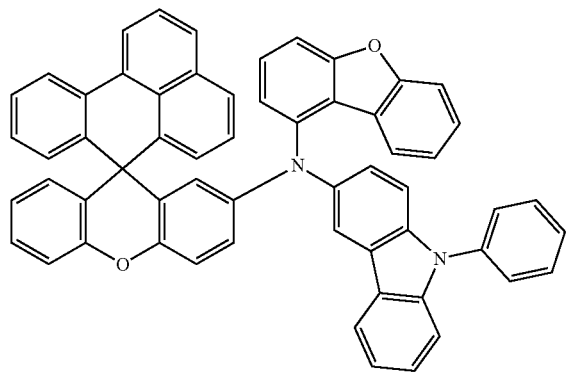
599
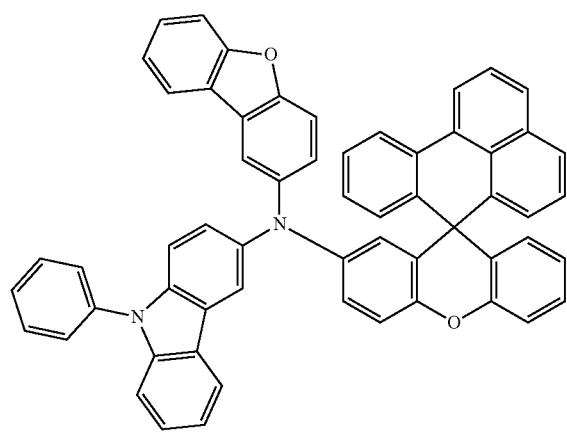
600
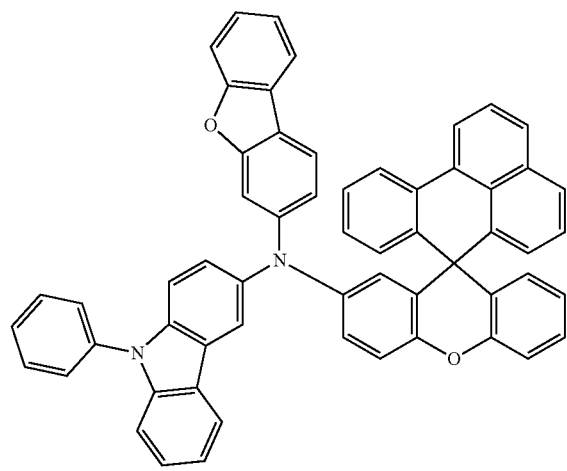
-continued
606
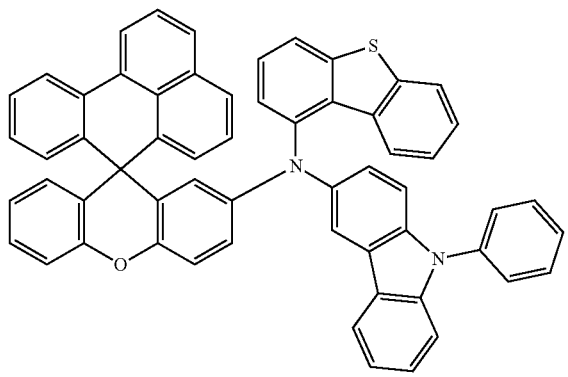
607
608
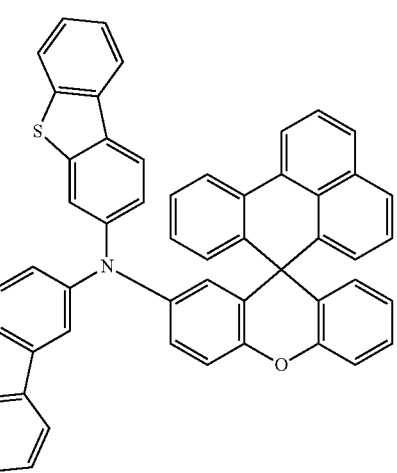

731
-continued
732
-continued
609
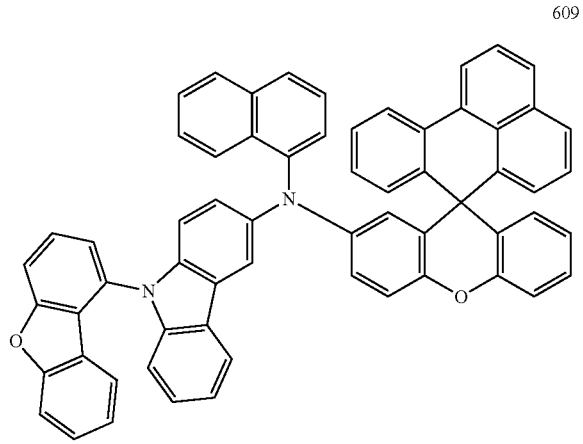
613
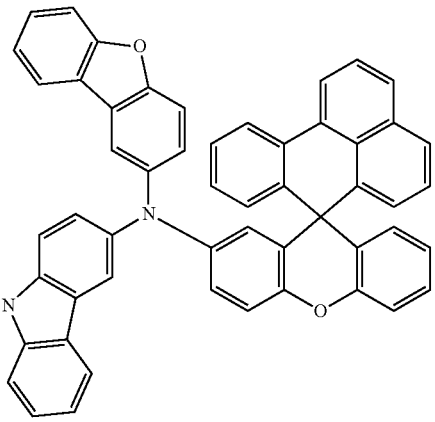
610
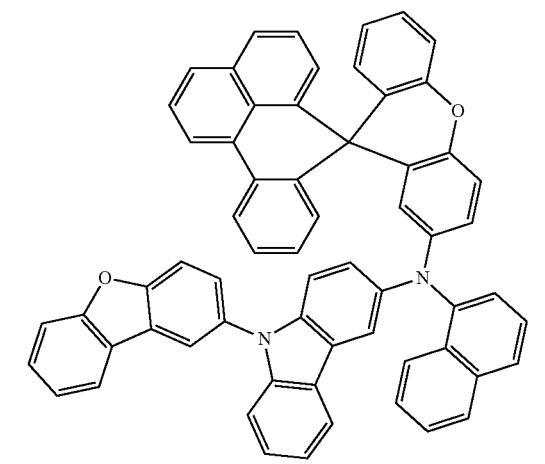
611
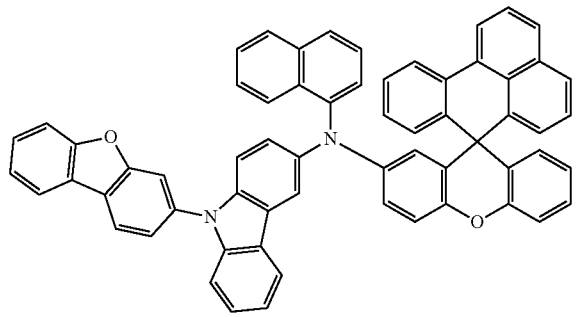
614
612
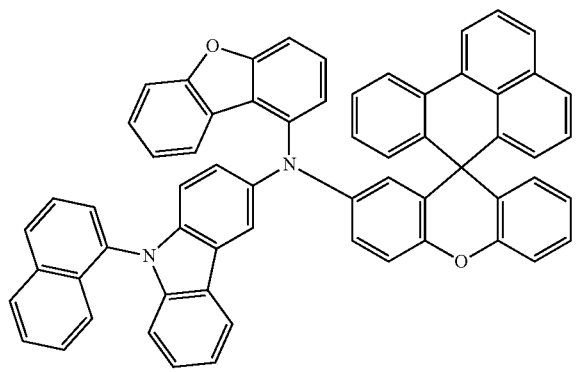
615

616
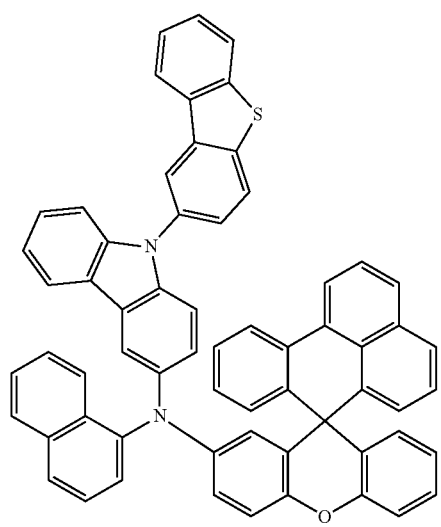
619
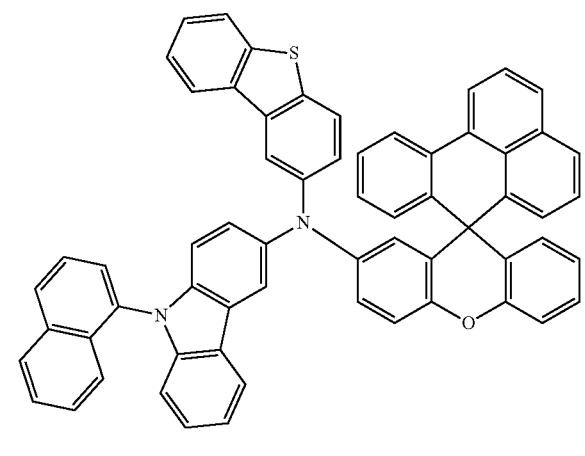
617
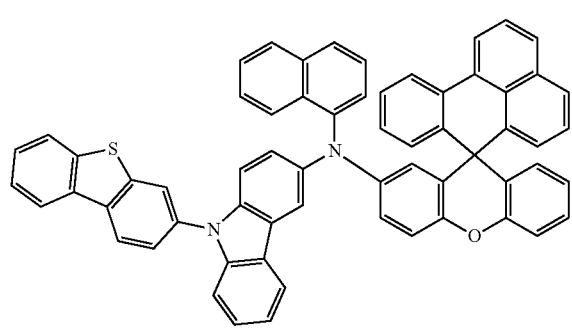
620
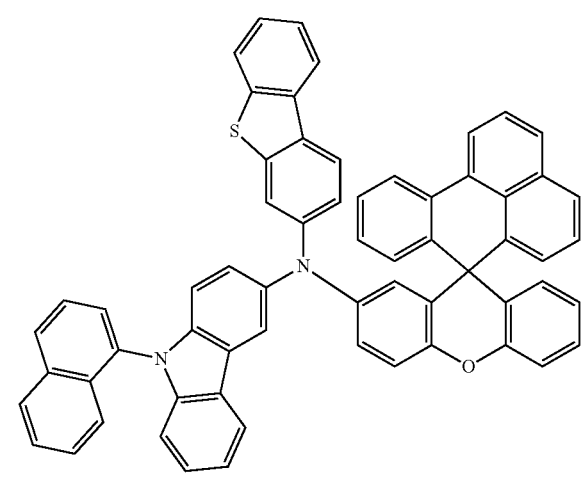
618
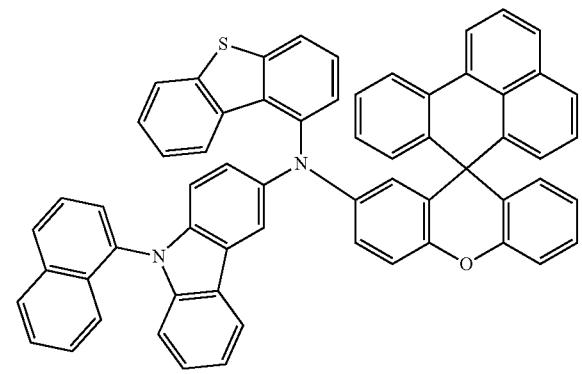
624
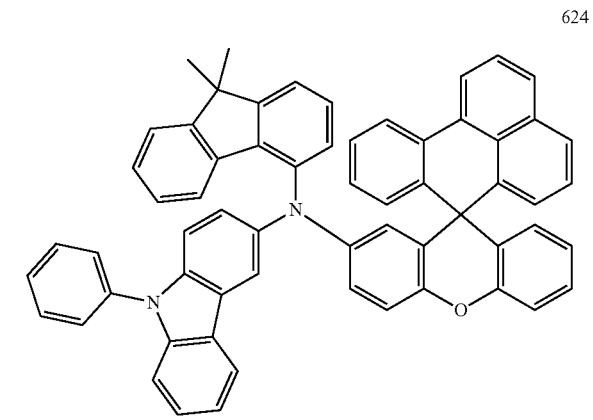

735
-continued
625
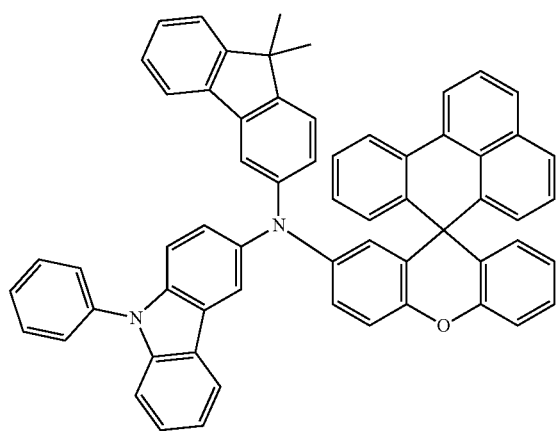
626
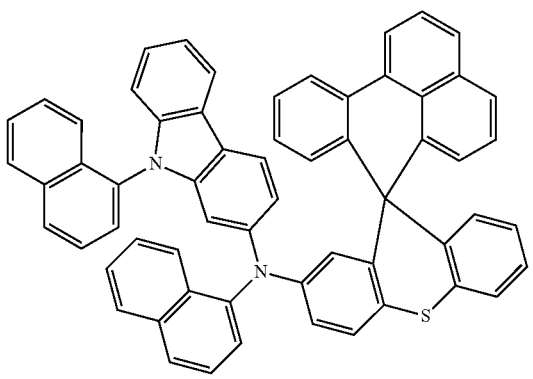
634
736
-continued
635
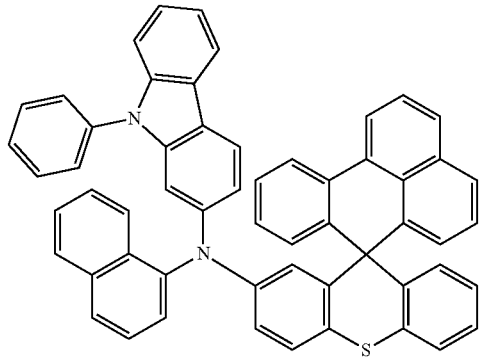
637
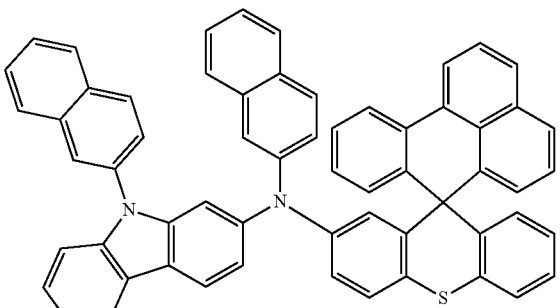
638
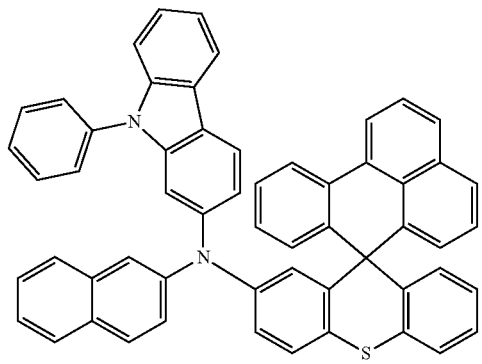
642

643
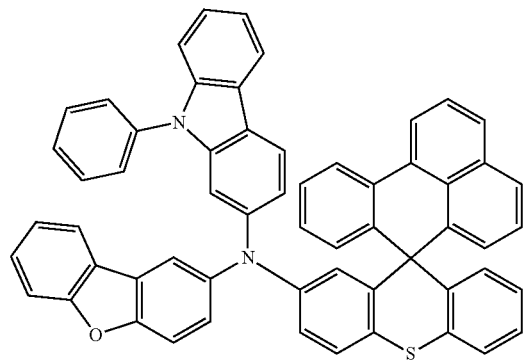
644
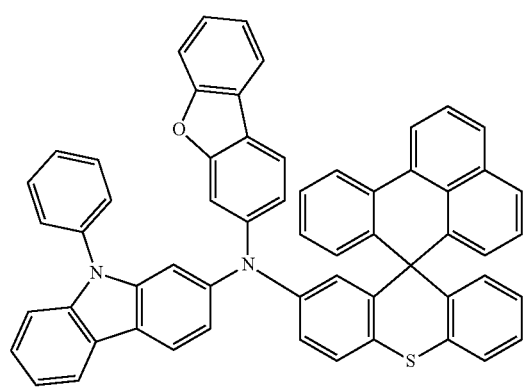
650
651
652
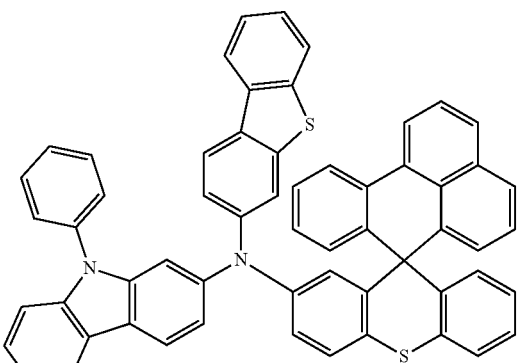
653
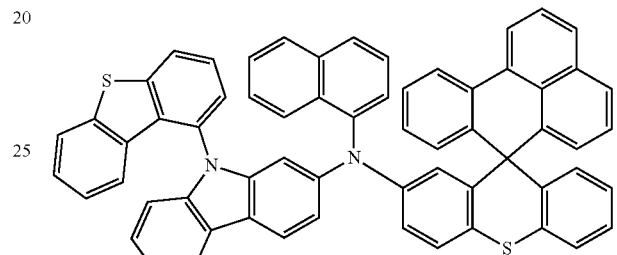
654
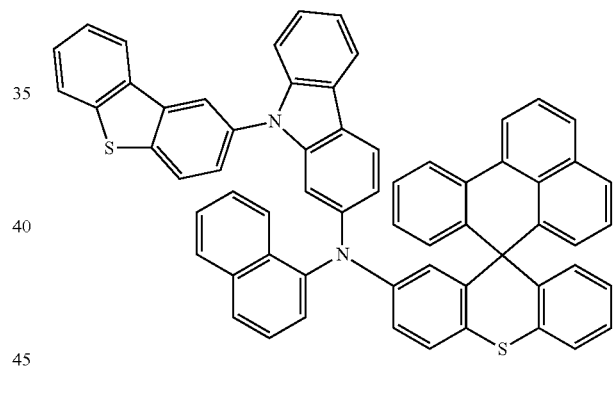
655
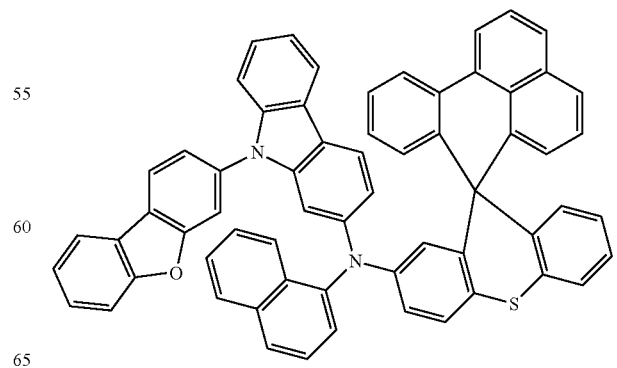

739
-continued
656
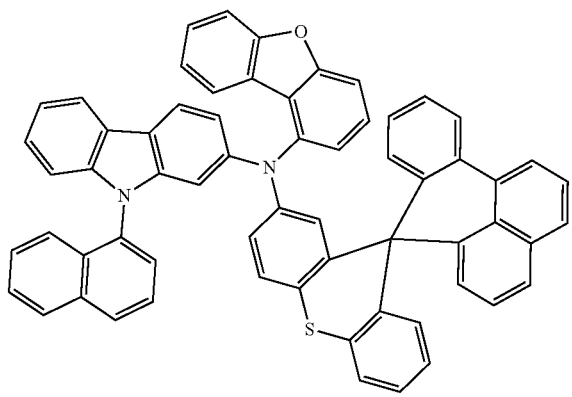
657
658
659
740
-continued
660
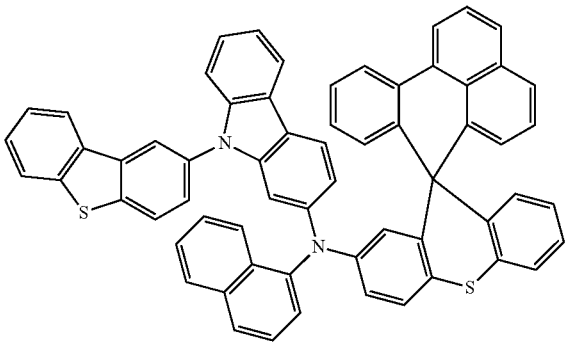
661
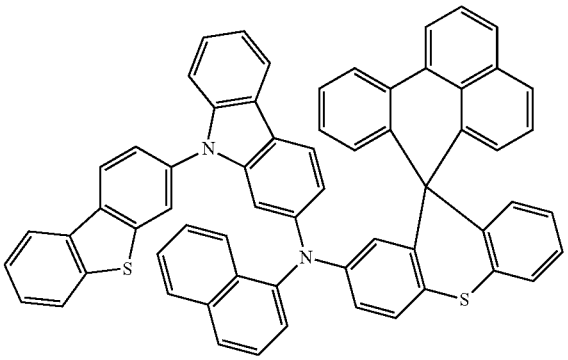
662
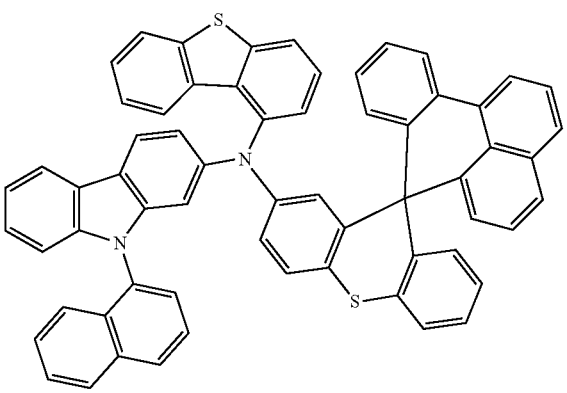
663
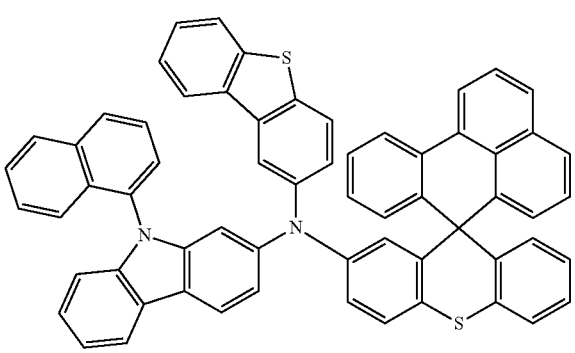

741
-continued
664
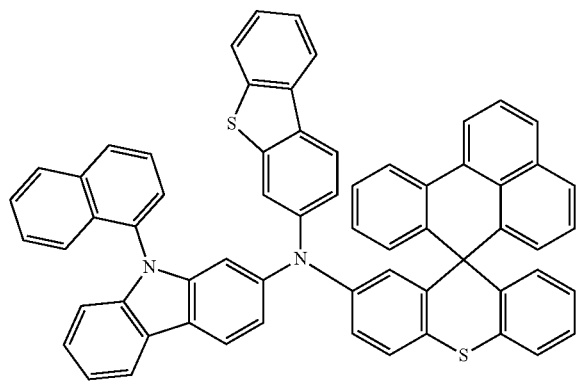
668
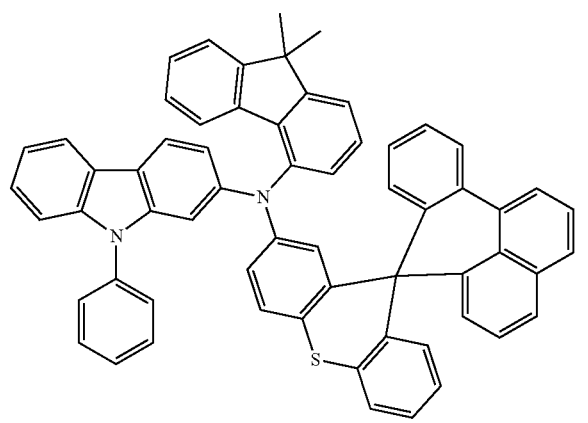
669
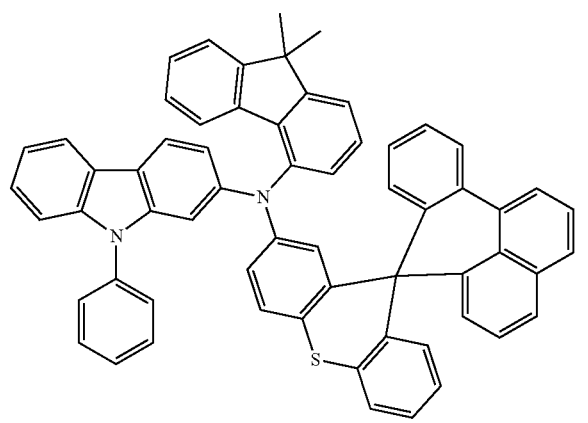
742
-continued
670
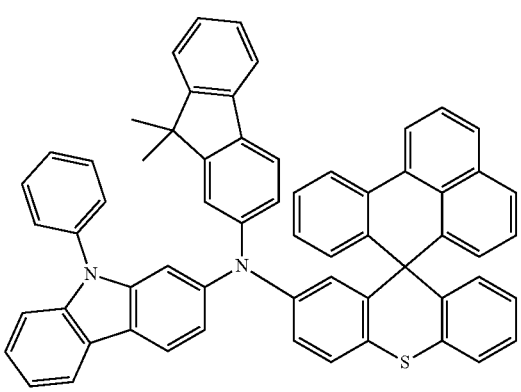
678
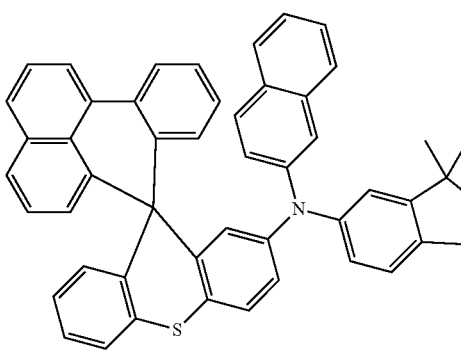
679
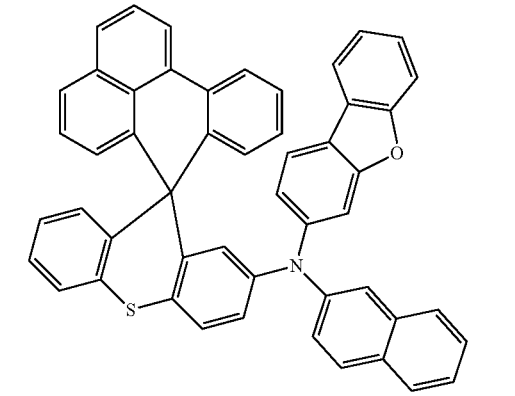
680
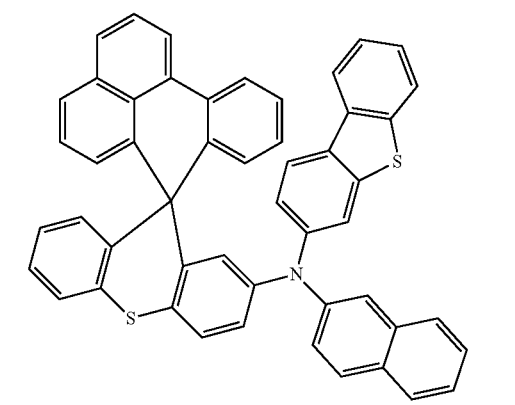

681
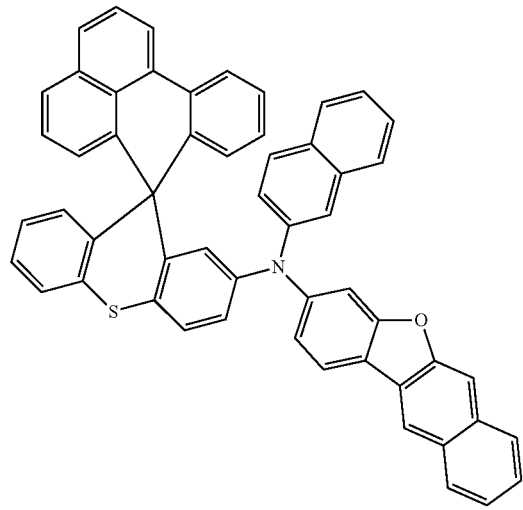
682
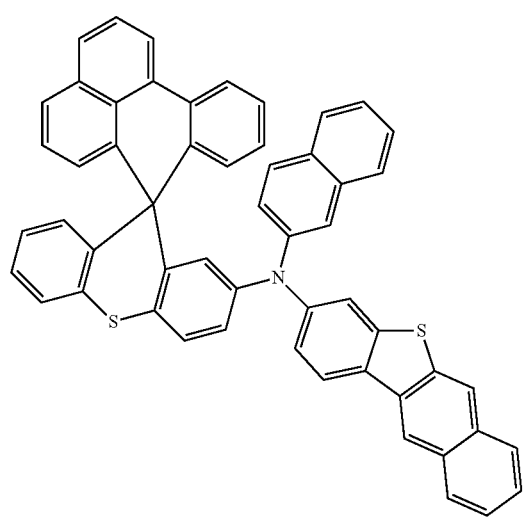
683
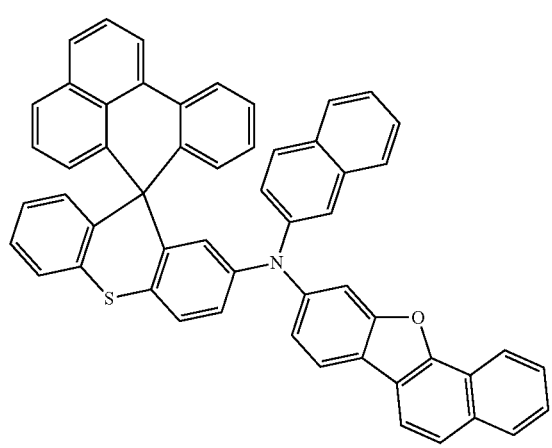
684
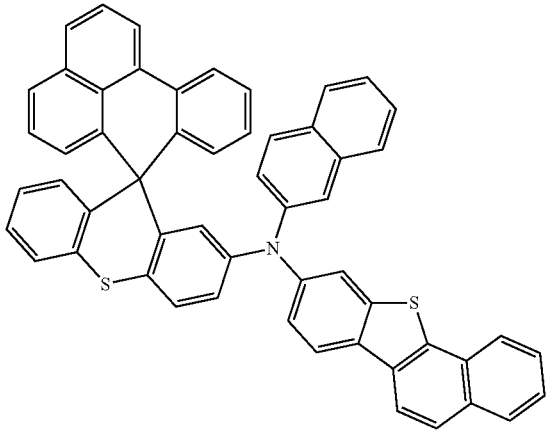
685
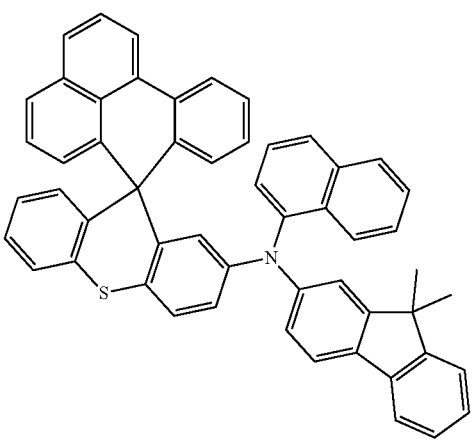
686
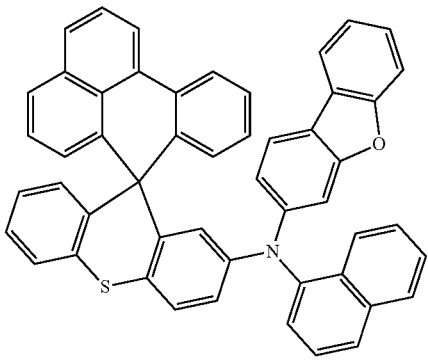
687
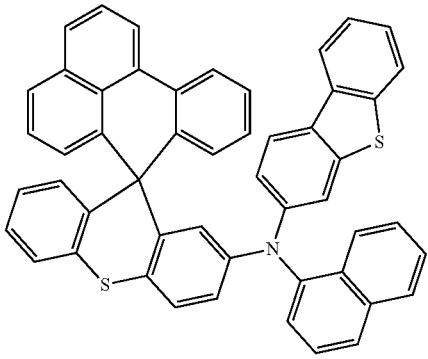

745
-continued
688
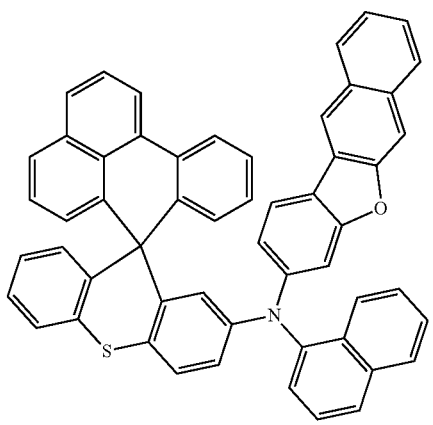
689
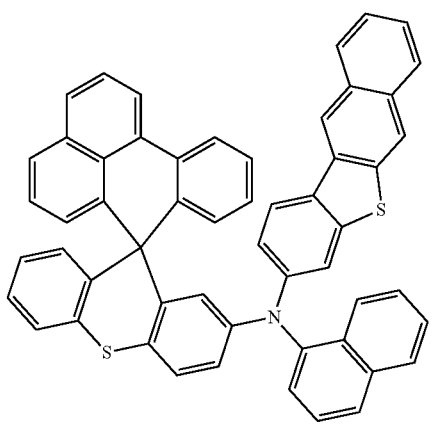
690
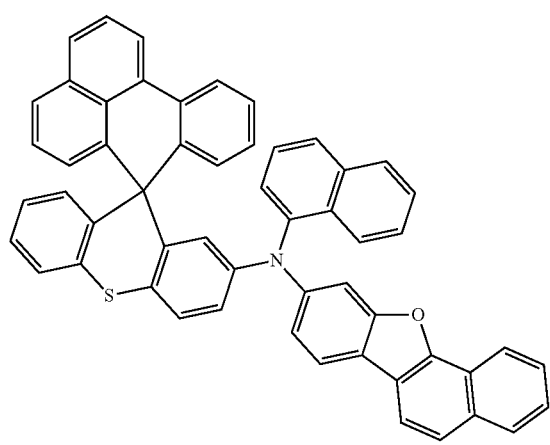
746
-continued
691
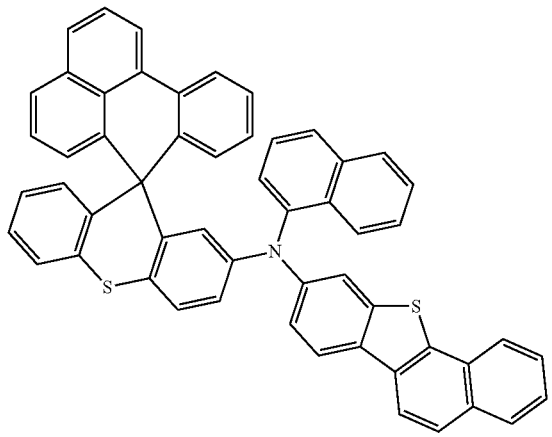
696
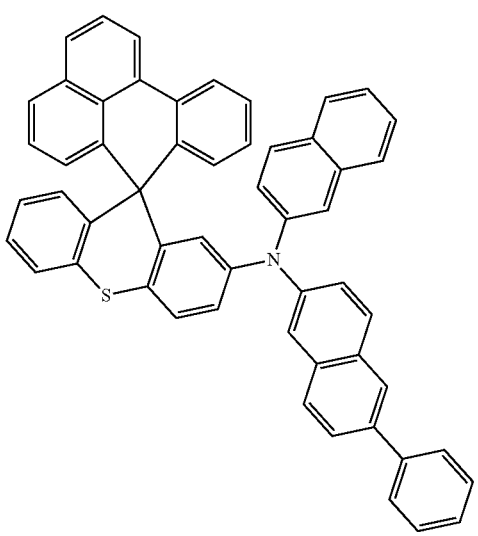
697

747
-continued
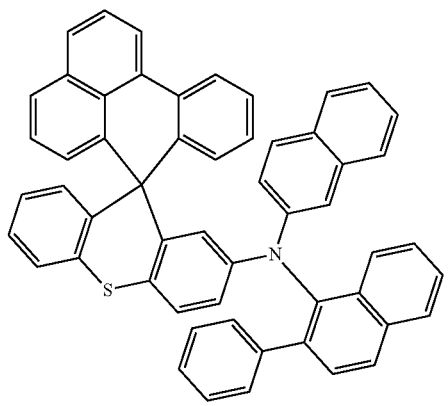
698
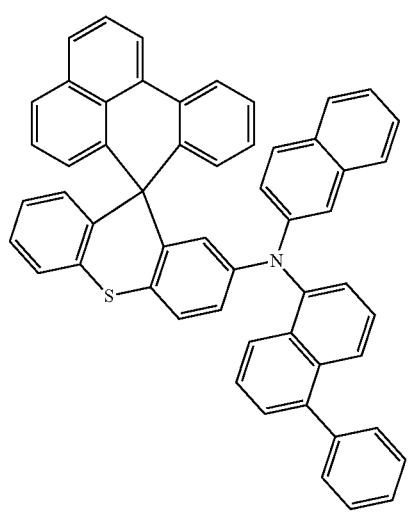
699
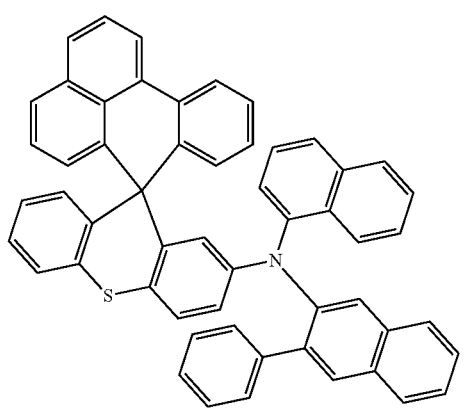
700
748
-continued
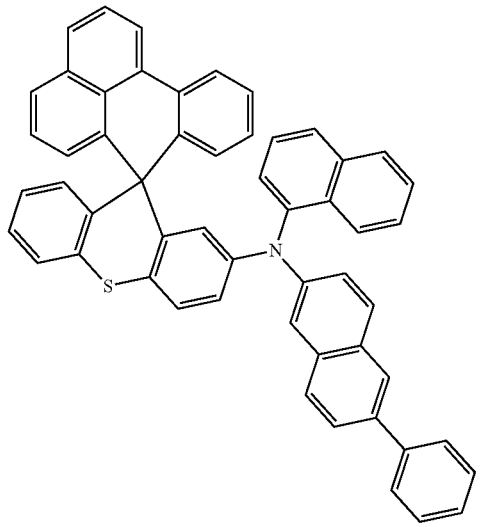
701
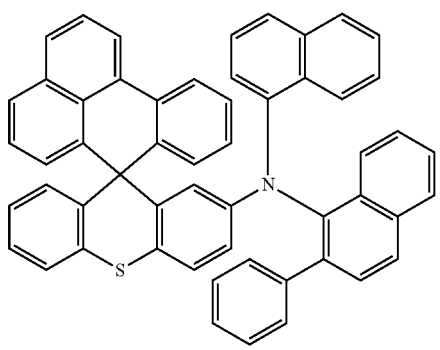
702
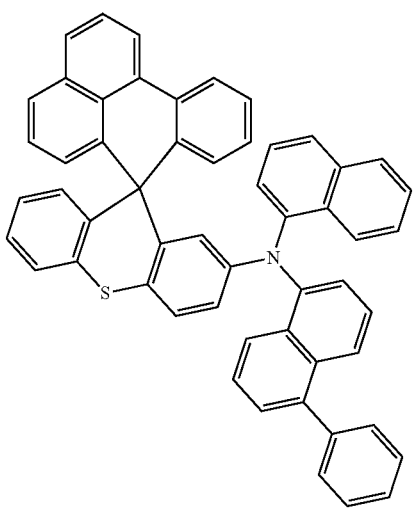
703

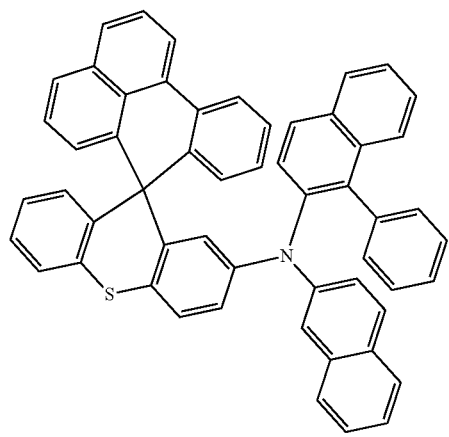
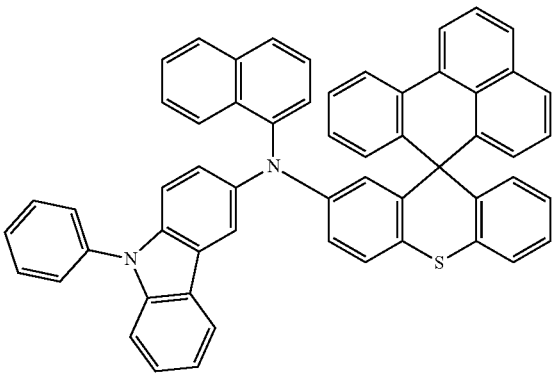
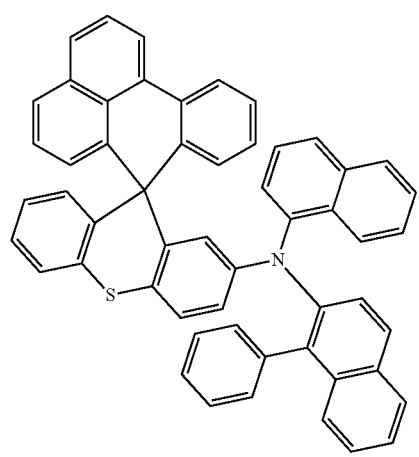
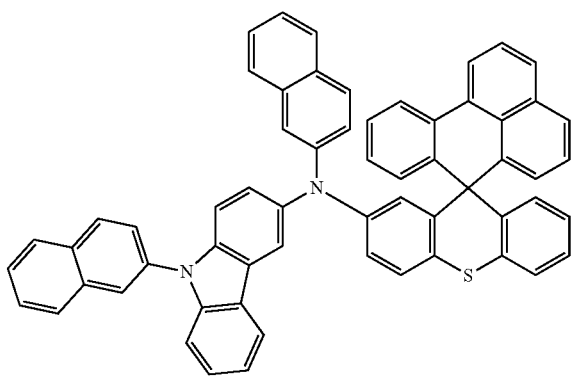
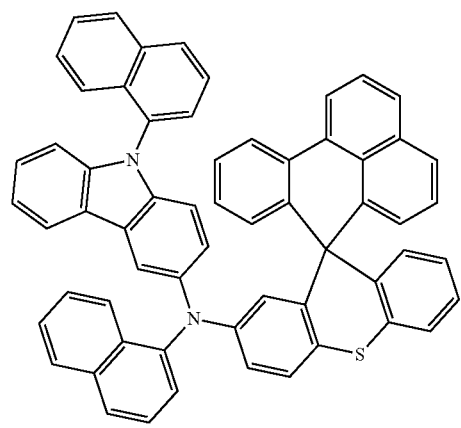
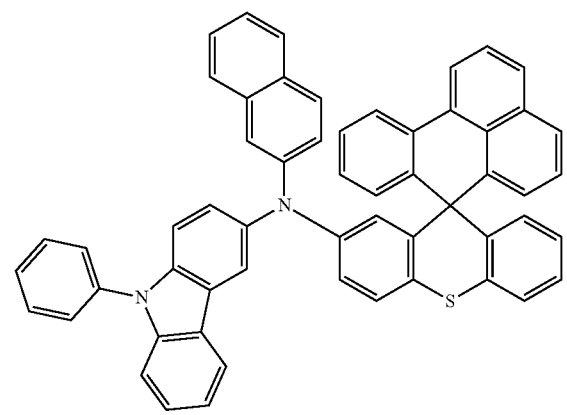
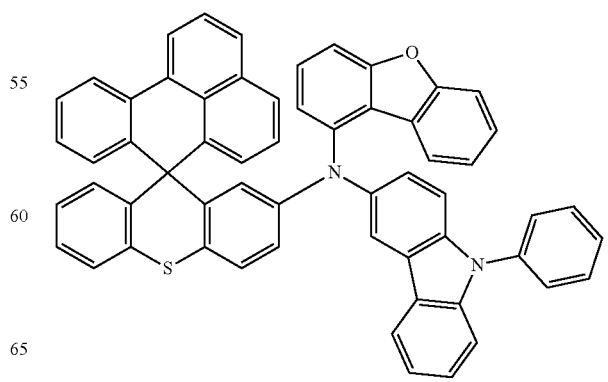

751
-continued
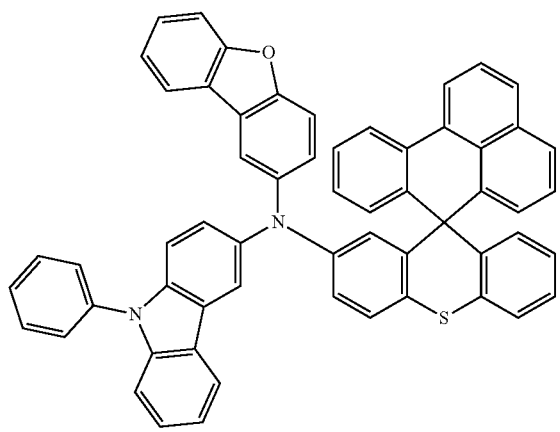
723
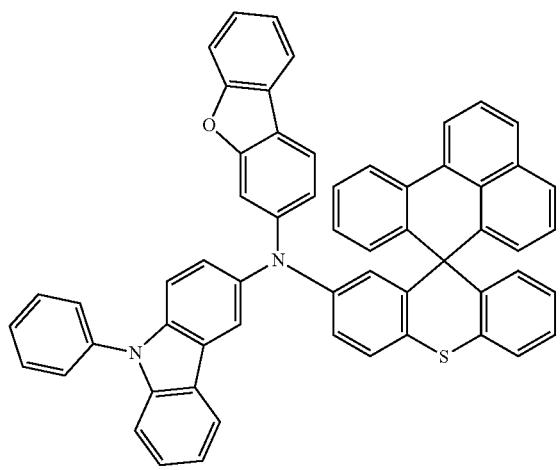
724
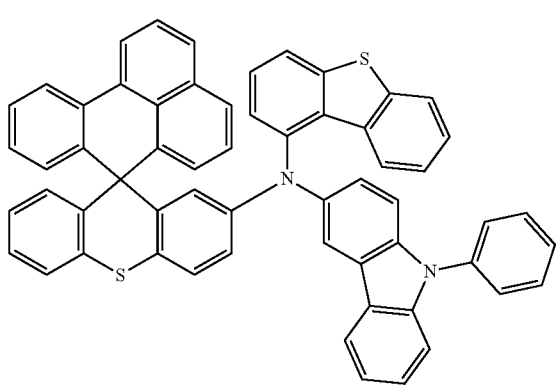
730
752
-continued
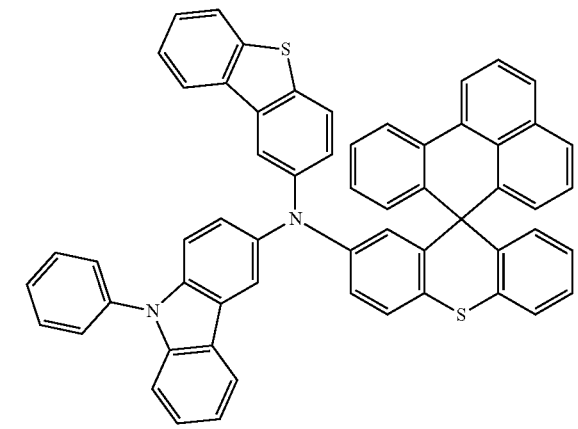
731
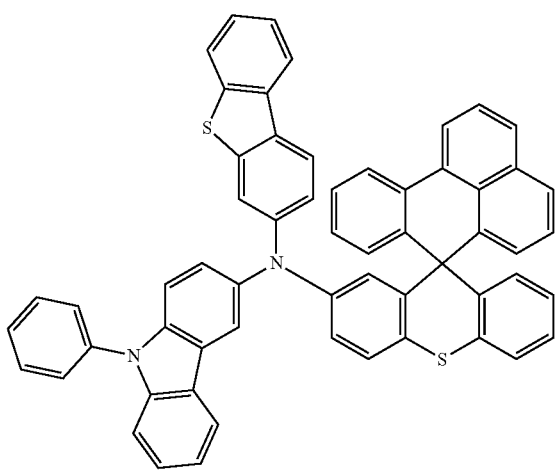
732
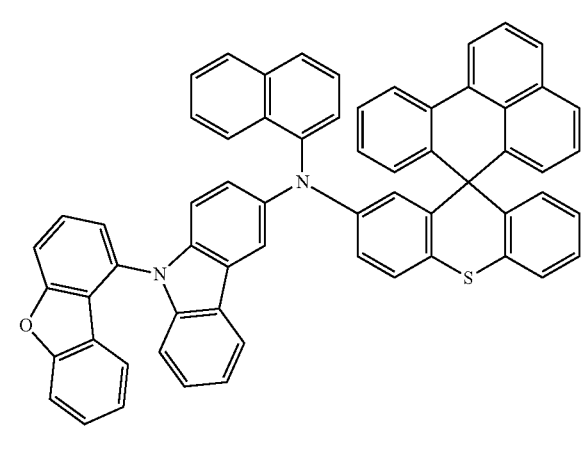
733

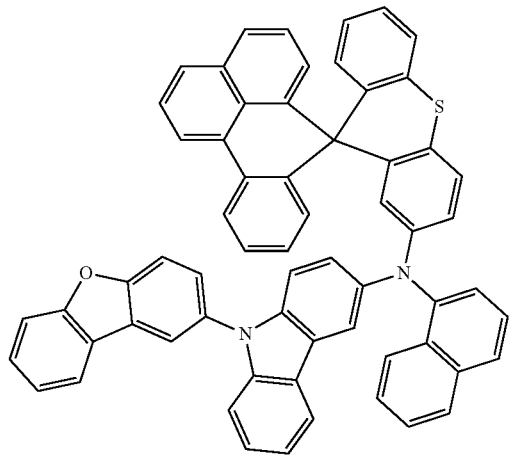
734
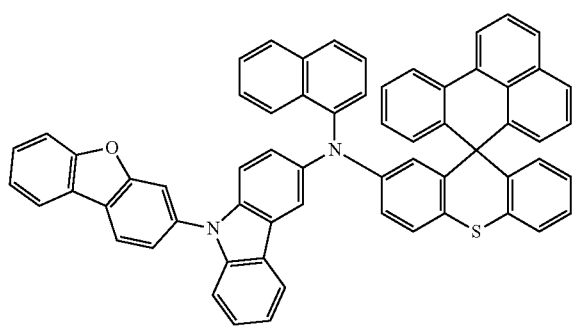
735
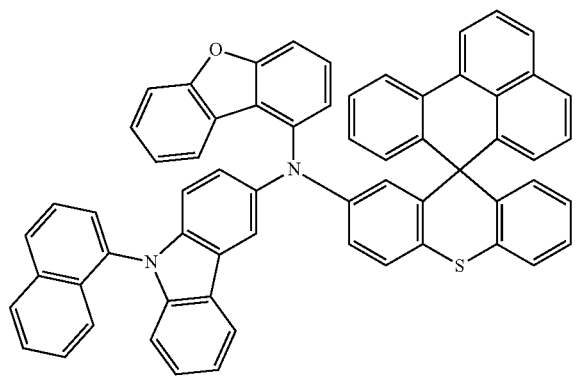
736
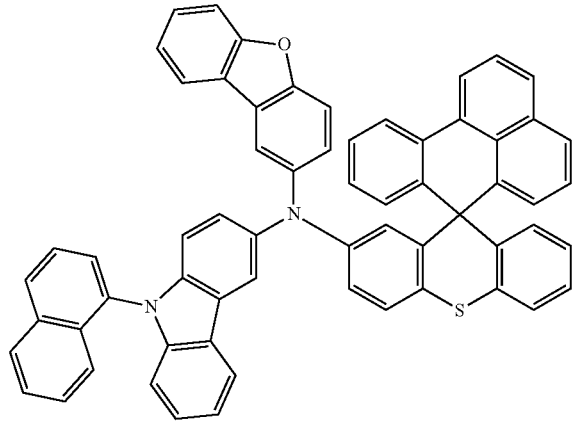
737
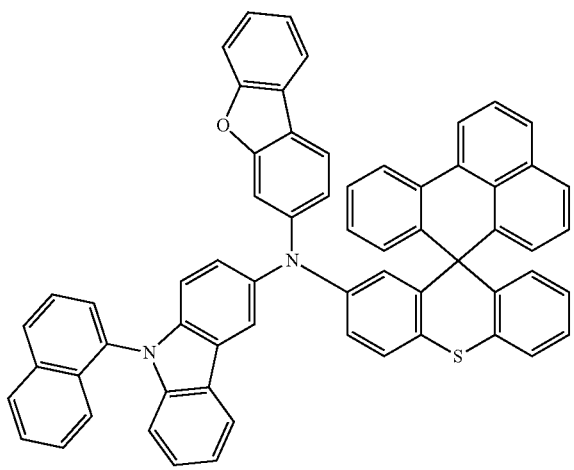
738
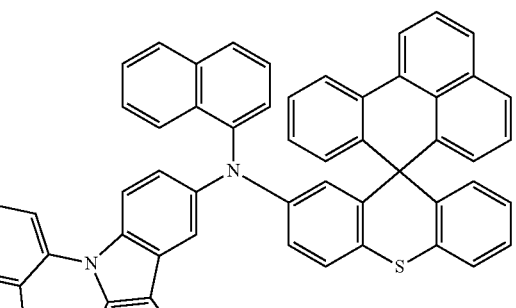
739
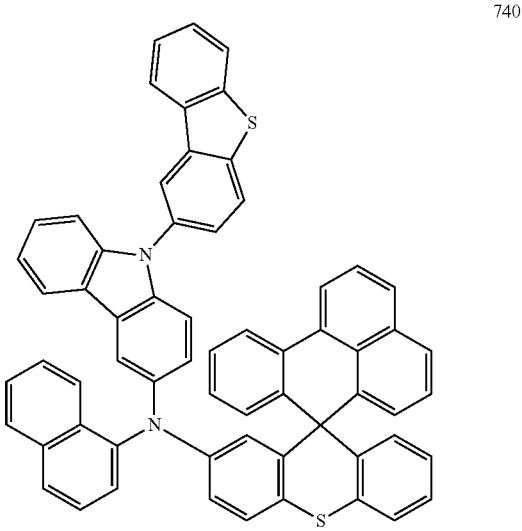
740

741
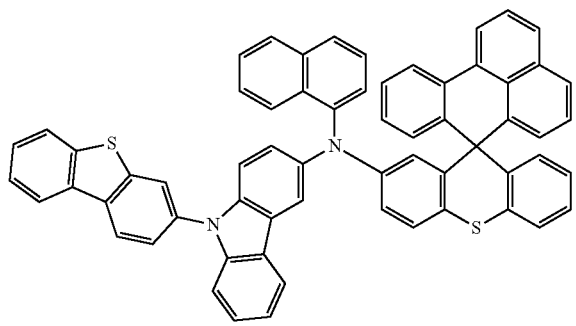
744
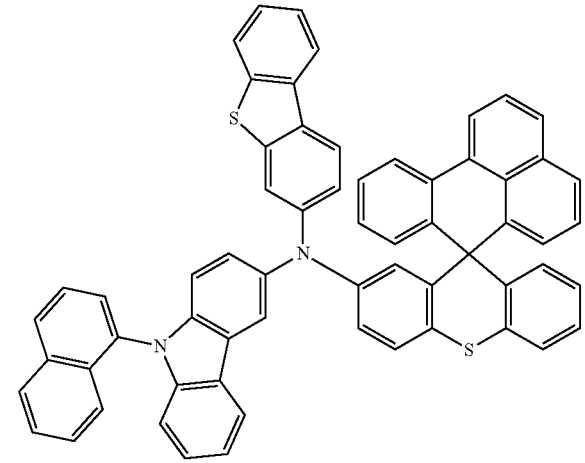
742
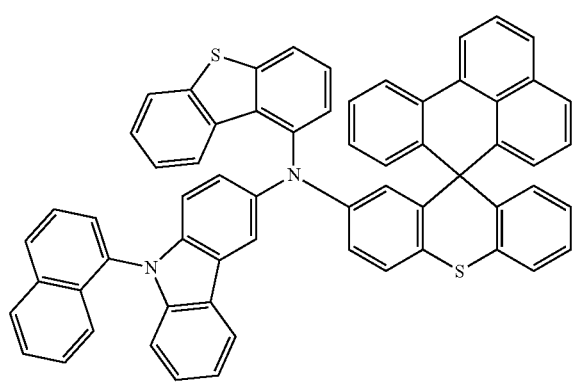
748
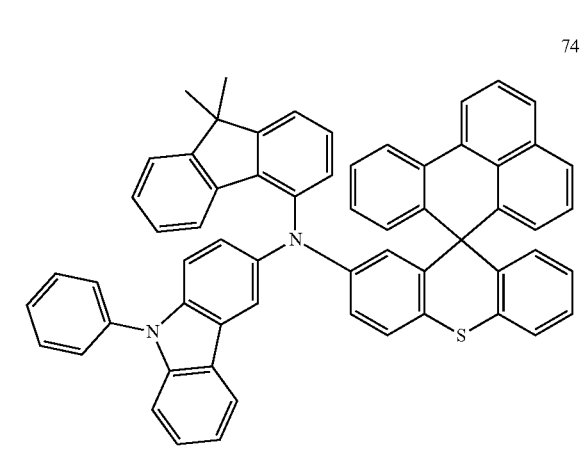
743
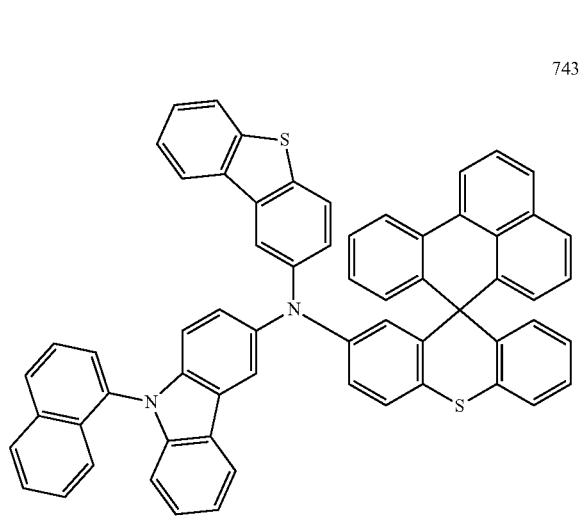
749
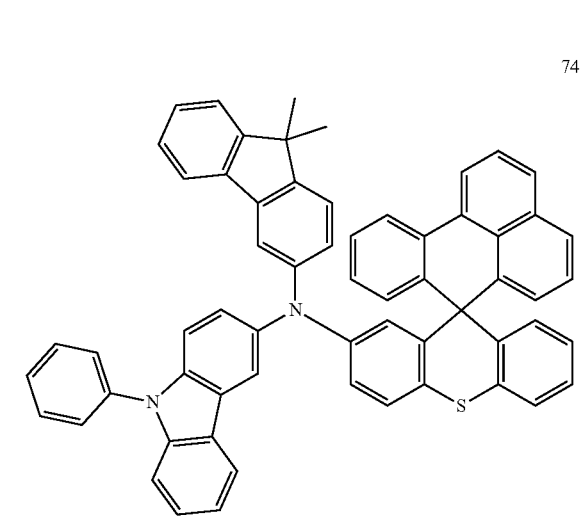

757
-continued
750
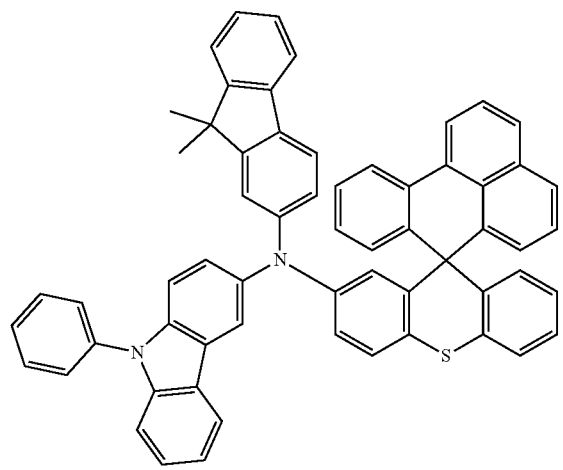
758
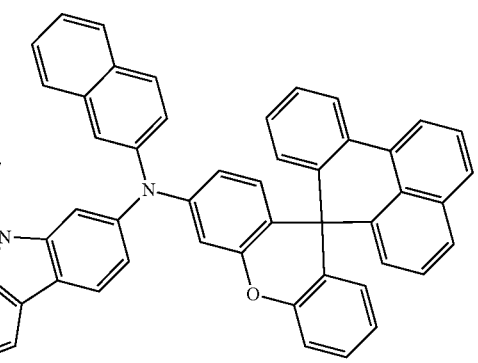
762
766
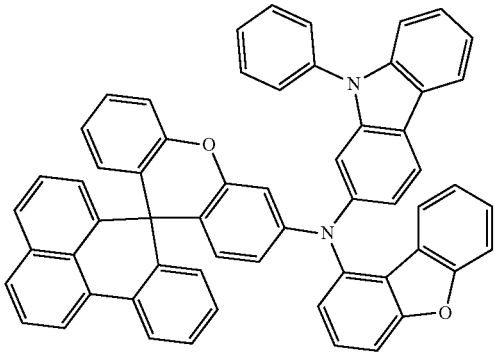
767
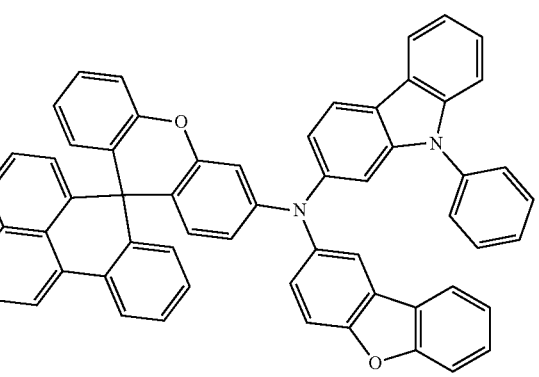
768
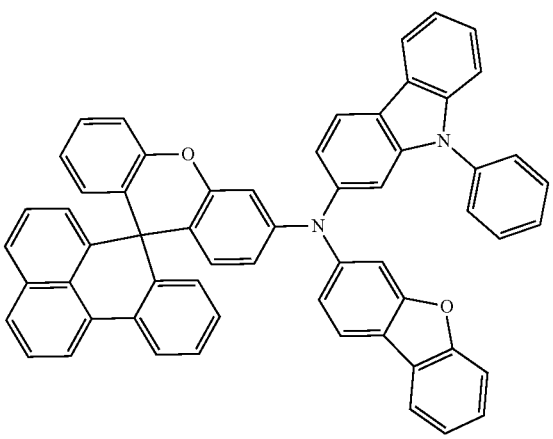

759
-continued
769
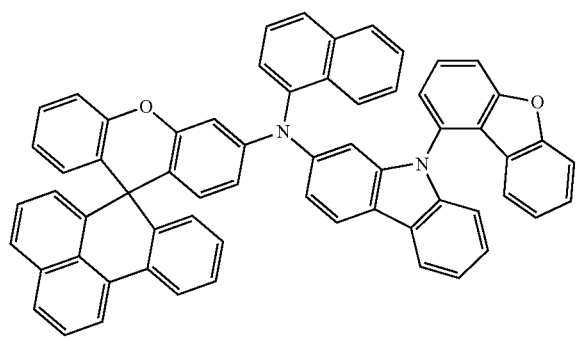
770
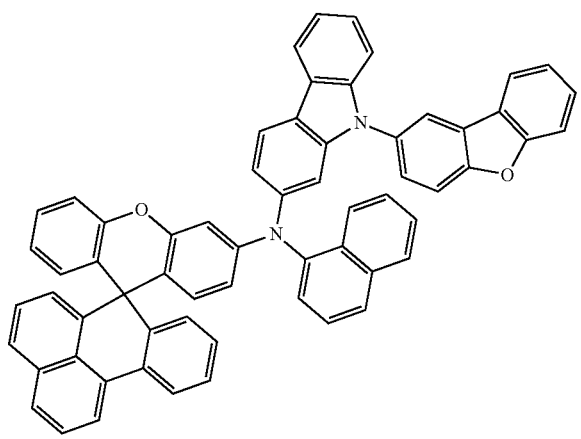
774
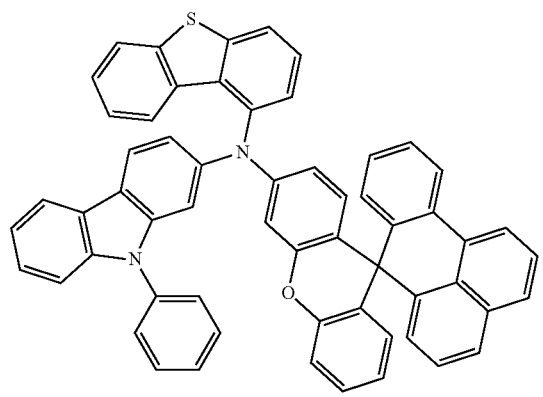
760
-continued
775
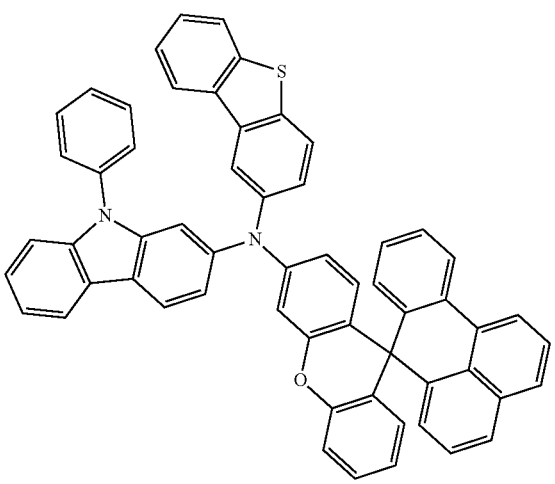
776
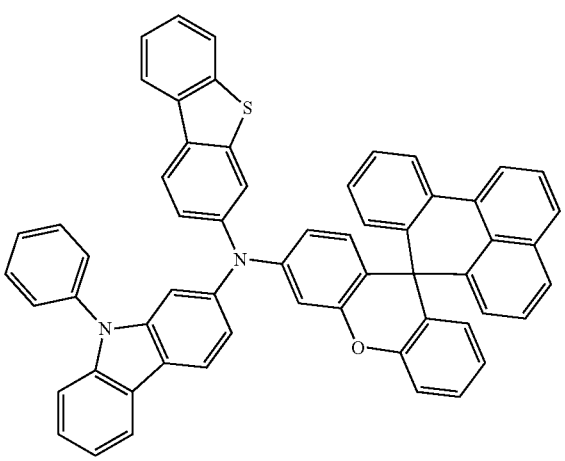
777
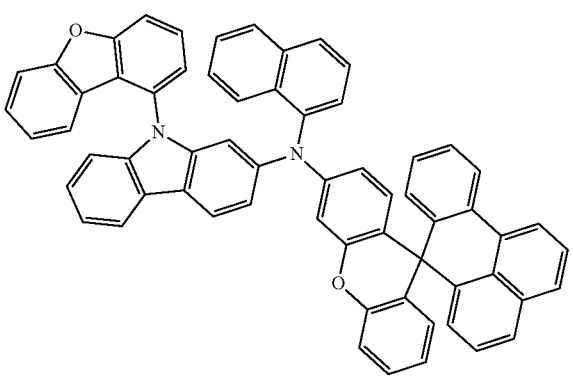

| 778 | 782 |
|---|---|
| 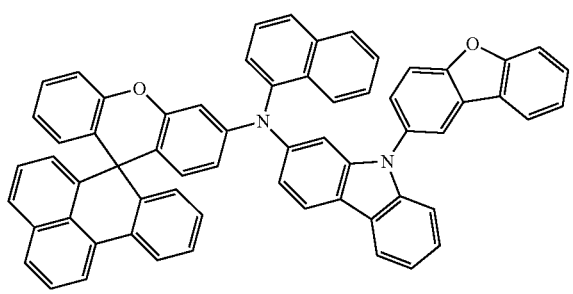 | 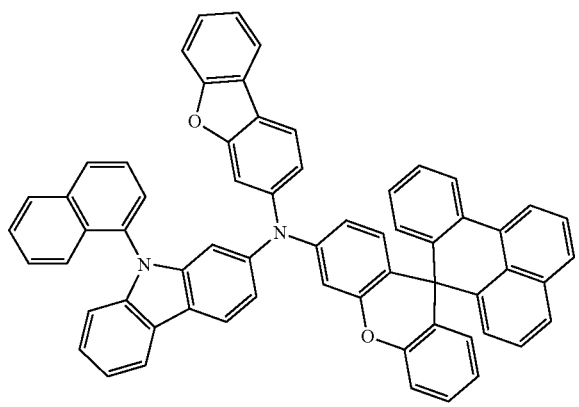 |
| 779 | 783 |
| 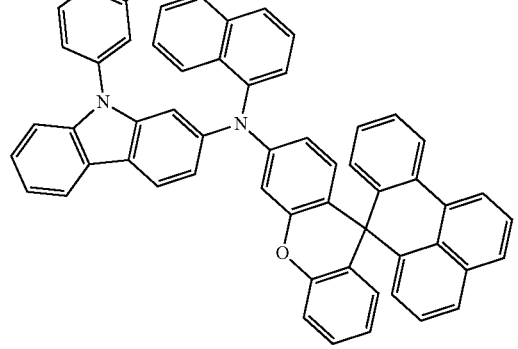 | 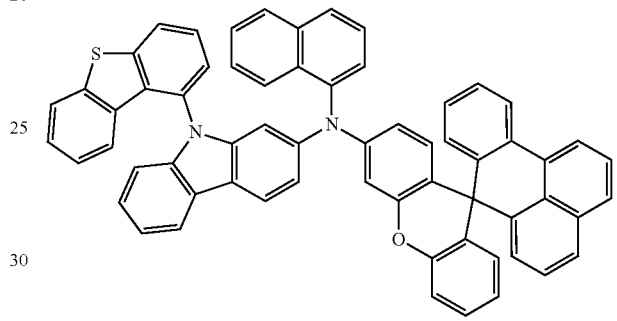 |
| 780 | 784 |
| 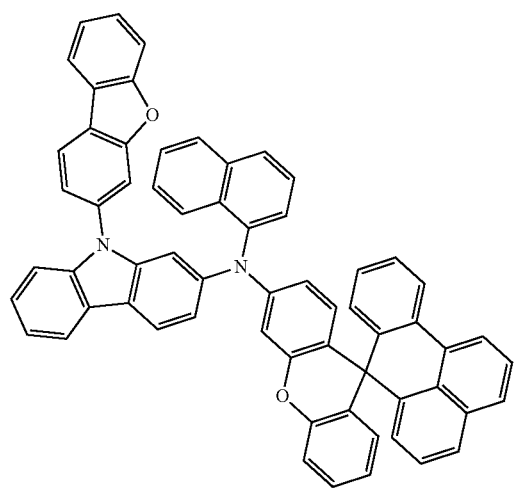 | |
| 781 | 785 |
| 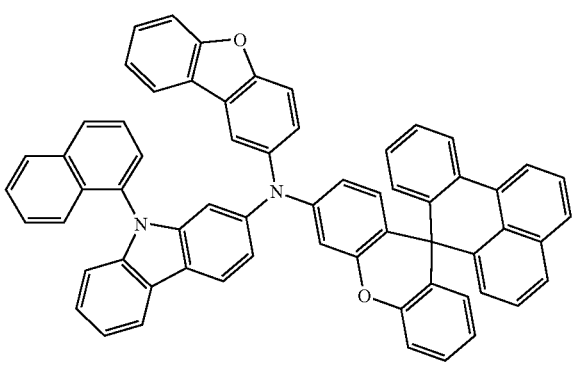 | 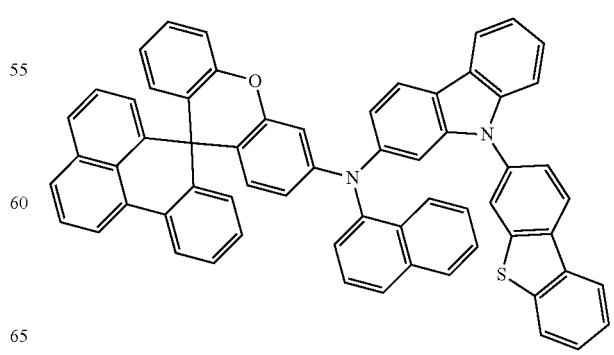 |
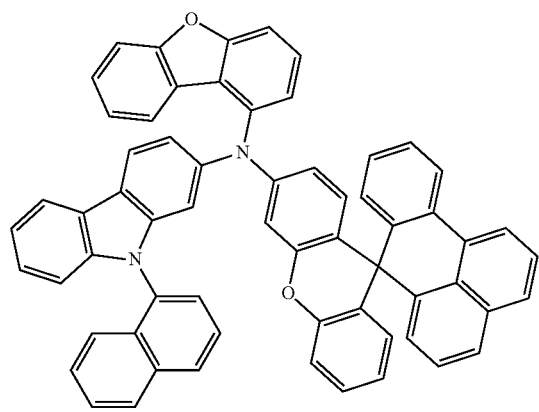

763
-continued
786
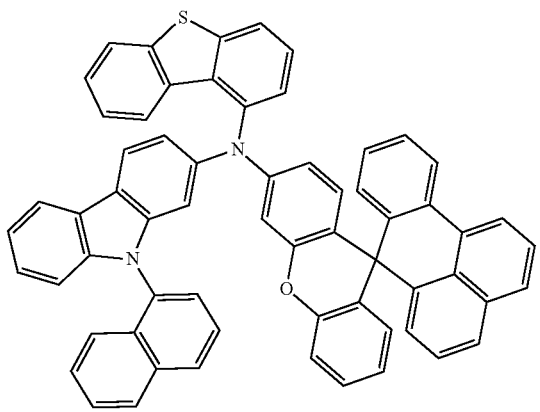
787
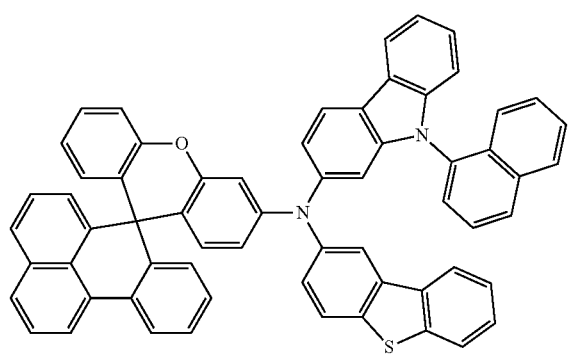
788
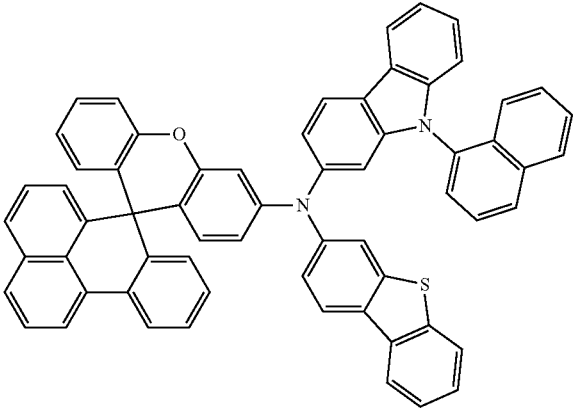
792
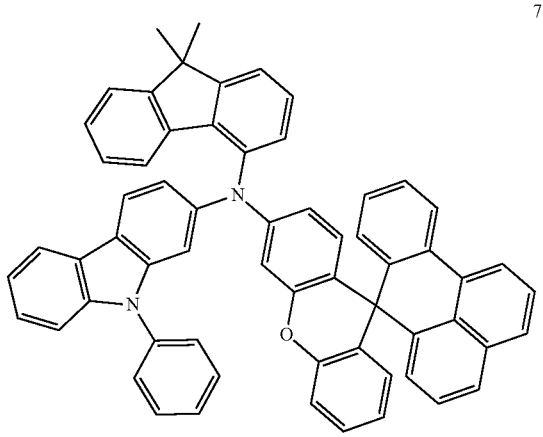
764
-continued
793
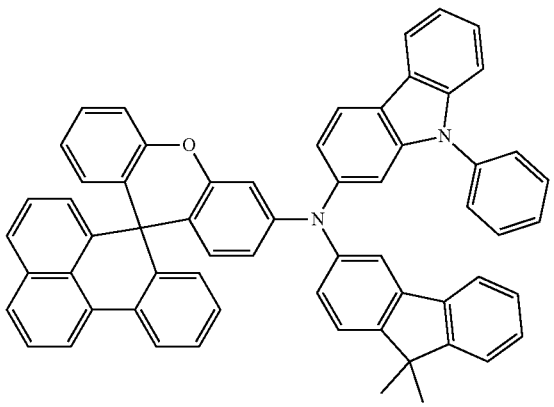
794
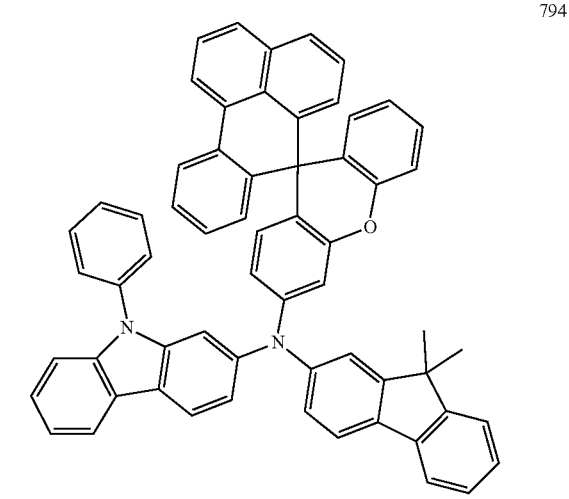
802
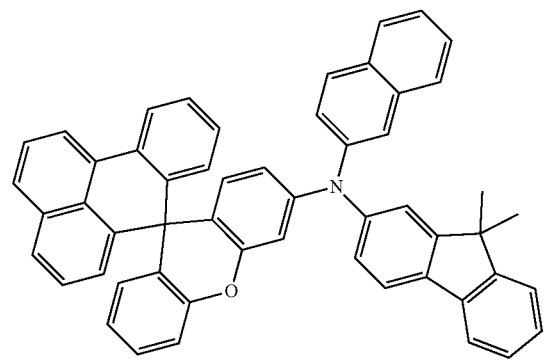

803
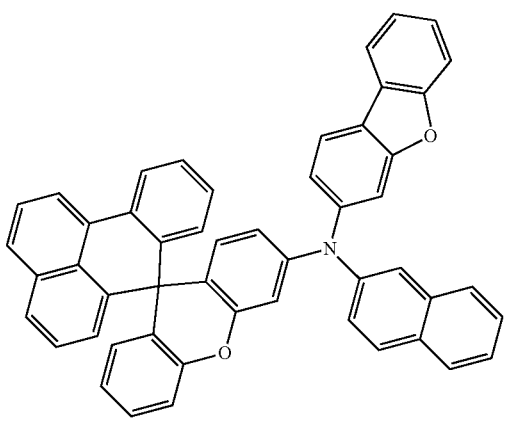
804
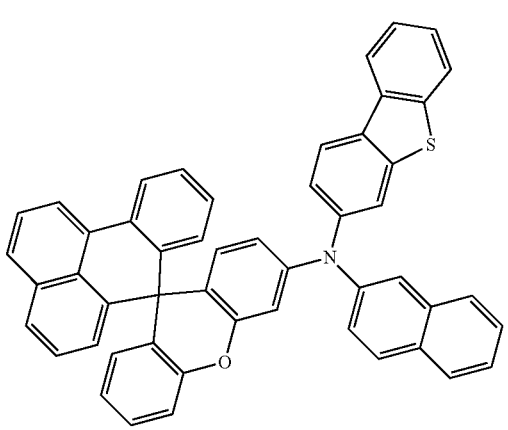
805
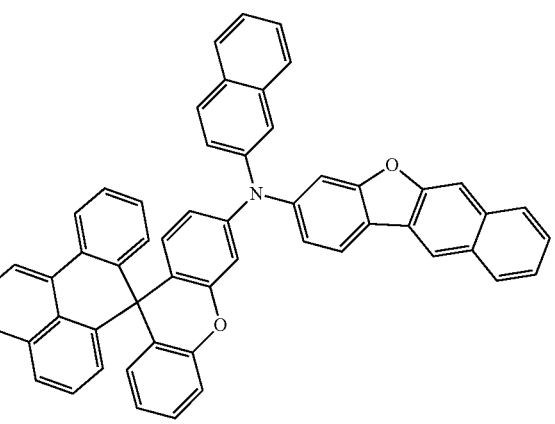
806
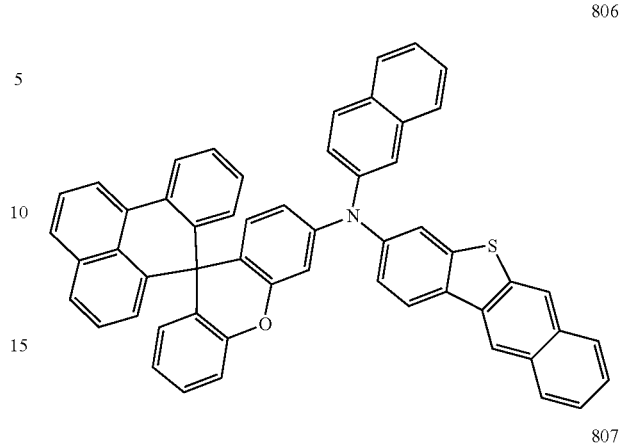
807
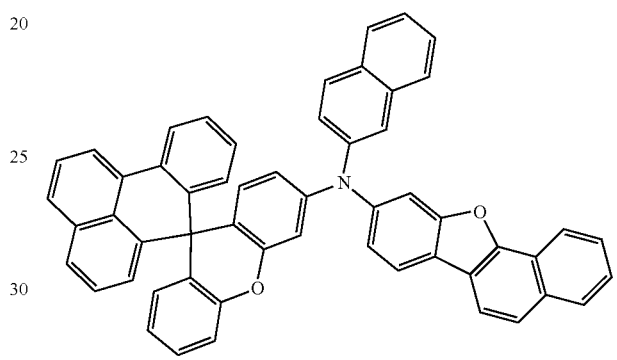
808
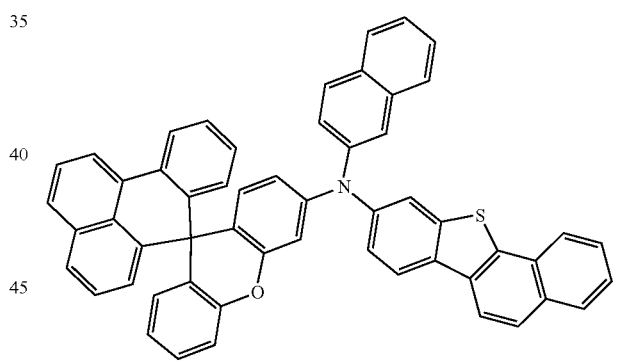
809
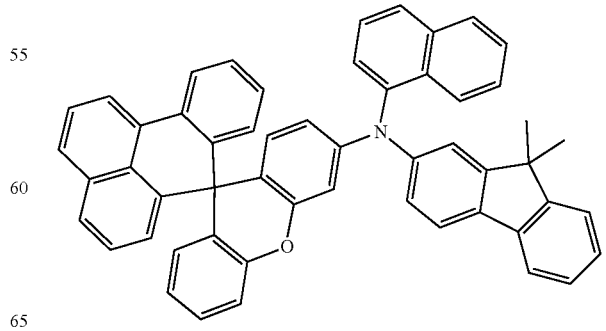

767
-continued
810
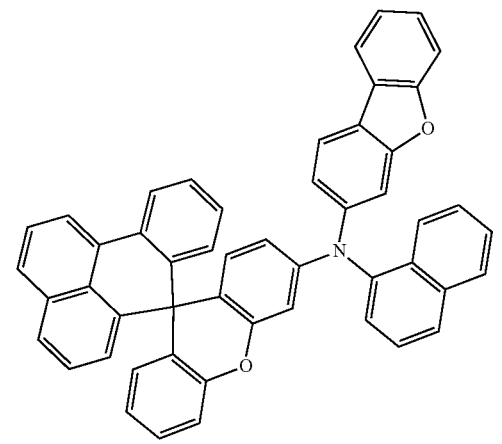
811
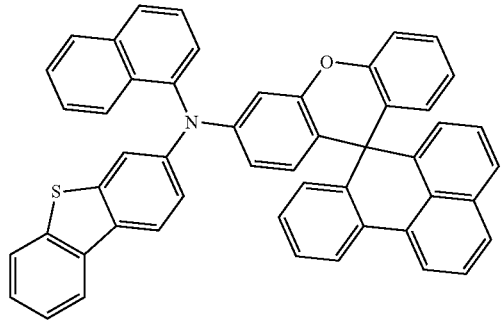
812
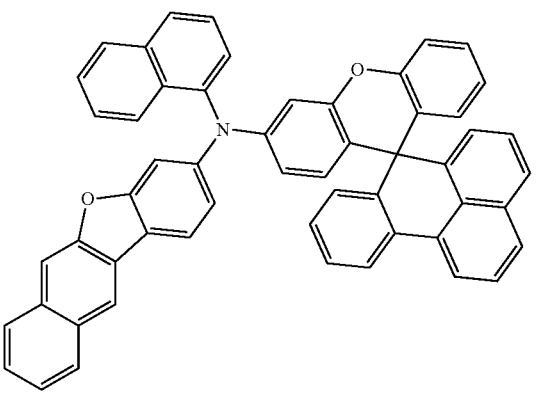
813
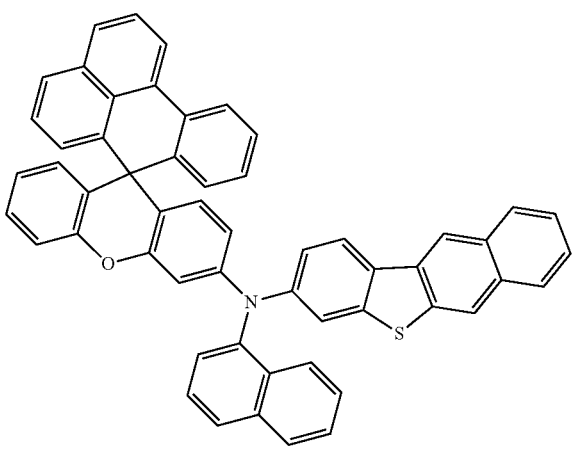
768
-continued
814
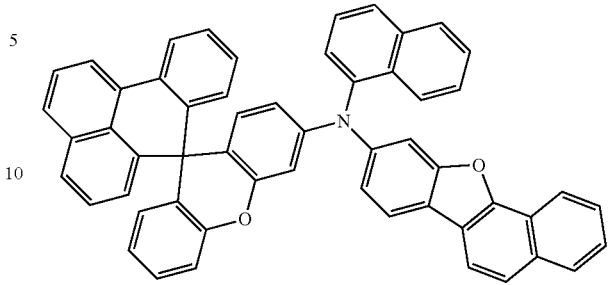
815
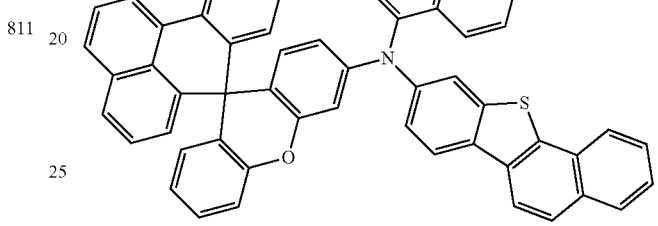
820
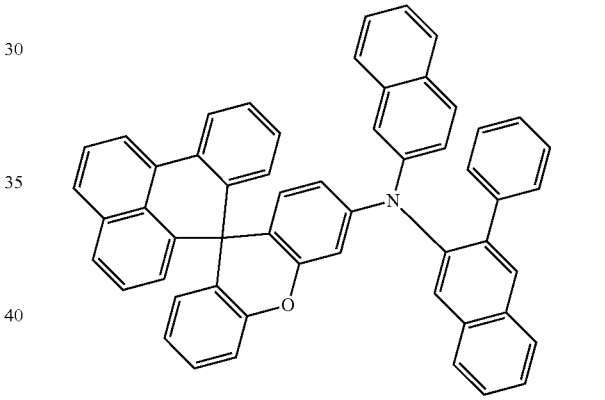
821
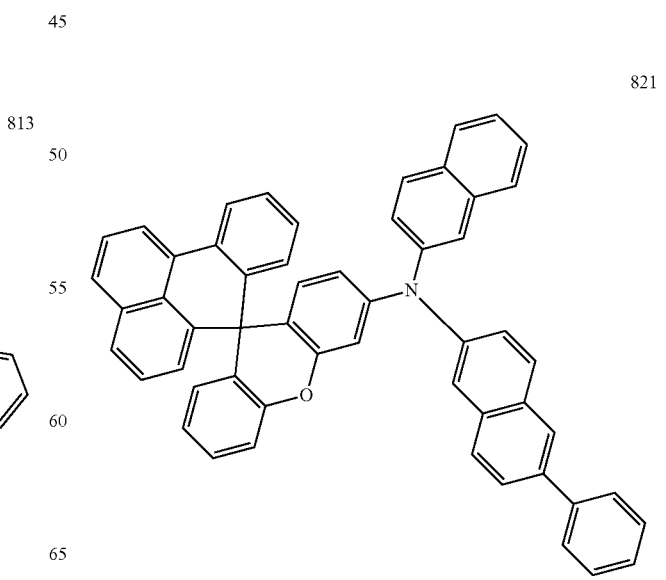

769
-continued
822
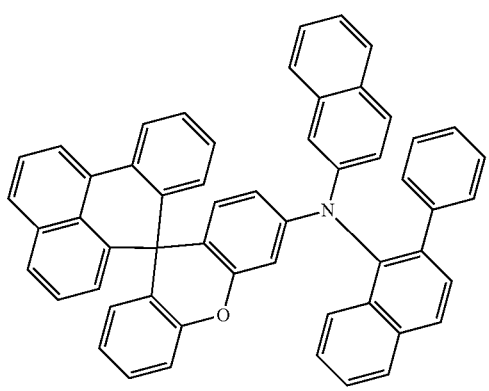
823
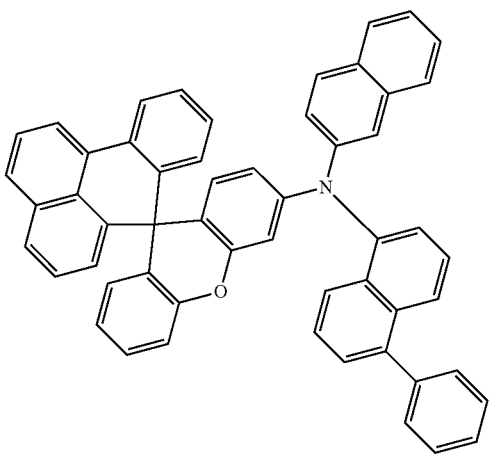
824
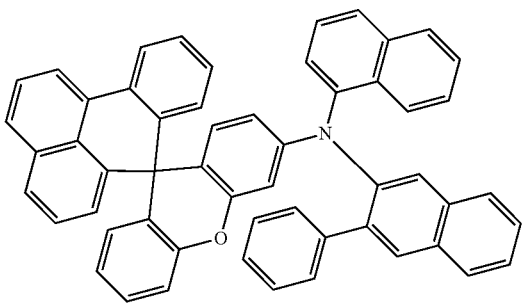
825
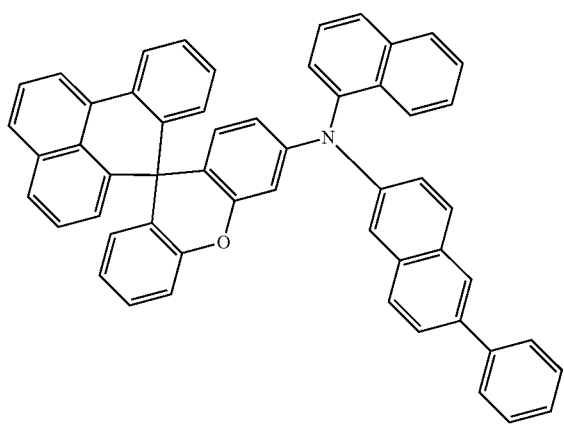
770
-continued
826
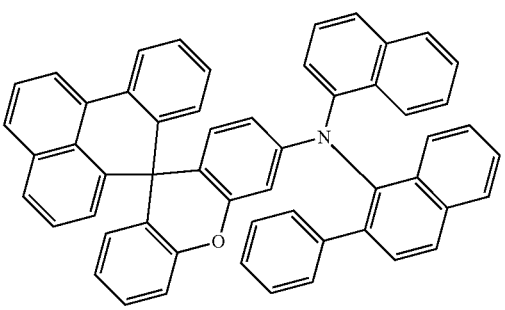
827
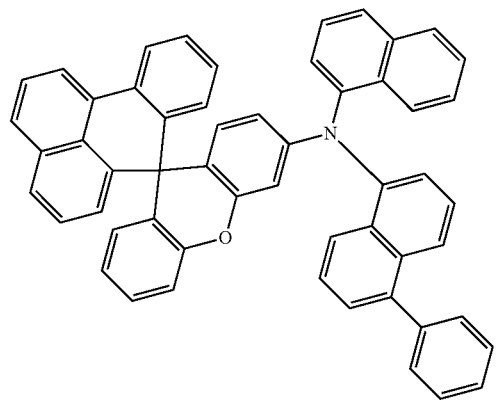
829
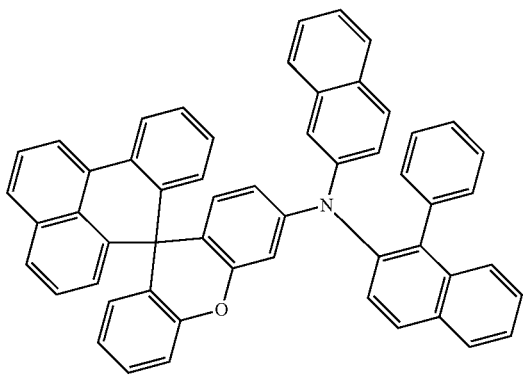
830
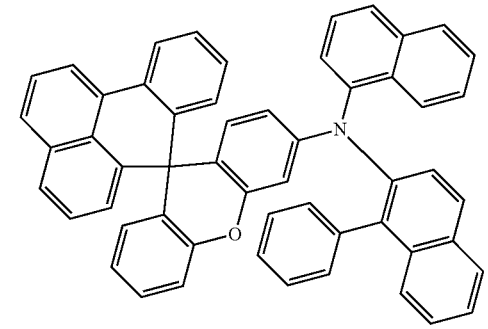

771
-continued
838
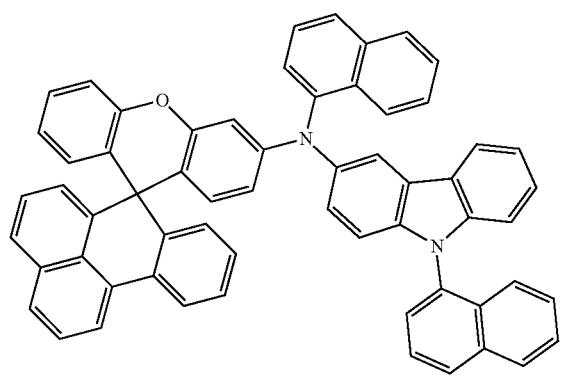
842
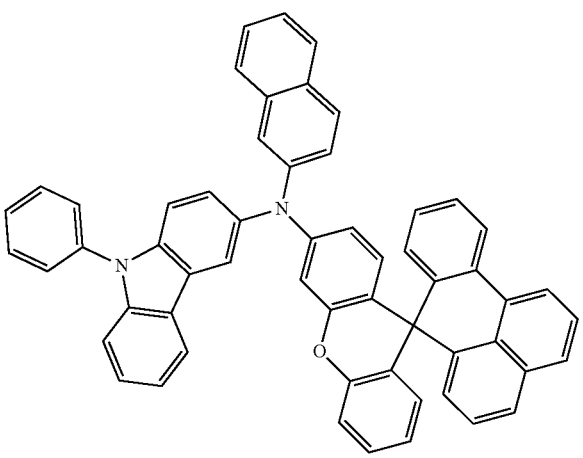
839
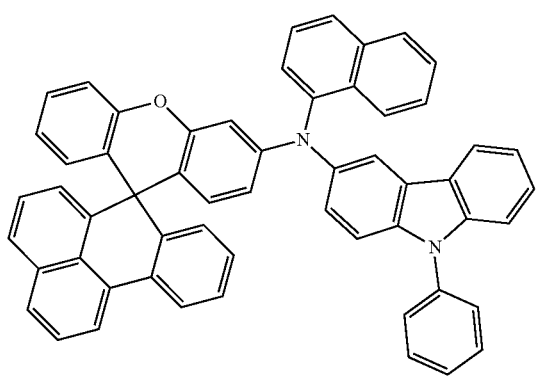
846
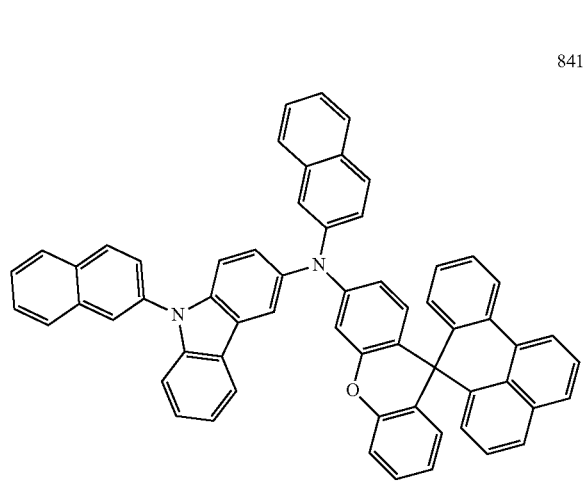
841
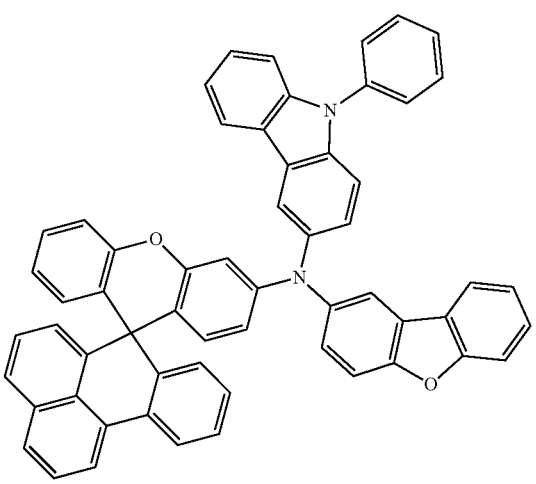
847

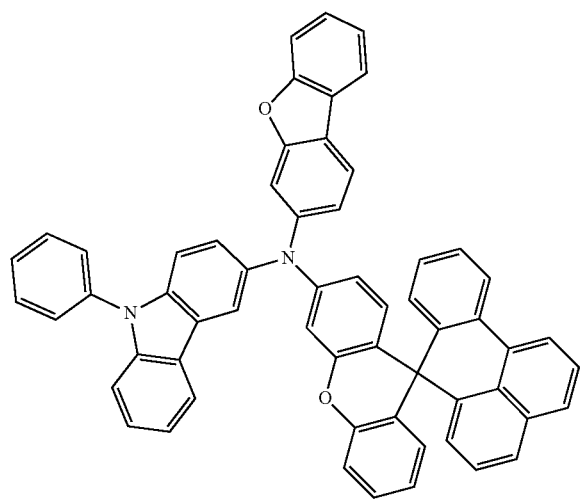
848
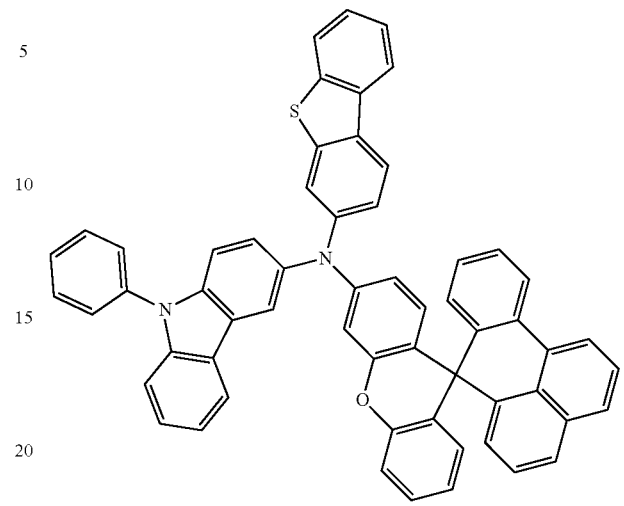
856
854
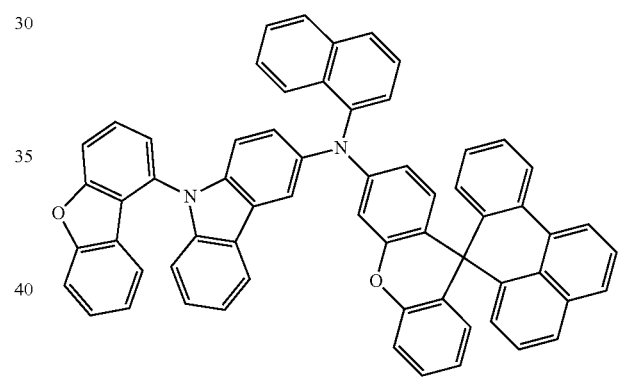
857
855
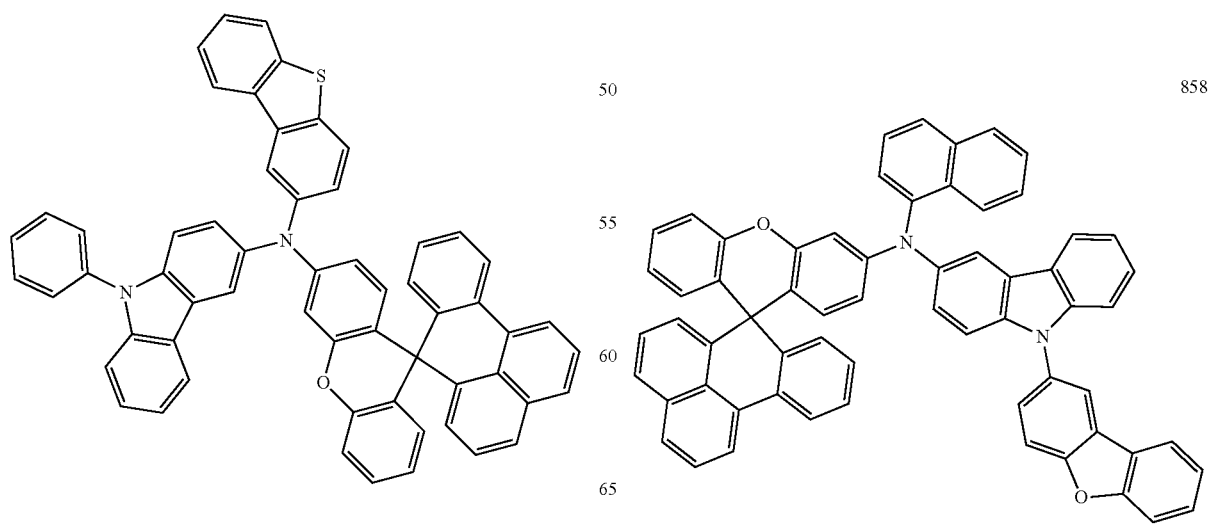
858

859
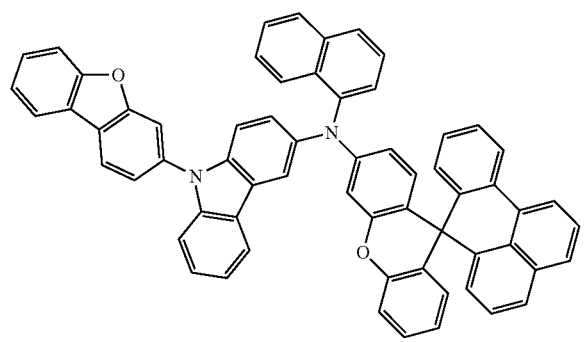
860
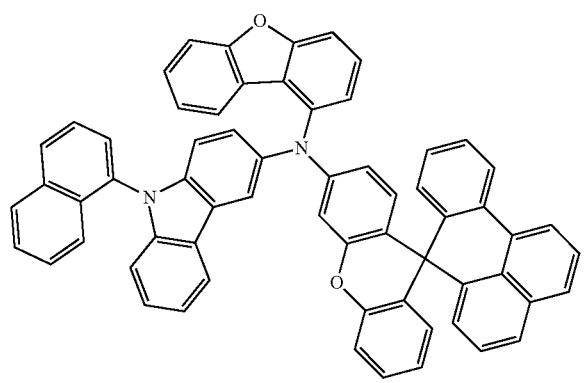
861
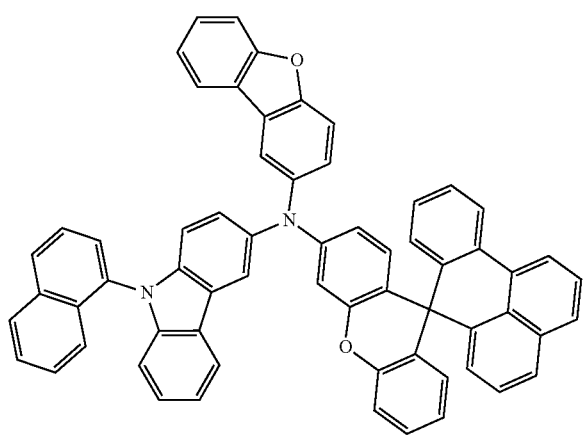
862
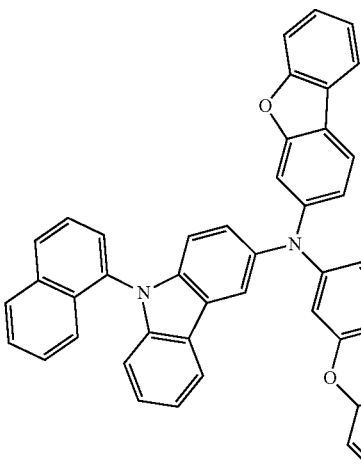
863
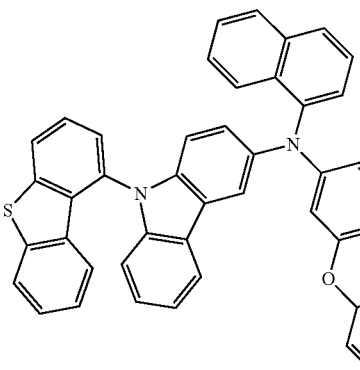
864
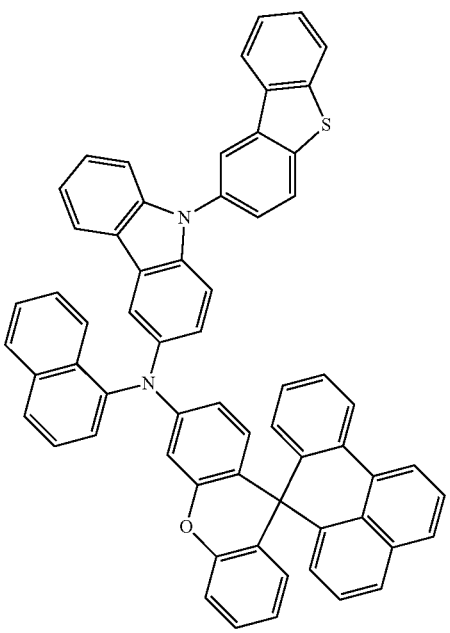

-continued
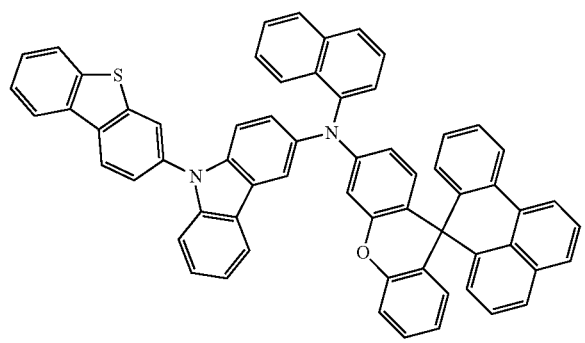
865
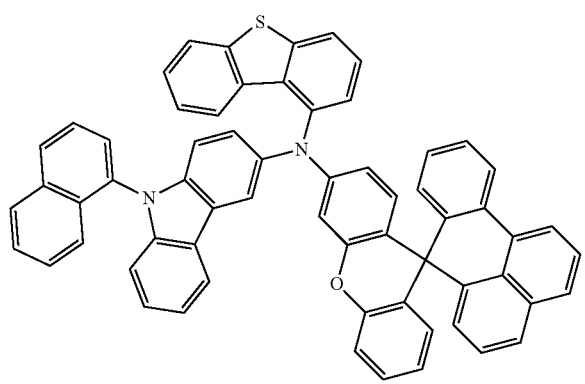
866
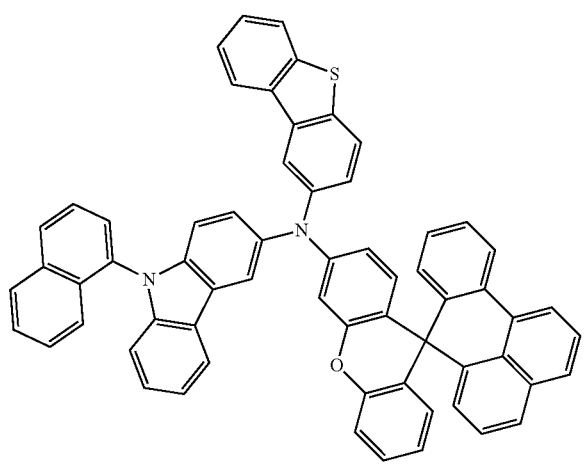
867
-continued
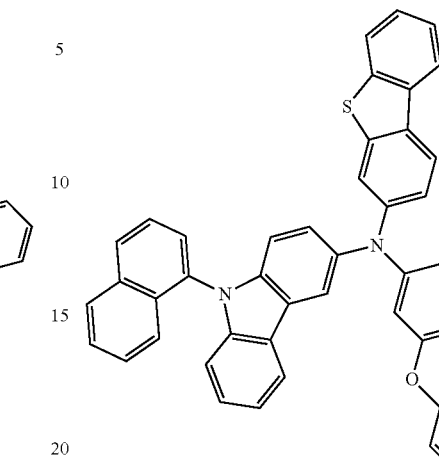
868
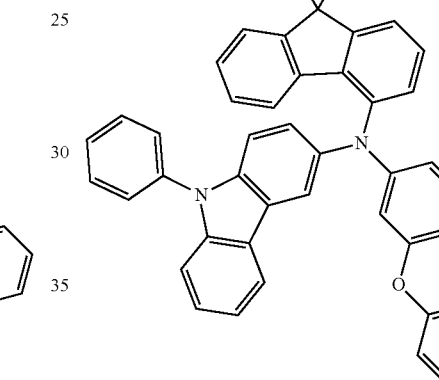
872
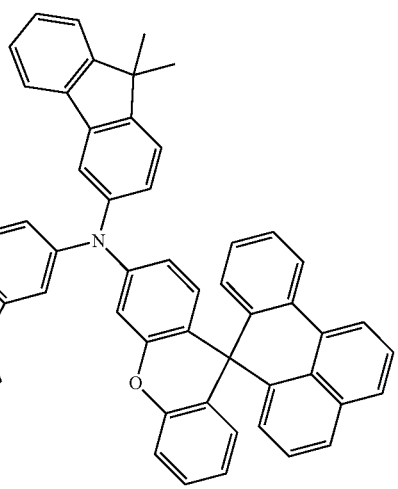
873

874
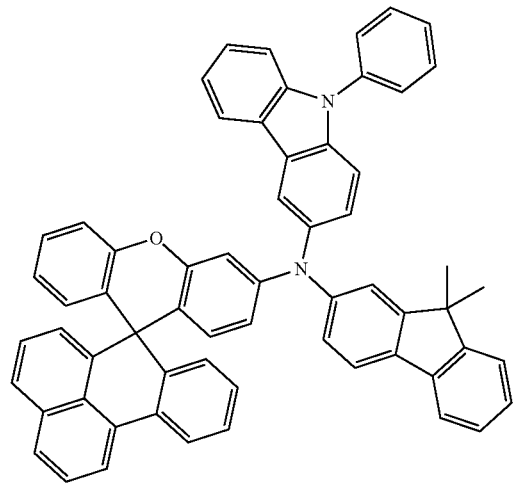
877
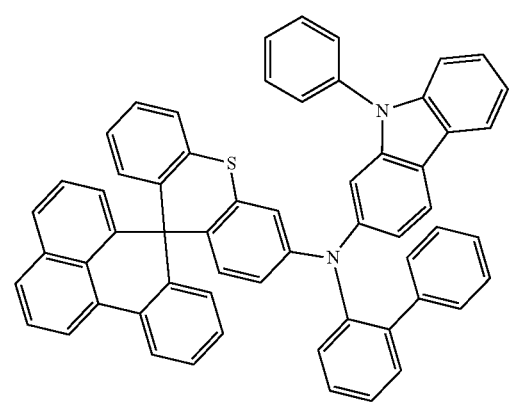
878
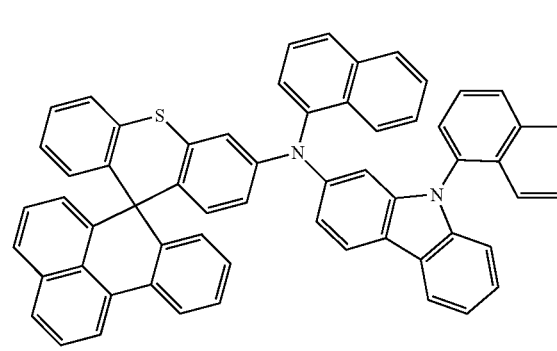
882
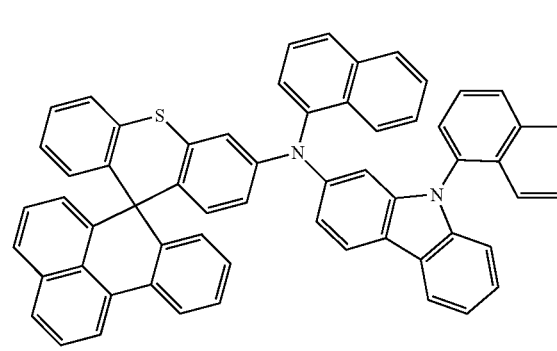
883
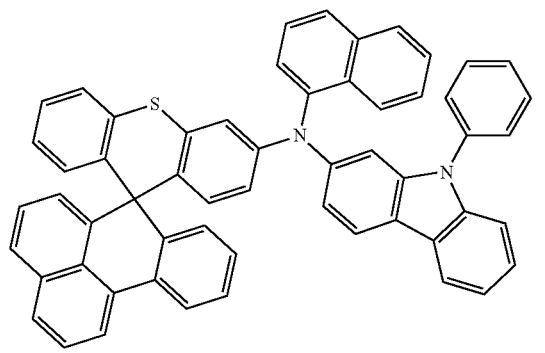
885
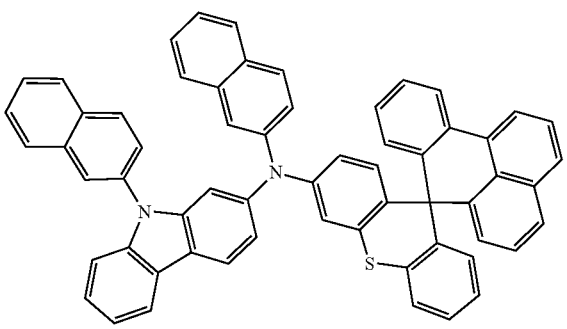
886
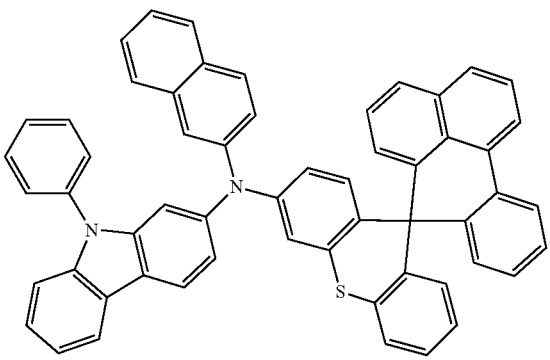
890
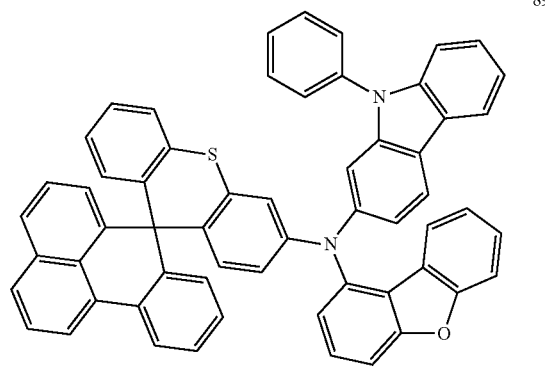

781
-continued
891
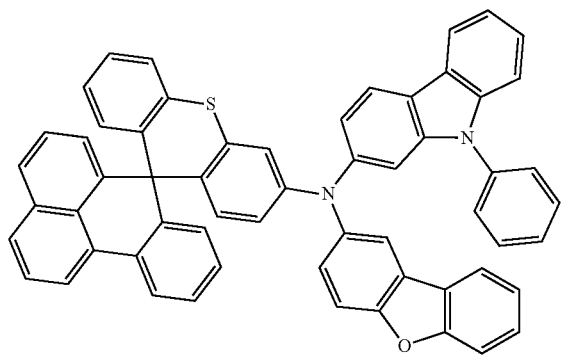
892
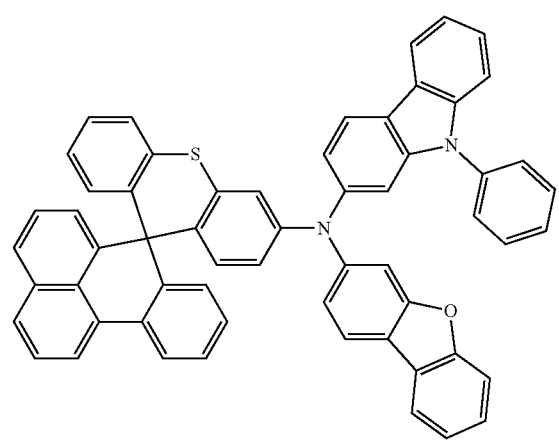
898
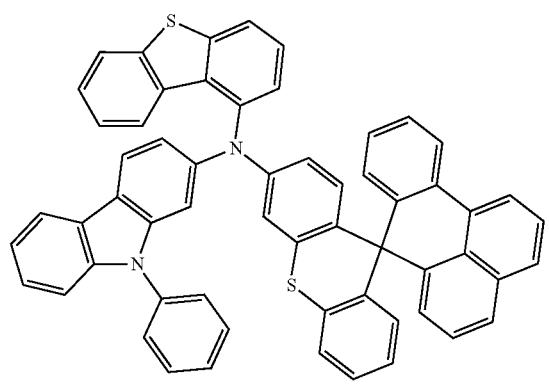
782
-continued
899
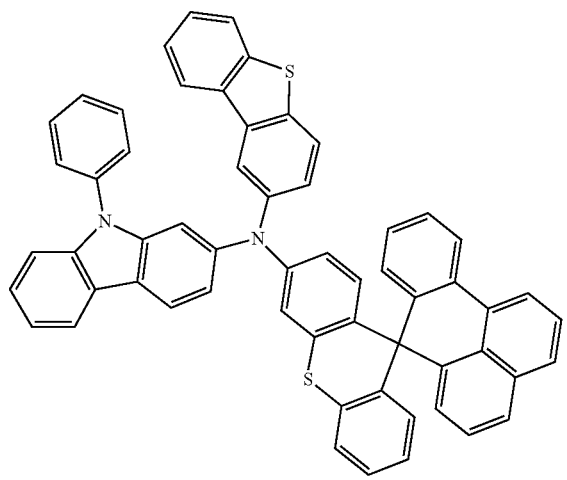
900
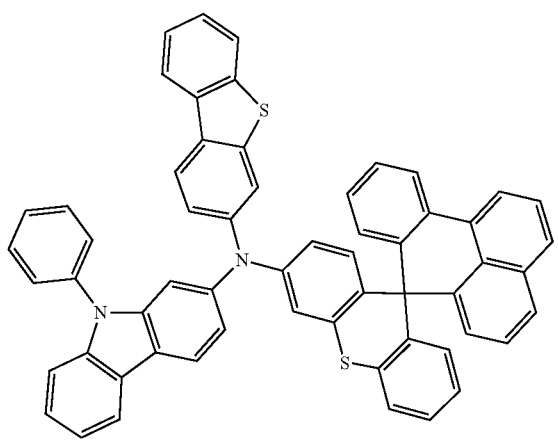
901
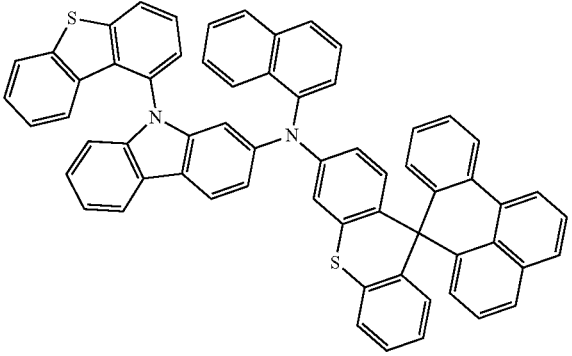

902
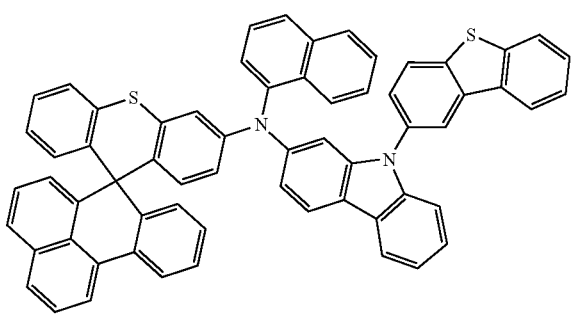
903
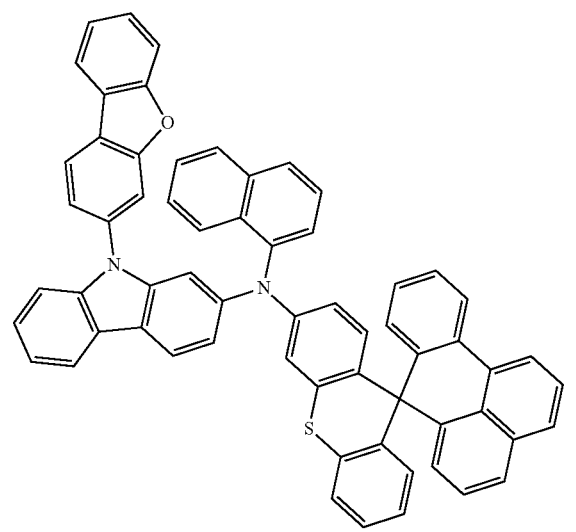
904
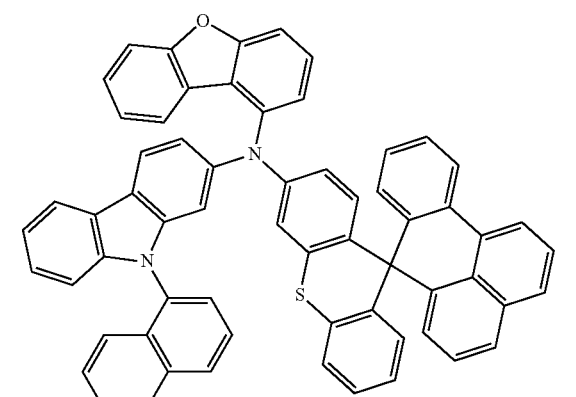
905
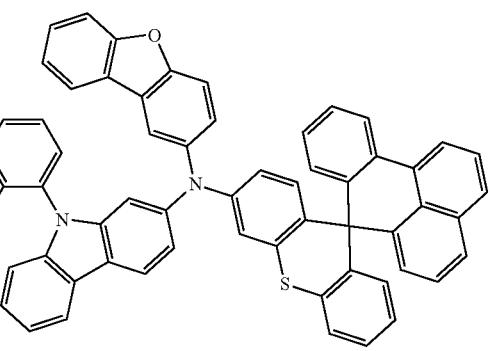
906
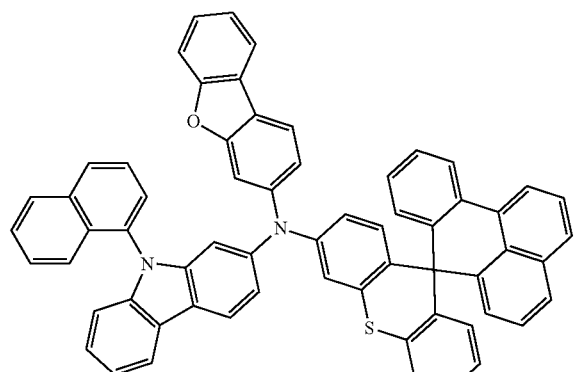
907
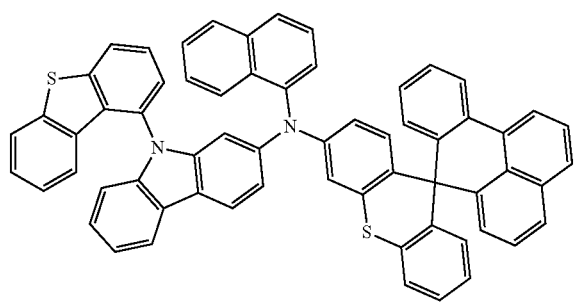
908
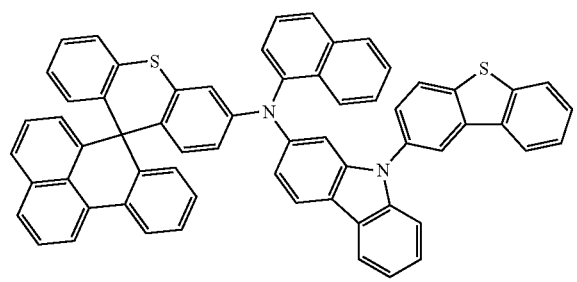

909
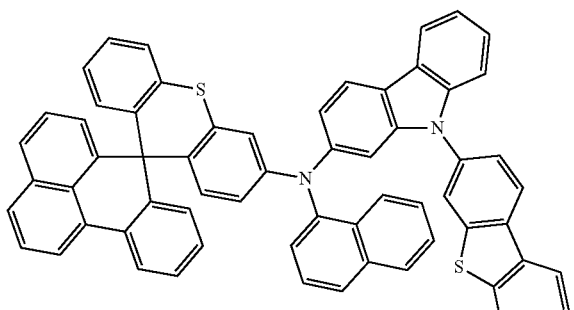
910
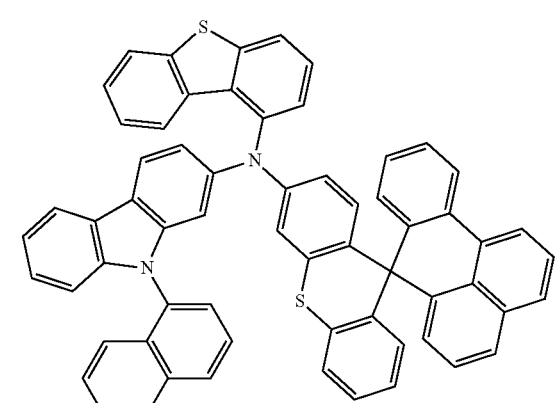
911
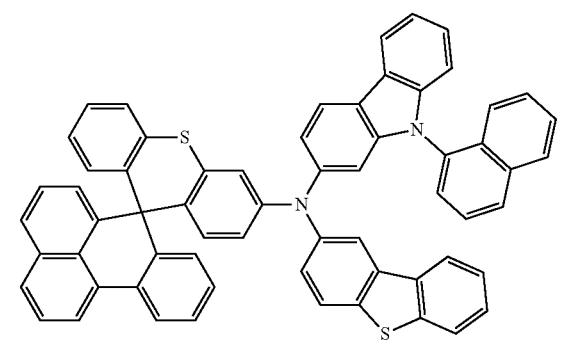
912
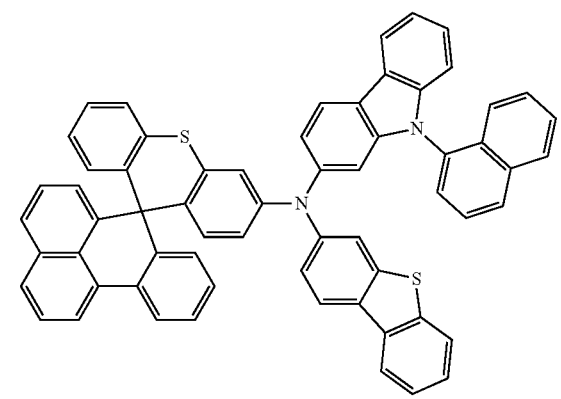
916
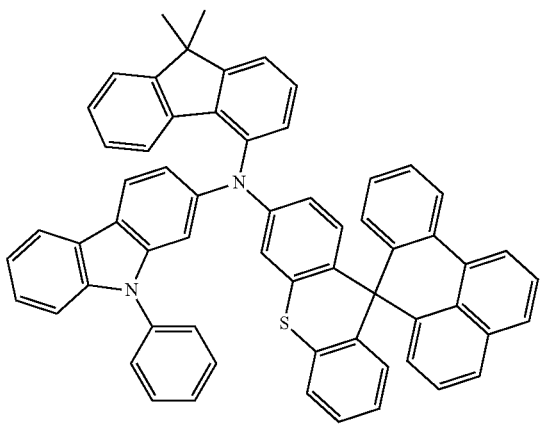
917
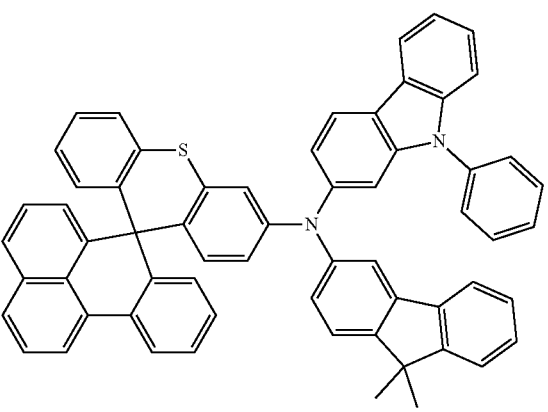
918
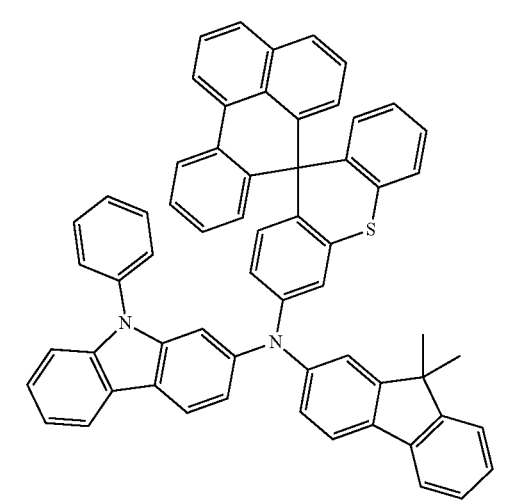

787
-continued
926
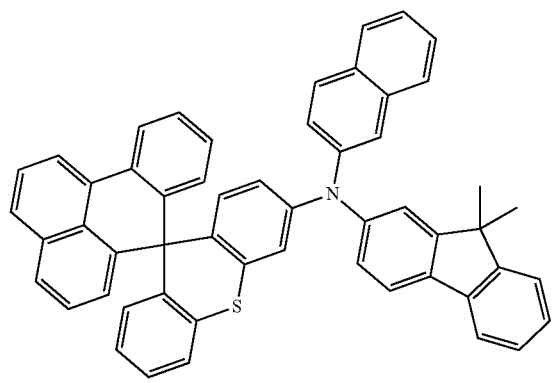
927
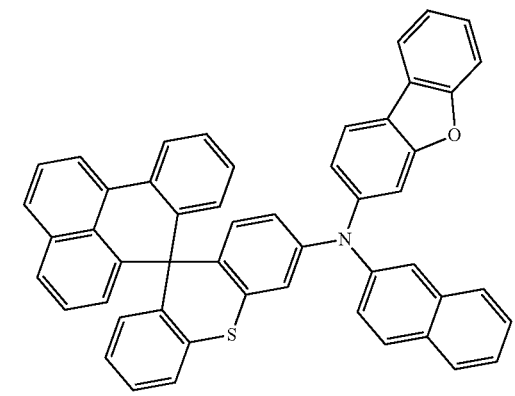
928
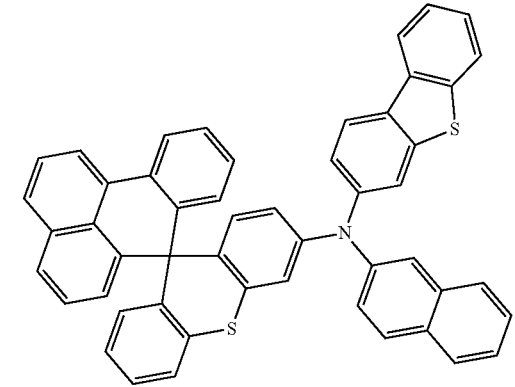
929
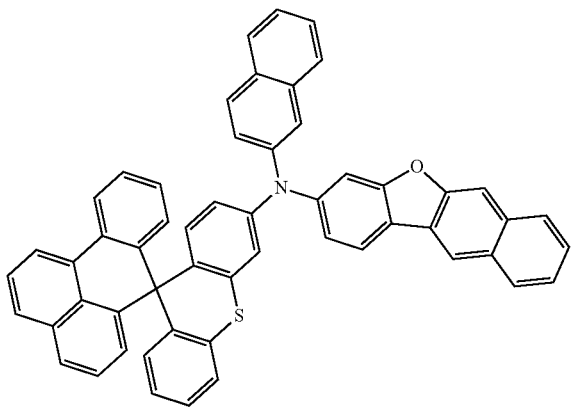
788
-continued
930
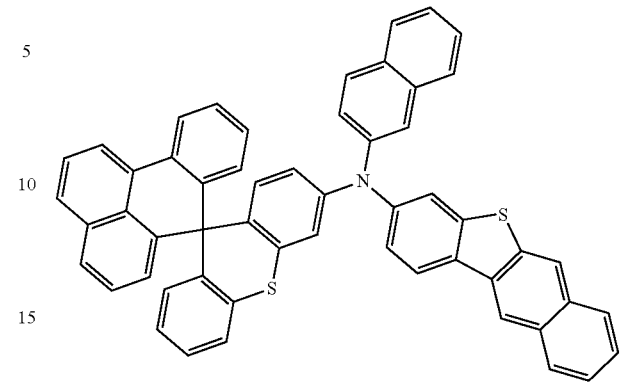
931
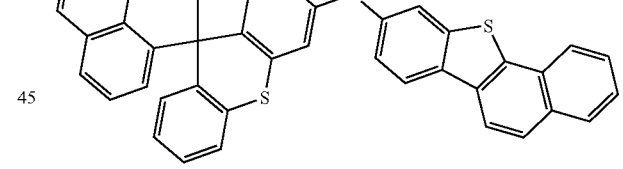
932
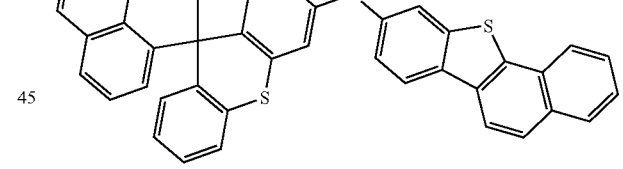
933
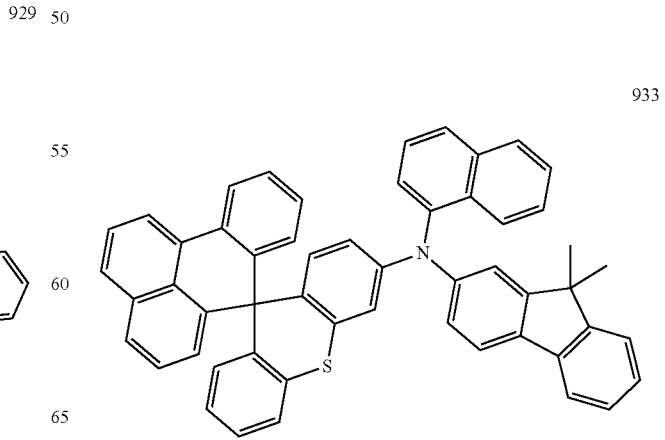

789
-continued
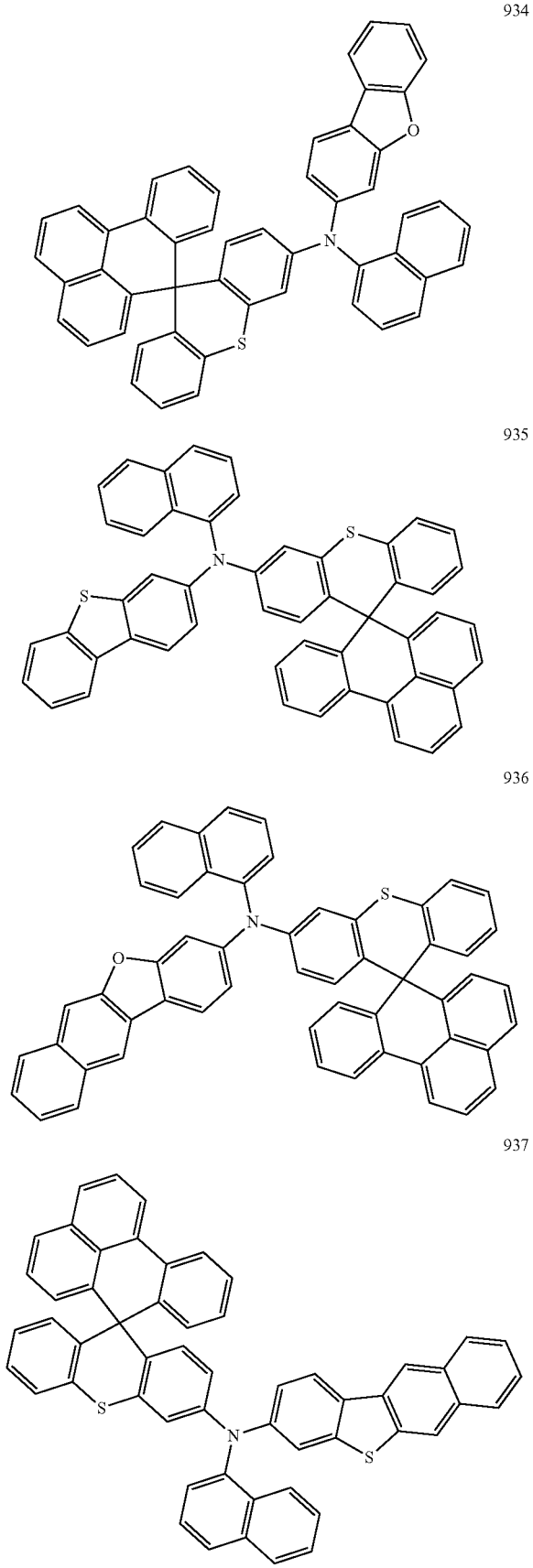
790
-continued
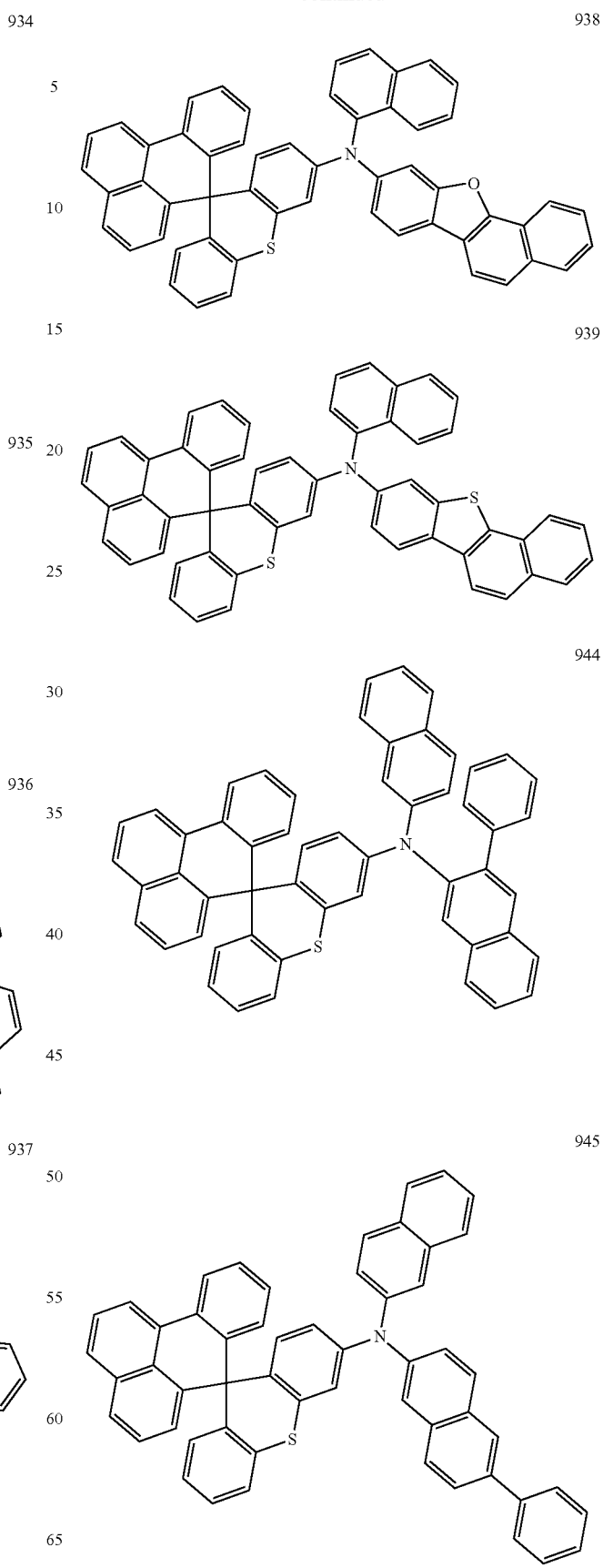

| 946 | 950 |
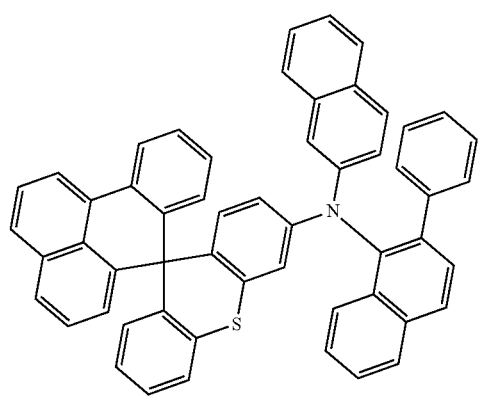
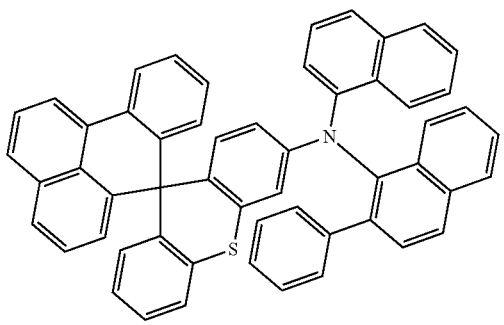
| 947 | 951 |
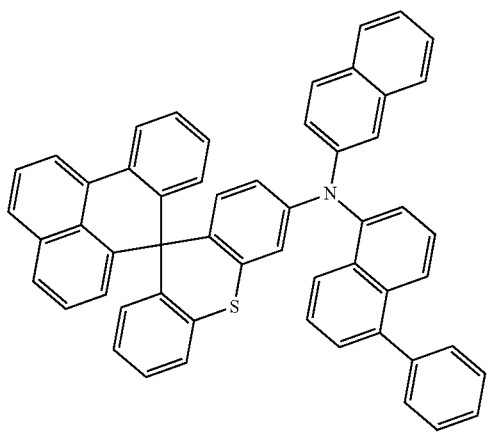
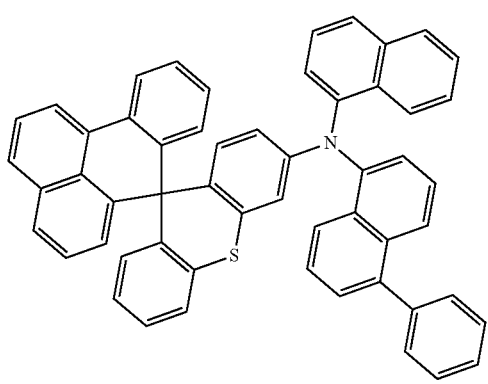
| 948 | 953 |
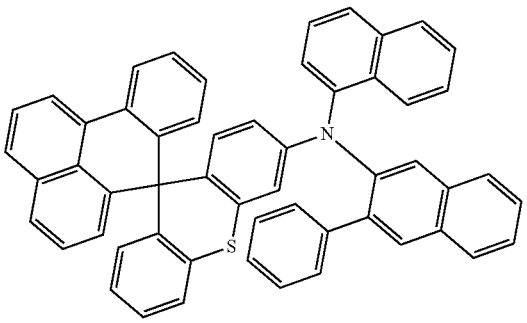
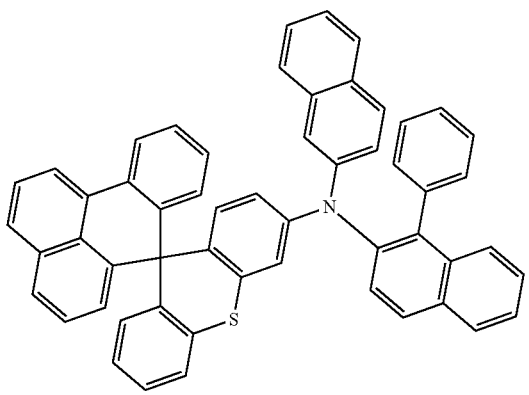
| 949 | 954 |
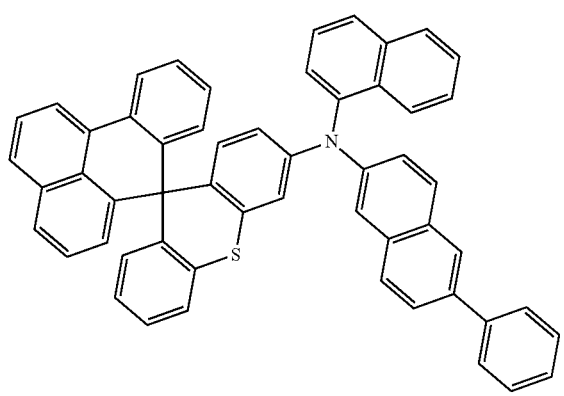
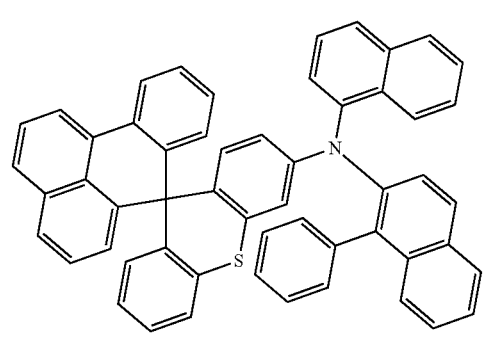

-continued
962
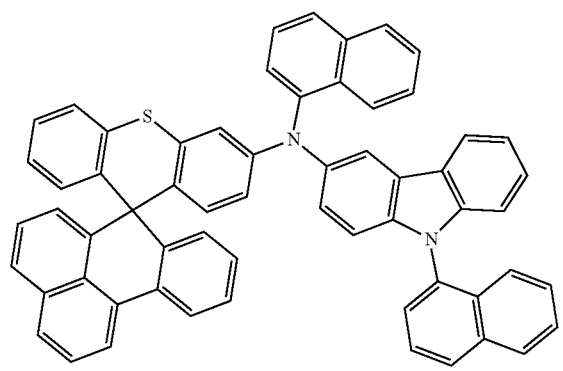
963
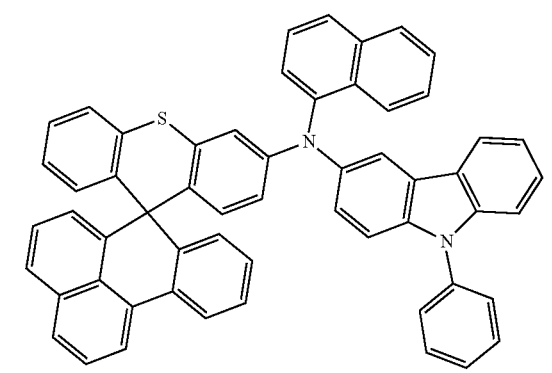
965
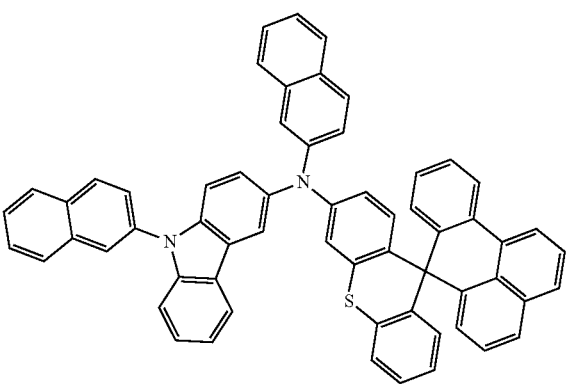
966
-continued
970
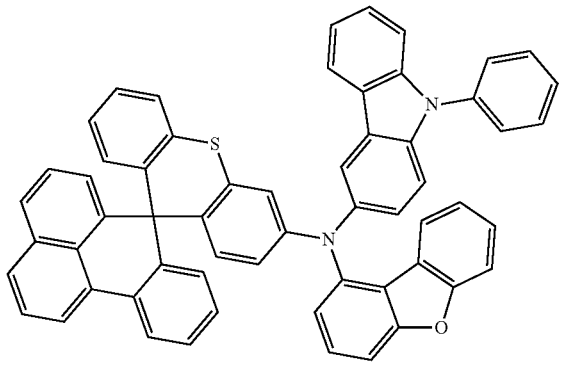
971
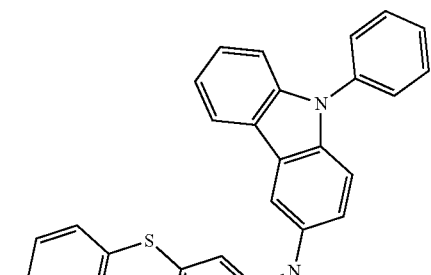
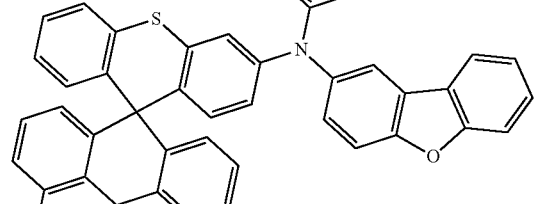
972
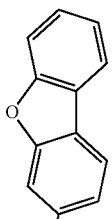
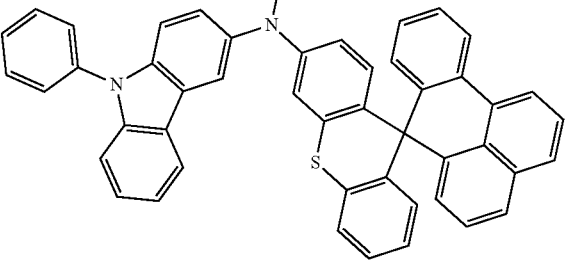

978
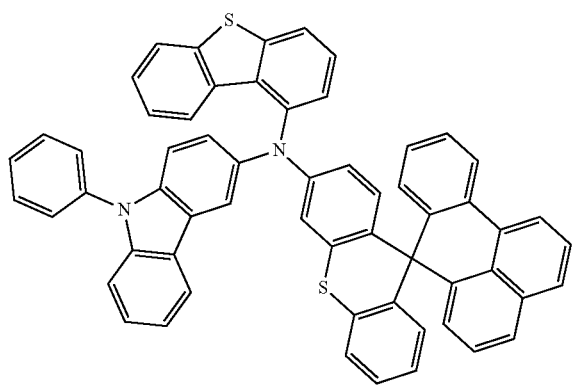
981
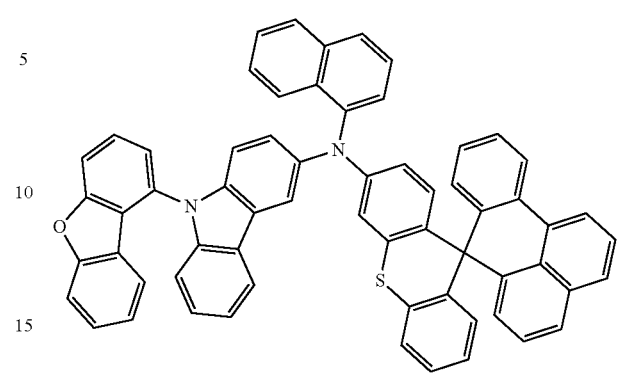
979
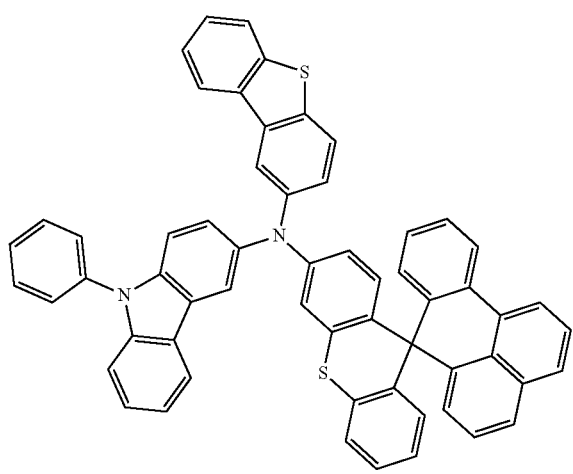
982
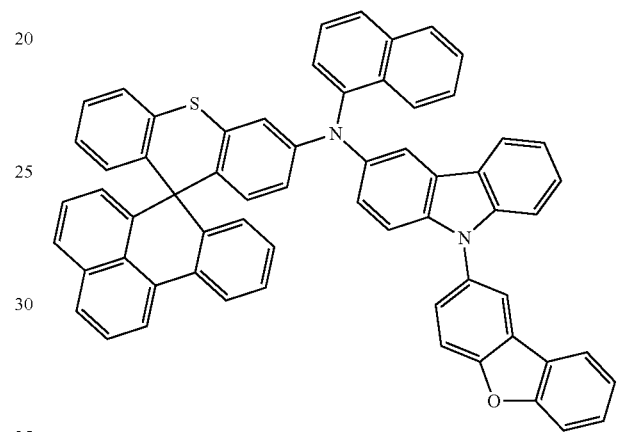
983
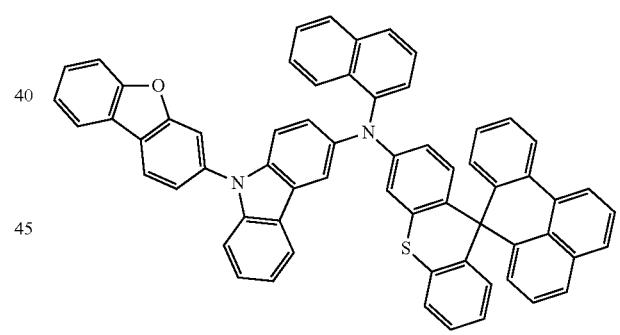
980
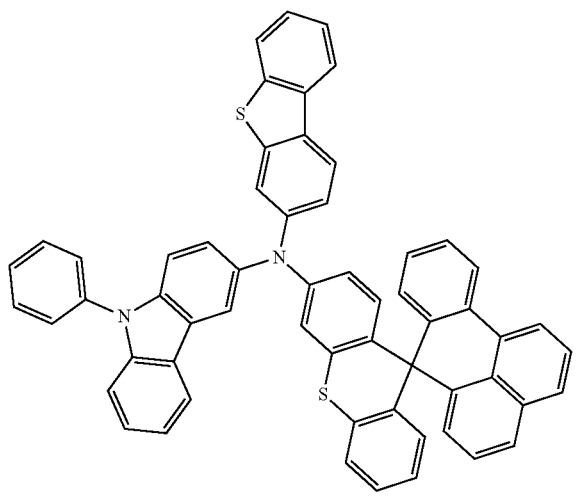
984
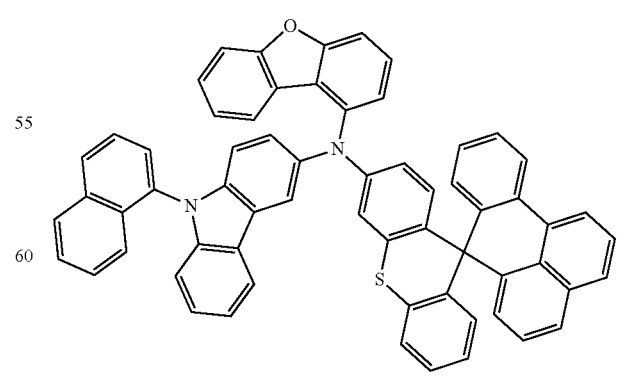

-continued
985
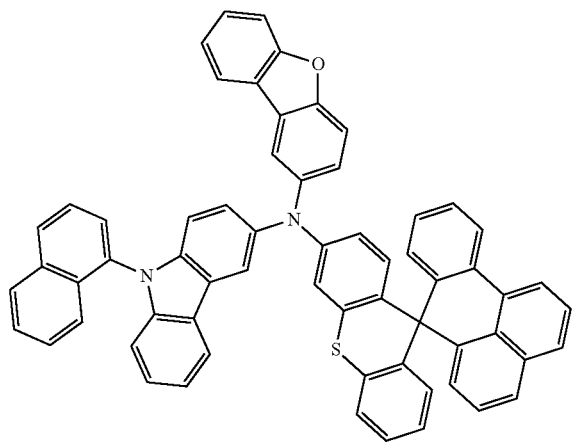
986
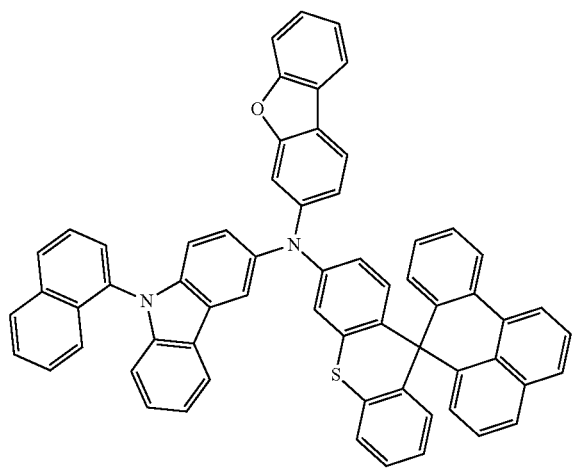
987
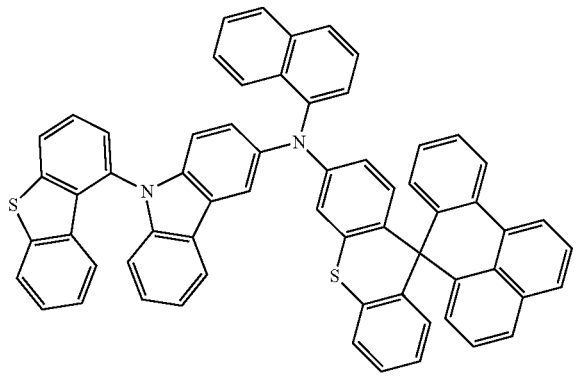
-continued
988
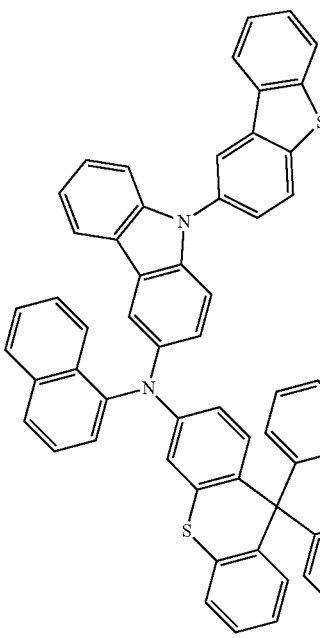
989
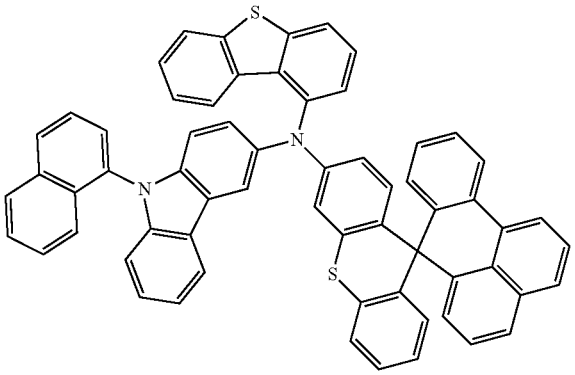
990

799
-continued
991
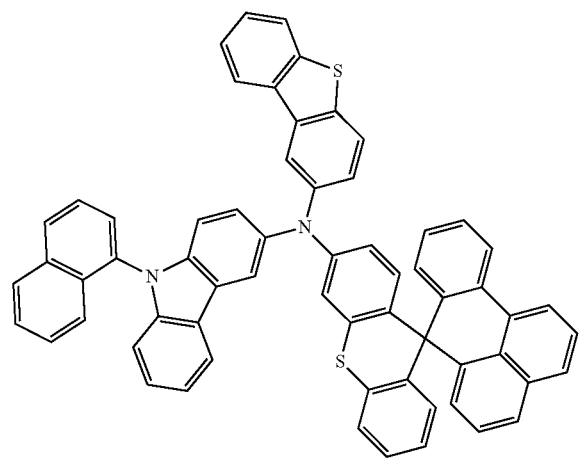
992
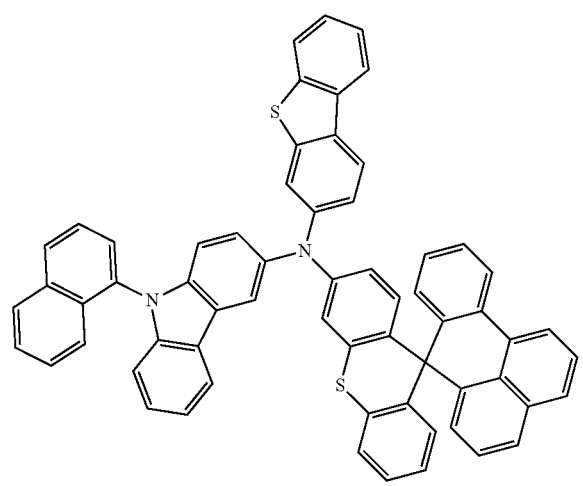
996
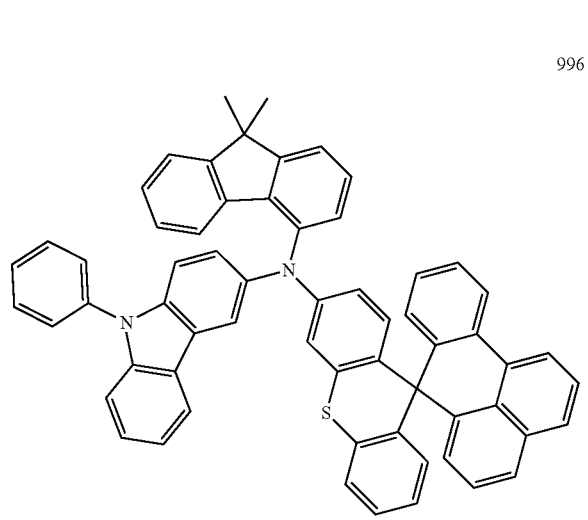 [SMILES: CC1(C)c2ccccc2-c2c(N(c3ccc4c(c3)Oc3ccccc3C43c4ccccc4-c4cccc5cccc3c45)c3ccc4c(c3)c3ccccc3n4-c3ccccc3)cccc21]
800
-continued
997
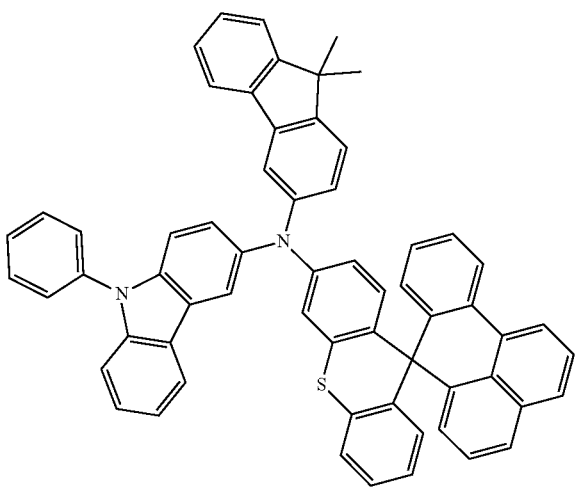
998
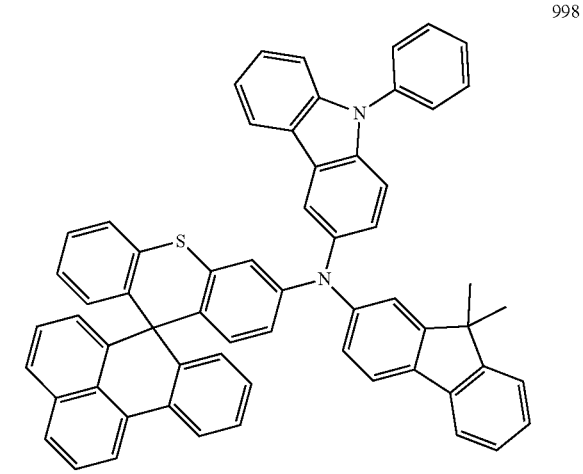
999
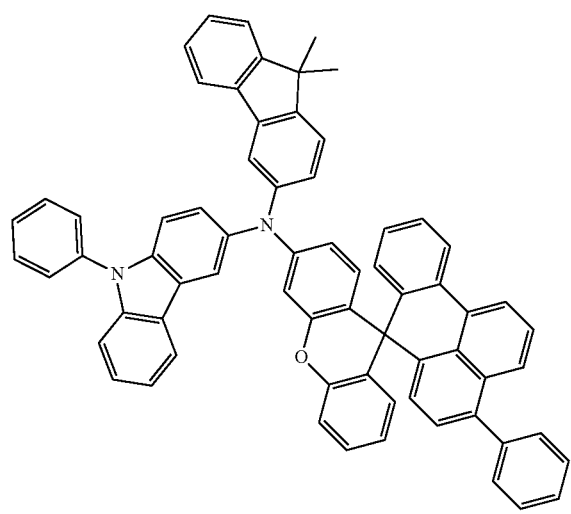

801
-continued
1000
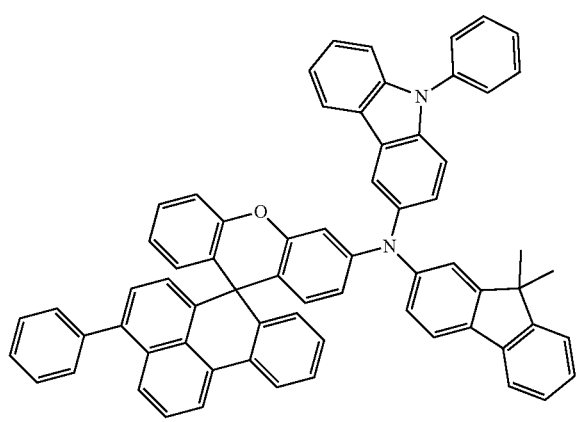
1001
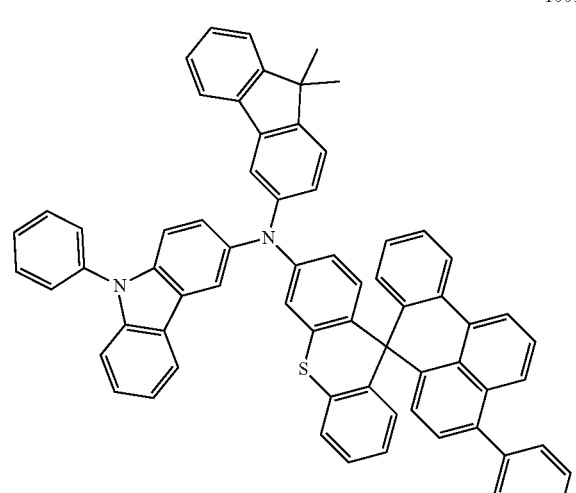
1002
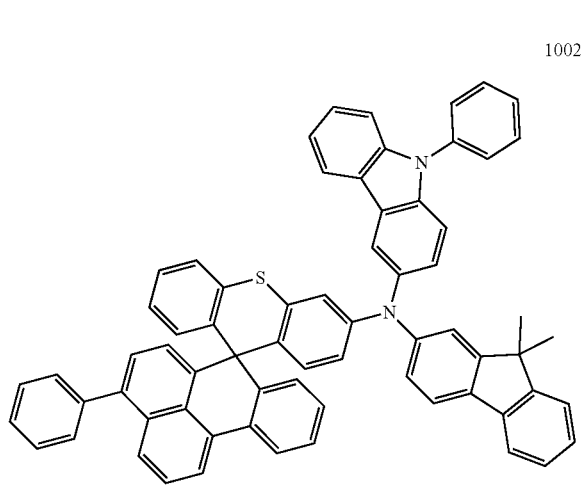
802
-continued
1003
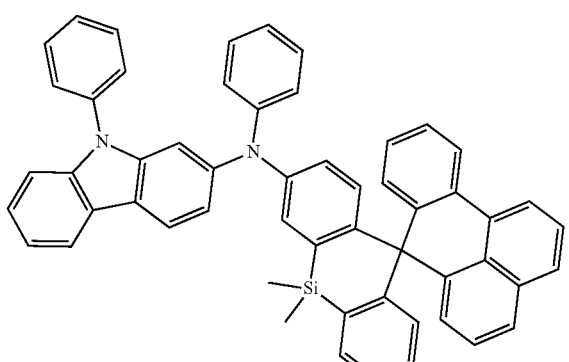
1004
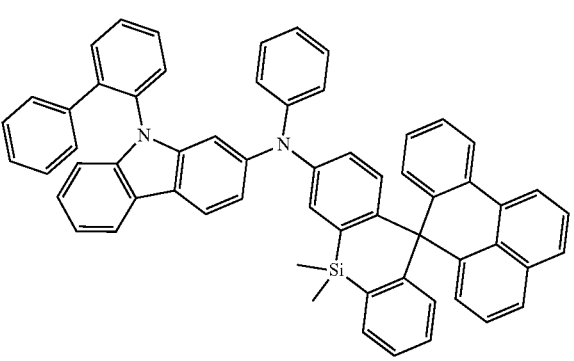
1005
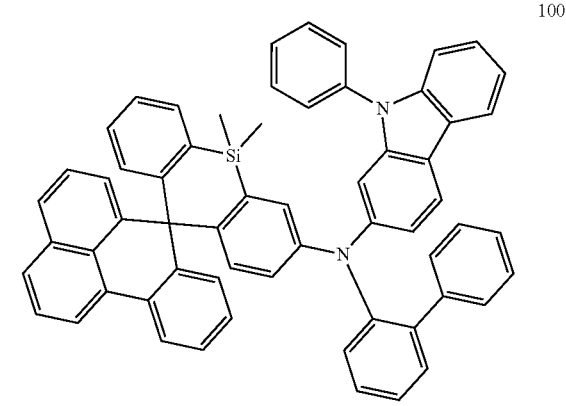
1006
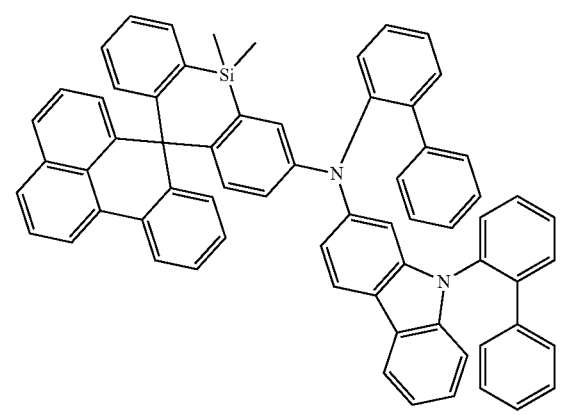

803
-continued
1007
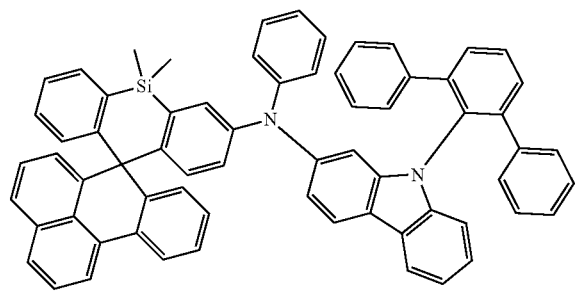
1008
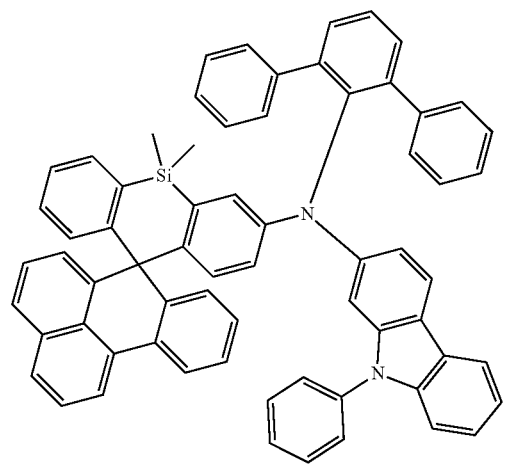
1009
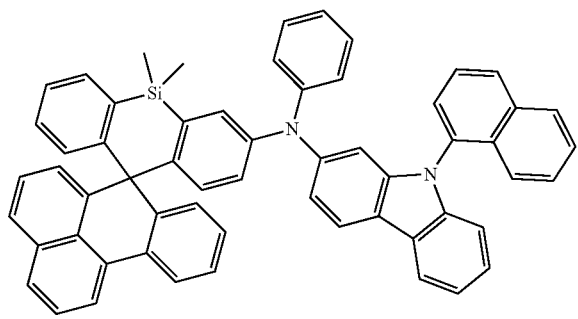
1010
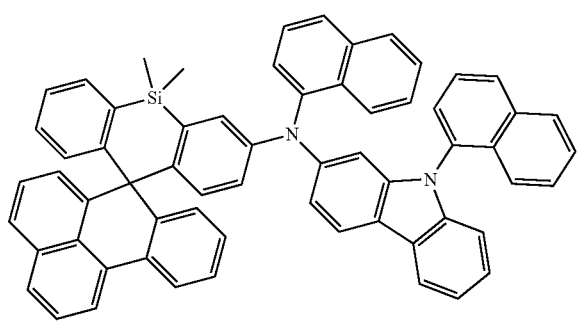
804
-continued
1011
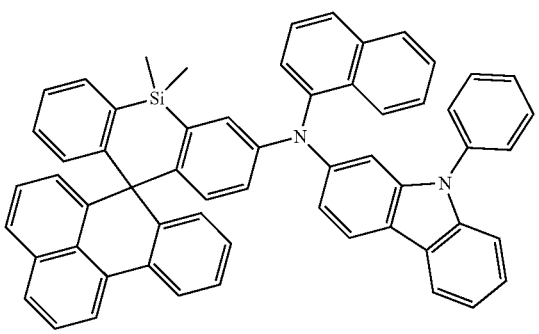
1012
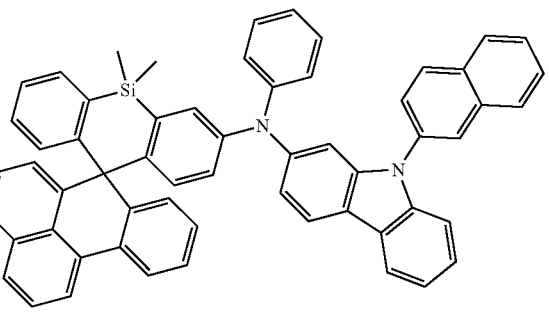
1013
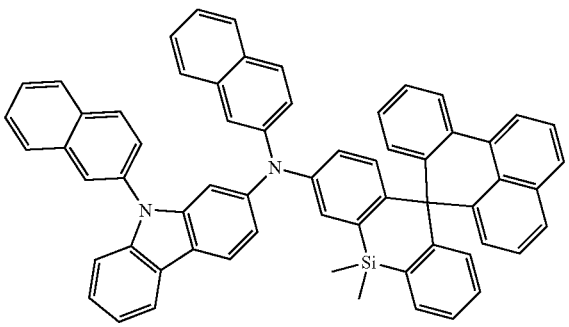
1014
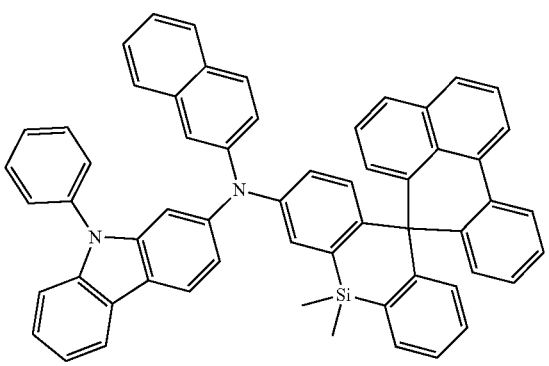

1015
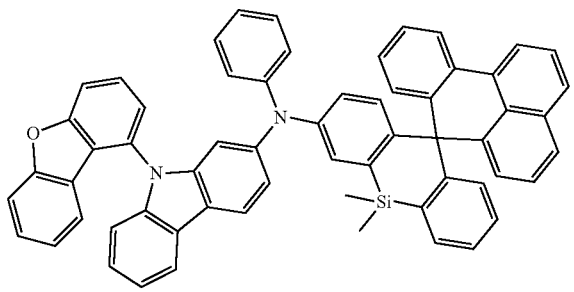
1016
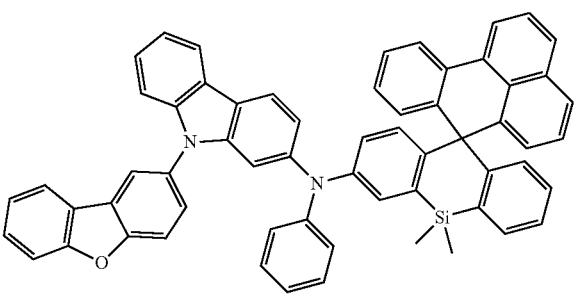
1017
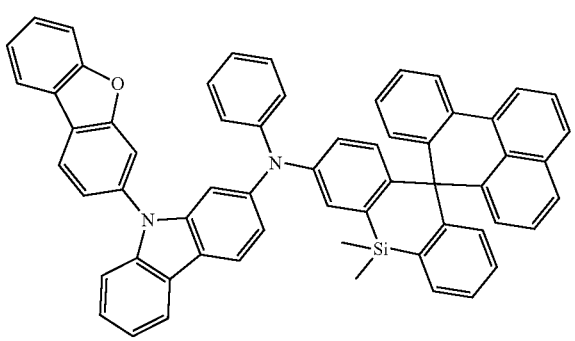
1018
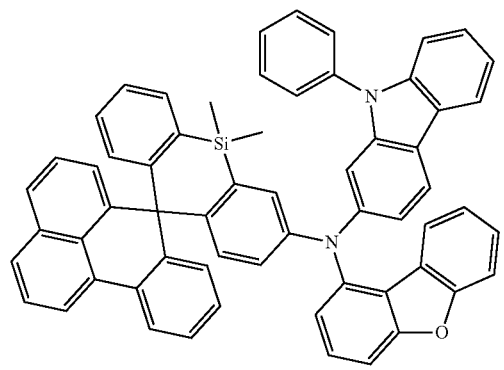
1019
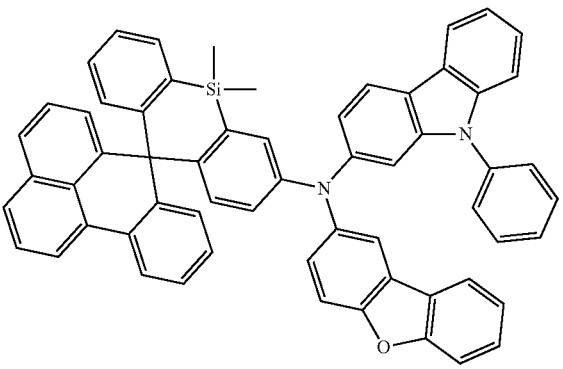
1020
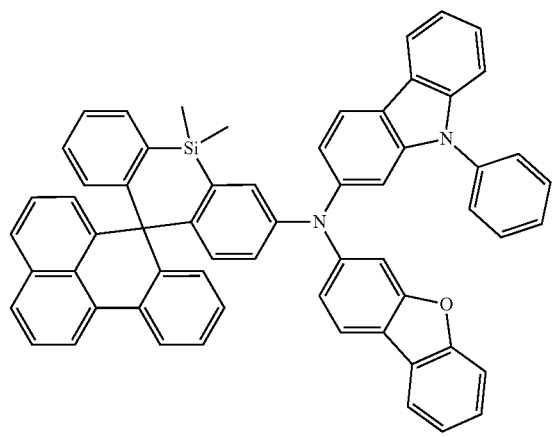
1021
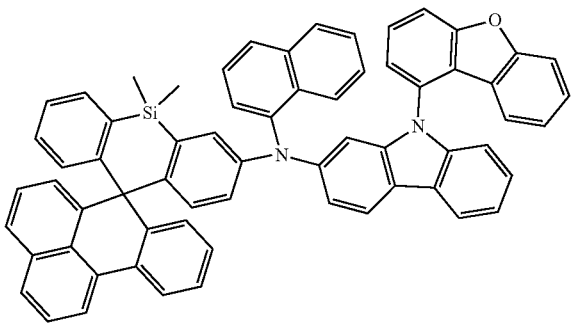
1022
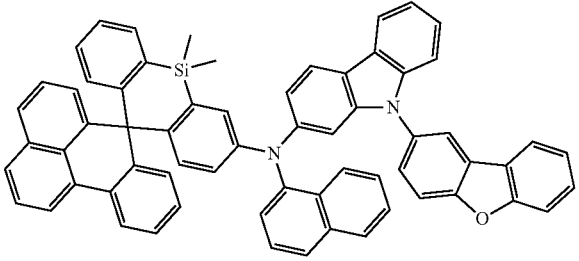

1023
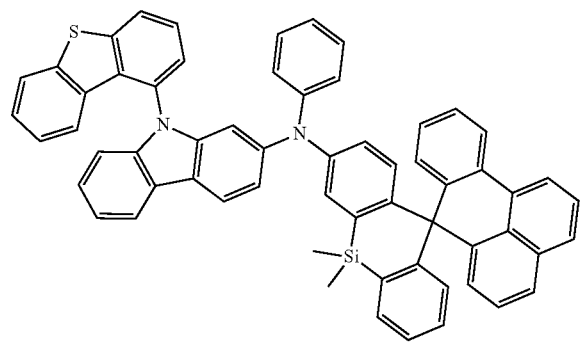
1024
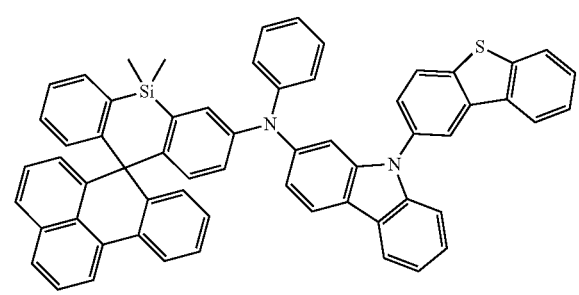
1025
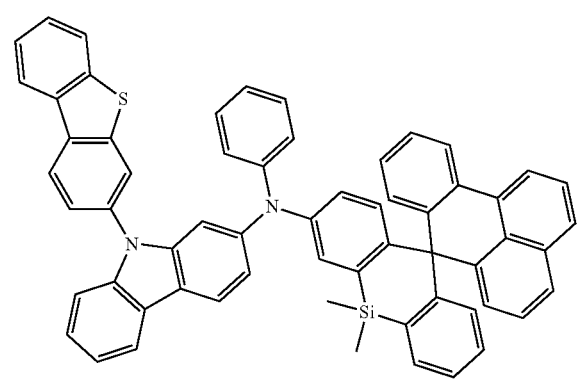
1026
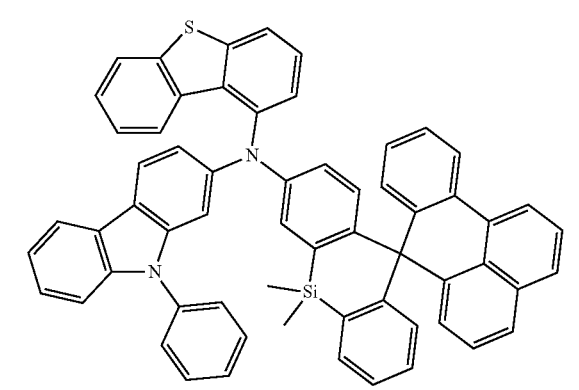
1027
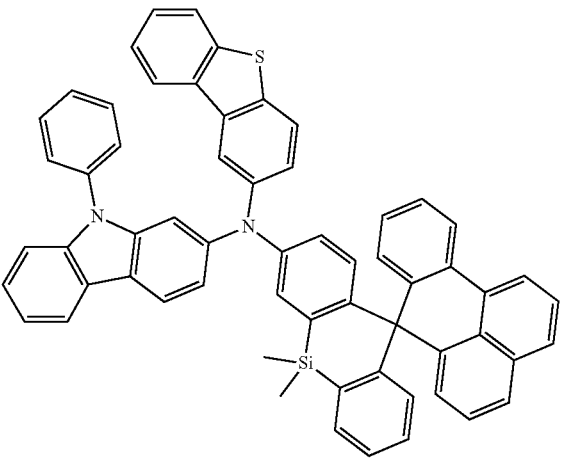
1028
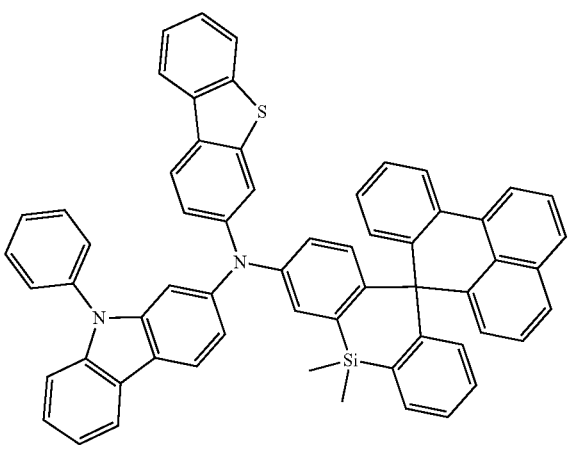
1029
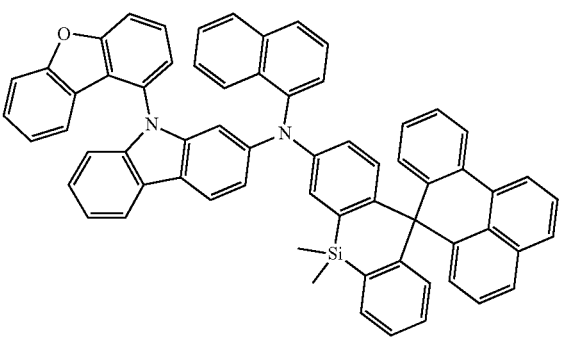
1030
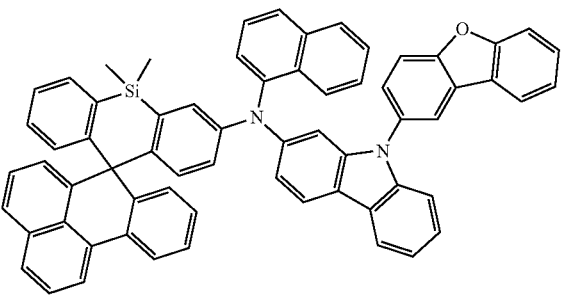

1031
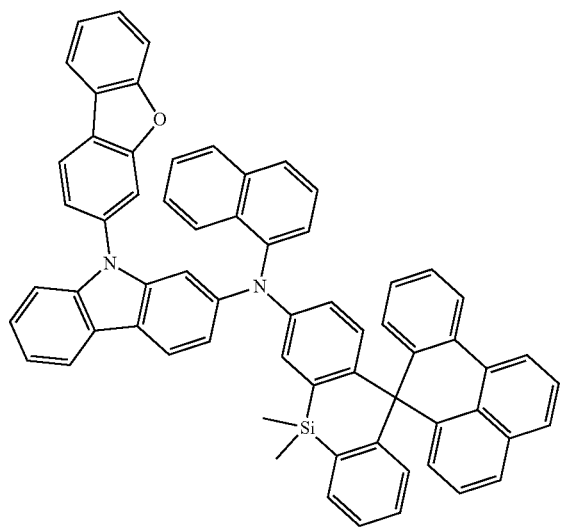
1032
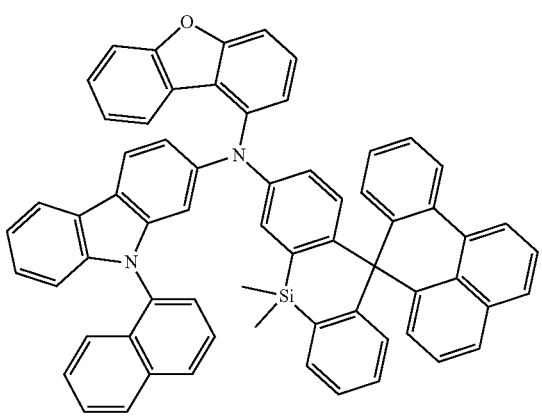
1033
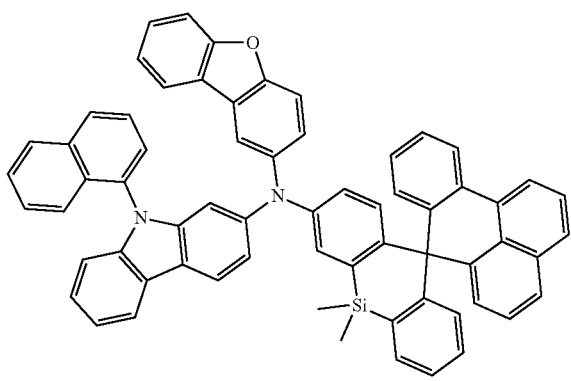
-continued
1034
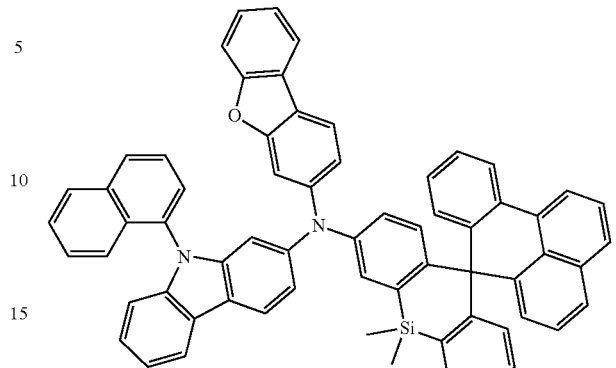
1035
1036
1037
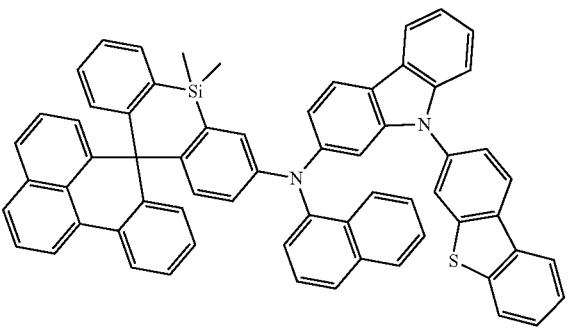

| 1038 | 1042 |
|---|---|
| 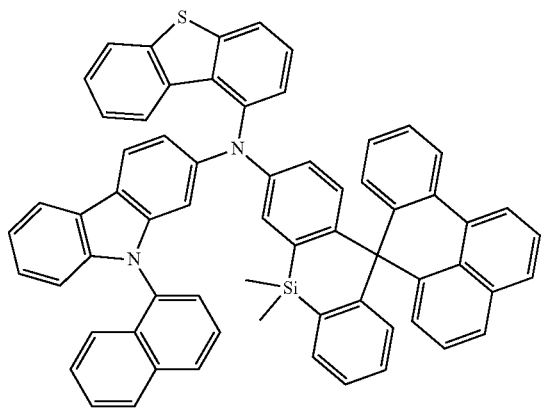 | 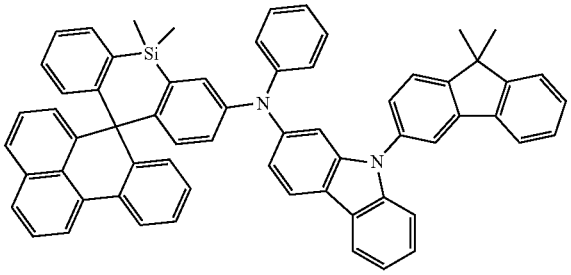 |
| 1039 | 1043 |
| 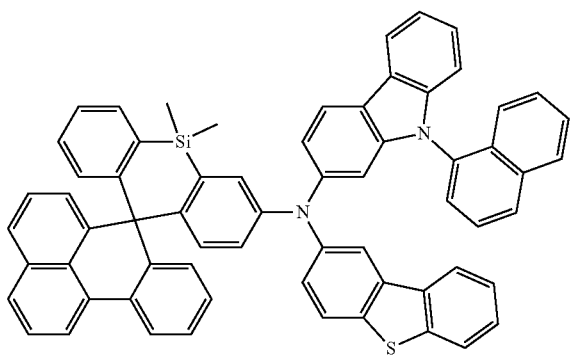 | 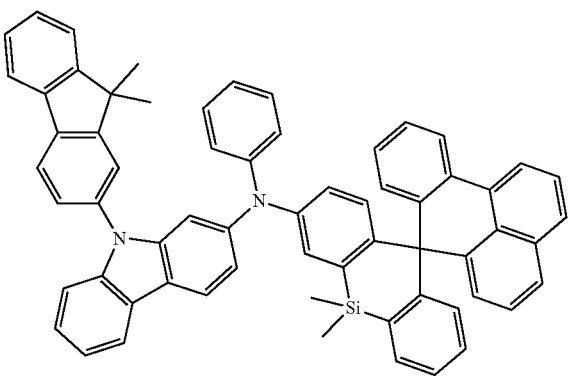 |
| 1040 | 1044 |
| 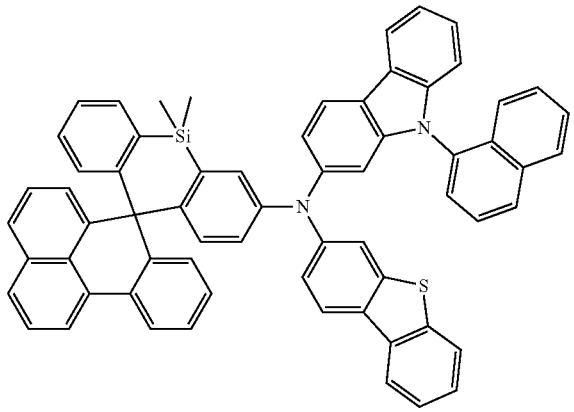 | 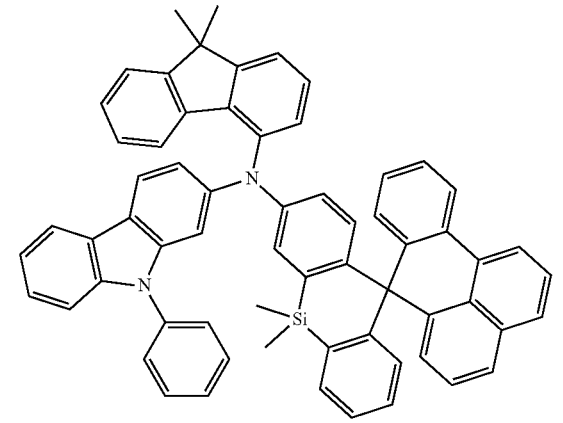 |
| 1041 | 1045 |
| 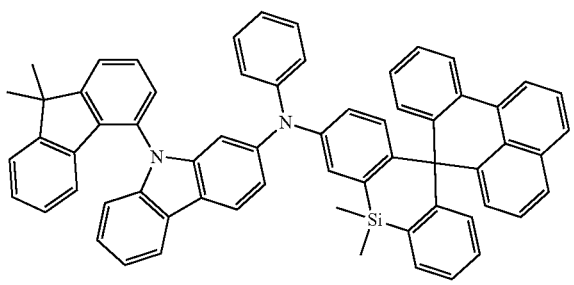 | 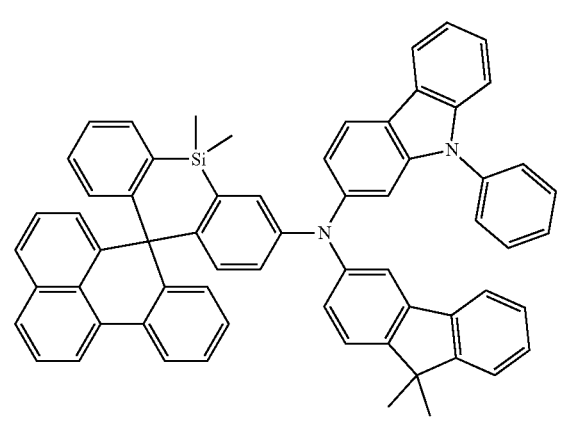 |

1046
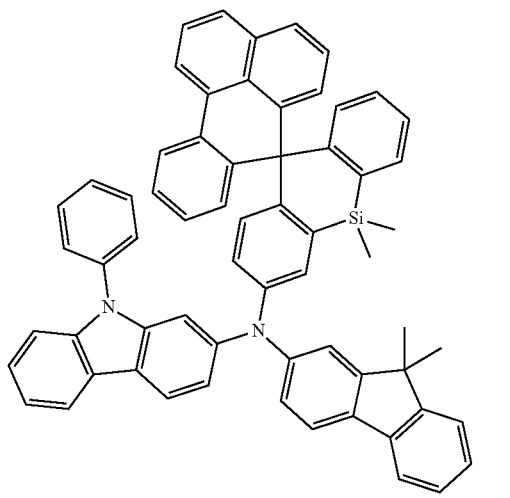
1047
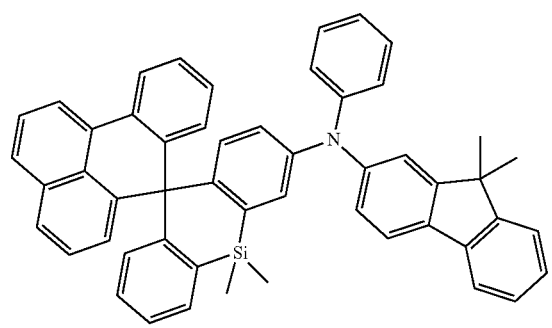
1048
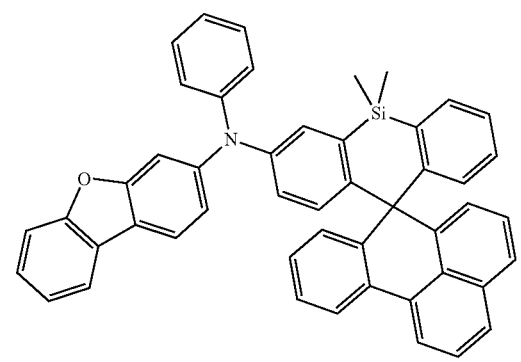
1049
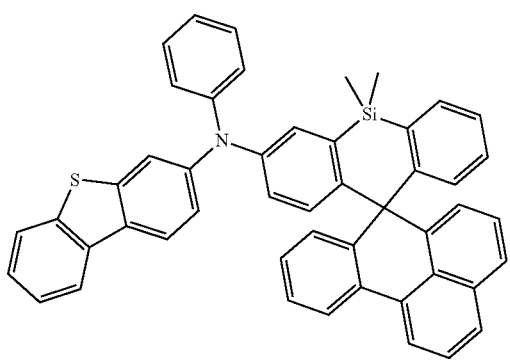
1050
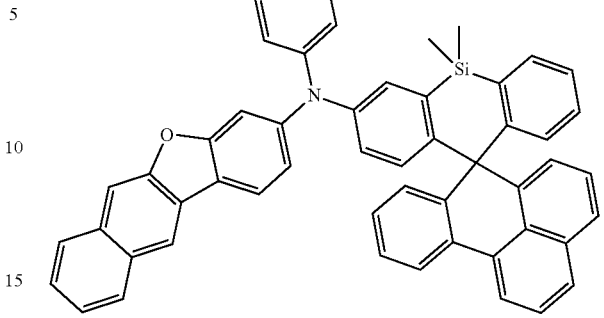
1051
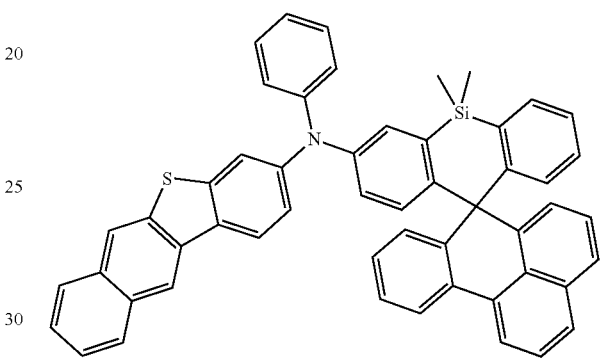
1052
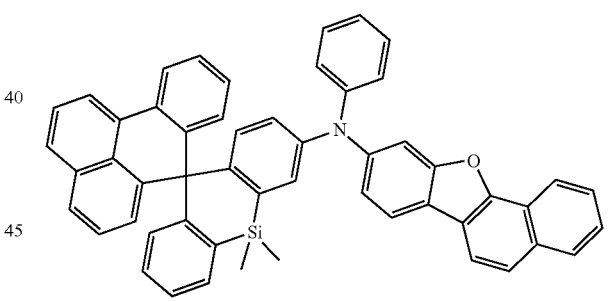
1053
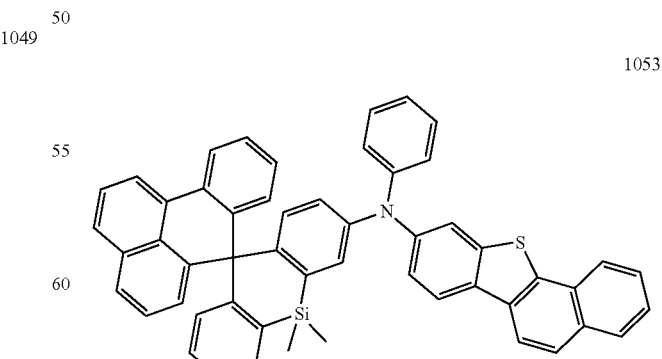

815
-continued
1054
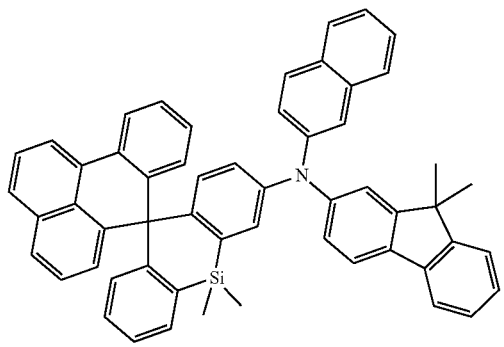
1055
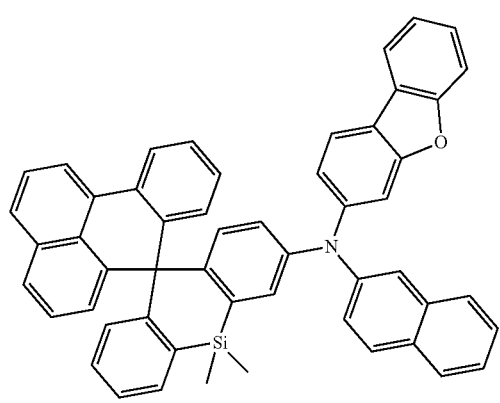
1056
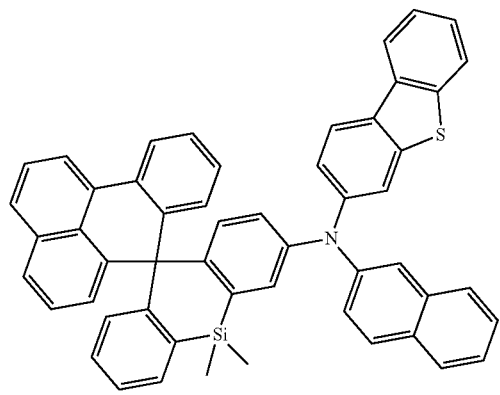
1057
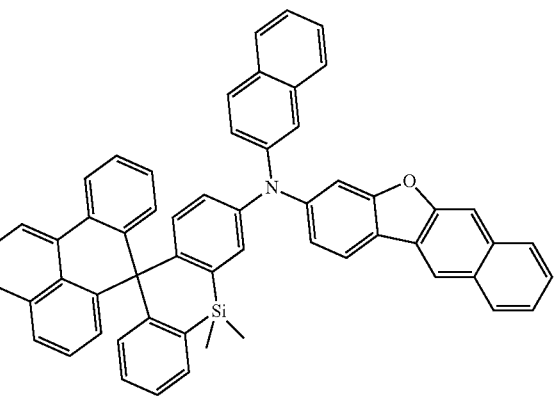
816
-continued
1058
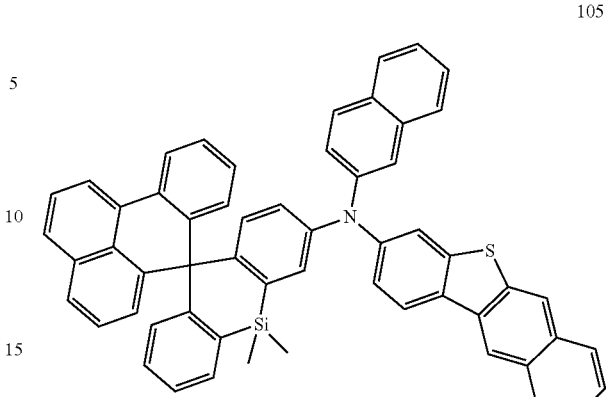
1059
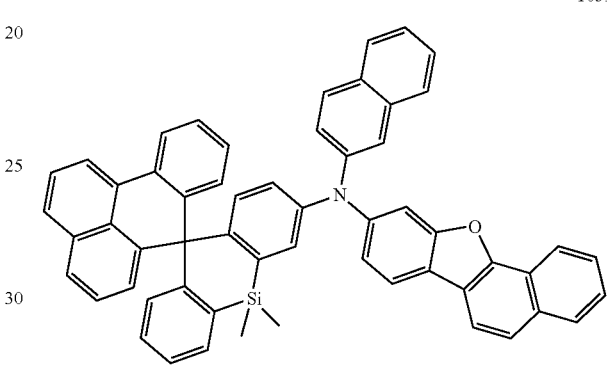
1060
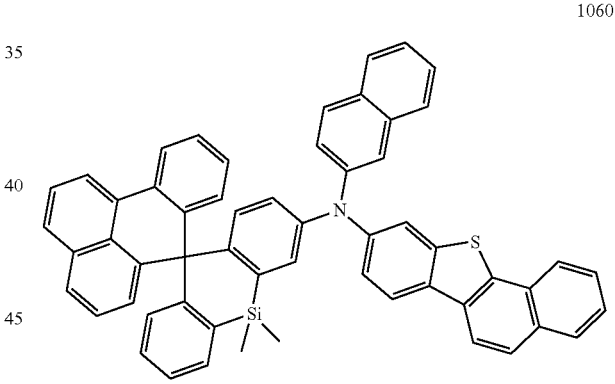
1061
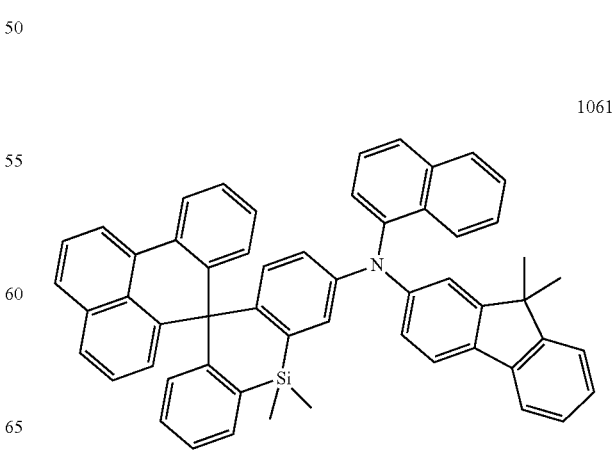

817
-continued
1062
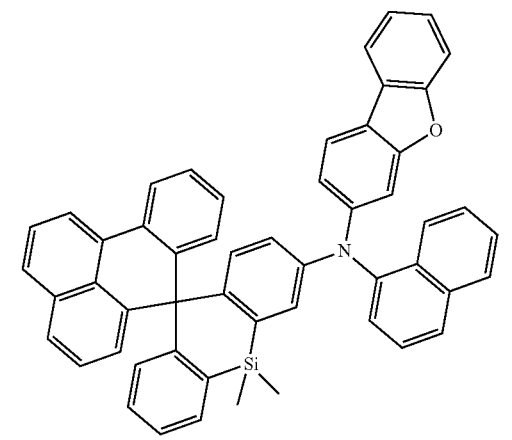
1063
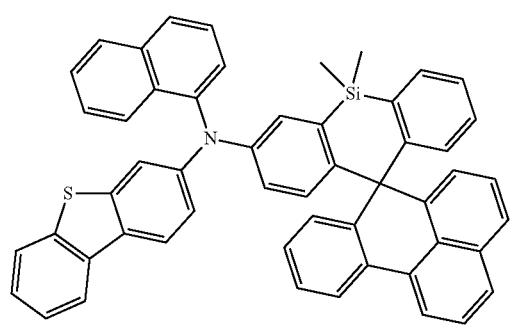
1064
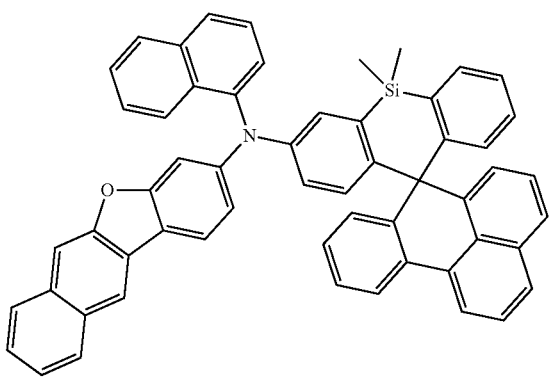
1065
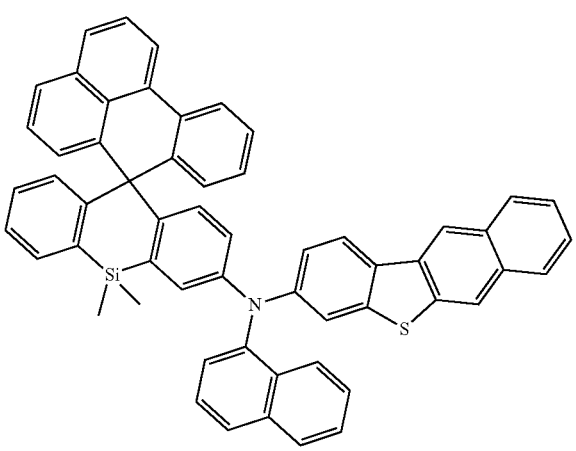
818
-continued
1066
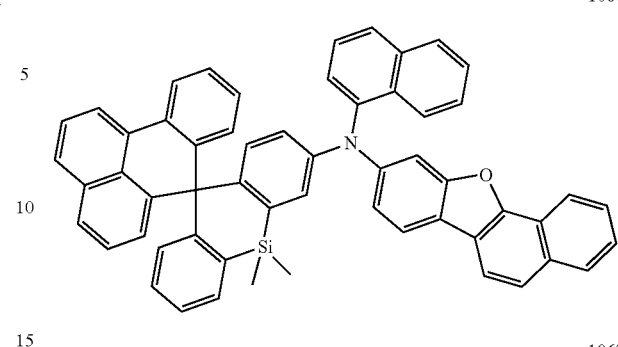
1067
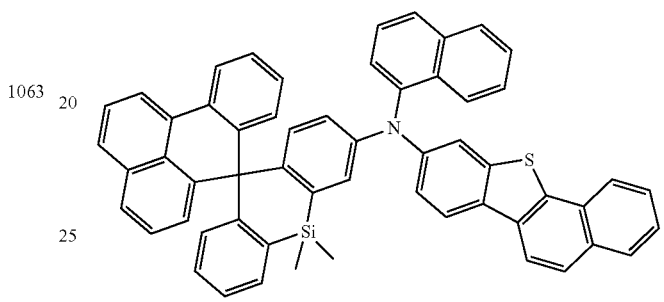
1068
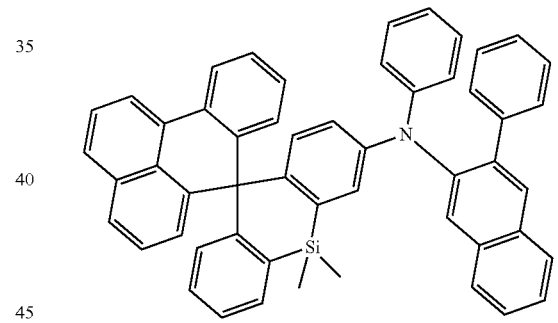
1069
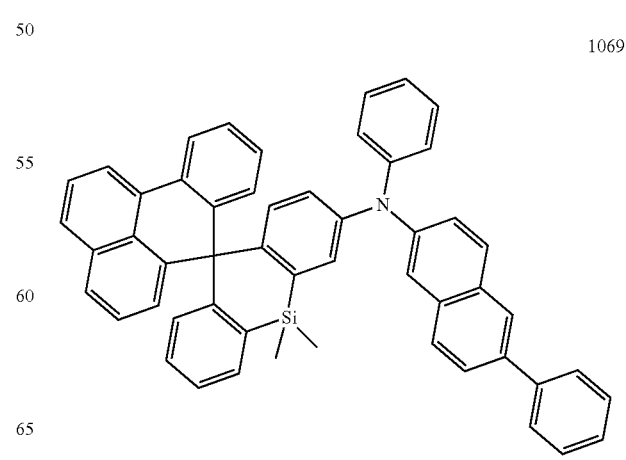

819
-continued
1070
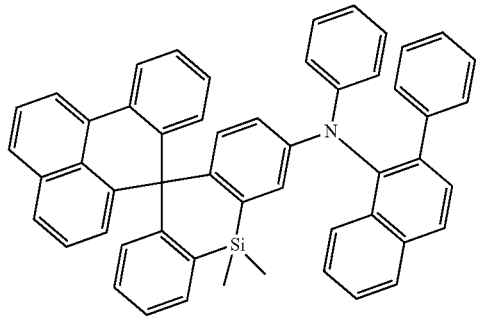
1071
1072
1073
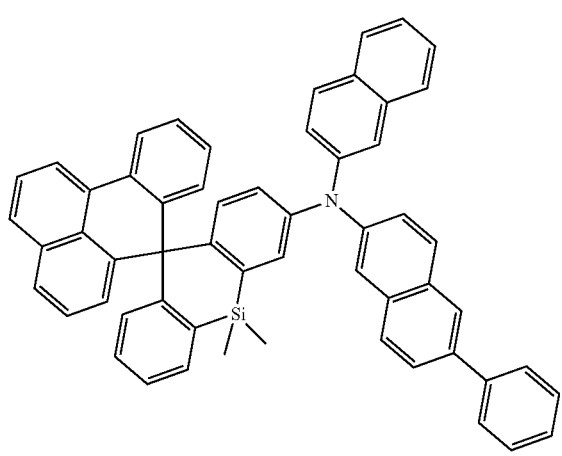
820
-continued
1074
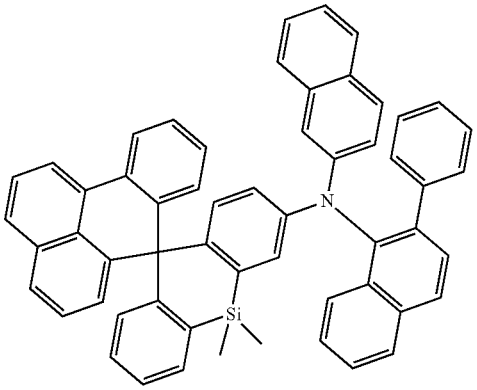
1075
1076
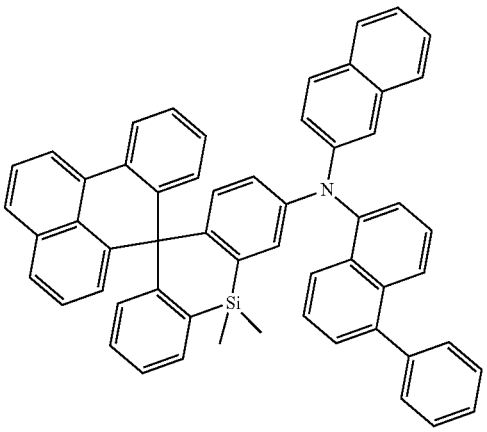
1077
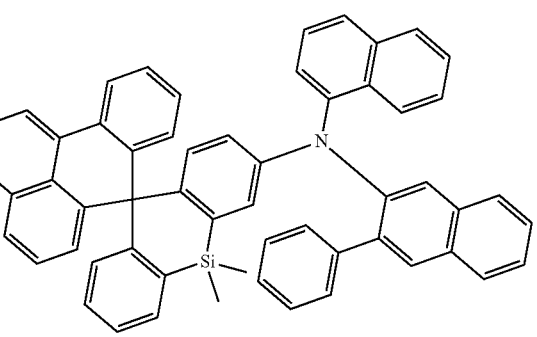

821
-continued
1078
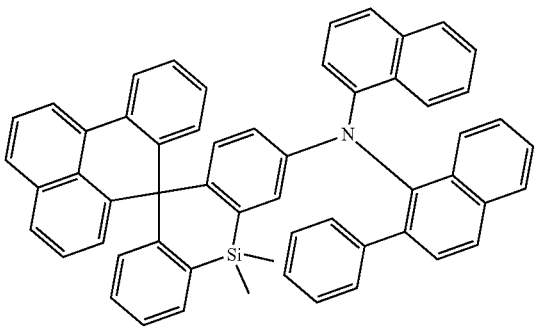
1079
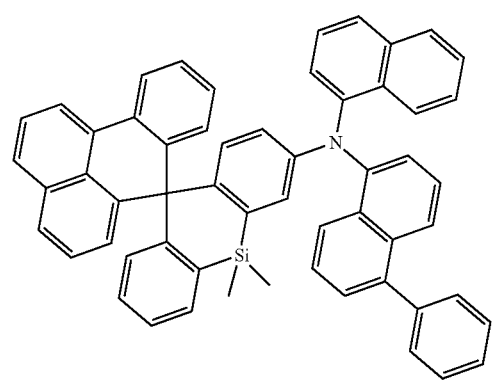
1080
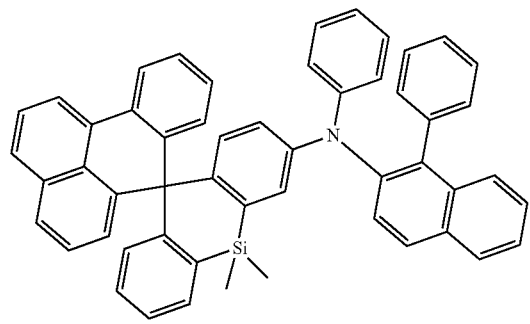
1081
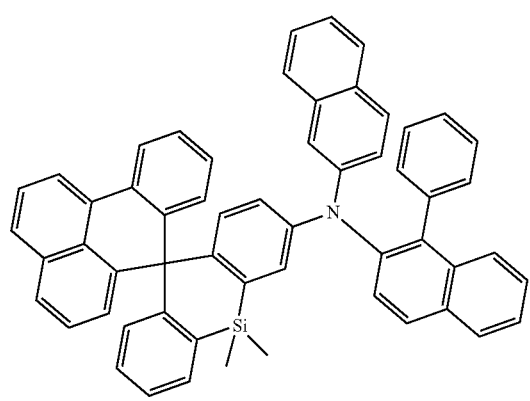
822
-continued
1082
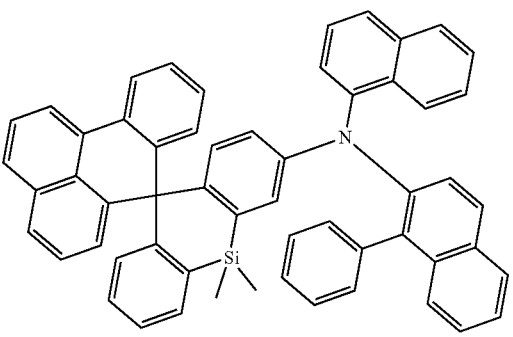
1083
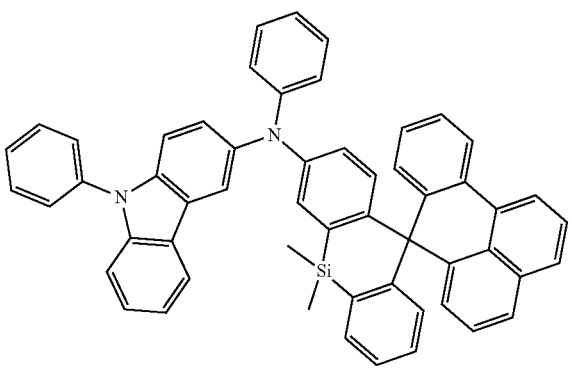
1084
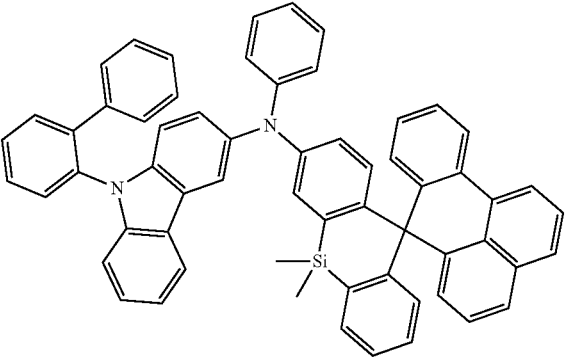
1085
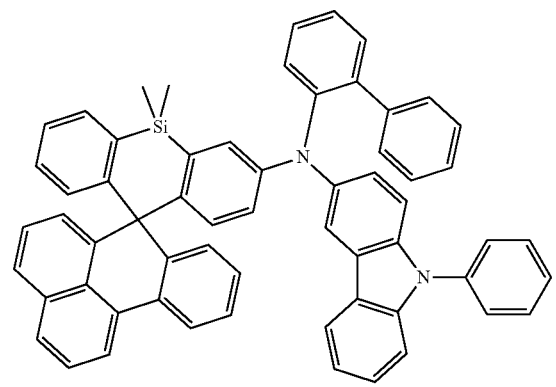

1086
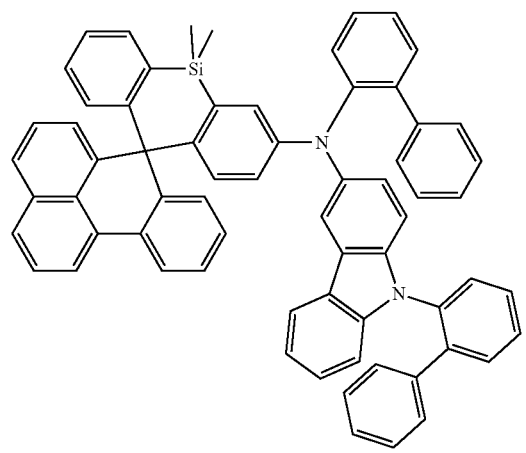
1087
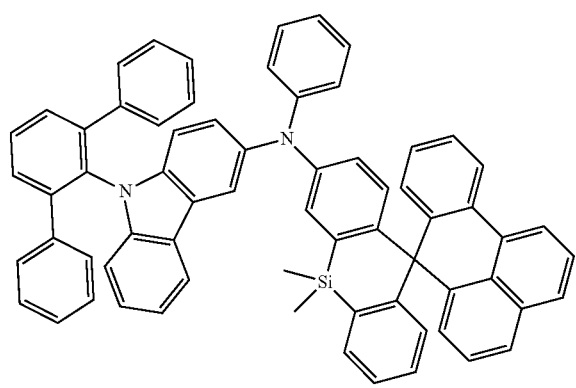
1088
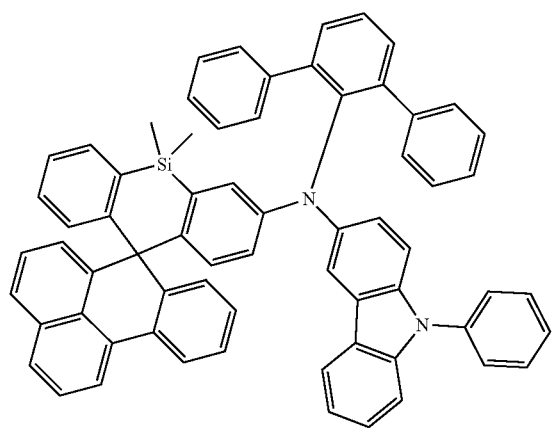
1089
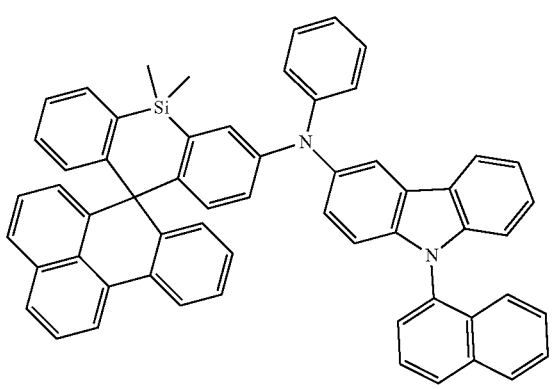
1090
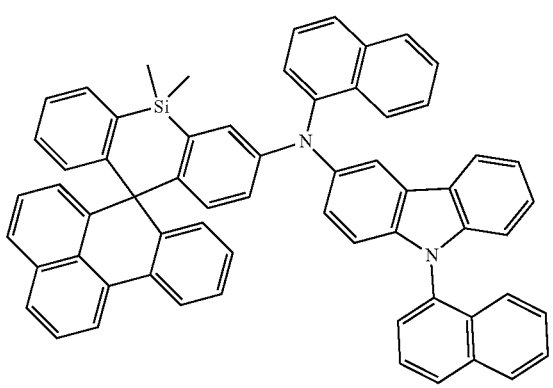
1091
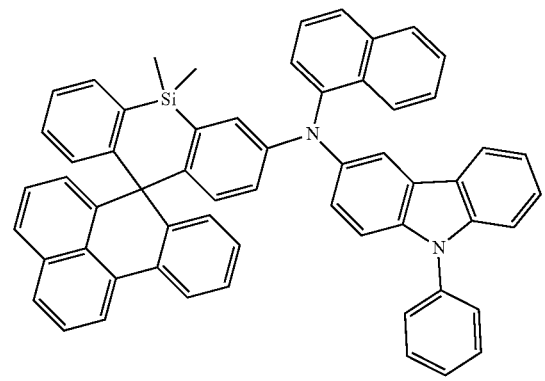

825
-continued
1092
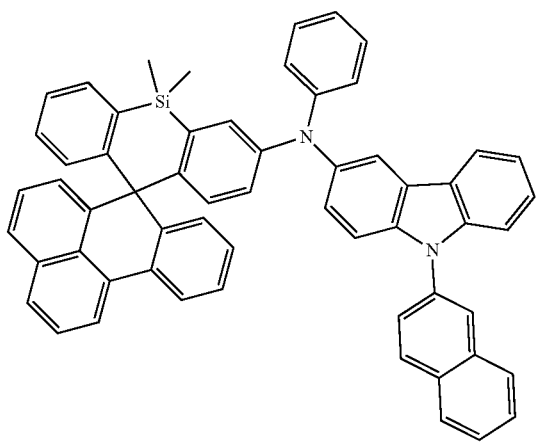
1093
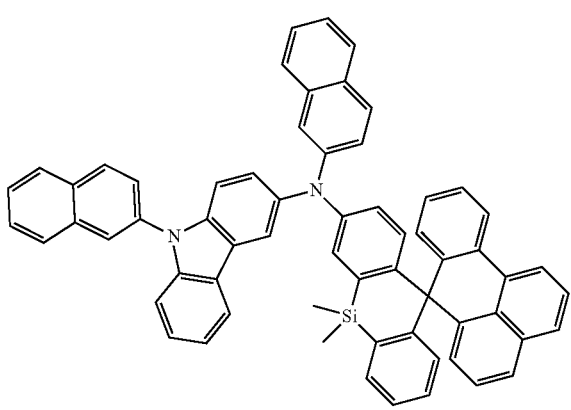
1094
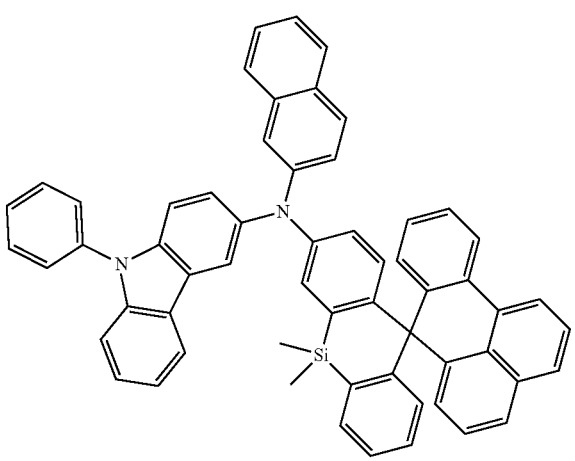
826
-continued
1095
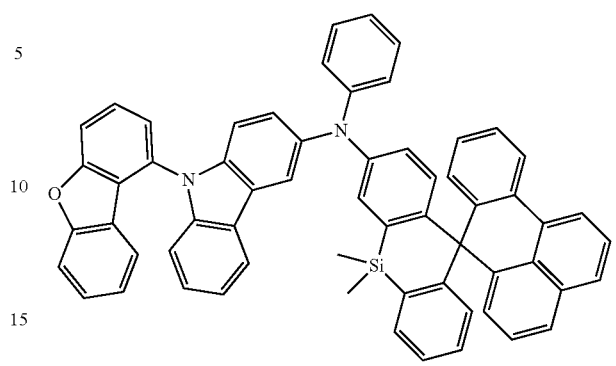
1096
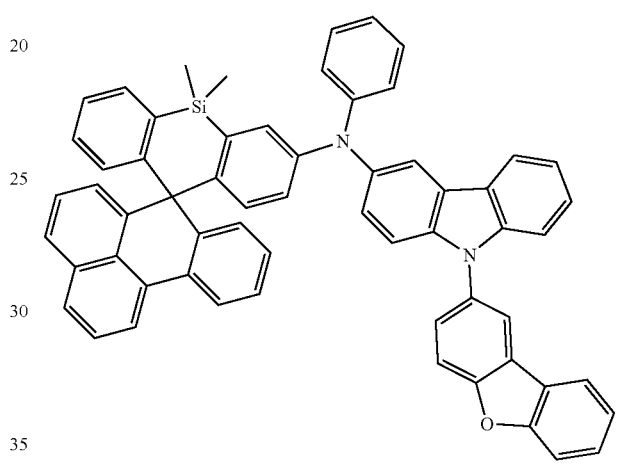
1097
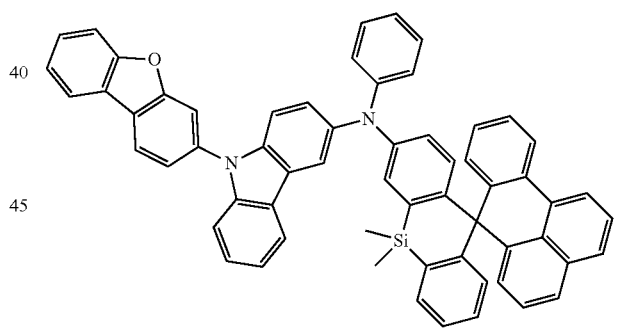
1098
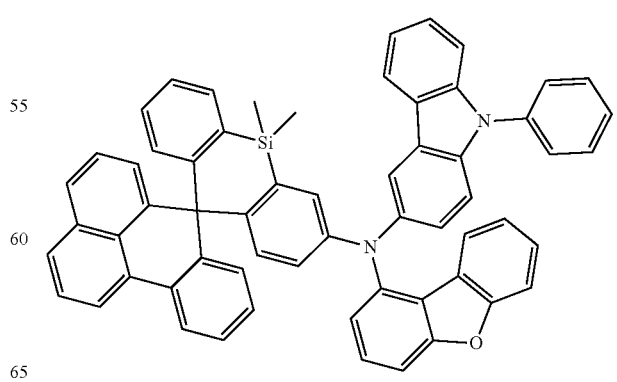

-continued
1099
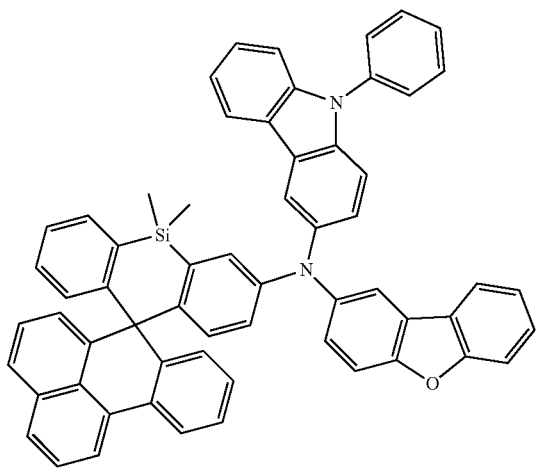
1100
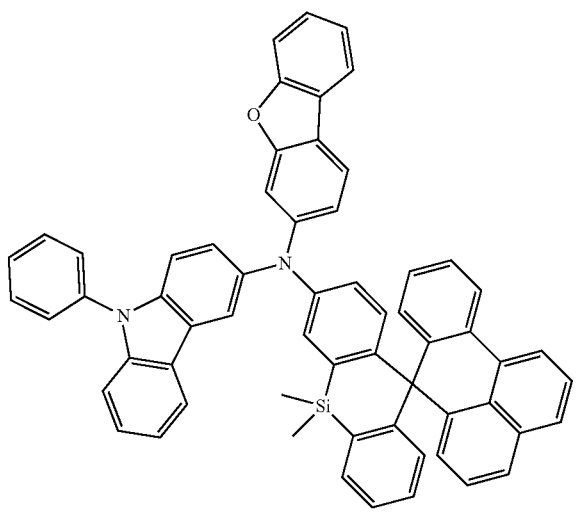
1101
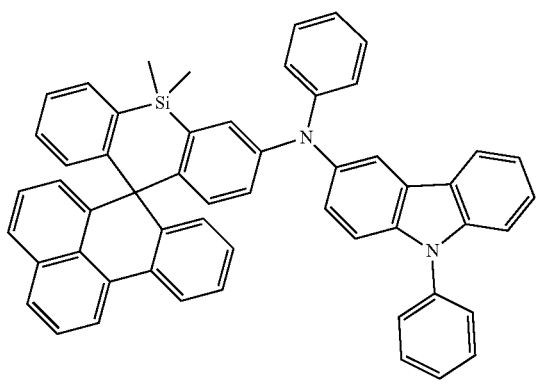
-continued
1102
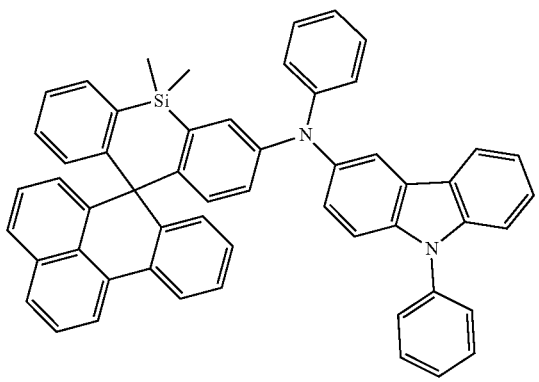
1103
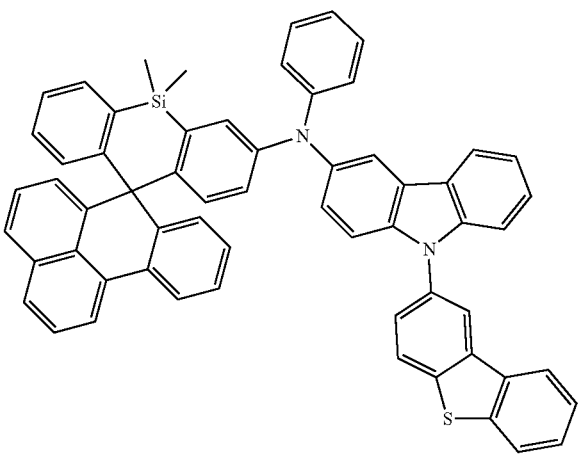
1104
1105
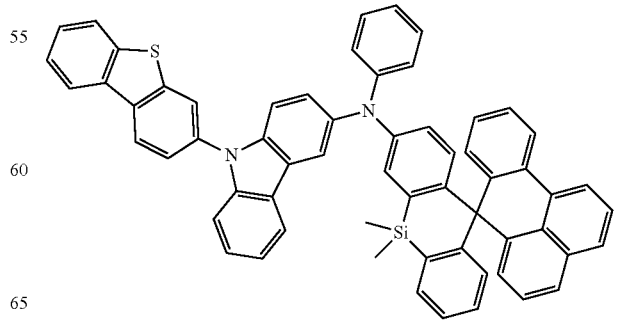

829
-continued
1106
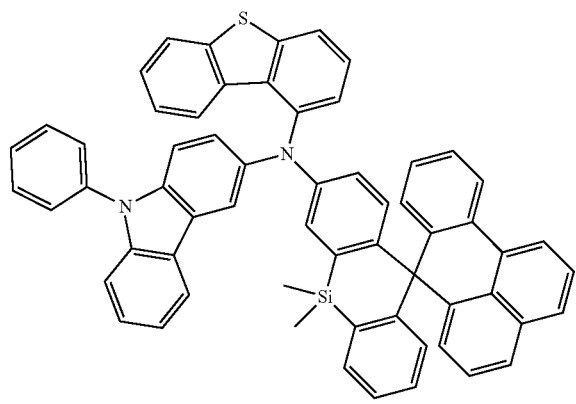
1107
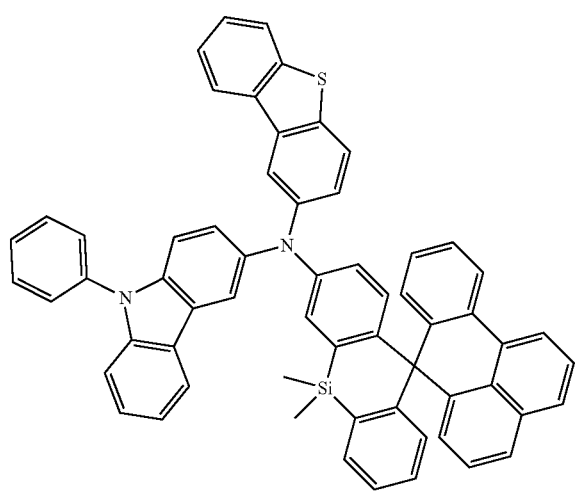
1108
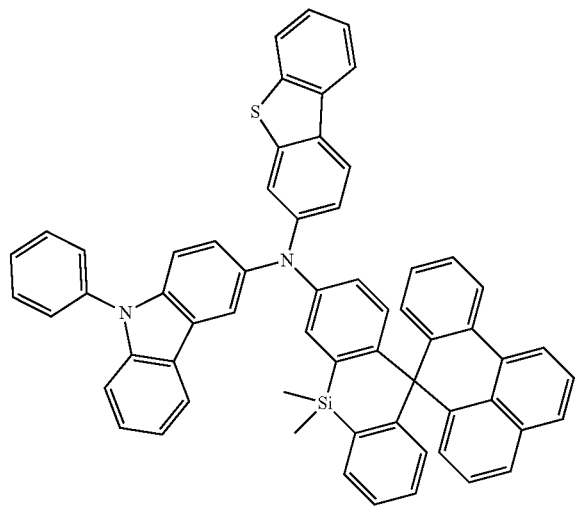
830
-continued
1109
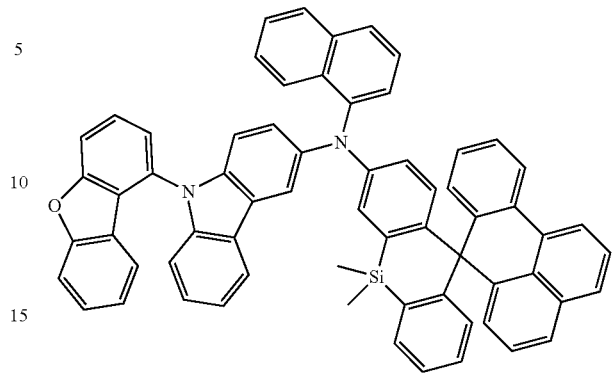
1110
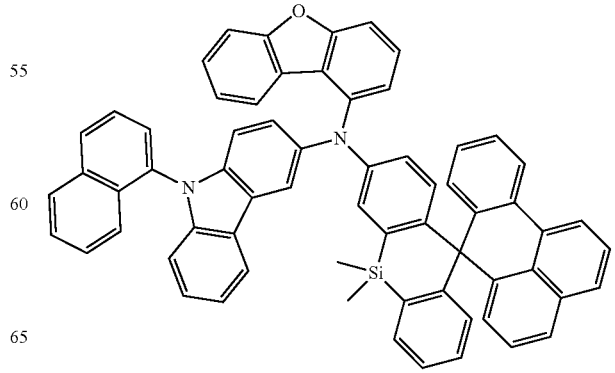
1111
1112

831
-continued
1113
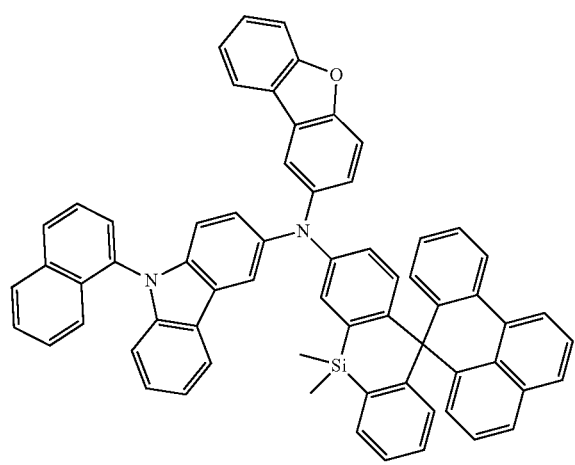
1114
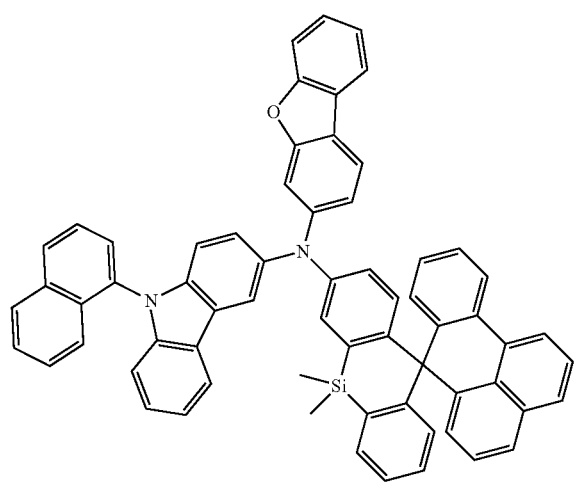
1115
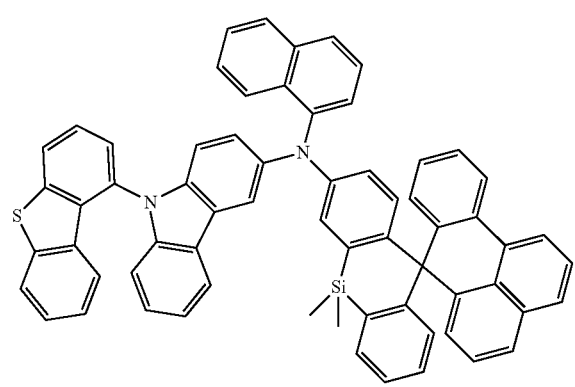
832
-continued
1116
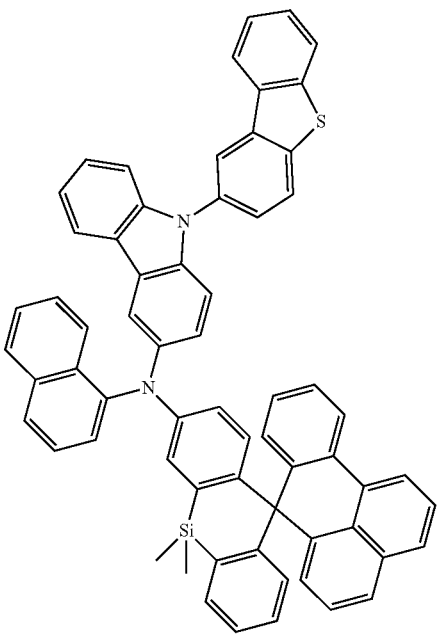
1117
1118
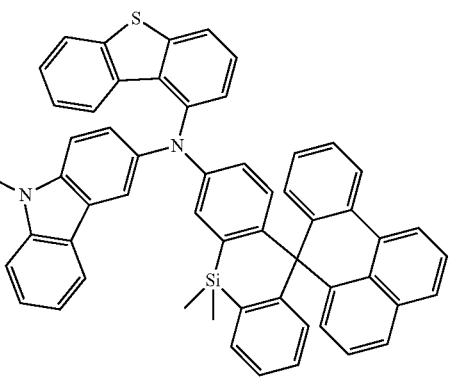

1119
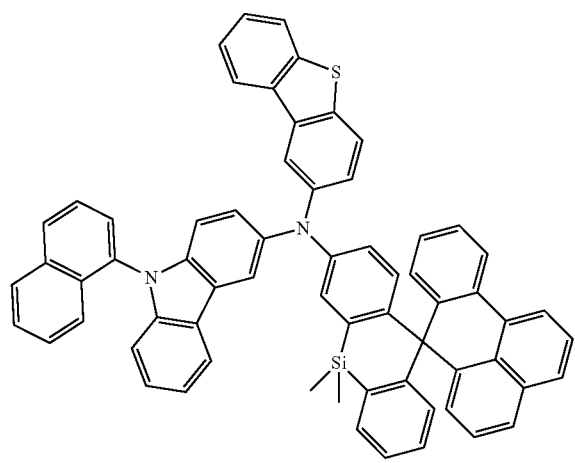
1120
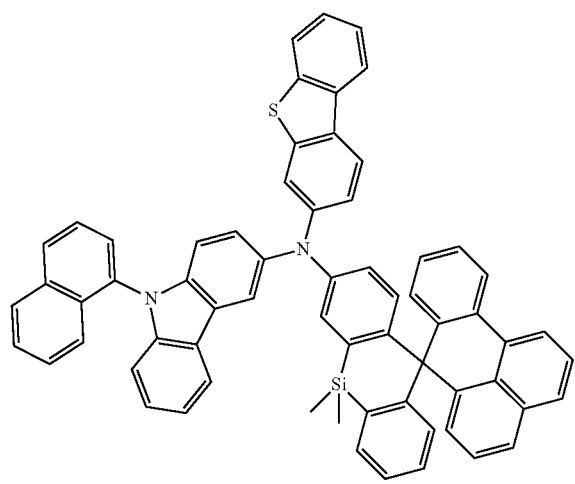
1121
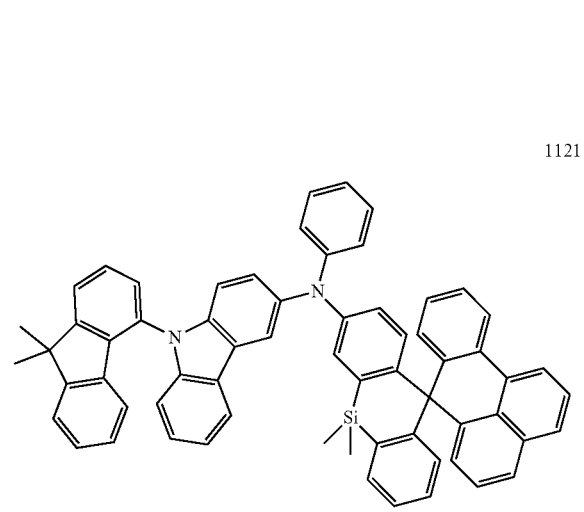
1122
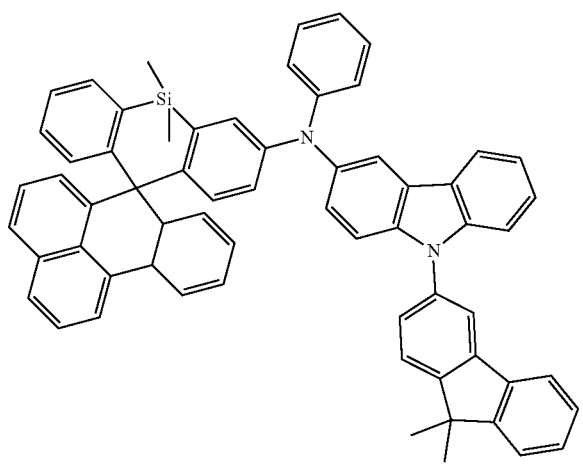
1123
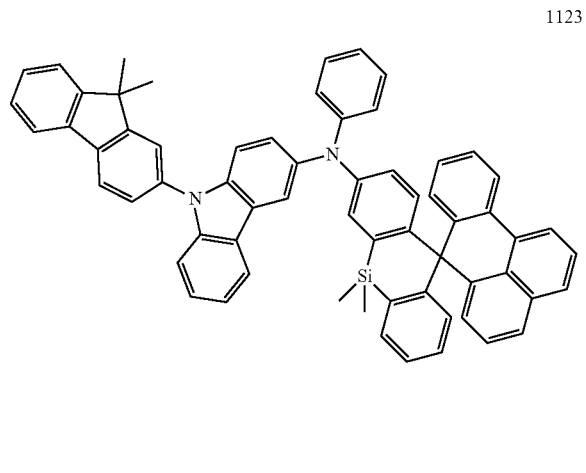
1124
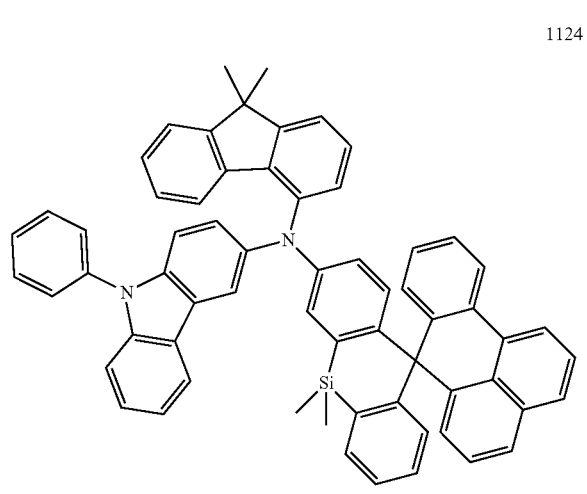

835
-continued
1125
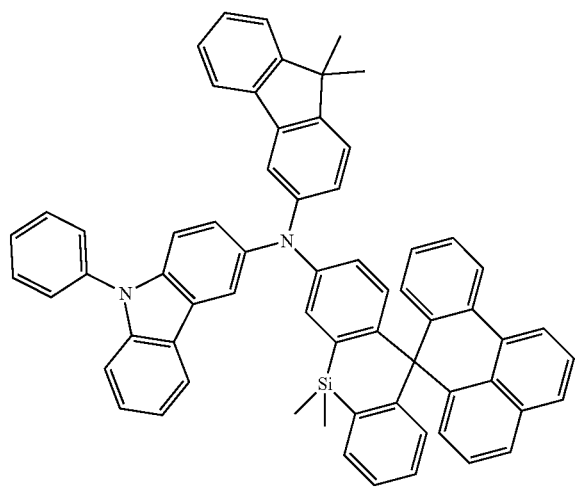
1126
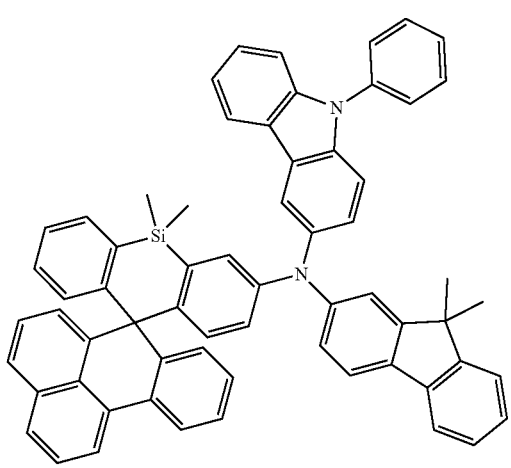
1127
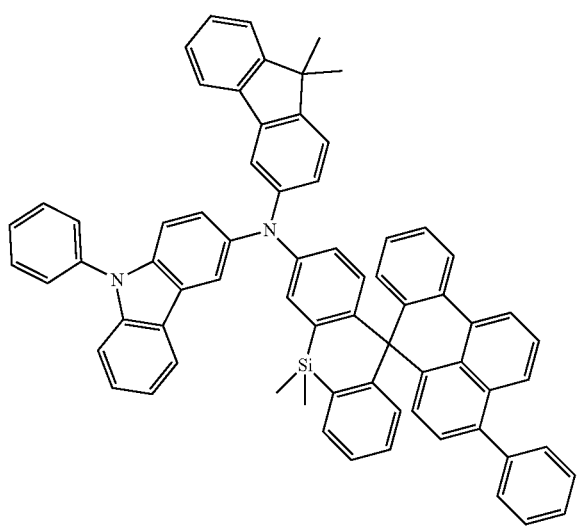
836
-continued
1128
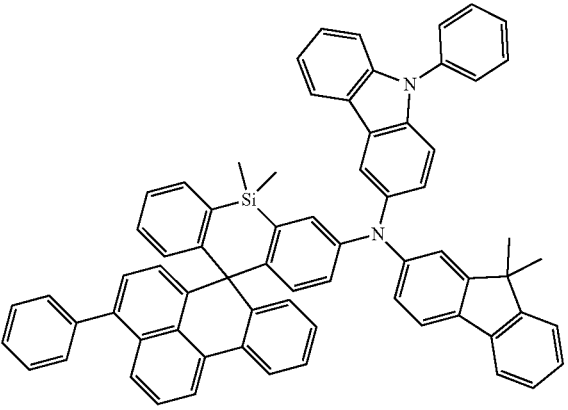
1129
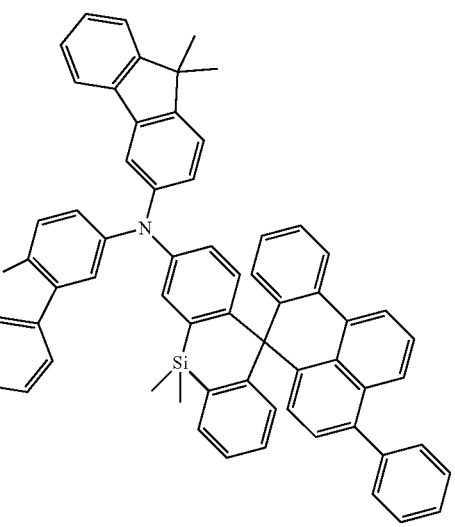
1130
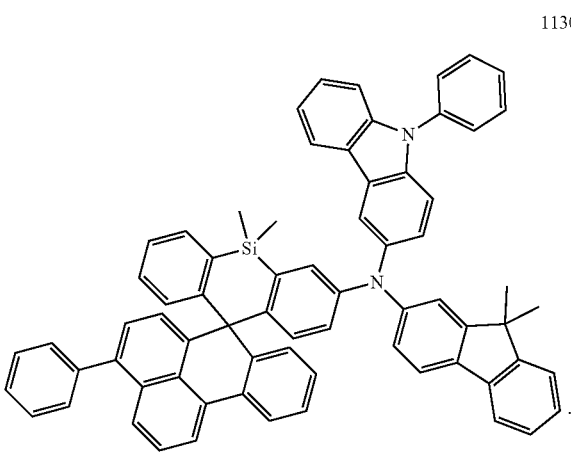
* * * * *

UNITED STATES PATENT AND TRADEMARK OFFICE
CERTIFICATE OF CORRECTION

PATENT NO. : 12,250,878 B2
APPLICATION NO. : 17/445484
DATED : March 11, 2025
INVENTOR(S) : Hankyu Pak et al.

It is certified that error appears in the above-identified patent and that said Letters Patent is hereby corrected as shown below:

In the Claims

In Column 410, Line 65, in Claim 10, below " 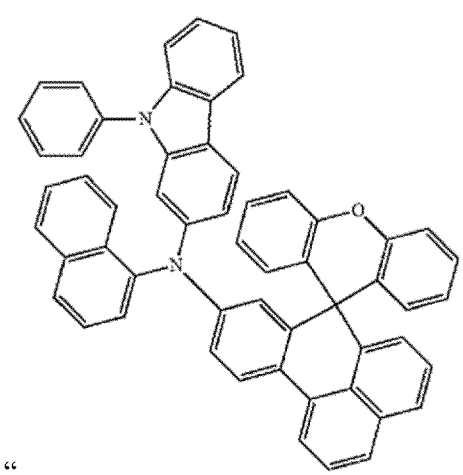 " insert

Signed and Sealed this
Fifteenth Day of July, 2025

Coke Morgan Stewart
*Acting Director of the United States Patent and Trademark Office*

CERTIFICATE OF CORRECTION (continued)
U.S. Pat. No. 12,250,878 B2

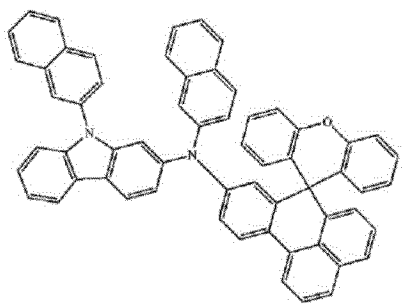

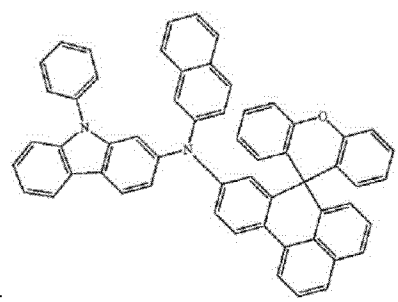

-- --.

In Column 445, Lines 53-66, in Claim 10, below " 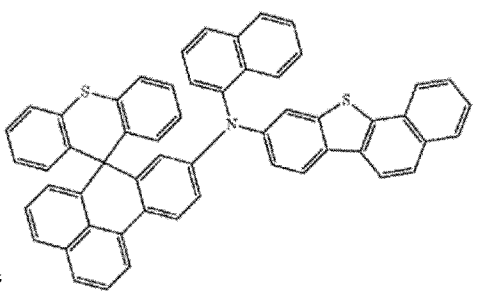 " delete

" 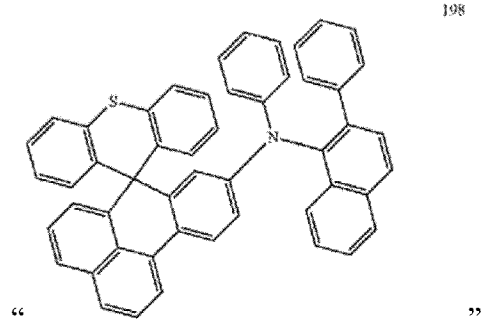 ".

In Column 446, Lines 3-16, in Claim 10, above " 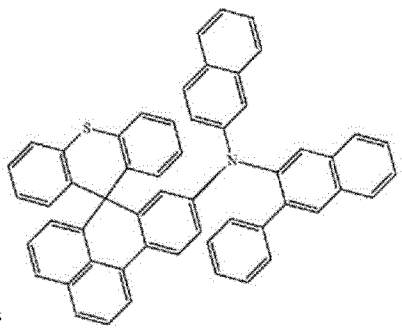 " delete
" 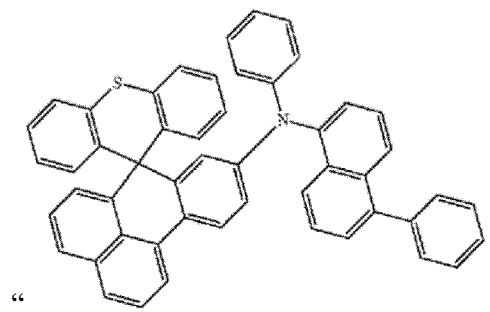 ".
In Column 450, Line 20, in Claim 10, below " 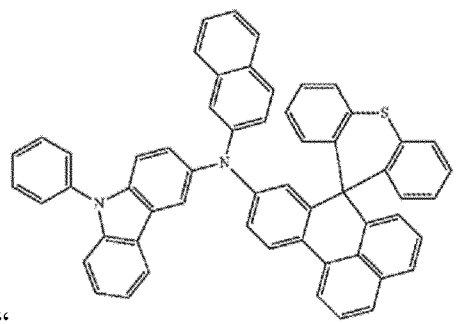 " insert
-- 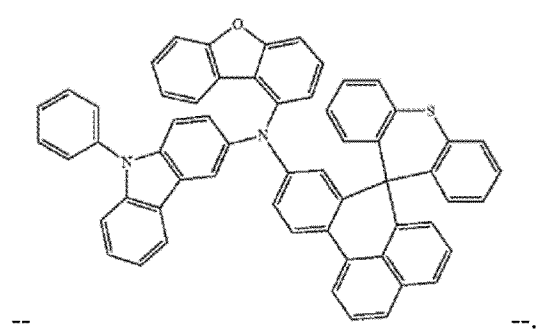 --.

In Column 485, Lines 48-63, in Claim 10, Compound 435, delete
" 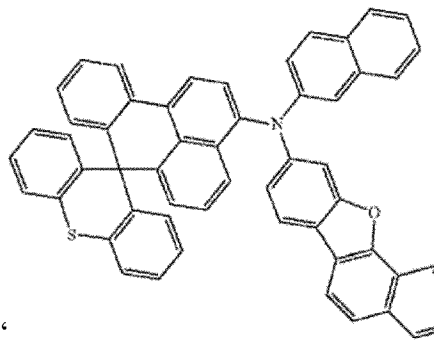 " and insert -- 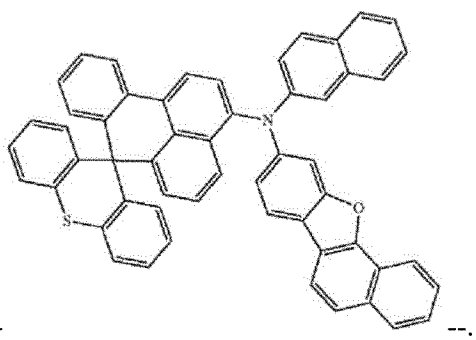 --.
In Column 501, Line 15, in Claim 10, above " 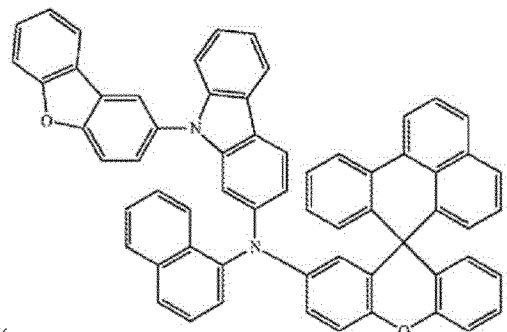 " insert
-- 522 --.
In Column 542, Lines 29-42, in Claim 10, Compound 748, delete
" 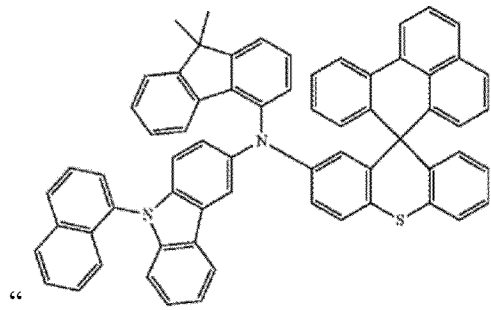 " and insert -- 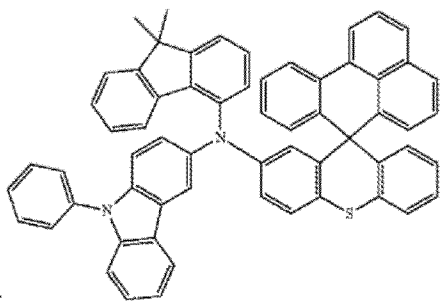 --.
In Column 550, Lines 3-19, in Claim 10, Compound 792, delete " 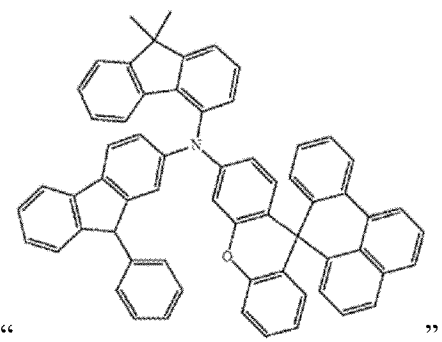 "

and insert -- 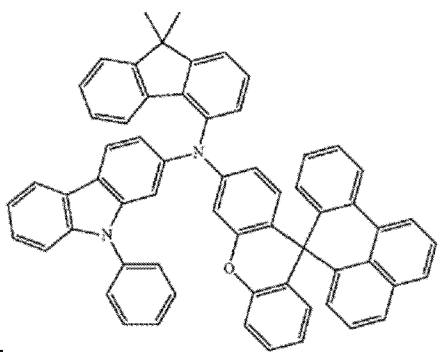 --.
In Column 551, Lines 49-63, in Claim 10, Compound 805, delete " 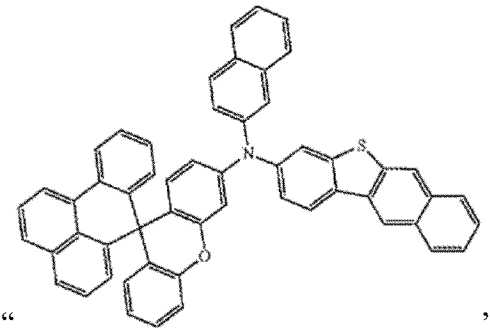 " and insert -- 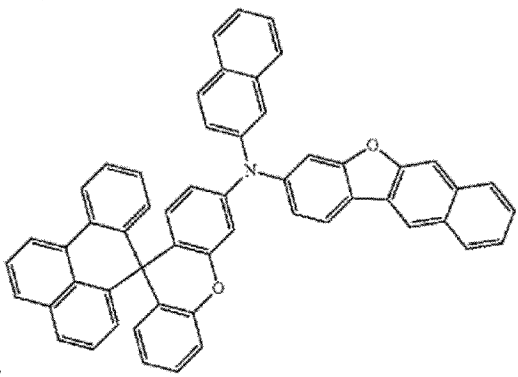 --.
In Column 606, Lines 16-30, in Claim 10, Compound 1079, delete " 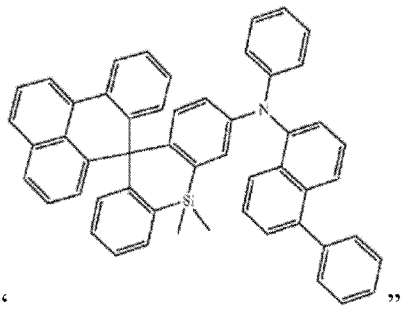 "
and insert -- 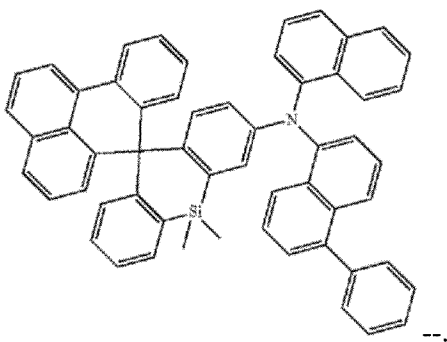 --.

In Column 608, Lines 4-17, in Claim 10, Compound 1086, delete
" 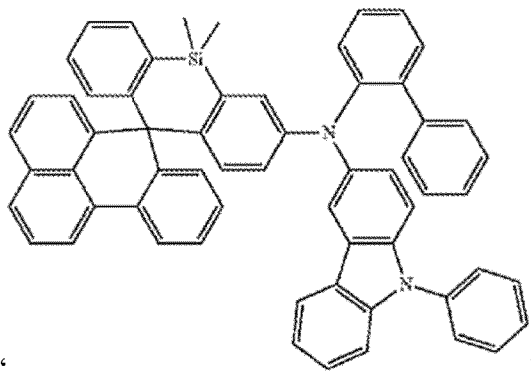 " and insert -- 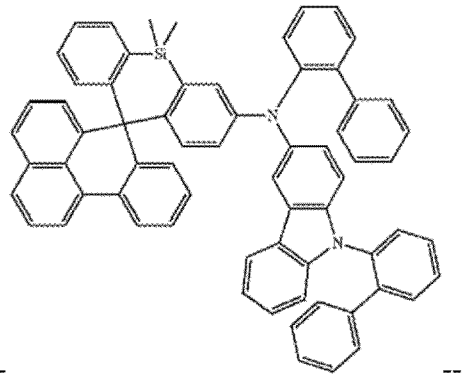 --.
In Column 677, Line 34, in Claim 18, delete "307" and insert -- 308 --.
In Column 683, Lines 26-40, in Claim 18, Compound 342, delete
" 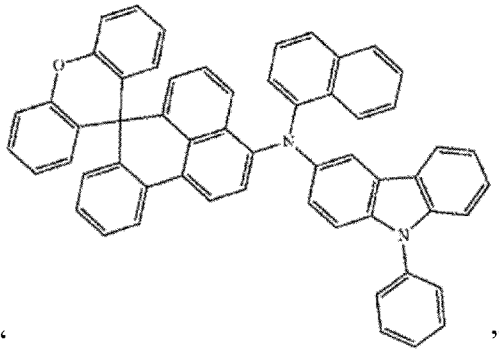 " and insert -- 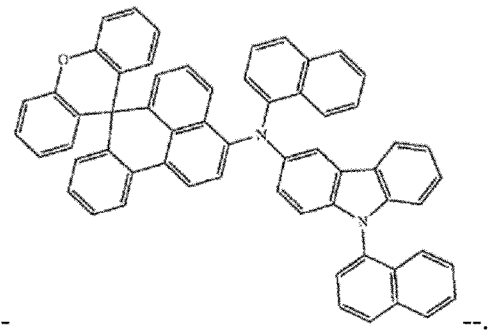 --.
In Column 834, Lines 4-20, in Claim 18, Compound 1122, delete
" 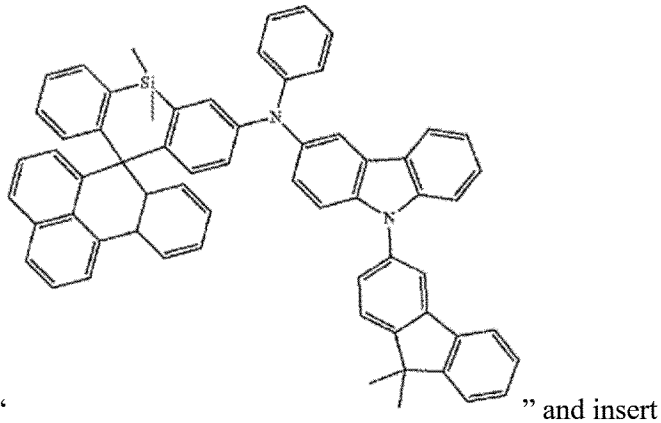 " and insert